(12) United States Patent
Kinoshita et al.

(10) Patent No.: US 9,440,922 B2
(45) Date of Patent: Sep. 13, 2016

(54) TETRACYCLIC COMPOUND

(71) Applicant: Chugai Seiyaku Kabushiki Kaisha, Kita-ku, Tokyo (JP)

(72) Inventors: Kazutomo Kinoshita, Kanagawa (JP); Kohsuke Asoh, Kanagawa (JP); Noriyuki Furuichi, Kanagawa (JP); Toshiya Ito, Kanagawa (JP); Hatsuo Kawada, Kanagawa (JP); Nobuya Ishii, Kanagawa (JP); Hiroshi Sakamoto, Kanagawa (JP); WooSang Hong, Gyeonggi-do (KR); MinJeong Park, Gyeonggi-do (KR); Yoshiyuki Ono, Shizuoka (JP); Yasuharu Kato, Shizuoka (JP); Kenji Morikami, Shizuoka (JP); Takashi Emura, Shizuoka (JP); Nobuhiro Oikawa, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/619,242

(22) Filed: Feb. 11, 2015

(65) Prior Publication Data

US 2015/0150845 A1    Jun. 4, 2015

Related U.S. Application Data

(62) Division of application No. 13/377,300, filed as application No. PCT/JP2010/059785 on Jun. 9, 2010, now Pat. No. 9,126,931.

(30) Foreign Application Priority Data

Jun. 10, 2009   (JP) .................. 2009-139691

(51) Int. Cl.
| | |
|---|---|
| A61K 31/506 | (2006.01) |
| C07D 209/56 | (2006.01) |
| C07D 209/88 | (2006.01) |
| C07D 307/77 | (2006.01) |
| C07D 307/92 | (2006.01) |
| C07D 333/50 | (2006.01) |
| C07D 333/76 | (2006.01) |
| C07D 401/04 | (2006.01) |
| C07D 401/06 | (2006.01) |

(Continued)

(52) U.S. Cl.
CPC ........... *C07D 209/56* (2013.01); *A61K 31/404* (2013.01); *A61K 31/4178* (2013.01); *A61K 31/4439* (2013.01); *A61K 31/454* (2013.01); *A61K 31/496* (2013.01); *A61K 31/506* (2013.01); *A61K 31/5377* (2013.01); *A61K 31/541* (2013.01); *A61K 31/7056* (2013.01); *C07D 209/88* (2013.01); *C07D 307/77* (2013.01); *C07D 307/92* (2013.01); *C07D 333/50* (2013.01); *C07D 333/76* (2013.01); *C07D 401/04* (2013.01); *C07D 401/06* (2013.01); *C07D 403/04* (2013.01); *C07D 405/12* (2013.01); *C07D 405/14* (2013.01); *C07D 471/04* (2013.01); *C07D 491/107* (2013.01)

(58) Field of Classification Search
CPC  C07D 209/56; C07D 209/88; C07D 307/77; C07D 307/92; C07D 333/50; C07D 333/76; C07D 401/04; C07D 401/06; C07D 403/04; C07D 405/12; C07D 405/14; C07D 471/04; C07D 491/107; A61K 31/404; A61K 31/4178; A61K 31/4439; A61K 31/454; A61K 31/496; A61K 31/506; A61K 31/5377; A61K 31/541; A61K 31/7056
See application file for complete search history.

(56) References Cited

U.S. PATENT DOCUMENTS 5,721,267 A    2/1998   Broka
5,936,084 A    8/1999   Jirousek et al.

(Continued)

FOREIGN PATENT DOCUMENTS

CN    1902200 A      1/2007
EA    001450 B1      4/2001

(Continued)

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*

(Continued)

*Primary Examiner* — Alexander R Pagano
(74) *Attorney, Agent, or Firm* — Foley & Lardner LLP

(57) ABSTRACT

A compound represented by the general Formula (I) below, or a salt or solvate thereof, which is useful as an ALK inhibitor, and is useful for prophylaxis or treatment of a disease accompanied by abnormality in ALK, for example, cancer, cancer metastasis, depression or cognitive function disorder:

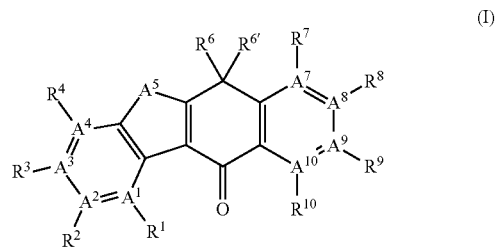

(meanings of the symbols that are included in the formula are as given in the specification).

34 Claims, No Drawings

(51) Int. Cl.

| | | |
|---|---|---|
| C07D 403/04 | (2006.01) | |
| C07D 405/12 | (2006.01) | |
| C07D 405/14 | (2006.01) | |
| C07D 471/04 | (2006.01) | |
| C07D 491/107 | (2006.01) | |
| A61K 31/404 | (2006.01) | |
| A61K 31/4178 | (2006.01) | |
| A61K 31/4439 | (2006.01) | |
| A61K 31/454 | (2006.01) | |
| A61K 31/496 | (2006.01) | |
| A61K 31/5377 | (2006.01) | |
| A61K 31/541 | (2006.01) | |
| A61K 31/7056 | (2006.01) | |

(56) References Cited

U.S. PATENT DOCUMENTS

| | | | |
|---|---|---|---|
| 9,126,931 B2* | 9/2015 | Kinoshita | C07D 209/56 |
| 2005/0107364 A1 | 5/2005 | Hutchinson et al. | |
| 2007/0031907 A1 | 2/2007 | Pinna et al. | |
| 2007/0099893 A1 | 5/2007 | Boyd et al. | |
| 2007/0249653 A1 | 10/2007 | Jagtap et al. | |
| 2008/0058320 A1 | 3/2008 | Herold et al. | |
| 2008/0262021 A1 | 10/2008 | Capraro et al. | |
| 2009/0221555 A1 | 9/2009 | Ahmed et al. | |
| 2010/0099658 A1 | 4/2010 | Kondoh et al. | |
| 2012/0083488 A1* | 4/2012 | Kinoshita | C07D 209/56 514/217.03 |

FOREIGN PATENT DOCUMENTS

| | | |
|---|---|---|
| JP | 08-092090 A | 4/1996 |
| RU | 2162089 C2 | 1/2001 |
| WO | WO 00/69856 A1 | 11/2000 |
| WO | WO 2004/080980 A1 | 9/2004 |
| WO | WO 2005/009389 A2 | 2/2005 |
| WO | WO 2005/097765 A1 | 10/2005 |
| WO | WO 2006/021884 A2 | 3/2006 |
| WO | WO 2007/023310 A2 | 3/2007 |
| WO | WO 2007/056497 A1 | 5/2007 |
| WO | WO 2007/130468 A2 | 11/2007 |
| WO | WO 2008/021369 A2 | 2/2008 |
| WO | WO 2008/051547 A1 | 5/2008 |
| WO | WO 2008/130951 A1 | 10/2008 |
| WO | WO 2009/008371 A1 | 1/2009 |
| WO | WO 2009/013126 A1 | 1/2009 |
| WO | WO 2009/073620 A2 | 6/2009 |
| WO | WO 2010/128324 A1 | 11/2010 |
| WO | WO 2010/142423 A2 | 12/2010 |
| WO | WO 2010/142685 A1 | 12/2010 |

OTHER PUBLICATIONS

National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
H.A. Fine, Neoplasms of the Central Nervous System in, 2 Cancer Principles & Practice of Oncology 1834-1887 (V.T. DeVita, Jr. et al. eds., 5th ed., 2005).*
D. Glick et al., 35 Journal of Psychiatric Research, 187-191, 187 (2001).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*
Kinase Inhibitors, Methods in Molecular Biology 795 (B. Kuster ed., 2012).*
H. Hermann, 86 Blood, 1694-1700 (1995).*
R. Piva et al., 107 Blood 689-697 (2006).*
L. Lamant et al., 18 Leukemia, 1693-1698 (2004).*
A Rosenwald et al., 94 Blood, 362-364 (1999).*
G.S. Wood, 88 Blood, 1765-1770 (1996).*
R.E. George et al., 455 Nature, 975-978 (2008).*
J. Cools et al., 34 Genes, Chromosomes & Cancer, 354-362 (2002).*
E.L. Kwak et al., 363 New England Journal of Medicine, 1693-1703 (2010).*
A.T. Shaw et al., 17 Clinical Cancer Research, 2081-2086 (2011).*
G. Husbinger et al., 20 Oncogene, 590-598 (2001).*
J. Wanner et al., 19 Heterocycles, 2295-2300 (1982).*
Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.
Chen et al., "Oncogenic mutations of ALK kinase in neuroblastoma," Nature, Oct. 16, 2008, 455:971-974, and Methods page.
Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
Goel et al., "Mice transgenic for BRAF V600E demonstrate phenotype affecting melanocyte and neural lineages," Proceedings of the American Association for Cancer Research, Apr. 2006, 47:#273.
Griffin et al., "Recurrent involvement of 2p23 in Inflammatory Myofibroblastic Tumors," Cancer Research, Jun. 15, 1999, 59:2776-2780.
Huang et al., "An in vivo model to study human GSTP1 polymorphisms in osteosarcoma," Proceedings of the American Association for Cancer Research, Apr. 2006, 47:#271.
Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Kirsch, Gilbert H., "Heterocyclic Analogues of Carbazole Alkaloids," Current Organic Chemistry, 2001, 5:507-518.
Mosse et al., "Identification of ALK as a major familial neuroblastoma predisposition gene," Nature, Oct. 16, 2008, 455:930-935, and Methods page.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soda et al., "Identification of the transforming EML4-ALK fusion gene in non-small-cell lung cancer," Nature, Aug. 2, 2007, 448:561-566, and Methods page.

(56) References Cited

OTHER PUBLICATIONS

Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Zhao et al., "The progress of the research on anaplastic lymphoma kinase genetic abnormality of anaplastic large cell lymphoma," Foreign Medical Sciences (Section of Blood Transfusion and Heanatology), Oct. 15, 2004, 27(5):403-406.

CAS RN 6008-29-3, STN Entry Date Nov. 16, 1984.
CAS RN 100863-39-6, STN Entry Date Mar. 15, 1986.
CAS RN 4355-38-8, STN Entry Date Nov. 16, 1984.
CAS RN 74205-47-3, STN Entry Date Nov. 16, 1984.
CAS RN 93257-39-7, STN Entry Date Dec. 18, 1984.
CAS RN 61492-49-7, STN Entry Date Nov. 16, 1984.
CAS RN 36263-63-5, STN Entry Date Nov. 16, 1984.
CAS RN 222318-66-3, STN Entry Date May 7, 1999.
CAS RN 24716-14-1, STN Entry Date Nov. 16, 1984.
CAS RN 89579-57-7, STN Entry Date Nov. 16, 1984.

\* cited by examiner

TETRACYCLIC COMPOUND

CROSS-REFERENCE TO RELATED APPLICATIONS

This application is a Divisional of U.S. application Ser. No. 13/377,300, which is the U.S. National Stage application of PCT/JP2010/059785, filed Jun. 9, 2010, which claims priority from Japanese application JP 2009-139691, filed Jun. 10, 2009.

TECHNICAL FIELD

The present invention relates to tetracyclic compounds, salts or solvates thereof. More specifically, the present invention relates to the tetracyclic compounds and provides a medicament, pharmaceutical compositions comprising the compounds, ALK inhibitors, and pharmaceuticals for the prophylaxis or treatment of the diseases including cancer, cancer metastasis, depression or cognitive function disorder comprising the compounds. Furthermore, the present invention relates to a method for the treatment of the diseases comprising administering to the patient who is in need of the treatment of the disease the compounds described herein, salts or solvates thereof in an effective amount for the treatment of the diseases, and use of the tetracyclic compounds for the preparation of the pharmaceutical composition.

BACKGROUND ART

Anaplastic Lymphoma Kinase (ALK) is one of the receptor tyrosine kinases belonging to insulin receptor family (Non-Patent Document Nos. 1 and 2).

It was reported that, due to gene alteration of ALK (translocation, point mutation and gene amplification), an abnormal activation of ALK is eventually involved in oncogenesis.

For example, in lung cancer, ALK forms EML4-ALK due to chromosomal translocation, leading to constitutive activation of tyrosine kinase, and it acquires a tumorigenic activity (Non-Patent Document 1). In addition, the ALK translocation were reported in systemic anaplastic large cell lymphoma (ALCL) and inflammatory myofibroblastic tumors (IMTs) (Non-Patent Document Nos. 3 and 4), and esophageal cancer (Non-Patent Document 5). It was also found that active point mutation (approximately 10%) or gene amplification of ALK is involved in oncogenesis of neuroblastoma (Non-Patent Document Nos. 6 and 7).

On the other hand, it was also reported in tumors activated by pleiotrophin (PTN) or midkine (MK) (Non-Patent Document Nos. 8 and 9), both a ligand for ALK.

Further, from the study using ALK knock-out mouse, it was suggested that an inhibitor for ALK is useful as an anti-depression agent or as a preventive or therapeutic agent for cognitive function disorders (Non-Patent Document 10 and Patent Document 1).

Therefore, a compound having an inhibitory activity on ALK will be very useful for the prevention and treatment of cancer, depression and cognitive function disorders, etc.

Meanwhile, as an ALK inhibiting material, there are some compounds among multi-kinase inhibitors which have an inhibitory activity on ALK as one of their activities. For example, as an inhibitor for c-MET (mesenchymal-epithelial transition factor) and ALK, PF02341066 having a 2-aminopyridine structure was reported (Patent Document 2, Non-Patent Document Nos. 11 and 12). As an inhibitor for FAK, ZAP70, IGF-1R and ALK, etc., NVP-TAE684 having a 2,4-diaminopyrimidine structure was reported (Patent Document 3 and Non-Patent Document 13). In addition, 2,4-diaminopyrimidines and 2,4-diaminoquinazolines (Patent Document 4), pyridopyrazines (Patent Document 5), pyrazolo[3,4-C]isoquinolines (Patent Document 6), thiazoles (Patent Document 7), tricyclic compounds (Patent Document 8), and indazoles (Patent Document 9) and the like have been reported.

However, the tetracyclic compounds of the present invention are not disclosed in any of the documents described above.

As a tetracyclic compound exhibiting an anti-tumor activity, tetracyclic compounds comprising carbazole structure like ellipticine are known.

However, their action mechanism is based on interaction with DNA to exhibit cell toxicity (Non-Patent Document 15), and there is no description at all regarding the activity of inhibiting ALK by the tetracyclic compounds.

DOCUMENT LIST

[Patent Document 1] WO 2007/023310 A2
[Patent Document 2] WO 2006/021884 A2
[Patent Document 3] WO 2004/080980 A1
[Patent Document 4] WO 2009/008371 A1
[Patent Document 5] WO 2007/130468 A2
[Patent Document 6] WO 2005/009389 A2
[Patent Document 7] WO 2005/097765 A1
[Patent Document 8] WO 2008/021369 A2
[Patent Document 9] WO 2009/013126 A1
[Non-Patent Document 1] Proc Natl Acad Sci USA, Vol. 101, pages 13306-13311, 2004
[Non-Patent Document 2] Nature, Vol. 448, pages 561-566, 2007
[Non-Patent Document 3] Blood, Vol. 72, pages 234-240, 1988
[Non-Patent Document 4] Cancer Res, Vol. 59, pages 2776-2780, 1999
[Non-Patent Document 5] World J Gastroenterol, Vol. 12, pages 7104-7112, 2006
[Non-Patent Document 6] Nature, Vol. 455, pages 930-935, 2008
[Non-Patent Document 7] Nature, Vol. 455, pages 971-974, 2008
[Non-Patent Document 8] J Biol Chem, Vol. 276, pages 16772-16779, 2001
[Non-Patent Document 9] J Biol Chem, Vol. 277, pages 35990-35999, 2002
[Non-Patent Document 10] Neuropsychopharmacology, Vol. 33, pages 685-700, 2008
[Non-Patent Document 11] Proc Am Assoc Cancer Res (AACR) 2006, 47: Abst LB-271
[Non-Patent Document 12] Proc Am Assoc Cancer Res (AACR) 2006, 47: Abst LB-273
[Non-Patent Document 13] Proc Natl Acad Sci USA Vol. 104, pages 270-275, 2007
[Non-Patent Document 14] Current Organic Chemistry, Vol. 5, Issue No. 5, pages 507-518, 2001
[Non-Patent Document 15] Current Medicinal Chemistry: Anti-Cancer Agents, Vol. 4, Issue No. 2, pages 149-172, 2004

SUMMARY OF THE INVENTION

Problems to be Solved by the Invention

The present invention is to provide ALK-inhibiting compounds having a novel structure. In addition, object of the present invention is to provide a pharmaceuticals for the prophylaxis or treatment comprising the ALK-inhibiting compounds that is effective for prophylaxising or treating a disease accompanied by abnormality in ALK, for example, cancer, cancer metastasis, depression and cognitive function disorder.

Means for Solving the Problems

As a result of extensive studies by the inventors of the present invention, it was found that the tetracyclic compounds that are represented by the following Formula (1) with a structure clearly different from any other existing pharmaceutical compounds have an excellent ALK-inhibiting activity, are useful for the treatment and prophylaxis of the diseases including cancer, cancer metastasis, depression and cognitive function disorder, and have a remarkable efficacy against said diseases. Accordingly, the present invention was completed.

Thus, according to one aspect of the present invention, the tetracyclic compounds, a medicament and a pharmaceutical composition comprising the compounds, etc. shown below are provided.

[1] A compound or salt or solvate thereof represented by Formula (I):

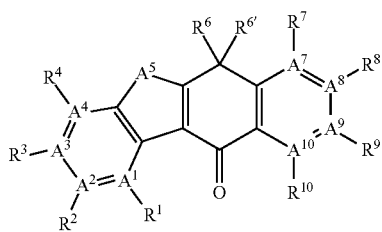

(I)

[wherein, $A^1$, $A^2$, $A^3$, $A^4$, $A^7$, $A^8$, $A^9$ and $A^{10}$ all represent C, or any one of $A^2$, $A^3$, $A^4$, $A^2$, $A^8$ and $A^9$ represents N (with the proviso that, when it represents N, no substituent group exists therefor) and the remainings represent C;

$A^5$ is selected from $NR^5$, O and S;

$R^1$ and $R^{10}$ each independently represent [1] a hydrogen atom, [2] a cyano group, [3] a halogen atom or [4] a 4- to 10-membered heterocycloalkyl group which may be substituted by 4- to 10-membered heterocycloalkyl group(s);

$R^2$ is selected from the group consisting of:
(1) a hydrogen atom,
(2) a $C_{1-8}$ alkyl group,
(3) a $C_{2-8}$ alkenyl group,
(4) a $C_{2-8}$ alkynyl group,
(5) a cyano group,
(6) a halogen atom,
(7) a $(C_{1-8}$ alkyl$)_{m2}$-amino group which may be substituted by $C_{1-8}$ alkylsulfonyl group(s),
m2: 0~2, and
(8) a nitro group;

$R^3$ is selected from the group consisting of:
(1) a hydrogen atom,
(2) a $C_{1-8}$ alkyl group which may be substituted by [1] halogen atom(s), [2] hydroxy group(s) or [3] $C_{1-8}$ alkoxy group(s),
(3) a $C_{6-10}$ aryl group,
(4) a cyano group, (5) a $C_{1-8}$ alkanoyl group which may be substituted by $C_{6-10}$ aryl group(s),
(6) a (C1-8 alkyl$)_{m3a}$-aminocarbonyl group which may be substituted by one or more $R^{3A}$,
$R^{3A}$: [1] a $C_{6-10}$ aryl group, [2] a $C_{1-8}$ alkoxy group, [3] a 5- to 14-membered heteroaryl group, or [4] a $C_{6-10}$ aryl sulfonyl group,
m3a: 0~2,
(7) a hydroxycarbonyl group,
(8) a $C_{1-8}$ alkoxycarbonyl group which may be substituted by [1] hydroxy group(s) or [2] $C_{1-8}$ alkoxy group(s),
(9) a halogen atom,
(10) a $(C_{1-8}$ alkyl$)_{m3b}$-amino group which may be substituted by $C_{6-10}$ aryl group(s),
m3b: 0~2,
(11) a $C_{1-8}$ alkylcarbonyl $(C_{0-8}$ alkyl) amino group which may be substituted by [1] $C_{6-10}$ aryl group(s) or [2] $C_{6-10}$ aryloxy group(s),
(12) a $C_{6-10}$ arylcarbonyl $(C_{0-8}$ alkyl) amino group which may be substituted by $C_{1-8}$ alkyl group(s) which may be substituted by halogen atom(s),
(13) a $(C_{1-8}$ alkyl$)_{m3c}$-aminocarbonyl $(C_{0-8}$ alkyl) amino group which may be substituted by $C_{6-10}$ aryl group(s),
m3c: 0~2,
(14) a nitro group,
(15) a hydroxy group,
(16) a $C_{1-8}$ alkoxy group which may be substituted by one or more $R^{3B}$,
$R^{3B}$: [1] a hydroxy group, [2] a $C_{1-8}$ alkoxy group, [3] a $C_{6-10}$ aryl $(C_{0-8}$ alkyl) aminocarbonyl group, [4] a $(C_{1-8}$ alkyl$)_{m3d}$ amino group, or [5] a halogen atom,
m3 d: 0~2,
(17) a 4- to 10-membered heterocycloalkyloxy group,
(18) a 5- to 14-membered heteroaryloxy group,
(19) a $(C_{1-8}$ alkyl$)_{m3e}$-aminocarbonyloxy group which may be substituted by $C_{6-10}$ aryl group(s)
m3e: 0~2,
(20) a 4- to 10-membered nitrogen-containing heterocycloalkylcarbonyl group,
(21) a $C_{1-8}$ alkylsulfonyloxy group which may be substituted by halogen atom(s),
(22) a $C_{1-8}$ alkylthio group,
(23) a $C_{1-8}$ alkylsulfonyl group which may be substituted by $C_{6-10}$ aryl group(s),
(24) a 5- to 14-membered heteroaryl group which may be substituted by $C_{1-8}$ alkyl group(s) which may be substituted by $C_{1-8}$ alkoxy group(s),
(25) a $C_{1-8}$ alkoxycarbonyl $(C_{0-8}$ alkyl) amino group which may be substituted by $C_{1-8}$ alkoxy group(s),
(26) a $C_{6-10}$ aryloxycarbonyl $(C_{0-8}$ alkyl) amino group which may be substituted by $C_{1-8}$ alkyl group(s) which may be substituted by halogen atom(s),
(27) a $C_{6-10}$ aryl $(C_{0-8}$ alkyl) aminocarbonyl $(C_{0-8}$ alkyl) amino group which may be substituted by one or more $R^{3C}$,
$R^{3C}$: [1] a $C_{1-8}$ alkyl group which may be substituted by halogen atom(s), or [2] a $C_{1-8}$ alkoxy group,
(28) a $C_{3-8}$ cycloalkyl $(C_{0-8}$ alkyl) aminocarbonyloxy group, and
(29) a $C_{6-10}$ aryl $(C_{0-8}$ alkyl) aminocarbonyloxy group which may be substituted by substituent(s) selected from the group consisting of [1] a $C_{1-8}$ alkyl group and [2] a $C_{1-8}$ alkoxy group;

$R^4$ is selected from the group consisting of:
(1) a hydrogen atom,
(2) a $C_{1-8}$ alkyl group which may be substituted by halogen atom(s),
(3) a $C_{2-8}$ alkenyl group, (4) a $C_{2-8}$ alkynyl group,
(5) a $C_{3-8}$ cycloalkyl group,
(6) a cyano group,
(7) an aminocarbonyl group,
(8) a $(C_{1-8}$ alkyl$)_{m4a}$-aminocarbonyl group,
m4a: 1~2,
(9) a hydroxycarbonyl group,
(10) a $C_{1-8}$ alkoxycarbonyl group,
(11) a halogen atom,
(12) a $(C_{1-8}$ alkyl$)_{m4b}$-amino group,
m4b: 0~2,
(13) a hydroxy group, and
(14) a $C_{1-8}$ alkoxy group which may be substituted by hydroxy group(s);

$R^5$ is selected from the group consisting of:
(1) a hydrogen atom,
(2) a $C_{1-8}$ alkyl group which may be substituted by one or more $R^{5A}$,
$R^{5A}$: [1] a hydroxycarbonyl group, [2] a $C_{1-8}$ alkoxycarbonyl group, [3] a hydroxy group, [4] a $C_{1-8}$ alkoxy group, [5] a $(C_{1-8}$ alkyl$)_{m5}$-amino group, [6] a $C_{6-10}$ aryl group, or [7] a $C_{1-8}$ alkylthio group,
m5: 0~2,
(3) a $C_{2-8}$ alkenyl group,
(4) a $C_{2-8}$ alkynyl group,
(5) a $C_{3-8}$ cycloalkyl group, and
(6) a $C_{1-8}$ alkylsulfonyl group;

$R^6$ and $R^{6'}$ are each independently selected from the group consisting of:
(1) a $C_{1-8}$ alkyl group which may be substituted by halogen atom(s),
(2) a $C_{2-8}$ alkenyl group, and
(3) a $C_{2-8}$ alkynyl group; or
$R^6$ and $R^{6'}$ are taken together with the carbon atoms to which they are bound to form:
(4) a $C_{3-8}$ cycloalkyl group, or
(5) a 4- to 10-membered heterocycloalkyl group which may be substituted by $C_{1-8}$ alkyl $C_{6-10}$ aryl sulfonyl group(s) which may be substituted by $C_{1-8}$ alkyl group(s);

$R^7$ is selected from the group consisting of:
(1) a hydrogen atom,
(2) a halogen atom,
(3) a $C_{1-8}$ alkoxy group which may be substituted by one or more $R^{7A}$,
$R^{7A}$: [1] a $(C_{1-8}$ alkyl)m7a-amino group, [2] a hydroxy, [3] a 4- to 10-membered heterocycloalkyl group which may be substituted by $C_{1-8}$ alkyl group(s),
m7a: 0~2,
(4) a $C_{1-8}$ alkylsulfonyl group,
(5) a nitro group, and
(6) a hydroxyl group;

$R^8$ is selected from the group consisting of:
(1) a hydrogen atom,
(2) a $C_{1-8}$ alkyl group which may be substituted by one or more $R^{8A}$,
$R^{8A}$: [1] a 4- to 10-membered heterocycloalkyl group which may be substituted by one or more $R^{8A1}$, [2] a $(C_{1-8}$ alkyl$)_{m8a}$-amino group which may be substituted by a halogen atom, and [3] a hydroxy group,
m8a: 0~2,
$R^{8A1}$: [1] a $C_{1-8}$ alkyl group, [2] a $C_{1-8}$ alkylsulfonyl group, [3] a $(C_{1-8}$ alkyl$)_{m8b}$-aminosulfonyl group, [4] an oxo group, [5] a $C_{1-8}$ alkoxycarbonyl, or [6] a $C_{1-8}$ alkoxycarbonyl $(C_{0-8}$ alkyl) aminosulfonyl,
m8b: 0~2, (3) a $C_{2-8}$ alkenyl group,
(4) a 4- to 10-membered heterocycloalkyl group which may be substituted by one or more $R^{8B}$,
$R^{8B}$:
<1> a $C_{1-8}$ alkyl group which may be substituted by one or more $R^{8B1}$,
<2> a $C_{2-8}$ alkenyl group,
<3> a $C_{2-8}$ alkynyl group,
<4> a $C_{3-8}$ cycloalkyl group which may be substituted by [1] cyano group(s) or [2] $C_{1-8}$ alkyl group(s),
<5> a 4- to 10-membered heterocycloalkyl group which may be substituted by one or more $R^{8B2}$,
<6> a $C_{1-8}$ alkoxy group which may be substituted by substituent(s) selected from the group consisting of [1] a $C_{1-8}$ alkoxy group and [2] a $C_{3-8}$ cycloalkyl group,
<7> a $C_{1-8}$ alkoxycarbonyl group,
<8> a $C_{1-8}$ alkylsulfonyl group,
<9> a 5- to 14-membered heteroarylsulfonyl group,
<10> an oxo group,
<11> a cyano group,
<12> a $C_{1-8}$ alkanoyl group which may be substituted by one or more $R^{8B3}$,
<13> a $C_{3-8}$ cycloalkylcarbonyl group,
<14> a $(C_{1-8}$ alkyl$)_{m8c}$-aminosulfonyl group,
<15> a $C_{1-8}$ alkylsulfonyl $(C_{0-8}$ alkyl) amino group,
<16> a $(C_{1-8}$ alkyl$)_{m8d}$-amino group which may be substituted by one or more $R^{8B4}$,
<17> a hydroxy group,
<18> a $(C_{1-8}$ alkyl$)_{m8e}$-aminocarbonyl group, or
<19> a $C_{1-8}$ alkoxycarbonyl $(C_{0-8}$ alkyl) amino group
m8c: 0~2
m8d: 0~2
m8e: 0~2
$R^{8B1}$: [1] a $C_{3-8}$ cycloalkyl group, [2] a hydroxy group, or [3] a $C_{1-8}$ alkoxy group(s),
$R^{8B2}$: [1] a halogen atom, [2] a $C_{1-8}$ alkyl group, [3] an oxo group, [4] a hydroxy group, or [5] a deuterium atom,
$R^{8B3}$: a $(C_{1-8}$ alkyl$)_{m8f}$-amino group,
m8f: 0~2,
$R^{8B4}$: [1] a $C_{3-8}$ cycloalkyl group, or [2] a hydroxy group,
(5) a 5- to 14-membered heteroaryl group which may be substituted by a $C_{1-8}$ alkyl group,
(6) a $(C_{1-8}$ alkyl$)_{m8g}$-aminocarbonyl group which may be substituted by one or more $R^{8C}$,
m8g: 0~2,
$R^{8C}$: [1] a hydroxy group, [2] a $(C_{1-8}$ alkyl$)_{m8h}$-amino group which may be substituted by substituent(s) selected from the group consisting of <1> a $(C_{1-8}$ alkyl$)_{m8i}$-aminosulfonyl group, <2> a $C_{1-8}$ alkylsulfonyl group, <3> a $C_{1-8}$ alkoxycarbonyl group and <4> a $C_{1-8}$ alkoxycarbonyl$(C_{0-8}$ alkyl) aminosulfonyl group, [3] a $C_{1-8}$ alkylsulfonyl group, or [4] a $C_{1-8}$ alkoxy group which may be substituted by a hydroxy group,
m8h: 0~2,
m8i: 0~2,
(7) a 4- to 10-membered heterocycloalkyl $(C_{0-8}$ alkyl) aminocarbonyl group which may be substituted by oxo group(s),
(8) a 4- to 10-membered nitrogen-containing heterocycloalkylcarbonyl group which may be substituted by one or more $R^{8D}$,
$R^{8D}$: [1] a $C_{1-8}$ alkyl group which may be substituted by one or more $R^{8D1}$, [2] a hydroxy group, [3] a $C_{1-8}$ alkylsulfonyl group, or [4] a $C_{1-8}$ alkoxycarbonyl group,
$R^{8D1}$: [1] a hydroxy group, or [2] a $C_{1-8}$ alkoxy group,
(9) a hydroxycarbonyl group,
(10) a $C_{0-8}$ alkoxy $(C_{0-8}$ alkyl) aminocarbonyl group which may be substituted by hydroxy group(s),

(11) a halogen atom,
(12) a $(C_{1-8}\ alkyl)_{m8j}$-amino group which may be substituted by one or more $R^{8H}$,
  m8j: 0~2,
  $R^{8H}$: [1] a hydroxy group, or [2] a 4- to 10-membered heterocycloalkyl group,
(13) a hydroxyl group,
(14) a $C_{1-8}$ alkoxy group which may be substituted by one or more $R^{8E}$, $R^{8E}$:
  <1> a hydroxy group,
  <2> halogen atom,
  <3> a hydroxycarbonyl group,
  <4> a $C_{1-8}$ alkoxycarbonyl group,
  <5> a 4- to 10-membered nitrogen-containing heterocycloalkylcarbonyl group which may be substituted by one or more $R^{8E1}$,
  <6> a $(C_{1-8}\ alkyl)_{m8k1}$-amino group which may be substituted by one or more $R^{8E2}$,
    m8k1: 0~2,
  <7> a 4- to 10-membered heterocycloalkyl group which may be substituted by one or more $R^{8E3}$,
  <8> a 5- to 14-membered heteroaryl group,
  <9> a $(C_{1-8}\ alkyl)_{m8k2}$-aminocarbonyl group which may be substituted by one or more $R^{8E6}$,
    m8k2: 0~2,
  <10> a $C_{1-8}$ alkoxy group which may be substituted by one or more $R^{8E7}$,
  <11> a $C_{1-8}$ alkylthio group,
  <12> a $C_{1-8}$ alkylsulfinyl group,
  <13> a $C_{1-8}$ alkylsulfonyl group,
  $R^{8E1}$:
  <1> a $C_{1-8}$ alkoxycarbonyl group,
  <2> a $C_{1-8}$ alkanoyl group,
  <3> a $C_{1-8}$ alkylsulfonyl group,
  <4> a $(C_{1-8}\ alkyl)_{m8k3}$-aminosulfonyl group,
    m8k3: 0~2, or
  <5> a 4- to 10-membered heterocycloalkyl group,
  $R^{8E2}$:
  <1> a hydroxy group,
  <2> a $C_{1-8}$ alkoxycarbonyl group which may be substituted by halogen atom(s),
  <3> a $C_{3-8}$ cycloalkyl group which may be substituted by $C_{1-8}$ alkyl group(s) which may be substituted by hydroxy group(s),
  <4> a $C_{1-8}$ alkanoyl group which may be substituted by substituent(s) selected from the group consisting of [1] a $(C_{1-8}\ alkyl)_{m8k4}$-amino group and [2] a halogen atom(s),
    m8k4: 0~2,
  <5> a $(C_{1-8}\ alkyl)_{m8k5}$-aminocarbonyl group,
    m8k5: 0~2,
  <6> a $C_{1-8}$ alkylsulfonyl group,
  <7> a 4- to 10-membered nitrogen-containing heterocycloalkylsulfonyl group which may be substituted by $C_{1-8}$ alkyl group(s),
  <8> a $(C_{1-8}\ alkyl)_{m8k6}$-aminosulfonyl group which may be substituted by $C_{1-8}$ alkoxycarbonyl group(s),
    m8k6: 0~2, or
  $R^{8E3}$:
  <1> a $C_{1-8}$ alkyl group which may be substituted by substituent(s) selected from the group consisting of [1] a hydroxy group and [2] a $C_{1-8}$ alkylcarbonyloxy group,
  <2> a $C_{1-8}$ alkylcarbonyloxy group,
  <3> a hydroxy group,
  <4> a $C_{3-8}$ cycloalkyl group,
  <5> a $C_{1-8}$ alkoxy group,
  <6> a $C_{1-8}$ alkoxycarbonyl group,
  <7> a $C_{1-8}$ alkylsulfonyl group,
  <8> a $(C_{1-8}\ alkyl)_{m8k8}$-aminocarbonyl group
    m8k8: 0~2,
  <9> a $C_{1-8}$ alkanoyl group which may be substituted by hydroxy group(s),
  <10> an oxo group, or <11> a 4- to 10-membered heterocycloalkyl group which may be substituted by substituent(s) selected from the group consisting of [1] a $C_{1-8}$ alkanoyl group, [2] a $C_{1-8}$ alkoxycarbonyl group and [3] a $C_{1-8}$ alkylsulfonyl group,
  $R^{8E6}$:
  <1> a $C_{2-8}$ alkenylcarbonyloxy group,
  <2> a hydroxy group,
  <3> a cyano group,
  <4> a $(C_{1-8}\ alkyl)_{m8k9}$-amino group which may be substituted by hydroxy group(s)
    m8k9: 0~2,
  <5> a $C_{1-8}$ alkoxy group which may be substituted by hydroxy group(s),
  <6> a $C_{1-8}$ alkylcarbonyloxy group,
  <7> a 4- to 10-membered heterocycloalkyl group which may be substituted by $C_{1-8}$ alkyl group(s), or
  <8> a 5- to 14-membered heteroaryl group,
  $R^{8E7}$:
  <1> a hydroxy group, or
  <2> a $C_{1-8}$ alkoxy group which may be substituted by hydroxy group(s),
(15) a 4- to 10-membered heterocycloalkyloxy group which may be substituted by one or more $R^{8F}$,
  $R^{8F}$:
  <1> a $C_{1-8}$ alkyl group which may be substituted by one or more $R^{8F1}$,
  <2> a $C_{3-8}$ cycloalkyl group,
  <3> a $C_{1-8}$ alkanoyl group which may be substituted by halogen atom(s),
  <4> a $C_{1-8}$ alkylcarbonyloxy group,
  <5> a $C_{1-8}$ alkoxycarbonyl group,
  <6> a 4- to 10-membered heterocycloalkyl group which may be substituted by one or more $R^{8F2}$,
  <7> a $C_{1-8}$ alkyl sulfonyl group,
  <8> a hydroxy group, or
  [9] a $C_{6-10}$ aryl group,
  $R^{8F1}$: [1] a hydroxy group, [2] a $C_{1-8}$ alkoxy group, or [3] a halogen atom,
  $R^{8F2}$: [1] a 4- to 10-membered heterocycloalkyl group, [2] a $C_{1-8}$ alkoxycarbonyl group, or [3] a $C_{1-8}$ alkylsulfonyl group,
(16) a 5- to 14-membered heteroaryloxy group,
(17) a 4- to 10-membered heterocycloalkylcarbonyloxy group,
(18) a $(C_{1-8}\ alkyl)_{m8l1}$-aminosulfonyloxy group,
  m8l1: 0~2,
(19) a $C_{1-8}$ alkyl thio group which may be substituted by [1] $(C_{1-8}\ alkyl)_{m8l2}$-amino group(s), [2] hydroxy group(s) or [3] hydroxycarbonyl group(s),
  m8l2: 0~2,
(20) a $C_{1-8}$ alkylsulfonyl group which may be substituted by one or more $R^{8G}$,
  $R^{8G}$: [1] a hydroxycarbonyl group, [2] a hydroxy group, or [3] a $(C_{1-8}\ alkyl)_{m8l3}$-amino group,
  m8l3: 0~2,
(21) a 4- to 10-membered nitrogen-containing heterocycloalkylsulfonyloxy group which may be substituted by $C_{1-8}$ alkyl group(s),
(22) a $C_{2-8}$ alkenyloxy group, and
(23) a $C_{1-8}$ alkylsulfonyloxy group which may be substituted by halogen atom(s);

9

$R^9$ is selected from the group consisting of:
(1) a hydrogen atom,
(2) a $C_{1-8}$ alkyl group which may be substituted by one or more $R^{9A}$,
$R^{9A}$: [1] a $C_{3-8}$ cycloalkyl group, [2] a 4- to 10-membered heterocycloalkyl group which may be substituted by one or more $R^{9A1}$, [3] a hydroxy group, [4] a $C_{1-8}$ alkoxy group, or [5] a hydroxycarbonyl group,
$R^{9A1}$: [1] a $C_{1-8}$ alkyl group, [2] a $C_{3-8}$ cycloalkyl group, or [3] a 4- to 10-membered heterocycloalkyl group,
(3) a $C_{2-8}$ alkenyl group which may be substituted by one or more $R^{9B}$,
$R^{9B}$: [1] a $(C_{1-8}$ alkyl$)_{m9a}$-amino group, [2] a 4- to 10-membered heterocycloalkyl group which may be substituted by one or more group $R^{9B1}$,
$R^{9B1}$: [1] a $C_{3-8}$ cycloalkyl group, or [2] a 4- to 10-membered heterocycloalkyl group,
m9a: 0~2,
(4) a $C_{2-8}$ alkynyl group which may be substituted by one or more $R^{9C}$,
$R^{9C}$: [1] a $C_{1-8}$ alkoxy group, [2] a $(C_{1-8}$ alkyl$)_{m9b}$-amino group which may be substituted by $C_{6-10}$ aryl group(s), [3] a 4- to 10-membered heterocycloalkyl group which may be substituted by one or more $R^{9C1}$, [4] a $C_{3-8}$ cycloalkyl group, [5] a hydroxy group, [6] a hydroxycarbonyl group, or [7] a $C_{1-8}$ alkyloxycarbonyl group,
m9b: 0~2,
$R^{9C1}$: [1] a $C_{3-8}$ cycloalkyl group, [2] a 4- to 10-membered heterocycloalkyl group, or [3] an oxo group,
(5) a $C_{3-8}$ cycloalkyl group,
(6) a 4- to 10-membered heterocycloalkyl group which may be substituted by one or more $R^{9D}$,
$R^{9D}$: [1] a $C_{1-8}$ alkyl group which may be substituted by 4- to 10-membered heterocycloalkyl group(s), [2] a $C_{3-8}$ cycloalkyl group, [3] a 4- to 10-membered heterocycloalkyl group, or [4] a $C_{1-6}$ alkylsulfonyl group, or [5] a $C_{1-8}$ alkoxycarbonyl group,
(7) a $C_{6-10}$ aryl group which may be substituted by one or more $R^{9E}$,
$R^{9E}$: [1] a halogen atom, [2] a hydroxy group, [3] a hydroxycarbonyl group, or [4] a $C_{1-8}$ alkyl group which may be substituted by hydroxy group(s), or [5] a $C_{1-8}$ alkoxy group,
(8) a 5- to 14-membered heteroaryl group which may be substituted by $C_{1-8}$ alkyl group(s),
(9) a cyano group,
(10) a $C_{1-8}$ alkanoyl group,
(11) a 4- to 10-membered nitrogen-containing heterocycloalkylcarbonyl group which may be substituted by $C_{1-8}$ alkyl group(s),
(12) a halogen atom,
(13) a $(C_{1-8}$ alkyl$)_{m9c}$-amino group which may be substituted by one or more $R^{9F}$,
m9c: 0~2,
(14) a $C_{1-8}$ alkylcarbonyl($C_{0-8}$ alkyl)amino group which may be substituted by $(C_{1-8}$ alkyl$)_{m9d}$-amino group(s),
m9d: 0~2,
(15) a $C_{1-8}$ alkylsulfonyl($C_{0-8}$ alkyl)amino group, (16) a $(C_{1-8}$ alkyl$)_{m9e}$-aminosulfonyl($C_{0-8}$ alkyl)amino group,
m9e: 0~2,
(17) a nitro group,
(18) a hydroxy group,
(19) a $C_{1-8}$ alkoxy group which may be substituted by one or more $R^{9G}$,
$R^{9G}$: [1] a hydroxy group, [2] a hydroxycarbonyl group, [3] a $C_{6-10}$ aryl group which may be substituted by $C_{1-8}$ alkoxy group(s), [4] a $(C_{1-8}$ alkyl$)_{m9g1}$-amino group, [5] a

10

$C_{1-8}$ alkoxy group which may be substituted by one or more $R^{9G1}$, [6] a 5- to 14-membered heteroaryl group, or [7] a 4- to 10-membered heterocycloalkyloxy group which may be substituted by $C_{1-8}$ alkyl group(s),
m9g1: 0~2,
$R^{9G1}$: [1] a $C_{1-8}$ alkoxy group, or [2] a hydroxycarbonyl group,
(20) a 4- to 10-membered heterocycloalkyloxy group which may be substituted by [1] 4- to 10-membered heterocycloalkyl group(s), or [2] $C_{1-8}$ alkoxycarbonyl group(s),
(21) a $C_{1-8}$ alkylsulfonyloxy group which may be substituted by halogen atom(s),
(22) a $C_{1-8}$ alkylthio group which may be substituted by $(C_{1-8}$ alkyl$)_{m9f}$-amino group(s),
m9f: 0~2,
(23) a $C_{1-8}$ alkylsulfonyl group which may be substituted by $(C_{1-8}$ alkyl$)_{m9g}$-amino group(s),
m9g: 0~2,
(24) a $(C_{1-8}$ alkyl$)_{m9h}$-aminosulfonyl group,
m9h: 0~2,
(25) a 4- to 10-membered nitrogen-containing heterocycloalkylsulfonyl group which may be substituted by $C_{1-8}$ alkyl group(s), and
(26) a hydroxycarbonyl group].

[2] The compound according to the above [1], or a salt or solvate thereof, wherein $R^3$ is a cyano group or a halogen atom.

[3] The compound according to the above [1], or a salt or solvate thereof, wherein $A^5$ is $NR^5$ and $R^5$ is a hydrogen atom.

[4] The compound according to the above [1], or a salt or solvate thereof, wherein all of the $A^1, A^2, A^3, A^4, A^7, A^8, A^9$ and $A^{10}$ are a carbon atom.

[5] The compound according to claim 1, or a salt or solvate thereof, wherein: $A^1, A^2, A^3, A^4, A^7, A^8, A^9$ and $A^{10}$ all represent C, or any one of $A^2, A^3, A^4, A^7, A^8$ and $A^9$ represents N (with the proviso that, when it represents N, no substituent group exists therefor) and the remainings represent C;
$A^5$ is selected from $NR^5$, O and S;
$R^1$ represents [1] a hydrogen atom, [2] a cyano group, or [3] a halogen atom;
$R^2$ is selected from the group consisting of:
(1) a hydrogen atom,
(2) a $C_{1-8}$ alkyl group,
(3) a cyano group,
(4) a halogen atom, and
(5) a $(C_{1-8}$ alkyl$)_{m2}$-amino group which may be substituted by $C_{1-8}$ alkylsulfonyl group(s),
m2: 0~2;
$R^3$ is selected from the group consisting of:
(1) a hydrogen atom,
(2) a $C_{1-8}$ alkyl group which may be substituted by halogen atom(s),
(3) a cyano group,
(4) a $(C_{1-8}$ alkyl$)_{m3a}$-aminocarbonyl group which may be substituted by one or more $R^{3A}$, $R^{3A}$: [1] a $C_{6-10}$ aryl group, [2] a $C_{1-8}$ alkoxy group, [3] a 5- to 14-membered heteroaryl group, or [4] a $C_{6-10}$ aryl sulfonyl group,
m3a: 0~2,
(5) a hydroxycarbonyl group,
(6) a $C_{1-8}$ alkoxycarbonyl group which may be substituted by hydroxy group(s),
(7) a halogen atom,
(8) a $(C_{1-8}$ alkyl$)_{m3b}$-amino group which may be substituted by $C_{6-10}$ aryl group(s),
m3b: 0~2, (9) a $C_{1-8}$ alkylcarbonyl ($C_{0-8}$ alkyl) amino group which may be substituted by [1] $C_{6-10}$ aryl group(s) or [2] $C_{6-10}$ aryloxy group(s), (10) a $C_{6-10}$ arylcarbonyl ($C_{0-8}$ alkyl) amino group which may be substituted by $C_{1-8}$ alkyl group(s) which may be substituted by halogen atom(s),

(11) a nitro group,

(12) a hydroxy group,

(13) a $C_{1-8}$ alkoxy group which may be substituted by one or more $R^{3B}$, $R^{3B}$: [1] a hydroxy group, [2] a $C_{1-8}$ alkoxy group, [3] a $C_{6-10}$ aryl ($C_{0-8}$ alkyl) aminocarbonyl group, [4] a ($C_{1-8}$ alkyl)$_{m3d}$ amino group, or [5] a halogen atom, m3d: 0~2,

(14) a 4- to 10-membered heterocycloalkyloxy group,

(15) a 5- to 14-membered heteroaryloxy group,

(16) a ($C_{1-8}$ alkyl)$_{m3e}$-aminocarbonyloxy group which may be substituted by $C_{0-10}$ aryl group(s), m3e: 0~2,

(17) a 4- to 10-membered nitrogen-containing heterocycloalkylcarbonyl group,

(18) a $C_{1-8}$ alkylthio group,

(19) a 5- to 14-membered heteroaryl group which may be substituted by $C_{1-8}$ alkyl group(s) which may be substituted by $C_{1-8}$ alkoxy group(s),

(20) a $C_{1-8}$ alkoxycarbonyl ($C_{0-8}$ alkyl) amino group which may be substituted by $C_{1-8}$ alkoxy group(s),

(21) a $C_{6-10}$ aryloxycarbonyl ($C_{0-8}$ alkyl) amino group which may be substituted by $C_{1-8}$ alkyl group(s) which may be substituted by halogen atom(s),

(22) a $C_{6-10}$ aryl ($C_{0-8}$ alkyl) aminocarbonyl ($C_{0-8}$ alkyl) amino group which may be substituted by $C_{1-8}$ alkoxy group(s),

(23) a $C_{3-8}$ cycloalkyl ($C_{0-8}$ alkyl) aminocarbonyloxy group, and

(24) a $C_{6-10}$ aryl ($C_{0-8}$ alkyl) aminocarbonyloxy group which may be substituted by substituent(s) selected from the group consisting of [1] a $C_{1-8}$ alkyl group and [2] a $C_{1-8}$ alkoxy group;

$R^4$ is selected from the group consisting of:

(1) a hydrogen atom, (2) a $C_{1-8}$ alkyl group which may be substituted by halogen atom(s), (3) a $C_{3-8}$ cycloalkyl group, (4) a cyano group, (5) an aminocarbonyl group, (6) a hydroxycarbonyl group, (7) a halogen atom, (8) a ($C_{1-8}$ alkyl)$_{m4b}$-amino group, m4b: 0~2, (9) a hydroxy group, and

(10) a $C_{1-8}$ alkoxy group which may be substituted by hydroxy group(s);

$R^5$ is selected from the group consisting of:

(1) a hydrogen atom, (2) a $C_{1-8}$ alkyl group which may be substituted by one or more $R^{5A}$, $R^{5A}$: [1] a hydroxycarbonyl group, [2] a $C_{1-8}$ alkoxycarbonyl group, [3] a hydroxy group, [4] a $C_{1-8}$ alkoxy group, [5] a ($C_{1-8}$ alkyl)$_{m5}$-amino group, or [6], a $C_{1-8}$ alkylthio group, m5: 0~2, and (3) a $C_{1-8}$ alkylsulfonyl group;

$R^6$ and $R^{6'}$ are each independently:

(1) a $C_{1-8}$ alkyl group, or $R^6$ and $R^{6'}$ are taken together with the carbon atoms to which they are bound to form, (2) a $C_{3-8}$ cycloalkyl group, or (3) a 4- to 10-membered heterocycloalkyl group;

$R^7$ is selected from the group consisting of:

(1) a hydrogen atom, (2) a halogen atom, and (3) a $C_{1-8}$ alkoxy group which may be substituted by one or more $R^{7A}$, $R^{7A}$: [1] a ($C_{1-8}$ alkyl)$_{m7a}$-amino group, or [2] a hydroxy group, m7a: 0~2;

$R^8$ is selected from the group consisting of:

(1) a hydrogen atom, (2) a $C_{1-8}$ alkyl group which may be substituted by one or more $R^{8A}$, $R^{8A}$: [1] a 4- to 10-membered heterocycloalkyl group which may be substituted by one or more $R^{8A1}$, [2] a ($C_{1-8}$ alkyl)$_{m8a}$-amino group which may be substituted by a halogen atom, and [3] a hydroxy group, m8a: 0~2, $R^{8A1}$: [1] a $C_{1-8}$ alkyl group, [2] a $C_{1-8}$ alkylsulfonyl group, [3] a ($C_{1-8}$ alkyl)$_{m8b}$-aminosulfonyl group, or [4] an oxo group, m8b: 0~2, (3) a $C_{2-8}$ alkenyl group, (4) a 4- to 10-membered heterocycloalkyl group which may be substituted by one or more $R^{8B}$, $R^{8B}$:

<1> a $C_{1-8}$ alkyl group which may be substituted by one or more $R^{8B1}$,

<2> a $C_{2-8}$ alkynyl group,

<3> a $C_{3-8}$ cycloalkyl group which may be substituted by [1] cyano group(s) or [2] $C_{1-8}$ alkyl group(s), <4> a 4- to 10-membered heterocycloalkyl group which may be substituted by one or more $R^{8B2}$, <5> a $C_{1-8}$ alkoxy group which may be substituted by substituent(s) selected from the group consisting of [1] a $C_{1-8}$ alkoxy group and [2] a $C_{3-8}$ cycloalkyl group, <6> a $C_{1-8}$ alkylsulfonyl group, <7> an oxo group, <8> a cyano group, <9> a $C_{1-8}$ alkanoyl group which may be substituted by one or more $R^{8B3}$, <10> a $C_{3-8}$ cycloalkylcarbonyl group, <11> a ($C_{1-8}$ alkyl)$_{m8c}$-aminosulfonyl group, <12> a $C_{1-8}$ alkylsulfonyl ($C_{0-8}$ alkyl) amino group, <13> a ($C_{1-8}$ alkyl)$_{m8d}$-amino group which may be substituted by one or more $R^{8B4}$, <14> a hydroxy group, or <15> a ($C_{1-8}$ alkyl)$_{m8e}$-aminocarbonyl group, m8c: 0~2, m8d: 0~2, m8e: 0~2, $R^{8B1}$: [1] a $C_{3-8}$ cycloalkyl group, [2] a hydroxy group, or [3] $C_{1-8}$ alkoxy group which may be substituted by $C_{1-8}$ alkoxy group(s), $R^{8B2}$: [1] a halogen atom, [2] a $C_{1-8}$ alkyl group, [3] an oxo group, or [4] a hydroxy group, $R^{8B3}$: a ($C_{1-8}$ alkyl)$_{m8f}$-amino group, m8f: 0~2, $R^{8B4}$: [1] a $C_{3-8}$ cycloalkyl group, or [2] a hydroxy group, (5) a 5- to 14-membered heteroaryl group which may be substituted by a $C_{1-8}$ alkyl group, (6) a ($C_{1-8}$ alkyl)$_{m8g}$-aminocarbonyl group which may be substituted by one or more $R^{8C}$, m8g: 0~2, $R^{8C}$: [i] a hydroxy group, [2] a ($C_{1-8}$ alkyl)$_{m8h}$-amino group which may be substituted by substituent(s) selected from the group consisting of <1> a ($C_{1-8}$ alkyl)$_{m8i}$-aminosulfonyl group and <2> a $C_{1-8}$ alkylsulfonyl group, or [3] a $C_{1-8}$ alkylsulfonyl group, m8h: 0~2, m8i: 0~2, (7) a 4- to 10-membered heterocycloalkyl ($C_{0-8}$ alkyl) aminocarbonyl group which may be substituted by oxo group(s), (8) a 4- to 10-membered nitrogen-containing heterocycloalkylcarbonyl group which may be substituted by one or more $R^{BD}$, $R^{8D}$: [1] a $C_{1-8}$ alkyl group which may be substituted by one or more $R^{8D1}$, [2] a hydroxy group, or [3] a $C_{1-8}$ alkylsulfonyl group, $R^{8D1}$: [1] a hydroxy group, or [2] a $C_{1-8}$ alkoxy group, (9) a hydroxycarbonyl group,

(10) a $C_{0-8}$ alkoxy ($C_{0-8}$ alkyl) aminocarbonyl group which may be substituted by hydroxy group(s),

(11) a halogen atom,

(12) a ($C_{1-8}$ alkyl)$_{m8j}$-amino group which may be substituted by 4- to 10-membered heterocycloalkyl group(s), m8j: 0~2,

(13) a hydroxyl group,

(14) a $C_{1-8}$ alkoxy group which may be substituted by one or more $R^{8E}$, $R^{8E}$:

<1> a hydroxy group,

<2> a $C_{1-8}$ alkoxycarbonyl group,

<3> a 4- to 10-membered nitrogen-containing heterocycloalkylcarbonyl group which may be substituted by one or more $R^{8E1}$, <4> a ($C_{1-8}$ alkyl)$_{m8k1}$-amino group which may be substituted by one or more $R^{8E2}$, m8k1: 0~2, <5> a 4- to 10-membered heterocycloalkyl group which may be substituted by one or more $R^{8E3}$, <6> a 5- to 14-membered heteroaryl group, <7> a ($C_{1-8}$ alkyl)$_{m8k2}$-aminocarbonyl group which may be substituted by one or more $R^{8E6}$ m8k2: 0~2, <8> a $C_{1-8}$ alkoxy group which may be substituted by one or more $R^{8E7}$, <9> a $C_{1-8}$ alkylthio group, <10> a $C_{1-8}$ alkylsulfinyl group, or <11> a $C_{1-8}$ alkylsulfonyl group, $R^{8E1}$:

<1> a $C_{1-8}$ alkoxycarbonyl group,

<2> a $C_{1-8}$ alkanoyl group,

<3> a $C_{1-8}$ alkylsulfonyl group,

<4> a ($C_{1-8}$ alkyl)$_{m8k3}$-aminosulfonyl group m8k3: 0~2, or

<5> a 4- to 10-membered heterocycloalkyl group, $R^{8E2}$:

<1> a hydroxy group,

<2> a $C_{1-8}$ alkoxycarbonyl group,

<3> a $C_{3-8}$ cycloalkyl group which may be substituted by $C_{1-8}$ alkyl group(s) which may be substituted by hydroxy group(s), <4> a $C_{1-8}$ alkanoyl group which may be substituted by substituent(s) selected from the group consisting of [1] a ($C_{1-8}$ alkyl)$_{m8k4}$-amino group and [2] a halogen atom, m8k4: 0~2, <5> a ($C_{1-8}$ alkyl)$_{m8k5}$-aminocarbonyl group, m8k5: 0~2, <6> a $C_{1-8}$ alkylsulfonyl group, <7> a 4- to 10-membered nitrogen-containing heterocycloalkylsulfonyl group which may be substituted by $C_{1-8}$ alkyl group(s), <8> a ($C_{1-8}$ alkyl)$_{m8k6}$-aminosulfonyl group, m8k6: 0~2, or $R^{8E3}$:

<1> a $C_{1-8}$ alkyl group which may be substituted by substituent(s) selected from the group consisting of [1] a hydroxy group and [2] a $C_{1-8}$ alkylcarbonyloxy group, <2> a hydroxy group, <3> a $C_{3-8}$ cycloalkyl group, <4> a $C_{1-8}$ alkylsulfonyl group, <5> a ($C_{1-8}$ alkyl)$_{m8k8}$-aminocarbonyl group, m8k8: 0~2, <6> a $C_{1-8}$ alkanoyl group which may be substituted by hydroxy group(s), <7> an oxo group, or <8> a 4- to 10-membered heterocycloalkyl group which may be substituted by substituent(s) selected from the group consisting of [1] a $C_{1-8}$ alkanoyl group, and [2] a $C_{1-8}$ alkylsulfonyl group, $R^{8E6}$:

<1> a $C_{2-8}$ alkenylcarbonyloxy group,

<2> a hydroxy group,

<3> a cyano group,

<4> a ($C_{1-8}$ alkyl)$_{m8k9}$-amino group which may be substituted by hydroxy group(s), m8k9: 0~2, <5> a $C_{1-8}$ alkoxy group which may be substituted by hydroxy group(s), <6> a 4- to 10-membered heterocycloalkyl group which may be substituted by $C_{1-8}$ alkyl group(s), or <7> a 5- to 14-membered heteroaryl group, $R^{8E7}$:

<1> a hydroxy group, or

<2> a $C_{1-8}$ alkoxy group which may be substituted by hydroxy group(s),

(15) a 4- to 10-membered heterocycloalkyloxy group which may be substituted by one or more $R^{8F}$:

$R^{8F}$:

<1> a $C_{1-8}$ alkyl group which may be substituted by one or more $R^{8''}$,

<2> a $C_{3-8}$ cycloalkyl group,

<3> a $C_{1-8}$ alkanoyl group which may be substituted by halogen atom(s),

<4> a $C_{1-8}$ alkoxycarbonyl group,

<5> a 4- to 10-membered heterocycloalkyl group which may be substituted by one or more $R^{8F2}$, <6> a $C_{1-8}$ alkyl sulfonyl group, or <7> a hydroxy group, $R^{8F1}$: [1] a hydroxy group, [2] a $C_{1-8}$ alkoxy group, or [3] a halogen atom, $R^{8F2}$: [1] a 4- to 10-membered heterocycloalkyl group, [2] a $C_{1-8}$ alkoxycarbonyl group, or [3] a $C_{1-8}$ alkylsulfonyl group,

(16) a 5- to 14-membered heteroaryloxy group,

(17) a ($C_{1-8}$ alkyl)$_{m8l1}$-aminosulfonyloxy group, m8l1: 0~2,

(18) a $C_{1-8}$ alkylthio group which may be substituted by ($C_{1-8}$ alkyl)$_{m8l2}$-amino group(s), m8l2: 0~2,

(19) a $C_{1-8}$ alkylsulfonyl group which may be substituted by one or more $R^{8G}$, $R^{8G}$: [1] a hydroxycarbonyl group, [2] a hydroxy group, or [3] a ($C_{1-8}$ alkyl)$_{m8l3}$-amino group, m8l3: 0~2,

(20) a $C_{2-8}$ alkenyloxy group, and

(21) a C$_{1-8}$ alkylsulfonyloxy group which may be substituted by halogen atom(s);

R$^9$ is selected from the group consisting of:
(1) a hydrogen atom,
(2) a C$_{1-8}$ alkyl group which may be substituted by one or more R$^{9A}$,
R$^{9A}$: [1] a C$_{3-8}$ cycloalkyl group, [2] a 4- to 10-membered heterocycloalkyl group which may be substituted by one or more R$^{9A1}$, [3] a hydroxy group, or [4] a C$_{1-8}$ alkoxy group,
R$^{9A1}$: [1] a C$_{1-8}$ alkyl group, [2] a C$_{3-8}$ cycloalkyl group, or [3] a 4- to 10-membered heterocycloalkyl group,
(3) a C$_{2-8}$ alkenyl group,
(4) a C$_{2-8}$ alkynyl group which may be substituted by one or more R$^{9C}$,
R$^{9C}$: [1] a C$_{1-8}$ alkoxy group, [2] a (C$_{1-8}$ alkyl)$_{m9b}$-amino group which may be substituted by C$_{6-10}$ aryl group(s), [3] a 4- to 10-membered heterocycloalkyl group which may be substituted by one or more R$^{9C1}$, [4] a C$_{3-8}$ cycloalkyl group, [5] a hydroxy group, or [6] a hydroxycarbonyl group, m9b: 0~2,
R$^{9C1}$: [1] a C$_{3-8}$ cycloalkyl group, [2] a 4- to 10-membered heterocycloalkyl group, or [3] an oxo group,
(5) a C$_{3-8}$ cycloalkyl group,
(6) a 4- to 10-membered heterocycloalkyl group which may be substituted by one or more R$^{9D}$,
R$^{9D}$: [1] a C$_{1-8}$ alkyl group which may be substituted by 4- to 10-membered heterocycloalkyl group(s), [2] a C$_{3-8}$ cycloalkyl group, [3] a 4- to 10-membered heterocycloalkyl group, or [4] a C$_{1-6}$ alkylsulfonyl group,
(7) a C$_{6-10}$ aryl group which may be substituted by one or more R$^{9E}$,
R$^{9E}$: [1] a halogen atom, [2] a hydroxy group, [3] a hydroxycarbonyl group, or [4] a C$_{1-8}$ alkyl group which may be substituted by hydroxy group(s),
(8) a 5- to 14-membered heteroaryl group which may be substituted by C$_{1-8}$ alkyl group(s),
(9) a cyano group,
(10) a C$_{1-8}$ alkanoyl group,
(11) a 4- to 10-membered nitrogen-containing heterocycloalkylcarbonyl group which may be substituted by C$_{1-8}$ alkyl group(s),
(12) a halogen atom,
(13) a (C$_{1-8}$ alkyl)$_{m9c}$-amino group,
m9c: 0~2,
(14) a C$_{1-8}$ alkylcarbonyl(C$_{0-8}$ alkyl)amino group which may be substituted by (C$_{1-8}$ alkyl)$_{m9d}$-amino group(s),
m9d: 0~2,
(15) a C$_{1-8}$ alkylsulfonyl(C$_{0-8}$ alkyl)amino group,
(16) a (C$_{1-8}$ alkyl)$_{m9e}$-aminosulfonyl(C$_{0-8}$ alkyl)amino group,
m9e: 0~2,
(17) a nitro group,
(18) a hydroxy group,
(19) a C$_{1-8}$ alkoxy group which may be substituted by one or more R$^{9G}$,
R$^{9G}$: [1] a hydroxy group, [2] a hydroxycarbonyl group, [3] a C$_{6-10}$ aryl group which may be substituted by C$_{1-8}$ alkoxy group(s), [4] a (C$_{1-8}$ alkyl)$_{m9o}$-amino group, [5] a C$_{1-8}$ alkoxy group which may be substituted by one or more R$^{9G1}$, or [6] a 5- to 14-membered heteroaryl group,
m9g1: 0~2,
R$^{9G1}$: [1] a C$_{1-8}$ alkoxy group, or [2] a hydroxycarbonyl group,
(20) a 4- to 10-membered heterocycloalkyloxy group which may be substituted by 4- to 10-membered heterocycloalkyl group(s),

(21) a C$_{1-8}$ alkylthio group which may be substituted by (C$_{1-8}$ alkyl)$_{m9f}$-amino group(s),
m9f: 0~2,
(22) a C$_{1-8}$ alkylsulfonyl group which may be substituted by (C$_{1-8}$ alkyl)$_{m9g}$-amino group(s),
m9g: 0~2,
(23) a (C$_{1-8}$ alkyl)$_{m9h}$-aminosulfonyl group,
m9h: 0~2, and
(24) a 4- to 10-membered nitrogen-containing heterocycloalkylsulfonyl group which may be substituted by C$_{1-8}$ alkyl group(s);
R$^{10}$ represents [1] a hydrogen atom, or [2] a 4- to 10-membered heterocycloalkyl group which may be substituted by 4- to 10-membered heterocycloalkyl group(s)].

[6] A compound according to claim 1, or salt or solvate thereof, which said compound is selected from the group consisting of:
9-(4-isopropyl-piperazin-1-yl)-6,6-dimethyl-11-oxo-6,11-dihydro-5H-benzo[b]carbazole-3-carbonitrile;
6,6-dimethyl-8-(4-oxetan-3-yl-piperazin-1-yl)-11-oxo-9-prop-1-ynyl-6,11-dihydro-5H-benzo[b]carbazole-3-carbonitrile;
9-cyclopropylethynyl-6,6-dimethyl-8-(4-oxetan-3-yl-piperazin-1-yl)-11-oxo-6,11-dihydro-5H-benzo[b]carbazole-3-carbonitrile;
6,6-dimethyl-8-(1-oxetan-3-yl-piperidin-4-yl)-11-oxo-6,11-dihydro-5H-benzo[b]carbazole-3-carbonitrile;
9-bromo-6,6-dimethyl-8-(4-oxetan-3-yl-piperazin-1-yl)-11-oxo-6,11-dihydro-5H-benzo[b]carbazole-3-carbonitrile;
9-bromo-8-(4-cyclopropyl-piperazin-1-yl)-6,6-dimethyl-11-oxo-6,11-dihydro-5H-benzo[b]carbazole-3-carbonitrile;
9-chloro-6,6-dimethyl-8-(4-morpholin-4-yl-piperidin-1-yl)-11-oxo-6,11-dihydro-5H-benzo[b]carbazole-3-carbonitrile;
8-(4-cyclobutyl-piperazin-1-yl)-6,6-dimethyl-11-oxo-9-prop-1-ynyl-6,11-dihydro-5H-benzo[b]carbazole-3-carbonitrile;
6,6,9-trimethyl-8-(4-morpholin-4-yl-piperidin-1-yl)-11-oxo-6,11-dihydro-5H-benzo[b]carbazole-3-carbonitrile;
9-ethyl-6,6-dimethyl-8-(4-oxetan-3-yl-piperazin-1-yl)-11-oxo-6,11-dihydro-5H-benzo[b]carbazole-3-carbonitrile;
9-ethyl-6,6-dimethyl-8-(4-morpholin-4-yl-piperidin-1-yl)-11-oxo-6,11-dihydro-5H-benzo[b]carbazole-3-carbonitrile;
9-ethynyl-6,6-dimethyl-8-(4-oxetan-3-yl-piperazin-1-yl)-11-oxo-6,11-dihydro-5H-benzo[b]carbazole-3-carbonitrile;
8-(4-cyclobutyl-piperazin-1-yl)-9-ethyl-6,6-dimethyl-11-oxo-6,11-dihydro-5H-benzo[b]carbazole-3-carbonitrile;
9-ethynyl-6,6-dimethyl-11-oxo-8-(4-pyrrolidin-1-yl-piperidin-1-yl)-6,11-dihydro-5H-benzo[b]carbazole-3-carbonitrile;
6,6-dimethyl-11-oxo-8-(4-pyrrolidin-1-yl-piperidin-1-yl)-6,11-dihydro-5H-benzo[b]carbazole-3-carbonitrile;
8-(4-cyclobutyl-piperazin-1-yl)-9-ethynyl-6,6-dimethyl-11-oxo-6,11-dihydro-5H-benzo[b]carbazole-3-carbonitrile;
8-(4-cyclobutyl-piperazin-1-yl)-6,6-dimethyl-11-oxo-9-propyl-6,11-dihydro-5H-benzo[b]carbazole-3-carbonitrile;
8-(1-isopropyl-piperidin-4-yl)-6,6-dimethyl-11-oxo-6,11-dihydro-5H-benzo[b]carbazole-3-carbonitrile;
8-(4-isopropyl-piperazin-1-yl)-6,6-dimethyl-11-oxo-6,11-dihydro-5H-benzo[b]carbazole-3-carbonitrile;
8-(4-cyclobutyl-piperazin-1-yl)-9-cyclopropyl-6,6-dimethyl-11-oxo-6,11-dihydro-5H-benzo[b]carbazole-3-carbonitrile;
8-(2-tert-butylamino-ethoxy)-6,6-dimethyl-11-oxo-6,11-dihydro-5H-benzo[b]carbazole-3-carbonitrile;

9-ethynyl-8-(4-methanesulfonyl-piperazin-1-yl)-6,6-dimethyl-11-oxo-6,11-dihydro-5H-benzo[b]carbazole-3-carbonitrile;

9-bromo-8-(4-cyclobutyl-piperazin-1-yl)-6,6-dimethyl-11-oxo-6,11-dihydro-5H-benzo[b]carbazole-3-carbonitrile;

6,6-dimethyl-8-(4-oxetan-3-yl-piperazin-1-yl)-11-oxo-9-propyl-6,11-dihydro-5H-benzo[b]carbazole-3-carbonitrile; and 9-ethynyl-6,6-dimethyl-8-morpholin-4-yl-11-oxo-6,11-dihydro-5H-benzo[b]carbazole-3-carbonitrile.

[7] A medicament comprising as an active ingredient the compound according to any one of the above [1] to [5], or a salt or solvate thereof.

[8] An ALK inhibitor comprising as an active ingredient the compound according to any one of the above [1] to [5], or a salt or solvate thereof.

[9] A pharmaceutical for the prophylaxis or treatment of cancer, cancer metastasis, depression or cognitive function disorder, comprising as an active ingredient the compound according to any one of the above [1] to [5], or a salt or solvate thereof.

[10] A pharmaceutical composition comprising the compound according to any one of the above [1] to [5], or a salt or solvate thereof and a pharmaceutically acceptable carrier(s).

[11] A method of treating a patient suffering from the disease including cancer, cancer metastasis, depression or cognitive function disorder, comprising administering to the patient who is in need of the treatment of the disease the compound described in any one of the above [1] to [5], salt or solvate thereof in an effective amount for the treatment of the disease.

[12] Use of the compound described in any one of the above [1] to [5], salt or solvate thereof in the manufacture of a pharmaceutical.

[13] The use according to above [11] in the manufacture of a pharmaceutical composition for the treatment or prophylaxis of the disease of mammals including human, wherein the disease is related with ALK activity.

Effect of the Invention

The compounds of the present invention or salts or salvates thereof have an excellent activity of inhibiting ALK, excellent stability in organisms, and excellent solubility in water, and therefore are useful as a prophylactic or therapeutic agent for proliferative disorders (in particular, therapeutic agent). Further, the compounds of the present invention or salts salts or solvates thereof are useful as a prophylactic or therapeutic agent (in particular, therapeutic agent) for various diseases such as cancers including leukemia (acute myelogenous leukemia, chronic myelogenous leukemia, acute lymphatic leukemia, chronic lymphatic leukemia and the like), malignant lymphoma (Hodgkin lymphoma, non-Hodgkin lymphoma and the like), brain tumor, neuroblastoma, gliomatosis, thyroid cancer, myelodysplastic syndrome, head and neck cancer, esophageal cancer, stomach cancer, colon cancer, colorectal cancer, breast cancer, ovarian cancer, lung cancer, pancreatic cancer, liver cancer, gall bladder cancer, skin cancer, malignant melanoma, kidney cancer, renal pelvis-ureter cancer, bladder cancer, uterine cancer, testicle cancer, prostate cancer, and the like. Further, the compounds of the present invention are useful as a prophylactic or therapeutic agent (in particular, therapeutic agent) for infiltration/metastasis of solid tumors. Still further, the compounds of the present invention are useful as a prophylactic or therapeutic agent for other diseases that are related with ALK, for example, depression or a cognitive function disorder.

The method of the present invention comprises a step of administering a pharmaceutically effective amount of the pharmaceutical composition comprising the compounds of the present invention or salts or solvates thereof to a patient who is in need of such treatment or suffers from such diseases or conditions.

MODE FOR CARRYING OUT THE INVENTION

Hereinbelow, the compounds of the present invention, the method of preparing the same, and the pharmaceutical agent comprising the same will be explained.

DEFINITION

According to the present invention, the "halogen atom" means a fluorine atom, a chlorine atom, a bromine atom, an iodine atom and the like. According to the present invention, when the halogen atom is a substituent group for an aromatic carbon ring, an aromatic heterocycle and the like, the preferred halogen atom includes a fluorine atom, a chlorine atom and a bromine atom. According to the present invention, when the halogen atom is a substituent group for an alkyl group or a group which comprises the alkyl as at least a part of the group (e.g., alkoxy, alkenyl, unsaturated carbocycle, unsaturated heterocycle and the like), the preferred halogen atom includes a fluorine atom. Specifically, examples thereof include a trifluoromethyl group, a pentafluoroethyl group, a heptafluoropropyl group, a nonafluorobutyl group, a trifluoromethoxy group, a pentafluoroethoxy group, a heptafluoropropoxy group, a nonafluorobutoxy group, a trifluoroacetyl group, a pentafluoropropionyl group, a heptafluorobutyryl group and a nonafluoropentanoyl group.

The "$C_{1-8}$ alkyl group" means a monovalent group which is derived by removing any one of hydrogen atoms from a linear or branched aliphatic hydrocarbon having 1 to 8 carbon atoms. Specifically, examples thereof include a methyl group, an ethyl group, an isopropyl group, a butyl group, a n-butyl group, an isobutyl group, a sec-butyl group, a t-butyl group, a pentyl group, an isopentyl group, a 2,3-dimethyl propyl group, a hexyl group, a 2,3-dimethyl hexyl group, a 1,1-dimethyl pentyl group, a heptyl group and an octyl group. Preferably, it is a $C_{1-6}$ alkyl group, more preferably a $C_{1-5}$ alkyl group, still more preferably a $C_{1-4}$ alkyl group, and still even more preferably a $C_{1-3}$ alkyl group.

The "$C_{1-8}$ alkyl group which may be substituted" means an unsubstituted $C_{1-8}$ alkyl group or a $C_{1-8}$ alkyl group of which at least one hydrogen atom on the alkyl group is substituted by a defined substituent(s). When two or more substituent groups are present, each substituent group can be the same or different from each other. In addition, the alkyl group may be substituted by a cyclic substituent group through a spiro bond. Preferably, it is a $C_{1-8}$ alkyl group which may be substituted by 1 to 3 substituent(s). More preferably, it is 1 to 3 substituent(s) for $C_{1-6}$ alkyl group and a $C_{1-4}$ alkyl group, and 1 to 2 substituent(s) for a $C_{1-3}$ alkyl group.

The "$C_{2-8}$ alkenyl group" means a monovalent group wherein at least one double bond (two adjacent SP2 carbon atoms) is comprised in a linear or branched aliphatic hydrocarbon group having 1 to 8 carbon atoms. Specific examples of the $C_{2-8}$ alkenyl group include a vinyl group, an allyl group, a 1-propenyl group, a 2-propenyl group, a 1-butenyl group, a 2-butenyl group (including both cis and trans), a 3-butenyl group, a pentenyl group and a hexenyl group. Preferably, it is a $C_{2-6}$ alkenyl group, more preferably a $C_{2-5}$ alkenyl group, still more preferably a $C_{2-4}$ alkenyl group, and still even more preferably a $C_{2-3}$ alkenyl group.

The "$C_{2-8}$ alkenyl group which may be substituted" means the unsubstituted $C_{2-8}$ alkenyl group described above or a $C_{2-8}$ alkenyl group of which at least one hydrogen atom on the alkenyl group is substituted by a defined substituent(s). When two or more substituent groups are present, each substituent group can be the same or different from each other. In addition, the single-bonded carbon atom may be substituted by a cyclic substituent group through a spiro bond. Preferably, it is a $C_{2-8}$ alkenyl group which may be substituted by 1 to 3 substituent(s). More preferably, it is 1 to 3 substituent(s) for a $C_{2-6}$ alkenyl group and a $C_{2-4}$ alkenyl group, 1 to 2 substituent(s) for a $C_{2-3}$ alkenyl group.

The "$C_{2-8}$ alkynyl group" means a monovalent group wherein at least one triple bond (two adjacent SP carbon atoms) is comprised in a linear or branched aliphatic hydrocarbon group having 1 to 8 carbon atoms. Specific examples of the $C_{2-8}$ alkynyl group include an ethynyl group, a 1-propynyl group, a propargyl group and a 3-butynyl group. Preferably, it is a $C_{2-6}$ alkynyl group, more preferably a $C_{2-5}$ alkynyl group, still more preferably a $C_{2-4}$ alkynyl group, and still even more preferably a $C_{2-3}$ alkynyl group.

The "$C_{2-8}$ alkynyl group which may be substituted" means the unsubstituted $C_{2-8}$ alkynyl group described above or a $C_{2-8}$ alkynyl group of which at least one hydrogen atom on the alkynyl group is substituted by a defined substituent(s). When two or more substituent groups are present, each substituent group can be the same or different from each other. In addition, the single-bonded carbon atom may be substituted by a cyclic substituent group through a spiro bond. Preferably, it is a $C_{2-8}$ alkynyl group which may be substituted by 1 to 3 substituent(s). More preferably, it is 1 to 3 substituent(s) for a $C_{2-6}$ alkynyl group and a $C_{2-4}$ alkynyl group, and 1 to 2 substituent(s) for $C_{2-3}$ alkynyl group.

The "$C_{3-8}$ cycloalkyl group" means an aliphatic hydrocarbon group in cyclic form. Preferably, it includes a $C_{3-6}$ cycloalkyl group. Specifically, examples thereof include a cyclopropyl group, a cyclobutyl group, a cyclopentyl group, a cyclohexyl group, a cycloheptyl group and a cyclooctyl group. Preferably, it is a $C_{3-6}$ cycloalkyl group.

The "$C_{3-8}$ cycloalkyl group which may be substituted" means the unsubstituted $C_{3-8}$ cycloalkyl group described above or a $C_{3-8}$ cycloalkyl group of which at least one hydrogen atom is substituted by a defined substituent group(s). When two or more substituent groups are present, each substituent group can be the same or different from each other. In addition, the single-bonded carbon atom may be substituted by a cyclic substituent group through a spiro bond. Preferably, it is a $C_{3-8}$ cycloalkyl group which may be substituted by 1 to 3 substituent(s).

The "4- to 10-membered heterocycloalkyl group" means a saturated or partially unsaturated heterocyclic group which consists of 4 to 10 ring-constituting atoms and comprises 1 to 3 hetero atoms that are selected from O, S and N. The heterocycloalkyl group can be a monocyclic, a bicyclic or a spirocyclic type heterocycloalkyl group. Specifically, examples thereof include an oxetanyl group, a tetrahydrofuryl group, a tetrahydrothienyl group, a tetrahydropyranyl group, a pyrrolidino group, a pyrrolidinyl group, a piperidino group, a piperidinyl group, a piperazino group, a piperazinyl group, a morpholino group, a morpholinyl group, a tetrahydrothiopyranyl group, a thiomorpholino group, an imidazolidinyl group, a 1,3-dioxolanyl group, a tetrahydropyranyl group, a 1,3-dioxanyl group, a 1,2,3,6-tetrahydropyridinyl group, a 1,4-Dioxa-8-aza-spiro[4.5]decanyl group, and a 1-oxa-8-aza-spiro[4.5]decanyl group. Preferably, it is a 4- to 8-membered heterocycloalkyl group, more preferably, 4- to 6-membered heterocycloalkyl group.

The "4- to 10-membered heterocycloalkyl group which may be substituted" means the unsubstituted 4- to 10-membered heterocycloalkyl group described above or a 4- to 10-membered heterocycloalkyl group of which at least one hydrogen atom on the heterocycloalkyl group is substituted by a defined substituent(s). When two or more substituent groups are present, each substituent group can be the same or different from each other. In addition, the alkyl group may be substituted by a cyclic substituent group through a spiro bond. Preferably, it is a 4- to 10-membered heterocycloalkyl group which may be substituted by 1 to 4 substituent(s). More preferably, it is 1 to 4 substituent(s) for a 4- to 8-membered heterocycloalkyl group, and 1 to 3 substituent(s) for a 4- to 6-membered heterocycloalkyl group. When the substituent is an oxo group, 2 oxo group can combine with the same sulfur atom. When the salt is formed, 2 alkyl group can combine with the same nitrogen atom.

The "$C_{6-10}$ aryl group" means a monovalent aromatic hydrocarbon ring. Specific examples of the $C_{6-10}$ aryl group include a phenyl group, a 1-naphthyl group and a 2-naphthyl group. Preferably, it is a $C_6$ aryl group or a $C_{10}$ aryl group.

The "$C_{6-10}$ aryl group which may be substituted" means the unsubstituted $C_{6-10}$ aryl group described above or a $C_{6-10}$ aryl group of which at least one hydrogen atom is substituted by a defined substituent group(s). When two or more substituent groups are present, each substituent group can be the same or different from each other. Preferably, it is a $C_{6-10}$ aryl group which may be substituted by 1 to 3 substituent(s).

The "5- to 14-membered heteroaryl group" means an aromatic cyclic group comprising one or more hetero atoms among 5 to 14 ring-constituting atoms. The cycle can be a monocyclic or bicyclic heteroaryl group fused to a benzene ring or a monocyclic heteroaryl ring. Specific examples thereof include a furyl group, a thienyl group, a pyrrolyl group, an imidazolyl group, a pyrazolyl group, a thiazolyl group, an isothiazolyl group, an oxazolyl group, an isooxazolyl group, an oxadiazolyl group, a thiadiazolyl group, a triazolyl group, a tetrazolyl group, a pyridyl group, a pyrimidyl group, a pyridazinyl group, a pyrazinyl group, a triazinyl group, a benzofuranyl group, a benzothienyl group, a benzothiadiazolyl group, a benzothiazolyl group, a benzoxazolyl group, a benzoxadiazolyl group, a benzoimidazolyl group, an indolyl group, an isoindolyl group, an indazolyl group, a quinolyl group, an isoquinolyl group, a cinnolinyl group, a quinazolinyl group, a quinoxalinyl group, a benzodioxolyl group, an indolizinyl group, an imidazopyridyl group and the like. Preferably, it is a 5- to 6-membered heteroaryl group.

The "5- to 14-membered heteroaryl group which may be substituted" means the unsubstituted 5- to 14-membered ring heteroaryl group described above or a 5- to 14-membered ring heteroaryl group of which at least one hydrogen atom on the heteroaryl group is substituted by a defined substituent(s). When two or more substituent groups are present, each substituent group can be the same or different from each other. Preferably, it is a 5- to 14-membered heteroaryl group which may be substituted by 1 to 3 substituent(s). More preferably, it is 1 to 3 substituent(s) or 1 to 2 substituent(s) for a 5- to 6-membered heteroaryl group.

The "$C_{1-8}$ alkanoyl group" means a $C_{1-8}$ alkyl-C(O)— group, and the $C_{1-8}$ alkyl group is described above. Specifically, examples thereof include acetyl, propionyl, butyryl, isobutyryl, pentanoyl, tert-butylcarbonyl and a hexanoyl group. Preferably, it is a $C_{1-6}$ alkanoyl group, and more preferably a $C_{1-3}$ alkanoyl group.

The "$C_{1-8}$ alkanoyl group which may be substituted" means the unsubstituted $C_{1-8}$ alkanoyl group described above or a $C_{1-8}$ alkanoyl group of which at least one hydrogen atom on the alkanoyl group is substituted by a defined substituent(s). When two or more substituent groups are present, each substituent group can be the same or different from each other. Preferably, it is a $C_{1-8}$ alkanoyl group which may be substituted by 1 to 3 substituent(s). More preferably, it is 1 to 2 substituent(s) for a $C_{1-6}$ alkanoyl group and a $C_{1-3}$ alkanoyl group.

The "$C_{3-8}$ cycloalkylcarbonyl group" means a $C_{3-8}$ cycloalkyl-C(O)— group, and the $C_{3-8}$ cycloalkyl group is described above. Specifically, examples thereof include a cyclopropylcarbonyl group, a cyclobutylcarbonyl group, a cyclopentylcarbonyl group, a cyclohexylcarbonyl group, a cycloheptylcarbonyl group and a cyclooctylcarbonyl group.

The "4- to 10-membered heterocycloalkylcarbonyl group" means a 4- to 10-membered heterocycloalkyl-CO— group, and the 4- to 10-membered heterocycloalkyl is described above.

The "4- to 10-membered heterocycloalkylcarbonyl group which may be substituted" means the unsubstituted 4- to 10-membered heterocycloalkylcarbonyl group described above or a 4- to 10-membered heterocycloalkylcarbonyl group in which at least one hydrogen atom of the heterocycloalkyl moiety is substituted by a defined substituent(s). When two or more substituent groups are present, each substituent group can be the same or different from each other. In addition, the heterocycloalkyl moiety may be substituted by a cyclic substituent group through a spiro bond. Preferably, it is a 4- to 10-membered heterocycloalkylcarbonyl group which may be substituted by 1 to 3 substituent(s).

The "aminocarbonyl group which may be substituted" means an unsubstituted aminocarbonyl group or an aminocarbonyl group in which one or two hydrogen atoms on the nitrogen atom are substituted by a defined substituent(s). When two substituent groups are present, each substituent group can be the same or different from each other.

The "$C_{3-8}$ cycloalkyl ($C_{0-8}$ alkyl) aminocarbonyloxy group" means a $C_{3-8}$ cycloalkyl-NHC(O)O— group or a $C_{3-8}$ cycloalkyl-N($C_{1-8}$ alkyl) C(O)O— group, and the $C_{3-8}$ cycloalkyl group is described above. Specifically, examples thereof include a cyclopropylaminocarbonyloxy group, a cyclobutylaminocarbonyloxy group, a cyclopentylaminocarbonyloxy group, a cyclohexylaminocarbonyloxy group, a cyclopropyl(N-methyl)aminocarbonyloxy group, and a cyclobutyl(N-methyl)aminocarbonyloxy group.

The "($C_{1-8}$ alkyl)$_x$-aminocarbonyl group", wherein x is a symbol defined in claims, means a $NH_2C(O)$— group, a ($C_{1-8}$ alkyl)NH—C(O)— group, or a ($C_{1-8}$ alkyl)$_2$N—C(O)— group.

Specifically, examples thereof include a N-methyl-aminocarbonyl group, N-ethyl-aminocarbonyl group, N-n-buthyl-aminocarbonyl group, a N,N-dimethyl-aminocarbonyl group.

The "($C_{1-8}$ alkyl)$_x$-aminocarbonyl group which may be substituted" means an unsubstituted ($C_{1-8}$ alkyl)$_x$-aminocarbonyl group described above or an ($C_{1-8}$ alkyl)$_x$-aminocarbonyl group in which at least one hydrogen atom on the nitrogen atom or the alkyl moiety are substituted by a defined substituent(s). When plural substituent groups are present, each substituent group can be the same or different from each other.

The "$C_{0-10}$ aryl($C_{0-8}$ alkyl)aminocarbonyl group" means a $C_{6-10}$ aryl-NHC(O)— group, or a $C_{6-10}$ aryl-N($C_{1-8}$ alkyl)-C(O)— group. Specifically, examples thereof include a phenyl-NHC(O)— group, or a phenyl-(N-methyl)-aminocarbonyl group, wherein the $C_{6-10}$ aryl group and $C_{1-8}$ alkyl are described above. Specifically, examples thereof include a phenylaminocarbonylamino group and a phenylaminocarbonyl(N-methyl)amino group.

The "4- to 10-membered nitrogen-containing heterocycloalkylcarbonyl group" means a carbonyl group to which a 4- to 10-membered nitrogen-containing heterocycloalkyl group is bonded. Herein, the 4- to 10-membered nitrogen-containing heterocycloalkyl group (i.e., 4- to 10-membered heterocycloalkyl group comprising a nitrogen atom(s)) means a heterocycloalkyl group which consists of 4 to 10 ring-constituting atoms and comprises at least one nitrogen atom as a hetero atom. Preferably, it is bonded to the carbonyl group via a nitrogen atom that is comprised in the heterocycloalkyl ring. Specific examples of the 4- to 10-membered nitrogen-containing heterocycloalkyl group include a pyrrolidinyl group, an imidazolidinnyl group, a morpholino group, a thiomorphorino group, a piperazino group and a piperidino group. As for the 4- to 10-membered nitrogen-containing heterocycloalkylcarbonyl group, examples thereof include a pyrrolidinocarbonyl group, a piperidinocarbonyl group, a piperazinocarbonyl group and a morpholinocarbonyl group.

The "4- to 10-membered nitrogen-containing heterocycloalkylcarbonyl group, which may be substituted" means the unsubstituted 4- to 10-membered nitrogen-containing heterocycloalkylcarbonyl group as described above or a 4- to 10-membered heterocycloalkylcarbonyl group in which at least one hydrogen atom of the heterocycloalkyl moiety is substituted by a defined substituent(s). When two or more substituent groups are present, each substituent group can be the same or different from each other. In addition, the heterocycloalkyl moiety may be substituted by a cyclic substituent group through a spiro bond. Preferably, it is a 4- to 10-membered nitrogen-containing heterocycloalkylcarbonyl group which may be substituted by 1 to 3 substituent(s).

The "4- to 10-membered heterocycloalkyl ($C_{0-8}$ alkyl) aminocarbonyl group" means 4- to 10-membered heterocycloalkyl NHC(O)— group, or a 4- to 10-membered heterocycloalkyl N($C_{1-8}$ alkyl)-C(O)— group. Specifically, examples thereof include a oxetan-3-yl amide group, and a (1,1-dioxo-tetrahydro-thiophen-3-yl)-amide group.

The "4- to 10-membered heterocycloalkyl ($C_{0-8}$ alkyl) aminocarbonyl group which may be substituted by one or more oxo groups" means the unsubstituted 4- to 10-membered heterocycloalkylaminocarbonyl group described above or the 4- to 10-membered heterocycloalkylaminocarbonyl group in which the heterocycloalkyl moiety is substituted by at least one oxo group.

The "$C_{6-10}$ arylsulfonyl group" means a $C_{6-10}$ aryl-$S(O)_2$— group and the $C_{6-10}$ aryl group is described above. Specifically, examples thereof include a phenylsulfonyl group.

The "5- to 14-membered heteroarylsulfonyl group" means a 5- to 14-membered heteroaryl-$S(O)_2$— group, and the 5- to 14-membered heteroaryl is described above. Specifically, examples thereof include a imidazol-sulfonyl group.

The "($C_{1-8}$ alkyl)$_x$-amino group", wherein x is a symbol defined in claims, means an amino group, a NH($C_{1-8}$ alkyl) group, or a N($C_{1-8}$ alkyl)$_2$-group. Specifically, examples thereof include amino, methylamino, ethylamino, butylamino, isopropylamino, dimethylamino and diethylamino Preferably, it is a $C_{1-3}$ alkylamino group.

The "($C_{1-8}$ alkyl)$_x$-amino group which may be substituted" means an unsubstituted ($C_{1-8}$ alkyl)$_x$-amino group or an amino group in which one or two hydrogen atoms on the nitrogen atom or the alkyl moiety are substituted by a defined substituent(s). When two substituent groups are present, each substituent group can be the same or different from each other.

The "$C_{1-8}$ alkylcarbonyl ($C_{0-8}$ alkyl) amino group" means a $C_{1-8}$ alkyl-C(O)—NH— group or a $C_{1-8}$ alkyl-C(O)—N ($C_{1-8}$ alkyl)-group, and the $C_{1-8}$ alkyl is described above. Specifically, examples thereof include a methylcarbonylamino group, an ethylcarbonylamino group, a propylcarbonylamino group and a butylcarbonylamino group.

The "$C_{1-8}$ alkylcarbonyl ($C_{0-8}$ alkyl) amino group which may be substituted" means the unsubstituted $C_{1-8}$ alkylcarbonyl ($C_{0-8}$ alkyl) amino group described above or the $C_{1-8}$ alkylcarbonyl ($C_{0-8}$ alkyl) amino group in which at least one hydrogen atoms of the terminal alkyl moiety is substituted by a defined substituent(s). When two or more substituent groups are present, each substituent group can be the same or different from each other. In addition, the alkyl moiety may be substituted by a cyclic substituent group through a spiro bond. Preferably, it is a $C_{1-8}$ alkylcarbonyl ($C_{0-8}$ alkyl) amino group which may be substituted by 1 to 3 substituent(s).

The "$C_{6-10}$ arylcarbonyl ($C_{0-8}$ alkyl) amino group" means a $C_{6-10}$ aryl-C(O)—NH— group or a $C_{6-10}$ aryl-C(O)—N ($C_{1-8}$ alkyl)-group and the $C_{6-10}$ aryl group and the $C_{1-8}$ alkyl group are described above. Specifically, examples thereof include a phenylcarbonylamino group.

The "$C_{6-10}$ arylcarbonyl ($C_{0-8}$ alkyl) amino group which may be substituted" means the unsubstituted $C_{6-10}$ arylcarbonyl ($C_{0-8}$ alkyl) amino group described above or the $C_{6-10}$ arylcarbonyl ($C_{0-8}$ alkyl) amino group in which at least one hydrogen atoms of the aryl moiety is substituted by a defined substituent(s). When two or more substituent groups are present, each substituent group can be the same or different from each other. Preferably, it is a $C_{6-10}$ arylcarbonyl ($C_{0-8}$ alkyl) amino group which may be substituted by 1 to 3 substituent(s).

The "($C_{1-8}$ alkyl)$_x$-aminocarbonyl ($C_{0-8}$ alkyl) amino group", wherein x is a symbol defined in claims, means a NH$_2$C(O)NH— group, a ($C_{1-8}$ alkyl)NHC(O)NH— group, a NH$_2$C(O)N($C_{1-8}$ alkyl)-group, or a ($C_{1-8}$ alkyl)NHC(O)N ($C_{1-8}$ alkyl)-group, and the $C_{1-8}$ alkyl is described above. Specifically, examples thereof include aminocarbonyl-(N-methyl)amino, and (N-methyl)aminocarbonyl-(N'-methyl)amino.

The "($C_{1-8}$ alkyl)$_x$-aminocarbonyl ($C_{0-8}$ alkyl) amino group which may be substituted" means an unsubstituted ($C_{1-8}$ alkyl)$_x$-aminocarbonyl ($C_{0-8}$ alkyl) amino group, or a ($C_{1-8}$ alkyl)$_x$-aminocarbonyl ($C_{0-8}$ alkyl) amino group in which at least one hydrogen atom on the nitrogen atom or the alkyl moiety is substituted by a defined substituent. Preferably, it is a ($C_{1-8}$ alkyl)$_x$-aminocarbonyl ($C_{0-8}$ alkyl) amino group which may be substituted by a phenyl group.

The "$C_{1-8}$ alkylsulfonylamino group" means a $C_{1-8}$ alkyl-S(O)$_2$—NH— group and the $C_{1-6}$ alkyl group is described above. Specifically, examples thereof include a methylsulfonylamino group and an ethylsulfonylamino group.

The "($C_{1-8}$ alkyl)$_x$-aminosulfonyl($C_{0-8}$ alkyl)amino group", wherein x is a symbol defined in claims, means a NH$_2$S(O)$_2$NH— group, a NH($C_{1-8}$ alkyl)-S(O)$_2$NH— group, or a N($C_{1-8}$ alkyl)$_2$-S(O)$_2$NH— group, a NH$_2$S(O)$_2$ N($C_{1-8}$ alkyl)-group, a NH($C_{1-8}$ alkyl)-S(O)$_2$($C_{1-8}$ alkyl)N— group, or a N($C_{1-8}$ alkyl)$_2$-S(O)$_2$ ($C_{1-8}$ alkyl)N— group, and the $C_{1-8}$ alkyl group is described above. Specifically, examples thereof include a methylamino-sulfonylamino group and a dimethylamino-sulfonylamino group.

The "$C_{1-8}$ alkoxy group" means a $C_{1-8}$ alkyl-O— group. Specifically, examples thereof include a methoxy group, an ethoxy group, a 1-propoxy group, a 2-propoxy group, a n-butoxy group, an i-butoxy group, a sec-butoxy group, a t-butoxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, a 2,3-dimethyl-2-butyloxy group and a 1-methyl-cyclopropylmethoxy group. Preferably, it is a $C_{1-6}$ alkoxy group, more preferably a $C_{1-5}$ alkoxy group, still more preferably a $C_{1-4}$ alkoxy group, and still even more preferably a $C_{1-3}$ alkoxy group.

The "$C_{1-8}$ alkoxy group which may be substituted" means an unsubstituted $C_{1-8}$ alkoxy group or a $C_{1-8}$ alkoxy group in which at least one hydrogen atom of the alkyl moiety is substituted by a defined substituent(s). When two or more substituent groups are present, each substituent group can be the same or different from each other. In addition, the alkyl moiety may be substituted by a cyclic substituent group through a spiro bond. Preferably, it is a $C_{1-8}$ alkoxy group which may be substituted by 1 to 3 substituent(s). More preferably, it is 1 to 3 substituent(s) for $C_{1-6}$ alkoxy group and a $C_{1-4}$ alkoxy group, and 1 to 2 substituent(s) for a $C_{1-3}$ alkoxy group.

The "$C_{1-8}$ alkoxycarbonyl group" means a $C_{1-8}$ alkyl-O—C(O)— group and the $C_{1-8}$ alkyl group is described above. Specifically, examples thereof include a methoxycarbonyl group, an ethoxycarbonyl group, a n-propoxycarbonyl group and an i-propoxycarbonyl group. Preferably, it is a $C_{1-6}$ alkoxycarbonyl group, and more preferably a $C_{1-3}$ alkoxycarbonyl group.

The "$C_{1-8}$ alkoxycarbonyl group which may be substituted" means the unsubstituted $C_{1-8}$ alkoxycarbonyl group described above or a $C_{1-8}$ alkoxycarbonyl group of which at least one hydrogen atom is substituted by a defined substituent(s). When two or more substituent groups are present, each substituent group can be the same or different from each other. In addition, the alkyl moiety of the alkoxycarbonyl group may be substituted by a cyclic substituent group through a spiro bond. Preferably, it is a $C_{1-8}$ alkoxycarbonyl group which may be substituted by 1 to 3 substituent(s).

The "$C_{0-8}$ alkoxy ($C_{0-8}$ alkyl) aminocarbonyl group" means a HO—NH—C(O)— group, a $C_{1-8}$ alkyl-NH—C(O)— group, a HO—N($C_{1-8}$ alkyl)-C(O)— group, or a $C_{1-8}$ alkyl-N($C_{1-8}$ alkyl)-C(O)— group, and has a $C_{1-8}$ alkoxy group or a $C_{1-8}$ alkyl group as described above. Specifically, examples thereof include a methoxyaminocarbonyl group, an ethoxyaminocarbonyl group, a n-propoxyaminocarbonyl group and an i-propoxyaminocarbonyl group. Preferably, it is a $C_{1-6}$ alkoxyaminocarbonyl group, and more preferably a $C_{1-3}$ alkoxyaminocarbonyl group.

The "$C_{0-8}$ alkoxy ($C_{0-8}$ alkyl) aminocarbonyl group which may be substituted" means the unsubstituted hydroxyaminocarbonyl group described above, or a $C_{1-8}$ alkoxyaminocarbonyl group, a hydroxy ($C_{1-8}$ alkyl) aminocarbonyl group or a $C_{1-8}$ alkoxy ($C_{1-8}$ alkyl) aminocarbonyl group, wherein at least one hydrogen atom of the alkyl moiety is substituted by a defined substituent(s). When two or more substituent groups are present, each substituent group can be the same or different from each other. In addition, the alkyl moiety may be substituted by a cyclic substituent group through a spiro bond. Preferably, it is a $C_{1-8}$ alkoxy aminocarbonyl group which may be substituted by 1 to 3 substituent(s).

The "4- to 10-membered heterocycloalkyloxy group" means a 4- to 10-membered heterocycloalkyl-O— group, and the 4- to 10-membered heterocycloalkyl is described above.

The "4- to 10-membered heterocycloalkyloxy group which may be substituted" means the unsubstituted 4- to 10-membered heterocycloalkyloxy group described above or a 4- to 10-membered heterocycloalkyloxy group in which at least one hydrogen atom of the heterocycloalkyl moiety is substituted by a defined substituent(s). When two or more substituent groups are present, each substituent group can be the same or different from each other. In addition, the heterocycloalkyl moiety may be substituted by a cyclic substituent group through a spiro bond. Preferably, it is a 4- to 10-membered heterocycloalkyloxy group which may be substituted by 1 to 3 substituent(s).

The "$C_{6-10}$ aryloxy group" means a $C_{6-10}$ aryl-O— group, and the $C_{6-10}$ aryl group is described above.

The "5- to 14-membered heteroaryloxy group" means a 5- to 14-membered heteroaryl-O— group, and the 5- to 14-membered heteroaryl is described above. Specifically, examples thereof include a pyrimidinyloxy group.

The "$C_{1-8}$ alkylcarbonyloxy group" means a $C_{1-8}$ alkyl-C(O)—O— group, and the $C_{1-8}$ alkyl is described above. Specifically, examples thereof include a methylcarbonyloxy group, an ethylcarbonyloxy group and a propylcarbonyloxy group.

The "$C_{2-8}$ alkenylcarbonyloxy group" means a $C_{2-8}$ alkenyl-C(O)—O— group, and the $C_{2-8}$ alkenyl is described above. Specifically, examples thereof include a 2-methyl-2-butenoyloxy group.

The "4- to 10-membered heterocycloalkylcarbonyloxy group" means a 4- to 10-membered heterocycloalkyl-C(O)—O— group, and the 4- to 10-membered heterocycloalkyl is described above.

The "($C_{1-8}$ alkyl)$_x$-aminocarbonyloxy group", wherein x is a symbol defined in claims, means a NH2C(O)—O— group, a NH($C_{1-8}$ alkyl)-C(O)—O— group, or a N($C_{1-8}$ alkyl)$_2$-C(O)—O— group. Specifically, examples thereof include a methylamino-carbonyloxy group, an ethylamino-carbonyloxy group and a propylamino-carbonyloxy group.

The "($C_{1-8}$ alkyl)$_x$-aminocarbonyloxy group which may be substituted" means an unsubstituted ($C_{1-8}$ alkyl)$_x$-aminocarbonyloxy group or a ($C_{1-8}$ alkyl)$_x$-aminocarbonyloxy group in which one or two hydrogen atoms on the nitrogen atom or the alkyl moiety are substituted by a defined substituent(s). When two substituent groups are present, each substituent group can be the same or different from each other.

The "4- to 10-membered nitrogen-containing heterocycloalkylsulfonyl group" means the 4- to 10-membered nitrogen-containing heterocycloalkyl-S(O)$_2$— group described above. Specifically, examples thereof include a morphorino-sulfonyl group.

The "4- to 10-membered nitrogen-containing heterocycloalkylsulfonyl group which may be substituted" means the unsubstituted 4- to 10-membered nitrogen-containing heterocycloalkylsulfonyl group described above or the 4- to 10-membered nitrogen-containing heterocycloalkylsulfonyloxy group in which at least one hydrogen atom of the 4- to 10-membered nitrogen-containing heterocycloalkyl moiety is substituted by a defined substituent(s). When two or more substituent groups are present, each substituent group can be the same or different from each other. Preferably, it is a 4- to 10-membered nitrogen-containing heterocycloalkylsulfonyl which may be substituted by 1 to 3 substituent(s).

The "4- to 10-membered nitrogen-containing heterocycloalkylsulfonyloxy group" means the 4- to 10-membered nitrogen-containing heterocycloalkyl-S(O)$_2$—O— group described above. Specifically, examples thereof include a morphorino-sulfonyloxy group and a piperadino-sulfonyloxy group.

The "4- to 10-membered nitrogen-containing heterocycloalkylsulfonyloxy group which may be substituted" means the unsubstituted 4- to 10-membered nitrogen-containing heterocycloalkylsulfonyloxy group described above or the 4- to 10-membered nitrogen-containing heterocycloalkylsulfonyloxy group in which at least one hydrogen atom of the 4- to 10-membered nitrogen-containing heterocycloalkyl moiety is substituted by a defined substituent(s). When two or more substituent groups are present, each substituent group can be the same or different from each other. Preferably, it is a 4- to 10-membered nitrogen-containing heterocycloalkylsulfonyloxy which may be substituted by 1 to 3 substituent(s).

The "$C_{1-8}$ alkylsulfonyloxy group" means a $C_{1-8}$ alkyl-S(O)$_2$—O— group, and the $C_{1-8}$ alkyl is described above.

The "$C_{1-8}$ alkylsulfonyloxy group which may be substituted" means the unsubstituted $C_{1-8}$ alkylsulfonyloxy group described above or a $C_{1-8}$ alkylsulfonyloxy group in which at least one hydrogen atom of the alkyl moiety is substituted by a defined substituent(s). When two or more substituent groups are present, each substituent group can be the same or different from each other. In addition, the alkyl moiety may be substituted by a cyclic substituent group through a spiro bond. Preferably, it is a $C_{1-8}$ alkylsulfonyloxy group which may be substituted by 1 to 3 substituent(s). Specifically, examples thereof include a trifluoromethylsulfonyloxy group.

The "($C_{1-8}$ alkyl)$_x$-aminosulfonyloxy group" wherein x is a symbol defined in claims, means a NH$_2$S(O)$_2$— group, a N($C_{1-8}$ alkyl)S(O)$_2$— group, or a N($C_{1-8}$ alkyl)$_2$S(O)$_2$— group. Specifically, examples thereof include a N-methyl-aminosulfonyloxy group.

The "$C_{1-8}$ alkylthio group" means a $C_{1-8}$ alkyl-S— group, and the $C_{1-8}$ alkyl group is described above. Examples thereof include methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, and 2-ethylbutylthio and the like. Preferably, it is a $C_{1-6}$ alkylthio group, and more preferably a $C_{1-3}$ alkylthio group.

The "$C_{1-8}$ alkylthio group which may be substituted" means an unsubstituted $C_{1-8}$ alkylthio group or a $C_{1-8}$ alkylthio group in which at least one hydrogen atom of the alkyl moiety is substituted by a defined substituent(s). When two or more substituent groups are present, each substituent group can be the same or different from each other. In addition, the alkyl moiety may be substituted by a cyclic substituent group through a spiro bond. Preferably, it is a $C_{1-8}$ alkylthio group which may be substituted by 1 to 3 substituent(s).

The "$C_{1-8}$ alkylsulfonyl group" means a $C_{1-8}$ alkyl-S(O)$_2$— group, and the $C_{1-8}$ alkyl group is described above. Specifically, examples thereof include a methylsulfonyl group, an ethylsulfonyl group and a n-propylsulfonyl group. Preferably, it is a $C_{1-6}$ alkylsulfonyl group, and more preferably a $C_{1-3}$ alkylsulfonyl group.

The "$C_{1-8}$ alkylsulfinyl group" means a $C_{1-8}$ alkyl-S(O)— group, and the $C_{1-8}$ alkyl group is described above. Specifically, examples thereof include a methylsulfinyl group, an ethylsulfinyl group and a n-propylsulfinyl group. Preferably, it is a $C_{1-6}$ alkylsulfinyl group, and more preferably a $C_{1-3}$ alkylsulfinyl group.

The "$C_{1-8}$ alkylsulfonyl group which may be substituted" means the unsubstituted $C_{1-8}$ alkylsulfonyl group described above or a $C_{1-8}$ alkylsulfonyl group in which at least one hydrogen atom of the alkyl moiety is substituted by a defined substituent(s). When two or more substituent groups are present, each substituent group can be the same or different from each other. Preferably, it is a $C_{1-8}$ alkylsulfonyl group which may be substituted by 1 to 3 substituent(s).

The "$C_{1-8}$ alkylsulfinyl group which may be substituted" means the unsubstituted $C_{1-8}$ alkylsulfinyl group described above or a $C_{1-8}$ alkylsulfinyl group in which at least one hydrogen atom of the alkyl moiety is substituted by a defined substituent(s). When two or more substituent groups are present, each substituent group can be the same or different from each other. Preferably, it is a $C_{1-8}$ alkylsulfinyl group which may be substituted by 1 to 3 substituent(s).

The "4- to 10-membered heterocycloalkylsulfonyl group" means a 4- to 10-membered heterocycloalkyl-S(O)$_2$— group, and the 4- to 10-membered heterocycloalkyl is described above.

The "4- to 10-membered heterocycloalkylsulfonyl group which may be substituted" means the unsubstituted 4- to 10-membered heterocycloalkylsulfonyl group described above or a 4- to 10-membered heterocycloalkylsulfonyl group in which at least one hydrogen atom of the heterocycloalkyl moiety is substituted by a defined substituent(s). When two or more substituent groups are present, each substituent group can be the same or different from each other. In addition, the heterocycloalkyl moiety may be substituted by a cyclic substituent group through a spiro bond. Preferably, it is a 4- to 10-membered heterocycloalkylsulfonyl group which may be substituted by 1 to 3 substituent(s).

The "($C_{1-8}$ alkyl)$_x$-aminosulfonyl group", wherein x is a symbol defined in claims, means a NH$_2$—S(O)$_2$— group, a $C_{1-8}$ alkylamino-S(O)$_2$— group, or a ($C_{1-8}$ alkyl)$_2$amino-S(O)$_2$— group and the $C_{1-8}$ alkyl is described above. Specifically, examples thereof include an aminosulfonyl group, a methylaminosulfonyl group and a dimethylaminosulfonyl group.

The "($C_{1-8}$ alkyl)$_x$-aminosulfonyl group which may be substituted" means an unsubstituted aminosulfonyl group or a ($C_{1-8}$ alkyl)$_x$-aminosulfonyl group in which one or two hydrogen atoms on the nitrogen atom or the alkyl moiety are substituted by a defined substituent(s). When two substituent groups are present, each substituent group can be the same or different from each other.

The "$C_{1-8}$ alkoxycarbonyl ($C_{0-8}$ alkyl) amino group" means a $C_{1-8}$ alkoxy-C(O)— NH— group or a $C_{1-8}$ alkoxy-C(O)—N($C_{1-8}$ alkyl)-group, wherein the $C_{1-8}$ alkoxy group and $C_{1-8}$ alkyl) are described above. Specifically, examples thereof include a methoxycarbmamoyl group and an N-ethylcarbonyl-N-methyl-amino group.

The "$C_{1-8}$ alkoxycarbony($C_{0-8}$ alkyl) amino group which may be substituted" means the unsubstituted $C_{1-8}$ alkoxycarbony($C_{0-8}$ alkyl) amino group described above, or a $C_{1-8}$ alkoxycarbony($C_{0-8}$ alkyl) amino group, wherein at least one hydrogen atom of the alkyl moiety is substituted by a defined substituent(s). When two or more substituent groups are present, each substituent group can be the same or different from each other. Preferably, it is a $C_{1-8}$ alkoxycarbony($C_{0-8}$ alkyl) amino group which may be substituted by 1 to 3 substituent(s).

The "$C_{1-8}$ alkoxycarbonyl ($C_{0-8}$ alkyl) aminosulfonyl group" means a $C_{1-8}$ alkoxy-C(O)—NHS(O)$_2$— group or a $C_{1-8}$ alkoxy-C(O)—N($C_{1-8}$ alkyl)S(O)$_2$— group, wherein the $C_{1-8}$ alkoxy group and $C_{1-8}$ alkyl group are described above. Specifically, examples thereof include a methoxycarbonylaminosulfonyl group and an ethoxycarbonyl-N-methyl-aminosulfonyl group.

The "$C_{6-10}$ aryloxycarbonyl ($C_{0-8}$ alkyl) amino group" means a $C_{6-10}$ aryl-O—C(O)—NH— group or a $C_{6-10}$ aryl-O—C(O)—N($C_{1-8}$ alkyl)-group, wherein the $C_{6-10}$ aryl group and $C_{1-8}$ alkyl are described above. Specifically, examples thereof include a phenyloxycarbonylamino group and a N-methyl-N-phenyloxycarbonyl-amino group.

The "$C_{6-10}$ aryloxycarbonyl ($C_{0-8}$ alkyl) amino group which may be substituted" means the unsubstituted $C_{6-10}$ aryloxycarbonyl ($C_{0-8}$ alkyl) amino group described above or the $C_{6-10}$ aryloxycarbonyl ($C_{0-8}$ alkyl) amino group in which at least one hydrogen atoms of the aryl moiety is substituted by a defined substituent(s). When two or more substituent groups are present, each substituent group can be the same or different from each other. Preferably, it is a $C_{6-10}$ aryloxycarbonyl ($C_{0-8}$ alkyl) amino group which may be substituted by 1 to 3 substituent(s).

The "$C_{6-10}$ aryl ($C_{0-8}$ alkyl) aminocarbonyl ($C_{0-8}$ alkyl) amino group" means a $C_{6-10}$ aryl NHC(O)NH— group, a $C_{6-10}$ aryl-N($C_{1-8}$ alkyl)-C(O)NH— group, a $C_{6-10}$ aryl-N($C_{1-8}$ alkyl)-C(O)N($C_{1-8}$ alkyl)-group, or a $C_{6-10}$ aryl-NH—C(O)N($C_{1-8}$ alkyl)-group, wherein the $C_{6-10}$ aryl group and $C_{1-8}$ alkyl are described above. Specifically, examples thereof include a phenylaminocarbonylamino group and a phenylaminocarbonyl(N-methyl)amino group.

The "$C_{6-10}$ aryl ($C_{0-8}$ alkyl) aminocarbonyl ($C_{0-8}$ alkyl) amino group which may be substituted" means the unsubstituted $C_{6-10}$ aryl ($C_{0-8}$ alkyl) aminocarbonyl ($C_{0-8}$ alkyl) amino group described above or the $C_{6-10}$ aryl ($C_{0-8}$ alkyl) aminocarbonyl ($C_{0-8}$ alkyl) amino group in which at least one hydrogen atoms of the aryl moiety is substituted by a defined substituent(s). When two or more substituent groups are present, each substituent group can be the same or different from each other. Preferably, it is a $C_{6-10}$ aryl ($C_{0-8}$ alkyl) aminocarbonyl ($C_{0-8}$ alkyl) amino group which may be substituted by 1 to 3 substituent(s).

The "$C_{6-10}$ aryl ($C_{0-8}$ alkyl) aminocarbonyloxy group" means a $C_{6-10}$ aryl-NHC(O)—O—, or a $C_{6-10}$ aryl-N($C_{1-8}$ alkyl)-C(O)—O— group, wherein the $C_{6-10}$ aryl group and $C_{1-8}$ alkyl are described above. Specifically, examples thereof include a phenylaminocarbonyloxy group and a phenylaminocarbonyl(N-methyl)amino carbonyloxy group.

The "$C_{6-10}$ aryl ($C_{0-8}$ alkyl) aminocarbonyloxy group which may be substituted" means the unsubstituted $C_{6-10}$ aryl ($C_{0-8}$ alkyl) aminocarbonyloxy group described above or the $C_{6-10}$ aryl ($C_{0-8}$ alkyl) aminocarbonyloxy group in which at least one hydrogen atoms of the aryl moiety is substituted by a defined substituent(s). When two or more substituent groups are present, each substituent group can be the same or different from each other. Preferably, it is a $C_{6-10}$ aryl ($C_{0-8}$ alkyl) aminocarbonyloxy group which may be substituted by 1 to 3 substituent(s).

The "$C_{1-8}$ alkylsulfonyl ($C_{0-8}$ alkyl) amino group" means a $C_{1-8}$ alkyl-S(O)$_2$—NH— group, or a $C_{1-8}$ alkyl-S(O)$_2$—N($C_{1-8}$ alkyl)-group. Specifically, examples thereof include a methylsulphonylamino group and a methylsulphonyl-(N-methyl)amino group.

The "$C_{2-8}$ alkenyloxy group" means a $C_{2-8}$ alkenyl-O— group, wherein the $C_{2-8}$ alkenyl group is described above. Specific examples of the $C_{2-8}$ alkenyloxy group include a vinyloxy group and a allyloxy group.

Preferably, all of $A^1$, $A^2$, $A^3$, $A^4$, $A^7$, $A^8$, $A^9$ and $A^{10}$ are C, or any one of $A^2$, $A^4$, $A^7$ and $A^9$ is N and the remainings are C (with the proviso that, when $A^2$, $A^4$, $A^7$ or $A^9$ is N, they do not have a substituent group $R^2$, $R^4$, $R^7$ or $R^9$). More preferably, all of them are C, or $A^4$ is N while the remainings are C, even more preferably, all of them are C, or $A^4$, $A^7$, and $A^9$ is N and the remainings are C (with the proviso that, when $A^4$, $A^7$, or $A^9$ is N, they do not have a substituent group $R^4$, $R^7$, $R^9$).

$A^5$ is preferably $NR^5$ or O, more preferably $NR^5$, even more preferably NH.

$R^1$ is preferably
[1] a hydrogen atom,
[2] a halogen atom,
and more preferably
[1] a hydrogen atom,
[2] a fluorine atom,
[3] a chlorine atom.

$R^{10}$ is preferably a hydrogen atom.

$R^2$ is preferably
[1] a hydrogen atom,
[2] a $C_{1-5}$ alkyl group,
[3] a cyano,
[4] a halogen atom,
and more preferably
[1] a hydrogen atom,
[2] a $C_{1-3}$ alkyl group,
[3] a fluorine atom,
[4] a chlorine atom,
[5] a bromine atom.
And even more preferably
[1] a hydrogen atom,
[2] a halogen atom,
Still more preferably
[1] a hydrogen atom, $R^4$ is preferably
[1] a hydrogen atom,
[2] a $C_{1-5}$ alkyl group which may be substituted by 1-11 halogen atom(s),
[3] a $C_{3-6}$ cycloalkyl group,
[4] a cyano,
[5] a halogen atom,
[6] a ($C_{1-3}$ alkyl)$_{m4b}$-amino group (m4b: 0~2),
[7] a hydroxy,
[8] a $C_{1-5}$ alkoxy group which may be substituted by 1-4 hydroxy(s),
and more preferably
[1] a hydrogen atom,
[2] a $C_{1-3}$ alkyl group which may be substituted by 1-7 halogen atom(s),
[3] a $C_{3-5}$ cycloalkyl group,
[4] a cyano,
[5] a fluorine atom,
[6] a bromine atom,
[7] an amino (C1-3 alkyl)$_{m4b}$-amino group,
[8] a hydroxy,
[9] a $C_{1-3}$ alkoxy group which may be substituted by 1-2 hydroxy(s).
Even more preferably
[1] a hydrogen atom,
[2] a $C_{1-8}$ alkyl group which may be substituted by at least one halogen atom,
[3] a $C_{3-8}$ cycloalkyl group,
[4] a cyano,
[5] a halogen atom,
[6] a hydroxy,
[7] a $C_{1-8}$ alkoxy group which may be substituted by a hydroxy,
Still more preferably
[1] a hydrogen atom,
[2] a halogen atom, $R^5$ is preferably
[1] a hydrogen atom,
[2] a $C_{1-5}$ alkyl group which may be substituted by 1-5 $R^{5A}$ substituent(s),
[3] a $C_{1-5}$ alkylsulfonyl group,
and more preferably
[1] a hydrogen atom,
[2] a $C_{1-3}$ alkyl group which may be substituted by 1-3 $R^{5A}$ substituent(s),
[3] a $C_{1-3}$ alkylsulfonyl group.
Even more preferably
[1] a hydrogen atom,
[2] a $C_{1-8}$ alkyl group,
Still more preferably
[1] a hydrogen atom.

$R^{5A}$ is preferably
[1] a $C_{1-5}$ alkoxycarbonyl group,
[2] a hydroxy,
[3] a $C_{1-5}$ alkoxy group,
[4] a ($C_{1-5}$ alkyl)$_{m5}$-amino group (m5: 0-2),
[5] a $C_6$ aryl,
[6] a $C_{1-5}$ alkylthio group,
and more preferably
[1] a $C_{1-3}$ alkoxycarbonyl group,
[2] a hydroxy,
[3] a $C_{1-3}$ alkoxy group,
[4] a ($C_{1-3}$ alkyl)$_{m5}$-amino group (m5: 0-2),
[5] a $C_{1-3}$ alkylthio group,
even more preferably
[1] a hydroxy,
[2] a $C_{1-5}$ alkoxy group,
[3] a ($C_{1-5}$ alkyl)$_{m5}$-amino group (m5: 0-2),
[4] a $C_{1-5}$ alkylthio group.

$R^6$ and $R^{6'}$ are preferably
[1] a $C_{1-8}$ alkyl group,
taken together with carbon atoms to which they are bound to form
[2] a $C_{3-8}$ cycloalkyl group,
[3] a 4- to 10-membered heterocycloalkyl group,
more preferably
[1] a $C_{1-3}$ alkyl group,
taken together with carbon atoms to which they are bound to form
[2] a $C_{3-6}$ cycloalkyl group,
[3] a 4- to 6-membered heterocycloalkyl group,
even more preferably
[1] a methyl,
taken together with carbon atoms to which they are bound to form

[2] a cyclopentane,
[3] a tetrahydropyran,
[4] or a piperidine.

$R^7$ is preferably
[1] a hydrogen atom,
[2] a fluorine atom,
[3] a bromine atom,
[4] a chlorine atom,
[5] a $C_{1-5}$ alkoxy group which may be substituted by 1-4 $R^{7A}$ substituent(s),
and more preferably
[1] a hydrogen atom,
[2] a halogen atom,
and even more preferably
[1] a hydrogen atom,
[2] a fluorine atom,
[3] a bromine atom,
[4] a chlorine atom,
and still more preferably
[1] a hydrogen atom.

$R^{7A}$ is preferably
[1] a $(C_{1-5}$ alkyl$)_{m7}$-amino group (m7: 0~2),
[2] a hydroxy,
[3] a 4- to 6-membered heterocycloalkyl group which may be substituted by $C_{1-5}$ alkyl group(s), and more preferably
[1] a $(C_{1-3}$ alkyl$)_{m7}$-amino group (m7: 2),
[2] a hydroxy,
[3] a 4- to 6-membered heterocycloalkyl group which may be substituted by $C_{1-3}$ alkyl group(s).

$R^3$ is preferably
[1] a hydrogen atom,
[2] a $C_{1-5}$ alkyl group which may be substituted by 1-11 halogen atom(s),
[3] a cyano,
[4] a $(C_{1-5}$ alkyl$)_{m3a}$-aminocarbonyl group (m3a: 0~2) which may be substituted by 1-5 $R^{3A}$ substituents,
[5] a hydroxycarbonyl,
[6] a $C_{1-5}$ alkylcarbonyl group which may be substituted by 1-4 hydroxy(s),
[7] a halogen atom,
[8] a $(C_{1-3}$ alkyl$)_{m3b}$-amino group (m3b: 0~2) which may be substituted by 1-2 $C_6$ aryl(s),
[9] a $C_{1-5}$ alkyl carbonyl $(C_{0-3}$ alkyl) amino group which may be substituted by 1-2 $C_6$ aryl(s) or 1-2 $C_6$ aryloxy(s),
[10] a $C_6$ arylcarbonyl $(C_{0-3}$ alkyl) amino group which may be substituted by 1-5 $C_{1-3}$ alkyl group(s) which may be substituted by 1-7 halogen atom(s),
[11] a $(C_{1-3}$ alkyl$)_{m3c}$-aminocarbonyl$(C_{0-3}$ alkyl) amino group (m3c: 0-1) which may be substituted by a $C_6$ aryl,
[12] a nitro,
[13] a hydroxy,
[14] a $C_{1-5}$ alkoxy group which may be substituted by 1-4 $R^{3B}$(s),
[15] a 4- to 6-membered heterocycloalkyloxy group,
[16] a 6-membered heteroaryloxy,
[17] a $(C_{1-5}$ alkyl$)_{m3e}$-aminocarbonyloxy group (m3e: 0~2) which may be substituted by 1-3 $C_6$ aryl(s),
[18] a 4- to 6-membered nitrogen-containing heterocycloalkylaminocarbonyl group,
[19] a $C_{1-5}$ alkylthio group,
[20] a 5- to 6-membered heteroaryl group which may be substituted by 1-4 $C_{1-5}$ alkyl group(s) which may be substituted by 1-3 $C_{1-5}$ alkoxy group(s),
[21] a $C_{1-3}$ alkoxycarbonyl $(C_{0-3}$ alkyl) amino group which may be substituted by a $C_{1-3}$ alkoxy group,
[22] a $C_6$ aryloxycarbonyl $(C_{0-3}$ alkyl) amino group which may be substituted by 1-3 $C_{1-3}$ alkyl group(s) which may be substituted by 1-9 halogen atom(s),
[23] a $C_6$ aryloxycarbonyl $(C_{0-3}$ alkyl) aminocarbonyl $(C_{0-3}$ alkyl)amino group which may be substituted by 1-3 $R^{3C}$,
[24] a $C_{3-6}$ cycloalkyl $(C_{0-3}$ alkyl) aminocarbonyloxy group, and
[25] a $C_6$ aryl $(C_{0-3}$ alkyl) aminocarbonyloxy group which may be substituted by 1-3 substituent(s) selected from the group consisting of a $C_{1-5}$ alkyl group and a $C_{1-5}$ alkoxy group(s).

$R^3$ is more preferably
[1] a hydrogen atom,
[2] a $C_{1-3}$ alkyl group which may be substituted by 1-7 halogen atom(s),
[3] a cyano,
[4] a $(C_{1-4}$ alkyl$)_{m3a}$-aminocarbonyl group (m3a: 0~1) which may be substituted by 1-4 $R^{3A}$ substituents,
[5] a hydroxycarbonyl,
[6] a halogen atom,
[7] a $C_{1-4}$ alkyl carbonyl $(C_{1-3}$ alkyl) amino group which may be substituted by 1-2 $C_6$ aryl(s) or 1-2 $C_6$ aryloxy(s),
[8] a $C_6$ arylcarbonyl $(C_{0-3}$ alkyl) amino group which may be substituted by a $C_{1-3}$ alkyl group which may be substituted by 1-7 halogen atom(s),
[9] a nitro,
[10] a hydroxy,
[11] a $C_{1-4}$ alkoxy group which may be substituted by 1-3 $R^B$ substituent(s),
[12] a 4-membered heterocycloalkyloxy group,
[13] a $(C_{1-3}$ alkyl$)_{m3e}$-aminocarbonyloxy group (m3e:1) which may be substituted by a $C_6$ aryl(s),
[14] a 6-membered nitrogen-containing heterocycloalkylaminocarbonyl group,
[15] a $C_{1-3}$ alkylthio group,
[16] a 5-membered heteroaryl group which may be substituted by a $C_{1-5}$ alkyl group which may be substituted by a $C_{1-3}$ alkoxy group,
[17] a $C_6$ aryloxycarbonyl $(C_{0-3}$ alkyl) aminocarbonyl $(C_{0-3}$ alkyl)amino group which may be substituted by a $R^3$ substituent,
[18] a $C_6$ cycloalkyl (C0-2 alkyl) aminocarbonyloxy group, and
[19] a $C_6$ aryl $(C_{0-3}$ alkyl) aminocarbonyloxy group which may be substituted by 1-2 substituent(s) selected from the group consisting of a $C_{1-4}$ alkyl group and a $C_{1-3}$ alkoxy group.

$R^3$ is still more preferably
[1] a hydrogen atom,
[2] a cyano,
[3] a halogen atom, $R^3$ is still even more preferably
[1] a cyano,
[2] a halogen atom.

$R^{3A}$ is preferably
[1] a $C_6$ aryl,
[2] a $C_{1-5}$ alkoxy group,
[3] a 5- or 6-membered heteroaryl group,
[4] a $C_6$ arylsulfonyl.

$R^{3B}$ is preferably
[1] a hydroxy,
[2] a $C_{1-5}$ alkoxy group,
[3] a $C_6$ aryl $(C_{0-3}$ alkyl) aminocarbonyl group,
[4] a $(C_{1-3}$ alkyl$)_{m3d}$-amino group (m3d: 0~2),
[5] a halogen atom, more preferably
[1] a hydroxy,
[2] a $C_{1-5}$ alkoxy group.

$R^{3C}$ is preferably
[1] a $C_{1-5}$ alkyl group which may be substituted by 1-11 halogen atom(s),
[2] a $C_{1-5}$ alkoxy group,
more preferably
[1] a $C_{1-4}$ alkyl group which may be substituted by 1-9 halogen atom(s),
[2] a $C_{1-3}$ alkoxy group.
$R^8$ is preferably
[1] a hydrogen atom,
[2] a $C_{1-5}$ alkyl group which may be substituted by 1-5 $R^{8A}$ substituent(s),
[3] a $C_{2-5}$ alkenyl group,
[4] a 4- to 6-membered heterocycloalkyl group which may be substituted by 1-4 $R^{8B}$ substituent(s),
[5] a 5- to 6-membered heteroaryl group which may be substituted by 1-4 $C_{1-8}$ alkyl group(s),
[6] a $(C_{1-5}$ alkyl$)_{m8g}$-aminocarbonyl group (m8g: 0~2) which may be substituted by 1-3 $R^{8C}$ substituent(s),
[7] a 4- to 6-membered heterocycloalkyl $(C_{0-3}$ alkyl) aminocarbonyl group which may be substituted by 1-2 oxo group(s),
[8] a 4- to 6-membered nitrogen-containing heterocycloalkylcarbonyl group which may be substituted by 1-4 $R^{8D}$ substituent(s),
[9] a hydroxycarbonyl,
[10] a $C_{1-5}$ alkoxy $(C_{0-3}$ alkyl) aminocarbonyl group which may be substituted by 1-3 hydroxy group(s),
[11] a halogen atom,
[12] a $(C_{1-5}$ alkyl$)_{m8j}$-amino group (m8j: 0~2) which may be substituted by 1-2 $R^{8H}$ substituent(s),
[13] a hydroxyl,
[14] a $C_{1-5}$ alkoxy group which may be substituted by 1-4 $R^{8E}$ substituent(s),
[15] a 4- to 6-membered heterocycloalkyloxy group which may be substituted by 1-5 $R^{8F}$ substituent(s),
[16] a 6-membered heteroaryloxy group,
[17] a $(C_{1-5}$ alkyl$)_{m8l1}$-aminosulfonyloxy group (m8l1:0-2),
[18] a $C_{1-5}$ alkyl thio group which may be substituted by 1-4 $R^{8I}$ substituent(s),
[19] a $C_{1-5}$ alkylsulfonyl group which may be substituted by 1-4 $R^{8G}$ substituent(s),
[20] a 6-membered heterocycloalkylsulfonyl group which may be substituted by a $C_{1-3}$ alkyl group,
[21] a $C_{2-5}$ alkenyloxy group, and
[22] a $C_{1-3}$ alkylsulfonyloxy group which may be substituted by 1-7 halogen atom(s).
And more preferably
[1] a hydrogen atom,
[2] a $C_{1-3}$ alkyl group which may be substituted by 1-3 $R^{8A}$ substituent(s),
[3] a C2-4 alkenyl group,
[4] a 6-membered heterocycloalkyl group which may be substituted by 1-3 $R^{8B}$ substituent(s),
[5] a 5- to 6-membered heteroaryl group which may be substituted by 1-2 $C_{1-3}$ alkyl group(s),
[6] a $(C_{1-3}$ alkyl$)_{m8g}$-aminocarbonyl group (m8g: 0~2) which may be substituted by 1-2 $R^{8C}$ substituent(s),
[7] a 4- to 6-membered heterocycloalkyl $(C_{0-1}$ alkyl) aminocarbonyl group which may be substituted by 1-2 oxo group(s),
[8] a 6-membered nitrogen-containing heterocycloalkylcarbonyl group which may be substituted by 1-2 $R^{8D}$ substituent(s),
[9] a hydroxycarbonyl,
[10] a $C_{1-3}$ alkoxy $(C_{0-3}$ alkyl) aminocarbonyl group which may be substituted by 1-2 hydroxy group(s),
[11] a bromine atom,
[12] a $(C_{1-3}$ alkyl$)_{m8j}$-amino group (m8j: 0~2) which may be substituted by 1-2 $R^{8H}$ substituent(s),
[13] a hydroxyl,
[14] a $C_{1-5}$ alkoxy group which may be substituted by 1-3 $R^{8E}$ substituent(s),
[15] a 4- to 6-membered heterocycloalkyloxy group which may be substituted by 1-3 $R^{8F}$ substituent(s),
[16] a 6-membered heteroaryloxy group,
[17] a $(C_{1-3}$ alkyl$)_{m8l1}$-aminosulfonyloxy group (m8l1:0-2),
[18] a $C_{1-3}$ alkyl thio group which may be substituted by 1-2 $R^{8I}$ substituent(s),
[19] a $C_{1-3}$ alkylsulfonyl group which may be substituted by 1-2 $R^{8G}$ substituent(s),
[20] a 6-membered heterocycloalkylsulfonyl group which may be substituted by a $C_{1-3}$ alkyl group,
[21] a $C_{2-3}$ alkenyloxy group, and
[22] a trifluoromethylsulfonyloxy group,
Even more preferably
[1] a hydrogen atom,
[2] a $C_{1-3}$ alkyl group which may be substituted by 1-3 $R^{8A}$ substituent(s),
[3] a 6-membered heterocycloalkyl group which may be substituted by 1-3 $R^{8B}$ substituent(s),
[4] a 5- to 6-membered heteroaryl group which may be substituted by 1-2 $C_{1-3}$ alkyl group(s),
[5] a 4- to 6-membered heterocycloalkyl (C0-1 alkyl) aminocarbonyl group which may be substituted by 1-2 oxo group(s),
[6] a 6-membered nitrogen-containing heterocycloalkylcarbonyl group which may be substituted by 1-2 $R^{8D}$ substituent(s),
[7] a $(C_{1-3}$ alkyl$)_{m8j}$-amino group (m8j: 0~2) which may be substituted by 1-2 $R^{8H}$ substituent(s),
[8] a hydroxyl,
[9] a $C_{1-5}$ alkoxy group which may be substituted by 1-3 $R^{8E}$ substituent(s),
[10] a 4- to 6-membered heterocycloalkyloxy group which may be substituted by 1-3 $R^{8F}$ substituent(s),
[11] a 6-membered heteroaryloxy group,
[12] a $C_{1-3}$ alkyl thio group which may be substituted by 1-2 $R^{8I}$ substituent(s),
[13] a $C_{1-3}$ alkylsulfonyl group which may be substituted by 1-2 $R^{8G}$ substituent(s), and
[14] a $C_{2-3}$ alkenyloxy group,
further preferably
[1] a hydrogen atom,
[2] a $C_{1-3}$ alkyl group which may be substituted by 1-3 $R^{8A}$ substituent(s),
[3] a 6-membered heterocycloalkyl group which may be substituted by 1-3 $R^{8B}$ substituent(s),
[4] a $(C_{1-3}$ alkyl$)_{m8j}$-amino group (m8j: 0~2) which may be substituted by 1-2 $R^{8H}$ substituent(s),
[5] a $C_{1-5}$ alkoxy group which may be substituted by 1-3 $R^{8E}$ substituent(s), and
[6] a 4- to 6-membered heterocycloalkyloxy group which may be substituted by 1-3 $R^{8F}$ substituent(s),
Still more preferably
[1] a 4- to 10-membered heterocycloalkyl group which may be substituted by one or more $R^{8B}$ described below,
Still even more preferably
[1] a 4- to 10-membered heterocycloalkyl group which may be substituted by at least one halogen atom, $C_{1-8}$ alkyl group, or an oxo.
$R^{8A}$ is preferably
[8A-1] a 4- to 6-membered heterocycloalkyl group which may be substituted by 1-4 $R^{8A1}$ substituent(s),

[8A-2] a $(C_{1-5}$ alkyl)$_{m8a}$-amino group (m8a: 0~2) which may be substituted by 1-11 halogen atom(s), and
[8A-3] a hydroxy;
$R^{8A}$ is more preferably
[8A-1] a 6-membered heterocycloalkyl group which may be substituted by 1-2 $R^{8A1}$ substituent(s),
[8A-2] a $(C_{1-3}$ alkyl)$_{m8a}$-amino group (m8a: 0~2) which may be substituted by 1-11 halogen atom(s), and
[8A-3] a hydroxy;
$R^{8A1}$ is preferably
[8A1-1] a $C_{1-5}$ alkyl group,
[8A1-2] a $C_{1-5}$ alkylsulfonyl group,
[8A1-3] a $(C_{1-5}$ alkyl)$_{m8b}$-aminosulfonyl group (m8b: 0~2), or
[8A1-4] an oxo group,
more preferably
[8A1-1] a $C_{1-3}$ alkyl group,
[8A1-2] a $C_{1-3}$ alkylsulfonyl group, or
[8A1-3] a $(C_{1-3}$ alkyl)$_{m8b}$-aminosulfonyl group (m8b: 0),
$R^{8B}$ is preferably
[8B-1] a $C_{1-6}$ alkyl group which may be substituted by 1-13 $R^{8B1}$ substituent(s),
[8B-2] a C2-6 alkynyl group,
[8B-3] a $C_{3-6}$ cycloalkyl group which may be substituted by [1] cyano(s) or [2] $C_{1-6}$ alkyl group(s),
[8B-4] a 4- to 6-membered heterocycloalkyl group which may be substituted by 1-10 $R^{8B2}$ substituent(s),
[8B-5] a $C_{1-6}$ alkoxy group which may be substituted by 1-5 substituent(s) selected from the group consisting of [1] a $C_{1-5}$ alkoxy group and [2] a $C_{3-6}$ cycloalkyl group,
[8B-6] a $C_{1-5}$ alkoxycarbonyl group,
[8B-7] a $C_{1-5}$ alkylsulfonyl group,
[8B-8] a 5- to 6-membered heteroarylsulfonyl group,
[8B-9] a cyano,
[8B-10] a $C_{1-6}$ alkanoyl group which may be substituted by 1-2 $R^{8B3}$ substituent(s),
[8B-11] a $C_{3-8}$ cycloalkylcarbonyl group,
[8B-12] a $(C_{1-5}$ alkyl)$_{m8c}$-aminosulfonyl group (m8c:0-2),
[8B-13] a $C_{1-6}$ alkylsulfonyl $(C_{0-6}$ alkyl) amino group,
[8B-14] a $(C_{1-8}$ alkyl)$_{m8d}$-amino group (m8d:0-2) which may be substituted by 1-3 $R^{8B4}$ substituent(s),
[8B-15] a hydroxy,
[8B-16] a $(C_{1-6}$ alkyl)$_{m8e}$-aminocarbonyl group (m8e:0-2), or
[8B-17] a $C_{1-4}$ alkoxycarbonylamino group more preferably
[8B-1] a $C_{1-5}$ alkyl group which may be substituted by 1-3 $R^{8B1}$,
[8B-2] a $C_{2-5}$ alkynyl group,
[8B-3] a $C_{3-5}$ cycloalkyl group which may be substituted by [1] a cyano or [2] a $C_{1-6}$ alkyl group,
[8B-4] a 4- to 6-membered heterocycloalkyl group which may be substituted by 1-8 $R^{8B2}$ substituent(s),
[8B-5] a $C_{1-5}$ alkoxy group which may be substituted by 1-2 substituent(s) selected from the group consisting of [1] a $C_{1-3}$ alkoxy group and [2] a $C_{3-6}$ cycloalkyl group,
[8B-6] a $C_{1-3}$ alkylsulfonyl group,
[8B-7] a cyano,
[8B-8] a $C_{1-6}$ alkanoyl group which may be substituted by a $R^{8B3}$ substituent,
[8B-9] a $C_{3-5}$ cycloalkylcarbonyl group,
[8B-10] a $(C_{1-3}$ alkyl)$_{m8c}$-aminosulfonyl group (m8c:1-2),
[8B-11] a $C_{1-3}$ alkylsulfonyl $(C_{0-3}$ alkyl) amino group,
[8B-12] a $(C_{1-5}$ alkyl)$_{m8d}$-amino group (m8d:0-1) which may be substituted by 1-2 $R^{8B4}$ substituent(s),
[8B-13] a hydroxy, or
[8B-14] a $(C_{1-3}$ alkyl)$_{m8e}$-aminocarbonyl group (m8e:0-1).

$R^{8B1}$ is preferably
[8B1-1] a $C_{3-6}$ cycloalkyl group,
[8B1-2] a hydroxy,
[8B1-3] a $C_{1-8}$ alkoxy group which may be substituted by 1-2 $C_{1-5}$ alkoxy group(s), or
[8B1-4] a cyano,
More preferably
[8B1-1] a $C_{3-5}$ cycloalkyl group,
[8B1-2] a hydroxy,
[8B1-3] a $C_{1-8}$ alkoxy group which may be substituted by 1 $C_{1-3}$ alkoxy group, or
[8B1-4] a cyano,
$R^{8B2}$ is preferably
[8B2-1] a halogen atom,
[8B2-2] a $C_{1-6}$ alkyl group,
[8B2-3] an oxo,
[8B2-4] a hydroxy, or
[8B2-5] a deuterium atom,
more preferably
[8B2-1] a fluorine atom,
[8B2-2] a $C_{1-3}$ alkyl group,
[8B2-3] an oxo, or
[8B2-4] a hydroxyl.
$R^{8B3}$ is preferably
[8B3-1] a $(C_{1-6}$ alkyl)$_{m8f}$-amino group (m8f:0-2),
more preferably
[8B3-1] a $(C_{1-3}$ alkyl)$_{m8f}$-amino group (m8f: 2).
$R^{8B4}$ is preferably
[8B4-1] a $C_{3-6}$ cycloalkyl group, or
[8B4-2] a hydroxy;
$R^{8C}$ is preferably
[8C-1] a hydroxyl,
[8C-2] a $(C_{1-3}$ alkyl)$_{m8h}$-amino group (m8h:0-1) which may be substituted by a $(C_{1-3}$ alkyl)$_{m8i}$-aminosulfonyl group (m8i:0-2),
[8C-3] a $C_{1-3}$ alkylsulfonyl group,
$R^{8D}$ is preferably
[8D-1] a $C_{1-6}$ alkyl group which may be substituted by a $R^{8D1}$ substituent,
[8D-2] a hydroxy group,
[8D-3] a $C_{1-3}$ alkylsulfonyl group, or
[8D-4] a $C_{1-4}$ alkoxycarbonyl group;
$R^{8D1}$ is preferably
[8D1-1] a hydroxy group, or
[8D1-2] a $C_{1-3}$ alkoxy group;
$R^{8H}$ is preferably
[8H-1] a 4- to 6-membered heterocycloalkyl group,
$R^{8E}$ is preferably
[8E-1] a hydroxy group,
[8E-2] a $C_{1-8}$ alkoxy group which may be substituted by 1-2 $R^{8E7}$ substituent(s),
[8E-3] a $C_{1-3}$ alkylsulfonyl group,
[8E-4] a $C_{1-4}$ alkoxycarbonyl group,
[8E-5] a 4- to 6-membered nitrogen-containing heterocycloalkylcarbonyl group which may be substituted by 1-2 $R^{8E1}$ substituent(s),
[8E-6] a $(C_{1-5}$ alkyl)$_{m8k1}$-amino group (m8k1: 0~2) which may be substituted by a $R^{8E2}$ substituent,
[8E-7] a 4- to 6-membered heterocycloalkyl group which may be substituted by 1-4 $R^{8E3}$ substituent(s),
[8E-8] a 5- to 6-membered heteroaryl group,
[8E-9] a $(C_{1-6}$ alkyl)$_{m8k2}$-aminocarbonyl group (m8k2: 0~2) which may be substituted by 1-2 $R^{8E6}$ substituent(s),
[8E-10] a $C_{1-5}$ alkoxy group which may be substituted by a $R^{8E7}$ substituent,
[8E-11] a $C_{1-3}$ alkylthio group,
[8E-12] a $C_{1-3}$ alkylsulfinyl group,

[8E-13] a $C_{1-5}$ alkylsulfonyl group,
[8E-14] a $C_{1-3}$ alkylsulfonyl ($C_{0-8}$ alkyl) amino group,
[8E-15] a 4- to 6-membered heterocycloalkylsulfonyl ($C_{0-3}$ alkyl) amino group which may be substituted by 1-3 $C_{1-5}$ alkyl group(s);
more preferably
[8E-1] a ($C_{1-3}$ alkyl)$_{m8k1}$-amino group (m8k1: 2) which may be substituted by one or more $R^{8E2}$,
[8E-2] a $C_{1-8}$ alkoxy group which may be substituted by one or more $R^{8E7}$,
[8E-3] a $C_{1-3}$ alkylsulfonyl group,
[8E-4] a ($C_{1-5}$ alkyl)$_{m8k1}$-amino group (m8k1: 0~2) which may be substituted by a $R^{8E2}$ substituent,
[8E-5] a 4- to 6-membered heterocycloalkyl group which may be substituted by 1-4 $R^{8E3}$ substituent(s),
[8E-6] a 4- to 6-membered heterocycloalkylsulfonylamino group which may be substituted by 1-2 $C_{1-3}$ alkyl group(s);
$R^{8E1}$ is preferably
[8E1-1] a $C_{1-4}$ alkoxycarbonyl group,
[8E1-2] a $C_{1-3}$ alkanoyl group,
[8E1-3] a $C_{1-5}$ alkylsulfonyl group,
[8E1-4] a ($C_{1-3}$ alkyl)$_{m8k3}$-aminosulfonyl group (m8k3: 0~2),
[8E1-5] a 4- to 6-membered heterocycloalkyl group;
$R^{8E2}$ is preferably
[8E2-1] a hydroxy group,
[8E2-2] a $C_{1-6}$ alkoxycarbonyl group,
[8E2-3] a $C_{3-6}$ cycloalkyl group which may be substituted by a $C_{1-8}$ alkyl group which may be substituted by a hydroxy,
[8E1-4] a $C_{1-5}$ alkanoyl group which may be substituted by 1-3 substituent(s) selected from the group consisting of [1] a ($C_{1-3}$ alkyl)$_{m8k4}$-amino group (m8k4: 0~2) and [2] a halogen atom,
[8E2-5] a ($C_{1-3}$ alkyl)$_{m8k5}$-aminocarbonyl group (m8k5: 0~2),
[8E2-6] a $C_{1-3}$ alkylsulfonyl group,
[8E2-7] a ($C_{1-3}$ alkyl)$_{m8k6}$-aminosulfonyl group (m8k6: 0-1) which may be substituted by a $C_{1-4}$ alkoxycarbonyl group.
more preferably
[8E2-1] a hydroxy group.
$R^{8E3}$ is preferably
[8E3-1] a $C_{1-6}$ alkyl group which may be substituted by 1-3 substituent(s) selected from the group consisting of [1] a hydroxy group or [2] a $C_{1-3}$ alkylcarbonyloxy group,
[8E3-2] a $C_{1-4}$ alkylcarbonyloxy group,
[8E3-3] a hydroxy group,
[8E3-4] a $C_{3-5}$ cycloalkyl group,
[8E3-5] a $C_{1-4}$ alkoxycarbonyl group,
[8E3-6] a $C_{1-5}$ alkylsulfonyl group,
[8E3-7] a ($C_{1-3}$ alkyl)$_{m8k8}$-aminocarbonyl group (m8k8: 0~2),
[8E3-8] a $C_{1-3}$ alkanoyl group which may be substituted by a hydroxy,
[8E3-9] an oxo group, or
[8E3-10] a 4- to 6-membered heterocycloalkyl group which may be substituted by 1-3 substituent(s) selected from the group consisting of [1] a $C_{1-3}$ alkanoyl group, [2] a $C_{1-4}$ alkoxycarbonyl group, or [3] a $C_{1-3}$ alkylsulfonyl group;
more preferably
[8E3-1] a ($C_{1-3}$ alkyl)$_{m8k8}$-aminocarbonyl group (m8k8: 0~2), or
[8E3-2] an oxo group;
$R^{8E}4$ is preferably
[8E4-1] a 4- to 6-membered heterocycloalkyl group,
[8E4-2] a $C_{1-3}$ alkanoyl group,
[8E4-3] a $C_{1-3}$ alkoxycarbonyl group,
[8E4-4] a $C_{1-3}$ alkylsulfonyl group,
[8E4-5] a $C_{1-3}$ alkylaminosulfonyl group;
$R^{8E6}$ is preferably
[8E6-1] a $C_{2-3}$ alkenylcarbonyloxy group,
[8E6-2] a hydroxy group,
[8E6-3] a cyano,
[8E6-4] a ($C_{1-3}$ alkyl)$_{m8k9}$-amino group (m8k9: 0~2) which may be substituted by 1-2 hydroxy group(s),
[8E6-5] a $C_{1-3}$ alkoxy group which may be substituted by a hydroxy,
[8E6-6] a $C_{1-4}$ alkylcarbonyloxy group,
[8E6-7] a 4- to 6-membered heterocycloalkyl group which may be substituted by 1-3 $C_{1-8}$ alkyl group(s),
[8E6-8] a 5- to 6-membered heteroaryl group;
$R^{8E7}$ is preferably
[8E7-1] a hydroxy group,
[8E7-2] a $C_{1-3}$ alkoxy group which may be substituted by a hydroxy;
$R^{8F}$ is preferably
[8F-1] a $C_{1-5}$ alkyl group which may be substituted by 1-3 $R^{8F1}$ substituent(s),
[8F-2] a $C_{3-6}$ cycloalkyl group,
[8F-3] a $C_{1-3}$ alkanoyl group which may be substituted by 1-7 halogen atom(s),
[8F-4] a $C_{1-5}$ alkylcarbonyloxy group,
[8F-5] a $C_{1-5}$ alkoxycarbonyl group,
[8F-6] a 4- to 6-membered heterocycloalkyl group which may be substituted by 1-3 $R^{8F2}$ substituent(s),
[8F-7] a $C_{1-5}$ alkylsulfonyl group, or
[8F-8] a hydroxy group;
More preferably
[8F-1] a $C_{1-3}$ alkyl group which may be substituted by a $R^{8F1}$ substituent,]
[8F-2] a $C_{3-5}$ cycloalkyl group,
[8F-3] a 4- to 6-membered heterocycloalkyl group which may be substituted by a $R^{8F2}$ substituent,
[8F-4] a $C_{1-3}$ alkylsulfonyl group,
$R^{8F1}$ is preferably
[8F1-1] a hydroxy group,
[8F1-2] a $C_{1-5}$ alkoxy group, or
[8F1-3] a halogen atom;
$R^{8F2}$ is preferably
[8F2-1] a 4- to 6-membered heterocycloalkyl group,
[8F2-2] a $C_{1-5}$ alkoxycarbonyl group, or
[8F2-3] a $C_{1-3}$ alkylsulfonyl group,
$R^{8G}$ is preferably
[8G-1] a hydroxycarbonyl group,
[8G-2] a hydroxy group, or
[8G-3] a ($C_{1-5}$ alkyl)$_{m8l3}$-amino group (m8l3: 0~2),
$R^9$ is preferably
[1] a hydrogen atom,
[2] a $C_{1-8}$ alkyl group which may be substituted by 1-8 $R^{9A}$ substituent(s),
[3] a C2-6 alkenyl group,
[4] a $C_{2-8}$ alkynyl group which may be substituted by 1-6 $R^9$ substituent(s),
[5] a $C_{3-6}$ cycloalkyl group,
[6] a 4- to 6-membered heterocycloalkyl group which may be substituted by 1-5 $R^{9D}$ substituent(s),
[7] a $C_6$ aryl group which may be substituted by 1-2 $R^{9E}$ substituent(s),
[8] a 5- to 6-membered heteroaryl group which may be substituted by 1-3 $C_{1-5}$ alkyl group(s),
[9] a cyano,
[10] a $C_{1-6}$ alkanoyl group,
[11] a 4- to 6-membered nitrogen-containing heterocycloalkylcarbonyl group which may be substituted by a $C_{1-5}$ alkyl group,

[12] a halogen atom,
[13] a $(C_{1-4}$ alkyl$)_{m9c}$-amino group (m9c: 0~2) which may be substituted by a $R^{9F}$ substituent,
[14] a hydroxy,
[15] a $C_{1-6}$ alkoxy group which may be substituted by 1-5 $R^{9G}$ substituent(s),
[16] a 4- to 6-membered heterocycloalkyloxy group which may be substituted by one or two 4- to 6-membered heterocycloalkyl group(s),
[17] a $C_{1-5}$ alkylthio group which may be substituted by $(C_{1-3}$ alkyl$)_{m9f}$-amino group(s) (m9f: 0~2),
[18] a $C_{1-5}$ alkylsulfonyl group which may be substituted by $(C_{1-3}$ alkyl$)_{m9g}$-amino group(s) (m9g: 0~2),
[19] a $(C_{1-3}$ alkyl$)_{m9h}$-aminosulfonyl group (m9h: 0~2),
[20] a 4- to 6-membered nitrogen-containing heterocycloalkylsulfonyl group which may be substituted by a $C_{1-3}$ alkyl group;
More preferably
[1] a hydrogen atom,
[2] a $C_{1-6}$ alkyl group which may be substituted by a $R^{9A}$ substituent,
[3] a $C_{2-5}$ alkenyl group,
[4] a $C_{2-8}$ alkynyl group which may be substituted by a $R^{9C}$ substituent,
[5] a $C_{3-6}$ cycloalkyl group,
[6] a 4- to 6-membered heterocycloalkyl group which may be substituted by a $R^{9D}$ substituent,
[7] a 5- to 6-membered heteroaryl group which may be substituted by a $C_{1-5}$ alkyl group,
[8] a cyano,
[9] a $C_{1-3}$ alkanoyl group,
[10] a halogen atom,
[11] a (C1-4 alkyl$)_{m9b}$-n amino group (m9b: 0),
[12] a hydroxy,
[13] a $C_{1-6}$ alkoxy group which may be substituted by 1-3 $R^{9G}$ substituent(s),
[14] a 4- to 6-membered heterocycloalkyloxy group which may be substituted by a 4- to 6-membered heterocycloalkyl group,
Even more preferably
[1] a hydrogen atom,
[2] a $C_{1-8}$ alkyl group which may be substituted by one or more $R^{9A}$ substituent(s),
[3] a $C_{2-8}$ alkenyl group which may be substituted by one or more $R^{9B}$ substituent(s),
[4] a $C_{2-8}$ alkynyl group which may be substituted by one or more $R^{9C}$ substituent(s),
[5] a $C_{3-8}$ cycloalkyl group,
[6] a halogen atom,
Still more preferably
[1] a hydrogen atom,
[2] a $C_{1-8}$ alkyl group which may be substituted by one or more $R^{9A}$ substituent(s),
[3] a $C_{2-8}$ alkynyl group which may be substituted by one or more $R^{9C}$ substituent(s).
$R^{9A}$ is preferably
[9A-1] a $C_{3-6}$ cycloalkyl group,
[9A-2] a 4- to 6-membered heterocycloalkyl group which may be substituted by 1-3 $R^{9A1}$ substituent(s),
[9A-3] a hydroxy group, or
[9A-4] a $C_{1-6}$ alkoxy group,
More preferably
[9A-1] a 4- to 6-membered heterocycloalkyl group which may be substituted by a $R^{9A1}$ substituent,
[9A-2] a hydroxy group, or
[9A-3] a $C_{1-3}$ alkoxy group, $R^{9A1}$ is preferably
[9A1-1] a $C_{1-5}$ alkyl group,
[9A1-2] a $C_{3-5}$ cycloalkyl group, or
[9A1-3] a 4- to 6-membered heterocycloalkyl group, More preferably
[9A1-1] a $C_{1-3}$ alkyl group,
[9A1-2] a $C_3$ cycloalkyl group, or
[9A1-3] a 4-membered heterocycloalkyl group,
$R^{9C}$ is preferably
[9C-1] a $C_{1-8}$ alkoxy group,
[9C-2] a $(C_{1-5}$ alkyl$)_{m9b}$-amino group (m9b: 0~2) which may be substituted by 1-2 $C_6$ aryl group(s),
[9C-3] a 4- to 6-membered heterocycloalkyl group which may be substituted by 1-3 $R^{9C1}$ substituent(s),
[9C-4] a $C_{3-6}$ cycloalkyl group,
[9C-5] a hydroxy group, or
[9C-6] a hydroxycarbonyl group;
More preferably
[9C-1] a $C_{1-5}$ alkoxy group,
[9C-2] a $(C_{1-3}$ alkyl$)_{m9b}$-amino group (m9b: 2) which may be substituted by 1-2 $C_6$ aryl group(s),
[9C-3] a 4- to 6-membered heterocycloalkyl group which may be substituted by 1-2 $R^{9C1}$ substituent(s),
[9C-4] a $C_{3-5}$ cycloalkyl group,
[9C-5] a hydroxy group.
$R^{9C1}$ is preferably
[9C1-1] a $C_{3-5}$ cycloalkyl group,
[9C1-2] a 4- to 6-membered heterocycloalkyl group, or
[9C1-3] an oxo group,
More preferably
[9C1-1] a C3 cycloalkyl group,
[9C1-2] a 4- to 6-membered heterocycloalkyl group, or
[9C1-3] an oxo group,
$R^{9D}$ is preferably
[9D-1] a $C_{1-5}$ alkyl group which may be substituted by one or two 4- to 6-membered heterocycloalkyl group(s),
[9D-2] a $C_{3-5}$ cycloalkyl group,
[9D-3] a 4- to 6-membered heterocycloalkyl group, or
[9D-4] a $C_{1-3}$ alkylsulfonyl group;
More preferably
[9D-1] a $C_{1-5}$ alkyl group which may be substituted by a 4- to 6-membered heterocycloalkyl group,
[9D-2] a 4- to 6-membered heterocycloalkyl group, or
[9D-3] a methylsulfonyl group;
$R^{9E}$ is preferably
[9E-1] a halogen atom,
[9E-2] a hydroxy group,
[9E-3] a hydroxycarbonyl group, or
[9E-4] a $C_{1-3}$ alkyl group which may be substituted by a hydroxy;
$R^{9F}$ is preferably
[9F-1] a $C_{1-3}$ alkylsulfonyl group,
[9F-2] a $(C_{1-3}$ alkyl$)_{m9f1}$-aminosulfonyl group (m9f1: 0~2), or
[9F-3] a $C_{1-3}$ alkanoyl group which may be substituted by $(C_{1-3}$ alkyl$)_{m9f2}$-amino group(s) (m9f2: 0~2),
$R^{9G}$ is preferably
[9G-1] a hydroxy group,
[9G-2] a hydroxycarbonyl group,
[9G-3] a $C_6$ aryl group which may be substituted by $C_{1-3}$ alkoxy group(s),
[9G-4] a $(C_{1-3}$ alkyl$)_{m9g1}$-amino group (m9g1: 0~2),
[9G-5] a $C_{1-5}$ alkoxy group which may be substituted by 1-3 $R^{9G1}$ substituent(s), or
[9G-6] a 5- to 6-membered heteroaryl group;
More preferably
[9G-1] a hydroxy group,
[9G-2] a $(C_{1-3}$ alkyl$)_{m9g1}$-amino group (m9g1: 0~2),

[9G-3] a $C_{1-3}$ alkoxy group which may be substituted by a $R^{9G1}$ substituent, or

[9G-4] a 5- to 6-membered heteroaryl group;

$R^{9G1}$ is preferably

[9G1-1] a $C_{1-3}$ alkoxy group, or

[9G1-2] a hydroxycarbonyl group.

Preferably, $A^5$ is NH, while the remaining are C, $R^3$ is a cyano group, $R^6$ and $R^{6'}$ are methyl, $R^8$ is (1) a hydrogen atom, (2) a $C_{1-8}$ alkyl group which may be substituted by one or more $R^{8A}$, (3) a $C_{2-8}$ alkenyl group, (4) a 4- to 10-membered heterocycloalkyl group which may be substituted by one or more $R^{8B}$, (5) a 5- to 14-membered heteroaryl group which may be substituted by a $C_{1-8}$ alkyl group, (6) a $(C_{1-8}$ alkyl$)_{m8g}$-aminocarbonyl group which may be substituted by one or more $R^{8C}$, (7) a 4- to 10-membered nitrogen-containing heterocycloalkylcarbonyl group which may be substituted by one or more $R^{8D}$, (8) a hydroxycarbonyl group, (9) a $C_{0-8}$ alkoxy ($C_{0-8}$ alkyl) aminocarbonyl group which may be substituted by one or more hydroxy group(s), (10) a halogen atom, (11) a hydroxy group, (12) a $C_{1-8}$ alkoxy group which may be substituted by one or more $R^{8B}$, (13) a 4- to 10-membered heterocycloalkyloxy group which may be substituted by one or more $R^{8F}$, (14) an aminosulfonyloxy group which may be substituted by one or more $C_{1-8}$ alkyl group(s), (15) a $C_{1-8}$ alkyl thio group which may be substituted by a $(C_{1-8}$ alkyl$)_n$-amino group, or (16) a $C_{1-8}$ alkylsulfonyl group which may be substituted by $R^{8G}$, $R^9$ is (1) a hydrogen atom, (2) a $C_{1-8}$ alkyl group which may be substituted by one or more $R^{9A}$, (3) a $C_{2-8}$ alkenyl group which may be substituted by one or more $R^{9B}$, (4) a $C_{2-8}$ alkynyl group which may be substituted by one or more $R^{9C}$, (5) a $C_{3-8}$ cycloalkyl group, (6) a 4- to 10-membered heterocycloalkyl group which may be substituted by one or more $R^{9D}$, (7) a $C_{6-10}$ aryl group which may be substituted by one or more $R^{9B}$, (8) a 5- to 14-membered heteroaryl group which may be substituted by a $C_{1-8}$ alkyl group, (9) a cyano group, (10) a $C_{1-8}$ alkanoyl group, (11) a 4- to 10-membered nitrogen-containing heterocycloalkylcarbonyl group which may be substituted by a $C_{1-8}$ alkyl group, (12) a halogen atom, (13) a $(C_{1-8}$ alkyl$)_{m9e}$-amino group which may be substituted by one or more $R^{9F}$, (14) a $C_{1-8}$ alkylsulfonylamino group, (15) a nitro group, (16) a hydroxy group, (17) a $C_{1-8}$ alkoxy group which may be substituted by one or more $R^{9G}$, (18) a $C_{1-8}$ alkyl thio group which may be substituted by a $(C_{1-8}$ alkyl$)_{m9f}$-amino group, (19) a $C_{1-8}$ alkylsulfonyl group which may be substituted by a $(C_{1-8}$ alkyl$)_{m9g}$-amino group, (20) a $(C_{1-8}$ alkyl$)_{m9h}$-aminosulfonyl group, or (21) a 4- to 10-membered nitrogen-containing heterocycloalkylsulfonyl group which may be substituted by a $C_{1-8}$ alkyl group, and $R^1$, $R^2$, $R^5$, $R^7$ and $R^{16}$ are defined above.

More preferably, $A^5$ is NH while the remaining are C, $R^3$ is a cyano group, $R^6$ and $R^{6'}$ are methyl groups, $R^8$ is (1) a hydrogen atom, (2) a $C_{1-8}$ alkyl group which may be substituted by one or more $R^{8A}$, (3) a 4- to 10-membered heterocycloalkyl group which may be substituted by one or more $R^{8B}$, or (4) a $C_{1-8}$ alkoxy group which may be substituted by one or more $R^{8E}$, R9 is (1) a hydrogen atom, (2) a $C_{1-8}$ alkyl group which may be substituted by one or more $R^{9A}$, (3) a $C_{2-8}$ alkynyl group which may be substituted by one or more $R^{9G}$, (4) a $C_{3-8}$ cycloalkyl group, or (5) a halogen atom, and $R^1$, $R^2$, $R^5$, $R^7$ and $R^{16}$ are an hydrogen atom.

According to the present invention, examples of the salts of the compounds that are represented by the Formula (I) include hydrochloric acid salt, hydrobromic acid salt, hydriodic acid salt, phosphoric acid salt, phosphonic acid salt, sulfuric acid salt, sulfonic acid salt such as methanesulfonic acid salt, p-toluene sulfonic acid salt and the like, carboxylic acid salt such as acetic acid salt, citric acid salt, malic acid salt, tartaric acid salt, succinic acid salt, salicylic acid salt and the like, or alkali metal salt such as sodium salt, potassium salt and the like, alkaline earth metal salt such as magnesium salt, calcium salt and the like, ammonium salt such as ammonium salt, alkyl ammonium salt, dialkyl ammonium salt and trialkyl ammonium salt tetraalkyl ammonium salt. Preferably, the salts are pharmaceutically acceptable salts. These salts are produced by brining the compounds described above in contact with an acid or a base which can be used for the production of a pharmaceutical product.

According to the present invention, the compounds that are represented by the Formula (I) or salts thereof can be an anhydride or a solvate such as a hydrate and the like. Herein, the term "solvate (d)" indicates a phenomenon by which solute molecules or ions contained in a solution strongly attract neighboring solvent molecules to form a huge group of molecules. When the solvent is water, it is called "hydrate (d)." The solvate can be any one of a hydrate and a non-hydrate. Preferably, the solvates are pharmaceutically acceptable solvates. For the non-hydrate, alcohol (for example, methanol, ethanol, n-propanol), dimethylformamide and the like can be used.

The compounds of the present invention and salts thereof may be present in several tautomer forms, for example, enol and imine form, keto and enamine form, and a mixture thereof. In a solution, a tautomer is present as a mixture of tautomeric set. In case of solid form, one type of tautomer is generally present in dominant ratio. In this regard, even if only one type of tautomer is described, the present invention includes all types of tautomer of the compounds of the present invention.

The present invention includes all types of stereoisomer of the compounds of the present invention that are represented by the Formula (I) (for example, enantiomer, diastereomer (including cis and trans geometric isomer)), racemate of the isomer and a mixture thereof. For example, the compounds having the Formula (I) of the present invention may have one or more asymmetric center, and the present invention includes a racemic mixture, a diastereomer mixture and enantiomer of such compound.

When the compounds of the present invention are obtained in free form, they can be converted into a salt, a hydrate or solvate thereof which can be formed from the compounds according to a method generally known in the art.

Further, when the compounds of the present invention are obtained in the form of a salt, hydrate or solvate of the compounds, they can be converted to free form according to a method generally known in the art.

The present invention include all isotopes of compounds that are represented by the Formula (I). The isotopes of the compounds of the present invention indicate the compounds of the present invention in which at least one atom is substituted by an atom with the same atomic number (i.e., number of protons) but with different mass number (sum of the number of protons and the number of neutrons). Example of the isotopes that are included in the compounds of the present invention includes a hydrogen atom, a carbon atom, a nitrogen atom, an oxygen atom, a phosphorus atom, a sulfur atom, a fluorine atom, a chlorine atom and the like, and $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$ and the like are included. In particular, a radioisotope which decays by emitting radiation, for example $^3$H and $^{14}$C, are useful for determining the distribution of a pharmaceutical agent or a compound in a living tissue, etc. On the other hand, a stable isotope does not degrade and remains in almost the same amount without exhibiting radioactivity, and therefore can be safely used. Isotopes of the compounds of the present invention can be converted by replacing a chemical reagent used for synthesis with a chemical reagent comprising a corresponding radioisotope according to a method generally known in the art.

Further, the compounds (I) of the present invention can be administered in the form of prodrug. Herein, the term "prodrug" indicates the derivatives of the compounds having the Formula (I) that can be converted to the compounds having the Formula (I) or salts or solvates thereof after administration by enzymatic or non-enzymatic degradation under a physiological condition. The prodrug can be in inactive form when it is administered to a patient. However, in organisms, it converts to the compounds having the Formula (I) and present therein in the active form.

For example, the prodrug converts into desired drug form at specific pH or by an enzymatic action. Conventional prodrug is a compound having a hydrolyzable ester residue which produces a free acid in organisms. Examples of such hydrolyzable ester residue include a residue having a carboxyl moiety of which free hydrogen (for example, a free hydrogen in a carboxyl group when Y in the Formula (I) has a carboxyl group) is replaced by a $C_{1-4}$ alkyl group, a $C_{2-7}$ alkanoyloxymethyl group, a 1-(alkanoyloxy)ethyl group having 4 to 9 carbon atoms, a 1-methyl-1-(alkanoyloxy)-ethyl group having 5 to 10 carbon atoms, an alkoxycarbonyloxymethyl group having 3 to 5 carbon atoms, a 1-(alkoxycarbonyloxy)ethyl group having 4 to 7 carbon atoms, a 1-methyl-1-(alkoxycarbonyloxy)ethyl group having 5 to 8 carbon atoms, a N-(alkoxycarbonyl)aminomethyl having 3 to 9 carbon atoms, a 1-(N-(alkoxycarbonyl)amino)ethyl group having 4 to 10 carbon atoms, a 3-phthalidyl group, a 4-crotonolactonyl group, a γ-butyrolacton-4-yl group, a di-N,N—($C_{1-2}$)alkylamino($C_{2-3}$)alkyl group (for example, N,N-dimethylaminoethyl group), a carbamoyl ($C_{1-2}$)alkyl group, a N,N-di($C_{1-2}$)alkylcarbamoyl-($C_{1-2}$) alkyl group, a piperidino($C_{2-3}$)alkyl group, a pyrrolidino ($C_{2-3}$)alkyl group, or a morpholino($C_{2-3}$) alkyl group, but not limited thereto.

Representative Preparation Method

The compounds having the Formula (I) of the present invention can be produced by the method described below, for example. However, method of preparing the compounds of the present invention is not limited thereto. Further, depending on necessity, order of the reaction step like introduction of a substituent group, etc. can be changed. Although the compounds of the present invention are novel compounds which have not been described in literatures, they can be prepared according to a chemical method that is generally known in the art. Still further, as for the reacting compounds that are used for the preparation, commercially available ones can be used or they can be produced according to a method that is generally known in the art depending on necessity.

In the following reaction schemes showing the reaction step, $A^1$ to $A^{10}$ and $R^1$ to $R^{10}$ are as defined in the Formula (I). $PR^1$ to $PR^{10}$ are the same as $R^1$ to $R^{10}$ that are defined in the Formula (I) or represent a group which can be converted to $R^1$ to $R^{10}$ according to modification or deprotection of a functional group.

Other abbreviated symbols described in the following reaction schemes have the general meanings that can be understood by a skilled person in the art.

PG represents a protecting group (for example, methyl, ethyl, t-butyl, benzyl, substituted benzyl, acetyl, t-butoxycarbonyl, benzyloxycarbonyl, methanesulfonyl, trifluoromethanesulfonyl, trimethylsilyl, triethylsilyl, triisopropylsilyl, t-butyldimethylsilyl, tetrahydropyranyl and the like). In the preparation method described below, when a defined group is subjected to undesirable chemical modification under a condition for implementing the method, the preparation can be carried out by using means such as protection and deprotection of a functional group, etc.

Herein, regarding selection, addition and removal of a protecting group include the methods described in "Protective Groups in Organic Synthesis" (Greene and Wuts, 4$^{th}$ edition, John Wiley & Sons 2007), and they can be suitably employed according to each reaction condition.

LG represents a leaving group such as fluorine, chlorine, bromine, iodine, methanesulfonate, trifluoromethanesulfonate and the like, which can be applied for the reaction described above.

In addition, abbreviated symbols that are typically used to describe the general synthetic method and examples below and names of the chemical reagents and solvents corresponding to the chemical formulae are listed in the following.

9-BBN 9-borabicyclo[3.3.1]nonane
AcOH acetic acid
BINAP 2,2'-bis(diphenylphosphino)-1,1'-binaphthyl
BF$_3$OEt$_2$ trifluoroboron etherate
t-BuOK potassium t-butoxy
n-BuLi n-butyl lithium
t-BuONa sodium t-butoxy
CDI carbonyl diimidazole
CPME c-pentylmethyl ether
DBU 1,8-diazabicyclo[5.4.0]-7-undecene
DCM dichloromethane
DEAD diethyl azodicarboxylate
DDQ 2,3-dichloro-5,6-dicyano-p-benzoquinone
DIPEA N,N-diisopropylethylamine
DMA N,N-dimethylacetamide
DME dimethoxyethane
DMF N,N-dimethyl formamide
DMSO dimethyl sulfoxide
DPPF bis(diphenylphosphino)ferrocene
EDC 1-ethyl-3-(3-dimethylaminopropyl)carbodiimide hydrochloride
EtOAc ethyl acetate
HOBt 1-hydroxybenzotriazole
KHMDS potassium hexamethyldisilazide
LDA lithium diisopropylamide
LiHMDS lithium hexamethyldisilazide
MeCN acetonitrile
MeI methyl iodide
MeOH methanol
MTBE t-butylmethyl ether
NaHMDS sodium hexamethyldisilazide
NMP N-methylpyrrolidone
Pd$_2$(dba)$_3$ tris(dibenzylideneacetone)dipalladium (0)
Pd(OAc)$_2$ palladium acetate
PdCl$_2$(CH$_3$CN)$_2$ dichloro(bisacetonitrile) palladium (II)
PdCl$_2$(PPh$_3$)$_2$ dichlorobis(triphenylphosphine) palladium (II)
Pd(PPh$_3$)$_4$ tetrakis(triphenylphosphine) palladium (0)
P(t-Bu)$_3$ tri t-butylphosphine
PPh$_3$ triphenylphosphine P(o-tol)₃ tri o-tolylphosphine
TEA triethylamine
TEMPO 2,2,6,6-tetramethylpiperidin-1-oxyl
TFA trifluoroacetic acid
TFAA trifluoroacetic anhydride
TFE trifluoroethanol
THF tetrahydrofuran
TMAD 1,1'-azobis(N,N-dimethylformamide)
TMSCl trimethylsilyl chloride
TMSI trimethylsilyl iodide
DavePhos 2-dicyclohexylphosphino-2'-(N,N-dimethylamino)biphenyl
JohnPhos 2-(di-t-butylphosphino)biphenyl
c-Hexyl JohnPhos 2-(dicyclohexylphosphino)biphenyl
S-Phos 2',6'-dimethoxy-2-(dicyclohexylphosphino)biphenyl
X-Phos 2',4',6'-triisopropyl-2-(dicyclohexylphosphino)biphenyl
t-ButylX-Phos 2',4',6'-triisopropyl-2-(di-t-butylphosphino)biphenyl
Xantphos 4,5'-bis(diphenylphosphino)-9,9'-dimethylxanthene Preparation Method I This is one of the methods for producing the compounds of the Formula (I) in which $A^5$ is N and $R^5$ is H.

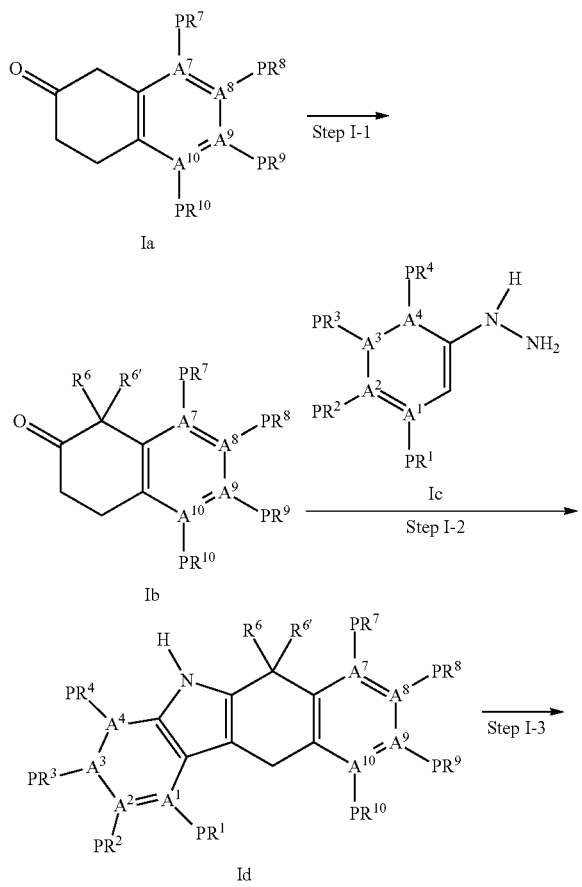

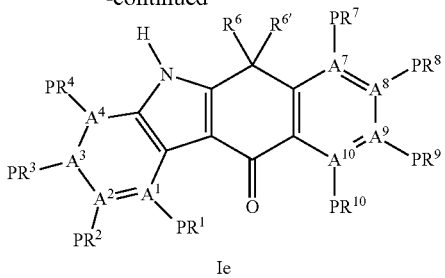

Step I-1

It is an alkylation step of a cyclic ketone derivative Ia. The step can be carried out by reacting cyclic ketone derivative Ia with an alkylating agent corresponding to $R^6$ and $R^{6'}$ in the presence of a base. For example, it can be carried out in view of the method described in Journal of the American Chemical Society, 115(23), 10628-36; 1993 and Organic Letters, 9(24), 5027-5029; 2007, etc. The reaction is carried out in a solvent under the condition of a reaction temperature of −20° C. to boiling point of the solvent, in the presence or the absence of a catalyst. When $R^6$ and $R^{6'}$ are atomic groups other than a hydrogen atom, the reaction order can be optionally selected, and separation and purification can be carried out at each step or the reaction can be carried out continuously.

As for the alkylating agent, examples thereof include an alkyl halide such as MeI, ethyl iodide, 2-iodopropane, 1,4-dibromobutane, 1,1'-oxybis(2-bromoethane) and the like, dimethyl sulfate, and sulfonic acid ester such as methylmethanesulfonate, methyl tosylate and methyltrifluoromethanesulfonate. Preferably, it is an alkyl halide such as MeI and the like. As for the catalyst, examples thereof include a phase transfer catalyst such as tetrabutylammonium chloride and tetrabutylammonium hydrogen sulfate. Preferably, it is tetrabutylammonium hydrogen sulfate. As for the base, examples thereof include an inorganic base such as sodium hydroxide, potassium hydroxide, sodium carbonate, potassium carbonate, cesium carbonate, sodium hydride, potassium hydride, calcium hydride and the like or an organic base such as t-BuOK, t-BuONa, pyridine, TEA, DIPEA, LDA, LiHMDS and n-BuLi. Preferably, it is potassium hydroxide, potassium t-butoxy, or sodium t-butoxy. As for the solvent, examples thereof include toluene, xylene, n-hexane, cyclohexane, DMF, DMA, EtOAc, DMSO, dichloromethane, carbon tetrachloride, THF, dioxane, acetonitrile, water, methanol, ethanol and a mixture thereof. Preferably, it is a mixture solvent of water-THF or THF.

Step I-2

It is the synthesis of carbazole skeleton Id according to Fischer method. This step is generally carried out by using cyclic ketone Ib in the presence of hydrazine compound Ic and an acid in a solvent or by using an acid as a solvent under the condition of a reaction temperature of 0° C. to boiling point of the solvent, and also can be carried out in view of the method described in Journal of Heterocyclic Chemistry, 28(2), 321-3; 1991 and Bioorganic & Medicinal Chemistry Letters (2008), 18(24), 6479-6481. Further, when the reaction proceeds slowly, a zinc chloride catalyst and the like can be also used in view of the reaction condition disclosed in Organic Letters (2006), 8(3), 367-370. The reaction consists of a step of producing phenyl hydrazone and a step of sigmatropic rearrangement. Separation and purification can be carried out at each step or the reaction can be carried out continuously. Further, according to the structure of aryl hydrazine, which is a reacting material of this reaction step, mixture of a position isomer can be obtained as a reaction product. Such position isomer can be separated from each other or used as a mixture for the next reaction step.

As for the acid used for the reaction, examples thereof include formic acid, acetic acid, methanesulfonic acid, p-toluenesulfonic acid, benzenesulfonic acid, TFA, hydrochloric acid, sulfuric acid and pyridinium p-toluenesulfonate. Preferably, it is acetic acid, sulfuric acid, or TFA. As for the solvent, examples thereof include toluene, xylene, NMP, DMF, DMA, DMSO, sulfolane, dioxane, DME, TFE, diethylene glycol, triethylene glycol and a mixture thereof.

Step I-3

It is a step of oxidation at benzyl at 11-position of carbazole skeleton Id. This step is carried out by applying an oxidizing agent to a substrate in a solvent in the presence or absence of a catalyst under the condition of a reaction temperature of −20° C. to boiling point of the solvent. As for the reaction condition, the method described in Journal of Medicinal Chemistry, 51(13), 3814-3824; 2008, etc. can be considered.

As for the oxidizing agent and the catalyst used for the reaction, DDQ, peracid such as, mCPBA and the like, cerium ammonium nitrate (IV) (CAN), permanganate such as potassium permanganate, barium permanganate and the like, sodium chlorite, hydrogen peroxide, or N-hydroxyphthalimide and the like can be used alone or in a combination thereof. Preferably, it is DDQ or N-hydroxyphthalimide. As for the reaction solvent used for the reaction, examples thereof include water, t-butanol, acetonitrile, THF, dichloromethane, ethyl acetate and a mixture thereof. Preferably, it is THF.

Preparation Method II

It is an exemplary method of producing β-ketoester intermediate IIg, which is used for constructing the skeleton of the compounds that are represented by the Formula (I).

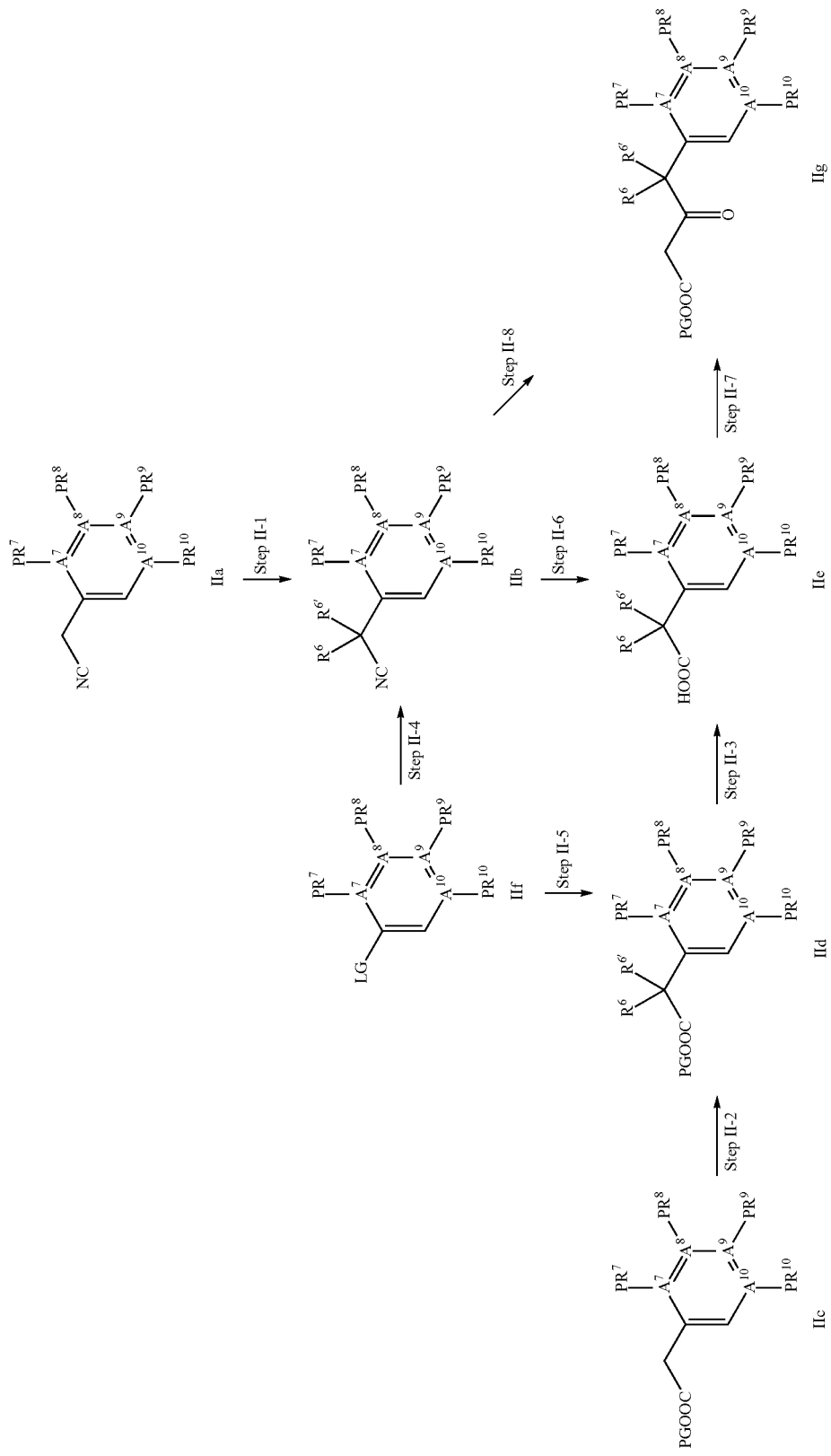

Step II-1, Step II-2

It is an alkylation step at α position of carboxylic acid ester IIc or nitrile IIa. The step can be carried out by reacting with an alkylating agent corresponding to $R^6$ and $R^{6'}$ in a solvent under the condition of a reaction temperature of −20° C. to boiling point of the solvent, in the presence of a base. For example, it can be carried out in view of the method described in J. Org. Chem., 2007, 72 (25), 9541-9549 and European Journal of Organic Chemistry (21), 3449-3462, etc. The reagents and the condition for the reaction are the same as those described for Step I-1.

Step II-3

It is an ester hydrolysis step of carboxylic acid ester IId. This step can be carried out by hydrolysis in an aqueous solvent at the reaction temperature of 0° C. to boiling point of the solvent in the presence of an inorganic base, for example in view of the method described in Tetrahedron Lett. 3529, 1977. Alternatively, it can be carried out according to a method in which hydrolysis is carried out in the presence of an acid, in view of the method described in J. Am. Chem. Soc, 1977, 99, 2353, for example. As for the inorganic base, examples thereof include sodium hydroxide, potassium hydroxide, sodium carbonate, potassium carbonate and cesium carbonate. Preferably, it is sodium hydroxide or potassium hydroxide. As for the solvent, water, methanol, ethanol, tetrahydrofuran, dioxane, and the like can be used alone or in a combination thereof. Preferably, it is methanol comprising water or ethanol comprising water. As for the acid which can be used for acid hydrolysis, hydrochloric acid, sulfuric acid, trifluoroacetic acid and methanesulfonic acid can be used alone in a combination thereof. Preferably, it is sulfuric acid.

Step II-4, Step II-5

It is a direct (hetero)arylation step at α position of carboxylic acid ester or nitrile. This step can be carried out by $S_NAr$ reaction in which carboxylic acid ester or nitrile is reacted with aromatic compound IIf having a leaving group in the presence of a base. It can be carried out in view of the method described in J. Am. Chem. Soc. 2000, 122, 712-713. Alternatively, it can be also carried out according to a method in which carboxylic acid ester or nitrile is reacted with aromatic compound IIf having a leaving group in the presence of a catalyst, a ligand and a base. For example, it can be carried out in view of the method described in Org. Lett, 2008, 10(8), 1545, J. Org. Chem. 2003, 68, 8003 and Angew. Chem. Int. Ed. 2003, 42, 5051, etc.

As for the base used for the reaction, sodium phosphate, potassium phosphate, sodium carbonate, potassium carbonate, cesium carbonate, sodium hydride, LiHMDS, NaHMDS, LDA, lithium dicyclohexylamide, lithium 2,2,6,6-tetramethyl pyrrolidide, KHMDS, t-BuONa, t-BuOK and the like can be used. Preferably, it is NaHMDS, KHMDS, or t-BuONa. As for the catalyst, ligand, or catalyst-ligand complex which are used for the reaction, palladium acetate, $Pd_2(dba)_3$, m-allyl palladium chloride dimer, $PdCl_2(CH_3CN)_2$, trialkylproazaphosphatrane, $\{P(t-Bu)_3PdBr\}_2$, $PPh_3$, $P(o-tol)_3$, BINAP, DPPF, $P(t-Bu)_3$, DavePhos, JohnPhos, c-Hexyl JohnPhos, S-Phos, X-Phos, t-ButylX-Phos, Xantphos, 4,5-bis[bis(3,5-bistrifluoromethylphenyl)phosphanyl]-9,9-dimethyl-9H-xanthene, 1,3-diallyldihydroimidazolium salt and the like can be used, for example. Preferably, it is triisobutylproazaphosphatrane.

Step II-6

It is a step of hydrolyzing nitrile IIb to carboxylic acid. This step can be carried out by hydrolysis in the presence of an acid under the condition of a reaction temperature of 0° C. to boiling point of the solvent, and the reaction conditions include that described in, for example, Tetrahedron, 64(36), 8464-8475; 2008, etc. For the reaction, the acid itself can be used as a solvent or diluted with other solvent. Alternatively, it can be carried out by hydrolysis in the presence of an inorganic base under the condition of a reaction temperature of 0° C. to boiling point of the solvent, and the reaction condition described in, for example, Bioorganic & Medicinal Chemistry Letters, 18(2), 749-754; 2008, etc. can be employed.

The reaction consists of the hydrolysis of nitrile Ith to acid amide and further conversion into carboxylic acid. Separation and purification can be carried out at each step or the reaction can be carried out continuously.

As for the acid which is used for the reaction, examples thereof include methanesulfonic acid, p-toluenesulfonic acid, benzenesulfonic acid, trifluoroacetic acid, hydrochloric acid and sulfuric acid. As for the solvent, examples thereof include toluene, xylene, dioxane, dimethoxyethane, diethylene glycol, triethylene glycol, TFE and the like and a mixture thereof. As for the inorganic base, examples thereof include sodium hydroxide, potassium hydroxide, sodium carbonate, potassium carbonate and cesium carbonate.

Step II-7

It is a step of converting carboxylic acid IIe to β-ketoester. According to this step, the carboxylic acid as a reacting material is converted into an acid chloride, active ester and the like by an action of an activating agent in a solvent under the condition of a reaction temperature of 0° C. to boiling point of the solvent. Thereafter, the acid chloride or active ester is reacted with enolate of malonic acid monoester under the condition of a reaction temperature of 0° C. to boiling point of the solvent to give a target compound through decarboxylation. As for the reaction condition, a method described in J. Chem. Soc. Perkin Trans. 1 1988, 2345-2352 and Synthesis 1993, 290-292 can be used, for example. As for the method of activating carboxylic acid, examples thereof include a method of converting into an acid chloride by using thionyl chloride, oxalyl chloride, phosphorus oxychloride, etc. or a method of converting into an active ester by using CDI. Preferably, thionyl chloride or CDI is used. The activated carboxylic acid itself can be subjected to separation and purification, or can be used continuously for the next reaction. As for the method of producing an enolate of malonic acid monoester, a combination of magnesium salt like magnesium chloride, etc. and malonic acid monoester (and a salt thereof) or a Grignard reagent like i-propyl magnesium chloride, etc. and malonic acid monoester (and a salt thereof), etc. can be used. In order to improve the reaction yield, an organic base such as TEA, DIPEA and the like can be also added to the reaction system. As for the solvent, examples thereof include toluene, xylene, MeCN, THF, CPME, MTBE, NMP, DMF, DMA, DMSO, sulfolane, dioxane, DME, and the like and a mixture thereof. Preferably, it is MeCN, THF or DME.

Step II-8

It is a step of converting nitrile IIB to β-ketoester. This step can be carried out by so-called Blaise reaction in which 2-halo carboxylic acid ester is reacted with nitrile in the presence of activated zinc powder under the condition of a reaction temperature of 0° C. to boiling point of the solvent, and the reaction method described in, for example, SYNTHESIS 2004, No. 16, pp 2629-2632x. can be used. As for the method of activating zinc powder, a method in which acid washing and drying are carried out in advance, or a method in which a catalytic amount of an acid such as methanesulfonic acid, etc. is included in the reaction system can be employed.

Preparation Method III

It is an exemplary method of preparing compound IIIh from intermediate IIg that is obtained from Preparation method II.

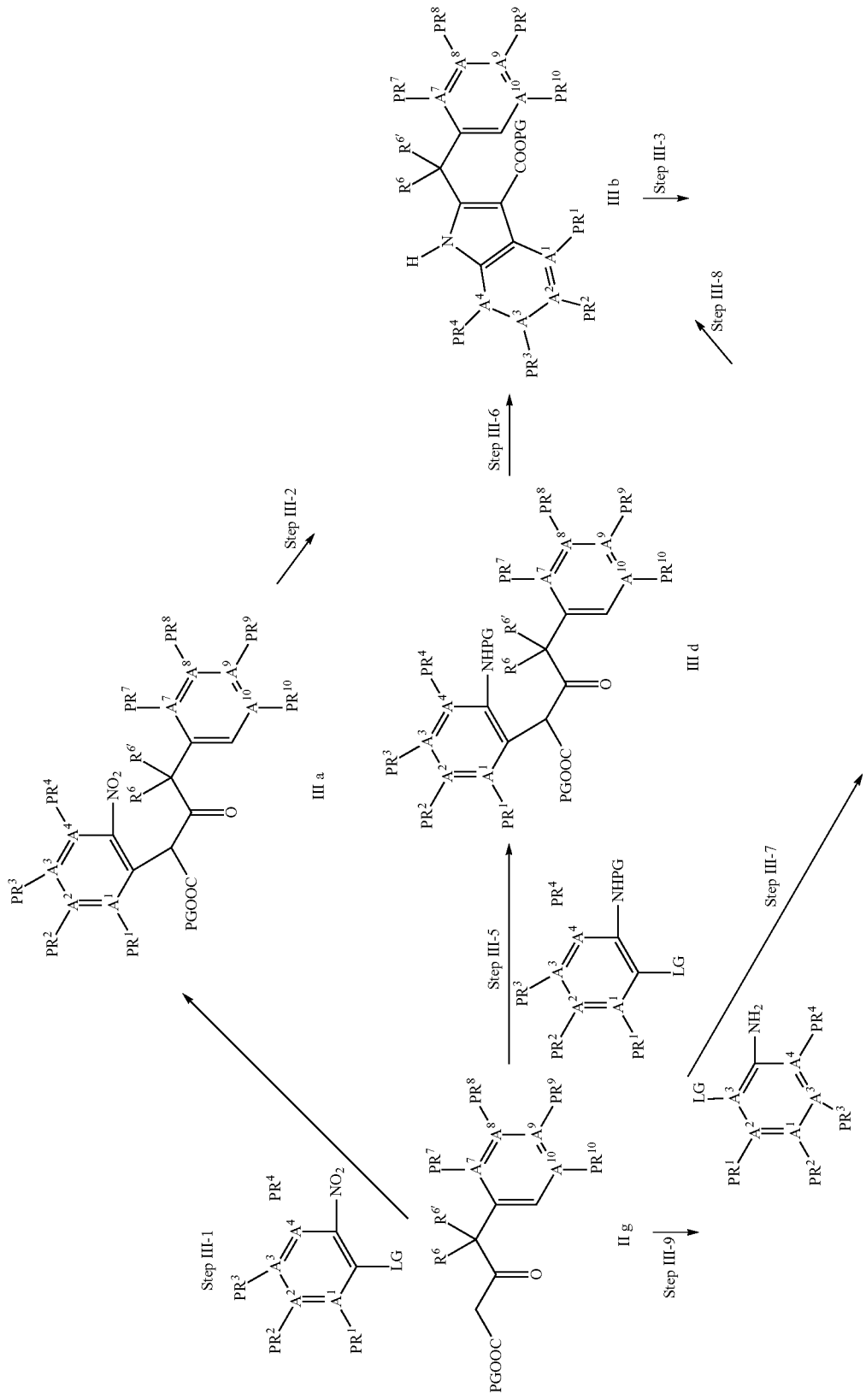

-continued
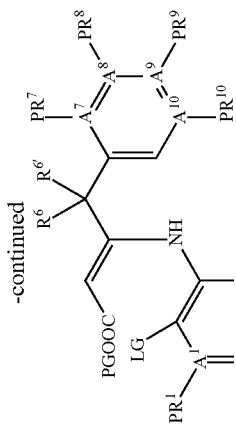
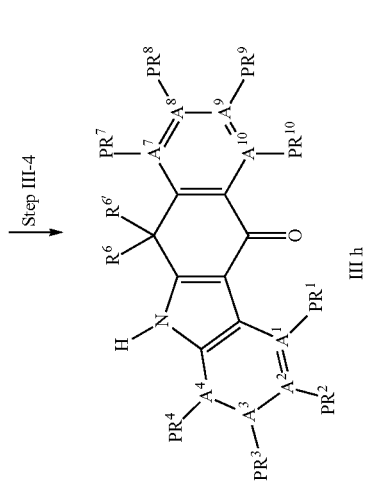
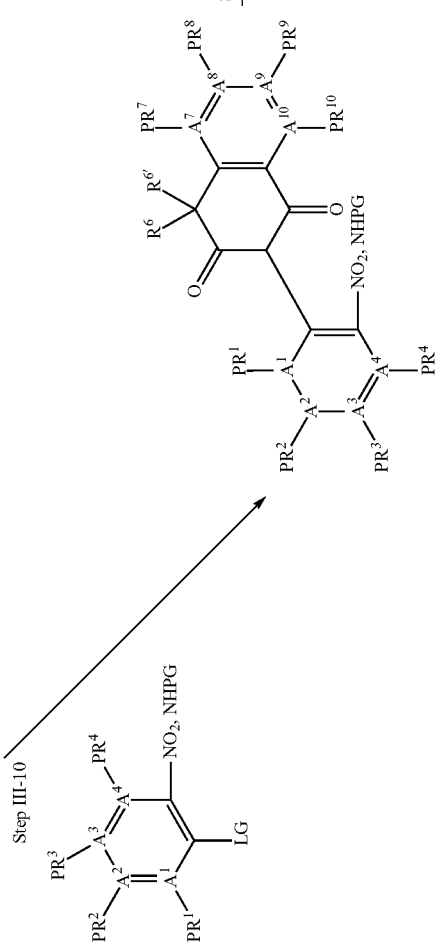
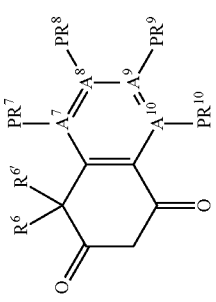

Step III-1

This step can be carried out by nucleophilic aromatic substitution reaction in which an aromatic nitro compound having a leaving group is reacted with β-ketoester IIg in the presence of a base under the condition of a reaction temperature of 0° C. to boiling point of the solvent, and the reaction method include that described in, for example, Synlett, (5), 883-885; 2004 and Tetrahedron, 38(23), 3479-83; 1982.

As for the base used for the reaction, sodium phosphate, potassium phosphate, sodium carbonate, potassium carbonate, cesium carbonate, sodium hydride, LiHMDS, NaHMDS, LDA, lithium dicyclohexylamide, lithium 2,2,6,6-tetramethylpyrrolidide, KHMDS, t-BuOK, t-BuONa and the like can be used. Preferably, it is potassium carbonate, cesium carbonate, t-BuOK, or t-BuONa. As for the solvent, examples thereof include toluene, xylene, MeCN, THF, CPME, MTBE, NMP, DMF, DMA, DMSO, sulfolane, dioxane, DME, acetone, methylethyl ketone, and a mixture thereof. Preferably, it is THF, DMF, DMA, NMP or a mixture thereof.

Further, the present step can be also carried out in the presence of a catalyst and a base, as described in Step III-5 or Journal of Organic Chemistry, 72(14), 5337-5341; 2007.

Step III-2

It is a reductive cyclization step to form an indole ring following the reduction of a nitro group. This reaction can be carried out by reacting β-ketoester IIIa with a reducing agent under the condition of a reaction temperature of 0° C. to boiling point of the solvent to reduce the nitro group. As for the reducing agent used for the reaction, the condition generally used for reduction of a nitro group, for example, iron as exemplified in Synthesis, (18), 2943-2952, 2008, zinc as exemplified in Tetrahedron, 64(40), 9607-9618, 2008, titanium (III) chloride as exemplified in Organic & Biomolecular Chemistry, 3(2), 213-215, 2005, tin (II) chloride as exemplified in Journal of Organic Chemistry, 58(19), 5209-5220, 1993, sodium hydrosulphite as exemplified in Gazzetta Chimica Italiana, 121(11), 499-504, 1991, and catalytic reduction condition as exemplified in Synlett, (17), 2689-2691, 2008, etc. can be employed. Preferably, the reducing agent is iron or sodium hydrosulphite.

Step III-3

It is a step of deprotecting an ester protecting group of indole-3-carboxylic acid ester IIIb. As an example of an ester protecting group, a methyl group, an ethyl group, a t-butyl group, a benzyl group, a substituted benzyl group and the like can be used.

Preferably, it is a t-butyl. As for the deprotection, examples thereof include a method described in "Protective Groups in Organic Synthesis" (Greene and Wuts, 4$^{th}$ edition, John Wiley & Sons 2007), and it can be appropriately used according to each reaction condition. When the ester protecting group is a t-butyl, as a deprotection condition, TMSI, TMSCI, and BF$_3$.OEt$_2$ can be used. As for the solvent, examples thereof include toluene, xylene, diethyl ether, THF, CPME, MTBE, NMP, DMF, DMA, DMSO, sulfolane, dioxane, DME, TFE and the like and a mixture thereof. Preferably, it is THF or TFE.

Step III-4

It is a step of cyclizing indole-3-carboxylic acid IIIc to carbazole based on Friedel-Crafts reaction. According to the reaction, a mixed acid anhydride is formed by using acetic anhydride, trifluoroacetic anhydride and the like, or acid chloride is formed by using thionyl chloride, oxalyl chloride, phosphorus oxychloride and the like, which results in activation of the carboxylic acid. Preferably, acetic anhydride or trifluoroacetic anhydride is used. The reaction is carried out in the absence or presence of a solvent. As for the solvent, examples thereof include toluene, xylene, diethyl ether, THF, CPME, MTBE, NMP, DMF, DMA, DMSO, sulfolane, dioxane, DME and the like and a mixture thereof. Preferably, it is THF, DMF, DMA or DME. Further, an organic base such as TEA, DIPEA, pyridine and the like can be used.

Thereafter, under the condition of a reaction temperature of 0° C. to boiling point of the solvent, the cyclization is carried out without a catalyst or with Bronsted acid or Lewis acid catalyst (Heterocycles 1999, 51, 2127). As for the Lewis acid catalyst, examples thereof include aluminum chloride, aluminum triflate, bismuth triflate, ytterbium triflate and BF$_3$.OEt$_2$. Preferably, it is BF$_3$.OEt$_2$. Depending on the type of a substituent group, it is also possible to carry out the reaction by applying methanesulfonic acid-phosphorus pentoxide (Eaton reagent), polyphosphoric acid and the like to indole-3-carboxylic acid ester IIIb without undergoing Step III-3.

Step III-5, III-6

The step can be carried out by reacting an aromatic acylamide compound having a leaving group with β-ketoester IIg in the presence of a base, a catalyst, and a ligand under the condition of a reaction temperature of 0° C. to boiling point of the solvent, followed by deprotection of an acyl protecting group. Examples thereof include a method described in Journal of Organic Chemistry 2007, 72, 9329-9334 and Organic Letters 10(4), 625-628, 2008. As for the metal catalyst, copper (I) iodide and palladium acetate can be used. As for the ligand, (S)-proline, tri t-butylphosphine, bis(t-butyl) (2'-methyl[1,1'-biphenyl]-2-yl)phosphine and the like can be used. As for the base which is used for the reaction, sodium phosphate, potassium phosphate, sodium carbonate, potassium carbonate, cesium carbonate, sodium hydride, LiHMDS, NaHMDS, LDA, lithium dicyclohexylamide, lithium 2,2,6,6-tetramethylpyrrolidide, potassium hexamethyldisilazide, t-BuONa, t-BuOK and the like can be used.

Step III-7, III-8

It is a step of reacting an aromatic amino compound with β-ketoester IIg to form an enamine intermediate followed by catalytic cyclization. Examples thereof include a method described in Journal of Organic Chemistry, 68(15), 6011-6019; 2003 and European Journal of Organic Chemistry, (24), 3977-3980; 2007.

Alternatively, the cyclization can be carried out based on an oxidative method. For example, a reaction condition described in Angewandte Chemie, International Edition, 47(38), 7230-7233; 2008 can be also employed, for example.

Step III-9

It is a step of synthesizing 1,3-diketone based on cyclization of β-keto ester IIg. As for the condition and reagents for the reaction, a method described in Bioorganic & Medicinal Chemistry Letters, 18(2), 568-570; 2008 wherein β-keto ester IIg is reacted in an solvent in the presence of Bronsted acid catalyst or Lewis acid catalyst, or a method of using a condensing agent such as methanesulfonic acid-phosphorus pentoxide (Eaton reagent), polyphosphoric acid and the like can be employed.

Step III-10, III-11

This step can be carried out in the same manner as Step III-1 and III-2 or Step III-5 and III-6.

Preparation Method IV

An exemplary method of producing compound IIIh wherein formula Iva is employed as a starting material.

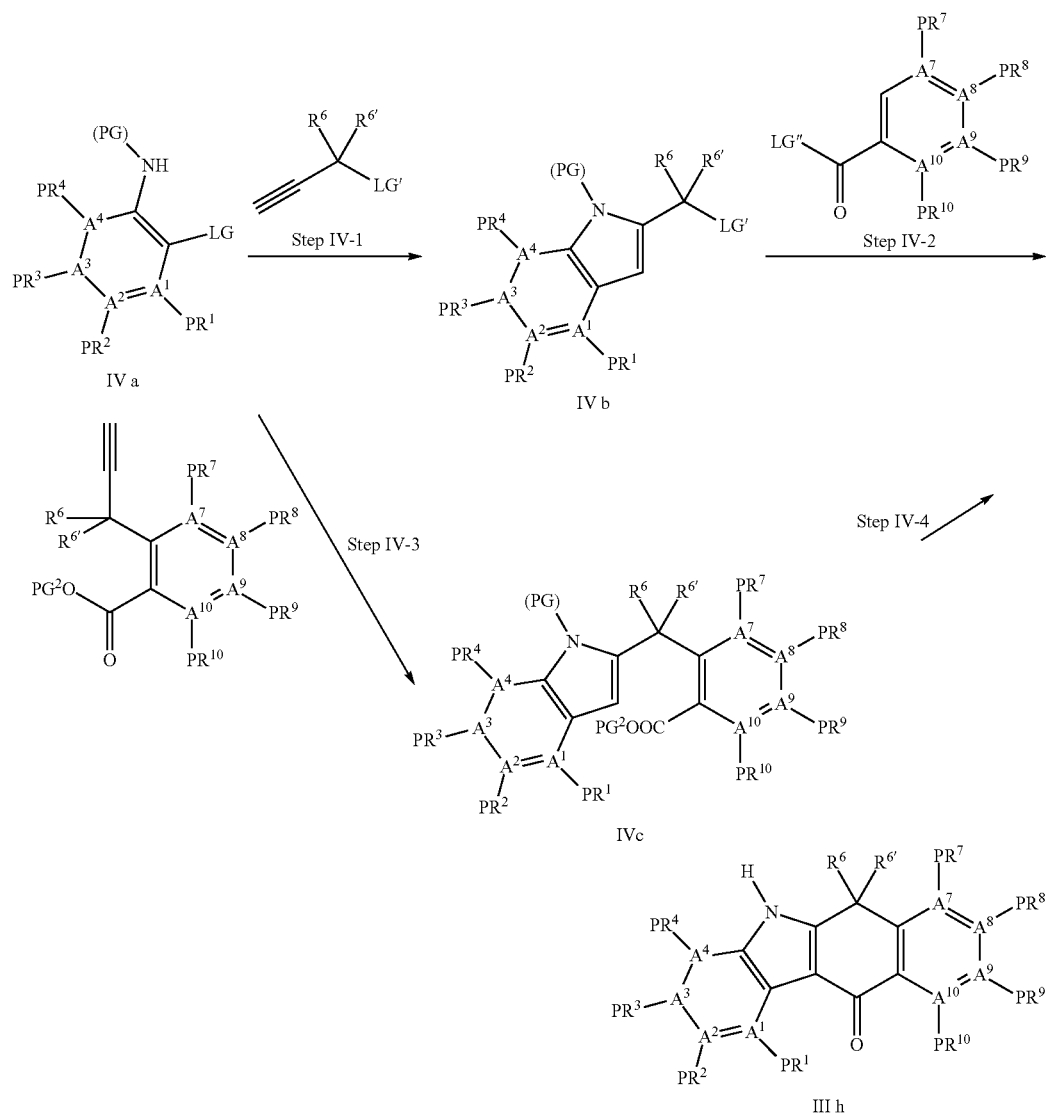

Step IV-1, IV-3

It is a step of constructing di-substituted indole derivatives based on Sonogashira reaction in which a terminal alkyne is reacted with aromatic amine derivative IVa having a leaving group at ortho position in the presence of a base and a catalyst with or without a catalytic amount of a copper reagent. Specifically, examples thereof include a method described in Organic Letters, 11(1), 221-224; 2009. The reaction is carried out in an appropriate solvent in the presence of a palladium catalyst and a ligand (or a complex thereof) with or without a base and a copper catalyst. Example of the copper catalyst used for the reaction include copper iodide. As an example of the catalyst and the ligand (or a complex thereof), palladium acetate, $Pd_2(dba)_3$, π-allyl palladium chloride dimer, $PdCl_2(CH_3CN)_2$, $PdCl_2(PPh_3)_2$, trialkylproazaphosphatrane, $\{P(t-Bu)_3PdBr\}_2$, $PPh_3$, P(o-tol)$_3$, BINAP, DPPF, P(t-Bu)$_3$, DavePhos, JohnPhos, c-Hexyl JohnPhos, S-Phos, X-Phos, t-ButylX-Phos, Xantphos, 4,5-bis[bis(3,5-bistrifluoromethylphenyl)phosphanyl]-9,9-dimethyl-9H-xanthene, 1,3-diallyldihydroimidazolium salt and the like can be used. As for the base used for the reaction, sodium phosphate, potassium phosphate, sodium carbonate, potassium carbonate, cesium carbonate, TEA, DIPEA and the like can be used. Preferably, it is cesium carbonate, TEA or DIPEA.

Step IV-2

This step corresponds to a tandem Friedel-Crafts reaction in which acylation at 3-position of di-substituted indole derivative IVb is carried out in the presence of Lewis acid catalyst under the condition of a reaction temperature of 0° C. to boiling point of the solvent, followed by intramolecular cyclization. As for the catalyst used for the reaction, examples thereof include aluminum chloride, aluminum triflate, bismuth triflate, ytterbium triflate and $BF_3.OEt_2$. Preferably, it is aluminum chloride.

Step IV-4

This step consists of deprotection of carboxylic acid ester comprised in di-substituted indole derivative IVc and subsequent intramolecular cyclization at 3-position of the indole either in catalytic or non-catalytic manner. As for the deprotection, examples thereof include a method described in "Protective Groups in Organic Synthesis" (Greene and Wuts, 4th edition, John Wiley & Sons 2007), and it can be appropriately used according to the type of each protecting group. When an activated indole derivative is used for the reaction, cyclization occurs more easily so that the reaction can be carried out in a non-catalytic manner. Further, the cylclization can be also carried out by using a condensing agent such as polyphosphoric acid, methanesulfonic acid-phosphorus pentoxide (Eaton reagent) and the like. Alternatively, it is also possible that carboxylic acid is first converted into carboxylic acid chloride, a mixed acid anhydride and the like under the same condition as defined in Step III-4 and the cyclization is carried out under Friedel-Crafts condition in the presence of Lewis acid catalyst. As for the Lewis acid catalyst used for the reaction, examples thereof include aluminum chloride, aluminum triflate, bismuth triflate, ytterbium triflate and $BF_3 \cdot OEt_2$.

Preparation Method V

It is one of the methods for constructing the skeleton of the compounds having the Formula (I) in which $A^5$ is O, S or NH.

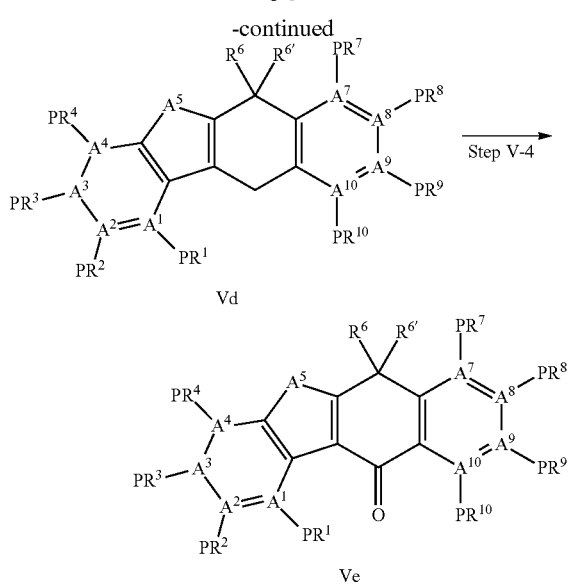

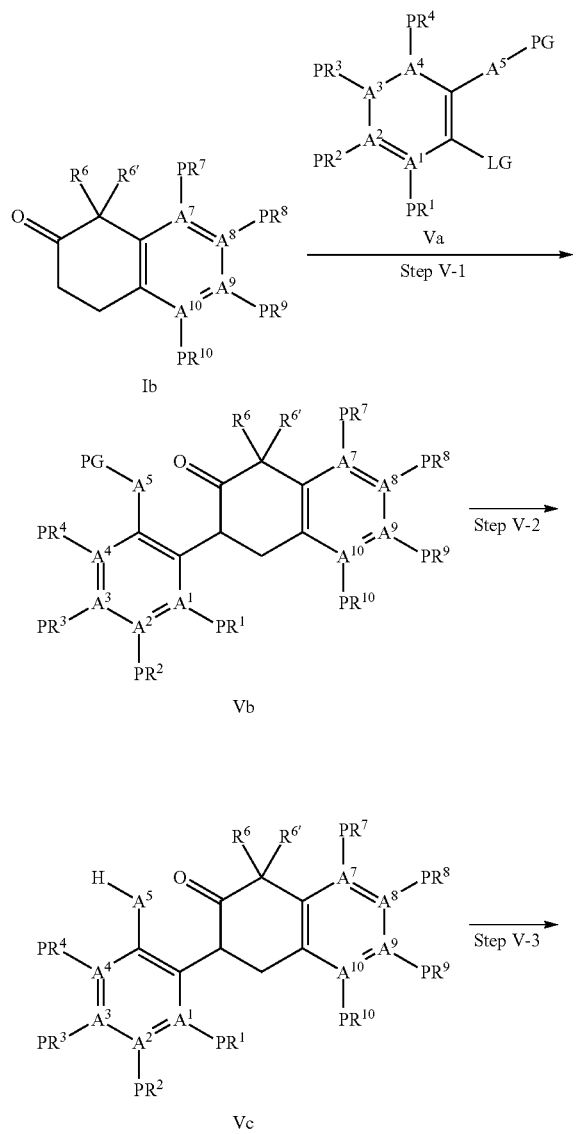

Step V-1

It is a step of arylation of cyclic ketone derivative Ib using aromatic compound Va having a leaving group. The reaction is catalytically carried out in the presence of a base with combination of a transition metal catalyst and a ligand, and the condition described in J. Am. Chem. Soc. 2000, 122, 1360-1370 and Journal of Organic Chemistry (2003), 68(25), 9865-9866 can be used, for example. As for the base used for the reaction, examples thereof include t-BuONa, t-BuOK, LiHMDS, NaHMDS, potassium phosphate, sodium carbonate, potassium carbonate and cesium carbonate. As for the catalyst and a ligand (or a catalyst-ligand complex), palladium acetate, $Pd_2(dba)_3$, m-allylpalladium chloride dimer, $PdCl_2(CH_3CN)_2$, $PdCl_2(PPh_3)_2$, trialkylproazaphosphatrane, $\{P(t-BU)_3PdBr\}_2$, $PPh_3$, $P(o-tol)_3$, BINAP, DPPF, $P(t-Bu)_3$, DavePhos, JohnPhos, c-Hexyl JohnPhos, S-Phos, X-Phos, t-ButylX-Phos, Xantphos, 4,5-bis[bis(3,5-bistrifluoromethylphenyl)phosphanyl]-9,9-dimethyl-9H-xanthene 1,3-diallyldihydroimidazolium salt and the like can be used.

Step V-2

It is a step of deprotecting a protecting group. When $A^5$ is O or S, a t-butyl group, a benzyl group and a substituted benzyl group can be used as a protecting group. When $A^5$ is O, a t-butyldimethylsilyl group and a tetrahydropyranyl group can be used. When it is NH, a t-butoxycarbonyl group, a benzyloxycarbonyl group, a methanesulfonyl group, a trifluoroacetyl group and the like can be used. As for the deprotection, examples thereof include a method described in "Protective Groups in Organic Synthesis" (Greene and Wuts, 4th edition, John Wiley & Sons 2007), and it can be appropriately used according to the type of each protecting group.

Step V-3

It is a cyclization step of cyclic α-aryl ketone derivative Vc to a benzofuran derivative, benzothiophene or indole Vd. The reaction can be carried out under condition of using an acid catalyst or dehydrating condition. For example, the reaction condition described in Acta Pharmaceutica Hungarica (2003), 73(3), 171-178 can be employed. In addition, depending on the type of a protecting group for hydroxyl group, it can be carried out simultaneously with the deprotection of Step V-2, as described in Heterocycles, 26(7), 1863-71; 1987. With respect to the condition for dehydration, a combination of an organic base and an acid anhydride such as trifluoromethanesulfonic acid and the like can be used.

Step V-4

It is a step of oxidation at benzyl at 11-position of tetracyclic compound Vd. This step is carried out by applying an oxidizing agent to a substrate in a solvent in the presence or absence of a catalyst under the condition of a reaction temperature of −20° C. to boiling point of the solvent. As for the reaction condition, the method described in Journal of Medicinal Chemistry, 51(13), 3814-3824; 2008, etc. can be employed.

As for the oxidizing agent and the catalyst used for the reaction, DDQ, peracid such as, mCPBA and the like, cerium ammonium nitrate (IV) (CAN), permanganate such as potassium permanganate, barium permanganate and the like, sodium chlorite, hydrogen peroxide, N-hydroxyphthalimide and the like can be used alone or in a combination thereof. As for the solvent used for the reaction, examples thereof include water, t-butanol, acetonitrile, tetrahydrofuran, dichloromethane, ethyl acetate and a mixture thereof.

Preparation Method VI

It is an exemplary method of constructing the skeleton of the compounds that are represented by the Formula (I) in which $A^5$ is S.

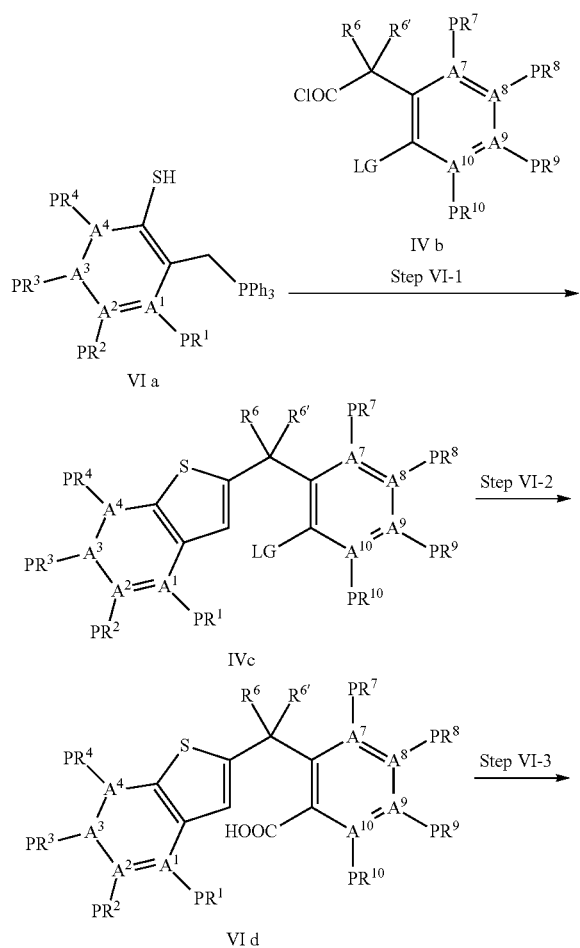

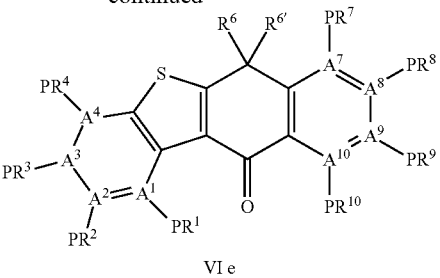

Step VI-1

It is a reaction to construct a benzothiophene ring based on the reaction between ylide VIa having a thiol at ortho position and acyl chloride VIb. The reaction can be carried out in the presence of a base, and the condition include that described in Synthesis, (2), 155-7; 1988, for example. As for the base, examples thereof include n-butyl lithium, sodium methylate and triethylamine.

Step VI-2

It is a reaction for the synthesis of an aromatic carboxylic acid. The reaction can be carried out by metallization like addition of lithium or magnesium based on exchange between halogen and metal in the presence of a base, followed by carboxylation using carbonate gas, dry ice, etc. The reaction condition as described in Journal of Organic Chemistry (2008), 73(19), 7785-7788 can be employed. As for the base, n-butyl lithium, s-butyl lithium, t-butyl lithium, a Grignard reagent, and various ate complexes can be used. Alternatively, as described in e-EROS Encyclopedia of Reagents for Organic Synthesis 2001 (electronic edition; http://www3.interscience.wiley.com/cgi-bin/mrwhome/104554785/HOME), carboxylation condition using a transition metal catalyst can be also employed.

Step VI-3

This step corresponds to intramolecular cyclization at 3-position of di-substituted benzothiophene derivative VId either in catalytic or non-catalytic manner. For example, the reaction condition as described in Journal of the American Chemical Society, 130(23), 7286-7299; 2008 can be employed. The reaction can be carried out by using a condensing agent such as polyphosphoric acid, methanesulfonic acid-phosphorus pentoxide (Eaton reagent) and the like. Alternatively, it is also possible that carboxylic acid is first converted into carboxylic acid chloride, a mixed acid anhydride and the like and the cyclization is carried out under Friedel-Crafts condition in the presence of Lewis acid catalyst. As for the Lewis acid catalyst used for the reaction, examples thereof include aluminum chloride, aluminum triflate, bismuth triflate, ytterbium triflate and $BF_3 \cdot OEt_2$.

Preparation Method VII Conversion and Modification of Functional Groups

To the functional groups $PR^1$ to $PR^{10}$ in the Formula (I) of the present invention, various substituent groups can be introduced based on a method of converting and modifying a functional group that is well known to a skilled person in the pertinent art. Hereinbelow, representative examples of functional group conversion will be explained. Further, although the following reaction scheme is specific in that examples of $PR^8$ and $PR^9$ are given for the tetracyclic compound that is already constructed, it can be also carried out to an intermediate during any steps explained in Preparation methods I to VI above or to a final compound. Further, it can be carried out at any substitution position of $PR^1$ to $PR^4$ and $R^6$ to $PR^{10}$.

In the following formula, $Q^1$ and $Q^2$ represent any substituent group which constitutes $PR^1$ to $PR^4$ and $R^6$ to $PR^{10}$.

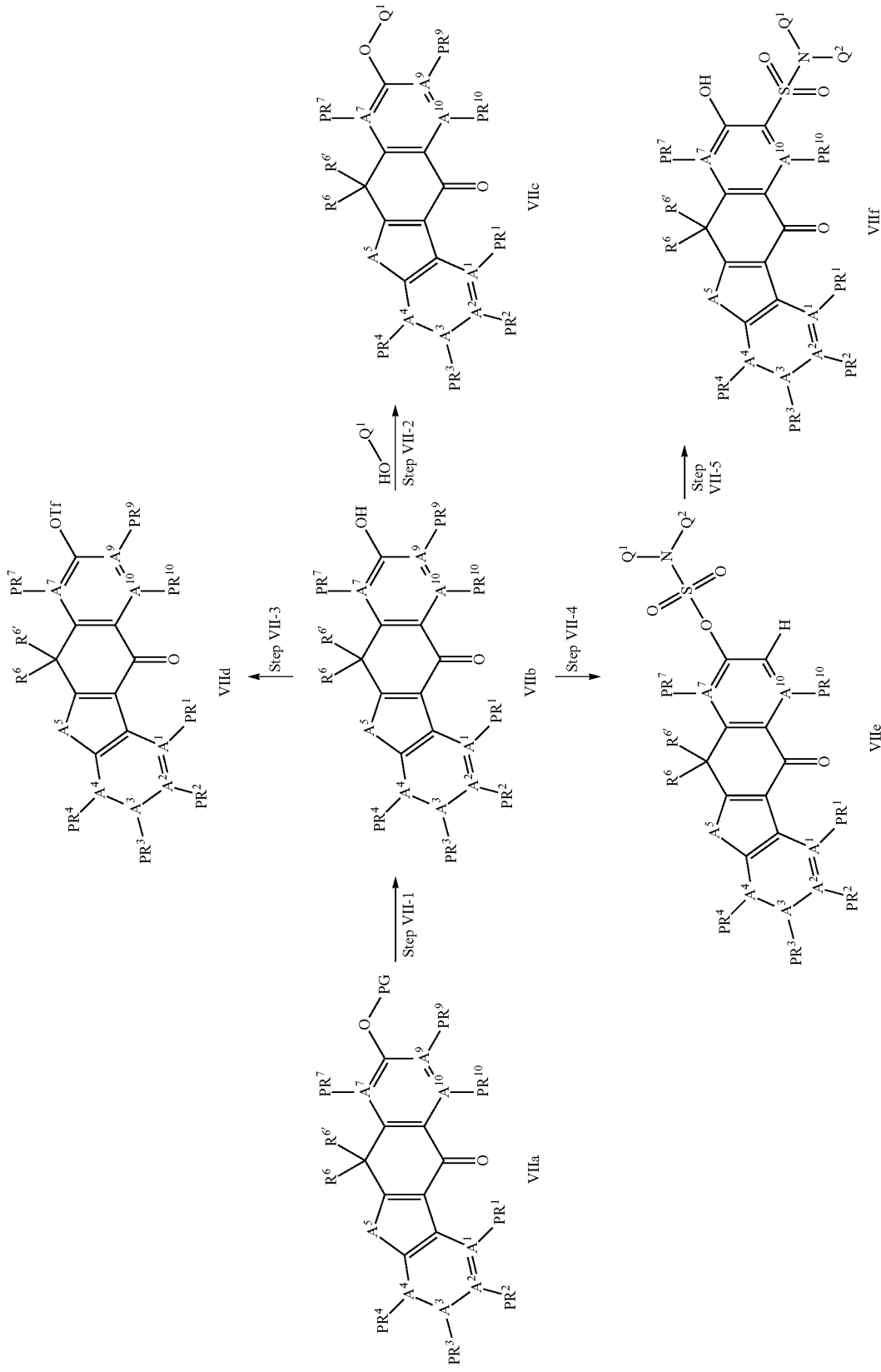

Step VII-1

It is a step of deprotecting a protecting group for an aromatic hydroxyl group. As an example of the protecting group, a methyl group, a t-butyl group, a benzyl group, a substituted benzyl group, a t-butyldimethylsilyl group, a tetrahydropyranyl group and the like can be used. Preferably, it is a methyl group. As for the deprotection, examples thereof include a method described in "Protective Groups in Organic Synthesis" (Greene and Wuts, 4$^{th}$ edition, John Wiley & Sons 2007), and it can be appropriately used according to the type of each protecting group. When a methyl group is used as a protecting group, various reaction conditions can be used selectively for the deprotection depending on reactivity. Examples thereof include heating in the presence of pyridine hydrochloric acid salt, heating in the presence of a solvent with dodecane thiol and sodium methylate and heating in the presence of a solvent with anhydrous lithium halide, boron tribromide, TMSI and the like.

Step VII-2

It is one of the methods for introducing a substituent group based on formation of ether bond with an aromatic hydroxyl group. For the formation of an ether bond, Mitsunobu reaction described in a known literature (Mitsunobu, et. al., Synthesis, Vol. 1, page 1, 1981) or a similar method can be used. Specifically, the reaction is carried out in the presence of a phosphorus compound and an azo compound in a solvent under the condition of a reaction temperature of −78° C. to boiling point of the solvent. As for the phosphorus compound, examples thereof include PPh$_3$ and tri-n-butylphosphine. As for the azo compound, examples thereof include DEAD, TMAD and diisopropyl azodicarboxylic acid. Also, by using them in any combination, the target compound can be obtained.

Step VII-3

It is a step of carrying out trifluoromethane sulfonylation on an aromatic hydroxyl group. The reaction is carried out by reacting with a reacting reagent such as trifluoromethanesulfonic acid and the like in the presence of a base with or without a solvent under the condition of a reaction temperature of −20° C. to boiling point of the solvent. As for the base used for the reaction, TEA, DIPEA, pyridine, 2,6-lutidine, dimethylaminopyridine and the like can be used. Preferably, pyridine is used without any solvent. The obtained trifluoromethanesulfonic acid ester VIId is a good leaving group and can be used for various derivatization.

Step VII-4

It is a step of obtaining sulfamic acid ester by carrying out sulfamoylation on an aromatic hydroxyl group. The reaction is carried out by reacting with a reacting reagent such as sulfamoyl chloride and the like in the presence of a base with a solvent under the condition of a reaction temperature of −20° C. to boiling point of the solvent. As for the base used for the reaction, sodium hydride, TEA, DIPEA, pyridine, 2,6-lutidine, dimethylaminopyridine and the like can be used. Preferably, it is sodium hydride. The obtained sulfamic acid ester VIIe is a substrate for the thiaFries rearrangement of Step VII-5 and can be used for various derivatization.

Step VII-5

This step corresponds to rearrangement of a sulfamoyl group to a neighboring position in the presence of a Lewis acid catalyst under the condition of a reaction temperature of 0° C. to boiling point of the solvent when the neighboring position of the sulfamic acid ester is unsubstituted (i.e., C—H), i.e., a reaction called thiaFries rearrangement. As for the catalyst used for the reaction, aluminum chloride, aluminum triflate, bismuth triflate, ytterbium triflate, BF$_3$.OEt$_2$ and the like can be used. Preferably, it is aluminum chloride.

Step VII-6

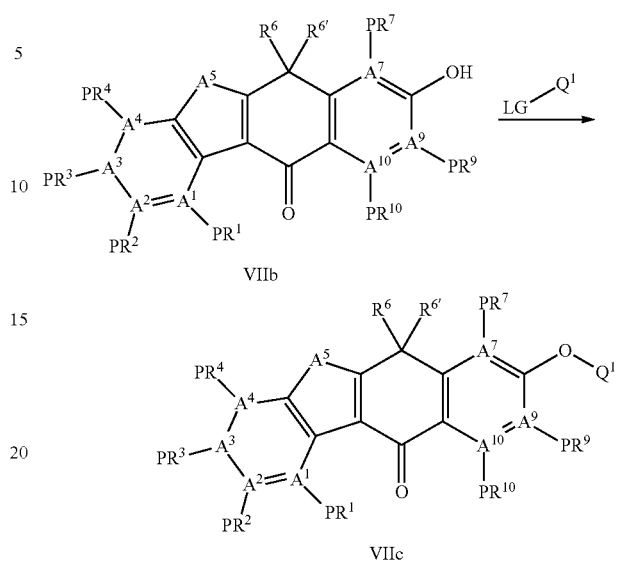

It is another step of introducing a substituent group based on formation of an ether bond. According to the present step, a reagent having an appropriate leaving group such as alkyl halide and the like is subjected to nucleophilic reaction with the hydroxyl group of compound VIIb in the presence of an appropriate base to form an ether bond. As for the base, examples thereof include an inorganic base such as sodium carbonate, potassium carbonate, cesium carbonate, sodium hydride, potassium hydride, calcium hydride and the like or an organic base such as pyridine, TEA, DIPEA and the like.

Further, by using aryl halide, aryl borate and the like as a reagent having a leaving group, formation of an diaryl ether bond can be also achieved and used. When reactivity is not satisfactory, a catalyst such as copper powder, copper acetate, copper iodide and the like or a ligand such as phenanthroline, trans-1,2-cyclohexanediamine and the like can be used.

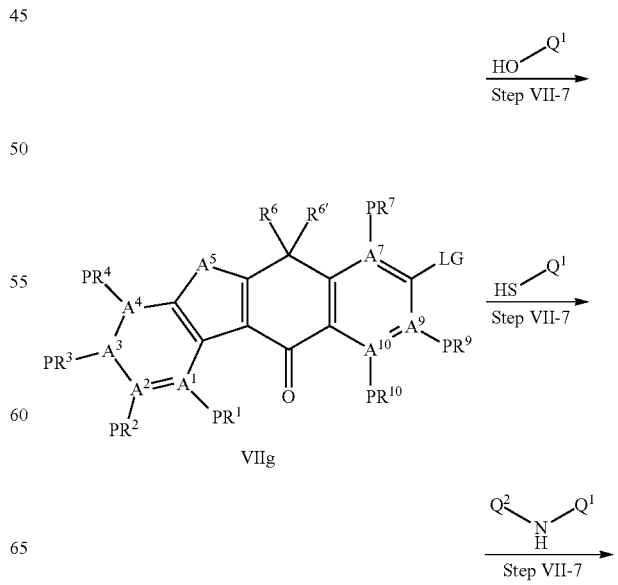

-continued

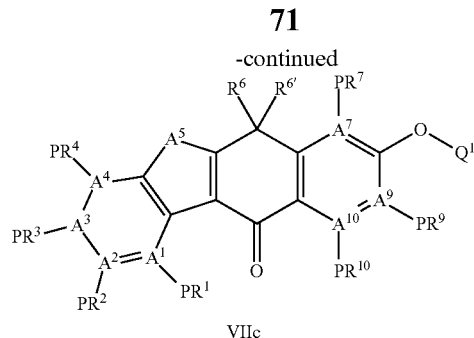

VIIc

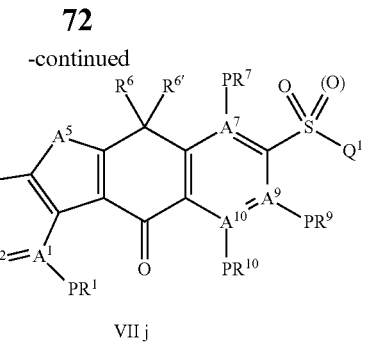

VIIj

Step VII-7

It is a reaction for forming a bond between aryl and a hetero atom by using compound VIIg having a leaving group. The reaction is carried out in an appropriate solvent inert to the reaction, in the presence of a base. As for the leaving group LG, a halogen, triflate and the like can be used. As for the solvent, examples thereof include toluene, xylene, n-hexane, cyclohexane, DMF, DMA, EtOAc, DMSO, NMP, THF, DME, dioxane, acetonitrile and the like and a mixture thereof. As for the base to be used for the reaction, examples thereof include t-BuONa, t-BuOK, LiHMDS, NaHMDS, KHMDS, potassium phosphate, sodium carbonate, potassium carbonate and cesium carbonate. This step can be also carried out by using a catalyst and a ligand. As for the catalyst and a ligand (or a catalyst-ligand complex), palladium acetate, $Pd_2(dba)_3$, m-allylpalladium chloride dimer, $PdCl_2(CH_3CN)_2$, $PdCl_2(PPh_3)_2$, trialkylproazaphosphatrane, ${P(t-Bu)_3PdBr}_2$, $PPh_3$, $P(o-tol)_3$, BINAP, DPPF, $P(t-Bu)_3$, DavePhos, JohnPhos, c-Hexyl JohnPhos, S-Phos, X-Phos, t-ButylX-Phos, Xantphos, 4,5-bis[bis(3,5-bistrifluoromethylphenyl)phosphanyl]-9,9-dimethyl-9H-xanthene, 1,3-diallyldihydroimidazolium salt and the like can be used, for example.

Step VII-8

When the reaction product of Step VII-7 is thio ether VIIh, it is possible to obtain sulfoxide or sulfone compound VIIj by oxidation with m-chloro perbenzoic acid, oxone, TEMPO and the like.

Step VII-9

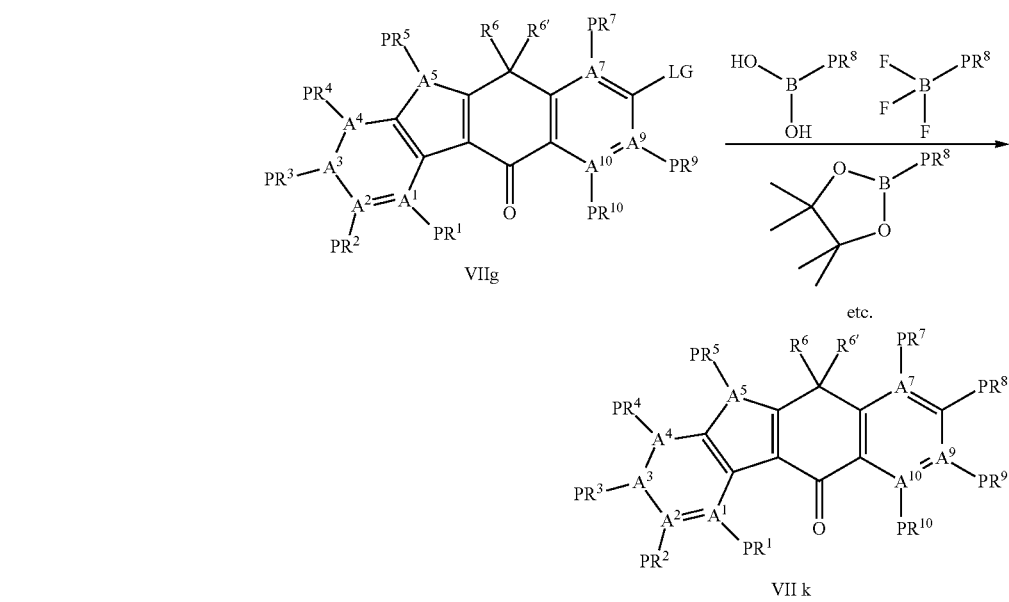

It is a reaction for forming a bond between aryl and SP$^2$ carbon or a bond between aryl and SP$^3$ carbon in which compound VIIg having a leaving group is used. The reaction is carried out in an appropriate solvent inert to the reaction, in the presence of a base. As for the leaving group LG, a halogen, triflate and the like can be used. As for the solvent, examples thereof include toluene, xylene, n-hexane, cyclohexane, DMF, DMA, EtOAc, DMSO, NMP, THF, DME, dioxane, acetonitrile, water, isopropanol and the like and a mixture thereof. As for the base to be used for the reaction, examples thereof include t-BuONa, t-BuOK, LiHMDS, NaHMDS, KHMDS, potassium phosphate, sodium carbonate, potassium carbonate, cesium carbonate, TEA and DIPEA. This step can be also carried out by using a catalyst and a ligand. As for the catalyst and a ligand (or a catalyst-ligand complex), palladium acetate, Pd$_2$(dba)$_3$, m-allylpalladium chloride dimer, PdCl$_2$(CH$_3$CN)$_2$, PdCl$_2$(PPh$_3$)$_2$, trialkylproazaphosphatrane, {P(t-Bu)$_3$PdBr}$_2$, PPh$_3$, P(o-tol)$_3$, BINAP, DPPF, P(t-Bu)$_3$, DavePhos, JohnPhos, c-Hexyl JohnPhos, S-Phos, X-Phos, t-ButylX-Phos, Xantphos, 4,5-bis[bis(3,5-bistrifluoromethylphenyl)phosphanyl]-9,9-dimethyl-9H-xanthene, 1,3-diallyldihydroimidazolium salt and the like can be used, for example.

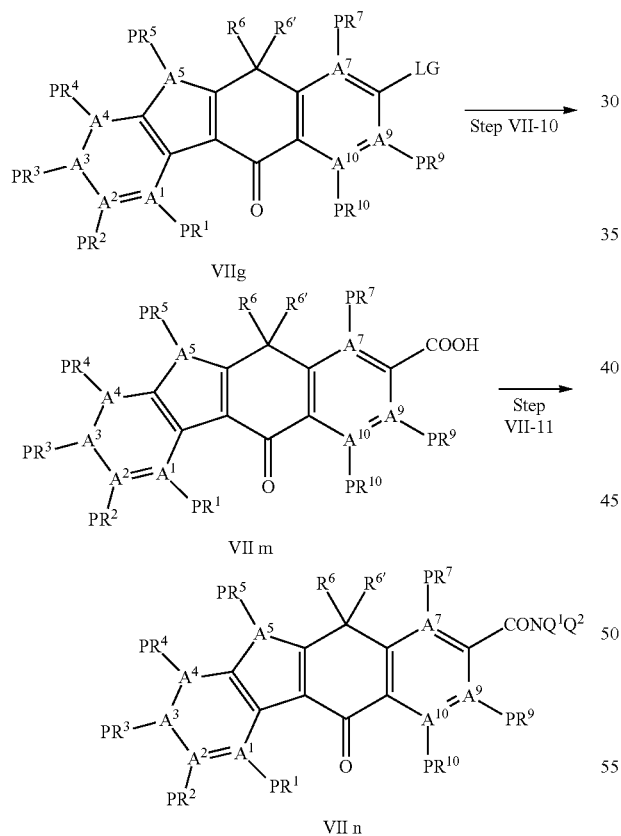

Step VII-10

It is a carboxylation reaction using compound VIIg having a leaving group. The reaction is carried out by reacting with formic acid (or a synthetic equivalent thereof) in an appropriate solvent inert to the reaction, in the presence of a base and a catalyst. As for the leaving group LG, a halogen, triflate and the like can be used. The solvent and the catalyst can be selected and used in the same manner as Step VII-9.

Step VII-11

It is an amidation reaction using carboxylic acid VIIm Specifically, the reaction can be carried out by dehydrating condensation reaction using various amines such as ammonia, primary amines, secondary amines, hydrazines, substituted hydrazines and the like. The reaction is carried out in the presence of an acid halogenating agent or a dehydrating condensing agent in an aprotic solvent under the condition of a reaction temperature of −20° C. to boiling point of the solvent, with or without an active esterifying agent and a base.

As for the acid halogenating agent, examples thereof include oxalyl chloride and thionyl chloride. As for the dehydrating condensing agent, examples thereof include 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), EDC and (benzotriazolyloxy)tripyrrolidino-phosphonium=hexafluorophosphate (PyBOP). As for the active esterifying agent, examples thereof include HOBt, di(N-succinimidyl) carbonate and carbonyl diimidazole. As for the base, examples thereof include TEA, DIPEA and DBU. As for the solvent, examples thereof include DMF, DMA, DCM, acetone, THF, dioxane, DME, ethyl acetate, MeCN, and a mixture thereof.

Step VII-12

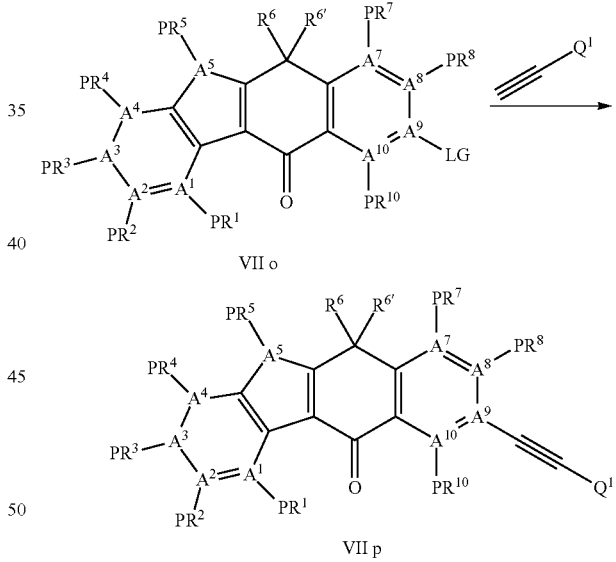

It is a step of forming a bond between aryl and SP carbon using compound VIIo having a leaving group. The reaction is carried out by reacting terminal alkyne in an appropriate solvent in the presence of a base and a catalyst with or without a catalytic amount of a copper reagent, and the reaction is referred to as Sonogashira reaction. The reagents and the condition for the reaction are as defined in Step IV-1 and Step IV-3. As a variant of Sonogashira reaction, examples thereof include a method disclosed in Tetrahedron, 63(43), 10671-10683; 2007. Specifically, by having secondary amines and the like in a reaction system and using propargyl bromide as an alkyne, a propargyl amine can be introduced.

Step VII-13

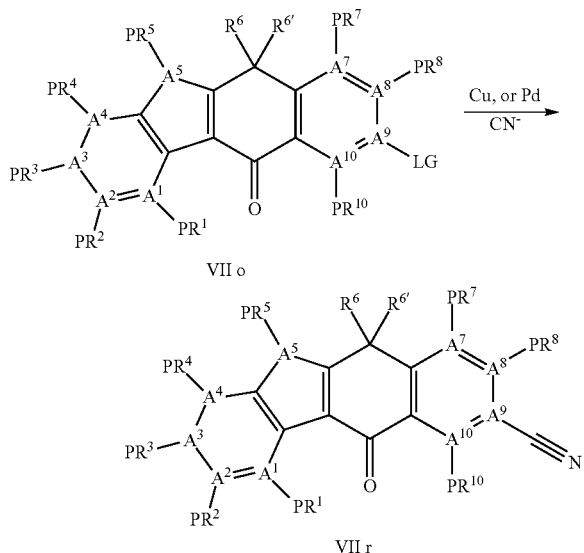

It is a reaction of forming a bond between aryl and CN by using compound VIIo having a leaving group. The reaction can be carried out by adding CN source in an appropriate solvent in the presence of a copper, zinc or palladium catalyst, with or without a ligand, in view of the reaction condition shown in Organic Letters, 10(23), 5325-5328; 2008, Tetrahedron Letters, 49(32), 4693-4694; 2008 and Bioorganic & Medicinal Chemistry, 16(13), 6489-6500; 2008. As for the CN-source, copper (I) cyanide, zinc (II) cyanide, iron (III) hexacyanide, sodium cyanide, potassium cyanide and the like can be used.

Synthesis of Starting Materials

Some of the starting materials for the present invention are novel compounds, and they can be easily synthesized in the same manner as known reacting compounds or according to the method well known to a skilled person in the art.

Hereinabove, examples of a method of preparing the compounds having the Formula (I) according to the present invention are described. However, separation and purification of the target compounds that are described in detail in each reaction step can be performed by applying common chemical treatments such as extraction, concentration, removal by distillation, crystallization, filtration, recrystallization, various chromatography, etc.

Pharmaceutical of the Present Invention

The pharmaceutical composition of the present invention comprises a pharmaceutically acceptable carrier, in addition to the compound that is selected as being useful for the invention. In the present specification, the term "pharmaceutically acceptable carrier" means one or more type of appropriate solid or liquid vehicle, diluent or an encapsulating material which is suitable for administration to mammals. In the present specification, the term "acceptable" means that it does not cause any reaction to substantially reduce the pharmaceutical efficacy of a composition under normal condition for use, and the components of the composition and the subject compound can be mixed well with each other. The pharmaceutically acceptable carrier should have substantially high purity and substantially low toxicity so that it can be suitably administered to a subject to be treated, preferably an animal, and more preferably a mammal.

As the materials which can be used as a pharmaceutically acceptable carrier, examples thereof include sugars such as lactose, glucose, sucrose, and the like; starch such as corn starch, potato starch and the like; cellulose and cellulose derivatives such as sodium carboxy methyl cellulose, ethyl cellulose, methyl cellulose and the like; tragacanth rubber powder; malt; gelatin; talc; solid lubricating agent such as stearic acid or magnesium stearate and the like; calcium sulfate; vegetable oils such as peanut oil, cotton seed oil, sesame oil, olive oil, corn oil, plant oil, cacao oil, and the like; polyhydric alcohols such as propylene glycol, glycerin, sorbitol, mannitol, polyethylene glycol and the like; alginic acid; an emulsifying agent such as TWEEN; humectant such as lecithin and the like; colorant; flavor; tabletting agent; stabilizer, anti-oxidant; preservative; pyrogen-free water; aqueous isotonic solution and phosphate buffer solution.

When the pharmaceutical composition of the present invention is used as an ALK inhibitor or a therapeutic or prophylactic agent for a proliferative disorder, or used against depression or cognitive function disorder, as an administration route, oral, rectal, parenteral (intravenous, intramuscular, subcutaneous), intracisternal, intravaginal, intraperitoneal, intrabladder, topical (drop, powder, ointment, gel or cream) administration or administration via inhalation (mouth or nasal spray) and the like can be considered. As for the administration form, examples thereof include a tablet, a capsule, a granule, powder, a pill, an aqueous or non-aqueous oral solution and suspension, and a parenteral solution which is filled in a container suitable to be divided into several small dosages. In addition, the administration form can be modified for various administration routes including subcutaneous transplant which gives controlled release of a drug compound.

The aforementioned preparation is prepared according to a method generally known in the art by using additives such as a vehicle, a lubricating agent (i.e., coating agent), a binding agent, a disintegrating agent, a stabilizing agent, a corrigent for taste and smell, a diluent and the like.

As a vehicle, examples thereof include starch such as starch, potato starch, corn starch, lactose, crystalline cellulose and calcium hydrogen phosphate.

As a coating agent, examples thereof include ethyl cellulose, hydroxypropyl cellulose, hydroxypropylmethyl cellulose, shellac, talc, carnauba wax and paraffin.

As a binding agent, examples thereof include polyvinyl pyrrolidone, Macrogol and the compounds described above as a vehicle.

As a disintegrating agent, examples thereof include the compounds described as a vehicle in the above and a chemically modified starch or cellulose such as sodium croscarmellose, sodium carboxymethyl starch and crosslinked polyvinyl pyrrolidone.

As a stabilizing agent, examples thereof include paraoxy benzoic acid esters such as methyl paraben, propyl paraben and the like; alcohols such as chlorobutanol, benzyl alcohol, phenylethyl alcohol and the like; benzalkonium chloride; phenols such as phenol, cresol and the like; thimerosal; dehydroacetic acid; and sorbic acid.

As a corrigent for taste and smell, examples thereof include a sweetener, an acid tasting agent, a flavor and the like that are commonly used in the art.

Further, as a solvent to prepare a liquid preparation, examples thereof include ethanol, phenol, chlorocresol, purified water and distilled water.

As a surface active agent or an emulsifying agent, examples thereof include polysorbate 80, polyoxyl 40 stearate and lauromacrogol.

When the pharmaceutical composition of the present invention is used as an ALK inhibitor or a therapeutic or prophylactic agent for a proliferative disorder, or used against depression or cognitive function disorder, the use amount of the compounds of the present invention or salts or solvates thereof varies depending on symptom, age, body weight, relative health state of a subject, administration of other drug compounds, administration method and the like. For example, the amount which is generally effective for a patient (i.e., warm-blooded animal, in particular human) is, in an effective component (i.e., the compound of the present invention that is represented by the Formula (I)), preferably 0.001 to 1000 mg per 1 kg body weight per day, more preferably 0.01 to 300 mg per 1 kg body weight per day in case of an orally administered agent, and dosage per day is preferably in the range of 1 to 800 mg for an adult patient with normal body weight. In case of a parenterally administered agent, it is preferably 0.001 to 1000 mg per 1 kg body weight per day, and more preferably, 0.01 to 300 mg per 1 kg body weight per day. It is preferable to administer them once a day or in divided dosages a day, depending on symptom of a subject to be treated.

Example

Hereinbelow, the present invention will be explained in greater detail in view of the following examples. However, the present invention is not limited by the examples.

NMR Analysis

NMR analysis was carried out by using JNM-EX270 (270 MHz, manufactured by JEOL), JNM-GSX400 (400 MHz, manufactured by JEOL), or 400 MR (400 MHz, manufactured by Varian). NMR data was expressed in ppm (parts per million; δ), while it was compared with the deuterium lock signal obtained from a sample solvent.

Mass Spectrum

The measurement was carried out by using JMS-DX303 or JMS-SX/SX102A (both manufactured by JEOL).

High Performance Liquid Chromatography-Mass Spectrum Data (LC-MS)

Measurement was carried out by using Micromass (ZMD, manufactured by Micromass) equipped with 996-600E gradient high performance liquid chromatography (manufactured by Waters) or Micromass (ZQ, manufactured by Micromass) equipped with 2525 gradient high performance liquid chromatography (manufactured by Waters).

One of the following conditions that are described in the Table 1 below was taken as a condition for high performance liquid chromatography.

TABLE 1

| Analysis Condition | Apparatus | Column used | Column Temperature | Mobile phase, Gradient | Flow Rate (mL/min) | Detection Wavelength |
|---|---|---|---|---|---|---|
| A | ZMD | Cadenza CD-C18 (Intakt) 3.0 mm I.D. × 30 mm, 3 um | 35 deg. | A) 0.05% TFA, H2O B) 0.05% TFA, MeCN (A/B):95/5 => 0/100 (3.5 min) => 0/100 (1 min) | 1.5 | 210-400 nm PDA total |
| B | ZMD | Cadenza CD-C18 (Intakt) 3.0 mm I.D. × 30 mm, 3 um | 35 deg. | A) 0.05% TFA, H2O B) 0.05% TFA, MeCN (A/B):95/5 => 0/100 (9.5 min) => 0/100 (2.5 min) | 1.0 | 210-400 nm PDA total |
| C | ZQ | Chromolith Flash RP-18e (Merck KGaA) 4.6 mm I.D. × 25 mm | Room Temp. | A) 10 mM AcONH4, H2O B) MeOH (A/B):95/5 => 0/100 (3 min) => 0/100 (2 min) | 2.0 | 210-400 nm PDA total |
| D | ZQ | Chromolith Flash RP-18e (Merck KGaA) 4.6 mm I.D. × 25 mm | Room Temp. | A) 10 mM AcONH4, H2O B) MeCN (A/B):95/5 => 0/100 (3 min) => 0/100 (2 min) | 2.0 | 210-400 nm PDA total |
| F | ZQ | Cadenza CD-C18 (Intakt) 3.0 mm I.D. × 30 mm, 3 um | 35 deg. | A) 0.05% TFA, H2O B) 0.05% TFA, MeCN (A/B):95/5 => 0/100 (3.5 min) => 0/100 (1 min) | 1.5 | 210-400 nm PDA total |
| H | ZQ | Cadenza CD-C18 (Intakt) 3.0 mm I.D. × 30 mm, 3 um | 35 deg. | A) 0.05% TFA, H2O B) 0.05% TFA, MeCN (A/B):95/5 => 0/100 (9.5 min) => 0/100 (2.5 min) | 1.0 | 210-400 nm PDA total |
| I | ZQ | Ascentis Express C18 (Sigma Aldrich) 2.1 mm I.D. × 50 mm | Room Temp. | A) 10 mM AcONH4, H2O B) MeOH (A/B):95/5 => 0/100 (9.5 min) => 0/100 (1 min) | 1.0 | 210-400 nm PDA total |
| S | ZQ | Sunfire C18 (Waters) 4.5 mm I.D. × 50 mm, 5 um | Room Temp. | A) 0.05% TFA, H2O B) 0.05% TFA, MeCN (A/B):90/10 => 5/95 (3.5 min) => 90/10 (1 min) => 90/10 (0.5 min) | 4.0 | 210-400 nm PDA total |
| T | ZQ | Sunfire C18 (Waters) 4.5 mm I.D. × 50 mm, 5 um | Room Temp. | A) 0.05% TFA, H2O B) 0.05% TFA, MeCN (A/B):90/10 => 5/95 (2 min) => 5/95 (1.5 min) => 90/10 (1.0 min) => 90/10 (0.5 min) | 4.0 | 210-400 nm PDA total |
| U | ZQ | WAKOsil 3c18 AR, (Wako Pure Chemical Industries. Ltd.) 4.6 mm I.D. × 30 mm | Room Temp. | A) 0.05% TFA, H2O B) 0.05% TFA, MeCN (A/B):90/10 => 90/10 (0.2 min) => 5/95 (3.1 min) => 5/95 (1.4 min) | 2.0 | 210-400 nm PDA total |
| W | ZMD | Sunfire C18 (Waters) 4.5 mm I.D. × 50 mm, 5 um | Room Temp. | A) 0.05% TFA, H2O B) 0.05% TFA, MeCN (A/B):90/10 => 5/95 (3.5 min) => 90/10 (1 min) => 90/10 (0.5 min | 4.0 | 210-400 nm PDA total |

TABLE 1-continued

| Analysis Condition | Apparatus | Column used | Column Temperature | Mobile phase, Gradient | Flow Rate (mL/min) | Detection Wavelength |
|---|---|---|---|---|---|---|
| Y | ZMD | Sunfire C18 (Waters) 4.5 mm I.D. × 50 mm, 7 um | Room Temp. | A) 0.05% TFA, H2O B) 0.05% TFA, MeCN (A/B):90/10 => 0/100 (3.5 min) => 0/100 (1 min) | 2.0 | 210-400 nm PDA total |

Microwave Reaction

The reaction was carried out by using a snap cap reaction vial together with an Explorer™ (manufactured by CEM Microwave Technology) or an initiator (manufactured by Biotage). Maximum output setting includes cooling of the reaction vessel by air in order to avoid temperature increase caused by microwave irradiation.

Commercially available reagents were obtained and used without any further purification. The room temperature indicates the temperature range of between about 20 to 25° C. All the non-aqueous reaction was carried out in anhydrous solvent under nitrogen or argon atmosphere. For concentration under reduced pressure or removal of a solvent by distillation, a rotary evaporator was used.

For preparing the compounds, when there is a possibility of having an undesirable side reaction, a functional group was protected using a protecting group to produce a target molecule, and the protecting group was removed later, if desired. Selection, addition and removal of a protecting group were carried out according to the method described in the literature [Greene and Wuts, "Protective Groups in Organic Synthesis" ($4^{th}$ edition, John Wiley & Sons 2007)], for example.

Example 1

Compound A2

7-Methoxy-1,1-dimethyl-3,4-dihydro-1H-naphthalen-2-one

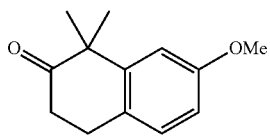

7-Methoxy-3,4-dihydro-1H-naphthalen-2-one (Compound A1, 209 g, 1.18 mol), tetrabutylammonium hydrogen sulfate (40 g, 0.118 mol) and methyl iodide (162 g, 2.60 mol) were suspended in THF (500 ml) at room temperature. Under stirring, the mixture was added with 50% aqueous solution of potassium hydroxide (400 g) over 5 min. Reflux occurred as the inner temperature rapidly increases. Once the inner temperature stopped to increase, stirring was continued for 45 min. The reaction solution was diluted with distilled water (1 L) and extracted twice with CPME (1.5 L). The combined organic layer was washed (distilled water 1 L×3), dried over anhydrous sodium sulfate, and concentrated under reduced pressure. The resulting crude product was recrystallized with MeOH (1 L) and distilled water (500 ml) to obtain the title compound as a colorless needle-like crystal (177 g, 73%).

$^1$H-NMR (400 MHz, CDCl$_3$) δ: 1.43 (6H, s), 2.65 (2H, t, 12 Hz), 3.02 (2H, t, 12 Hz), 3.79 (3H, s), 6.74 (1H, m), 6.87 (1H, m), 7.24 (1H, m).

LCMS: m/z 205 [M+H]$^+$

Example 2

Compound A3-1, Compound A3-2

3-Bromo-8-methoxy-6,6-dimethyl-6,11-dihydro-5H-benzo[b]carbazole

1-Bromo-8-methoxy-6,6-dimethyl-6,11-dihydro-5H-benzo[b]carbazole

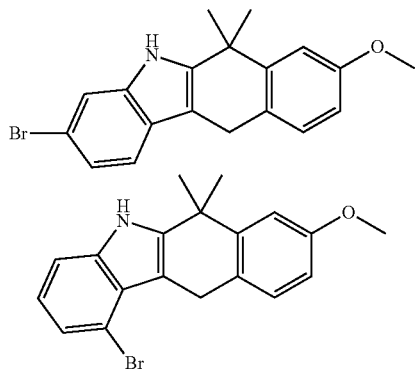

7-Methoxy-1,1-dimethyl-3,4-dihydro-1H-naphthalen-2-one (Compound A2, 66.2 g, 324 mmol) and 3-bromophenylhydrazine hydrochloric acid salt (71.0 g, 318 mmol) were dissolved in AcOH (350 ml) and refluxed under stirring for 6 hr. The reaction solvent was removed by distillation under reduced pressure to obtain the crude product as a mixture of the title compound A3-1 and A3-2.

Example 3

Compound A4

3-Bromo-8-methoxy-6,6-dimethyl-5,6-dihydrobenzo[b]carbazol-11-one

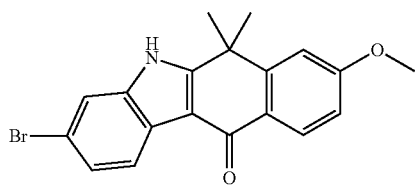 [SMILES: COc1ccc2c(c1)C(C)(C)c1[nH]c3cc(Br)ccc3c1C2=O]

The crude product obtained from the above (i.e., mixture of A3-1 and A3-2) was dissolved in a mixture solvent of THF (450 ml) and distilled water (50 ml), added once with DDQ (115 g, 509 mmol), and then stirred at room temperature for 1 hr. The reaction mixture was diluted with CPME 3 L, and the organic layer was washed three times with 0.5 N aqueous solution of sodium hydroxide (1 L) and twice with distilled water (1 L) in order and dried over anhydrous sodium sulfate. The organic layer was concentrated to 500 ml under reduced pressure. The precipitated product was collected by filtration and washed with a small amount of CPME to obtain the title compound as a yellow crystal (48 g, 40%).

$^1$H-NMR (400 MHz, DMSO-$d_6$) δ: 1.73 (6H, s), 3.90 (3H, s), 7.06-7.09 (1H, m), 7.32-7.38 (2H, m), 7.65-7.66 (1H, m), 8.09-8.17 (2H, m), 12.32 (1H, br. s).

LCMS: m/z 370, 372 [M+H]$^+$

Example 4

Compound AA1

4-Methoxy-2-(3-trimethylsilanylprop-2-ynyl)-benzoic acid methyl ester

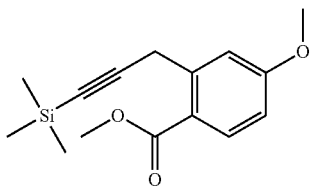

To the THF (16 ml) solution of 2-bromomethyl-4-methoxy-benzoic acid methyl ester (961 mg, 4.09 mmol), triphenylphosphine (107 mg, 0.1 eq.), cesium carbonate (1.87 g, 1.4 eq.), copper iodide (59 mg, 0.076 eq.) and tris(dibenzylideneacetone)dipalladium (86 mg, 0.023 eq.) were added, degassed, flushed with nitrogen gas, added with trimethylsilylacetylene (734 μl, 1.3 eq.), and then stirred overnight at 55° C. To the reaction solution, saturated aqueous solution of ammonium chloride was added followed by extraction with ethyl acetate. The organic layer was washed with brine and dried over magnesium sulfate. The drying agent was removed by filtration and the residues obtained after concentration under reduced pressure were purified by silica gel column chromatography (ethyl acetate/hexane) to obtain the title compound (brown oily substance, 606 mg, 54%).

$^1$H-NMR (400 MHz, CDCl$_3$) δ: 7.93 (1H, d, J=8.8 Hz), 7.33 (1H, d, J=2.6 Hz), 6.78 (1H, dd, J=8.8, 2.6 Hz), 4.09 (2H, s), 3.86 (3H, s), 3.84 (3H, s), 0.14 (9H, s).

LCMS: m/z 277 [M+H]$^+$

HPLC retention time: 3.30 min (analysis condition U)

Example 5

Compound AA2

2-(1,1-Dimethyl-3-trimethylsilanylprop-2-ynyl)-4-methoxy-benzoic acid methyl ester

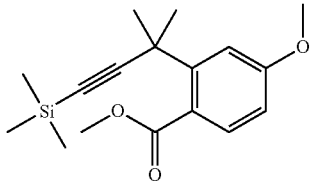

To the toluene (4 ml) solution of 4-methoxy-2-(3-trimethylsilanyl-prop-2-ynyl)-benzoic acid methyl ester (Compound AA1, 273 mg, 0.988 mmol), sodium bis(trimethylsilyl) amide (2.1 ml, 1.9 m solution, 4 eq.) and iodomethane (308 μl, 5 eq.) were added at −78° C. After allowing the reaction temperature to increase to the room temperature, the mixture was stirred for 2 hr. To the reaction solution, saturated aqueous solution of ammonium chloride was added followed by extraction with ethyl acetate. The organic layer was washed with brine and dried over magnesium sulfate. The drying agent was removed by filtration and the residues obtained after concentration under reduced pressure were purified by silica gel column chromatography (ethyl acetate/hexane) to obtain the title compound (yellow oily substance, 226 mg, 75%).

$^1$H-NMR (400 MHz, CDCl$_3$) δ: 7.45 (1.0H, d, J=8.4 Hz), 7.09 (1.1H, d, J=2.6 Hz), 6.75 (1H, m), 3.84 (3H, s), 3.82 (3H, s), 1.70 (6H, s), 0.14 (9H, s)

LCMS: m/z 305 [M+H]$^+$

HPLC retention time: 3.38 min (analysis condition U)

Example 6

Compound AA3

2-(1,1-Dimethylprop-2-ynyl)-4-methoxy-benzoic acid methyl ester

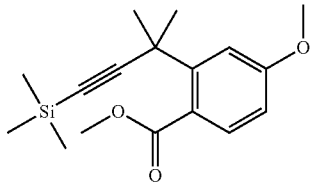

To the THF (18 ml) solution of 2-(1,1-dimethyl-3-trimethylsilanylprop-2-ynyl)-4-methoxy-benzoic acid methyl ester (Compound AA2, 912 mg, 3 mmol), tetrabutylammonium fluoride (2.061 g, 2.6 eq.) was added, and then stirred for 3 hr at room temperature. To the reaction solution, saturated aqueous solution of ammonium chloride was added followed by extraction with ethyl acetate. The organic layer was washed with brine and dried over magnesium sulfate. The drying agent was removed by filtration and the residues obtained after concentration under reduced pressure were purified by silica gel column chromatography (ethyl acetate/hexane) to obtain the title compound (yellow oily substance, 524 mg, 75%).

$^1$H-NMR (400 MHz, CDCl$_3$) δ: 7.44 (1H, d, J=8.4 Hz), 7.05 (1H, d, J=2.3 Hz), 6.76 (1H, dd, J=8.4, 2.3 Hz), 3.84 (3H, s), 3.82 (3H, s), 1.73 (6H, s)

LCMS: m/z 223 [M+H]$^+$

HPLC retention time: 2.55 min (analysis condition U)

Example 7

Compound AA4

2-[1-(6-Cyano-1-methanesulfonyl-1H-indol-2-yl)-1-methylethyl]-4-methoxy-benzoic acid methyl ester

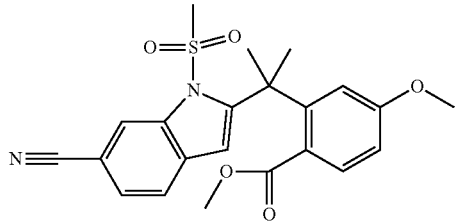 [SMILES: COC(=O)c1ccc(OC)cc1C(C)(C)c1cc2ccc(C#N)cc2n1S(C)(=O)=O]

To the DMF (2 ml) solution of 2-(1,1-dimethylprop-2-ynyl)-4-methoxy-benzoic acid methyl ester (Compound AA3, 134 mg, 0.577 mmol) and N-(2-bromo-5-cyanophenyl)methanesulfonamide (Compound AA3, 167 mg, 1.05 eq.), copper iodide (9 mg, 0.08 eq.) and TEA (129 μl, 1.6 eq.) were added, degassed and flushed with nitrogen gas, added with dicholorobis(triphenylphosphine) palladium (20 mg, 0.05 eq.), and then degassed and flushed again with nitrogen gas. After stirring for 2 hr at 90° C., the reaction solution was added with water, extracted with ethyl acetate. The organic layer was washed with an brine and dried over magnesium sulfate. The drying agent was removed by filtration and the residues obtained after concentration under reduced pressure were purified by silica gel column chromatography (ethyl acetate/hexane) to obtain the title compound (white solid, 152 mg, 62%).

¹H-NMR (400 MHz, DMSO-$d_6$) δ: 8.19 (1H, dd, J=0.6, 0.6 Hz), 7.84 (1H, dd, J=8.0, 0.6 Hz), 7.67 (1H, dd, J=8.0, 1.3 Hz), 7.13 (1H, d, J=8.4 Hz), 6.99 (1H, s), 6.96 (1H, br. s), 6.85 (1H, dd, J=8.4, 2.5 Hz), 3.78 (3H, s), 3.12 (3H, s), 3.09 (3H, br. s), 1.89 (6H, s).

LCMS: m/z 427 [M+H]⁺

HPLC retention time: 2.77 min (analysis condition U)

Example 8

Compound AA5

N-(2-Bromo-5-cyanophenyl)methanesulfonamide

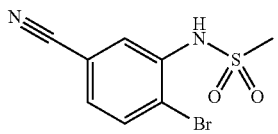

To a mixture of 3-amino-4-bromo-benzonitrile (1.98 g, 10 mmol), TEA (5.06 g, 50 mmol), and methylene chloride (50 ml), mesyl chloride (2.71 ml, 35 mmol) was added at 0° C. and the mixture was stirred at room temperature for 30 min. Water was added to the reaction solution, which was then extracted with dichloromethane. The organic layer was dried over sodium sulfate. The drying agent was removed by filtration and the residues obtained after concentration under reduced pressure were added with tetrahydrofuran (100 ml), water (400 μl) and sodium hydride (540 mg, 15.5 mmol), and stirred at room temperature for 16 hr. To the reaction solution, saturated aqueous solution of ammonium chloride (200 ml) was added followed by extraction with ethyl acetate. The organic layer was dried over sodium sulfate. The drying agent was removed by filtration and the residues obtained after concentration under reduced pressure were purified by silica gel column chromatography (hexane/ethyl acetate) to obtain the title compound (2.48 g, 90%).

¹H-NMR (400 MHz, DMSO-$d_6$) δ: 9.82 (1H, s), 7.87 (1H, d, J=4 Hz), 7.75 (1H, d, J=8 Hz), 7.70 (1H, dd, J=8 Hz, 4 Hz), 3.14 (3H, s)

HPLC retention time: 1.63 min (analysis condition U)

Example 9

Compound AA6

2-(1-Hydroxy-1-methylethyl)-1H-indole-6-carbonitrile

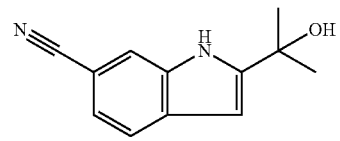

To N-(2-bromo-5-cyanophenyl)methanesulfonamide (Compound AA5, 230 mg, 1 mmol), 3-methyl-2-butyn-3-ol (0.15 ml, 1.5 mmol), X-Phos (72 mg, 15% mol), PdCl₂(CH₃CN)₂ (13 mg, 5% mol) and cesium carbonate (390 mg, 2 mmol), DMA (2 ml) was added, and the mixture was stirred at 100° C. for 3 hr. Water and 5 N hydrochloric acid solution were added to the reaction solution, which was then extracted with ethyl acetate. The organic layer was dried over sodium sulfate. The drying agent was removed by filtration and the residues obtained after concentration under reduced pressure were purified by silica gel column chromatography (hexane/ethyl acetate) to obtain the title compound (130 mg, 75%).

¹H-NMR (400 MHz, CDCl₃) δ: 8.76 (1H, s), 7.68 (1H, s), 7.60 (1H, d, J=8 Hz), 7.32 (1H, dd, J=8 Hz, 4 Hz), 6.37 (1H, m), 1.93 (1H, s), 1.70 (6H, s)

LCMS: m/z 201 [M+H]⁺

HPLC retention time: 2.12 min (analysis condition U)

Example 10

Compound A5-1

3-Bromo-8-hydroxy-6,6-dimethyl-5,6-dihydrobenzo[b]carbazol-11-one

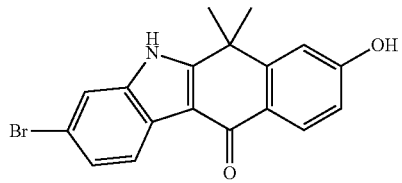

Under the same conditions as the method for synthesizing Compound A6, the title compound was synthesized from Compound A4.

¹H-NMR (400 MHz, DMSO-$d_6$) δ: 12.30 (1H, s), 10.21 (1H, s), 8.06-8.11 (1H, m), 8.01-8.05 (1H, m), 7.62-7.66 (1H, m), 7.32-7.37 (1H, m), 7.08-7.12 (1H, m), 6.84-6.90 (1H, m), 1.69 (6H, s).

LCMS: m/z 356, 358 [M+H]⁺

HPLC retention time: 2.30 min (analysis condition U)

Example 11

Compound A5-2

8-Methoxy-6,6-dimethyl-11-oxo-6,11-dihydro-5H-benzo[b]carbazole-3-carbonitrile

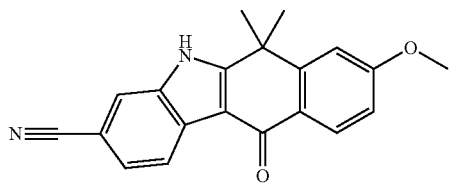 [SMILES: COc1ccc2c(c1)C(C)(C)c1[nH]c3cc(C#N)ccc3c1C2=O]

(Method 1) 3-Bromo-8-methoxy-6,6-dimethyl-5,6-dihydrobenzo[b]carbazol-11-one (Compound A4, 10.45 g, 28.2 mmol) and copper (I) cyanide (5.0 g, 50.2 mmol) were dissolved in NMP (100 ml), followed by stirring at 170° C. for 17 hr. The reaction mixture was suspended in ethyl acetate (500 mL) and distilled water (200 mL). The insoluble matters were removed by Celite filtration and washed twice with ethyl acetate (300 mL×2). The organic layer was washed once with an aqueous solution of disodium EDTA (200 mL) and twice with saturated brine (200 mL) in order, and dried over anhydrous sodium sulfate. The organic layer was concentrated under reduced pressure to yield a product, which was suspended and washed with a small amount of CPME to obtain the title compound as a colorless crystal (6.58 g, 73%).

(Method 2) To the THF (5.6 ml) solution of 2-[1-(6-cyano-1-methanesulfonyl-1H-indol-2-yl)-1-methylethyl]-4-methoxy-benzoic acid methyl ester (Compound AA4, 138 mg, 0.324 mmol), tetrabutylammonium fluoride (514 mg, 6 eq.) was added, and the mixture was stirred at room temperature overnight. Thereafter, 2 M aqueous solution of sodium hydroxide (5.6 ml) was added to the mixture, which was then stirred for 4 hr, added with 1 M HCl, and extracted with ethyl acetate. The organic layer was washed with brine and dried over magnesium sulfate. The drying agent was removed by filtration and the residues obtained after concentration under reduced pressure were dissolved in ethyl acetate (10 ml) and added with e 4 M HCl and ethyl acetate solution (10 ml) followed by stirring at room temperature for 30 min. The residues obtained after concentration of the reaction solution under reduced pressure were purified by silica gel column chromatography (ethyl acetate/hexane) to obtain the title compound (89.2 mg, 62%).

(Method 3) To nitrobenzene (5 ml) and aluminum chloride (400 mg, 3 mmol), 4-methoxybenzoyl chloride (400 mg, 2.3 mmol) was added. After stirring for 30 min at room temperature, 2-(1-hydroxy-1-methyl-ethyl)-1H-indole-6-carbonitrile (Compound AA6, 200 mg, 1 mmol) was added followed by stirring at room temperature for 3 hr. Water was added to the reaction solution, which was then extracted with ethyl acetate. The organic layer was dried over sodium sulfate. The drying agent was removed by filtration and the residues obtained after concentration under reduced pressure were purified by silica gel column chromatography (hexane/ethyl acetate) to obtain the title compound (127 mg, 40%).

$^1$H-NMR (400 MHz, DMSO-$d_6$) δ: 1.71 (6H, s), 3.89 (3H, s), 7.07-7.09 (1H, m), 7.34 (1H, s), 7.58-7.60 (1H, m), 7.99 (1H, s), 8.14-8.16 (1H, m), 8.30-8.32 (1H, m), 12.32 (1H, br. s),

LCMS: m/z 317 [M+H]$^+$

HPLC retention time: 2.56 min (analysis condition U)

Example 12

Compound A6

8-Hydroxy-6,6-dimethyl-11-oxo-6,11-dihydro-5H-benzo[b]carbazole-3-carbonitrile

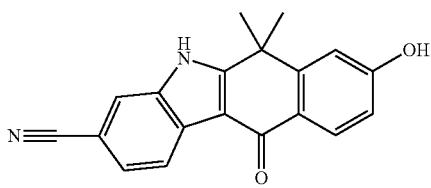 [SMILES: CC1(C)c2cc(O)ccc2C(=O)c2c1[nH]c1cc(C#N)ccc21]

8-Methoxy-6,6-dimethyl-11-oxo-6,11-dihydro-5H-benzo[b]carbazole-3-carbonitrile (Compound A5-2, 6.58 g, 20.8 mmol) was dissolved in pyridine hydrochloric acid salt (25.0 g), and stirred at 170° C. for 13 hr. The reaction mixture was partitioned in ethyl acetate (400 mL) and distilled water (400 mL), and the aqueous layer was extracted one more time with ethyl acetate (400 mL). The combined organic layer was washed twice with distilled water (100 mL) and once with saturated brine (100 mL) in order, and dried over anhydrous sodium sulfate. The organic layer was concentrated under reduced pressure to yield a product, which was suspended and washed with a small amount of CPME to obtain the title compound as a colorless crystal (5.91 g, 93%).

$^1$H-NMR (400 MHz, DMSO-$d_6$) δ: 1.73 (6H, s), 6.87-6.90 (1H, m), 7.11 (1H, s), 7.57-7.59 (1H, m), 7.97 (1H, s), 8.04-8.06 (1H, m), 8.29-8.31 (1H, m), 10.27 (1H, s), 12.66 (1H, br. s),

LCMS: m/z 303 [M+H]$^+$

Example 13

Compound A7-1

4-(3-Cyano-6,6-dimethyl-11-oxo-6,11-dihydro-5H-benzo[b]carbazol-8-yloxy)-piperidine-1-carboxylic acid tert-butyl ester

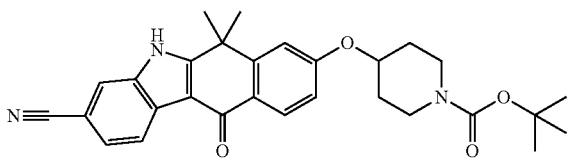 [SMILES: CC(C)(C)OC(=O)N1CCC(Oc2ccc3c(c2)C(C)(C)c2[nH]c4cc(C#N)ccc4c2C3=O)CC1]

8-Hydroxy-6,6-dimethyl-11-oxo-6,11-dihydro-5H-benzo[b]carbazole-3-carbonitrile (Compound A6, 30 mg, 0.099 mmol) was dissolved in THF (1 mL), added with 4-hydroxy-piperidine-1-carboxylic acid tert-butyl ester (40 mg, 2 eq.), triphenylphosphine (52 mg, 2 eq.), and diisopropyl azodicarboxlyate (43 μL, 2 eq.) in order, and stirred at room temperature for 4 hr. The reaction solution was poured to water, and then extracted with ethyl acetate. The organic layer was washed with saturated brine and dried over sodium sulfate. The drying agent was removed by filtration and the residues obtained after concentration under reduced pressure were purified by silica gel column chromatography (ethyl acetate/hexane) to obtain the title compound (37 mg, 76%).

¹H-NMR (400 MHz, CDCl₃) δ: 9.44 (1H, s), 8.77 (1H, d, J=7.8 Hz), 8.62 (1H, d, J=8.2 Hz), 8.00 (1H, s), 7.81 (1H, d, J=8.2 Hz), 7.34 (1H, s), 7.26 (1H, d, J=7.8 Hz), 4.85-4.93 (1H, m), 3.96-4.04 (2H, m), 3.60-3.70 (2H, m), 2.19-2.32 (2H, m), 1.89-2.15 (8H, m), 1.74 (9H, s)
LCMS: m/z 430 [M+H]⁺
HPLC retention time: 4.09 min (analysis condition W)

Example 14

Compound A7-2

6,6-Dimethyl-11-oxo-8-[2-(2-oxo-imidazolidin-1-yl)-ethoxy]-6,11-dihydro-5H-benzo[b]carbazole-3-carbonitrile

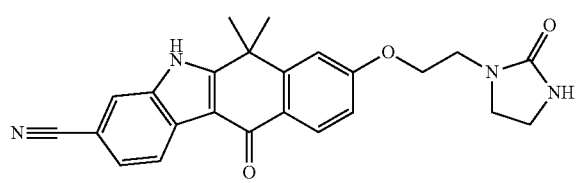 [SMILES: CC1(C)c2cc(OCCN3CCNC3=O)ccc2C(=O)c2c1[nH]c1cc(C#N)ccc21]

Under the same conditions as the method for synthesizing Compound A7-1, the title compound was prepared from Compound A6 and 1-(2-hydroxy-ethyl)-imidazolidin-2-one.
LCMS: m/z 415 [M+H]⁺
HPLC retention time: 2.96 min (analysis condition W)

Example 15

Compound A7-3

[2-(3-Cyano-6,6-dimethyl-11-oxo-6,11-dihydro-5H-benzo[b]carbazol-8-yloxy)-ethyl]-carbamic acid tert-butyl ester

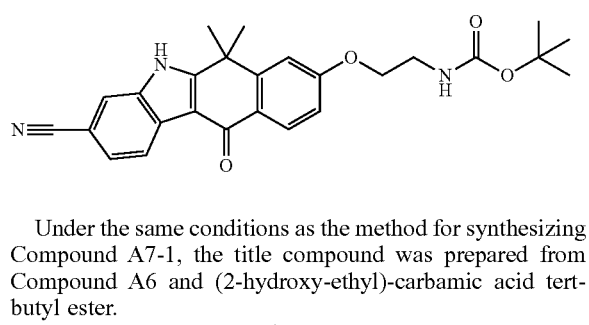

Under the same conditions as the method for synthesizing Compound A7-1, the title compound was prepared from Compound A6 and (2-hydroxy-ethyl)-carbamic acid tert-butyl ester.
LCMS: m/z 346 [M+H]⁺
HPLC retention time: 2.40 min (analysis condition W)

Example 16

Compound A7-4

6,6-Dimethyl-8-(2-methylsulfanyl-ethoxy)-11-oxo-6,11-dihydro-5H-benzo[b]carbazole-3-carbonitrile

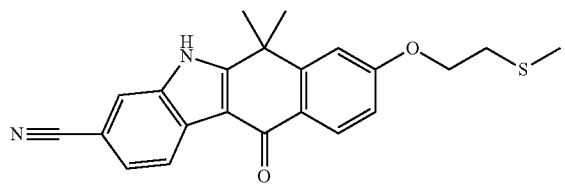 [SMILES: CSCCOc1ccc2c(c1)C(C)(C)c1[nH]c3cc(C#N)ccc3c1C2=O]

Under the same conditions as the method for synthesizing Compound A7-1, the title compound was prepared from Compound A6 and 2-methylthioethanol.
LCMS: m/z 451 [M+H]⁺
HPLC retention time: 4.23 min (analysis condition W)

Example 17

Compound A7-5

6,6-Dimethyl-8-(2-methylsulfanyl-ethoxy)-5-(2-methylsulfanyl-ethyl)-11-oxo-6,11-dihydro-5H-benzo[b]carbazole-3-carbonitrile

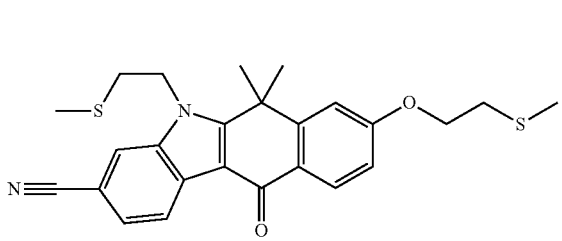 [SMILES: CSCCOc1ccc2c(c1)C(C)(C)c1c(c3ccc(C#N)cc3n1CCSC)C2=O]

The title compound was obtained as a by-product of the synthesis of Compound A7-4.
LCMS: m/z 377 [M+H]⁺
HPLC retention time: 3.75 min (analysis condition W)

Example 18

Compound A7-6

6,6-Dimethyl-11-oxo-8-(tetrahydro-pyran-4-yloxy)-6,11-dihydro-5H-benzo[b]carbazole-3-carbonitrile

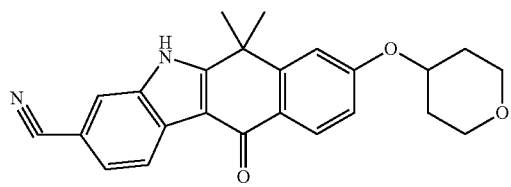 [SMILES: CC1(C)c2cc(OC3CCOCC3)ccc2C(=O)c2c1[nH]c1cc(C#N)ccc21]

Under the same conditions as the method for synthesizing Compound A7-1, the title compound was prepared from Compound A6 and tetrahydropyran-4-ol.
¹H-NMR (400 MHz, DMSO-d₆) δ: 12.72 (1H, br.s), 8.32 (1H, d, 8.5 Hz), 8.15 (1H, d, 8.5 Hz), 8.01 (1H, s), 7.61 (1H, d, 8.5 Hz), 7.38 (1H, s), 7.15 (1H, d, 8.5 Hz), 4.86-4.81 (1H, m), 3.93-3.88 (2H, m), 3.58-3.52 (2H, m), 2.06-2.00 (2H, m), 1.85 (6H, s), 1.69-1.60 (2H, m)
LCMS: m/z 387 [M+H]⁺
HPLC retention time: 3.47 min (analysis condition W)

Example 19

Compound A7-7

6,6-Dimethyl-11-oxo-8-(pyridin-4-ylmethoxy)-6,11-dihydro-5H-benzo[b]carbazole-3-carbonitrile

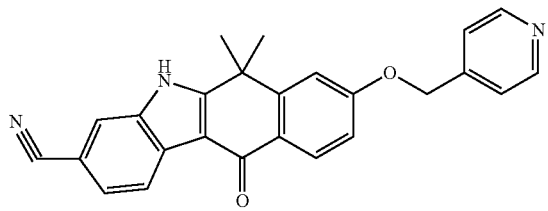 [SMILES: CC1(C)c2cc(OCc3ccncc3)ccc2C(=O)c2c1[nH]c1cc(C#N)ccc21]

Under the same conditions as the method for synthesizing Compound A7-1, the title compound was prepared from Compound A6 and pyridin-4-yl-methanol.
LCMS: m/z 394 [M+H]$^+$
HPLC retention time: 2.56 min (analysis condition W)

Example 20

Compound A7-8

8-(2-Methoxyethoxy)-6,6-dimethyl-11-oxo-6,11-dihydro-5H-benzo[b]carbazole-3-carbonitrile

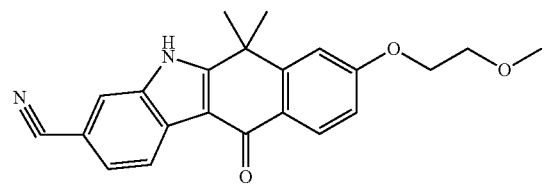 [SMILES: COCCOc1ccc2c(c1)C(C)(C)c1[nH]c3cc(C#N)ccc3c1C2=O]

Under the same conditions as the method for synthesizing Compound A7-1, the title compound was prepared from Compound A6 and 2-methoxyethanol.
$^1$H-NMR (400 MHz, DMSO-d$_6$) δ: 11.69 (1H, br. s), 8.27 (1H, d, 7.9 Hz), 8.10 (1H, d, 8.5 Hz), 7.95 (1H, s), 7.55 (1H, d, 7.9 Hz), 7.32 (1H, d, 2.4 Hz), 7.05 (1H, d, 8.5 Hz), 4.22 (2H, t, 4.3 Hz), 3.67 (2H, t, 4.3 Hz), 1.72 (6H, s)
LCMS: m/z 361 [M+H]$^+$
HPLC retention time: 3.38 min (analysis condition W)

Example 21

Compound A7-9

8-[2-(2-Methoxyethoxyl)ethoxy]-6,6-dimethyl-11-oxo-6,11-dihydro-5H-benzo[b]carbazole-3-carbonitrile

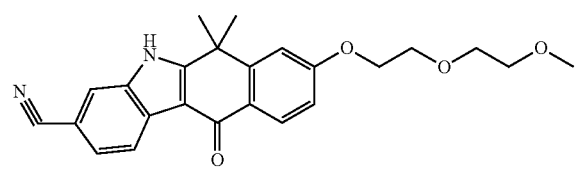 [SMILES: COCCOCCOc1ccc2c(c1)C(C)(C)c1[nH]c3cc(C#N)ccc3c1C2=O]

Under the same conditions as the method for synthesizing Compound A7-1, the title compound was prepared from Compound A6 and 2-(2-methoxyethoxyl)ethanol.
LCMS: m/z 405 [M+H]$^+$
HPLC retention time: 3.32 min (analysis condition W)

Example 22

Compound A7-10

6,6-Dimethyl-8-(3-methyloxetan-3-ylmethoxy)-11-oxo-6,11-dihydro-5H-benzo[b]carbazole-3-carbonitrile

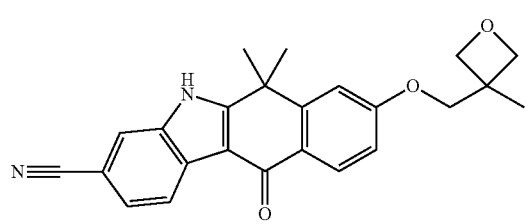 [SMILES: CC1(COc2ccc3c(c2)C(C)(C)c2[nH]c4cc(C#N)ccc4c2C3=O)COC1]

Under the same conditions as the method for synthesizing Compound A7-17, the title compound was prepared from Compound A6 and 3-chloromethyl-3-methyloxetane.
LCMS: m/z 387 [M+H]$^+$
HPLC retention time: 2.23 min (analysis condition S)

Example 23

Compound A7-11-1

[2-(3-Cyano-6,6-dimethyl-11-oxo-6,11-dihydro-5H-benzo[b]carbazol-8-yloxy)ethyl]ethyl-carbamic acid tert-butyl ester

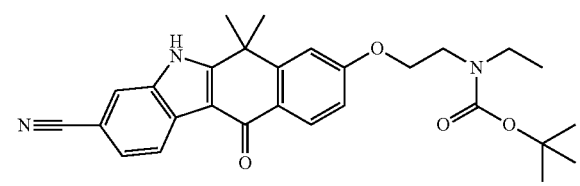 [SMILES: CCN(CCOc1ccc2c(c1)C(C)(C)c1[nH]c3cc(C#N)ccc3c1C2=O)C(=O)OC(C)(C)C]

Under the same conditions as the method for synthesizing Compound A7-1, the title compound was prepared from Compound A6 and ethyl-(2-hydroxy-ethyl)-carbamic acid tert-butyl ester.
LCMS: m/z 474 [M+H]$^+$
HPLC retention time: 2.93 min (analysis condition U)

Example 24

Compound A7-11-2

8-(2-Ethylaminoethoxy)-6,6-dimethyl-11-oxo-6,11-dihydro-5H-benzo[b]carbazole-3-carbonitrile

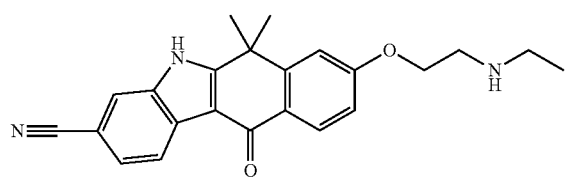 [SMILES: CCNCCOc1ccc2c(c1)C(C)(C)c1[nH]c3cc(C#N)ccc3c1C2=O]

Under the same conditions as the method for synthesizing Compound A8-1, the title compound was prepared from Compound A7-11-1.
LCMS: m/z 374 [M+H]$^+$
HPLC retention time: 1.35 min (analysis condition U)

Example 25

Compound A7-12

8-(2-Hydroxyethoxy)-6,6-dimethyl-11-oxo-6,11-dihydro-5H-benzo[b]carbazole-3-carbonitrile

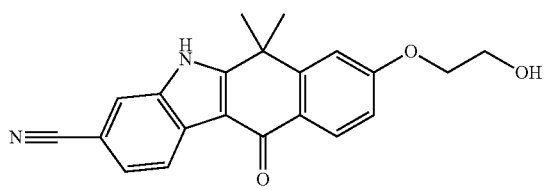 [SMILES: CC1(C)c2cc(OCCO)ccc2C(=O)c2c1[nH]c1cc(C#N)ccc21]

Under the same conditions as the method for synthesizing Compound A7-17, the title compound was prepared from Compound A6 and 2-bromo-ethanol.
LCMS: m/z 437 [M+H]$^+$
HPLC retention time: 2.93 min (analysis condition U)

Example 26

Compound A7-13-1

6,6-Dimethyl-11-oxo-8-(2-phenyl-[1,3]dioxan-5-yloxy)-6,11-dihydro-5H-benzo[b]carbazole-3-carbonitrile

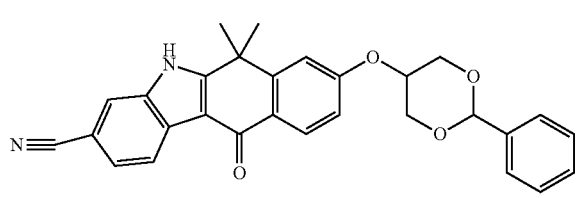 [SMILES: CC1(C)c2cc(OC3COC(c4ccccc4)OC3)ccc2C(=O)c2c1[nH]c1cc(C#N)ccc21]

Under the same conditions as the method for synthesizing Compound A7-1, the title compound was prepared from Compound A6 and 2-phenyl-[1,3]dioxan-5-ol.

LCMS: m/z 465 [M+H]$^+$
HPLC retention time: 4.10 min (analysis condition W)

Example 27

Compound A7-13-2

8-(2-Hydroxy-1-hydroxymethylethoxy)-6,6-dimethyl-11-oxo-6,11-dihydro-5H-benzo[b]carbazole-3-carbonitrile

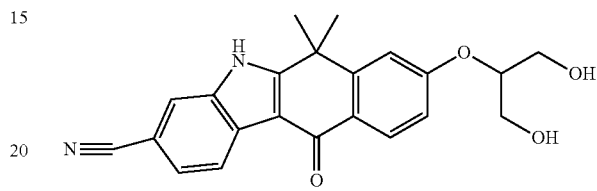

Anhydrous ferric trichloride (56 mg, 5 eq.) was added to the dichloromethane (2 mL) suspension of 6,6-dimethyl-11-oxo-8-(2-phenyl-[1,3]dioxan-5-yloxy)-6,11-dihydro-5H-benzo[b]carbazole-3-carbonitrile (Compound A7-13-1, 13 mg, 0.028 mmol), and stirred at room temperature for 1 hr. The reaction solution was added to water, and then extracted with ethyl acetate. The organic layer was washed with saturated brine and dried over sodium sulfate. The drying agent was removed by filtration and the residues obtained after concentration under reduced pressure were purified by high performance liquid chromatography to obtain the title compound (7 mg, 46%).
LCMS: m/z 377 [M+H]$^+$
HPLC retention time: 2.70 min (analysis condition W)

Example 28

Compound A7-14-1

8-((S)-2,2-Dimethyl-[1,3]dioxolan-4-ylmethoxy)-6,6-dimethyl-11-oxo-6,11-dihydro-5H-benzo[b]carbazole-3-carbonitrile

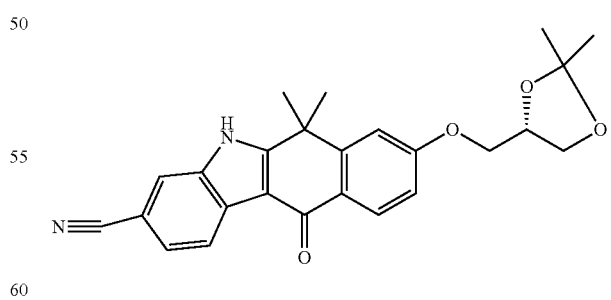

Under the same conditions as the method for synthesizing Compound A7-17, the title compound was prepared from Compound A6 and toluene-4-sulfonic acid (R)-2,2-dimethyl-[1,3]dioxolan-4-ylmethyl ester.
LCMS: m/z 417 [M+H]$^+$
HPLC retention time: 3.47 min (analysis condition Y)

Example 29

Compound A7-14-2

8-((R)-2,3-Dihydroxy-propoxy)-6,6-dimethyl-11-oxo-6,11-dihydro-5H-benzo[b]carbazole-3-carbonitrile

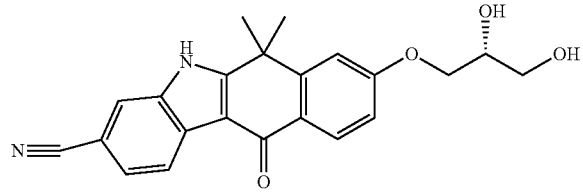 [SMILES: CC1(C)c2cc(OC[C@H](O)CO)ccc2C(=O)c2c1[nH]c1cc(C#N)ccc21]

To the solution of THF and water (4:1, 1 mL) of 8-(2,2-dimethyl-[1,3]dioxolan-4-ylmethoxy)-6,6-dimethyl-11-oxo-6,11-dihydro-5H-benzo[b]carbazole-3-carbonitrile (Compound A14-1, 30 mg, 0.07 mmol), camphor sulfonic acid (36 mg, 0.14 mmol) was added at room temperature. After stirring at room temperature for 38 hr, the mixture was extracted with ethyl acetate. The organic layer was dried over sodium sulfate. The drying agent was removed by filtration and the residues obtained after concentration under reduced pressure were purified by silica gel column chromatography (dichloromethane/methanol) to obtain the title compound (white solid, 28 mg, 72%).

$^1$H-NMR (300 MHz, DMSO-$d_6$) σppm; 12.7 (s, 1H), 8.31 (d, 1H, J=8.01 Hz), 8.15 (d, 1H, J=8.77 Hz), 8.00 (s, 1H), 7.60 (d, 1H, J=8.01 Hz), 7.12 (s, 1H), 7.09 (d, 1H, J=8.77 Hz), 4.46 (m, 1H), 4.15 (m, 3H), 3.78 (m, 1H), 1.76 (s, 6H), 1.38 (s, 3H), 1.32 (s, 3H)

LCMS: m/z 377 [M+H]$^+$

HPLC retention time: 1.80 min (analysis condition U)

Example 30

Compound A7-14-3

8-((S)-2,2-Dimethyl-[1,3]dioxolan-4-ylmethoxy)-5,6,6-trimethyl-11-oxo-6,11-dihydro-5H-benzo[b]carbazole-3-carbonitrile

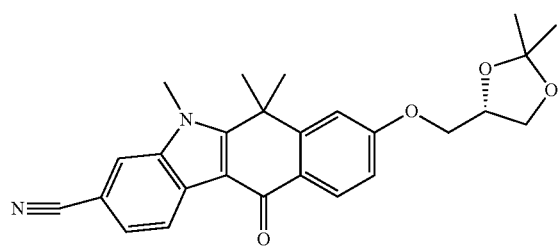 [SMILES: Cn1c2c(c3ccc(C#N)cc31)C(=O)c1ccc(OC[C@H]3COC(C)(C)O3)cc1C2(C)C]

Under the same conditions as the method for synthesizing Compound B3-4, the title compound was prepared as a crude product from Compound A7-14-1.

Example 31

Compound A7-14-4

8-((R)-2,3-Dihydroxy-propoxy)-5,6,6-trimethyl-11-oxo-6,11-dihydro-5H-benzo[b]carbazole-3-carbonitrile

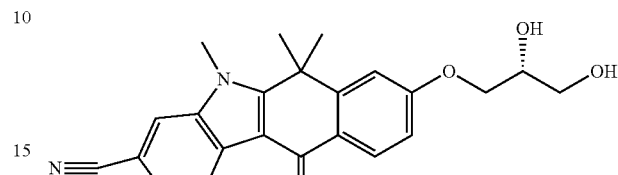

Under the same conditions as the method for synthesizing Compound A7-14-2, the title compound was prepared from Compound A7-14-3 (303 mg, 98%).

LCMS: m/z 484 [M+H]$^+$

HPLC retention time: 2.08 min (analysis condition D)

Example 32

Compound A7-15-1

8-[(4R,5S)-5-(Tert-butyl-dimethyl-silanyloxymethyl)-2,2-dimethyl-[1,3]dioxolan-4-ylmethoxy]-6,6-dimethyl-11-oxo-6,11-dihydro-5H-benzo[b]carbazole-3-carbonitrile

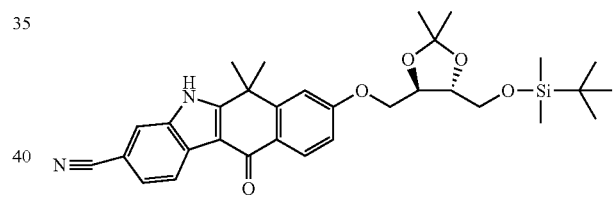

Under the same conditions as the method for synthesizing Compound A7-1, the title compound was prepared from Compound A6 and [(R4R,5R)-5-(tert-butyl-dimethyl-silanyloxymethyl)-2,2-dimethyl-[1,3]dioxolan-4-yl]-methanol.

LCMS: m/z 516 [M+H]$^+$

HPLC retention time: 3.97 min (analysis condition Y)

Example 33

Compound A7-15-2

6,6-Dimethyl-11-oxo-8-((2R,3R)-2,3,4-trihydroxy-butoxy)-6,11-dihydro-5H-benzo[b]carbazole-3-carbonitrile

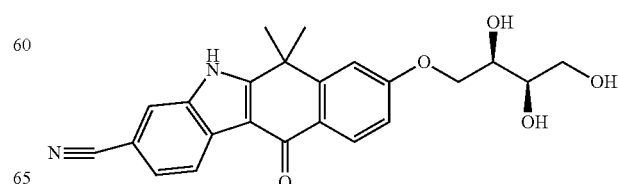

Under the same conditions as the method for synthesizing Compound A7-14-2, the title compound was prepared from Compound A7-15-1.
LCMS: m/z 407 [M+H]+
HPLC retention time: 1.73 min (analysis condition U)

Example 34

Compound A7-16

6,6-Dimethyl-8-(1-methyl-piperidin-4-yloxy)-11-oxo-6,11-dihydro-5H-benzo[b]carbazole-3-carbonitrile

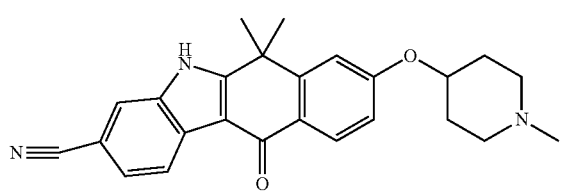 [SMILES: CN1CCC(Oc2ccc3c(c2)C(C)(C)c2[nH]c4cc(C#N)ccc4c2C3=O)CC1]

Under the same conditions as the method for synthesizing Compound A7-1, the title compound was prepared from Compound A6 and 1-methylpiperidin-4-ol.
$^1$H-NMR (400 MHz, DMSO-$d_6$) δ: 12.75 (1H, s), 8.32 (1H, d, J=7.9 Hz), 8.14 (1H, d, J=9.8 Hz), 8.00 (1H, s), 7.60 (1H, d, J=7.9 Hz), 7.34 (1H, s), 7.11 (1H, d, J=9.1 Hz), 4.62 (1H, m), 2.64 (2H, m), 2.23 (2H, m), 2.21 (s, 3H), 1.99 (2H, m), 1.77 (s, 6H), 1.73 (2H, m).
LCMS: m/z 400 [M+H]+
HPLC retention time: 1.42 min (analysis condition S)

Example 35

Compound A7-17

8-(2-Diethylamino-ethoxy)-6,6-dimethyl-11-oxo-6,11-dihydro-5H-benzo[b]carbazole-3-carbonitrile

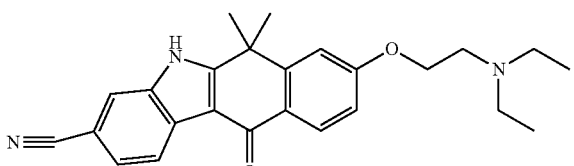

8-Hydroxy-6,6-dimethyl-11-oxo-6,11-dihydro-5H-benzo[b]carbazole-3-carbonitrile (Compound A6, 25 mg, 0.083 mmol) was dissolved in N,N-dimethylacetamide (1 mL), added with 2-chloroethyldiethylamine (16 mg, 1.1 eq.) and cesium carbonate (54 mg, 2 eq.) in order and stirred at 100° C. for 4 hr. The reaction solution was poured over water and extracted with ethyl acetate. The organic layer was washed with saturated brine and dried over sodium sulfate. The drying agent was removed by filtration and the residues obtained after concentration under reduced pressure were purified by amino silica gel column chromatography (ethyl acetate/hexane) to obtain the title compound (11 mg, 32%).
$^1$H-NMR (400 MHz, DMSO-$d_6$) δ: 8.32 (1H, d, J=8.2 Hz), 8.15 (1H, d, J=8.7 Hz), 8.01 (1H, s), 7.61 (1H, d, J=8.2 Hz), 7.35 (1H, d, J=1.8 Hz), 7.09 (1H, dd, J=8.7, 1.8 Hz), 4.19 (2H, t, J=5.9 Hz), 2.83 (2H, t, J=5.9 Hz), 2.58 (4H, q, J=7.0 Hz), 1.78 (6H, s), 1.00 (6H, t, J=7.0 Hz)
LCMS: m/z 402 [M+H]+
HPLC retention time: 2.52 min (analysis condition W)

Example 36

Compound A7-18

N-[2-(3-Cyano-6,6-dimethyl-11-oxo-6,11-dihydro-5H-benzo[b]carbazol-8-yloxy)-ethyl]-acetamide

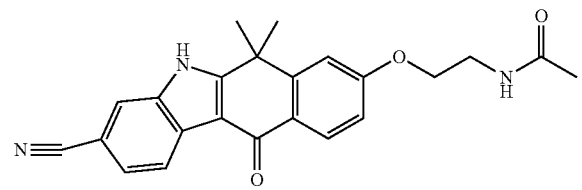 [SMILES: CC(=O)NCCOc1ccc2c(c1)C(C)(C)c1[nH]c3cc(C#N)ccc3c1C2=O]

Under the same conditions as the method for synthesizing Compound A7-17, the title compound was prepared from Compound A6 and 2-chloroethylacetamide.
LCMS: m/z 388 [M+H]+
HPLC retention time: 2.91 min (analysis condition W)

Example 37

Compound A7-19

[2-(3-Cyano-6,6-dimethyl-11-oxo-6,11-dihydro-5H-benzo[b]carbazol-8-yloxy)-ethyl]-carbamic acid ethyl ester

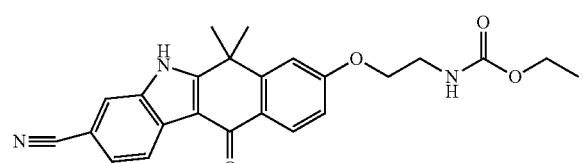

Under the same conditions as the method for synthesizing Compound A7-17, the title compound was prepared from Compound A6 and ethyl-2-chloroethylcarbamate.
LCMS: m/z 418 [M+H]+
HPLC retention time: 3.35 min (analysis condition W)

Example 38

Compound A7-20

[2-(3-Cyano-6,6-dimethyl-11-oxo-6,11-dihydro-5H-benzo[b]carbazol-8-yloxy)-ethyl]-urea

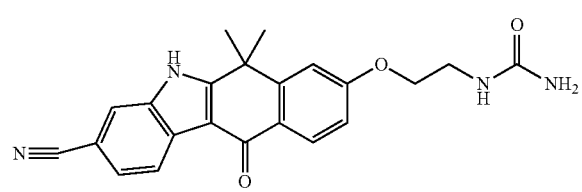 [SMILES: CC1(C)c2cc(OCCNC(N)=O)ccc2C(=O)c2c1[nH]c1cc(C#N)ccc21]

Under the same conditions as the method for synthesizing Compound A7-17, the title compound was prepared from Compound A6 and 2-chloroethylurea.
LCMS: m/z 399 [M+H]+
HPLC retention time: 2.80 min (analysis condition W)

Example 39

Compound A7-21

6,6-Dimethyl-8-(oxetan-3-yloxy)-11-oxo-6,11-di-hydro-5H-benzo[b]carbazole-3-carbonitrile

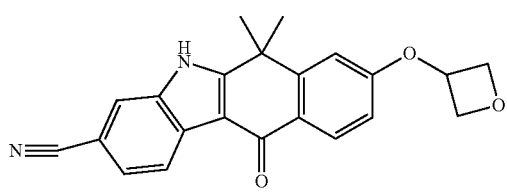 [SMILES: CC1(C)c2cc(OC3COC3)ccc2C(=O)c2c1[nH]c1cc(C#N)ccc21]

Under the same conditions as the method for synthesizing Compound A7-17, the title compound was prepared from Compound A6 and toluene-4-sulfonic acid oxetan-3-yl ester.
LCMS: m/z 359 [M+H]+
HPLC retention time: 2.00 min (analysis condition S)

Example 40

Compound A7-22

6,6-Dimethyl-11-oxo-8-(pyrimidin-2-yloxy)-6,11-dihydro-5H-benzo[b]carbazole-3-carbonitrile

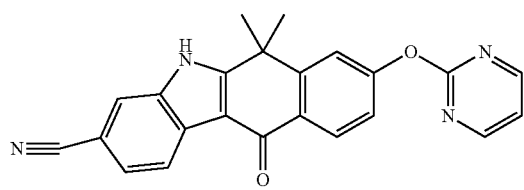 [SMILES: CC1(C)c2cc(Oc3ncccn3)ccc2C(=O)c2c1[nH]c1cc(C#N)ccc21]

Under the same conditions as the method for synthesizing Compound A7-17, the title compound was prepared from Compound A6 and 2-bromopyrimidine.
LCMS: m/z 381 [M+H]+
HPLC retention time: 2.00 min (analysis condition S)

Example 41

Compound A7-23

(3-Cyano-6,6-dimethyl-11-oxo-6,11-dihydro-5H-benzo[b]carbazol-8-yloxy)-ethyl acetate ester

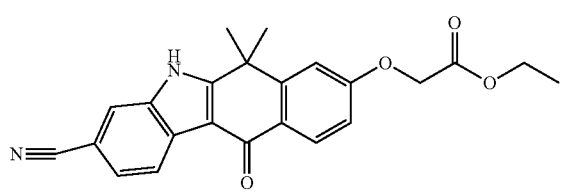 [SMILES: CCOC(=O)COc1ccc2c(c1)C(C)(C)c1[nH]c3cc(C#N)ccc3c1C2=O]

Under the same conditions as the method for synthesizing Compound A7-17, the title compound was prepared from Compound A6 and 3-chloro-propionic acid ethyl ester.
LCMS: m/z 389 [M+H]+
HPLC retention time: 3.37 min (analysis condition U)

Example 42

Compound A7-24

8-(2-Bromo-ethoxy)-6,6-dimethyl-11-oxo-6,11-dihydro-5H-benzo[b]carbazole-3-carbonitrile

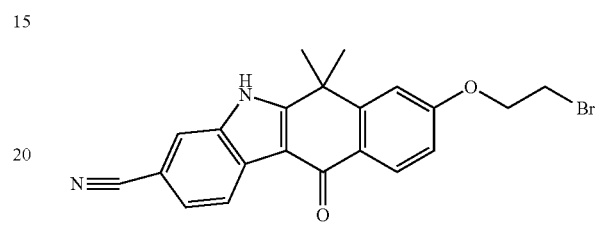

Under the same conditions as the method for synthesizing Compound A7-1, the title compound was prepared from Compound A6 and 2-bromoethanol.
$^1$H-NMR (270 MHz, DMSO-$d_6$) δ: 12.75 (1H, br.s), 8.32 (1H, d, J=8.2 Hz), 8.17 (1H, d, J=8.6 Hz), 8.01 (1H, s), 7.61 (1H, dd, J=8.2, 1.4 Hz), 7.40 (1H, d, J=2.2 Hz), 7.12 (1H, dd, J=8.6, 2.2 Hz), 4.50 (2H, t, J=5.3 Hz), 3.88 (2H, t, J=5.3 Hz), 1.77 (6H, s).
LCMS: m/z 409, 411 [M+H]+
HPLC retention time: 2.48 min (analysis condition S)

Example 43

Compound A7-25

6,6-Dimethyl-11-oxo-8-(piperidin-4-ylmethoxy)-6,11-dihydro-5H-benzo[b]carbazole-3-carbonitrile hydrochloric acid salt

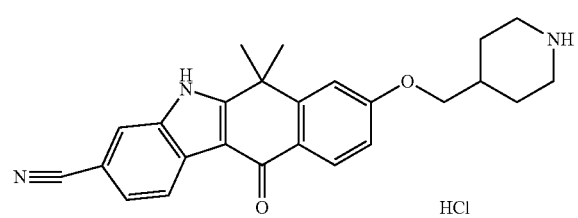 [SMILES: CC1(C)c2cc(OCC3CCNCC3)ccc2C(=O)c2c1[nH]c1cc(C#N)ccc21 ; Cl]

Under nitrogen atmosphere, 3-cyano-8-hydroxy-6,6-dimethyl-5,6-dihydro-benzo[b]carbazol-11-one (Compound A6, 85 mg, 0.28 mmol) and triphenylphosphine (150 mg, 2 eq.) were added with THF (2 ml), and then further added dropwise with 4-hydroxymethyl-piperidine-1-carboxylic acid tert-butyl ester (120 mg, 2 eq.) and 2.19 N toluene solution of diethyl azodicarboxylic acid (0.26 mL, 2 eq.). The resultant was stirred at room temperature for 12 hr under nitrogen atmosphere. The residues obtained after concentrating the reaction solution under reduced pressure were purified by silica gel column chromatography (ethyl acetate/dichloromethane) to obtain 4-(3-cyano-6,6-dimethyl-11- oxo-6,11-dihydro-5H-benzo[b]carbazol-8-yloxymethyl)-piperidine-1-carboxylic acid tert-butyl ester (white powder, 120 mg).

To the resulting compound, 4 N hydrochloric acid and dioxane solution was added under cooling. After stirring at room temperature for 2 hr, the solvent was removed under nitrogen stream. Then, the residues were washed with diethyl ether and then subjected to azeotropic treatment with toluene, followed by drying under vacuum and filtration to obtain the title compound (79 mg).

LCMS: m/z 399 [M+H]$^+$
HPLC retention time: 2.22 min (analysis condition C)

Example 44

Compound A8-1

6,6-Dimethyl-11-oxo-8-(piperidin-4-yloxy)-6,11-dihydro-5H-benzo[b]carbazole-3-carbonitrile

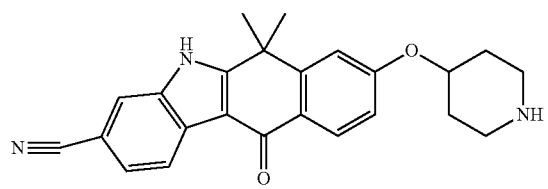 [SMILES: CC1(C)c2cc(OC3CCNCC3)ccc2C(=O)c2c1[nH]c1cc(C#N)ccc21]

THF (0.5 mL) and TFA (0.5 mL) were added to 4-(3-cyano-6,6-dimethyl-11-oxo-6,11-dihydro-5H-benzo[b]carbazol-8-yloxy)-piperidine-1-carboxylic acid tert-butyl ester (Compound A7-1, 35 mg, 0.072 mmol), and the mixture was stirred at room temperature until Compound A7-1 disappears. The reaction solution was concentrated under reduced pressure and the residue was desalinated by using anion exchanger PL StratoSpheres (trademark) PL-HCO3 MP to obtain the title compound (37 mg, 76%).

$^1$H-NMR (400 MHz, CD$_3$OD) δ: 8.38 (1H, d, J=7.9 Hz), 8.24 (1H, d, J=8.5 Hz), 7.85 (1H, s), 7.53 (1H, d, J=7.9 Hz), 7.27 (1H, s), 7.09 (1H, d, J=8.5 Hz), 4.67-4.76 (1H, m), 3.07-3.20 (2H, m), 2.77-2.87 (2H, m), 2.03-2.15 (2H, m), 1.80 (6H, s), 1.69-1.77 (2H, m)

LCMS: m/z 386 [M+H]$^+$
HPLC retention time: 2.51 min (analysis condition W)

Example 45

Compound A8-2

8-(2-Amino-ethoxy)-6,6-dimethyl-11-oxo-6,11-dihydro-5H-benzo[b]carbazole-3-carbonitrile

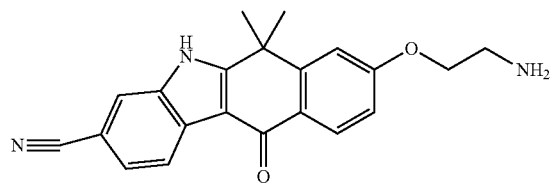 [SMILES: CC1(C)c2cc(OCCN)ccc2C(=O)c2c1[nH]c1cc(C#N)ccc21]

Under the same conditions as the method for synthesizing Compound A8-1, the title compound was prepared from Compound A7-3.

LCMS: m/z 346 [M+H]$^+$
HPLC retention time: 2.40 min (analysis condition W)

Example 46

Compound A8-3

8-(2-Methanesulfonyl-ethoxy)-6,6-dimethyl-11-oxo-6,11-dihydro-5H-benzo[b]carbazole-3-carbonitrile

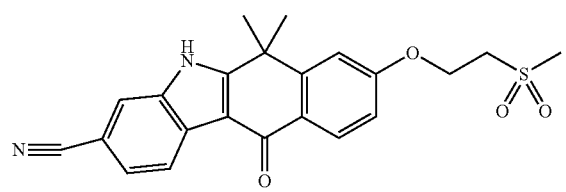 [SMILES: CC1(C)c2cc(OCCS(C)(=O)=O)ccc2C(=O)c2c1[nH]c1cc(C#N)ccc21]

Under the same conditions as the method for synthesizing Compound B3-8, the title compound was prepared from Compound A7-5.

LCMS: m/z 409 [M+H]$^+$
HPLC retention time: 3.13 min (analysis condition W)

Example 47

Compound A8-4

8-(2-Methanesulfinyl-ethoxy)-6,6-dimethyl-11-oxo-6,11-dihydro-5H-benzo[b]carbazole-3-carbonitrile

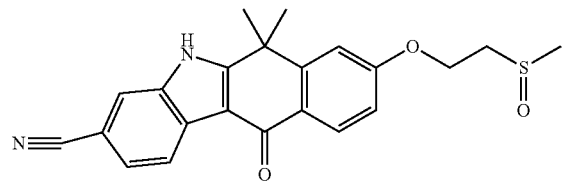 [SMILES: CS(=O)CCOc1ccc2c(c1)C(C)(C)c1[nH]c3cc(C#N)ccc3c1C2=O]

The title compound was obtained as a by-product of the synthesis of Compound A8-3.

LCMS: m/z 393 [M+H]$^+$
HPLC retention time: 2.87 min (analysis condition W)

Example 48

Compound A8-5

5,6,6-Trimethyl-11-oxo-8-(tetrahydro-pyran-4-yloxy)-6,11-dihydro-5H-benzo[b]carbazole-3-carbonitrile

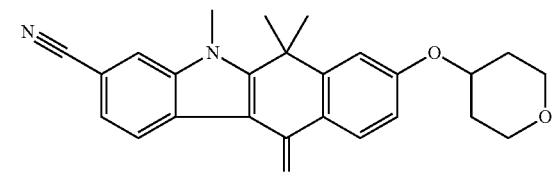

Under the same conditions as the method for synthesizing Compound A10-1, the title compound was prepared from Compound A7-6.

LCMS: m/z 401 [M+H]+
HPLC retention time: 2.72 min (analysis condition S)

Example 49

Compound A8-6-1

2-Bromo-8-methoxy-6,6-dimethyl-11-oxo-6,11-dihydro-5H-benzo[b]carbazole-3-carbonitrile

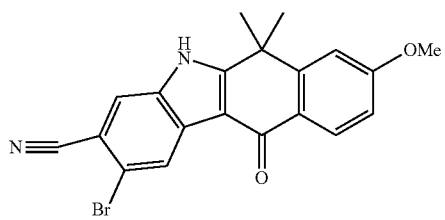 [SMILES: COc1ccc2c(c1)C(C)(C)c1[nH]c3cc(C#N)c(Br)cc3c1C2=O]

8-Methoxy-6,6-dimethyl-11-oxo-6,11-dihydro-5H-benzo[b]carbazole-3-carbonitrile (Compound A5-2, 50 mg, 0.158 mmol) was dissolved in CH$_3$CN (1 mL), added with NBS (56 mg, 2 eq.), and stirred at 80° C. overnight. The reaction solution was added to water, and then extracted with ethyl acetate. The organic layer was washed with saturated brine and dried over sodium sulfate. The drying agent was removed by filtration and the residues obtained after concentration under reduced pressure were added with MeOH and the solid remained after dissolution was filtered to obtain the target compound (yellow powder, 20 mg, 38%).

$^1$H-NMR (400 MHz, DMSO-d$_6$) δ: 12.92 (1H, s), 8.50 (1H, s), 8.16 (1H, d, J=8.5 Hz), 8.14 (1H, s), 7.36 (1H, d, J=2.4 Hz), 7.11 (1H, dd, J=8.5, 2.4 Hz), 3.92 (3H, s), 1.78 (6H, s).

LCMS: m/z 395, 397 [M+H]+
HPLC retention time: 2.57 min (analysis condition S)

Example 50

Compound A8-6-2

2-Bromo-8-hydroxy-6,6-dimethyl-11-oxo-6,11-dihydro-5H-benzo[b]carbazole-3-carbonitrile

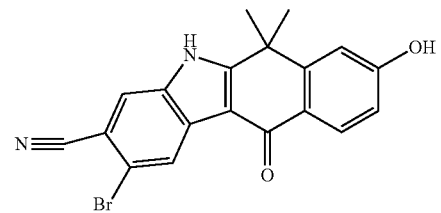 [SMILES: CC1(C)c2cc(O)ccc2C(=O)c2c1[nH]c1cc(C#N)c(Br)cc21]

Under the same conditions as the method for synthesizing Compound A6, the title compound was prepared from Compound A8-6-1.

$^1$H-NMR (400 MHz, DMSO-d$_6$) δ: 8.46 (1H, s), 8.10 (1H, s), 8.05 (1H, d, J=8.6 Hz), 7.13 (1H, d, J=2.1 Hz), 6.89 (1H, dd, J=8.5, 2.1 Hz), 1.71 (6H, s).

LCMS: m/z 381, 383 [M+H]+
HPLC retention time: 2.10 min (analysis condition S)

Example 51

Compound A8-6-3

2-Bromo-8-(2-diethylamino-ethoxy)-6,6-dimethyl-11-oxo-6,11-dihydro-5H-benzo[b]carbazole-3-carbonitrile

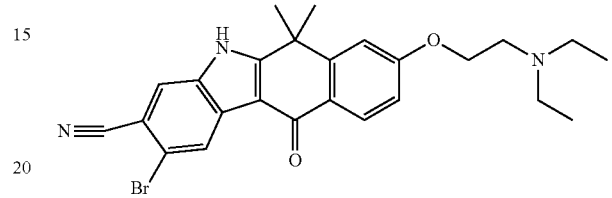

Under the same conditions as the method for synthesizing Compound A7-17, the title compound was prepared from Compound A8-6-2.

$^1$H-NMR (400 MHz, CD$_3$OD) δ: 8.53 (1H, d, J=0.5 Hz), 8.20 (1H, d, J=8.7 Hz), 7.88 (1H, d, J=0.5 Hz), 7.28 (1H, d, J=2.3 Hz), 7.05 (1H, dd, J=8.9, 2.5 Hz), 4.24 (2H, t, J=5.7 Hz), 2.96 (2H, t, J=5.7 Hz), 2.70 (4H, q, J=7.1 Hz), 1.79 (6H, s), 1.12 (6H, t, J=7.2 Hz).

LCMS: m/z 480, 482 [M+H]+
HPLC retention time: 1.73 min (analysis condition S)

Example 52

Compound A8-7

(3-Cyano-6,6-dimethyl-11-oxo-6,11-dihydro-5H-benzo[b]carbazol-8-yloxy)-acetic acid

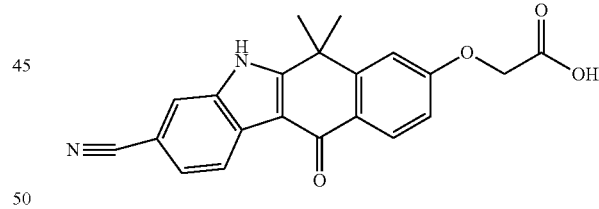

(3-Cyano-6,6-dimethyl-11-oxo-6,11-dihydro-5H-benzo[b]carbazol-8-yloxy)-ethyl acetate ester (Compound A7-23, 180 mg, 0.464 mmol) and potassium hydroxide (130 mg, 2.32 mmol) were dissolved in THF (10 ml) and water (1.8 mL), and stirred at 70° C. for 2 hr. After cooling to room temperature, the mixture was extracted with dichloromethane. Water layer (日本語誤変換) was adjusted to be acidic by using 1 N hydrochloric acid, and the precipitated solid was filtered and washed several times with water to obtain the title compound (white solid, 130 mg, 78%).

$^1$H-NMR (300 MHz, DMSO) σppm 13.09 (s, 1H), 8.31 (d, 1H, J=8.1 Hz), 8.11 (d, 1H, J=8.4 Hz), 8.01 (s, 1H), 7.58 (d, 1H, J=7.8 Hz), 7.25 (d, 1H, J=2.1 Hz), 6.97 (d, 1H, J=8.4 Hz), 4.51 (s, 2H), 1.73 (s, 6H)

LCMS: m/z 361 [M+H]+
HPLC retention time: 2.97 min (analysis condition U)

Example 53

Compound A8-8

6,6-Dimethyl-8-(2-morpholin-4-yl-ethoxy)-11-oxo-6,11-dihydro-5H-benzo[b]carbazole-3-carbonitrile

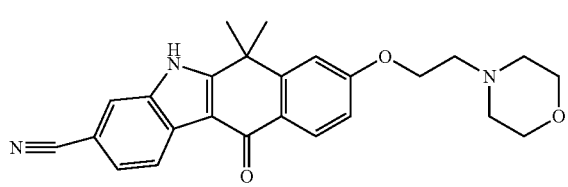 [SMILES: CC1(C)c2cc(OCCN3CCOCC3)ccc2C(=O)c2c1[nH]c1cc(C#N)ccc21]

Under the same conditions as the method for synthesizing Compound A8-17, the title compound was prepared from Compound A7-24 and morpholine.

$^1$H-NMR (500 MHz, CD$_3$OD+CDCl$_3$) σ ppm; 8.4 (d, 1H, J=8.2 Hz), 8.3 (d, 1H, J=8.7 Hz), 7.8 (s, 1H), 7.5 (dd, 1H, J=1.1 Hz, J=8.2 Hz), 7.2 (d, 1H, J=2.3 Hz), 7.0 (dd, 1H, J=2.2 Hz, J=8.7 Hz), 4.2 (t, 2H, J=5.3 Hz), 3.7 (t, 4H, J=4.5 Hz), 2.9 (t, 2H, J=5.3 Hz), 2.6 (t, 4H, J=4.5 Hz), 1.8 (s, 6H)

LCMS: m/z 416 [M+H]$^+$

HPLC retention time: 2.40 min (analysis condition U)

Example 54

Compound A8-9

8-[2-(1,1-Dioxothiomorpholino)-ethoxy]-6,6-dimethyl-11-oxo-6,11-dihydro-5H-benzo[b]carbazole-3-carbonitrile

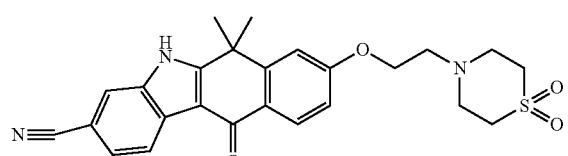

Under the same conditions as the method for synthesizing Compound A7-17, the title compound was prepared from Compound A7-24 and thiomorpholine-1,1-dioxide.

$^1$H-NMR (400 MHz, DMSO-d$_6$) δ: 12.72 (1H, s), 8.31 (1H, d, 8.5 Hz), 8.15 (1H, d, 8.5 Hz), 8.00 (1H, s), 7.60 (1H, d, 8.5 Hz), 7.36 (1H, d, 1.8 Hz), 7.10 (1H, dd, 1.8, 8.5), 4.25 (2H, t, 5.5 Hz), 3.06-3.33 (8H, m), 2.97 (2H, t, 5.5), 1.77 (6H, s)

LCMS: m/z 464 [M+H]$^+$

HPLC retention time: 2.70 min (analysis condition W)

Example 55

Compound A8-10

8-(2-Tert-butylamino-ethoxy)-6,6-dimethyl-11-oxo-6,11-dihydro-5H-benzo[b]carbazole-3-carbonitrile

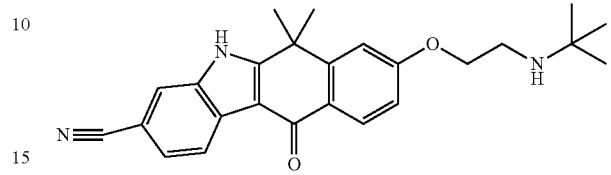

Under the same conditions as the method for synthesizing Compound A7-17, the title compound was prepared from Compound A7-24 and tert-butylamine.

$^1$H-NMR (400 MHz, DMSO-d6) δ: 12.71 (1H, s), 8.32 (1H, d, 7.9 Hz), 8.15 (1H, d, 9.1 Hz), 8.07 (1 d, 1.8 Hz), 7.60 (1H, dd, 1.8, 7.9 Hz), 7.35 (1H, d, 2.4 Hz), 7.09 (1H, dd, 2.4, 9.1 Hz), 4.16 (2H, t, 6.1 Hz), 2.91 (2H, t, 6.1 Hz), 1.77 (6H, s), 1.08 (9H, s)

LCMS: m/z 402 [M+H]$^+$

HPLC retention time: 2.55 min (analysis condition W)

Example 56

Compound A8-11

8-(2-Sec-butylamino-ethoxy)-6,6-dimethyl-11-oxo-6,11-dihydro-5H-benzo[b]carbazole-3-carbonitrile

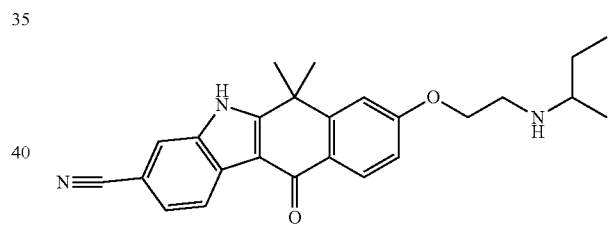

Under the same conditions as the method for synthesizing Compound A8-17, the title compound was prepared from Compound A7-24 and sec-butylamine.

LCMS: m/z 402 [M+H]$^+$

HPLC retention time: 1.88 min (analysis condition U)

Example 57

Compound A8-12

8-[2-(2-Hydroxy-1,1-dimethyl-ethylamino)-ethoxy]-6,6-dimethyl-11-oxo-6,11-dihydro-5H-benzo[b]carbazole-3-carbonitrile

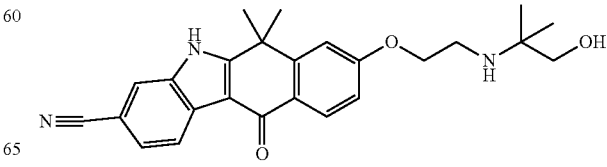

Under the same conditions as the method for synthesizing Compound A8-17, the title compound was prepared from Compound A7-24 and 2-amino-2-methyl-propan-1-ol.

¹H-NMR (300 MHz, DMSO-d6) σppm; 12.65 (brs, 1H), 8.31 (d, 1H, J=8.0 Hz), 8.15 (d, 1H, J=8.8 Hz), 7.99 (s, 1H), 7.59 (d, 1H, J=8.0 Hz), 7.34 (d, 1H, J=2.3 Hz), 7.08 (dd, 1H, J=2.2 Hz, J=8.8 Hz), 4.58 (brs, 1H), 4.16 (t, 2H, J=5.7 Hz), 3.20 (s, 2H), 2.88 (t, 2H, J=5.7 Hz), 1.76 (s, 6H), 0.97 (s, 6H)

LCMS: m/z 418 [M+H]⁺
HPLC retention time: 2.47 min (analysis condition U)

Example 58

Compound A8-13

8-[2-(4-Ethyl-piperazin-1-yl)-ethoxy]-6,6-dimethyl-11-oxo-6,11-dihydro-5H-benzo[b]carbazole-3-carbonitrile

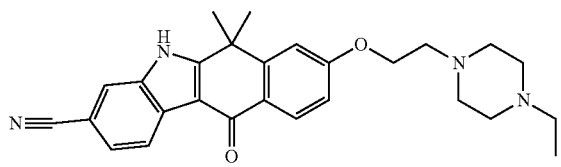 [SMILES: CCN1CCN(CCOc2ccc3c(c2)C(C)(C)c2[nH]c4cc(C#N)ccc4c2C3=O)CC1]

Under the same conditions as the method for synthesizing Compound A8-17, the title compound was prepared from Compound A7-24 and 1-ethyl-piperazine.

LCMS: m/z 443 [M+H]⁺
HPLC retention time: 1.68 min (analysis condition U)

Example 59

Compound A8-14

8-(2-Imidazol-1-yl-ethoxy)-6,6-dimethyl-11-oxo-6,11-dihydro-5H-benzo[b]carbazole-3-carbonitrile

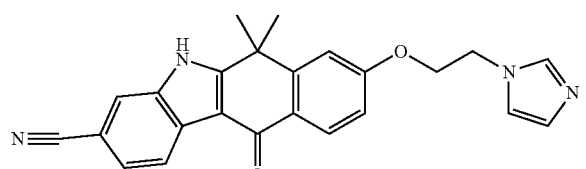

Under the same conditions as the method for synthesizing Compound A7-1, the title compound was prepared from Compound A6 and 2-imidazol-1-yl-ethanol.

¹H-NMR (300 MHz, DMSO-d6) σ ppm; 12.71 (s, 1H), 8.31 (d, 1H, J=8.3 Hz), 8.14 (d, 1H, J=8.8 Hz), 7.99 (s, 1H), 7.73 (s, 1H), 7.60 (d, 1H, J=8.3 Hz), 7.34 (s, 1H), 7.29 (s, 1H), 7.09 (d, 1H, J=8.8 Hz), 6.91 (s, 1H), 4.20 (s, 4H), 1.76 (s, 6H)

LCMS: m/z 387 [M+H]⁺
HPLC retention time: 1.77 min (analysis condition U)

Example 60

Compound A8-15

8-{2-[Bis-(2-hydroxy-ethyl)-amino]-ethoxy}-6,6-dimethyl-11-oxo-6,11-dihydro-5H-benzo[b]carbazole-3-carbonitrile

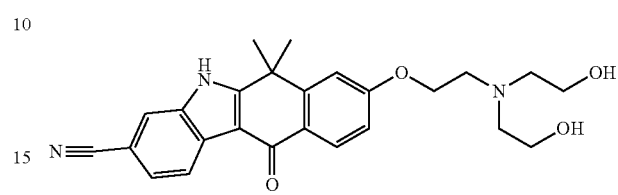

According to the same method as the method for synthesizing Compound A7-17, the title compound was prepared from Compound A7-24 and 2-(2-hydroxy-ethylamino)-ethanol.

LCMS: m/z 434 [M+H]⁺
HPLC retention time: 2.40 min (analysis condition U)

Example 61

Compound A8-16

1-[2-(3-Cyano-6,6-dimethyl-11-oxo-6,11-dihydro-5H-benzo[b]carbazol-8-yloxy)-ethyl]-piperidine-4-carboxylic acid amide

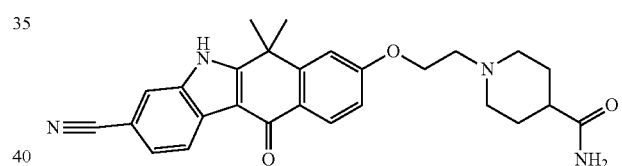

Under the same conditions as the method for synthesizing Compound A8-17, the title compound was prepared from Compound A7-24 and piperidine-4-carboxylic acid amide.

LCMS: m/z 457 [M+H]⁺
HPLC retention time: 1.28 min (analysis condition S)

Example 62

Compound A8-17

6,6-Dimethyl-11-oxo-8-[2-(3-oxo-piperazin-1-yl)-ethoxy]-6,11-dihydro-5H-benzo[b]carbazole-3-carbonitrile

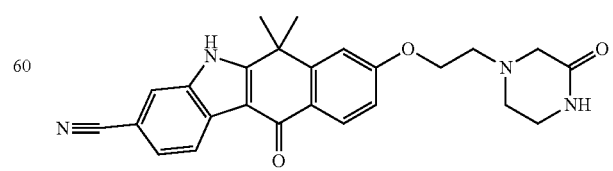

To DMF solution (5 mL) of 8-(2-bromo-ethoxy)-6,6-dimethyl-11-oxo-6,11-dihydro-5H-benzo[b]carbazole-3- carbonitrile (Compound A7-24, 30 mg, 0.07 mmol), piperazin-2-one (44.9 mg, 0.35 mmol) and N,N-diisopropylethylamine (0.061 mL, 0.35 mmol) were added at room temperature and stirred at 80° C. for 18 hr. After cooling to room temperature, the mixture was extracted with ethyl acetate washed with saturated brine. The organic layer was dried over magnesium sulfate. The drying agent was removed by filtration and the residues obtained after concentration under reduced pressure were purified by preparative TLC (dichloromethane/methanol) to obtain the title compound (white solid, 24 mg, 80%).

$^1$H-NMR (300 MHz, DMSO-d6) σppm; 12.71 (s, 1H), 8.32 (d, 1H, J=8.4 Hz), 8.15 (d, 1H, J=8.8 Hz), 8.00 (s, 1H), 7.75 (s, 1H), 7.60 (d, 1H, J=8.4 Hz), 7.37 (d, 1H, J=2.3 Hz), 7.09 (dd, 1H, J=2.3 Hz, J=8.8 Hz), 4.27 (t, 2H, J=5.7 Hz), 3.19 (m, 2H), 3.08 (s, 2H), 2.83 (t, 2H, J=5.7 Hz), 2.70 (t, 2H, J=5.7 Hz), 1.8 (s, 6H)

LCMS: m/z 429 [M+H]$^+$

HPLC retention time: 1.29 min (analysis condition S)

Example 63

Compound A8-18

Morpholine-4-sulfonic acid[2-(3-cyano-6,6-dimethyl-11-oxo-6,11-dihydro-5H-benzo[b]carbazol-8-yloxy)-ethyl]-amide

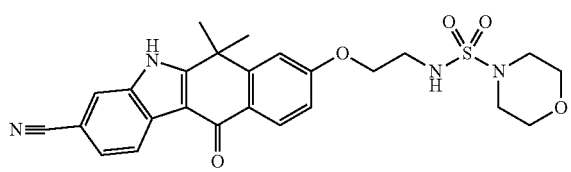 [SMILES: CC1(C)c2cc(OCCNS(=O)(=O)N3CCOCC3)ccc2C(=O)c2c1[nH]c1cc(C#N)ccc21]

The title compound was obtained as a by-product of the synthesis of Compound C1-2.

LCMS: m/z 495 [M+H]$^+$

HPLC retention time: 2.00 min (analysis condition S)

Example 64

Compound A8-19

4-Methyl-piperazine-1-sulfonic acid[2-(3-cyano-6,6-dimethyl-11-oxo-6,11-dihydro-5H-benzo[b]carbazol-8-yloxy)-ethyl]-amide

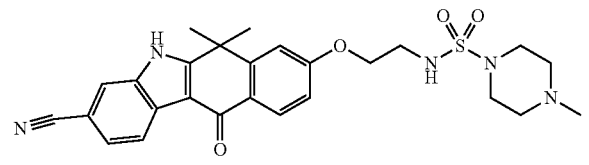 [SMILES: CN1CCN(S(=O)(=O)NCCOc2ccc3c(c2)C(C)(C)c2[nH]c4cc(C#N)ccc4c2C3=O)CC1]

The title compound was obtained as a by-product of the synthesis of Compound C1-4.

$^1$H-NMR (300 MHz, DMSO-d6) δ: 1.77 (6H, s), 2.16 (3H, s), 2.34 (4H, m), 3.08 (4H, m), 3.35 (2H, m), 4.19 (2H, t, 5.34 Hz), 7.09 (1H, dd, 8.77 Hz, 2.99 Hz), 7.37 (1H, bs, 1.91 Hz), 7.59 (2H, m), 8.01 (1H, s), 8.16 (1H, d, 8.40 Hz), 8.32 (1H, d, 8.01 Hz), 12.7 (1H, s).

LCMS: m/z 501 [M+H]$^+$

HPLC retention time: 1.43 min (analysis condition S)

Example 65

Compound A8-20

6,6-Dimethyl-8-(1-oxetan-3-yl-piperidin-4-yl-methoxy)-11-oxo-6,11-dihydro-5H-benzo[b]carbazole-3-carbonitrile

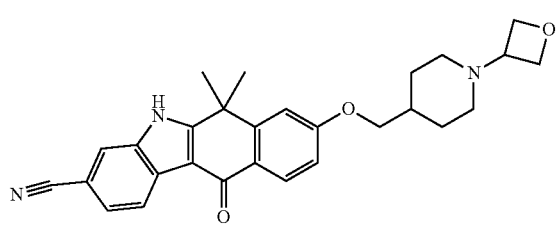 [SMILES: CC1(C)c2cc(OCC3CCN(C4COC4)CC3)ccc2C(=O)c2c1[nH]c1cc(C#N)ccc21]

6,6-Dimethyl-11-oxo-8-(piperidin-4-ylmethoxy)-6,11-dihydro-5H-benzo[b]carbazole-3-carbonitrile hydrochloric acid salt (Compound A7-25, 30 mg, 0.075 mmol) and oxetan-3-one (38 mg, 7 eq.) were dissolved in acetic acid (0.2 ml), THF (1 ml) and methanol (1 ml), added with sodium cyanoborohydride (33 mg, 7 eq.) at room temperature, and stirred overnight. The reaction solution was added with water, and then extracted with ethyl acetate. The solution was dried over sodium sulfate and the solvent was removed under vacuum and the resulting residues were purified by preparative TLC (chloroform: 2 N ammonia methanol=9:1) to obtain the target compound (15 mg).

LCMS: m/z 456 [M+H]$^+$

HPLC retention time: 2.78 min (analysis condition C)

Example 66

Compound A8-21

6,6-Dimethyl-8-[2-(1-oxetan-3-yl-piperidin-4-yl)-ethoxy]-11-oxo-6,11-dihydro-5H-benzo[b]carbazole-3-carbonitrile

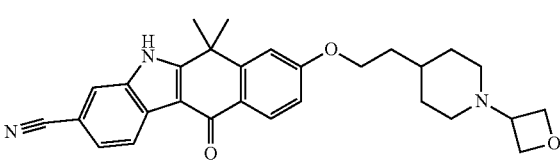 [SMILES: CC1(C)c2cc(OCCC3CCN(C4COC4)CC3)ccc2C(=O)c2c1[nH]c1cc(C#N)ccc21]

Under the same conditions as the method for synthesizing Compound A7-25, and Compound A8-20, the title compound was prepared from Compound A6 and 4-(2-hydroxy-ethyl)-piperidine-1-carboxylic acid tert-butyl ester (15 mg).

LCMS: m/z 470 [M+H]$^+$

HPLC retention time: 2.85 min (analysis condition C)

Example 67

Compound A9-1

N-[2-(3-Cyano-6,6-dimethyl-11-oxo-6,11-dihydro-5H-benzo[b]carbazol-8-yloxy)-ethyl]-methanesulfonamide

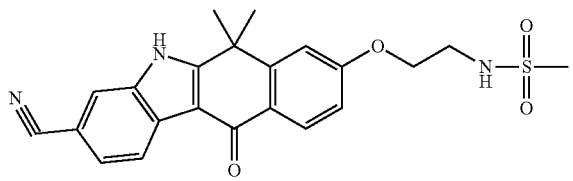 [SMILES: CC1(C)c2cc(OCCNS(C)(=O)=O)ccc2C(=O)c2c1[nH]c1cc(C#N)ccc21]

Trifluoroacetic acid salt of 8-(2-amino-ethoxy)-6,6-dimethyl-11-oxo-6,11-dihydro-5H-benzo[b]carbazole-3-carbonitrile (Compound A8-2, 19 mg, 0.044 mmol) was suspended in dichloromethane (0.5 mL), added with diisopropylethylamine (0.0157 mL, 2 eq.) and methanesulfonyl chloride (0.0034 mL, 1 eq.), and then stirred at room temperature for 2 hr. The reaction solution was added to water, and then extracted with dichloromethane. After washing with saturated brine, the organic layer was dried over sodium sulfate. The drying agent was removed by filtration and the residues obtained after concentration under reduced pressure were separated by silica gel preparative TLC (ethyl acetate 100%) to obtain the target compound (5.5 mg, 29%).

$^1$H-NMR (400 MHz, DMSO-d$_6$) δ: 8.47 (1H, d, J=8.2 Hz), 8.32 (1H, d, J=8.7 Hz), 8.16 (1H, s), 7.76 (1H, d, J=8.2 Hz), 7.53-7.46 (2H, m), 7.26 (1H, d, J=8.7 Hz), 4.39-4.33 (2H, m), 3.58-3.51 (2H, m), 3.12 (3H, s), 1.93 (6H, s)

LCMS: m/z 424 [M+H]$^+$

HPLC retention time: 3.10 min (analysis condition W)

Example 68

Compound A9-2

N-[2-(3-Cyano-6,6-dimethyl-11-oxo-6,11-dihydro-5H-benzo[b]carbazol-8-yloxy)-ethyl]-2,2,2-trifluoroacetamide

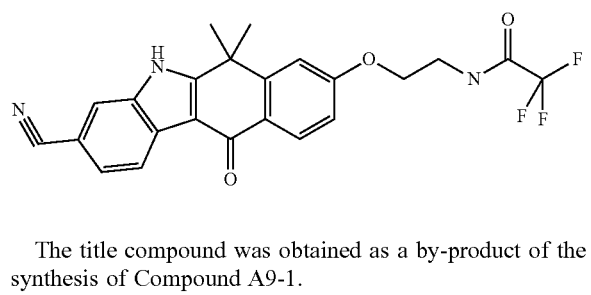

The title compound was obtained as a by-product of the synthesis of Compound A9-1.

LCMS: m/z 442 [M+H]$^+$

HPLC retention time: 3.45 min (analysis condition W)

Example 69

Compound A9-3-1

8-{2-(Tert-butyloxycarbonylaminosulfonyl)amino-ethoxy}-6,6-dimethyl-11-oxo-6,11-dihydro-5H-benzo[b]carbazole-3-carbonitrile

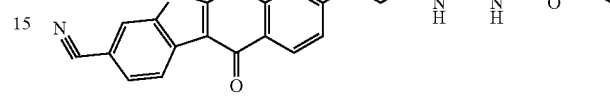

Trifluoroacetic acid salt of 8-(2-amino-ethoxy)-6,6-dimethyl-11-oxo-6,11-dihydro-5H-benzo[b]carbazole-3-carbonitrile (Compound A8-2, 20 mg, 0.044 mmol) was dissolved in pyridine (0.5 mL), added with N-(tert-butoxycarbonyl)-N-[4-(dimethyl azaniumylidene)-1,4-dihydropyridin-1-yl sulfonyl]azanide (13.5 mg, 1 eq.), and then stirred at room temperature for 14 hr. The reaction solution was added to water, and then extracted with ethyl acetate. After washing with saturated brine, the organic layer was dried over sodium sulfate. The drying agent was removed by filtration and the residues obtained after concentration under reduced pressure were separated by silica gel preparative TLC (ethyl acetate) to obtain the title compound (16.1 mg, 68%).

$^1$H-NMR (400 MHz, DMSO-d$_6$) δ: 12.74 (1H, s), 10.94 (1H, s), 8.33 (1H, d, J=8.5 Hz), 8.16 (1H, d, J=9.1 Hz), 8.02 (1H, s), 7.84 (1H, br. s), 7.62 (1H, d, J=7.9 Hz), 7.36 (1H, s), 7.10 (1H, d, J=7.9 Hz). 4.24-4.18 (2H, m), 1.78 (6H, s), 1.32 (9H, s)

LCMS: m/z 525 [M+H]$^+$

HPLC retention time: 3.48 min (analysis condition W)

Example 70

Compound A9-3-2

8-{2-(Methylaminosulfonyl)amino-ethoxy}-6,6-dimethyl-11-oxo-6,11-dihydro-5H-benzo[b]carbazole-3-carbonitrile

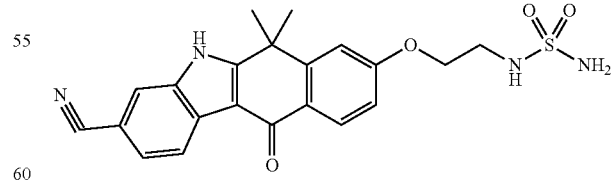

Under the same conditions as the method for synthesizing Compound A8-1, the title compound was prepared from Compound A9-3-1.

LCMS: m/z 425 [M+H]$^+$

HPLC retention time: 2.95 min (analysis condition W)

Example 71

Compound A9-4

8-(1-Methanesulfonyl-piperidin-4-yloxy)-6,6-dimethyl-11-oxo-6,11-dihydro-5H-benzo[b]carbazole-3-carbonitrile

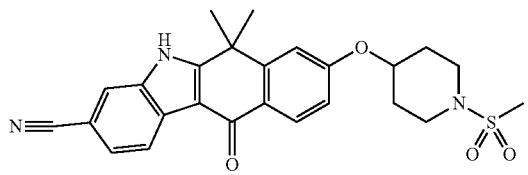 [SMILES: CC1(C)c2cc(OC3CCN(S(C)(=O)=O)CC3)ccc2C(=O)c2c1[nH]c1cc(C#N)ccc21]

According to the same method as the method for synthesizing Compound A7-17, the title compound was prepared from Compound A8-1 and methanesulfonyl chloride.

$^1$H-NMR (400 MHz, DMSO-d$_6$) δ: 12.72 (1H, s), 8.30 (1H, d, J=8.5 Hz), 8.14 (1H, d, J=8.5 Hz), 8.00 (1H, s), 7.59 (1H, d, J=7.9 Hz), 7.38 (1H, s), 7.13 (1H, d, J=8.5 Hz), 4.81 (1H, s), 3.39-3.38 (2H, m), 3.19-3.13 (2H, m), 2.93 (3H, s), 2.11-2.04 (2H, m), 1.83-1.75 (8H, m).

LCMS: m/z 464 [M+H]$^+$

HPLC retention time: 3.41 min (analysis condition U)

Example 72

Compound A9-5

8-[1-(2-Methoxy-ethyl)-piperidin-4-yloxy]-6,6-dimethyl-11-oxo-6,11-dihydro-5H-benzo[b]carbazole-3-carbonitrile

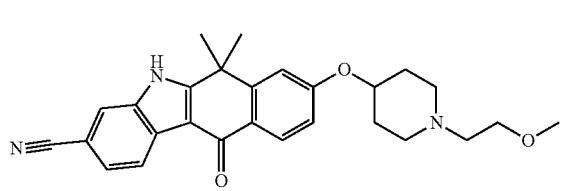 [SMILES: COCCN1CCC(Oc2ccc3c(c2)C(C)(C)c2[nH]c4cc(C#N)ccc4c2C3=O)CC1]

Under the same conditions as the method for synthesizing Compound A9-1, the title compound was prepared from Compound A8-1 and 1-bromo-2-methoxy-ethane.

$^1$H-NMR (400 MHz, CDCl$_3$) δ: 8.48-8.53 (1H, m), 8.32-8.38 (1H, m), 7.74-7.77 (1H, m), 7.50-7.55 (1H, m), 7.07-7.10 (1H, m), 6.95-7.00 (1H, m), 4.43-4.51 (1H, m), 3.53 (2H, t, J=5.6 Hz), 3.36 (3H, s), 2.77-2.87 (2H, m), 2.62 (2H, t, J=5.6 Hz), 2.35-2.47 (2H, m), 2.02-2.12 (2H, m), 1.78-1.95 (2H, m), 1.82 (6H, s).

LCMS: m/z 444 [M+H]$^+$

HPLC retention time: 2.00 min (analysis condition U)

Example 73

Compound A9-6-2

8-[1-(2-Hydroxy-ethyl)-piperidin-4-yloxy]-6,6-dimethyl-11-oxo-6,11-dihydro-5H-benzo[b]carbazole-3-carbonitrile

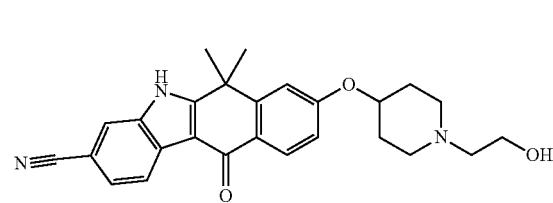 [SMILES: CC1(C)c2cc(OC3CCN(CCO)CC3)ccc2C(=O)c2c1[nH]c1cc(C#N)ccc21]

According to the same method as the method for synthesizing Compound A7-17, the title compound was prepared from Compound A8-1 and (2-bromoethoxy)-tert-butyldimethylsilane, followed by treatment with tetrabutylammonium fluoride.

LCMS: m/z 430 [M+H]$^+$

HPLC retention time: 1.45 min (analysis condition S)

Example 74

Compound A9-7

8-[1-(2-Fluoro-ethyl)-piperidin-4-yloxy]-6,6-dimethyl-11-oxo-6,11-dihydro-5H-benzo[b]carbazole-3-carbonitrile

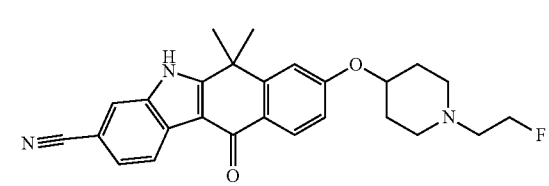 [SMILES: CC1(C)c2cc(OC3CCN(CCF)CC3)ccc2C(=O)c2c1[nH]c1cc(C#N)ccc21]

According to the same method as the method for synthesizing Compound A7-17, the title compound was prepared from Compound A8-1 and methanesulfonic acid 2-fluoro-ethyl ester.

$^1$H-NMR (300 MHz, DMSO-d6) δ: 1.67 (2H, m), 1.76 (6H, s), 2.01 (2H, m), 2.37 (2H, t, 11.0 Hz), 2.61 (1H, t, 4.20 Hz), 2.70 (1H, t, 4.58), 2.78 (2H, m), 4.46 (1H, t, 4.58 Hz), 4.62 (2H, t, 5.34 Hz), 7.10 (1H, dd, 9.16 Hz, 2.29 Hz), 7.34 (1H, bs, 1.53 Hz), 7.60 (1H, dd, 8.40 Hz, 1.53 Hz), 7.99 (1H, s), 8.13 (1H, d, 8.39 Hz), 8.30 (1H, d, 8.39 Hz), 12.7 (1H, s).

LCMS: m/z 432 [M+H]$^+$

HPLC retention time: 1.52 min (analysis condition S)

Example 75

Compound A9-8

8-(1-Acetyl-piperidin-4-yloxy)-6,6-dimethyl-11-oxo-6,11-dihydro-5H-benzo[b]carbazole-3-carbonitrile

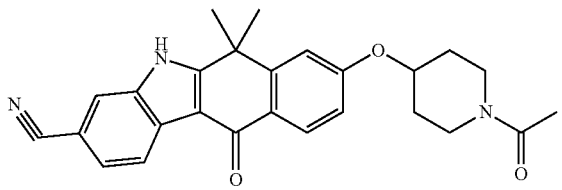 [SMILES: CC(=O)N1CCC(Oc2ccc3c(c2)C(C)(C)c2[nH]c4cc(C#N)ccc4c2C3=O)CC1]

According to the same method as the method for synthesizing Compound A7-17, the title compound was prepared from Compound A8-1 and acetyl chloride.
LCMS: m/z 428 [M+H]$^+$
HPLC retention time: 1.91 min (analysis condition S)

Example 76

Compound A9-9

2-(3-Cyano-6,6-dimethyl-11-oxo-6,11-dihydro-5H-benzo[b]carbazol-8-yloxy)-acetamide

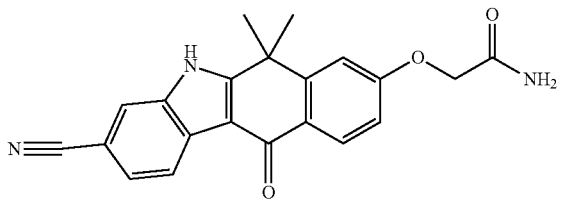 [SMILES: CC1(C)c2cc(OCC(N)=O)ccc2C(=O)c2c1[nH]c1cc(C#N)ccc21]

Under the same conditions as the method for synthesizing Compound A7-17, the title compound was prepared from Compound A6 and 2-bromo-acetamide.
LCMS: m/z 360 [M+H]$^+$
HPLC retention time: 2.83 min (analysis condition U)

Example 77

Compound A9-10

2-(3-Cyano-6,6-dimethyl-11-oxo-6,11-dihydro-5H-benzo[b]carbazol-8-yloxy)-N-methyl-acetamide

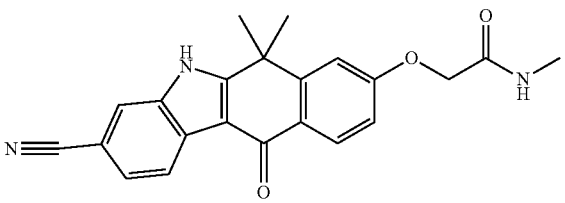 [SMILES: CNC(=O)COc1ccc2c(c1)C(C)(C)c1[nH]c3cc(C#N)ccc3c1C2=O]

(3-Cyano-6,6-dimethyl-11-oxo-6,11-dihydro-5H-benzo[b]carbazol-8-yloxy)-acetic acid (Compound A8-7, 30 mg, 0.0838 mmol), methylamine hydrochloric acid salt (28.1 mg, 0.417 mmol), EDC (32 mg, 0.167 mmol) and HOBT (0.023 mg, 0.167 mmol) were dissolved in DMF (1 mL), and added with diisopropylethylamine (0.145 mL, 0.833 mmol) at room temperature. After stirring at room temperature for 18 hr, water was added and the extraction was carried out with ethyl acetate. After washing with saturated brine, the organic layer was dried over magnesium sulfate. The drying agent was removed by filtration and the residues obtained after concentration under reduced pressure were dissolved in dichloromethane, added with diethyl ether, and the precipitated title compound was obtained (white solid, 19.7 mg, 63%).
$^1$H-NMR (300 MHz, DMSO) σ ppm 12.73 (s, 1H), 8.33 (d, 1H, J=8.1 Hz), 8.17 (d, 1H, J=8.7 Hz), 8.13 (s, 1H), 8.00 (s, 1H), 7.62 (d, 1H, J=8.1 Hz), 7.39 (d, 1H, J=2.4 Hz), 7.11 (dd, 1H, J=8.7 Hz, 2.4 Hz), 4.64 (s, 2H), 3.17 (d, 1H, J=5.4 Hz), 2.69 (d, 1H, J=4.5 Hz), 1.76 (s, 6H)
LCMS: m/z 374 [M+H]$^+$
HPLC retention time: 2.43 min (analysis condition U)

Example 78

Compound A9-11

2-(3-Cyano-6,6-dimethyl-11-oxo-6,11-dihydro-5H-benzo[b]carbazol-8-yloxy)-N-(2,2-dimethyl-[1,3]dioxolan-4-ylmethyl)-acetamide

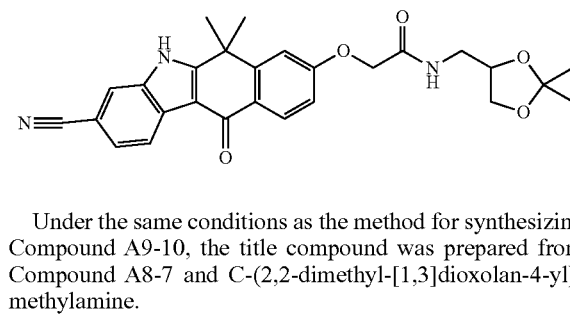

Under the same conditions as the method for synthesizing Compound A9-10, the title compound was prepared from Compound A8-7 and C-(2,2-dimethyl-[1,3]dioxolan-4-yl)-methylamine.
LCMS: m/z 474 [M+H]$^+$
HPLC retention time: 2.20 min (analysis condition U)

Example 79

Compound A9-12

2-(3-Cyano-6,6-dimethyl-11-oxo-6,11-dihydro-5H-benzo[b]carbazol-8-yloxy)-N-(2,3-dihydroxy-propyl)-acetamide

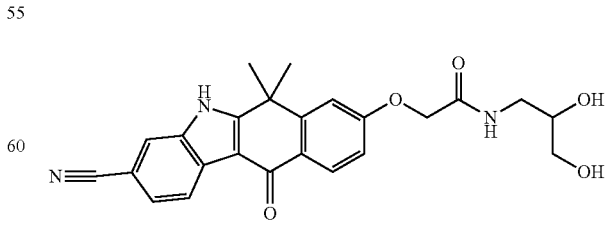

Under the same conditions as the method for synthesizing Compound A7-14-2, the title compound was prepared from Compound A9-11.

LCMS: m/z 434 [M+H]+

HPLC retention time: 1.72 min (analysis condition U)

Example 80

Compound A9-13

2-Methyl-acrylic acid 2-[2-(3-cyano-6,6-dimethyl-11-oxo-6,11-dihydro-5H-benzo[b]carbazol-8-yloxy)-acetylamino]-ethyl ester

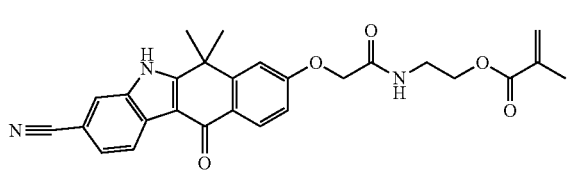 [SMILES: C=C(C)C(=O)OCCNC(=O)COc1ccc2c(c1)C(C)(C)c1[nH]c3cc(C#N)ccc3c1C2=O]

Under the same conditions as the method for synthesizing Compound A9-10, the title compound was prepared from Compound A8-7 and 2-methyl-acrylic acid 2-amino-ethyl ester.

LCMS: m/z 472 [M+H]+

HPLC retention time: 3.30 min (analysis condition U)

Example 81

Compound A9-14

2-(3-Cyano-6,6-dimethyl-11-oxo-6,11-dihydro-5H-benzo[b]carbazol-8-yloxy)-N-(2-hydroxy-ethyl)-acetamide

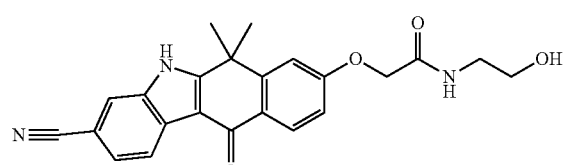

2-Methyl-acrylic acid 2-[2-(3-cyano-6,6-dimethyl-11-oxo-6,11-dihydro-5H-benzo[b]carbazol-8-yloxy)-acetylamino]-ethyl ester (Compound A9-13, 40 mg, 0.085 mmol) was dissolved in a mixture solvent of methanol (2 mL) and water (2 mL), added with potassium hydroxide (48 mg, 0.85 mmol), and then stirred at room temperature for 18 hr. After the neutralization with 1 N hydrochloric acid, the reaction solution was concentrated under reduced pressure. The resulting residues were purified by amino silica gel to obtain the title compound (white solid, 8.9 mg, 26%).

$^1$H-NMR (300 MHz, DMSO) σ ppm 12.75 (s, 1H), 8.32 (d, 1H, J=8.1 Hz), 8.17-8.13 (m, 2 Hz), 7.99 (s, 1H), 7.60 (d, 1H, J=8.1 Hz), 7.38 (d, 1H, J=1.8 Hz), 7.11 (dd, 1H, J=2.1 Hz, 8.7 Hz), 4.72 (t, 1H, J=5.7 Hz), 4.65 (s, 1H), 3.48 (dd, 2H, J=12.0 Hz, 6.0 Hz), 3.26 (dd, 2H, J=12.0 Hz, 6.0 Hz), 1.76 (s, 6H)

LCMS: m/z 404 [M+H]+

HPLC retention time: 2.83 min (analysis condition U)

Example 82

Compound A9-15-1

4-[2-(3-Cyano-6,6-dimethyl-11-oxo-6,11-dihydro-5H-benzo[b]carbazol-8-yloxy)-acetyl]-piperazine-1-carboxylic acid tert-butyl ester

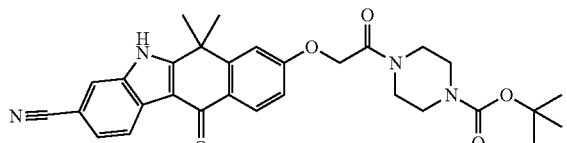

(3-Cyano-6,6-dimethyl-11-oxo-6,11-dihydro-5H-benzo[b]carbazol-8-yloxy)-acetic acid (Compound A8-7, 30 mg, 0.083 mmol), piperazine-1-carboxylic acid tert-butyl ester (31 mg, 2 eq.), and HOBt (30 mg, 3 eq.) were dissolved in 0.5 ml DMF, added with EDC (48 mg, 3 eq.), and stirred at room temperature overnight. Thereafter, the solvent was removed under reduced pressure and the resulting residues were purified by preparative TLC to obtain the title compound (20 mg).

LCMS: m/z 527, 471, 427[M−H]−

HPLC retention time: 2.77 min (analysis condition C)

Example 83

Compound A9-15-2

6,6-Dimethyl-11-oxo-8-(2-oxo-2-piperazin-1-yl-ethoxy)-6,11-dihydro-5H-benzo[b]carbazole-3-carbonitrile hydrochloric acid salt

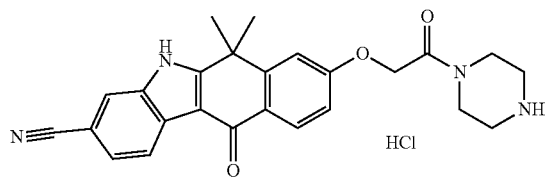 [SMILES: CC1(C)c2cc(OCC(=O)N3CCNCC3)ccc2C(=O)c2c1[nH]c1cc(C#N)ccc21 ; Cl]

4-[2-(3-Cyano-6,6-dimethyl-11-oxo-6,11-dihydro-5H-benzo[b]carbazol-8-yloxy)-acetyl]-piperazine-1-carboxylic acid tert-butyl ester (Compound A9-15-1, 20 mg) was added with 4 N hydrochloric acid and dioxane solution (1 ml), and stirred in an water bath at 10° C. for 4 hr. Water was added to the reaction solution and the resulting precipitates were filtered and dried to obtain the title compound (15 mg, white powder).

LCMS: m/z 429 [M+H]+

HPLC retention time: 0.81 min (analysis condition I)

Example 84

Compound A9-16

2-(3-Cyano-6,6-dimethyl-11-oxo-6,11-dihydro-5H-benzo[b]carbazol-8-yloxy)-N-(2-cyano-ethyl)-acetamide

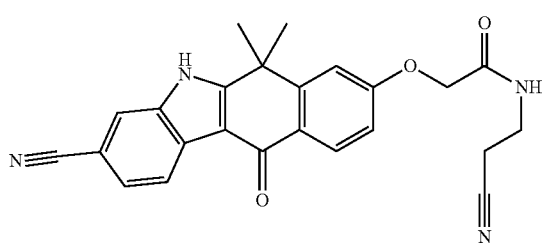 [SMILES: CC1(C)c2cc(OCC(=O)NCCC#N)ccc2C(=O)c2c1[nH]c1cc(C#N)ccc21]

(3-Cyano-6,6-dimethyl-11-oxo-6,11-dihydro-5H-benzo[b]carbazol-8-yloxy)-acetic acid (Compound A8-7, 30 mg, 0.083 mmol), 3-aminopropionitrile (12 mg, 2 eq.) and HOBt (30 mg, 3 eq.) were dissolved in 0.5 ml DMF, added with EDC (48 mg, 3 eq.), and stirred at room temperature overnight. Thereafter, the solvent was removed under reduced pressure and the resulting residues were purified by preparative TLC to obtain the title compound (23 mg).

LCMS: m/z 411 [M+H]$^+$

HPLC retention time: 2.27 min (analysis condition C)

Example 85

Compound A9-17

2-(3-Cyano-6,6-dimethyl-11-oxo-6,11-dihydro-5H-benzo[b]carbazol-8-yloxy)-N-(2-cyano-ethyl)-N-methyl-acetamide

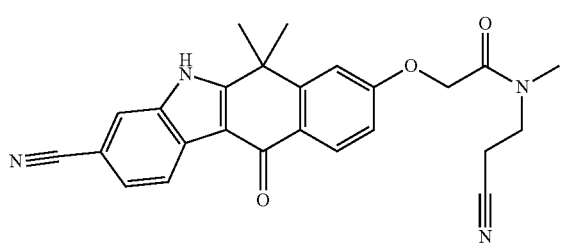 [SMILES: CN(CCC#N)C(=O)COc1ccc2c(c1)C(C)(C)c1[nH]c3cc(C#N)ccc3c1C2=O]

(3-Cyano-6,6-dimethyl-11-oxo-6,11-dihydro-5H-benzo[b]carbazol-8-yloxy)-acetic acid (Compound A8-7, 30 mg, 0.083 mmol), N-methyl-3-aminopropionitrile (14 mg, 2 eq.) and HOBt (30 mg, 3 eq.) were dissolved in 0.5 ml DMF, added with EDC (48 mg, 3 eq.), and stirred at room temperature overnight. Thereafter, the solvent was removed under reduced pressure and the resulting residues were purified by preparative TLC to obtain the title compound (7 mg).

LCMS: m/z 411 [M+H]$^+$

HPLC retention time: 2.33 min (analysis condition C)

Example 86

Compound A10

8-(Tert-butyl-dimethyl-silanyloxy)-6,6-dimethyl-11-oxo-6,11-dihydro-5H-benzo[b]carbazole-3-carbonitrile

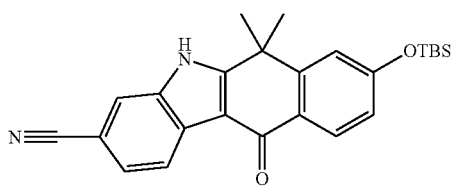 [SMILES: CC1(C)c2cc(O[Si](C)(C)C(C)(C)C)ccc2C(=O)c2c1[nH]c1cc(C#N)ccc21]

The DMF solution of 8-methoxy-6,6-dimethyl-11-oxo-6,11-dihydro-5H-benzo[b]carbazole-3-carbonitrile (Compound A6, 100 mg, 0.331 mmol), imidazole (67.5 mg, 3 eq.) and tert-butylchlorodimethylsilane (92.4 mg, 1.5 eq.) was stirred overnight at room temperature. To the reaction solution, saturated aqueous solution of sodium hydrogen carbonate was added followed by extraction with tert-butylmethyl ether. The organic layer was washed with brine and dried over sodium sulfate. The drying agent was removed by filtration and the residues obtained after concentration under reduced pressure were purified by silica gel column chromatography (ethyl acetate/hexane) to obtain the target compound (white solid, 170 mg, 100%).

LCMS: m/z 417 [M+H]$^+$

HPLC retention time: 3.38 min (analysis condition S)

Example 87

Compound A10-1

8-Methoxy-5,6,6-trimethyl-11-oxo-6,11-dihydro-5H-benzo[b]carbazole-3-carbonitrile

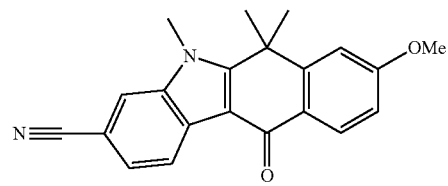

To the THF solution of triphenylphosphine (260 mg, 3 eq.), azodicarboxylic acid diisopropyl ester (0.195 ml, 3 eq.) was added and the mixture was stirred at room temperature for 1 hr. Thereafter, 8-(tert-butyldimethylsilanyloxy)-6,6-dimethyl-11-oxo-6,11-dihydro-5H-benzo[b]carbazole-3-carbonitrile (Compound A10, 138 mg, 0.331 mmol) and methanol (1 ml) were added and stirred overnight. The reaction solution was purified by HPLC to obtain the target compound (44.8 mg, 41%).

$^1$H-NMR (270 MHz, DMSO-d$_6$) δ: 8.44 (1H, d, J=8.1 Hz), 8.33 (1H, s), 8.14 (1H, d, J=8.7 Hz), 7.66 (1H, dd, J=8.2, 1.1 Hz), 7.39 (1H, d, J=2.3 Hz), 7.09 (1H, dd, J=8.7, 2.3 Hz), 4.17 (3H, s), 3.92 (3H, s), 1.88 (6H, s).

LCMS: m/z 331 [M+H]$^+$

HPLC retention time: 2.35 min (analysis condition S)

Example 88

Compound A10-2

8-(1-Methanesulfonyl-piperidin-4-yloxy)-5,6,6-trimethyl-11-oxo-6,11-dihydro-5H-benzo[b]carbazole-3-carbonitrile

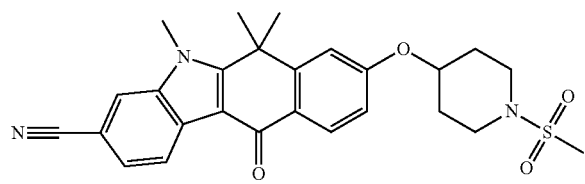 [SMILES: Cn1c2c(c3ccc(C#N)cc31)C(=O)c1ccc(OC3CCN(S(C)(=O)=O)CC3)cc1C2(C)C]

Under the same conditions as the method for synthesizing Compound B3-4, the title compound was prepared from Compound A9-4.

LCMS: m/z 478 [M+H]$^+$

HPLC retention time: 2.68 min (analysis condition U)

Example 89

Compound B1

Trifluoro-methanesulfonic acid 3-cyano-6,6-dimethyl-11-oxo-6,11-dihydro-5H-benzo[b]carbazol-8-yl ester

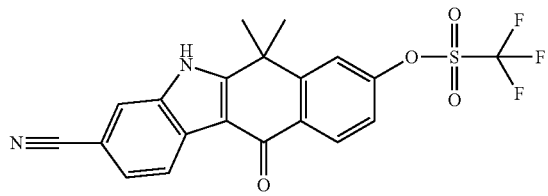 [SMILES: CC1(C)c2cc(OS(=O)(=O)C(F)(F)F)ccc2C(=O)c2c1[nH]c1cc(C#N)ccc21]

8-Hydroxy-6,6-dimethyl-11-oxo-6,11-dihydro-5H-benzo[b]carbazole-3-carbonitrile (Compound A6, 550 mg, 0.189 mmol) was dissolved in pyridine (18 mL), added with anhydrous trifluoromethanesulfonic acid (0.758 ml, 3 eq.), and stirred at room temperature for 30 min. The reaction solution was added to water and then extracted with dichloromethane. The organic layer was dried over magnesium sulfate. The drying agent was removed by filtration and the residues obtained after concentration under reduced pressure were purified by silica gel column chromatography (ethyl acetate/hexane) to obtain the target compound (white powder, 641 mg, 81%).

$^1$H-NMR (400 MHz, DMSO-d$_6$) δ: 12.89 (1H, br. s), 8.36 (1H, d, J=8.8 Hz), 8.31 (1H, dd, J=8.1, 0.7 Hz), 8.11 (1H, d, J=2.3 Hz), 8.04 (1H, dd, J=1.5, 0.7 Hz), 7.65-7.60 (2H, m). 1.76 (6H, s)

LCMS: m/z 435 [M+H]$^+$

HPLC retention time: 3.10 min (analysis condition U)

Example 90

Compound B2-1

8-(4-Isopropyl-piperazin-1-yl)-6,6-dimethyl-11-oxo-6,11-dihydro-5H-benzo[b]carbazole-3-carbonitrile

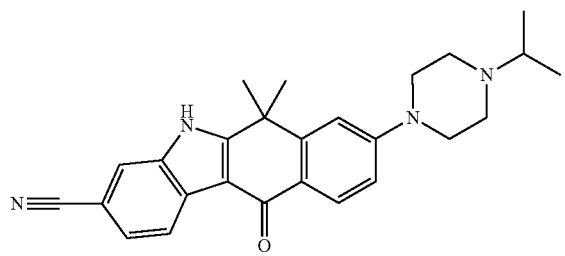 [SMILES: CC(C)N1CCN(c2ccc3c(c2)C(C)(C)c2[nH]c4cc(C#N)ccc4c2C3=O)CC1]

Trifluoro-methanesulfonic acid 3-cyano-6,6-dimethyl-11-oxo-6,11-dihydro-5H-benzo[b]carbazol-8-yl ester (Compound B1, 40 mg, 0.0921 mmol) was dissolved in NMP (1 ml) and added with 1-isopropylpiperazine (236 mg, 20 eq.). The mixture was stirred at 120° C. for 3 hr. After cooling to room temperature, purification was carried out by HPLC to obtain the target compound (white powder, 12.8 mg, 34%).

$^1$H-NMR (270 MHz, DMSO-d$_6$) δ: 8.30 (1H, d, 8.1 Hz), 8.03 (1H, d, 8.6 Hz), 7.98 (1H, s), 7.56 (1H, d, 8.6 Hz), 7.21 (1H, s), 7.04 (1H, d, 9.1 Hz), 3.40-3.37 (4H, m), 2.73-2.65 (1H, m), 2.61-2.58 (4H, m), 1.75 (6H, s), 1.02 (6H, d, 6.6 Hz)

LCMS: m/z 413 [M+H]$^+$

Example 91

Compound B2-2

8-[4-(2-Hydroxy-ethyl)-piperazin-1-yl]-6,6-dimethyl-11-oxo-6,11-dihydro-5H-benzo[b]carbazole-3-carbonitrile

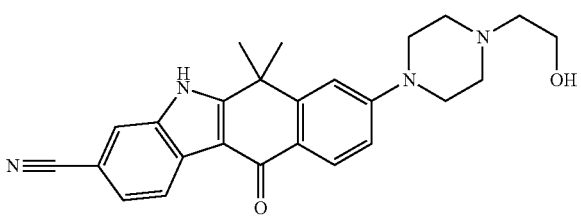 [SMILES: CC1(C)c2cc(N3CCN(CCO)CC3)ccc2C(=O)c2c1[nH]c1cc(C#N)ccc21]

According to the same method as the method for synthesizing Compound B2-1, the title compound was prepared from Compound B1 and N-(2-hydroxyethyl)piperazine.

$^1$H-NMR (270 MHz, DMSO-d$_6$) δ: 8.30 (1H, d, 8.1 Hz), 8.03 (1H, d, 8.7 Hz), 7.99 (1H, s), 7.58 (1H, d, 7.9 Hz), 7.21 (1H, s), 7.04 (1H, d, 8.7 Hz), 4.50-4.46 (1H, br m), 3.59-3.53 (2H, m), 3.39-3.35 (4H, m), 2.59-2.56 (4H, m), 2.45 (2H, t, 6.1 Hz), 1.76 (6H, s)

LCMS: m/z 415 [M+H]$^+$

HPLC retention time: 1.27 min (analysis condition S)

Example 92

Compound B2-3

6,6-Dimethyl-8-morpholin-4-yl-11-oxo-6,11-dihydro-5H-benzo[b]carbazole-3-carbonitrile

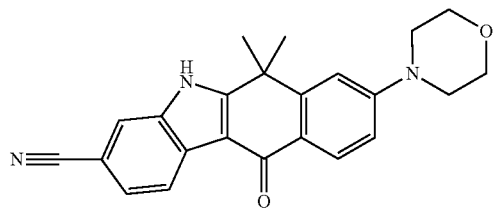 [SMILES: CC1(C)c2cc(N3CCOCC3)ccc2C(=O)c2c1[nH]c1cc(C#N)ccc21]

Under the same conditions as the method for synthesizing Compound B2-1, the title compound was prepared from Compound B1 and morpholine.

$^1$H-NMR (400 MHz, DMSO-$d_6$) δ: 12.62 (1H, br. s), 8.29 (1H, d, 8.2 Hz), 8.04 (1H, d, 9.0 Hz), 7.96 (1H, s), 7.56 (1H, d, 8.2 Hz), 7.22 (1H, s), 7.04 (1H, d, 9.0 Hz), 3.77-3.75 (4H, m), 3.35-3.30 (4H, m), 1.74 (6H, s)

LCMS: m/z 372 [M+H]$^+$

HPLC retention time: 2.45 min (analysis condition U)

Example 93

Compound B2-4

6,6-Dimethyl-11-oxo-8-(4-pyrrolidin-1-yl-piperidin-1-yl)-6,11-dihydro-5H-benzo[b]carbazole-3-carbonitrile

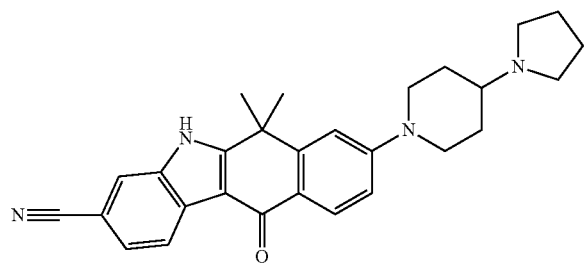 [SMILES: CC1(C)c2cc(N3CCC(N4CCCC4)CC3)ccc2C(=O)c2c1[nH]c1cc(C#N)ccc21]

Under the same conditions as the method for synthesizing Compound B2-1, the title compound was prepared from Compound B1 and 4-pyrrolidin-1-yl-piperidine.

$^1$H-NMR (270 MHz, DMSO-$d_6$) δ: 8.30 (1H, d, 8.1 Hz), 8.01 (1H, d, 8.7 Hz), 7.97 (1H, s), 7.56 (1H, d, 8.6 Hz), 7.20 (1H, s), 3.94-3.90 (2H, m), 3.30-3.28 (4H, m), 2.95 (2H, t, 11.8 Hz), 2.24-2.20 (1H, m), 1.95-1.91 (2H, m), 1.75 (6H, s), 1.70-1.66 (4H, m), 1.54-1.52 (2H, m)

LCMS: m/z 439 [M+H]$^+$

Example 94

Compound B2-5-1

4-(3-Cyano-6,6-dimethyl-11-oxo-6,11-dihydro-5H-benzo[b]carbazol-8-yl)-piperazine-1-carboxylic acid tert-butyl ester

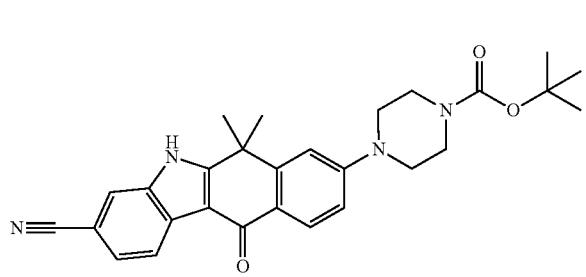 [SMILES: CC(C)(C)OC(=O)N1CCN(c2ccc3c(c2)C(C)(C)c2[nH]c4cc(C#N)ccc4c2C3=O)CC1]

Under the same conditions as the method for synthesizing Compound B2-1, the title compound was prepared from Compound B1 and piperazine-1-carboxylic acid tert-butyl ester.

LCMS: m/z 471 [M+H]$^+$

HPLC retention time: 2.67 min (analysis condition S)

Example 95

Compound B2-5-2

6,6-Dimethyl-11-oxo-8-piperazin-1-yl-6,11-dihydro-5H-benzo[b]carbazole-3-carbonitrile

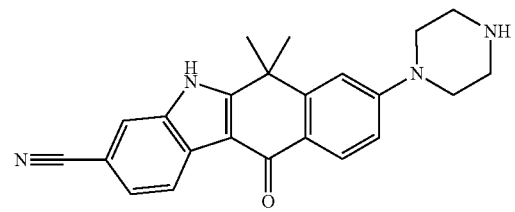 [SMILES: CC1(C)c2cc(N3CCNCC3)ccc2C(=O)c2c1[nH]c1cc(C#N)ccc21]

Under the same conditions as the method for synthesizing Compound A8-1, the title compound was prepared from Compound B2-5-1.

$^1$H-NMR (400 MHz, DMSO-$d_6$) δ: 8.32 (1H, d, 8.5 Hz), 8.03 (1H, d, 9.1 Hz), 7.99 (1H, s), 7.59 (1H, dd, 8.2, 1.5 Hz), 7.20 (1H, d, 2.4 Hz), 7.04 (1H, dd, 8.8, 2.1 Hz), 3.32-3.30 (4H, m), 2.88-2.87 (4H, m), 1.77 (6H, s)

LCMS: m/z 371 [M+H]$^+$

Example 96

Compound B2-6

6,6-Dimethyl-11-oxo-8-piperidin-1-yl-6,11-dihydro-5H-benzo[b]carbazole-3-carbonitrile

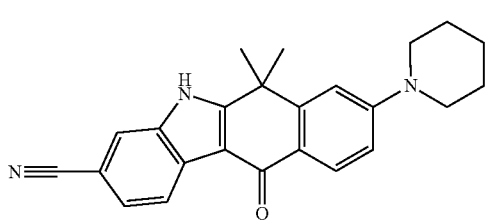 [SMILES: CC1(C)c2cc(N3CCCCC3)ccc2C(=O)c2c1[nH]c1cc(C#N)ccc21]

Under the same conditions as the method for synthesizing Compound B2-1, the title compound was prepared from Compound B1 and piperidine.

LCMS: m/z 370 [M+H]$^+$

HPLC retention time: 2.40 min (analysis condition U)

Example 97

Compound B2-7-1

8-(4-Hydroxy-piperidin-1-yl)-6,6-dimethyl-11-oxo-6,11-dihydro-5H-benzo[b]carbazole-3-carbonitrile

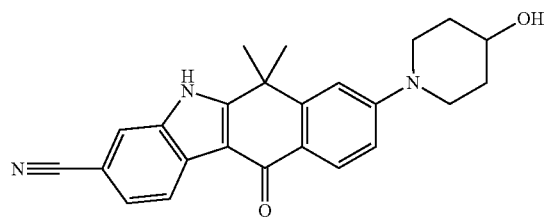 [SMILES: CC1(C)c2cc(N3CCC(O)CC3)ccc2C(=O)c2c1[nH]c1cc(C#N)ccc21]

Under the same conditions as the method for synthesizing Compound B2-1, the title compound was prepared from Compound B1 and piperidin-4-ol.

$^1$H-NMR (270 MHz, DMSO-d$_6$) δ: 8.30 (1H, d, 8.1 Hz), 8.01 (1H, d, 8.7 Hz), 7.97 (1H, s), 7.56 (1H, d, 7.7 Hz), 7.19 (1H, s), 7.04 (1H, d, 10.6 Hz), 4.76-4.71 (1H, br m), 3.81-3.75 (3H, m), 3.08 (2H, t, 10.2 Hz), 1.86-1.82 (2H, m), 1.75 (6H, s), 1.49-1.42 (2H, m)

LCMS: m/z 386 [M+H]$^+$

Example 98

Compound B2-7-2

6,6-Dimethyl-11-oxo-8-(4-oxo-piperidin-1-yl)-6,11-dihydro-5H-benzo[b]carbazole-3-carbonitrile

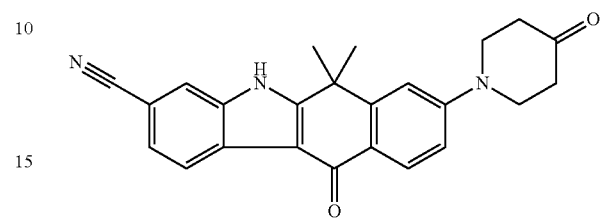

8-(4-Hydroxy-piperidin-1-yl)-6,6-dimethyl-11-oxo-6,11-dihydro-5H-benzo[b]carbazole-3-carbonitrile (Compound B2-7-1, 210 mg, 0.545 mmol), was dissolved in the DCM (2 mL) and DMF (0.6 mL) mixture solvent, added with 1,1,1-triacetoxy-1,1-dihydro-1,2-benzoiodoxol-3(1H)-one (300 mg, 1.3 eq.), and the mixture was stirred at room temperature for 2 hr. To the reaction solution, 0.25 mol/L aqueous solution of sodium thiosulfate, saturated sodium bicarbonate solution and CPME were added followed by further stirring at room temperature for 1 hr. The reaction solution was filtered and the filtrate was subjected to liquid separation. The organic layer was washed with saturated brine and dried over sodium sulfate. The drying agent was removed by filtration and the residues obtained after concentration under reduced pressure were purified by silica gel column chromatography (ethyl acetate/hexane) to obtain the target compound (yellowish white powder, 109 mg, 52%).

LCMS: m/z 384 [M+H]$^+$

HPLC retention time: 2.17 min (analysis condition U)

Example 99

Compound B2-8

8-(4-Methanesulfonyl-piperazin-1-yl)-6,6-dimethyl-11-oxo-6,11-dihydro-5H-benzo[b]carbazole-3-carbonitrile

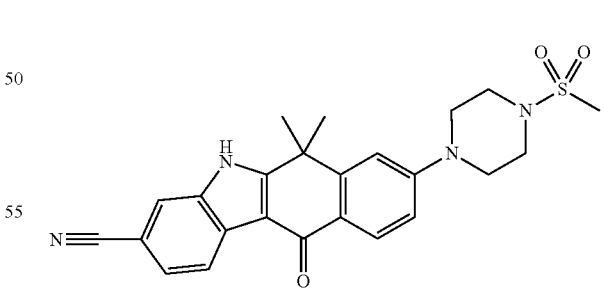

Under the same conditions as the method for synthesizing Compound B2-1, the title compound was prepared from Compound B1 and 1-methanesulfonylpiperazine.

$^1$H-NMR (270 MHz, DMSO-d$_6$) δ: 12.66 (1H, br.s), 8.31 (1H, d, J=8.2 Hz), 8.06 (1H, d, J=8.7 Hz), 7.99 (1H, s), 7.59 (1H, d, J=8.2 Hz), 7.30 (1H, d, J=1.8 Hz), 7.09 (1H, dd, J=8.7, 1.8 Hz), 3.53 (4H, t, J=4.8 Hz), 3.27 (4H, t, J=4.8 Hz), 2.94 (3H, s), 1.77 (6H, s).

LCMS: m/z 449 [M+H]+

HPLC retention time: 1.98 min (analysis condition S)

Example 100

Compound B2-9

8-(3-Methanesulfonyl-pyrrolidin-1-yl)-6,6-dimethyl-11-oxo-6,11-dihydro-5H-benzo[b]carbazole-3-carbonitrile

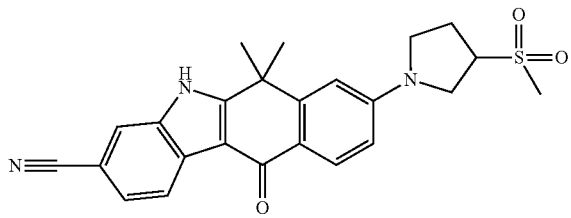 [SMILES: CC1(C)c2cc(N3CCC(S(C)(=O)=O)C3)ccc2C(=O)c2c1[nH]c1cc(C#N)ccc21]

Under the same conditions as the method for synthesizing Compound B2-1, the title compound was prepared from Compound B1 and 3-methanesulfonylpyrrolidine.

LCMS: m/z 434 [M+H]+

HPLC retention time: 1.83 min (analysis condition S)

Example 101

Compound B2-10

8-(1,1-Dioxothiomorpholino)-6,6-dimethyl-11-oxo-6,11-dihydro-5H-benzo[b]carbazole-3-carbonitrile

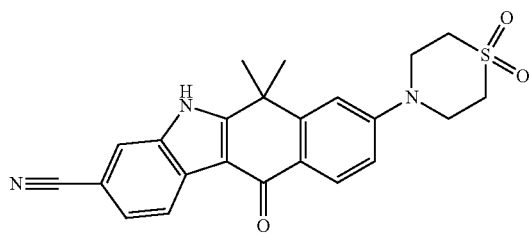 [SMILES: CC1(C)c2cc(N3CCS(=O)(=O)CC3)ccc2C(=O)c2c1[nH]c1cc(C#N)ccc21]

Trifluoro-methanesulfonic acid 3-cyano-6,6-dimethyl-11-oxo-6,11-dihydro-5H-benzo[b]carbazol-8-yl ester (Compound B1, 30 mg, 0.069 mmol) was dissolved in 1,4-dioxane (1 mL), added with thiomorpholine 1,1-dioxide (19 mg, 2 eq.), $Pd_2(dba)_3$ (6.3 mg, 0.1 eq.), BINAP (8.6 mg, 0.2 eq.) and $K_3PO_4$ (29 mg, 2 eq.), and stirred at 100° C. overnight. The reaction solution was added to water, and then extracted with ethyl acetate. The organic layer was washed with saturated brine and dried over sodium sulfate. The drying agent was removed by filtration and the residues obtained after concentration under reduced pressure were purified by silica gel column chromatography (ethyl acetate/hexane) to obtain the target compound (white powder, 2.1 mg, 7%).

$^1$H-NMR (270 MHz, DMSO-$d_6$) δ: 8.29 (1H, d, J=8.6 Hz), 8.07 (1H, d, J=8.9 Hz), 8.00 (1H, s), 7.55 (1H, dd, J=8.5, 1.7 Hz), 7.34 (1H, d, J=2.0 Hz), 7.15 (1H, dd, J=9.1, 2.7 Hz), 4.01 (4H, s), 3.16 (4H, s), 1.77 (6H, s).

LCMS: m/z 420 [M+H]+

HPLC retention time: 1.80 min (analysis condition S)

Example 102

Compound B2-11

8-(4-Cyclopentyl-2-oxo-piperazin-1-yl)-6,6-dimethyl-11-oxo-6,11-dihydro-5H-benzo[b]carbazole-3-carbonitrile

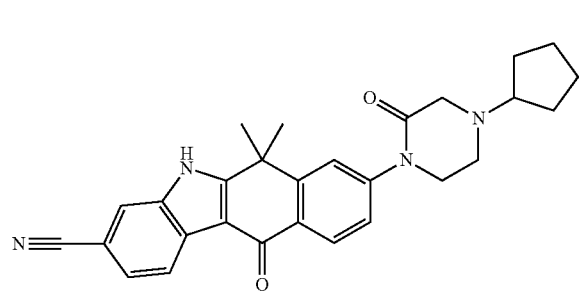 [SMILES: CC1(C)c2cc(N3CCN(C4CCCC4)CC3=O)ccc2C(=O)c2c1[nH]c1cc(C#N)ccc21]

Under the same conditions as the method for synthesizing Compound B2-10, the title compound was prepared from Compound B1 and 4-cyclopentylpiperazin-2-one.

LCMS: m/z 453 [M+H]+

HPLC retention time: 1.30 min (analysis condition S)

Example 103

Compound B2-12

6,6-Dimethyl-8-(4-morpholin-4-yl-piperidin-1-yl)-11-oxo-6,11-dihydro-5H-benzo[b]carbazole-3-carbonitrile

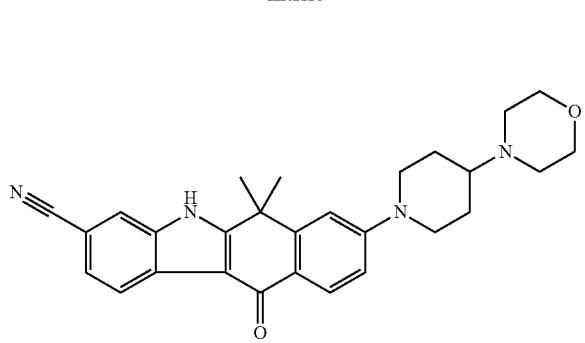

Under the same conditions as the method for synthesizing Compound B2-1, the title compound was prepared from Compound B1 and 4-piperidin-4-yl morpholine.

$^1$H-NMR (400 MHz, DMSO-$d_6$) δ: 12.73 (1H, s), 8.27-8.31 (1H, m), 7.98-8.02 (1H, m), 7.95-7.97 (1H, m), 7.53-7.58 (1H, m), 7.17-7.21 (1H, m), 6.99-7.05 (1H, m), 3.97-4.05 (2H, m), 3.53-3.59 (4H, m), 2.80-2.90 (2H, m), 2.43-2.51 (4H, m), 2.31-2.40 (1H, m), 1.83-1.92 (2H, m), 1.74 (6H, s), 1.39-1.52 (2H, m)

LCMS: m/z 455 [M+H]+

HPLC retention time: 1.73 min (analysis condition U)

Example 104

Compound B2-13

8-(4,4-Difluoro-1,4'-bipiperidin-1'-yl)-6,6-dimethyl-11-oxo-6,11-dihydro-5H-benzo[b]carbazole-3-carbonitrile

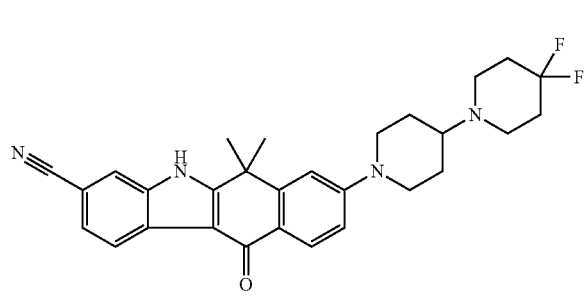 [SMILES: CC1(C)c2cc(N3CCC(N4CCC(F)(F)CC4)CC3)ccc2C(=O)c2c1[nH]c1cc(C#N)ccc21]

Under the same conditions as the method for synthesizing Compound B3-32, the title compound was prepared from Compound B2-7-2 and 4,4-difluoropiperidine hydrochloric acid salt.

$^1$H-NMR (400 MHz, DMSO-d$_6$) δ: 12.59 (1H, s), 8.25-8.32 (1H, m), 7.97-8.02 (1H, m), 7.96 (1H, s), 7.52-7.59 (1H, m), 7.16-7.21 (1H, m), 6.99-7.05 (1H, mz), 4.00-4.09 (2H, m), 3.55-3.62 (2H, m), 2.79-2.90 (2H, m), 2.55-2.67 (4H, m), 1.78-1.98 (5H, m), 1.74 (6H, s), 1.44-1.58 (2H, m)

LCMS: m/z 489 [M+H]$^+$

HPLC retention time: 1.88 min (analysis condition U)

Example 105

Compound B2-14

8-[4-((2R,6S)-2,6-Dimethyl-morpholin-4-yl)-piperidin-1-yl]-6,6-dimethyl-11-oxo-6,11-dihydro-5H-benzo[b]carbazole-3-carbonitrile

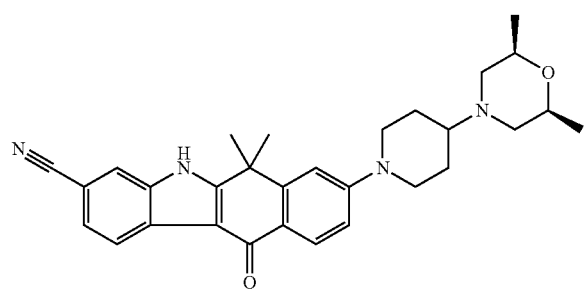 [SMILES: C[C@@H]1CN(C2CCN(c3ccc4c(c3)C(C)(C)c3[nH]c5cc(C#N)ccc5c3C4=O)CC2)C[C@H](C)O1]

Under the same conditions as the method for synthesizing Compound B3-32, the title compound was prepared from Compound B2-7-2 and (2R,6S)-2,6-dimethylmorpholine.

$^1$H-NMR (400 MHz, DMSO-d$_6$) δ: 12.60 (1H, s), 8.25-8.31 (1H, m), 7.97-8.02 (1H, m), 7.95 (1H, s), 7.51-7.58 (1H, m), 7.18 (1H, s), 6.99-7.05 (1H, m), 3.96-4.06 (2H, m), 3.45-3.55 (2H, m), 2.80-2.91 (2H, m), 2.72-2.79 (2H, m), 2.29-2.41 (1H, m), 1.70-1.90 (10H, m), 1.40-1.53 (2H, m), 1.03 (6H, d, 6.3 Hz)

LCMS: m/z 483 [M+H]$^+$

HPLC retention time: 1.83 min (analysis condition U)

Example 106

Compound B2-15

8-((3R,5S)-3,5-Dimethylpiperazin-1-yl)-6,6-dimethyl-11-oxo-6,11-dihydro-5H-benzo[b]carbazole-3-carbonitrile

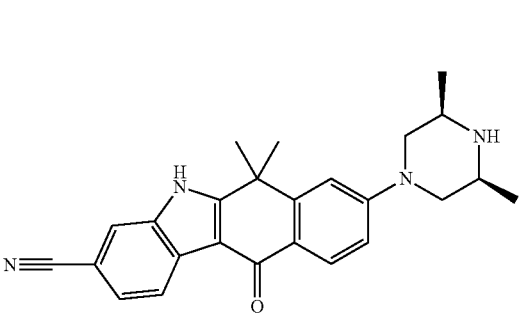 [SMILES: C[C@@H]1CN(c2ccc3c(c2)C(C)(C)c2[nH]c4cc(C#N)ccc4c2C3=O)C[C@H](C)N1]

Under the same conditions as the method for synthesizing Compound B2-1, the title compound was prepared from Compound B1 and 2,6-dimethylpiperazine.

LCMS: m/z 399 [M+H]$^+$

HPLC retention time: 1.76 min (analysis condition U)

Example 107

Compound B2-16-1

(S)-4-(3-Cyano-6,6-dimethyl-11-oxo-6,11-dihydro-5H-benzo[b]carbazol-8-yl)-3-methyl-piperazine-1-carboxylic acid tert-butyl ester

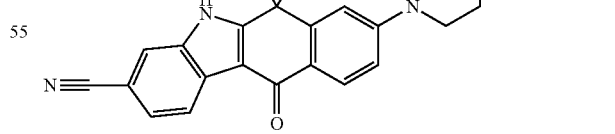

Under the same conditions as the method for synthesizing Compound B2-10, the title compound was prepared from Compound B1 and (S)-3-methylpiperazine-1-carboxylic acid tert-butyl ester.

LCMS: m/z 485 [M+H]$^+$

HPLC retention time: 3.97 min (analysis condition W)

Example 108

Compound B2-16-2

6,6-Dimethyl-8-((S)-2-methyl-piperazin-1-yl)-11-oxo-6,11-dihydro-5H-benzo[b]carbazole-3-carbonitrile

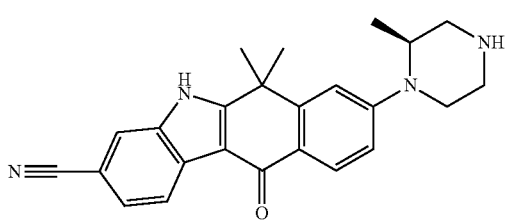 [SMILES: C[C@H]1CNCCN1c1ccc2c(c1)C(C)(C)c1[nH]c3cc(C#N)ccc3c1C2=O]

Under the same conditions as the method for synthesizing Compound A8-1, the title compound was prepared from Compound 2-16-1.

LCMS: m/z 385 [M+H]$^+$

HPLC retention time: 2.43 min (analysis condition W)

Example 109

Compound B2-16-3

8-((S)-4-Cyclobutyl-2-methyl-piperazin-1-yl)-6,6-dimethyl-11-oxo-6,11-dihydro-5H-benzo[b]carbazole-3-carbonitrile

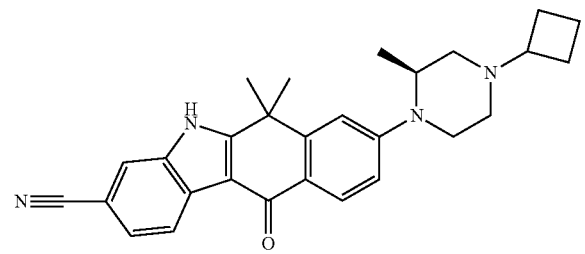 [SMILES: C[C@H]1CN(C2CCC2)CCN1c1ccc2c(c1)C(C)(C)c1[nH]c3cc(C#N)ccc3c1C2=O]

Under the same conditions as the method for synthesizing Compound B3-32, the title compound was prepared from Compound B2-16-2 and cyclobutanone.

$^1$H-NMR (400 MHz, DMSO-d$_6$) δ: 8.31 (1H, d, 8 Hz), 8.03 (1H, d, 12 Hz), 7.98 (1H, s), 7.59 (1H, d, 12 Hz), 7.13 (1H, s), 6.98 (1H, d, 8 Hz), 4.35-4.28 (1H, m), 3.70 (1H, d, 12 Hz), 3.02 (1H, ddd, 12, 12, 4 Hz), 2.87 (1H, d, 8 Hz), 2.74-2.67 (2H, m), 2.08-1.99 (2H, m), 1.92-1.64 (10H, m), 1.70-1.62 (2H, m), 1.12 (3H, d, 8 Hz)

LCMS: m/z 439 [M+H]$^+$

HPLC retention time: 2.59 min (analysis condition W)

Example 110

Compound B2-17

8-(2-Diethylamino-ethylsulfanyl)-6,6-dimethyl-11-oxo-6,11-dihydro-5H-benzo[b]carbazole-3-carbonitrile

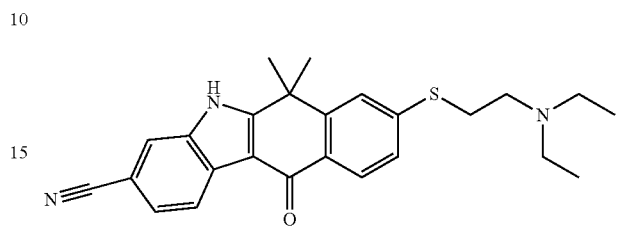

Trifluoro-methanesulfonic acid 3-cyano-6,6-dimethyl-11-oxo-6,11-dihydro-5H-benzo[b]carbazol-8-yl ester (Compound B1, 25 mg, 0.057 mmol) was dissolved in dimethoxyethane (0.5 mL), added with 2-diethylaminoethanethiol hydrochloric acid salt (19.6 mg, 2 eq.), Pd$_2$(dba)$_3$ (2.6 mg, 0.05 eq.), Xantphos (3.3 mg, 0.1 eq.) and DIPEA (0.06 mg, 6 eq.), and the mixture was stirred at 160° C. for 30 min. The reaction solution was added to water, extracted with ethyl acetate, and dried over magnesium sulfate. The drying agent was removed by filtration and the residues obtained after concentration under reduced pressure were purified by silica gel column chromatography (dichloromethane/methanol) to obtain the target compound (white amorphous, 22.4 mg, 93%).

$^1$H-NMR (400 MHz, CDCl$_3$) δ: 9.60 (1H, s), 8.53-8.48 (1H, m), 8.32 (1H, d, J=8.4 Hz), 7.77 (1H, s), 7.53-7.50 (2H, m), 7.38-7.35 (1H, m), 3.18-3.12 (2H, m), 2.81-2.75 (2H, m), 2.65-2.57 (4H, m), 1.76 (6H, s), 1.08-1.04 (6H, m)

LCMS: m/z 418 [M+H]$^+$

HPLC retention time: 2.10 min (analysis condition U)

Example 111

Compound B2-18

8-(2-Diisopropylamino-ethylsulfanyl)-6,6-dimethyl-11-oxo-6,11-dihydro-5H-benzo[b]carbazole-3-carbonitrile

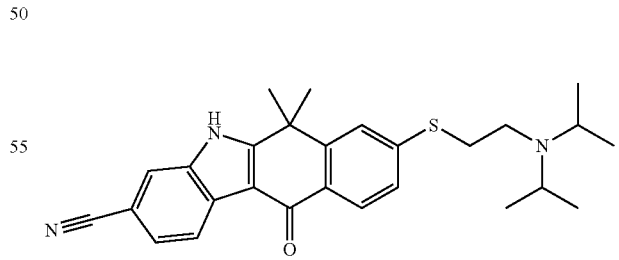

Under the same conditions as the method for synthesizing Compound B2-17, the title compound was prepared from Compound B1 and 2-diisopropylaminoethanethiol hydrochloric acid salt.

LCMS: m/z 446 [M+H]$^+$

HPLC retention time: 2.22 min (analysis condition U)

Example 112

Compound B2-19

8-(2-Dimethylamino-ethylsulfanyl)-6,6-dimethyl-11-oxo-6,11-dihydro-5H-benzo[b]carbazole-3-carbonitrile

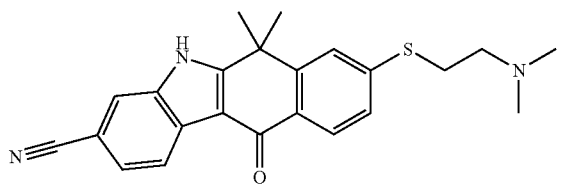 [SMILES: CN(C)CCSc1ccc2c(c1)C(C)(C)c1[nH]c3cc(C#N)ccc3c1C2=O]

Under the same conditions as the method for synthesizing Compound B2-17, the title compound was prepared from Compound B1 and 2-dimethylaminoethanethiol hydrochloric acid salt.
LCMS: m/z 390 [M+H]$^+$
HPLC retention time: 1.98 min (analysis condition U)

Example 113

Compound B2-20

3-(3-Cyano-6,6-dimethyl-11-oxo-6,11-dihydro-5H-benzo[b]carbazol-8-yl sulfanyl)-propionic acid

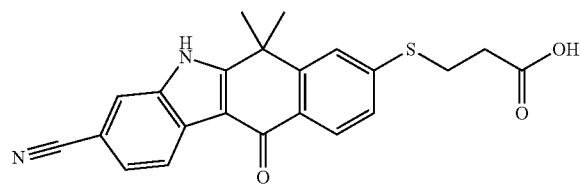 [SMILES: CC1(C)c2cc(SCCC(=O)O)ccc2C(=O)c2c1[nH]c1cc(C#N)ccc21]

Under the same conditions as the method for synthesizing Compound B2-17, the title compound was prepared from Compound B1 and 3-mercaptopropionic acid.
LCMS: m/z 391 [M+H]$^+$
HPLC retention time: 2.45 min (analysis condition U)

Example 114

Compound B2-21

8-(2,3-Dihydroxy-propylsulfanyl)-6,6-dimethyl-11-oxo-6,11-dihydro-5H-benzo[b]carbazole-3-carbonitrile

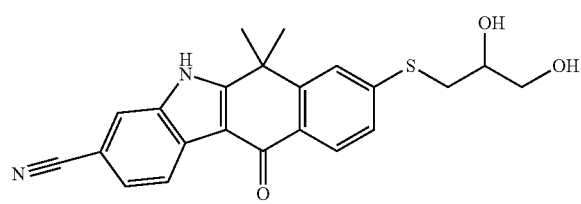 [SMILES: CC1(C)c2cc(SCC(O)CO)ccc2C(=O)c2c1[nH]c1cc(C#N)ccc21]

Under the same conditions as the method for synthesizing Compound B2-17, the title compound was prepared from Compound B1 and 3-mercaptopropane-1,2-diol.
LCMS: m/z 393 [M+H]$^+$
HPLC retention time: 2.15 min (analysis condition U)

Example 115

Compound B2-22-1

4-(3-Cyano-6,6-dimethyl-11-oxo-6,11-dihydro-5H-benzo[b]carbazol-8-yl)-3,6-dihydro-2H-pyridine-1-carboxylic acid tert-butyl ester

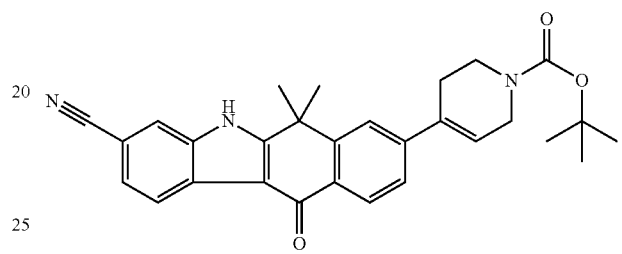

To trifluoro-methanesulfonic acid 3-cyano-6,6-dimethyl-11-oxo-6,11-dihydro-5H-benzo[b]carbazol-8-yl ester (Compound B1, 7.80 g, 18.0 mmol), 4-(4,4,5,5-tetramethyl-[1,3,2]dioxaborolan-2-yl)-3,6-dihydro-2H-pyridine-1-carboxylic acid tert-butyl ester (6.11 g, 19.8 mmol, 1.1 eq.), Pd(PPh$_3$)$_2$Cl$_2$ (630 mg, 0.898 mmol, 0.05 eq.), and sodium carbonate (5.71 g, 53.9 mmol, 3.0 eq.), DME (125 ml) and water (25 ml) were added. The mixture was subjected to reduced pressure under ultrasonication treatment, followed by flushing with nitrogen gas. This procedure was repeated five times and then degassed. After further stirring at 80° C. for 2 hr under nitrogen atmosphere, the mixture was cooled to room temperature, added with water (250 ml), and further stirred for 30 min. The precipitates were filtered and washed with water (50 ml). They were further washed with CH$_3$CN (50 ml) to obtain the target compound as a crude product (gray powder, 7.54 g, 90%).
LCMS: m/z 468 [M+H]$^+$
HPLC retention time: 2.90 min (analysis condition S)

Example 116

Compound B2-22-2

6,6-Dimethyl-11-oxo-8-(1,2,3,6-tetrahydro-pyridin-4-yl)-6,11-dihydro-5H-benzo[b]carbazole-3-carbonitrile

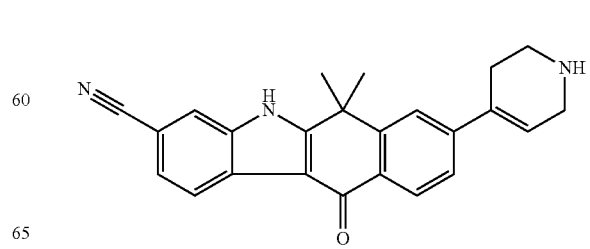

Under the same conditions as the method for synthesizing Compound A8-1, the title compound was prepared from Compound B2-22-1.

LCMS: m/z 368 [M+H]+
HPLC retention time: 1.47 min (analysis condition S)

Example 117

Compound B2-23

6,6-Dimethyl-8-(1-methyl-1H-pyrazol-4-yl)-11-oxo-6,11-dihydro-5H-benzo[b]carbazole-3-carbonitrile

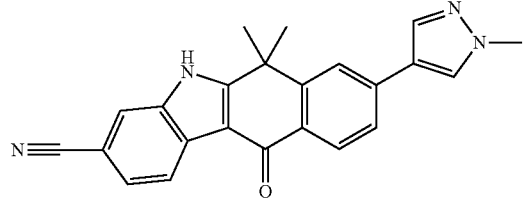 [SMILES: Cn1cc(-c2ccc3c(c2)C(C)(C)c2[nH]c4cc(C#N)ccc4c2C3=O)cn1]

Under the same conditions as the method for synthesizing Compound B2-22-1, the title compound was prepared from Compound B1 and 1-methyl-4-(4,4,5,5-tetramethyl-1,3,2-dioxaborolan-2-yl)-1H-pyrazole.

LCMS: m/z 367 [M+H]+
HPLC retention time: 2.42 min (analysis condition U)

Example 118

Compound B2-24

6,6-Dimethyl-11-oxo-8-vinyl-6,11-dihydro-5H-benzo[b]carbazole-3-carbonitrile

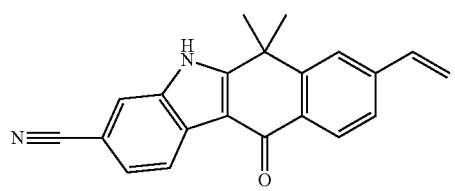 [SMILES: C=Cc1ccc2c(c1)C(C)(C)c1[nH]c3cc(C#N)ccc3c1C2=O]

Under nitrogen atmosphere, trifluoro-methanesulfonic acid 3-cyano-6,6-dimethyl-11-oxo-6,11-dihydro-5H-benzo[b]carbazol-8-yl ester (Compound B1, 1.00 g, 2.302 mmol) was added with n-propanol (20 mL), potassium vinyltrifluoroborate (854 mg, 3.0 eq.), dichloro-((bis-diphenylphosphino)ferrocenyl)palladium (217 mg, 0.1 eq.) and triethylamine (1.11 ml, 3.0 eq.) in order and the resultant was stirred at 60° C. for 4 hr. Upon the completion of the reaction, water was added to the reaction solution. The resulting precipitates were filtered and washed with distilled water, and the residues were dried to obtain the title compound (666 mg, 80%).

$^1$H-NMR (400 MHz, CDCl$_3$) δ: 8.90 (1H, s), 8.55 (1H, d, J=7.9 Hz), 8.40 (1H, d, J=8.5 Hz), 7.79 (1H, s), 7.58-7.61 (3H, m), 6.85 (1H, dd, J=17.7, 11.0 Hz), 5.95 (1H, d, J=17.1 Hz), 5.46 (1H, d, J=11.0 Hz), 1.84 (6H, s)

LCMS: m/z 313 [M+H]+
HPLC retention time: 3.75 min (analysis condition W)

Example 119

Compound B2-25-1

4-(3-Cyano-6,6-dimethyl-11-oxo-6,11-dihydro-5H-benzo[b]carbazol-8-yl methyl)-piperidine-1-carboxylic acid tert-butyl ester

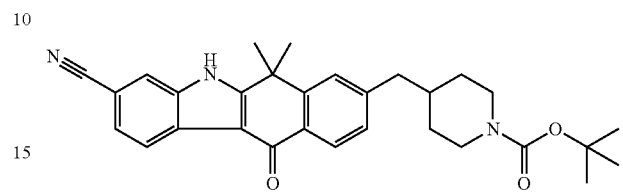

4-Methylene-piperidine-1-carboxylic acid tert-butyl ester (409 mg, 2.07 mmol, 1.2 eq.) was dissolved in THF (2 ml), added under nitrogen atmosphere with 9-BBN (0.5 M THF solution, 4.83 ml, 2.42 mmol, 1.4 eq.) and then stirred at 60° C. for 1 hr. Thereafter, 9-BBN (0.5 M THF solution, 5.52 ml, 2.77 mmol, 1.6 eq.) was further added and the mixture was stirred at 60° C. for 1 hr. The resulting mixture was cooled to room temperature, added with cesium fluoride (1.31 g, 8.60 mmol, 5.0 eq.), and stirred at room temperature for 30 min.

To the solution obtained from the above, DMF (18 ml) suspension comprising trifluoro-methanesulfonic acid 3-cyano-6,6-dimethyl-11-oxo-6,11-dihydro-5H-benzo[b]carbazol-8-yl ester (Compound B1, 750 mg, 1.73 mmol) and dichloro-((bisdiphenylphosphino)ferrocenyl)palladium (70.5 mg, 0.0863 mmol, 0.05 eq.) was added, and the mixture was stirred at 100° C. for 3 hr. After cooling to the room temperature, water (50 ml) was added, followed by extraction with ethyl acetate. The organic layer was washed with saturated brine and dried over sodium sulfate. The drying agent was removed by filtration and the residues obtained after concentration under reduced pressure were purified by silica gel column chromatography (ethyl acetate/hexane) to obtain 4-(3-cyano-6,6-dimethyl-11-oxo-6,11-dihydro-5H-benzo[b]carbazol-8-yl methyl)-piperidine-1-carboxylic acid tert-butyl ester (yellow powder, 763 mg, 91%).

LCMS: m/z 484 [M+H]+
HPLC retention time: 2.97 min (analysis condition S)

Example 120

Compound B2-25-2

6,6-Dimethyl-11-oxo-8-piperidin-4-yl methyl-6,11-dihydro-5H-benzo[b]carbazole-3-carbonitrile

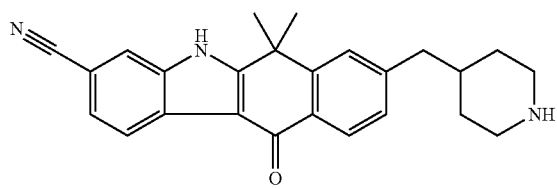 [SMILES: CC1(C)c2cc(CC3CCNCC3)ccc2C(=O)c2c1[nH]c1cc(C#N)ccc21]

Under the same conditions as the method for synthesizing Compound A8-1, the title compound was prepared from Compound B2-25-1.

LCMS: m/z 384 [M+H]+
HPLC retention time: 1.40 min (analysis condition S)

Example 121

Compound B2-26-1

Tert-butyl 4-((3-cyano-6,6-dimethyl-11-oxo-6,11-dihydro-5H-benzo[b]carbazol-8-yl)methyl)piperidin-1-yl sulfonylcarbamic acid

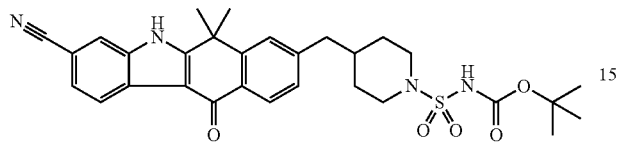

Under the same conditions as the method for synthesizing Compound A9-1, the title compound was prepared from Compound B2-25-2 and N-(tert-butoxycarbonyl)-N-[4-(dimethylazaniumylidene)-1,4-dihydropyridin-1-yl sulfonyl]azanide (CAS No. 872496-91-8).
LCMS: m/z 563 [M+H]+
HPLC retention time: 2.63 min (analysis condition S)

Example 122

Compound B2-26-2

4-(3-Cyano-6,6-dimethyl-11-oxo-6,11-dihydro-5H-benzo[b]carbazol-8-ylmethyl)-piperidine-1-sulfonic acid amide

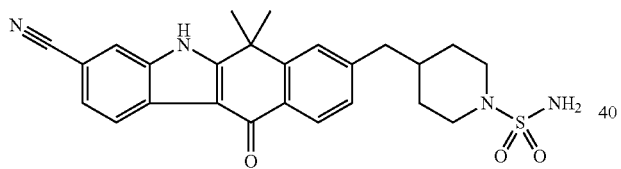

Under the same conditions as the method for synthesizing Compound A8-1, the title compound was prepared from Compound B2-26-1.
LCMS: m/z 463 [M+H]+
HPLC retention time: 2.10 min (analysis condition S)

Example 123

Compound B2-27

8-(1-Isopropyl-piperidin-4-ylmethyl)-6,6-dimethyl-11-oxo-6,11-dihydro-5H-benzo[b]carbazole-3-carbonitrile

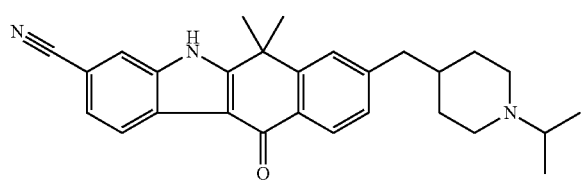 [SMILES: CC(C)N1CCC(Cc2ccc3c(c2)C(C)(C)c2[nH]c4cc(C#N)ccc4c2C3=O)CC1]

Under the same conditions as the method for synthesizing Compound B3-32, the title compound was prepared from Compound B2-25-2 and acetone.
1H-NMR (400 MHz, DMSO-d6) δ: 12.80 (1H, s), 8.32 (1H, d, 7.9 Hz), 8.12 (1H, d, 7.9 Hz), 8.01 (1H, s), 7.65 (1H, s), 7.61 (1H, d, 9.1 Hz), 7.30 (1H, d, 7.9 Hz), 2.75 (2H, d, 11.0 Hz), 2.65 (3H, q, 6.5 Hz), 2.04 (2H, t, 11.0 Hz), 1.77 (6H, s), 1.60-1.57 (3H, m), 1.22 (2H, t, 11.6 Hz), 0.94 (6H, d, 6.7 Hz)
LCMS: m/z 426 [M+H]+

Example 124

Compound B2-28

3-Cyano-6,6-dimethyl-11-oxo-6,11-dihydro-5H-benzo[b]carbazol-8-carboxylic acid

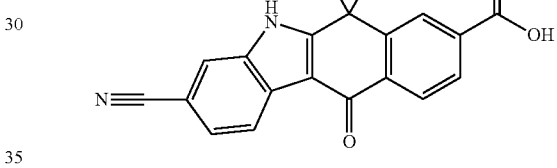

Under nitrogen atmosphere, to the dimethyl formamide (3 ml) solution comprising trifluoro-methanesulfonic acid 3-cyano-6,6-dimethyl-11-oxo-6,11-dihydro-5H-benzo[b]carbazol-8-yl ester (Compound B1, 150 mg, 0.345 mmol), lithium formate monohydrate (90 mg, 5.0 eq.), 4,5-bis(diphenylphosphino)-9,9-dimethylxanthene (Xantphos) (20 mg, 0.1 eq.), Pd2(dba)3 (32 mg, 0.1 eq.), lithium chloride (88 mg, 6.0 eq.), N,N-diisopropylethylamine (241 µl, 4.0 eq.), and acetic anhydride (131 µl, 4.0 eq.) were added, and the mixture was stirred at 80° C. for 15 hr. Upon the completion of the reaction, ethyl acetate was added to the reaction solution. The organic layer was washed in order with 1 M hydrochloric acid, distilled water, and brine. The organic layer was dried over sodium sulfate. The drying agent was removed by filtration and the residues obtained after concentration under reduced pressure were purified by silica gel column chromatography (ethyl acetate/hexane) to obtain the title compound (88 mg, 76%).
1H-NMR (400 MHz, DMSO-d6) δ: 13.17 (1H, s), 8.35 (1H, d, J=7.9 Hz), 8.34 (1H, s), 8.23 (1H, d, J=7.9 Hz), 8.07 (1H, s), 8.02 (1H, d, J=9.1 Hz), 7.64 (1H, d, J=7.9 Hz), 1.80 (6H, s)
LCMS: m/z 331 [M+H]+
HPLC retention time: 3.08 min (analysis condition W)

Example 125

Compound B2-29

8-Formyl-6,6-dimethyl-11-oxo-6,11-dihydro-5H-benzo[b]carbazole-3-carbonitrile

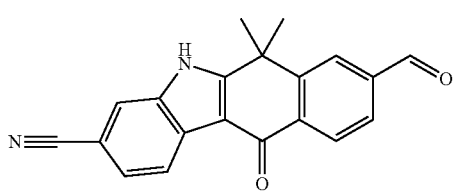 [SMILES: CC1(C)c2cc(C=O)ccc2C(=O)c2c1[nH]c1cc(C#N)ccc21]

To the THF (24 ml) and distilled water (6 ml) suspension of 6,6-dimethyl-11-oxo-8-vinyl-6,11-dihydro-5H-benzo[b]carbazole-3-carbonitrile (Compound B2-24, 600 mg, 1.920 mmol), t-butanol solution of osmium tetraoxide (192 μl, 0.1 eq.) and sodium meta periodate (821 mg, 2.0 eq.) were added and the mixture was stirred at room temperature for 3 hr. Aqueous solution of sodium thiosulfate (0.3 M) was added to the solution, which was then extracted with an ethyl acetate. The organic layer was washed with 10% aqueous solution of disodium ethylenediamine tetraacetic acid. The organic layer was dried over sodium sulfate. The drying agent was removed by filtration and the residues obtained after concentration under reduced pressure were purified by silica gel column chromatography (ethyl acetate/hexane) to obtain the title compound (470 mg, 77%).

$^1$H-NMR (400 MHz, DMSO-$d_6$) δ: 12.95 (1H, s), 10.20 (1H, s), 8.48 (1H, s), 8.42 (1H, d, J=8.5 Hz), 8.36 (1H, d, J=8.5 Hz), 8.07 (1H, s), 8.02 (1H, d, J=7.9 Hz), 7.67 (1H, d, J=7.9 Hz), 1.85 (6H, s)

LCMS: m/z 315 [M+H]$^+$

HPLC retention time: 3.38 min (analysis condition W)

Example 126

Compound B3-1

5,6,6-Trimethyl-8-morpholin-4-yl-11-oxo-6,11-dihydro-5H-benzo[b]carbazole-3-carbonitrile

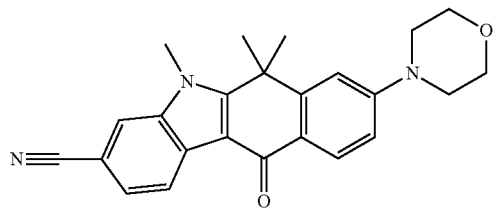 [SMILES: Cn1c2c(c3ccc(C#N)cc31)C(=O)c1ccc(N3CCOCC3)cc1C2(C)C]

Under the same conditions as the method for synthesizing Compound A10-1, the title compound was prepared from Compound B2-3.

LCMS: m/z 386 [M+H]$^+$

HPLC retention time: 2.62 min (analysis condition U)

Example 127

Compound B3-2-1

Tert-butyl 4-(3-cyano-6,6-dimethyl-11-oxo-6,11-dihydro-5H-benzo[b]carbazol-8-yl)piperazin-1-yl sulfonylcarbamic acid

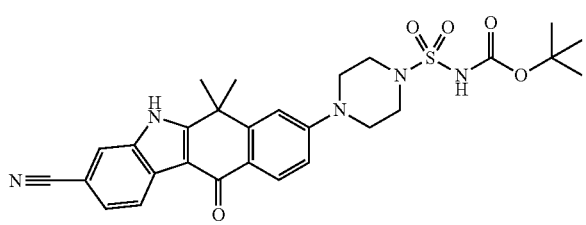 [SMILES: CC(C)(C)OC(=O)NS(=O)(=O)N1CCN(c2ccc3c(c2)C(C)(C)c2[nH]c4cc(C#N)ccc4c2C3=O)CC1]

Under the same conditions as the method for synthesizing Compound A9-1, the title compound was prepared from Compound B2-5-2 and N-(tert-butoxycarbonyl)-N-[4-(dimethylazaniumylidene)-1,4-dihydropyridin-1-yl sulfonyl]azanide (CAS No. 872496-91-8).

LCMS: m/z 550 [M+H]$^+$

HPLC retention time: 2.39 min (analysis condition S)

Example 128

Compound B3-2-2

4-(3-Cyano-6,6-dimethyl-11-oxo-6,11-dihydro-5H-benzo[b]carbazol-8-yl)-piperazine-1-sulfonic acid amide

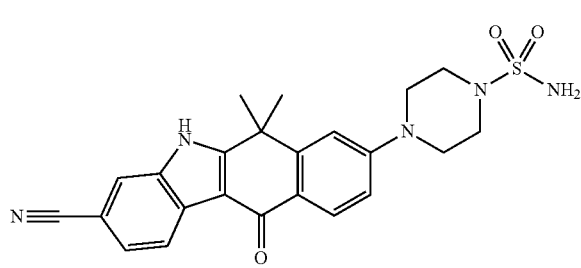 [SMILES: CC1(C)c2cc(N3CCN(S(N)(=O)=O)CC3)ccc2C(=O)c2c1[nH]c1cc(C#N)ccc21]

Under the same conditions as the method for synthesizing Compound A8-1, the title compound was prepared from Compound B3-2-1.

LCMS: m/z 450 [M+H]$^+$

HPLC retention time: 1.82 min (analysis condition S)

Example 129

Compound B3-3

4-(3-Cyano-6,6-dimethyl-11-oxo-6,11-dihydro-5H-benzo[b]carbazol-8-yl)-piperazine-1-sulfonic acid dimethylamide

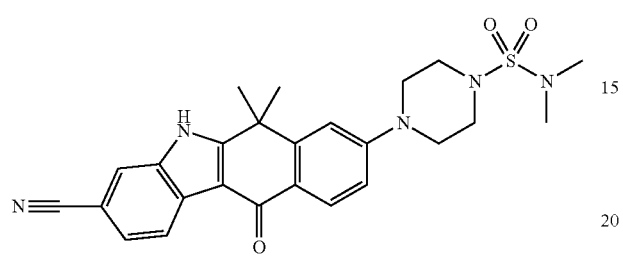

Under the same conditions as the method for synthesizing Compound A9-1, the title compound was prepared from Compound B2-5-2 and dimethylsulfamoyl chloride.

LCMS: m/z 478 [M+H]$^+$

HPLC retention time: 2.45 min (analysis condition S)

Example 130

Compound B3-4

4-(3-Cyano-5,6,6-trimethyl-11-oxo-6,11-dihydro-5H-benzo[b]carbazol-8-yl)-piperazine-1-sulfonic acid dimethylamide

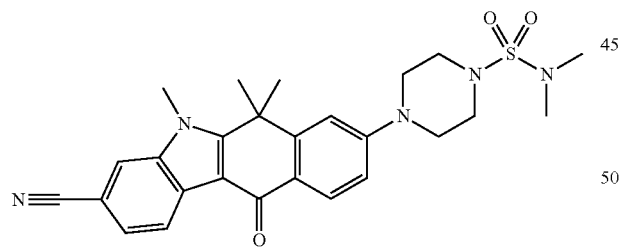

To the DMF suspension of 4-(3-cyano-6,6-dimethyl-11-oxo-6,11-dihydro-5H-benzo[b]carbazol-8-yl)-piperazine-1-sulfonic acid amide (Compound B3-2-2, 20 mg, 0.04 mmol) and sodium hydride (21.4 mg, 12 eq.), iodomethane (28 µl, 10 eq.) was added and stirred at room temperature overnight. Water was added to the reaction solution, followed by filtration to obtain the target compound (25.8 mg, 100%).

$^1$H-NMR (270 MHz, DMSO-d$_6$) δ: 8.43 (1H, d, J=8.2 Hz), 8.31 (1H, s), 8.03 (1H, d, J=8.9 Hz), 7.64 (1H, dd, J=8.1, 1.3 Hz), 7.30 (1H, d, J=2.0 Hz), 7.08 (1H, dd, J=8.9, 2.0 Hz), 4.16 (3H, s), 3.43-3.53 (4H, t, J=4.7 Hz), 3.26-3.41 (4H, s), 2.82 (6H, s), 1.87 (6H, s).

LCMS: m/z 492 [M+H]$^+$

HPLC retention time: 2.69 min (analysis condition S)

Example 131

Compound B3-5

8-(4-Cyclopropyl-piperazin-1-yl)-6,6-dimethyl-11-oxo-6,11-dihydro-5H-benzo[b]carbazole-3-carbonitrile

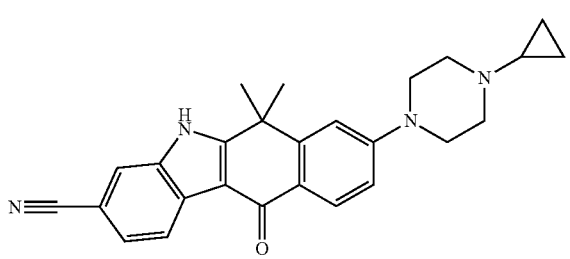 [SMILES: CC1(C)c2cc(N3CCN(C4CC4)CC3)ccc2C(=O)c2c1[nH]c1cc(C#N)ccc21]

The title compound was obtained as a by-product of the synthesis of Compound F5-36.

LCMS: m/z 411 [M+H]$^+$

HPLC retention time: 1.31 min (analysis condition S)

Example 132

Compound B3-6

8-(4-Cyclobutyl-piperazin-1-yl)-6,6-dimethyl-11-oxo-6,11-dihydro-5H-benzo[b]carbazole-3-carbonitrile

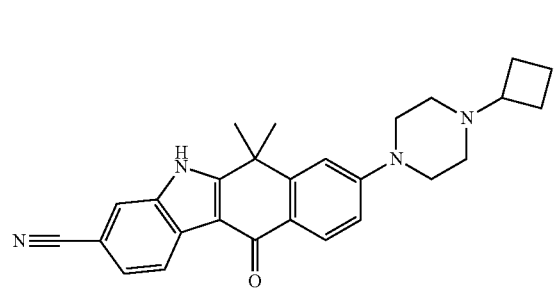 [SMILES: CC1(C)c2cc(N3CCN(C4CCC4)CC3)ccc2C(=O)c2c1[nH]c1cc(C#N)ccc21]

Under the same conditions as the method for synthesizing Compound B3-32, the title compound was prepared from Compound B2-5-2 and cyclobutanone.

$^1$H-NMR (400 MHz, DMSO-d$_6$) δ: 8.29 (1H, d, J=8.2 Hz), 8.01 (1H, d, J=8.8 Hz), 7.96 (1H, s), 7.55 (1H, d, J=8.2 Hz), 7.19 (1H, d, J=2.2 Hz), 7.03 (1H, dd, J=2.4, 8.8 Hz), 2.71-2.75 (1H, m), 2.37-2.39 (4H, m), 1.98-2.00 (2H, m), 1.77-1.85 (2H, m), 1.74 (6H, s), 1.63-1.68 (2H, m).

LCMS: m/z 425 [M+H]$^+$

HPLC retention time: 1.80 min (analysis condition U)

Example 133

Compound B3-7

6,6-Dimethyl-8-(4-oxetan-3-yl-piperazin-1-yl)-11-oxo-6,11-dihydro-5H-benzo[b]carbazole-3-carbonitrile

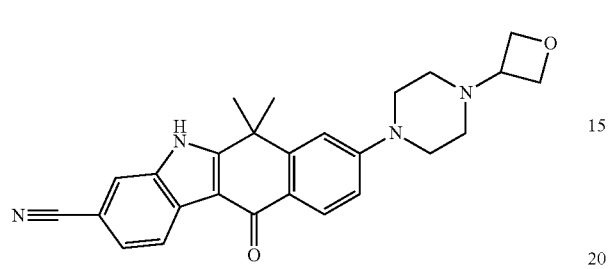

Under the same conditions as the method for synthesizing Compound B3-32, the title compound was prepared from Compound B2-5-2 and 3-oxetanone.

$^1$H-NMR (400 MHz, DMSO-d$_6$) δ: 8.29 (1H, dd, J=8.2, 0.59 Hz), 8.02 (1H, d, J=9.0 Hz), 7.97 (1H, d, J=0.59 Hz), 7.56 (1H, dd, J=8.0, 1.4 Hz), 7.22 (1H, d, J=2.3 Hz), 7.04 (1H, dd, J=8.8, 2.2 Hz), 4.56-4.59 (2H, m), 4.47-4.50 (2H, m), 3.43-3.48 (1H, m), 3.39-3.42 (4H, m), 2.40-2.42 (4H, m), 1.74 (6H, s)

LCMS: m/z 427 [M+H]$^+$

HPLC retention time: 1.67 min (analysis condition U)

Example 134

Compound B3-8

8-(2-Diethylamino-ethanesulfonyl)-6,6-dimethyl-11-oxo-6,11-dihydro-5H-benzo[b]carbazole-3-carbonitrile

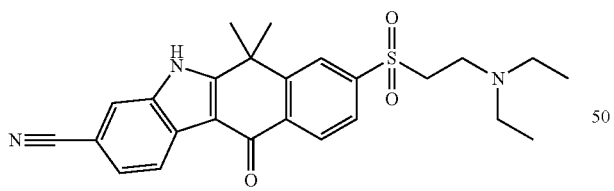

8-(2-Diethylamino-ethylsulfanyl)-6,6-dimethyl-11-oxo-6,11-dihydro-5H-benzo[b]carbazole-3-carbonitrile (Compound B2-17, 16.8 mg, 0.0402 mmol) was dissolved in methanol (1.5 mL), added with oxone (54.3 mg, 2.2 eq.) which had been dissolved in water (0.5 mL), and then stirred at room temperature for 2 hr. The reaction solution was concentrated, extracted with ethyl acetate, washed with saturated sodium hydrogen carbonate, and dried over magnesium sulfate. The drying agent was removed by filtration and the residues obtained after concentration under reduced pressure were purified by silica gel column chromatography (dichloromethane/methanol) to obtain the target compound (white solid, 5.8 mg, 32%).

$^1$H-NMR (400 MHz, CDCl$_3$) δ: 9.29 (1H, s), 8.61 (1H, d, J=8.2 Hz), 8.52 (1H, d, J=8.0 Hz), 8.21 (1H, s), 8.01 (1H, d, J=8.2 Hz), 7.81 (1H, s), 7.61 (1H, d, J=8.2 Hz), 3.33 (2H, t, J=7.4 Hz), 2.95 (2H, t, J=7.4 Hz), 2.41 (4H, q, J=7.2 Hz), 1.86 (6H, s), 0.89 (4H, t, J=7.1 Hz)

LCMS: m/z 450 [M+H]$^+$

HPLC retention time: 2.05 min (analysis condition U)

Example 135

Compound B3-9

8-(2-Diisopropylamino-ethanesulfonyl)-6,6-dimethyl-11-oxo-6,11-dihydro-5H-benzo[b]carbazole-3-carbonitrile

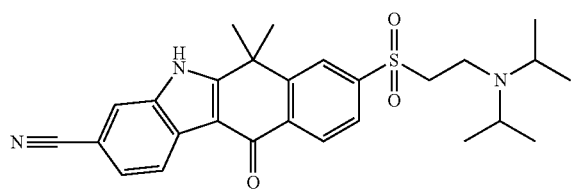 [SMILES: CC(C)N(CCS(=O)(=O)c1ccc2c(c1)C(C)(C)c1[nH]c3cc(C#N)ccc3c1C2=O)C(C)C]

Under the same conditions as the method for synthesizing Compound B3-8, the title compound was prepared from Compound B2-18.

LCMS: m/z 478 [M+H]$^+$

HPLC retention time: 2.18 min (analysis condition U)

Example 136

Compound B3-10

8-(2-Dimethylamino-ethanesulfonyl)-6,6-dimethyl-11-oxo-6,11-dihydro-5H-benzo[b]carbazole-3-carbonitrile

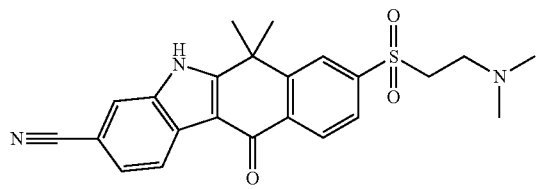 [SMILES: CN(C)CCS(=O)(=O)c1ccc2c(c1)C(C)(C)c1[nH]c3cc(C#N)ccc3c1C2=O]

Under the same conditions as the method for synthesizing Compound B3-8, the title compound was prepared from Compound B2-19.

LCMS: m/z 422 [M+H]$^+$

HPLC retention time: 2.03 min (analysis condition U)

Example 137

Compound B3-11

3-(3-Cyano-6,6-dimethyl-11-oxo-6,11-dihydro-5H-benzo[b]carbazol-8-sulfonyl)-propionic acid

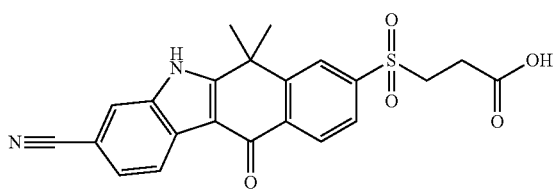 [SMILES: CC1(C)c2cc(S(=O)(=O)CCC(=O)O)ccc2C(=O)c2c1[nH]c1cc(C#N)ccc21]

Under the same conditions as the method for synthesizing Compound B3-8, the title compound was prepared from Compound B2-20.
LCMS: m/z 423 [M+H]$^+$
HPLC retention time: 2.28 min (analysis condition U)

Example 138

Compound B3-12

8-(2,3-Dihydroxy-propane-1-sulfonyl)-6,6-dimethyl-11-oxo-6,11-dihydro-5H-benzo[b]carbazole-3-carbonitrile

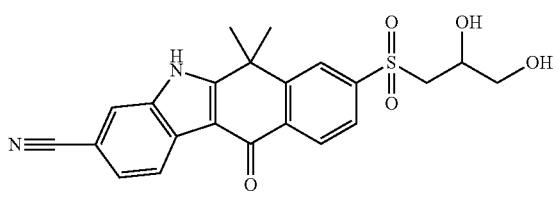 [SMILES: CC1(C)c2cc(S(=O)(=O)CC(O)CO)ccc2C(=O)c2c1[nH]c1cc(C#N)ccc21]

Under the same conditions as the method for synthesizing Compound B3-8, the title compound was prepared from Compound B2-21.
LCMS: m/z 425 [M+H]$^+$
HPLC retention time: 2.17 min (analysis condition U)

Example 139

Compound B3-13-1

4-(3-Cyano-6,6-dimethyl-11-oxo-6,11-dihydro-5H-benzo[b]carbazol-8-yl)-piperidine-1-carboxylic acid tert-butyl ester

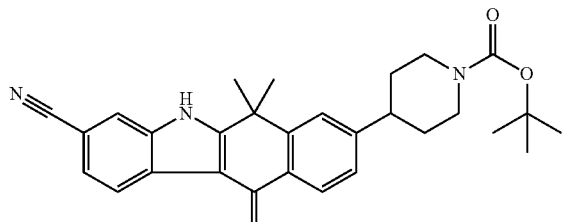

4-(3-Cyano-6,6-dimethyl-11-oxo-6,11-dihydro-5H-benzo[b]carbazol-8-yl)-3,6-dihydro-2H-pyridine-1-carboxylic acid tert-butyl ester (Compound B2-22-1, 16.2 g, 34.6 mmol) was dissolved in THF (800 ml) and methanol (230 ml), added with 10 wt % Pd/C (3.2 g), and stirred under hydrogen atmosphere for 19 hr. The solid was filtered through Celite, eluted with a mixture solvent (400 ml; THF/methanol=4/1), and concentrated under reduced pressure. The residues were dissolved in ethyl acetate (400 ml), and then washed with 1% aqueous solution of N-acetylcysteine, saturated aqueous solution of NaHCO$_3$ and saturated brine. The organic layer was dried over sodium sulfate. The drying agent was removed by filtration and the residues were concentrated under reduced pressure to obtain the title compound as a crude product (white powder, 14.0 g, 86%).
LCMS: m/z 470 [M+H]$^+$
HPLC retention time: 2.88 min (analysis condition S)

Example 140

Compound B3-13-2

6,6-Dimethyl-11-oxo-8-piperidin-4-yl-6,11-dihydro-5H-benzo[b]carbazole-3-carbonitrile

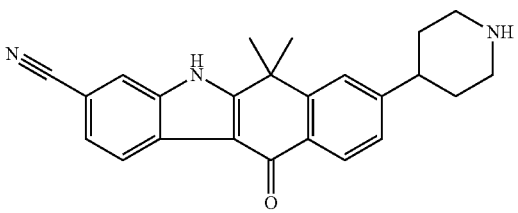 [SMILES: CC1(C)c2cc(C3CCNCC3)ccc2C(=O)c2c1[nH]c1cc(C#N)ccc21]

Under the same conditions as the method for synthesizing Compound A8-1, the title compound was prepared from Compound B3-13-1.
LCMS: m/z 370 [M+H]$^+$
HPLC retention time: 1.30 min (analysis condition S)

Example 141

Compound B3-14

8-(1,2-Dihydroxy-ethyl)-6,6-dimethyl-11-oxo-6,11-dihydro-5H-benzo[b]carbazole-3-carbonitrile

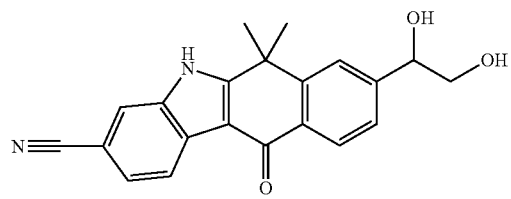 [SMILES: CC1(C)c2cc(C(O)CO)ccc2C(=O)c2c1[nH]c1cc(C#N)ccc21]

To the THF (1 ml) solution of 6,6-dimethyl-11-oxo-8-vinyl-6,11-dihydro-5H-benzo[b]carbazole-3-carbonitrile (Compound B2-24, 20 mg, 0.064 mmol), t-butanol solution of osmium tetraoxide (19 µl, 0.3 eq.) and 50% aqueous solution of N-methylmorpholine-N-oxide (30 µl, 2.0 eq.) were added and the mixture was stirred at room temperature for 3 hr. To the reaction solution, 10% aqueous solution of disodium ethylenediamine tetraacetic acid was added, followed by extraction with ethyl acetate. The organic layer was dried over sodium sulfate. The drying agent was removed by filtration and the residues obtained after concentration under reduced pressure were purified by high performance liquid chromatography to obtain the title compound (21 mg, 63%).

$^1$H-NMR (400 MHz, CD$_3$OD) δ: 8.41 (1H, d, J=7.9 Hz), 8.29 (1H, d, J=7.9 Hz), 7.87 (1H, s), 7.86 (1H, s), 7.57 (1H, d, J=7.9 Hz), 7.52 (1H, d, J=6.7 Hz), 4.85 (1H, dd, J=7.0, 4.6 Hz), 3.73 (1H, dd, J=11.3, 4.6 Hz), 3.68 (1H, dd, J=11.3, 7.0 Hz), 1.83 (6H, s)

LCMS: m/z 347 [M+H]$^+$

HPLC retention time: 2.68 min (analysis condition W)

Example 142

Compound B3-15

6,6-Dimethyl-8-(morpholine-4-carbonyl)-11-oxo-6,11-dihydro-5H-benzo[b]carbazole-3-carbonitrile

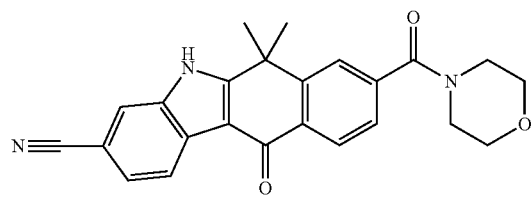 [SMILES: CC1(C)c2cc(C(=O)N3CCOCC3)ccc2C(=O)c2c1[nH]c1cc(C#N)ccc21]

To the tetrahydrofuran (1 ml) solution of 3-cyano-6,6-dimethyl-11-oxo-6,11-dihydro-5H-benzo[b]carbazol-8-carboxylic acid (Compound B2-28, 15 mg, 0.045 mmol), morpholine (6 μl, 1.5 eq.), hexafluorophosphoric acid uronium 2-(1H-7-azabenzotriazol-1-yl)-1,1,3,3-tetramethylmethane aminium (HATU) (26 mg, 1.5 eq.), and N,N-diisopropylethylamine (24 μl, 3.0 eq.) were added and the mixture was stirred at room temperature for 3 hr. The reaction solution was filtered to remove insoluble matters and the residues obtained after concentration under reduced pressure were purified by high performance liquid chromatography to obtain the title compound (11 mg, 55%).

$^1$H-NMR (400 MHz, DMSO-d$_6$) δ: 12.85 (1H, s), 8.33 (1H, d, J=8.5 Hz), 8.27 (1H, d, J=7.9 Hz), 8.03 (1H, s), 7.92 (1H, s), 7.63 (1H, d, J=8.5 Hz), 7.54 (1H, d, J=7.9 Hz), 3.52-3.77 (6H, m), 3.30-3.42 (2H, m), 1.79 (6H, s)

LCMS: m/z 400 [M+H]$^+$

HPLC retention time: 2.96 min (analysis condition W)

Example 143

Compound B3-16

8-(4-Methanesulfonyl-piperazin-1-carbonyl)-6,6-dimethyl-11-oxo-6,11-dihydro-5H-benzo[b]carbazole-3-carbonitrile

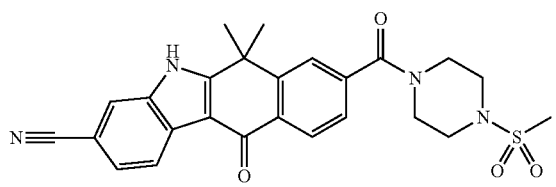 [SMILES: CC1(C)c2cc(C(=O)N3CCN(S(C)(=O)=O)CC3)ccc2C(=O)c2c1[nH]c1cc(C#N)ccc21]

Under the same conditions as the method for synthesizing Compound B3-15, the title compound was prepared from Compound B2-28 and 1-methanesulfonylpiperazine.

LCMS: m/z 477 [M+H]$^+$

HPLC retention time: 3.03 min (analysis condition W)

Example 144

Compound B3-17

8-(4-Hydroxy-piperidin-1-carbonyl)-6,6-dimethyl-11-oxo-6,11-dihydro-5H-benzo[b]carbazole-3-carbonitrile

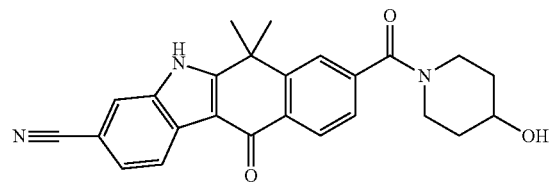 [SMILES: CC1(C)c2cc(C(=O)N3CCC(O)CC3)ccc2C(=O)c2c1[nH]c1cc(C#N)ccc21]

Under the same conditions as the method for synthesizing Compound B3-15, the title compound was prepared from Compound B2-28 and piperidin-4-ol.

LCMS: m/z 414 [M+H]$^+$

HPLC retention time: 2.75 min (analysis condition W)

Example 145

Compound B3-18

3-Cyano-6,6-dimethyl-11-oxo-6,11-dihydro-5H-benzo[b]carbazol-8-carboxylic acid (2-hydroxy-1-hydroxymethyl-ethyl)-amide

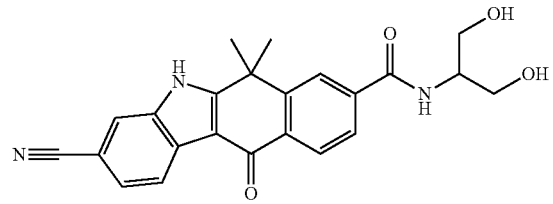 [SMILES: CC1(C)c2cc(C(=O)NC(CO)CO)ccc2C(=O)c2c1[nH]c1cc(C#N)ccc21]

Under the same conditions as the method for synthesizing Compound B3-15, the title compound was prepared from Compound B2-28 and 2-aminopropane-1,3-diol.

LCMS: m/z 404 [M+H]$^+$

HPLC retention time: 2.60 min (analysis condition W)

Example 146

Compound B3-19

3-Cyano-6,6-dimethyl-11-oxo-6,11-dihydro-5H-benzo[b]carbazol-8-carboxylic acid (2-methanesulfonyl-ethyl)-amide

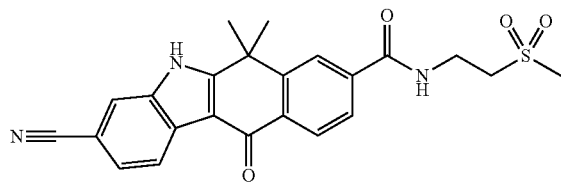

Under the same conditions as the method for synthesizing Compound B3-15, the title compound was prepared from Compound B2-28 and 2-methanesulfonylethylamine.
LCMS: m/z 436 [M+H]$^+$
HPLC retention time: 2.87 min (analysis condition W)

Example 147

Compound B3-20

3-Cyano-6,6-dimethyl-11-oxo-6,11-dihydro-5H-benzo[b]carbazol-8-carboxylic acid (1,1-dioxo-tetrahydro-thiophen-3-yl)-amide

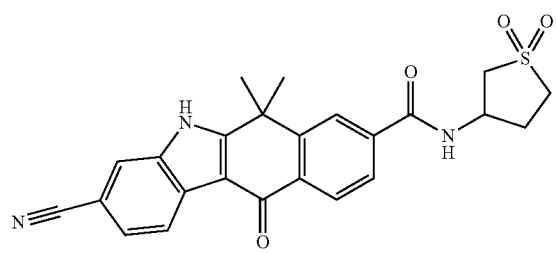

Under the same conditions as the method for synthesizing Compound B3-15, the title compound was prepared from Compound B2-28 and (1,1-dioxotetrahydrothiophen-3-yl) amine
LCMS: m/z 448 [M+H]$^+$
HPLC retention time: 1.70 min (analysis condition S)

Example 148

Compound B3-21

3-Cyano-6,6-dimethyl-11-oxo-6,11-dihydro-5H-benzo[b]carbazol-8-carboxylic acid ((R)-2,3-dihydroxy-propyl)-amide

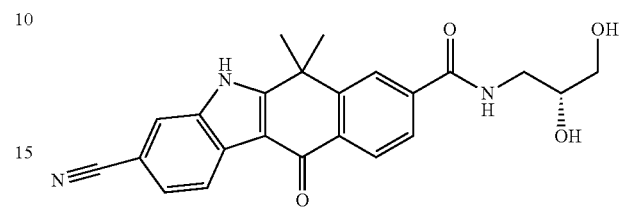

Under the same conditions as the method for synthesizing Compound B3-15, the title compound was prepared from Compound B2-28 and (R)-(+)-3-amino-1,2-propanediol.
LCMS: m/z 404 [M+H]$^+$
HPLC retention time: 1.38 min (analysis condition S)

Example 149

Compound B3-22

3-Cyano-6,6-dimethyl-11-oxo-6,11-dihydro-5H-benzo[b]carbazol-8-carboxylic acid bis-(2-hydroxy-ethyl)-amide

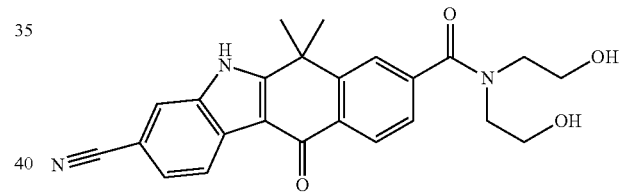

Under the same conditions as the method for synthesizing Compound B3-15, the title compound was prepared from Compound B2-28 and N,N-diethanolamine.
LCMS: m/z 418 [M+H]$^+$
HPLC retention time: 1.35 min (analysis condition S)

Example 150

Compound B3-23

3-Cyano-6,6-dimethyl-11-oxo-6,11-dihydro-5H-benzo[b]carbazol-8-carboxylic acid oxetan-3-yl amide

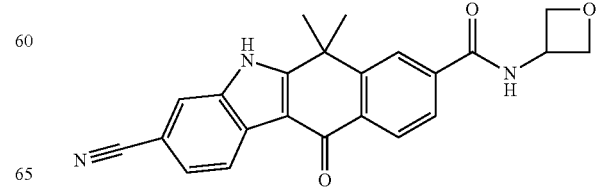

Under the same conditions as the method for synthesizing Compound B3-15, the title compound was prepared from Compound B2-28 and oxetan-3-yl amine.
LCMS: m/z 386 [M+H]+
HPLC retention time: 1.63 min (analysis condition S)

Example 151

Compound B3-24

3-Cyano-6,6-dimethyl-11-oxo-6,11-dihydro-5H-benzo[b]carbazol-8-carboxylic acid (2-hydroxy-ethoxy)-amide

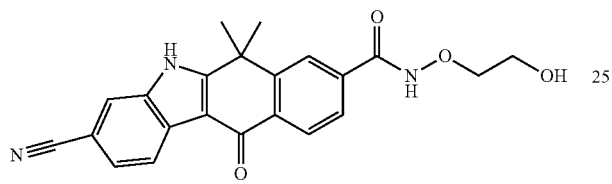

Under the same conditions as the method for synthesizing Compound B3-15, the title compound was prepared from Compound B2-28 and 2-aminooxy-ethanol.
LCMS: m/z 390 [M+H]+
HPLC retention time: 1.54 min (analysis condition S)

Example 152

Compound B3-25-1

2-[(3-Cyano-6,6-dimethyl-11-oxo-6,11-dihydro-5H-benzo[b]carbazol-8-carbonyl)-amino]-ethyl}-carbamic acid tert-butyl ester

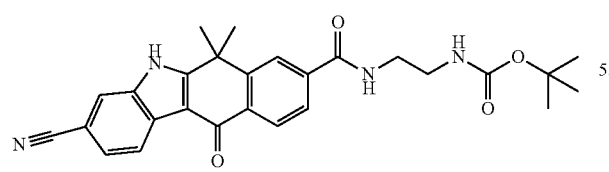

Under the same conditions as the method for synthesizing Compound B3-15, the title compound was prepared from Compound B2-28 and (2-amino-ethyl)-carbamic acid tert-butyl ester.
LCMS: m/z 473 [M+H]+
HPLC retention time: 2.08 min (analysis condition S)

Example 153

Compound B3-25-2

3-Cyano-6,6-dimethyl-11-oxo-6,11-dihydro-5H-benzo[b]carbazol-8-carboxylic acid (2-amino-ethyl)-amide

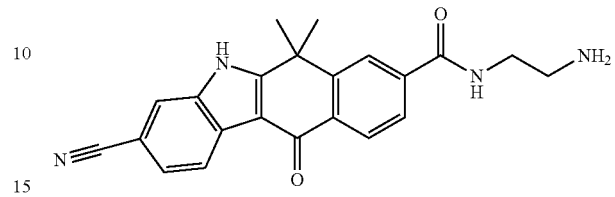

Under the same conditions as the method for synthesizing Compound A8-1, the title compound was prepared from Compound B3-25-1.
LCMS: m/z 373 [M+H]+
HPLC retention time: 1.19 min (analysis condition S)

Example 154

Compound B3-25-3

3-Cyano-6,6-dimethyl-11-oxo-6,11-dihydro-5H-benzo[b]carbazol-8-carboxylic acid (2-methanesulfonylamino-ethyl)-amide

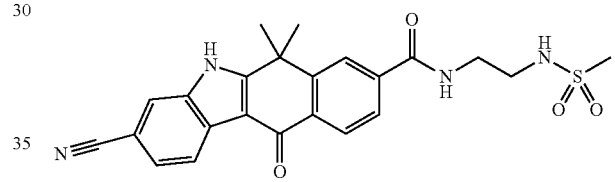

Under the same conditions as the method for synthesizing Compound A9-1, the title compound was prepared from Compound B3-25-2.
LCMS: m/z 451 [M+H]+
HPLC retention time: 1.62 min (analysis condition S)

Example 155

Compound B3-26

3-Cyano-6,6-dimethyl-11-oxo-6,11-dihydro-5H-benzo[b]carbazol-8-carboxylic acid (2-hydroxy-ethyl)-methyl-amide

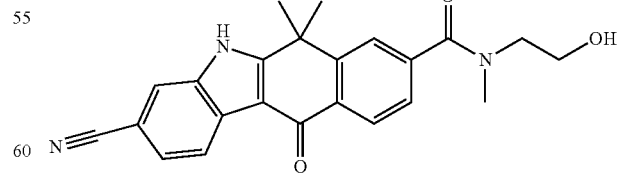

Under the same conditions as the method for synthesizing Compound B3-15, the title compound was prepared from Compound B2-28 and 2-methylamino-ethanol.
LCMS: m/z 388 [M+H]+
HPLC retention time: 1.53 min (analysis condition S)

Example 156

Compound B3-27-1

Tert-butyl N-(2-(3-cyano-6,6-dimethyl-11-oxo-6,11-dihydro-5H-benzo[b]carbazol-8carboxamide)ethyl) sulfamoylcarbamic acid

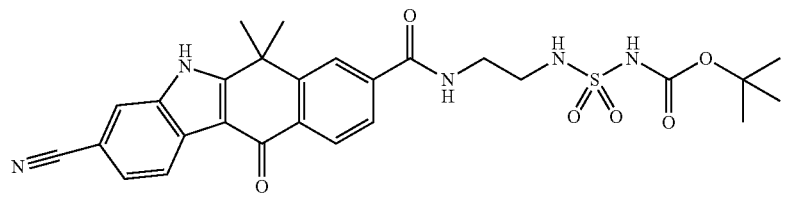

Under the same conditions as the method for synthesizing Compound A9-1, the title compound was prepared from Compound B3-25-2 and N-(tert-butoxycarbonyl)-N-[4-(dimethylazaniumylidene)-1,4-dihydropyridin-1-yl sulfonyl] azanide (CAS No. 872496-91-8).
LCMS: m/z 552 [M+H]⁺
HPLC retention time: 2.03 min (analysis condition S)

Example 157

Compound B3-27-2

3-Cyano-6,6-dimethyl-11-oxo-N-(2-(sulfamoylamino)ethyl)-6,11-dihydro-5H-benzo[b]carbazol-8-carboxamide

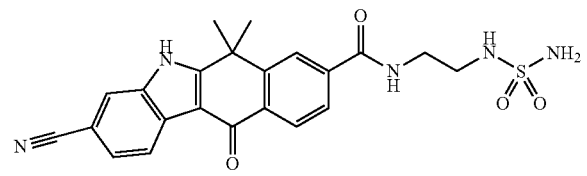

Under the same conditions as the method for synthesizing Compound A8-1, the title compound was prepared from Compound B3-27-1.
LCMS: m/z 452 [M+H]⁺
HPLC retention time: 1.57 min (analysis condition S)

Example 158

Compound B3-28

8-[4-(2-Hydroxy-ethyl)-piperazin-1-carbonyl]-6,6-dimethyl-11-oxo-6,11-dihydro-5H-benzo[b]carbazole-3-carbonitrile

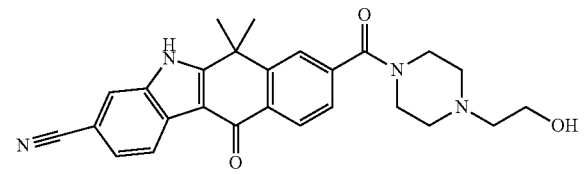

Under the same conditions as the method for synthesizing Compound B3-15, the title compound was prepared from Compound B2-28 and 2-piperazin-1-yl ethanol.
LCMS: m/z 443 [M+H]⁺
HPLC retention time: 1.75 min (analysis condition U)

Example 159

Compound B3-29

8-(4-Tert-butyl-piperazin-1-carbonyl)-6,6-dimethyl-11-oxo-6,11-dihydro-5H-benzo[b]carbazole-3-carbonitrile


Under the same conditions as the method for synthesizing Compound B3-15, the title compound was prepared from Compound B2-28 and 1-tert-butylpiperazine.
LCMS: m/z 455 [M+H]⁺
HPLC retention time: 1.88 min (analysis condition U)

Example 160

Compound B3-30

8-[4-(2-Methoxy-ethyl)-piperazin-1-carbonyl]-6,6-dimethyl-11-oxo-6,11-dihydro-5H-benzo[b]carbazole-3-carbonitrile


Under the same conditions as the method for synthesizing Compound B3-15, the title compound was prepared from Compound B2-28 and 1-(2-methoxyethyl)piperazine.
LCMS: m/z 457 [M+H]⁺
HPLC retention time: 1.83 min (analysis condition U)

Example 161

Compound B3-31-1

4-(3-Cyano-6,6-dimethyl-11-oxo-6,11-dihydro-5H-benzo[b]carbazol-8-carbonyl)-piperazine-1-carboxylic acid tert-butyl ester

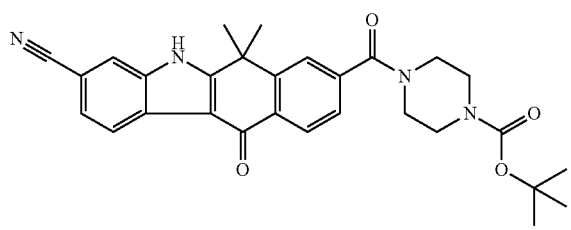 [SMILES: CC(C)(C)OC(=O)N1CCN(C(=O)c2ccc3c(c2)C(C)(C)c2[nH]c4cc(C#N)ccc4c2C3=O)CC1]

Under the same conditions as the method for synthesizing Compound B3-15, the title compound was prepared from Compound B2-28 and piperazine-1-carboxylic acid tert-butyl ester.
LCMS: m/z 499 [M+H]$^+$
HPLC retention time: 2.63 min (analysis condition U)

Example 162

Compound B3-31-2

6,6-Dimethyl-11-oxo-8-(piperazin-1-carbonyl)-6,11-dihydro-5H-benzo[b]carbazole-3-carbonitrile

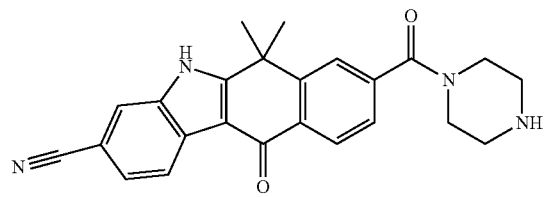 [SMILES: CC1(C)c2cc(C(=O)N3CCNCC3)ccc2C(=O)c2c1[nH]c1cc(C#N)ccc21]

Under the same conditions as the method for synthesizing Compound A8-1, the title compound was prepared from Compound B3-31-1.
LCMS: m/z 399 [M+H]$^+$
HPLC retention time: 1.78 min (analysis condition U)

Example 163

Compound B3-32

6,6-Dimethyl-8-morpholin-4-yl methyl-11-oxo-6,11-dihydro-5H-benzo[b]carbazole-3-carbonitrile

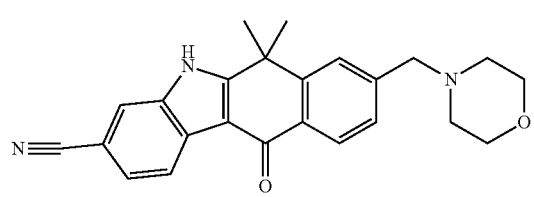 [SMILES: CC1(C)c2cc(CN3CCOCC3)ccc2C(=O)c2c1[nH]c1cc(C#N)ccc21]

To the THF (1 ml) solution of Compound B2-29 (30 mg, 0.095 mmol), morpholine (6 μl, 1.5 eq.) and sodium triacetoxyborohydride (81 mg, 2.0 eq.) were added and stirred at room temperature for 1 hr. The reaction solution was filtered to remove insoluble matters, and the residues obtained after concentration under reduced pressure were purified by high performance liquid chromatography to obtain the title compound (19 mg, 50%).
$^1$H-NMR (400 MHz, CD$_3$OD) δ: 8.41 (1H, d, 7.9 Hz), 8.27 (1H, d, 8.5 Hz), 7.87 (1 s), 7.81 (1H, s), 7.56 (1H, d, 8.5 Hz), 7.49 (1H, d, 7.9 Hz), 3.71 (4H, t, 4.6 Hz), 3.68 (2H, s), 2.51 (4H, t, 4.6 Hz), 1.82 (6H, s)
LCMS: m/z 386 [M+H]$^+$
HPLC retention time: 2.41 min (analysis condition W)

Example 164

Compound B3-33

6,6-Dimethyl-8-(4-methyl-piperazin-1-yl methyl)-11-oxo-6,11-dihydro-5H-benzo[b]carbazole-3-carbonitrile

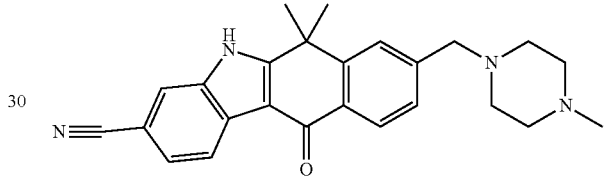

Under the same conditions as the method for synthesizing Compound B3-32, the title compound was prepared from Compound B2-29 and 1-methylpiperazine.
$^1$H-NMR (400 MHz, CD$_3$OD) δ: 8.41 (1H, d, 7.9 Hz), 8.26 (1H, d, 7.9 Hz), 7.88 (1 s), 7.81 (1H, s), 7.56 (1H, d, 7.9 Hz), 7.48 (1H, d, 7.9 Hz), 3.70 (2H, s), 2.42-2.78 (8H, m), 2.31 (3H, s), 1.82 (6H, s)
LCMS: m/z 399 [M+H]$^+$
HPLC retention time: 2.30 min (analysis condition W)

Example 165

Compound B3-34

8-[4-(1,1-Dioxide-4-thiomorpholinyl)methyl]-6,6-dimethyl-11-oxo-6,11-dihydro-5H-benzo[b]carbazole-3-carbonitrile

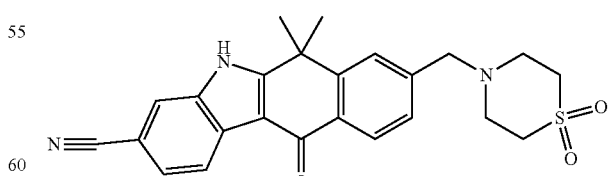

Under the same conditions as the method for synthesizing Compound B3-32, the title compound was prepared from Compound B2-29 and thiomorpholine 1,1-dioxide.
LCMS: m/z 434 [M+H]$^+$
HPLC retention time: 2.75 min (analysis condition W)

Example 166

Compound B3-35

8-(4-Methanesulfonyl-piperazin-1-yl methyl)-6,6-dimethyl-11-oxo-6,11-dihydro-5H-benzo[b]carbazole-3-carbonitrile

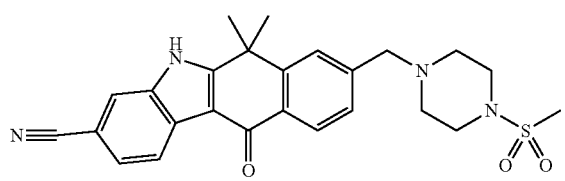 [SMILES: CC1(C)c2cc(CN3CCN(S(C)(=O)=O)CC3)ccc2C(=O)c2c1[nH]c1cc(C#N)ccc21]

Under the same conditions as the method for synthesizing Compound B3-32, the title compound was prepared from Compound B2-29 and 1-methanesulfonylpiperazine.

$^1$H-NMR (400 MHz, CD$_3$OD) δ: 8.41 (1H, d, 8.5 Hz), 8.28 (1H, d, 7.9 Hz), 7.87 (1 s), 7.80 (1H, s), 7.56 (1H, d, 8.5 Hz), 7.50 (1H, d, 7.9 Hz), 3.73 (2H, s), 3.24-3.28 (4H, m), 2.85 (3H, s), 2.59-2.65 (4H, m), 1.82 (6H, s)

LCMS: m/z 463 [M+H]$^+$

HPLC retention time: 2.47 min (analysis condition W)

Example 167

Compound B3-36

4-(3-Cyano-6,6-dimethyl-11-oxo-6,11-dihydro-5H-benzo[b]carbazol-8-ylmethyl)-piperazine-1-sulfonic acid dimethylamide

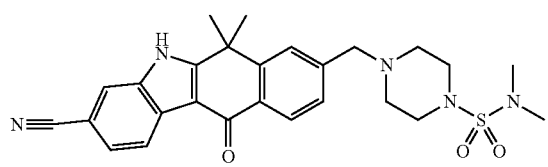 [SMILES: CN(C)S(=O)(=O)N1CCN(Cc2ccc3c(c2)C(C)(C)c2[nH]c4cc(C#N)ccc4c2C3=O)CC1]

Under the same conditions as the method for synthesizing Compound B3-32, the title compound was prepared from Compound B2-29 and piperazine-1-sulfonic acid dimethylamide.

$^1$H-NMR (400 MHz, DMSO-d$_6$) δ: 12.79 (1H, s), 8.32 (1H, d, 7.9 Hz), 8.18 (1H, d, 7.9 Hz), 8.00 (1 s), 7.77 (1H, s), 7.60 (1H, d, 7.9 Hz), 7.46 (1H, d, 7.9 Hz), 3.67 (2H, s), 3.18-3.23 (4H, m), 2.76 (6H, s), 2.45-2.50 (4H, m), 1.77 (6H, s)

LCMS: m/z 492 [M+H]$^+$

HPLC retention time: 2.58 min (analysis condition W)

Example 168

Compound B3-37

6,6-Dimethyl-11-oxo-8-[(2,2,2-trifluoro-ethyl-amino)-methyl]-6,11-dihydro-5H-benzo[b]carbazole-3-carbonitrile

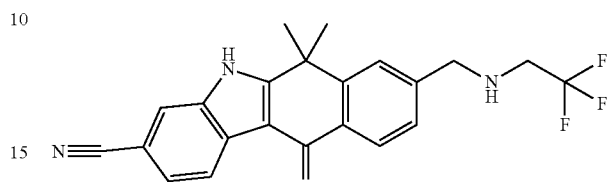

Under the same conditions as the method for synthesizing Compound B3-32, the title compound was prepared from Compound B2-29 and 2,2,2-trifluoroethylamine.

LCMS: m/z 398 [M+H]$^+$

HPLC retention time: 2.73 min (analysis condition W)

Example 169

Compound B3-38

8-Hydroxymethyl-6,6-dimethyl-11-oxo-6,11-dihydro-5H-benzo[b]carbazole-3-carbonitrile

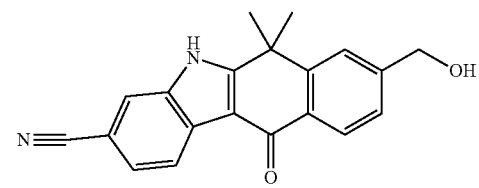 [SMILES: CC1(C)c2cc(CO)ccc2C(=O)c2c1[nH]c1cc(C#N)ccc21]

The by-product obtained from the synthesis of Compound B3-37 was purified by high performance liquid chromatography to obtain the target compound.

LCMS: m/z 317 [M+H]$^+$

HPLC retention time: 2.91 min (analysis condition W)

Example 170

Compound B4-1

8-(1-Cyclobutyl-piperidin-4-yl)-6,6-dimethyl-11-oxo-6,11-dihydro-5H-benzo[b]carbazole-3-carbonitrile

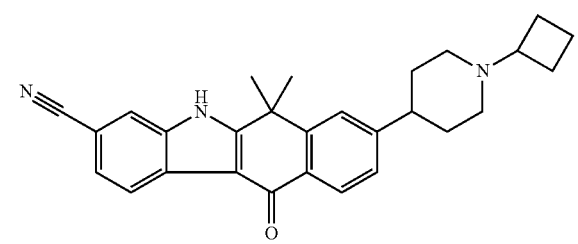 [SMILES: CC1(C)c2cc(C3CCN(C4CCC4)CC3)ccc2C(=O)c2c1[nH]c1cc(C#N)ccc21]

Under the same conditions as the method for synthesizing Compound B3-32, the title compound was prepared from Compound B3-13-2 and cyclobutanone.

$^1$H-NMR (400 MHz, DMSO-d$_6$) δ: 12.73 (1H, s), 8.28-8.33 (1H, m), 8.09-8.14 (1H, m), 7.99 (1H, s), 7.72 (1H, s), 7.56-7.62 (1H, m), 7.34-7.41 (1H, m), 3.52-3.64 (2H, m), 2.85-2.95 (2H, m), 2.56-2.75 (2H, m), 1.91-2.04 (2H, m), 1.56-1.84 (14H, m)

LCMS: m/z 424 [M+H]$^+$

HPLC retention time: 1.87 min (analysis condition U)

Example 171

Compound B4-2

8-(1-Methanesulfonyl-piperidin-4-yl)-6,6-dimethyl-11-oxo-6,11-dihydro-5H-benzo[b]carbazole-3-carbonitrile

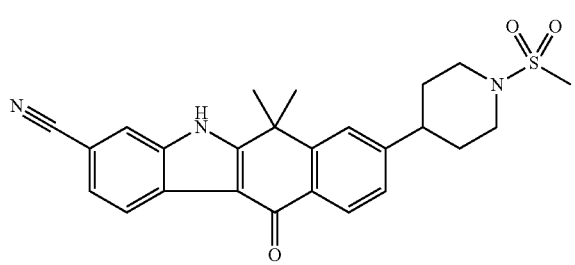 [SMILES: CC1(C)c2cc(C3CCN(S(C)(=O)=O)CC3)ccc2C(=O)c2c1[nH]c1cc(C#N)ccc21]

Under the same conditions as the method for synthesizing Compound A9-1, the title compound was prepared from Compound B3-13-2 and mesyl chloride.

$^1$H-NMR (270 MHz, DMSO-d$_6$) δ: 12.77 (1H, s), 8.31 (1H, d, 8.6 Hz), 8.15 (1H, d, 8.2 Hz), 8.00 (1H, s), 7.77 (1H, s), 7.59 (1H, d, 7.3 Hz), 7.42 (1H, d, 8.6 Hz), 3.74-3.70 (1H, m), 2.93 (3H, s), 2.86-2.77 (4H, m), 1.93-1.87 (4H, m), 1.77 (6.0H, s)

LCMS: m/z 448 [M+H]$^+$

HPLC retention time: 2.37 min (analysis condition S)

Example 172

Compound B4-3-1

Tert-butyl4-(3-cyano-6,6-dimethyl-11-oxo-6,11-dihydro-5H-benzo[b]carbazol-8-yl)piperidin-1-yl sulfonylcarbamic acid

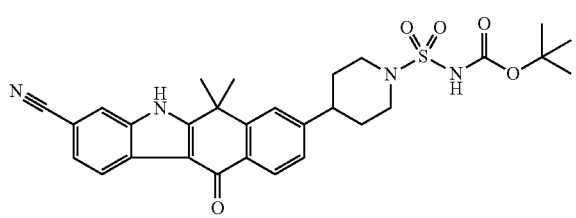 [SMILES: CC(C)(C)OC(=O)NS(=O)(=O)N1CCC(c2ccc3c(c2)C(C)(C)c2[nH]c4cc(C#N)ccc4c2C3=O)CC1]

Under the same conditions as the method for synthesizing Compound A9-1, the title compound was prepared from Compound B3-13-2 and N-(tert-butoxycarbonyl)-N-[4-(dimethylazaniumylidene)-1,4-dihydropyridine-1-yl-sulfonyl]azanide.

LCMS: m/z 549 [M+H]$^+$

HPLC retention time: 2.72 min (analysis condition S)

Example 173

Compound B4-3-2

4-(3-Cyano-6,6-dimethyl-11-oxo-6,11-dihydro-5H-benzo[b]carbazol-8-yl)-piperidine-1-sulfonic acid amide

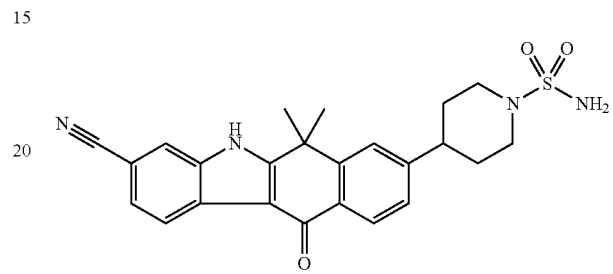

Under the same conditions as the method for synthesizing Compound A8-1, the title compound was prepared from Compound B4-3-1.

$^1$H-NMR (400 MHz, DMSO-d$_6$) δ: 12.78 (1H, s), 8.29 (1H, d, 7.9 Hz), 8.14 (1H, d, 8.5 Hz), 7.97 (1H, s), 7.76 (1H, s), 7.55 (1H, d, 8.5 Hz), 7.41 (1H, d, 7.9 Hz), 6.79 (2H, s), 3.63 (2H, d, 12.2 Hz), 2.80-2.73 (1H, m), 2.70-2.64 (2H, m), 1.96-1.93 (2H, m), 1.87-1.81 (2H, m), 1.77 (6H, s)

LCMS: m/z 449 [M+H]$^+$

HPLC retention time: 2.03 min (analysis condition S)

Example 174

Compound B4-4

4-(3-Cyano-6,6-dimethyl-11-oxo-6,11-dihydro-5H-benzo[b]carbazol-8-yl)-piperidine-1-sulfonic acid methylamide

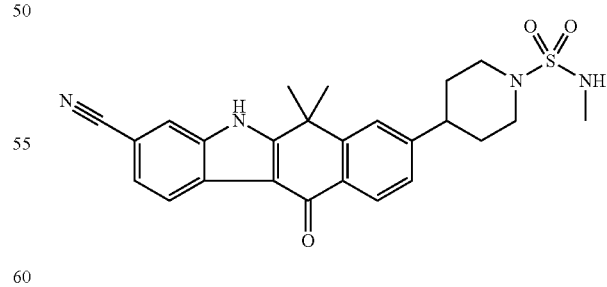

Under the same conditions as the method for synthesizing Compound A9-1, the title compound was prepared from Compound B3-13-2 and 2-oxooxazolidine-3-sulfonic acid methylamide.

LCMS: m/z 463 [M+H]$^+$

HPLC retention time: 2.40 min (analysis condition S)

Example 175

Compound B4-5

4-(3-Cyano-6,6-dimethyl-11-oxo-6,11-dihydro-5H-benzo[b]carbazol-8-yl)-piperidine-1-sulfonic acid dimethylamide

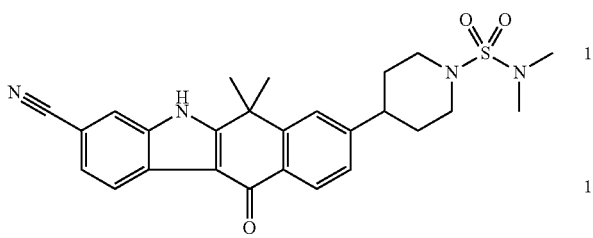

Under the same conditions as the method for synthesizing Compound A9-1, the title compound was prepared from Compound B3-13-2 and dimethylsulfamoyl chloride.
LCMS: m/z 477 [M+H]$^+$
HPLC retention time: 2.65 min (analysis condition S)

Example 176

Compound B4-6

6,6-Dimethyl-8-(1-methyl-piperidin-4-yl)-11-oxo-6,11-dihydro-5H-benzo[b]carbazole-3-carbonitrile

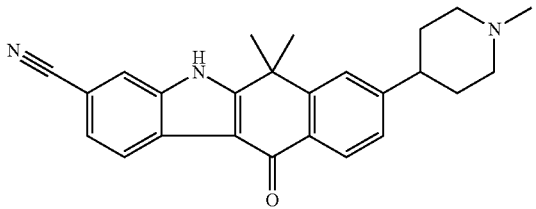 [SMILES: CN1CCC(c2ccc3c(c2)C(C)(C)c2[nH]c4cc(C#N)ccc4c2C3=O)CC1]

Under the same conditions as the method for synthesizing Compound A9-1, the title compound was prepared from Compound B3-13-2 and iodomethane.
LCMS: m/z 384 [M+H]$^+$
HPLC retention time: 1.50 min (analysis condition S)

Example 177

Compound B4-7

8-(1-Isopropyl-piperidin-4-yl)-6,6-dimethyl-11-oxo-6,11-dihydro-5H-benzo[b]carbazole-3-carbonitrile

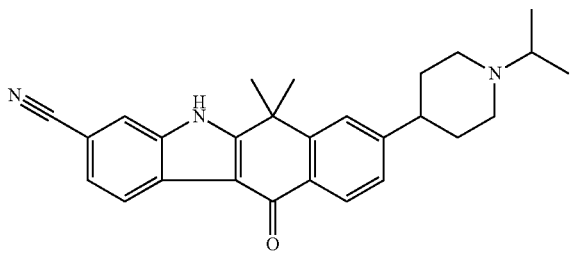 [SMILES: CC(C)N1CCC(c2ccc3c(c2)C(C)(C)c2[nH]c4cc(C#N)ccc4c2C3=O)CC1]

Under the same conditions as the method for synthesizing Compound B3-32, the title compound was prepared from Compound B3-13-2 and acetone.

$^1$H-NMR (400 MHz, DMSO-d$_6$) δ: 12.77 (1H, s), 8.32 (1H, d, 7.9 Hz), 8.13 (1H, d, 7.9 Hz), 8.01 (1H, s), 7.73 (1H, s), 7.61 (1H, d, 9.1 Hz), 7.39 (1H, d, 9.8 Hz), 2.93 (2H, d, 11.0 Hz), 2.77-2.71 (1H, m), 2.67-2.62 (1H, m), 2.25 (2H, t, 10.1 Hz), 1.80-1.73 (10H, m), 1.02 (6H, d, 6.7 Hz)
LCMS: m/z 412 [M+H]$^+$
HPLC retention time: 1.60 min (analysis condition S)

Example 178

Compound B4-8

6,6-Dimethyl-8-(1-oxetan-3-yl-piperidin-4-yl)-11-oxo-6,11-dihydro-5H-benzo[b]carbazole-3-carbonitrile

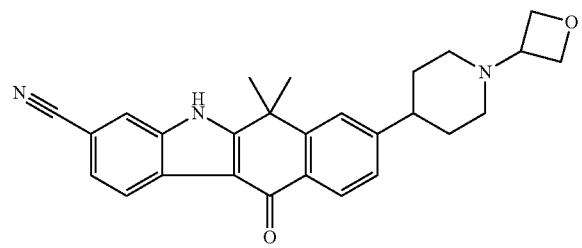 [SMILES: CC1(C)c2cc(C3CCN(C4COC4)CC3)ccc2C(=O)c2c1[nH]c1cc(C#N)ccc21]

Under the same conditions as the method for synthesizing Compound B3-32, the title compound was prepared from Compound B3-13-2 and oxetan-3-one.
$^1$H-NMR (400 MHz, DMSO-d$_6$) δ: 12.74 (1H, s), 8.32 (1H, d, 7.9 Hz), 8.13 (1H, d, 7.9 Hz), 8.00 (1H, s), 7.74 (1H, s), 7.61 (1H, d, 9.8 Hz), 7.40 (1H, d, 7.9 Hz), 4.56 (2H, t, 6.7 Hz), 4.46 (2H, t, 6.1 Hz), 3.46-3.39 (1H, m), 2.85-2.82 (2H, m), 2.71-2.64 (1H, m), 1.92-1.86 (2H, m), 1.82-1.79 (4H, m), 1.77 (6H, s)
LCMS: m/z 426 [M+H]$^+$
HPLC retention time: 1.53 min (analysis condition S)
Sulfuric Acid Salt of Compound B4-8
6,6-Dimethyl-8-(1-oxetan-3-yl-piperidin-4-yl)-11-oxo-6,11-dihydro-5H-benzo[b]carbazole-3-carbonitrile was dissolved at 80° C. in a mixture of 5 volumes of DMA and 1.4 volumes of 2 N sulfuric acid. After cooling to room temperature, 15 volumes of acetone were added dropwise, and the precipitated solids were filtered and dried to obtain sulfuric acid salt of 6,6-dimethyl-8-(1-oxetan-3-yl-piperidin-4-yl)-11-oxo-6,11-dihydro-5H-benzo[b]carbazole-3-carbonitrile.
$^1$H-NMR (400 MHz, DMSO-d$_6$) δ: 12.81 (1H, s), 10.26 (1H, br. s), 8.33 (1H, d, 8.3 Hz), 8.21 (1H, d, 8.3 Hz), 8.04 (1H, s), 7.75 (1H, s), 7.63 (1H, d, 8.3 Hz), 7.41 (1H, d, 8.3 Hz), 4.85-4.70 (4H, m), 4.50-4.40 (1H, br. s), 3.60-3.00 (6H, br. m), 2.20-2.10 (2H, m), 2.05-1.90 (2H, m), 1.79 (6H, s)
LCMS: m/z 426 [M+H]$^+$

Example 179

Compound B4-9

4-(3-Cyano-6,6-dimethyl-11-oxo-6,11-dihydro-5H-benzo[b]carbazol-8-yl)-piperidine-1-carboxylic acid ethylamide

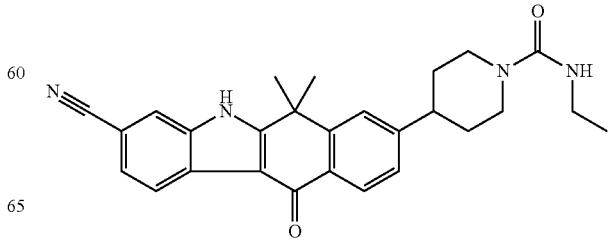

Under the same conditions as the method for synthesizing Compound A9-1, the title compound was prepared from Compound B-3-13-2 and ethylisocyanate.

LCMS: m/z 441 [M+H]$^+$

HPLC retention time: 2.20 min (analysis condition S)

Example 180

Compound B4-10

8-[1-(Imidazole-1-sulfonyl)-piperidin-4-yl]-6,6-dimethyl-11-oxo-6,11-dihydro-5H-benzo[b]carbazole-3-carbonitrile

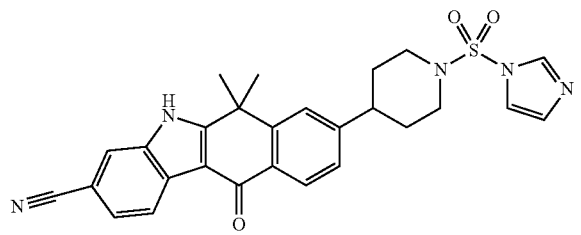 [SMILES: CC1(C)c2cc(C3CCN(S(=O)(=O)n4ccnc4)CC3)ccc2C(=O)c2c1[nH]c1cc(C#N)ccc21]

According to the method disclosed in Journal of Organic Chemistry, 2003, page 115, 6,6-dimethyl-11-oxo-8-piperidin-4-yl-6,11-dihydro-5H-benzo[b]carbazole-3-carbonitrile (Compound B3-13-2, 10 mg, 0.027 mmol) was reacted with 3-(imidazole-1-sulfonyl)-1-methyl-3H-imidazol-1-ium (19 mg, 2 eq.). After removing the solvent, the residues were purified by liquid chromatography to obtain the title compound (3 mg).

LCMS: m/z 500 [M+H]$^+$

HPLC retention time: 2.80 min (analysis condition C)

Example 181

Compound CC1

3-Methoxy-5,5-dimethyl-6-oxo-5,6,7,8-tetrahydro-naphthalen-2-sulfonyl chloride

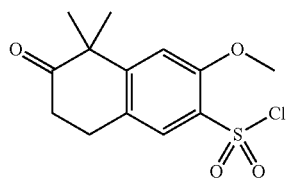 [SMILES: COc1cc2c(cc1S(=O)(=O)Cl)CCC(=O)C2(C)C]

To the dichloromethane (2 ml) solution of 7-methoxy-1,1-dimethyl-3,4-dihydro-1H-naphthalen-2-one (Compound A2, 200 mg, 0.980 mmol), chlorosulfonic acid (110 μl, 1.70 eq.) was added and the mixture was stirred at room temperature for 2 hr. To the reaction solution, oxalyl chloride (297 μl, 3.0 eq.) and N,N-dimethyl formamide (45 μl, 0.6 eq.) were added in three divided portions, and the mixture was stirred at room temperature for 30 min. The reaction solution was concentrated under reduced pressure to obtain the title compound (295 mg). Since the title compound is unstable, its structure was identified in the next step.

Example 182

Compound CC2-1

7-Methoxy-1,1-dimethyl-6-(pyrrolidine-1-sulfonyl)-3,4-dihydro-1H-naphthalen-2-one

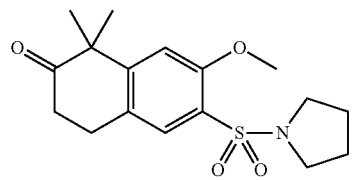 [SMILES: COc1cc2c(cc1S(=O)(=O)N1CCCC1)CCC(=O)C2(C)C]

The THF (4 ml) solution of 3-methoxy-5,5-dimethyl-6-oxo-5,6,7,8-tetrahydro-naphthalen-2-sulfonyl chloride (Compound CC1, 295 mg, 0.974 mmol) was cooled to 0° C., and the tetrafuran (1 ml) solution combining pyrrolidine (121 μl, 1.5 eq.) and triethylamine (272 μl, 2 eq.) was added dropwise thereto over 2 min. The mixture was stirred at 0° C. until Compound CC-1 disappears. The reaction solution was added with distilled water and extracted with ethyl acetate. The organic layer was washed with 10% aqueous solution of disodium ethylenediamine tetraacetic acid. The organic layer was washed with brine and dried over sodium sulfate. The drying agent was removed by filtration and the residues obtained after concentration under reduced pressure were purified by silica gel column chromatography (ethyl acetate/hexane) to obtain the title compound (246 mg, 75%).

$^1$H-NMR (400 MHz, CDCl$_3$) δ: 7.76 (1H, s), 6.93 (1H, s), 3.95 (3H, s), 3.37-3.46 (4H, m), 3.09 (0.0H, t, J=6.9 Hz), 2.69 (0.0H, t, J=6.9 Hz), 1.82-1.91 (4H, m), 1.47 (6H, s)

LCMS: m/z 338 [M+H]$^+$

HPLC retention time: 3.21 min (analysis condition W)

Example 183

Compound CC2-2

7-Methoxy-1,1-dimethyl-6-(4-methyl-piperazine-1-sulfonyl)-3,4-dihydro-1H-naphthalen-2-one

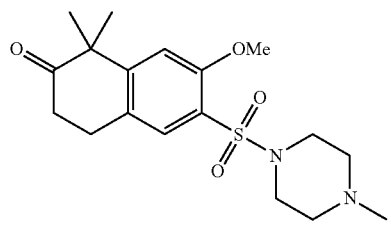 [SMILES: COc1cc2c(cc1S(=O)(=O)N1CCN(C)CC1)CCC(=O)C2(C)C]

Under the same conditions as the method for synthesizing Compound CC2-1, the title compound was prepared from Compound CC1 and N-methylpiperazine.

LCMS: m/z 367 [M+H]$^+$

HPLC retention time: 2.22 min (analysis condition Y)

Example 184

Compound CC3-1

8-Methoxy-6,6-dimethyl-9-(pyrrolidine-1-sulfonyl)-6,11-dihydro-5H-benzo[b]carbazole-3-carbonitrile

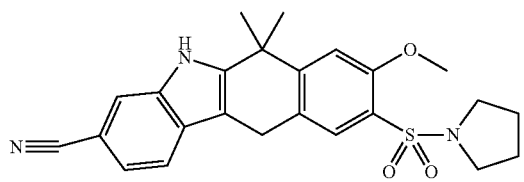 [SMILES: COc1cc2c(cc1S(=O)(=O)N1CCCC1)Cc1c([nH]c3cc(C#N)ccc13)C2(C)C]

Under the same conditions as the method for synthesizing Compound E2-1, the title compound was prepared from Compound CC2-1.
LCMS: m/z 436 [M+H]$^+$
HPLC retention time: 3.76 min (analysis condition W)

Example 185

Compound CC3-2

3-Bromo-8-methoxy-6,6-dimethyl-9-(4-methyl-piperazine-1-sulfonyl)-6,11-dihydro-5H-benzo[b]carbazole

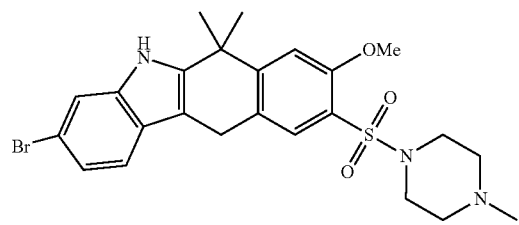 [SMILES: COc1cc2c(cc1S(=O)(=O)N1CCN(C)CC1)Cc1c([nH]c3cc(Br)ccc13)C2(C)C]

Under the same conditions as the method for synthesizing Compound A3-1, the title compound was prepared from Compound CC2-2.
LCMS: m/z 519 [M+H]$^+$
HPLC retention time: 2.99 min (analysis condition Y)

Example 186

Compound CC4-1

8-Methoxy-6,6-dimethyl-11-oxo-9-(pyrrolidine-1-sulfonyl)-6,11-dihydro-5H-benzo[b]carbazole-3-carbonitrile

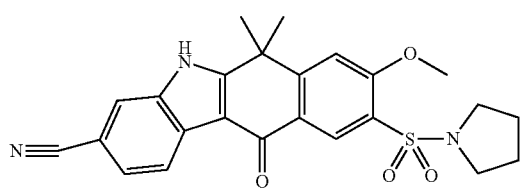 [SMILES: COc1cc2c(cc1S(=O)(=O)N1CCCC1)C(=O)c1c([nH]c3cc(C#N)ccc13)C2(C)C]

Under the same conditions as the method for synthesizing Compound A4, the title compound was prepared from Compound CC3-1.
$^1$H-NMR (400 MHz, DMSO-d$_6$) δ: 12.86 (1H, s), 8.60 (1H, s), 8.30 (1H, d, J=8.5 Hz), 8.01 (1H, s), 7.60 (1H, s), 7.59 (1H, d, J=8.5 Hz), 4.09 (3H, s), 3.21-3.42 (4H, m), 1.72-1.90 (10H, m)
LCMS: m/z 450 [M+H]$^+$
HPLC retention time: 3.40 min (analysis condition W)

Example 187

Compound CC4-2

3-Bromo-8-methoxy-6,6-dimethyl-9-(4-methyl-piperazine-1-sulfonyl)-5,6-dihydro-benzo[b]carbazol-11-one

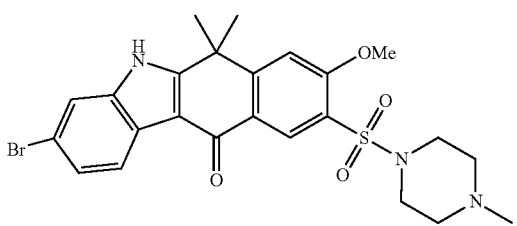 [SMILES: COc1cc2c(cc1S(=O)(=O)N1CCN(C)CC1)C(=O)c1c([nH]c3cc(Br)ccc13)C2(C)C]

Under the same conditions as the method for synthesizing Compound A4, the title compound was prepared from Compound CC3-2.
LCMS: m/z 532, 534 [M+H]$^+$
HPLC retention time: 2.18 min (analysis condition U)

Example 188

Compound CC-4-3

8-Methoxy-6,6-dimethyl-9-(4-methyl-piperazine-1-sulfonyl)-11-oxo-6,11-dihydro-5H-benzo[b]carbazole-3-carbonitrile

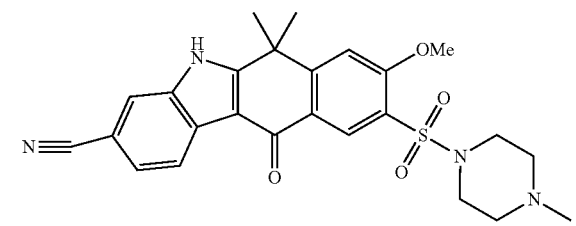 [SMILES: COc1cc2c(cc1S(=O)(=O)N1CCN(C)CC1)C(=O)c1c([nH]c3cc(C#N)ccc13)C2(C)C]

Under the same conditions as the method for synthesizing Compound A5-2, the title compound was prepared from Compound CC4-2.
LCMS: m/z 479 [M+H]$^+$
HPLC retention time: 1.93 min (analysis condition U)

Example 189

Compound C1-1

Dimethyl-sulfamic acid 3-cyano-6,6-dimethyl-11-oxo-6,11-dihydro-5H-benzo[b]carbazol-8-yl ester

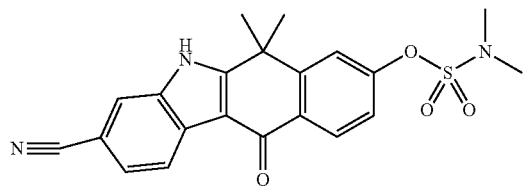 [SMILES: CN(C)S(=O)(=O)Oc1ccc2c(c1)C(C)(C)c1[nH]c3cc(C#N)ccc3c1C2=O]

8-Hydroxy-6,6-dimethyl-11-oxo-6,11-dihydro-5H-benzo[b]carbazole-3-carbonitrile (Compound A6, 50 mg, 0.165 mmol) was dissolved in DMF (1.5 mL), added with sodium hydride (13 mg, 2.0 eq.) and dimethylsulfamoyl chloride (0.02 mL, 1.2 eq.), and then stirred at room temperature for 1 hr. Water was added to the reaction solution, which was then extracted with ethyl acetate. The organic layer was washed with saturated brine and dried over sodium sulfate. The drying agent was removed by filtration and the residues were concentrated under reduced pressure to obtain the target compound (yellowish white powder, 62 mg, 92%).

$^1$H-NMR (270 MHz, DMSO-$d_6$) δ: 12.87 (1H, s), 8.40-8.30 (2H, m), 8.05 (1H, s), 7.82 (1H, d, J=1.8 Hz), 7.64 (1H, d, J=7.9 Hz), 7.50 (1H, dd, J=8.5, 2.4 Hz), 2.96 (6H, s), 1.81 (6H, s)

LCMS: m/z 410 [M+H]$^+$

HPLC retention time: 2.38 min (analysis condition S)

Example 190

Compound C1-2

Morpholine-4-sulfonic acid 3-cyano-6,6-dimethyl-11-oxo-6,11-dihydro-5H-benzo[b]carbazol-8-yl ester

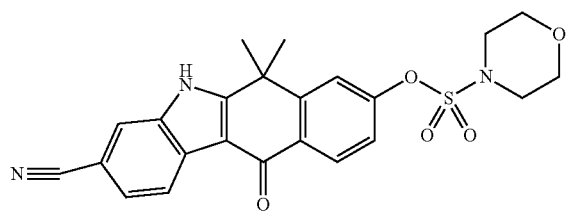 [SMILES: CC1(C)c2cc(OS(=O)(=O)N3CCOCC3)ccc2C(=O)c2c1[nH]c1cc(C#N)ccc21]

According to the same method as the method for synthesizing Compound A8-17, the title compound was prepared as a crude product from Compound A6 and Compound A8-18-0.

Example 191

Compound C1-4

4-Methyl-piperazine-1-sulfonic acid 3-cyano-6,6-dimethyl-11-oxo-6,11-dihydro-5H-benzo[b]carbazol-8-yl ester

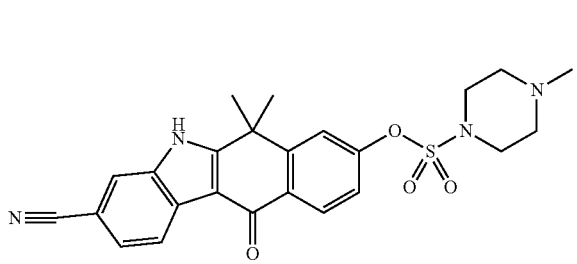 [SMILES: CN1CCN(S(=O)(=O)Oc2ccc3c(c2)C(C)(C)c2[nH]c4cc(C#N)ccc4c2C3=O)CC1]

According to the same method as the method for synthesizing Compound A8-17, the title compound was prepared as a crude product from Compound A6 and Compound A8-19-0.

Example 192

Compound C2-1

3-Cyano-8-hydroxy-6,6-dimethyl-11-oxo-6,11-dihydro-5H-benzo[b]carbazole-9-sulfonic acid dimethylamide

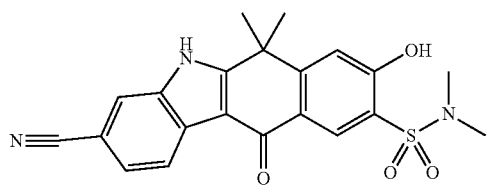

To dimethyl-sulfamic acid 3-cyano-6,6-dimethyl-11-oxo-6,11-dihydro-5H-benzo[b]carbazol-8-yl ester (Compound C1-1, 250 mg, 0.610 mmol), aluminum chloride (1.0 M, nitromethane solution (1.8 mL, 3.0 eq.)) was added and the mixture was stirred at 160° C. for 10 min under irradiation with microwave. Water was added to the reaction solution, which was then extracted with dichloromethane. The organic layer was washed with saturated brine and dried over sodium sulfate. The drying agent was removed by filtration and the residues obtained after concentration under reduced pressure were purified by silica gel column chromatography (dichloromethane/methanol) to obtain the target compound (yellowish white powder, 99 mg, 40%).

$^1$H-NMR (270 MHz, DMSO-$d_6$) δ: 12.78 (1H, s), 11.72 (1H, s), 8.50 (1H, s), 8.32 (1H, d, J=8.5 Hz), 8.02 (1H, s), 7.62 (1H, d, J=7.9 Hz), 7.25 (1H, s), 2.80 (6H, s), 1.75 (6H, s).

LCMS: m/z 410 [M+H]$^+$

HPLC retention time: 2.00 min (analysis condition S)

Example 193

Compound C2-2

8-Hydroxy-6,6-dimethyl-11-oxo-9-(pyrrolidine-1-sulfonyl)-6,11-dihydro-5H-benzo[b]carbazole-3-carbonitrile

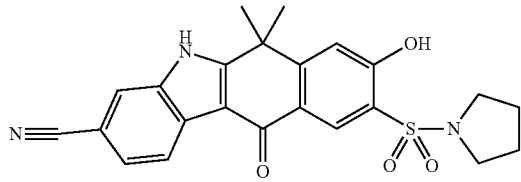 [SMILES: CC1(C)c2cc(O)c(S(=O)(=O)N3CCCC3)cc2C(=O)c2c1[nH]c1cc(C#N)ccc21]

Under the same conditions as the method for synthesizing Compound E3-2, the title compound was prepared from Compound CC4-1.
LCMS: m/z 436 [M+H]$^+$
HPLC retention time: 3.32 min (analysis condition W)

Example 194

Compound C2-3

8-Hydroxy-6,6-dimethyl-9-(morpholine-4-sulfonyl)-11-oxo-6,11-dihydro-5H-benzo[b]carbazole-3-carbonitrile

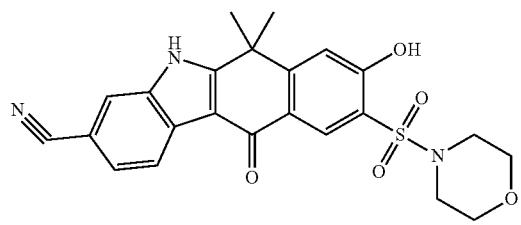 [SMILES: CC1(C)c2cc(O)c(S(=O)(=O)N3CCOCC3)cc2C(=O)c2c1[nH]c1cc(C#N)ccc21]

Under the same conditions as the method for synthesizing Compound C2-1, the title compound was prepared from Compound C1-2.
LCMS: m/z 452 [M+H]$^+$
HPLC retention time: 1.89 min (analysis condition S)

Example 195

Compound C2-4

8-Hydroxy-6,6-dimethyl-9-(4-methyl-piperazine-1-sulfonyl)-11-oxo-6,11-dihydro-5H-benzo[b]carbazole-3-carbonitrile

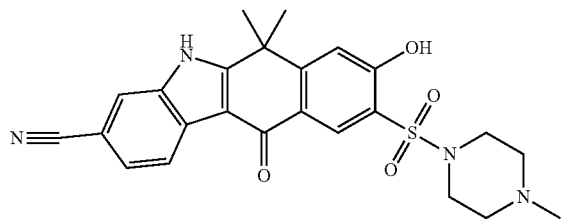 [SMILES: CN1CCN(S(=O)(=O)c2cc3c(cc2O)C(C)(C)c2[nH]c4cc(C#N)ccc4c2C3=O)CC1]

Under the same conditions as the method for synthesizing Compound E3-2, the title compound was prepared from Compound CC4-3.
LCMS: m/z 465 [M+H]$^+$
HPLC retention time: 1.87 min (analysis condition U)

Example 196

Compound C3-1

Trifluoro-methanesulfonic acid 3-cyano-9-dimethyl-sulfamoyl-6,6-dimethyl-11-oxo-6,11-dihydro-5H-benzo[b]carbazol-8-yl ester

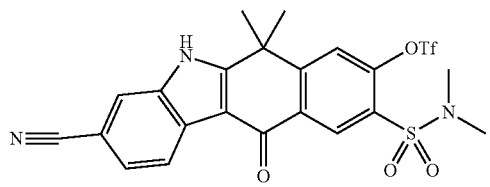 [SMILES: CN(C)S(=O)(=O)c1cc2c(cc1OS(=O)(=O)C(F)(F)F)C(C)(C)c1[nH]c3cc(C#N)ccc3c1C2=O]

Under the same conditions as the method for synthesizing Compound B1, the title compound was prepared from Compound C2-1.
$^1$H-NMR (270 MHz, DMSO-d$_6$) δ: 13.05 (1H, s), 8.67 (1H, s), 8.32 (1H, d, J=8.2 Hz), 8.06 (2H, m), 7.67 (1H, dd, J=7.9, 1.3 Hz), 2.79 (6H, s), 1.84 (6H, s).
LCMS: m/z 542 [M+H]$^+$
HPLC retention time: 2.67 min (analysis condition S)

Example 197

Compound C3-2

Trifluoro-methanesulfonic acid 3-cyano-6,6-dimethyl-11-oxo-9-(pyrrolidine-1-sulfonyl)-6,11-dihydro-5H-benzo[b]carbazol-8-yl ester

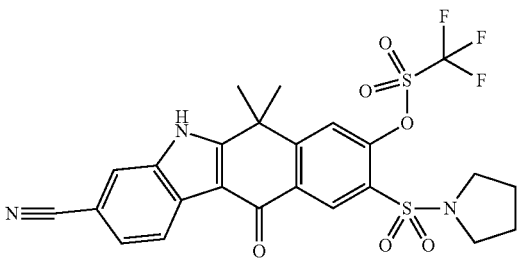 [SMILES: CC1(C)c2cc(OS(=O)(=O)C(F)(F)F)c(S(=O)(=O)N3CCCC3)cc2C(=O)c2c1[nH]c1cc(C#N)ccc21]

Under the same conditions as the method for synthesizing Compound B1, the title compound was prepared from Compound C2-2.
LCMS: m/z 568 [M+H]$^+$
HPLC retention time: 4.00 min (analysis condition W)

Example 198

Compound C4-1

3-Cyano-8-(2-methoxy-ethoxy)-6,6-dimethyl-11-oxo-6,11-dihydro-5H-benzo[b]carbazole-9-sulfonic acid dimethylamide

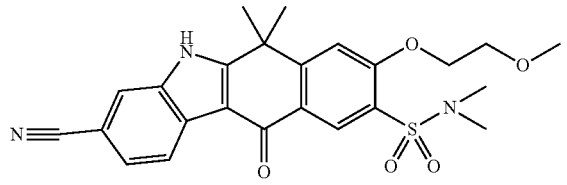 [SMILES: COCCOc1cc2c(cc1S(=O)(=O)N(C)C)C(=O)c1c([nH]c3cc(C#N)ccc13)C2(C)C]

Under the same conditions as the method for synthesizing Compound A7-17, the title compound was prepared from Compound C2-1 and 1-bromo-2-methoxy-ethane.

$^1$H-NMR (300 MHz, DMSO-d$_6$) σppm; 12.8 (s, 1H), 8.58 (s, 1H), 8.31 (d, 1H, J=8.4 Hz), 8.03 (s, 1H), 7.62 (m, 2H), 4.47 (m, 2H), 3.75 (m, 2H), 3.32 (s, 3H), 2.27 (s, 6H), 1.83 (s, 6H)

LCMS: m/z 468 [M+H]$^+$
HPLC retention time: 2.68 min (analysis condition U)

Example 199

Compound C4-2

3-Cyano-8-(2-diethylamino-ethoxy)-6,6-dimethyl-11-oxo-6,11-dihydro-5H-benzo[b]carbazole-9-sulfonic acid dimethylamide

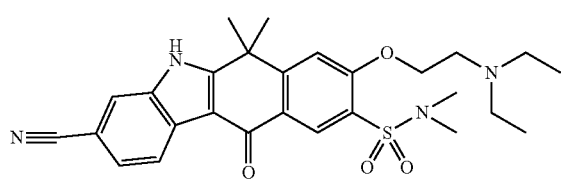 [SMILES: CCN(CC)CCOc1cc2c(cc1S(=O)(=O)N(C)C)C(=O)c1c([nH]c3cc(C#N)ccc13)C2(C)C]

Under the same conditions as the method for synthesizing Compound A7-17, the title compound was prepared from Compound C2-1.

$^1$H-NMR (270 MHz, DMSO-d$_6$) δ: 8.57 (1H, s), 8.29 (1H, d, J=8.4 Hz), 8.02 (1H, s), 7.70-7.60 (2H, m), 4.37 (2H, t, J=6.3 Hz), 2.84 (2H, m), 2.80 (6H, s), 2.64-2.53 (4H, m), 1.83 (6H, s), 0.98 (6H, t, J=7.1 Hz).

LCMS: m/z 509 [M+H]$^+$
HPLC retention time: 1.55 min (analysis condition S)

Example 200

Compound C4-3

3-Cyano-8-methoxy-6,6-dimethyl-11-oxo-6,11-dihydro-5H-benzo[b]carbazole-9-sulfonic acid dimethylamide

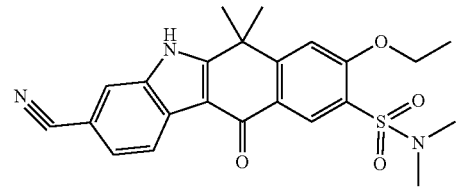 [SMILES: CCOc1cc2c(cc1S(=O)(=O)N(C)C)C(=O)c1c([nH]c3cc(C#N)ccc13)C2(C)C]

Under the same conditions as the method for synthesizing Compound A7-17, the title compound was prepared from Compound C2-1 and iodomethane.

LCMS: m/z 424 [M+H]$^+$
HPLC retention time: 2.17 min (analysis condition S)

Example 201

Compound C4-4

3-Cyano-6,6-dimethyl-11-oxo-8-(piperidin-4-yl oxy)-6,11-dihydro-5H-benzo[b]carbazole-9-sulfonic acid dimethylamide

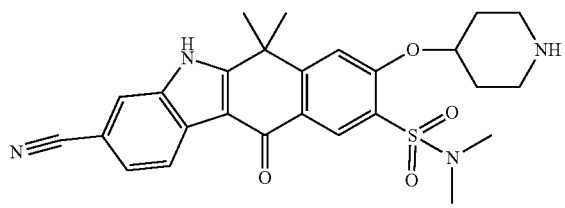 [SMILES: CN(C)S(=O)(=O)c1cc2c(cc1OC1CCNCC1)C(C)(C)c1[nH]c3cc(C#N)ccc3c1C2=O]

Under the same conditions as the method for synthesizing Compound A7-1 and Compound A8-1, the title compound was prepared from Compound C2-1 and 4-hydroxy-piperidine-1-carboxylic acid tert-butyl ester.

LCMS: m/z 493 [M+H]$^+$
HPLC retention time: 1.49 min (analysis condition S)

Example 202

Compound C4-5

3-Cyano-6,6-dimethyl-8-(2-morpholin-4-yl-ethoxy)-11-oxo-6,11-dihydro-5H-benzo[b]carbazole-9-sulfonic acid dimethylamide

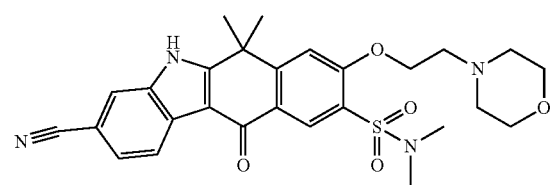 [SMILES: CN(C)S(=O)(=O)c1cc2c(cc1OCCN1CCOCC1)C(C)(C)c1[nH]c3cc(C#N)ccc3c1C2=O]

Under the same conditions as the method for synthesizing Compound A7-1, the title compound was prepared from Compound C2-1 and 2-morpholin-4-yl-ethanol.

LCMS: m/z 523 [M+H]+

HPLC retention time: 1.64 min (analysis condition S)

Example 203

Compound C4-6

3-Cyano-8-[2-(1,1-dioxo-thiomorpholin-4-yl)-ethoxy]-6,6-dimethyl-11-oxo-6,11-dihydro-5H-benzo[b]carbazole-9-sulfonic acid dimethylamide

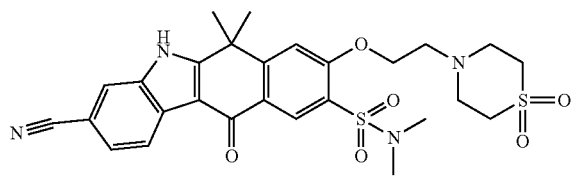 [SMILES: CN(C)S(=O)(=O)c1cc2c(cc1OCCN1CCS(=O)(=O)CC1)C(C)(C)c1[nH]c3cc(C#N)ccc3c1C2=O]

Under the same conditions as the method for synthesizing Compound A7-1, the title compound was prepared from Compound C2-1 and 2-(1,1-dioxothiomorpholino)ethanol.

LCMS: m/z 571 [M+H]+

HPLC retention time: 1.75 min (analysis condition S)

Example 204

Compound C4-7

3-Cyano-8-(1-ethyl-piperidin-4-yl oxy)-6,6-dimethyl-11-oxo-6,11-dihydro-5H-benzo[b]carbazole-9-sulfonic acid dimethylamide

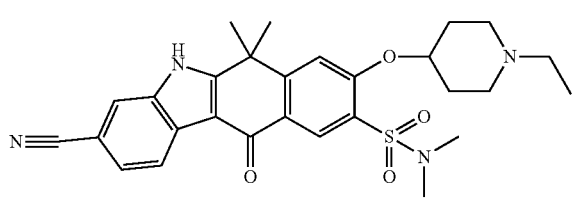 [SMILES: CCN1CCC(Oc2cc3c(cc2S(=O)(=O)N(C)C)C(=O)c2c([nH]c4cc(C#N)ccc24)C3(C)C)CC1]

Under the same conditions as the method for synthesizing Compound A7-1, the title compound was prepared from Compound C2-1 and 1-ethyl-piperidin-4-ol.

LCMS: m/z 521 [M+H]+

HPLC retention time: 1.52 min (analysis condition S)

Example 205

Compound C4-8

3-Cyano-8-(4-isopropyl-piperazin-1-yl)-6,6-dimethyl-11-oxo-6,11-dihydro-5H-benzo[b]carbazole-9-sulfonic acid dimethylamide Under the same conditions as the method for synthesizing Compound B2-1, the title compound was prepared from Compound C3-1.

$^1$H-NMR (270 MHz, DMSO-$d_6$) δ: 8.61 (1H, s), 8.30 (1H, d, J=8.1 Hz), 8.04 (1H, s), 7.87 (1H, s), 7.62 (1H, dd, J=8.2, 1.8 Hz), 3.17-3.06 (2H, m), 2.75-2.70 (6H, s), 2.67-2.58 (2H, m), 1.81 (6H, s), 1.02 (6H, d, J=6.4 Hz).

LCMS: m/z 520 [M+H]+

HPLC retention time: 1.52 min (analysis condition S)

Example 206

Compound C4-9

3-Cyano-8-[4-(2-hydroxy-ethyl)-piperazin-1-yl]-6,6-dimethyl-11-oxo-6,11-dihydro-5H-benzo[b]carbazole-9-sulfonic acid dimethylamide Under the same conditions as the method for synthesizing Compound B2-1, the title compound was prepared from Compound C3-1 and 2-piperazin-1-yl-ethanol.

LCMS: m/z 522 [M+H]+

HPLC retention time: 1.40 min (analysis condition S)

Example 207

Compound C4-10

3-Cyano-6,6-dimethyl-8-morpholin-4-yl-11-oxo-6,11-dihydro-5H-benzo[b]carbazole-9-sulfonic acid dimethylamide

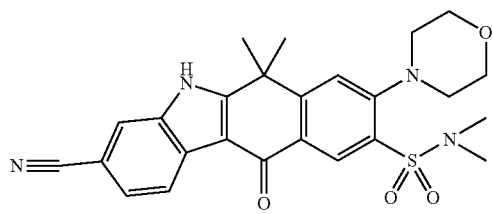 [SMILES: CN(C)S(=O)(=O)c1cc2c(cc1N1CCOCC1)C(C)(C)c1[nH]c3cc(C#N)ccc3c1C2=O]

Under the same conditions as the method for synthesizing Compound B2-1, the title compound was prepared from Compound C3-1 and morpholine.
LCMS: m/z 479 [M+H]$^+$
HPLC retention time: 2.22 min (analysis condition S)

Example 208

Compound C4-11

4-(3-Cyano-9-dimethylsulfamoyl-6,6-dimethyl-11-oxo-6,11-dihydro-5H-benzo[b]carbazol-8-yl)-piperazine-1-carboxylic acid tert-butyl ester

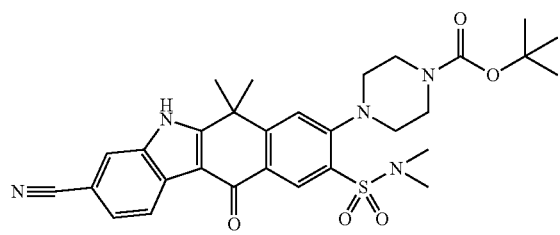 [SMILES: CN(C)S(=O)(=O)c1cc2c(cc1N1CCN(C(=O)OC(C)(C)C)CC1)C(C)(C)c1[nH]c3cc(C#N)ccc3c1C2=O]

Under the same conditions as the method for synthesizing Compound B2-1, the title compound was prepared from Compound C3-1 and piperazine-1-carboxylic acid tert-butyl ester.
LCMS: m/z 578 [M+H]$^+$
HPLC retention time: 2.72 min (analysis condition S)

Example 209

Compound C4-12

3-Cyano-6,6-dimethyl-11-oxo-8-piperazin-1-yl-6,11-dihydro-5H-benzo[b]carbazole-9-sulfonic acid dimethylamide

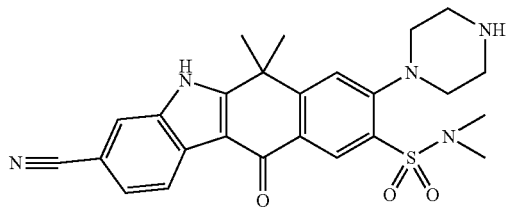 [SMILES: CN(C)S(=O)(=O)c1cc2c(cc1N1CCNCC1)C(C)(C)c1[nH]c3cc(C#N)ccc3c1C2=O]

Under the same conditions as the method for synthesizing Compound A8-1, the title compound was prepared from C4-11.

$^1$H-NMR (270 MHz, CD$_3$OD) δ: 8.78 (1H, s), 8.39 (1H, dd, J=8.2, 0.7 Hz), 7.88 (1H, m), 7.75 (1.1H, s), 7.55 (1H, dd, J=8.2, 1.5 Hz), 3.15 (4H, m), 3.04 (4H, m), 2.82 (s, 6H), 1.85 (6H, s)
LCMS: m/z 478 [M+H]$^+$
HPLC retention time: 1.43 min (analysis condition S)

Example 210

Compound C4-13

6,6-Dimethyl-11-oxo-9-(pyrrolidine-1-sulfonyl)-8-(4-pyrrolidin-1-yl-piperidin-1-yl)-6,11-dihydro-5H-benzo[b]carbazole-3-carbonitrile

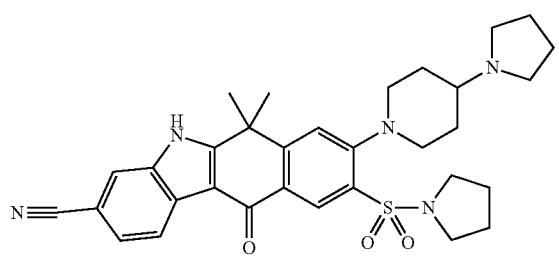 [SMILES: CC1(C)c2cc(N3CCC(N4CCCC4)CC3)c(S(=O)(=O)N3CCCC3)cc2C(=O)c2c1[nH]c1cc(C#N)ccc21]

Under the same conditions as the method for synthesizing Compound B2-1, the title compound was prepared from Compound C3-2 and 4-(1-pyrrolidyl)-piperidine.

$^1$H-NMR (400 MHz, DMSO-d$_6$) δ: 12.83 (1H, s), 8.64 (1H, s), 8.32 (1H, d, 8.2 Hz), 8.03 (1H, s), 7.80 (1H, s), 7.63 (1H, d, 8.2 Hz), 2.87-2.94 (4H, m), 1.94-1.99 (4H, m), 1.80 (6H, s), 1.58-1.76 (10H, m)
LCMS: m/z 572 [M+H]$^+$
HPLC retention time: 2.81 min (analysis condition W)

Example 211

Compound C4-14

8-(2-Diethylamino-ethoxy)-6,6-dimethyl-9-(morpholine-4-sulfonyl)-11-oxo-6,11-dihydro-5H-benzo[b]carbazole-3-carbonitrile

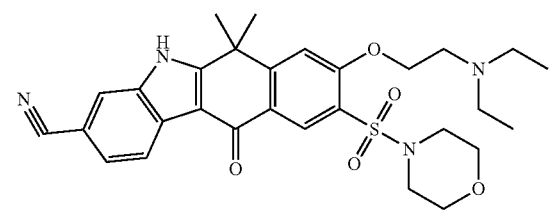 [SMILES: CCN(CC)CCOc1cc2c(cc1S(=O)(=O)N1CCOCC1)C(=O)c1c([nH]c3cc(C#N)ccc13)C2(C)C]

Under the same conditions as the method for synthesizing Compound A7-17, the title compound was prepared from Compound C2-3.
LCMS: m/z 551 [M+H]$^+$
HPLC retention time: 1.46 min (analysis condition S)

Example 212

Compound C4-15

6,6-Dimethyl-9-(morpholine-4-sulfonyl)-11-oxo-8-(tetrahydro-pyran-4-yl oxy)-6,11-dihydro-5H-benzo[b]carbazole-3-carbonitrile

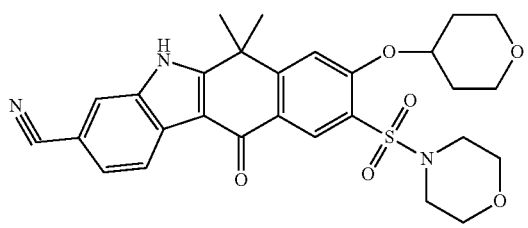 [SMILES: CC1(C)c2cc(OC3CCOCC3)c(S(=O)(=O)N3CCOCC3)cc2C(=O)c2c1[nH]c1cc(C#N)ccc21]

Under the same conditions as the method for synthesizing Compound A7-1, the title compound was prepared from Compound C2-3 and tetrahydropyran-4-ol.
LCMS: m/z 536 [M+H]+
HPLC retention time: 2.05 min (analysis condition S)

Example 213

Compound C4-16

6,6-Dimethyl-9-(4-methyl-piperazine-1-sulfonyl)-11-oxo-8-(tetrahydro-pyran-4-yl oxy)-6,11-dihydro-5H-benzo[b]carbazole-3-carbonitrile

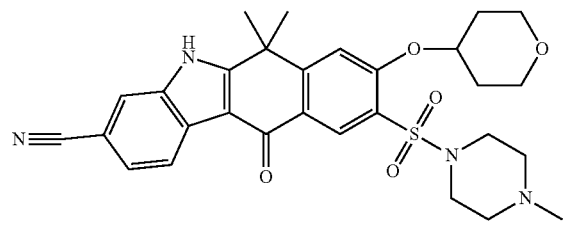 [SMILES: CN1CCN(S(=O)(=O)c2cc3c(cc2OC2CCOCC2)C(C)(C)c2[nH]c4cc(C#N)ccc4c2C3=O)CC1]

Under the same conditions as the method for synthesizing Compound A7-1, the title compound was prepared from Compound C2-4 and tetrahydropyran-4-ol.
LCMS: m/z 549 [M+H]+
HPLC retention time: 2.03 min (analysis condition U)

Example 214

Compound C4-17

8-(2-Diethylamino-ethoxy)-6,6-dimethyl-9-(4-methyl-piperazine-1-sulfonyl)-11-oxo-6,11-dihydro-5H-benzo[b]carbazole-3-carbonitrile

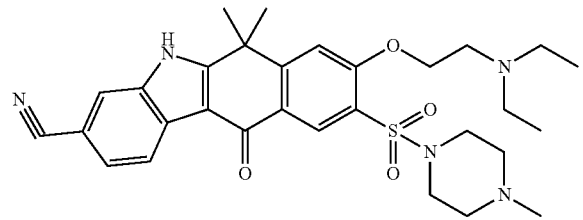 [SMILES: CCN(CC)CCOc1cc2c(cc1S(=O)(=O)N1CCN(C)CC1)C(=O)c1c([nH]c3cc(C#N)ccc13)C2(C)C]

Under the same conditions as the method for synthesizing Compound A7-1, the target compound was prepared from Compound C2-3.

LCMS: m/z 564 [M+H]+
HPLC retention time: 1.20 min (analysis condition S)

Example 215

Compound C5

3-Cyano-8-methoxy-5,6,6-trimethyl-11-oxo-6,11-dihydro-5H-benzo[b]carbazole-9-sulfonic acid dimethylamide

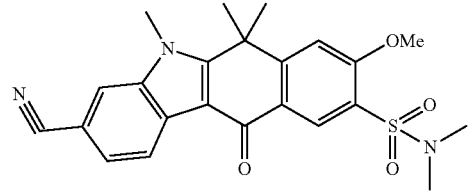 [SMILES: COc1cc2c(cc1S(=O)(=O)N(C)C)C(=O)c1c(n(C)c3cc(C#N)ccc13)C2(C)C]

The title compound was obtained as a by-product of the synthesis of Compound C4-3.
LCMS: m/z 438 [M+H]+
HPLC retention time: 2.29 min (analysis condition S)

Example 216

Compound D0-1-1

7-Methoxy-1,1-dimethyl-6-nitro-3,4-dihydro-1H-naphthalen-2-one

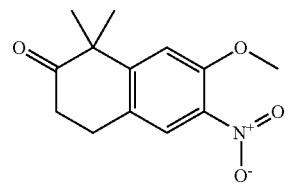 [SMILES: COc1cc2c(cc1[N+](=O)[O-])CCC(=O)C2(C)C]

Tetrabutylammonium nitrate (2.47 g, 1.07 eq.) was dissolved in dichloromethane, and added with trifluoromethanesulfonic anhydride (1.33 ml, 1.07 eq.) at 0° C. The mixture was stirred for 1 hr, added with DCM solution of 7-methoxy-1,1-dimethyl-3,4-dihydro-1H-naphthalen-2-one (Compound A2, 1.55 g, 7.59 mmol), and then stirred at 0° C. for 2 hr and 30 min. The reaction solution was added to saturated aqueous solution of sodium hydrogen carbonate and then extracted with ethyl acetate. The organic layer was washed with brine and dried over sodium sulfate. The drying agent was removed by filtration and the residues obtained after concentration under reduced pressure were purified by silica gel column chromatography (ethyl acetate/hexane) to obtain the title compound (pale yellow solid, 1.144 g, 60%).
$^1$H-NMR (270 MHz, DMSO-$d_6$) δ: 7.79 (1H, s), 7.28 (1H, s), 3.95 (3H, s), 3.06 (2H, t, J=6.9 Hz), 2.64 (2H, t, J=6.9 Hz), 1.41 (6H, s).
HPLC retention time: 2.03 min (analysis condition S)

Example 217

Compound D0-1-2

7-Methoxy-1,1-dimethyl-8-nitro-3,4-dihydro-1H-naphthalen-2-one

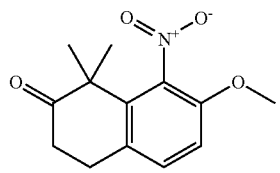 [SMILES: COc1ccc2c(c1[N+](=O)[O-])C(C)(C)C(=O)CC2]

The title compound was obtained as a by-product of the synthesis of Compound D0-1-1.

$^1$H-NMR (270 MHz, DMSO-$d_6$) δ: 7.44 (1H, d, J=8.6 Hz), 7.23 (1H, d, J=8.6 Hz), 3.84 (3H, s), 3.07 (2H, t, J=6.9 Hz), 2.65 (2H, t, J=6.9 Hz), 1.35 (6H, s)

HPLC retention time: 2.15 min (analysis condition S)

Example 218

Compound D0-2-1

3-Bromo-8-methoxy-6,6-dimethyl-9-nitro-6,11-dihydro-5H-benzo[b]carbazole

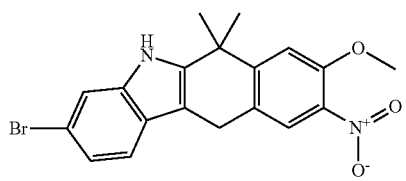

Under the same conditions as the method for synthesizing Compound A3-1, the title compound was prepared from Compound D0-1-1.

LCMS: m/z 401, 403 [M+H]$^+$

HPLC retention time: 3.07 min (analysis condition S)

Example 219

Compound D0-2-2

3-Bromo-8-methoxy-6,6-dimethyl-7-nitro-6,11-dihydro-5H-benzo[b]carbazole

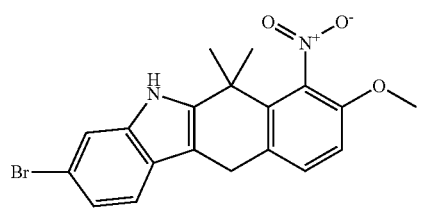 [SMILES: COc1ccc2c(c1[N+](=O)[O-])C(C)(C)c1[nH]c3cc(Br)ccc3c1C2]

Under the same conditions as the method for synthesizing Compound A3-1, the title compound was prepared from Compound D0-1-2.

LCMS: m/z 401, 403 [M+H]$^+$

HPLC retention time: 3.10 min (analysis condition S)

Example 220

Compound D0-3-1

3-Bromo-8-methoxy-6,6-dimethyl-9-nitro-5,6-dihydro-benzo[b]carbazol-11-one

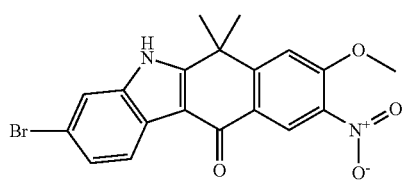 [SMILES: COc1cc2c(cc1[N+](=O)[O-])C(=O)c1c([nH]c3cc(Br)ccc13)C2(C)C]

Under the same conditions as the method for synthesizing Compound A4, the title compound was prepared from Compound D0-2-1.

LCMS: m/z 415, 417 [M+H]$^+$

HPLC retention time: 3.07 min (analysis condition S)

Example 221

Compound D0-3-2

3-Bromo-8-methoxy-6,6-dimethyl-7-nitro-5,6-dihydro-benzo[b]carbazol-11-one

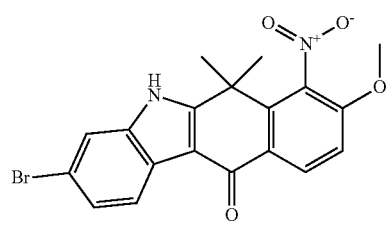 [SMILES: COc1ccc2c(c1[N+](=O)[O-])C(C)(C)c1[nH]c3cc(Br)ccc3c1C2=O]

Under the same conditions as the method for synthesizing Compound A4, the title compound was prepared from Compound D0-2-2.

LCMS: m/z 415, 417 [M+H]$^+$

HPLC retention time: 2.72 min (analysis condition S)

Example 222

Compound D0-4-1

8-Methoxy-6,6-dimethyl-9-nitro-11-oxo-6,11-dihydro-5H-benzo[b]carbazole-3-carbonitrile

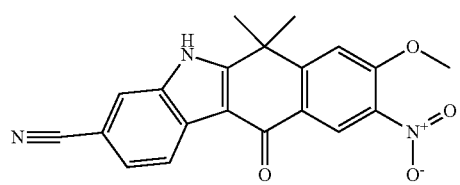 [SMILES: COc1cc2c(cc1[N+](=O)[O-])C(=O)c1c([nH]c3cc(C#N)ccc13)C2(C)C]

Under the same conditions as the method for synthesizing Compound A5-2, the title compound was prepared from Compound D0-3-1.

LCMS: m/z 362 [M+H]+

HPLC retention time: 2.35 min (analysis condition S)

Example 223

Compound D0-4-2

8-Methoxy-6,6-dimethyl-7-nitro-11-oxo-6,11-di-hydro-5H-benzo[b]carbazole-3-carbonitrile Under the same conditions as the method for synthesizing Compound A5-2, the title compound was prepared from Compound D0-3-2.

LCMS: m/z 362 [M+H]+

HPLC retention time: 2.35 min (analysis condition S)

Example 224

Compound D0-5-1

8-Hydroxy-6,6-dimethyl-9-nitro-11-oxo-6,11-di-hydro-5H-benzo[b]carbazole-3-carbonitrile Under the same conditions as the method for synthesizing Compound A6, the title compound was prepared from Compound D0-4-1.

LCMS: m/z 348 [M+H]+

HPLC retention time: 2.28 min (analysis condition S)

Example 225

Compound D0-5-2

8-Hydroxy-6,6-dimethyl-7-nitro-11-oxo-6,11-di-hydro-5H-benzo[b]carbazole-3-carbonitrile

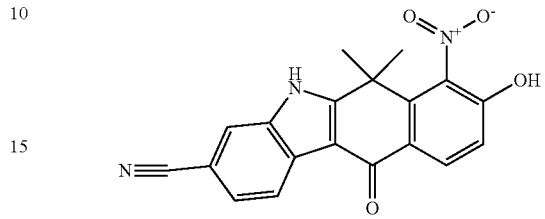

Under the same conditions as the method for synthesizing Compound A6, the title compound was prepared from Compound D0-4-2.

LCMS: m/z 348 [M+H]+

HPLC retention time: 2.23 min (analysis condition S)

Example 226

Compound D1

6,6-Dimethyl-8-(1-methyl-piperidin-4-yl oxy)-9-nitro-11-oxo-6,11-dihydro-5H-benzo[b]carbazole-3-carbonitrile

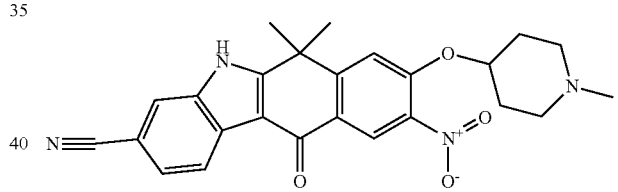

Under the same conditions as the method for synthesizing Compound A7-1, the title compound was prepared from Compound D0-5-1 and 1-methylpiperidin-4-ol.

LCMS: m/z 445 [M+H]+

HPLC retention time: 1.64 min (analysis condition S)

Example 227

Compound D2

9-Amino-6,6-dimethyl-8-(1-methyl-piperidin-4-yl oxy)-11-oxo-6,11-dihydro-5H-benzo[b]carbazole-3-carbonitrile

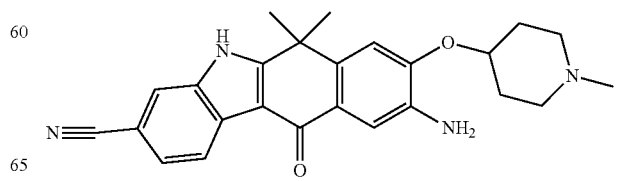

6,6-Dimethyl-8-(1-methyl-piperidin-4-yl oxy)-9-nitro-11-oxo-6,11-dihydro-5H-benzo[b]carbazole-3-carbonitrile (Compound D1, 83 mg, 0.19 mmol) was dissolved in ethanol, added with aqueous solution of ammonium acetate and aqueous solution of titanium (III) chloride, and then the mixture was stirred at room temperature for 45 min. The reaction solution was added to saturated aqueous solution of sodium hydrogen carbonate and then extracted with ethyl acetate. The organic layer was washed with brine and dried over sodium sulfate. The drying agent was removed by filtration and the residues were concentrated under reduced pressure to obtain the title compound (yellow solid, 60 mg, 78%).

$^1$H-NMR (270 MHz, DMSO-$d_6$) δ: 12.61 (1H, br. s), 8.28-8.34 (1H, m), 7.94-8.00 (1H, m), 7.57 (1H, dd, J=8.2, 1.4 Hz), 7.46 (1H, s), 7.19 (1H, s), 4.93 (1.8H, s), 4.65 (1.0H, s), 4.06-4.15 (1H, m), 3.34 (5.7H, s), 3.16-3.18 (2H, m), 2.55-2.67 (2H, m), 2.17-2.33 (5H, m), 1.89-2.07 (2H, m), 1.65-1.81 (8H, m)

LCMS: m/z 415 [M+H]$^+$

HPLC retention time: 1.12 min (analysis condition S)

Example 228

Compound D3-1

N-[3-Cyano-6,6-dimethyl-8-(1-methyl-piperidin-4-yl oxy)-11-oxo-6,11-dihydro-5H-benzo[b]carbazol-9-yl]-methanesulfonamide

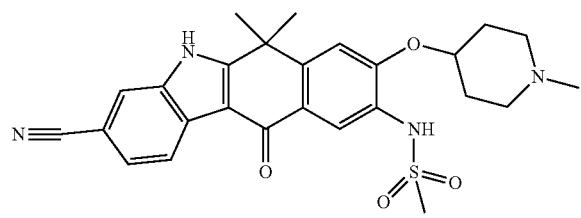 [SMILES: CN1CCC(Oc2cc3c(cc2NS(C)(=O)=O)C(=O)c2c([nH]c4cc(C#N)ccc24)C3(C)C)CC1]

Under the same conditions as the method for synthesizing Compound A9-1, the title compound was prepared from Compound D2 and methanesulfonyl chloride.

LCMS: m/z 493 [M+H]$^+$

HPLC retention time: 1.43 min (analysis condition S)

Example 229

Compound D3-2

3-Cyano-6,6-dimethyl-11-oxo-8-(1-methylpiperidin-4-yl oxy)-6,11-dihydro-5H-benzo[b]carbazole-9-sulfonic acid dimethylamide

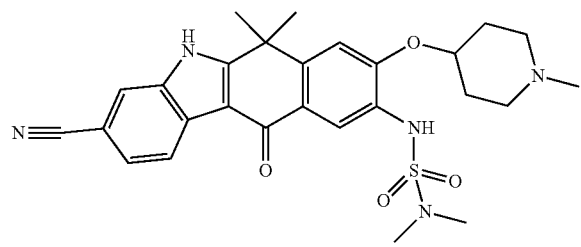 [SMILES: CN1CCC(Oc2cc3c(cc2NS(=O)(=O)N(C)C)C(=O)c2c([nH]c4cc(C#N)ccc24)C3(C)C)CC1]

Under the same conditions as the method for synthesizing Compound A9-1, the title compound was prepared from Compound D2 and dimethylsulfamoyl chloride.

$^1$H-NMR (270 MHz, CD$_3$OD) δ: 8.34-8.42 (2. OH, m), 7.85 (1.0H, s), 7.47-7.58 (1.0H, m), 7.32 (1.0H, s), 4.73-4.89 (1H, m), 2.75-2.91 (8H, m), 2.38-2.52 (2H, m), 2.34 (3H, s), 2.06-2.21 (2H, m), 1.87-2.05 (2H, m), 1.80 (6H, s).

LCMS: m/z 522 [M+H]$^+$

HPLC retention time: 1.66 min (analysis condition S)

Example 230

Compound D3-3

N-[3-Cyano-6,6-dimethyl-8-(1-methyl-piperidin-4-yl oxy)-11-oxo-6,11-dihydro-5H-benzo[b]carbazol-9-yl]-2-dimethylamino-acetamide

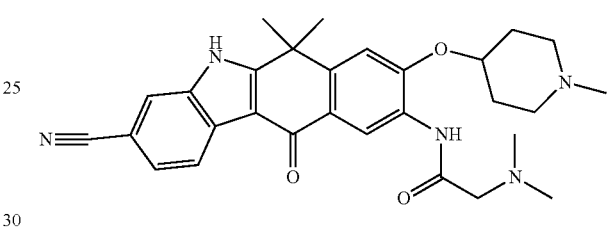

Under the same conditions as the method for synthesizing Compound A9-10, the title compound was prepared from Compound D2 and N,N-dimethylglycine.

LCMS: m/z 500 [M+H]$^+$

HPLC retention time: 1.31 min (analysis condition S)

Example 231

Compound E1

6-Bromo-7-methoxy-1,1-dimethyl-3,4-dihydro-1H-naphthalen-2-one

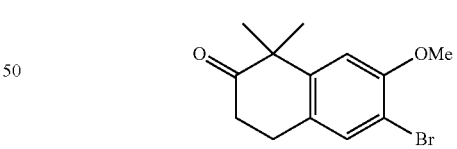

7-Methoxy-1,1-dimethyl-3,4-dihydro-1H-naphthalen-2-one (Compound A2, 2.0 g, 9.791 mmol) was dissolved in CH$_3$CN (40 mL), added with NBS (1.92 g, 1.1 eq.), and the mixture was stirred at room temperature for 2.5 hr. The reaction solution was added to water (40 mL), and the precipitated solid was filtered to obtain the title compound (white powder, 2.55 g, 92%).

$^1$H-NMR (270 MHz, CDCl$_3$) δ: 7.36 (1H, s), 6.84 (1H, s), 3.91 (3H, s), 3.02 (2H, t, J=6.8 Hz), 2.66 (2H, t, J=6.8 Hz), 1.42 (6H, s).

LCMS: m/z 283, 285 [M+H]$^+$

HPLC retention time: 2.67 min (analysis condition S)

Example 232

Compound E2-1

9-Bromo-8-methoxy-6,6-dimethyl-6,11-dihydro-5H-benzo[b]carbazole-3-carbonitrile

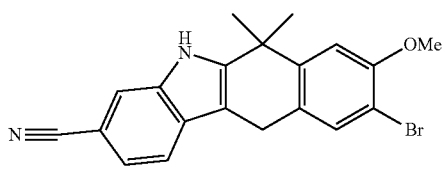 [SMILES: COc1cc2c(cc1Br)Cc1c([nH]c3cc(C#N)ccc13)C2(C)C]

6-Bromo-7-methoxy-1,1-dimethyl-3,4-dihydro-1H-naphthalen-2-one (Compound E1, 7.89 g, 27.85 mmol) and 3-hydrazino-benzonitrile (4.45 g, 1.2 eq.) were dissolved in TFA (250 mL), and stirred at 100° C. for 2 hr. TFA was removed under reduced pressure and the residues were added with saturated aqueous solution of NaHCO$_3$ (500 mL), followed by extraction with ethyl acetate. The organic layer was washed with saturated brine and dried over sodium sulfate. The drying agent was removed by filtration and the residues obtained after concentration under reduced pressure were added with ethyl acetate. After stirring at room temperature, the precipitated solid was separated by filtration (Compound E2-2). The filtrate was concentrated under reduced pressure to obtain the title compound as a mixture with E2-2 (yellowish white powder, 2.65 g).

LCMS: m/z 381, 383 [M+H]$^+$

HPLC retention time: 3.03 min (analysis condition S)

Example 233

Compound E2-2

9-Bromo-8-methoxy-6,6-dimethyl-6,11-dihydro-5H-benzo[b]carbazole-1-carbonitrile

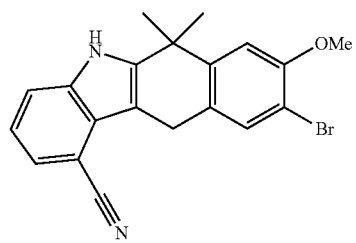 [SMILES: COc1cc2c(cc1Br)Cc1c([nH]c3cccc(C#N)c13)C2(C)C]

The title compound was obtained as a by-product of the synthesis of Compound E2-1.

$^1$H-NMR (270 MHz, DMSO-d$_6$) δ: 11.70 (1H, s), 7.69 (1H, dd, J=8.1, 0.8 Hz), 7.55 (1H, s), 7.48 (1H, dd, J=7.4, 0.8 Hz), 7.27 (1H, s), 7.22 (1H, dd, J=8.1, 7.4 Hz), 4.23 (2H, s), 3.91 (3H, s), 1.70 (6H, s).

LCMS: m/z 381, 383 [M+H]$^+$

HPLC retention time: 2.92 min (analysis condition S)

Example 234

Compound E2-3, Compound E2-4

3,9-Dibromo-8-methoxy-6,6-dimethyl-6,11-dihydro-5H-benzo[b]carbazole 1,9-Dibromo-8-methoxy-6,6-dimethyl-6,11-dihydro-5H-benzo[b]carbazole

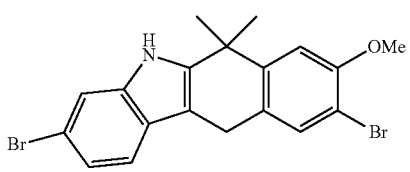

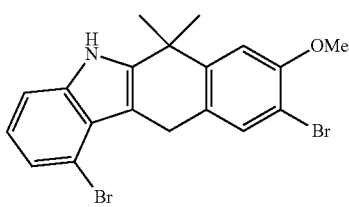

Under the same conditions as the method for synthesizing Compound A4, the title compound was prepared (as a mixture) from Compound E1.

Example 235

Compound E3-1-1

9-Bromo-8-methoxy-6,6-dimethyl-11-oxo-6,11-dihydro-5H-benzo[b]carbazole-3-carbonitrile

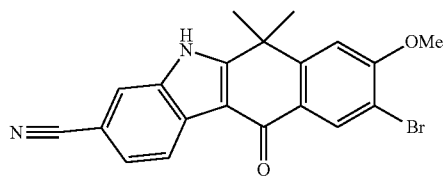 [SMILES: COc1cc2c(cc1Br)C(=O)c1c([nH]c3cc(C#N)ccc13)C2(C)C]

Under the same conditions as the method for synthesizing Compound A4, the title compound was prepared from Compound E2-1.

$^1$H-NMR (270 MHz, DMSO-d$_6$) δ: 12.82 (1H, s), 8.30 (2H, s+d), 8.03 (1H, s), 7.61 (1H, dd, J=8.2, 1.4 Hz), 7.49 (1H, s), 4.04 (3H, s), 1.81 (6H, s).

LCMS: m/z 395, 397 [M+H]$^+$

HPLC retention time: 2.77 min (analysis condition S)

Example 236

Compound E3-1-2

9-Bromo-8-methoxy-6,6-dimethyl-11-oxo-6,11-dihydro-5H-benzo[b]carbazole-1-carbonitrile

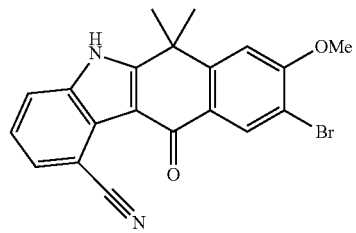 [SMILES: COc1cc2c(cc1Br)C(=O)c1c([nH]c3cccc(C#N)c13)C2(C)C]

The title compound was obtained as a by-product of the synthesis of Compound E3-1-1.

$^1$H-NMR (270 MHz, DMSO-$d_6$) δ: 12.84 (1H, s), 8.31 (1H, s), 7.86 (1H, dd, J=8.2, 0.9 Hz), 7.70 (1H, d, J=7.1 Hz), 7.47 (1H, s), 7.43 (1H, t, J=7.8 Hz), 4.04 (3H, s), 1.81 (6H, s).

LCMS: m/z 395, 397 [M+H]$^+$

HPLC retention time: 2.42 min (analysis condition S)

Example 237

Compound E3-1-3

3,9-Dibromo-8-methoxy-6,6-dimethyl-5,6-dihydro-benzo[b]carbazol-11-one

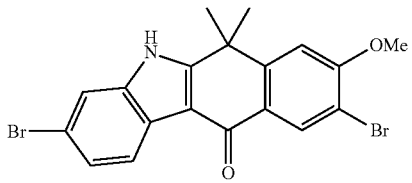 [SMILES: COc1cc2c(cc1Br)C(=O)c1c([nH]c3cc(Br)ccc13)C2(C)C]

Under the same conditions as the method for synthesizing Compound A4, the title compound was prepared from Compound E2-3 and Compound E2-4 (mixture).

$^1$H-NMR (270 MHz, DMSO-$d_6$) δ: 12.42 (1H, s), 8.28 (1H, s), 8.09 (1H, d, J=8.2 Hz), 7.68 (1H, d, J=1.6 Hz), 7.47 (1H, s), 7.39 (1H, dd, J=8.3, 1.7 Hz), 4.03 (3H, s), 1.78 (6H, s).

LCMS: m/z 448, 450, 452 [M+H]$^+$

HPLC retention time: 2.93 min (analysis condition S)

Example 238

Compound E3-2

9-Bromo-8-hydroxy-6,6-dimethyl-11-oxo-6,11-dihydro-5H-benzo[b]carbazole-3-carbonitrile

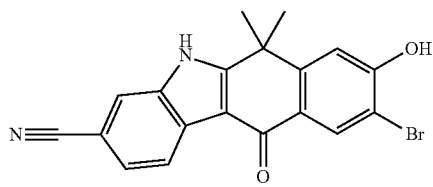 [SMILES: CC1(C)c2cc(O)c(Br)cc2C(=O)c2c1[nH]c1cc(C#N)ccc21]

9-Bromo-8-methoxy-6,6-dimethyl-11-oxo-6,11-dihydro-5H-benzo[b]carbazole-3-carbonitrile (Compound E3-1-1, 1.0 g, 2.53 mmol) was dissolved in NMP (10 mL), added with NaOMe (683 mg, 5 eq.) and 1-dodecanethiol (3.0 mL, 5 eq.), and stirred at 160° C. for 1 hr. The reaction solution was added to 0.5 N aqueous solution of hydrochloric acid, and then extracted with ethyl acetate. The organic layer was washed with saturated brine and dried over sodium sulfate. The drying agent was removed by filtration and the residues obtained after concentration under reduced pressure were added with MeOH, and the solid remaining after dissolution was filtered to obtain the title compound (yellow powder, 1.88 g, 65%).

$^1$H-NMR (400 MHz, DMSO-$d_6$) δ: 12.77 (1H, s), 11.13 (1H, d, J=2.4 Hz), 8.31 (1H, dd, J=7.9, 2.4 Hz), 8.25 (1H, d, J=3.0 Hz), 8.01 (1H, s), 7.61 (1H, d, J=7.9 Hz), 7.28 (1H, d, J=2.4 Hz), 1.74 (6H, s).

LCMS: m/z 381, 383 [M+H]$^+$

HPLC retention time: 2.40 min (analysis condition S)

Example 239

Compound E3-3

9-Bromo-8-isopropoxy-6,6-dimethyl-11-oxo-6,11-dihydro-5H-benzo[b]carbazole-3-carbonitrile

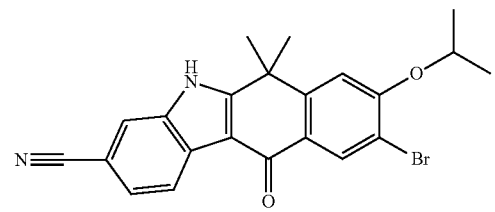 [SMILES: CC(C)Oc1cc2c(cc1Br)C(=O)c1c([nH]c3cc(C#N)ccc13)C2(C)C]

Under the same conditions as the method for synthesizing Compound A7-17, the title compound was prepared from Compound E3-2 and 2-bromopropane.

$^1$H-NMR (270 MHz, DMSO-$d_6$) δ: 12.77 (1H, s), 8.29 (2H, s+d), 8.01 (1H, s), 7.60 (1H, d, J=8.1 Hz), 7.50 (1H, s), 5.03 (1H, m), 1.79 (6H, s), 1.36 (6H, d, J=5.9 Hz).

LCMS: m/z 423, 425 [M+H]$^+$

HPLC retention time: 2.98 min (analysis condition S)

Example 240

Compound E4-1

8-Methoxy-6,6-dimethyl-11-oxo-6,11-dihydro-5H-benzo[b]carbazole-3,9-dicarbonitrile

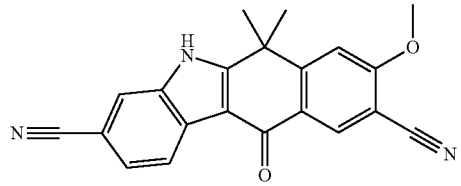 [SMILES: COc1cc2c(cc1C#N)C(=O)c1c([nH]c3cc(C#N)ccc13)C2(C)C]

Under the same conditions as the method for synthesizing Compound A5-2, the title compound was prepared from Compound E3-1-1.

$^1$H-NMR (270 MHz, DMSO-$d_6$) δ: 12.88 (1H, br. s), 8.43 (1H, s), 8.30 (1H, d, J=8.2 Hz), 8.05 (1H, d, J=0.5 Hz), 7.65-7.62 (2H, m), 4.11 (3H, s), 1.84 (6H, s).

LCMS: m/z 342 [M+H]$^+$

HPLC retention time: 2.23 min (analysis condition S)

Example 241

Compound E4-2-1

9-(3-Hydroxy-3-methyl-but-1-ynyl)-8-methoxy-6,6-dimethyl-11-oxo-6,11-dihydro-5H-benzo[b]carbazole-3-carbonitrile

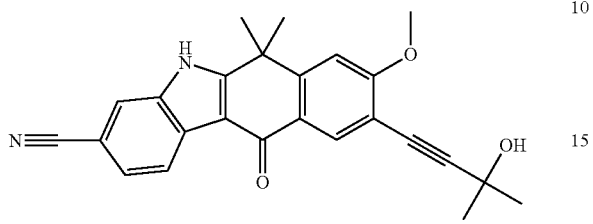

9-Bromo-8-methoxy-6,6-dimethyl-11-oxo-6,11-dihydro-5H-benzo[b]carbazole-3-carbonitrile (Compound E3-1-1, 50 mg, 0.13 mmol), bis(acetonitrile)dichloropalladium (II) (1.64 mg, 0.05 eq.), XPhos (9.05 mg, 0.15 eq.), cesium carbonate (185 mg, 4.5 eq.) and 3-methyl-1-butyn-1-ol (18.6 µl, 1.5 eq.) were dissolved in acetonitrile and stirred at 85° C. for 2 hr. The reaction solution was added to water, and then extracted with ethyl acetate. The organic layer was washed with brine and dried over sodium sulfate. The drying agent was removed by filtration and the residues obtained after concentration under reduced pressure were purified by HPLC to obtain the title compound (brown solid, 21.3 mg, 42%).

$^1$H-NMR (270 MHz, DMSO-$d_6$) δ: 8.29 (1H, d, J=8.1 Hz), 8.11 (1H, s), 8.00 (1H, s), 7.57 (1H, d, J=8.1 Hz), 7.40 (1H, s), 5.50 (1H, s), 3.95 (3H, s), 2.54 (1H, s), 1.79 (6H, s), 1.49 (6H, s).

LCMS: m/z 399 [M+H]$^+$

HPLC retention time: 2.10 min (analysis condition S)

Example 242

Compound E4-2-2

9-Ethynyl-8-methoxy-6,6-dimethyl-11-oxo-6,11-dihydro-5H-benzo[b]carbazole-3-carbonitrile

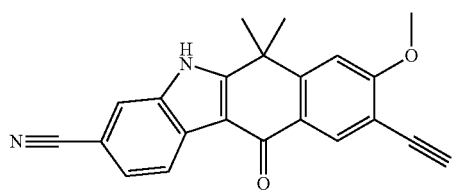 [SMILES: C#Cc1cc2c(cc1OC)C(C)(C)c1[nH]c3cc(C#N)ccc3c1C2=O]

9-(3-Hydroxy-3-methyl-but-1-ynyl)-8-methoxy-6,6-dimethyl-11-oxo-6,11-dihydro-5H-benzo[b]carbazole-3-carbonitrile (Compound E4-2-1, 21.3 mg, 0.05 mmol) and sodium hydride (3.2 mg, 1.5 eq.) were dissolved in THF, and the mixture was stirred overnight at 50° C. Water was added to the reaction solution and the residues obtained after concentration under reduced pressure were purified by HPLC to obtain the title compound (brown solid, 9.6 mg, 31%).

$^1$H-NMR (270 MHz, DMSO-$d_6$) δ: 8.26 (1H, d, J=8.2 Hz), 8.16 (1H, s), 7.97 (1H, s), 7.53 (1H, d, J=8.2 Hz), 7.41 (1H, s), 4.32 (1H, s), 4.00 (3H, s), 1.79 (6H, s).

LCMS: m/z 341 [M+H]$^+$

HPLC retention time: 2.27 min (analysis condition S)

Example 243

Compound E4-3

8-Methoxy-6,6-dimethyl-11-oxo-9-vinyl-6,11-dihydro-5H-benzo[b]carbazole-3-carbonitrile

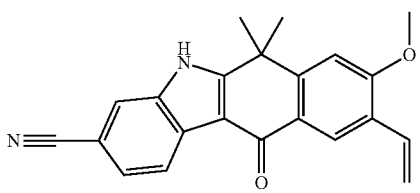 [SMILES: C=Cc1cc2c(cc1OC)C(C)(C)c1[nH]c3cc(C#N)ccc3c1C2=O]

9-Bromo-8-methoxy-6,6-dimethyl-11-oxo-6,11-dihydro-5H-benzo[b]carbazole-3-carbonitrile (Compound E3-1-1, 50 mg, 0.13 mmol), [1,1'-bis(diphenylphosphino)ferrocene]palladium (II) dichloride dichloromethane complex (1:1) (10.3 mg, 0.1 eq.), TEA (53 µl, 3 eq.) and potassium vinyltrifluoroborate (51 mg, 3 eq.) were dissolved in n-propanol and the mixture was stirred at 60° C. for 5 days. The reaction solution was added to water and then extracted with ethyl acetate. The organic layer was washed with brine and dried over sodium sulfate. The drying agent was removed by filtration and the residues obtained after concentration under reduced pressure were purified by silica gel column chromatography (ethyl acetate/hexane) to obtain the title compound (brown powder, 25 mg, 19%).

LCMS: m/z 343 [M+H]$^+$

HPLC retention time: 2.55 min (analysis condition S)

Example 244

Compound E4-4

9-(2-Diethylamino-ethylsulfanyl)-8-methoxy-6,6-dimethyl-11-oxo-6,11-dihydro-5H-benzo[b]carbazole-3-carbonitrile

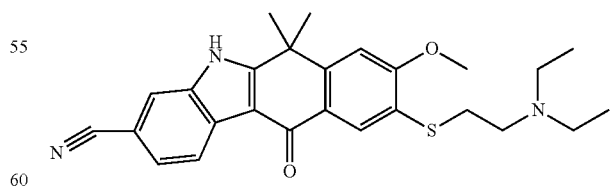

Under the same conditions as the method for synthesizing Compound B2-17, the title compound was prepared from Compound E3-1-1.

LCMS: m/z 448 [M+H]$^+$

HPLC retention time: 2.05 min (analysis condition U)

Example 245

Compound E4-5

9-Isopropylsulfanyl-8-methoxy-6,6-dimethyl-11-oxo-6,11-dihydro-5H-benzo[b]carbazole-3-carbonitrile

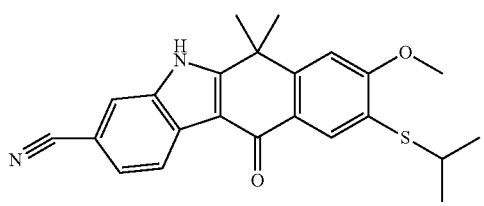 [SMILES: COc1cc2c(cc1SC(C)C)C(=O)c1c([nH]c3cc(C#N)ccc13)C2(C)C]

Under the same conditions as the method for synthesizing Compound B2-17, the title compound was prepared from Compound E3-1-1 and sodium salt of propane-2-thiol.

LCMS: m/z 391 [M+H]$^+$

HPLC retention time: 2.98 min (analysis condition U)

Example 246

Compound E4-6

8-Methoxy-6,6-dimethyl-9-(4-methylpiperazin-1-yl)-11-oxo-6,11-dihydro-5H-benzo[b]carbazole-3-carbonitrile

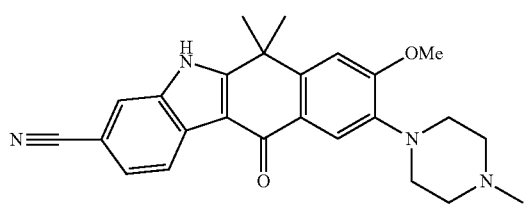 [SMILES: COc1cc2c(cc1N1CCN(C)CC1)C(=O)c1c([nH]c3cc(C#N)ccc13)C2(C)C]

Under the same conditions as the method for synthesizing Compound B2-10, the title compound was prepared from Compound E3-1-1 and 1-methylpiperazine.

$^1$H-NMR (400 MHz, DMSO-d$_6$) δ: 8.25 (1H, d, J=7.8 Hz), 7.93 (1H, s), 7.65 (1H, s), 7.50 (1H, d, J=6.8 Hz), 7.25 (1H, s), 3.93 (3H, s), 3.02 (4H, br), 2.22 (3H, s), 1.73 (6H, s).

LCMS: m/z 415 [M+H]$^+$

HPLC retention time: 1.80 min (analysis condition U)

Example 247

Compound E4-7-1

4-(3-Cyano-8-methoxy-6,6-dimethyl-11-oxo-6,11-dihydro-5H-benzo[b]carbazol-9-yl)-3,6-dihydro-2H-pyridine-1-carboxylic acid tert-butyl ester

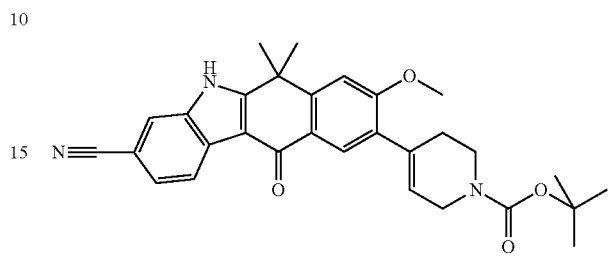

To 9-bromo-8-methoxy-6,6-dimethyl-11-oxo-6,11-dihydro-5H-benzo[b]carbazole-3-carbonitrile (Compound E3-1-1, 300 mg, 0.759 mmol), 4-(4,4,5,5-tetramethyl-[1,3,2]dioxaborolan-2-yl)-3,6-dihydro-2H-pyridine-1-carboxylic acid tert-butyl ester (282 mg, 0.911 mmol, 1.2 eq.), Pd(PPh$_3$)$_2$Cl$_2$ (26.6 mg, 0.0379 mmol, 0.05 eq.) and sodium carbonate (241 mg, 2.28 mmol, 3.0 eq.), DME (5 ml) and water (1 ml) were added. The mixture was subjected to reduced pressure under ultrasonication treatment, followed by flushing with nitrogen gas. This procedure was repeated five times and then degassed. The mixture was stirred at 80° C. for 80 min under nitrogen atmosphere. Pd(PPh$_3$)$_2$Cl$_2$ (26.6 mg, 0.0379 mmol, 0.05 eq.) was added and the mixture was further stirred at 80° C. for 20 min. Then, the mixture was cooled to room temperature, and added with water and ethyl acetate. The insoluble matters were filtered through Celite. The organic layer was dried over sodium sulfate. The drying agent was removed by filtration, followed by concentration under reduced pressure to obtain the title compound as a crude product (gray powder).

LCMS: m/z 498 [M+H]$^+$

HPLC retention time: 2.85 min (analysis condition S)

Example 248

Compound E4-7-2

8-Methoxy-6,6-dimethyl-11-oxo-9-(1,2,3,6-tetrahydro-pyridin-4-yl)-6,11-dihydro-5H-benzo[b]carbazole-3-carbonitrile

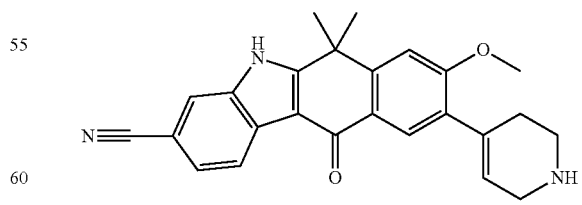

Under the same conditions as the method for synthesizing Compound A8-1, the title compound was prepared from Compound B4-4-1.

LCMS: m/z 368 [M+H]$^+$

HPLC retention time: 1.27 min (analysis condition S)

Example 249

Compound E4-8-1

4-(3-Cyano-8-methoxy-6,6-dimethyl-11-oxo-6,11-dihydro-5H-benzo[b]carbazol-9-yl)-piperidine-1-carboxylic acid tert-butyl ester

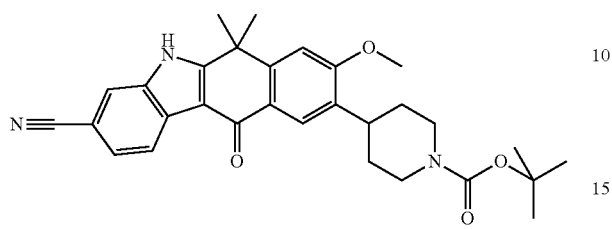

Under the same conditions as the method for synthesizing Compound B3-13-1, the title compound was prepared from Compound B4-7-1.
LCMS: m/z 500 [M+H]$^+$
HPLC retention time: 4.18 min (analysis condition W)

Example 250

Compound E4-8-2

8-Methoxy-6,6-dimethyl-11-oxo-9-piperidin-4-yl-6,11-dihydro-5H-benzo[b]carbazole-3-carbonitrile

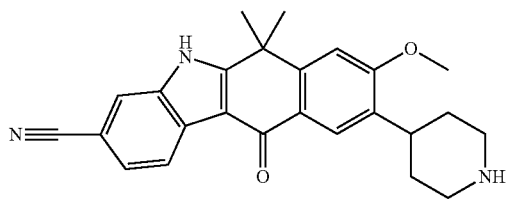 [SMILES: COc1cc2c(cc1C1CCNCC1)C(=O)c1c([nH]c3cc(C#N)ccc13)C2(C)C]

Under the same conditions as the method for synthesizing Compound A8-1, the title compound was prepared from Compound B4-8-1.
LCMS: m/z 400 [M+H]$^+$
HPLC retention time: 1.35 min (analysis condition S)

Example 251

Compound E4-9-1

4-(3-Cyano-8-isopropoxy-6,6-dimethyl-11-oxo-6,11-dihydro-5H-benzo[b]carbazol-9-yl)-3,6-dihydro-2H-pyridine-1-carboxylic acid tert-butyl ester

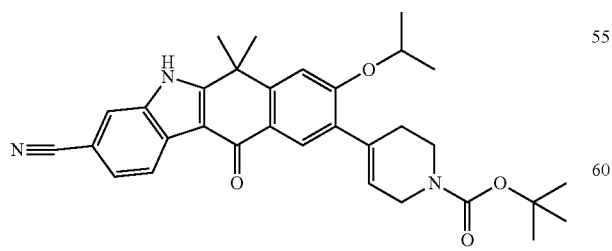

Under the same conditions as the method for synthesizing Compound E4-7-1, the title compound was prepared from Compound E3-3.
LCMS: m/z 526 [M+H]$^+$
HPLC retention time: 3.13 min (analysis condition S)

Example 252

Compound E4-9-2

8-Isopropoxy-6,6-dimethyl-11-oxo-9-(1,2,3,6-tetrahydro-pyridin-4-yl)-6,11-dihydro-5H-benzo[b]carbazole-3-carbonitrile

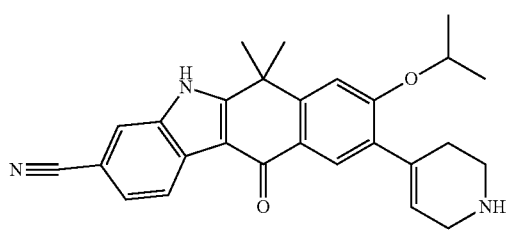 [SMILES: CC(C)Oc1cc2c(cc1C1=CCNCC1)C(=O)c1c([nH]c3cc(C#N)ccc13)C2(C)C]

Under the same conditions as the method for synthesizing Compound A8-1, the title compound was prepared from Compound E4-9-1.
LCMS: m/z 426 [M+H]$^+$
HPLC retention time: 1.40 min (analysis condition S)

Example 253

Compound E4-10

9-Cyclopropyl-8-methoxy-6,6-dimethyl-11-oxo-6,11-dihydro-5H-benzo[b]carbazole-3-carbonitrile

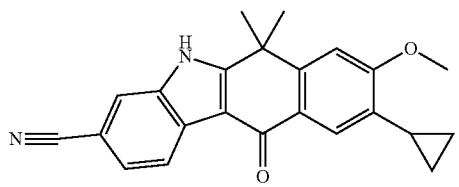 [SMILES: COc1cc2c(cc1C1CC1)C(=O)c1c([nH]c3cc(C#N)ccc13)C2(C)C]

Under the same conditions as the method for synthesizing Compound E4-7-1, the title compound was prepared from Compound E3-1-1 and potassium cyclopropyltrifluoroborate.
LCMS: m/z 357 [M+H]$^+$
HPLC retention time: 2.62 min (analysis condition S)

Example 254

Compound E4-11

3-Cyano-8-methoxy-6,6-dimethyl-11-oxo-6,11-dihydro-5H-benzo[b]carbazol-9-carboxylic acid

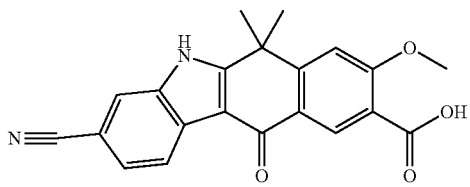 [SMILES: COc1cc2c(cc1C(=O)O)C(=O)c1c([nH]c3cc(C#N)ccc13)C2(C)C]

Under the same conditions as the method for synthesizing Compound B2-28, the title compound was prepared from Compound E3-1-1.

LCMS: m/z 361 [M+H]+
HPLC retention time: 1.68 min (analysis condition S)

Example 255

Compound E5-1

9-Ethyl-8-methoxy-6,6-dimethyl-11-oxo-6,11-di-
hydro-5H-benzo[b]carbazole-3-carbonitrile

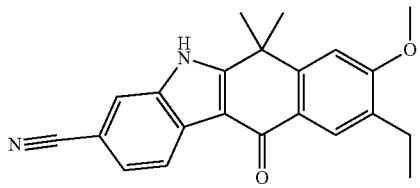 [SMILES: CCc1cc2c(cc1OC)C(C)(C)c1[nH]c3cc(C#N)ccc3c1C2=O]

The ethyl acetate suspension of 8-methoxy-6,6-dimethyl-11-oxo-9-vinyl-6,11-dihydro-5H-benzo[b]carbazole-3-carbonitrile (Compound E4-3, 25 mg, 0.07 mmol) and palladium carbon (25 mg) were stirred at room temperature for 1 hr under hydrogen atmosphere. The reaction solution was filtered through Celite. The filtrate was concentrated under reduced pressure and the resulting residues were purified by high performance liquid chromatography to obtain the title compound (white solid, 3.2 mg, 13%).
LCMS: m/z 345 [M+H]+
HPLC retention time: 2.62 min (analysis condition S)

Example 256

Compound E5-2

9-(2-Diethylamino-ethanesulfonyl)-8-methoxy-6,6-
dimethyl-11-oxo-6,11-dihydro-5H-benzo[b]carba-
zole-3-carbonitrile

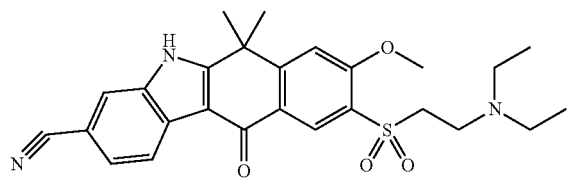 [SMILES: CCN(CC)CCS(=O)(=O)c1cc2c(cc1OC)C(C)(C)c1[nH]c3cc(C#N)ccc3c1C2=O]

Under the same conditions as the method for synthesizing Compound B3-8, the title compound was prepared from Compound E4-4.
LCMS: m/z 480 [M+H]+
HPLC retention time: 1.97 min (analysis condition U)

Example 257

Compound E5-3

8-Methoxy-6,6-dimethyl-11-oxo-9-(propane-2-sulfo-
nyl)-6,11-dihydro-5H-benzo[b]carbazole-3-carboni-
trile

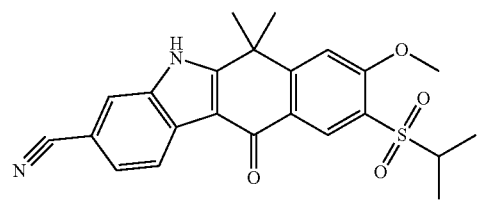 [SMILES: COc1cc2c(cc1S(=O)(=O)C(C)C)C(=O)c1c([nH]c3cc(C#N)ccc13)C2(C)C]

Under the same conditions as the method for synthesizing Compound B3-8, the title compound was prepared from Compound E4-5.
LCMS: m/z 423 [M+H]+
HPLC retention time: 2.40 min (analysis condition U)

Example 258

Compound E5-4

9-(1-Isopropyl-piperidin-4-yl)-8-methoxy-6,6-dim-
ethyl-11-oxo-6,11-dihydro-5H-benzo[b]carbazole-3-
carbonitrile

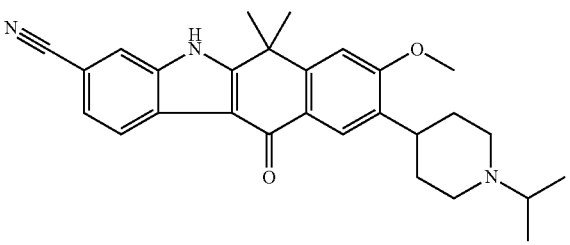 [SMILES: COc1cc2c(cc1C1CCN(C(C)C)CC1)C(=O)c1c([nH]c3cc(C#N)ccc13)C2(C)C]

Under the same conditions as the method for synthesizing Compound B3-32, the title compound was prepared from Compound E4-8-2 and acetone.
LCMS: m/z 442 [M+H]+
HPLC retention time: 1.48 min (analysis condition S)

Example 259

Compound E5-5

8-Methoxy-6,6-dimethyl-9-(1-oxetan-3-yl-1,2,3,6-
tetrahydro-pyridin-4-yl)-11-oxo-6,11-dihydro-5H-
benzo[b]carbazole-3-carbonitrile

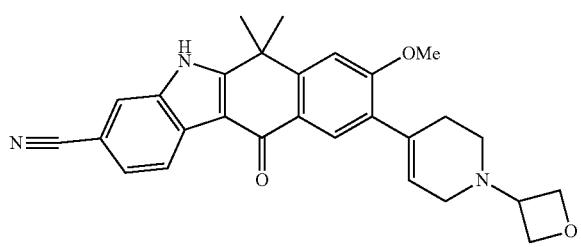 [SMILES: COc1cc2c(cc1C1=CCN(C3COC3)CC1)C(=O)c1c([nH]c3cc(C#N)ccc13)C2(C)C]

Under the same conditions as the method for synthesizing Compound B3-32, the title compound was prepared from Compound E4-7-2 and oxetan-3-one.
LCMS: m/z 454 [M+H]+
HPLC retention time: 1.32 min (analysis condition S)

Example 260

Compound E5-6

8-Isopropoxy-6,6-dimethyl-9-(1-oxetan-3-yl-1,2,3,6-tetrahydro-pyridin-4-yl)-11-oxo-6,11-dihydro-5H-benzo[b]carbazole-3-carbonitrile

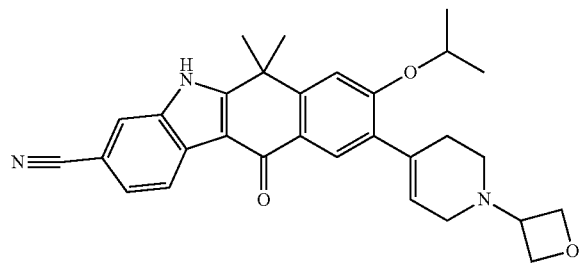 [SMILES: CC(C)Oc1cc2c(cc1C1=CCN(C3COC3)CC1)C(=O)c1c([nH]c3cc(C#N)ccc13)C2(C)C]

Under the same conditions as the method for synthesizing Compound B3-32, the title compound was prepared from Compound E4-9-2 and oxetan-3-one.

$^1$H-NMR (270 MHz, DMSO-d$_6$) δ: 12.71 (1H, s), 8.31 (1H, d, J=8.2 Hz), 7.99 (1H, s), 7.94 (1H, s), 7.58 (1H, d, J=7.6 Hz), 7.33 (1H, s), 5.84 (1. OH, m), 4.95 (1H, m), 4.56 (4H, dt, J=17.4, 6.3 Hz), 3.56 (1H, m), 3.01 (2H, br), 1.78 (6H, s), 1.34 (6H, d, J=5.9 Hz).

LCMS: m/z 482 [M+H]$^+$

HPLC retention time: 1.43 min (analysis condition S)

Example 261

Compound E5-7

9-(4-Isopropyl-piperazin-1-carbonyl)-8-methoxy-6,6-dimethyl-11-oxo-6,11-dihydro-5H-benzo[b]carbazole-3-carbonitrile

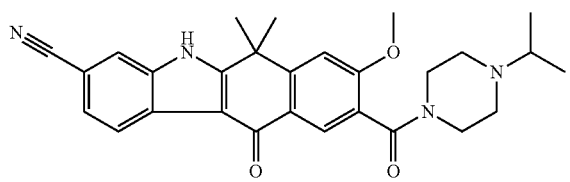 [SMILES: COc1cc2c(cc1C(=O)N1CCN(C(C)C)CC1)C(=O)c1c([nH]c3cc(C#N)ccc13)C2(C)C]

Under the same conditions as the method for synthesizing Compound B3-15, the title compound was prepared from Compound E4-11 and 1-isopropylpiperazine.

LCMS: m/z 471 [M+H]$^+$

HPLC retention time: 1.18 min (analysis condition S)

Example 262

Compound E5-8

8-Methoxy-6,6-dimethyl-9-(morpholine-4-carbonyl)-11-oxo-6,11-dihydro-5H-benzo[b]carbazole-3-carbonitrile

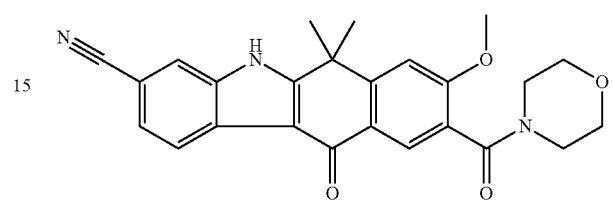

Under the same conditions as the method for synthesizing Compound B3-15, the title compound was prepared from Compound E4-11 and morpholine.

LCMS: m/z 430 [M+H]$^+$

HPLC retention time: 1.68 min (analysis condition S)

Example 263

Compound E6-1

(3-Cyano-8-methoxy-6,6-dimethyl-11-oxo-6,11-dihydro-5H-benzo[b]carbazol-9-yl)-propionic acid methyl ester

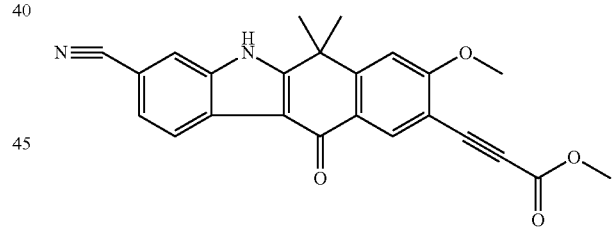

To the mixture of 9-ethynyl-8-methoxy-6,6-dimethyl-11-oxo-6,11-dihydro-5H-benzo[b]carbazole-3-carbonitrile (Compound E4-2, 27 mg, 0.079 mmol), palladium (II) chloride (2.0 mg, 0.14 eq.), copper (II) chloride (25.0 mg, 2.2 eq.), and sodium acetate (14.1 mg, 2.13 eq.), methanol (1.5 mL) was added, and then the mixture was stirred at room temperature for 2 days under carbon monoxide atmosphere. The mixture was extracted with water and ethyl acetate and the insoluble matters were filtered off. The organic layer was washed with brine and dried over magnesium sulfate. The residues obtained after filtration and concentration under reduced pressure were washed with dichloromethane to obtain the title compound (13.9 mg, 44%).

LCMS: m/z 399 [M+H]$^+$

HPLC retention time: 2.81 min (analysis condition F)

Example 264

Compound E6-2

(3-Cyano-8-methoxy-6,6-dimethyl-11-oxo-6,11-dihydro-5H-benzo[b]carbazol-9-yl)-propynoic acid

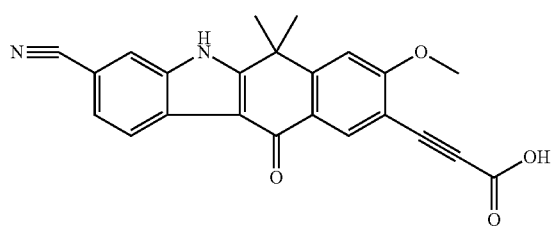 [SMILES: COc1cc2c(cc1C#CC(=O)O)C(=O)c1c([nH]c3cc(C#N)ccc13)C2(C)C]

(3-Cyano-8-methoxy-6,6-dimethyl-11-oxo-6,11-dihydro-5H-benzo[b]carbazol-9-yl)-propynoic acid methyl ester (Compound E6-1, 15.2 mg, 0.038 mmol) was dissolved in a mixture solvent of methanol (1.5 mL) and THF (0.5 mL), added with 2 N aqueous solution of potassium hydroxide (5 drops), and then stirred at room temperature overnight. 0.5 N Hydrochloric acid was added to the reaction solution, which was then extracted with ethyl acetate. The organic layer was washed with brine and dried over magnesium sulfate. The solids obtained after filtration and concentration under reduced pressure were washed with dichloromethane and purified by HPLC to obtain the title compound (white solid, 9.6 mg, 66%).

LCMS: m/z 385 [M+H]$^+$
HPLC retention time: 2.35 min (analysis condition F)

Example 265

Compound E6-3

9-(3-Hydroxy-3-methyl-butyl)-8-methoxy-6,6-dimethyl-11-oxo-6,11-dihydro-5H-benzo[b]carbazole-3-carbonitrile

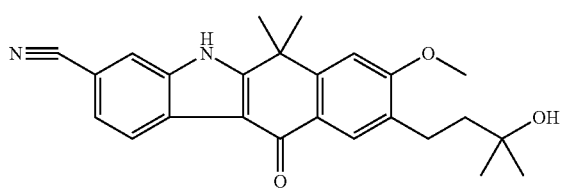 [SMILES: COc1cc2c(cc1CCC(C)(C)O)C(=O)c1c([nH]c3cc(C#N)ccc13)C2(C)C]

9-(3-Hydroxy-3-methyl-but-1-ynyl)-8-methoxy-6,6-dimethyl-11-oxo-6,11-dihydro-5H-benzo[b]carbazole-3-carbonitrile (Compound E4-2-1, 21.0 mg, 0.0527 mmol) was dissolved in ethanol (15 mL) and N,N-dimethylacetamide (2 mL), added with 10% Pd/C (6.7 mg), and then stirred at room temperature overnight under hydrogen atmosphere. The reaction solution was filtered and concentrated under reduced pressure. The resulting residues were diluted with ethyl acetate, washed with brine, dried over magnesium sulfate, filtered, and concentrated under reduced pressure. The resulting solid was washed with dichloromethane to obtain the title compound (yellow powder, 16.9 mg, 80%).

LCMS: m/z 403 [M+H]$^+$
HPLC retention time: 5.39 min (analysis condition H)

Example 266

Compound F1-1

4-(9-Bromo-3-cyano-6,6-dimethyl-11-oxo-6,11-dihydro-5H-benzo[b]carbazol-8-yl oxy)-piperidine-1-carboxylic acid tert-butyl ester

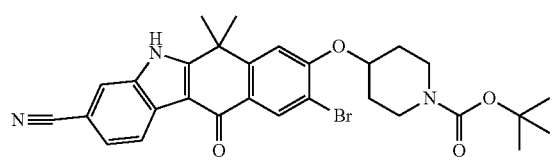 [SMILES: CC(C)(C)OC(=O)N1CCC(Oc2cc3c(cc2Br)C(=O)c2c([nH]c4cc(C#N)ccc24)C3(C)C)CC1]

According to the same method as the method for synthesizing Compound A7-17, the title compound was prepared from Compound E3-2 and 4-trifluoromethanesulfonyloxy-piperidine-1-carboxylic acid tert-butyl ester.

LCMS: m/z 564, 566 [M+H]$^+$
HPLC retention time: 3.30 min (analysis condition S)

Example 267

Compound F1-2

9-Bromo-6,6-dimethyl-11-oxo-8-(piperidin-4-yl oxy)-6,11-dihydro-5H-benzo[b]carbazole-3-carbonitrile

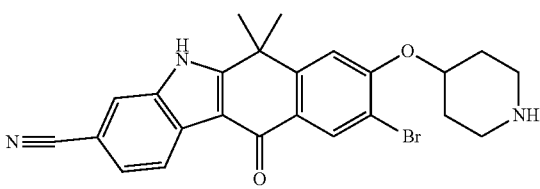 [SMILES: CC1(C)c2cc(OC3CCNCC3)c(Br)cc2C(=O)c2c1[nH]c1cc(C#N)ccc21]

Under the same conditions as the method for synthesizing Compound A8-1, the title compound was prepared from Compound F1-1.

LCMS: m/z 464, 466 [M+H]$^+$
HPLC retention time: 1.52 min (analysis condition S)

Example 268

Compound F1-3

9-Bromo-8-(1-methanesulfonyl-piperidin-4-yl oxy)-6,6-dimethyl-11-oxo-6,11-dihydro-5H-benzo[b]carbazole-3-carbonitrile

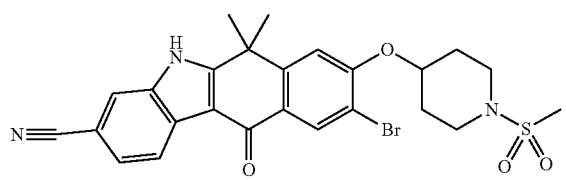 [SMILES: CC1(C)c2cc(OC3CCN(S(C)(=O)=O)CC3)c(Br)cc2C(=O)c2c1[nH]c1cc(C#N)ccc21]

Under the same conditions as the method for synthesizing Compound A9-1, the title compound was prepared from Compound F1-2 and methanesulfonyl chloride.

LCMS: m/z 542, 544 [M+H]+

HPLC retention time: 2.57 min (analysis condition S)

Example 269

Compound F1-4

9-Bromo-6,6-dimethyl-11-oxo-8-(tetrahydro-pyran-4-yl oxy)-6,11-dihydro-5H-benzo[b]carbazole-3-carbonitrile

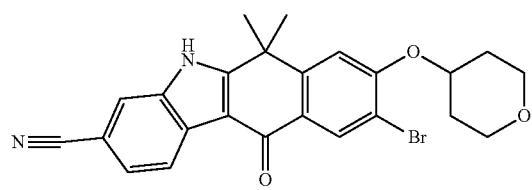 [SMILES: CC1(C)c2cc(OC3CCOCC3)c(Br)cc2C(=O)c2c1[nH]c1cc(C#N)ccc21]

Under the same conditions as the method for synthesizing Compound A7-1, the title compound was prepared from Compound E3-2 and tetrahydropyran-4-ol.

LCMS: m/z 465, 467 [M+H]+

HPLC retention time: 2.70 min (analysis condition S)

Example 270

Compound F2

Trifluoro-methanesulfonic acid 9-bromo-3-cyano-6,6-dimethyl-11-oxo-6,11-dihydro-5H-benzo[b]carbazol-8-yl ester

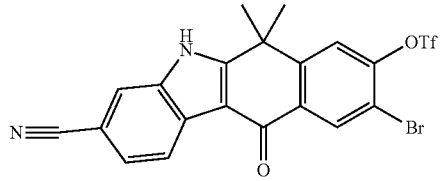 [SMILES: CC1(C)c2cc(OS(=O)(=O)C(F)(F)F)c(Br)cc2C(=O)c2c1[nH]c1cc(C#N)ccc21]

Under the same conditions as the method for synthesizing Compound B1, the title compound was prepared from Compound E3-2.

1H-NMR (270 MHz, DMSO-d6) δ: 12.99 (1H, s), 8.51 (1H, s), 8.31 (1H, dd, J=8.2, 0.7 Hz), 8.17 (1H, s), 8.07 (1H, s), 7.67 (1H, dd, J=8.2, 1.4 Hz), 1.81 (6H, s).

LCMS: m/z 513, 515 [M+H]+

HPLC retention time: 3.13 min (analysis condition S)

Example 271

Compound F3-1

9-Bromo-6,6-dimethyl-8-(1-oxetan-3-yl-piperidin-4-yloxy)-11-oxo-6,11-dihydro-5H-benzo[b]carbazole-3-carbonitrile

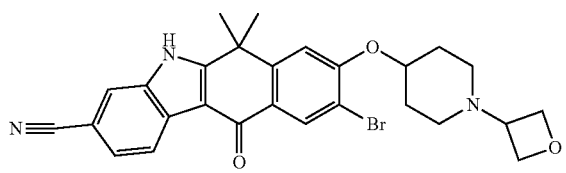 [SMILES: CC1(C)c2cc(OC3CCN(C4COC4)CC3)c(Br)cc2C(=O)c2c1[nH]c1cc(C#N)ccc21]

Under the same conditions as the method for synthesizing Compound B3-32, the title compound was prepared from Compound F1-2 and oxetan-3-one.

1H-NMR (400 MHz, DMSO-d6) δ: 8.29 (1H, d, 8 Hz), 8.29 (1H, s), 8.01 (1H, s), 7.60 (1H, d, 8 Hz), 7.55 (1H, s), 5.00-4.95 (1H, m), 4.55 (2H, dd, 8, 8 Hz), 4.44 (2H, dd, 8, 8 Hz), 2.52-2.46 (1H, m), 2.33-2.29 (2H, m), 1.96-1.94 (2H, m), 1.79 (8H, br. s)

LCMS: m/z 519, 521 [M+H]+

HPLC retention time: 2.78 min (analysis condition W)

Example 272

Compound F3-2

9-Bromo-6,6-dimethyl-11-oxo-8-(4-pyrrolidin-1-yl-piperidin-1-yl)-6,11-dihydro-5H-benzo[b]carbazole-3-carbonitrile

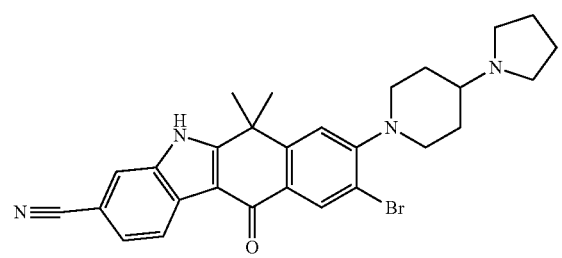 [SMILES: CC1(C)c2cc(N3CCC(N4CCCC4)CC3)c(Br)cc2C(=O)c2c1[nH]c1cc(C#N)ccc21]

Under the same conditions as the method for synthesizing Compound B2-1, the title compound was prepared from Compound F2 and 4-pyrrolidin-1-yl-piperidine.

LCMS: m/z 517, 519 [M+H]+

HPLC retention time: 1.70 min (analysis condition S)

Example 273

Compound F3-3

9-Bromo-8-(4-methanesulfonyl-piperazin-1-yl)-6,6-dimethyl-11-oxo-6,11-dihydro-5H-benzo[b]carbazole-3-carbonitrile

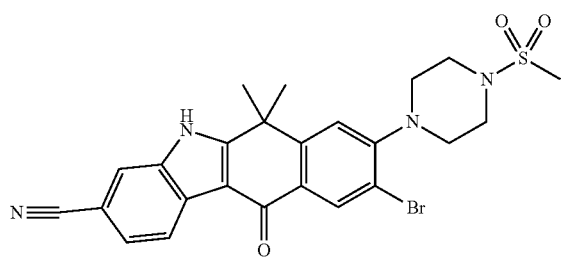 [SMILES: CC1(C)c2cc(N3CCN(S(C)(=O)=O)CC3)c(Br)cc2C(=O)c2c1[nH]c1cc(C#N)ccc21]

Under the same conditions as the method for synthesizing Compound B2-1, the title compound was prepared from Compound F2 and 1-methanesulfonylpiperazine.
LCMS: m/z 527, 529 [M+H]+
HPLC retention time: 2.48 min (analysis condition S)

Example 274

Compound F3-4

9-Bromo-6,6-dimethyl-8-morpholin-4-yl-11-oxo-6,11-dihydro-5H-benzo[b]carbazole-3-carbonitrile

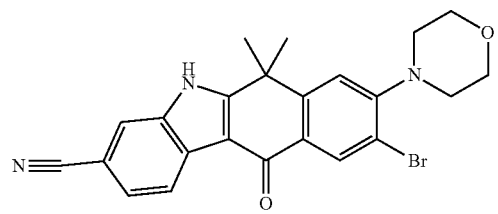 [SMILES: CC1(C)c2cc(N3CCOCC3)c(Br)cc2C(=O)c2c1[nH]c1cc(C#N)ccc21]

Under the same conditions as the method for synthesizing Compound B2-1, the title compound was prepared from Compound F2 and morpholine.
LCMS: m/z 450, 452 [M+H]+
HPLC retention time: 2.65 min (analysis condition S)

Example 275

Compound F3-5

9-Bromo-8-[4-(2-hydroxy-ethyl)-piperazin-1-yl]-6,6-dimethyl-11-oxo-6,11-dihydro-5H-benzo[b]carbazole-3-carbonitrile

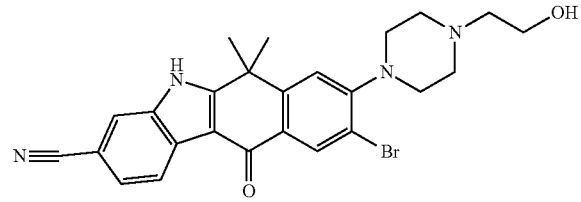 [SMILES: CC1(C)c2cc(N3CCN(CCO)CC3)c(Br)cc2C(=O)c2c1[nH]c1cc(C#N)ccc21]

Under the same conditions as the method for synthesizing Compound B2-1, the title compound was prepared from Compound F2 and 2-piperazin-1-yl ethanol.

$^{1}$H-NMR (270 MHz, DMSO-d$_6$) δ: 8.26 (2.0H, s+d), 7.97 (1H, s), 7.54 (1H, d, J=8.7 Hz), 7.43 (1H, s), 4.45 (1H, t, J=5.4 Hz), 3.55 (2H, q, J=5.8 Hz), 3.17 (4H, br), 2.66 (2H, br), 1.76 (6H, s).
LCMS: m/z 493, 495 [M+H]+
HPLC retention time: 1.43 min (analysis condition S)

Example 276

Compound F3-6-1

[1-(9-Bromo-3-cyano-6,6-dimethyl-11-oxo-6,11-dihydro-5H-benzo[b]carbazol-8-yl)-piperidin-4-yl]-carbamic acid tert-butyl ester

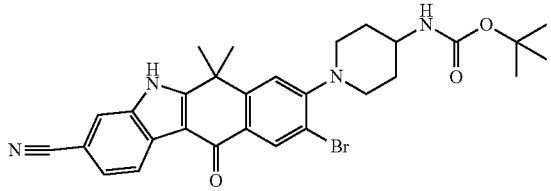 [SMILES: CC(C)(C)OC(=O)NC1CCN(c2cc3c(cc2Br)C(=O)c2c([nH]c4cc(C#N)ccc24)C3(C)C)CC1]

Under the same conditions as the method for synthesizing Compound B2-1, the title compound was prepared from Compound F2 and piperidin-4-yl-carbamic acid tert-butyl ester.
LCMS: m/z 563, 565 [M+H]+
HPLC retention time: 3.05 min (analysis condition S)

Example 277

Compound F3-6-2

8-(4-Amino-piperidin-1-yl)-9-bromo-6,6-dimethyl-11-oxo-6,11-dihydro-5H-benzo[b]carbazole-3-carbonitrile

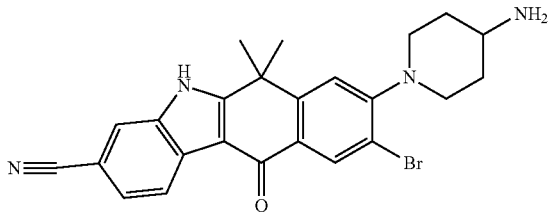 [SMILES: CC1(C)c2cc(N3CCC(N)CC3)c(Br)cc2C(=O)c2c1[nH]c1cc(C#N)ccc21]

Under the same conditions as the method for synthesizing Compound A8-1, the title compound was prepared from Compound F3-6-1.
LCMS: m/z 463, 465 [M+H]+
HPLC retention time: 1.47 min (analysis condition S)

Example 278

Compound F3-7

9-Bromo-8-(4-hydroxy-piperidin-1-yl)-6,6-dimethyl-11-oxo-6,11-dihydro-5H-benzo[b]carbazole-3-carbonitrile

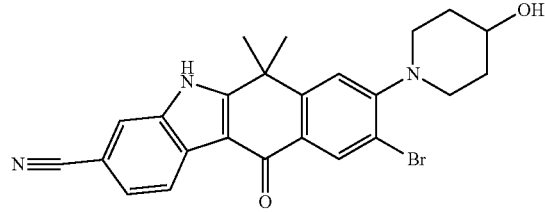 [SMILES: CC1(C)c2cc(N3CCC(O)CC3)c(Br)cc2C(=O)c2c1[nH]c1cc(C#N)ccc21]

Under the same conditions as the method for synthesizing Compound B2-1, the title compound was prepared from Compound F2 and piperidin-4-ol.

LCMS: m/z 464, 466 [M+H]+

HPLC retention time: 2.25 min (analysis condition S)

Example 279

Compound F3-8

9-Bromo-8-(4-isopropyl-piperazin-1-yl)-6,6-dimethyl-11-oxo-6,11-dihydro-5H-benzo[b]carbazole-3-carbonitrile

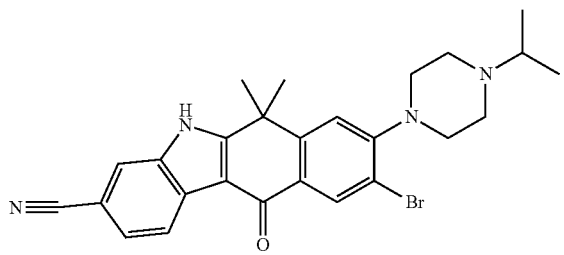 [SMILES: CC(C)N1CCN(c2cc3c(cc2Br)C(=O)c2c([nH]c4cc(C#N)ccc24)C3(C)C)CC1]

Under the same conditions as the method for synthesizing Compound B2-1, the title compound was prepared from Compound F2 and 1-isopropylpiperazine.

LCMS: m/z 491, 493 [M+H]+

HPLC retention time: 1.58 min (analysis condition S)

Example 280

Compound F3-9

9-Bromo-6,6-dimethyl-11-oxo-8-piperazin-1-yl-6,11-dihydro-5H-benzo[b]carbazole-3-carbonitrile

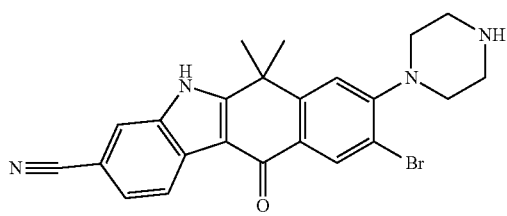 [SMILES: CC1(C)c2cc(N3CCNCC3)c(Br)cc2C(=O)c2c1[nH]c1cc(C#N)ccc21]

Under the same conditions as the method for synthesizing Compound B2-1, the title compound was prepared from Compound F2 and piperazine.

$^1$H-NMR (DMSO-$d_6$) δ: 8.30-8.24 (2H, m), 8.00 (1H, s), 7.63-7.58 (1H, m), 7.37 (1H, s), 3.10-3.01 (4H, m), 2.91-2.85 (4H, m), 1.76 (6H, s)

LCMS: m/z 449, 451 [M+H]+

HPLC retention time: 1.45 min (analysis condition S)

Example 281

Compound F3-10

4-(9-Bromo-3-cyano-6,6-dimethyl-11-oxo-6,11-dihydro-5H-benzo[b]carbazol-8-yl)-piperazine-1-carboxylic acid tert-butyl ester

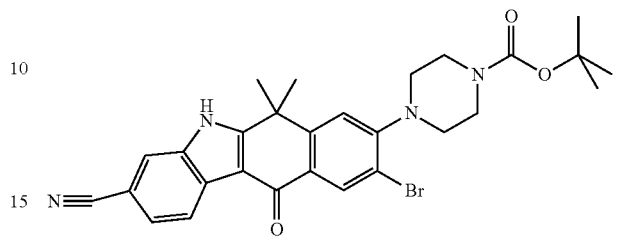

Under the same conditions as the method for synthesizing Compound B2-1, the title compound was prepared from Compound F2 and piperazine-1-carboxylic acid tert-butyl ester.

LCMS: m/z 549, 551 [M+H]+

HPLC retention time: 4.61 min (analysis condition W)

Example 282

Compound F3-11

9-Bromo-6,6-dimethyl-8-(4-morpholin-4-yl-piperidin-1-yl)-11-oxo-6,11-dihydro-5H-benzo[b]carbazole-3-carbonitrile

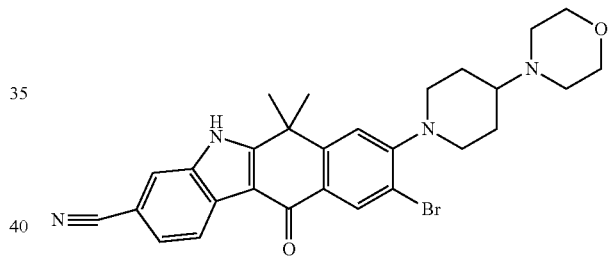

Under the same conditions as the method for synthesizing Compound B2-1, the title compound was prepared from Compound F2 and 4-piperidin-4-yl morpholine.

$^1$H-NMR (DMSO-$d_6$) δ: 8.30-8.24 (2H, m), 8.00 (1H, s), 7.59 (1H, d, J=8.2 Hz), 7.42 (1H, s), 3.66-3.45 (6H, m), 2.80 (2H, t, J=11.1 Hz), 2.38-2.28 (1H, m), 1.96-1.87 (2H, m), 1.75 (6H, s), 1.66-1.56 (2H, m)

LCMS: m/z 533, 535 [M+H]+

HPLC retention time: 1.53 min (analysis condition S)

Example 283

Compound F4-1-1

9-Ethynyl-6,6-dimethyl-8-(1-oxetan-3-yl-piperidin-4-yl oxy)-11-oxo-6,11-dihydro-5H-benzo[b]carbazole-3-carbonitrile

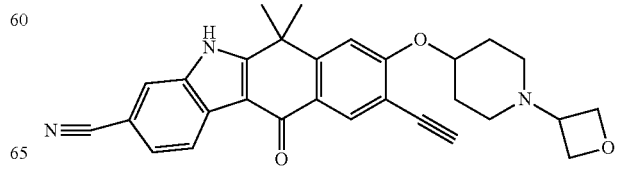

Under the same conditions as the method for synthesizing Compound F5-43, the title compound was prepared from Compound F3-1.

¹H-NMR (400 MHz, DMSO-d₆) δ: 8.30 (1H, d, 8 Hz), 8.17 (1H, s), 8.01 (1H, s), 7.60 (1H, d, 8 Hz), 7.50 (1H, s), 4.87-4.83 (1H, m), 4.55 (2H, dd, 4, 4 Hz), 4.45 (2H, dd, 4, 4 Hz), 3.44 (1H, ddd, 4, 4, 4 Hz), 2.33-2.24 (2H, m), 1.99-1.91 (2H, m), 1.78 (8H, br. s)

LCMS: m/z 466 [M+H]⁺

HPLC retention time: 2.67 min (analysis condition W)

Example 284

Compound F4-1-2

9-Ethyl-6,6-dimethyl-8-(1-oxetan-3-yl-piperidin-4-yl oxy)-11-oxo-6,11-dihydro-5H-benzo[b]carbazole-3-carbonitrile

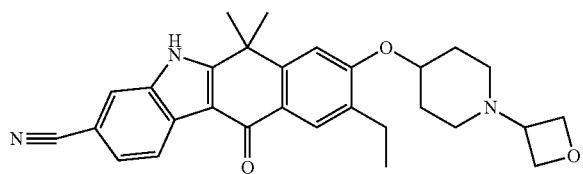 [SMILES: CCc1cc2c(cc1OC1CCN(C3COC3)CC1)C(C)(C)c1[nH]c3cc(C#N)ccc3c1C2=O]

Under the same conditions as the method for synthesizing Compound B3-13-1, the title compound was prepared from Compound F4-1-1.

LCMS: m/z 470 [M+H]⁺

HPLC retention time: 2.74 min (analysis condition W)

Example 285

Compound F4-2

N-[1-(9-Bromo-3-cyano-6,6-dimethyl-11-oxo-6,11-dihydro-5H-benzo[b]carbazol-8-yl)-piperidin-4-yl]-methanesulfonamide

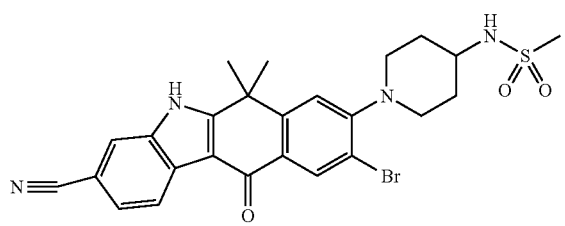 [SMILES: CC1(C)c2cc(N3CCC(NS(C)(=O)=O)CC3)c(Br)cc2C(=O)c2c1[nH]c1cc(C#N)ccc21]

Under the same conditions as the method for synthesizing Compound A9-1, the title compound was prepared from Compound F3-6-2 and methanesulfonyl chloride.

LCMS: m/z 541, 543 [M+H]⁺

HPLC retention time: 2.37 min (analysis condition S)

Example 286

Compound F4-3

9-Bromo-6,6-dimethyl-8-(4-oxetan-3-yl-piperazin-1-yl)-11-oxo-6,11-dihydro-5H-benzo[b]carbazole-3-carbonitrile

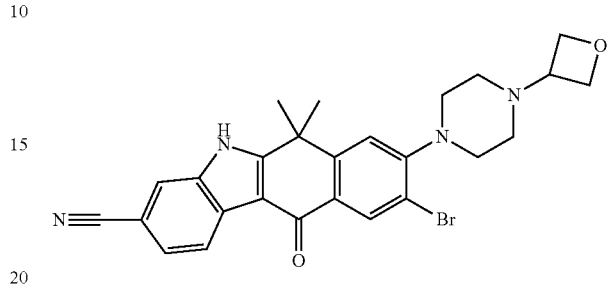

Under the same conditions as the method for synthesizing Compound B3-32, the title compound was prepared from Compound F3-9 and 1-oxetan-3-one.

¹H-NMR (270 MHz, DMSO-d₆) δ: 12.83 (1H, br. s), 8.31-8.32 (1H, m), 8.27-8.29 (1H, m), 8.01-8.04 (1H, m), 7.59-7.64 (1H, m), 7.48 (1H, s), 4.59 (2H, dd, J=6.3, 6.3 Hz), 4.48 (2H, dd, J=6.3, 6.3 Hz), 3.52 (1H, t, J=6.3 Hz), 3.12-3.25 (4H, m), 2.44-2.54 (4H, m), 1.78 (6H, s).

LCMS: m/z 505, 507 [M+H]⁺

HPLC retention time: 1.45 min (analysis condition S)

Hydrochloric Acid Salt of Compound F4-3

9-Bromo-6,6-dimethyl-8-(4-oxetan-3-yl-piperazin-1-yl)-11-oxo-6,11-dihydro-5H-benzo[b]carbazole-3-carbonitrile was added with DMSO and 6 N hydrochloric acid (1.05 eq.) and dissolved therein. After freeze-drying, crystallization was performed by using ethanol comprising 25% water to obtain monohydrochloric acid salt of 9-bromo-6,6-dimethyl-8-(4-oxetan-3-yl-piperazin-1-yl)-11-oxo-6,11-dihydro-5H-benzo[b]carbazole-3-carbonitrile.

¹H-NMR (270 MHz, DMSO-d₆) δ: 12.91 (1H, br.s), 11.70 (1H, br. s), 8.32-8.29 (2H, m), 8.04 (1H, s), 7.64-7.62 (1H, m), 7.52 (1H, s), 4.89-4.62 (4H, br. m), 3.66-3.39 (1H, m), 3.31-3.05 (8H, br. m), 1.81 (6H, s)

LCMS: m/z 505, 507 [M+H]⁺

Example 287

Compound F4-4

9-Bromo-8-{4-[2-(2-methoxy-ethoxy)-ethyl]-piperazin-1-yl}-6,6-dimethyl-11-oxo-6,11-dihydro-5H-benzo[b]carbazole-3-carbonitrile

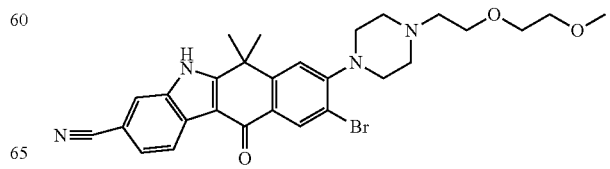

Under the same conditions as the method for synthesizing Compound A7-17, the title compound was prepared from Compound F3-9 and 1-bromo-2-(2-methoxyethoxyl)ethane.

LCMS: m/z 551, 553 [M+H]$^+$

HPLC retention time: 2.80 min (analysis condition W)

Example 288

Compound F4-5

9-Bromo-6,6-dimethyl-11-oxo-8-[4-(tetrahydro-pyran-4-yl)-piperazin-1-yl]-6,11-dihydro-5H-benzo[b]carbazole-3-carbonitrile

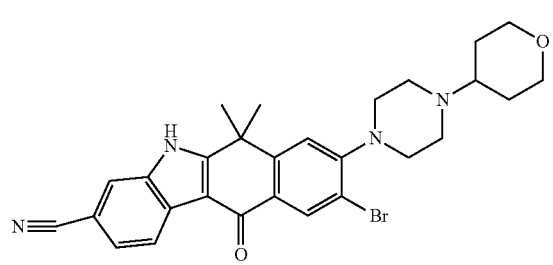

Under the same conditions as the method for synthesizing Compound B3-32, the title compound was prepared from Compound F3-9 and tetrahydropyran-4-one.

LCMS: m/z 533, 535 [M+H]$^+$

HPLC retention time: 2.67 min (analysis condition W)

Example 289

Compound F4-6

9-Bromo-6,6-dimethyl-11-oxo-8-[4-(tetrahydro-thio-pyran-4-yl)-piperazin-1-yl]-6,11-dihydro-5H-benzo[b]carbazole-3-carbonitrile

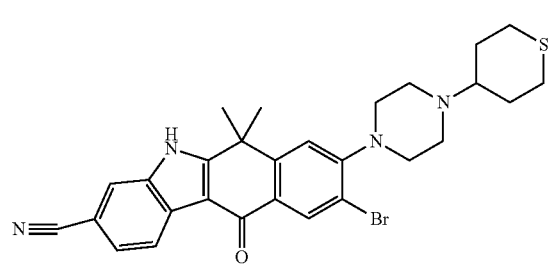 [SMILES: CC1(C)c2cc(N3CCN(C4CCOCC4)CC3)c(Br)cc2C(=O)c2c1[nH]c1cc(C#N)ccc21]

Under the same conditions as the method for synthesizing Compound B3-32, the title compound was prepared from Compound F3-9 and tetrahydrothiopyran-4-one.

LCMS: m/z 549, 551 [M+H]$^+$

HPLC retention time: 2.86 min (analysis condition W)

Example 290

Compound F4-7

9-Bromo-8-[4-(1,1-dioxo-hexahydro-16-thiopyran-4-yl)-piperazin-1-yl]-6,6-dimethyl-11-oxo-6,11-dihydro-5H-benzo[b]carbazole-3-carbonitrile

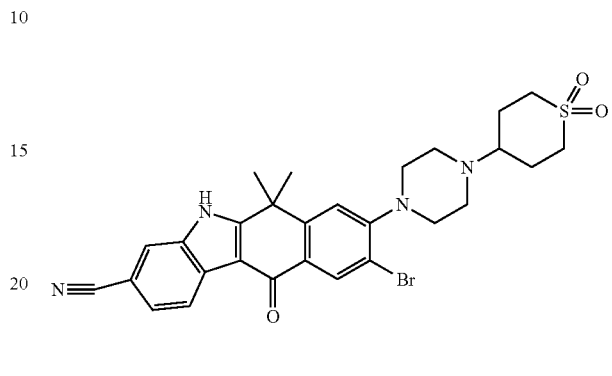

Under the same conditions as the method for synthesizing Compound B3-8, the title compound was prepared from Compound F4-6.

LCMS: m/z 581, 583 [M+H]$^+$

HPLC retention time: 2.66 min (analysis condition W)

Example 291

Compound F4-8

9-Bromo-8-(4-cyclopropylmethyl-piperazin-1-yl)-6,6-dimethyl-11-oxo-6,11-dihydro-5H-benzo[b]carbazole-3-carbonitrile

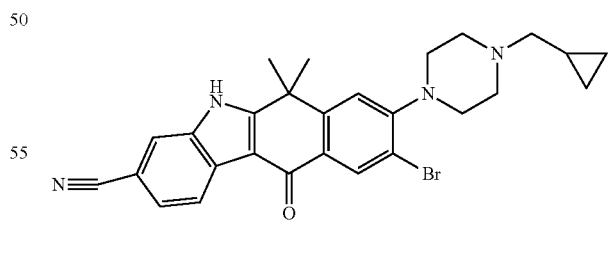

Under the same conditions as the method for synthesizing Compound A7-17, the title compound was prepared from Compound F3-9 and bromomethylcyclopropane.

LCMS: m/z 503, 505 [M+H]$^+$

HPLC retention time: 2.81 min (analysis condition W)

Example 292

Compound F4-9

9-Bromo-8-(4-cyclopropyl-piperazin-1-yl)-6,6-dimethyl-11-oxo-6,11-dihydro-5H-benzo[b]carbazole-3-carbonitrile

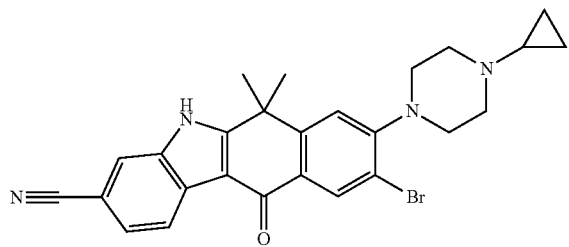 [SMILES: CC1(C)c2cc(N3CCN(C4CC4)CC3)c(Br)cc2C(=O)c2c1[nH]c1cc(C#N)ccc21]

Under the same conditions as the method for synthesizing Compound B3-32, the title compound was prepared from Compound F3-9 and (1-ethoxy-cyclopropoxy)-trimethyl-silane.

$^1$H-NMR (270 MHz, DMSO-$d_6$) δ: 8.22-8.30 (2H, m), 8.00 (1H, s), 7.56 (1H, d, J=7.9 Hz), 7.43 (1H, s), 3.30 (1H, d, J=5.8 Hz), 3.11 (4H, s), 2.75 (4H, s), 1.75 (6H, s), 0.47 (2H, d, J=5.8 Hz), 0.34 (2H, d, J=5.8 Hz)

LCMS: m/z 489, 491 [M+H]$^+$

HPLC retention time: 1.68 min (analysis condition S)

Example 293

Compound F4-10

9-Bromo-8-(4-cyclobutyl-piperazin-1-yl)-6,6-dimethyl-11-oxo-6,11-dihydro-5H-benzo[b]carbazole-3-carbonitrile

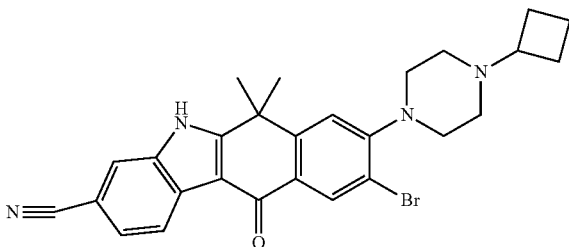

Under the same conditions as the method for synthesizing Compound B3-32, the title compound was prepared from Compound F3-9 and cyclobutanone.

$^1$H-NMR (400 MHz, DMSO-$d_6$) δ: 8.23-8.29 (2H, m), 8.00 (1H, s), 7.55 (1H, d, 7.9 Hz), 7.45 (1H, s), 4.04-4.15 (1H, m), 3.10-3.20 (4H, m), 2.39-2.48 (4H, m), 1.97-2.06 (2H, m), 1.78-1.88 (2H, m), 1.77 (6H, s), 1.61-1.72 (2H, m)

LCMS: m/z 503, 505 [M+H]$^+$

HPLC retention time: 2.78 min (analysis condition W)

Example 294

Compound F5-1

9-Ethynyl-8-(4-methanesulfonyl-piperazin-1-yl)-6,6-dimethyl-11-oxo-6,11-dihydro-5H-benzo[b]carbazole-3-carbonitrile

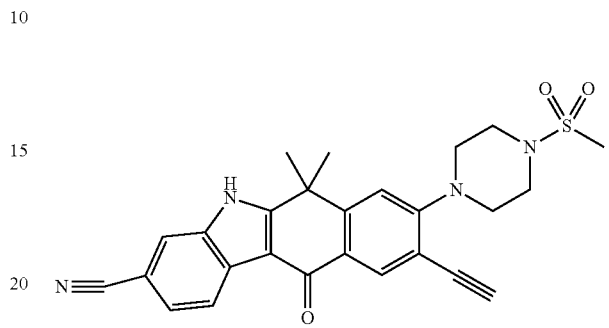

Under the same conditions as the method for synthesizing Compound F5-43, the title compound was prepared from Compound F3-3.

$^1$H-NMR (270 MHz, DMSO-$d_6$) δ: 12.78 (1H, s), 8.31 (1H, dd, J=8.1, 0.7 Hz), 8.19 (1H, s), 8.02 (1H, dd, J=1.4, 0.7 Hz), 7.61 (1H, dd, J=8.2, 1.4 Hz), 7.33 (1H, s), 4.55 (1H, s), 3.43 (4H, br), 2.98 (3H, s), 1.79 (6H, s).

LCMS: m/z 473 [M+H]$^+$

HPLC retention time: 2.27 min (analysis condition S)

Example 295

Compound F5-2

N-[1-(3-Cyano-9-ethynyl-6,6-dimethyl-11-oxo-6,11-dihydro-5H-benzo[b]carbazol-8-yl)-piperidin-4-yl]-methanesulfonamide

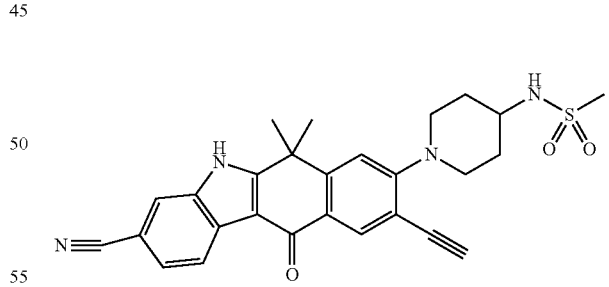

Under the same conditions as the method for synthesizing Compound F5-43, the title compound was prepared from Compound F4-2.

$^1$H-NMR (270 MHz, DMSO-$d_6$) δ: 12.98 (1H, s), 8.30 (1H, d, J=8.1 Hz), 8.15 (1H, s), 8.02 (1H, s), 7.61 (1H, d, J=7.9 Hz), 7.23 (2H, s+d), 4.55 (1H, s), 3.79 (2H, brd), 2.95 (4H, br), 1.96 (2H, brd), 1.78 (3H, s), 1.65 (2H, brd).

LCMS: m/z 487 [M+H]$^+$

HPLC retention time: 2.15 min (analysis condition S)

Example 296

Compound F5-3

6,6-Dimethyl-11-oxo-8-(4-pyrrolidin-1-yl-piperidin-1-yl)-6,11-dihydro-5H-benzo[b]carbazole-3,9-dicarbonitrile

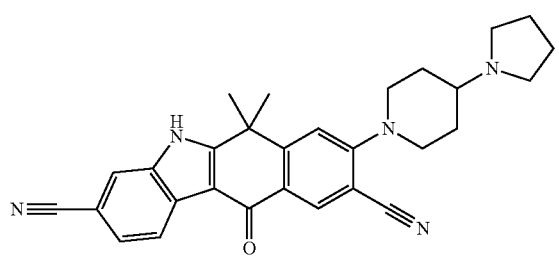 [SMILES: CC1(C)c2cc(N3CCC(N4CCCC4)CC3)c(C#N)cc2C(=O)c2c1[nH]c1cc(C#N)ccc21]

Under the same conditions as the method for synthesizing Compound A5-2, the target compound was prepared from Compound F3-2.

$^1$H-NMR (270 MHz, DMSO-$d_6$) δ: 8.33 (1H, d, J=1.3 Hz), 8.27 (1H, dd, J=7.7, 1.3 Hz), 8.00 (1H, s), 7.57 (1H, d, J=7.7 Hz), 7.40 (1H, s), 3.74 (2H, m), 3.19-3.33 (1H, m), 2.98-3.12 (2H, m), 2.35-2.62 (2H, m), 2.11-2.29 (2H, m), 1.89-2.06 (2H, m), 1.78 (6H, s), 1.54-1.70 (6H, m).

LCMS: m/z 464 [M+H]$^+$

HPLC retention time: 1.55 min (analysis condition S)

Example 297

Compound F5-4

9-Ethynyl-6,6-dimethyl-11-oxo-8-(4-pyrrolidin-1-yl-piperidin-1-yl)-6,11-dihydro-5H-benzo[b]carbazole-3-carbonitrile

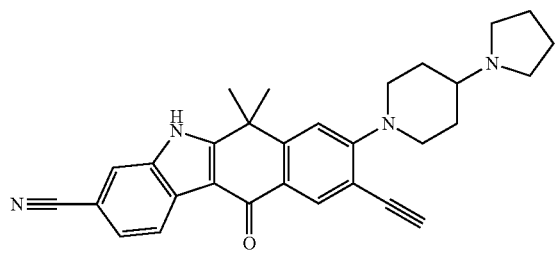 [SMILES: C#Cc1cc2c(cc1N1CCC(N3CCCC3)CC1)C(C)(C)c1[nH]c3cc(C#N)ccc3c1C2=O]

Under the same conditions as the method for synthesizing Compound E4-2-1 and Compound E4-2-2, the title compound was prepared from Compound F3-2.

$^1$H-NMR (270 MHz, DMSO-$d_6$) δ: 8.29 (1H, d, J=8.2 Hz), 8.14 (1H, s), 8.00 (1H, s), 7.58 (1H, dd, J=8.1, 1.3 Hz), 7.24 (1H, s), 4.50 (1H, s), 3.70-3.83 (2H, m), 3.34-3.48 (1H, m), 2.83-2.98 (2H, m), 2.45-2.58 (2H, m), 2.10-2.23 (2H, m), 1.90-2.03 (2H, m), 1.76 (6H, s), 1.51-1.74 (6H, m).

LCMS: m/z 463 [M+H]$^+$

HPLC retention time: 1.60 min (analysis condition S)

Example 298

Compound F5-5

9-Ethynyl-6,6-dimethyl-8-morpholin-4-yl-11-oxo-6,11-dihydro-5H-benzo[b]carbazole-3-carbonitrile

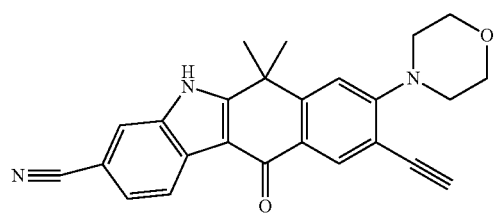 [SMILES: C#Cc1cc2c(cc1N1CCOCC1)C(C)(C)c1[nH]c3cc(C#N)ccc3c1C2=O]

Under the same conditions as the method for synthesizing Compound E4-2-1 and Compound E4-2-2, the title compound was prepared from Compound F3-4.

$^1$H-NMR (400 MHz, DMSO-$d_6$) δ: 12.82 (1H, s), 8.31 (1H, d, J=7.9 Hz), 8.18 (1H, s), 8.02 (1H, s), 7.61 (1H, d, J=7.9 Hz), 7.28 (1H, s), 4.53 (1H, s), 3.80 (4H, s), 3.36 (4H, s), 1.79 (6H, s).

LCMS: m/z 396 [M+H]$^+$

HPLC retention time: 2.32 min (analysis condition S)

Example 299

Compound F5-6

9-(3-Dimethylamino-prop-1-ynyl)-6,6-dimethyl-8-morpholin-4-yl-11-oxo-6,11-dihydro-5H-benzo[b]carbazole-3-carbonitrile

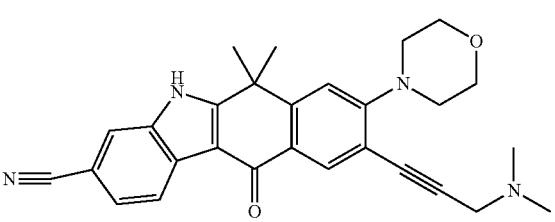 [SMILES: CN(C)CC#Cc1cc2c(cc1N1CCOCC1)C(C)(C)c1[nH]c3cc(C#N)ccc3c1C2=O]

Under the same conditions as the method for synthesizing Compound E4-2-1, the title compound was prepared from Compound F3-4 and 3-dimethylaminopropyne.

$^1$H-NMR (270 MHz, CDCl$_3$) δ: 8.52 (1H, d, J=7.8 Hz), 8.47 (1H, s), 7.76 (1H, s), 7.56 (1H, d, J=7.8 Hz), 7.03 (1H, s), 3.92 (4H, m), 3.55 (2H, s), 3.39 (4H, m), 2.37 (6H, s), 1.83 (6H, s)

LCMS: m/z 453 [M+H]$^+$

Example 300

Compound F5-7

6,6-Dimethyl-8-morpholin-4-yl-9-(3-morpholin-4-yl-prop-1-ynyl)-11-oxo-6,11-dihydro-5H-benzo[b]carbazole-3-carbonitrile

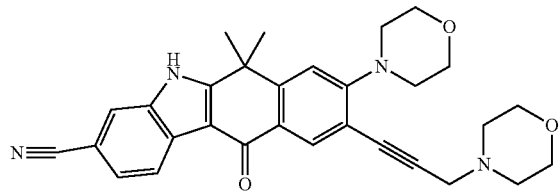 [SMILES: CC1(C)c2cc(N3CCOCC3)c(C#CCN3CCOCC3)cc2C(=O)c2c1[nH]c1cc(C#N)ccc21]

To 9-bromo-6,6-dimethyl-8-morpholin-4-yl-11-oxo-6,11-dihydro-5H-benzo[b]carbazole-3-carbonitrile (Compound F3-4, 30 mg, 0.067 mmol), 3-bromopropyne (0.01 ml, 0.13 mmol), morpholine (0.029 ml, 0.33 mmol), X-Phos (4.8 mg, 15% mol), $PdCl_2$ $(CH_3CN)_2$ (0.9 mg, 5% mol) and cesium carbonate (87 mg, 0.27 mmol), acetonitrile (2 ml) was added and the mixture was stirred at 80° C. for 2 hr. The reaction solution was added to water, and then extracted with dichloromethane. The organic layer was dried over sodium sulfate. The drying agent was removed by filtration and the residues obtained after concentration under reduced pressure were purified by silica gel column chromatography (dichloromethane/methanol) to obtain the target compound (pale brown solid, 18 mg, 64%).

$^1$H-NMR (270 MHz, DMSO-$d_6$) δ: 8.29 (1H, d, J=7.8 Hz), 8.14 (1H, s), 8.00 (1H, s), 7.59 (1H, d, J=7.8 Hz), 7.27 (1H, s), 3.79 (4H, m), 3.64 (4H, m), 3.61 (2H, s), 3.33 (4H, m), 2.56 (4H, m), 1.77 (6H, s)

LCMS: m/z 495 [M+H]$^+$

Example 301

Compound F5-8

6,6-Dimethyl-8-morpholin-4-yl-11-oxo-9-pent-1-ynyl-6,11-dihydro-5H-benzo[b]carbazole-3-carbonitrile

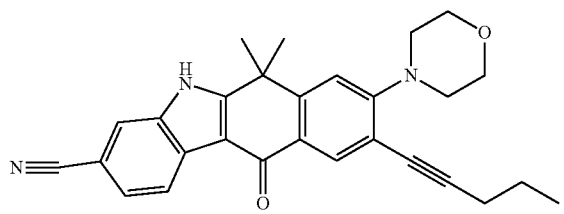 [SMILES: CCCC#Cc1cc2c(cc1N1CCOCC1)C(C)(C)c1[nH]c3cc(C#N)ccc3c1C2=O]

Under the same conditions as the method for synthesizing Compound E4-2-1, the title compound was prepared from Compound F3-4 and 1-pentyne.

LCMS: m/z 438 [M+H]$^+$

HPLC retention time: 2.88 min (analysis condition S)

Example 302

Compound F5-9

9-(3-Methoxy-prop-1-ynyl)-6,6-dimethyl-8-morpholin-4-yl-11-oxo-6,11-dihydro-5H-benzo[b]carbazole-3-carbonitrile

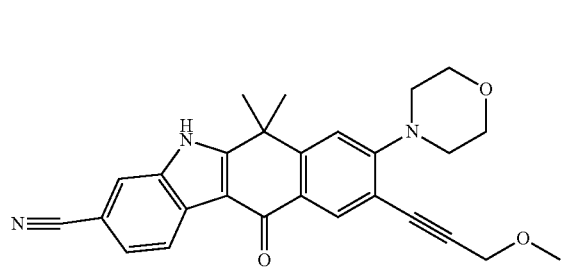 [SMILES: COCC#Cc1cc2c(cc1N1CCOCC1)C(C)(C)c1[nH]c3cc(C#N)ccc3c1C2=O]

Under the same conditions as the method for synthesizing Compound E4-2-1, the title compound was prepared from Compound F3-4 and 3-methoxypropyne.

$^1$H-NMR (270 MHz, DMSO-$d_6$) δ: 8.30 (1H, d, J=7.8 Hz), 8.15 (1H, s), 8.01 (1H, s), 7.60 (1H, d, J=7.8 Hz), 7.28 (1H, s), 4.41 (2H, s), 3.79 (4H, m), 3.37 (3H, s), 3.34 (4H, m), 1.78 (6H, s)

LCMS: m/z 440 [M+H]$^+$

Example 303

Compound F5-10

9-[3-(4-Cyclopropyl-piperazin-1-yl)-prop-1-ynyl]-6,6-dimethyl-8-morpholin-4-yl-11-oxo-6,11-dihydro-5H-benzo[b]carbazole-3-carbonitrile

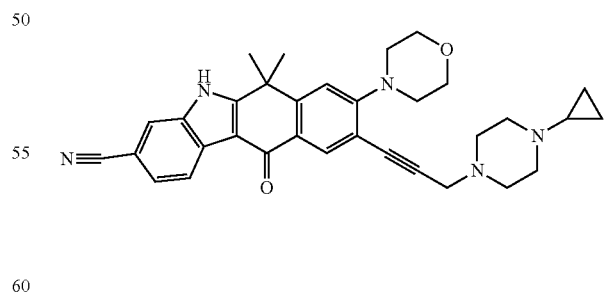

Under the same conditions as the method for synthesizing Compound F5-7, the title compound was prepared from Compound F3-4 and 3-bromopropyne and 4-cyclopropylpiperazine.

LCMS: m/z 534 [M+H]$^+$

HPLC retention time: 1.40 min (analysis condition S)

Example 304

Compound F5-11

6,6-Dimethyl-9-(1-methyl-1H-pyrazol-4-yl)-8-morpholin-4-yl-11-oxo-6,11-dihydro-5H-benzo[b]carbazole-3-carbonitrile

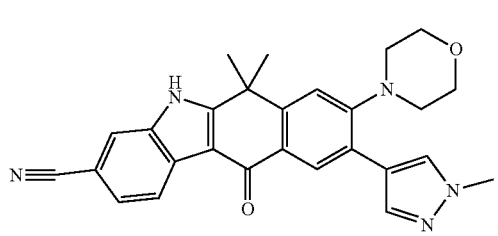 [SMILES: Cn1cc(-c2cc3c(cc2N2CCOCC2)C(C)(C)c2[nH]c4cc(C#N)ccc4c2C3=O)cn1]

Under the same conditions as the method for synthesizing Compound E4-7-1, the title compound was prepared from Compound F3-4 and 1-methyl-4-(4,4,5,5-tetramethyl-1,3,2-dioxaborolan-2-yl)-1H-pyrazole.

$^1$H-NMR (400 MHz, DMSO-$d_6$) δ: 8.29 (1H, d, J=7.8 Hz), 8.22 (1H, s), 8.09 (1H, s), 7.99 (1H, s), 7.95 (1H, s), 7.56-7.61 (1H, m), 7.36 (1H, s), 3.90 (3H, s), 3.73 (4H, s), 2.95 (4H, s), 1.77 (6H, s).

LCMS: m/z 452 [M+H]$^+$

HPLC retention time: 2.18 min (analysis condition U)

Example 305

Compound F5-12

9-Cyclopropyl-6,6-dimethyl-8-morpholin-4-yl-11-oxo-6,11-dihydro-5H-benzo[b]carbazole-3-carbonitrile

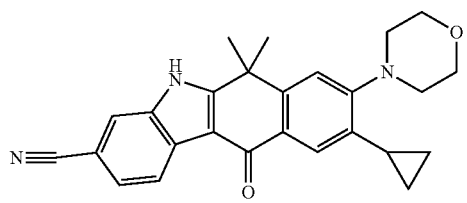 [SMILES: CC1(C)c2cc(N3CCOCC3)c(C3CC3)cc2C(=O)c2c1[nH]c1cc(C#N)ccc21]

Under the same conditions as the method for synthesizing Compound E4-7-1, the title compound was prepared from Compound F3-4 and potassium cyclopropyltrifluoroborate.

$^1$H-NMR (270 MHz, CD$_3$OD+CDCl$_3$) δ: 8.45 (1H, d, J=7.8 Hz), 7.83 (2H, m), 7.54 (1H, d, J=7.8 Hz), 7.20 (1H, s), 3.96 (4H, m), 3.24 (4H, m), 2.25 (1H, m), 1.80 (6H, s), 1.09 (2H, m), 0.93 (2H, m)

LCMS: m/z 412 [M+H]$^+$

Example 306

Compound F5-13

6,6-Dimethyl-8-morpholin-4-yl-11-oxo-9-vinyl-6,11-dihydro-5H-benzo[b]carbazole-3-carbonitrile

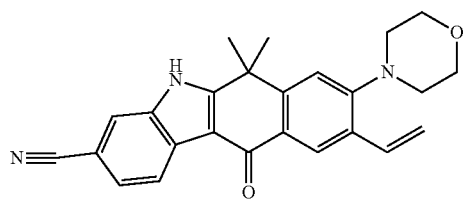 [SMILES: C=Cc1cc2c(cc1N1CCOCC1)C(C)(C)c1[nH]c3cc(C#N)ccc3c1C2=O]

Under the same conditions as the method for synthesizing Compound B2-24, the title compound was prepared from Compound F3-4 and potassium vinyltrifluoroborate.

LCMS: m/z 398 [M+H]$^+$

HPLC retention time: 2.67 min (analysis condition U)

Example 307

Compound F5-14

9-Ethynyl-8-(4-isopropyl-piperazin-1-yl)-6,6-dimethyl-11-oxo-6,11-dihydro-5H-benzo[b]carbazole-3-carbonitrile

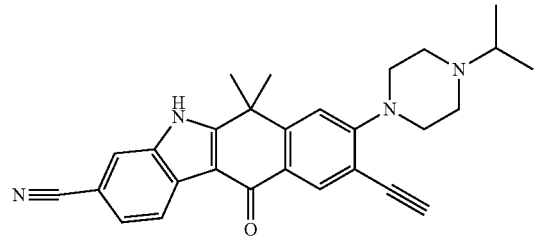 [SMILES: C#Cc1cc2c(cc1N1CCN(C(C)C)CC1)C(C)(C)c1[nH]c3cc(C#N)ccc3c1C2=O]

Under the same conditions as the method for synthesizing Compound F5-43, the title compound was prepared from Compound F3-8.

$^1$H-NMR (400 MHz, DMSO-$d_6$) δ: 12.73 (1H, s), 8.31 (1H, d, J=9.1 Hz), 8.16 (1H, d, J=1.2 Hz), 8.00 (1H, s), 7.60 (1H, d, J=7.9 Hz), 7.25 (1H, s), 4.50 (1H, d, J=1.8 Hz), 2.72 (1H, m), 2.65 (4H, s), 1.78 (6H, s), 1.04 (6H, d, J=5.5 Hz).

LCMS: m/z 437 [M+H]$^+$

HPLC retention time: 1.48 min (analysis condition S)

Example 308

Compound F5-15-1

4-(3-Cyano-9-cyclopropyl-6,6-dimethyl-11-oxo-6,11-dihydro-5H-benzo[b]carbazol-8-yl)-piperazine-1-carboxylic acid tert-butyl ester

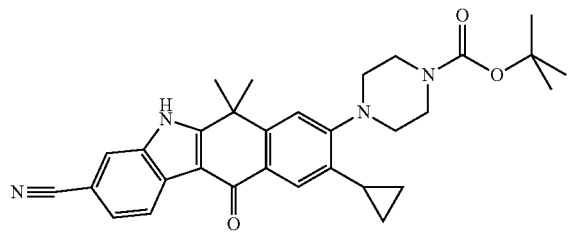 [SMILES: CC(C)(C)OC(=O)N1CCN(c2cc3c(cc2C2CC2)C(=O)c2c([nH]c4cc(C#N)ccc24)C3(C)C)CC1]

Under the same conditions as the method for synthesizing Compound E4-7-1, the title compound was prepared from Compound F3-10 and potassium cyclopropyltrifluoroborate.

$^1$H-NMR (400 MHz, DMSO-d$_6$) δ: 8.55 (1H, s), 8.28-8.25 (1H, m), 7.98-7.95 (1H, m), 7.62 (1H, s), 7.32 (1H, s), 3.56-3.53 (4 h, m), 3.09-3.07 (4H, m), 2.22-2.18 (1H, m), 1.73 (6H, br s), 1.44 (9H, s), 1.08-1.05 (2H, m), 0.77-0.76 (2H, m)

LCMS: m/z 511 [M+H]$^+$

HPLC retention time: 4.50 min (analysis condition W)

Example 309

Compound F5-15-2

9-Cyclopropyl-6,6-dimethyl-11-oxo-8-piperazin-1-yl-6,11-dihydro-5H-benzo[b]carbazole-3-carbonitrile

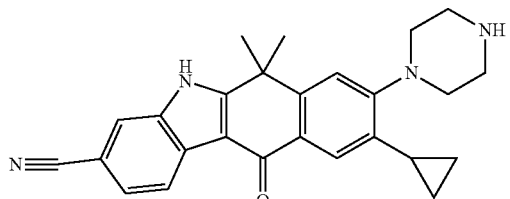

Under the same conditions as the method for synthesizing Compound A8-1, the title compound was prepared from Compound F5-15-1.

LCMS: m/z 411 [M+H]$^+$

HPLC retention time: 2.67 min (analysis condition W)

Example 310

Compound F5-16

9-Ethynyl-6,6-dimethyl-8-(4-oxetan-3-yl-piperazin-1-yl)-11-oxo-6,11-dihydro-5H-benzo[b]carbazole-3-carbonitrile

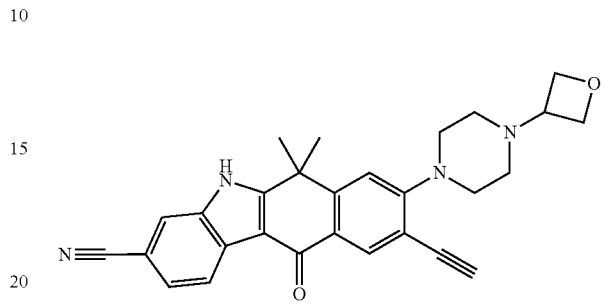

Under the same conditions as the method for synthesizing Compound F5-43, the title compound was prepared from Compound F4-3.

$^1$H-NMR (270 MHz, DMSO-d$_6$) δ: 12.77 (1H, br. s), 8.31 (1H, d, J=8.2 Hz), 8.16 (1H, s), 8.02 (1H, s), 7.61 (1H, dd, J=8.2, 1.3 Hz), 7.27 (1H, s), 4.59 (2H, dd, J=6.6, 6.6 Hz), 4.51 (1H, s), 4.49 (2H, dd, J=6.6, 6.6 Hz), 3.51 (1H, t, J=6.6 Hz), 3.35-3.43 (4H, m), 2.43-2.50 (4H, s), 1.78 (6H, s).

LCMS: m/z 451 [M+H]$^+$

HPLC retention time: 1.40 min (analysis condition S)

Example 311

Compound F5-17

6,6-Dimethyl-8-(4-oxetan-3-yl-piperazin-1-yl)-11-oxo-6,11-dihydro-5H-benzo[b]carbazole-3,9-dicarbonitrile

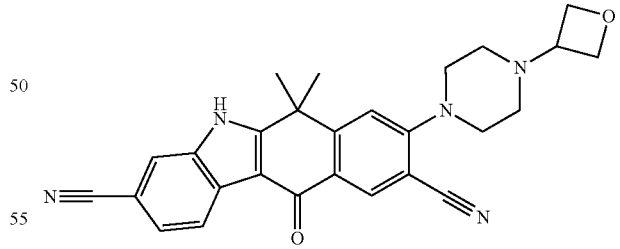

According to the same method as the method for synthesizing Compound A5-2, the title compound was prepared from Compound F4-3.

$^1$H-NMR (270 MHz, DMSO-d$_6$) δ: 12.84 (1H, br. s), 8.36 (1H, s), 8.32-8.29 (1H, d, 8.08 Hz), 8.04 (1H, s), 7.65-7.62 (1H, d, 8.08 Hz), 7.44 (1H, s), 4.62-4.57 (2H, m), 4.52-4.47 (2H, m), 3.81-3.78 (2H, t, 4.61 Hz), 3.57-3.50 (1H, m), 3.43 (4H, m) 2.51 (4H, m), 1.80 (6H, s)

LCMS: m/z 452 [M+H]$^+$

Example 312

Compound F5-18

9-(3-Methoxy-prop-1-ynyl)-6,6-dimethyl-8-(4-oxetan-3-yl-piperazin-1-yl)-11-oxo-6,11-dihydro-5H-benzo[b]carbazole-3-carbonitrile

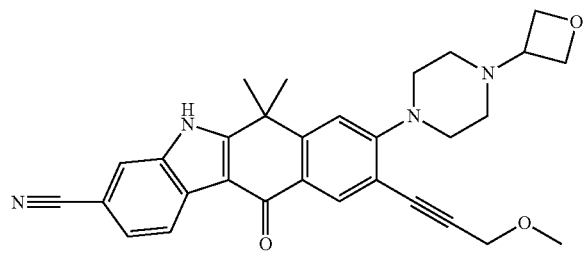 [SMILES: COCC#Cc1cc2c(cc1N1CCN(C3COC3)CC1)C(C)(C)c1[nH]c3cc(C#N)ccc3c1C2=O]

Under the same conditions as the method for synthesizing Compound E4-2-1, the title compound was prepared from Compound F4-3 and 3-methoxypropyne.

$^1$H-NMR (270 MHz, DMSO-$d_6$) δ: 12.77 (1H, br. s), 8.32-8.29 (1H, d, 8.08 Hz), 8.13 (1H, s), 8.01 (1H, s), 7.62-7.59 (1H, d, 8.08 Hz), 7.27 (1H, s), 4.62-4.57 (2H, m), 4.52-4.47 (2H, m), 4.39 (2H, s), 3.53-3.47 (1H, m), 3.38 (4H, m), 3.36 (3H, s), 2.51 (4H, m), 1.77 (6H, s)

LCMS: m/z 495 [M+H]$^+$

Example 314

Compound F5-20

6,6-Dimethyl-8-(4-oxetan-3-yl-piperazin-1-yl)-9-[3-(4-oxetan-3-yl-piperazin-1-yl)-prop-1-ynyl]-11-oxo-6,11-dihydro-5H-benzo[b]carbazole-3-carbonitrile

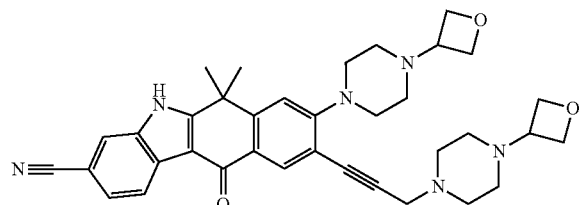

Under the same conditions as the method for synthesizing Compound F5-7, the title compound was prepared from Compound F4-3, 3-bromopropyne and 4-oxetan-3-yl-piperazine.

$^1$H-NMR (270 MHz, DMSO-$d_6$) δ: 8.30 (1H, d, J=7.8 Hz), 8.12 (1H, s), 8.00 (1H, s), 7.59 (1H, d, J=7.8 Hz), 7.26 (1H, s), 4.60-4.42 (8H, m), 3.61 (2H, s), 3.60-3.30 (6H, m), 2.60-2.30 (12H, m), 1.77 (6H, s)

LCMS: m/z 605 [M+H]$^+$

Example 313

Compound F5-19

9-(3-Dimethylamino-prop-1-ynyl)-6,6-dimethyl-8-(4-oxetan-3-yl-piperazin-1-yl)-11-oxo-6,11-dihydro-5H-benzo[b]carbazole-3-carbonitrile

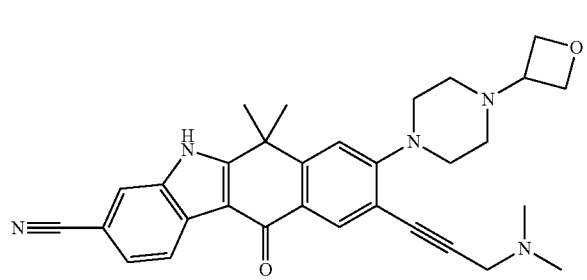

Under the same conditions as the method for synthesizing Compound E4-2-1, the title compound was prepared from Compound F4-3 and dimethyl-prop-2-ynylamine.

LCMS: m/z 508 [M+H]$^+$

HPLC retention time: 1.07 min (analysis condition S)

Example 315

Compound F5-21

9-Cyclopentylethynyl-6,6-dimethyl-8-(4-oxetan-3-yl piperazin-1-yl)-11-oxo-6,11-dihydro-5H-benzo[b] carbazole-3-carbonitrile

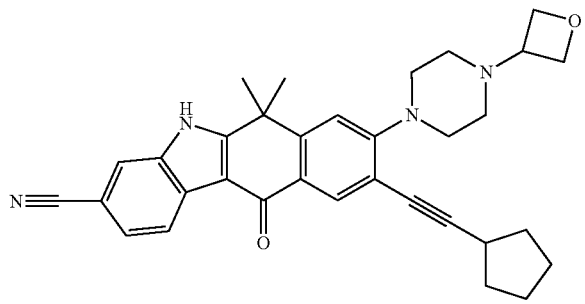 [SMILES: CC1(C)c2cc(N3CCN(C4COC4)CC3)c(C#CC3CCCC3)cc2C(=O)c2c1[nH]c1cc(C#N)ccc21]

Under the same conditions as the method for synthesizing Compound E4-2-1, the title compound was prepared from Compound F4-3 and cyclopentylacetylene.

LCMS: m/z 519 [M+H]$^+$

HPLC retention time: 1.80 min (analysis condition S)

Example 316

Compound F5-22

6,6-Dimethyl-8-(4-oxetan-3-yl-piperazin-1-yl)-11-oxo-9-prop-1-ynyl-6,11-dihydro-5H-benzo[b]carbazole-3-carbonitrile

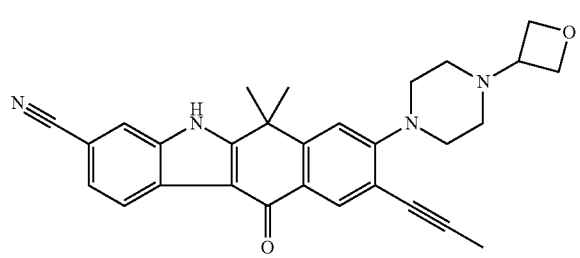 [SMILES: CC#Cc1cc2c(cc1N1CCN(C3COC3)CC1)C(C)(C)c1[nH]c3cc(C#N)ccc3c1C2=O]

Under the same conditions as the method for synthesizing Compound E4-2-1, the title compound was prepared from Compound F4-3 and propyne.

$^1$H-NMR (400 MHz, CD$_3$OD) δ: 8.37 (1H, d, J=8.2 Hz), 8.18 (1H, s), 7.84 (1H, s), 7.53 (1H, d, J=8.2 Hz), 7.19 (1H, s), 4.70-4.77 (2H, m), 4.62-4.68 (2H, m), 3.57-3.63 (1H, m), 3.38-3.45 (4H, m), 2.54-2.61 (4H, m), 2.10 (3H, s), 1.79 (6H, s)

LCMS: m/z 465 [M+H]$^+$

HPLC retention time: 1.90 min (analysis condition U)

Example 317

Compound F5-23

9-(3-Hydroxy-prop-1-ynyl)-6,6-dimethyl-8-(4-oxetan-3-yl-piperazin-1-yl)-11-oxo-6,11-dihydro-5H-benzo[b]carbazole-3-carbonitrile

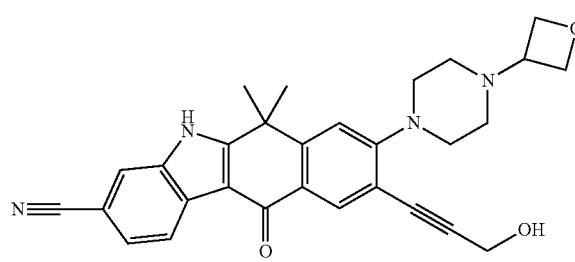

Under the same conditions as the method for synthesizing Compound E4-2-1, the TMS complex of the title compound was prepared from Compound F4-3 and trimethylprop-2-ynyloxysilane. By treating the resulting TMS complex with tetrabutylammonium fluoride, the title compound was obtained.

LCMS: m/z 481 [M+H]$^+$

HPLC retention time: 1.30 min (analysis condition S)

Example 318

Compound F5-24

6,6-Dimethyl-9-(4-methyl-pent-1-ynyl)-8-(4-oxetan-3-yl-piperazin-1-yl)-11-oxo-6,11-dihydro-5H-benzo[b]carbazole-3-carbonitrile

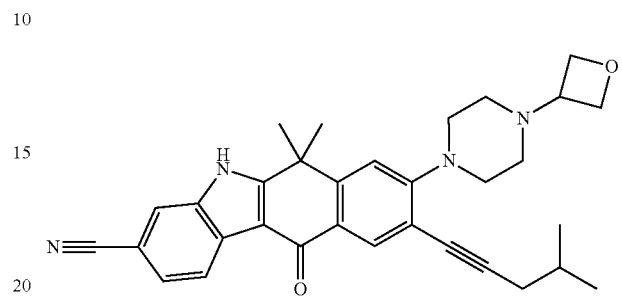

Under the same conditions as the method for synthesizing Compound E4-2-1, the title compound was prepared from Compound F4-3 and 4-methylpent-1-yne.

$^1$H-NMR (270 MHz, DMSO-d$_6$) δ: 12.75 (1H, br. s), 8.32-8.29 (1H, d, 8.08 Hz), 8.08 (1H, s), 8.01 (1H, s), 7.62-7.59 (1H, m), 7.23 (1H, s), 4.61-4.57 (2H, m), 4.51-4.46 (2H, m), 3.51-3.47 (1H, m), 3.37 (4H, m), 2.46 (4H, m), 2.41-2.39 (2H, d, 5.94 Hz), 1.92-1.80 (1H, m), 1.77 (6H, s), 1.04 (3H, s), 1.01 (3H, s)

LCMS: m/z 507 [M+H]$^+$

Example 319

Compound F5-25

9-Cyclopropylethynyl-6,6-dimethyl-8-(4-oxetan-3-yl-piperazin-1-yl)-11-oxo-6,11-dihydro-5H-benzo[b]carbazole-3-carbonitrile

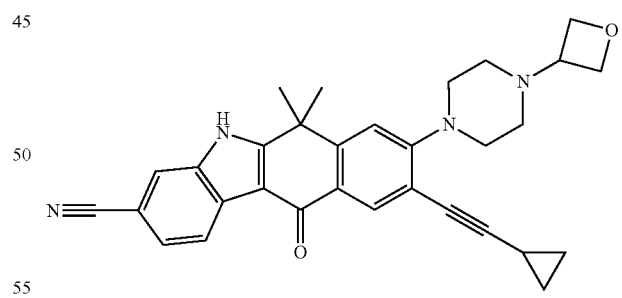

Under the same conditions as the method for synthesizing Compound E4-2-1, the title compound was prepared from Compound F4-3 and ethynylcyclopropane.

$^1$H-NMR (270 MHz, DMSO-d$_6$) δ: 12.74 (1H, br. s), 8.32-8.29 (1H, d, 8.08 Hz), 8.05 (1H, s), 8.00 (1H, s), 7.62-7.58 (1H, m), 7.21 (1H, s), 4.62-4.57 (2H, m), 4.51-4.47 (2H, m), 3.53-3.48 (1H, m), 3.34 (4H, m), 2.46 (4H, m), 1.76 (6H, s), 1.64-1.58 (1H, m), 0.97-0.89 (2H, m), 0.76-0.70 (2H, m)

LCMS: m/z 491 [M+H]$^+$

Example 320

Compound F5-26

6,6-Dimethyl-9-(3-morpholin-4-yl-prop-1-ynyl)-8-(4-oxetan-3-yl-piperazin-1-yl)-11-oxo-6,11-dihydro-5H-benzo[b]carbazole-3-carbonitrile

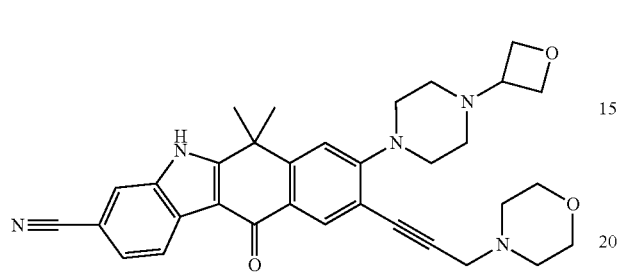

Under the same conditions as the method for synthesizing Compound F5-7, the title compound was prepared from Compound F4-3, 3-bromopropyne and morpholine.

$^1$H-NMR (270 MHz, DMSO-$d_6$) δ: 8.29 (1H, d, J=7.8 Hz), 8.13 (1H, s), 8.02 (1H, s), 7.59 (1H, d, J=7.8 Hz), 7.25 (1H, s), 4.61-4.48 (4H, m), 3.64-3.32 (11H, m), 2.60-2.40 (8H, m), 1.78 (6H, s)

LCMS: m/z 550 [M+H]$^+$

Example 321

Compound F5-27

6,6-Dimethyl-8-(4-oxetan-3-yl-piperazin-1-yl)-11-oxo-9-pent-1-ynyl-6,11-dihydro-5H-benzo[b]carbazole-3-carbonitrile

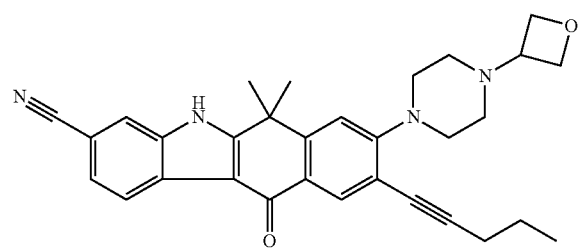 [SMILES: CCCC#Cc1cc2c(cc1N1CCN(C3COC3)CC1)C(C)(C)c1[nH]c3cc(C#N)ccc3c1C2=O]

Under the same conditions as the method for synthesizing Compound E4-2-1, the title compound was prepared from Compound F4-3 and 1-pentyne.

$^1$H-NMR (400 MHz, DMSO-$d_6$) δ: 12.72 (1H, br. s), 8.28 (1H, d, 8.1 Hz), 8.06 (1H, s), 7.98 (1H, s), 7.58 (1H, d, 8.1 Hz), 7.21 (1H, s), 4.60-4.43 (4H, m), 3.53-3.44 (1H, m), 3.39-3.32 (2H, m), 1.75 (6H, s), 1.60-1.53 (4H, m), 1.01 (3H, t, 7.3 Hz)

LCMS: m/z 493 [M+H]$^+$

HPLC retention time: 2.17 min (analysis condition U)

Example 322

Compound F5-28

6,6-Dimethyl-9-(5-methyl-hex-1-ynyl)-8-(4-oxetan-3-yl-piperazin-1-yl)-11-oxo-6,11-dihydro-5H-benzo[b]carbazole-3-carbonitrile

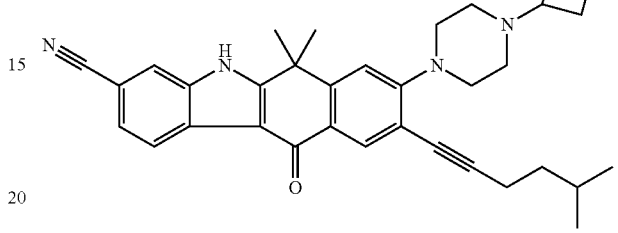

Under the same conditions as the method for synthesizing Compound E4-2-1, the title compound was prepared from Compound F4-3 and 5-methylhex-1-yne.

LCMS: m/z 521 [M+H]$^+$

HPLC retention time: 2.37 min (analysis condition U)

Example 323

Compound F5-29

9-(3-Diethylamino-prop-1-ynyl)-6,6-dimethyl-8-(4-oxetan-3-yl-piperazin-1-yl)-11-oxo-6,11-dihydro-5H-benzo[b]carbazole-3-carbonitrile

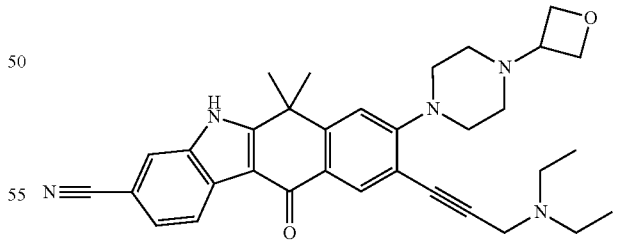

Under the same conditions as the method for synthesizing Compound E4-2-1, the title compound was prepared from Compound F4-3 and 3-diethylaminopropyne.

LCMS: m/z 536 [M+H]$^+$

HPLC retention time: 1.13 min (analysis condition S)

Example 324

Compound F5-30

9-[3-(Benzyl-ethyl-amino)-prop-1-ynyl]-6,6-dimethyl-8-(4-oxetan-3-yl-piperazin-1-yl)-11-oxo-6,11-dihydro-5H-benzo[b]carbazole-3-carbonitrile

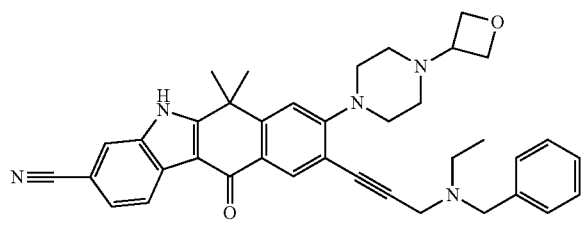 [SMILES: CCN(CC#Cc1cc2c(cc1N1CCN(C3COC3)CC1)C(C)(C)c1[nH]c3cc(C#N)ccc3c1C2=O)Cc1ccccc1]

Under the same conditions as the method for synthesizing Compound E4-2-1, the title compound was prepared from Compound F4-3 and 3-benzyl-3-ethylaminopropyne.

LCMS: m/z 584 [M+H]$^+$

HPLC retention time: 1.32 min (analysis condition S)

Example 325

Compound F5-31

9-[3-(1,1-Dioxo-1λ6-thiomorpholin-4-yl)-prop-1-ynyl]-6,6-dimethyl-8-(4-oxetan-3-yl-piperazin-1-yl)-11-oxo-6,11-dihydro-5H-benzo[b]carbazole-3-carbonitrile

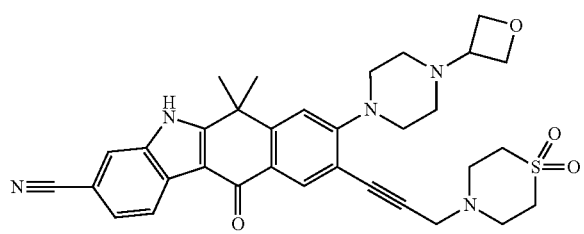 [SMILES: CC1(C)c2cc(N3CCN(C4COC4)CC3)c(C#CCN3CCS(=O)(=O)CC3)cc2C(=O)c2c1[nH]c1cc(C#N)ccc21]

Under the same conditions as the method for synthesizing Compound E4-2-1, the title compound was prepared from Compound F4-3 and 3-(1,1-dioxo-1λ6-thiomorpholin-4-yl)-propyne.

LCMS: m/z 598 [M+H]$^+$

HPLC retention time: 1.35 min (analysis condition S)

Example 326

Compound F5-32

9-Isopropenyl-6,6-dimethyl-8-(4-oxetan-3-yl-piperazin-1-yl)-11-oxo-6,11-dihydro-5H-benzo[b]carbazole-3-carbonitrile

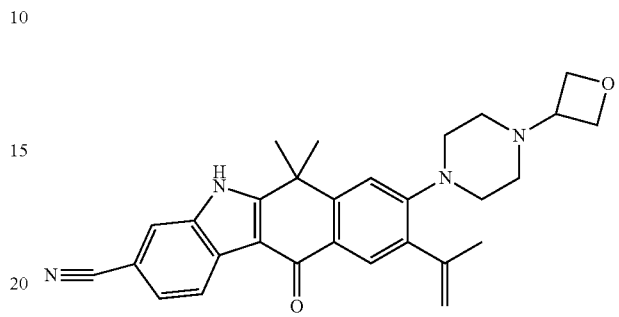

Under the same conditions as the method for synthesizing Compound E4-7-1, the title compound was prepared from Compound F4-3 and 2-isopropenyl-4,4,5,5-tetramethyl-[1,3,2]dioxaborolane.

$^1$H-NMR (270 MHz, CD$_3$OD+CDCl$_3$) δ: 8.44 (1H, d, J=7.8 Hz), 8.09 (1H, s), 7.83 (1H, s), 7.54 (1H, d, J=7.8 Hz), 7.18 (1H, s), 5.24-5.20 (2H, m), 4.81-4.68 (4H, m), 3.66 (1H, m), 3.30 (4H, m), 2.57 (4H, m), 2.21 (3H, s), 1.82 (6H, s)

LCMS: m/z 467 [M+H]$^+$

Example 327

Compound F5-33

6,6,9-Trimethyl-8-(4-oxetan-3-yl-piperazin-1-yl)-11-oxo-6,11-dihydro-5H-benzo[b]carbazole-3-carbonitrile

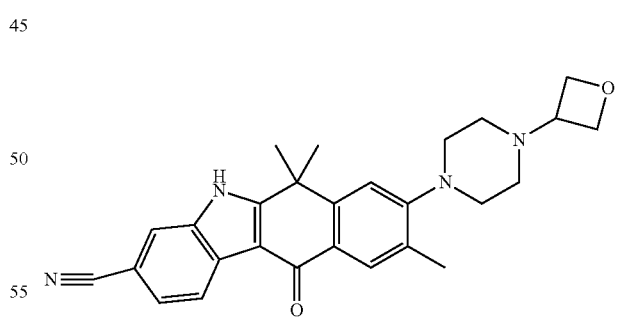

Under the same conditions as the method for synthesizing Compound F5-47, the title compound was prepared from Compound F4-3.

$^1$H-NMR (270 MHz, DMSO-d$_6$) δ: 12.71 (1H, br. s), 8.33-8.31 (1H, d, 8.08 Hz), 8.01 (1H, s), 7.97 (1H, s), 7.62-7.59 (1H, m), 7.32 (1H, s), 4.61-4.57 (2H, m), 4.51-4.47 (2H, m), 3.55-3.49 (1H, m), 3.05 (4H, m), 2.47 (4H, m), 2.33 (3H, s), 1.76 (6H, s)

LCMS: m/z 441 [M+H]$^+$

Example 328

Compound F5-34

9-Cyclopropyl-6,6-dimethyl-8-(4-oxetan-3-yl-piper-azin-1-yl)-11-oxo-6,11-dihydro-5H-benzo[b]carba-zole-3-carbonitrile

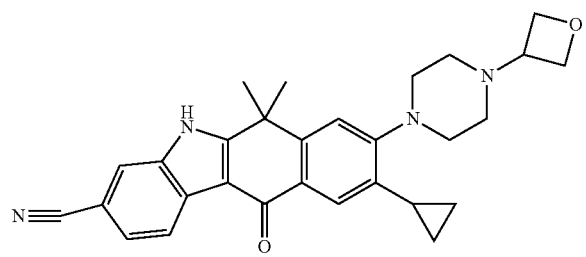 [SMILES: CC1(C)c2cc(N3CCN(C4COC4)CC3)c(C3CC3)cc2C(=O)c2c1[nH]c1cc(C#N)ccc21]

Under the same conditions as the method for synthesizing Compound B3-32, the title compound was prepared from Compound F5-15-2 and oxetan-3-one.

$^1$H-NMR (400 MHz, DMSO-d$_6$) δ: 8.32-8.29 (1H, m), 8.00-7.99 (1H, m), 7.62-7.58 (2H, m), 7.32-7.31 (1H, m), 4.61-4.57 (2H, m), 4.52-4.49 (2H, m), 3.53 (1H, br. s), 3.18 (4H, br. s), 1.75 (6H, s), 1.25-1.23 (1H, m), 1.09-1.04 (2H, m), 0.79-0.75 (2H, m)

LCMS: m/z 467 [M+H]$^+$

HPLC retention time: 2.74 min (analysis condition W)

Example 329

Compound F5-35

6,6-Dimethyl-9-(1-methyl-1H-pyrazol-4-yl)-8-(4-oxetan-3-yl-piperazin-1-yl)-11-oxo-6,11-dihydro-5H-benzo[b]carbazole-3-carbonitrile

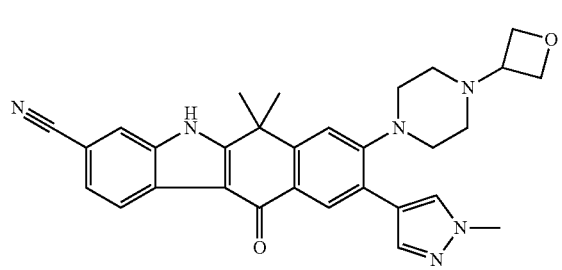 [SMILES: Cn1cc(-c2cc3c(cc2N2CCN(C4COC4)CC2)C(C)(C)c2[nH]c4cc(C#N)ccc4c2C3=O)cn1]

Under the same conditions as the method for synthesizing Compound E4-7-1, the title compound was prepared from Compound F4-3 and 1-methyl-4-(4,4,5,5-tetramethyl-[1,3,2]dioxaborolan-2-yl)-1H-pyrazole.

LCMS: m/z 507 [M+H]$^+$

HPLC retention time: 1.75 min (analysis condition U)

Example 330

Compound F5-36-1

4-[3-Cyano-6,6-dimethyl-11-oxo-8-(4-pyrrolidin-1-yl-piperidin-1-yl)-6,11-dihydro-5H-benzo[b]carba-zol-9-yl]-3,6-dihydro-2H-pyridine-1-carboxylic acid tert-butyl ester

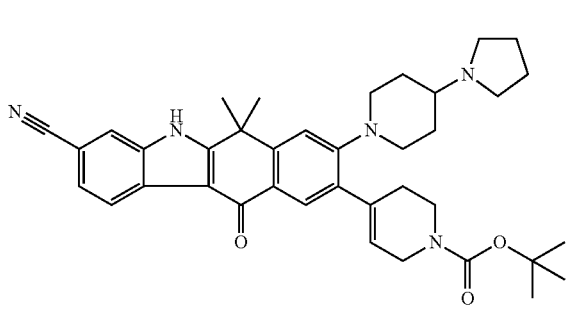 [SMILES: CC(C)(C)OC(=O)N1CC=C(c2cc3c(cc2N2CCC(N4CCCC4)CC2)C(C)(C)c2[nH]c4cc(C#N)ccc4c2C3=O)CC1]

Under the same conditions as the method for synthesizing Compound E4-7-1, the title compound was prepared from Compound F3-2.

LCMS: m/z 621 [M+H]$^+$

HPLC retention time: 2.58 min (analysis condition U)

Example 331

Compound F5-36-2

6,6-Dimethyl-11-oxo-8-(4-pyrrolidin-1-yl-piperidin-1-yl)-9-(1,2,3,6-tetrahydro-pyridin-4-yl)-6,11-di-hydro-5H-benzo[b]carbazole-3-carbonitrile

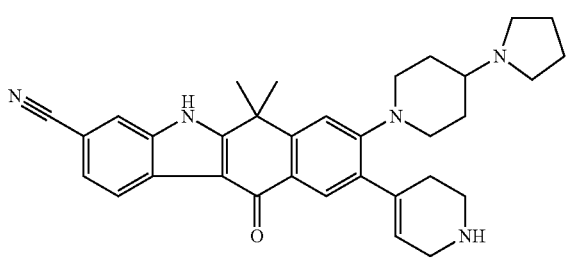 [SMILES: CC1(C)c2cc(N3CCC(N4CCCC4)CC3)c(C3=CCNCC3)cc2C(=O)c2c1[nH]c1cc(C#N)ccc21]

Under the same conditions as the method for synthesizing Compound A8-1, the title compound was prepared from Compound F5-36-1.

LCMS: m/z 520 [M+H]$^+$

HPLC retention time: 1.82 min (analysis condition U)

Example 332

Compound F5-37

8-(4-Cyclopropyl-piperazin-1-yl)-9-ethynyl-6,6-dimethyl-11-oxo-6,11-dihydro-5H-benzo[b]carbazole-3-carbonitrile

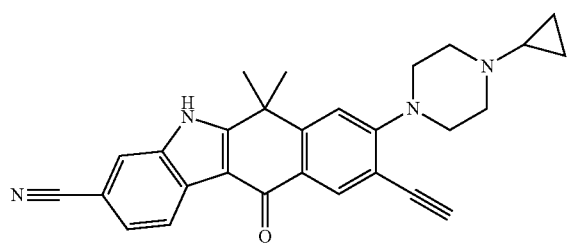 [SMILES: C#Cc1cc2c(cc1N1CCN(C3CC3)CC1)C(C)(C)c1[nH]c3cc(C#N)ccc3c1C2=O]

Under the same conditions as the method for synthesizing Compound F5-43, the title compound was prepared from Compound F4-9.

$^1$H-NMR (270 MHz, DMSO-$d_6$) δ: 12.76 (1H, br. s), 8.31 (1H, d, J=8.1 Hz), 8.15 (1H, s), 8.01 (1H, s), 7.61 (1H, dd, J=8.1, 1.5 Hz), 7.24 (1H, s), 4.52 (1H, s), 3.28-3.36 (4H, m), 3.17 (1H, d, J=5.3 Hz), 2.70-2.77 (4H, m), 1.76 (6H, s), 0.47 (2H, d, J=5.3 Hz), 0.36 (2H, d, J=5.3 Hz).

LCMS: m/z 435 [M+H]$^+$

HPLC retention time: 1.57 min (analysis condition S)

Example 333

Compound F5-38

8-(4-Cyclopropyl-piperazin-1-yl)-6,6-dimethyl-11-oxo-9-prop-1-ynyl-6,11-dihydro-5H-benzo[b]carbazole-3-carbonitrile

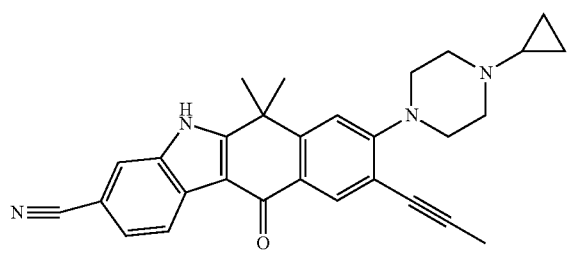 [SMILES: CC#Cc1cc2c(cc1N1CCN(C3CC3)CC1)C(C)(C)c1[nH]c3cc(C#N)ccc3c1C2=O]

Under the same conditions as the method for synthesizing Compound E4-2-1, the title compound was prepared from Compound F4-9 and propyne.

$^1$H-NMR (270 MHz, DMSO-$d_6$) δ: 12.76 (1H, br. s), 8.31-8.28 (1H, d, 8.08 Hz), 8.06 (1H, s), 8.00 (1H, s), 7.60-7.57 (1H, m), 7.19 (1H, s), 3.29 (4H, m), 2.74 (4H, m), 2.55 (1H, m), 2.13 (3H, s), 1.75 (6H, s), 0.51-0.43 (2H, m), 0.38-0.32 (2H, m)

LCMS: m/z 449 [M+H]$^+$

Example 334

Compound F5-39

8-(4-Cyclopropyl-piperazin-1-yl)-6,6-dimethyl-11-oxo-9-phenyl-6,11-dihydro-5H-benzo[b]carbazole-3-carbonitrile

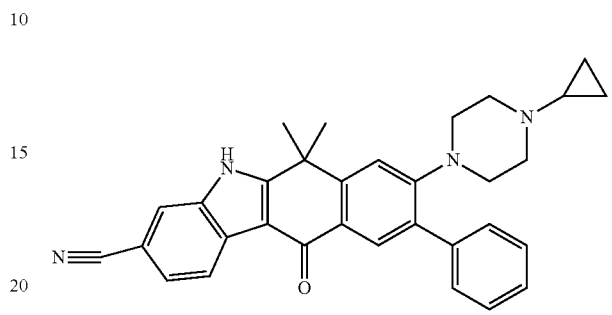

Under the same conditions as the method for synthesizing Compound E4-7-1, the title compound was prepared from Compound F4-9 and phenylboric acid.

LCMS: m/z 487 [M+H]$^+$

HPLC retention time: 2.15 min (analysis condition U)

Example 335

Compound F5-40

8-(4-Cyclopropyl-piperazin-1-yl)-6,6-dimethyl-11-oxo-9-pyridin-3-yl-6,11-dihydro-5H-benzo[b]carbazole-3-carbonitrile

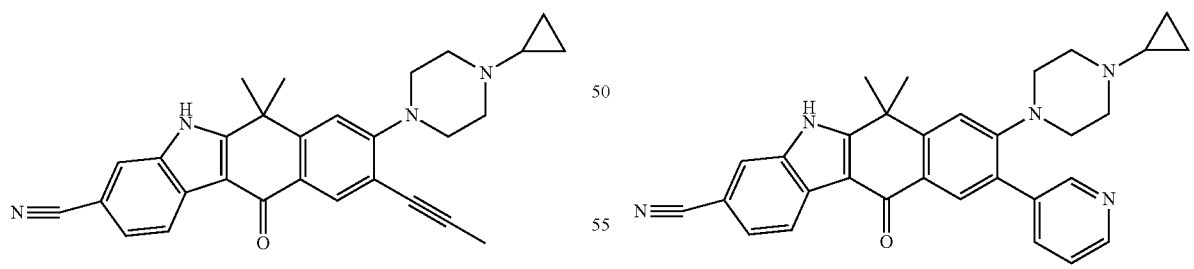

Under the same conditions as the method for synthesizing Compound E4-7-1, the title compound was prepared from Compound F4-9 and pyridine-3-boric acid.

LCMS: m/z 488 [M+H]$^+$

HPLC retention time: 1.53 min (analysis condition U)

Example 336

Compound F5-41

8-(4-Cyclopropyl-piperazin-1-yl)-6,6-dimethyl-11-oxo-9-thiophene-2-yl-6,11-dihydro-5H-benzo[b]carbazole-3-carbonitrile

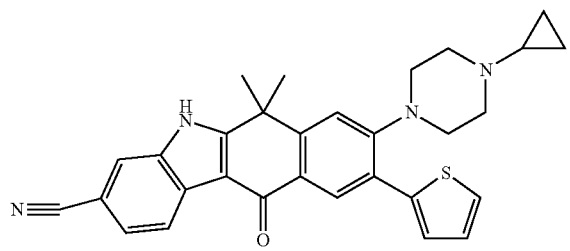 [SMILES: CC1(C)c2cc(N3CCN(C4CC4)CC3)c(-c3cccs3)cc2C(=O)c2c1[nH]c1cc(C#N)ccc21]

Under the same conditions as the method for synthesizing Compound E4-7-1, the title compound was prepared from Compound F4-9 and thiophene-2-boric acid.

LCMS: m/z 493 [M+H]$^+$

HPLC retention time: 2.13 min (analysis condition U)

Example 337

Compound F5-42

8-(4-Cyclopropyl-piperazin-1-yl)-6,6,9-trimethyl-11-oxo-6,11-dihydro-5H-benzo[b]carbazole-3-carbonitrile

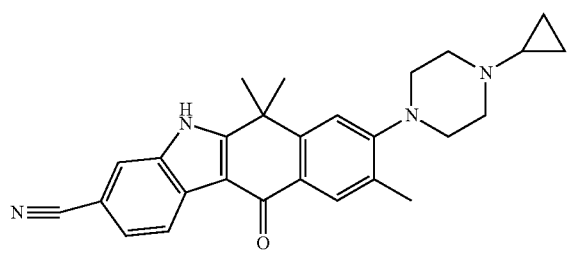 [SMILES: Cc1cc2c(cc1N1CCN(C3CC3)CC1)C(C)(C)c1[nH]c3cc(C#N)ccc3c1C2=O]

Under the same conditions as the method for synthesizing Compound F5-47, the title compound was prepared from Compound F4-9.

$^1$H-NMR (270 MHz, DMSO-d$_6$) δ: 12.71 (1H, br. s), 8.33-8.30 (1H, d, 8.08 Hz), 8.00 (1H, s), 7.96 (1H, s), 7.61-7.58 (1H, m), 7.29 (1H, s), 2.97 (4H, m), 2.73 (4H, m), 2.56 (1H, m), 2.34 (3H, s), 1.76 (6H, s), 1.64-1.58 (1H, m), 0.50-0.44 (2H, m), 0.37-0.32 (2H, m)

LCMS: m/z 425 [M+H]$^+$

Example 338

Compound F5-43

8-(4-Cyclobutyl-piperazin-1-yl)-9-ethynyl-6,6-dimethyl-11-oxo-6,11-dihydro-5H-benzo[b]carbazole-3-carbonitrile

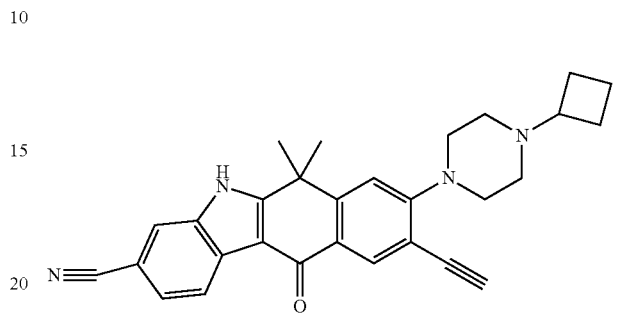

Under nitrogen atmosphere, to the MeCN (8 ml) suspension of 9-bromo-8-(4-cyclobutyl-piperazin-1-yl)-6,6-dimethyl-11-oxo-6,11-dihydro-5H-benzo[b]carbazole-3-carbonitrile (Compound F4-10, 200 mg, 0.397 mmol), ethynyltriisopropylsilane (268 mg, 3.0 eq.), 2-dicyclohexylphosphino-2',4',6'-triisopropylbiphenyl (Xphos) (39 mg, 0.2 eq.), Pd(CH$_3$CN)$_2$Cl$_2$ (11 mg, 0.1 eq.) and cesium carbonate (518 mg, 4.0 eq.) were added and the mixture was stirred and heated under reflux condition until the reaction is completed. Upon the completion of the reaction, distilled water was added to the reaction solution, which was then extracted with ethyl acetate. The organic layer was washed with brine and dried over sodium sulfate. The drying agent was removed by filtration and the residues obtained after concentration under reduced pressure were purified by silica gel column chromatography (ethyl acetate/methanol) to obtain 8-(4-cyclobutyl-piperazin-1-yl)-6,6-dimethyl-11-oxo-9-[(triisopropylsilanyl)-ethynyl]-6,11-dihydro-5H-benzo[b]carbazole-3-carbonitrile (179 mg, 74%).

To the THF (6 ml) solution of the obtained compound (179 mg, 0.295 mmol), 1 M THF solution (710 μl) of tetrabutylammonium fluoride was added and the mixture was stirred until the reaction is completed. Upon the completion of the reaction, ethyl acetate was added to the reaction solution, which was then washed with distilled water and dried over sodium sulfate. The drying agent was removed by filtration and the residues obtained after concentration under reduced pressure were washed with a mixture solvent of ethanol and distilled water to obtain the title compound (67 mg, 92%).

$^1$H-NMR (400 MHz, DMSO-d$_6$) δ: 12.85 (1H, s), 8.31 (1H, d, 7.9 Hz), 8.20 (1H, s), 8.03 (1H, s), 7.62 (1H, d, 7.9 Hz), 7.35 (1H, s), 4.62 (1H, s), 3.94-4.03 (2H, m), 3.79-3.89 (1H, m), 3.48-3.54 (2H, m), 3.27-3.38 (2H, m), 2.96-3.16 (2H, m), 2.30-2.41 (2H, m), 2.16-2.26 (2H, m), 1.72-1.85 (8H, m)

LCMS: m/z 449 [M+H]$^+$

HPLC retention time: 2.69 min (analysis condition W)

Example 339

Compound F5-44

8-(4-Cyclobutyl-piperazin-1-yl)-6,6-dimethyl-11-oxo-9-prop-1-ynyl-6,11-dihydro-5H-benzo[b]carbazole-3-carbonitrile

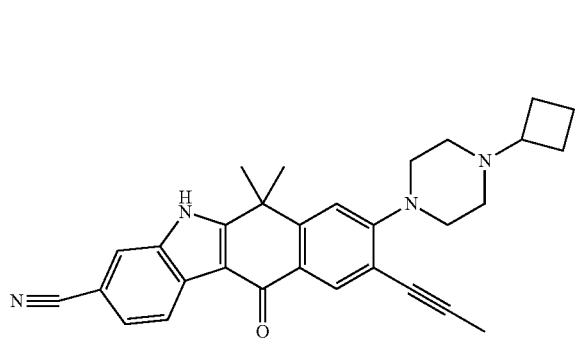 [SMILES: CC#Cc1cc2c(cc1N1CCN(C3CCC3)CC1)C(C)(C)c1[nH]c3cc(C#N)ccc3c1C2=O]

Under the same conditions as the method for synthesizing Compound E4-2-1, the title compound was prepared from Compound F4-10 under propyne gas atmosphere.

$^1$H-NMR (400 MHz, DMSO-$d_6$) δ: 12.71 (1H, s), 8.30 (1H, d, 7.9 Hz), 8.06 (1H, s), 8.00 (1H, s), 7.59 (1H, d, 7.9 Hz), 7.20 (1H, s), 2.75-2.83 (1H, m), 2.40-2.48 (4H, m), 2.11 (3H, s), 1.97-2.06 (2H, m), 1.76 (6H, s), 1.62-1.71 (2H, m)

LCMS: m/z 463 [M+H]$^+$

HPLC retention time: 2.80 min (analysis condition W)

Example 340

Compound F5-45

9-Cyclobutylethynyl-8-(4-cyclobutyl-piperazin-1-yl)-6,6-dimethyl-11-oxo-6,11-dihydro-5H-benzo[b]carbazole-3-carbonitrile

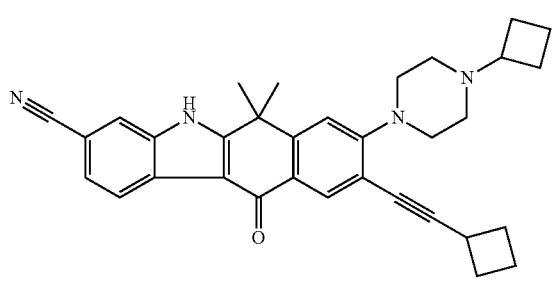 [SMILES: CC1(C)c2cc(N3CCN(C4CCC4)CC3)c(C#CC3CCC3)cc2C(=O)c2c1[nH]c1cc(C#N)ccc21]

Under the same conditions as the method for synthesizing Compound E4-2-1, the title compound was prepared from Compound F4-10 and ethynylcyclobutane.

LCMS: m/z 503 [M+H]$^+$

HPLC retention time: 1.85 min (analysis condition S)

Example 341

Compound F5-46

8-(4-Cyclobutyl-piperazin-1-yl)-9-cyclopropyl-6,6-dimethyl-11-oxo-6,11-dihydro-5H-benzo[b]carbazole-3-carbonitrile

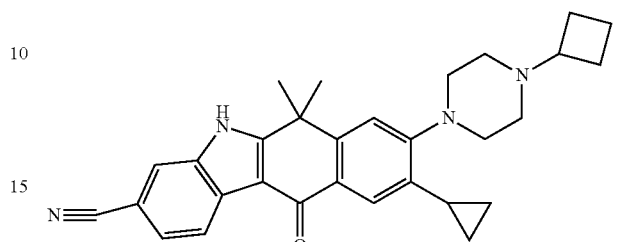

Under the same conditions as the method for synthesizing Compound B3-32, the title compound was prepared from Compound F5-15-2 and cyclobutanone.

$^1$H-NMR (400 MHz, DMSO-$d_6$) δ: 8.23 (1H, d, 8 Hz), 7.92 (1H, br. s), 7.59 (1H, s), 7.47 (1H, br. d, 8 Hz), 7.28 (1H, s), 3.12 (4H, br. s), 2.80 (1H, dddd, 8, 8, 8, 8 Hz), 2.20-2.13 (1H, m), 2.01 (2H, br. s), 1.86-1.68 (10H, m), 1.05 (2H, d, 8 Hz), 0.76 (2H, d, 4 Hz)

LCMS: m/z 465 [M+H]$^+$

HPLC retention time: 2.79 min (analysis condition W)

Hydrochloric Acid Salt of Compound F5-46

8-(4-Cyclobutyl-piperazin-1-yl)-9-cyclopropyl-6,6-dimethyl-11-oxo-6,11-dihydro-5H-benzo[b]carbazole-3-carbonitrile was added with DMSO and 6 N hydrochloric acid (1.05 eq.) and dissolved therein. After freeze-drying, crystallization was performed by using ethanol comprising 25% water to obtain monohydrochloric acid salt of 8-(4-cyclobutyl-piperazin-1-yl)-9-cyclopropyl-6,6-dimethyl-11-oxo-6,11-dihydro-5H-benzo[b]carbazole-3-carbonitrile.

$^1$H-NMR (400 MHz, DMSO-$d_6$) δ: 12.81 (1H, s), 10.64 (1H, br. s), 8.32-8.29 (1H, m), 8.01 (1H, s), 7.67 (1H, s), 7.61-7.60 (1H, m), 7.33 (1H, s), 4.00-3.39 (6H, m), 3.28-3.02 (3H, m), 2.45-2.05 (5H, m), 1.83-1.77 (8H, m), 1.09-1.07 (2H, m), 0.81-0.80 (2H, m)

LCMS: m/z 465 [M+H]$^+$

Example 342

Compound F5-47

8-(4-Cyclobutyl-piperazin-1-yl)-6,6,9-trimethyl-11-oxo-6,11-dihydro-5H-benzo[b]carbazole-3-carbonitrile

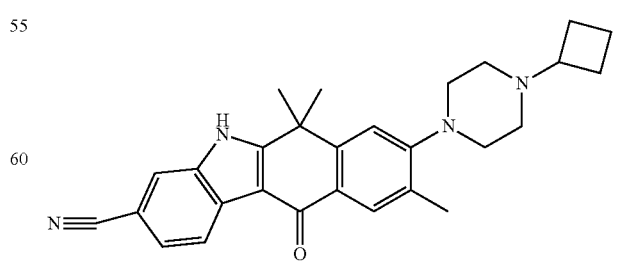

Under nitrogen atmosphere, to the N,N-dimethyl formamide (1.5 ml) solution of 9-bromo-8-(4-cyclobutyl-piperazin-1-yl)-6,6-dimethyl-11-oxo-6,11-dihydro-5H-benzo[b]carbazole-3-carbonitrile (Compound F4-10, 50 mg, 0.099 mmol), trimethyl boroxine (12 mg, 0.1 eq.), tetrakis triphenylphosphine palladium (39 mg, 0.2 eq.), and potassium carbonate (41 mg, 3.0 eq.) were added, and the mixture was stirred at 100° C. for 24 hr. Upon the completion of the reaction, distilled water was added to the reaction solution, which was then extracted with ethyl acetate. The organic layer was washed with brine and dried over sodium sulfate. The drying agent was removed by filtration and the residues obtained after concentration under reduced pressure were purified by silica gel column chromatography (ethyl acetate/methanol) to obtain the title compound (25 mg, 58%).

$^1$H-NMR (400 MHz, DMSO-$d_6$) δ: 12.67 (1H, s), 8.31 (1H, d, 7.9 Hz), 7.98 (1H, s), 7.95 (1H, s), 7.59 (1H, d, 7.9 Hz), 7.30 (1H, s), 2.96-3.04 (4H, m), 2.76-2.84 (1H, m), 2.39-2.48 (4H, m), 2.32 (3H, s), 1.78-1.87 (2H, m), 1.75 (6H, s), 1.63-1.71 (2H, m)

LCMS: m/z 439 [M+H]$^+$

HPLC retention time: 2.66 min (analysis condition W)

Example 343

Compound F5-48

8-(4-Cyclobutyl-piperazin-1-yl)-9-isopropenyl-6,6-dimethyl-11-oxo-6,11-dihydro-5H-benzo[b]carbazole-3-carbonitrile

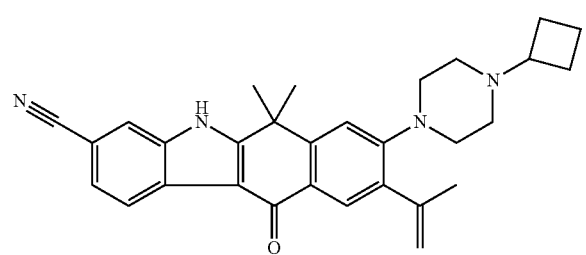 [SMILES: C=C(C)c1cc2c(cc1N1CCN(C3CCC3)CC1)C(C)(C)c1[nH]c3cc(C#N)ccc3c1C2=O]

Under the same conditions as the method for synthesizing Compound E4-7-1, the title compound was prepared from Compound F4-10 and 2-isopropenyl-4,4,5,5-tetramethyl-[1,3,2]dioxaborolane.

LCMS: m/z 465 [M+H]$^+$

HPLC retention time: 1.63 min (analysis condition S)

Example 344

Compound F5-49

9-Ethynyl-6,6-dimethyl-8-(4-morpholin-4-yl-piperidin-1-yl)-11-oxo-6,11-dihydro-5H-benzo[b]carbazole-3-carbonitrile

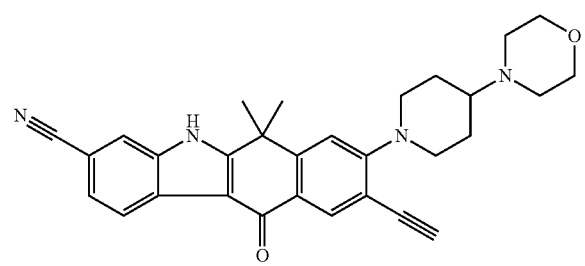 [SMILES: C#Cc1cc2c(cc1N1CCC(N3CCOCC3)CC1)C(C)(C)c1[nH]c3cc(C#N)ccc3c1C2=O]

Under the same conditions as the method for synthesizing Compound F5-43, the title compound was prepared from Compound F3-11.

LCMS: m/z 479 [M+H]$^+$

HPLC retention time: 1.90 min (analysis condition U)

Example 345

Compound F5-50

6,6-Dimethyl-8-(4-morpholin-4-yl-piperidin-1-yl)-11-oxo-9-prop-1-ynyl-6,11-dihydro-5H-benzo[b]carbazole-3-carbonitrile

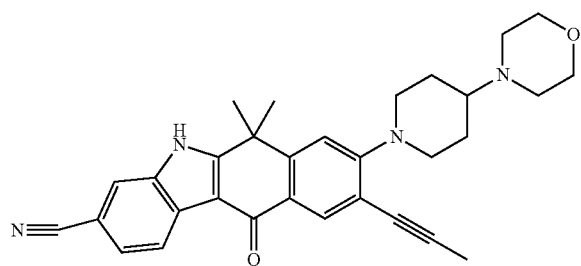 [SMILES: CC#Cc1cc2c(cc1N1CCC(N3CCOCC3)CC1)C(C)(C)c1[nH]c3cc(C#N)ccc3c1C2=O]

Under the same conditions as the method for synthesizing Compound E4-2-1, the title compound was prepared from Compound F3-11 and propyne gas.

$^1$H-NMR (270 MHz, CD$_3$OD+CDCl$_3$) δ: 8.40 (1H, d, J=7.8 Hz), 8.24 (1H, s), 7.84 (1H, s), 7.54 (1H, d, J=7.8 Hz), 7.14 (1H, s), 4.01-3.96 (2H, m), 3.78 (4H, m), 2.88-2.84 (2H, m), 2.68 (4H, m), 2.16-1.73 (5H, m), 2.16 (3H, s), 1.80 (6H, s)

LCMS: m/z 493 [M+H]$^+$

Example 346

Compound F5-51

6,6,9-Trimethyl-8-(4-morpholin-4-yl-piperidin-1-yl)-11-oxo-6,11-dihydro-5H-benzo[b]carbazole-3-carbonitrile

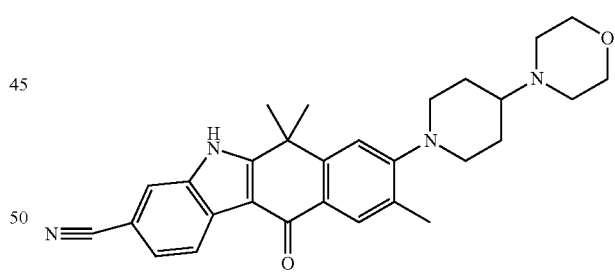

Under the same conditions as the method for synthesizing Compound F5-47, the title compound was prepared from Compound F3-11

$^1$H-NMR (270 MHz, DMSO-$d_6$) δ: 12.70 (1H, br. s), 8.33-8.30 (1H, d, 8.08 Hz), 8.00 (1H, s), 7.95 (1H, s), 7.61-7.58 (1H, m), 7.28 (1H, s), 3.60 (4H, m), 3.32-3.26 (2H, m), 2.79-2.69 (2H, m), 2.32 (3H, s), 1.95-1.90 (2H, m), 1.74 (6H, s), 1.65-1.52 (2H, m),

LCMS: m/z 469 [M+H]$^+$

Methanesulfonic Acid Salt of Compound F5-51

6,6,9-Trimethyl-8-(4-morpholin-4-yl-piperidin-1-yl)-11-oxo-6,11-dihydro-5H-benzo[b]carbazole-3-carbonitrile was added with DMSO and 2 N methanesulfonic acid (1.05 eq.) and dissolved therein. After freeze-drying, crystallization was performed with ethanol to obtain methanesulfonic acid salt of 6,6,9-trimethyl-8-(4-morpholin-4-yl-piperidin-1-yl)-11-oxo-6,11-dihydro-5H-benzo[b]carbazole-3-carbonitrile.

$^1$H-NMR (270 MHz, DMSO-$d_6$) δ: 12.72 (1H, br.s), 9.60 (1H, br. s), 8.33-8.31 (1H, d, 9.8 Hz), 8.01 (1H, s), 7.99 (1H, s), 7.61-7.59 (1H, m), 7.31 (1H, s), 4.07-4.04 (2H, m), 3.73-3.67 (2H, m), 3.55-3.40 (8H, m), 3.32-3.26 (1H, m), 2.70-2.60 (2H, m), 2.34 (3H, s), 2.30 (3H, s), 1.95-1.90 (2H, m), 1.75 (6H, s)

LCMS: m/z 469 [M+H]$^+$

Example 347

Compound F6-1

9-(1-Isopropyl-1,2,3,6-tetrahydro-pyridin-4-yl)-6,6-dimethyl-11-oxo-8-(4-pyrrolidin-1-yl-piperidin-1-yl)-6,11-dihydro-5H-benzo[b]carbazole-3-carbonitrile

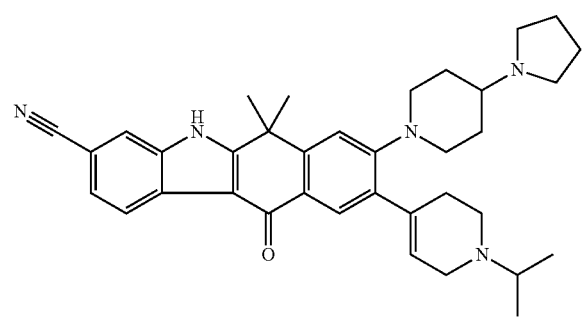 [SMILES: CC(C)N1CC=C(c2cc3c(cc2N2CCC(N4CCCC4)CC2)C(C)(C)c2[nH]c4cc(C#N)ccc4c2C3=O)CC1]

Under the same conditions as the method for synthesizing Compound B3-32, the title compound was prepared from Compound F5-36-2 and acetone.

$^1$H-NMR (400 MHz, DMSO-$d_6$) δ: 12.68 (1H, br. s), 8.30 (1H, d, 8.1 Hz), 7.98 (1H, s), 7.82 (1H, s), 7.58 (1H, d, 8.1 Hz), 7.20 (1H, s), 5.85 (1H, s), 3.56-3.44 (2H, m), 3.21-3.14 (2H, m), 2.77-2.66 (5H, m), 2.12-2.09 (1H, m), 1.98-1.88 (2H, m), 1.74 (6H, s), 1.70-1.63 (1H, m), 1.58-1.45 (2H, m), 1.09-1.00 (6H, m)

LCMS: m/z 563 [M+H]$^+$

HPLC retention time: 1.90 min (analysis condition U)

Example 348

Compound F6-2

9-(1-Methanesulfonyl-1,2,3,6-tetrahydro-pyridin-4-yl)-6,6-dimethyl-11-oxo-8-(4-pyrrolidin-1-yl-piperidin-1-yl)-6,11-dihydro-5H-benzo[b]carbazole-3-carbonitrile

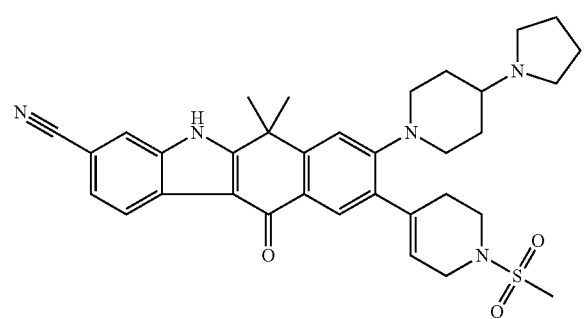 [SMILES: CC1(C)c2cc(N3CCC(N4CCCC4)CC3)c(C3=CCN(S(C)(=O)=O)CC3)cc2C(=O)c2c1[nH]c1cc(C#N)ccc21]

Under the same conditions as the method for synthesizing Compound A9-1, the title compound was prepared from Compound F5-36-2.

LCMS: m/z 598 [M+H]$^+$

HPLC retention time: 1.52 min (analysis condition S)

Example 349

Compound F6-3

9-[3-(4-Cyclopropyl-piperazin-1-yl)-propyl]-6,6-dimethyl-8-morpholin-4-yl-11-oxo-6,11-dihydro-5H-benzo[b]carbazole-3-carbonitrile

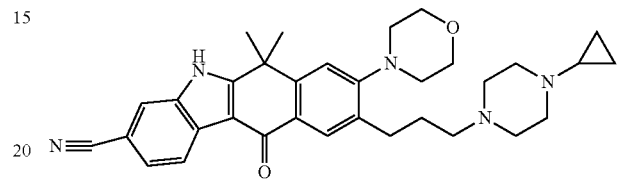

Under the same conditions as the method for synthesizing Compound B3-13-1, the title compound was prepared from Compound F5-10.

LCMS: m/z 538 [M+H]$^+$

HPLC retention time: 1.32 min (analysis condition S)

Example 350

Compound F6-4

9-Ethyl-6,6-dimethyl-8-(4-oxetan-3-yl-piperazin-1-yl)-11-oxo-6,11-dihydro-5H-benzo[b]carbazole-3-carbonitrile

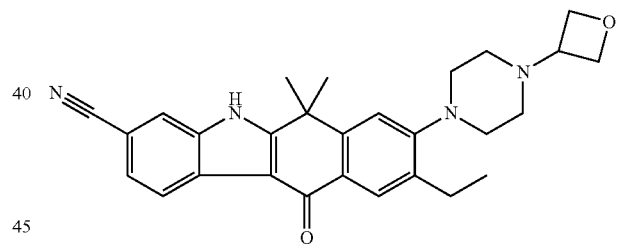

Under the same conditions as the method for synthesizing Compound B3-13-1, the title compound was prepared from Compound F5-16.

$^1$H-NMR (400 MHz, DMSO-$d_6$) δ: 12.70 (1H, br. s), 8.29 (1H, d, 8.0 Hz), 8.03-7.94 (2H, m), 7.59-7.55 (1H, m), 7.38 (1H, s), 4.59-4.47 (4H, m), 3.53-5.47 (1H, m), 3.03-2.97 (2H, m), 2.73-2.62 (2H, m), 1.74 (6H, s), 1.29-1.98 (3H, m)

LCMS: m/z 455 [M+H]$^+$

HPLC retention time: 1.92 min (analysis condition U)

Hydrochloric acid salt of Compound F6-4

9-Ethyl-6,6-dimethyl-8-(4-oxetan-3-yl-piperazin-1-yl)-11-oxo-6,11-dihydro-5H-benzo[b]carbazole-3-carbonitrile was added with DMSO and 6 N hydrochloric acid (1.05 eq.) and dissolved therein. After freeze-drying, crystallization was performed with ethanol comprising 25% water to obtain monohydrochloric acid salt of 9-ethyl-6,6-dimethyl-8-(4-oxetan-3-yl-piperazin-1-yl)-11-oxo-6,11-dihydro-5H-benzo[b]carbazole-3-carbonitrile.

¹H-NMR (270 MHz, DMSO-d₆) δ: 12.83 (1H, br.s), 11.59 (1H, br. s), 8.33-8.31 (1H, m), 8.09 (1H, s), 8.02 (1H, s), 7.63-7.61 (1H, m), 7.39 (1H, s), 4.91-4.60 (4H, br. m), 3.58-3.40 (1H, m), 3.31-3.05 (8H, br. m), 2.73 (2H, q, J=7.3), 1.81 (6H, s), 1.29 (3H, t, J=7.3)

LCMS: m/z 455 [M+H]⁺

Example 351

Compound F6-5

9-(3-Methoxy-propyl)-6,6-dimethyl-8-(4-oxetan-3-yl-piperazin-1-yl)-11-oxo-6,11-dihydro-5H-benzo[b]carbazole-3-carbonitrile

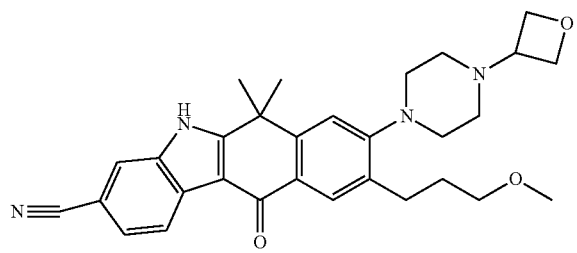 [SMILES: COCCCc1cc2c(cc1N1CCN(C3COC3)CC1)C(C)(C)c1[nH]c3cc(C#N)ccc3c1C2=O]

Under the same conditions as the method for synthesizing Compound B3-13-1, the title compound was prepared from Compound F5-18.

¹H-NMR (270 MHz, DMSO-d₆) δ: 12.73 (1H, br. s), 8.33-8.30 (1H, d, 8.08 Hz), 8.01 (1H, s), 8.00 (1H, s), 7.62-7.59 (1H, d, 8.08 Hz), 7.42 (1H, s), 4.61-4.56 (2H, m), 4.51-4.46 (2H, m), 3.53-3.47 (1H, m), 3.42-3.37 (2H, m), 3.02 (4H, m), 2.75-2.68 (2H, m), 2.51 (4H, m), 1.93-1.82 (2H, m), 1.76 (6H, s)

LCMS: m/z 499 [M+H]⁺

Example 352

Compound F6-6

6,6-Dimethyl-8-(4-oxetan-3-yl-piperazin-1-yl)-9-[3-(4-oxetan-3-yl-piperazin-1-yl)-propyl]-11-oxo-6,11-dihydro-5H-benzo[b]carbazole-3-carbonitrile

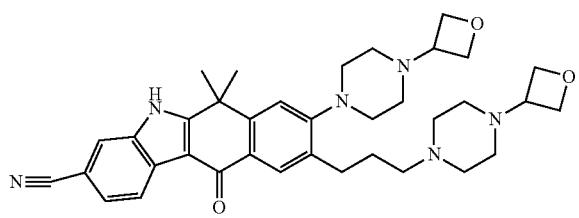 [SMILES: CC1(C)c2cc(N3CCN(C4COC4)CC3)c(CCCN3CCN(C4COC4)CC3)cc2C(=O)c2c1[nH]c1cc(C#N)ccc21]

Under the same conditions as the method for synthesizing Compound B3-13-1, the title compound was prepared from Compound F5-20.

LCMS: m/z 609 [M+H]⁺

HPLC retention time: 1.00 min (analysis condition S)

Example 353

Compound F6-7

9-(2-Cyclopentyl-ethyl)-6,6-dimethyl-8-(4-oxetan-3-yl-piperazin-1-yl)-11-oxo-6,11-dihydro-5H-benzo[b]carbazole-3-carbonitrile

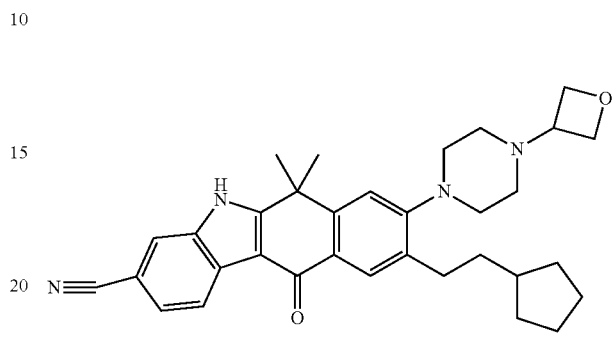

Under the same conditions as the method for synthesizing Compound B3-13-1, the title compound was prepared from Compound F5-21.

LCMS: m/z 523 [M+H]⁺

HPLC retention time: 1.92 min (analysis condition S)

Example 354

Compound F6-8

6,6-Dimethyl-8-(4-oxetan-3-yl-piperazin-1-yl)-11-oxo-9-propyl-6,11-dihydro-5H-benzo[b]carbazole-3-carbonitrile

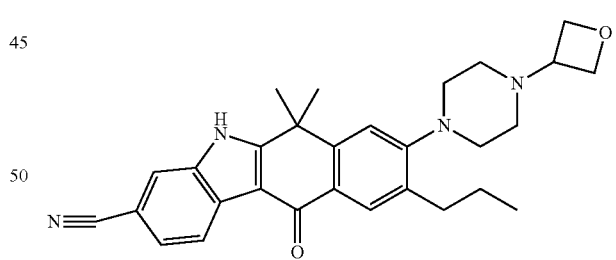

Under the same conditions as the method for synthesizing Compound B3-13-1, the title compound was prepared from Compound F5-22.

¹H-NMR (270 mHz DMSO-d₆) δ: 12.75 (1H, s), 8.30 (1H, d, J=8.2 Hz), 8.01-7.97 (2H, m), 7.59 (1H, d, J=7.1 Hz), 7.38 (1H, s), 4.51 (4H, dt, J=27.7, 6.3 Hz), 3.55-3.49 (1H, m), 3.02-2.96 (4H, m), 2.63 (2H, t, J=7.3 Hz), 2.47-2.41 (4H, m), 1.73 (6H, s), 1.70-1.61 (2H, m), 0.94 (3H, t, J=7.4 Hz).

LCMS: m/z 469 [M+H]⁺

HPLC retention time: 1.57 min (analysis condition S)

Example 355

Compound F6-9

8-[4-(4-Hydroxy-butyl)-piperazin-1-yl]-6,6-dimethyl-11-oxo-9-propyl-6,11-dihydro-5H-benzo[b]carbazole-3-carbonitrile

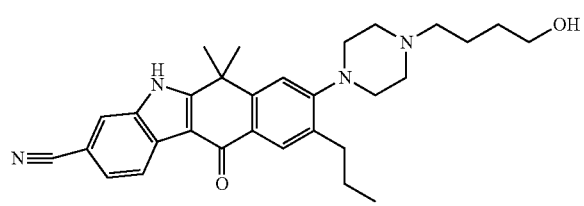 [SMILES: CCCc1cc2c(cc1N1CCN(CCCCO)CC1)C(C)(C)c1[nH]c3cc(C#N)ccc3c1C2=O]

The title compound was obtained as a by-product of the synthesis of Compound F6-8.
LCMS: m/z 485 [M+H]+
HPLC retention time: 1.61 min (analysis condition S)

Example 356

Compound F6-10

9-(3-Hydroxy-propyl)-6,6-dimethyl-8-(4-oxetan-3-yl-piperazin-1-yl)-11-oxo-6,11-dihydro-5H-benzo[b]carbazole-3-carbonitrile

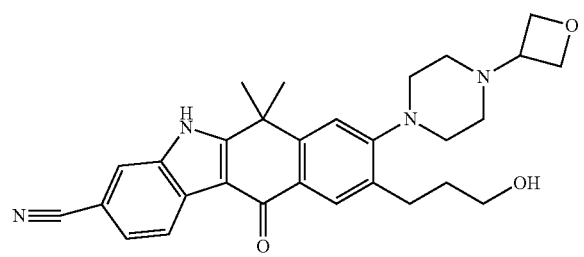 [SMILES: CC1(C)c2cc(N3CCN(C4COC4)CC3)c(CCCO)cc2C(=O)c2c1[nH]c1cc(C#N)ccc21]

Under the same conditions as the method for synthesizing Compound B3-13-1, the title compound was prepared from Compound F5-23.
LCMS: m/z 499 [M+H]+
HPLC retention time: 1.42 min (analysis condition S)

Example 357

Compound F6-11

6,6-Dimethyl-9-(3-morpholin-4-yl-propyl)-8-(4-oxetan-3-yl-piperazin-1-yl)-11-oxo-6,11-dihydro-5H-benzo[b]carbazole-3-carbonitrile

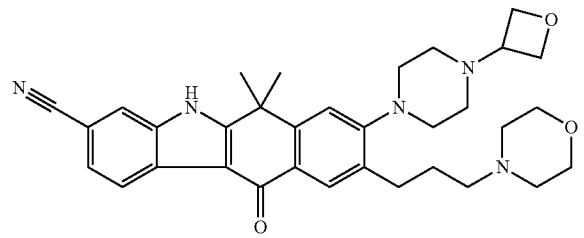 [SMILES: CC1(C)c2cc(N3CCN(C4COC4)CC3)c(CCCN3CCOCC3)cc2C(=O)c2c1[nH]c1cc(C#N)ccc21]

Under the same conditions as the method for synthesizing Compound B3-13-1, the title compound was prepared from Compound F5-26.
LCMS: m/z 554 [M+H]+
HPLC retention time: 1.50 min (analysis condition U)

Example 358

Compound F6-12

6,6-Dimethyl-8-(4-oxetan-3-yl-piperazin-1-yl)-11-oxo-9-pentyl-6,11-dihydro-5H-benzo[b]carbazole-3-carbonitrile

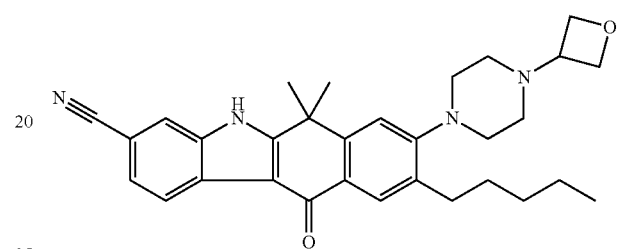

Under the same conditions as the method for synthesizing Compound B3-13-1, the title compound was prepared from Compound F5-27.
LCMS: m/z 497 [M+H]+
HPLC retention time: 2.25 min (analysis condition U)

Example 359

Compound F6-13

9-(3-Isopropoxy-prop-1-ynyl)-6,6-dimethyl-8-(4-oxetan-3-yl-piperazin-1-yl)-11-oxo-6,11-dihydro-5H-benzo[b]carbazole-3-carbonitrile

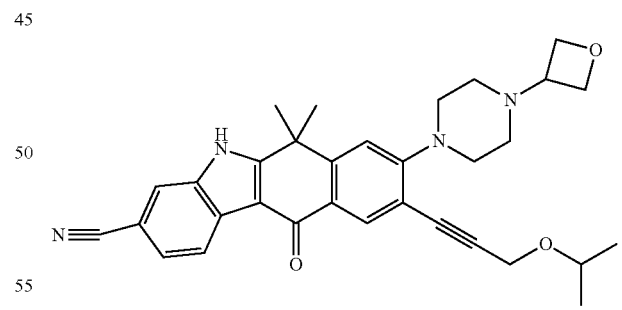

Under the same conditions as the method for synthesizing Compound A7-17, the title compound was prepared from Compound F5-23 and 2-bromopropane.
$^1$H-NMR (270 MHz, CD$_3$OD+CDCl$_3$) δ: 8.40 (1H, d, J=7.8 Hz), 8.32 (1H, s), 7.84 (1H, s), 7.53 (1H, d, J=7.8 Hz), 7.18 (1H, s), 4.80-4.68 (4H, m), 4.46 (2H, s), 3.95 (1H, m), 3.64 (1H, m), 3.46 (4H, m), 2.62 (4H, m), 1.82 (6H, s), 1.24 (6H, d, J=7.0 Hz)
LCMS: m/z 523 [M+H]+

Example 360

Compound F6-14

9-Isopropyl-6,6-dimethyl-8-(4-oxetan-3-yl-piperazin-1-yl)-11-oxo-6,11-dihydro-5H-benzo[b]carbazole-3-carbonitrile

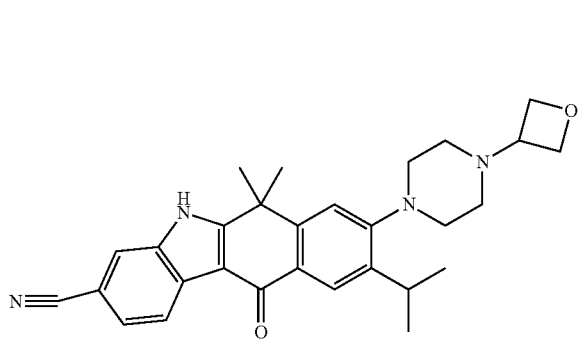

Under the same conditions as the method for synthesizing Compound B3-13-1, the title compound was prepared from Compound F5-32.

$^1$H-NMR (270 MHz, CD$_3$OD+CDCl$_3$) δ: 8.44 (1H, d, J=7.8 Hz), 8.27 (1H, s), 7.84 (1H, s), 7.54 (1H, d, J=7.8 Hz), 7.36 (1H, s), 4.82-4.70 (4H, m), 3.68 (1H, m), 3.45 (1H, m), 3.13-3.09 (4H, m), 2.64-2.62 (4H, m), 1.81 (6H, s), 1.31 (6H, d, J=7.0 Hz)

LCMS: m/z 469 [M+H]$^+$

Example 361

Compound F6-15

8-(4-Cyclopropyl-piperazin-1-yl)-9-ethyl-6,6-dimethyl-11-oxo-6,11-dihydro-5H-benzo[b]carbazole-3-carbonitrile

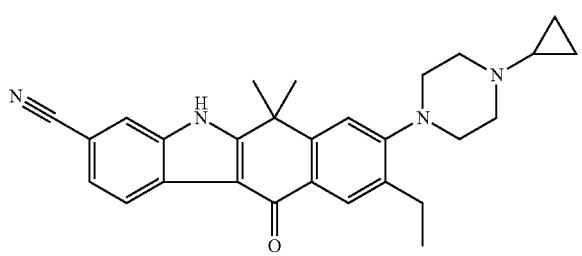 [SMILES: CCc1cc2c(cc1N1CCN(C3CC3)CC1)C(C)(C)c1[nH]c3cc(C#N)ccc3c1C2=O]

Under the same conditions as the method for synthesizing Compound B3-13-1, the title compound was prepared from Compound F5-37.

LCMS: m/z 439 [M+H]$^+$

HPLC retention time: 1.98 min (analysis condition U)

Example 362

Compound F6-16

8-(4-Cyclopropyl-piperazin-1-yl)-6,6-dimethyl-11-oxo-9-propyl-6,11-dihydro-5H-benzo[b]carbazole-3-carbonitrile

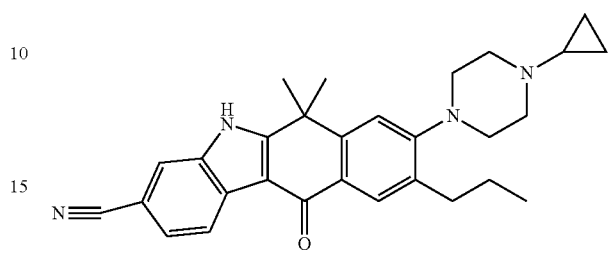

Under the same conditions as the method for synthesizing Compound B3-13-1, the title compound was prepared from Compound F5-38.

LCMS: m/z 453 [M+H]$^+$

HPLC retention time: 1.63 min (analysis condition S)

Example 363

Compound F6-17

8-(4-Cyclobutyl-piperazin-1-yl)-9-ethyl-6,6-dimethyl-11-oxo-6,11-dihydro-5H-benzo[b]carbazole-3-carbonitrile

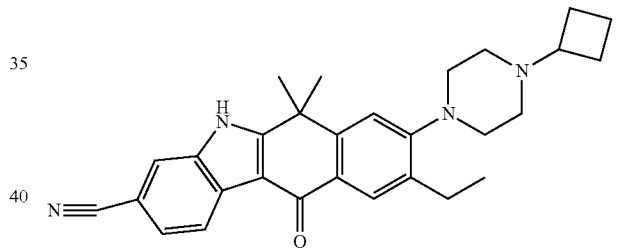

Under the same conditions as the method for synthesizing Compound B3-13-1, the title compound was prepared from Compound F5-43.

$^1$H-NMR (400 MHz, DMSO-d$_6$) δ: 12.80 (1H, s), 8.32 (1H, d, 7.9 Hz), 8.10 (1H, s), 8.02 (1H, s), 7.62 (1H, d, 7.9 Hz), 7.38 (1H, s), 3.78-3.88 (1H, m), 3.79-3.89 (1H, m), 3.48-3.54 (2H, m), 3.40-3.47 (2H, m), 3.30-3.39 (2H, m), 3.02-3.24 (4H, m), 2.73 (2H, q, 7.3 Hz), 2.30-2.41 (2H, m), 2.17-2.26 (2H, m), 1.71-1.86 (8H, m), 1.29 (3H, t, 7.3 Hz)

LCMS: m/z 453 [M+H]$^+$

HPLC retention time: 2.76 min (analysis condition W)

Methanesulfonic acid salt of Compound F6-17

8-(4-Cyclobutyl-piperazin-1-yl)-9-ethyl-6,6-dimethyl-11-oxo-6,11-dihydro-5H-benzo[b]carbazole-3-carbonitrile was dissolved in 6 volumes of DMF at room temperature and added dropwise with aqueous solution of methanesulfonic acid (2 M, 1.05 eq.). The resulting solution was added dropwise to 60 volumes of acetonitrile, and the precipitated solid was filtered and dried to obtain monomethanesulfonic acid salt of 8-(4-cyclobutyl-piperazin-1-yl)-9-ethyl-6,6-dimethyl-11-oxo-6,11-dihydro-5H-benzo[b]carbazole-3-carbonitrile.

¹H-NMR (400 MHz, DMSO-d₆) δ: 12.75 (1H, s), 8.31 (1H, J=8.4 Hz), 8.07 (1H, s), 8.01 (1H, s), 7.59 (1H, d, J=7.9 Hz), 7.38 (1H, s), 3.58-2.84 (10H, m), 2.71 (2H, q, J=7.5 Hz), 2.34 (3H, s), 2.20-2.04 (4H, m), 1.76-1.68 (8H, m), 1.26 (3H, t, J=7.5 Hz)

FABMS: m/z 453 [M+H]⁺

Example 364

Compound F6-18

8-(4-Cyclobutyl-piperazin-1-yl)-6,6-dimethyl-11-oxo-9-propyl-6,11-dihydro-5H-benzo[b]carbazole-3-carbonitrile

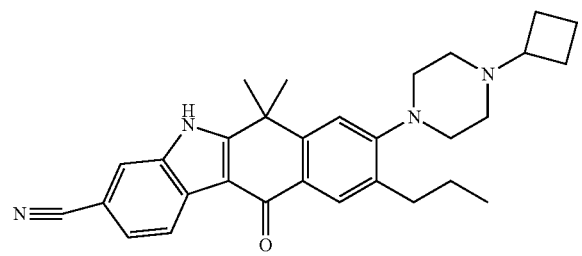

Under the same conditions as the method for synthesizing Compound B3-13-1, the title compound was prepared from Compound F5-44.

¹H-NMR (400 MHz, DMSO-d₆) δ: 12.69 (1H, s), 8.31 (1H, d, 7.9 Hz), 8.01 (1H, s), 7.99 (1H, s), 7.60 (1H, d, 7.9 Hz), 7.39 (1H, s), 2.92-3.02 (4H, m), 2.75-2.84 (1H, m), 2.65 (2H, t, 7.3 Hz), 2.38-2.48 (4H, m), 1.96-2.06 (2H, m), 1.78-1.87 (2H, m), 1.75 (6H, s), 1.62-1.73 (4H, m), 0.97 (3H, t, 7.3 Hz)

LCMS: m/z 467 [M+H]⁺

HPLC retention time: 2.96 min (analysis condition W)

Example 365

Compound F6-19

8-(4-Cyclobutyl-piperazin-1-yl)-9-isopropyl-6,6-dimethyl-11-oxo-6,11-dihydro-5H-benzo[b]carbazole-3-carbonitrile

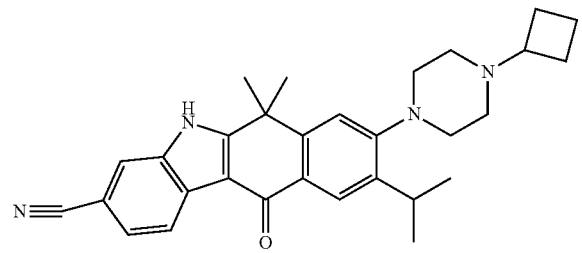 [SMILES: CCc1cc2c(cc1N1CCN(C3CCC3)CC1)C(C)(C)c1[nH]c3cc(C#N)ccc3c1C2=O]

Under the same conditions as the method for synthesizing Compound B3-13, the title compound was prepared from Compound F5-48.

LCMS: m/z 467 [M+H]⁺

HPLC retention time: 1.67 min (analysis condition S)

Example 366

Compound F6-20

9-Ethyl-6,6-dimethyl-8-(4-morpholin-4-yl-piperidin-1-yl)-11-oxo-6,11-dihydro-5H-benzo[b]carbazole-3-carbonitrile

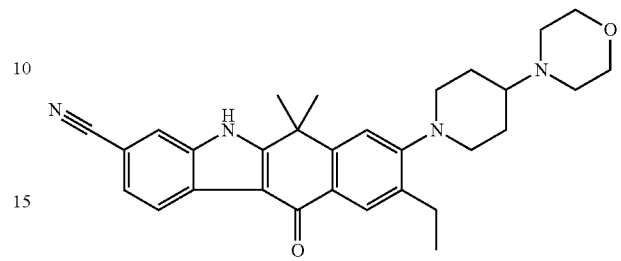

Under the same conditions as the method for synthesizing Compound B3-13-1, the title compound was prepared from Compound F5-49.

¹H-NMR (400 MHz, DMSO-d₆) δ: 12.70 (1H, s), 8.32 (1H, d, J=7.9 Hz), 8.04 (1H, s), 8.00 (1H, s), 7.61 (1H, d, J=8.5 Hz), 7.34 (1H, s), 3.64-3.57 (4H, m), 3.27-3.18 (2H, m), 2.82-2.66 (4H, m), 2.39-2.28 (1H, m), 1.96-1.87 (2H, m), 1.76 (6H, s), 1.69-1.53 (2H, m), 1.29 (3H, t, J=7.3 Hz)

LCMS: m/z 483 [M+H]⁺

HPLC retention time: 1.98 min (analysis condition U)

Hydrochloric Acid Salt of Compound F6-20

9-Ethyl-6,6-dimethyl-8-(4-morpholin-4-yl-piperidin-1-yl)-11-oxo-6,11-dihydro-5H-benzo[b]carbazole-3-carbonitrile was dissolved in a mixture solution of methylethyl ketone (10 volumes), water (4 volumes) and acetic acid (3 volumes) at 60° C. To the dissolved solution, hydrochloric acid (2 N) was added dropwise (1 volume). After stirring at 60° C. for 30 min, ethanol (25 volume) was added dropwise. The precipitated solid was filtered and dried to obtain monohydrochloric acid salt of 9-ethyl-6,6-dimethyl-8-(4-morpholin-4-yl-piperidin-1-yl)-11-oxo-6,11-dihydro-5H-benzo[b]carbazole-3-carbonitrile.

¹H-NMR (400 MHz, DMSO-d₆) δ: 12.78 (1H, s), 10.57 (1H, br. s), 8.30 (1H, J=8.4 Hz), 8.05 (1H, s), 7.99 (1H, s), 7.59 (1H, d, J=7.9 Hz), 7.36 (1H, s), 4.02-3.99 (2H, m), 3.84-3.78 (2H, m), 3.51-3.48 (2H, m), 3.15-3.13 (1H, s), 2.83-2.73 (2H, s), 2.71-2.67 (2H, s), 2.23-2.20 (2H, m), 1.94-1.83 (2H, m), 1.75 (6H, s), 1.27 (3H, t, J=7.5 Hz)

FABMS: m/z 483 [M+H]⁺

Example 367

Compound F6-21

6,6-Dimethyl-8-(4-morpholin-4-yl-piperidin-1-yl)-11-oxo-9-propyl-6,11-dihydro-5H-benzo[b]carbazole-3-carbonitrile

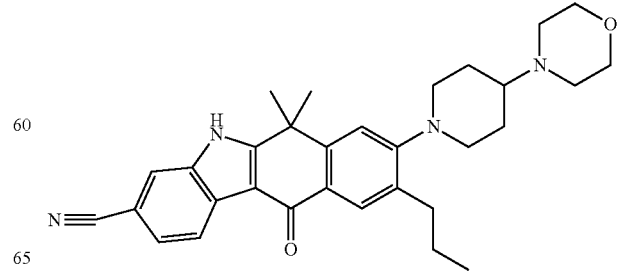

Under the same conditions as the method for synthesizing Compound B3-13-1, the title compound was prepared from Compound F5-50.

$^1$H-NMR (270 MHz, CD$_3$OD+CDCl$_3$) δ: 8.41 (1H, d, J=7.8 Hz), 8.14 (1H, s), 7.84 (1H, s), 7.53 (1H, d, J=7.8 Hz), 7.31 (1H, s), 3.77 (4H, m), 3.32 (2H, m), 2.86-2.66 (8H, m), 2.43-2.05 (3H, m), 1.79 (6H, s), 1.79-1.66 (4H, m), 1.02 (3H, t, J=7.3 Hz)

LCMS: m/z 497 [M+H]$^+$

Example 368

Compound G2

8-Methoxy-10,10-dimethyl-10,11-dihydro-5H-1,11-diaza-benzo[B]fluorene

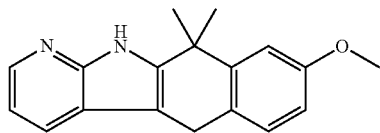 [SMILES: COc1ccc2c(c1)C(C)(C)c1[nH]c3ncccc3c1C2]

2-Hydrazinopyridine (1.3 g, 11.8 mmol) and 7-methoxy-1,1-dimethyl-3,4-dihydro-1H-naphthalen-2-one (Compound A2, 2.4 g, 11.8 mmol) were dissolved in NMP (60 mL), and stirred at 190° C. for 48 hr. The reaction solution was diluted with ethyl acetate, washed with water and dried over magnesium sulfate. The drying agent was removed by filtration and the residues obtained after concentration under reduced pressure were purified by silica gel column chromatography (hexane/ethyl acetate) to obtain the target compound (white solid, 101 mg, 3%).

$^1$H-NMR (400 MHz, DMSO-d$_6$) δ: 11.53 (1H, s), 8.16-8.12 (1H, m), 7.84 (1H, d, J=7.8 Hz), 7.23 (1H, d, J=8.4 Hz), 7.11 (1H, s), 7.03-6.98 (1H, m), 6.85-6.81 (1H, m), 3.96 (2H, s), 3.77 (3H, s), 1.64 (6H, s)

LCMS: m/z 279 [M+H]$^+$

HPLC retention time: 2.08 min (analysis condition U)

Example 369

Compound G3

8-Methoxy-10,10-dimethyl-10,11-dihydro-1,11-diaza-benzo[b]fluoren-5-one

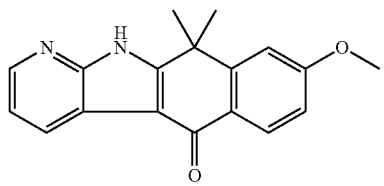 [SMILES: COc1ccc2c(c1)C(C)(C)c1[nH]c3ncccc3c1C2=O]

Under the same conditions as the method for synthesizing Compound A4, the title compound was prepared from Compound G2.

$^1$H-NMR (400 MHz, CDCl$_3$) δ: 12.95 (1H, br. s), 8.78 (1H, d, J=7.8 Hz), 8.52 (1H, d, J=4.9 Hz), 8.41 (1H, d, J=8.8 Hz), 7.37 (1H, dd, J=7.7, 5.0 Hz), 7.15 (1H, s), 7.04-7.00 (1H, m), 3.94 (3H, s), 1.98 (6H, s)

LCMS: m/z 293 [M+H]$^+$

HPLC retention time: 2.13 min (analysis condition U)

Example 370

Compound G4

8-Hydroxy-10,10-dimethyl-10,11-dihydro-1,11-diaza-benzo[b]fluoren-5-one

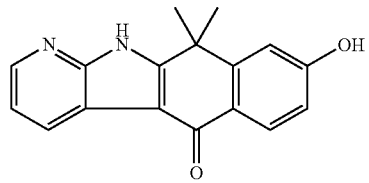 [SMILES: CC1(C)c2cc(O)ccc2C(=O)c2c1[nH]c1ncccc21]

Under the same conditions as the method for synthesizing Compound E3-2, the title compound was prepared from Compound G3.

$^1$H-NMR (400 MHz, CDCl$_3$) δ: 8.66 (1H, d, J=7.7 Hz), 8.29 (1H, d, J=4.9 Hz), 8.23 (1H, d, J=13.8 Hz), 7.29 (1H, dd, J=7.7, 5.0 Hz), 7.12 (1H, s), 6.93 (1H, d, J=8.6 Hz), 1.71 (6H, s)

LCMS: m/z 279 [M+H]$^+$

HPLC retention time: 1.72 min (analysis condition U)

Example 371

Compound G5

Trifluoro-methanesulfonic acid 10,10-dimethyl-5-oxo-10,11-dihydro-5H-1,11-diaza-benzo[b]fluoren-8-yl ester

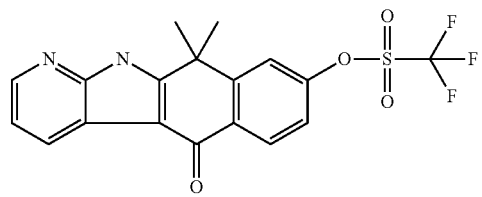 [SMILES: CC1(C)c2cc(OS(=O)(=O)C(F)(F)F)ccc2C(=O)c2c1[nH]c1ncccc21]

Under the same conditions as the method for synthesizing Compound B1, the title compound was prepared from Compound G4.

$^1$H-NMR (400 MHz, CDCl$_3$) δ: 8.81 (1H, d, J=7.8 Hz), 8.60-8.52 (2H, m), 7.55 (1H, s), 7.46-7.40 (2H, m), 2.01 (6H, s)

LCMS: m/z 411 [M+H]$^+$

HPLC retention time: 1.75 min (analysis condition U)

Example 372

Compound G6

10,10-Dimethyl-8-(4-pyrrolidin-1-yl-piperidin-1-yl)-10,11-dihydro-1,11-diaza-benzo[b]fluoren-5-one

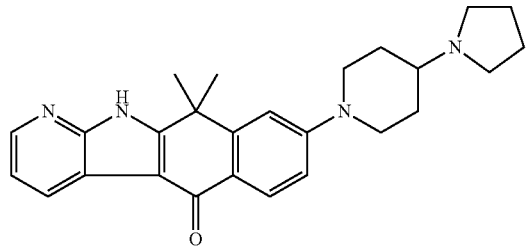 [SMILES: CC1(C)c2cc(N3CCC(N4CCCC4)CC3)ccc2C(=O)c2c1[nH]c1ncccc21]

Under the same conditions as the method for synthesizing Compound B2-1, the title compound was prepared from Compound G5 and 4-pyrrolidin-1-yl-piperidine.

$^1$H-NMR (400 MHz, CDCl$_3$) δ: 13.12 (1H, s), 8.78 (1H, d, J=7.8 Hz), 8.49 (1H, d, J=4.9 Hz), 8.29 (1H, d, J=8.8 Hz), 7.34 (1H, dd, J=7.7, 5.0 Hz), 7.06-6.98 (2H, m), 3.96-3.88 (2H, m), 3.02-3.92 (2H, m), 2.69-2.60 (4H, m), 2.32-2.23 (1H, m), 2.09-2.00 (4H, m), 1.92 (6H, s), 1.26-1.19 (4H, m)

LCMS: m/z 415 [M+H]$^+$

HPLC retention time: 1.57 min (analysis condition U)

Example 373

Compound H1

6-Acetyl-7-methoxy-1,1-dimethyl-3,4-dihydro-1H-naphthalen-2-one

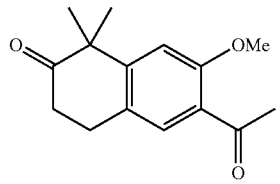 [SMILES: COc1cc2c(cc1C(C)=O)CCC(=O)C2(C)C]

To the dichloromethane (70 ml) solution of 7-methoxy-1,1-dimethyl-3,4-dihydro-1H-naphthalen-2-one (Compound A2, 3 g, 14.7 mmol), acetic anhydride (1.7 ml, 1.2 eq.) and aluminum chloride-nitrobenzene solution (1 M, 44 ml, 3 eq.) was added at 0° C., and stirred for 3 hr. Thereafter, the reaction solution was added with saturated aqueous solution of sodium hydrogen carbonate and extracted twice with dichloromethane. The organic layer was washed with brine and dried over magnesium sulfate. The drying agent was removed by filtration and the residues obtained after concentration under reduced pressure were purified by silica gel column chromatography (ethyl acetate/hexane) to obtain the title compound as a crude product.

Example 374

Compound H2-1

1-(3-Bromo-8-methoxy-6,6-dimethyl-6,11-dihydro-5H-benzo[b]carbazol-9-yl)-ethanone

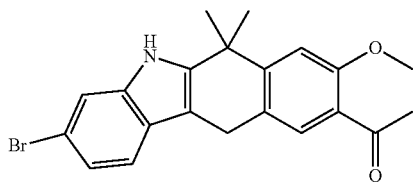 [SMILES: COc1cc2c(cc1C(C)=O)Cc1c([nH]c3cc(Br)ccc13)C2(C)C]

Under the same conditions as the method for synthesizing Compound A3-1, the title compound was prepared from Compound H1 and (3-bromo-phenyl)-hydrazine.

LCMS: m/z 398 [M+H]$^+$

HPLC retention time: 3.97 min (analysis condition Y)

Example 375

Compound H2-2

1-(1-Bromo-8-methoxy-6,6-dimethyl-6,11-dihydro-5H-benzo[b]carbazol-9-yl)-ethanone

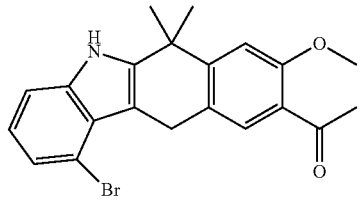 [SMILES: COc1cc2c(cc1C(C)=O)Cc1c([nH]c3cccc(Br)c13)C2(C)C]

The title compound was obtained as a by-product of the synthesis of Compound H2-1.

LCMS: m/z 398 [M+H]$^+$

HPLC retention time: 3.97 min (analysis condition Y)

Example 376

Compound H3

9-Acetyl-3-bromo-8-methoxy-6,6-dimethyl-5,6-dihydro-benzo[b]carbazol-11-one

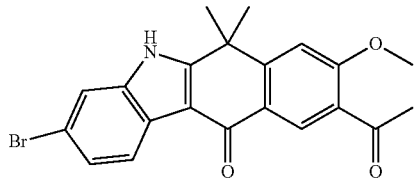 [SMILES: COc1cc2c(cc1C(C)=O)C(=O)c1c([nH]c3cc(Br)ccc13)C2(C)C]

Under the same conditions as the method for synthesizing Compound A4, the title compound was prepared from Compound H2.

$^1$H-NMR (300 MHz, DMSO-d$_6$) δ: 1.80 (6H, s), 2.58 (3H, s), 4.06 (3H, s), 7.38 (1H, dd, 8.39 Hz, 1.91 Hz), 7.51 (1H, s), 7.67 (1H, bs, 1.53 Hz), 8.10 (1H, d, 8.39 Hz), 8.41 (1H, s), 12.3 (1H, s)

LCMS: m/z 412, 414 [M+H]$^+$

HPLC retention time: 2.73 min (analysis condition U)

Example 377

Compound H4

9-Acetyl-8-methoxy-6,6-dimethyl-11-oxo-6,11-dihydro-5H-benzo[b]carbazole-3-carbonitrile

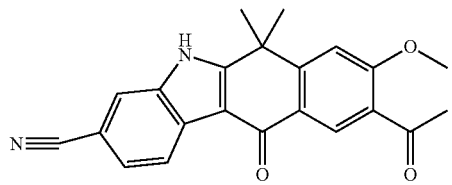 [SMILES: COc1cc2c(cc1C(C)=O)C(=O)c1c([nH]c3cc(C#N)ccc13)C2(C)C]

According to the same method as the method for synthesizing Compound A5-2, the title compound was prepared from Compound H3.

$^1$H-NMR (300 MHz, DMSO-d$_6$) δ: 1.83 (6H, s), 2.58 (3H, s), 4.07 (3H, s), 7.53 (1H, s), 7.61 (1H, d, 8.01 Hz), 8.03 (1H, s), 8.31 (1H, d, 8.77 Hz), 8.42 (1H, s), 12.8 (1H, s).

LCMS: m/z 359 [M+H]$^+$

HPLC retention time: 2.47 min (analysis condition U)

Example 378

Compound H5

9-Acetyl-8-hydroxy-6,6-dimethyl-11-oxo-6,11-di-hydro-5H-benzo[b]carbazole-3-carbonitrile

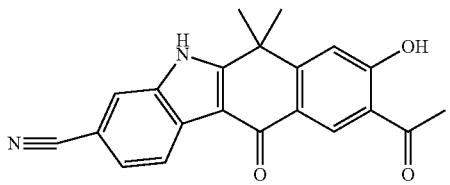 [SMILES: CC(=O)c1cc2c(cc1O)C(C)(C)c1[nH]c3cc(C#N)ccc3c1C2=O]

Under the same conditions as the method for synthesizing Compound A6, the title compound was prepared from Compound H4.

$^1$H-NMR (300 MHz, DMSO-$d_6$) δ: 1.77 (6H, s), 2.75 (3H, s), 7.43 (1H, s), 7.63 (1H, d, 8.01 Hz), 8.02 (1H, s), 8.32 (1H, d, 8.01 Hz), 8.67 (1H, s), 12.2 (1H, s), 12.8 (1H, s).
LCMS: m/z 345 [M+H]$^+$
HPLC retention time: 2.27 min (analysis condition S)

Example 379

Compound H6-1

9-Acetyl-6,6-dimethyl-11-oxo-8-(tetrahydro-pyran-4-yloxy)-6,11-dihydro-5H-benzo[b]carbazole-3-carbonitrile

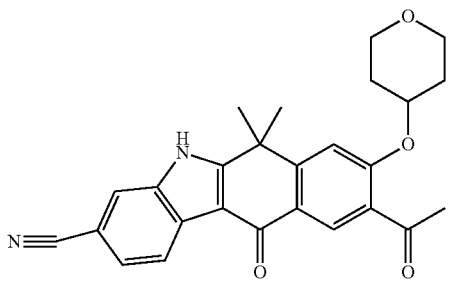 [SMILES: CC(=O)c1cc2c(cc1OC1CCOCC1)C(C)(C)c1[nH]c3cc(C#N)ccc3c1C2=O]

Under the same conditions as the method for synthesizing Compound A7-1, the title compound was prepared from Compound H5 and tetrahydropyran-4-ol.
LCMS: m/z 429 [M+H]$^+$
HPLC retention time: 2.48 min (analysis condition U)

Example 380

Compound H6-2

9-Acetyl-8-(2-diethylamino-ethoxy)-6,6-dimethyl-11-oxo-6,11-dihydro-5H-benzo[b]carbazole-3-carbonitrile

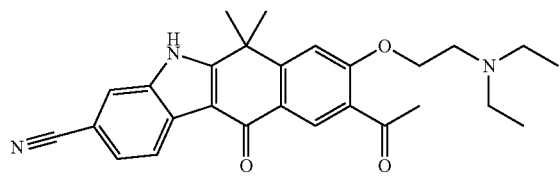 [SMILES: CCN(CC)CCOc1cc2c(cc1C(C)=O)C(=O)c1c([nH]c3cc(C#N)ccc13)C2(C)C]

Under the same conditions as the method for synthesizing Compound A7-17, the title compound was prepared from Compound H5.
LCMS: m/z 444 [M+H]$^+$
HPLC retention time: 2.05 min (analysis condition U)

Example 381

Compound H7

Trifluoro-methanesulfonic acid 9-acetyl-3-cyano-6,6-dimethyl-11-oxo-6,11-dihydro-5H-benzo[b]carbazol-8-yl ester

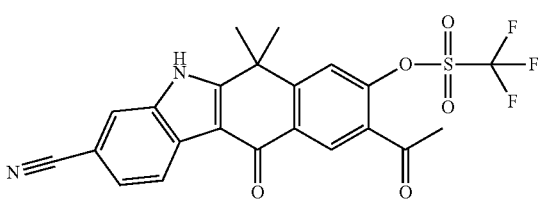 [SMILES: CC(=O)c1cc2c(cc1OS(=O)(=O)C(F)(F)F)C(C)(C)c1[nH]c3cc(C#N)ccc3c1C2=O]

Under the same conditions as the method for synthesizing Compound B1, the title compound was prepared from Compound H5.

$^1$H-NMR (300 MHz, DMSO-$d_6$) δ: 1.83 (6H, s), 2.74 (3H, s), 7.68 (1H, dd, 8.01 Hz, 1.53 Hz), 8.08 (2H, s), 8.33 (1H, d, 8.77 Hz), 8.79 (1H, s), 12.9 (1H, s).

Example 382

Compound H8-1

9-Acetyl-6,6-dimethyl-11-oxo-8-(4-pyrrolidin-1-yl-piperidin-1-yl)-6,11-dihydro-5H-benzo[b]carbazole-3-carbonitrile

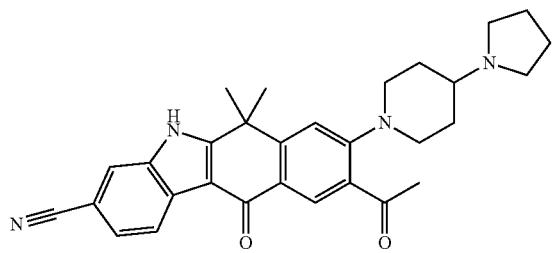 [SMILES: CC(=O)c1cc2c(cc1N1CCC(N3CCCC3)CC1)C(C)(C)c1[nH]c3cc(C#N)ccc3c1C2=O]

Under the same conditions as the method for synthesizing Compound B2-1, the title compound was prepared from Compound H7 and 4-pyrrolidin-1-yl-piperidine.

$^1$H-NMR (300 MHz, DMSO-$d_6$) δ: 1.65 (2H, m), 1.69 (4H, s), 1.79 (6H, s), 1.95 (2H, m), 2.18 (1H, m), 2.54 (4H, s), 2.59 (3H, s), 2.93 (2H, t, 11.8 Hz), 3.37 (2H, m), 7.36 (1H, s), 7.60 (1H, d, 8.01), 8.01 (1H, s), 8.13 (1H, s), 8.30 (1H, d, 8.39), 12.7 (1H, s).
LCMS: m/z 481 [M+H]$^+$
HPLC retention time: 2.03 min (analysis condition U)

Example 383

Compound H8-2

9-Acetyl-8-(4-isopropyl-piperazin-1-yl)-6,6-dimethyl-11-oxo-6,11-dihydro-5H-benzo[b]carbazole-3-carbonitrile

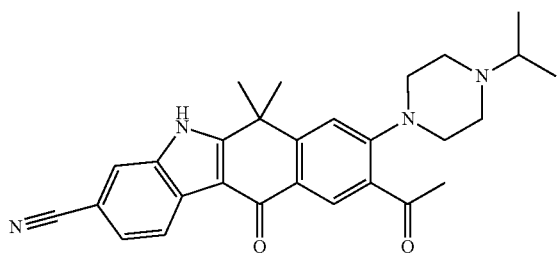 [SMILES: CC(=O)c1cc2c(cc1N1CCN(C(C)C)CC1)C(C)(C)c1[nH]c3cc(C#N)ccc3c1C2=O]

Under the same conditions as the method for synthesizing Compound B2-1, the title compound was prepared from Compound H7.
LCMS: m/z 455 [M+H]$^+$
HPLC retention time: 2.02 min (analysis condition U)

Example 384

Compound H8-3

9-Acetyl-6,6-dimethyl-8-morpholin-4-yl-11-oxo-6,11-dihydro-5H-benzo[b]carbazole-3-carbonitrile

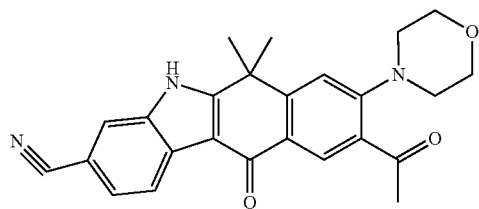 [SMILES: CC(=O)c1cc2c(cc1N1CCOCC1)C(C)(C)c1[nH]c3cc(C#N)ccc3c1C2=O]

Under the same conditions as the method for synthesizing Compound B2-1, the title compound was prepared from Compound H7 and morpholine.
LCMS: m/z 414 [M+H]$^+$
HPLC retention time: 2.11 min (analysis condition S)

Example 385

Compound H8-4

9-Acetyl-6,6-dimethyl-8-(4-morpholin-4-yl-piperidin-1-yl)-11-oxo-6,11-dihydro-5H-benzo[b]carbazole-3-carbonitrile

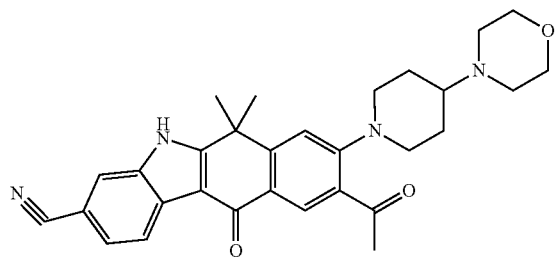 [SMILES: CC(=O)c1cc2c(cc1N1CCC(N3CCOCC3)CC1)C(C)(C)c1[nH]c3cc(C#N)ccc3c1C2=O]

Under the same conditions as the method for synthesizing Compound B2-1, the title compound was prepared from Compound H7 and 4-piperidin-4-yl-morpholine.
LCMS: m/z 497 [M+H]$^+$
HPLC retention time: 1.45 min (analysis condition S)

Example 386

Compound H8-5

9-Acetyl-6,6-dimethyl-11-oxo-8-piperazin-1-yl-6,11-dihydro-5H-benzo[b]carbazole-3-carbonitrile

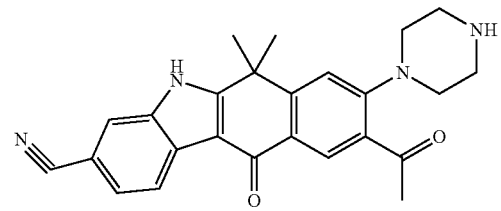 [SMILES: CC(=O)c1cc2c(cc1N1CCNCC1)C(C)(C)c1[nH]c3cc(C#N)ccc3c1C2=O]

Under the same conditions as the method for synthesizing Compound B2-1, the title compound was prepared from Compound H7 and piperazine.
LCMS: m/z 413 [M+H]$^+$
HPLC retention time: 1.71 min (analysis condition U)

Example 387

Compound H9-1

9-Acetyl-8-(4-cyclobutyl-piperazin-1-yl)-6,6-dimethyl-11-oxo-6,11-dihydro-5H-benzo[b]carbazole-3-carbonitrile

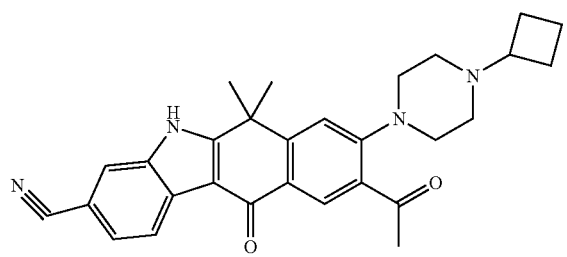 [SMILES: CC(=O)c1cc2c(cc1N1CCN(C3CCC3)CC1)C(C)(C)c1[nH]c3cc(C#N)ccc3c1C2=O]

Under the same conditions as the method for synthesizing Compound B3-32, the title compound was prepared from Compound H8-5 and cyclobutanone.
LCMS: m/z 467 [M+H]$^+$
HPLC retention time: 1.82 min (analysis condition U)

Example 388

Compound H9-2

9-Acetyl-6,6-dimethyl-11-oxo-8-[4-(tetrahydropyran-4-yl)-piperazin-1-yl]-6,11-dihydro-5H-benzo[b]carbazole-3-carbonitrile

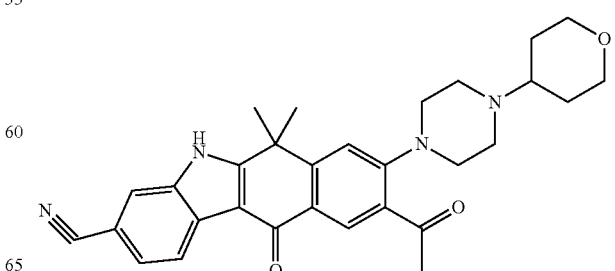

Under the same conditions as the method for synthesizing Compound B3-32, the title compound was prepared from Compound H8-5 and tetrahydropyran-4-one.
LCMS: m/z 497 [M+H]+
HPLC retention time: 1.76 min (analysis condition U)

Example 389

Compound H9-3

9-Acetyl-8-[4-(1,1-dimethyl-prop-2-ynyl)-piperazin-1-yl]-6,6-dimethyl-11-oxo-6,11-dihydro-5H-benzo[b]carbazole-3-carbonitrile

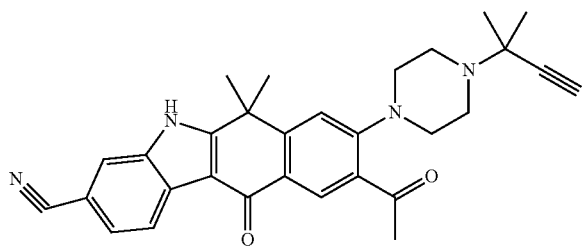 [SMILES: C#CC(C)(C)N1CCN(c2cc3c(cc2C(C)=O)C(=O)c2c([nH]c4cc(C#N)ccc24)C3(C)C)CC1]

To the anhydrous THF solution (0.5 mL) of 9-acetyl-6,6-dimethyl-11-oxo-8-piperazin-1-yl-6,11-dihydro-5H-benzo[b]carbazole-3-carbonitrile (Compound H8-5, 25 mg, 0.06 mmol), 3-chloro-3-methyl-but-1-yne (0.013 mL, 0.12 mmol), copper (I) chloride (0.6 mg, 0.006 mmol) and triethylamine (0.017 mL, 0.12 mmol) were added at room temperature. After stirring for 30 min, the mixture was added with water and extracted with ethyl acetate. The organic layer was dried over magnesium sulfate. The drying agent was removed by filtration and the residues obtained after concentration under reduced pressure were purified by amino silica gel column chromatography (dichloromethane/methanol) to obtain the title compound (white solid, 9.8 mg, 35%).
LCMS: m/z 479 [M+H]+
HPLC retention time: 1.88 min (analysis condition U)

Example 390

Compound I1-1

6-Chloro-7-methoxy-1,1-dimethyl-3,4-dihydro-1H-naphthalen-2-one

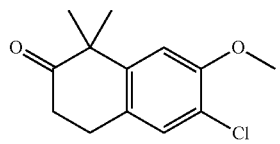 [SMILES: COc1cc2c(cc1Cl)CCC(=O)C2(C)C]

7-Methoxy-1,1-dimethyl-3,4-dihydro-1H-naphthalen-2-one (Compound A2, 3.37 g, 16.5 mmol) was dissolved in CH₃CN (82 mL), added with NCS (2.42 g, 1.1 eq.) and stirred at 90° C. for 1.5 hr. The reaction solution was extracted with ethyl acetate. The organic layer was washed with saturated brine and dried over sodium sulfate. The drying agent was removed and the target compound was obtained after concentration under reduced pressure (yellow oily substance, 4.45 g).
¹H-NMR (400 MHz, CDCl₃) δ: 7.16 (1H, s), 6.85 (1H, s), 3.90 (3H, s), 3.00 (2H, t, J=6.8 Hz), 2.65 (2H, t, J=6.8 Hz), 1.42 (6H, s).

LCMS: m/z 239 [M+H]+
HPLC retention time: 2.80 min (analysis condition U)

Example 391

Compound I1-2

9-Chloro-8-methoxy-6,6-dimethyl-6,11-dihydro-5H-benzo[b]carbazole-3-carbonitrile

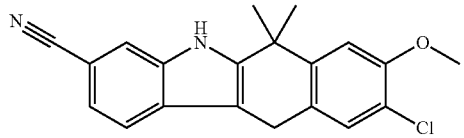 [SMILES: COc1cc2c(cc1Cl)Cc1c([nH]c3cc(C#N)ccc13)C2(C)C]

6-Chloro-7-methoxy-1,1-dimethyl-3,4-dihydro-1H-naphthalen-2-one (Compound I1-1, 4.45 g, 16.5 mmol) and 3-hydrazinobenzonitrile (2.63 g, 1.2 eq.) were dissolved in TFA (91 mL), and stirred at 90° C. for 3 hr. According to the concentration under reduced pressure, TFA was removed and the residues were added with saturated aqueous solution of NaHCO₃, followed by extraction with ethyl acetate. The organic layer was washed with saturated brine and dried over sodium sulfate. The drying agent was removed by filtration and the residues obtained after concentration under reduced pressure were added with ethyl acetate. After stirring at room temperature, the precipitated solid was separated by filtration. The filtrate was concentrated under reduced pressure to obtain the title compound as a mixture with I1-3 (red powder, 6.46 g).

Example 392

Compound I1-3

9-Chloro-8-methoxy-6,6-dimethyl-6,11-dihydro-5H-benzo[b]carbazole-1-carbonitrile

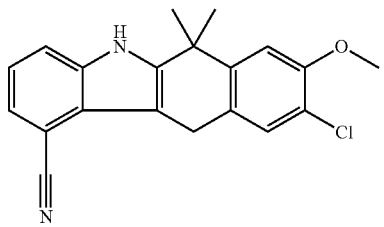 [SMILES: COc1cc2c(cc1Cl)Cc1c([nH]c3cccc(C#N)c13)C2(C)C]

The title compound was obtained as a by-product of the synthesis of Compound I1-2.
¹H-NMR (400 MHz, DMSO-d₆) δ: 11.66 (1H, s), 7.65-7.69 (1H, m), 7.44-7.48 (1H, m), 7.39 (1H, s), 7.29 (1H, s), 7.17-7.23 (1H, m), 4.21 (2H, s), 3.91 (3H, s), 1.69 (6H, s).
LCMS: m/z 337 [M+H]+
HPLC retention time: 3.15 min (analysis condition U)

Example 393

Compound I2-1

2-(4-Chloro-3-methoxy-phenyl)-2-methyl-propionitrile

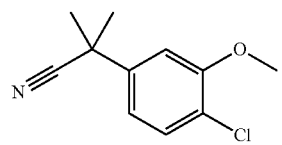

1-Chloro-4-fluoro-2-methoxy-benzene (4.3 g, 26.78 mmol) and isobutyronitrile (9.61 mL, 4.0 eq.) were dissolved in toluene (9.0 mL), added with KHMDS (80 mL, 0.5 M toluene solution) and stirred at 65° C. for 2 hr. The reaction solution was cooled to room temperature, added with aqueous solution of 1 N hydrochloric acid and then extracted with MTBE. The organic layer was washed with saturated brine and dried over magnesium sulfate. The drying agent was removed by filtration and the residues obtained after concentration under reduced pressure were purified by silica gel column chromatography (hexane/ethyl acetate) to obtain the title compound (1.72 g, 31%).

$^1$H-NMR (270 MHz, CDCl$_3$) δ: 7.37 (1H, d, J=8.4 Hz), 7.05 (1H, d, J=2.1 Hz), 6.97 (1H, dd, J=8.2, 2.1 Hz), 3.95 (3H, s), 1.73 (6H, s).

HPLC retention time: 2.33 min (analysis condition S)

Example 394

Compound I2-2

4-(4-Chloro-3-methoxy-phenyl)-4-methyl-3-oxo-pentanoic acid ethyl ester

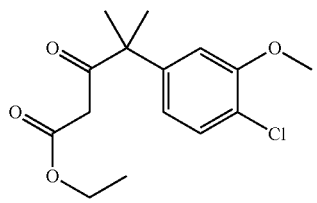 [SMILES: CCOC(=O)CC(=O)C(C)(C)c1ccc(Cl)c(OC)c1]

Under the same conditions as the method for synthesizing Compound K3, the title compound was prepared from Compound I2-1.

$^1$H-NMR (270 MHz, DMSO-d$_6$) δ: 7.42 (1H, d, J=8.1 Hz), 6.92 (1H, d, J=2.1 Hz), 6.86 (1H, dd, J=8.2, 2.3 Hz), 4.01 (2H, q, J=7.1 Hz), 3.87 (3H, s), 3.43 (2H, s), 1.44 (6H, s), 1.12 (3H, t, J=7.2 Hz).

LCMS: m/z 299, 301 [M+H]$^+$

HPLC retention time: 2.52, 3.05 min (analysis condition S)

Example 395

Compound I2-3

4-(4-Chloro-3-methoxy-phenyl)-2-(4-cyano-2-nitro-phenyl)-4-methyl-3-oxo-pentanoic acid ethyl ester

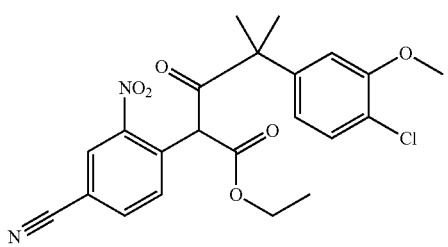 [SMILES: CCOC(=O)C(C(=O)C(C)(C)c1ccc(Cl)c(OC)c1)c1ccc(C#N)cc1[N+](=O)[O-]]

Under the same conditions as the method for synthesizing Compound K4, the title compound was obtained as a crude product from Compound I2-2.

Example 396

Compound I2-4

2-[1-(4-Chloro-3-methoxy-phenyl)-1-methyl-ethyl]-6-cyano-1H-indole-3-carboxylic acid ethyl ester

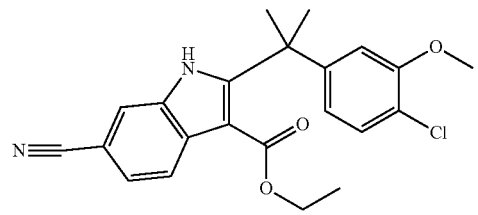 [SMILES: CCOC(=O)c1c(C(C)(C)c2ccc(Cl)c(OC)c2)[nH]c2cc(C#N)ccc12]

Under the same conditions as the method for synthesizing Compound K5, the title compound was obtained from Compound I2-3.

LCMS: m/z 397, 399 [M+H]$^+$

HPLC retention time: 2.83 min (analysis condition S)

Example 397

Compound I3

9-Chloro-8-methoxy-6,6-dimethyl-11-oxo-6,11-dihydro-5H-benzo[b]carbazole-3-carbonitrile

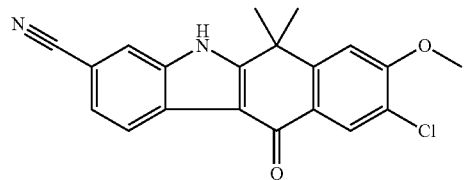 [SMILES: COc1cc2c(cc1Cl)C(=O)c1c([nH]c3cc(C#N)ccc13)C2(C)C]

(Method 1) Under the same conditions as the method for synthesizing Compound A4, the title compound was obtained from Compound I1-2.

(Method 2) Under the same conditions as the method for synthesizing Compound L8-1, the title compound was obtained from Compound I2-4.

$^1$H-NMR (400 MHz, DMSO-d$_6$) δ: 12.79 (1H, s), 8.27-8.31 (1H, m), 8.12 (1H, s), 8.00-8.02 (1H, m), 7.58-7.63 (1H, m), 7.51 (1H, s), 4.03 (3H, s), 1.80 (6H, s).

LCMS: m/z 351 [M+H]$^+$

HPLC retention time: 2.87 min (analysis condition U)

Example 398

Compound I4

9-Chloro-8-hydroxy-6,6-dimethyl-11-oxo-6,11-dihydro-5H-benzo[b]carbazole-3-carbonitrile

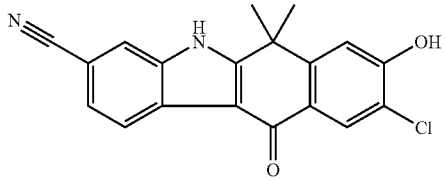 [SMILES: CC1(C)c2cc(O)c(Cl)cc2C(=O)c2c1[nH]c1cc(C#N)ccc21]

Under the same conditions as the method for synthesizing Compound E3-2, the title compound was prepared from Compound I3.

LCMS: m/z 337 [M+H]+
HPLC retention time: 2.47 min (analysis condition U)

Example 399

Compound I5

Trifluoro-methanesulfonic acid 9-chloro-3-cyano-6,6-dimethyl-11-oxo-6,11-dihydro-5H-benzo[b]carbazol-8-yl ester

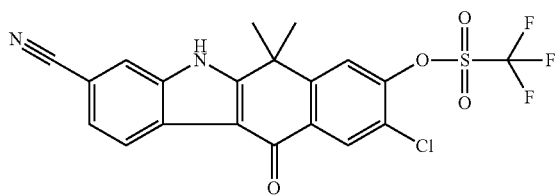 [SMILES: CC1(C)c2cc(OS(=O)(=O)C(F)(F)F)c(Cl)cc2C(=O)c2c1[nH]c1cc(C#N)ccc21]

Under the same conditions as the method for synthesizing Compound B1, the title compound was prepared from Compound I4.
LCMS: m/z 469 [M+H]+
HPLC retention time: 3.40 min (analysis condition U)

Example 400

Compound I6-1

9-Chloro-6,6-dimethyl-11-oxo-8-(4-pyrrolidin-1-yl-piperidin-1-yl)-6,11-dihydro-5H-benzo[b]carbazole-3-carbonitrile

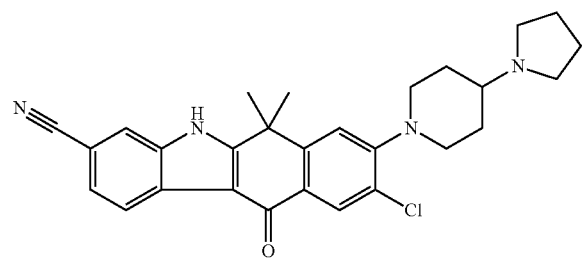 [SMILES: CC1(C)c2cc(N3CCC(N4CCCC4)CC3)c(Cl)cc2C(=O)c2c1[nH]c1cc(C#N)ccc21]

Under the same conditions as the method for synthesizing Compound B2-1, the title compound was prepared from Compound I5 and 4-pyrrolidin-1-yl-piperidine.
LCMS: m/z 473 [M+H]+
HPLC retention time: 2.25 min (analysis condition U)

Example 401

Compound I6-2

9-Chloro-8-(4-isopropyl-piperazin-1-yl)-6,6-dimethyl-11-oxo-6,11-dihydro-5H-benzo[b]carbazole-3-carbonitrile

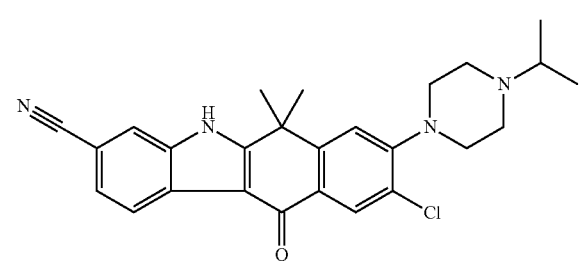 [SMILES: CC(C)N1CCN(c2cc3c(cc2Cl)C(=O)c2c([nH]c4cc(C#N)ccc24)C3(C)C)CC1]

Under the same conditions as the method for synthesizing Compound B2-1, the title compound was prepared from Compound I5.
LCMS: m/z 447 [M+H]+
HPLC retention time: 2.30 min (analysis condition U)

Example 402

Compound I6-3

9-Chloro-6,6-dimethyl-8-morpholin-4-yl-11-oxo-6,11-dihydro-5H-benzo[b]carbazole-3-carbonitrile

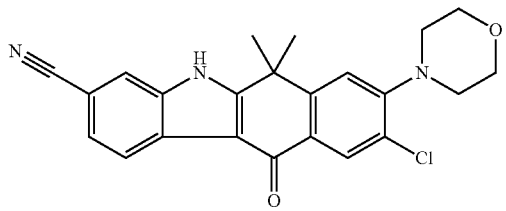 [SMILES: CC1(C)c2cc(N3CCOCC3)c(Cl)cc2C(=O)c2c1[nH]c1cc(C#N)ccc21]

Under the same conditions as the method for synthesizing Compound B2-1, the title compound was prepared from 15 and morpholine.
$^1$H-NMR (400 MHz, DMSO-$d_6$) δ: 12.79 (1H, s), 8.28 (1H, d, 8.0 Hz), 8.09 (1H, s), 8.00 (1H, s), 7.59 (1H, d, 8.0 Hz), 7.45 (1H, s), 3.75-3.81 (4H, m), 3.13-3.19 (4H, m), 1.76 (6H, s)
LCMS: m/z 406 [M+H]+
HPLC retention time: 2.88 min (analysis condition U)

Example 403

Compound I6-4

9-Chloro-6,6-dimethyl-8-(4-morpholin-4-yl-piperidin-1-yl)-11-oxo-6,11-dihydro-5H-benzo[b]carbazole-3-carbonitrile

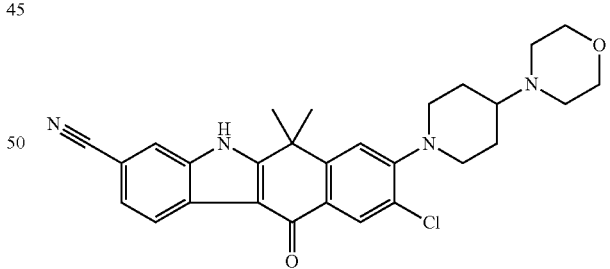

Under the same conditions as the method for synthesizing Compound B2-1, the title compound was prepared from Compound I5 and 4-piperidin-4-yl-morpholine.
$^1$H-NMR (400 MHz, DMSO-$d_6$) δ: 12.75 (1H, s), 8.28 (1H, d, 8.0 Hz), 8.07 (1H, s), 8.00 (1H, s), 7.59 (1H, d, 8.0 Hz), 7.41 (1H, s), 3.55-3.62 (4H, m), 3.47-3.56 (4H, m), 2.75-2.86 (2H, m), 2.45-2.55 (4H, m), 2.28-2.39 (1H, m), 1.86-1.96 (2H, m), 1.76 (6H, s), 1.52-1.66 (2H, m)
LCMS: m/z 489 [M+H]+
HPLC retention time: 1.97 min (analysis condition U)

Example 404

Compound I6-5-1

[1-(9-Chloro-3-cyano-6,6-dimethyl-11-oxo-6,11-dihydro-5H-benzo[b]carbazol-8-yl)-piperidin-4-yl]-carbamic acid tert-butyl ester

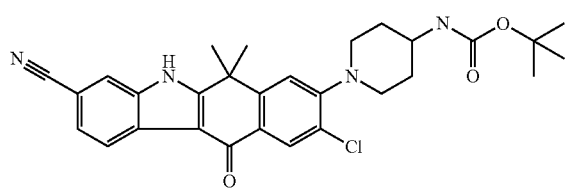 [SMILES: CC(C)(C)OC(=O)NC1CCN(c2cc3c(cc2Cl)C(=O)c2c([nH]c4cc(C#N)ccc24)C3(C)C)CC1]

Under the same conditions as the method for synthesizing Compound B2-1, the title compound was prepared from Compound I5 and piperidin-4-yl-carbamic acid tert-butyl ester.
LCMS: m/z 519 [M+H]$^+$
HPLC retention time: 3.27 min (analysis condition U)

Example 405

Compound I6-5-2

8-(4-Amino-piperidin-1-yl)-9-chloro-6,6-dimethyl-11-oxo-6,11-dihydro-5H-benzo[b]carbazole-3-carbonitrile

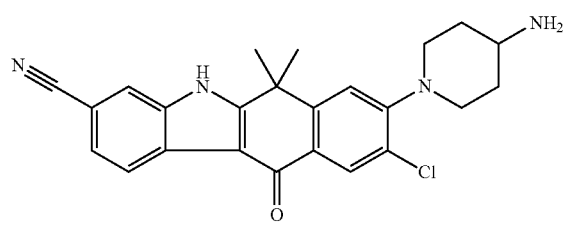

Under the same conditions as the method for synthesizing Compound A8-1, the title compound was prepared from Compound I6-5-1.
LCMS: m/z 419 [M+H]$^+$
HPLC retention time: 2.12 min (analysis condition U)

Example 406

Compound I6-6

9-Chloro-6,6-dimethyl-11-oxo-8-piperazin-1-yl-6,11-dihydro-5H-benzo[b]carbazole-3-carbonitrile

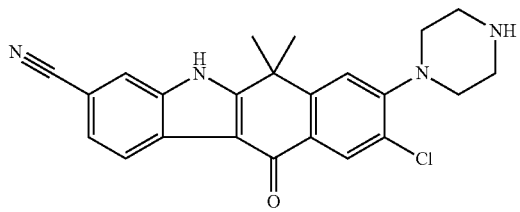 [SMILES: CC1(C)c2cc(N3CCNCC3)c(Cl)cc2C(=O)c2c1[nH]c1cc(C#N)ccc21]

Under the same conditions as the method for synthesizing Compound B2-1, the title compound was prepared from Compound I5 and piperazine.
LCMS: m/z 405 [M+H]$^+$
HPLC retention time: 1.87 min (analysis condition U)

Example 407

Compound I7-1

N-[1-(9-Chloro-3-cyano-6,6-dimethyl-11-oxo-6,11-dihydro-5H-benzo[b]carbazol-8-yl)-piperidin-4-yl]-methanesulfonamide

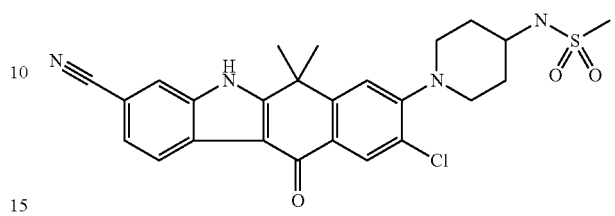

Under the same conditions as the method for synthesizing Compound A9-1, the title compound was prepared from Compound I6-5-2.
LCMS: m/z 497 [M+H]$^+$
HPLC retention time: 2.62 min (analysis condition U)

Example 408

Compound I7-2

9-Chloro-6,6-dimethyl-8-(4-oxetan-3-yl-piperazin-1-yl)-11-oxo-6,11-dihydro-5H-benzo[b]carbazole-3-carbonitrile

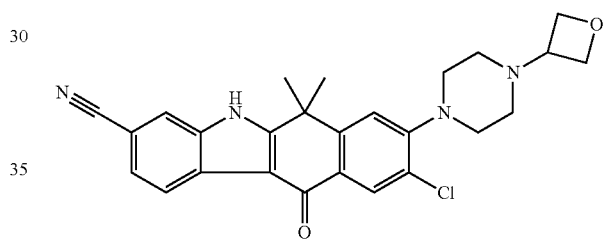

Under the same conditions as the method for synthesizing Compound B2-1, the title compound was prepared from Compound I5 and 1-oxetan-3-yl-piperazine.
$^1$H-NMR (400 MHz, DMSO-d$_6$) δ: 12.78 (1H, s), 8.27-8.31 (1H, m), 8.07-8.09 (1H, s), 7.99-8.02 (1H, m), 7.59-7.62 (1H, m), 7.44-7.46 (1H, s), 4.54-4.60 (2H, m), 4.44-4.51 (2H, m), 3.47-3.55 (1H, m), 3.16-3.24 (4H, m), 2.40-2.55 (4H, m), 1.77 (6H, s)
LCMS: m/z 461 [M+H]$^+$
HPLC retention time: 2.13 min (analysis condition U)

Example 409

Compound I7-3

9-Chloro-8-(4-cyclopropyl-piperazin-1-yl)-6,6-dimethyl-11-oxo-6,11-dihydro-5H-benzo[b]carbazole-3-carbonitrile

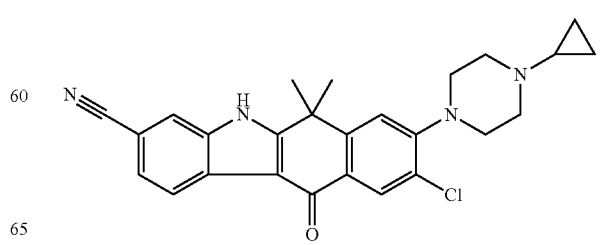

Under the same conditions as the method for synthesizing Compound B2-1, the title compound was prepared from Compound I5 and 1-cyclopropylpiperazine.
LCMS: m/z 445 [M+H]+
HPLC retention time: 1.97 min (analysis condition U)

Example 410

Compound I7-4

9-Chloro-8-(4-cyclobutyl-piperazin-1-yl)-6,6-dimethyl-11-oxo-6,11-dihydro-5H-benzo[b]carbazole-3-carbonitrile

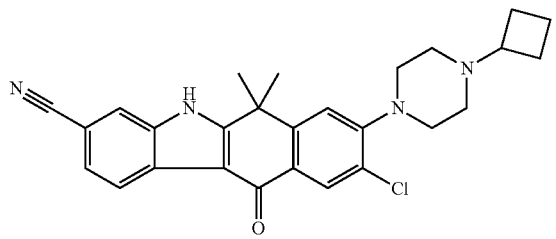 [SMILES: CC1(C)c2cc(N3CCN(C4CCC4)CC3)c(Cl)cc2C(=O)c2c1[nH]c1cc(C#N)ccc21]

Under the same conditions as the method for synthesizing Compound B3-32, the title compound was prepared from Compound I6-6 and cyclobutanone.
$^1$H-NMR (400 MHz, DMSO-d$_6$) δ: 12.78 (1H, s), 8.29 (1H, d, 8.5 Hz), 8.08 (1H, s), 8.01 (1H, s), 7.60 (1H, d, 8.5 Hz), 7.44 (1H, s), 3.17-3.15 (4H, m), 2.83-2.76 (1H, m), 2.47-2.44 (4H, m), 2.04-1.97 (2H, m), 1.82 (2H, t, 9.8 Hz), 1.77 (6H, s), 1.70-1.63 (2H, m)
LCMS: m/z 459, 461 [M+H]+
HPLC retention time: 1.63 min (analysis condition S)

Example 411

Compound J2

6-Methoxy-1,1-dimethyl-3,4-dihydro-1H-naphthalen-2-one

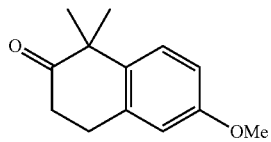

Under the same conditions as the method for synthesizing Compound A2, the title compound was prepared from 6-methoxy-3,4-dihydro-1H-naphthalen-2-one and iodomethane.
LCMS: m/z 205 [M+H]+
HPLC retention time: 1.54 min (analysis condition S)

Example 412

Compound J3-1

9-Methoxy-6,6-dimethyl-6,11-dihydro-5H-benzo[b]carbazole-3-carbonitrile

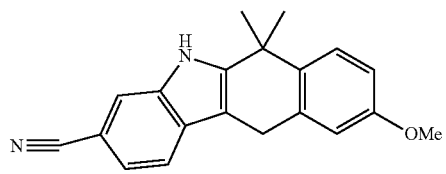 [SMILES: COc1ccc2c(c1)Cc1c([nH]c3cc(C#N)ccc13)C2(C)C]

Under the same conditions as the method for synthesizing Compound E2-1, the title compound was prepared from Compound J2 and 3-hydrazino-benzonitrile.
LCMS: m/z 303 [M+H]+
HPLC retention time: 2.73 min (analysis condition S)

Example 413

Compound J3-2

9-Methoxy-6,6-dimethyl-6,11-dihydro-5H-benzo[b]carbazole-1-carbonitrile

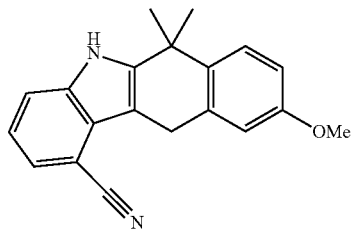 [SMILES: COc1ccc2c(c1)Cc1c([nH]c3cccc(C#N)c13)C2(C)C]

Compound J3-2 was obtained as a by-product of the synthesis of Compound J3-1.
LCMS: m/z 303 [M+H]+
HPLC retention time: 2.67 min (analysis condition S)

Example 414

Compound J4

9-Methoxy-6,6-dimethyl-11-oxo-6,11-dihydro-5H-benzo[b]carbazole-3-carbonitrile

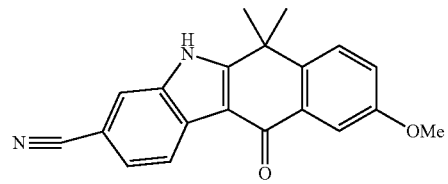 [SMILES: COc1ccc2c(c1)C(=O)c1c([nH]c3cc(C#N)ccc13)C2(C)C]

Under the same conditions as the method for synthesizing Compound A4, the title compound was prepared from Compound J3-1 and Compound J3-2 (mixture).
$^1$H-NMR (DMSO-d$_6$) δ: 12.79 (1H, s), 8.33 (1H, d, J=8.2 Hz), 8.02 (1H, s), 7.81 (1H, d, J=8.6 Hz), 7.69 (1H, d, J=3.0 Hz), 7.63 (1H, dd, J=8.3, 1.4 Hz), 7.28 (1H, dd, J=8.7, 3.0 Hz), 3.87 (3H, s), 1.74 (6H, s).
LCMS: m/z 317 [M+H]+
HPLC retention time: 2.25 min (analysis condition S)

Example 415

Compound J5

9-Hydroxy-6,6-dimethyl-11-oxo-6,11-dihydro-5H-benzo[b]carbazole-3-carbonitrile

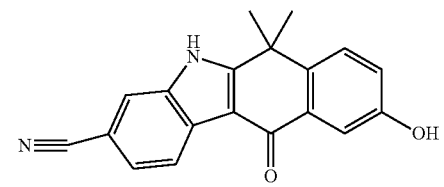 [SMILES: CC1(C)c2ccc(O)cc2C(=O)c2c1[nH]c1cc(C#N)ccc21]

Under the same conditions as the method for synthesizing Compound A6, the title compound was prepared from Compound J4.

$^1$H-NMR (DMSO-$d_6$) δ: 12.75 (1H, s), 9.77 (1H, s), 8.32 (1H, dd, J=8.2, 0.7 Hz), 8.01 (1H, s), 7.68 (1H, d, J=8.6 Hz), 7.62 (1H, dd, J=8.2, 1.4 Hz), 7.58 (1H, d, J=2.8 Hz), 7.10 (1H, dd, J=8.6, 2.8 Hz), 1.72 (6H, s).

LCMS: m/z 303 [M+H]$^+$

HPLC retention time: 1.75 min (analysis condition S)

Example 416

Compound J6

Trifluoro-methanesulfonic acid 3-cyano-6,6-dimethyl-11-oxo-6,11-dihydro-5H-benzo[b]carbazole-9-yl ester

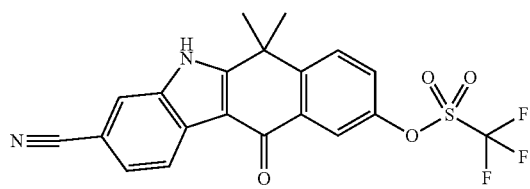 [SMILES: CC1(C)c2ccc(OS(=O)(=O)C(F)(F)F)cc2C(=O)c2c1[nH]c1cc(C#N)ccc21]

Under the same conditions as the method for synthesizing Compound B1, the title compound was prepared from Compound J5.

$^1$H-NMR (DMSO-$d_6$) δ: 12.95 (1H, s), 8.31 (1H, d, J=8.2 Hz), 8.15 (2H, m), 8.05 (1H, s), 7.87 (1H, dd, J=9.0, 2.7 Hz), 7.65 (1H, d, J=8.2 Hz), 1.80 (6H, s).

LCMS: m/z 435 [M+H]$^+$

HPLC retention time: 2.75 min (analysis condition S)

Example 417

Compound J7-1

9-Isopropoxy-6,6-dimethyl-11-oxo-6,11-dihydro-5H-benzo[b]carbazole-3-carbonitrile

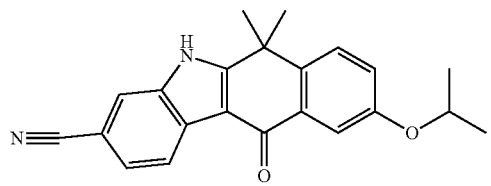 [SMILES: CC(C)Oc1ccc2c(c1)C(=O)c1c([nH]c3cc(C#N)ccc13)C2(C)C]

Under the same conditions as the method for synthesizing Compound A7-1, the title compound was prepared from Compound J4 and isopropanol.

LCMS: m/z 345 [M+H]$^+$

HPLC retention time: 3.87 min (analysis condition W)

Example 418

Compound J7-2-1

4-(3-Cyano-6,6-dimethyl-11-oxo-6,11-dihydro-5H-benzo[b]carbazol-9-yl oxy)-piperidine-1-carboxylic acid tert-butyl ester

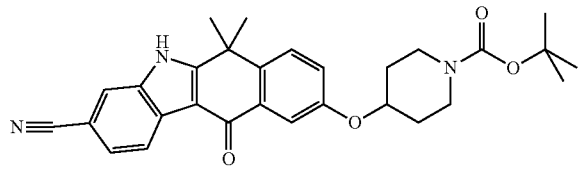 [SMILES: CC(C)(C)OC(=O)N1CCC(Oc2ccc3c(c2)C(=O)c2c([nH]c4cc(C#N)ccc24)C3(C)C)CC1]

Under the same conditions as the method for synthesizing Compound A7-1, the title compound was prepared from Compound J5.

LCMS: m/z 486 [M+H]$^+$

HPLC retention time: 4.15 min (analysis condition W)

Example 419

Compound J7-2-2

6,6-Dimethyl-11-oxo-9-(piperidin-4-yl oxy)-6,11-dihydro-5H-benzo[b]carbazole-3-carbonitrile

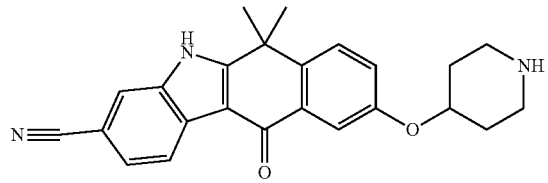 [SMILES: CC1(C)c2ccc(OC3CCNCC3)cc2C(=O)c2c1[nH]c1cc(C#N)ccc21]

Under the same conditions as the method for synthesizing Compound A8-1, the title compound was prepared from Compound J7-2-1.

LCMS: m/z 386 [M+H]$^+$

HPLC retention time: 2.48 min (analysis condition W)

Example 420

Compound J7-2-3

6,6-Dimethyl-9-(1-oxetan-3-yl-piperidin-4-yl oxy)-11-oxo-6,11-dihydro-5H-benzo[b]carbazole-3-carbonitrile

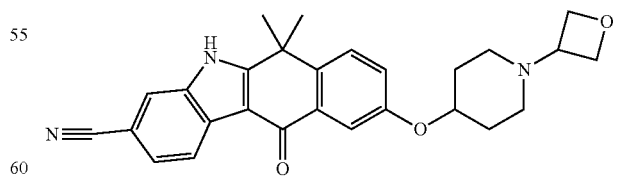

Under the same conditions as the method for synthesizing Compound B3-32, the title compound was prepared from Compound J7-2-2 and oxetan-3-one.

LCMS: m/z 442 [M+H]$^+$

HPLC retention time: 2.61 min (analysis condition W)

Example 421

Compound J7-3

6,6-Dimethyl-11-oxo-9-(4-pyrrolidin-1-yl-piperidin-1-yl)-6,11-dihydro-5H-benzo[b]carbazole-3-carbonitrile

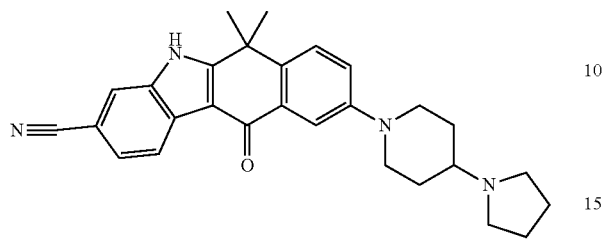

Under the same conditions as the method for synthesizing Compound B2-10, the title compound was prepared from Compound J6 and 4-pyrrolidin-1-yl-piperidine.

$^1$H-NMR (270 MHz, DMSO-$d_6$) δ: 13.12 (1H, s), 8.32 (1H, d, J=8.1 Hz), 8.01 (1H, s), 7.72 (1H, d, J=8.7 Hz), 7.68 (1H, d, J=2.6 Hz), 7.62 (1H, dd, J=8.2, 1.2 Hz), 7.38 (1H, dd, J=9.1, 2.8 Hz), 3.90 (2H, d, J=11.5 Hz), 2.76 (2H, t, J=12.2 Hz), 2.14 (2H, d, J=10.9 Hz), 1.91 (4H, br), 1.74 (6H, s).

LCMS: m/z 439 [M+H]$^+$

HPLC retention time: 1.35 min (analysis condition S)

Example 422

Compound J7-4

9-(4-Isopropyl-piperazin-1-yl)-6,6-dimethyl-11-oxo-6,11-dihydro-5H-benzo[b]carbazole-3-carbonitrile

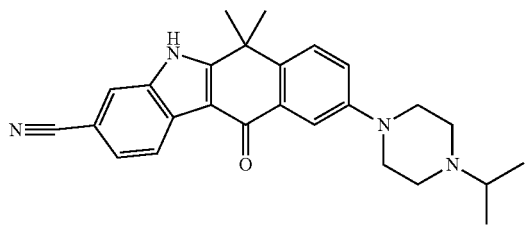 [SMILES: CC(C)N1CCN(c2ccc3c(c2)C(=O)c2c([nH]c4cc(C#N)ccc24)C3(C)C)CC1]

Under the same conditions as the method for synthesizing Compound B2-10, the title compound was prepared from Compound J6 and 1-isopropyl-piperazine.

$^1$H-NMR (270 MHz, DMSO-$d_6$) δ: 12.80 (1H, s), 8.33 (1H, d, J=7.6 Hz), 8.02 (1H, s), 7.66 (3H, m), 7.33 (1H, d, J=8.2 Hz), 3.21 (4H, br), 2.66 (5H, m), 1.72 (6H, s), 1.02 (6H, d, J=6.3 Hz).

LCMS: m/z 413 [M+H]$^+$

HPLC retention time: 1.38 min (analysis condition S)

Example 423

Compound J7-5

6,6-Dimethyl-11-oxo-9-pyrrolidin-1-yl-6,11-dihydro-5H-benzo[b]carbazole-3-carbonitrile

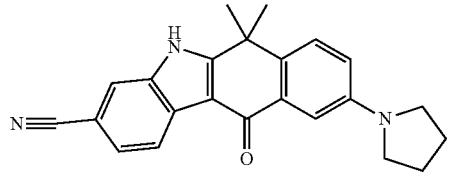 [SMILES: CC1(C)c2ccc(N3CCCC3)cc2C(=O)c2c1[nH]c1cc(C#N)ccc21]

Under the same conditions as the method for synthesizing Compound B2-10, the title compound was prepared from Compound J6 and pyrrolidine.

$^1$H-NMR (270 MHz, DMSO-$d_6$) δ: 8.24 (1H, d, J=8.1 Hz), 7.91 (1H, s), 7.59 (1H, d, J=8.6 Hz), 7.45 (1H, d, J=7.9 Hz), 7.30 (1H, d, J=2.6 Hz), 6.85 (1H, dd, J=8.6, 2.8 Hz), 3.31 (4H, t, J=6.3 Hz), 1.99 (4H, t, J=6.2 Hz), 1.67 (6H, s).

LCMS: m/z 356 [M+H]$^+$

HPLC retention time: 2.38 min (analysis condition S)

Example 424

Compound J7-6

6,6-Dimethyl-11-oxo-9-((S)-2-pyrolidin-1-yl methyl-pyrolidin-1-yl)-6,11-dihydro-5H-benzo[b]carbazole-3-carbonitrile

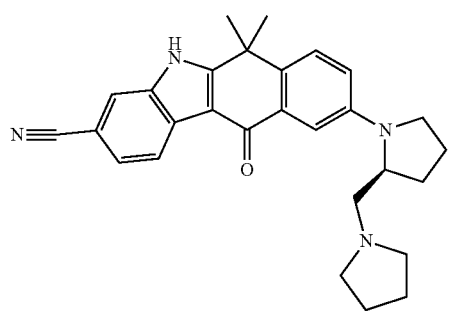 [SMILES: CC1(C)c2ccc(N3CCC[C@H]3CN3CCCC3)cc2C(=O)c2c1[nH]c1cc(C#N)ccc21]

Under the same conditions as the method for synthesizing Compound B2-10, the title compound was prepared from Compound J6 and (S)-2-pyrrolidin-1-yl methyl-pyrrolidine.

LCMS: m/z 439 [M+H]$^+$

HPLC retention time: 1.50 min (analysis condition S)

Example 425

Compound J7-7

6,6-Dimethyl-11-oxo-9-piperazin-1-yl-6,11-dihydro-5H-benzo[b]carbazole-3-carbonitrile

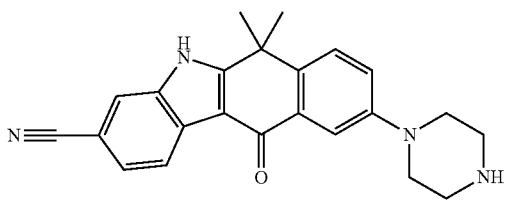 [SMILES: CC1(C)c2ccc(N3CCNCC3)cc2C(=O)c2c1[nH]c1cc(C#N)ccc21]

Under the same conditions as the method for synthesizing Compound B2-10, the title compound was prepared from Compound J6 and piperazine.

LCMS: m/z 371 [M+H]$^+$

HPLC retention time: 1.31 min (analysis condition S)

Example 426

Compound J7-8

9-(3-Hydroxy-3-methyl-but-1-ynyl)-6,6-dimethyl-11-oxo-6,11-dihydro-5H-benzo[b]carbazole-3-carbonitrile

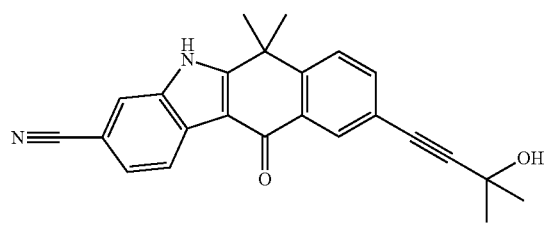 [SMILES: CC(C)(O)C#Cc1ccc2c(c1)C(=O)c1c([nH]c3cc(C#N)ccc13)C2(C)C]

Under the same conditions as the method for synthesizing Compound E4-2-1, the title compound was prepared from Compound J6.
LCMS: m/z 369 [M+H]$^+$
HPLC retention time: 2.16 min (analysis condition S)

Example 427

Compound J7-9

9-Ethynyl-6,6-dimethyl-11-oxo-6,11-dihydro-5H-benzo[b]carbazole-3-carbonitrile

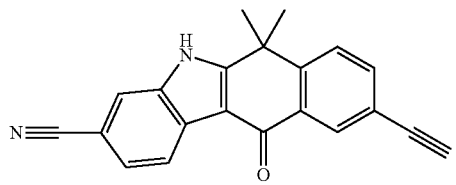 [SMILES: C#Cc1ccc2c(c1)C(=O)c1c([nH]c3cc(C#N)ccc13)C2(C)C]

Under the same conditions as the method for synthesizing Compound E4-2-2, the title compound was prepared from Compound J7-8.
$^1$H-NMR (270 MHz, DMSO-d$_6$) δ: 8.31 (1H, d, J=8.1 Hz), 8.23 (1H, d, J=1.8 Hz), 8.02 (1H, d, J=1.3 Hz), 7.93 (1H, d, J=8.2 Hz), 7.78 (1H, dd, J=8.2, 1.8 Hz), 7.61 (1H, dd, J=8.1, 1.3 Hz), 4.31 (1H, s), 1.77 (6H, s).
LCMS: m/z 311 [M+H]$^+$
HPLC retention time: 2.40 min (analysis condition S)

Example 428

Compound J7-10-1

4-(3-Cyano-6,6-dimethyl-11-oxo-6,11-dihydro-5H-benzo[b]carbazol-9-yl)-3,6-dihydro-2H-pyridine-1-carboxylic acid tert-butyl ester

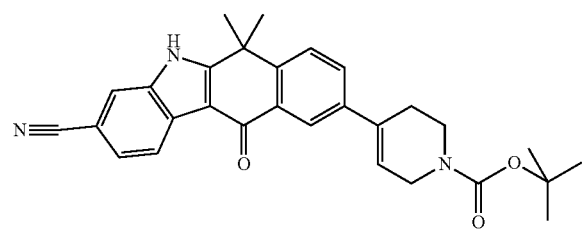 [SMILES: CC(C)(C)OC(=O)N1CC=C(c2ccc3c(c2)C(=O)c2c([nH]c4cc(C#N)ccc24)C3(C)C)CC1]

Under the same conditions as the method for synthesizing Compound B2-22-1, the title compound was prepared from Compound J6.
LCMS: m/z 468 [M+H]$^+$
HPLC retention time: 2.90 min (analysis condition S)

Example 429

Compound J7-10-2

6,6-Dimethyl-11-oxo-9-(1,2,3,6-tetrahydro-pyridin-4-yl)-6,11-dihydro-5H-benzo[b]carbazole-3-carbonitrile

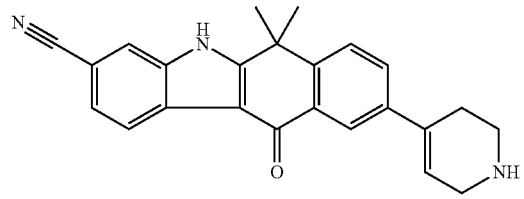 [SMILES: CC1(C)c2ccc(C3=CCNCC3)cc2C(=O)c2c1[nH]c1cc(C#N)ccc21]

Under the same conditions as the method for synthesizing Compound A8-1, the title compound was prepared from Compound J7-10-1.
LCMS: m/z 368 [M+H]$^+$
HPLC retention time: 1.27 min (analysis condition S)

Example 430

Compound J7-11-1

9-(Piperidin-4-ylmethyl)-6,6-dimethyl-11-oxo-6,11-dihydro-5H-benzo[b]carbazole-3-carbonitrile

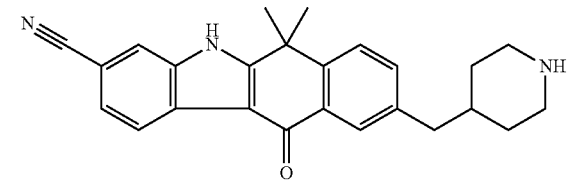 [SMILES: CC1(C)c2ccc(CC3CCNCC3)cc2C(=O)c2c1[nH]c1cc(C#N)ccc21]

Under the same conditions as the method for synthesizing Compound B2-25-1 and Compound B2-25-2, the title compound was prepared from Compound J6.
LCMS: m/z 384 [M+H]$^+$
HPLC retention time: 1.42 min (analysis condition S)

Example 431

Compound J7-11-2

9-(1-Isopropyl-piperidin-4-ylmethyl)-6,6-dimethyl-11-oxo-6,11-dihydro-5H-benzo[b]carbazole-3-carbonitrile

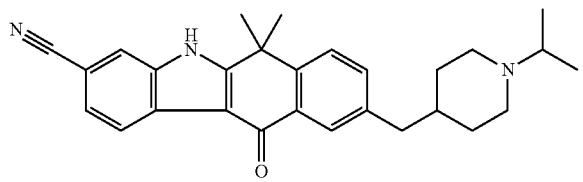 [SMILES: CC(C)N1CCC(Cc2ccc3c(c2)C(=O)c2c([nH]c4cc(C#N)ccc24)C3(C)C)CC1]

Under the same conditions as the method for synthesizing Compound B3-32, the title compound was prepared from Compound J7-11-1 and acetone.

¹H-NMR (400 MHz, DMSO-d₆) δ: 12.79 (1H, s), 8.33 (1H, d, 7.9 Hz), 8.01 (1H, s), 7.98 (1H, d, 1.8 Hz), 7.79 (1H, d, 7.9 Hz), 7.61 (1H, d, 7.9 Hz), 7.51-7.49 (1H, m), 2.74 (2H, d, 11.0 Hz), 2.64-2.60 (3H, m), 2.04 (2H, t, 10.7 Hz), 1.77 (6H, s), 1.60-1.51 (3H, m), 1.23-1.14 (2H, m), 0.94 (6H, d, 6.7 Hz)

LCMS: m/z 426 [M+H]⁺

Example 432

Compound J7-12

4-(3-Cyano-6,6-dimethyl-11-oxo-6,11-dihydro-5H-benzo[b]carbazol-9-yl oxy)-butyric acid

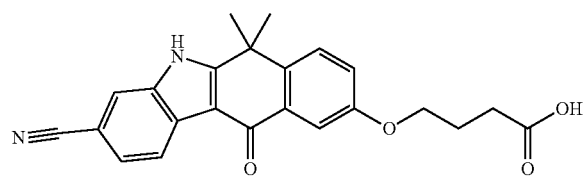 [SMILES: CC1(C)c2ccc(OCCCC(=O)O)cc2C(=O)c2c1[nH]c1cc(C#N)ccc21]

9-Hydroxy-6,6-dimethyl-11-oxo-6,11-dihydro-5H-benzo[b]carbazole-3-carbonitrile (Compound J5, 30 mg, 0.099 mmol), 4-bromo-butyric acid methyl ester (24.9 µl, 0.198 mmol) and cesium carbonate (64.5 mg, 0.198 mmol) were dissolved in DMA (0.20 ml) and stirred at room temperature for 4 hr. Water was added to the reaction solution, which was then extracted with diethyl ether. The organic layer was washed with saturated brine and dried over anhydrous magnesium sulfate. The yellow solid obtained after concentration under reduced pressure was purified by silica gel column chromatography (methylene chloride/MeOH) to obtain 4-(3-cyano-6,6-dimethyl-11-oxo-6,11-dihydro-5H-benzo[b]carbazol-9-yl oxy)-butyric acid methyl ester as an intermediate.

The intermediate was dissolved in MeOH (0.50 ml), added with aqueous solution of sodium hydroxide (6 mol/l) and stirred at room temperature for 30 min. The reaction solution was added with hydrochloric acid (3 mol/l), extracted with diethyl ether. The organic layer was washed with saturated brine and dried over anhydrous magnesium sulfate. After concentration under reduced pressure, white solid was obtained, which was then washed with methylene chloride to obtain the title compound (19.0 mg, 70%).

LCMS: m/z 389 [M+H]⁺

HPLC retention time: 2.39 min (analysis condition F)

Example 433

Compound J7-13

5-(3-Cyano-6,6-dimethyl-11-oxo-6,11-dihydro-5H-benzo[b]carbazol-9-yl oxy)-pentanoic acid

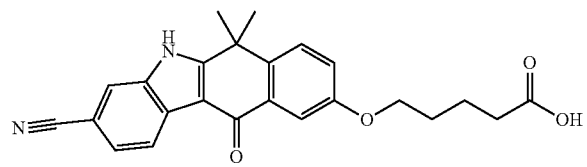 [SMILES: CC1(C)c2ccc(OCCCCC(=O)O)cc2C(=O)c2c1[nH]c1cc(C#N)ccc21]

Under the same conditions as the method for synthesizing Compound J7-12, Compound J5 and 5-bromo-pentanoic acid methyl ester were reacted to obtain the target compound (19.5 mg, 64%).

LCMS: m/z 403 [M+H]⁺

HPLC retention time: 2.49 min (analysis condition F)

Example 434

Compound J7-14

6-(3-Cyano-6,6-dimethyl-11-oxo-6,11-dihydro-5H-benzo[b]carbazol-9-yl oxy)-hexanoic acid

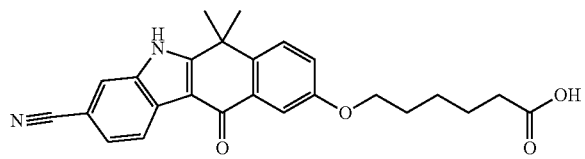 [SMILES: CC1(C)c2ccc(OCCCCCC(=O)O)cc2C(=O)c2c1[nH]c1cc(C#N)ccc21]

Under the same conditions as the method for synthesizing Compound J7-12, Compound J5 and 6-bromo-hexanoic acid ethyl ester were reacted to obtain the target compound (19.6 mg, 66%).

LCMS: m/z 417 [M+H]⁺

HPLC retention time: 2.61 min (analysis condition F)

Example 435

Compound J7-15

3-[2-(3-Cyano-6,6-dimethyl-11-oxo-6,11-dihydro-5H-benzo[b]carbazol-9-yl oxy)-ethoxy]-propionic acid

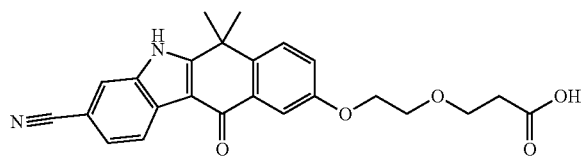 [SMILES: CC1(C)c2ccc(OCCOCCC(=O)O)cc2C(=O)c2c1[nH]c1cc(C#N)ccc21]

Under the same conditions as the method for synthesizing Compound A7-1, Compound JJ2 and 3-(2-hydroxy-ethoxy)-propionic acid tert-butyl ester were reacted to obtain 3-[2-(3-bromo-6,6-dimethyl-11-oxo-6,11-dihydro-5H-benzo[b]carbazol-9-yl oxy)-ethoxy]-propionic acid tert-butyl ester.

The resultant was dissolved in DMA (0.30 ml), added with copper cyanide (25.5 mg, 0.285 mmol), and stirred at 200° C. for 1 hr under irradiation with microwave. The reaction solution was diluted with ethyl acetate, washed with saturated brine and dried over anhydrous magnesium sulfate. The residues obtained after concentration under reduced pressure were dissolved in methylene chloride (0.75 ml). The solution was added with TFA (250 µl) and stirred at room temperature for 5 min. Thereafter, the residues obtained from the reaction solution after concentration under reduced pressure were purified by silica gel column chromatography (methylene chloride/MeOH) to obtain the title compound (5.6 mg, 14%).

LCMS: m/z 419 [M+H]⁺

HPLC retention time: 2.31 min (analysis condition F)

Example 436

Compound J7-16

6,6-Dimethyl-11-oxo-9-(pyridin-4-ylmethoxy)-6,11-dihydro-5H-benzo[b]carbazole-3-carbonitrile

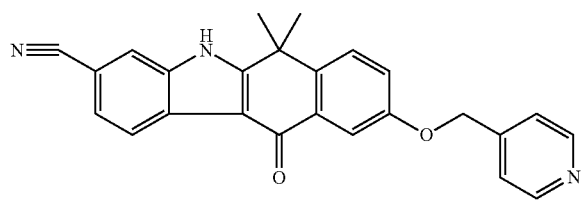 [SMILES: CC1(C)c2ccc(OCc3ccncc3)cc2C(=O)c2c1[nH]c1cc(C#N)ccc21]

Under the same conditions as the method for synthesizing Compound A7-1, the title compound was prepared from Compound J5 and pyridin-4-yl-methanol (pale yellow solid, 6.1 mg, 31%).
LCMS: m/z 394 [M+H]$^+$
HPLC retention time: 1.97 min (analysis condition F)

Example 437

Compound J7-17

6,6-Dimethyl-11-oxo-9-(pyridin-3-ylmethoxy)-6,11-dihydro-5H-benzo[b]carbazole-3-carbonitrile

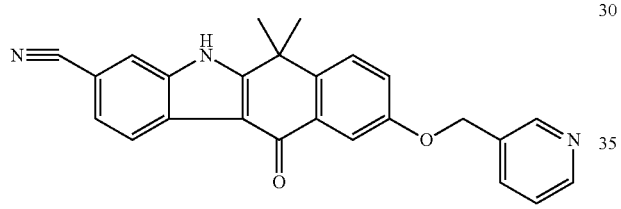

Under the same conditions as the method for synthesizing Compound JJ3-1, the title compound was prepared from Compound J5 and pyridin-3-yl-methanol (pale yellow solid, 7.9 mg, 38%).
LCMS: m/z 394 [M+H]$^+$
HPLC retention time: 1.99 min (analysis condition F)

Example 438

Compound J8-1

6,6-Dimethyl-9-(4-oxetan-3-yl-piperazin-1-yl)-11-oxo-6,11-dihydro-5H-benzo[b]carbazole-3-carbonitrile

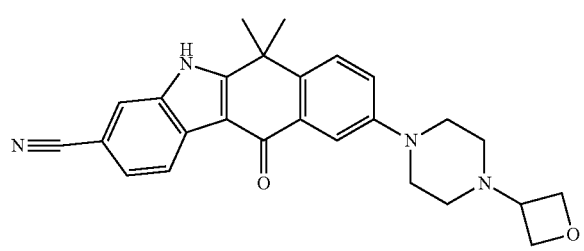 [SMILES: CC1(C)c2ccc(N3CCN(C4COC4)CC3)cc2C(=O)c2c1[nH]c1cc(C#N)ccc21]

Under the same conditions as the method for synthesizing Compound B3-32, the title compound was prepared from Compound J7-7 and oxetan-3-one.

LCMS: m/z 427 [M+H]$^+$
HPLC retention time: 1.31 min (analysis condition S)

Example 439

Compound J8-2

9-(4-Cyclopropyl-piperazin-1-yl)-6,6-dimethyl-11-oxo-6,11-dihydro-5H-benzo[b]carbazole-3-carbonitrile

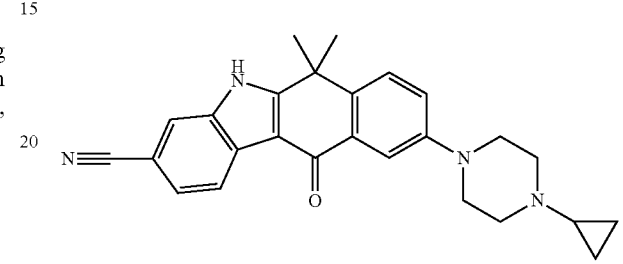

Under the same conditions as the method for synthesizing Compound B3-32, the title compound was prepared from Compound J7-7 and (1-ethoxycyclopropoxy)trimethylsilane.
LCMS: m/z 411 [M+H]$^+$
HPLC retention time: 1.39 min (analysis condition S)

Example 440

Compound J8-3

9-(1-Methanesulfonyl-1,2,3,6-tetrahydro-pyridin-4-yl)-6,6-dimethyl-11-oxo-6,11-dihydro-5H-benzo[b]carbazole-3-carbonitrile

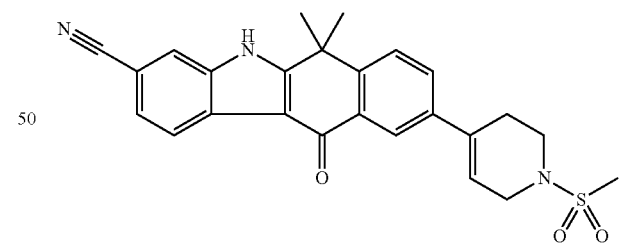

Under the same conditions as the method for synthesizing Compound A9-1, the title compound was prepared from Compound J7-10-2.
$^1$H-NMR (400 MHz, DMSO-d$_6$) δ: 12.81 (1H, s), 8.33 (1H, d, 7.9 Hz), 8.26 (1H, d, 2.4 Hz), 8.01 (1H, s), 7.88-7.81 (2H, m), 7.61 (1H, d, 7.9 Hz), 6.36 (1H, s), 3.93 (2H, d, 3.0 Hz), 3.45 (2H, t, 5.8 Hz), 2.97 (3H, s), 2.73-2.70 (2H, m), 1.78 (6H, s)
LCMS: m/z 446 [M+H]$^+$
HPLC retention time: 2.15 min (analysis condition S)

Example 441

Compound J8-4

9-(1-Isopropyl-1,2,3,6-tetrahydro-pyridin-4-yl)-6,6-dimethyl-11-oxo-6,11-dihydro-5H-benzo[b]carbazole-3-carbonitrile

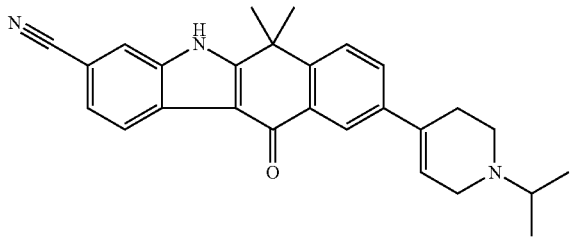

Under the same conditions as the method for synthesizing Compound B3-32, the title compound was prepared from Compound J7-10-2 and acetone.

$^1$H-NMR (400 MHz, DMSO-d$_6$) δ: 12.82 (1H, s), 8.33 (1H, d, 7.9 Hz), 8.22 (1H, d, 1.8 Hz), 8.02 (1H, s), 7.84 (1H, d, 8.5 Hz), 7.78 (1H, dd, 8.2, 2.1 Hz), 7.62 (1H, d, 7.9 Hz), 6.32 (1H, t, 3.7 Hz), 3.23-3.20 (2H, m), 2.83-2.76 (1H, m), 2.72 (2H, t, 5.5 Hz), 2.56-2.54 (2H, m), 1.78 (6H, s), 1.06 (6H, d, 6.7 Hz)

LCMS: m/z 410 [M+H]$^+$

HPLC retention time: 1.38 min (analysis condition S)

Example 442

Compound J8-5

6,6-Dimethyl-9-(1-oxetan-3-yl-1,2,3,6-tetrahydro-pyridin-4-yl)-11-oxo-6,11-dihydro-5H-benzo[b]carbazole-3-carbonitrile

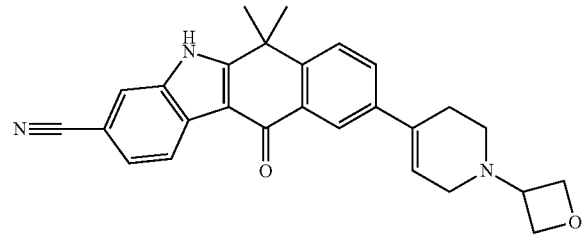 [SMILES: CC1(C)c2ccc(C3=CCN(C4COC4)CC3)cc2C(=O)c2c1[nH]c1cc(C#N)ccc21]

Under the same conditions as the method for synthesizing Compound B3-32, the title compound was prepared from Compound J7-10-2 and oxetan-3-one.

$^1$H-NMR (270 MHz, DMSO-d$_6$) δ: 12.81 (1H, br. s), 8.34 (1H, d, J=8.2 Hz), 8.22 (1H, d, J=1.8 Hz), 8.03 (1H, s), 7.76-7.90 (2H, m), 7.64 (1H, dd, J=8.2, 1.8 Hz), 6.25-6.34 (1H, m), 4.60 (2H, dd, J=6.6, 6.0 Hz), 4.52 (2H, dd, J=6.6, 6.0 Hz), 3.57 (1H, t, J=6.0 Hz), 3.03 (2H, m), 2.55 (4H, m), 1.77 (6H, s).

LCMS: m/z 424 [M+H]$^+$

HPLC retention time: 1.34 min (analysis condition S)

Example 443

Compound J8-6

9-(1-Cyclopropyl-1,2,3,6-tetrahydro-pyridin-4-yl)-6,6-dimethyl-11-oxo-6,11-dihydro-5H-benzo[b]carbazole-3-carbonitrile

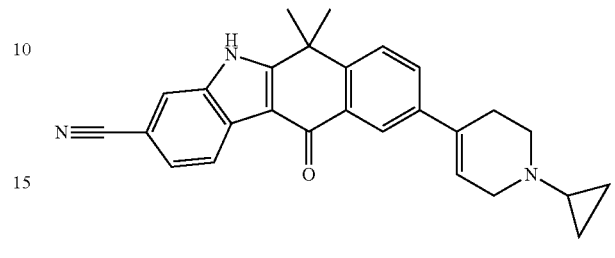

Under the same conditions as the method for synthesizing Compound B3-32, the title compound was prepared from Compound J7-10-2 and (1-ethoxycyclopropoxy)trimethylsilane.

LCMS: m/z 408 [M+H]$^+$

HPLC retention time: 1.36 min (analysis condition S)

Example 444

Compound J9-1

4-(3-Cyano-6,6-dimethyl-11-oxo-6,11-dihydro-5H-benzo[b]carbazol-9-yl)-piperidine-1-carboxylic acid tert-butyl ester

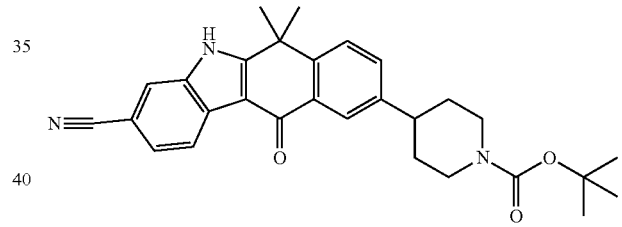

Under the same conditions as the method for synthesizing Compound B3-13-1, the title compound was prepared from Compound J7-10-1.

LCMS: m/z 414, 470 [M+H]$^+$

HPLC retention time: 2.83 min (analysis condition S)

Example 445

Compound J9-2

6,6-Dimethyl-11-oxo-9-piperidin-4-yl-6,11-dihydro-5H-benzo[b]carbazole-3-carbonitrile

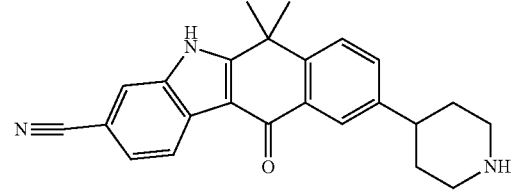 [SMILES: CC1(C)c2ccc(C3CCNCC3)cc2C(=O)c2c1[nH]c1cc(C#N)ccc21]

Under the same conditions as the method for synthesizing Compound A8-1, the title compound was prepared from Compound J9-1.

LCMS: m/z 370 [M+H]+

HPLC retention time: 1.30 min (analysis condition S)

Example 446

Compound J9-3

9-(1-Isopropyl-piperidin-4-yl)-6,6-dimethyl-11-oxo-6,11-dihydro-5H-benzo[b]carbazole-3-carbonitrile

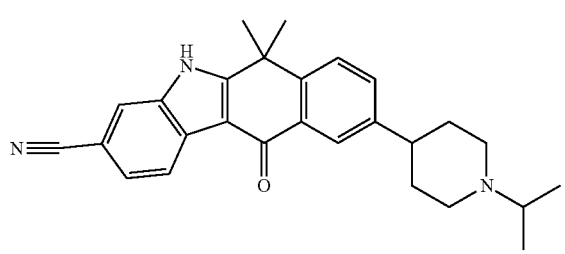 [SMILES: CC(C)N1CCC(c2ccc3c(c2)C(=O)c2c([nH]c4cc(C#N)ccc24)C3(C)C)CC1]

Under the same conditions as the method for synthesizing Compound A9-1, the title compound was prepared from Compound J9-2 and 2-bromopropane.

$^1$H-NMR (270 MHz, DMSO-$d_6$) δ: 12.83 (1H, s), 8.34 (2H, d, J=8.1 Hz), 8.05 (2H, m), 7.82 (1H, d, J=8.1 Hz), 7.61 (2H, m), 3.02 (2H, br), 2.42 (2H, br), 1.76 (6H, s), 1.06 (6H, d, J=6.4 Hz).

LCMS: m/z 412 [M+H]+

HPLC retention time: 1.45 min (analysis condition S)

Example 447

Compound J9-4

6,6-Dimethyl-9-(1-oxetan-3-yl-piperidin-4-yl)-11-oxo-6,11-dihydro-5H-benzo[b]carbazole-3-carbonitrile

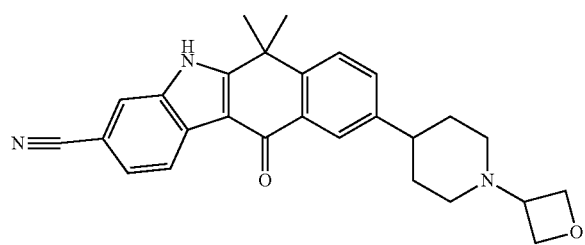

Under the same conditions as the method for synthesizing Compound B3-13-1, the title compound was prepared from Compound J8-5.

LCMS: m/z 426 [M+H]+

HPLC retention time: 1.26 min (analysis condition S)

Example 448

Compound J9-5

9-(1-Cyclopropyl-piperidin-4-yl)-6,6-dimethyl-11-oxo-6,11-dihydro-5H-benzo[b]carbazole-3-carbonitrile

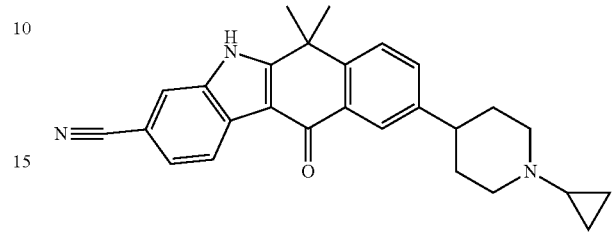

Under the same conditions as the method for synthesizing Compound B3-13-1, the title compound was prepared from Compound J8-6.

LCMS: m/z 410 [M+H]+

HPLC retention time: 1.43 min (analysis condition S)

Example 449

Compound JJ1

3-Bromo-9-methoxy-6,6-dimethyl-5,6-dihydro-benzo[b]carbazol-11-one

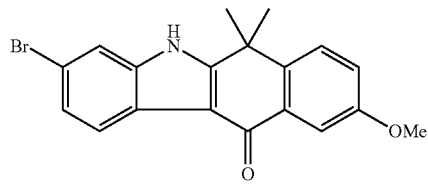 [SMILES: COc1ccc2c(c1)C(=O)c1c([nH]c3cc(Br)ccc13)C2(C)C]

6-Methoxy-1,1-dimethyl-3,4-dihydro-1H-naphthalen-2-one (Compound J2, 2.15 g, 10.5 mmol) and 3-bromophenylhydrazine hydrochloric acid salt (3.11 g, 1.3 eq.) were dissolved in acetic acid (12 mL), and stirred at 100° C. for 2.5 hr under nitrogen atmosphere. After cooling, the reaction solution was added with ethyl acetate, washed with water, saturated aqueous solution of sodium hydrogen carbonate, and saturated brine, and dried over magnesium sulfate. After the filtration, it was concentrated under reduced pressure. The resulting residues were dissolved in THF (30 mL) and water (3 mL), added with DDQ (5.96 g, 2.5 eq.) at 0° C., and then stirred at room temperature overnight. The reaction solution was added with MTBE, washed with 0.5 N aqueous solution of sodium hydroxide and saturated brine, and dried over magnesium sulfate. After filtration and the concentration under reduced pressure, the resulting residues were washed with MTBE to obtain the title compound (brown solid, 1.80 g, 46%).

$^1$H-NMR (270 MHz, DMSO-$d_6$) δ: 12.4 (1H, s), 8.12 (1H, d, J=8.6 Hz), 7.79 (1H, d, J=8.9 Hz), 7.67-7.68 (2H, m), 7.40 (1H, dd, J=1.7, 8.6 Hz), 7.26 (1H, dd, J=2.6, 8.9 Hz), 3.86 (3H, s), 1.72 (6H, s),

LCMS: m/z 370 [M+H]+

HPLC retention time: 6.45 min (analysis condition H)

Example 450

Compound JJ2

3-Bromo-9-hydroxy-6,6-dimethyl-5,6-dihydro-benzo[b]carbazol-11-one

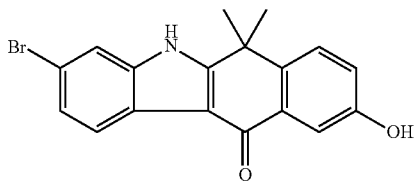 [SMILES: CC1(C)c2ccc(O)cc2C(=O)c2c1[nH]c1cc(Br)ccc21]

3-Bromo-9-methoxy-6,6-dimethyl-5,6-dihydro-benzo[b]carbazol-11-one (Compound JJ1, 1.50 g, 4.05 mmol) and pyridinium chloride (15.2 g, 32.5 eq.) were stirred at 160° C. for 12 hr under nitrogen atmosphere. After cooling, water and ethyl acetate were added and the resulting suspension was filtered. The organic layer was washed with water and saturated brine and dried over magnesium sulfate. After filtration and the concentration under reduced pressure, the resulting residues were washed with MTBE to obtain the title compound (brown solid, 1.47 g, 100%).

$^1$H-NMR (270 MHz, DMSO-$d_6$) δ: 12.4 (1H, s), 9.71 (1H, s), 8.11 (1H, d, J=8.2 Hz), 7.64-7.68 (2H, m), 7.57 (1H, d, J=3.0 Hz), 7.38 (1H, dd, J=1.7, 8.2 Hz), 7.07 (1H, dd, J=3.0, 8.6 Hz), 1.69 (6H, s),

LCMS: m/z 356 [M+H]$^+$

HPLC retention time: 2.52 min (analysis condition F)

Example 451

Compound JJ3-1

3-Bromo-9-((S)-2,2-dimethyl-[1,3]dioxolan-4-ylmethoxy)-6,6-dimethyl-5,6-dihydro-benzo[b]carbazol-11-one

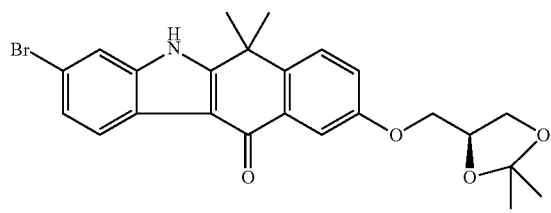 [SMILES: CC1(C)OC[C@H](COc2ccc3c(c2)C(=O)c2c([nH]c4cc(Br)ccc24)C3(C)C)O1]

Under nitrogen atmosphere, 3-bromo-9-hydroxy-6,6-dimethyl-5,6-dihydro-benzo[b]carbazol-11-one (Compound JJ2, 356 mg, 1.00 mmol) and triphenylphosphine (317 mg, 1.2 eq.) were added with THF (3 ml), followed by dropwise addition of ((S)-2,2-dimethyl-[1,3]dioxolan-4-yl)-methanol (148 μl, 1.2 eq.) and diisopropyl azodicarboxylic acid (252 μl, 1.3 eq.). The mixture was then stirred at 50° C. for 2 hr. After cooling, the reaction solution was added with ethyl acetate, washed with brine and dried over magnesium sulfate. After filtration and the concentration under reduced pressure, the resulting residues were purified by silica gel column chromatography (ethyl acetate/dichloromethane) to yield the solid, which was then washed with dichloromethane to obtain the title compound (white powder, 241.6 mg, 51%).

$^1$H-NMR (270 MHz, DMSO-$d_6$) δ: 12.4 (1H, s), 8.12 (1H, d, J=8.2 Hz), 7.79 (1H, d, J=8.9 Hz), 7.67-7.69 (2H, m), 7.40 (1H, dd, J=1.8, 8.2 Hz), 7.28 (1H, dd, J=3.0, 8.9 Hz), 4.41-4.48 (1H, m), 4.06-4.17 (2H, m), 3.79-3.85 (1H, m), 1.72 (3H, s), 1.38 (3H, s), 1.33 (3H, s),

LCMS: m/z 470 [M+H]$^+$

HPLC retention time: 3.08 min (analysis condition F)

Example 452

Compound JJ3-2

3-Bromo-9-((R)-2,3-dihydroxy-propoxy)-6,6-dimethyl-5,6-dihydro-benzo[b]carbazol-11-one

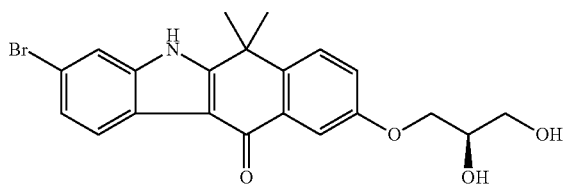 [SMILES: CC1(C)c2ccc(OC[C@H](O)CO)cc2C(=O)c2c1[nH]c1cc(Br)ccc21]

3-Bromo-9-((S)-2,2-dimethyl-[1,3]dioxolan-4-ylmethoxy)-6,6-dimethyl-5,6-dihydro-benzo[b]carbazol-11-one (Compound JJ3-1, 18.7 mg, 0.0398 mmol) was dissolved in methanol (1 mL) and THF (0.3 mL), added with 1 N hydrochloric acid (5 drops) and stirred at 50° C. for 1 hr. After cooling, the reaction solution was concentrated under reduced pressure, and the resulting residues were added with dichloromethane, and the solid was separated by filtration to obtain the title compound (yellow powder, 16.8 mg, 98%).

$^1$H-NMR (270 MHz, DMSO-$d_6$) δ: 12.43 (1H, s), 8.12 (1H, d, J=8.6 Hz), 7.78 (1H, d, J=8.9 Hz), 7.67-7.70 (2H, m), 7.40 (2H, dd, J=1.8, 8.6 Hz), 7.27 (2H, dd, J=2.8, 8.9 Hz), 4.43 (2H, brs), 4.12 (1H, dd, J=9.9, 4.3 Hz), 3.96 (1H, dd, J=9.7, 6.1 Hz), 3.85 (1H, dd, J=9.9, 5.6 Hz), 3.48 (2H, d, J=5.6 Hz), 1.72 (6H, s), LCMS: m/z 430 [M+H]$^+$ HPLC retention time: 2.02 min (analysis condition F)

Example 453

Compound JJ4-1

3-Bromo-9-((S)-2,2-dimethyl-[1,3]dioxolan-4-ylmethoxy)-5,6,6-trimethyl-5,6-dihydro-benzo[b]carbazol-11-one

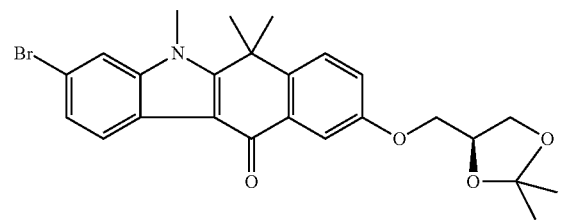 [SMILES: Cn1c2c(c3ccc(Br)cc31)C(=O)c1cc(OC[C@H]3COC(C)(C)O3)ccc1C2(C)C]

To the mixture of 3-bromo-9-((S)-2,2-dimethyl-[1,3]dioxolan-4-ylmethoxy)-6,6-dimethyl-5,6-dihydro-benzo[b]carbazol-11-one (Compound JJ3-1, 33.2 mg, 0.0706 mmol) and sodium hydride (60% in oil, 6.4 mg, 2.3 eq.), DMA (0.55 mL) and methyl iodide (0.015 mL, 3.4 eq.) were added under nitrogen atmosphere at 0° C., and the mixture was stirred at room temperature overnight. The reaction solution was added with water and extracted with ethyl acetate. The organic layer was washed with brine and dried over magnesium sulfate. After filtration and the concentration under reduced pressure, the resulting solid was washed with MTBE to obtain the title compound (white solid, 31.2 mg, 91%).

LCMS: m/z 484 [M+H]+

HPLC retention time: 3.34 min (analysis condition F)

Example 454

Compound JJ4-2

3-Bromo-9-((R)-2,3-dihydroxy-propoxy)-5,6,6-trimethyl-5,6-dihydro-benzo[b]carbazol-11-one

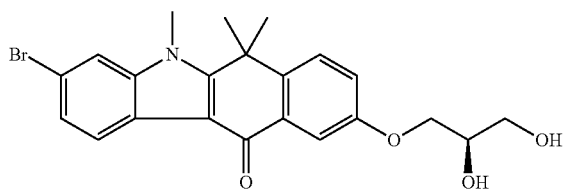 [SMILES: Cn1c2c(c3ccc(Br)cc31)C(=O)c1cc(OC[C@H](O)CO)ccc1C2(C)C]

Under the same conditions as the method for synthesizing Compound JJ3-2, the title compound was prepared from Compound JJ4-1 (yellow solid, 13.3 mg, 83%).

LCMS: m/z 444 [M+H]+

HPLC retention time: 2.47 min (analysis condition F)

Example 455

Compound JJ5

(3-Bromo-6,6-dimethyl-11-oxo-6,11-dihydro-5H-benzo[b]carbazol-9-yl oxy)-acetic acid

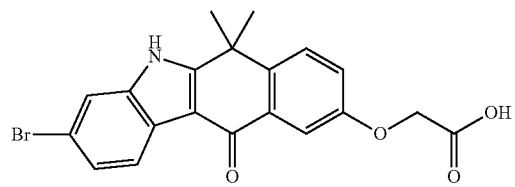 [SMILES: CC1(C)c2ccc(OCC(=O)O)cc2C(=O)c2c1[nH]c1cc(Br)ccc21]

Under the same conditions as the method for synthesizing Compound A7-1, (3-bromo-6,6-dimethyl-11-oxo-6,11-dihydro-5H-benzo[b]carbazol-9-yl oxy)-acetic acid methyl ester was prepared from Compound JJ2 and hydroxy-acetic acid methyl ester. The resultant was dissolved in MeOH (0.35 ml), added with aqueous solution of sodium hydroxide (6 mol/1), and stirred at room temperature for 10 min. The reaction solution was added with hydrochloric acid (3 mol/1), extracted with diethyl ether and dried over anhydrous magnesium sulfate. After the concentration under reduced pressure, white solid was obtained, which was then washed with methylene chloride to obtain the title compound (11.2 mg, 48%).

LCMS: m/z 414 [M+H]+

HPLC retention time: 2.50 min (analysis condition F)

Example 456

Compound JJ6

4-(3-Bromo-6,6-dimethyl-11-oxo-6,11-dihydro-5H-benzo[b]carbazol-9-yl oxy)-butyric acid

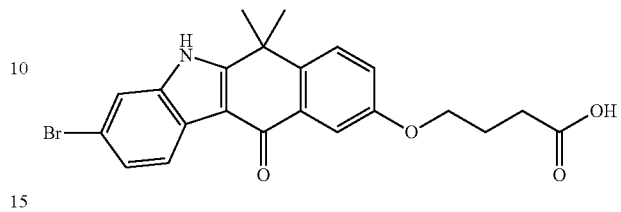

3-Bromo-9-hydroxy-6,6-dimethyl-5,6-dihydro-benzo[b]carbazol-11-one (Compound JJ2, 20 mg, 0.056 mmol), 4-bromo-butyric acid methyl ester (7.0 µl, 0.056 mmol) and cesium carbonate (36.6 mg, 0.112 mmol) were dissolved in DMA (0.09 ml), and then stirred at room temperature for 1 hr. Thereafter, 4-bromo-butyric acid methyl ester (7.0 µl, 0.056 mmol) was added thereto and the mixture was stirred at room temperature for 3 hr, followed by further stirring at 45° C. for 30 min. The reaction solution was added with water, extracted with diethyl ether and dried over anhydrous magnesium sulfate. After the concentration under reduced pressure, the resulting residues were purified by silica gel column chromatography (ethyl acetate/hexane) to obtain 4-(3-bromo-6,6-dimethyl-11-oxo-6,11-dihydro-5H-benzo[b]carbazol-9-yl oxy)-butyric acid methyl ester. This compound was dissolved in MeOH (0.50 ml), added with aqueous solution of sodium hydroxide (6 mol/1), and then stirred at room temperature for 10 min. The reaction solution was added with hydrochloric acid (3 mol/1), extracted with diethyl ether, and dried over anhydrous magnesium sulfate and concentrated under reduced pressure to obtain white solid. This white solid was washed with methylene chloride to obtain the title compound (6.1 mg, 25%).

LCMS: m/z 442 [M+H]+

HPLC retention time: 2.65 min (analysis condition F)

Example 457

Compound JJ7-1

3-Bromo-9-[(4R,5R)-5-(tert-butyl-dimethyl-silanyloxymethyl)-2,2-dimethyl-[1,3]dioxolan-4-yl methoxy]-6,6-dimethyl-5,6-dihydro-benzo[b]carbazol-11-one

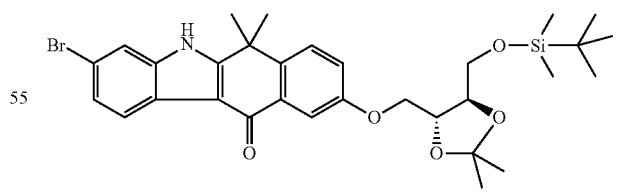

Under the same conditions as the method for synthesizing Compound A7-1, the title compound (white solid, 111.5 mg, 65%) was prepared from Compound JJ2 and [(4R,5R)-5-(tert-butyl-dimethyl-silanyloxymethyl)-2,2-dimethyl-[1,3]dioxolan-4-yl]-methanol.

LCMS: m/z 614 [M+H]+

HPLC retention time: 4.04 min (analysis condition F)

Example 458

Compound JJ7-2

3-Bromo-6,6-dimethyl-9-((2R,3R)-2,3,4-trihydroxy-butoxy)-5,6-dihydro-benzo[b]carbazol-11-one

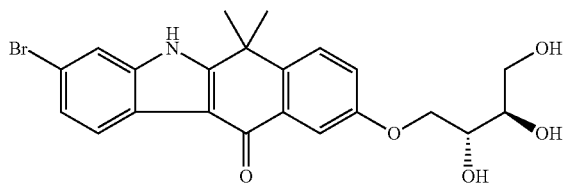 [SMILES: CC1(C)c2ccc(OC[C@@H](O)[C@H](O)CO)cc2C(=O)c2c1[nH]c1cc(Br)ccc21]

3-Bromo-9-[(4R,5R)-5-(tert-butyl-dimethyl-silanyloxymethyl)-2,2-dimethyl-[1,3]dioxolan-4-yl methoxy]-6,6-dimethyl-5,6-dihydro-benzo[b]carbazol-11-one (Compound JJ7-1, 13.7 mg, 0.0223 mmol) was dissolved in THF (0.15 mL) and methanol (0.1 mL), added with 0.5 M sulfuric acid (0.05 mL), and then stirred at 60° C. for 3 hr. After cooling, the reaction solution was added with saturated aqueous solution of sodium hydrogen carbonate and extracted with ethyl acetate. The organic layer was washed with brine and dried over magnesium sulfate. After filtration and the concentration under reduced pressure, the resulting solid was washed with dichloromethane to obtain the title compound (white solid, 8.4 mg, 82%).

LCMS: m/z 460 [M+H]$^+$

HPLC retention time: 2.18 min (analysis condition F)

Example 459

Compound JJ8-1

9-[(4R,5R)-5-(Tert-butyl-dimethyl-silanyloxymethyl)-2,2-dimethyl-[1,3]dioxolan-4-yl methoxy]-6,6-dimethyl-11-oxo-6,11-dihydro-5H-benzo[b]carbazole-3-carbonitrile

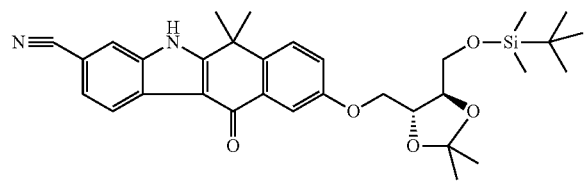 [SMILES: CC1(C)O[C@H](COc2ccc3c(c2)C(=O)c2c([nH]c4cc(C#N)ccc24)C3(C)C)[C@@H](CO[Si](C)(C)C(C)(C)C)O1]

According to the same method as the method for synthesizing Compound A5-2, the title compound (11.1 mg, 50%) was prepared from Compound JJ7-1 and [(4R,5R)-5-(tert-butyl-dimethyl-silanyloxymethyl)-2,2-dimethyl-[1,3]dioxolan-4-yl]-methanol.

LCMS: m/z 561 [M+H]$^+$

HPLC retention time: 3.84 min (analysis condition F)

Example 460

Compound JJ8-2

6,6-Dimethyl-11-oxo-9-((2R,3R)-2,3,4-trihydroxy-butoxy)-6,11-dihydro-5H-benzo[b]carbazole-3-carbonitrile

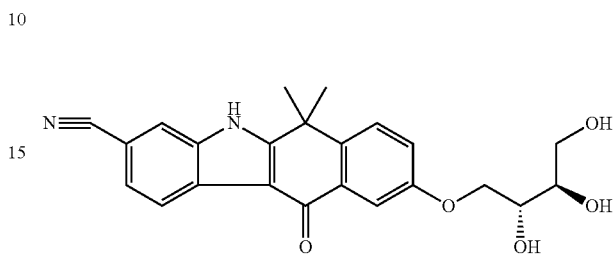

Under the same conditions as the method for synthesizing Compound JJ7-2, the title compound was prepared from 9-[(4R,5R)-5-(tert-butyl-dimethyl-silanyloxymethyl)-2,2-dimethyl-[1,3]dioxolan-4-yl methoxy]-6,6-dimethyl-11-oxo-6,11-dihydro-5H-benzo[b]carbazole-3-carbonitrile (Compound JJ8-1) (white solid, 7.8 mg, 97%).

LCMS: m/z 407 [M+H]$^+$

HPLC retention time: 1.92 min (analysis condition F)

Example 461

Compound JJ9-1

9-((R)-2,3-Dihydroxy-propoxy)-6,6-dimethyl-11-oxo-6,11-dihydro-5H-benzo[b]carbazole-3-carbonitrile

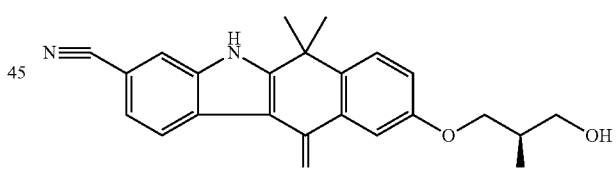

3-Bromo-9-((S)-2,2-dimethyl-[1,3]dioxolan-4-yl-methoxy)-6,6-dimethyl-5,6-dihydro-benzo[b]carbazol-11-one (Compound JJ3-1, 49.5 mg, 0.105 mmol) and copper cyanide (90%, 35.3 mg, 3.4 eq.) were added with DMA (0.5 mL), and the mixture was irradiated with microwave at 200° C. for 1 hr under nitrogen atmosphere. After cooling, the reaction solution was added with water and extracted with ethyl acetate. The insoluble matters were separated off by filtration, and the organic layer was washed with brine and dried over magnesium sulfate. After filtration and the concentration under reduced pressure, the resulting residues were purified by preparative TLC (methanol/dichloromethane) to obtain the title compound (white solid, 8.5 mg, 22%).

LCMS: m/z 377 [M+H]$^+$

HPLC retention time: 2.02 min (analysis condition F)

Example 462

Compound JJ9-2

9-((S)-2,2-Dimethyl-[1,3]dioxolan-4-ylmethoxy)-6,6-dimethyl-11-oxo-6,11-dihydro-5H-benzo[b]carbazole-3-carbonitrile

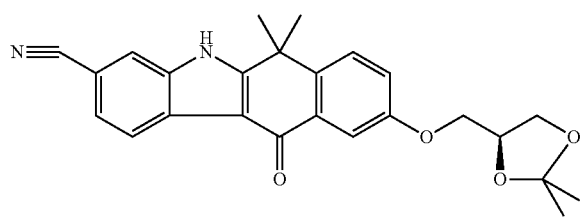 [SMILES: CC1(C)OC[C@H](COc2ccc3c(c2)C(=O)c2c([nH]c4cc(C#N)ccc24)C3(C)C)O1]

The title compound was obtained as a by-product of the synthesis of Compound JJ9-1 (white solid, 24.8 mg, 57%).
LCMS: m/z 417 [M+H]$^+$
HPLC retention time: 2.81 min (analysis condition F)

Example 463

Compound JJ9-3

9-((S)-2,2-Dimethyl-[1,3]dioxolan-4-yl methoxy)-5,6,6-trimethyl-11-oxo-6,11-dihydro-5H-benzo[b]carbazole-3-carbonitrile

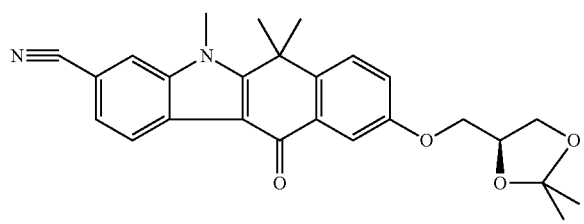 [SMILES: Cn1c2c(c3ccc(C#N)cc31)C(=O)c1cc(OC[C@H]3COC(C)(C)O3)ccc1C2(C)C]

Under the same conditions as the method for synthesizing Compound JJ4-1, the title compound was prepared from 9-((S)-2,2-dimethyl-[1,3]dioxolan-4-ylmethoxy)-6,6-dimethyl-11-oxo-6,11-dihydro-5H-benzo[b]carbazole-3-carbonitrile (Compound JJ9-2) (17.0 mg, 84%).
LCMS: m/z 431 [M+H]$^+$
HPLC retention time: 3.00 min (analysis condition F)

Example 464

Compound JJ9-4

9-((R)-2,3-Dihydroxy-propoxy)-5,6,6-trimethyl-11-oxo-6,11-dihydro-5H-benzo[b]carbazole-3-carbonitrile

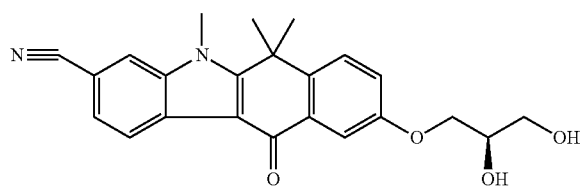 [SMILES: Cn1c2c(c3ccc(C#N)cc31)C(=O)c1cc(OC[C@H](O)CO)ccc1C2(C)C]

Under the same conditions as the method for synthesizing Compound JJ3-2, the title compound was prepared from 9-((S)-2,2-dimethyl-[1,3]dioxolan-4-ylmethoxy)-5,6,6-trimethyl-11-oxo-6,11-dihydro-5H-benzo[b]carbazole-3-carbonitrile (JJ9-3) (white solid, 12.1 mg, 90%).
LCMS: m/z 391 [M+H]$^+$
HPLC retention time: 2.13 min (analysis condition F)

Example 465

Compound JJ10-1

9-Benzyloxy-3-bromo-6,6-dimethyl-5,6-dihydro-benzo[b]carbazol-11-one

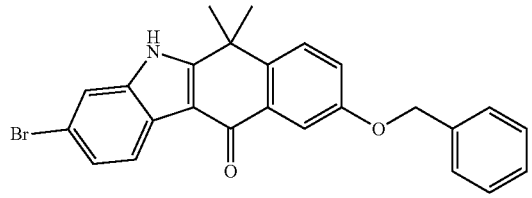 [SMILES: CC1(C)c2ccc(OCc3ccccc3)cc2C(=O)c2c1[nH]c1cc(Br)ccc21]

Under the same conditions as the method for synthesizing Compound A7-17, the title compound was prepared from Compound JJ2 and benzyl bromide (18.2 mg, 61%).
LCMS: m/z 446 [M+H]$^+$
HPLC retention time: 2.68 min (analysis condition D)

Example 466

Compound JJ10-2

5-Benzyl-9-benzyloxy-3-bromo-6,6-dimethyl-5,6-dihydro-benzo[b]carbazol-11-one

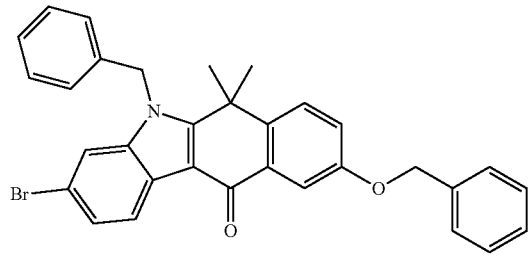 [SMILES: CC1(C)c2ccc(OCc3ccccc3)cc2C(=O)c2c1n(Cc1ccccc1)c1cc(Br)ccc21]

The title compound was obtained as a by-product of the synthesis of Compound JJ10-1 (5.3 mg, 21%).
LCMS: m/z 536 [M+H]$^+$
HPLC retention time: 3.17 min (analysis condition D)

Example 467

Compound JJ10-3

3-Bromo-9-(4-methoxy-benzyloxy)-6,6-dimethyl-5,6-dihydro-benzo[b]carbazol-11-one

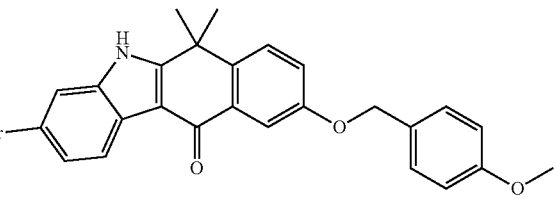

Under the same conditions as the method for synthesizing Compound A7-1, the title compound was prepared by reacting Compound JJ2 and (4-methoxyphenyl)-methanol (7.5 mg, 28%).

LCMS: m/z 476 [M+H]+
HPLC retention time: 2.70 min (analysis condition D)

Example 468

Compound K2

2-(3-Bromo-4-methoxy-phenyl)-2-methyl-propionitrile

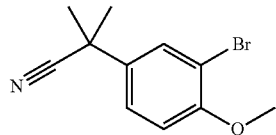

To the THF suspension of potassium tert-butoxide (15.35 g, 3 eq.), (3-bromo-4-methoxyphenyl)acetonitrile (Compound K1, 10 g, 0.044 mmol) was added, and then stirred at 0° C. for 1 hr. Then, iodomethane (8.26 ml, 3 eq.) was added and the mixture was stirred at room temperature for 1 hr. To the reaction solution, saturated aqueous solution of ammonium chloride and water were added followed by extraction with ethyl acetate. The organic layer was washed with brine and dried over sodium sulfate. The drying agent was removed by filtration and the residues obtained after concentration under reduced pressure were purified by silica gel column chromatography (ethyl acetate/hexane) to obtain the title compound (colorless oily substance, 11.24 g, 100%).
$^1$H-NMR (270 MHz, DMSO-$d_6$) δ: 7.69 (1H, d, J=2.5 Hz), 7.50 (1H, dd, J=8.6, 2.5 Hz), 7.16 (1H, d, J=8.6 Hz), 3.86 (3H, s), 1.67 (6H, s).
HPLC retention time: 2.30 min (analysis condition S)

Example 469

Compound K3

4-(3-Bromo-4-methoxy-phenyl)-4-methyl-3-oxo-pentanoic acid ethyl ester

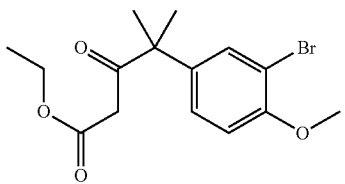 [SMILES: CCOC(=O)CC(=O)C(C)(C)c1ccc(OC)c(Br)c1]

To the THF suspension of zinc (5.72 g, 2 eq.), methanesulfonic acid (25.6 µl, 0.01 eq.) was added, and then stirred at 80° C. for 10 min. Then, the THF solution of 2-(3-bromo-4-methoxy-phenyl)-2-methyl-propionitrile (10 g, 39.35 mmol) was added, followed by addition of bromoethyl acetate (11.07 ml, 1.6 eq.) over 1 hr. The mixture was further stirred for 30 min. To the reaction solution, 4 M hydrochloric acid was added, and stirred at room temperature overnight. After extraction with ethyl acetate, the organic layer was washed with brine and dried over sodium sulfate. The drying agent was removed by filtration and the residues obtained after concentration under reduced pressure were purified by silica gel column chromatography (ethyl acetate/hexane) to obtain the title compound (orange oily substance, 9.74 g, 72%).
$^1$H-NMR (270 MHz, CDCl$_3$) δ: 7.46 (1H, d, J=2.5 Hz), 7.16 (1H, dd, J=8.6, 2.5 Hz), 6.89 (1H, d, J=8.6 Hz), 4.17-4.08 (2H, m), 3.90 (3H, s), 3.26 (2H, s), 1.49 (6H, s), 1.23 (3H, t, J=7.2 Hz).

LCMS: m/z 343, 345 [M+H]+
HPLC retention time: 2.64 min (analysis condition S)

Example 470

Compound K4

4-(3-Bromo-4-methoxy-phenyl)-2-(4-cyano-2-nitro-phenyl)-4-methyl-3-oxo-pentanoic acid ethyl ester

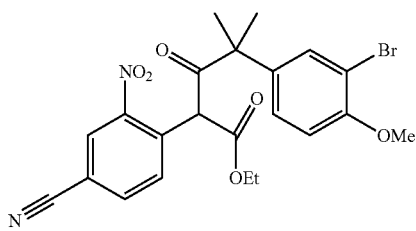 [SMILES: CCOC(=O)C(C(=O)C(C)(C)c1ccc(OC)c(Br)c1)c1ccc(C#N)cc1[N+](=O)[O-]]

4-(3-Bromo-4-methoxy-phenyl)-4-methyl-3-oxo-pentanoic acid ethyl ester (Compound K3, 10.3 g, 30.01 mmol) was dissolved in DMF (80 mL), added with cesium carbonate (24.4 g, 2.5 eq.) and 4-chloro-3-nitro-benzonitrile (7.12 g, 1.3 eq.), and then stirred at 45° C. for 4 hr. The reaction solution was added to 1 N aqueous solution of hydrochloric acid, and extracted with ethyl acetate. The organic layer was washed with saturated brine and dried over sodium sulfate. The drying agent was removed by filtration, and after concentration under reduced pressure the title compound was obtained as a crude product (yellow oily substance).
LCMS: m/z 489, 491 [M+H]+
HPLC retention time: 2.85, 3.20 min (analysis condition S)

Example 471

Compound K5

2-[1-(3-Bromo-4-methoxy-phenyl)-1-methyl-ethyl]-6-cyano-1H-indole-3-carboxylic acid ethyl ester

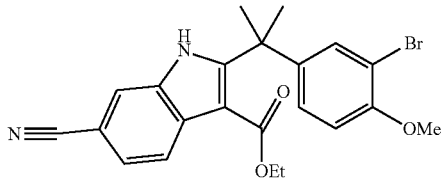 [SMILES: CCOC(=O)c1c(C(C)(C)c2ccc(OC)c(Br)c2)[nH]c2cc(C#N)ccc12]

4-(3-Bromo-4-methoxy-phenyl)-2-(4-cyano-2-nitro-phenyl)-4-methyl-3-oxo-pentanoic acid ethyl ester (Compound K4), which had been obtained from the above, was dissolved in THF (140 mL) and water (70 mL), added with Na$_2$S$_2$O$_4$ (26.13 g, 5.0 eq.) and stirred at 50° C. overnight. The reaction solution was added to saturated brine and extracted with ethyl acetate. The organic layer was washed with 1 M aqueous solution of potassium carbonate and saturated brine in order, and dried over sodium sulfate. The drying agent was removed by filtration and the residues obtained after concentration under reduced pressure were purified by crystallization in MeCN (80 ml) to obtain the title compound (yellow solid, 8.20 g, 62%).
$^1$H-NMR (270 MHz, DMSO-$d_6$) δ: 12.15 (1H, s), 8.07 (1H, d, J=8.4 Hz), 7.94 (1H, s), 7.51 (1H, dd, J=8.5, 1.2 Hz), 7.33 (1H, d, J=2.1 Hz), 7.03 (1H, dd, J=8.7, 2.4 Hz), 6.96 (1H, d, J=8.4 Hz), 3.97 (2H, q, J=7.3 Hz), 3.78 (3H, s), 1.80 (6H, s), 1.09 (3H, t, J=7.2 Hz).

LCMS: m/z 441, 443 [M+H]+

HPLC retention time: 2.85 min (analysis condition S)

Example 472

Compound K6

8-Bromo-9-methoxy-6,6-dimethyl-11-oxo-6,11-dihydro-5H-benzo[b]carbazole-3-carbonitrile

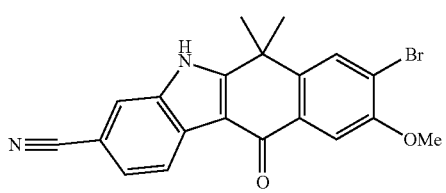 [SMILES: COc1cc2c(cc1Br)C(C)(C)c1[nH]c3cc(C#N)ccc3c1C2=O]

Phosphorus pentoxide-methanesulfonic acid (12 mL) was added with 2-[1-(3-bromo-4-methoxy-phenyl)-1-methyl-ethyl]-6-cyano-1H-indole-3-carboxylic acid ethyl ester (Compound K5, 1.0 g, 2.27 mmol), and the mixture was stirred at room temperature for 20 min. The reaction solution was diluted with MeCN (20 mL), poured into water (20 mL), and the precipitated solid was filtered to obtain the title compound (yellow solid, 763 mg, 85%).

$^1$H-NMR (270 MHz, DMSO-d$_6$) δ: 12.84 (1H, s), 8.32 (1H, d, J=8.1 Hz), 8.15 (1H, s), 8.03 (1H, s), 7.77 (1H, s), 7.64 (1H, dd, J=8.2, 1.4 Hz), 3.97 (3H, s), 1.75 (6H, s).

LCMS: m/z 395, 397 [M+H]+

HPLC retention time: 2.58 min (analysis condition S)

Example 473

Compound K7-1

9-Methoxy-6,6-dimethyl-11-oxo-8-(4-pyrrolidin-1-yl-piperidin-1-yl)-6,11-dihydro-5H-benzo[b]carbazole-3-carbonitrile

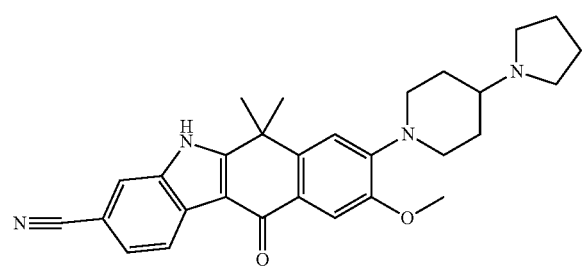 [SMILES: COc1cc2c(cc1N1CCC(N3CCCC3)CC1)C(C)(C)c1[nH]c3cc(C#N)ccc3c1C2=O]

Under the same conditions as the method for synthesizing Compound B2-1, the title compound was prepared from Compound K6 and 4-pyrrolidin-1-yl-piperidine.

LCMS: m/z 469 [M+H]+

HPLC retention time: 1.37 min (analysis condition S)

Example 474

Compound K7-2

9-Methoxy-6,6-dimethyl-8-(4-morpholin-1-yl-piperidin-1-yl)-11-oxo-6,11-dihydro-5H-benzo[b]carbazole-3-carbonitrile

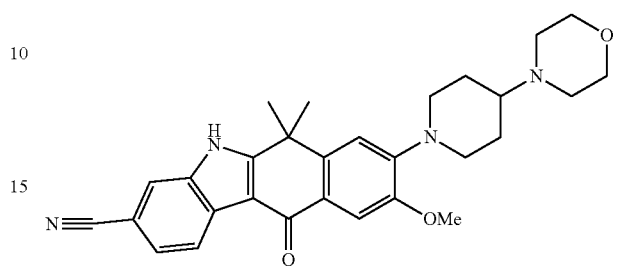

Under the same conditions as the method for synthesizing Compound B2-1, the title compound was prepared from Compound K6 and 4-piperidin-4-yl-morpholine.

$^1$H-NMR (270 MHz, DMSO-d$_6$) δ: 12.70 (1H, s), 8.31 (1H, d, J=8.2 Hz), 7.99 (1H, s), 7.63 (1H, s), 7.60 (1H, dd, J=8.2, 1.2 Hz), 7.16 (1H, s), 3.89 (3H, s), 3.64 (2H, brd), 2.72 (2H, brd), 1.91 (2H, brd), 1.73 (6H, s), 1.57 (2H, brd).

LCMS: m/z 485 [M+H]+

HPLC retention time: 1.33 min (analysis condition S)

Example 475

Compound K7-3

9-Methoxy-6,6-dimethyl-11-oxo-8-piperazin-1-yl-6,11-dihydro-5H-benzo[b]carbazole-3-carbonitrile

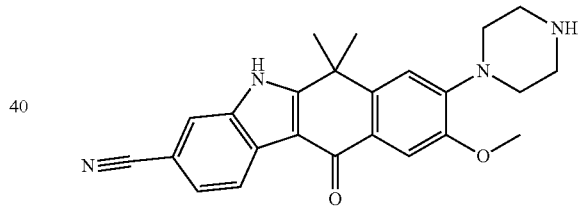

Under the same conditions as the method for synthesizing Compound B2-1, the target compound was prepared from Compound K6 and piperazine.

LCMS: m/z 401 [M+H]+

HPLC retention time: 1.31 min (analysis condition S)

Example 476

Compound K7-4

9-Methoxy-6,6-dimethyl-8-morpholin-4-yl-11-oxo-6,11-dihydro-5H-benzo[b]carbazole-3-carbonitrile

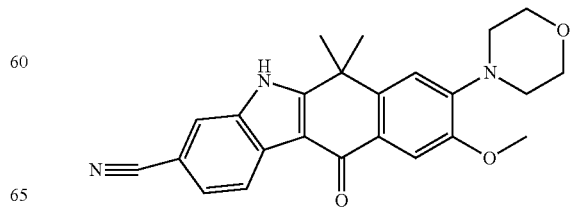

Under the same conditions as the method for synthesizing Compound B2-1, the title compound was prepared from Compound K6 and morpholine.

LCMS: m/z 402 [M+H]⁺

HPLC retention time: 2.10 min (analysis condition S)

Example 477

Compound K8

8-(4-Cyclobutyl-piperazin-1-yl)-9-methoxy-6,6-dimethyl-11-oxo-6,11-dihydro-5H-benzo[b]carbazole-3-carbonitrile

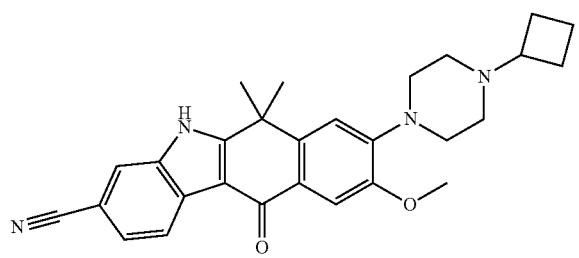 [SMILES: COc1cc2c(cc1N1CCN(C3CCC3)CC1)C(C)(C)c1[nH]c3cc(C#N)ccc3c1C2=O]

Under the same conditions as the method for synthesizing Compound B3-32, the title compound was prepared from Compound K7-3 and cyclobutanone.

$^1$H-NMR (270 MHz, DMSO-$d_6$) δ: 12.70 (1H, br. s), 8.31 (1H, d, J=8.2 Hz), 8.00 (1H, s), 7.64 (1H, s), 7.61 (1H, dd, J=8.1, 1.3 Hz), 7.16 (1H, s), 3.88 (3H, s), 3.60 (1H, t, J=6.2 Hz), 3.10-3.25 (4H, m), 2.77 (1H, t, J=7.1 Hz), 2.35-2.51 (4H, m), 1.74 (6H, s), 1.58-2.08 (6H, m).

LCMS: m/z 455 [M+H]⁺

HPLC retention time: 1.45 min (analysis condition S)

Example 478

Compound K9-1

9-Hydroxy-6,6-dimethyl-11-oxo-8-(4-pyrrolidin-1-yl-piperidin-1-yl)-6,11-dihydro-5H-benzo[b]carbazole-3-carbonitrile

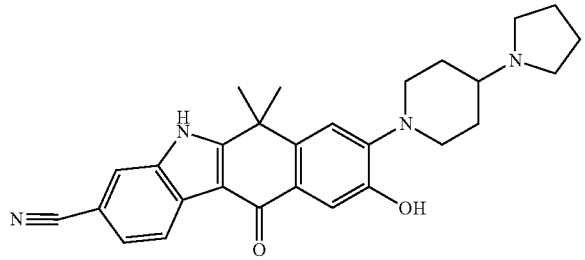 [SMILES: CC1(C)c2cc(N3CCC(N4CCCC4)CC3)c(O)cc2C(=O)c2c1[nH]c1cc(C#N)ccc21]

The title compound was obtained as a by-product of the synthesis of Compound K7-1.

LCMS: m/z 455 [M+H]⁺

HPLC retention time: 1.22 min (analysis condition S)

Example 479

Compound K9-2

9-Hydroxy-6,6-dimethyl-8-(4-morpholin-4-yl-piperidin-1-yl)-11-oxo-6,11-dihydro-5H-benzo[b]carbazole-3-carbonitrile

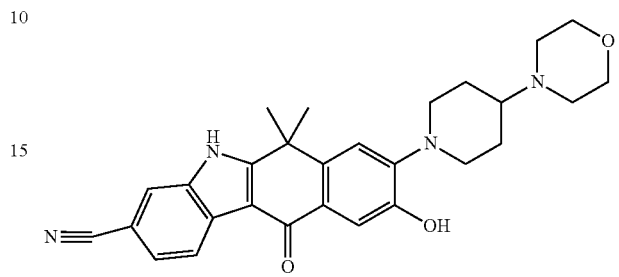

Under the same conditions as the method for synthesizing Compound E3-2, the title compound was prepared from Compound K7-2.

$^1$H-NMR (270 MHz, DMSO-$d_6$) δ: 12.65 (1H, s), 9.61 (1H, s), 8.30 (1H, d, J=8.2 Hz), 7.98 (1H, s), 7.59-7.56 (2H, m), 7.10 (1H, s), 3.71 (2H, brd, J=11.2 Hz), 3.60 (4H, m), 2.66 (2H, m), 1.88 (2H, brd, J=9.7 Hz), 1.71 (6H, s), 1.57 (2H, brd).

LCMS: m/z 471 [M+H]⁺

HPLC retention time: 1.20 min (analysis condition S)

Example 480

Compound K9-3

8-(4-Cyclobutyl-piperazin-1-yl)-9-hydroxy-6,6-dimethyl-11-oxo-6,11-dihydro-5H-benzo[b]carbazole-3-carbonitrile

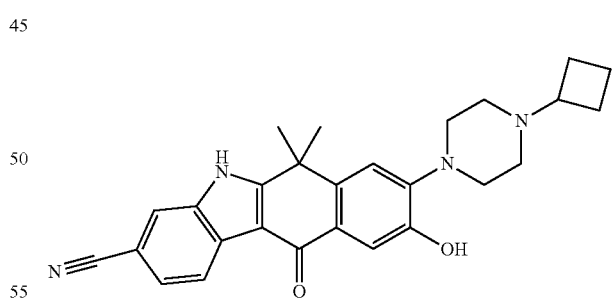

Under the same conditions as the method for synthesizing Compound E3-2, the title compound was prepared from Compound K8.

$^1$H-NMR (270 MHz, DMSO-$d_6$) δ: 12.66 (1H, br. s), 9.67 (1H, s), 8.31 (1H, d, J=8.2 Hz), 7.98 (1H, s), 7.56-7.60 (2H, m), 7.09 (1H, s), 3.10-3.24 (4H, m), 2.77 (1H, t, J=7.5 Hz), 2.37-2.49 (4H, m), 1.52-2.07 (6H, m), 1.72 (6H, s).

LCMS: m/z 441 [M+H]⁺

HPLC retention time: 1.31 min (analysis condition S)

Example 481

Compound K9-4

9-Hydroxy-6,6-dimethyl-8-morpholin-4-yl-11-oxo-6,11-dihydro-5H-benzo[b]carbazole-3-carbonitrile

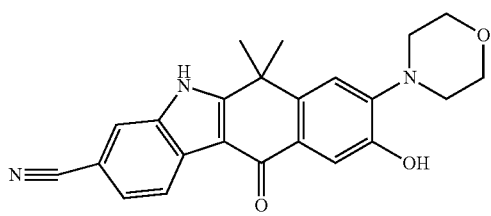 [SMILES: CC1(C)c2cc(N3CCOCC3)c(O)cc2C(=O)c2c1[nH]c1cc(C#N)ccc21]

Under the same conditions as the method for synthesizing Compound E3-2, the title compound was prepared from Compound K7-4.

LCMS: m/z 388 [M+H]$^+$

HPLC retention time: 1.67 min (analysis condition S)

Example 482

Compound K10-1

9-Isopropoxy-6,6-dimethyl-8-(4-morpholin-4-yl-piperidin-1-yl)-11-oxo-6,11-dihydro-5H-benzo[b]carbazole-3-carbonitrile

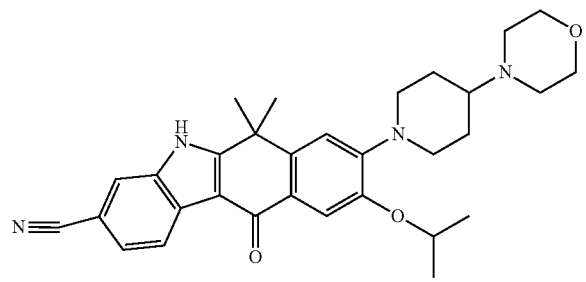 [SMILES: CC(C)Oc1cc2c(cc1N1CCC(N3CCOCC3)CC1)C(C)(C)c1[nH]c3cc(C#N)ccc3c1C2=O]

Under the same conditions as the method for synthesizing Compound A7-17, the title compound was prepared from Compound K9-2 and 2-bromopropane.

$^1$H-NMR (270 MHz, DMSO-d$_6$) δ: 12.68 (1H, s), 8.30 (1H, d, J=8.1 Hz), 7.99 (1H, s), 7.60 (2H, m), 7.14 (1H, s), 4.72-4.63 (2H, m), 3.71 (2H, brd, J=10.7 Hz), 3.59 (6H, m), 2.68 (2H, t, J=12.9 Hz), 2.27 (2H, brd), 1.90 (2H, brd), 1.73 (6H, s), 1.56 (2H, br), 1.34 (6H, d, J=5.9 Hz).

LCMS: m/z 513 [M+H]$^+$

HPLC retention time: 1.48 min (analysis condition S)

Example 483

Compound K10-2

8-(4-Cyclobutyl-piperazin-1-yl)-9-isopropoxy-6,6-dimethyl-11-oxo-6,11-dihydro-5H-benzo[b]carbazole-3-carbonitrile

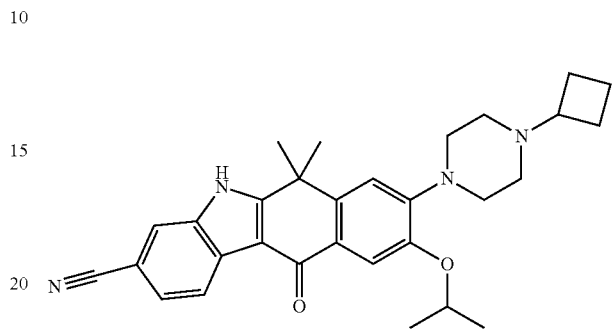

Under the same conditions as the method for synthesizing Compound A7-17, the title compound was prepared from Compound K9-3 and 2-iodopropane.

$^1$H-NMR (270 MHz, DMSO-d$_6$) δ: 8.29 (1H, d, J=8.1 Hz), 7.98 (1H, s), 7.56-7.63 (2H, m), 7.14 (1H, s), 4.62-4.74 (1H, m), 3.10-3.26 (4H, m), 2.69-2.85 (1H, m), 2.35-2.48 (4H, m), 1.57-2.08 (6H, m), 1.73 (6H, s), 1.32 (6H, d, J=6.1 Hz).

LCMS: m/z 483 [M+H]$^+$

HPLC retention time: 1.65 min (analysis condition S)

Example 484

Compound K10-3

9-(2-Methoxy-ethoxy)-6,6-dimethyl-8-morpholin-4-yl-11-oxo-6,11-dihydro-5H-benzo[b]carbazole-3-carbonitrile

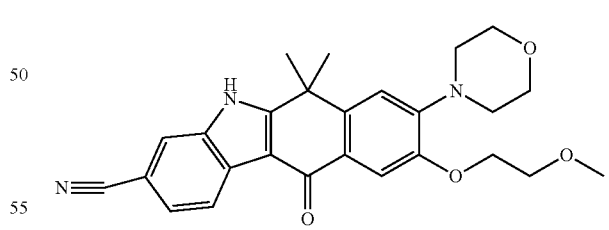

Under the same conditions as the method for synthesizing Compound A7-17, the title compound was prepared from Compound K9-4 and 1-bromo-2-methoxyethane.

$^1$H-NMR (400 MHz, DMSO-d$_6$) δ: 12.67 (1H, s), 8.30 (1H, d, 7.9 Hz), 7.98 (1H, s), 7.64 (1, s), 7.58 (1H, d, 7.9 Hz), 7.16 (1H, s), 4.18-4.22 (2H, m), 3.72-3.80 (6H, m), 3.35 (3H, s), 3.18-3.24 (4H, s), 1.74 (1H, s)

LCMS: m/z 446 [M+H]$^+$

HPLC retention time: 3.23 min (analysis condition W)

Example 485

Compound K10-4

9-[2-(2-Methoxy-ethoxy)-ethoxy]-6,6-dimethyl-8-morpholin-4-yl-11-oxo-6,11-dihydro-5H-benzo[b]carbazole-3-carbonitrile

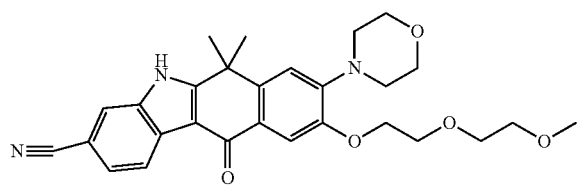 [SMILES: COCCOCCOc1cc2c(cc1N1CCOCC1)C(C)(C)c1[nH]c3cc(C#N)ccc3c1C2=O]

Under the same conditions as the method for synthesizing Compound A7-17, the title compound was prepared from Compound K9-4 and 1-bromo-2-(2-methoxyethoxyl)ethane.
LCMS: m/z 490 [M+H]⁺
HPLC retention time: 3.16 min (analysis condition W)

Example 486

Compound K10-5

6,6-Dimethyl-8-morpholin-1-yl-11-oxo-9-[(S)-(tetrahydro-furan-3-yl)oxy]-6,11-dihydro-5H-benzo[b]carbazole-3-carbonitrile

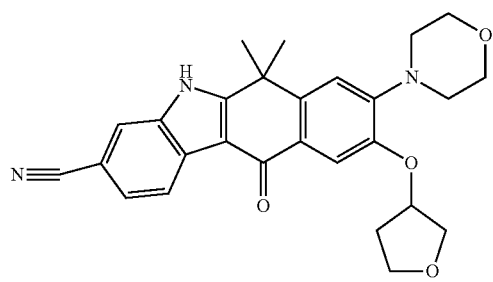 [SMILES: CC1(C)c2cc(N3CCOCC3)c(OC3CCOC3)cc2C(=O)c2c1[nH]c1cc(C#N)ccc21]

Under the same conditions as the method for synthesizing Compound A7-17, the title compound was prepared from Compound K9-4 and 3-mesyloxytetrahydrofurane.
LCMS: m/z 458 [M+H]⁺
HPLC retention time: 3.20 min (analysis condition W)

Example 487

Compound K10-6

9-Isopropoxy-6,6-dimethyl-8-morpholin-4-yl-11-oxo-6,11-dihydro-5H-benzo[b]carbazole-3-carbonitrile

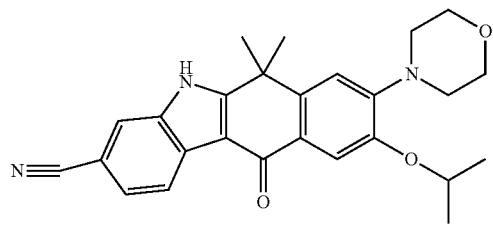 [SMILES: CC(C)Oc1cc2c(cc1N1CCOCC1)C(C)(C)c1[nH]c3cc(C#N)ccc3c1C2=O]

Under the same conditions as the method for synthesizing Compound A7-17, the title compound was prepared from Compound K9-4 and 2-bromopropane.
$^1$H-NMR (270 MHz, DMSO-$d_6$) δ: 12.70 (1H, br. s), 8.32-8.29 (1H, d, 8.08 Hz), 8.00 (1H, s), 7.63 (1H, s), 7.62-7.59 (1H, d, 8.08 Hz), 7.16 (1H, s), 4.75-4.66 (1H, m), 3.77 (4H, m) 3.19 (4H, m), 1.74 (6H, s), 1.35 (3H, s), 1.33 (3H, s)
LCMS: m/z 430 [M+H]⁺

Example 488

Compound K10-7

9-(2-Hydroxy-ethoxy)-6,6-dimethyl-8-morpholin-4-yl-11-oxo-6,11-dihydro-5H-benzo[b]carbazole-3-carbonitrile

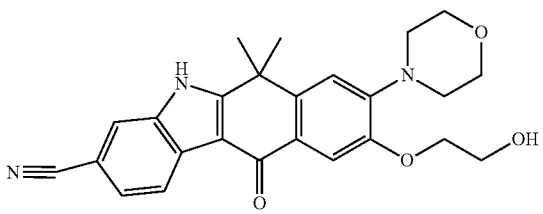 [SMILES: CC1(C)c2cc(N3CCOCC3)c(OCCO)cc2C(=O)c2c1[nH]c1cc(C#N)ccc21]

Under the same conditions as the method for synthesizing Compound A7-17, the title compound was prepared from Compound K9-4 and 2-bromoethanol.
$^1$H-NMR (270 MHz, DMSO-$d_6$) δ: 12.71 (1H, br. s), 8.33-8.30 (1H, d, 8.08 Hz), 8.00 (1H, s), 7.63 (1H, s), 7.62-7.59 (1H, d, 8.08 Hz), 7.16 (1H, s), 4.13-4.09 (2H, t, 4.61 Hz), 3.81-3.78 (2H, t, 4.61 Hz), 3.78 (4H, m) 3.23 (4H, m), 1.75 (6H, s)
LCMS: m/z 432 [M+H]⁺

Example 489

Compound L2-1

(4-Isopropoxy-3-methoxy-phenyl)-ethyl acetate ester

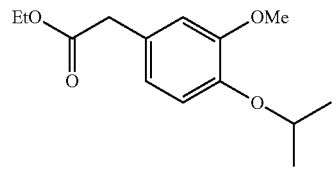 [SMILES: CCOC(=O)Cc1ccc(OC(C)C)c(OC)c1]

(4-Hydroxy-3-methoxy-phenyl)-ethyl acetate ester (Compound L1-1, 3.0 g, 14.27 mmol) was dissolved in DMF (70 mL), added with 2-iodopropane (2.9 mL, 2.0 eq.) and potassium carbonate (3.94 g, 2.0 eq.), and stirred at 80° C. overnight. The reaction solution was added to water and extracted with ethyl acetate. The organic layer was washed with saturated brine and dried over sodium sulfate. The drying agent was removed by filtration and the residues obtained after concentration under reduced pressure were purified by silica gel column chromatography (ethyl acetate/hexane) to obtain the target compound (yellow oily substance, 2.61 g, 73%).
$^1$H-NMR (270 MHz, DMSO-$d_6$) δ: 6.88 (2H, m), 6.74 (1H, dd, J=8.1, 2.1 Hz), 4.52-4.43 (1H, m), 4.07 (2H, q, J=7.1 Hz), 3.72 (3H, s), 3.56 (2H, s), 1.23 (6H, d, J=6.1 Hz), 1.18 (3H, t, J=7.1 Hz).

LCMS: m/z 253 [M+H]+

HPLC retention time: 2.18 min (analysis condition S)

Example 490

Compound L2-2

(4-Isopropoxy-3-methoxy-phenyl)-acetic acid isopropyl ester

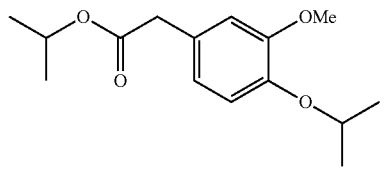 [SMILES: COc1cc(CC(=O)OC(C)C)ccc1OC(C)C]

(4-Hydroxy-3-methoxy-phenyl)-acetic acid (Compound L1-2, 1.5 g, 8.23 mmol) was dissolved in DMF (30 mL), added with 2-iodopropane (3.3 mL, 4.0 eq.) and potassium carbonate (4.55 g, 4.0 eq.), and stirred at 80° C. overnight. The reaction solution was added to water and extracted with ethyl acetate. The organic layer was washed with saturated brine and dried over sodium sulfate. The drying agent was removed by filtration and the residues obtained after concentration under reduced pressure were purified by silica gel column chromatography (ethyl acetate/hexane) to obtain the target compound (yellow oily substance, 1.21 g, 55%).

$^1$H-NMR (270 MHz, DMSO-$d_6$) δ: 6.87 (2H, s+d), 6.73 (1H, dd, J=8.1, 2.1 Hz), 4.94-4.84 (1H, m), 4.52-4.43 (1H, m), 3.72 (3H, s), 3.52 (2H, s), 1.23 (6H, d, J=6.1 Hz), 1.18 (6H, d, J=6.1 Hz).

LCMS: m/z 267 [M+H]+

HPLC retention time: 2.40 min (analysis condition S)

Example 491

Compound L3-1

2-(4-Isopropoxy-3-methoxy-phenyl)-2-methyl-propionic acid ethyl ester

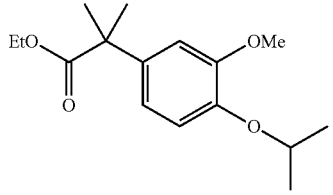 [SMILES: CCOC(=O)C(C)(C)c1ccc(OC(C)C)c(OC)c1]

Under the same conditions as the method for synthesizing Compound K2, the title compound was prepared from Compound L2-1.

$^1$H-NMR (270 MHz, DMSO-$d_6$) δ: 6.90-6.76 (3H, m), 4.53-4.44 (1H, m), 4.06 (2H, q, J=7.1 Hz), 3.73 (3H, s), 1.47 (6H, s), 1.23 (6H, d, J=6.1 Hz), 1.12 (3H, t, J=7.0 Hz).

LCMS: m/z 281 [M+H]+

HPLC retention time: 2.57 min (analysis condition S)

Example 492

Compound L3-2

2-(4-Isopropoxy-3-methoxy-phenyl)-2-methyl-propionic acid isopropyl ester

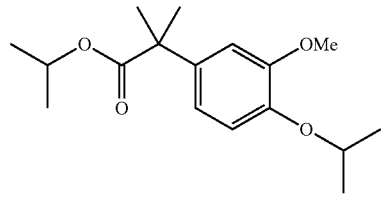 [SMILES: COc1cc(C(C)(C)C(=O)OC(C)C)ccc1OC(C)C]

Under the same conditions as the method for synthesizing Compound K2, the title compound was prepared from Compound L2-2.

$^1$H-NMR (270 MHz, DMSO-$d_6$) δ: 6.88 (1H, d, J=8.2 Hz), 6.79 (2H, m), 4.94-4.84 (1H, m), 4.53-4.44 (1H, m), 3.72 (3H, s), 1.45 (6H, s), 1.23 (6H, d, J=6.1 Hz), 1.12 (6H, d, J=6.3 Hz).

LCMS: m/z 295 [M+H]+

HPLC retention time: 2.75 min (analysis condition S)

Example 493

Compound L4

2-(4-Isopropoxy-3-methoxy-phenyl)-2-methyl-propionic acid

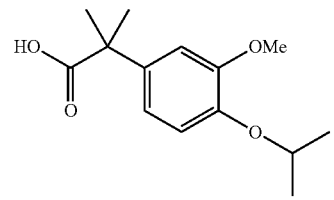 [SMILES: COc1cc(C(C)(C)C(=O)O)ccc1OC(C)C]

2-(4-Isopropoxy-3-methoxy-phenyl)-2-methyl-propionic acid ethyl ester (Compound L3-1, 1.45 g, 5.17 mmol) was dissolved in THF (13 mL) and EtOH (13 mL), added with 1 N aqueous solution of sodium hydroxide (10.3 mL, 2.0 eq.), and stirred at 80° C. overnight. The reaction solution was added to water and extracted with ethyl acetate. The aqueous layer was acidified by using 1 N aqueous solution of hydrochloric acid, extracted with ethyl acetate, washed with saturated brine and dried over sodium sulfate. The drying agent was removed by filtration and the residues obtained after concentration under reduced pressure were purified by silica gel column chromatography (ethyl acetate/hexane) to obtain the target compound (white solid, 1.10 g, 84%).

$^1$H-NMR (270 MHz, DMSO-$d_6$) δ: 12.26 (1H, s), 6.90-6.80 (3H, m), 4.49 (1H, m), 3.73 (3H, s), 1.45 (6H, s), 1.23 (6H, d, J=6.1 Hz).

LCMS: m/z 253 [M+H]+

HPLC retention time: 1.83 min (analysis condition S)

Example 494

Compound L5

4-(4-Isopropoxy-3-methoxy-phenyl)-4-methyl-3-oxo-pentanoic acid ethyl ester

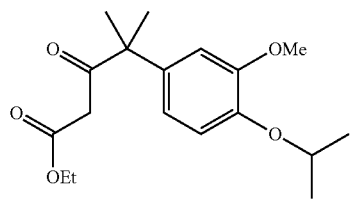 [SMILES: CCOC(=O)CC(=O)C(C)(C)c1ccc(OC(C)C)c(OC)c1]

2-(4-Isopropoxy-3-methoxy-phenyl)-2-methyl-propionic acid (Compound L4, 1.4 g, 5.55 mmol) was added with thionyl chloride (10 mL), and then stirred at room temperature for 5 hr. According to the concentration under reduced pressure, unreacted thionyl chloride was removed to obtain corresponding acid chloride.

To MeCN (40 mL), malonic acid monoethyl ester potassium salt (1.98 g, 2.1 eq.), triethylamine (2.47 mL, 3.2 eq.), and magnesium chloride (1.32 g, 2.5 eq.) were added and the mixture was stirred at room temperature for 2 hr. To the reaction solution, MeCN (15 mL) solution of the acid chloride prepared from the above was added dropwise. Upon the completion of the dropwise addition, the mixture was further stirred at room temperature for overnight. MeCN was removed by distillation and concentrated under reduced pressure, and the resulting residues were added with 1 N aqueous solution of hydrochloric acid, extracted with toluene, washed with saturated brine, and dried over sodium sulfate. The drying agent was removed by filtration and the residues obtained after concentration under reduced pressure were purified by silica gel column chromatography (ethyl acetate/hexane) to obtain the target compound (yellow oily substance, 1.45 g, 81%).

$^1$H-NMR (270 MHz, DMSO-$d_6$) δ: 6.94 (1H, d, J=8.2 Hz), 6.76 (2H, m), 4.56-4.47 (1H, m), 4.00 (2H, q, J=7.1 Hz), 3.74 (3H, s), 3.38 (2H, s), 1.41 (6H, s), 1.24 (6H, d, J=6.1 Hz), 1.12 (3H, t, J=7.3 Hz).

LCMS: m/z 323 [M+H]$^+$

HPLC retention time: 2.45, 3.03 min (analysis condition S)

Example 495

Compound L6

2-(4-Cyano-2-nitro-phenyl)-4-(4-isopropoxy-3-methoxy-phenyl)-4-methyl-3-oxo-pentanoic acid ethyl ester

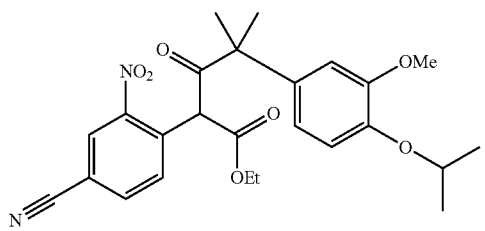 [SMILES: CCOC(=O)C(C(=O)C(C)(C)c1ccc(OC(C)C)c(OC)c1)c1ccc(C#N)cc1[N+](=O)[O-]]

Under the same conditions as the method for synthesizing Compound K4, the title compound was prepared from Compound L5.

$^1$H-NMR (270 MHz, DMSO-$d_6$) δ: 8.35 (1H, d, J=1.8 Hz), 8.14 (1H, dd, J=8.2, 1.9 Hz), 7.67 (1H, d, J=8.2 Hz), 6.68 (1H, d, J=8.4 Hz), 6.59 (1H, dd, J=8.4, 2.0 Hz), 6.45 (1H, d, J=2.1 Hz), 5.44 (1H, s), 4.43 (1H, m), 4.09 (2H, q, J=7.1 Hz), 3.53 (3H, s), 1.59 (3H, s), 1.35 (3H, s), 1.24 (6H, dx2), 1.13 (3H, t, J=7.1 Hz).

LCMS: m/z 469 [M+H]$^+$

HPLC retention time: 2.85, 3.10 min (analysis condition S)

Example 496

Compound L7

6-Cyano-2-[1-(4-isopropoxy-3-methoxy-phenyl)-1-methyl-ethyl]-1H-indole-3-carboxylic acid ethyl ester

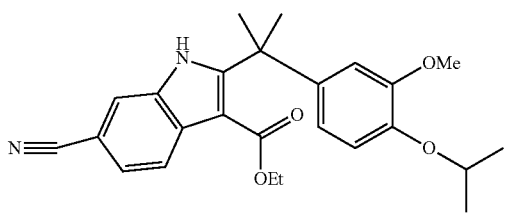 [SMILES: CCOC(=O)c1c(C(C)(C)c2ccc(OC(C)C)c(OC)c2)[nH]c2cc(C#N)ccc12]

Under the same conditions as the method for synthesizing Compound K5, the title compound was prepared from Compound L6.

$^1$H-NMR (270 MHz, DMSO-$d_6$) δ: 12.04 (1H, s), 8.05 (1H, d, J=8.4 Hz), 7.93 (1H, s), 7.49 (1H, dd, J=8.4, 1.5 Hz), 6.79 (2H, m), 6.54 (1H, dd, J=8.3, 1.9 Hz), 4.43 (1H, t, J=6.1 Hz), 3.94 (2H, q, J=7.0 Hz), 3.65 (3H, s), 1.81 (6H, s), 1.21 (6H, d, J=5.9 Hz), 1.05 (3H, t, J=7.1 Hz).

LCMS: m/z 421 [M+H]$^+$

HPLC retention time: 2.82 min (analysis condition S)

Example 497

Compound L8-1

9-Hydroxy-8-methoxy-6,6-dimethyl-11-oxo-6,11-dihydro-5H-benzo[b]carbazole-3-carbonitrile

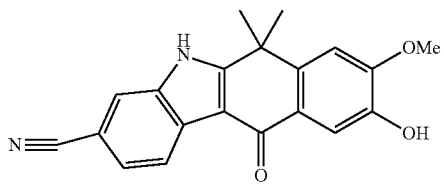 [SMILES: COc1cc2c(cc1O)C(=O)c1c([nH]c3cc(C#N)ccc13)C2(C)C]

6-Cyano-2-[1-(4-isopropoxy-3-methoxy-phenyl)-1-methyl-ethyl]-1H-indole-3-carboxylic acid ethyl ester (Compound L7, 1.25 g, 2.97 mmol) was dissolved in MeCN (18 mL), added with methanesulfonic acid (3.75 mL), and then stirred at 50° C. for 8 hr. Hexane was added to the reaction solution, and the precipitated solid was filtered to obtain the title compound (yellow solid, 185 mg, 19%).

$^1$H-NMR (270 MHz, DMSO-$d_6$) δ: 12.67 (1H, s), 8.30 (1H, d, J=8.2 Hz), 7.99 (1H, s), 7.59 (2H, m), 7.28 (1H, s), 3.93 (3H, s), 1.75 (6H, s).

LCMS: m/z 333 [M+H]$^+$

HPLC retention time: 1.73 min (analysis condition S)

Example 498

Compound L8-2

9-Isopropoxy-8-methoxy-6,6-dimethyl-11-oxo-6,11-dihydro-5H-benzo[b]carbazole-3-carbonitrile

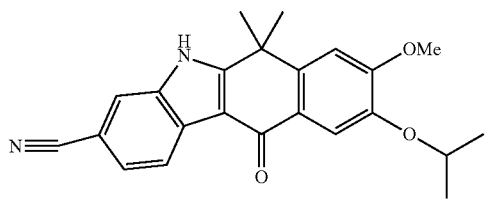 [SMILES: COc1cc2c(cc1OC(C)C)C(=O)c1c([nH]c3cc(C#N)ccc13)C2(C)C]

To the filtrate obtained from the synthesis of Compound L8-1, water was added and the extraction was carried out with ethyl acetate. The resultant was washed with saturated brine and dried over sodium sulfate. The drying agent was removed by filtration and the concentration was performed under reduced pressure to obtain the target compound (red amorphous, 830 mg, 75%).

$^1$H-NMR (270 MHz, DMSO-$d_6$) δ: 12.72 (1H, s), 8.31 (1H, d, J=8.4 Hz), 8.01 (1H, d, J=0.7 Hz), 7.66 (1H, s), 7.61 (1H, dd, J=8.2, 1.4 Hz), 7.33 (1H, s), 4.65 (1H, m), 3.93 (3H, s), 1.77 (6H, s), 1.32 (6H, d, J=6.1 Hz).

LCMS: m/z 375 [M+H]$^+$

HPLC retention time: 2.38 min (analysis condition S)

Example 499

Compound L9

8-Hydroxy-9-isopropoxy-6,6-dimethyl-11-oxo-6,11-dihydro-5H-benzo[b]carbazole-3-carbonitrile

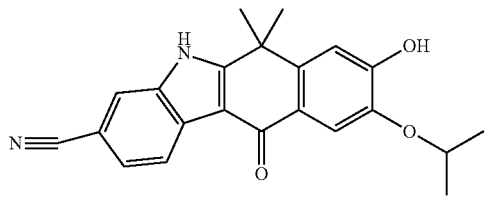 [SMILES: CC(C)Oc1cc2c(cc1O)C(C)(C)c1[nH]c3cc(C#N)ccc3c1C2=O]

Under the same conditions as the method for synthesizing Compound E3-2, the title compound was prepared from Compound L8-2.

$^1$H-NMR (270 MHz, DMSO-$d_6$) δ: 12.69 (1H, s), 9.69 (1H, s), 8.30 (1H, d, J=8.1 Hz), 7.99 (1H, s), 7.65 (1H, s), 7.60 (1H, dd, J=8.2, 1.2 Hz), 7.17 (1H, s), 4.64 (1H, m), 1.69 (6H, s), 1.32 (6H, d, J=6.1 Hz).

LCMS: m/z 361 [M+H]$^+$

HPLC retention time: 2.20 min (analysis condition S)

Example 500

Compound L10-1

8-(1-Cyclobutyl-piperidin-4-yloxy)-9-isopropoxy-6,6-dimethyl-11-oxo-6,11-dihydro-5H-benzo[b]carbazole-3-carbonitrile

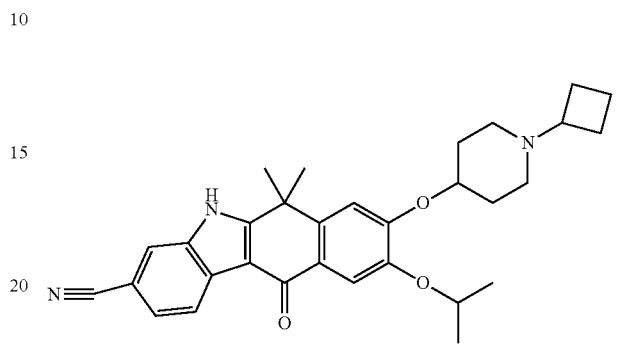

Under the same conditions as the method for synthesizing Compound A7-1, the title compound was prepared from Compound L9 and 1-cyclobutylpiperidin-4-ol.

$^1$H-NMR (270 MHz, CDCl$_3$) δ: 9.31 (1H, br. s), 8.54-8.50 (1H, d, 8.08 Hz), 7.90 (1H, s), 7.77 (1H, s), 7.59-7.55 (1H, m), 7.09 (1H, s), 4.70-4.61 (1H, m), 4.52-4.43 (1H, m), 2.79-2.73 (1H, m), 2.70-2.60 (2H, m), 2.25-2.16 (2H, m), 2.09-1.99 (4H, m), 1.98-1.88 (4H, m), 1.77 (6H, s), 1.72-1.58 (2H, m), 1.39 (3H, s), 1.37 (3H, s)

LCMS: m/z 498 [M+H]$^+$

Example 501

Compound L10-2

8-((R)-1-Cyclobutyl-pyrrolidin-3-yl oxy)-9-isopropoxy-6,6-dimethyl-11-oxo-6,11-dihydro-5H-benzo[b]carbazole-3-carbonitrile

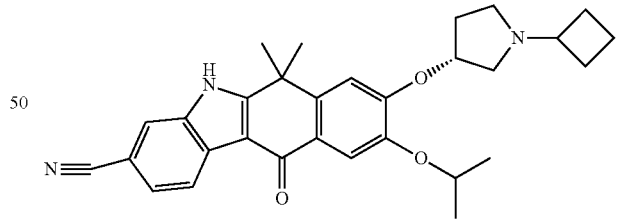

Under the same conditions as the method for synthesizing Compound A7-1, the title compound was prepared from Compound L9 and (S)-1-cyclobutylpyrrolidin-3-ol.

$^1$H-NMR (270 MHz, CDCl$_3$) δ: 10.63 (1H, br. s), 8.51-8.48 (1H, d, 8.08 Hz), 7.89 (1H, s), 7.85 (1H, s), 7.55-7.51 (1H, m), 6.99 (1H, s), 5.03-4.97 (1H, m), 4.71-4.62 (1H, m), 3.07-292 (2H, m), 2.84-2.73 (2H, m), 2.64-2.53 (1H, m), 2.36-2.23 (2H, m), 2.10-1.97 (2H, m), 1.83-1.67 (2H, m), 1.78 (6H, s), 1.53-1.46 (2H, m), 1.39 (3H, s), 1.37 (3H, s)

LCMS: m/z 484 [M+H]$^+$

Example 502

Compound M1

7-Methoxy-3,4-dihydro-2H-spiro[cyclopentane-1,1'-naphthalen]-2-one

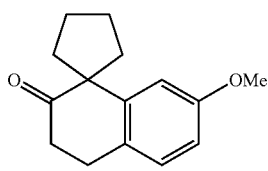 [SMILES: COc1ccc2c(c1)C1(CCCC1)C(=O)CC2]

To the THF (300 ml) solution of 7-methoxy-3,4-dihydro-1H-naphthalen-2-one (Compound A1, 0.5 g, 2.84 mmol), sodium hydride (36.4 mg, 2.2 eq.) was added at 0° C. After stirring for 20 min, 1,4-dibromobutane (0.74 ml, 1.2 eq.) was added dropwise thereto, and the mixture was stirred at 80° C. for 4 hr. To the reaction solution, saturated aqueous solution of ammonium chloride was added followed by extraction with ethyl acetate. The organic layer was washed with saturated aqueous solution of ammonium chloride and dried over magnesium sulfate. The drying agent was removed by filtration and the residues obtained after concentration under reduced pressure were purified by silica gel column chromatography (ethyl acetate/hexane) to obtain the title compound (yellow solid, 0.31 g, 47%).

$^1$H-NMR (CDCl$_3$, 300 MHz) δ: 1.79-1.92 (6H, m), 2.42-2.27 (m, 2H), 3.03 (t, 2H, J=6.5 Hz), 3.81 (t, 2H, J=6.5 Hz), 3.81 (s, 3H), 6.73 (dd, 1H, J=2.7 Hz, 8.0 Hz), 6.83 (d, 1H, J=2.7 Hz), 7.09 (d, 1H, J=8.0 Hz)

LCMS: m/z 231 [M+H]$^+$

Example 503

Compound M2

3-Bromo-8-methoxy-5,11-dihydrospiro[benzo[b]carbazole-6,1'-cyclopentane]

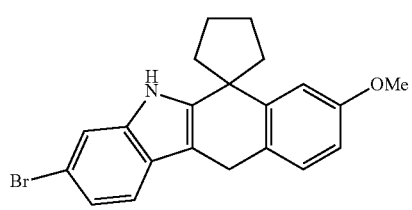 [SMILES: COc1ccc2c(c1)C1(CCCC1)c1[nH]c3cc(Br)ccc3c1C2]

Under the same conditions as the method for synthesizing Compound A3-1, the title compound was prepared from Compound M1 and (3-bromo-phenyl)-hydrazine.

LCMS: m/z 380, 382 [M+H]$^+$

HPLC retention time: 2.90 min (analysis condition Y)

Example 504

Compound M3

3-Bromo-8-methoxyspiro[benzo[b]carbazole-6,1'-cyclopentan]-11(5H)-one

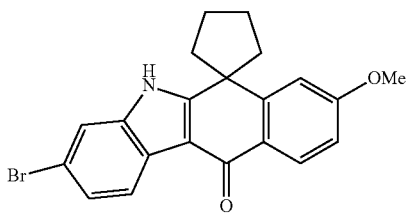 [SMILES: COc1ccc2c(c1)C1(CCCC1)c1[nH]c3cc(Br)ccc3c1C2=O]

Under the same conditions as the method for synthesizing Compound A4, the title compound was prepared from Compound M2.

$^1$H-NMR (CDCl$_3$, 300 MHz) δ: 2.11-2.51 (8H, m), 3.91 (s, 3H), 6.98 (dd, 1H, J=2.3 Hz, 8.8 Hz), 7.01 (d, 1H, J=2.3 Hz), 7.41 (dd, 1H, J=1.5 Hz, 8.4 Hz), 7.57 (d, 1H, J=1.5 Hz), 8.30 (d, 1H, J=8.4 Hz), 8.35 (d, 1H, J=8.8 Hz), 8.69 (s, 1H)

LCMS: m/z 396, 398 [M+H]$^+$

Example 505

Compound M4

8-Methoxy-11-oxo-5,11-dihydrospiro[benzo[b]carbazole-6,1'-cyclopentane]-3-carbonitrile

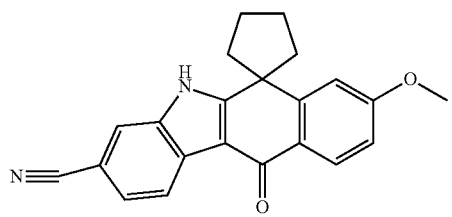 [SMILES: COc1ccc2c(c1)C1(CCCC1)c1[nH]c3cc(C#N)ccc3c1C2=O]

Under the same conditions as the method for synthesizing Compound A5-2, the title compound was prepared from Compound M3.

$^1$H-NMR (DMSO-d$_6$, 300 MHz) δ: 2.14-2.37 (m, 8H), 3.90 (s, 3H), 7.05-7.10 (m, 2H), 7.60 (dd, 1H, J=1.5 Hz, 8.4 Hz), 7.95 (s, 1H), 8.13 (d, 1H, J=9.5 Hz), 8.30 (d, 1H, J=8.4 Hz), 12.24 (s, 1H)

LCMS: m/z 343 [M+H]$^+$

Example 506

Compound M5

8-Hydroxy-11-oxo-5,11-dihydrospiro[benzo[b]carbazole-6,1'-cyclopentane]-3-carbonitrile

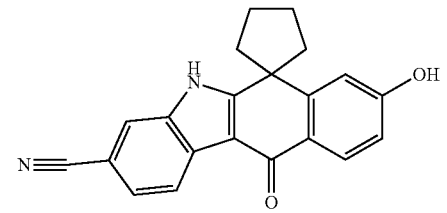 [SMILES: N#Cc1ccc2c3c([nH]c2c1)C1(CCCC1)c1cc(O)ccc1C3=O]

Under the same conditions as the method for synthesizing Compound A6, the title compound was prepared from Compound M4.

¹H-NMR (DMSO-d₆, 300 MHz) δ: 2.06-2.39 (m, 8H), 6.87 (dd, 1H, J=1.9 Hz, 8.8 Hz), 6.90 (d, 1H, J=1.9 Hz), 7.57 (dd, 1H, J=1.1 Hz, 8.0 Hz), 7.95 (s, 1H), 8.02 (d, 1H, J=8.8 Hz), 8.30 (d, 1H, J=8.0 Hz), 10.29 (s, 1H), 12.25 (s, 1H)

LCMS: m/z 329 [M+H]⁺

Example 507

Compound M6-1

(S)-8-((2,2-Dimethyl-1,3-dioxolan-4-yl)methoxy)-11-oxo-5,11-dihydrospiro[benzo[b]carbazole-6,1'-cyclopentane]-3-carbonitrile

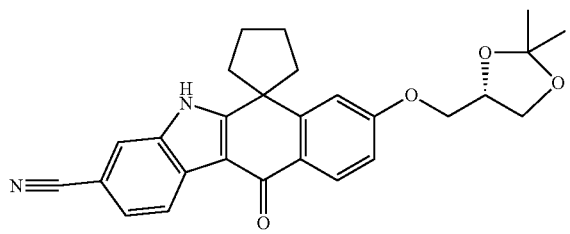 [SMILES: CC1(C)OC[C@H](COc2ccc3c(c2)C2(CCCC2)c2[nH]c4cc(C#N)ccc4c2C3=O)O1]

Under the same conditions as the method for synthesizing Compound A7-17, the title compound was prepared as a crude product from Compound M5 and toluene-4-sulfonic acid (R)-2,2-dimethyl-[1,3]dioxolan-4-yl methyl ester.

Example 508

Compound M6-2

(R)-8-(2,3-Dihydroxypropoxy)-11-oxo-5,11-dihydrospiro[benzo[b]carbazole-6,1'-cyclopentane]-3-carbonitrile

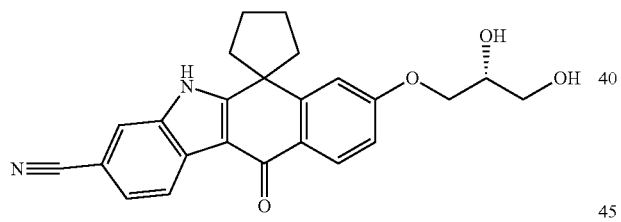

Under the same conditions as the method for synthesizing Compound A7-14-2, the title compound was prepared from Compound M6-1.

LCMS: m/z 403 [M+H]⁺

HPLC retention time: 2.88 min (analysis condition U)

Example 509

Compound N1

7-Methoxy-2',3,3',4,5',6'-hexahydro-2H-spiro[naphthalene-1,4'-pyran]-2-one

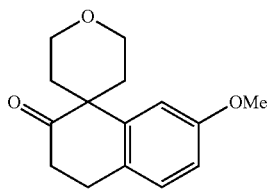 [SMILES: COc1ccc2c(c1)C1(CCOCC1)C(=O)CC2]

To the THF (300 ml) solution of 7-methoxy-3,4-dihydro-1H-naphthalen-2-one (Compound A1, 20 g, 0.11 mol), sodium hydride (9.9 g, 3.7 eq.) was added at 0° C. After stirring for 10 min, 1-bromo-2-(2-bromo-ethoxy)-ethane (19 ml, 12 eq.) was added dropwise thereto, and the mixture was stirred at 80° C. for 3 hr. To the reaction solution, saturated aqueous solution of ammonium chloride was added and the extraction was carried out twice with ethyl acetate. The organic layer was dried over magnesium sulfate. The drying agent was removed by filtration and the residues obtained after concentration under reduced pressure were purified by silica gel column chromatography (ethyl acetate/hexane) to obtain the title compound (white solid, 13 g, 51%).

¹H-NMR (300 MHz, CDCl₃) δ: 2.07 (4H, m), 2.70 (t, 2H, 6.8 Hz), 3.12 (t, 2H, 6.8 Hz), 3.81 (s, 3H), 3.89 (m, 4H), 6.75 (dd, 1H, 2.6 Hz, 8.3 Hz), 6.9 (d, 1H, 2.6 Hz), 7.0 (d, 1H, 8.3 Hz)

LCMS: m/z 247 [M+H]⁺

Example 510

Compound N2-1, Compound N2-2

3-Bromo-8-methoxy-2',3',5,5',6',11-hexahydrospiro[benzo[b]carbazole-6,4'-pyran]

1-Bromo-8-methoxy-2',3',5,5',6',11-hexahydrospiro[benzo[b]carbazole-6,4'-pyran]

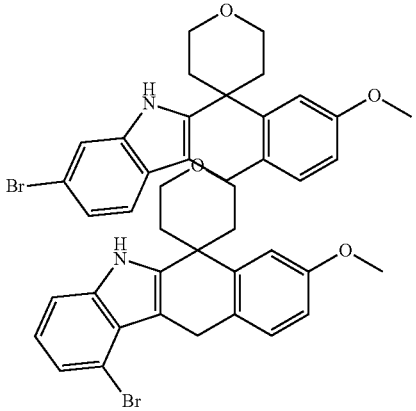

Under the same conditions as the method for synthesizing Compound A3-1, the title compound was prepared as a mixture from Compound N1.

Example 511

Compound N3

3-Bromo-8-methoxy-2',3',5',6'-tetrahydrospiro[benzo[b]carbazole-6,4'-pyran]-11(5H)-one

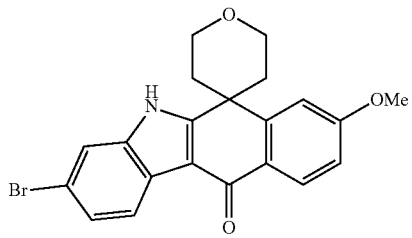 [SMILES: COc1ccc2c(c1)C1(CCOCC1)c1[nH]c3cc(Br)ccc3c1C2=O]

Under the same conditions as the method for synthesizing Compound A4, the title compound was prepared from Compound N2-1.

¹H-NMR (300 MHz, DMSO-d₆) δ: 1.9 (2H, m), 2.4 (m, 2H), 3.9 (s, 3H), 4.0 (m, 2H), 4.2 (m, 2H), 7.1 (dd, 1H, 2.2 Hz, 8.7 Hz), 7.3 (m, 2H), 7.8 (d, 1H, 2.2 Hz), 8.1 (d, 2H, 8.7 Hz), 11.8 (s, 1H)

LCMS: m/z 413 (M+1)⁺

Example 512

Compound N4

8-Methoxy-11-oxo-2',3',5,5',6',11-hexahydrospiro[benzo[b]carbazole-6,4'-pyran]-3-carbonitrile

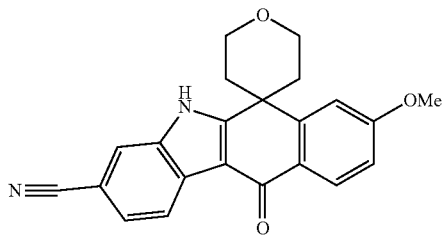 [SMILES: COc1ccc2c(c1)C1(CCOCC1)c1[nH]c3cc(C#N)ccc3c1C2=O]

Under the same conditions as the method for synthesizing Compound A5-2, the title compound was prepared from Compound N3.

¹H-NMR (300 MHz, DMSO-d₆) δ: 1.9 (m, 2H), 2.4 (m, 2H), 3.9 (s, 3H), 4.0 (m, 2H), 4.1 (m, 2H), 7.1 (dd, 1H, 2.2 Hz, 8.7 Hz), 7.4 (d, 1H, 2.2 Hz), 7.6 (dd, 1H, 1.5 Hz, 8.3 Hz), 8.0 (s, 1H), 8.1 (d, 1H, 8.7 Hz), 8.3 (d, 1H, 8.3 Hz), 12.2 (s, 1H)

LCMS: m/z 359 [M+H]⁺
HPLC retention time: 2.80 min (analysis condition U)

Example 513

Compound N5

8-Hydroxy-11-oxo-2',3',5,5',6',11-hexahydrospiro[benzo[b]carbazole-6,4'-pyran]-3-carbonitrile

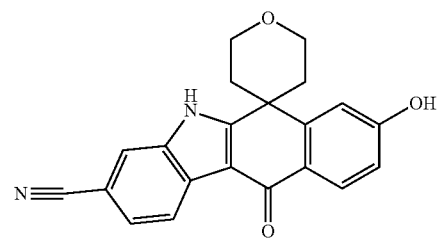 [SMILES: N#Cc1ccc2c3c([nH]c2c1)C1(CCOCC1)c1cc(O)ccc1C3=O]

Under the same conditions as the method for synthesizing Compound A6, the title compound was prepared from Compound N4.

¹H-NMR (300 MHz, DMSO-d₆) d ppm 2.0 (m, 2H), 2.3 (m, 2H), 4.0 (m, 2H), 4.1 (m, 2H), 6.9 (dd, 1H, 1.9 Hz, 8.3 Hz), 7.3 (d, 1H, 1.9 Hz), 7.6 (dd, 1H, 1.5 Hz, 8.3 Hz), 8.0 (s, 1H), 8.1 (d, 1H, 8.3 Hz), 8.3 (d, 1H, 8.3 Hz), 10.3 (s, 1H), 12.2 (s, 1H)

LCMS: m/z 345 [M+H]⁺
HPLC retention time: 2.37 min (analysis condition U)

Example 514

Compound N6-1-1

(S)-8-((2,2-Dimethyl-1,3-dioxolan-4-yl) methoxy)-11-oxo-2',3',5,5',6',11-hexahydrospiro[benzo[b]carbazole-6,4'-pyran]-3-carbonitrile

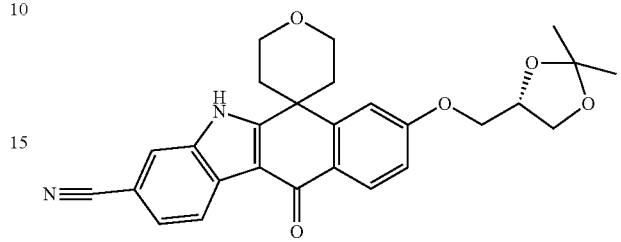

Under the same conditions as the method for synthesizing Compound A7-1, the title compound was prepared from Compound N6-2 and (S)-2,2-dimethyl-4-p-tolyloxymethyl-[1,3] dioxolane.

LCMS: m/z 459 [M+H]⁺
HPLC retention time: 2.93 min (analysis condition Y)

Example 515

Compound N6-1-2

(R)-8-(2,3-Dihydroxypropoxy)-11-oxo-2',3',5,5',6',11-hexahydrospiro[benzo[b]carbazole-6,4'-pyran]-3-carbonitrile

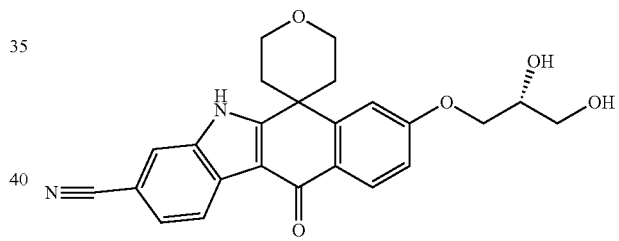

Under the same conditions as the method for synthesizing Compound A7-14-2, the title compound was prepared from Compound N6-1-1.

LCMS: m/z 419 [M+H]⁺
HPLC retention time: 1.52 min (analysis condition S)

Example 516

Compound N6-2

11-Oxo-8-(piperidin-4-yloxy)-2',3',5,5',6',11-hexahydrospiro[benzo[b]carbazole-6,4'-pyran]-3-carbonitrile

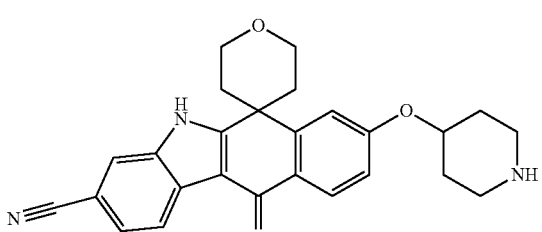

Under the same conditions as the method for synthesizing Compound A7-1 and Compound A8-1, the title compound was prepared from Compound N5.
LCMS: m/z 428 [M+H]+
HPLC retention time: 1.38 min (analysis condition S)

Example 517

Compound N6-3

8-(3-Morpholinoethoxy)-11-oxo-2',3',5,5',6',11-hexahydrospiro[benzo[b]carbazole-6,4'-pyran]-3-carbonitrile

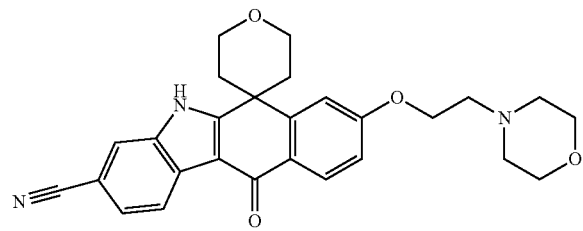 [SMILES: N#Cc1ccc2c3c([nH]c2c1)C1(CCOCC1)c1cc(OCCN2CCOCC2)ccc1C3=O]

Under the same conditions as the method for synthesizing Compound A8-17, the title compound was prepared from Compound N5.
LCMS: m/z 458 [M+H]+
HPLC retention time: 1.33 min (analysis condition S)

Example 518

Compound N6-4

8-(3-Morpholinopropoxy)-11-oxo-2',3',5,5',6',11-hexahydrospiro[benzo[b]carbazole-6,4'-pyran]-3-carbonitrile

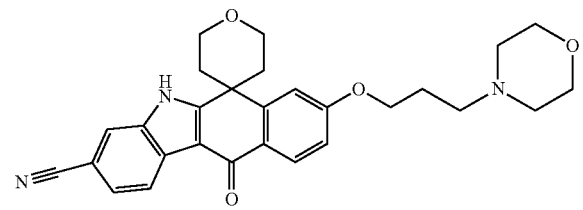 [SMILES: N#Cc1ccc2c3c([nH]c2c1)C1(CCOCC1)c1cc(OCCCN2CCOCC2)ccc1C3=O]

Under the same conditions as the method for synthesizing Compound A8-17, the title compound was prepared from Compound N5.
LCMS: m/z 472 [M+H]+
HPLC retention time: 1.41 min (analysis condition S)

Example 519

Compound N6-5

3-Cyano-8-[2-(1,1-dioxo-thiomorpholin-4-yl)-ethoxy]-6,6-dimethyl-11-oxo-6,11-dihydro-5H-benzo[b]carbazole-9-sulfonic acid dimethylamide

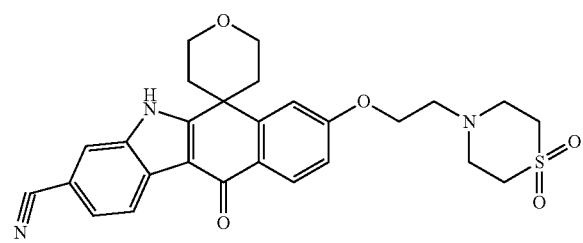 [SMILES: N#Cc1ccc2c3c([nH]c2c1)C1(CCOCC1)c1cc(OCCN2CCS(=O)(=O)CC2)ccc1C3=O]

Under the same conditions as the method for synthesizing Compound A8-17, the title compound was prepared from Compound N5.
LCMS: m/z 506 [M+H]+
HPLC retention time: 1.53 min (analysis condition S)

Example 520

Compound N6-6

8-(1-Ethylpiperidin-4-yloxy)-11-oxo-2',3',5,5',6',11-hexahydrospiro[benzo[b]carbazole-6,4'-pyran]-3-carbonitrile

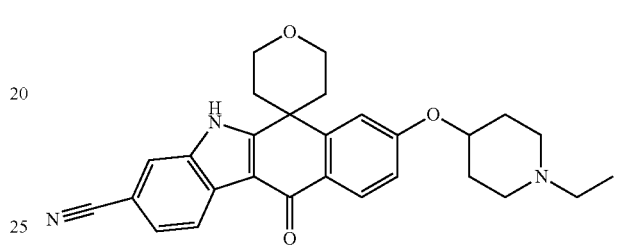

Under the same conditions as the method for synthesizing Compound A7-1, the title compound was prepared from Compound N6-2.
$^1$H-NMR (300 MHz, DMSO-$d_6$) δ: 1.02 (3H, t, 7.25 Hz), 1.18 (2H, m), 1.71 (2H, m), 1.97 (4H, m), 2.27 (2H, m), 2.38 (3H, m), 2.71 (2H, m), 4.03 (2H, m), 4.21 (2H, m), 4.66 (1H, s), 7.13 (1H, dd, 8.77 Hz, 1.91 Hz), 7.39 (1H, bs, 1.91 Hz), 7.60 (1H, d, 8.40 Hz), 8.07 (1H, s), 8.15 (1H, d, 8.40 Hz), 8.37 (1H, d, 8.01 Hz), 12.2 (1H, s).
LCMS: m/z 456 [M+H]+
HPLC retention time: 1.48 min (analysis condition S)

Example 521

Compound N7

Trifluoromethanesulfonic acid 3-cyano-11-oxo-2',3',5,5',6',11-hexahydrospiro[benzo[b]carbazole-6,4'-pyran]-8-yl

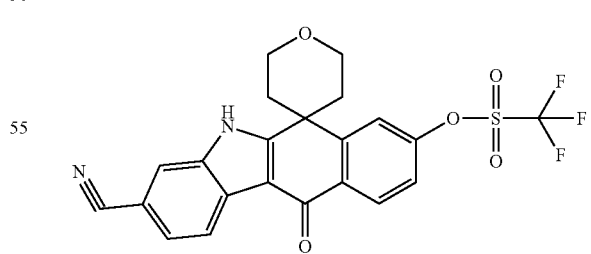

Under the same conditions as the method for synthesizing Compound B1, the title compound was prepared from Compound N5.
LCMS: m/z 477 [M+H]+
HPLC retention time: 3.58 min (analysis condition Y)

Example 522

Compound N8-1

11-Oxo-8-(4-(pyrrolidin-1-yl)piperidin-1-yl)-2',3',5,5',6',11-hexahydrospiro[benzo[b]carbazole-6,4'-pyran]-3-carbonitrile

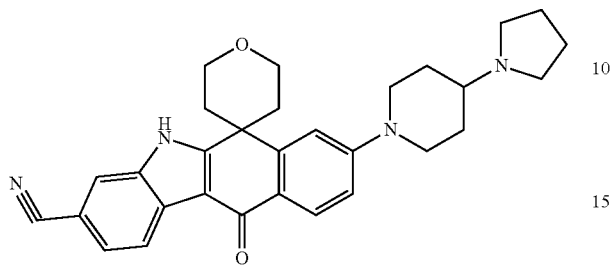

Under the same conditions as the method for synthesizing Compound B2-1, the title compound was prepared from Compound N7 and 4-pyrrolidin-1-yl-piperidine.
LCMS: m/z 481 [M+H]+
HPLC retention time: 1.75 min (analysis condition U)

Example 523

Compound N8-2

8-(4-Morpholinopiperidin-1-yl)-11-oxo-2',3',5,5',6',11-hexahydrospiro[benzo[b]carbazole-6,4'-pyran]-3-carbonitrile

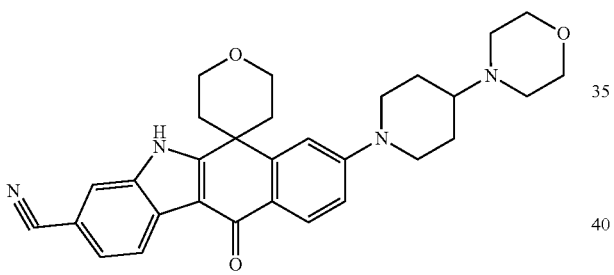

Under the same conditions as the method for synthesizing Compound B2-1, the title compound was prepared from Compound N7 and 4-piperidin-4-yl-morpholine.
LCMS: m/z 497 [M+H]+
HPLC retention time: 1.70 min (analysis condition U)

Example 524

Compound O1

6-Bromo-7-methoxy-2',3,3',4,5',6'-hexahydro-2H-spiro[naphthalene-1,4'-pyran]-2-one

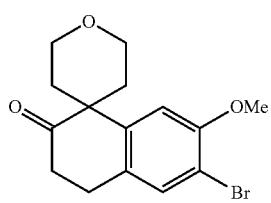 [SMILES: COc1cc2c(cc1Br)CCC(=O)C21CCOCC1]

Under the same conditions as the method for synthesizing Compound E-1, the title compound was prepared from Compound N1.

$^1$H-NMR (300 MHz, DMSO-d$_6$) δ: 2.01 (4H, m), 2.66 (2H, t, 6.87 Hz), 3.08 (2H, t, 6.87 Hz), 3.62 (2H, m), 3.78 (2H, m), 3.87 (3H, s), 7.00 (1H, s), 7.43 (1H, s)

Example 525

Compound O2

9-Bromo-8-methoxy-2',3',5,5',6',11-hexahydrospiro[benzo[b]carbazole-6,4'-pyran]-3-carbonitrile

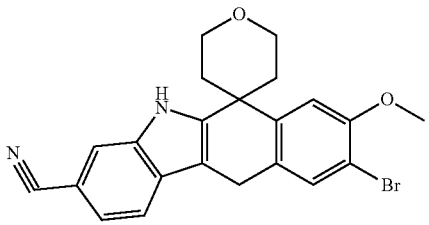 [SMILES: COc1cc2c(cc1Br)Cc1c([nH]c3cc(C#N)ccc13)C21CCOCC1]

Under the same conditions as the method for synthesizing Compound E2-1, the title compound was prepared as a crude product from Compound O1.

Example 526

Compound O3

9-Bromo-8-methoxy-11-oxo-2',3',5,5',6',11-hexahydrospiro[benzo[b]carbazole-6,4'-pyran]-3-carbonitrile

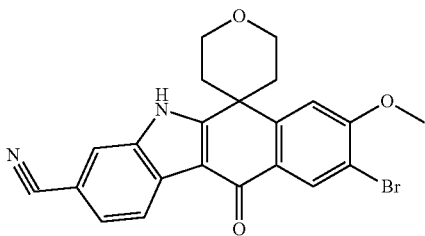 [SMILES: COc1cc2c(cc1Br)C(=O)c1c([nH]c3cc(C#N)ccc13)C21CCOCC1]

Under the same conditions as the method for synthesizing Compound A4, the title compound was prepared from Compound O2.
$^1$H-NMR (300 MHz, DMSO-d$_6$) δ: 1.95 (2H, d, 14.87 Hz), 2.55 (2H, m), 4.04 (2H, m), 4.09 (3H, s), 4.22 (2H, m), 7.51 (1H, s), 7.63 (1H, dd, 8.01 Hz, 1.53 Hz), 8.09 (1H, s), 8.30 (1H, s), 8.36 (1H, d, 8.01 Hz), 12.3 (1H, s).
LCMS: m/z 437, 439 [M+H]+
HPLC retention time: 2.65 min (analysis condition U)

Example 527

Compound O4

9-Fluoro-8-methoxy-11-oxo-2',3',5,5',6',11-hexahydrospiro[benzo[b]carbazole-6,4'-pyran]-3-carbonitrile

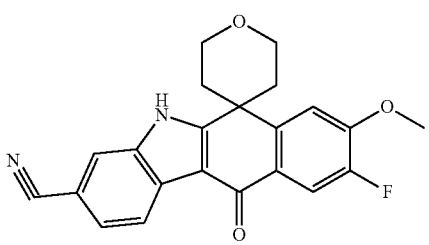 [SMILES: COc1cc2c(cc1F)C(=O)c1c([nH]c3cc(C#N)ccc13)C21CCOCC1]

Example 528

Compound O5-1

9-Fluoro-8-hydroxy-11-oxo-2',3',5,5',6',11-hexahydrospiro[benzo[b]carbazole-6,4'-pyran]-3-carbonitrile Under the same conditions as the method for synthesizing Compound O5-3, the title compound was prepared from Compound O3.

LCMS: m/z 377 [M+H]$^+$
HPLC retention time: 2.29 min (analysis condition S)

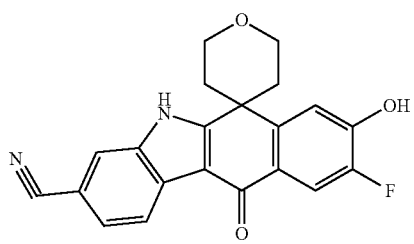 [SMILES: N#Cc1ccc2c3c([nH]c2c1)C1(CCOCC1)c1cc(O)c(F)cc1C3=O]

Under the same conditions as the method for synthesizing Compound E3-2, the title compound was prepared from Compound O4.

LCMS: m/z 363 [M+H]$^+$
HPLC retention time: 1.88 min (analysis condition S)

Example 529

Compound O5-2

Trifluoromethanesulfonic acid 3-cyano-9-fluoro-11-oxo-2',3',5,5',6',11-hexahydrospiro[benzo[b]carbazole-6,4'-pyran]-8-yl

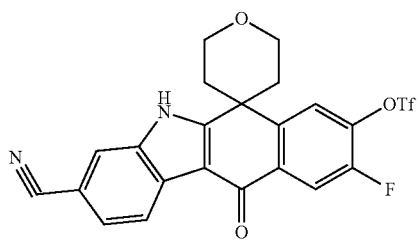 [SMILES: N#Cc1ccc2c3c([nH]c2c1)C1(CCOCC1)c1cc(OS(=O)(=O)C(F)(F)F)c(F)cc1C3=O]

Under the same conditions as the method for synthesizing Compound B1, the title compound was prepared from Compound O5-1.

LCMS: m/z 495 [M+H]$^+$
HPLC retention time: 3.47 min (analysis condition Y)

Example 530

Compound O5-3

9-Fluoro-11-oxo-8-(4-(pyrrolidin-1-yl)piperidin-1-yl)-2',3',5,5',6',11-hexahydrospiro[benzo[b]carbazole-6,4'-pyran]-3-carbonitrile

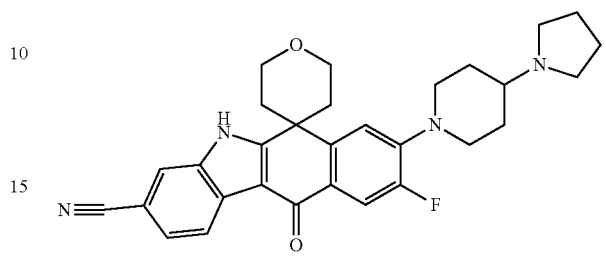

To the THF (0.9 ml) solution of 9-bromo-6-tetrahydropyran-8-pyrrolidinopiperidin-11-oxo-6,11-dihydro-5H-benzo[b]carbazole-3-carbonitrile (Compound O8-1, 90 mg, 0.161 mmol), THF solution of n-butyl lithium (2 M solution, 0.241 ml, 3 eq.) was added at −78° C. After stirring for 30 min, THF (1 ml) solution of N-fluorobenzenesulfonimide (152 mg, 3 eq.) was added dropwise thereto. After rising to room temperature, the mixture was stirred for 18 hr. To the reaction solution, water was added and the extraction was carried out with ethyl acetate. The organic layer was washed with brine and dried over magnesium sulfate. The drying agent was removed by filtration and the residues obtained after concentration under reduced pressure were purified by high performance chromatography to obtain the target compound (white solid, 0.44 mg, 0.5%).

$^1$H-NMR (CDCl$_3$+CD$_3$OD, 300 MHz) δ: 1.75-1.94 (m, 11H), 2.02-2.01 (m, 2H), 2.30-2.27 (m, 1H), 2.75-2.72 (m, 2H), 2.90-3.00 (m, 2H), 3.61-3.47 (m, 4H), 4.01-3.90 (m, 4H), 7.08 (dd, 1H, J=1, 2 Hz, 8.4 Hz), 7.29 (dd, 1H, J=1, 5 Hz, 8.1 Hz), 7.68 (d, 1H, J=12.9 Hz), 7.72 (s, 1H), 8.22 (d, 1H, J=8.4 Hz)

LCMS: m/z 499 [M+H]$^+$
HPLC retention time: 1.95 min (analysis condition U)

Example 531

Compound O5-4

8-(4-Cyclobutylpiperazin-1-yl)-9-fluoro-11-oxo-2',3',5,5',6',11-hexahydrospiro[benzo[b]carbazole-6,4'-pyran]-3-carbonitrile

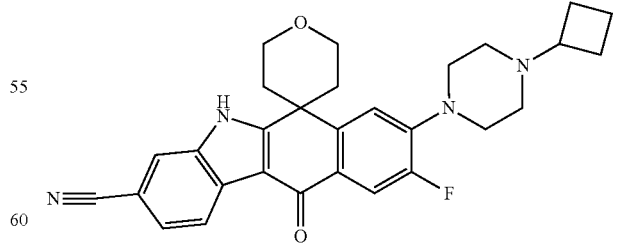

Under the same conditions as the method for synthesizing Compound B2-1, the title compound was prepared from Compound O5-2 and 1-cyclobutylpiperazine.

LCMS: m/z 485 [M+H]$^+$
HPLC retention time: 1.97 min (analysis condition U)

Example 532

Compound O6-1

9-Bromo-8-hydroxy-11-oxo-2',3',5,5',6',11-hexahydrospiro[benzo[b]carbazole-6,4'-pyran]-3-carbonitrile

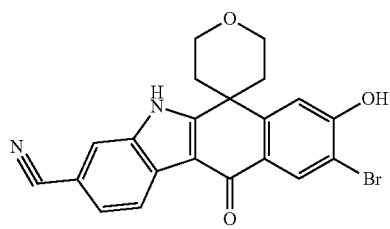 [SMILES: N#Cc1ccc2c3c([nH]c2c1)C1(CCOCC1)c1cc(O)c(Br)cc1C3=O]

Under the same conditions as the method for synthesizing Compound A6, the title compound was prepared from Compound O3.
LCMS: m/z 423, 425 [M+H]+
HPLC retention time: 2.30 min (analysis condition U)

Example 533

Compound O6-2

Trifluoromethanesulfonic acid 9-bromo-3-cyano-11-oxo-2',3',5,5',6',11-hexahydrospiro[benzo[b]carbazole-6,4'-pyran]-8-yl

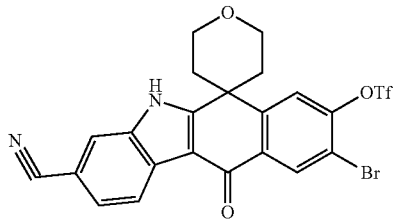 [SMILES: N#Cc1ccc2c3c([nH]c2c1)C1(CCOCC1)c1cc(OS(=O)(=O)C(F)(F)F)c(Br)cc1C3=O]

Under the same conditions as the method for synthesizing Compound B1, the title compound was prepared from Compound O6-1.
LCMS: m/z 555, 557 [M+H]+
HPLC retention time: 3.13 min (analysis condition U)

Example 534

Compound O7-1

9-Bromo-11-oxo-8-(piperazin-1-yl)-2',3',5,5',6',11-hexahydrospiro[benzo[b]carbazole-6,4'-pyran]-3-carbonitrile

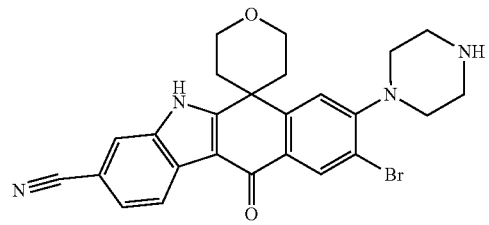 [SMILES: N#Cc1ccc2c3c([nH]c2c1)C1(CCOCC1)c1cc(N2CCNCC2)c(Br)cc1C3=O]

Under the same conditions as the method for synthesizing Compound B2-1, the title compound was prepared from Compound O6-2 and piperazine.

LCMS: m/z 491, 493 [M+H]+
HPLC retention time: 1.88 min (analysis condition U)

Example 535

Compound O7-2

4-(9-Bromo-3-cyano-11-oxo-2',3',5,5',6',11-hexahydrospiro[benzo[b]carbazole-6,4'-pyran]-8-yl)piperazine-1-carboxylic acid tert-butyl

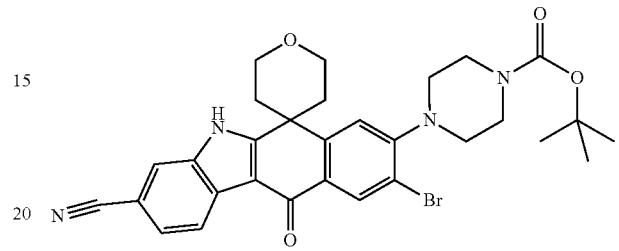

To the dichloromethane (5 mL) solution of 9-bromo-11-oxo-8-(piperazin-1-yl)-2',3',5,5',6',11-hexahydrospiro[benzo[b]carbazole-6,4'-pyran]-3-carbonitrile (Compound O7-1, 250 mg, 0.509 mmol) and mono-tert-butyl ester carbonic anhydride (122 mg, 0.560 mmol), triethylamine (0.21 mL, 1.53 mmol) was added at 0° C., and stirred at room temperature for 1 hr. The reaction mixture was concentrated under reduced pressure and the residues were purified by silica gel column chromatography (methanol/dichloromethane) to obtain the target compound as a white solid (212 mg, 70%).

$^1$H-NMR (300 MHz, DMSO-$d_6$) d ppm: 1.44 (9H, s), 1.97 (2H, m), 2.44 (2H, m), 1.35 (4H, m), 3.54 (4H, m), 4.06 (2H, m), 4.18 (2H, m), 7.57 (1H, s), 7.63 (1H, dd, 8.01 Hz, 1.52 Hz), 8.08 (1H, d, 1.52 Hz), 8.31 (1H, s), 8.36 (1H, d, 8.01 Hz), 12.3 (1H, s)
LCMS: m/z 591, 593 [M+H]+
HPLC retention time: 3.23 min (analysis condition T)

Example 536

Compound O7-3

Tert-butyl 4-(3-cyano-11-oxo-9-(prop-1-ynyl)-2',3',5,5',6',11-hexahydrospiro[benzo[b]carbazole-6,4'-pyran]-8-yl)piperazine-1-carboxylic acid

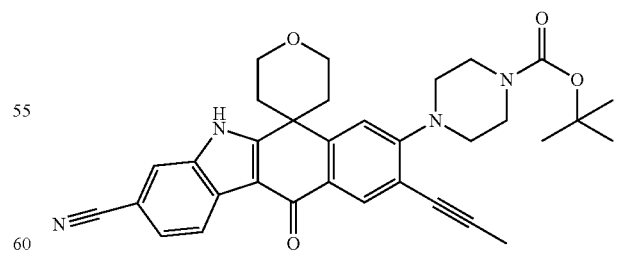

Under the same conditions as the method for synthesizing Compound O9-1, the title compound was prepared from Compound O7-2.
LCMS: m/z 551 [M+H]+
HPLC retention time: 3.92 min (analysis condition Y)

Example 537

Compound O7-4

11-Oxo-8-(piperazin-1-yl)-9-(prop-1-ynyl)-2',3',5,5', 6',11-hexahydrospiro[benzo[b]carbazole-6,4'-pyran]-3-carbonitrile

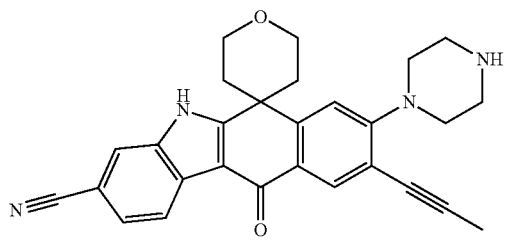 [SMILES: CC#Cc1cc2c(cc1N1CCNCC1)C1(CCOCC1)c1[nH]c3cc(C#N)ccc3c1C2=O]

Under the same conditions as the method for synthesizing Compound A8-1, the title compound was prepared from Compound O7-3.
LCMS: 451 m/z [M+H]+
HPLC retention time: 1.87 min (analysis condition U)

Example 538

Compound O7-5

4-(3-Cyano-9-ethynyl-11-oxo-2',3',5,5',6',11-hexahydrospiro[benzo[b]carbazole-6,4'-pyran]-8-yl)piperazine-1-carboxylic acid tert-butyl

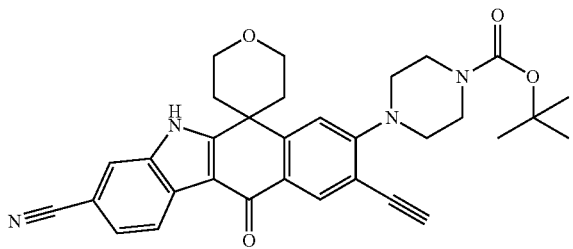 [SMILES: C#Cc1cc2c(cc1N1CCN(C(=O)OC(C)(C)C)CC1)C1(CCOCC1)c1[nH]c3cc(C#N)ccc3c1C2=O]

LCMS: m/z 537 [M+H]+
HPLC retention time: 3.82 min (analysis condition Y)

Example 539

Compound O8-1

9-Bromo-11-oxo-8-(4-(pyrrolidin-1-yl)piperidin-1-yl)-2',3',5,5',6',11-hexahydrospiro[benzo[b]carbazole-6,4'-pyran]-3-carbonitrile

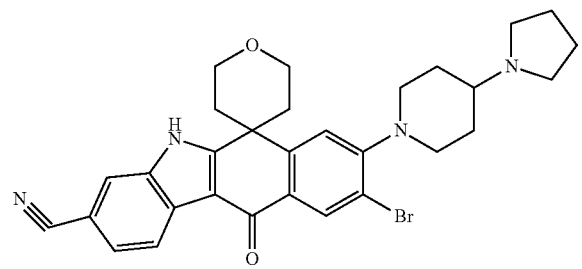 [SMILES: N#Cc1ccc2c3c([nH]c2c1)C1(CCOCC1)c1cc(N2CCC(N4CCCC4)CC2)c(Br)cc1C3=O]

Under the same conditions as the method for synthesizing Compound B2-1, the title compound was prepared from Compound O6-2 and 4-pyrrolidin-1-yl-piperidine.
LCMS: m/z 559, 561 [M+H]+
HPLC retention time: 2.05 min (analysis condition U)

Example 540

Compound O8-2

9-Bromo-8-(4-cyclobutylpiperazin-1-yl)-11-oxo-2', 3',5,5',6',11-hexahydrospiro[benzo[b]carbazole-6,4'-pyran]-3-carbonitrile Under the same conditions as the method for synthesizing Compound B2-1, the title compound was prepared from Compound O6-2 and 1-cyclobutylpiperazine.
LCMS: m/z 547 [M+H]+
HPLC retention time: 1.61 min (analysis condition S)

Example 541

Compound O8-3

9-Bromo-8-(4-morpholinopiperidin-1-yl)-11-oxo-2', 3',5,5',6',11-hexahydrospiro[benzo[b]carbazole-6,4'-pyran]-3-carbonitrile Under the same conditions as the method for synthesizing Compound B2-1, the title compound was prepared from Compound O6-2 and 4-piperidin-4-yl-morpholine.
LCMS: m/z 575, 577 [M+H]+
HPLC retention time: 1.95 min (analysis condition U)

Example 542

Compound O8-4

9-Bromo-8-(4-(oxetan-3-yl)piperazin-1-yl)-11-oxo-2',3',5,5',6',11-hexahydrospiro[benzo[b]carbazole-6,4'-pyran]-3-carbonitrile

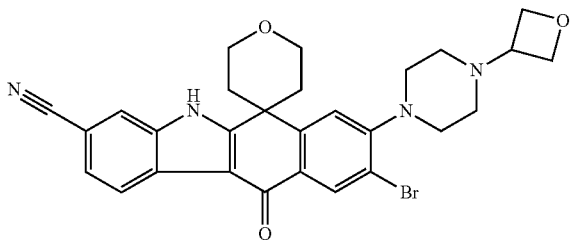 [SMILES: N#Cc1ccc2c3c([nH]c2c1)C1(CCOCC1)c1cc(N2CCN(C4COC4)CC2)c(Br)cc1C3=O]

Under the same conditions as the method for synthesizing Compound B3-32, the title compound was prepared from Compound O7-1 and oxetan-3-one.

LCMS: m/z 547, 549 [M+H]$^+$

HPLC retention time: 1.43 min (analysis condition S)

Example 543

Compound O8-5

9-Bromo-8-(4-tert-butylpiperazin-1-yl)-11-oxo-2',3',5,5',6',11-hexahydrospiro[benzo[b]carbazole-6,4'-pyran]-3-carbonitrile

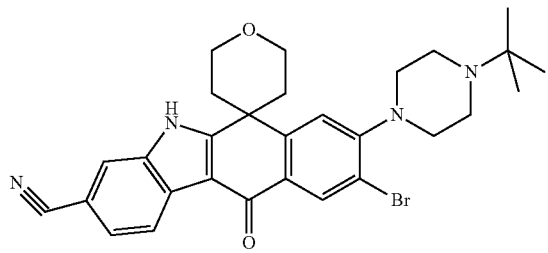 [SMILES: CC(C)(C)N1CCN(c2cc3c(cc2Br)C(=O)c2c([nH]c4cc(C#N)ccc24)C32CCOCC2)CC1]

Under the same conditions as the method for synthesizing Compound B2-1, the title compound was prepared from Compound O6-2 and 1-tert-butylpiperazine.

LCMS: 547, 549 m/z [M+H]$^+$

HPLC retention time: 2.07 min (analysis condition U)

Example 544

Compound O9-1

11-Oxo-9-(prop-1-ynyl)-8-(4-(pyrrolidin-1-yl)piperidin-1-yl)-2',3',5,5',6',11-hexahydrospiro[benzo[b]carbazole-6,4'-pyran]-3-carbonitrile

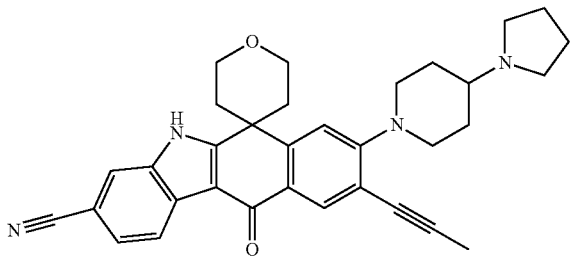 [SMILES: CC#Cc1cc2c(cc1N1CCC(N3CCCC3)CC1)C1(CCOCC1)c1[nH]c3cc(C#N)ccc3c1C2=O]

9-Bromo-11-oxo-8-(4-(pyrrolidin-1-yl)piperidin-1-yl)-2',3',5,5',6',11-hexahydrospiro[benzo[b]carbazole-6,4'-pyran]-3-carbonitrile (Compound O8-1, 100 mg, 0.170 mmol), tributyl(1-propynyl) (0.082 mL, 0.268 mmol), bis(acetonitrile) palladium dichloride (II) (2.64 mg, 0.00895 mmol), X-Phos (12.8 mg, 0.0269 mmol), and cesium carbonate (262.4 mg, 0.806 mmol) were suspended in acetonitrile (1 mL), and then stirred at 80° C. for 2 hr. The reaction mixture was cooled to room temperature followed by addition of water and extracted with ethyl acetate. The organic layer was washed with saturated brine and dried over anhydrous magnesium sulfate. The drying agent was removed by filtration and the residues obtained after concentration under reduced pressure were purified by silica gel column chromatography (dichloromethane/methanol) to obtain the target compound (pale yellow solid, 3.8 mg, 4.1%).

$^1$H-NMR (300 MHz, DMSO) σppm 12.20 (bs, 1H), 8.35 (d, 1H, J=8.1 Hz), 8.06 (s, 1H), 8.06 (d, 1H, J=10.8 Hz), 7.58 (d, 1H, J=8.4 Hz), 7.29 (s, 1H), 4.25-4.23 (m, 2H), 4.02-3.98 (m, 2H), 3.78 (d, 2H, J=11.4 Hz), 2.93 (t, 2H, J=11.1 Hz), 2.55 (s, 1H), 2.45-2.28 (m, 2H), 2.24-2.05 (m, 4H), 2.08-1.81 (m, 4H), 1.75-1.50 (m, 7H)

LCMS: m/z 519 [M+H]$^+$

HPLC retention time: 1.98 min (analysis condition U)

Example 545

Compound O9-2

9-Ethynyl-11-oxo-8-(4-(pyrrolidin-1-yl)piperidin-1-yl)-2',3',5,5',6',11-hexahydrospiro[benzo[b]carbazole-6,4'-pyran]-3-carbonitrile

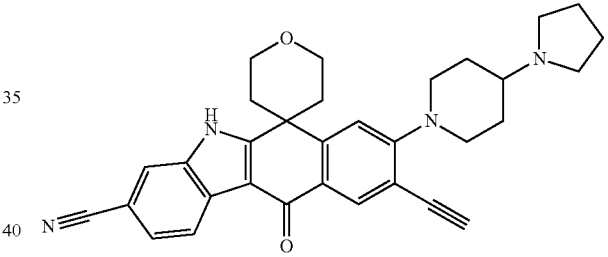

Under the same conditions as the method for synthesizing Compound F5-43, the title compound was prepared from Compound O8-1.

LCMS: m/z 505 [M+H]$^+$

HPLC retention time: 1.92 min (analysis condition U)

Example 546

Compound O9-3

11-Oxo-8-(4-(pyrrolidin-1-yl)piperidin-1-yl)-2',3',5,5',6',11-hexahydrospiro[benzo[b]carbazole-6,4'-pyran]-3,9-dicarbonitrile

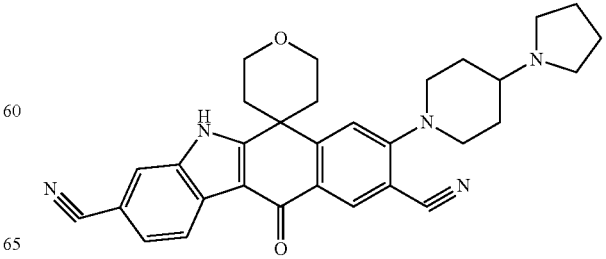

Under the same conditions as the method for synthesizing Compound A5-2, the title compound was prepared from Compound O8-1.

LCMS: 506 m/z [M+H]$^+$

HPLC retention time: 1.87 min (analysis condition U)

Example 547

Compound O9-4

9-(3-Hydroxy-3-methylbut-1-ynyl)-11-oxo-8-(4-(pyrrolidin-1-yl)piperidin-1-yl)-2',3',5,5',6',11-hexahydrospiro[benzo[b]carbazole-6,4'-pyran]-3-carbonitrile

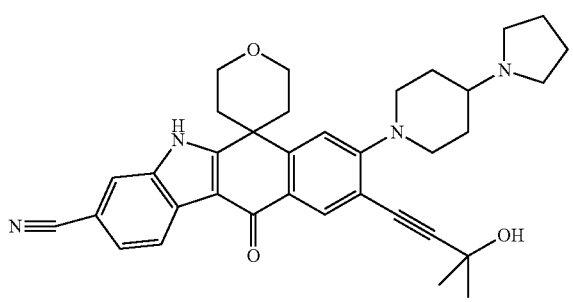 [SMILES: CC(C)(O)C#Cc1cc2c(cc1N1CCC(N3CCCC3)CC1)C1(CCOCC1)c1[nH]c3cc(C#N)ccc3c1C2=O]

Under the same conditions as the method for synthesizing Compound E4-2-1, the title compound was prepared from Compound O8-1.

LCMS: m/z 563 [M+H]$^+$

HPLC retention time: 1.92 min (analysis condition U)

Example 548

Compound O9-5

8-(4-Cyclobutylpiperazin-1-yl)-11-oxo-9-(prop-1-ynyl)-2',3',5,5',6',11-hexahydrospiro[benzo[b]carbazole-6,4'-pyran]-3-carbonitrile

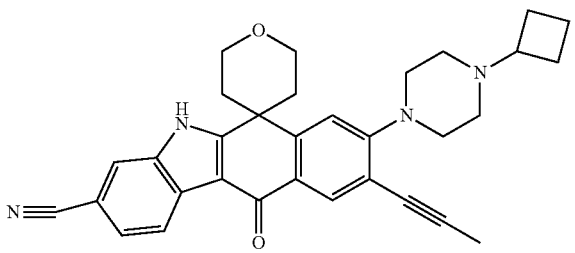 [SMILES: CC#Cc1cc2c(cc1N1CCN(C3CCC3)CC1)C1(CCOCC1)c1[nH]c3cc(C#N)ccc3c1C2=O]

Under the same conditions as the method for synthesizing Compound O9-1, the title compound was prepared from Compound O8-2.

$^1$H-NMR (300 MHz, DMSO-d$_6$) δ: 1.6 (m, 2H), 1.8 (m, 2H), 1.9 (m, 4H), 2.1 (s, 3H), 2.4 (m, 6H), 2.8 (m, 1H), 3.4 (m, 4H), 4.0 (m, 2H), 4.1 (m, 2H), 7.3 (s, 1H), 7.6 (d, 1H, 8.0 Hz), 8.0 (m, 2H), 8.3 (d, 1H, 8.0 Hz), 12.2 (s, 1H)

LCMS: m/z 505 [M+H]$^+$

HPLC retention time: 2.03 min (analysis condition U)

Example 549

Compound O9-6

8-(4-Cyclobutylpiperazin-1-yl)-9-ethynyl-11-oxo-2',3',5,5',6',11-hexahydrospiro[benzo[b]carbazole-6,4'-pyran]-3-carbonitrile

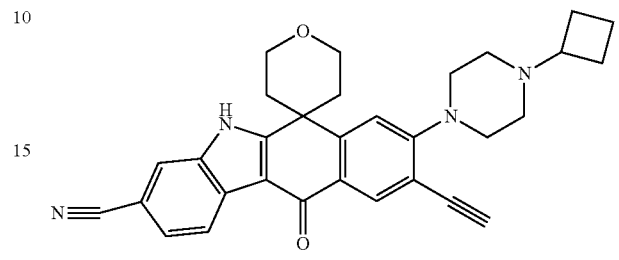

Under the same conditions as the method for synthesizing Compound F5-43, the title compound was prepared from Compound O8-2.

$^1$H-NMR (300 MHz, DMSO-d$_6$) δ: 1.66 (2H, m), 1.83 (2H, t, 8.77 Hz), 1.99 (4H, m), 2.41 (6H, m), 2.79 (1H, t, 7.63 Hz), 3.35 (4H, m), 4.01 (2H, m), 4.27 (2H, m), 4.51 (1H, s), 7.33 (1H, s), 7.54 (1H, m), 8.03 (1H, s), 8.16 (1H, s), 8.32 (1H, d, 8.40 Hz), 12.3 (1H, s).

LCMS: m/z 491 [M+H]$^+$

HPLC retention time: 1.95 min (analysis condition U)

Example 550

Compound O9-7

8-(4-Morpholinopiperidin-1-yl)-11-oxo-9-(prop-1-ynyl)-2',3',5,5',6',11-hexahydrospiro[benzo[b]carbazole-6,4'-pyran]-3-carbonitrile

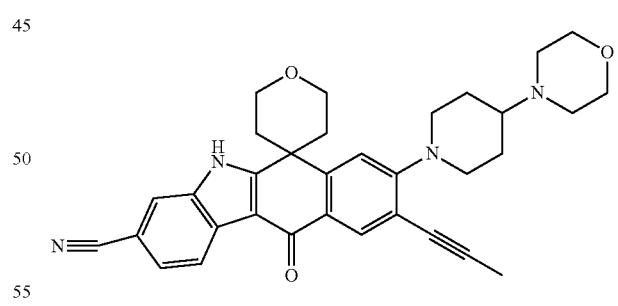

Under the same conditions as the method for synthesizing Compound O9-1, the title compound was prepared from Compound O8-3.

$^1$H-NMR (300 MHz, DMSO-d$_6$) δ: 1.57 (2H, m), 1.95 (4H, m), 2.14 (3H, s), 2.37 (3H, m), 3.35 (4H, m), 2.83 (2H, t, 12.6 Hz), 3.56 (4H, s), 3.86 (2H, d, 11.8 Hz), 4.04 (2H, m), 4.17 (2H, m), 7.31 (1H, s), 7.61 (1H, d, 8.01 Hz), 8.06 (1H, s), 8.07 (1H, s), 8.36 (1H, d, 8.01 Hz), 12.3 (1H, s).

LCMS: m/z 535 [M+H]$^+$

HPLC retention time: 1.95 min (analysis condition U)

Example 551

Compound O9-8

9-Ethynyl-8-(4-morpholinopiperidin-1-yl)-11-oxo-2', 3',5,5',6',11-hexahydrospiro[benzo[b]carbazole-6,4'-pyran]-3-carbonitrile

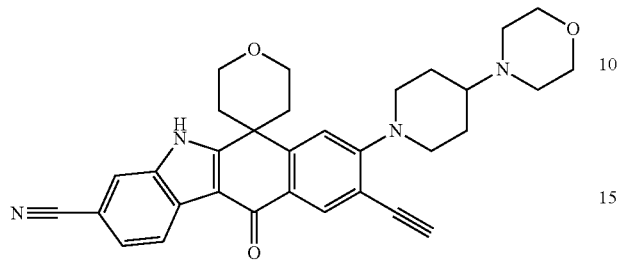

Under the same conditions as the method for synthesizing Compound F5-43, the title compound was prepared from compound O8-3.
LCMS: m/z 521 [M+H]+
HPLC retention time: 1.90 min (analysis condition U)

Example 552

Compound O9-9

8-(4-(Oxetan-3-yl)piperazin-1-yl)-11-oxo-9-(prop-1-ynyl)-2',3',5,5',6',11-hexahydrospiro[benzo[b]carbazole-6,4'-pyran]-3-carbonitrile

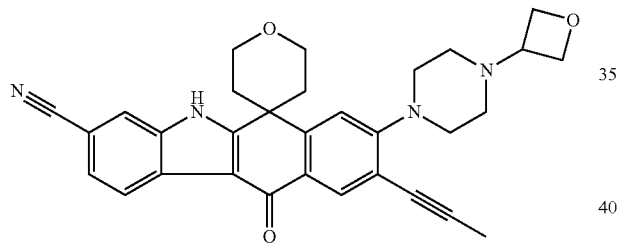

Under the same conditions as the method for synthesizing Compound B3-32, the title compound was prepared from Compound O7-4 and oxetan-3-one.
LCMS: m/z 507 [M+H]+
HPLC retention time: 1.43 min (analysis condition S)

Example 553

Compound O10-1-1

Tert-butyl4-(3-cyano-9-ethyl-11-oxo-2',3',5,5a,5',6', 11,11a-octahydrospiro[benzo[b]carbazole-6,4'-pyran]-8-yl)piperazine-1-carboxylic acid

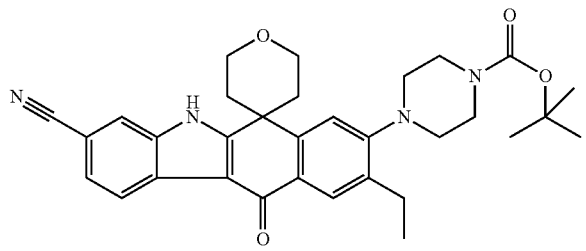 [SMILES: CCc1cc2c(cc1N1CCN(C(=O)OC(C)(C)C)CC1)C1(CCOCC1)c1[nH]c3cc(C#N)ccc3c1C2=O]

Under the same conditions as the method for synthesizing Compound B3-13-1, the title compound was prepared from Compound O7-5.
LCMS: m/z 541 [M+H]+
HPLC retention time: 3.08 min (analysis condition S)

Example 554

Compound O10-1-2

9-Ethyl-11-oxo-8-(piperazin-1-yl)-2',3',5,5',6',11-hexahydrospiro[benzo[b]carbazole-6,4'-pyran]-3-carbonitrile

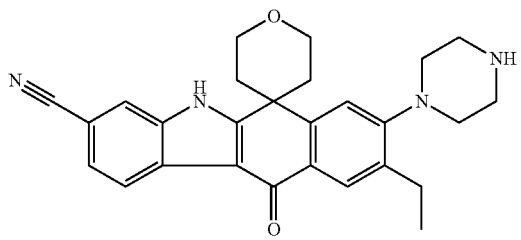 [SMILES: CCc1cc2c(cc1N1CCNCC1)C1(CCOCC1)c1[nH]c3cc(C#N)ccc3c1C2=O]

Under the same conditions as the method for synthesizing Compound A8-1, the title compound was prepared from Compound O10-1-1.
LCMS: m/z 441 [M+H]+
HPLC retention time: 1.42 min (analysis condition S)

Example 555

Compound O10-2

9-Ethyl-8-(4-morpholinopiperidin-1-yl)-11-oxo-2',3', 5,5',6',11-hexahydrospiro[benzo[b]carbazole-6,4'-pyran]-3-carbonitrile

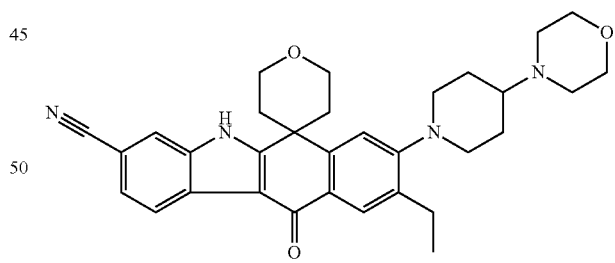

According to the same method as the method for synthesizing Compound B3-13-1, the title compound was prepared from Compound O9-8.

$^1$H-NMR (400 MHz, DMSO-d$_6$) δ: 8.23-8.21 (1H, m), 8.02-8.00 (1H, m), 7.88-7.86 (1H, m), 7.39-7.36 (2H, m), 4.63-4.59 (2H, m), 3.89-3.85 (2H, m), 3.60-3.56 (6H, m), 3.22-3.19 (4H, m), 2.76-2.68 (4H, m), 2.37-2.32 (3H, m), 1.92-1.88 (2H, m), 1.75-1.72 (2H, m), 1.61-1.57 (2H, m), 1.27-1.25 (3H, m)
LCMS: m/z 525 [M+H]+
HPLC retention time: 1.48 min (analysis condition S)

Example 556

Compound O10-3

9-Ethyl-8-(4-(oxetan-3-yl)piperazin-1-yl)-11-oxo-2',3',5,5',6',11-hexahydrospiro[benzo[b]carbazole-6,4'-pyran]-3-carbonitrile

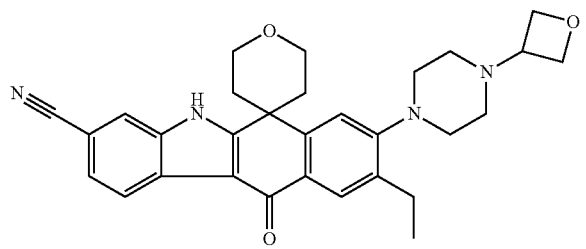 [SMILES: CCc1cc2c(cc1N1CCN(C3COC3)CC1)C1(CCOCC1)c1[nH]c3cc(C#N)ccc3c1C2=O]

Under the same conditions as the method for synthesizing Compound B3-32, the title compound was prepared from Compound O10-1-2 and oxetan-3-one.

$^1$H-NMR (400 MHz, DMSO-d$_6$) δ: 12.26 (1H, s), 8.39 (1H, d, 7.9 Hz), 8.09-8.07 (2H, m), 7.63 (1H, d, 8.5 Hz), 7.51 (1H, s), 4.60-4.50 (4H, m), 4.20-4.09 (4H, m), 3.56-3.51 (1H, m), 3.07-3.05 (4H, m), 2.76-2.70 (2H, m), 2.44-2.40 (2H, m), 2.02-1.98 (2H, m), 1.29-1.26 (4H, m)

LCMS: m/z 497 [M+H]$^+$

HPLC retention time: 1.42 min (analysis condition S)

Example 557

Compound O10-4

8-(4-Cyclobutylpiperazin-1-yl)-9-ethyl-11-oxo-2',3',5,5',6',11-hexahydrospiro[benzo[b]carbazole-6,4'-pyran]-3-carbonitrile

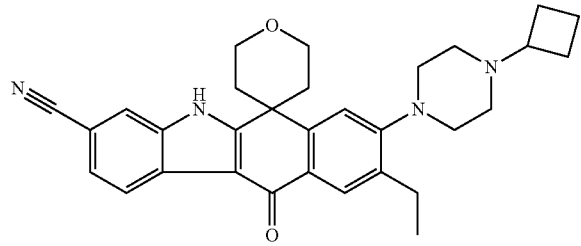 [SMILES: CCc1cc2c(cc1N1CCN(C3CCC3)CC1)C1(CCOCC1)c1[nH]c3cc(C#N)ccc3c1C2=O]

Under the same conditions as the method for synthesizing Compound B3-32, the title compound was prepared from Compound O10-1-2 and cyclobutanone.

LCMS: m/z 495 [M+H]$^+$

HPLC retention time: 1.57 min (analysis condition S)

Example 558

Compound P1

Intermediate

8-Methoxy-6,6-dimethyl-2-nitro-6,11-dihydro-5H-benzo[b]carbazole

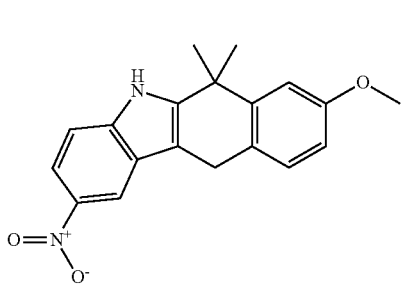 [SMILES: COc1ccc2c(c1)C(C)(C)c1[nH]c3ccc([N+](=O)[O-])cc3c1C2]

Under the same conditions as the method for synthesizing Compound A3-1, the title compound was prepared from Compound A2 and 4-nitrophenylhydrazine.

LCMS: m/z 323 [M+H]$^+$

HPLC retention time: 4.08 min (analysis condition W)

Example 559

Compound P2

Intermediate

8-Methoxy-6,6-dimethyl-2-nitro-5,6-dihydro-benzo[b]carbazol-11-one

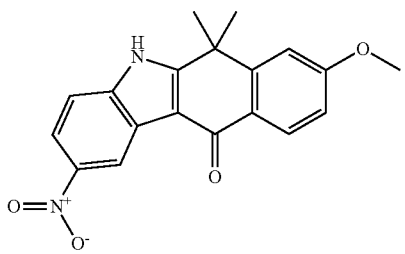 [SMILES: COc1ccc2c(c1)C(C)(C)c1[nH]c3ccc([N+](=O)[O-])cc3c1C2=O]

Under the same conditions as the method for synthesizing Compound A4, the title compound was prepared from Compound P1.

$^1$H-NMR (400 MHz, DMSO-d$_6$) δ: 12.85 (1H, s), 9.03 (1H, d, J=1.9 Hz), 8.17-8.20 (2H, m), 7.71 (1H, d, J=9.1 Hz), 7.38 (1H, d, J=2.4 Hz), 7.12 (1H, dd, J=8.5, 2.4 Hz), 3.93 (3H, s), 1.79 (6H, s)

LCMS: m/z 337 [M+H]$^+$

HPLC retention time: 3.55 min (analysis condition W)

Example 560

Compound P3

Intermediate

8-Hydroxy-6,6-dimethyl-2-nitro-5,6-dihydro-benzo[b]carbazol-11-one

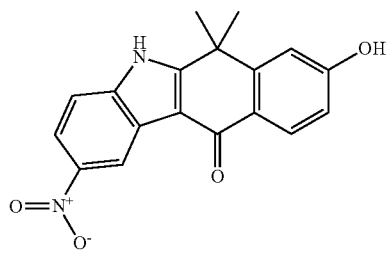 [SMILES: CC1(C)c2cc(O)ccc2C(=O)c2c1[nH]c1ccc([N+](=O)[O-])cc21]

Under the same conditions as the method for synthesizing Compound A6, the title compound was prepared from Compound P2.

LCMS: m/z 323 [M+H]$^+$

HPLC retention time: 3.11 min (analysis condition W)

Example 561

Compound P4

Intermediate 4-(6,6-Dimethyl-2-nitro-11-oxo-6,11-dihydro-5H-benzo[b]carbazole-8-yl oxy)-piperidine-1-carboxylic acid tert-butyl ester

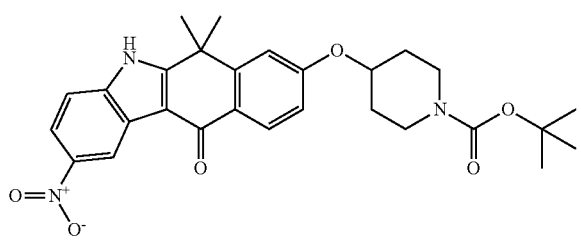 [SMILES: CC(C)(C)OC(=O)N1CCC(Oc2ccc3c(c2)C(C)(C)c2[nH]c4ccc([N+](=O)[O-])cc4c2C3=O)CC1]

Under the same conditions as the method for synthesizing Compound A7-1, the title compound was prepared from Compound P3.

$^1$H-NMR (400 MHz, CDCl$_3$) δ: 9.40 (1H, s), 9.37 (1H, s), 8.41 (1H, d, J=8.5 Hz), 8.24 (1H, d, J=11.0 Hz), 7.51 (1H, d, J=8.5 Hz), 7.13 (1H, s), 7.03 (1H, d, J=9.1 Hz), 4.61-4.71 (1H, m), 3.69-3.84 (2H, m), 3.35-3.49 (2H, m), 1.94-2.10 (2H, m), 1.75-1.93 (8H, m), 1.50 (9H, s)

LCMS: m/z 506 [M+H]$^+$

HPLC retention time: 4.17 min (analysis condition W)

Example 562

Compound P5

2-Amino-6,6-dimethyl-8-(piperidin-4-yloxy)-5,6-dihydro-benzo[b]carbazol-11-one

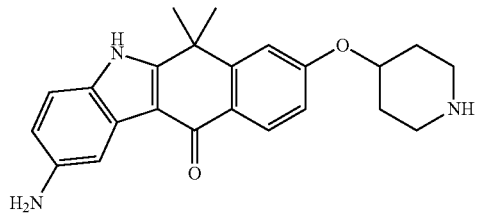 [SMILES: CC1(C)c2cc(OC3CCNCC3)ccc2C(=O)c2c1[nH]c1ccc(N)cc21]

Under the same conditions as the method for synthesizing Compound A8-1, the title compound was prepared from Compound P6.

$^1$H-NMR (400 MHz, CD$_3$OD) δ: 8.23 (1H, d, J=8.5 Hz), 7.68 (1H, d, J=2.4 Hz), 7.26 (1H, d, J=8.5 Hz), 7.24 (1H, d, J=2.4 Hz), 7.06 (1H, dd, J=8.5, 2.4 Hz), 6.80 (1H, dd, J=8.5, 2.4 Hz), 4.64-4.71 (1H, m), 3.06-3.15 (2H, m), 2.73-2.83 (2H, m), 2.02-2.13 (2H, m), 1.67-1.82 (8H, m)

LCMS: m/z 506 [M+H]$^+$

HPLC retention time: 4.17 min (analysis condition W)

Example 563

Compound P6

Intermediate 4-(2-Amino-6,6-dimethyl-11-oxo-6,11-dihydro-5H-benzo[b]carbazole-8-yl oxy)-piperidine-1-carboxylic acid tert-butyl ester

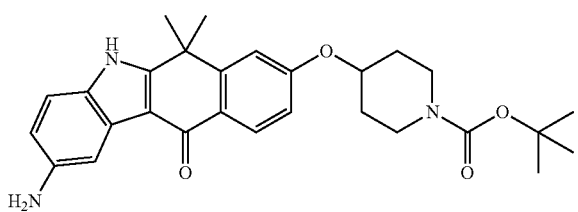 [SMILES: CC(C)(C)OC(=O)N1CCC(Oc2ccc3c(c2)C(C)(C)c2[nH]c4ccc(N)cc4c2C3=O)CC1]

To the ethanol (8 ml) suspension of 4-(6,6-dimethyl-2-nitro-11-oxo-6,11-dihydro-5H-benzo[b]carbazole-8-yl oxy)-piperidine-1-carboxylic acid tert-butyl ester (Compound P4, 103 mg, 0.204 mmol), iron powder (228 mg, 20 eq.), ammonium chloride (109 mg, 10 eq.), and distilled water (4 ml) were added and the mixture was stirred at 90° C. for 30 min. Upon the completion of the reaction, insoluble matters were filtered off, and the filtrate was extracted with ethyl acetate. The organic layer was washed with brine and dried over sodium sulfate. The drying agent was removed by filtration and the residues obtained after concentration under reduced pressure were purified by silica gel column chromatography (ethyl acetate/hexane) to obtain the title compound (115 mg, 57%).

LCMS: m/z 476 [M+H]$^+$

HPLC retention time: 2.82 min (analysis condition W)

Example 564

Compound P7

Intermediate 4-(2-Methanesulfonylamino-6,6-dimethyl-11-oxo-6,11-dihydro-5H-benzo[b]carbazole-8-yl oxy)-piperidine-1-carboxylic acid tert-butyl ester

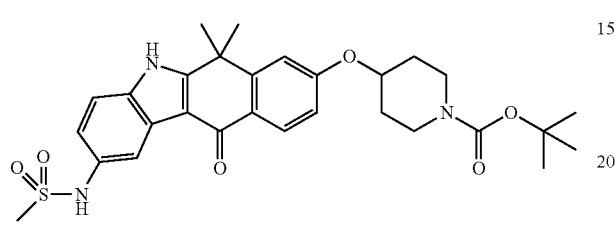

To the pyridine (2 ml) solution of 4-(2-amino-6,6-dimethyl-11-oxo-6,11-dihydro-5H-benzo[b]carbazole-8-yl oxy)-piperidine-1-carboxylic acid tert-butyl ester (Compound P6, 50 mg, 0.105 mmol), mesyl chloride (9 μl, 1.2 eq.) was added and stirred at room temperature for 30 min. Upon the completion of the reaction, the reaction solution was concentrated under reduced pressure to obtain the title compound as an unpurified product.

LCMS: m/z 554 [M+H]$^+$

HPLC retention time: 3.60 min (analysis condition W)

Example 565

Compound P8

N-[6,6-Dimethyl-11-oxo-8-(piperidin-4-yloxy)-6,11-dihydro-5H-benzo[b]carbazole-2-yl]-methanesulfonamide

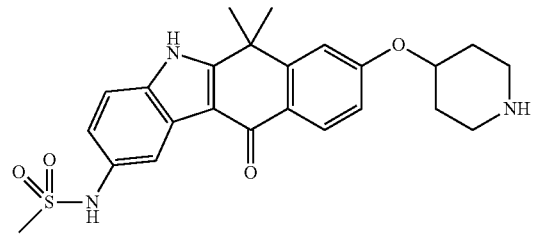 [SMILES: CC1(C)c2cc(OC3CCNCC3)ccc2C(=O)c2c1[nH]c1ccc(NS(C)(=O)=O)cc21]

Under the same conditions as the method for synthesizing Compound A8-1, the title compound was prepared from Compound P7.

$^1$H-NMR (400 MHz, CD$_3$OD) δ: 8.25 (1H, d, J=8.5 Hz), 8.16 (1H, d, J=1.8 Hz), 7.46 (1H, d, J=9.1 Hz), 7.27-7.29 (2H, m), 7.09 (1H, dd, J=9.1, 1.8 Hz), 4.67-4.75 (1H, m), 3.09-3.18 (2H, m), 2.95 (3H, s), 2.77-2.87 (2H, m), 1.70-1.84 (8H, m)

LCMS: m/z 454 [M+H]$^+$

HPLC retention time: 2.22 min (analysis condition W)

Example 566

Compound Q3

Intermediate

2-Fluoro-8-methoxy-6,6-dimethyl-6,11-dihydro-5H-benzo[b]carbazole-3-carbonitrile

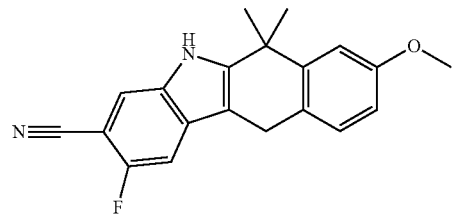 [SMILES: COc1ccc2c(c1)C(C)(C)c1[nH]c3cc(C#N)c(F)cc3c1C2]

Under the same conditions as the method for synthesizing Compound A3-1, the title compound was prepared from Compound A2 and 3-cyano-4-fluorophenylhydrazine.

LCMS: m/z 321 [M+H]$^+$

HPLC retention time: 4.13 min (analysis condition W)

Example 567

Compound Q4

Intermediate

2-Fluoro-8-methoxy-6,6-dimethyl-11-oxo-6,11-dihydro-5H-benzo[b]carbazole-3-carbonitrile

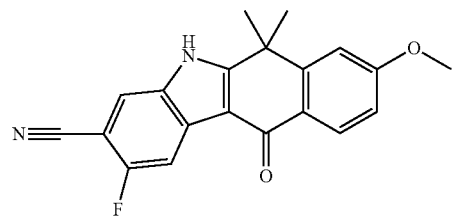 [SMILES: COc1ccc2c(c1)C(C)(C)c1[nH]c3cc(C#N)c(F)cc3c1C2=O]

Under the same conditions as the method for synthesizing Compound A4, the title compound was prepared from Compound Q3.

$^1$H-NMR (400 MHz, DMSO-d$_6$) δ: 12.89 (1H, s), 8.16 (1H, d, J=8.5 Hz), 8.07 (1H, d, J=4.9 Hz), 8.04 (1H, d, J=9.8 Hz), 7.36 (1H, d, J=2.4 Hz), 7.10 (1H, dd, J=8.5, 2.4 Hz), 3.91 (3H, s), 1.78 (3H, s)

LCMS: m/z 335 [M+H]$^+$

HPLC retention time: 3.61 min (analysis condition W)

Example 568

Compound Q5

Intermediate

2-Fluoro-8-hydroxy-6,6-dimethyl-11-oxo-6,11-dihydro-5H-benzo[b]carbazole-3-carbonitrile

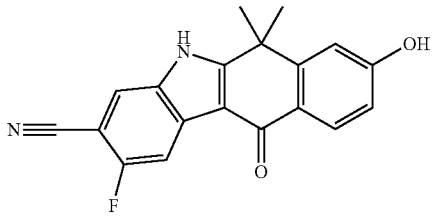 [SMILES: CC1(C)c2cc(O)ccc2C(=O)c2c1[nH]c1cc(C#N)c(F)cc21]

Under the same conditions as the method for synthesizing Compound A6, the title compound was prepared from Compound Q4.
LCMS: m/z 321 [M+H]$^+$
HPLC retention time: 3.16 min (analysis condition W)

Example 569

Compound Q6

Intermediate 4-(3-Cyano-2-fluoro-6,6-dimethyl-11-oxo-6,11-dihydro-5H-benzo[b]carbazole-8-yl oxy)-piperidine-1-carboxylic acid tert-butyl ester

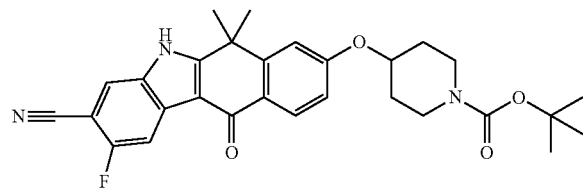 [SMILES: CC(C)(C)OC(=O)N1CCC(Oc2ccc3c(c2)C(C)(C)c2[nH]c4cc(C#N)c(F)cc4c2C3=O)CC1]

Under the same conditions as the method for synthesizing Compound A7-1, the title compound was prepared from Compound Q5.
LCMS: m/z 504 [M+H]$^+$
HPLC retention time: 4.25 min (analysis condition W)

Example 570

Compound Q7

8-(2-Diethylamino-ethoxy)-2-fluoro-6,6-dimethyl-11-oxo-6,11-dihydro-5H-benzo[b]carbazole-3-carbonitrile

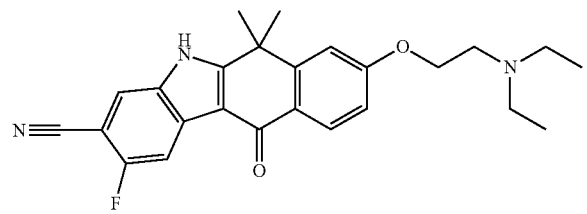 [SMILES: CCN(CC)CCOc1ccc2c(c1)C(C)(C)c1[nH]c3cc(C#N)c(F)cc3c1C2=O]

Under the same conditions as the method for synthesizing Compound A7-17, the title compound was prepared from Compound Q5.

$^1$H-NMR (400 MHz, CD$_3$OD) δ: 8.25 (1H, d, J=8.5 Hz), 8.09 (1H, d, J=9.8 Hz), 7.83 (1H, d, J=5.5 Hz), 7.30 (1H, d, J=2.4 Hz), 7.09 (1H, dd, J=8.5, 2.4 Hz), 4.26 (2H, t, J=5.7 Hz), 2.98 (2H, t, J=5.7 Hz), 2.72 (4H, q, J=7.2 Hz), 1.81 (6H, s), 1.13 (6H, t, J=7.2 Hz)
LCMS: m/z 420 [M+H]$^+$
HPLC retention time: 2.65 min (analysis condition W)

Example 571

Compound Q8

2-Fluoro-6,6-dimethyl-11-oxo-8-(piperidin-4-yloxy)-6,11-dihydro-5H-benzo[b]carbazole-3-carbonitrile

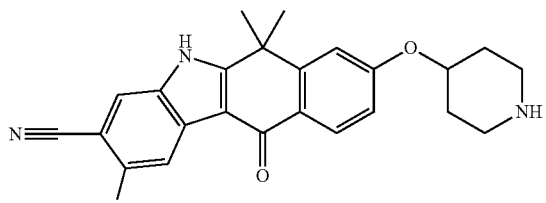

Under the same conditions as the method for synthesizing Compound A8-1, the title compound was prepared from Compound Q6.
$^1$H-NMR (400 MHz, DMSO-d$_6$) δ: 8.11 (1H, d, J=8.5 Hz), 7.98 (1H, d, J=5.5 Hz), 7.96 (1H, d, J=9.8 Hz), 7.29 (1H, s), 7.08 (1H, d, J=8.5 Hz), 4.58-4.69 (1H, m), 2.93-3.05 (2H, m), 2.60-2.69 (2H, m), 1.94-2.03 (2H, m), 1.74 (6H, s), 1.45-1.57 (2H, m)
LCMS: m/z 404 [M+H]$^+$
HPLC retention time: 2.67 min (analysis condition W)

Example 572

Compound R2

2-Fluoro-3-hydrazinylbenzonitrile

3-Amino-2-fluoro-benzonitrile (100 mg, 0.735 mmol) was dissolved in water (0.94 mL), added with conc. hydrochloric acid (0.74 mL) at 0° C., and then further added with an aqueous solution (0.294 mL) of sodium nitrite (61 mg, 0.882 mmol). The resulting mixture was stirred at 0° C. for 1 hr. To the reaction mixture, conc. hydrochloric acid solution (0.94 mL) of tin chloride (321 mg, 1.69 mmol) was added and stirred at room temperature for 1 hr. Thereafter, the reaction solution was neutralized with aqueous solution of sodium hydroxide, and extracted with dichloromethane. The organic layer was washed with saturated brine and dried over anhydrous magnesium sulfate. The drying agent was removed by filtration and the residues were obtained after concentration under reduced pressure to give the target compound as a crude product.

Example 573

Compound R3

4-Fluoro-8-methoxy-6,6-dimethyl-6,11-dihydro-5H-benzo[b]carbazole-3-carbonitrile

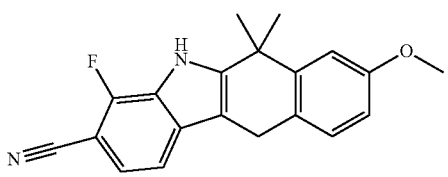 [SMILES: COc1ccc2c(c1)C(C)(C)c1[nH]c3c(F)c(C#N)ccc3c1C2]

Under the same conditions as the method for synthesizing Compound E2-1, the title compound was prepared as a crude product from Compound A2 and Compound R2.

Example 574

Compound R4

4-Fluoro-8-methoxy-6,6-dimethyl-11-oxo-6,11-dihydro-5H-benzo[b]carbazole-3-carbonitrile

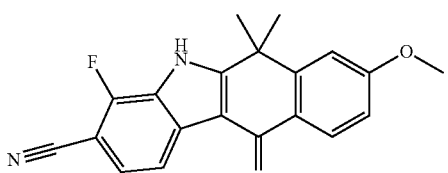

Under the same conditions as the method for synthesizing Compound A4, the title compound was prepared from Compound R3.

LCMS: m/z 335 [M+H]$^+$

HPLC retention time: 2.70 min (analysis condition U)

Example 575

Compound R5

4-Fluoro-8-hydroxy-6,6-dimethyl-11-oxo-6,11-dihydro-5H-benzo[b]carbazole-3-carbonitrile

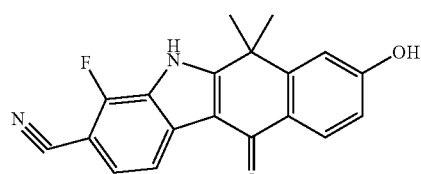

Under the same conditions as the method for synthesizing Compound A6, the title compound was prepared from Compound R4.

LCMS: m/z 321 [M+H]$^+$

HPLC retention time: 2.32 min (analysis condition U)

Example 576

Compound R6

8-(2-Diethylamino-ethoxy)-4-fluoro-6,6-dimethyl-11-oxo-6,11-dihydro-5H-benzo[b]carbazole-3-carbonitrile

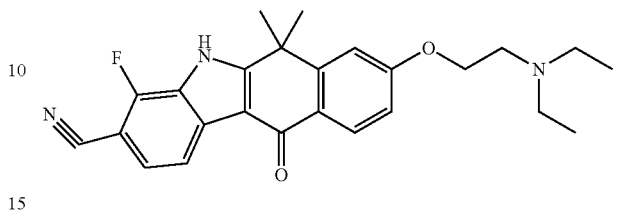

Under the same conditions as the method for synthesizing Compound A7-17, the title compound was prepared from Compound R5.

LCMS: m/z 420 [M+H]$^+$

HPLC retention time: 1.51 min (analysis condition S)

Example 577

Compound R7

Trifluoromethanesulfonic acid 3-cyano-4-fluoro-6,6-dimethyl-11-oxo-6,11-dihydro-5H-benzo[b]carbazole-8-yl

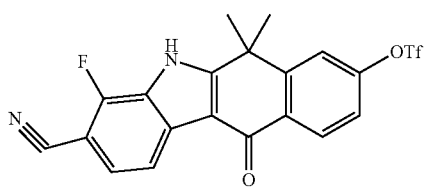 [SMILES: CC1(C)c2cc(OS(=O)(=O)C(F)(F)F)ccc2C(=O)c2c1[nH]c1c(F)c(C#N)ccc21]

Under the same conditions as the method for synthesizing Compound B1, the title compound was prepared from Compound R5.

LCMS: m/z 453 [M+H]$^+$

HPLC retention time: 3.82 min (analysis condition Y)

Example 578

Compound R8-1

4-Fluoro-6,6-dimethyl-11-oxo-8-(4-pyrrolidin-1-yl-piperidin-1-yl)-6,11-dihydro-5H-benzo[b]carbazole-3-carbonitrile

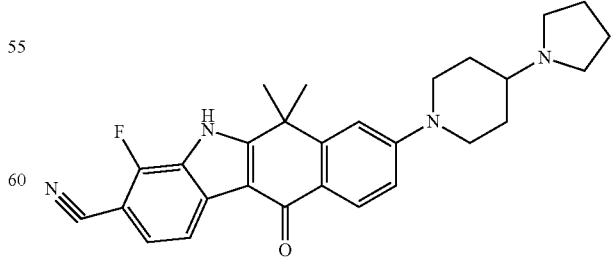

Under the same conditions as the method for synthesizing Compound B2-1, the title compound was prepared from Compound R7 and 4-pyrrolidin-1-yl-piperidine.

LCMS: m/z 457 [M+H]⁺

HPLC retention time: 2.10 min (analysis condition U)

Example 579

Compound R8-2

4-Fluoro-8-(4-isopropyl-piperazin-1-yl)-6,6-dimethyl-11-oxo-6,11-dihydro-5H-benzo[b]carbazole-3-carbonitrile

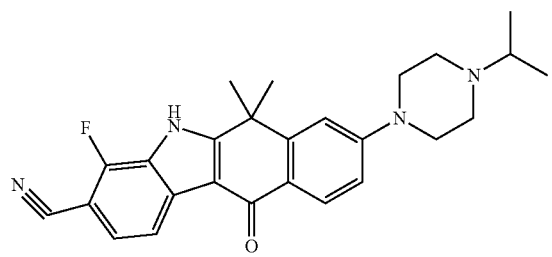 [SMILES: CC(C)N1CCN(c2ccc3c(c2)C(C)(C)c2[nH]c4c(F)c(C#N)ccc4c2C3=O)CC1]

Under the same conditions as the method for synthesizing Compound B2-1, the title compound was prepared from Compound R7.

LCMS: m/z 431 [M+H]⁺

HPLC retention time: 2.07 min (analysis condition U)

Example 580

Compound R9-1

8-((S)-2,2-Dimethyl-[1,3]dioxolan-4-ylmethoxy)-4-fluoro-6,6-dimethyl-11-oxo-6,11-dihydro-5H-benzo[b]carbazole-3-carbonitrile

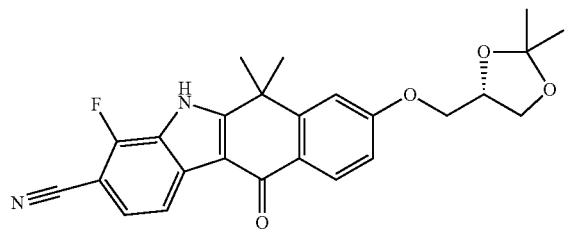 [SMILES: CC1(C)OC[C@H](COc2ccc3c(c2)C(C)(C)c2[nH]c4c(F)c(C#N)ccc4c2C3=O)O1]

Under the same conditions as the method for synthesizing Compound A7-1, the title compound was prepared as a crude product from Compound R5 and (R)-(−) 2,2-dimethyl-1,3-dioxolan-4-methanol.

Example 581

Compound R9-2

8-((R)-2,3-Dihydroxy-propoxy)-4-fluoro-6,6-dimethyl-11-oxo-6,11-dihydro-5H-benzo[b]carbazole-3-carbonitrile

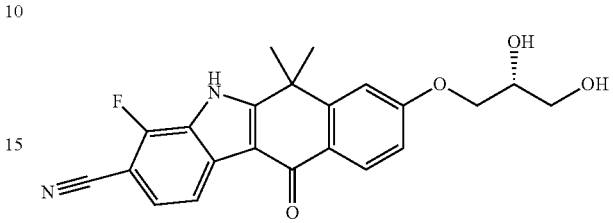

Under the same conditions as the method for synthesizing Compound A7-14-2, the title compound was prepared from Compound R9-1 (9.9 mg, 80%).

LCMS: m/z 395 [M+H]⁺

HPLC retention time: 2.38 min (analysis condition C)

Example 582

Compound S1-1

3-Chloro-8-methoxy-6,6-dimethyl-5,6-dihydrobenzo[b]carbazol-11-one

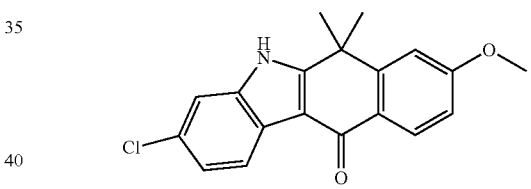

Under the same conditions as the method for synthesizing Compound A3-1 and Compound A4, the title compound was prepared as a crude product from Compound A2 and (3-chlorophenyl)-hydrazine hydrochloric acid salt.

Example 583

Compound S1-2

3-Chloro-8-methoxy-2,6,6-trimethyl-5,6-dihydro-benzo[b]carbazol-11-one

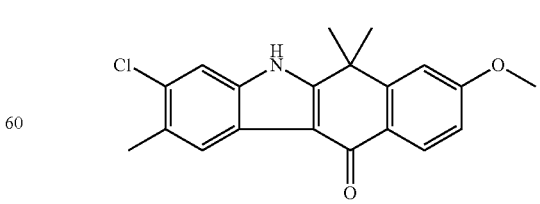

7-Methoxy-1,1-dimethyl-3,4-dihydro-1H-naphthalen-2-one (Compound A2, 99.1 mg, 0.485 mmol) and (3-chloro-4-methyl-phenyl)hydrazine hydrochloric acid salt (100.4 mg, 1.1 eq.) were dissolved in TFA (1 mL) and the mixture was irradiated with microwave at 80° C. for 10 min under nitrogen atmosphere. After cooling, the reaction solution was added with ethyl acetate, washed with water, saturated aqueous solution of sodium hydrogen carbonate and saturated brine and dried over magnesium sulfate. After filtration and concentration under reduced pressure, the residues obtained therefrom were dissolved in THF (2 mL) and water (0.2 mL), added with DDQ (125.7 mg, 1.1 eq.), and stirred at room temperature overnight. The reaction solution was added with the mixture solvent of hexane and ethyl acetate, and the starting-point components were removed by dry type silica gel column. The eluent was concentrated under reduced pressure, and the resulting residues were purified by preparative TLC (methanol/dichloromethane) to obtain the title compound (19.4 mg, 12%).

$^1$H-NMR (400 MHz, DMSO-d$_6$) δ: 12.2 (1H, s), 8.15 (1H, d, J=8.8 Hz), 8.12 (1H, s), 7.52 (1H, s), 7.32 (1H, s), 7.07 (1H, dd, J=2.4, 8.8 Hz), 3.90 (3H, s), 2.45 (3H, s), 1.73 (6H, s),

LCMS: m/z 340 [M+H]$^+$
HPLC retention time: 2.80 min (analysis condition F)

Example 584

Compound S1-3

3-Chloro-4-fluoro-8-methoxy-6,6-dimethyl-5,6-dihydro-benzo[b]carbazol-11-one

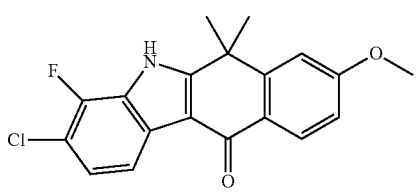 [SMILES: COc1ccc2c(c1)C(C)(C)c1[nH]c3c(F)c(Cl)ccc3c1C2=O]

According to the same method as the method for synthesizing Compound A3-1, the title compound was prepared from Compound A2 and (3-chloro-2-fluoro-phenyl)-hydrazine.
LCMS: m/z 344, 346 [M+H]$^+$
HPLC retention time: 2.68 min (analysis condition S)

Example 585

Compound S1-4

9-Bromo-3-chloro-8-methoxy-6,6-dimethyl-5,6-dihydro-benzo[b]carbazol-11-one

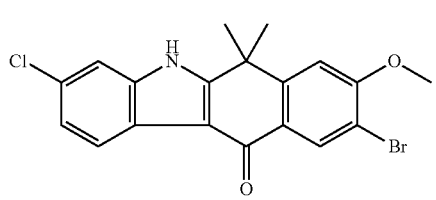 [SMILES: COc1cc2c(cc1Br)C(=O)c1c([nH]c3cc(Cl)ccc13)C2(C)C]

6-Bromo-7-methoxy-1,1-dimethyl-3,4-dihydro-1H-naphthalen-2-one (Compound E1, 0.2 g, 0.71 mmol) and 3-chlorophenylhydrazine hydrochloric acid salt (0.17 g, 1.3 eq.) were dissolved in acetic acid (0.5 mL). Under nitrogen atmosphere, the reaction solution was stirred at 90° C. for 8 hr. After cooling to room temperature, the reaction solution was added with ethyl acetate, washed with water, saturated aqueous solution of sodium hydrogen carbonate and saturated brine and dried over magnesium sulfate. After filtration and concentration under reduced pressure, the residues obtained therefrom were dissolved in THF (3 mL) comprising 10% water, added with DDQ (227 mg, 3 eq.) at room temperature, and the mixture was stirred at room temperature for 2 hr. The reaction solution was added with the mixture liquid of THF/diethyl ether (1:1) and washed with 0.5 N aqueous solution of sodium hydroxide and saturated brine. After drying with sodium sulfate, the mixture was filtered and the resulting residues obtained after concentration under reduced pressure were washed with the mixture liquid of hexane/diethyl ether (1:1) to obtain the title compound (brown powder, 86 mg).

LCMS: m/z 404, 406, 408 [M+H]$^+$
HPLC retention time: 3.02 min (analysis condition C)

Example 586

Compound S2-1

3-Chloro-8-hydroxy-6,6-dimethyl-5,6-dihydrobenzo[b]carbazol-11-one

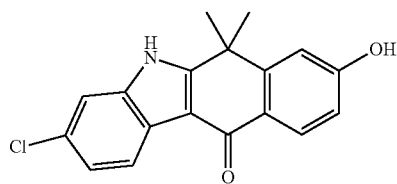 [SMILES: CC1(C)c2cc(O)ccc2C(=O)c2c1[nH]c1cc(Cl)ccc21]

Under the same conditions as the method for synthesizing Compound A6, the title compound was prepared from Compound S1-1.
LCMS: m/z 312 [M+H]$^+$
HPLC retention time: 4.18 min (analysis condition H)

Example 587

Compound S2-2

3-Chloro-8-hydroxy-2,6,6-trimethyl-5,6-dihydro-benzo[b]carbazol-11-one

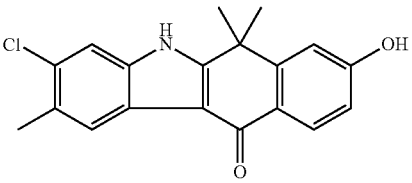 [SMILES: Cc1cc2c3c([nH]c2cc1Cl)C(C)(C)c1cc(O)ccc1C3=O]

3-Chloro-8-methoxy-2,6,6-trimethyl-5,6-dihydro-benzo[b]carbazol-11-one (Compound S1-2, 18.9 mg, 0.0556 mmol) and pyridinium chloride (220 mg, 34 eq.) were stirred at 185° C. for 2.5 hr. After cooling, the reaction solution was added with water and ethyl acetate, and the organic layer was washed with water and saturated brine, dried over magnesium sulfate, filtered and concentrated under reduced pressure to obtain the title compound as a crude product.

Example 588

Compound S2-3

3-Chloro-4-fluoro-8-hydroxy-6,6-dimethyl-5,6-dihydro-benzo[b]carbazol-11-one

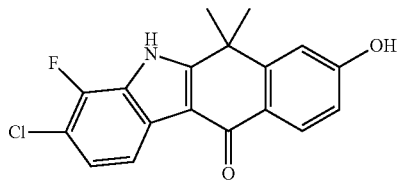 [SMILES: CC1(C)c2cc(O)ccc2C(=O)c2c1[nH]c1c(F)c(Cl)ccc21]

3-Chloro-4-fluoro-8-methoxy-6,6-dimethyl-5,6-dihydro-benzo[b]carbazol-11-one (Compound S1-3, 220.0 mg, 0.640 mmol) and pyridinium chloride (800 mg, 6.922 mmol) were mixed with each other, heated to 160° C., and then stirred for 20 hr. The reaction solution was added with water. As a result, black solid was obtained as a precipitate, which was then filtered and subjected to purification by silica gel column chromatography (ethyl acetate/hexane) to obtain the title compound (139.4 mg, 66%).

LCMS: m/z 330 [M+H]$^+$

HPLC retention time: 2.60 min (analysis condition F)

Example 589

Compound S2-4

9-Bromo-3-chloro-8-hydroxy-6,6-dimethyl-5,6-dihydro-benzo[b]carbazol-11-one

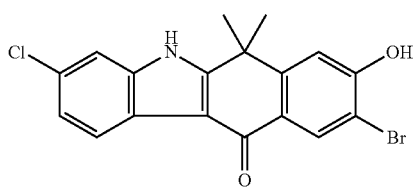 [SMILES: CC1(C)c2cc(O)c(Br)cc2C(=O)c2c1[nH]c1cc(Cl)ccc21]

Under the same conditions as the method for synthesizing Compound A6, the title compound was prepared from Compound S1-4.

LCMS: m/z 390, 392, 394 [M+H]$^+$

HPLC retention time: 2.75 min (analysis condition C)

Example 590

Compound S3

3-Chloro-8-(2-diethylaminoethoxy)-6,6-dimethyl-5, 6-dihydro-benzo[b]carbazol-11-one (CH5263231-000)

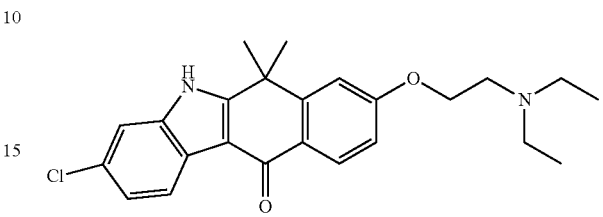

3-Chloro-8-hydroxy-6,6-dimethyl-5,6-dihydro-benzo[b]carbazol-11-one (Compound S2-1, 10 mg, 0.03207 mmol) was dissolved in DMF (0.1 mL), added with (2-chloroethyl)diethylamine (5.5 mg, 0.03207 mmol) and cesium carbonate (20.9 mg, 0.06414 mmol), and stirred at 80° C. for 2 hr. The reaction solution was added to water and extracted with ethyl acetate. The organic layer was dried over magnesium sulfate. The residues obtained after concentration under reduced pressure were purified by NH silica gel column chromatography (ethyl acetate/hexane) to obtain the title compound (11.6 mg, 76%).

LCMS: m/z 411 [M+H]$^+$

HPLC retention time: 4.49 min (analysis condition H)

Example 591

Compound S4

3-Chloro-2,6,6-trimethyl-8-((2R,3R)-2,3,4-trihydroxy-butoxy)-5,6-dihydro-benzo[b]carbazol-11-one

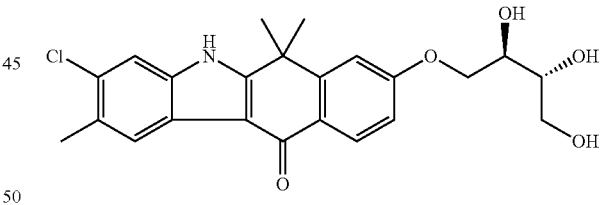

Crude product of Compound S2-2 was dissolved in THF (0.4 mL) under nitrogen atmosphere, together with THF (0.2 mL) solution of triphenylphosphine (18.9 mg, 1.3 eq.) and [(4R,5R)-5-(tert-butyl-dimethyl-silanyloxymethyl)-2,2-dimethyl-[1,3]dioxolan-4-yl]-methanol (17 mg, 1.2 eq.). DEAD (40% toluene solution, 0.0031 mL, 1.2 eq.) was added to the solution, which was then stirred at room temperature for 40 min and at 40° C. for 4 hr. The reaction solution was added with triphenylphosphine (18.9 mg, 1.3 eq.) and DEAD (40% toluene solution, 0.002 mL, 0.8 eq.) and stirred at 40° C. overnight. The reaction solution was added with ethyl acetate, washed with water and saturated brine, dried over magnesium sulfate, and filtered. The residues obtained after concentration under reduced pressure were purified by preparative TLC (ethyl acetate/hexane) to obtain the crude product of 8-[(4R,5R)-5-(tert-butyl-dimethyl-silanyloxymethyl)-2,2-dimethyl-[1,3]dioxolan-4-yl methoxy]-3-chloro-2,6,6-trimethyl-5,6-dihydro-benzo[b]carbazol-11-one (12.6 mg).

The resultant was dissolved in THF (0.15 mL) and methanol (0.03 mL) under nitrogen atmosphere, added with 0.5 M sulfuric acid (0.05 mL) and stirred at 60° C. for 3 hr. After cooling, diethyl ether was added and sodium hydrogen carbonate (8.4 mg) and water were further added thereto. The organic layer was washed with saturated brine. The aqueous layer was extracted with ethyl acetate, and the combined organic layer was dried over magnesium sulfate, and filtered. The solid obtained from the concentration under reduced pressure was washed with dichloromethane to obtain the target compound (white solid, 5.3 mg, 22%).

$^1$H-NMR (400 MHz, DMSO-$d_6$) δ: 12.18 (1H, s), 8.14 (1H, d, J=8.8 Hz), 8.12 (1H, s), 7.52 (1H, s), 7.31 (1H, d, J=2.4 Hz), 7.06 (1H, dd, J=2.4, 8.8 Hz), 4.78 (1H, d, J=5.9 Hz), 4.60 (1H, d, J=5.9 Hz), 4.52 (1H, t, J=5.4 Hz), 4.18-4.22 (1H, m), 4.02-4.06 (1H, m), 3.85-3.95 (1H, m), 3.50-3.60 (2H, m), 3.40-3.46 (1H, m), 2.45 (3H, s), 1.73 (3H, s),

LCMS: m/z 430 [M+H]$^+$

HPLC retention time: 2.27 min (analysis condition F)

Example 592

Compound S5

3-Chloro-8-ethoxy-4-fluoro-6,6-dimethyl-5,6-dihydro-benzo[b]carbazol-11-one

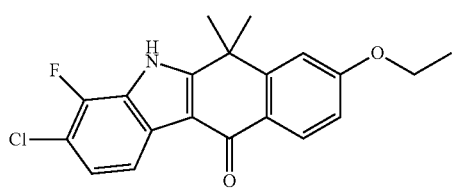 [SMILES: CCOc1ccc2c(c1)C(C)(C)c1[nH]c3c(F)c(Cl)ccc3c1C2=O]

The title compound was obtained as a by-product of the synthesis of Compound S6.
LCMS: m/z 358 [M+H]$^+$
HPLC retention time: 3.16 min (analysis condition F)

Example 593

Compound S6

3-Chloro-8-((R)-2,3-dihydroxy-propoxy)-4-fluoro-6,6-dimethyl-5,6-dihydro-benzo[b]carbazol-11-one

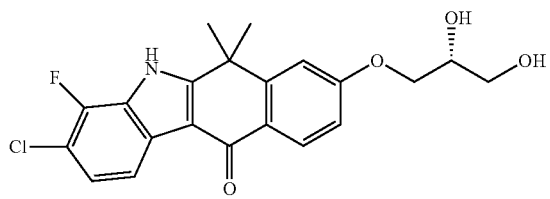 [SMILES: CC1(C)c2cc(OC[C@H](O)CO)ccc2C(=O)c2c1[nH]c1c(F)c(Cl)ccc21]

3-Chloro-4-fluoro-8-hydroxy-6,6-dimethyl-5,6-dihydro-benzo[b]carbazol-11-one (Compound S2-3, 20.0 mg, 0.061 mmol) was dissolved in THF (0.25 mL), added with ((S)-2,2-dimethyl-[1,3]dioxolan-4-yl)-methanol (9.8 μL, 0.079 mmol), triphenylphosphine (20.7 mg, 0.079 mmol) and diethyl azodicarboxylic acid (35.9 μl, 0.079 mmol), and then stirred at 40° C. for 5 hr. The reaction solution was concentrated under reduced pressure, and the resulting residues were purified by silica gel column chromatography (ethyl acetate/hexane) to obtain the intermediate, 3-chloro-8-((S)-2,2-dimethyl-[1,3]dioxolan-4-yl methoxy)-4-fluoro-6,6-dimethyl-5,6-dihydro-benzo[b]carbazol-11-one. This compound was dissolved in THF (0.10 mL) and MeOH (0.08 ml), added with sulfuric acid (0.5 M, 0.045 ml), and then stirred at 60° C. for 1 hr. The reaction solution was added with saturated aqueous solution of sodium hydrogen carbonate, extracted with ethyl acetate and dried over anhydrous magnesium sulfate. The yellow solid obtained after concentration under reduced pressure was washed with methylene chloride/hexane solvent and filtered to obtain the title compound (4.3 mg, 18%).

LCMS: m/z 404 [M+H]$^+$

HPLC retention time: 2.34 min (analysis condition F)

Example 594

Compound S7-1

3-Chloro-9-bromo-8-((S)-2,2-dimethyl-[1,3]dioxolan-4-ylmethoxy)-6,6-dimethyl-5,6-dihydro-benzo[b]carbazol-11-one

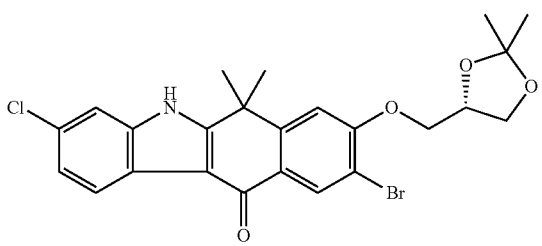 [SMILES: CC1(C)OC[C@H](COc2cc3c(cc2Br)C(=O)c2c([nH]c4cc(Cl)ccc24)C3(C)C)O1]

Under nitrogen atmosphere, 9-bromo-3-chloro-8-hydroxy-6,6-dimethyl-5,6-dihydro-benzo[b]carbazol-11-one (Compound S2-4, 76 mg, 0.2 mmol) and triphenylphosphine (69 mg, 1.3 eq.) were added with THF (2 ml), and ((S)-2,2-dimethyl-[1,3]dioxolan-4-yl)-methanol (35 mg, 1.3 eq.) and 2.19 N toluene solution (118 μL, 1.3 eq.) of diethyl azodicarboxylic acid were added dropwise thereto, followed by stirring at 50° C. for 2 hr. After cooling, the reaction solution was added with ethyl acetate, washed with brine, dried over sodium sulfate and filtered. The residues obtained after concentration under reduced pressure were purified by silica gel column chromatography (ethyl acetate/dichloromethane) to give a solid, which was then washed with dichloromethane to obtain the title compound (brown powder, 53 mg).

LCMS: m/z 504, 506, 508 [M+H]$^+$

HPLC retention time: 3.17 min (analysis condition C)

Example 595

Compound S7-2

9-Bromo-3-chloro-8-((R)-2,3-dihydroxy-propoxy)-6,6-dimethyl-5,6-dihydro-benzo[b]carbazol-11-one

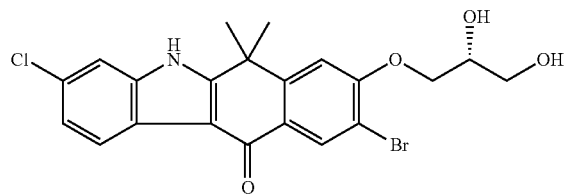 [SMILES: CC1(C)c2cc(OC[C@H](O)CO)c(Br)cc2C(=O)c2c1[nH]c1cc(Cl)ccc21]

3-Chloro-9-bromo-8-((S)-2,2-dimethyl-[1,3]dioxolan-4-ylmethoxy)-6,6-dimethyl-5,6-dihydro-benzo[b]carbazol-11-one (Compound S7-1, 56 mg, 0.11 mmol) was dissolved in methanol (5 mL), added with 1 N hydrochloric acid (0.2 ml), and stirred at 50° C. for 2 hr. After cooling, the reaction solution was concentrated under reduced pressure and the resulting residues were added with methanol to obtain a precipitated solid, which was then filtered to obtain the title compound (white powder, 26 mg).

LCMS: m/z 464, 466, 468 [M+H]$^+$

HPLC retention time: 2.77 min (analysis condition C)

Example 596

Compound S7-3

3-Chloro-9-bromo-8-((S)-2,2-dimethyl-[1,3]dioxolan-4-yl methoxy)-6,6-dimethyl-5,6-dihydro-benzo[b]carbazol-11-one

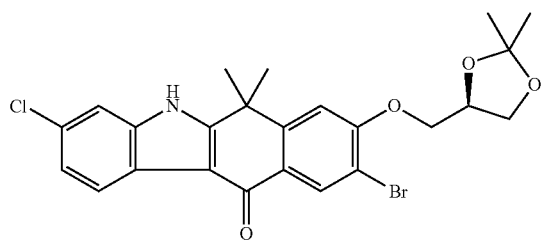 [SMILES: CC1(C)OC[C@@H](COc2cc3c(cc2Br)C(=O)c2c([nH]c4cc(Cl)ccc24)C3(C)C)O1]

Under nitrogen atmosphere, 9-bromo-3-chloro-8-hydroxy-6,6-dimethyl-5,6-dihydro-benzo[b]carbazol-11-one (Compound S2-4, 112 mg, 0.29 mmol) and triphenylphosphine (227 mg, 3 eq.) were added with THF (2 ml), and ((R)-2,2-dimethyl-[1,3]dioxolan-4-yl)-methanol (114 mg, 3 eq.) and 2.19 N toluene solution (0.4 mL, 3 eq.) of diethyl azodicarboxylic acid were added dropwise thereto, followed by stirring at 40° C. for 12 hr under nitrogen atmosphere. The residues obtained from the reaction solution after concentration under reduced pressure were purified by silica gel column chromatography (ethyl acetate/dichloromethane) to obtain the title compound (white powder, 100 mg).

LCMS: m/z 504, 506, 508 [M+H]$^+$

HPLC retention time: 3.15 min (analysis condition C)

Example 597

Compound S7-4

9-Bromo-3-chloro-8-((S)-2,3-dihydroxy-propoxy)-6,6-dimethyl-5,6-dihydro-benzo[b]carbazol-11-one

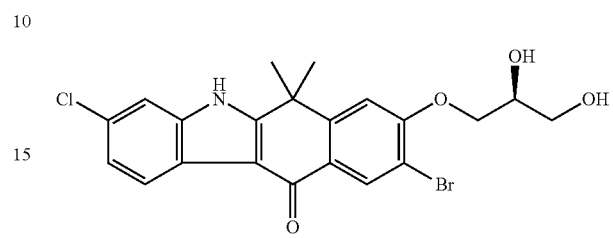

Under the same conditions as the method for synthesizing Compound S7-2, the title compound was prepared from Compound S7-3.

LCMS: m/z 464, 466, 468 [M+H]$^+$

HPLC retention time: 2.77 min (analysis condition C)

Example 598

Compound S8-1

9-Hydroxy-3-chloro-8-((S)-2,2-dimethyl-[1,3]dioxolan-4-ylmethoxy)-6,6-dimethyl-5,6-dihydro-benzo[b]carbazol-11-one

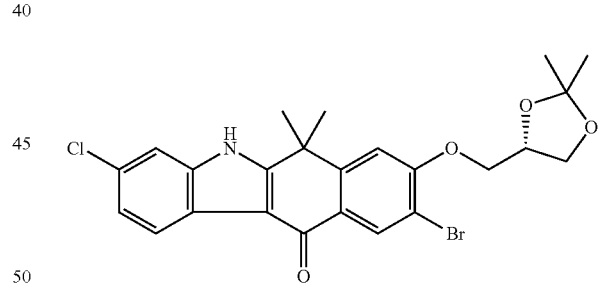

9-Bromo-3-chloro-8-((S)-2,2-dimethyl-[1,3]dioxolan-4-ylmethoxy)-6,6-dimethyl-5,6-dihydro-benzo[b]carbazol-11-one (Compound S7-1, 30 mg, 0.06 mmol) was dissolved in the mixture solvent of water.dioxane (1:1) (0.5 mL), added with tris(benzylidenacetone dipalladium)chloroform complex (3.1 mg, 0.05 eq.), 2-di-tert-butylphosphino-2',4',6'-triisopropylbiphenyl (2.5 mg, 0.1 eq.) and KOH (0.5 N aqueous solution 180 µL, 1.5 eq.), and stirred at 60° C. for 12 hr. After cooling, the reaction solution was concentrated under reduced pressure, and the resulting residues were purified by HPLC to obtain the title compound (white solid, 4.6 mg).

LCMS: m/z 442, 444 [M+H]$^+$

HPLC retention time: 2.78 min (analysis condition C)

Example 599

Compound S8-2

3-Chloro-8-((R)-2,3-dihydroxy-propoxy)-9-hydroxy-6,6-dimethyl-5,6-dihydro-benzo[b]carbazol-11-one

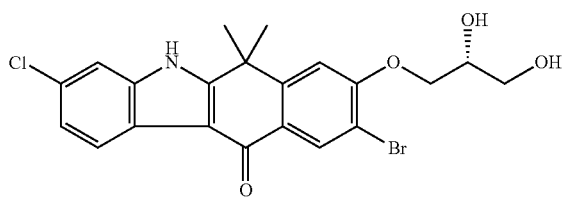 [SMILES: CC1(C)c2cc(OC[C@H](O)CO)c(Br)cc2C(=O)c2c1[nH]c1cc(Cl)ccc21]

Under the same conditions as the method for synthesizing Compound S7-2, the title compound was prepared from Compound S8-1.

LCMS: m/z 402, 404 [M+H]+
HPLC retention time: 0.90 min (analysis condition I)

Example 600

Compound S9-1

8-Hydroxy-6,6-dimethyl-11-oxo-9-(1H-tetrazol-5-yl)-6,11-dihydro-5H-benzo[b]carbazole-3-carbonitrile

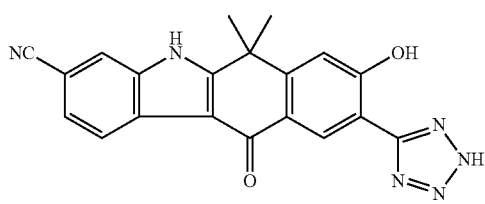 [SMILES: CC1(C)c2cc(O)c(-c3nn[nH]n3)cc2C(=O)c2c1[nH]c1cc(C#N)ccc21]

9-Bromo-3-chloro-8-methoxy-6,6-dimethyl-5,6-dihydro-benzo[b]carbazol-11-one (Compound S1-4, 150 mg, 0.37 mMol) was dissolved in NMP, added with CuCN (100 mg, 3 eq.), and stirred at 210° C. for 1.5 hr under irradiation with microwave. After cooling, the reaction solution was added with water and ethyl acetate, and the precipitated solid was filtered to remove the solvent. The obtained residues were dissolved in DMF (1 ml), added with sodium azide (100 mg, 8 eq.) and ammonium chloride (5 mg), and then stirred at 120° C. for 24 hr in a sealed tube. After adding water, the insoluble matters were filtered and purified by HPLC to obtain the title compound (6.5 mg).

LCMS: m/z 371 [M+H]+
HPLC retention time: 2.22 min (analysis condition C)

Example 601

Compound S9-2

3-Chloro-8-hydroxy-6,6-dimethyl-9-(1H-tetrazol-5-yl)-5,6-dihydro-benzo[b]carbazol-11-one

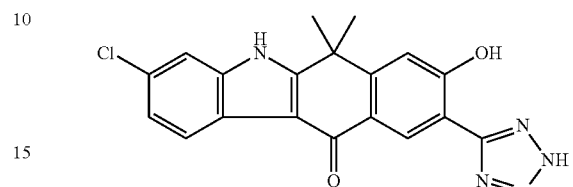

The title compound was obtained as an intermediate for the synthesis of Compound S9-1.

LCMS: m/z 380, 382 [M+H]+
HPLC retention time: 2.38 min (analysis condition C)

Example 602

Compound S10

3-Chloro-8-((R)-2,3-dihydroxy-propoxy)-9-(3-hydroxy-3-methyl-but-1-ynyl)-6,6-dimethyl-5,6-dihydro-benzo[b]carbazol-11-one

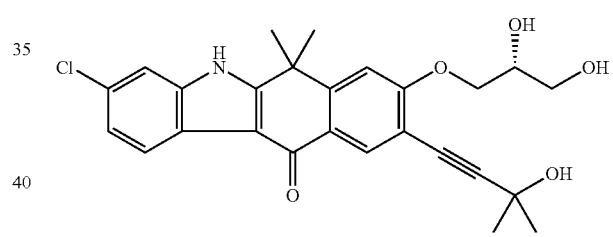

To the mixture of 9-bromo-3-chloro-8-((S)-2,2-dimethyl-[1,3]dioxolan-4-yl methoxy)-6,6-dimethyl-5,6-dihydro-benzo[b]carbazol-11-one (Compound S7-1, 50 mg, 0.1 mmol), bis(acetonitrile) palladium (II) dichloride (2.6 mg, 0.01 eq.), cesium carbonate (195 mg, 6 eq.) and 2-dicyclohexylphosphino-2',4',6'-triisopropylbiphenyl (14.3 mg, 0.03 eq.), acetonitrile (2 mL) was added and stirred at 80° C. for 12 hr. Tar-like residues obtained after concentration under reduced pressure were purified by silica gel column chromatography (ethyl acetate/hexane) to obtain 3-chloro-8-((S)-2,2-dimethyl-[1,3]dioxolan-4-yl methoxy)-9-(3-hydroxy-3-methyl-but-1-ynyl)-6,6-dimethyl-5,6-dihydro-benzo[b]carbazol-11-one (brown powder, 105 mg).

The resulting 3-chloro-8-((S)-2,2-dimethyl-[1,3]dioxolan-4-yl methoxy)-9-(3-hydroxy-3-methyl-but-1-ynyl)-6,6-dimethyl-5,6-dihydro-benzo[b]carbazol-11-one (20 mg, 0.04 mmol) was dissolved in methanol (3 mL), added with 1 N hydrochloric acid (1 ml), and stirred at room temperature for 12 hr. After cooling, the reaction solution was concentrated under reduced pressure, and the resulting residues were washed with methylene chloride to obtain the title compound (pale yellow powder, 5.2 mg).

LCMS: m/z 468, 470 [M+H]+
HPLC retention time: 2.70 min (analysis condition C)

Example 603

Compound S11-1

3-Chloro-8-((R)-2,3-dihydroxy-propoxy)-6,6-dimethyl-11-oxo-6,11-dihydro-5H-benzo[b]carbazole-9-carbonitrile

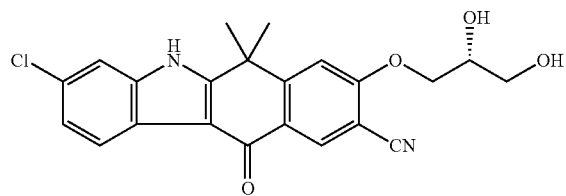 [SMILES: CC1(C)c2cc(OC[C@H](O)CO)c(C#N)cc2C(=O)c2c1[nH]c1cc(Cl)ccc21]

3-Chloro-9-bromo-8-((S)-2,2-dimethyl-[1,3]dioxolan-4-yl methoxy)-6,6-dimethyl-5,6-dihydro-benzo[b]carbazol-11-one (Compound S7-2, 17 mg, 37 µmol) was dissolved in DMA, added with CuCN (17 mg, 5 eq.), and stirred at 220° C. for 2 hr under irradiation with microwave. After cooling, the reaction solution was added with ethyl acetate, and the precipitated solid was filtered to remove the solvent. The resulting residues were purified by HPLC to obtain the title compound (4 mg).
LCMS: m/z 409, 411 [M+H]$^+$
HPLC retention time: 2.65 min (analysis condition C)

Example 604

Compound S11-2

3-Chloro-8-hydroxy-6,6-dimethyl-11-oxo-6,11-dihydro-5H-benzo[b]carbazole-9-carbonitrile

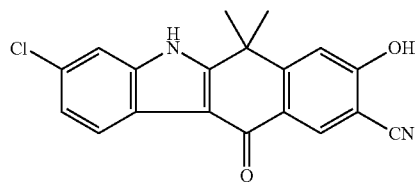

The title compound was obtained as a by-product of the synthesis of Compound S11-1.
LCMS: m/z 337, 339 [M+H]$^+$
HPLC retention time: 2.35 min (analysis condition C)

Example 605

Compound T1-1

3-Bromo-6,6-dimethyl-8-[(R)-(tetrahydro-furan-3-yl)oxy]-5,6-dihydro-benzo[b]carbazol-11-one

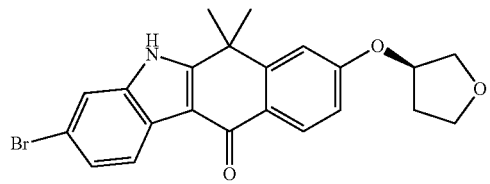 [SMILES: CC1(C)c2cc(O[C@@H]3CCOC3)ccc2C(=O)c2c1[nH]c1cc(Br)ccc21]

According to the same method as the method for synthesizing Compound A7-1, the title compound was prepared from Compound A5-1 and (S)-tetrahydro-furan-3-ol.
LCMS: m/z 426 [M+H]$^+$
HPLC retention time: 2.08 min (analysis condition D)

Example 606

Compound T1-2

6,6-Dimethyl-11-oxo-8-[(R)-(tetrahydro-furan-3-yl)oxy]-6,11-dihydro-5H-benzo[b]carbazole-3-carbonitrile

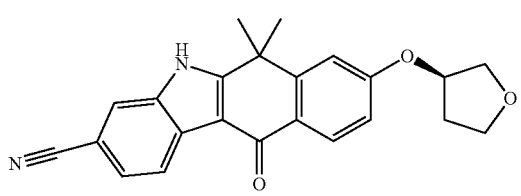 [SMILES: CC1(C)c2cc(O[C@@H]3CCOC3)ccc2C(=O)c2c1[nH]c1cc(C#N)ccc21]

According to the same method as the method for synthesizing Compound A5-2, the title compound was prepared from Compound T1-1.
LCMS: m/z 373 [M+H]$^+$
HPLC retention time: 1.98 min (analysis condition A)

Example 607

Compound T2-1

3-Bromo-6,6-dimethyl-8-[(S)-(tetrahydro-furan-3-yl)oxy]-5,6-dihydro-benzo[b]carbazol-11-one

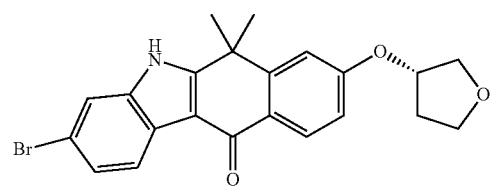 [SMILES: CC1(C)c2cc(O[C@H]3CCOC3)ccc2C(=O)c2c1[nH]c1cc(Br)ccc21]

According to the same method as the method for synthesizing Compound A7-1, the title compound was prepared from Compound A5-1 and (R)-tetrahydro-furan-3-ol.
LCMS: m/z 426 [M+H]$^+$
HPLC retention time: 6.12 min (analysis condition H)

Example 608

Compound T2-2

6,6-Dimethyl-11-oxo-8-[(S)-(tetrahydro-furan-3-yl)oxy]-6,11-dihydro-5H-benzo[b]carbazole-3-carbonitrile

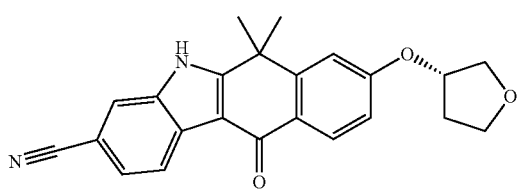 [SMILES: CC1(C)c2cc(O[C@H]3CCOC3)ccc2C(=O)c2c1[nH]c1cc(C#N)ccc21]

According to the same method as the method for synthesizing Compound A5-2, the title compound was prepared from Compound T2-1.
LCMS: m/z 373 [M+H]$^+$
HPLC retention time: 2.00 min (analysis condition D)

Example 609

Compound T3-1

3-Bromo-6,6-dimethyl-8-(tetrahydro-pyran-4-yl oxy)-5,6-dihydro-benzo[b]carbazol-11-one

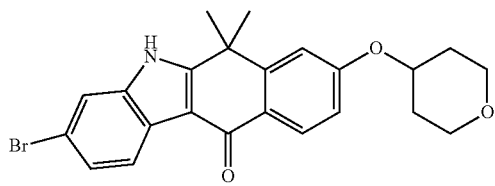 [SMILES: CC1(C)c2cc(OC3CCOCC3)ccc2C(=O)c2c1[nH]c1cc(Br)ccc21]

According to the same method as the method for synthesizing Compound A7-1, the title compound was prepared from Compound A5-1 and tetrahydro-pyran-4-ol.

LCMS: m/z 440 [M+H]$^+$
HPLC retention time: 8.07 min (analysis condition H)

Example 610

Compound T3-2

3-Bromo-5,6,6-trimethyl-8-(tetrahydro-pyran-4-yl oxy)-5,6-dihydro-benzo[b]carbazol-11-one

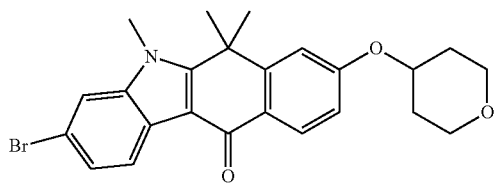 [SMILES: Cn1c2c(c3ccc(Br)cc31)C(=O)c1ccc(OC3CCOCC3)cc1C2(C)C]

According to the same method as the method for synthesizing Compound A10-2, the title compound was prepared from Compound T3-1.

LCMS: m/z 454 [M+H]$^+$
HPLC retention time: 6.88 min (analysis condition H)

Example 611

Compound T4-1

3-Bromo-6,6-dimethyl-8-(2-phenyl-[1,3]dioxan-5-yl oxy)-5,6-dihydro-benzo[b]carbazol-11-one

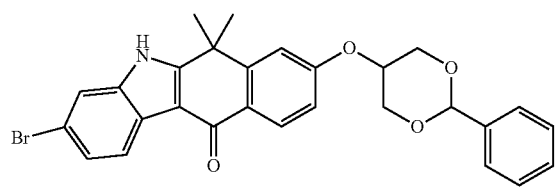 [SMILES: CC1(C)c2cc(OC3COC(c4ccccc4)OC3)ccc2C(=O)c2c1[nH]c1cc(Br)ccc21]

According to the same method as the method for synthesizing Compound A7-1, the title compound was prepared from Compound A5-1 and 5-phenyl-[1,3]dioxan-2-ol.

LCMS: m/z 518[M+H]$^+$
HPLC retention time: 2.68 min (analysis condition D)

Example 612

Compound T4-2

3-Bromo-8-(2-hydroxy-1-hydroxymethyl-ethoxy)-6,6-dimethyl-5,6-dihydro-benzo[b]carbazol-11-one

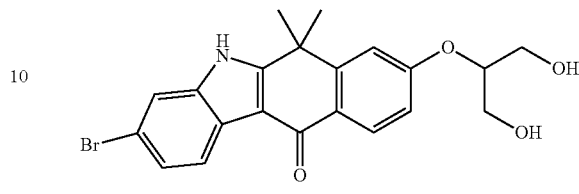

According to the same method as the method for synthesizing Compound A7-13-2, the title compound was prepared from Compound T4-1.

LCMS: m/z 430 [M+H]$^+$
HPLC retention time: 4.64 min (analysis condition H)

Example 613

Compound T5-1

4-(3-Bromo-6,6-dimethyl-11-oxo-6,11-dihydro-5H-benzo[b]carbazole-8-yloxy)-piperidine-1-carboxylic acid tert-butyl ester

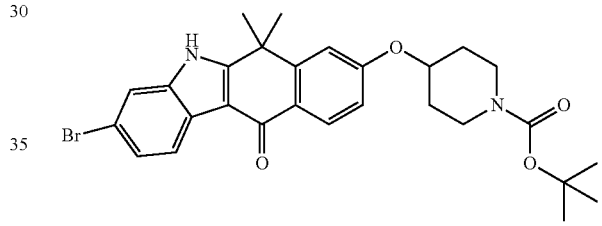

According to the same method as the method for synthesizing Compound A7-1, the title compound was prepared from Compound A5-1 and 4-hydroxy-piperidine-1-carboxylic acid tert-butyl ester.

LCMS: m/z 539 [M+H]$^+$
HPLC retention time: 2.72 min (analysis condition D)

Example 614

Compound T5-2

4-(3-Bromo-5,6,6-trimethyl-11-oxo-6,11-dihydro-5H-benzo[b]carbazole-8-yl oxy)-piperidine-1-carboxylic acid tert-butyl ester

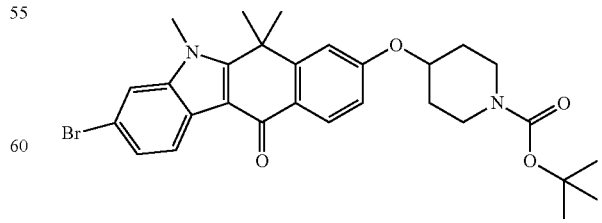

According to the same method as the method for synthesizing Compound A10-1, the title compound was prepared from Compound T5-1.

LCMS: m/z 553 [M+H]+
HPLC retention time: 2.93 min (analysis condition D)

Example 615

Compound T5-3

3-Bromo-5,6,6-trimethyl-8-(piperidin-4-yloxy)-5,6-dihydro-benzo[b]carbazol-11-one

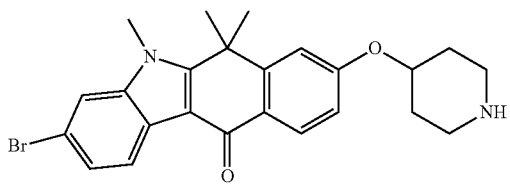 [SMILES: Cn1c2c(c3ccc(Br)cc31)C(=O)c1ccc(OC3CCNCC3)cc1C2(C)C]

According to the same method as the method for synthesizing Compound A8-1, the title compound was prepared from Compound T5-2.
LCMS: m/z 453 [M+H]+
HPLC retention time: 1.98 min (analysis condition D)

Example 616

Compound T5-4

3-Bromo-8-(1-methanesulfonyl-piperidin-4-yloxy)-5,6,6-trimethyl-5,6-dihydro-benzo[b]carbazol-11-one

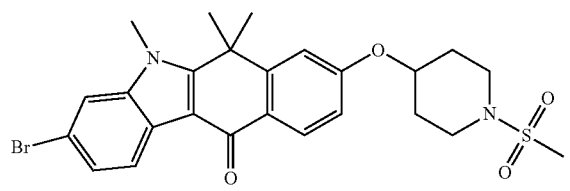 [SMILES: Cn1c2c(c3ccc(Br)cc31)C(=O)c1ccc(OC3CCN(S(C)(=O)=O)CC3)cc1C2(C)C]

According to the same method as the method for synthesizing Compound A9-7, the title compound was prepared from Compound T5-3 and methanesulfonyl chloride.
LCMS: m/z 531 [M+H]+
HPLC retention time: 2.38 min (analysis condition D)

Example 617

Compound T5-5

8-(1-Acetyl-piperidin-4-yloxy)-3-bromo-6,6-dimethyl-5,6-dihydro-benzo[b]carbazol-11-one

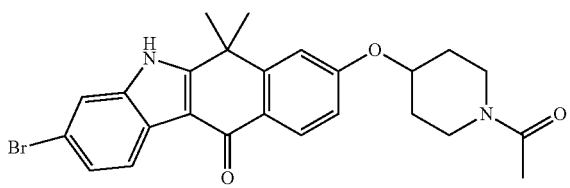 [SMILES: CC(=O)N1CCC(Oc2ccc3c(c2)C(C)(C)c2[nH]c4cc(Br)ccc4c2C3=O)CC1]

According to the same method as the method for synthesizing Compound A9-1, the title compound was prepared from Compound T5-3 and acetic anhydride.
LCMS: m/z 482 [M+H]+
HPLC retention time: 2.10 min (analysis condition D)

Example 618

Compound T6-1

3-Bromo-6,6-dimethyl-8-[1-(2,2,2-trifluoro-acetyl)-piperidin-4-yloxy]-5,6-dihydro-benzo[b]carbazol-11-one

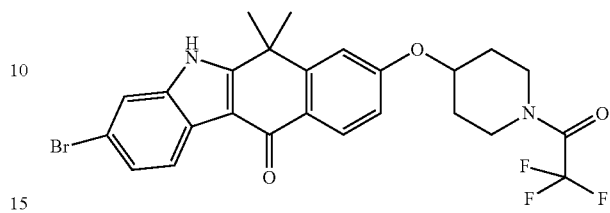

According to the same method as the method for synthesizing Compound A9-1, the title compound was prepared from Compound T6-2 and trifluoroacetic anhydride.
LCMS: m/z 535 [M+H]+
HPLC retention time: 2.53 min (analysis condition D)

Example 619

Compound T6-2

3-Bromo-6,6-dimethyl-8-(piperidin-4-yloxy)-5,6-dihydro-benzo[b]carbazol-11-one

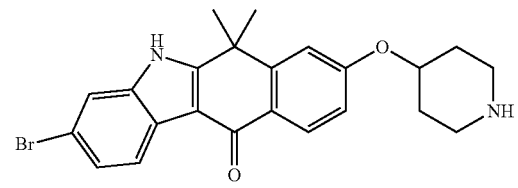 [SMILES: CC1(C)c2cc(OC3CCNCC3)ccc2C(=O)c2c1[nH]c1cc(Br)ccc21]

3-Bromo-6,6-dimethyl-8-[1-(2,2,2-trifluoro-acetyl)-piperidin-4-yloxy]-5,6-dihydro-benzo[b]carbazol-11-one (Compound T6-1, 28.0 mg, 52.3 µmol) was dissolved in THF (1.00 mL) and methanol (0.50 mL), added with aqueous solution of potassium hydroxide (1.00 mL, 20 wt %), and stirred at room temperature for 1 hr. The reaction solution was added to water, and extracted with mixture solution of chloroform and methanol, and dried over sodium sulfate. Then, after filtering and concentration under reduced pressure, 3-bromo-6,6-dimethyl-8-(piperidin-4-yloxy)-5,6-dihydro-benzo[b]carbazol-11-one was obtained as a crude product.
LCMS: m/z 439 [M+H]+
HPLC retention time: 1.83 min (analysis condition D)

Example 620

Compound T6-3

3-Bromo-8-(1-methanesulfonyl-piperidin-4-yloxy)-6,6-dimethyl-5,6-dihydro-benzo[b]carbazol-11-one

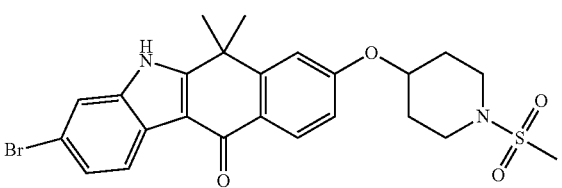

According to the same method as the method for synthesizing Compound A9-1, the title compound was prepared from Compound T6-2 and mesyl chloride.
LCMS: m/z 517 [M+H]+
HPLC retention time: 2.23 min (analysis condition D)

Example 621

Compound T6-4

8-(1-Acetyl-piperidin-4-yloxy)-3-bromo-5,6,6-trimethyl-5,6-dihydro-benzo[b]carbazol-11-one

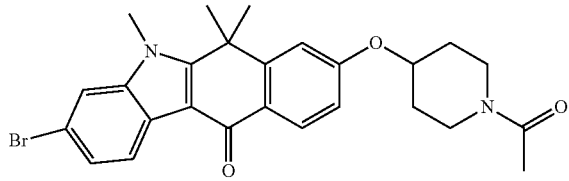 [SMILES: CC(=O)N1CCC(Oc2ccc3c(c2)C(C)(C)c2c(c4ccc(Br)cc4n2C)C3=O)CC1]

According to the same method as the method for synthesizing Compound A9-1, the title compound was prepared from Compound T6-2 and acetic anhydride.
LCMS: m/z 496 [M+H]+
HPLC retention time: 2.27 min (analysis condition D)

Example 622

Compound T7-1

3-Bromo-8-isopropoxy-6,6-dimethyl-5,6-dihydro-benzo[b]carbazol-11-one

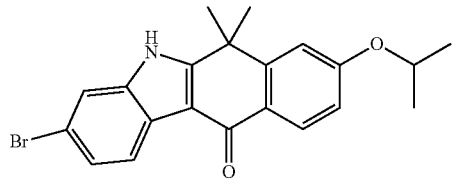 [SMILES: CC(C)Oc1ccc2c(c1)C(C)(C)c1[nH]c3cc(Br)ccc3c1C2=O]

The title compound was obtained as a by-product of the synthesis of Compound T4-1.
LCMS: m/z 398 [M+H]+
HPLC retention time: 3.18 min (analysis condition F)

Example 623

Compound T7-2

3-Bromo-8-isopropoxy-5,6,6-trimethyl-5,6-dihydro-benzo[b]carbazol-11-one

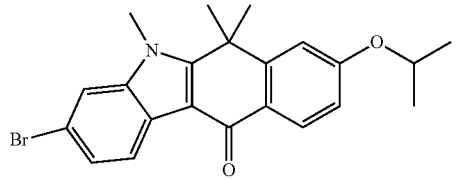 [SMILES: CC(C)Oc1ccc2c(c1)C(C)(C)c1c(c3ccc(Br)cc3n1C)C2=O]

According to the same method as the method for synthesizing Compound A10-2, the title compound was prepared from Compound T7-1.
LCMS: m/z 413 [M+H]+
HPLC retention time: 2.70 min (analysis condition D)

Example 624

Compound T8-1

3-Bromo-5,6,6-trimethyl-8-(2-phenyl-[1,3]dioxan-5-yl oxy)-5,6-dihydro-benzo[b]carbazol-11-one

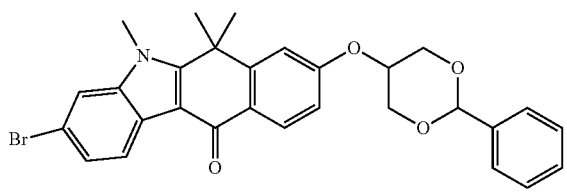 [SMILES: Cn1c2c(c3ccc(Br)cc31)C(=O)c1ccc(OC3COC(c4ccccc4)OC3)cc1C2(C)C]

According to the same method as the method for synthesizing Compound A10-2, the title compound was prepared from Compound T4-1.
LCMS: m/z 532 [M+H]+
HPLC retention time: 2.90 min (analysis condition D)

Example 625

Compound T8-2

3-Bromo-8-(2-hydroxy-1-hydroxymethyl-ethoxy)-5,6,6-trimethyl-5,6-dihydro-benzo[b]carbazol-11-one

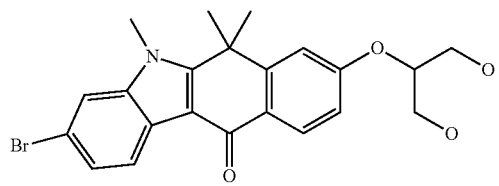 [SMILES: Cn1c2c(c3ccc(Br)cc31)C(=O)c1ccc(OC(CO)CO)cc1C2(C)C]

According to the same method as the method for synthesizing Compound A7-13-2, the title compound was prepared from Compound T4-1.
LCMS: m/z 444 [M+H]+
HPLC retention time: 1.90 min (analysis condition D)

Example 626

Compound T9

N-[2-(3-Bromo-6,6-dimethyl-11-oxo-6,11-dihydro-5H-benzo[b]carbazole-8-yl oxy)-ethyl]-acetamide

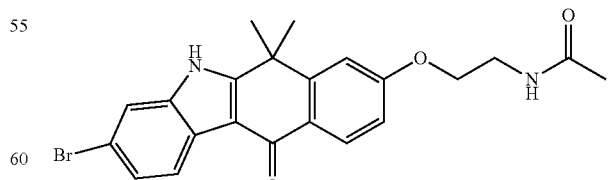

According to the same method as the method for synthesizing Compound A7-17, the title compound was prepared from Compound A5-1 and (N-(2-chloro-ethyl)-acetamide.
LCMS: m/z 441 [M+H]+

Example 627

Compound T10

3-Bromo-6,6-dimethyl-8-(oxetan-3-yl oxy)-5,6-dihydro-benzo[b]carbazol-11-one

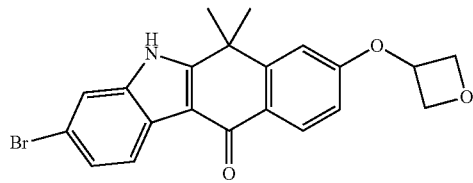 [SMILES: CC1(C)c2cc(OC3COC3)ccc2C(=O)c2c1[nH]c1cc(Br)ccc21]

According to the same method as the method for synthesizing Compound A7-17, the title compound was prepared from Compound A5-1 and toluene-4-sulfonic acid oxetan-3-yl ester.

LCMS: m/z 412 [M+H]$^+$

HPLC retention time: 2.17 min (analysis condition D)

Example 628

Compound T11

3-Bromo-8-(4-hydroxy-tetrahydro-furan-3-yl oxy)-6,6-dimethyl-5,6-dihydro-benzo[b]carbazol-11-one

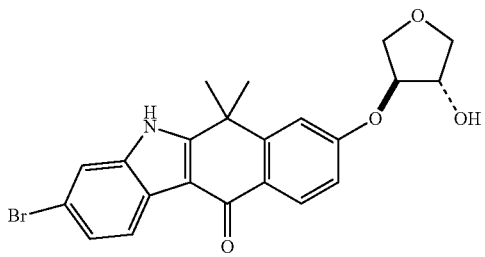

Under nitrogen atmosphere, tetrahydro-furo[3,4-d][1,3,2]dioxathiol 2,2-dioxide (71.5 mg, 0.420 mmol) was dissolved in DMF (1.40 mL), added with 3-bromo-8-hydroxy-6,6-dimethyl-5,6-dihydro-benzo[b]carbazol-11-one (Compound A5-1, 50.0 mg, 0.140 mmol) and cesium carbonate (228 mg, 0.700 mmol), and stirred at 80° C. for 15 hr. Subsequently, sulfuric acid (0.10 mL, 18 M), THF (3.00 mL) and water (0.50 mL) were added to the mixture, which was then stirred at room temperature for 24 hr and further at 60° C. for 24 hr. The reaction solution was added to water, extracted with ethyl acetate, washed with water, saturated aqueous solution of sodium bicarbonate, and saturated brine, and dried over sodium sulfate. After filtering and concentration under reduced pressure, the resulting residues were washed with dichloromethane and purified by NH silica gel column chromatography (ethyl acetate/THF) to obtain the target compound (44.7 mg, 72%).

LCMS: m/z 442 [M+H]$^+$

HPLC retention time: 1.98 min (analysis condition D)

Example 629

Compound T12-1

Acetic acid (2 S,3R,4S,5R,6R)-4,5-diacetoxy-6-(3-bromo-6,6-dimethyl-11-oxo-6,11-dihydro-5H-benzo[b]carbazole-8-yl oxymethyl)-2-methoxy-tetrahydro-pyran-3-yl ester

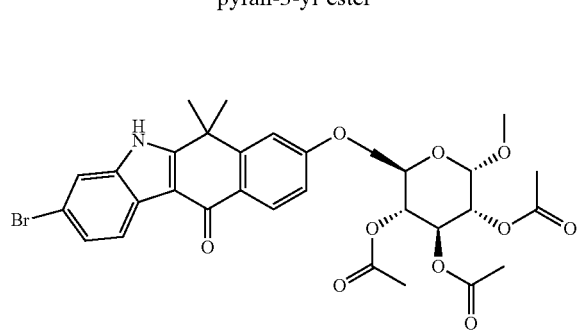

According to the same method as the method for synthesizing Compound A7-1, the title compound was prepared from Compound A5-1 and methyl 2,3,4-tri-O-acetyl-α-D-glucopyranoside.

LCMS: m/z 658 [M+H]$^+$

HPLC retention time: 2.38 min (analysis condition D)

Example 630

Compound T12-2

3-Bromo-6,6-dimethyl-8-((2R,3S,4S,5R,6S)-3,4,5-trihydroxy-6-methoxy-tetrahydro-pyran-2-yl methoxy)-5,6-dihydro-benzo[b]carbazol-11-one

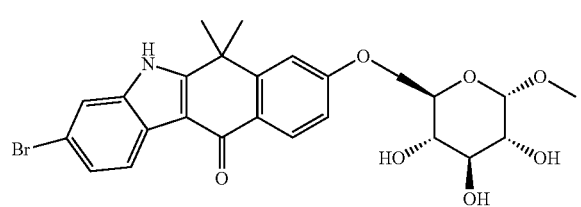 [SMILES: CO[C@H]1O[C@H](COc2ccc3c(c2)C(C)(C)c2[nH]c4cc(Br)ccc4c2C3=O)[C@@H](O)[C@H](O)[C@H]1O]

Under nitrogen atmosphere, to acetic acid (2S,3R,4S,5R,6R)-4,5-diacetoxy-6-(3-bromo-6,6-dimethyl-11-oxo-6,11-dihydro-5H-benzo[b]carbazole-8-yl oxymethyl)-2-methoxy-tetrahydro-pyran-3-yl ester (Compound T12-1, 34.0 mg, 51.63 μmol), methanol solution (2.50 mL, 2 M) of ammonia was added, and the mixture was stirred at room temperature for 21 hr. The reaction solution was concentrated under reduced pressure, and the resulting resides were washed with diethyl ether to obtain the target compound (25.7 mg, 94%).

LCMS: m/z 532 [M+H]$^+$

HPLC retention time: 2.42 min (analysis condition D)

Example 631

Compound T13-1

(3-Bromo-6,6-dimethyl-11-oxo-6,11-dihydro-5H-benzo[b]carbazole-8-yl oxy)-acetic acid tert-butyl ester

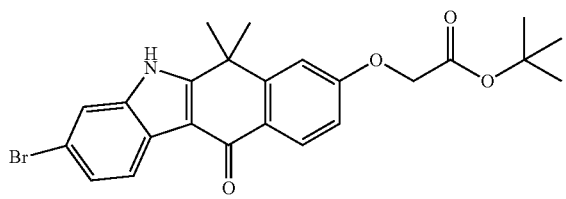 [SMILES: CC(C)(C)OC(=O)COc1ccc2c(c1)C(C)(C)c1[nH]c3cc(Br)ccc3c1C2=O]

According to the same method as the method for synthesizing Compound A7-17, the title compound was prepared from Compound A5-1 and bromo-acetic acid tert-butyl ester.
LCMS: m/z 470 [M+H]$^+$
HPLC retention time: 2.53 min (analysis condition D)

Example 632

Compound T13-2

(3-Bromo-6,6-dimethyl-11-oxo-6,11-dihydro-5H-benzo[b]carbazole-8-yl oxy)-acetic acid

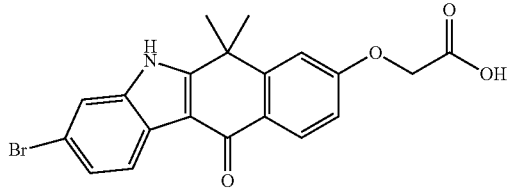 [SMILES: CC1(C)c2cc(OCC(=O)O)ccc2C(=O)c2c1[nH]c1cc(Br)ccc21]

According to the same method as the method for synthesizing Compound A8-1, the title compound was prepared from Compound T13-1.
LCMS: m/z 414 [M+H]$^+$
HPLC retention time: 1.50 min (analysis condition D)

Example 633

Compound T13-3

2-(3-Bromo-6,6-dimethyl-11-oxo-6,11-dihydro-5H-benzo[b]carbazole-8-yloxy)-N-(3-ethyl-3-hydroxy-pentyl)-acetamide

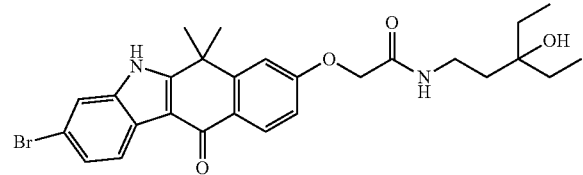 [SMILES: CCC(O)(CC)CCNC(=O)COc1ccc2c(c1)C(C)(C)c1[nH]c3cc(Br)ccc3c1C2=O]

Under nitrogen atmosphere, (3-azide-1,1-diethyl-propoxy)-trimethyl-silane (16.6 mg, 72.42 µmol) was dissolved in toluene (0.48 mL), added with 3-bromo-6,6-dimethyl-11-oxo-6,11-dihydro-5H-benzo[b]carbazole-8-yl oxy)-acetic acid (20.0 mg, 48.28 µmol) and Molecular Sieves 4 angstrom, and the mixture was stirred at room temperature for 5 min. Thereafter, the mixture was added with trimethylphosphine (10.2 µL, 96.56 µmol) and stirred at 80° C. for 22 hr. The reaction solution was added to hydrochloric acid (1 M), extracted with ethyl acetate, washed with water, saturated aqueous solution of sodium bicarbonate, saturated brine and dried over sodium sulfate. After filtering and concentration under reduced pressure, the resulting residues were purified by silica gel column chromatography (methanol/dichloromethane) to obtain the target compound (0.7 mg, 3%).
LCMS: m/z 527 [M+H]$^+$
HPLC retention time: 2.93 min (analysis condition D)

Example 634

Compound T13-4

4-[2-(3-Bromo-6,6-dimethyl-11-oxo-6,11-dihydro-5H-benzo[b]carbazole-8-yl oxy)-acetyl]-piperazine-1-carboxylic acid tert-butyl ester

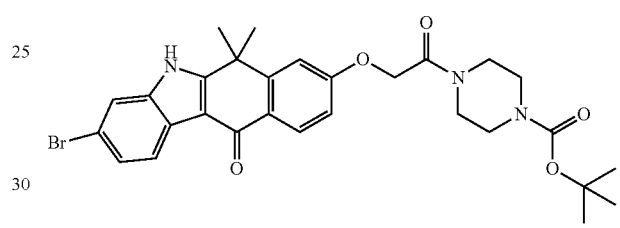

According to the same method as the method for synthesizing Compound A9-10, the title compound was prepared from Compound T13-2 and 1-(tert-butoxycarbonyl)piperazine.
LCMS: m/z 582 [M+H]$^+$
HPLC retention time: 2.32 min (analysis condition D)

Example 635

Compound T13-5

3-Bromo-6,6-dimethyl-8-(2-oxo-2-piperazin-1-yl-ethoxy)-5,6-dihydro-benzo[b]carbazol-11-one hydrochloric acid salt

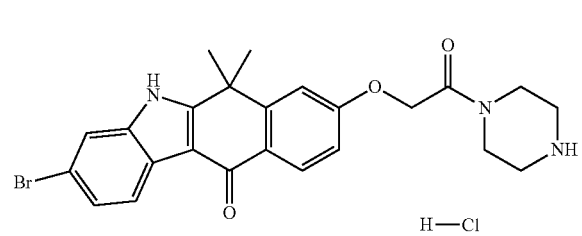 [SMILES: CC1(C)c2cc(OCC(=O)N3CCNCC3)ccc2C(=O)c2c1[nH]c1cc(Br)ccc21 ; Cl]

According to the same method as the method for synthesizing Compound A8-1, the title compound was prepared from Compound T13-4.
LCMS: m/z 482 [M+H]$^+$
HPLC retention time: 1.75 min (analysis condition D)

Example 636

Compound T13-6

3-Bromo-8-[2-(4-methanesulfonyl-piperazin-1-yl)-2-oxo-ethoxy]-6,6-dimethyl-5,6-dihydro-benzo[b]carbazol-11-one

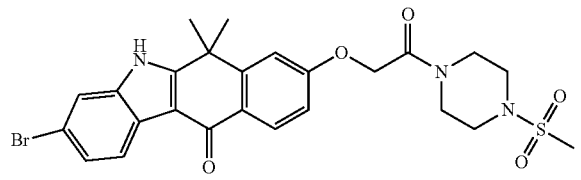 [SMILES: CC1(C)c2cc(OCC(=O)N3CCN(S(C)(=O)=O)CC3)ccc2C(=O)c2c1[nH]c1cc(Br)ccc21]

According to the same method as the method for synthesizing Compound A9-1, the title compound was prepared from Compound T13-5 and methanesulfonyl chloride.
LCMS: m/z 560 [M+H]$^+$
HPLC retention time: 2.00 min (analysis condition D)

Example 637

Compound T13-7

3-Bromo-6,6-dimethyl-8-{2-oxo-2-[4-(propane-2-sulfonyl)-piperazin-1-yl]-ethoxy}-5,6-dihydro-benzo[b]carbazol-11-one

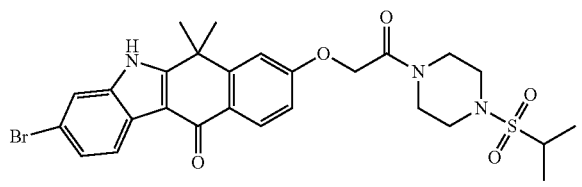 [SMILES: CC(C)S(=O)(=O)N1CCN(C(=O)COc2ccc3c(c2)C(C)(C)c2[nH]c4cc(Br)ccc4c2C3=O)CC1]

According to the same method as the method for synthesizing Compound A9-1, the title compound was prepared from Compound T13-5 and isopropylsulfonyl chloride.
LCMS: m/z 588 [M+H]$^+$
HPLC retention time: 2.47 min (analysis condition D)

Example 638

Compound T13-8

8-[2-(4-Acetyl-piperazin-1-yl)-2-oxo-ethoxy]-3-bromo-6,6-dimethyl-5,6-dihydro-benzo[b]carbazol-11-one

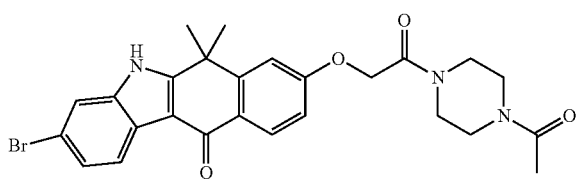 [SMILES: CC(=O)N1CCN(C(=O)COc2ccc3c(c2)C(C)(C)c2[nH]c4cc(Br)ccc4c2C3=O)CC1]

According to the same method as the method for synthesizing Compound A9-1, the title compound was prepared from Compound T13-5 and acetic anhydride.
LCMS: m/z 524 [M+H]$^+$
HPLC retention time: 1.85 min (analysis condition D)

Example 639

Compound T13-9

3-Bromo-6,6-dimethyl-8-[2-(4-oxetan-3-yl-piperazin-1-yl)-2-oxo-ethoxy]-5,6-dihydro-benzo[b]carbazol-11-one


According to the same method as the method for synthesizing Compound B3-32, the title compound was prepared from Compound T13-5 and 3-oxetanone.
LCMS: m/z 538 [M+H]$^+$
HPLC retention time: 1.88 min (analysis condition D)

Example 640

Compound T13-10

4-[2-(3-Bromo-6,6-dimethyl-11-oxo-6,11-dihydro-5H-benzo[b]carbazole-8-yl-oxy)-acetyl]-piperazine-1-sulfonic acid methylamide


According to the same method as the method for synthesizing Compound A9-1, the title compound was prepared from Compound T13-5 and 2-oxo-oxazolidine-3-sulfonic acid methylamide.
LCMS: m/z 575 [M+H]$^+$
HPLC retention time: 2.29 min (analysis condition A)

Example 641

Compound T14-1

4-(3-Bromo-6,6-dimethyl-11-oxo-6,11-dihydro-5H-benzo[b]carbazole-8-yl oxymethyl)-piperidine-1-carboxylic acid tert-butyl ester

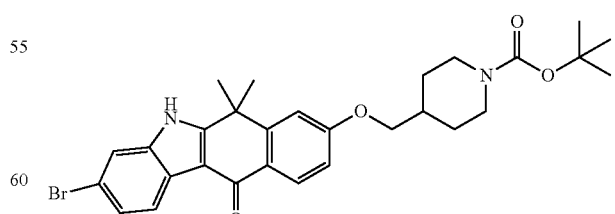

According to the same method as the method for synthesizing Compound A7-1, the title compound was prepared from Compound A5-1 and 1-(tert-butoxycarbonyl)-4-(hydroxymethyl)piperidine.

LCMS: m/z 553 [M+H]+

HPLC retention time: 2.80 min (analysis condition D)

Example 642

Compound T14-2

3-Bromo-6,6-dimethyl-8-(piperidin-4-ylmethoxy)-5,6-dihydro-benzo[b]carbazol-11-one hydrochloric acid salt

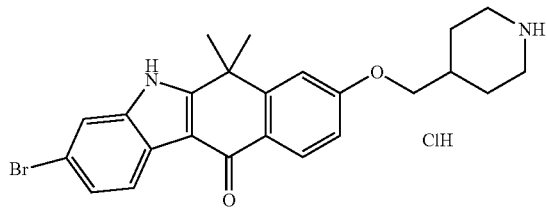 [SMILES: CC1(C)c2cc(OCC3CCNCC3)ccc2C(=O)c2c1[nH]c1cc(Br)ccc21 ; Cl]

According to the same method as the method for synthesizing Compound A8-1, the title compound was prepared from Compound T14-1.

LCMS: m/z 454 [M+H]+

HPLC retention time: 1.90 min (analysis condition D)

Example 643

Compound T14-3

3-Bromo-6,6-dimethyl-8-(1-oxetan-3-yl-piperidin-4-ylmethoxy)-5,6-dihydro-benzo[b]carbazol-11-one

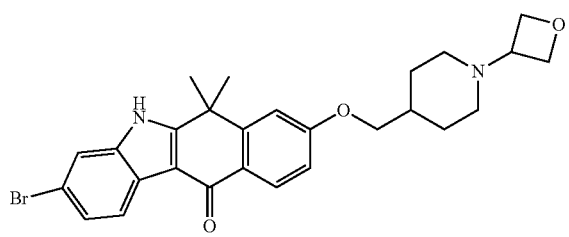 [SMILES: CC1(C)c2cc(OCC3CCN(C4COC4)CC3)ccc2C(=O)c2c1[nH]c1cc(Br)ccc21]

According to the same method as the method for synthesizing Compound B3-32, the title compound was prepared from Compound T14-2 and 3-oxetanone.

1H-NMR (400 MHz, CDCl3) δ: 9.24 (1H, s), 8.37 (1H, d, 8.8 Hz), 8.30 (1H, d, 8.3 Hz), 7.57 (1H, d, 1.5 Hz), 7.41 (1H, dd, 8.3, 1.5 Hz), 7.08 (1H, d, 2.4 Hz), 6.98 (1H, dd, 8.8, 2.4 Hz) 4.60-4.95 (7H, m), 3.93 (2H, d, 5.9 Hz), 3.50 (1H, m), 2.83 (2H, d, 11.2 Hz), 1.89 (4H, m), 1.78 (6H, s),

LCMS: m/z 509 [M+H]+

HPLC retention time: 2.10 min (analysis condition A)

Example 644

Compound T14-4

8-(1-Acetyl-piperidin-4-ylmethoxy)-3-bromo-6,6-dimethyl-5,6-dihydro-benzo[b]carbazol-11-one

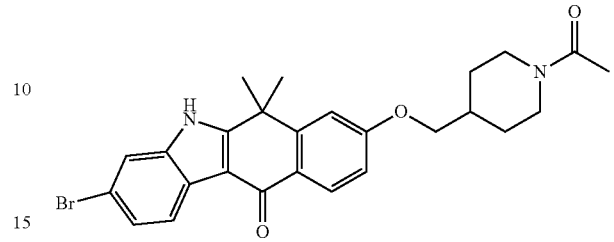

According to the same method as the method for synthesizing Compound A9-1, the title compound was prepared from Compound T14-2 and acetic anhydride.

LCMS: m/z 495 [M+H]+

HPLC retention time: 2.53 min (analysis condition A)

Example 645

Compound T14-5

3-Bromo-8-(1-methanesulfonyl-piperidin-4-ylmethoxy)-6,6-dimethyl-5,6-dihydro-benzo[b]carbazol-11-one


According to the same method as the method for synthesizing Compound A9-1, the title compound was prepared from Compound T14-2 and methanesulfonyl chloride.

LCMS: m/z 531 [M+H]+

HPLC retention time: 2.30 min (analysis condition D)

Example 646

Compound T14-6

3-Bromo-6,6-dimethyl-8-[1-(propane-2-sulfonyl)-piperidin-4-ylmethoxy]-5,6-dihydro-benzo[b]carbazol-11-one

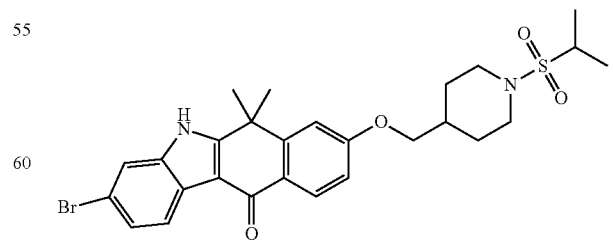

According to the same method as the method for synthesizing Compound A9-1, the title compound was prepared from Compound T14-2 and isopropylsulfonyl chloride.

LCMS: m/z 559 [M+H]+
HPLC retention time: 2.58 min (analysis condition D)

Example 647

Compound T14-7

3-[4-(3-Bromo-6,6-dimethyl-11-oxo-6,11-dihydro-5H-benzo[b]carbazole-8-yl oxymethyl)-piperidin-1-yl]-azetidine-1-carboxylic acid tert-butyl ester

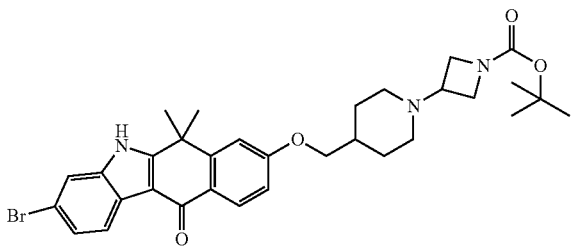 [SMILES: CC(C)(C)OC(=O)N1CC(N2CCC(COc3ccc4c(c3)C(C)(C)c3[nH]c5cc(Br)ccc5c3C4=O)CC2)C1]

According to the same method as the method for synthesizing Compound B3-32, the title compound was prepared from Compound T14-2 and 3-oxo-azetidine-1-carboxylic acid tert-butyl ester.
LCMS: m/z 608 [M+H]+
HPLC retention time: 2.29 min (analysis condition A)

Example 648

Compound T14-8

8-(1-Azetidin-3-yl-piperidin-4-ylmethoxy)-3-bromo-6,6-dimethyl-5,6-dihydro-benzo[b]carbazol-11-one

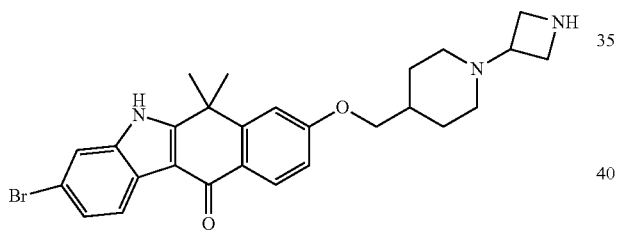

According to the same method as the method for synthesizing Compound A8-1, the title compound was prepared from Compound T14-7.
LCMS: m/z 508 [M+H]+
HPLC retention time: 1.90 min (analysis condition A)

Example 649

Compound T14-9

3-Bromo-8-[1-(1-methanesulfonyl-azetidin-3-yl)-piperidin-4-ylmethoxy]-6,6-dimethyl-5,6-dihydro-benzo[b]carbazol-11-one

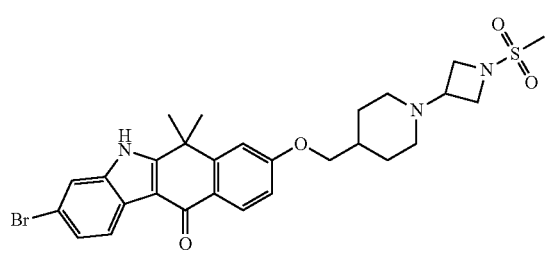 [SMILES: CC1(C)c2cc(OCC3CCN(C4CN(S(C)(=O)=O)C4)CC3)ccc2C(=O)c2c1[nH]c1cc(Br)ccc21]

According to the same method as the method for synthesizing Compound A9-1, the title compound was prepared from Compound T14-8 and mesyl chloride.
LCMS: m/z 586 [M+H]+
HPLC retention time: 2.06 min (analysis condition A)

Example 650

Compound T14-10

8-[1-(1-Acetyl-azetidin-3-yl)-piperidin-4-yl-methoxy]-3-bromo-6,6-dimethyl-5,6-dihydro-benzo[b]carbazol-11-one

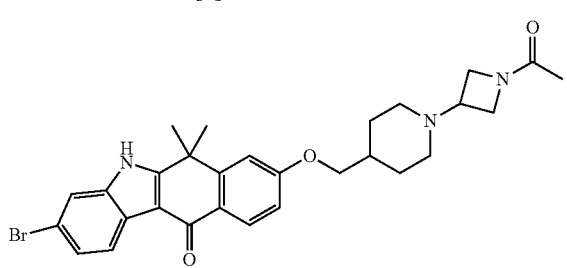

According to the same method as the method for synthesizing Compound A9-1, the title compound was prepared from Compound T14-8 and acetic anhydride.
LCMS: m/z 550 [M+H]+
HPLC retention time: 2.53 min (analysis condition A)

Example 651

Compound T15-1

4-[2-(3-Bromo-6,6-dimethyl-11-oxo-6,11-dihydro-5H-benzo[b]carbazole-8-yl oxy)-ethyl]-piperidine-1-carboxylic acid tert-butyl ester

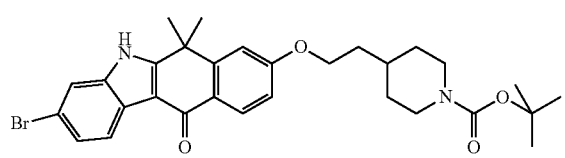 [SMILES: CC(C)(C)OC(=O)N1CCC(CCOc2ccc3c(c2)C(C)(C)c2[nH]c4cc(Br)ccc4c2C3=O)CC1]

According to the same method as the method for synthesizing Compound A7-1, the title compound was prepared from Compound A5-1 and N-(tert-butoxycarbonyl)-4-piperidine ethanol.
LCMS: m/z 567 [M+H]+
HPLC retention time: 2.29 min (analysis condition D)

Example 652

Compound T15-2

3-Bromo-6,6-dimethyl-8-(2-piperidin-4-yl-ethoxy)-5,6-dihydro-benzo[b]carbazol-11-one

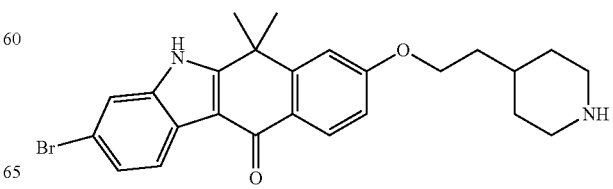

According to the same method as the method for synthesizing Compound A8-1, the title compound was prepared from Compound T15-1.

LCMS: m/z 467 [M+H]+

HPLC retention time: 1.95 min (analysis condition D)

Example 653

Compound T15-3

3-Bromo-6,6-dimethyl-8-[2-(1-oxetan-3-yl-piperidin-4-yl)-ethoxy]-5,6-dihydro-benzo[b]carbazol-11-one

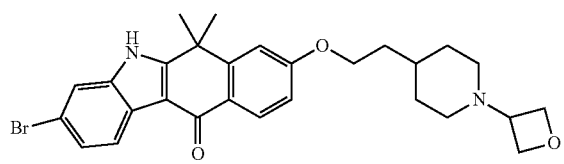 [SMILES: CC1(C)c2cc(OCCC3CCN(C4COC4)CC3)ccc2C(=O)c2c1[nH]c1cc(Br)ccc21]

According to the same method as the method for synthesizing Compound B3-32, the title compound was prepared from Compound T15-2 and 3-oxetanone.

LCMS: m/z 523 [M+H]+

HPLC retention time: 2.28 min (analysis condition D)

Example 654

Compound T16-1

4-(3-Bromo-6,6-dimethyl-11-oxo-6,11-dihydro-5H-benzo[b]carbazole-8-yl oxy)-1-oxa-8-aza-spiro[4.5]decane-8-carboxylic acid tert-butyl ester

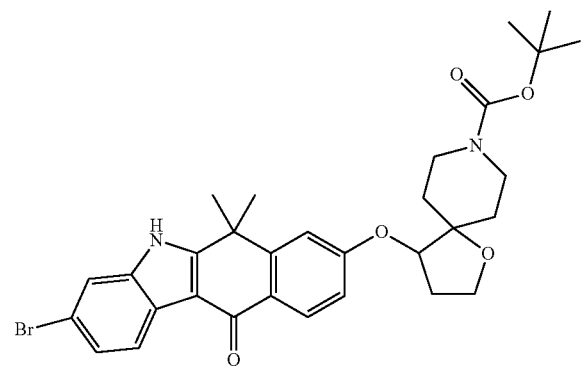 [SMILES: CC(C)(C)OC(=O)N1CCC2(CC1)OCCC2Oc1ccc2c(c1)C(C)(C)c1[nH]c3cc(Br)ccc3c1C2=O]

According to the same method as the method for synthesizing Compound A7-1, the title compound was prepared from Compound A5-1 and 3-hydroxy-1-oxa-8-aza-spiro[4.5]decane-8-carboxylic acid tert-butyl ester.

LCMS: m/z 595 [M+H]+

HPLC retention time: 3.08 min (analysis condition A)

Example 655

Compound T16-2

3-Bromo-6,6-dimethyl-8-(1-oxa-8-aza-spiro[4.5]decane-4-yl oxy)-5,6-dihydro-benzo[b]carbazol-11-one

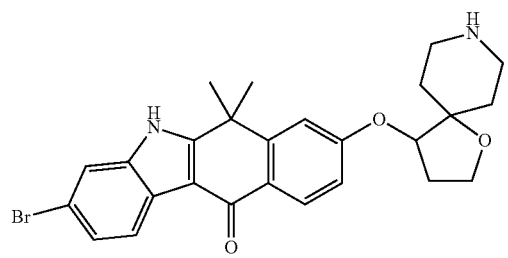 [SMILES: CC1(C)c2cc(OC3CCOC34CCNCC4)ccc2C(=O)c2c1[nH]c1cc(Br)ccc21]

According to the same method as the method for synthesizing Compound A8-1, the title compound was prepared from Compound T16-1.

LCMS: m/z 496 [M+H]+

HPLC retention time: 1.99 min (analysis condition A)

Example 656

Compound T16-3

3-Bromo-8-(8-methanesulfonyl-1-oxa-8-aza-spiro[4.5]decane-4-yl oxy)-6,6-dimethyl-5,6-dihydro-benzo[b]carbazol-11-one

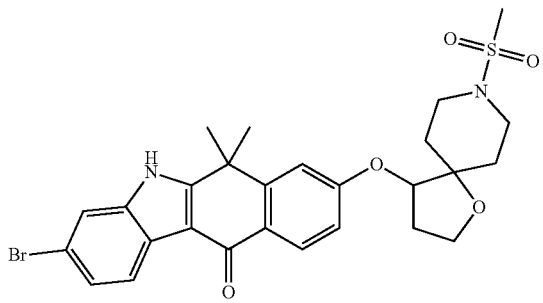 [SMILES: CC1(C)c2cc(OC3CCOC34CCN(S(C)(=O)=O)CC4)ccc2C(=O)c2c1[nH]c1cc(Br)ccc21]

According to the same method as the method for synthesizing Compound A9-1, the title compound was prepared from Compound T16-2 and mesyl chloride.

LCMS: m/z 573 [M+H]+

HPLC retention time: 2.56 min (analysis condition A)

Example 657

Compound T16-4

3-Bromo-6,6-dimethyl-8-(8-oxetan-3-yl-1-oxa-8-aza-spiro[4.5]decan-4-yl oxy)-5,6-dihydro-benzo[b]carbazol-11-one

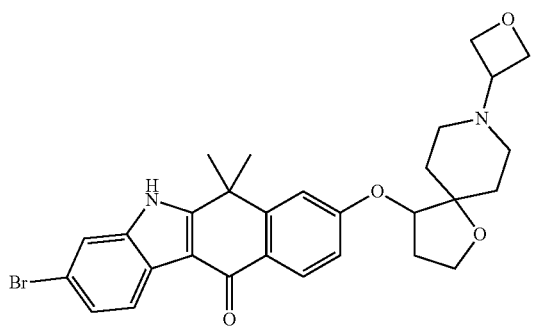 [SMILES: CC1(C)c2cc(OC3CCOC34CCN(C3COC3)CC4)ccc2C(=O)c2c1[nH]c1cc(Br)ccc21]

According to the same method as the method for synthesizing Compound B3-32, the title compound was prepared from Compound T16-2 and 3-oxetanone.
LCMS: m/z 551 [M+H]$^+$
HPLC retention time: 2.01 min (analysis condition A)

Example 658

Compound T17-1

3,7,9-Tribromo-8-hydroxy-6,6-dimethyl-5,6-dihydro-benzo[b]carbazol-11-one

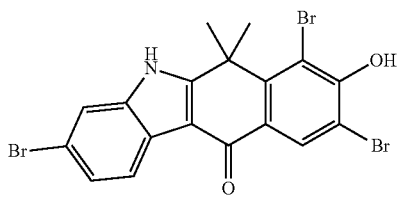 [SMILES: CC1(C)c2[nH]c3cc(Br)ccc3c2C(=O)c2cc(Br)c(O)c(Br)c21]

Under nitrogen atmosphere, 4-[1,3]dithian-2-ylidene-piperidine-1-carboxylic acid tert-butyl ester (100 g, 0.332 mmol) was dissolved in dichloromethane (2.50 mL), added with trifluoromethanesulfonic acid (30.8 µL, 0.348 mmol) at −20° C., and stirred at room temperature for 30 min. The reaction solution was cooled to −70° C., and then added dropwise with the dichloromethane (2.50 mL) solution of 3-bromo-8-hydroxy-6,6-dimethyl-5,6-dihydro-benzo[b]carbazol-11-one (Compound A5-1, 177 mg, 0.498 mmol) and triethylamine (78.6 µL, 0.564 mmol). Thereafter, triethylamine hydrotrifluoric acid salt (262 µL, 1.610 mmol) and 1,3-dibromo-5,5-dimethylhydantoin (460 mg, 1.610 mmol) were added thereto and stirred at −70° C. for 1 hr. The reaction solution was added to aqueous solution of sodium hydroxide (1 M), extracted with ethyl acetate, washed with water, saturated aqueous solution of sodium bicarbonate, saturated brine and dried over sodium sulfate. After filtering and concentration under reduced pressure, the resulting residues were purified by silica gel column chromatography (ethyl acetate/hexane) and aminosilica gel column chromatography (ethyl acetate/hexane) to obtain the target compound (42.0 mg, 25%).
LCMS: m/z 511 [M+H]$^+$
HPLC retention time: 6.34 min (analysis condition B)

Example 659

Compound T17-2

3,7,9-Tribromo-8-((S)-2,2-dimethyl-[1,3]dioxolan-4-ylmethoxy)-6,6-dimethyl-5,6-dihydro-benzo[b]carbazol-11-one

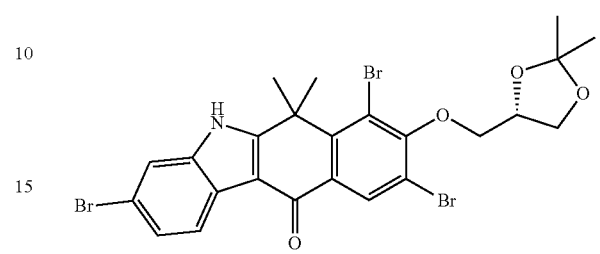

According to the same method as the method for synthesizing Compound A7-1, the title compound was prepared from Compound A17-1 and (S)-(+)-2,2-dimethyl-1,3-dioxolan-4-methanol.
LCMS: m/z 625 [M+H]$^+$
HPLC retention time: 3.41 min (analysis condition A)

Example 660

Compound T17-3

3,7,9-Tribromo-8-((R)-2,3-dihydroxy-propoxy)-6,6-dimethyl-5,6-dihydro-benzo[b]carbazol-11-one

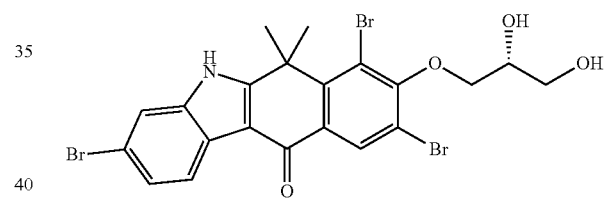

According to the same method as the method for synthesizing Compound A7-14-2, the title compound was prepared from Compound T17-2.
LCMS: m/z 585 [M+H]$^+$
HPLC retention time: 2.44 min (analysis condition A)

Example 661

Compound T18-1

3-Bromo-8-((S)-2,2-dimethyl-[1,3]dioxolan-4-ylmethoxy)-6,6-dimethyl-5,6-dihydro-benzo[b]carbazol-11-one

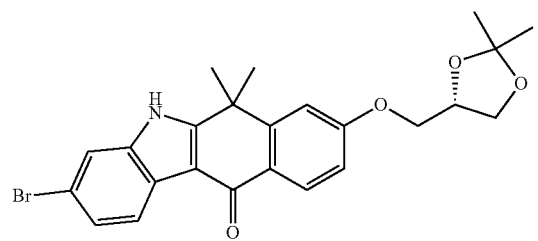 [SMILES: CC1(C)OC[C@H](COc2ccc3c(c2)C(C)(C)c2[nH]c4cc(Br)ccc4c2C3=O)O1]

3-Bromo-8-hydroxy-6,6-dimethyl-5,6-dihydro-benzo[b]carbazol-11-one (Compound A5-1, 18.0 mg, 50.5 µmol) was dissolved in DMF (0.18 mL), added with toluene-4-sulfonic acid (R)-2,2-dimethyl-[1,3]dioxolan-4-yl methyl ester (14.5 mg, 0.0505 mmol) and potassium carbonate (10.0 mg, 0.07575 mmol), and the mixture was stirred at 70° C. for 3 days. The reaction solution was added to water, extracted with ethyl acetate, and the organic layer was dried over magnesium sulfate. The residues obtained after concentration under reduced pressure were purified by preparative TLC (methylene chloride/methanol) to obtain the title compound (16.6 mg, 70%).

LCMS: m/z 470 [M+H]+

HPLC retention time: 3.01 min (analysis condition F)

Example 662

Compound T18-2

3-Bromo-8-((R)-2,3-dihydroxy-propoxy)-6,6-dimethyl-5,6-dihydro-benzo[b]carbazol-11-one

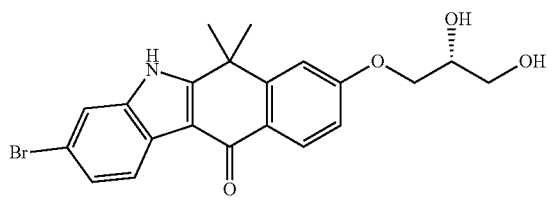 [SMILES: CC1(C)c2cc(OC[C@H](O)CO)ccc2C(=O)c2c1[nH]c1cc(Br)ccc21]

Under the same conditions as the method for synthesizing Compound A7-14-2, the title compound was prepared from Compound T18-1.

LCMS: m/z 430 [M+H]+

HPLC retention time: 4.72 min (analysis condition H)

Example 663

Compound T19-1-1

3-Bromo-8-methoxy-5,6,6-trimethyl-5,6-dihydro-benzo[b]carbazol-11-one

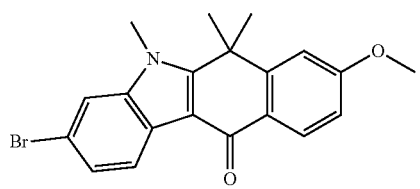 [SMILES: COc1ccc2c(c1)C(C)(C)c1c(c3ccc(Br)cc3n1C)C2=O]

Under the same conditions as the method for synthesizing Compound A10-1, the title compound was prepared from Compound A4.

LCMS: m/z 384 [M+H]+

HPLC retention time: 2.84 min (analysis condition D)

Example 664

Compound T19-1

3-Bromo-8-hydroxy-5,6,6-trimethyl-5,6-dihydro-benzo[b]carbazol-11-one

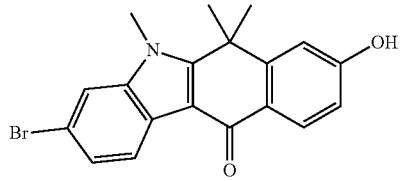 [SMILES: Cn1c2c(c3ccc(Br)cc31)C(=O)c1ccc(O)cc1C2(C)C]

Under the same conditions as the method for synthesizing Compound A6, the title compound was prepared from Compound T19-1-1.

LCMS: m/z 370 [M+H]+

HPLC retention time: 2.40 min (analysis condition D)

Example 665

Compound T19-2

3-Bromo-8-(2-diethylamino ethoxy)-6,6-trimethyl-5,6-dihydro-benzo[b]carbazol-11-one

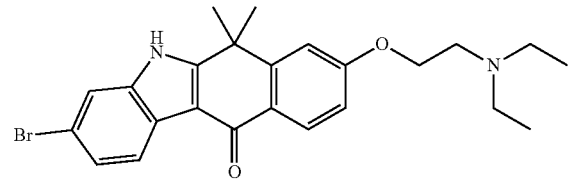 [SMILES: CCN(CC)CCOc1ccc2c(c1)C(C)(C)c1[nH]c3cc(Br)ccc3c1C2=O]

Under the same conditions as the method for synthesizing Compound A7-17, the title compound was prepared from Compound A5-1 (9.8 mg, 36%).

LCMS: m/z 455 [M+H]+

HPLC retention time: 1.96 min (analysis condition D)

Example 666

Compound T19-3

3-Bromo-8-(2-diethylaminoethoxy)-5,6,6-trimethyl-5,6-dihydro-benzo[b]carbazol-11-one

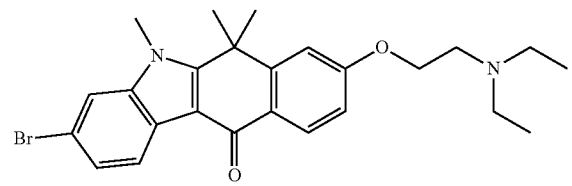 [SMILES: CCN(CC)CCOc1ccc2c(c1)C(C)(C)c1c(c3ccc(Br)cc3n1C)C2=O]

Under the same conditions as the method for synthesizing Compound A7-17, the title compound was prepared from Compound T19-1.

LCMS: m/z 469 [M+H]+

HPLC retention time: 2.09 min (analysis condition D)

Example 667

Compound T20

5-(3-Bromo-6,6-dimethyl-11-oxo-6,11-dihydro-5H-benzo[b]carbazol-8-yl oxy)-pentanoic acid

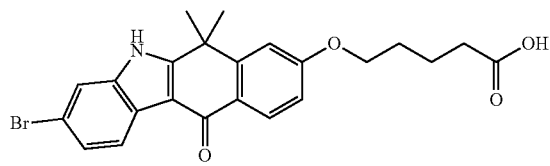 [SMILES: CC1(C)c2cc(OCCCCC(=O)O)ccc2C(=O)c2c1[nH]c1cc(Br)ccc21]

Under the same conditions as the method for synthesizing Compound A7-17, Compound A5-1 and methyl 5-bromovalerate were reacted, added with 1 N NaOH (140 μL), and then stirred at room temperature for 2 hr. The reaction mixture was added with 2 N HCl (70 μL), and concentrated under reduced pressure. The resulting residues were purified by preparative TLC (methylene chloride:methanol=15:1) to obtain 7 mg (55%).
LCMS: m/z 456 [M+H]$^+$
HPLC retention time: 5.88 min (analysis condition H)

Example 668

Compound T21

(R)-5-(3-Bromo-6,6-dimethyl-11-oxo-6,11-dihydro-5H-benzo[b]carbazol-8-yl oxy)-4-hydroxy-pentanoic acid

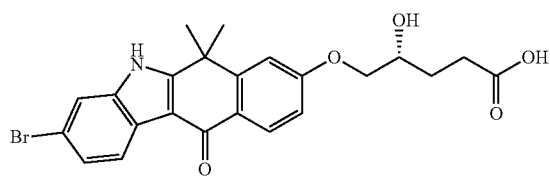 [SMILES: CC1(C)c2cc(OC[C@H](O)CCC(=O)O)ccc2C(=O)c2c1[nH]c1cc(Br)ccc21]

Under the same conditions as the method for synthesizing Compound T20, the title compound was prepared from the reaction between Compound A5-1 and toluene-4-sulfonic acid (R)-5-oxo-tetrahydrofuran-2-yl methyl ester.
LCMS: m/z 471 [M+H]$^+$
HPLC retention time: 4.57 min (analysis condition H)

Example 669

Compound T22-0

[5-(Tert-butyldimethylsilanyloxymethyl)-2,2-dimethyl-[1,3]dioxolan-4-yl]-methanol

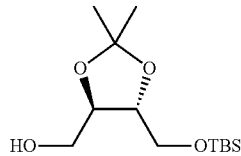 [SMILES: CC1(C)O[C@H](CO)[C@@H](CO[Si](C)(C)C(C)(C)C)O1]

To THF (50 mL), NaH (1.41 g, 0.032 mmol) was added at room temperature, followed by addition of ((4R,5R)-5-hydroxymethyl-2,2-dimethyl-[1,3]dioxolan-4-yl)-methanol (5.0 g, 0.031 mmol) at room temperature. The mixture was stirred at room temperature for 1 hr. After that, TBSCl (5.11 g, 0.034 mmol) was added at room temperature and stirred at room temperature overnight. The reaction solution was added with saturated aqueous solution of sodium hydrogen carbonate and extracted with ethyl acetate. The organic layer was dried over magnesium sulfate. The residues obtained after concentration under reduced pressure were purified by silica gel column chromatography (ethyl acetate/hexane) to obtain the title compound (8.21 g, 96%).
$^1$H-NMR (270 MHz, DMSO-d$_6$) δ: 3.64-4.98 (6H, m), 2.37 (1H, m), 1.41 (3H, s), 1.40 (3H, s), 0.90 (9H, s), 0.08 (6H, s)

Example 670

Compound T22-1

3-Bromo-8-[(4R,5R)-5-(tert-butyldimethylsilanyloxymethyl)-2,2-dimethyl-[1,3]dioxolan-4-yl methoxy]-6,6-dimethyl-5,6-dihydro-benzo[b]carbazol-11-one

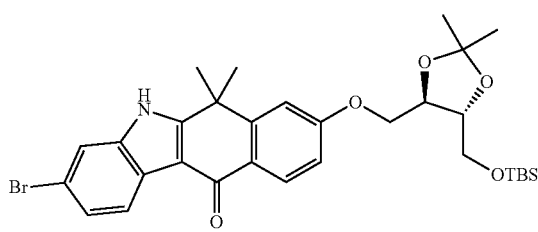 [SMILES: CC1(C)O[C@H](COc2ccc3c(c2)C(C)(C)c2[nH]c4cc(Br)ccc4c2C3=O)[C@@H](CO[Si](C)(C)C(C)(C)C)O1]

Under the same conditions as the method for synthesizing Compound A7-1, the title compound was prepared from Compound A5-1 and [5-(tert-butyldimethylsilanyloxymethyl)-2,2-dimethyl-[1,3]dioxolan-4-yl]-methanol (Compound T22-0) (704 mg, 80%).
LCMS: m/z 614 [M+H]$^+$
HPLC retention time: 4.00 min (analysis condition F)

Example 671

Compound T22-1-1

3-Bromo-8-((1R,5R)-5-hydroxymethyl-2,2-dimethyl-[1,3]dioxolan-4-ylmethoxy)-6,6-dimethyl-5,6-dihydro-benzo[b]carbazol-11-one

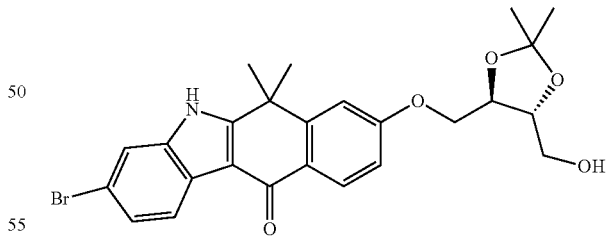

Under nitrogen atmosphere, to the DMF (0.4 mL) suspension of 3-bromo-8-[(1R,5R)-5-(tert-butyl-dimethyl-silanyloxymethyl)-2,2-dimethyl-[1,3]dioxolan-4-yl methoxy]-6,6-dimethyl-5,6-dihydro-benzo[b]carbazol-11-one (Compound T22-1, 50.3 mg, 0.0818 mmol) and copper (I) iodide (34 mg), sodium methoxide (1 M methanol solution, 0.82 mL, 0.818 mmol) was added and the mixture was stirred for 6 hr and 45 min at ambient temperature of 90° C. After cooling to room temperature, the reaction mixture was added with diethyl ether and ethyl acetate, and the insoluble matters were removed by Celite filtration. The concentrated residues were added with diethyl ether, hexane, ethyl acetate and water, and then the mixture was extracted twice with diethyl ether. The organic layer was washed with water and subsequently with brine, dried over sodium sulfate and concentrated under reduced pressure. The resulting crude product was purified by preparative TLC (Merck60 $F_{254}$, 0.5 mm) {solution for elution:hexane/ethyl acetate (1:2)} to obtain the title compound (colorless oily substance, 22.6 mg, 55%).

$^1$H-NMR (270 MHz, CDCl$_3$) δ: 8.44-8.38 (1H, b), 8.39 (1H, d, 8.6 Hz), 8.31 (1H, d, 8.2 Hz), 7.60 (1H, d, 1.3 Hz), 7.44 (1H, dd, 8.2 Hz, 1.3 Hz), 7.12 (1H, d, 2.3 Hz), 7.02 (1H, dd, 8.6 Hz, 2.3 Hz), 4.41-4.10 (4H, m), 4.00-3.88 (1H, m), 3.86-3.76 (1H, m), 1.78 (6H, s), 1.50 (3H, s), 1.49 (3H, s)

LCMS: m/z 500 [M+H]$^+$

HPLC retention time: 2.85 min (analysis condition C)

Example 672

Compound T22-1-2

Acetic acid (3R,4R)-5-(3-bromo-6,6-dimethyl-11-oxo-6,11-dihydro-5H-benzo[b]carbazol-8-yl oxymethyl)-2,2-dimethyl[1,3]dioxolan-4-yl methyl ester

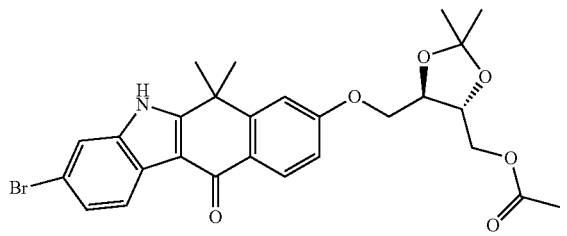 [SMILES: CC(=O)OC[C@H]1OC(C)(C)O[C@@H]1COc1ccc2c(c1)C(C)(C)c1[nH]c3cc(Br)ccc3c1C2=O]

The title compound was obtained as a by-product of the synthesis of T22-1-1 (white solid, 17.8 mg, 40%).

$^1$H-NMR (270 MHz, CDCl$_3$) δ: 8.92-8.80 (1H, b), 8.40 (1H, d, 8.9 Hz), 8.31 (1H, d, 8.6 Hz), 7.58 (1H, d, 1.7 Hz), 7.43 (1H, dd, 8.6 Hz, 1.7 Hz), 7.14 (1H, d, 2.3 Hz), 7.02 (1H, dd, 8.9 Hz, 2.3 Hz), 4.51-4.38 (1H, m), 4.34-4.16 (4H, m), 2.13 (3H, s), 1.78 (6H, s), 1.50 (6H, s)

LCMS: m/z 542 [M+H]$^+$

HPLC retention time: 3.00 min (analysis condition C)

Example 673

Compound T22-2

3-Bromo-6,6-dimethyl-8-((2R,3R)-2,3,4-trihydroxy-butoxy)-5,6-dihydro-benzo[b]carbazol-11-one

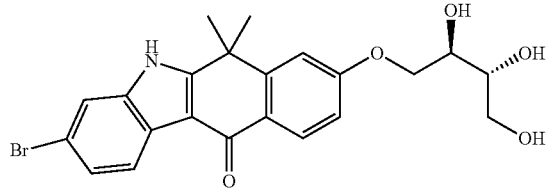 [SMILES: CC1(C)c2cc(OC[C@@H](O)[C@H](O)CO)ccc2C(=O)c2c1[nH]c1cc(Br)ccc21]

Under the same conditions as the method for synthesizing Compound A7-14-2, the title compound was prepared from Compound T22-1 (2.83 g, 95%).

LCMS: m/z 460 [M+H]$^+$

HPLC retention time: 4.50 min (analysis condition H)

Example 674

Compound T22-3

3-Bromo-8-[(4R,5R)-5-(tert-butyldimethylsilany-loxymethyl)-2,2-dimethyl-[1,3]dioxolan-4-yl-methoxy]-5,6,6-trimethyl-5,6-dihydro-benzo[b]car-bazol-11-one

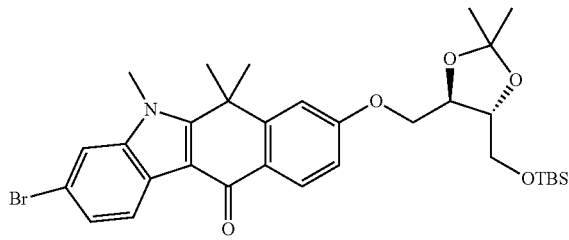 [SMILES: Cn1c2c(c3ccc(Br)cc31)C(=O)c1ccc(OC[C@H]3OC(C)(C)O[C@@H]3CO[Si](C)(C)C(C)(C)C)cc1C2(C)C]

Under the same conditions as the method for synthesizing Compound B3-4, the title compound was prepared from Compound T22-1.

LCMS: m/z 628 [M+H]$^+$

HPLC retention time: 4.74 min (analysis condition F)

Example 675

Compound T22-4

3-Bromo-8-((2R,3R)-2,3-dihydroxy-pentyloxy)-5,6,6-trimethyl-5,6-dihydro-benzo[b]carbazol-11-one

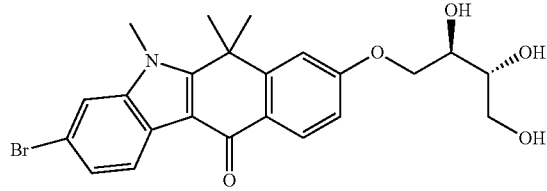 [SMILES: Cn1c2c(c3ccc(Br)cc31)C(=O)c1ccc(OC[C@@H](O)[C@H](O)CO)cc1C2(C)C]

Under the same conditions as the method for synthesizing Compound A7-14-2, the title compound was prepared from Compound T22-3.

LCMS: m/z 475 [M+H]$^+$

HPLC retention time: 4.86 min (analysis condition H)

Example 676

Compound T22-5

{3-Bromo-8-[(4R,5R)-5-(tert-butyldimethylsilany-loxymethyl)-2,2-dimethyl-[1,3]dioxolan-4-yl methoxy]-6,6-dimethyl-11-oxo-6,11-dihydro-benzo[b]carbazol-5-yl}-acetic acid methyl ester

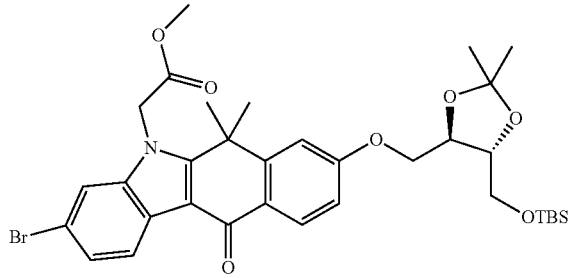 [SMILES: COC(=O)Cn1c2c(c3ccc(Br)cc31)C(=O)c1ccc(OC[C@H]3OC(C)(C)O[C@@H]3CO[Si](C)(C)C(C)(C)C)cc1C2(C)C]

Under nitrogen atmosphere, 3-bromo-8-[(4R,5R)-5-(tert-butyldimethylsilanyloxymethyl)-2,2-dimethyl-[1,3]dioxolan-4-yl methoxy]-6,6-dimethyl-5,6-dihydro-benzo[b]carbazol-11-one (Compound T22-1, 40.0 mg, 65.2 μmol) was dissolved in DMF (0.20 mL), added at 0° C. with methyl bromoacetate (30.5 μL, 134.5 μmol) and sodium hydride (4.5 mg, 132 μmol), and then stirred at room temperature for 2 hr. The residues obtained from the reaction solution after concentration under reduced pressure were purified by silica gel column chromatography (ethyl acetate/hexane) to obtain the title compound (44.5 mg, 85%).

LCMS: m/z 686 [M+H]+

HPLC retention time: 3.35 min (analysis condition D)

Example 677

Compound T22-6

{3-Bromo-8-[(4R,5R)-5-(tert-butyldimethylsilanyloxymethyl)-2,2-dimethyl-[1,3]dioxolan-4-yl methoxy]-6,6-dimethyl-11-oxo-6,11-dihydro-benzo[b]carbazol-5-yl}-acetic acid

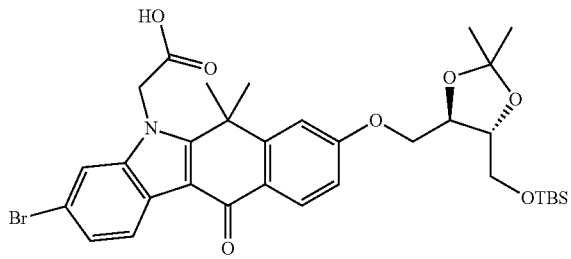 [SMILES: CC1(C)O[C@H](COc2ccc3c(c2)C(C)(C)c2c(c4ccc(Br)cc4n2CC(=O)O)C3=O)[C@@H](CO[Si](C)(C)C(C)(C)C)O1]

{3-Bromo-8-[(4R,5R)-5-(tert-butyl-dimethyl-silanyloxymethyl)-2,2-dimethyl-[1,3]dioxolan-4-yl methoxy]-6,6-dimethyl-11-oxo-6,11-dihydro-benzo[b]carbazol-5-yl}-acetic acid methyl ester (Compound T22-5, 40 mg, 60.0 μmol) was dissolved in the mixture solvent of methanol (120 μl) and water (30 μl), added with lithium hydroxide monohydrate (10 mg, 240 μmol), and then stirred 40° C. for 15 min. The residues obtained from the reaction solution after concentration under reduced pressure were purified by silica gel column chromatography (methylene chloride/methanol) to obtain the target compound (35.2 mg, 96%).

LCMS: m/z 672 [M+H]+

HPLC retention time: 3.41 min (analysis condition D)

Example 678

Compound T22-7

[3-Bromo-6,6-dimethyl-11-oxo-8-((2R,3R)-2,3,4-trihydroxy-butoxy)-6,11-dihydro-benzo[b]carbazol-5-yl]-acetic acid

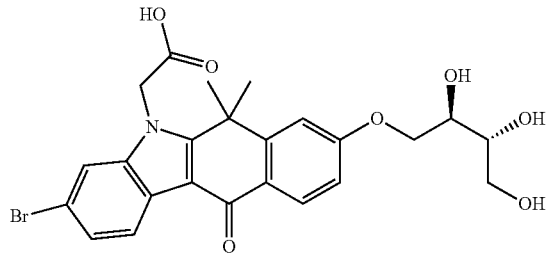 [SMILES: CC1(C)c2cc(OC[C@@H](O)[C@H](O)CO)ccc2C(=O)c2c1n(CC(=O)O)c1cc(Br)ccc21]

Under the same conditions as the method for synthesizing Compound A7-14-2, the title compound was prepared from Compound T22-6 (6.2 mg, 31%).

LCMS: m/z 518 [M+H]+

HPLC retention time: 1.30 min (analysis condition D)

Example 679

Compound T22-8

[3-Bromo-6,6-dimethyl-11-oxo-8-((2R,3R)-2,3,4-trihydroxy-butoxy)-6,11-dihydro-benzo[b]carbazol-5-yl]-acetic acid methyl ester

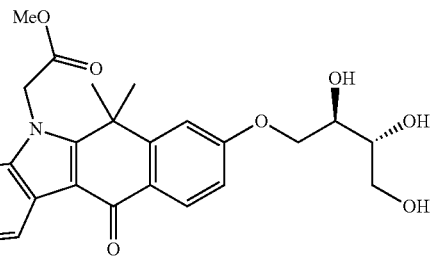

[3-Bromo-6,6-dimethyl-11-oxo-8-((2R,3R)-2,3,4-trihydroxy-butoxy)-6,11-dihydro-benzo[b]carbazol-5-yl]-acetic acid (Compound T22-6, 15.0 mg, 29.0 μmol) was dissolved in methanol (0.30 mL), added with trimethylsilyldiazomethane (0.10 mL), and then stirred at room temperature for 1 hr. The residues obtained from the reaction solution after concentration under reduced pressure were purified by silica gel column chromatography (methylene chloride/methanol) to obtain the target compound (15.2 mg, 96%).

LCMS: m/z 532 [M+H]+

HPLC retention time: 1.80 min (analysis condition D)

Example 680

Compound T23-1

3-Bromo-5-((R)-1,2-dihydroxyethyl)-8-methoxy-6,6-dimethyl-5,6-dihydro-benzo[b]carbazol-11-one

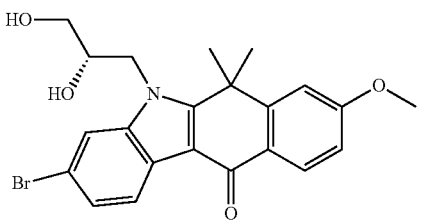 [SMILES: COc1ccc2c(c1)C(C)(C)c1c(c3ccc(Br)cc3n1C[C@H](O)CO)C2=O]

Under the same conditions as the method for synthesizing Compound T18-1 and Compound T18-2, the title compound was prepared from Compound A5-1 and toluene-4-sulfonic acid (R)-2,2-dimethyl-[1,3]dioxolan-4-yl methyl ester.

LCMS: m/z 366 [M+H]+

HPLC retention time: 4.50 min (analysis condition H)

Example 681

Compound T23-2

3-Bromo-5-((S)-1,2-dihydroxyethyl)-8-methoxy-6,6-dimethyl-5,6-dihydro-benzo[b]carbazol-11-one

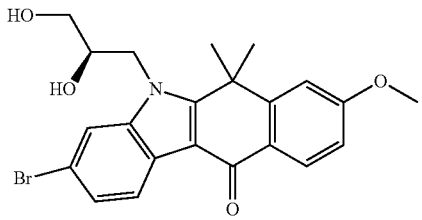 [SMILES: COc1ccc2c(c1)C(C)(C)c1c(c3ccc(Br)cc3n1C[C@@H](O)CO)C2=O]

Under the same conditions as the method for synthesizing Compound T18-1 and Compound T18-2, the title compound was prepared from Compound A4 and toluene-4-sulfonic acid (S)-2,2-dimethyl-[1,3]dioxolan-4-yl methyl ester.

LCMS: m/z 366 [M+H]+

HPLC retention time: 4.50 min (analysis condition H)

Example 682

Compound T24-1

3-Bromo-8-((S)-2,2-dimethyl-[1,3]dioxolan-4-yl methoxy)-5,6,6-trimethyl-5,6-dihydro-benzo[b]carbazol-11-one

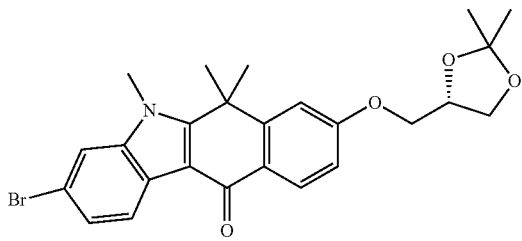 [SMILES: Cn1c2c(c3ccc(Br)cc31)C(=O)c1ccc(OC[C@H]3COC(C)(C)O3)cc1C2(C)C]

Under nitrogen atmosphere, to the DMF (1 mL) suspension of 3-bromo-8-((S)-2,2-dimethyl-[1,3]dioxolan-4-yl-methoxy)-6,6-dimethyl-5,6-dihydro-benzo[b]carbazol-11-one (Compound T18-1, 112.2 mg, 0.239 mmol) and sodium hydride (60%) (19 mg, 0.477 mmol), cooled in an ice bath, methyl iodide (37 mL, 0.596 mmol) was added. The reaction mixture was stirred at room temperature for 45 min, and then added with saturated aqueous solution of ammonium chloride and saturated aqueous solution of sodium thiosulfate under ice cooling. The mixture was extracted twice with ethyl acetate/diethyl ether/hexane. The organic layer was washed with water and subsequently with aqueous solution of ammonium chloride, dried over sodium sulfate, and then concentrated under reduced pressure. The resulting crude product was purified by flash column chromatography {Merck Kieselgel60, solution for elution:hexane/ethyl acetate (1:1)} to obtain the title compound (white solid, 107.3 mg, 93%).

$^1$H-NMR (270 MHz, CDCl$_3$) δ: 8.41 (1H, d, 8.6 Hz), 8.35 (1H, d, 8.9 Hz), 7.56 (1H, d, 1.7 Hz), 7.46 (1H, dd, 8.6 Hz, 1.7 Hz), 7.14 (1H, d, 2.3 Hz), 7.00 (1H, dd, 8.9 Hz, 2.3 Hz), 4.60-4.49 (1H, m), 4.20-3.90 (4H, m), 4.03 (3H, s), 1.88 (6H, s), 1.50 (3H, s), 1.43 (3H, s)

LCMS: m/z 484 [M+H]+

HPLC retention time: 6.59 min (analysis condition B)

Example 683

Compound T24-2

3-Bromo-8-((R)-2,3-dihydroxy-propoxy)-5,6,6-trimethyl-5,6-dihydro-benzo[b]carbazol-11-one

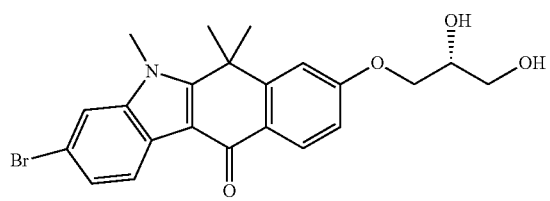 [SMILES: Cn1c2c(c3ccc(Br)cc31)C(=O)c1ccc(OC[C@H](O)CO)cc1C2(C)C]

Under nitrogen atmosphere, to the THF (0.15 mL)-MeOH (0.1 mL) solution of 3-bromo-8-((S)-2,2-dimethyl-[1,3]dioxolan-4-yl methoxy)-5,6,6-trimethyl-5,6-dihydro-benzo[b]carbazol-11-one (Compound T24-1, 15.5 mg, 0.0320 mmol), 0.5 M aqueous solution of sulfuric acid (128 μL, 0.0640 mmol) was added at room temperature. The reaction mixture was stirred at ambient temperature of 55° C. for 2 hr, cooled to room temperature, and then added with diethyl ether and subsequently with sodium hydrogen carbonate (11 mg). The mixture was extracted twice with diethyl ether/ethyl acetate, and the organic layer was washed with brine, dried over sodium sulfate and concentrated under reduced pressure to obtain the title compound (white solid, 11.9 mg, 84%).

$^1$H-NMR (270 MHz, CD$_3$OD) δ: 8.26 (1H, d, 8.6 Hz), 8.20 (1H, d, 8.9 Hz), 7.77 (1H, d, 1.7 Hz), 7.42 (1H, dd, 8.6 Hz, 1.7 Hz), 7.33 (1H, d, 2.3 Hz), 7.09 (1H, dd, 8.9 Hz, 2.3 Hz), 4.26-3.96 (3H, m), 4.10 (3H, s), 3.74-3.66 (1H, m), 1.92 (6H, s)

LCMS: m/z 444 [M+H]+

HPLC retention time: 4.65 min (analysis condition B)

Example 684

Compound T25

3-Bromo-6,6-dimethyl-5,6-dihydro-benzo[b]carbazol-11-one

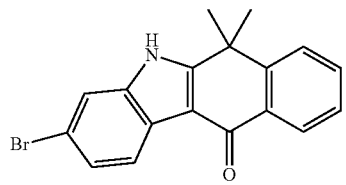 [SMILES: CC1(C)c2ccccc2C(=O)c2c1[nH]c1cc(Br)ccc21]

Under the same conditions as the method for synthesizing Compound A3-1 and Compound A4, the title compound was prepared from 3,4-dihydro-1H-naphthalen-2-one (560 mg).

LCMS: m/z 340 [M+H]+

HPLC retention time: 4.57 min (analysis condition H)

Example 685

Compound T26-1

8-[(4R,5R)-5-(Tert-butyldimethylsilanyloxymethyl)-2,2-dimethyl-[1,3]dioxolan-4-yl methoxy]-3-iodo-6,6-dimethyl-5,6-dihydro-benzo[b]carbazol-11-one

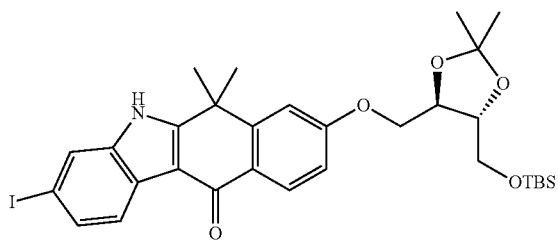 [SMILES: CC1(C)O[C@H](COc2ccc3c(c2)C(C)(C)c2[nH]c4cc(I)ccc4c2C3=O)[C@@H](CO[Si](C)(C)C(C)(C)C)O1]

Under nitrogen atmosphere, 3-bromo-8-[(4R,5R)-5-(tert-butyldimethylsilanyloxymethyl)-2,2-dimethyl-[1,3]dioxolan-4-yl methoxy]-6,6-dimethyl-5,6-dihydro-benzo[b]carbazol-11-one (Compound T22-1, 300 mg, 0.47 mmol), sodium iodide (147 mg, 0.94 mmol) and copper iodide (9.40 mg, 0.047 mmol) were dissolved in dioxane (1.00 ml), added with (1R,2R)—N,N,N',N'-tetramethyl-cyclohexane-1,2-diamine (15.4 µl, 0.094 mmol), and then stirred at 110° C. for 16 hr. The residues obtained from the reaction solution after concentration under reduced pressure were purified by silica gel column chromatography (methylene chloride/methanol) to obtain the title compound (220 mg, 70%).

LCMS: m/z 662 [M+H]+
HPLC retention time: 3.40 min (analysis condition D)

Example 686

Compound T26-2

3-Iodo-6,6-dimethyl-8-((2R,3R)-2,3,4-trihydroxy-butoxy)-5,6-dihydro-benzo[b]carbazol-11-one

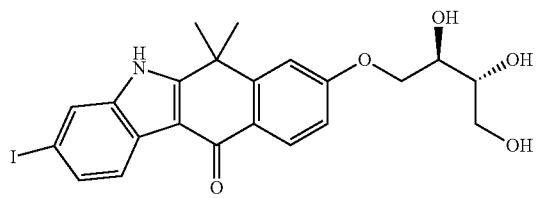 [SMILES: CC1(C)c2cc(OC[C@@H](O)[C@H](O)CO)ccc2C(=O)c2c1[nH]c1cc(I)ccc21]

Under the same conditions as the method for synthesizing Compound A7-14-2, the title compound was prepared from Compound T26-1 (17.0 mg, 90%).
LCMS: m/z 508 [M+H]+
HPLC retention time: 1.77 min (analysis condition D)

Example 687

Compound T27-1

3-Bromo-9-(2-fluoro-4-methoxy-phenyl)-8-methoxy-6,6-dimethyl-5,6-dihydro-benzo[b]carbazol-11-one

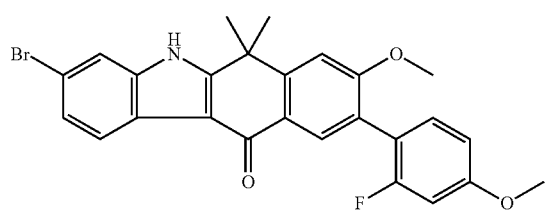 [SMILES: COc1ccc(-c2cc3c(cc2OC)C(C)(C)c2[nH]c4cc(Br)ccc4c2C3=O)c(F)c1]

To the mixture of 6-bromo-7-methoxy-1,1-dimethyl-3,4-dihydro-1H-naphthalen-2-one (Compound E1, 410 mg, 1.44 mmol), tetrakistriphenylphosphine palladium (80 mg, 0.05 eq.) and sodium carbonate (614 mg, 4 eq.), toluene (3 mL) and water (1 ml) were added and then stirred at room temperature and at 90° C. for 3 hr. The mixture was extracted by adding water and diethyl ether, and the organic layer was washed with brine, and dried over magnesium sulfate. The residues obtained after concentration under reduced pressure were purified by silica gel column chromatography (ethyl acetate/hexane) to obtain 6-(2-fluoro-4-methoxy-phenyl)-7-methoxy-1,1-dimethyl-3,4-dihydro-1H-naphthalen-2-one (white solid, 320 mg).

Thus-obtained 6-(2-fluoro-4-methoxy-phenyl)-7-methoxy-1,1-dimethyl-3,4-dihydro-1H-naphthalen-2-one (320 mg, 0.1 mmol) and 3-bromophenylhydrazine (0.29 g, 1.3 eq.) were dissolved in acetic acid (1 mL), and stirred under nitrogen atmosphere at 90° C. for 8 hr. After cooling, the reaction solution was added with ethyl acetate, washed with water, saturated aqueous solution of sodium hydrogen carbonate, and saturated brine, dried over magnesium sulfate, and then filtered. The residues obtained after concentration under reduced pressure were dissolved in THF (3 mL) comprising 10% water, added with DDQ (227 mg, 3 eq.) at room temperature, and stirred at room temperature for 2 hr. To the reaction solution, the mixture solution of THF/diethyl ether (1:1) was added, and the reaction solution was washed with 0.5 N aqueous solution of sodium hydroxide and saturated brine, dried over sodium sulfate, and then filtered. The residues obtained after concentration under reduced pressure were purified by silica gel column chromatography (ethyl acetate/hexane) to obtain the title compound (red solid, 75 mg).

LCMS: m/z 494, 496 [M+H]+
HPLC retention time: 3.10 min (analysis condition C)

Example 688

Compound T27-2

3-Bromo-9-(2-fluoro-4-hydroxy-phenyl)-8-hydroxy-6,6-dimethyl-5,6-dihydro-benzo[b]carbazol-11-one

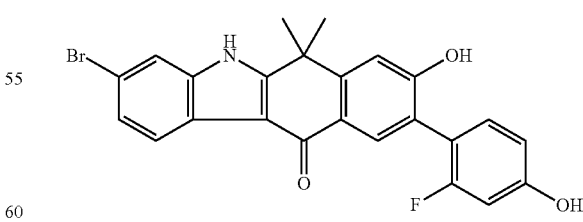

Under the same conditions as the method for synthesizing Compound A6, the title compound was prepared from Compound T27-1.
LCMS: m/z 464, 466 [M+H]+
HPLC retention time: 2.68 min (analysis condition C)

Example 689

Compound U5

4-Bromo-8-methoxy-6,6-dimethyl-11-oxo-6,11-dihydro-5H-benzo[b]carbazole-3-carbonitrile

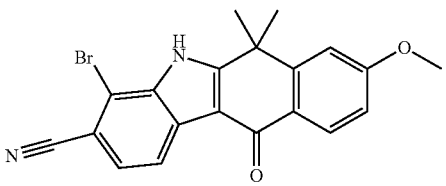 [SMILES: COc1ccc2c(c1)C(C)(C)c1[nH]c3c(Br)c(C#N)ccc3c1C2=O]

2-Bromo-3-nitro-benzonitrile (Compound U1, 678 mg, 2.987 mmol) was dissolved in ethanol (20.9 mL) and water (8.96 mL), added with acetic acid (2.39 mL, 41.81 mmol) and iron (1.17 g, 20.91 mmol), and stirred at 60° C. for 18 hr. The reaction solution was poured into aqueous solution of sodium hydroxide (1 M), extracted with ethyl acetate, washed with water and saturated brine, dried over sodium sulfate, and then filtered. After concentration under reduced pressure, 3-amino-2-bromo-benzonitrile (Compound U2) was obtained as a crude product.

The crude product obtained from the above was dissolved in 12 M aqueous solution of hydrochloric acid (4.00 mL), added slowly at 0° C. with aqueous solution in which sodium nitrite (247 mg, 3.584 mmol) is dissolved in water (3.58 mL), and then the mixture was stirred at 0° C. for 30 min. Under light-shielding conditions, aqueous solution in which tin chloride dihydrate (2.02 g, 8.961 mmol) is dissolved in 12 M aqueous solution of hydrochloric acid (4.00 mL) was slowly added to the reaction solution at 0° C., and then the mixture was stirred at 0° C. for 1 hr. The reaction solution was poured into 5 M aqueous solution of sodium hydroxide, extracted with ethyl acetate, washed with saturated brine, dried over sodium sulfate, and filtered. After concentration under reduced pressure, 2-bromo-3-hydrazino-benzonitrile (Compound U3) was obtained as a crude product. Under nitrogen atmosphere, the above crude product and 7-methoxy-1,1-dimethyl-3,4-dihydro-1H-naphthalen-2-one (Compound A2, 462 mg, 2.260 mmol) were added with TFA (6.78 mL) and stirred at 100° C. for 2 hr. After cooling, the reaction solution was poured into saturated aqueous solution of sodium bicarbonate, extracted with ethyl acetate, washed with water and saturated brine, dried over sodium sulfate, and filtered. After concentration under reduced pressure, 4-bromo-8-methoxy-6,6-dimethyl-6,11-dihydro-5H-benzo[b]carbazole-3-carbonitrile (Compound U4) was obtained as a crude product. The above crude product was dissolved in THF (10.0 mL) and water (1.00 mL), added with 2,3-dichloro-5,6-dicyano-1,4-benzoquinone (1.54 g, 6.780 mmol), and stirred at room temperature for 20 hr. The reaction solution was poured into 1 M aqueous solution of sodium hydroxide, extracted with cyclopentylmethyl ether, washed with 1 M aqueous solution of sodium hydroxide, water and saturated brine, dried over sodium sulfate, and filtered. The residues obtained after concentration under reduced pressure were washed with cyclopentylmethyl ether to obtain the title compound (460 mg, 52%).

LCMS: m/z 395 [M+H]$^+$

HPLC retention time: 2.25 min (analysis condition D)

Example 690

Compound U6

8-Hydroxy-6,6-dimethyl-11-oxo-6,11-dihydro-5H-benzo[b]carbazole-3-carbonitrile

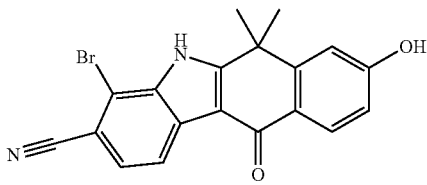 [SMILES: CC1(C)c2cc(O)ccc2C(=O)c2c1[nH]c1c(Br)c(C#N)ccc21]

4-Bromo-8-methoxy-6,6-dimethyl-11-oxo-6,11-dihydro-5H-benzo[b]carbazole-3-carbonitrile (Compound U5, 325 mg, 0.822 mmol) was added with pyridine hydrochloride salt (3.80 g, 32.89 mmol) and stirred at 160° C. for 28 hr. The reaction solution was poured into water, extracted with ethyl acetate, washed with water, dried over sodium sulfate, and filtered. After concentration under reduced pressure, the title compound was obtained as a crude product.

LCMS: m/z 381 [M+H]$^+$

HPLC retention time: 1.92 min (analysis condition D)

Example 691

Compound U7-1

4-Bromo-8-((R)-2,2-dimethyl-[1,3]dioxolan-4-yl-methoxy)-6,6-dimethyl-11-oxo-6,11-dihydro-5H-benzo[b]carbazole-3-carbonitrile

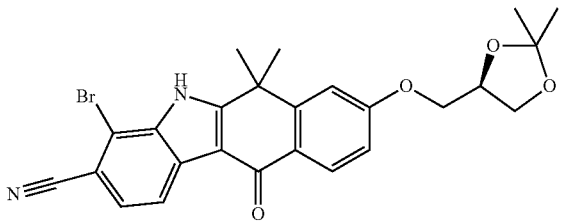 [SMILES: CC1(C)OC[C@@H](COc2ccc3c(c2)C(C)(C)c2[nH]c4c(Br)c(C#N)ccc4c2C3=O)O1]

Under the same conditions as the method for synthesizing Compound A7-1, the title compound was prepared from the reaction between Compound U6 and (R)-(−)-2,2-dimethyl-1,3-dioxolane-4-methanol (354 mg, 87%).

LCMS: m/z 495 [M+H]$^+$

HPLC retention time: 2.35 min (analysis condition D)

Example 692

Compound U7-2

4-Bromo-8-((S)-2,3-dihydroxy-propoxy)-6,6-dimethyl-11-oxo-6,11-dihydro-5H-benzo[b]carbazole-3-carbonitrile

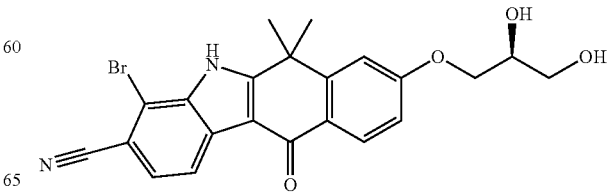

Under the same conditions as the method for synthesizing Compound A7-14-2, the title compound was prepared from Compound U7-1.
LCMS: m/z 455 [M+H]+
HPLC retention time: 2.40 min (analysis condition C)

Example 693

Compound U8-2

8-((R)-2,3-Dihydroxy-propoxy)-5,6,6-trimethyl-11-oxo-6,11-dihydro-5H-benzo[b]carbazole-3-carbonitrile

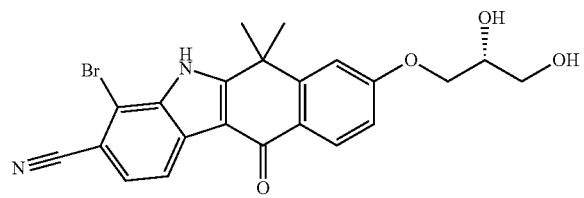 [SMILES: CC1(C)c2cc(OC[C@H](O)CO)ccc2C(=O)c2c1[nH]c1c(Br)c(C#N)ccc21]

Under the same conditions as the method for synthesizing Compound U7-1 and Compound U7-2, the title compound was prepared from the reaction between Compound U6 and (S)-(+)-2,2-dimethyl-1,3-dioxolane-4-methanol (4.5 mg, 29%).
LCMS: m/z 455 [M+H]+
HPLC retention time: 2.37 min (analysis condition C)

Example 694

Compound U8-3-1

8-((S)-2,2-Dimethyl-[1,3]dioxolan-4-ylmethoxy)-6,6-dimethyl-11-oxo-6,11-dihydro-5H-benzo[b]carbazole-3,4-dicarbonitrile

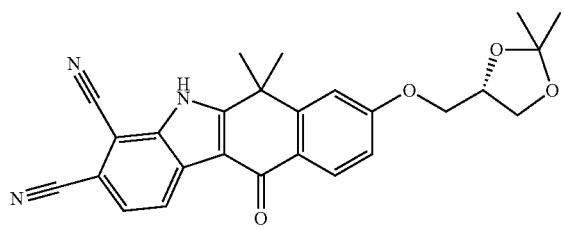 [SMILES: CC1(C)OC[C@H](COc2ccc3c(c2)C(C)(C)c2[nH]c4c(C#N)c(C#N)ccc4c2C3=O)O1]

Under nitrogen atmosphere, 4-bromo-8-((S)-2,2-dimethyl-[1,3]dioxolan-4-yl methoxy)-6,6-dimethyl-11-oxo-6,11-dihydro-5H-benzo[b]carbazole-3-carbonitrile (Compound U6, 20.0 mg, 40.37 μmol) was dissolved in DMA (0.35 mL), added with copper (I) cyanide (18.1 mg, 201.9 μmol), and stirred at 200° C. for 1 hr under irradiation with microwave. The reaction solution was poured into water, extracted with ethyl acetate, washed with water and saturated brine, dried over sodium sulfate, and then filtered. The residues obtained after concentration under reduced pressure were purified by silica gel column chromatography (ethyl acetate/hexane) to obtain the title compound as a crude product.
LCMS: m/z 442 [M+H]+
HPLC retention time: 2.30 min (analysis condition D)

Example 695

Compound U8-3-2

8-((R)-2,3-Dihydroxy-propoxy)-6,6-dimethyl-11-oxo-6,11-dihydro-5H-benzo[b]carbazole-3,4-dicarbonitrile

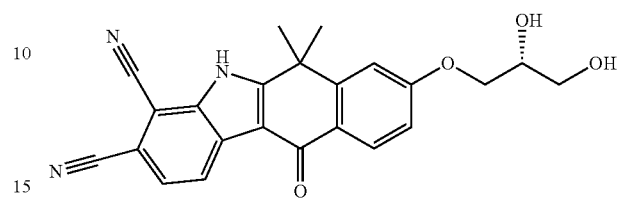

Under the same conditions as the method for synthesizing Compound A7-14-2, the title compound was prepared from Compound U8-3-1 (9.5 mg, 59%).
LCMS: m/z 402 [M+H]+
HPLC retention time: 2.40 min (analysis condition D)

Example 696

Compound U8-4-1

8-((R)-2,2-Dimethyl-[1,3]dioxolan-4-ylmethoxy)-4-hydroxy-6,6-dimethyl-11-oxo-6,11-dihydro-5H-benzo[b]carbazole-3-carbonitrile

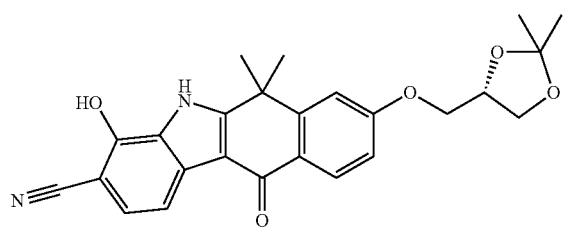 [SMILES: CC1(C)OC[C@H](COc2ccc3c(c2)C(C)(C)c2[nH]c4c(O)c(C#N)ccc4c2C3=O)O1]

Under the same conditions as the method for synthesizing Compound U9, the title compound was prepared as a crude product from Compound U8-1 (9.5 mg, 59%).
LCMS: m/z 433 [M+H]+
HPLC retention time: 2.34 min (analysis condition A)

Example 697

Compound U8-4-2

8-((R)-2,3-Dihydroxy-propoxy)-4-hydroxy-6,6-dimethyl-11-oxo-6,11-dihydro-5H-benzo[b]carbazole-3-carbonitrile

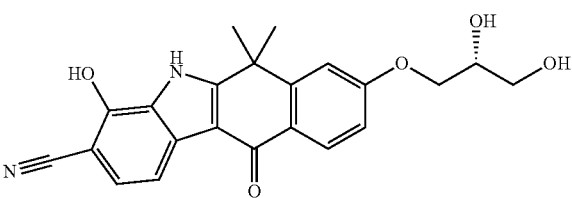 [SMILES: CC1(C)c2cc(OC[C@H](O)CO)ccc2C(=O)c2c1[nH]c1c(O)c(C#N)ccc21]

Under the same conditions as the method for synthesizing Compound A7-14-2, the title compound was prepared from Compound U8-4-1 (crude product) (9.7 mg, 52%).

LCMS: m/z 393 [M+H]+
HPLC retention time: 1.69 min (analysis condition A)

Example 698

Compound U8-4-3

8-((R)-2,3-Dihydroxy-propoxy)-4-methoxy-6,6-dimethyl-11-oxo-6,11-dihydro-5H-benzo[b]carbazole-3-carbonitrile

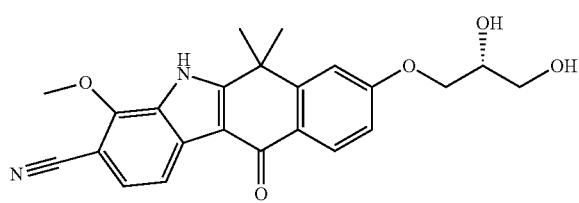 [SMILES: COc1c(C#N)ccc2c3c([nH]c12)C(C)(C)c1cc(OC[C@H](O)CO)ccc1C3=O]

Under nitrogen atmosphere, 8-((R)-2,3-dihydroxy-propoxy)-4-hydroxy-6,6-dimethyl-11-oxo-6,11-dihydro-5H-benzo[b]carbazole-3-carbonitrile (Compound U8-4-2, 8.0 mg, 20.39 μmol) was dissolved in methanol (2.0 mL) and chloroform (2.00 mL), added with trimethylsilyldiazomethane (diethyl ether solution, 2 M, 15.3 μL, 30.58 μmol) and diisopropylethylamine (0.05 mL), and then stirred at room temperature for 31 hr. The residues obtained from the reaction solution after concentration under reduced pressure were purified by silica gel column chromatography (methanol/dichloromethane) to obtain the title compound (5.1 mg, 62%).

LCMS: m/z 407 [M+H]+
HPLC retention time: 3.74 min (analysis condition A)

Example 699

Compound U8-5-1

8-((R)-2,2-Dimethyl-[1,3]dioxolan-4-ylmethoxy)-6,6-dimethyl-11-oxo-4-trifluoromethyl-6,11-dihydro-5H-benzo[b]carbazole-3-carbonitrile

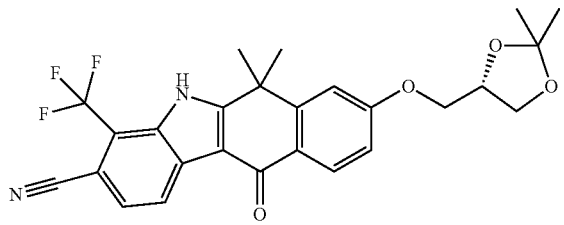 [SMILES: CC1(C)OC[C@H](COc2ccc3c(c2)C(C)(C)c2[nH]c4c(C(F)(F)F)c(C#N)ccc4c2C3=O)O1]

Under nitrogen atmosphere, 4-bromo-8-((S)-2,2-dimethyl-[1,3]dioxolan-4-yl methoxy)-6,6-dimethyl-11-oxo-6,11-dihydro-5H-benzo[b]carbazole-3-carbonitrile (Compound U8-1, 25.0 mg, 50.47 μmol) was dissolved in DMF (0.75 mL), added with copper iodide (I) (48.0 mg, 252.3 μmol) and difluoro-fluorosulfonyl-acetic acid methyl ester (31.9 μL, 252.3 μmol), and then stirred at 100° C. for 2 days. The reaction solution was poured into hydrochloric acid (1 M), extracted with ethyl acetate, washed with water, saturated aqueous solution of sodium bicarbonate and saturated brine, dried over sodium sulfate, and then filtered. The residues obtained after concentration under reduced pressure were purified by silica gel column chromatography (ethyl acetate/hexane) to obtain the title compound as a crude product.

LCMS: m/z 485 [M+H]+
HPLC retention time: 2.88 min (analysis condition A)

Example 700

Compound U8-5-2

8-((R)-2,3-Dihydroxy-propoxy)-6,6-dimethyl-11-oxo-4-trifluoromethyl-6,11-dihydro-5H-benzo[b]carbazole-3-carbonitrile

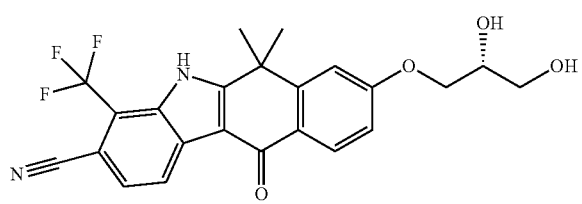 [SMILES: CC1(C)c2cc(OC[C@H](O)CO)ccc2C(=O)c2c1[nH]c1c(C(F)(F)F)c(C#N)ccc21]

Under the same conditions as the method for synthesizing Compound A7-14-2, the title compound was prepared from Compound U8-5-1 (4.0 mg, 30%).

LCMS: m/z 445 [M+H]+
HPLC retention time: 2.17 min (analysis condition A)

Example 701

Compound U8-6-1

4-Cyclopropyl-8-((S)-2,2-dimethyl-[1,3]dioxolan-4-ylmethoxy)-6,6-dimethyl-11-oxo-6,11-dihydro-5H-benzo[b]carbazole-3-carbonitrile

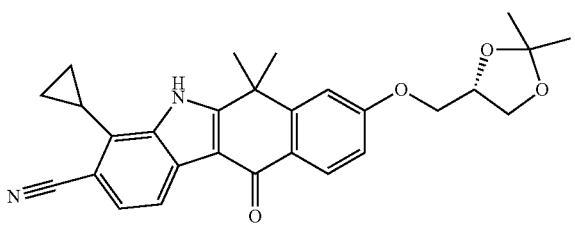 [SMILES: CC1(C)OC[C@H](COc2ccc3c(c2)C(C)(C)c2[nH]c4c(C5CC5)c(C#N)ccc4c2C3=O)O1]

Under nitrogen atmosphere, 2-cyclopropyl-4,4,5,5-tetramethyl-[1,3,2]dioxaborolane (13.2 mg, 78.73 μmol) and potassium phosphate (212.27 mg, 212.0 μmol) were dissolved in water (0.20 mL), and the mixture was stirred at room temperature for 15 min. To the reaction solution, 4-bromo-8-((S)-2,2-dimethyl-[1,3]dioxolan-4-yl methoxy)-6,6-dimethyl-11-oxo-6,11-dihydro-5H-benzo[b]carbazole-3-carbonitrile (Compound U8-1, 30.0 mg, 60.56 μmol), palladium acetate (1.36 mg, 6.056 μmol), and tricyclohexylphosphine (toluene solution, 20 wt %, 17.0 mg, 12.11 μmol) were added and the mixture was stirred at 80° C. for 24 hr. The reaction solution was poured into hydrochloric acid (1 M), extracted with ethyl acetate, washed with saturated aqueous solution of sodium bicarbonate and saturated brine, dried over sodium sulfate, and then filtered. The residues obtained after concentration under reduced pressure were purified by silica gel column chromatography (ethyl acetate/hexane) to obtain the title compound (13.6 mg, 49%).

LCMS: m/z 457 [M+H]+
HPLC retention time: 2.38 min (analysis condition D)

Example 702

Compound U8-6-2

4-Cyclopropyl-8-((R)-2,3-dihydroxy-propoxy)-6,6-dimethyl-11-oxo-6,11-dihydro-5H-benzo[b]carbazole-3-carbonitrile

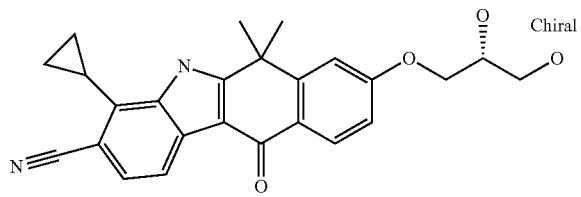 [SMILES: CC1(C)c2cc(OC[C@H](O)CO)ccc2C(=O)c2c1[nH]c1c(C3CC3)c(C#N)ccc21]

Under the same conditions as the method for synthesizing Compound A7-14-2, the title compound was prepared from Compound U8-6-1.

LCMS: m/z 417 [M+H]$^+$

HPLC retention time: 2.42 min (analysis condition A)

Example 703

Compound U8-7-1

(S)-8-((2,2-Dimethyl-1,3-dioxolan-4-yl)methoxy)-4,6,6-trimethyl-11-oxo-6,11-dihydro-5H-benzo[b]carbazole-3-carbonitrile

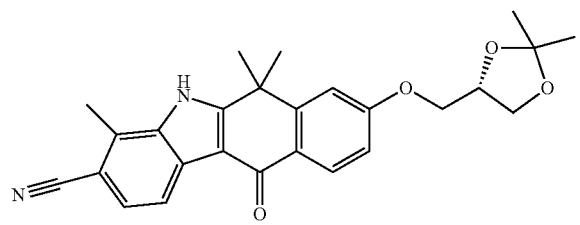 [SMILES: Cc1c(C#N)ccc2c3c([nH]c12)C(C)(C)c1cc(OC[C@H]2COC(C)(C)O2)ccc1C3=O]

Under nitrogen atmosphere, 4-bromo-8-((S)-2,2-dimethyl-[1,3]dioxolan-4-yl methoxy)-6,6-dimethyl-11-oxo-6,11-dihydro-5H-benzo[b]carbazole-3-carbonitrile (Compound U8-1, 30.0 mg, 60.56 µmol) and lithium chloride (7.70 mg, 181.7 µmol) were dissolved in DMF (1.00 mL), added with tetramethyl tin (12.5 µL, 90.84 µmol), tetrakistriphenylphosphine palladium (3.50 mg, 6.056 µmol) and tricyclohexylphosphine (toluene solution, 20 wt %, 17.0 mg, 3.028 µmol), and the mixture was stirred at 100° C. for 24 hr. The reaction solution was poured into hydrochloric acid (1 M), extracted with ethyl acetate, washed with water, saturated aqueous solution of sodium bicarbonate and saturated brine, dried over sodium sulfate, and then filtered. The residues obtained after concentration under reduced pressure were purified by silica gel column chromatography (ethyl acetate/hexane) to obtain 8-((S)-2,2-dimethyl-[1,3]dioxolan-4-ylmethoxy)-4,6,6-trimethyl-11-oxo-6,11-dihydro-5H-benzo[b]carbazole-3-carbonitrile as a crude product (20.9 mg, 80%).

Example 704

Compound U8-7-2

8-((R)-2,3-Dihydroxy-propoxy)-4,6,6-trimethyl-11-oxo-6,11-dihydro-5H-benzo[b]carbazole-3-carbonitrile

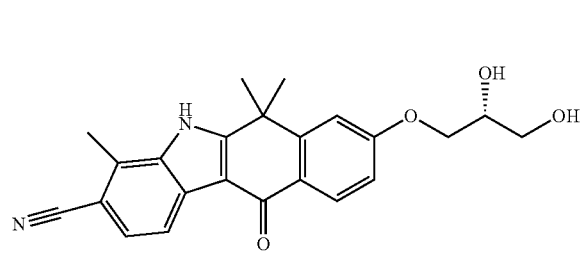 [SMILES: Cc1c(C#N)ccc2c3c([nH]c12)C(C)(C)c1cc(OC[C@H](O)CO)ccc1C3=O]

Under the same conditions as the method for synthesizing Compound A7-14-2, the title compound was prepared from Compound U8-7-1.

LCMS: m/z 391 [M+H]$^+$

HPLC retention time: 1.82 min (analysis condition A)

Example 705

Compound U8-8-1

3-Cyano-8-((S)-2,2-dimethyl-[1,3]dioxolan-4-ylmethoxy)-6,6-dimethyl-11-oxo-6,11-dihydro-5H-benzo[b]carbazole-4-carboxylic acid amide

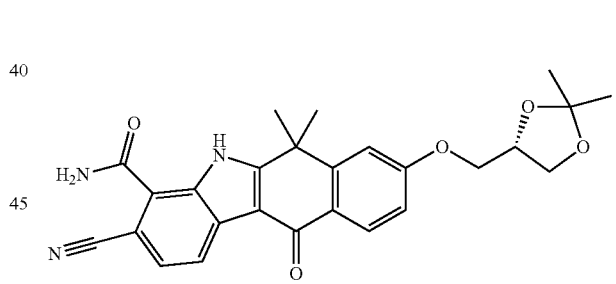

Under nitrogen atmosphere, 4-bromo-8-((S)-2,2-dimethyl-[1,3]dioxolan-4-yl methoxy)-6,6-dimethyl-11-oxo-6,11-dihydro-5H-benzo[b]carbazole-3-carbonitrile (Compound U8-1, 30.0 mg, 60.56 µmol), palladium acetate (1.36 mg, 6.056 µmol), 1,1'-bis(diphenylphosphino)ferrocene (3.36 mg, 6.056 µmol), imidazole (4.12 mg, 60.56 µmol) and tert-potassium butoxy (10.2 mg, 90.84 µmol) were dissolved in formamide (3.00 mL) and the mixture was stirred at 180° C. for 5 min under irradiation with microwave. The reaction solution was poured into water, extracted with ethyl acetate, washed with water and saturated brine, dried over sodium sulfate, and then filtered. The residues obtained after concentration under reduced pressure were purified by silica gel column chromatography (methanol/dichloromethane) to obtain the target compound (7.6 mg, 27%).

LCMS: m/z 460 [M+H]$^+$

HPLC retention time: 1.82 min (analysis condition A)

Example 706

Compound U8-8-2

3-Cyano-8-((R)-2,3-dihydroxy-propoxy)-6,6-dimethyl-11-oxo-6,11-dihydro-5H-benzo[b]carbazole-4-carboxylic acid

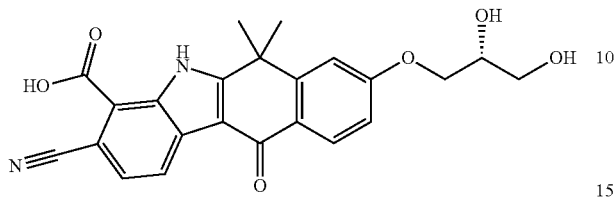

Under the same conditions as the method for synthesizing Compound A7-14-2, the title compound was prepared from Compound U8-8-1.
LCMS: m/z 421 [M+H]$^+$
HPLC retention time: 1.57 min (analysis condition A)

Example 707

Compound U8-8-3

3-Cyano-8-((R)-2,3-dihydroxy-propoxy)-6,6-dimethyl-11-oxo-6,11-dihydro-5H-benzo[b]carbazole-4-carboxylic acid amide

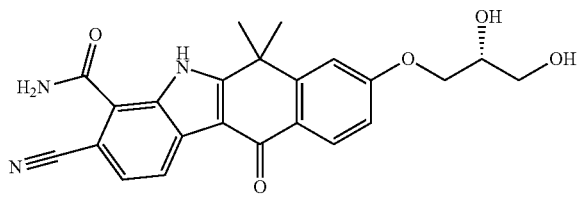 [SMILES: CC1(C)c2cc(OC[C@H](O)CO)ccc2C(=O)c2c1[nH]c1c(C(=O)O)c(C#N)ccc21]

The title compound was obtained as a by-product of the synthesis of Compound U8-8-2.
LCMS: m/z 420 [M+H]$^+$
HPLC retention time: 1.27 min (analysis condition A)

Example 708

Compound U9

4-Hydroxy-8-methoxy-6,6-dimethyl-11-oxo-6,11-dihydro-5H-benzo[b]carbazole-3-carbonitrile

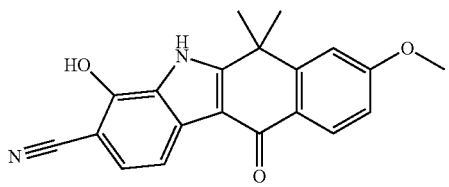

Under nitrogen atmosphere, 4-bromo-8-methoxy-6,6-dimethyl-11-oxo-6,11-dihydro-5H-benzo[b]carbazole-3-carbonitrile (Compound U5, 10.0 mg, 25.30 μmol), X-phos (1.07 mg, 2.530 μmol), sodium hydroxide (4.36 mg, 75.90 μmol) and Pd$_2$dba$_3$·CHCl$_3$ (1.31 mg, 1.265 μmol) were dissolved in dioxane (0.50 mL) and water (0.50 mL) and the mixture was stirred at 100° C. for 1 hr. The reaction solution was poured into hydrochloric acid (1 M), extracted with ethyl acetate, washed with saturated brine, dried over sodium sulfate, and then filtered. The residues obtained after concentration under reduced pressure were purified by silica gel column chromatography (ethyl acetate/hexane) and washed with dichloromethane to obtain the title compound (5.4 mg, 64%).
LCMS: m/z 333 [M+H]$^+$
HPLC retention time: 1.62 min (analysis condition D)

Example 709

Compound U10-1

4-((R)-2,3-Dihydroxy-propoxy)-8-methoxy-6,6-dimethyl-11-oxo-6,11-dihydro-5H-benzo[b]carbazole-3-carbonitrile

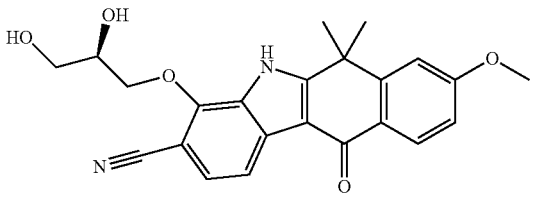 [SMILES: COc1ccc2c(c1)C(C)(C)c1[nH]c3c(OC[C@H](O)CO)c(C#N)ccc3c1C2=O]

Under the same conditions as the method for synthesizing Compound A7-1, the title compound was prepared from the reaction between Compound U9 and (S)-(+)-2,2-dimethyl-1,3-di oxo lane-4-methanol.
LCMS: m/z 407 [M+H]$^+$
HPLC retention time: 2.06 min (analysis condition A)

Example 710

Compound U10-2

4-((S)-2,3-Dihydroxy-propoxy)-8-methoxy-6,6-dimethyl-11-oxo-6,11-dihydro-5H-benzo[b]carbazole-3-carbonitrile

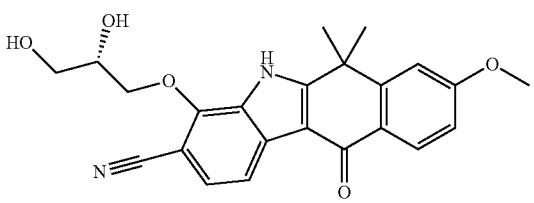 [SMILES: COc1ccc2c(c1)C(C)(C)c1[nH]c3c(OC[C@@H](O)CO)c(C#N)ccc3c1C2=O]

Under the same conditions as the method for synthesizing Compound A7-1, the title compound was prepared from the reaction between Compound U9 and (R)-(−)-2,2-dimethyl-1,3-dioxolane-4-methanol.
LCMS: m/z 407 [M+H]$^+$
HPLC retention time: 2.06 min (analysis condition A)

Example 711

Compound U11

4-Amino-8-methoxy-6,6-dimethyl-11-oxo-6,11-dihydro-5H-benzo[b]carbazole-3-carbonitrile

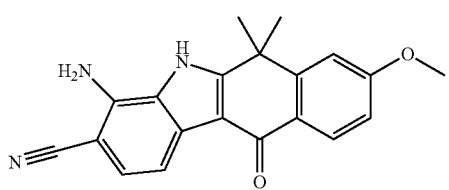 [SMILES: COc1ccc2c(c1)C(C)(C)c1[nH]c3c(N)c(C#N)ccc3c1C2=O]

Under nitrogen atmosphere, 4-bromo-8-methoxy-6,6-dimethyl-11-oxo-6,11-dihydro-5H-benzo[b]carbazole-3-carbonitrile (Compound U5, 25.0 mg, 63.25 µmol), copper iodide (2.41 mg, 12.65 µmol), sodium azide (20.6 mg, 316.3 µmol), (1S,2S)—N,N'-dimethyl-cyclohexane-1,2-diamine (2.70 mg, 18.98 µmol), and sodium ascorbate (1.25 mg, 6.325 µmol) were dissolved in ethanol (0.70 mL) and water (0.30 mL) and the mixture was stirred at 100° C. for 2 hr. The reaction solution was poured into aqueous solution of sodium hydroxide (1 M), extracted with ethyl acetate, washed with water and saturated brine, dried over sodium sulfate, and then filtered. The residues obtained after concentration under reduced pressure were purified by silica gel column chromatography (methanol/dichloromethane) to obtain the title compound (5.6 mg, 27%).

LCMS: m/z 332 [M+H]$^+$

HPLC retention time: 2.16 min (analysis condition A)

Example 712

Compound V2

3-Fluoro-8-methoxy-6,6-dimethyl-6,11-dihydro-5H-benzo[b]carbazole

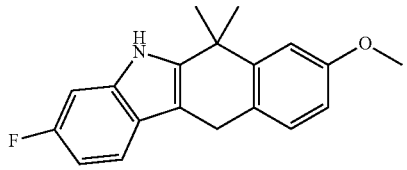 [SMILES: COc1ccc2c(c1)C(C)(C)c1[nH]c3cc(F)ccc3c1C2]

Under nitrogen atmosphere, the acetic acid (1 mL) suspension of 7-methoxy-1,1-dimethyl-3,4-dihydro-1H-naphthalen-2-one (Compound A2, 101.0 mg, 0.495 mmol) and (3-fluoro-phenyl)-hydrazine hydrochloric acid salt (Compound V1, 96.5 mg, 0.593 mmol) was stirred at ambient temperature of 95° C. for 3.75 hr. After cooling to room temperature, the reaction mixture was added with water (1 mL) and hexane/ethyl acetate (15:1) (0.5 mL), and stirred at room temperature for 15 min. The solid was filtered, washed with hexane/ethyl acetate (15:1), and then dried under reduced pressure to obtain the title compound (beige powder, 72.7 mg, 50%).

$^1$H-NMR (270 MHz, CDCl$_3$) δ: 7.92-7.82 (1H, b), 7.47 (1H, dd, 8.9 Hz, 5.6 Hz), 7.10-7.03 (2H, m), 6.95-6.81 (2H, m), 4.05 (2H, s), 3.86 (3H, s), 1.67 (6H, s)

Example 713

Compound V3

3-Fluoro-8-methoxy-6,6-dimethyl-5,6-dihydro-benzo[b]carbazol-11-one

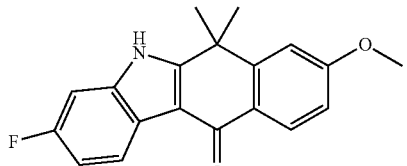

Under nitrogen atmosphere, to the THF (1.8 mL)-water (0.18 mL) solution of 3-fluoro-8-methoxy-6,6-dimethyl-6,11-dihydro-5H-benzo[b]carbazole (Compound V2, 72.4 mg, 0.245 mmol), DDQ (122.4 mg, 0.539 mmol) was added and the mixture was stirred at room temperature for 5 hr. The reaction mixture was added with diethyl ether and 0.5 N aqueous solution of sodium hydroxide (2 mL), and the resulting mixture was extracted twice with diethyl ether. The organic layer was washed twice with 0.5 N aqueous solution of sodium hydroxide (2 mL) and subsequently twice with brine (2 mL), and dried over sodium sulfate. After concentration under reduced pressure, hexane/ethyl acetate (5:1) and diethyl ether were added to the obtained crude product, and the solid was triturated. After removing the supernatant and drying under reduced pressure, the title compound was obtained (yellow solid, 57.0 mg, 75%).

$^1$H-NMR (270 MHz, CDCl$_3$) δ: 8.54-8.44 (1H, b), 8.43-8.33 (2H, m), 7.16-6.98 (4H, m), 3.93 (3H, s), 1.77 (6H, s)

Example 714

Compound V4

3-Fluoro-8-hydroxy-6,6-dimethyl-5,6-dihydro-benzo[b]carbazol-11-one

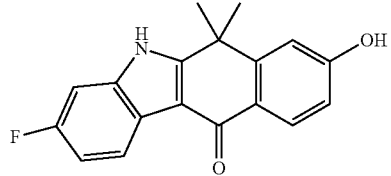 [SMILES: CC1(C)c2cc(O)ccc2C(=O)c2c1[nH]c1cc(F)ccc21]

Mixture of 3-fluoro-8-methoxy-6,6-dimethyl-5,6-dihydro-benzo[b]carbazol-11-one (Compound V3, 56.6 mg, 0.183 mmol) and pyridinium chloride (0.65 g) was stirred at ambient temperature of 160° C. for 12 hr. The reaction mixture was cooled to room temperature, added with ethyl acetate and water, and the resulting mixture was extracted four times with ethyl acetate. The organic layer was washed with water three times, dried over sodium sulfate, and concentrated under reduced pressure. The obtained crude product was used for the next step without further purification (brown solid, 61.6 mg, 100%).

$^1$H-NMR (270 MHz, CD$_3$OD) δ: 8.20 (1H, dd, 8.9 Hz, 5.3 Hz), 8.15 (1H, d, 9.6 Hz), 7.17 (1H, dd, 9.6 Hz, 2.3 Hz), 7.12 (1H, d, 2.3 Hz), 7.05-6.95 (1H, m), 6.88 (1H, dd, 8.9 Hz, 2.3 Hz), 1.74 (6H, s)

Example 715

Compound V5-1

8-[(1R,5R)-5-(Tert-butyl-dimethyl-silanyloxymethyl)-2,2-dimethyl-[1,3]dioxolan-4-yl methoxy]-3-fluoro-6,6-dimethyl-5,6-dihydro-benzo[b]carbazol-11-one

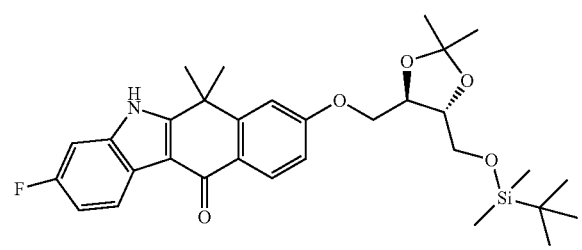 [SMILES: CC1(C)O[C@H](COc2ccc3c(c2)C(C)(C)c2[nH]c4cc(F)ccc4c2C3=O)[C@@H](CO[Si](C)(C)C(C)(C)C)O1]

Under nitrogen atmosphere, to the THF (1.5 mL) solution of 3-fluoro-8-hydroxy-6,6-dimethyl-5,6-dihydro-benzo[b]

carbazol-11-one (Compound V4, 0.183 mmol), (4S,5R)-5-(tert-butyl-dimethyl-silanyloxymethyl)-2,2-dimethyl[1,3]dioxolan-4-ol (75.9 mg, 0.275 mmol) and triphenylphosphine (72 mg, 0.275 mmol), toluene solution (125 μL, 0.275 mmol) of DEAD was added dropwise at room temperature. The reaction mixture was stirred at ambient temperature of 40° C. for 7 hr. After cooling to room temperature, the reaction mixture was concentrated under reduced pressure, and the resulting crude product was purified by preparative TLC (Merck 60 $F_{254}$, 0.5 mm) {solution for elution:hexane/ethyl acetate (3:1)} to obtain the title compound (pale orange amorphous, 54.1 mg, 53.4%).

$^1$H-NMR (270 MHz, $CDCl_3$) δ: 8.54-8.45 (1H, b), 8.42-8.33 (2H, m), 7.17-6.99 (4H, m), 4.41-4.27 (2H, m), 4.25-4.15 (1H, m), 4.06-3.96 (1H, m), 3.96-3.88 (1H, m), 3.83-3.74 (1H, m), 1.76 (3H, s), 1.75 (3H, s), 1.48 (3H, s), 1.47 (3H, s), 0.87 (9H, s), 0.092 (6H, s)

Example 716

Compound V5-2

3-Fluoro-6,6-dimethyl-8-((3R,4R)-2,3,4-trihydroxy-butoxy)-5,6-dihydro-benzo[b]carbazol-11-one

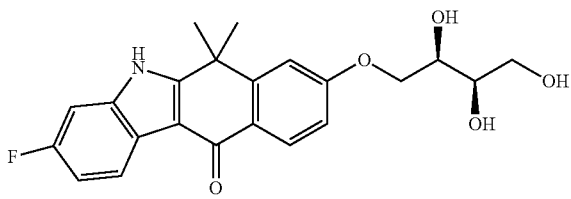 [SMILES: CC1(C)c2cc(OC[C@@H](O)[C@H](O)CO)ccc2C(=O)c2c1[nH]c1cc(F)ccc21]

Under nitrogen atmosphere, to the THF (0.3 mL)-MeOH (0.1 mL) solution of 8-[(1R,5R)-5-(tert-butyl-dimethyl-silanyloxymethyl)-2,2-dimethyl-[1,3]dioxolan-4-yl methoxy]-3-fluoro-6,6-dimethyl-5,6-dihydro-benzo[b]carbazol-11-one (Compound V5-1, 52.8 mg, 0.0954 mmol), 0.5 M aqueous solution of sulfuric acid (0.19 mL, 0.0954 mmol) was added at room temperature. The reaction mixture was stirred at ambient temperature of 55° C. for 4 hr, cooled to room temperature, and then added with diethyl ether, sodium hydrogen carbonate (20 mg) and water in order. The mixture was extracted twice with diethyl ether and subsequently twice with ethyl acetate, and the organic layer was washed with brine, dried over sodium sulfate, and concentrated under reduced pressure. The resulting crude product was washed with dichloromethane, and dried under reduced pressure to obtain the title compound (white powder, 29.9 mg, 78%).

$^1$H-NMR (270 MHz, $CD_3OD$) δ: 8.24 (1H, d, 8.9 Hz), 8.19 (1H, dd, 8.6 Hz, 5.3 Hz), 7.30 (1H, d, 2.3 Hz), 7.18 (1H, dd, 9.2 Hz, 2.3 Hz), 7.09 (1H, dd, 8.9 Hz, 2.3 Hz), 7.06-6.96 (1H, m), 4.32-4.22 (1H, m), 4.21-4.12 (1H, m), 4.11-4.02 (1H, m), 3.84-3.75 (1H, m), 3.74-3.61 (2H, m), 1.77 (6H, s)

LCMS: m/z 400 [M+H]$^+$

HPLC retention time: 4.02 min (analysis condition H)

Example 717

Compound W2

7-((S)-2,3-Dihydroxy-propoxy)-6,6-dimethyl-11-oxo-6,11-dihydro-5H-benzo[b]carbazole-3-carbonitrile

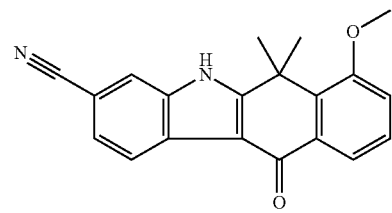 [SMILES: COc1cccc2c1C(C)(C)c1[nH]c3cc(C#N)ccc3c1C2=O]

To the toluene suspension of sodium t-butoxide (700 mg, 2.5 eq.), 8-methoxy-3,4-dihydro-1H-naphthalen-2-one (Compound W1, 500 mg, 2.9 mmol) was added dropwise at 0° C. After 15 minutes, the solution turned into blackish green color. The mixture solution was added dropwise with methyl iodide (1.03 g, 2.5 eq.) and stirred at 15° C. overnight. Brown solid precipitated. The reaction solution was added to saturated aqueous solution of ammonium chloride/diethyl ether under stirring and cooling. After that, the solution was extracted with diethyl ether, and dried over sodium sulfate. After removing the solvent under reduced pressure, the resulting residues were purified by silica gel column chromatography (ethyl acetate/hexane) to obtain 8-methoxy-1,1-dimethyl-3,4-dihydro-1H-naphthalen-2-one (350 mg).

Thus-obtained 8-methoxy-1,1-dimethyl-3,4-dihydro-1H-naphthalen-2-one (250 mg, 1.23 mmol) and 3-cyanophenyl-hydrazine (0.2 g, 1.2 eq.) were dissolved in trifluoroacetic acid (1 mL), and stirred at 120° C. for 1 hr under irradiation with microwave. After cooling, the reaction solution was added with ethyl acetate, washed with water, saturated aqueous solution of sodium hydrogen carbonate, and saturated brine, dried over magnesium sulfate, and filtered. The residues obtained after concentration under reduced pressure were dissolved in THF (3 mL) comprising 10% water and added at room temperature with DDQ (227 mg, 3 eq.). The mixture was then stirred at room temperature for 2 hr. The reaction solution was added with mixture solution of THF/diethyl ether (1:1), washed with 0.5 N aqueous solution of sodium hydroxide and saturated brine, dried over sodium sulfate, and then filtered. The residues obtained after concentration under reduced pressure were purified by silica gel column chromatography (ethyl acetate/hexane) to obtain 7-methoxy-6,6-dimethyl-11-oxo-6,11-dihydro-5H-benzo[b]carbazole-3-carbonitrile (brown solid, 54 mg).

LCMS: m/z 317 [M+H]$^+$

HPLC retention time: 1.00 min (analysis condition I)

Example 718

Compound W3

7-Hydroxy-6,6-dimethyl-11-oxo-6,11-dihydro-5H-benzo[b]carbazole-3-carbonitrile

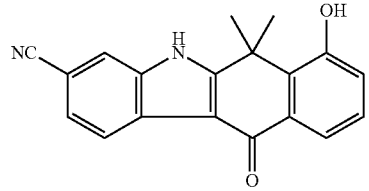 [SMILES: CC1(C)c2[nH]c3cc(C#N)ccc3c2C(=O)c2cccc(O)c21]

Under the same conditions as Compound A6, the title compound was prepared from Compound W2.

LCMS: m/z 316 [M+H]+

HPLC retention time: 0.93 min (analysis condition I)

Example 719

Compound W4-1

7-((R)-2,2-Dimethyl-[1,3]dioxolan-4-yl methoxy)-6,6-dimethyl-11-oxo-6,11-dihydro-5H-benzo[b]carbazole-3-carbonitrile

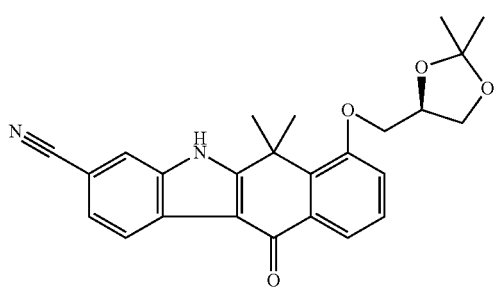 [SMILES: CC1(C)OC[C@@H](COc2cccc3c2C(C)(C)c2[nH]c4cc(C#N)ccc4c2C3=O)O1]

Under nitrogen atmosphere, 7-methoxy-6,6-dimethyl-11-oxo-6,11-dihydro-5H-benzo[b]carbazole-3-carbonitrile (Compound W3, 15 mg, 0.05 mmol) and triphenylphosphine (40 mg, 3 eq.) were added with THF (1 ml), further added dropwise with ((R)-2,2-dimethyl-[1,3]dioxolan-4-yl)-methanol (20 mg, 3 eq.) and 2.19 N toluene solution of diethyl azodicarboxylate (68 µL, 3 eq.), and the mixture was stirred at 50° C. for 2 hr. After cooling, the reaction solution was added with ethyl acetate, washed with brine, dried over sodium sulfate, and filtered. The residues obtained after concentration under reduced pressure were purified by preparative TLC (ethyl acetate/dichloromethane), and the resulting solid was washed with dichloromethane to obtain the target compound (brown powder, 5 mg).

LCMS: m/z 417 [M+H]+

HPLC retention time: 1.04 min (analysis condition I)

Example 720

Compound W4-2

7-((S)-2,3-Dihydroxy-propoxy)-6,6-dimethyl-11-oxo-6,11-dihydro-5H-benzo[b]carbazole-3-carbonitrile

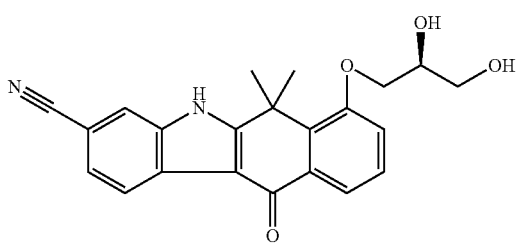 [SMILES: CC1(C)c2[nH]c3cc(C#N)ccc3c2C(=O)c2cccc(OC[C@@H](O)CO)c21]

Under the same conditions as Compound S7-2, the title compound was prepared from Compound W4-1.

LCMS: m/z 377 [M+H]+

HPLC retention time: 0.88 min (analysis condition I)

Example 721

Compound X1

1,1-Spiro-4-piperidine-N-paratoluenesulfonyl-7-methoxy-3,4-dihydro-1H-naphthalen-2-one

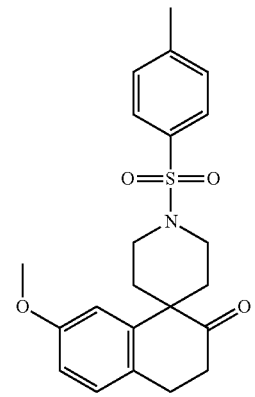 [SMILES: COc1ccc2c(c1)C1(CCN(S(=O)(=O)c3ccc(C)cc3)CC1)C(=O)CC2]

7-Methoxy-3,4-dihydro-1H-naphthalen-2-one (Compound A1, 100 mg, 0.568 mmol) was dissolved in toluene (4 mL), added with NaH (60% in oil, 68 mg, 3 eq.), and stirred at room temperature for 10 min. The mixture solution was added with bis-(2-iodo-ethyl)-p-toluenesulfonamide (172 mg, 0.568 mmol), and stirred at 70° C. for 2 hr under nitrogen stream. After cooling, the reaction solution was added to saturated aqueous solution of ammonium chloride, extracted with ethyl acetate, washed with saturated brine, and then dried over magnesium sulfate. The residues obtained after concentration under reduced pressure were purified by silica gel column chromatography (hexane:ethyl acetate/3:1) to obtain the title compound (colorless oily substance, 62 mg, 33%).

LCMS: m/z 400 [M+H]+

HPLC retention time: 2.02 min (analysis condition B)

Example 722

Compound X2

1,1-Spiro-4-piperidine-N-paratoluenesulfonyl-7-methoxy-3,4-dihydro-1H-naphthalen-2-one

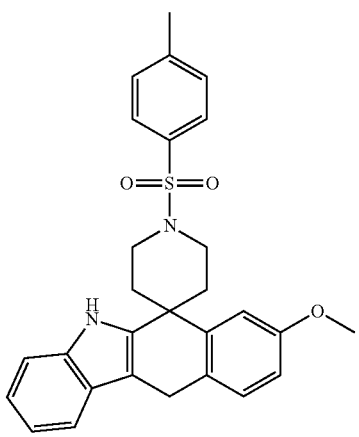 [SMILES: COc1ccc2c(c1)C1(CCN(S(=O)(=O)c3ccc(C)cc3)CC1)c1[nH]c3ccccc3c1C2]

1,1-Spiro-4-piperidine-N-paratoluenesulfonyl-7-methoxy-3,4-dihydro-1H-naphthalen-2-one (Compound X1, 400 mg, 1.0 mmol) and phenylhydrazine (217 mg, 1.5 eq.) were dissolved in acetic acid (6 mL), and the mixture was stirred at 120° C. for 4 hr under nitrogen atmosphere. After cooling, the reaction solution was added to water, extracted with ethyl acetate, washed with saturated brine, and then dried over magnesium sulfate. The residues obtained after concentration under reduced pressure were purified by silica gel column chromatography (hexane:ethyl acetate/4:1) to obtain the title compound (brown solid, 185 mg, 43%).

LCMS: m/z 473 [M+H]+

HPLC retention time: 7.23 min (analysis condition B)

Example 723

Compound X3

6,6-Spiro-4-piperidine-N-paratoluenesulfonyl-8-methoxy-5,6-dihydro-benzo[b]carbazol-11-one

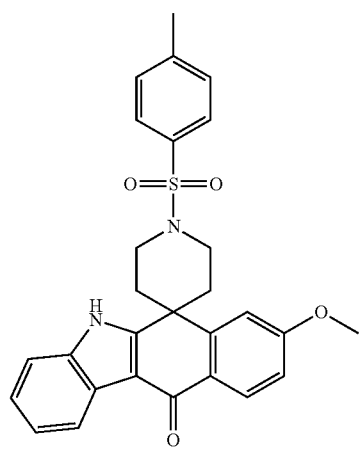 [SMILES: COc1ccc2c(c1)C1(CCN(S(=O)(=O)c3ccc(C)cc3)CC1)c1[nH]c3ccccc3c1C2=O]

6,6-Spiro-4-piperidine-N-paratoluenesulfonyl-8-methoxy-5,6-dihydro-5H-benzo[b]carbazole (Compound X2, 400 mg, 0.848 mmol) and DDQ (770 mg, 4 eq.) were dissolved in THF (10 mL) and water (2 mL), and then the mixture was stirred at 50° C. for 5 hr. After cooling, the reaction solution was added to saturated aqueous solution of sodium hydrogen carbonate, extracted with ethyl acetate, washed with saturated brine, and then dried over magnesium sulfate. The residues obtained after concentration under reduced pressure were purified by silica gel column chromatography (hexane:ethyl acetate/3:1) to give a solid, which was then washed with ethyl ether to obtain the title compound (yellow solid, 86 mg, 21%).

1H-NMR (400 MHz, DMSO-d6) δ: 11.9 (1H, s), 8.22 (2H, m), 7.75 (2H, d), 7.60 (4H, m) 7.30 (2H, m), 7.11 (1H, d), 3.81 (2H, m), 3.68 (3H, s), 3.62 (2H, m), 2.49 (3H, s), 2.21 (2H, m), 2.10 (2H, m),

LCMS: m/z 487 [M+H]+

HPLC retention time: 6.05 min (analysis condition B)

Example 724

Compound X4

6,6-Spiro-4-piperidine-8-hydroxy-5,6-dihydro-benzo[b]carbazol-11-one

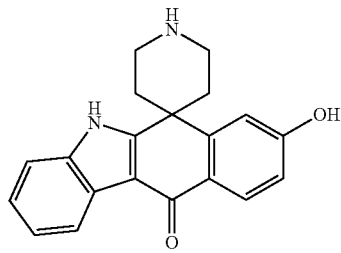 [SMILES: O=C1c2ccc(O)cc2C2(CCNCC2)c2[nH]c3ccccc3c21]

Mixture of 6,6-spiro-4-piperidine-N-paratoluenesulfonyl-8-methoxy-5,6-dihydro-benzo[b]carbazol-11-one (Compound X3, 35 mg, 0.072 mmol) and pyridine hydrochloride salt (800 mg) was stirred in a sealing tube at 160° C. for 10 hr. After cooling, the reaction solution was added to water, extracted with ethyl acetate, washed with saturated brine, and then dried over magnesium sulfate. The residues obtained after concentration under reduced pressure were purified by silica gel column chromatography (dichloromethane:methanol/4:1) to obtain the title compound (yellow solid, 30 mg, 98%).

1H-NMR (400 MHz, DMSO-d6) δ: 8.20 (1H, m), 8.10 (1H, m), 7.53 (1H, m), 7.25 (3H, m), 6.80 (1H, m), 3.60 (2H, m), 3.45 (2H, m), 2.52 (2H, m), 2.05 (2H, m).

LCMS: m/z 319 [M+H]+

HPLC retention time: 2.86 min (analysis condition B)

Example 725

Compound X5

8-(2-Diethylaminoethoxy)-6,6-spiro-4-piperidine-8-hydroxy-5,6-dihydro-benzo[b]carbazol-11-one

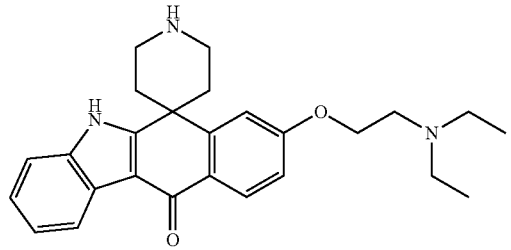 [SMILES: CCN(CC)CCOc1ccc2c(c1)C1(CCNCC1)c1[nH]c3ccccc3c1C2=O]

6,6-Spiro-4-piperidine-8-hydroxy-5,6-dihydro-benzo[b]carbazol-11-one (Compound X4, 30 mg, 0.094 mmol), diethylaminoethanol (22 mg, 2 eq.), triphenylphosphine (50 mg, 2 eq.) and DIAD (39 mg, 2 eq.) were dissolved in THF (4 mL) and the mixture was stirred at room temperature for 4 hr. The reaction solution was added to water, extracted with ethyl acetate, washed with saturated brine, and then dried over magnesium sulfate. The residues obtained after concentration under reduced pressure were purified by silica gel column chromatography (dichloromethane:methanol/4:1) to obtain the title compound (yellow oily substance, 6.8 mg, 17%).

LCMS: m/z 418 [M+H]+

HPLC retention time: 2.75 min (analysis condition B)

Example 726

Compound Y2

2,3-Dichloro-8-methoxy-6,6-dimethyl-6,11-dihydro-5H-benzo[b]carbazole

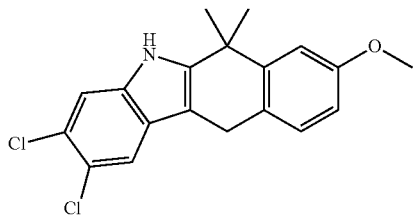 [SMILES: COc1ccc2c(c1)C(C)(C)c1[nH]c3cc(Cl)c(Cl)cc3c1C2]

Under nitrogen atmosphere, the acetic acid (1 mL) suspension of 7-methoxy-1,1-dimethyl-3,4-dihydro-1H-naphthalen-2-one (Compound A2, 92.3 mg, 0.452 mmol) and (3,4-dichlorophenyl)hydrazine hydrochloric acid salt (Compound Y1, 96.5 mg, 0.452 mmol) was stirred at ambient temperature of 90° C. for 3.5 hr. After cooling to room temperature, the reaction mixture was added with diethyl ether and water, and the resulting mixture was extracted twice with diethyl ether. The organic layer was washed three times with water, dried over sodium sulfate, and concentrated under reduced pressure. The resulting crude product was purified by flash column chromatography {Merck Kieselgel60, solution for elution:hexane/ethyl acetate (4:1)} to obtain the title compound (pale yellow solid, 62.1 mg, 40%).

$^1$H-NMR (270 MHz, CDCl$_3$) δ: 7.92-7.84 (1H, b), 7.62 (1H, s), 7.46 (1H, s), 7.05 (1H, d, 2.6), 6.84 (1H, dd, 8.6 Hz, 2.6 Hz), 4.01 (2H, s), 3.86 (3H, s), 1.67 (6H, s)

Example 727

Compound Y3

2,3-Dichloro-8-methoxy-6,6-dimethyl-5,6-dihydro-benzo[b]carbazol-11-one

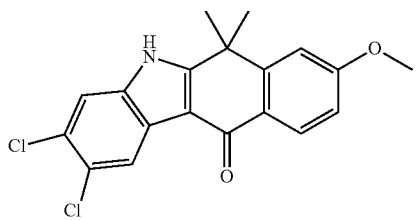 [SMILES: COc1ccc2c(c1)C(C)(C)c1[nH]c3cc(Cl)c(Cl)cc3c1C2=O]

Under nitrogen atmosphere, to the 1,4-dioxane (1.7 mL)-water (0.1 mL) solution of 2,3-dichloro-8-methoxy-6,6-dimethyl-6,11-dihydro-5H-benzo[b]carbazole (Compound Y2, 61.0 mg, 0.176 mmol), DDQ (120 mg, 0.529 mmol) was added and the mixture was stirred at room temperature for 16 hr and 15 min. The reaction mixture was purified by flash column chromatography {Merck Kieselgel60, solution for elution:hexane/ethyl acetate (2:1)} to obtain the title compound (pale orange solid, 16.7 mg, 26%).

$^1$H-NMR (270 MHz, CDCl$_3$) δ: 8.55 (1H, s), 8.42-8.36 (1H, b), 8.39 (1H, d, 8.6 Hz), 7.54 (1H, s), 7.08 (1H, d, 2.3 Hz), 7.03 (1H, dd, 8.6 Hz, 2.3 Hz), 3.93 (3H, s), 1.76 (6H, s)

Example 728

Compound Y4

2,3-Dichloro-8-hydroxy-6,6-dimethyl-5,6-dihydro-benzo[b]carbazol-11-one

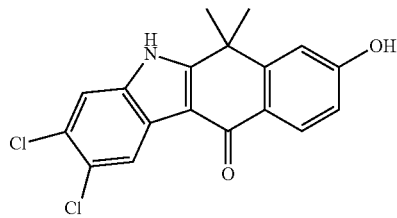 [SMILES: CC1(C)c2cc(O)ccc2C(=O)c2c1[nH]c1cc(Cl)c(Cl)cc21]

Mixture of 2,3-dichloro-8-methoxy-6,6-dimethyl-5,6-dihydro-benzo[b]carbazol-11-one (Compound Y3, 16.5 mg, 0.0457 mmol) and pyridinium chloride (0.2 g) was stirred at ambient temperature of 160° C. for 7 hr. The reaction mixture was cooled to room temperature and added with ethyl acetate and water. The mixture was extracted three times with ethyl acetate. The organic layer was washed twice with water, dried over sodium sulfate, and concentrated under reduced pressure. The resulting crude product was used for the next step without further purification (brown solid, 14.8 mg, 94%).

$^1$H-NMR (270 MHz, CD$_3$OD) δ: 8.34 (1H, s), 8.14 (1H, d, 8.6 Hz), 7.61 (1H, s), 7.10 (1H, d, 2.3 Hz), 6.89 (1H, dd, 8.6 Hz, 2.3 Hz), 1.75 (1H, s)

Example 729

Compound Y5-1

8-[(1R,5R)-5-(Tert-butyldimethylsilanyloxymethyl)-2,2-dimethyl-[1,3]dioxolan-4-yl methoxy]-2,3-dichloro-6,6-dimethyl-5,6-dihydro-benzo[b]carbazol-11-one Under nitrogen atmosphere, to the THF (0.3 mL) solution of 2,3-dichloro-8-hydroxy-6,6-dimethyl-5,6-dihydro-benzo[b]carbazol-11-one (Compound Y4, 12.9 mg, 0.0373 mmol), (4S,5R)-5-(tert-butyldimethylsilanyloxymethyl)-2,2-dimethyl-[1,3]dioxolan-4-ol (15.5 mg, 0.0559 mmol) and triphenylphosphine (14.7 mg, 0.0559 mmol), toluene solution (25.4 μL, 0.0559 mmol) of DEAD was added dropwise at room temperature. The reaction mixture was stirred at ambient temperature of 40° C. for 4 hr. After cooling to room temperature, the reaction mixture was concentrated under reduced pressure, and the resulting crude product was purified by preparative TLC (Merck 60 F$_{254}$, 0.5 mm) {solution for elution:hexane/ethyl acetate (3:1)} to obtain the title compound (white solid, 15.1 mg, 67%).

$^1$H-NMR (270 MHz, CDCl$_3$) δ: 8.55 (1H, s), 8.44-8.37 (1H, b), 8.37 (1H, d, 8.6 Hz), 7.54 (1H, s), 7.15 (1H, d, 2.6

Hz), 7.03 (1H, dd, 8.6 Hz, 2.6 Hz), 4.41-4.26 (2H, m), 4.25-4.15 (1H, m), 4.06-3.86 (2H, m), 3.83-3.73 (1H, m), 1.76 (3H, s), 1.75 (3H, s), 1.48 (3H, s), 1.47 (3H, s), 0.90 (9H, s), 0.092 (6H, s)

Example 730

Compound Y5-2

2,3-Dichloro-6,6-dimethyl-8-((3R,4R)-2,3,4-trihydroxy-butoxy)-5,6-dihydro-benzo[b]carbazol-11-one

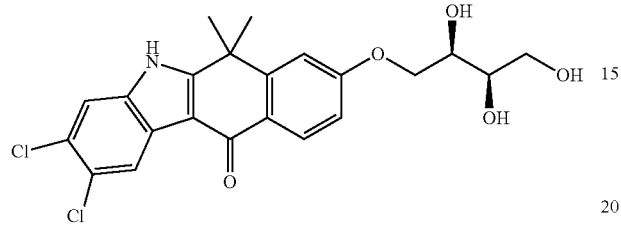

Under nitrogen atmosphere, to the THF (0.2 mL)-MeOH (0.1 mL) solution of 8-[(1R,5R)-5-(tert-butyldimethyl-silanyloxymethyl)-2,2-dimethyl-[1,3]dioxolan-4-yl methoxy]-2,3-dichloro-6,6-dimethyl-5,6-dihydro-benzo[b]carbazol-11-one (Compound Y5-1, 14.6 mg, 0.0242 mmol), 0.5 M aqueous solution of sulfuric acid (96.6 μL, 0.0483 mmol) was added at room temperature. The reaction mixture was stirred at ambient temperature of 55° C. for 3 hr, cooled to room temperature, and then added with diethyl ether and sodium hydrogen carbonate (10 mg) in order. The mixture was extracted twice with diethyl ether, and the organic layer was washed with water and brine, dried over sodium sulfate, and concentrated under reduced pressure. The resulting crude product was washed with dichloromethane, and dried under reduced pressure to obtain the title compound (white solid, 8.3 mg, 76%).

$^1$H-NMR (270 MHz, CD$_3$OD) δ: 8.35 (1H, s), 8.24 (1H, d, 8.9 Hz), 7.62 (1H, s), 7.31 (1H, d, 2.3 Hz), 7.10 (1H, dd, 8.9 Hz, 2.3 Hz), 4.31-4.23 (1H, m), 4.12-4.12 (1H, m), 4.11-4.02 (1H, m), 3.84-3.74 (1H, m), 3.73-3.61 (1H, m), 1.78 (6H, s)

LCMS: m/z 450 [M+H]$^+$

HPLC retention time: 4.92 min (analysis condition H)

Example 731

Compound Z3

2-[1-(2-Bromo-5-methoxy-phenyl)-1-methylethyl]-benzo[b]thiophene

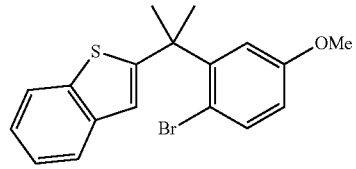 [SMILES: COc1ccc(Br)c(C(C)(C)c2cc3ccccc3s2)c1]

2-(2-Bromo-5-methoxyphenyl)-2-methyl-propinoic acid (1.5 g, 5.5 mmol) was dissolved in methylene chloride (15 mL), added with oxalyl chloride (1.5 mL) and dimethylformamide (2 micro liter) at room temperature, and the mixture was stirred at room temperature for 30 min. After removing the solvent, the residues were dissolved in toluene, added at room temperature with 2-[(triphenyl-5-phosphanyl)-methyl]-benzenethiol hydrobromide (2.56 g, 5.5 mmol) and triethylamine (2.27 mL), and then the mixture was refluxed under heating for 30 min. Thereafter, the mixture was cooled to 0° C., added with lithium hexamethyldisilazide (1 M tetrahydrofuran solution, 5.5 mL), and refluxed under heating for 24 hr. The reaction mixture was extracted with ethyl acetate and washed with water. The organic layer was dried over magnesium sulfate. The residues obtained after concentration under reduced pressure were purified by silica gel column chromatography (ethyl acetate/hexane) to obtain the title compound (0.55 g, 28%).

$^1$H-NMR (270 MHz, CDCl$_3$) δ: 6.61 (1H, s), 3.37 (3H, s), 1.83 (6H, s)

Example 732

Compound Z4

2-(1-Benzo[b]thiophen-2-yl-1-methyl-ethyl)-4-methoxy-benzoic acid

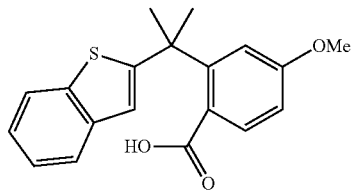 [SMILES: COc1ccc(C(=O)O)c(C(C)(C)c2cc3ccccc3s2)c1]

2-[1-(2-Bromo-5-methoxy-phenyl)-1-methylethyl]-benzo[b]thiophene (Compound Z3, 40 mg, 0.11 mmol) was dissolved in tetrahydrofuran (0.5 mL), cooled to −78° C., added with n-butyl lithium (1.57 M, hexane solution, 0.07 mL), and the mixture was stirred for 10 min. The reaction mixture was added with dry ice and then maintained for 1 hr. After that, the mixture was added with 0.5 N hydrochloric acid, extracted with ethyl acetate and washed with water. The organic layer was dried over magnesium sulfate. The residues obtained after concentration under reduced pressure were purified by silica gel column chromatography (ethyl acetate/hexane) to obtain the title compound (22 mg, 55%).

$^1$H-NMR (270 MHz, CDCl$_3$) δ: 7.46 (1H, d), 7.44 (1H, d), 6.92 (s, 1H), 6.70 (d, 1H), 3.84 (s, 3H), 1.89 (6H, s)

Example 733

Compound Z5

8-Methoxy-6,6-dimethyl-6H-benzo[b]naphth[2,3-d]thiophen-11-one

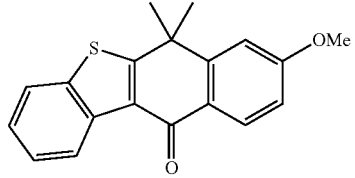 [SMILES: COc1ccc2c(c1)C(C)(C)c1sc3ccccc3c1C2=O]

To 2-(1-benzo[b]thiophen-2-yl-1-methylethyl)-4-methoxy-benzoic acid (Compound Z4, 68 mg, 0.22 mmol), polyphosphoric acid (3.5 g) was added, and the mixture was stirred for 1 hr at 100° C. under heating. The mixture was added with water, extracted with ethyl acetate and washed with water. The organic layer was dried over magnesium sulfate. The residues obtained after concentration under reduced pressure were purified by silica gel column chromatography (ethyl acetate/hexane) to obtain the title compound (41 mg, 63%).
LCMS: m/z 309 [M+H]$^+$
HPLC retention time: 2.89 min (analysis condition C)

Example 734

Compound Z6

8-Hydroxy-6,6-dimethyl-6H-benzo[b]naphth[2,3-d]thiophen-11-one

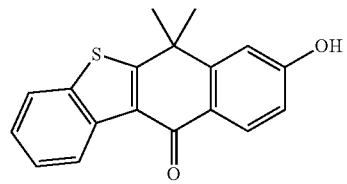 [SMILES: CC1(C)c2cc(O)ccc2C(=O)c2c1sc1ccccc21]

Under the same conditions as Compound A6, the title compound was prepared from Compound Z5.
LCMS: m/z 295 [M+H]$^+$
HPLC retention time: 2.91 min (analysis condition F)

Example 735

Compound Z7

8-(2-Diethylamino-ethoxy)-6,6-dimethyl-6H-benzo[b]naphth[2,3-d]thiophen-11-one

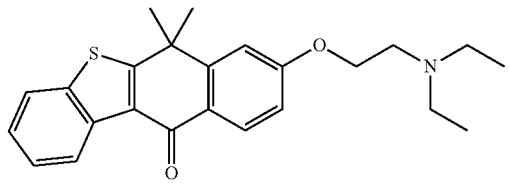 [SMILES: CCN(CC)CCOc1ccc2c(c1)C(C)(C)c1sc3ccccc3c1C2=O]

According to the same method as the method for synthesizing Compound A7-17, the title compound was prepared from Compound Z6.
LCMS: m/z 394 [M+H]$^+$
HPLC retention time: 5.06 min (analysis condition F)

Example 736

Compound Z9

2-Bromo-1,3-dihydroxytetrahydropyranbenzene

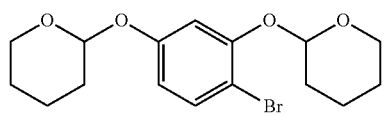 [SMILES: Brc1ccc(OC2CCCCO2)cc1OC1CCCCO1]

To 4-bromo-benzene-1,3-diol (Compound Z8, 20 g, 105.8 mmol) and 3,4-dihydro-2H-pyran (38.6 mL), pyridium para-toluenesulfonate (266 mg) was added, and the mixture was stirred at 50° C. for 1 hr. The residues obtained after concentration under reduced pressure were purified by silica gel column chromatography (ethyl acetate/hexane) to obtain the title compound (31.82 mg, 84%).
LCMS: m/z 358 [M+H]$^+$
HPLC retention time: 3.15 min (analysis condition C)

Example 737

Compound Z10

3-(2,4-Dihydroxy-phenyl)-7-methoxy-1,1-dimethyl-3,4-dihydro-1H-naphthalen-2-one

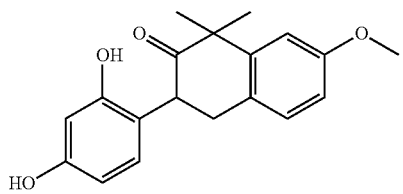 [SMILES: COc1ccc2c(c1)C(C)(C)C(=O)C(c1ccc(O)cc1O)C2]

To 7-methoxy-1,1-dimethyl-3,4-dihydro-1H-naphthalen-2-one (Compound A2, 10 g), 2-bromo-1,3-dihydroxytetrahydropyranbenzene (Compound Z9, 20.98 g), sodium t-butoxide (5.88 g), palladium acetate (550 mg) and tri-t-butylphosphonium tetrafluoroborate (710 mg), toluene (40 mL) was added and the mixture was stirred and heated at 70° C. under nitrogen atmosphere for 6 hr. After cooling, the reaction mixture was added with methanol (38 mL) and trifluoroacetic acid (14.54 mL) at room temperature, and then stirred at room temperature overnight. To the resulting residues, methylene chloride and saturated dipotassium hydrogen phosphate were added and the organic layer was washed with saturated brine. Thereafter, the organic layer was dried over magnesium sulfate. The residues obtained after concentration under reduced pressure were purified by silica gel column chromatography (ethyl acetate/hexane) to obtain the title compound (5.53 g, 36%).
LCMS: m/z 312 [M+H]$^+$
HPLC retention time: 2.39 min (analysis condition F)

Example 738

Compound Z11

Trifluoromethanesulfonic acid 8-methoxy-6,6-dimethyl-6,11-dihydro-benzo[b]naphth[2,3-d]furan-3-yl ester

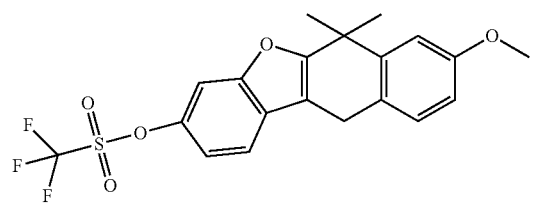 [SMILES: COc1ccc2c(c1)C(C)(C)c1oc3cc(OS(=O)(=O)C(F)(F)F)ccc3c1C2]

3-(2,4-Dihydroxy-phenyl)-7-methoxy-1,1-dimethyl-3,4-dihydro-1H-naphthalen-2-one (Compound Z10, 5.53 g) was dissolved in methylene chloride (40 mL), and added with trifluoromethanesulfonic anhydride (2.98 mL) at room temperature. After cooling to 5° C., diisopropylethylamine (9.25 mL) and trifluoromethanesulfonic anhydride (4.47 mL) were added thereto. To the reaction mixture, methylene chloride and saturated dipotassium hydrogen phosphate were added and the organic layer was washed with saturated brine. Thereafter, the organic layer was dried over magnesium sulfate. The residues obtained after concentration under reduced pressure were purified by silica gel column chromatography (ethyl acetate/hexane) to obtain the title compound (4.82 g, 64%).

LCMS: m/z 427 [M+H]$^+$

HPLC retention time: 8.95 min (analysis condition H)

Example 739

Compound Z12

Trifluoromethanesulfonic acid 8-methoxy-6,6-dimethyl-11-oxo-6,11-dihydro-benzo[b]naphth[2,3-d]furan-3-yl ester

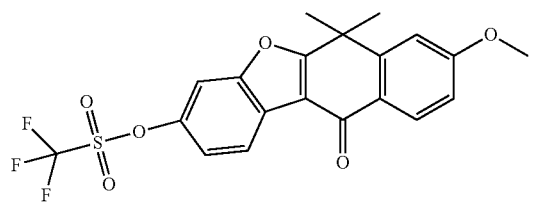 [SMILES: COc1ccc2c(c1)C(C)(C)c1oc3cc(OS(=O)(=O)C(F)(F)F)ccc3c1C2=O]

Trifluoromethanesulfonic acid 8-methoxy-6,6-dimethyl-6,11-dihydro-benzo[b]naphth[2,3-d]furan-3-yl ester (Compound Z11, 4.82 g) was dissolved in acetonitrile (48 mL) and water (24 mL), added with sodium chlorite (2.55 g) and N-hydroxyphthalimide (369 mg), and then the mixture was stirred at 40° C. for 1 hr. The reaction mixture was added with methylene chloride and the organic layer was washed with saturated brine. Thereafter, the organic layer was dried over magnesium sulfate. The residues obtained after concentration under reduced pressure were purified by silica gel column chromatography (ethyl acetate/hexane) to obtain the title compound (2.80 g, 56%).

LCMS: m/z 441 [M+H]$^+$

HPLC retention time: 8.02 min (analysis condition H)

Example 740

Compound Z13

Trifluoromethanesulfonic acid 8-hydroxy-6,6-dimethyl-11-oxo-6,11-dihydro-benzo[b]naphth[2,3-d]furan-3-yl ester

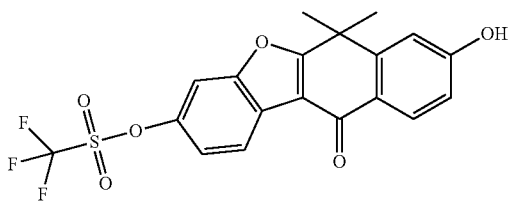 [SMILES: CC1(C)c2cc(O)ccc2C(=O)c2c1oc1cc(OS(=O)(=O)C(F)(F)F)ccc21]

Under the same conditions as Compound A6, the title compound was prepared as a crude product from Compound Z12.

Example 741

Compound Z14

Trifluoro-methanesulfonic acid 8-[(4R,5R)-5-(tert-butyl-dimethyl-silanyloxymethyl)-2,2-dimethyl-[1,3]dioxolan-4-yl methoxy]-6,6 dimethyl-11-oxo-6,11-dihydro-benzo[b]naphth[2,3-d]furan-3-yl ester

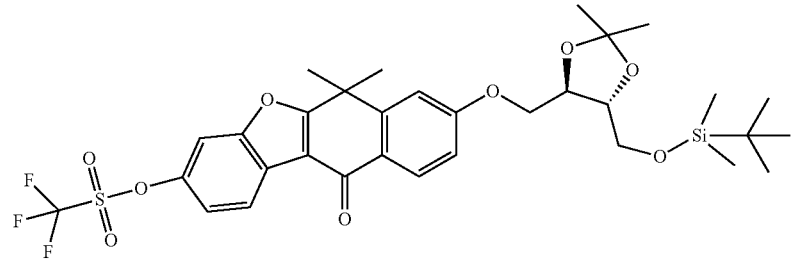 [SMILES: CC1(C)O[C@H](COc2ccc3c(c2)C(C)(C)c2oc4cc(OS(=O)(=O)C(F)(F)F)ccc4c2C3=O)[C@@H](CO[Si](C)(C)C(C)(C)C)O1]

Under the same conditions as the method for synthesizing Compound A7-1, the title compound was obtained as a crude product from Compound Z13 and [5-(tert-butyldimethylsilanyloxymethyl)-2,2-dimethyl-[1,3]dioxolan-4-yl]-methanol (Compound T22-0).

Example 742

Compound Z15

8-[(4R,5R)-5-(Tert-butyl-dimethyl-silanyloxymethyl)-2,2-dimethyl-[1,3]dioxolan-4-yl methoxy]-6,6-dimethyl-11-oxo-6,11-dihydro-benzo[b]naphth[2,3-d]furane-3-carbonitrile

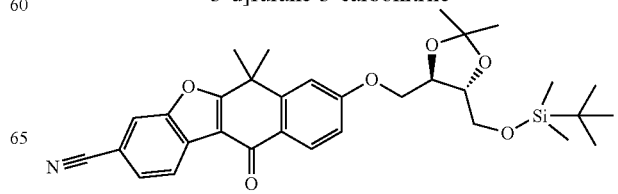

Trifluoro-methanesulfonic acid 8-[(4R,5R)-5-(tert-butyl-dimethyl-silanyloxymethyl)-2,2-dimethyl-[1,3]dioxolan-4-yl methoxy]-6,6 dimethyl-11-oxo-6,11-dihydro-benzo[b]naphth[2,3-d]furan-3-yl ester (Compound Z14, 24 mg) was dissolved in DMF (0.5 mL), added with zinc (II) cyanide (8.2 mg) and palladium tetrakistriphenylphosphine (2.0 mg), and the mixture was stirred under heating at 200° C. for 20 min with microwave irradiation. To the reaction mixture, ethyl acetate was added and the organic layer was washed with saturated brine. Thereafter, the organic layer was dried over magnesium sulfate. The residues obtained after concentration under reduced pressure were purified by silica gel column chromatography (ethyl acetate/hexane) to obtain the title compound (15 mg).

LCMS: m/z 562 [M+H]$^+$
HPLC retention time: 4.14 min (analysis condition F)

Example 743

Compound Z16

6,6-Dimethyl-11-oxo-8-((2R,3R)-2,3,4-trihydroxy-butoxy)-6,11-dihydro-benzo[b]naphth[2,3-d]furane-3-carbonitrile

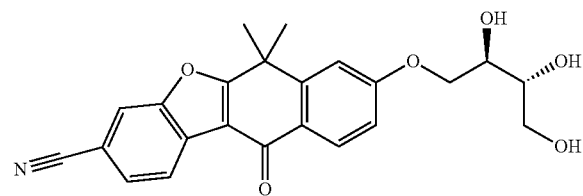 [SMILES: CC1(C)c2cc(OC[C@@H](O)[C@H](O)CO)ccc2C(=O)c2c1oc1cc(C#N)ccc21]

Under the same conditions as Compound S7-2, the title compound was prepared from Compound Z15.
LCMS: m/z 408 [M+H]$^+$
HPLC retention time: 4.51 min (analysis condition H)

Example 744

Compound K7-5

4-(3-Cyano-9-methoxy-6,6-dimethyl-11-oxo-6,11-dihydro-5H-benzo[b]carbazol-8-yl)-3,6-dihydro-2H-pyridine-1-carboxylic acid tert-butyl ester

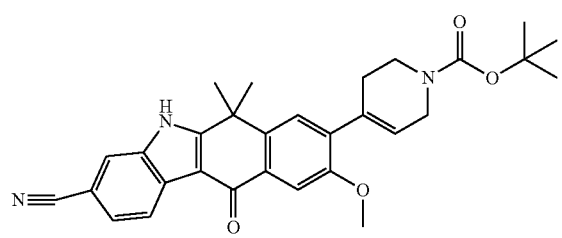 [SMILES: COc1cc2c(cc1C1=CCN(C(=O)OC(C)(C)C)CC1)C(C)(C)c1[nH]c3cc(C#N)ccc3c1C2=O]

Under the same conditions as the method for synthesizing Compound B2-22-1, the title compound was prepared from Compound K6 and 4-(4,4,5,5-tetramethyl-[1,3,2]dioxaborolan-2-yl)-3,6-dihydro-2H-pyridine-1-carboxylic acid tert-butyl ester.
LCMS: m/z 498 [M+H]$^+$
HPLC retention time: 4.24 min (analysis condition W)

Example 745

Compound K7-6

9-Methoxy-6,6-dimethyl-11-oxo-8-(1,2,3,6-tetrahydro-pyridin-4-yl)-6,11-dihydro-5H-benzo[b]carbazole-3-carbonitrile

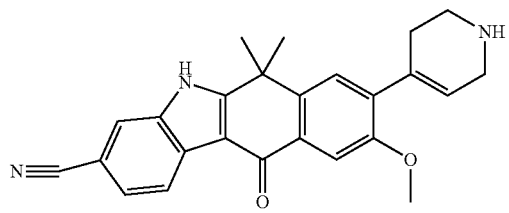 [SMILES: COc1cc2c(cc1C1=CCNCC1)C(C)(C)c1[nH]c3cc(C#N)ccc3c1C2=O]

Under the same conditions as the method for synthesizing Compound A8-1, the title compound was prepared from K7-5.
LCMS: m/z 398 [M+H]$^+$
HPLC retention time: 2.57 min (analysis condition W)

Example 746

Compound K8-1

8-(1-Cyclobutyl-1,2,3,6-tetrahydro-pyridin-4-yl)-9-methoxy-6,6-dimethyl-11-oxo-6,11-dihydro-5H-benzo[b]carbazole-3-carbonitrile

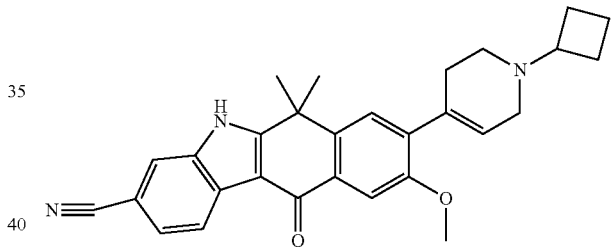

Under the same conditions as the method for synthesizing Compound B3-32, the title compound was prepared from Compound K7-6 and cyclobutanone.
LCMS: m/z 452 [M+H]$^+$
HPLC retention time: 2.72 min (analysis condition W)

Example 747

Compound K8-2

8-(1-Cyclobutyl-piperidin-4-yl)-9-methoxy-6,6-dimethyl-11-oxo-6,11-dihydro-5H-benzo[b]carbazole-3-carbonitrile

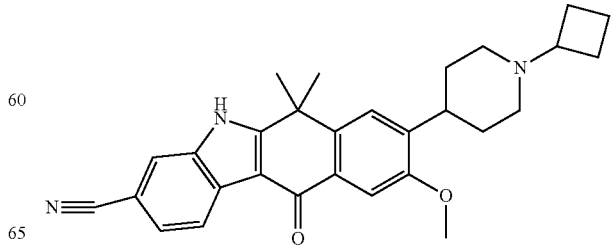

Under the same conditions as the method for synthesizing Compound B3-13-1, the title compound was prepared from Compound K8-1.
LCMS: m/z 454 [M+H]+
HPLC retention time: 2.76 min (analysis condition W)

Example 748

Compound K9-5

8-(1-Cyclobutyl-piperidin-4-yl)-9-hydroxy-6,6-dimethyl-11-oxo-6,11-dihydro-5H-benzo[b]carbazole-3-carbonitrile

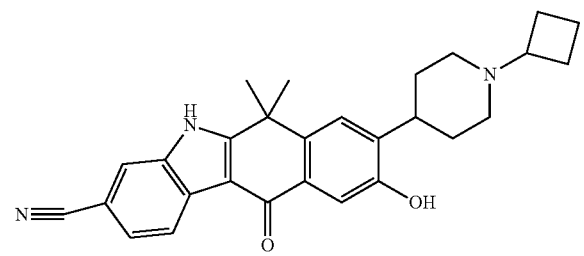 [SMILES: CC1(C)c2cc(C3CCN(C4CCC4)CC3)c(O)cc2C(=O)c2c1[nH]c1cc(C#N)ccc21]

Under the same conditions as the method for synthesizing Compound E3-2, the title compound was prepared from Compound K8-2.
LCMS: m/z 440 [M+H]+
HPLC retention time: 2.57 min (analysis condition W)

Example 749

Compound K10-8

8-(1-Cyclobutyl-piperidin-4-yl)-9-isopropoxy-6,6-dimethyl-11-oxo-6,11-dihydro-5H-benzo[b]carbazole-3-carbonitrile

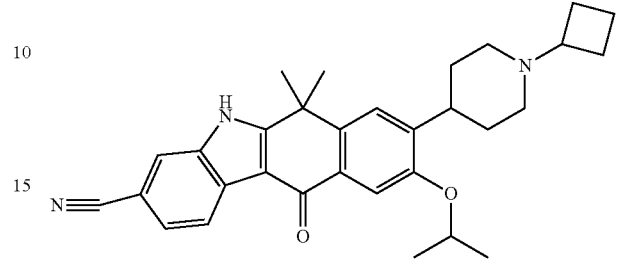

Under the same conditions as the method for synthesizing Compound A7-17, the title compound was prepared from Compound K9-5 and isopropyl iodide.
LCMS: m/z 482 [M+H]+
HPLC retention time: 1.74 min (analysis condition S)

The compounds described in the following Tables 2-3 were synthesized from the intermediates of Compound K or Compound L by alkylation of hydroxyl group according to Mitsunobu reaction used for preparing Compound A7-1 or the method used for the synthesis of Compound A7-17 (described in the Table).

TABLE 2

| Example No. | Comp. No. | Structure | Compound Name | HPLC Condition | Retention Time | m/z | Method |
|---|---|---|---|---|---|---|---|
| 750 | K10-9 | 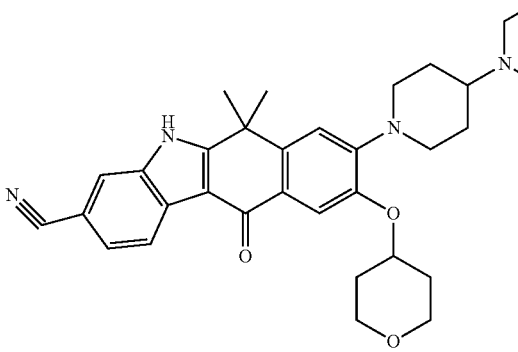 | 6,6-Dimethyl-8-(4-morpholin-4-yl-piperidin-1-yl)-11-oxo-9-(tetrahydro-pyran-4-yloxy)-6,11-dihydro-5H-benzo[b]carbazole-3-carbonitrile | U | 1.85 | 555 | A7-1 |
| 751 | K10-10 | 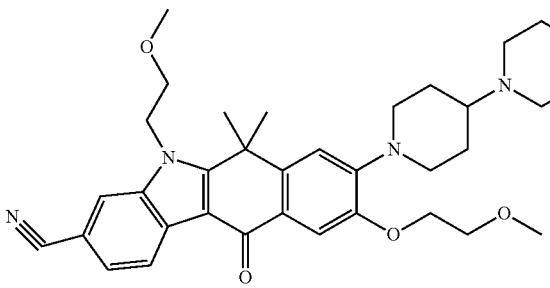 | 9-(2-Methoxy-ethoxy)-5-(2-methoxy-ethyl)-6,6-dimethyl-8-(4-morpholin-4-yl-piperidin-1-yl)-11-oxo-6,11-dihydro-5H-benzo[b]carbazole-3-carbonitrile | S | 1.50 | 587 | A7-17 |

TABLE 2-continued

| Example No. | Comp. No. | Structure | Compound Name | HPLC Condition | Retention Time | m/z | Method |
|---|---|---|---|---|---|---|---|
| 752 | K10-11 | 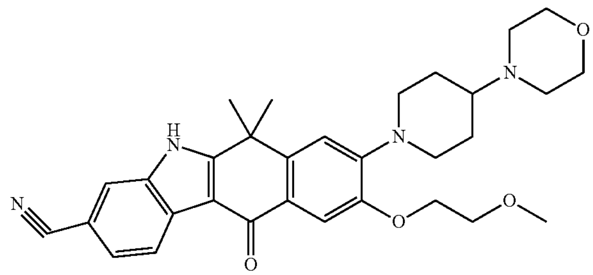 [SMILES: COCCOc1cc2c(cc1N1CCC(N3CCOCC3)CC1)C(C)(C)c1[nH]c3cc(C#N)ccc3c1C2=O] | 9-(2-Methoxy-ethoxy)-6,6-dimethyl-8-(4-morpholin-4-yl-piperidin-1-yl)-11-oxo-6,11-dihydro-5H-benzo[b]carbazole-3-carbonitrile | S | 1.37 | 529 | A7-17 |
| 753 | K10-12 | 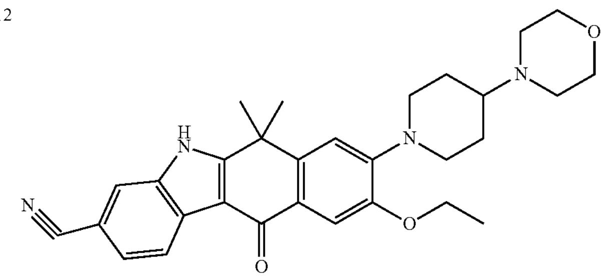 | 9-Ethoxy-6,6-dimethyl-8-(4-morpholin-4-yl-piperidin-1-yl)-11-oxo-6,11-dihydro-5H-benzo[b]carbazole-3-carbonitrile | U | 1.95 | 499 | A7-17 |
| 754 | K10-13 | 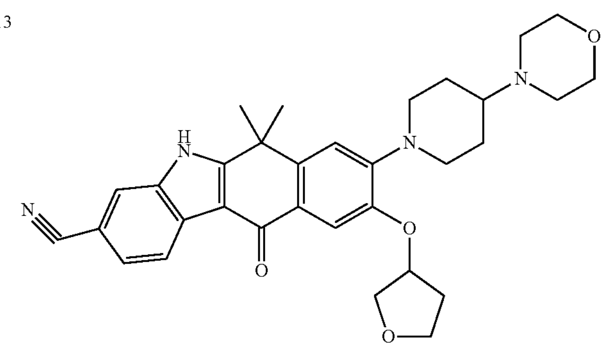 | 6,6-Dimethyl-8-(4-morpholin-4-yl-piperidin-1-yl)-11-oxo-9-(tetrahydro-furan-3-yloxy)-6,11-dihydro-5H-benzo[b]carbazole-3-carbonitrile | S | 1.40 | 541 | A7-1 |
| 755 | K10-14 | 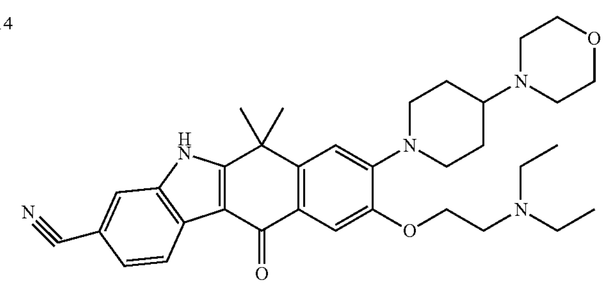 | 9-(2-Diethylamino-ethoxy)-6,6-dimethyl-8-(4-morpholin-4-yl-piperidin-1-yl)-11-oxo-6,11-dihydro-5H-benzo[b]carbazole-3-carbonitrile | S | 1.13 | 570 | A7-17 |
| 756 | K10-15 | 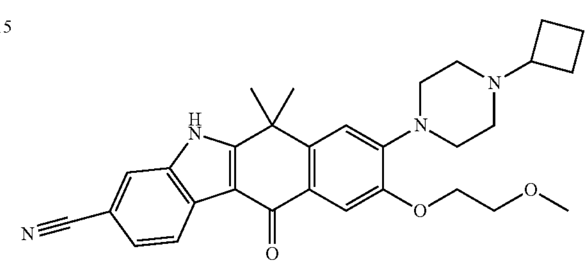 | 8-(4-Cyclobutyl-piperazin-1-yl)-9-(2-methoxy-ethoxy)-6,6-dimethyl-11-oxo-6,11-dihydro-5H-benzo[b]carbazole-3-carbonitrile | S | 1.45 | 499 | A7-17 |

TABLE 2-continued

| Example No. | Comp. No. | Structure | Compound Name | HPLC Condition | Retention Time | m/z | Method |
|---|---|---|---|---|---|---|---|
| 757 | K10-16 | 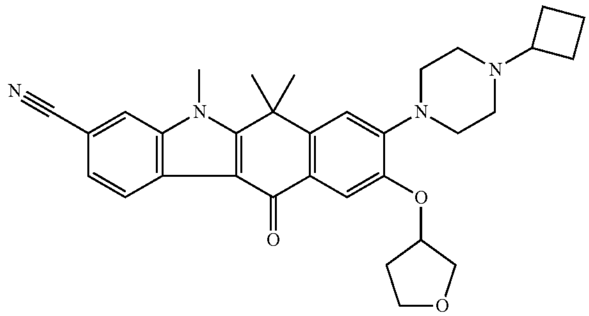 [SMILES: Cn1c2c(c3ccc(C#N)cc31)C(=O)c1cc(OC3CCOC3)c(N3CCN(C4CCC4)CC3)cc1C2(C)C] | 8-(4-Cyclobutyl-piperazin-1-yl)-5,6,6-trimethyl-11-oxo-9-(tetrahydro-furan-3-yloxy)-6,11-dihydro-5H-benzo[b]carbazole-3-carbonitrile | S | 1.98 | 525 | A7-1 |
| 758 | K10-17 | 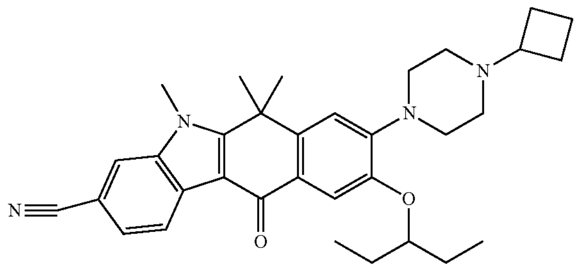 [SMILES: CCC(CC)Oc1cc2c(cc1N1CCN(C3CCC3)CC1)C(C)(C)c1c(c3ccc(C#N)cc3n1C)C2=O] | 8-(4-Cyclobutyl-piperazin-1-yl)-9-(1-ethyl-propoxy)-5,6,6-trimethyl-11-oxo-6,11-dihydro-5H-benzo[b]carbazole-3-carbonitrile | S | 2.43 | 525 | A7-1 |
| 759 | K10-18 | 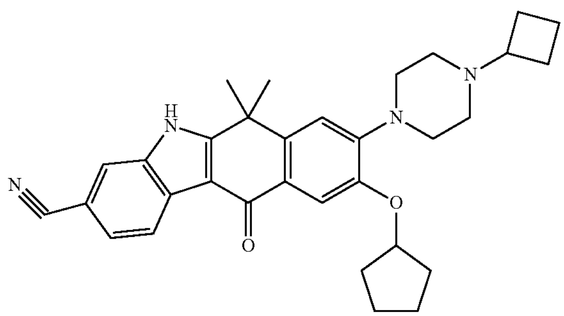 [SMILES: CC1(C)c2cc(N3CCN(C4CCC4)CC3)c(OC3CCCC3)cc2C(=O)c2c1[nH]c1cc(C#N)ccc21] | 8-(4-Cyclobutyl-piperazin-1-yl)-6,6-dimethyl-11-oxo-9-(tetrahydro-furan-3-yloxy)-6,11-dihydro-5H-benzo[b]carbazole-3-carbonitrile | S | 1.92 | 511 | A7-1 |
| 760 | K10-19 | 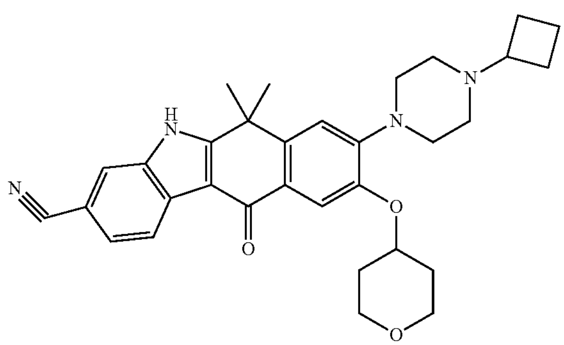 [SMILES: CC1(C)c2cc(N3CCN(C4CCC4)CC3)c(OC3CCOCC3)cc2C(=O)c2c1[nH]c1cc(C#N)ccc21] | 8-(4-Cyclobutyl-piperazin-1-yl)-6,6-dimethyl-11-oxo-9-(tetrahydro-pyran-4-yloxy)-6,11-dihydro-5H-benzo[b]carbazole-3-carbonitrile | U | 1.97 | 525 | A7-1 |
| 761 | K10-20 | 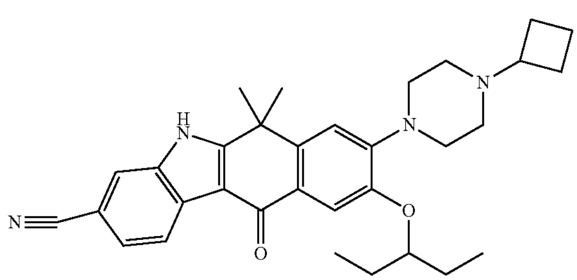 | 8-(4-Cyclobutyl-piperazin-1-yl)-9-(1-ethyl-propoxy)-6,6-dimethyl-11-oxo-6,11-dihydro-5H-benzo[b]carbazole-3-carbonitrile | S | 1.82 | 511 | A7-1 |

TABLE 2-continued

| Example No. | Comp. No. | Structure | Compound Name | HPLC Condition | Retention Time | m/z | Method |
|---|---|---|---|---|---|---|---|
| 762 | L10-3 | 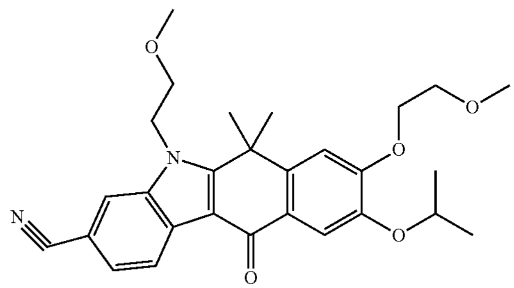 [SMILES: COCCOc1cc2c(cc1OC(C)C)C(=O)c1c(n(CCOC)c3cc(C#N)ccc13)C2(C)C] | 9-Isopropoxy-8-(2-methoxy-ethoxy)-5-(2-methoxy-ethyl)-6,6-dimethyl-11-oxo-6,11-dihydro-5H-benzo[b]carbazole-3-carbonitrile | S | 2.68 | 477 | A7-17 |
| 763 | L10-4 | 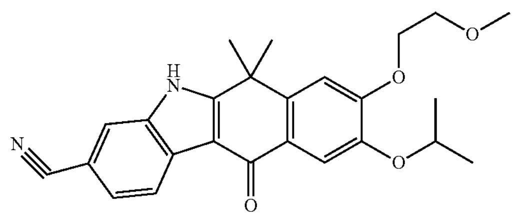 [SMILES: COCCOc1cc2c(cc1OC(C)C)C(=O)c1c([nH]c3cc(C#N)ccc13)C2(C)C] | 9-Isopropoxy-8-(2-methoxy-ethoxy)-6,6-dimethyl-11-oxo-6,11-dihydro-5H-benzo[b]carbazole-3-carbonitrile | S | 2.68 | 419 | A7-17 |

TABLE 3

| Example No. | Comp. No. | Structure | Compound Name | HPLC Condition | Retention Time | m/z | Method |
|---|---|---|---|---|---|---|---|
| 764 | L10-5 | 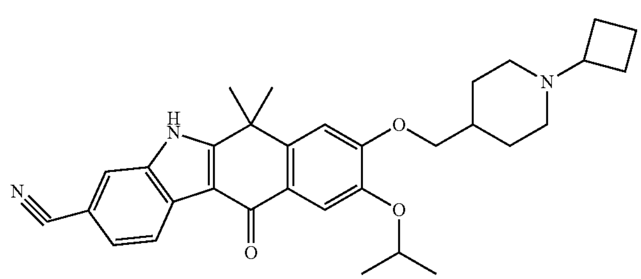 [SMILES: CC(C)Oc1cc2c(cc1OCC1CCN(C3CCC3)CC1)C(C)(C)c1[nH]c3cc(C#N)ccc3c1C2=O] | 8-(1-Cyclobutyl-piperidin-4-ylmethoxy)-9-isopropoxy-6,6-dimethyl-11-oxo-6,11-dihydro-5H-benzo[b]carbazole-3-carbonitrile | S | 1.65 | 512 | A7-1 |
| 765 | L10-6 | 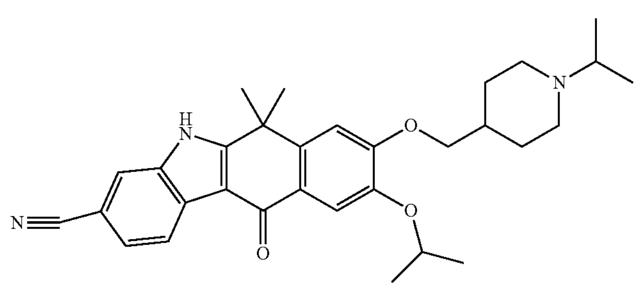 [SMILES: CC(C)Oc1cc2c(cc1OCC1CCN(C(C)C)CC1)C(C)(C)c1[nH]c3cc(C#N)ccc3c1C2=O] | 9-Isopropoxy-8-(1-isopropyl-piperidin-4-ylmethoxy)-6,6-dimethyl-11-oxo-6,11-dihydro-5H-benzo[b]carbazole-3-carbonitrile | S | 1.62 | 500 | A7-1 |
| 766 | L10-7 | 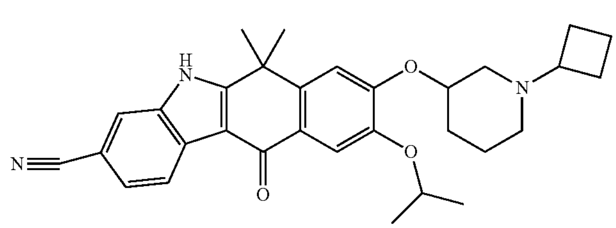 [SMILES: CC(C)Oc1cc2c(cc1OC1CCCN(C3CCC3)C1)C(C)(C)c1[nH]c3cc(C#N)ccc3c1C2=O] | 8-(1-Cyclobutyl-piperidin-3-yloxy)-9-isopropoxy-6,6-dimethyl-11-oxo-6,11-dihydro-5H-benzo[b]carbazole-3-carbonitrile | S | 1.65 | 498 | A7-1 |

TABLE 3-continued

| Example No. | Comp. No. | Structure | Compound Name | HPLC Condition | Retention Time | m/z | Method |
|---|---|---|---|---|---|---|---|
| 767 | L10-8 | 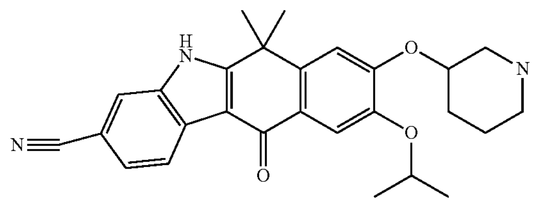 [SMILES: CC(C)Oc1cc2c(cc1OC1CCCNC1)C(C)(C)c1[nH]c3cc(C#N)ccc3c1C2=O] | 9-Isopropoxy-8-(1-isopropyl-piperidin-3-yloxy)-6,6-dimethyl-11-oxo-6,11-dihydro-5H-benzo[b]carbazole-3-carbonitrile | S | 1.59 | 486 | A7-1 |
| 768 | L10-9 | 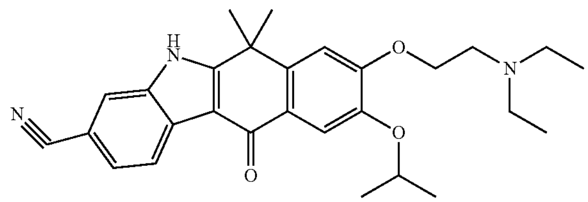 [SMILES: CCN(CC)CCOc1cc2c(cc1OC(C)C)C(=O)c1c([nH]c3cc(C#N)ccc13)C2(C)C] | 8-(2-Diethyl-aminoethoxy)-9-isopropoxy-6,6-dimethyl-11-oxo-6,11-dihydro-5H-benzo[b]carbazole-3-carbonitrile | U | 2.07 | 460 | A7-17 |
| 769 | L10-10 | 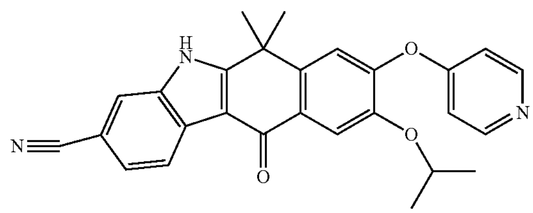 [SMILES: CC(C)Oc1cc2c(cc1Oc1ccncc1)C(C)(C)c1[nH]c3cc(C#N)ccc3c1C2=O] | 9-Isopropoxy-6,6-dimethyl-11-oxo-8-(pyridin-4-yloxy)-6,11-dihydro-5H-benzo[b]carbazole-3-carbonitrile | U | 2.07 | 438 | A7-17 |
| 770 | L10-11 | 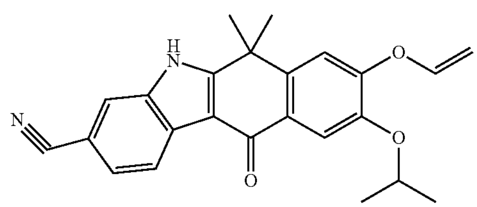 [SMILES: C=COc1cc2c(cc1OC(C)C)C(=O)c1c([nH]c3cc(C#N)ccc13)C2(C)C] | 9-Isopropoxy-6,6-dimethyl-11-oxo-8-vinyloxy-6,11-dihydro-5H-benzo[b]carbazole-3-carbonitrile | U | 2.77 | 387 | A7-17 |
| 771 | L10-12 | 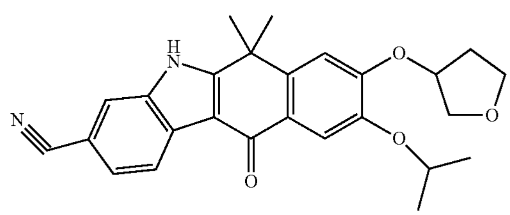 [SMILES: CC(C)Oc1cc2c(cc1OC1CCOC1)C(C)(C)c1[nH]c3cc(C#N)ccc3c1C2=O] | 9-Isopropoxy-6,6-dimethyl-11-oxo-8-(tetrahydro-furan-3-yloxy)-6,11-dihydro-5H-benzo[b]carbazole-3-carbonitrile | S | 2.45 | 431 | A7-1 |

The compounds described in the following Table 4 were synthesized from the intermediates of Compound B according to the method described in the Table.

TABLE 4

| Example No. | Comp. No. | Structure | Compound Name | HPLC Condition | Retention Time | m/z | Method |
|---|---|---|---|---|---|---|---|
| 772 | B3-39 | 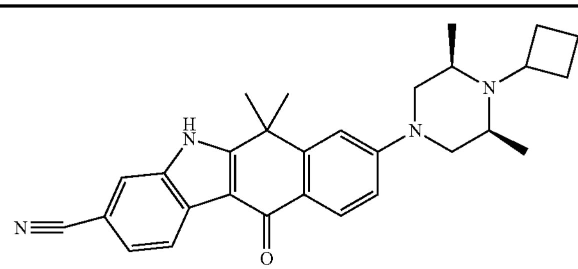 | 8-((3R,5S)-4-Cyclobutyl-3,5-dimethyl-piperazin-1-yl)-6,6-dimethyl-11-oxo-6,11-dihydro-5H-benzo[b]carbazole-3-carbonitrile | U | 1.90 | 453 | B3-32 |

TABLE 4-continued

| Example No. | Comp. No. | Structure | Compound Name | HPLC Condition | Retention Time | m/z | Method |
|---|---|---|---|---|---|---|---|
| 773 | B3-40 | 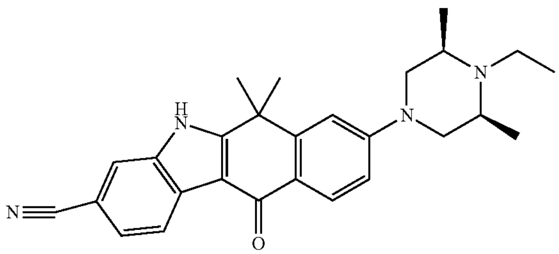 [SMILES: CCN1[C@H](C)CN(c2ccc3c(c2)C(C)(C)c2[nH]c4cc(C#N)ccc4c2C3=O)C[C@@H]1C] | 8-((3R,5S)-4-Ethyl-3,5-dimethyl-piperazin-1-yl)-6,6-dimethyl-11-oxo-6,11-dihydro-5H-benzo[b]carbazole-3-carbonitrile | U | 1.82 | 427 | B3-32 |
| 774 | B2-30 | 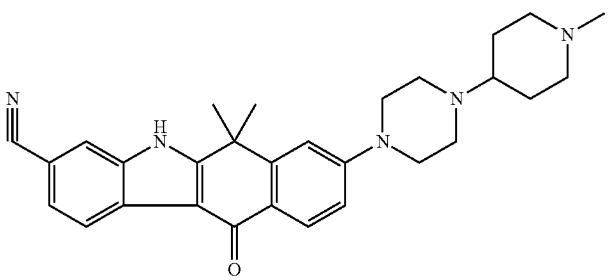 [SMILES: CN1CCC(N2CCN(c3ccc4c(c3)C(C)(C)c3[nH]c5cc(C#N)ccc5c3C4=O)CC2)CC1] | 6,6-Dimethyl-8-[4-(1-methyl-piperidin-4-yl)-piperazin-1-yl]-11-oxo-6,11-dihydro-5H-benzo[b]carbazole-3-carbonitrile | U | 1.58 | 468 | B2-1 |
| 775 | B3-41 | 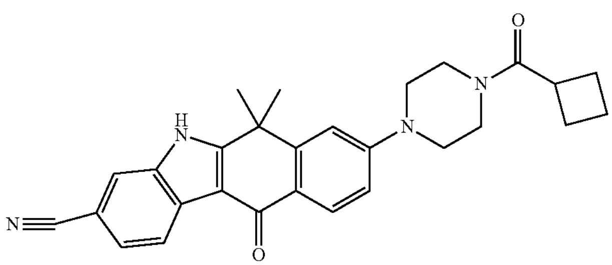 [SMILES: CC1(C)c2cc(N3CCN(C(=O)C4CCC4)CC3)ccc2C(=O)c2c1[nH]c1cc(C#N)ccc21] | 8-(4-Cyclobutanecarbonyl-piperazin-1-yl)-6,6-dimethyl-11-oxo-6,11-dihydro-5H-benzo[b]carbazole-3-carbonitrile | U | 2.35 | 453 | A9-10 |
| 776 | B3-42 | 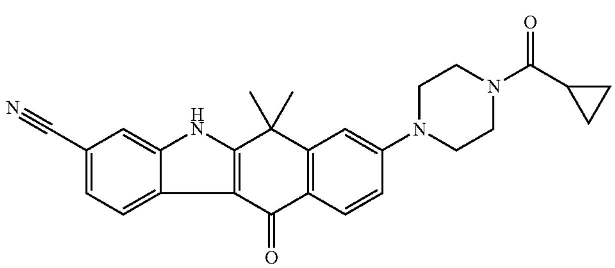 [SMILES: CC1(C)c2cc(N3CCN(C(=O)C4CC4)CC3)ccc2C(=O)c2c1[nH]c1cc(C#N)ccc21] | 8-(4-Cyclopropanecarbonyl-piperazin-1-yl)-6,6-dimethyl-11-oxo-6,11-dihydro-5H-benzo[b]carbazole-3-carbonitrile | U | 2.22 | 439 | A9-10 |

Example 777

Compound E6-4

9-Ethyl-8-hydroxy-6,6-dimethyl-11-oxo-6,11-dihydro-5H-benzo[b]carbazole-3-carbonitrile

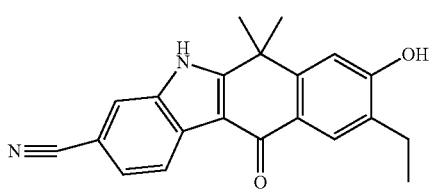 [SMILES: CCc1cc2c(cc1O)C(C)(C)c1[nH]c3cc(C#N)ccc3c1C2=O]

Under the same conditions as the method for synthesizing Compound E3-2, the title compound was prepared from Compound E5-1.

LCMS: m/z 331 [M+H]+
HPLC retention time: 3.42 min (analysis condition W)

Example 778

Compound E7

Trifuloro-methanesulfonic acid 3-cyano-9-ethyl-6,6-dimethyl-11-oxo-6,11-dihydro-5H-benzo[b]carbazol-8-yl ester

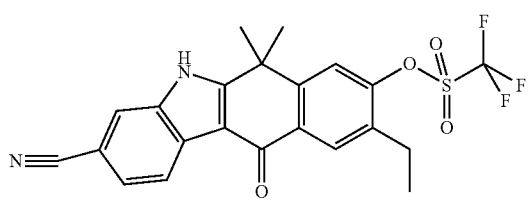 [SMILES: CCc1cc2c(cc1OS(=O)(=O)C(F)(F)F)C(C)(C)c1[nH]c3cc(C#N)ccc3c1C2=O]

Under the same conditions as the method for synthesizing Compound B1, the title compound was prepared from Compound E6-4.

LCMS: m/z 463 [M+H]$^+$
HPLC retention time: 4.39 min (analysis condition W)

Example 779

Compound E8-1

9-Ethyl-6,6-dimethyl-11-oxo-8-piperazin-1-yl-6,11-dihydro-5H-benzo[b]carbazole-3-carbonitrile

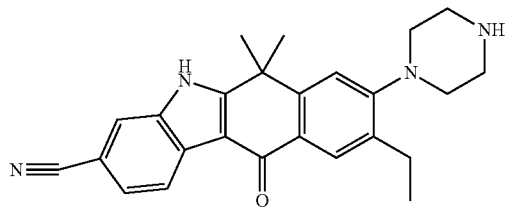 [SMILES: CCc1cc2c(cc1N1CCNCC1)C(C)(C)c1[nH]c3cc(C#N)ccc3c1C2=O]

The title compound was prepared from Compound E7 and piperazine in the same manner as the method for synthesizing Compound B2-1.

LCMS: m/z 399 [M+H]$^+$
HPLC retention time: 1.88 min (analysis condition U)

Example 780

Compound E8-2

9-Ethyl-6,6-dimethyl-8-((S)-3-methyl-piperazin-1-yl)-11-oxo-6,11-dihydro-5H-benzo[b]carbazole-3-carbonitrile

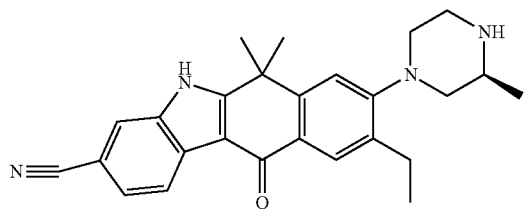 [SMILES: CCc1cc2c(cc1N1CCN[C@@H](C)C1)C(C)(C)c1[nH]c3cc(C#N)ccc3c1C2=O]

Under the same conditions as the method for synthesizing Compound B2-1, the title compound was prepared from Compound E7 and 2-(S)-methylpiperazine.

LCMS: m/z 413 [M+H]$^+$
HPLC retention time: 2.76 min (analysis condition W)

Example 781

Compound E8-3

8-((3R,5S)-3,5-Dimethyl-piperazin-1-yl)-9-ethyl-6,6-dimethyl-11-oxo-6,11-dihydro-5H-benzo[b]carbazole-3-carbonitrile

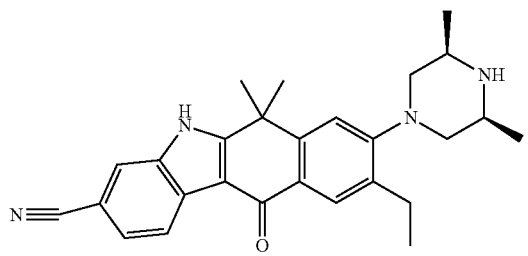 [SMILES: CCc1cc2c(cc1N1C[C@@H](C)N[C@@H](C)C1)C(C)(C)c1[nH]c3cc(C#N)ccc3c1C2=O]

Under the same conditions as the method for synthesizing Compound B2-1, the title compound was prepared from Compound E7 and cis-2,6-dimethylpiperazine.

LCMS: m/z 427 [M+H]$^+$
HPLC retention time: 2.00 min (analysis condition U)

Example 782

Compound E8-4

8-(1-Cyclobutyl-1,2,3,6-tetrahydro-pyridin-4-yl)-9-ethyl-6,6-dimethyl-11-oxo-6,11-dihydro-5H-benzo[b]carbazole-3-carbonitrile Compound 7 was converted in the same manner as Compound B2-22-1 and Compound 2, and subsequently subjected to reductive amination in the same manner as Compound B3-32 to obtain the title compound.

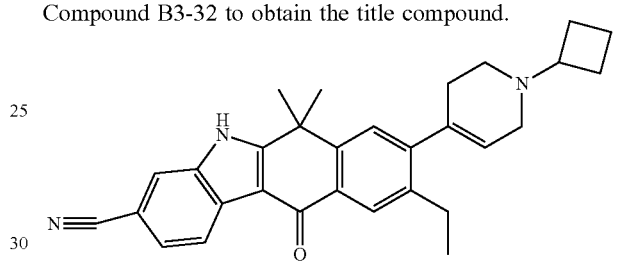

LCMS: m/z 450 [M+H]$^+$
HPLC retention time: 2.12 min (analysis condition U)

Example 783

Compound E9-1

8-((S)-4-Cyclobutyl-3-methyl-piperazin-1-yl)-9-ethyl-6,6-dimethyl-11-oxo-6,11-dihydro-5H-benzo[b]carbazole-3-carbonitrile

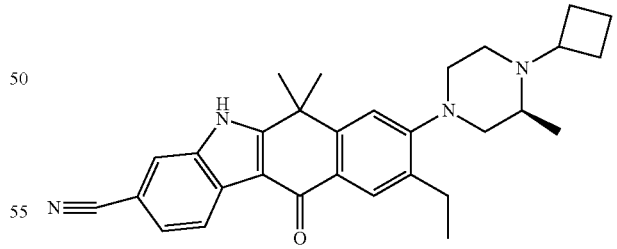

Under the same conditions as the method for synthesizing Compound B3-32, the title compound was prepared from Compound E8-2 and cyclobutanone.

LCMS: m/z 467 [M+H]$^+$
HPLC retention time: 2.90 min (analysis condition W)

The compounds described in the following Table 5 were prepared by acylation from Compound E8-1 in the same manner as the method for synthesizing Compound A9-10.

TABLE 5

| Example No. | Comp. No. | Structure | Compound Name | HPLC Condition | Retention Time | m/z |
|---|---|---|---|---|---|---|
| 784 | E9-2 | 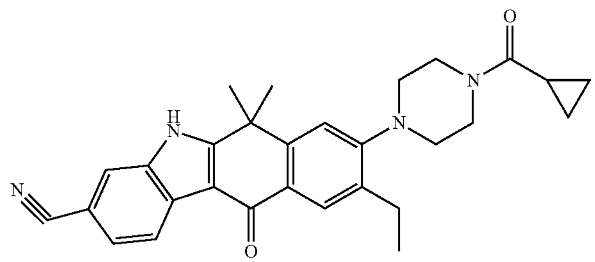 [SMILES: CCc1cc2c(cc1N1CCN(C(=O)C3CC3)CC1)C(C)(C)c1[nH]c3cc(C#N)ccc3c1C2=O] | 8-(4-Cyclopropanecarbonyl-piperazin-1-yl)-9-ethyl-6,6-dimethyl-11-oxo-6,11-dihydro-5H-benzo[b]carbazole-3-carbonitrile | U | 2.58 | 467 |
| 785 | E9-3 | 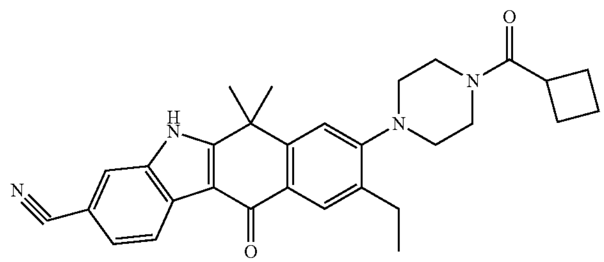 [SMILES: CCc1cc2c(cc1N1CCN(C(=O)C3CCC3)CC1)C(C)(C)c1[nH]c3cc(C#N)ccc3c1C2=O] | 8-(4-Cyclobutanecarbonyl-piperazin-1-yl)-9-ethyl-6,6-dimethyl-11-oxo-6,11-dihydro-5H-benzo[b]carbazole-3-carbonitrile | U | 2.74 | 481 |
| 786 | E9-4 | 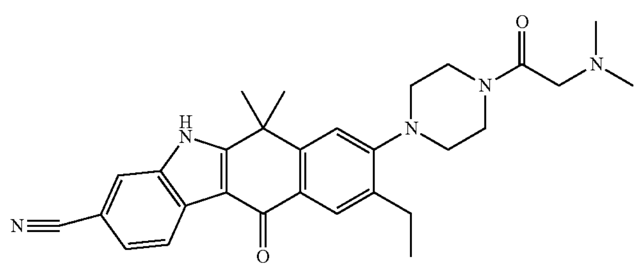 [SMILES: CCc1cc2c(cc1N1CCN(C(=O)CN(C)C)CC1)C(C)(C)c1[nH]c3cc(C#N)ccc3c1C2=O] | 8-[4-(2-Dimethylamino-acetyl)-piperazin-1-yl]-9-ethyl-6,6-dimethyl-11-oxo-6,11-dihydro-5H-benzo[b]carbazole-3-carbonitrile | U | 1.98 | 484 |
| 787 | E9-5 | 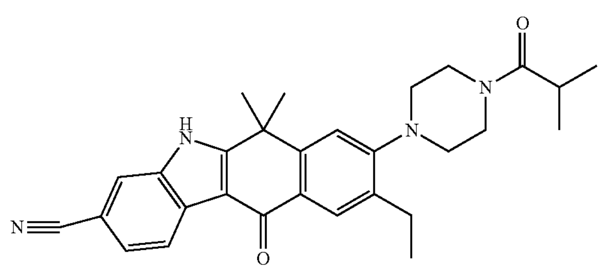 [SMILES: CCc1cc2c(cc1N1CCN(C(=O)C(C)C)CC1)C(C)(C)c1[nH]c3cc(C#N)ccc3c1C2=O] | 9-Ethyl-8-(4-isobutyryl-piperazin-1-yl)-6,6-dimethyl-11-oxo-6,11-dihydro-5H-benzo[b]carbazole-3-carbonitrile | U | 2.67 | 469 |
| 788 | E9-6 | 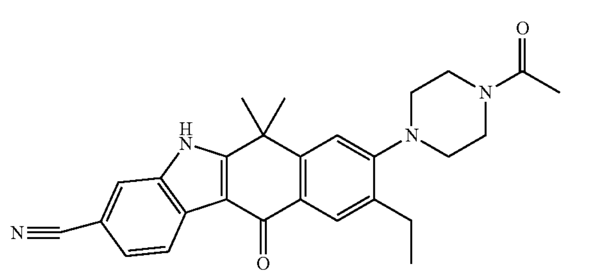 [SMILES: CCc1cc2c(cc1N1CCN(C(C)=O)CC1)C(C)(C)c1[nH]c3cc(C#N)ccc3c1C2=O] | 8-(4-Acetyl-piperazin-1-yl)-9-ethyl-6,6-dimethyl-11-oxo-6,11-dihydro-5H-benzo[b]carbazole-3-carbonitrile | U | 2.35 | 441 |

TABLE 5-continued

| Example No. | Comp. No. | Structure | Compound Name | HPLC Condition | Retention Time | m/z |
|---|---|---|---|---|---|---|
| 789 | E9-7 | 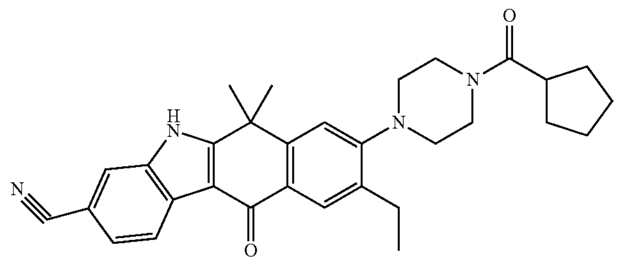 [SMILES: CCc1cc2c(cc1N1CCN(C(=O)C3CCCC3)CC1)C(C)(C)c1[nH]c3cc(C#N)ccc3c1C2=O] | 8-(4-Cyclopentanecarbonyl-piperazin-1-yl)-9-ethyl-6,6-dimethyl-11-oxo-6,11-dihydro-5H-benzo[b]carbazole-3-carbonitrile | S | 2.87 | 495 |
| 790 | E9-8 | 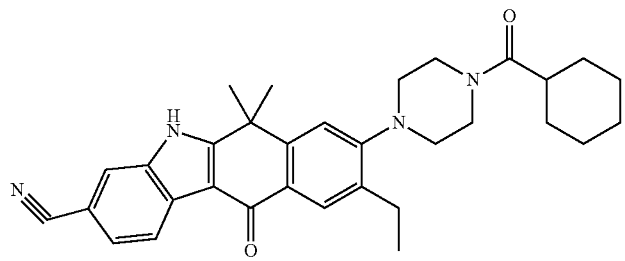 [SMILES: CCc1cc2c(cc1N1CCN(C(=O)C3CCCCC3)CC1)C(C)(C)c1[nH]c3cc(C#N)ccc3c1C2=O] | 8-(4-Cyclohexanecarbonyl-piperazin-1-yl)-9-ethyl-6,6-dimethyl-11-oxo-6,11-dihydro-5H-benzo[b]carbazole-3-carbonitrile | S | 2.97 | 509 |

Example 791

Compound E9-9

8-[4-(1-Cyano-cyclohexyl)-piperazin-1-yl]-9-ethyl-6,6-dimethyl-11-oxo-6,11-dihydro-5H-benzo[b]carbazole-3-carbonitrile

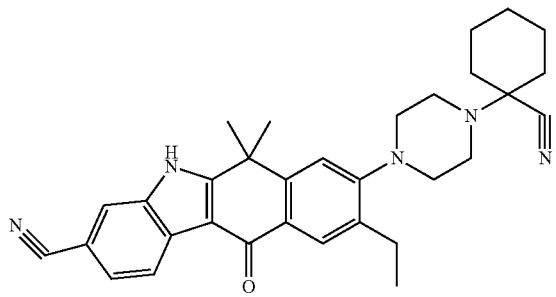 [SMILES: CCc1cc2c(cc1N1CCN(C3(C#N)CCCCC3)CC1)C(C)(C)c1[nH]c3cc(C#N)ccc3c1C2=O]

9-Ethyl-6,6-dimethyl-11-oxo-8-piperazin-1-yl-6,11-dihydro-5H-benzo[b]carbazole-3-carbonitrile (45 mg) and cyclohexanone (25 mg) were suspended in chloroform (2 ml), added with trimethylsilyl cyanide (30 mg) and zinc iodide (5 mg), and the mixture was stirred at 60° C. for 17 hrs. The reaction mixture was diluted with ethyl acetate (20 ml) and the organic layer was washed with 10% brine solution and concentrated under reduced pressure. The resulting residues were purified by silica gel column (dichloromethane/methanol (=99/1)) to obtain the title compound (12 mg, yield 30%).

LCMS: m/z 506 [M+H]$^+$

HPLC retention time: 3.00 min (analysis condition U)

The compounds described in the following Table 6 were synthesized from Compound E8-1 or Compound PR10-1 in the same manner as the method for Compound E9-9.

TABLE 6

| Example No. | Comp. No. | Structure | Compound Name | HPLC Condition | Retention Time | m/z |
|---|---|---|---|---|---|---|
| 792 | E9-10 | 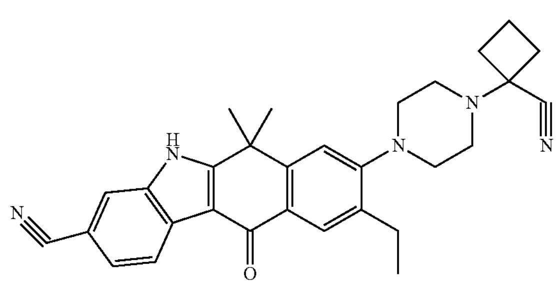 [SMILES: CCc1cc2c(cc1N1CCN(C3(C#N)CCC3)CC1)C(C)(C)c1[nH]c3cc(C#N)ccc3c1C2=O] | 8-[4-(1-Cyano-cyclobutyl)-piperazin-1-yl]-9-ethyl-6,6-dimethyl-11-oxo-6,11-dihydro-5H-benzo[b]carbazole-3-carbonitrile | U | 2.88 | 478 |

TABLE 6-continued

| Example No. | Comp. No. | Structure | Compound Name | HPLC Condition | Retention Time | m/z |
|---|---|---|---|---|---|---|
| 793 | PR11-20 | 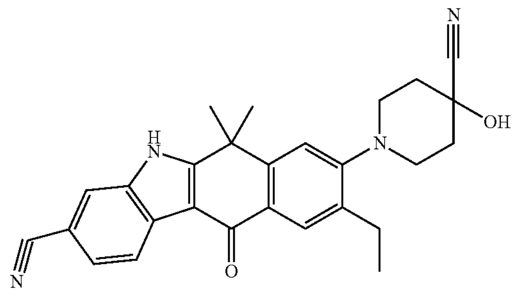 [SMILES: CCc1cc2c(cc1N1CCC(O)(C#N)CC1)C(C)(C)c1[nH]c3cc(C#N)ccc3c1C2=O] | 8-(4-Cyano-4-hydroxy-piperidine-1-yl)-9-ethyl-6,6-dimethyl-11-oxo-6,11-dihydro-5H-benzo[b]carbazole-3-carbonitrile | Y | 3.05 | 439 |
| 794 | PR11-21 | 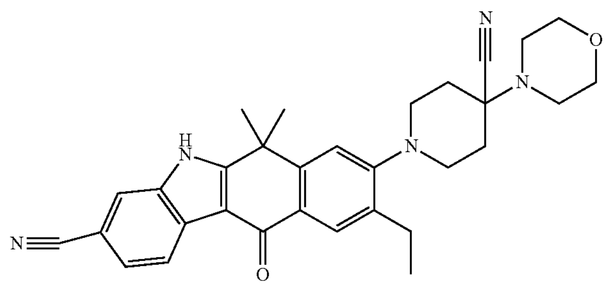 [SMILES: CCc1cc2c(cc1N1CCC(C#N)(N3CCOCC3)CC1)C(C)(C)c1[nH]c3cc(C#N)ccc3c1C2=O] | 8-(4-Cyano-4-morpholine-4-yl-piperidine-1-yl)-9-ethyl-6,6 dimethyl-11-oxo-6,11-dihydro-5H-benzo[b]carbazole-3-carbonitrile | Y | 3.35 | 508 |

With respect to the compounds described in the following Table 7, Compound F2 was subjected to amination in the same manner as Compound B2-1. Subsequently, the preparation was carried out by reductive amination in the same manner as the method for Compound B3-32.

TABLE 7

| Example No. | Comp. No. | Structure | Compound Name | HPLC Condition | Retention Time | m/z | Method |
|---|---|---|---|---|---|---|---|
| 795 | F3-12 | 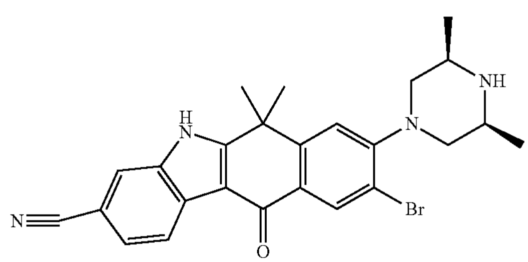 [SMILES: C[C@@H]1CN(c2cc3c(cc2Br)C(=O)c2c([nH]c4cc(C#N)ccc24)C3(C)C)C[C@H](C)N1] | 9-Bromo-8-((3R,5S)-3,5-dimethyl-piperazin-1-yl)-6,6-dimethyl-11-oxo-6,11-dihydro-5H-benzo[b]carbazole-3-carbonitrile | U | 2.05 | 477, 479 | B2-1 |
| 796 | F4-11 | 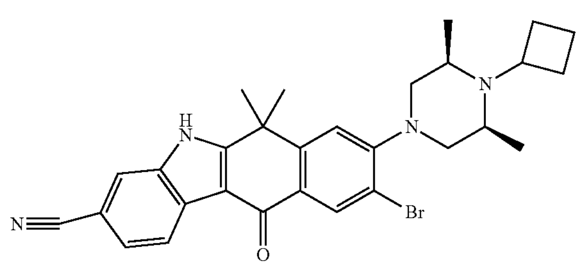 [SMILES: C[C@@H]1CN(c2cc3c(cc2Br)C(=O)c2c([nH]c4cc(C#N)ccc24)C3(C)C)C[C@H](C)N1C1CCC1] | 9-Bromo-8-((3R,5S)-4-cyclobutyl-3,5-dimethyl-piperazin-1-yl)-6,6-dimethyl-11-oxo-6,11-dihydro-5H-benzo[b]carbazole-3-carbonitrile | U | 2.28 | 531, 533 | B3-32 |

Example 797

Compound PR1

2-(4-Vinylphenyl)-2-methylpropanoic acid

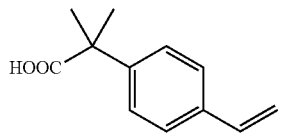

2-(4-Bromophenyl)-2-methylpropanoic acid (30 g), PPh$_3$ (5.0 g), potassium vinyltrifluoroborate (24.8 g), potassium carbonate (51.2 g), and palladium acetate (1.43 g) were dissolved in 1-propanol (198 ml) and distilled water (99 ml). After deaeration, the mixture was stirred under reflux for 6 hrs under nitrogen atmosphere. Insoluble matters were removed by filtration and washed with 1-propanol (210 ml). The filtrate was then concentrated under reduced pressure. Concentrated residues were partitioned between CPME (300 ml) and distilled water (150 ml, comprising 4.17 ml of ethylenediamine) The organic layer was removed and the aqueous layer was adjusted to pH 5 by using 2 N hydrochloric acid. The aqueous layer was extracted with a mixture of isopropyl acetate (240 ml) and heptane (240 ml). The organic layer was dried over anhydrous sodium sulfate and concentrated under reduced pressure. Ethanol (300 ml) was added thereto for suspending and washing the resultant. The solid was removed by Celite filtration, and the filtrate was concentrated under reduced pressure to obtain the title compound (21.7 g, 93%).

$^1$H-NMR (400 MHz CDCl$_3$) δ ppm 7.49-7.34 (4H, m), 6.69 (1H, dd, J=17.6, 11.0 Hz), 5.72 (1H, d, J=17.6 Hz), 5.23 (1H, d, 11.0 Hz), 1.59 (s, 6H)

HPLC retention time: 2.05 min (analysis condition S)

Example 798

Compound PR2

2-(4-Ethylphenyl)-2-methylpropanoic acid

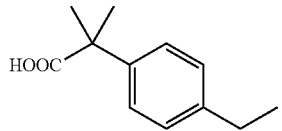

2-(4-Vinylphenyl)-2-methylpropanoic acid (58 g) was dissolved in ethanol, and then stirred for 3 hrs under atmospheric hydrogen pressure in the presence of 10% palladium carbon (5.8 g). The catalyst was removed by filtration, and the filtrate was concentrated to obtain a crude product, which was then suspended and washed with hexane to give the title compound (56.5 g, 94.8%).

$^1$H-NMR (270 MHz DMSO-d$_6$) δ ppm 12.28 (1H, s), 7.27-7.22 (2H, m), 7.18-7.14 (2H, m), 2.56 (2H, q, J=7.6 Hz), 1.45 (6H, s), 1.16 (3H, t, J=7.6 Hz)

LCMS: m/z 193 [M+H]$^+$

HPLC retention time: 2.18 min (analysis condition S)

Example 799

Compound PR3

2-(4-Ethyl-3-iodophenyl)-2-methylpropanoic acid

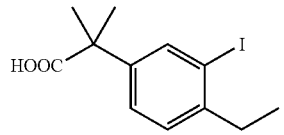

2-(4-Ethylphenyl)-2-methylpropanoic acid (58.1 g, 302.2 mmol) was dissolved in acetic acid (175 ml), added with N-iodosuccinimide (71.4 g, 317.3 mmol, 1.05 eq.) and conc. sulfuric acid (75 ml) at 0° C. Thereafter, the mixture was stirred at room temperature for 2 hrs. After cooling the reaction solution to 0° C., 10% aqueous solution of sodium hydrogen sulfite (100 ml) was added and the mixture was stirred for 1 hr. H$_2$O (450 ml) was added to the mixture and the precipitated solid was filtered to obtain the title compound as a crude product. Ethanol (150 ml) and 10% aqueous solution of sodium hydrogen sulfite (50 ml) were added to the crude product, and the mixture was dissolved under heating at 50° C. After confirming the dissolution, the solution was cooled to room temperature, added with H$_2$O (300 ml), and then stirred at 0° C. for 1 hr. The precipitated solid was filtered to obtain the title compound (95.8 g, 99%).

$^1$H-NMR (270 MHz DMSO-d$_6$) δ ppm 12.46 (1H, s), 7.70 (1H, d, J=1.8 Hz), 7.32 (1H, dd, J=8.1, 1.8 Hz), 7.26 (1H, d, J=8.1 Hz), 2.64 (2H, q, J=7.5 Hz), 1.43 (6H, s), 1.12 (3H, t, J=7.5 Hz)

HPLC retention time: 2.53 min (analysis condition S)

Example 800

Compound PR4

Tert-butyl 4-(4-ethyl-3-iodophenyl)-4-methyl-3-oxopentanoic acid

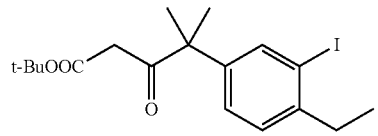

Mono-tert-butyl malonic acid (72.5 g) was dissolved in DME (360 ml), added with TEA (189 ml) and magnesium chloride (29.63 g) and the mixture was stirred for 2 hrs. In a separate vessel, CDI (52.75 g) was added to the DME (360 ml) solution of 2-(4-ethyl-3-iodophenyl)-2-methylpropanoic acid (90 g) and stirred at room temperature for 1 hr to prepare a solution. This solution was then added dropwise to the aforementioned mixture, and the resulting solution was washed with DME (90 ml) and stirred at 70° C. for 3 hrs. The reaction mixture was diluted with isopropyl acetate (225 ml) and heptane (225 ml), and the organic layer was washed with 2 N hydrochloric acid (684 ml), 0.17 N hydrochloric acid (540 ml), 15% aqueous solution of ammonium chloride (540 ml), 1 N aqueous solution of sodium hydroxide (540 ml) and 15% brine (540 ml) in order. The organic layer was concentrated under reduced pressure to obtain the title compound as a crude product, which was used for the next step without further purification.

¹H-NMR (270 MHz DMSO-d₆) δ: 7.64 (1H, d, J=2.0 Hz), 7.30 (1H, d, J=8.1 Hz), 7.24 (1H, d, J=8.0, 2.0 Hz), 3.32 (2H, s), 2.65 (2H, q, J=7.4 Hz), 1.40 (6H, s), 1.34 (9H, s), 1.13 (3H, t, J=7.4 Hz)

Example 801

Compound PR5-1

Tert-butyl 6-cyano-2-(2-(4-ethyl-3-iodophenyl)propan-2-yl)-1H-indole-3-carboxylic acid

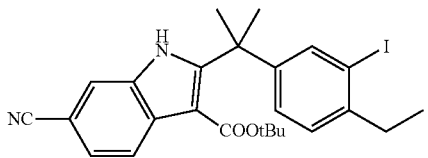 [SMILES: CCc1ccc(C(C)(C)c2[nH]c3cc(C#N)ccc3c2C(=O)OC)cc1I]

4-(4-Ethyl-3-iodophenyl)-4-methyl-3-oxopentanoic acid tert-butyl (117.76 g) was dissolved in DMF (471 ml) and added with cesium carbonate (276.5 g). DMF solution (176.6 ml) of 4-chloro-3-nitrobenzonitrile (63.9 g) was added dropwise thereto (washed with DMF 58.8 ml), and the mixture was stirred at 35° C. for 6 hrs. To the mixture, THF (588.8 ml), ethyl acetate (588.8 ml), acetic acid (72.87 ml) and distilled water (588.8 ml) were added for distillation, and the aqueous layer was removed. The organic layer was added with THF (588.8 ml) and water (588.8 ml), and under stirring sodium hydrosulfite (80%, 147.76 g) was added in small portions and the mixture was stirred at room temperature for 3 hrs. After removing the aqueous layer, the organic layer was washed with 15% brine (588.8 ml). The organic layer was added with 1 N hydrochloric acid (94.2 ml), stirred for 1 hr, and then added with 1 N aqueous solution of sodium hydroxide (329.7 ml). The aqueous layer was removed and the organic layer was concentrated under reduced pressure. The concentrated residues were dissolved in ethanol (824.3 ml) and added dropwise with distilled water (247.3 ml). The resulting precipitated crystals were filtered and collected, washed with water:ethanol (=1:2 mixture solution, 588.8 ml), and then dried to obtain the title compound (98.12 g, two-step 63.5%).

¹H-NMR (270 MHz DMSO-d₆) δ: 12.04 (1H, br. s), 8.01 (1H, d, J=8.4 Hz), 7.91 (1H, d, J=0.8 Hz), 7.55 (1H, d, J=1.8 Hz), 7.49 (1H, dd, J=1.5, 8.4 Hz), 7.16 (1H, d, J=8.1 Hz), 7.07 (1H, dd, J=2.0, 8.1 Hz), 2.58 (2H, q, J=7.4 Hz), 1.79 (6H, s), 1.23 (9H, s), 1.06 (3H, t, J=7.4 Hz)

LCMS: m/z 459, 515 [M+H]⁺

Example 802

Compound PR5-2

Methyl 6-cyano-2-(2-(4-ethyl-3-iodophenyl)propan-2-yl)-1H-indole-3-carboxylic acid

The title compound was prepared from monomethyl malonate and 2-(4-ethyl-3-iodophenyl)-2-methylpropanoic acid in the same manner as the method for Compound PR4 and Compound PR5-1.

¹H-NMR (270 MHz DMSO-D₆) δ: 12.20 (s, 1H), 8.06-8.03 (m, 1H), 7.95-7.94 (m, 1H), 7.58-7.57 (m, 1H), 7.53-7.49 (m, 1H), 7.17-7.14 (m, 1H), 7.06-7.02 (m, 1H), 3.46 (s, 3H), 2.65-2.56 (q, 2H, J=7.5 Hz), 1.78 (s, 6H), 1.12-1.07 (t, 3H, J=7.5 Hz)

LCMS: m/z 473 [M+H]⁺

Example 803

Compound PR6

Tert-butyl 6-cyano-2-(2-(4-ethyl-3-(4-morpholin-4-yl-piperidin-1-yl)phenyl)propan-2-yl)-1H-indole-3-carboxylic acid hydrochloric acid salt

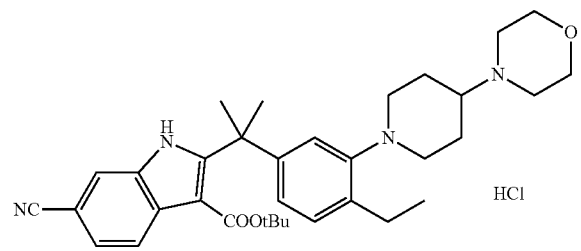

Tert-butyl 6-cyano-2-(2-(4-ethyl-3-iodophenyl)propan-2-yl)-1H-indole-3-carboxylic acid (390.5 g), 4-morpholin-4-yl piperidine (158 g), and 1,3-bis-(2,6-diisopropylphenyl)-imidazoyl-2-ylidene (allyl) palladium (II) chloride (8.83 g) were dissolved in a mixture of NaHMDS (1.9 M, THF solution 1.32 L) and DME (1.95 L) under nitrogen stream, and the mixture was stirred at 40° C. for 1 hr. The reaction mixture was then partitioned between isopropyl acetate (1.95 L) and 20% aqueous solution of ammonium chloride (1.95 L). The organic layer was washed twice with 10% brine (1.56 L), and then concentrated under reduced pressure. The resulting residues were dissolved in a mixture of DME (3.9 L) and water (78.1 ml), added with N-acetylcysteine (12.39 g), and stirred at 45° C. for 1 hr. After that, the insoluble matters were filtered and washed with DME (1.95 L). The filtrate was concentrated under reduced pressure. The resulting residues were dissolved in acetone (5.5 L) and added with the solution in which pyridinium chloride (96.5 g) is dissolved in acetone (195 ml) and ethanol (78 ml). The precipitated solid was filtered, collected, washed with acetone (1.95 L) and dried to obtain the title compound (373 g, 83%).

¹H-NMR (400 MHz DMSO-D₆) δ: 12.03 (1H, s), 10.75-10.88 (1H, m), 7.99 (1 H, d, J=8.3 Hz), 7.93 (1H, d, J=1.3 Hz), 7.46 (1H, dd, J=1.3, 8.1 Hz), 7.10 (1H, d, J=7.9 Hz), 6.88 (1H, dd, J=1.7, 7.9 Hz), 6.79 (1H, d, J=1.7 Hz), 3.91-4.01 (2H, m), 3.76-3.87 (2H, m), 3.37-3.46 (2H, m), 3.22 (1H, m), 2.94-3.11 (4H, m), 2.57 (2H, q, J=7.5 Hz), 2.45-2.53 (2H, m), 2.09-2.16 (2H, m), 1.80 (6H, s), 1.71-1.77 (2H, m), 1.19 (9H, s), 1.14 (3H, t, J=7.5 Hz)

LCMS: m/z 557 [M+H]⁺

Example 804

Compound PR7

6-Cyano-2-(2-(4-ethyl-3-(4-morpholin-4-yl-piperidin-1-yl)phenyl)propan-2-yl)-1H-indole-3-carboxylic acid

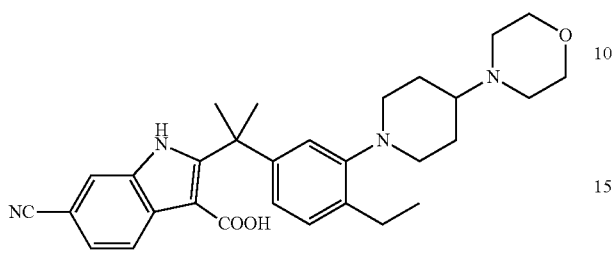

Tert-butyl 6-cyano-2-(2-(4-ethyl-3-(4-morpholin-4-yl-piperidin-1-yl)phenyl)propan-2-yl)-1H-indole-3-carboxylic acid hydrochloric acid salt (1400 g) was suspended in TFE (7 L) under nitrogen stream, and added dropwise with TMSCl (554 ml) at 8° C. After stirring for 3 hrs, the reaction solution was added with acetone (5.6 L) and aqueous solution of NaOH (1 N, 4.39 L), and 10% aqueous solution of $K_2HPO_4$ (1.4 L) was added thereto for neutralization. The precipitated solid was filtered and collected, washed twice with a mixture solution of water:acetone (=1:1, 2.8 L), and dried to obtain the title compound (1061 g, 96.6%).

$^1$H-NMR (270 MHz DMSO-D$_6$) δ: 11.95 (1H, s), 11.92 (1H, bs), 8.04 (1H, d, J=8.4 Hz), 7.89 (1H, d, J=1.3 Hz), 7.44 (1H, J=dd, 1.3, 8.4 Hz), 7.00 (1H, d, J=8.4 Hz), 6.88 (1H, d, J=1.8 Hz), 6.71 (1H, dd, J=2.2, 7.9 Hz), 3.50-3.55 (4H, m), 2.92-2.96 (2H, m), 2.54 (2H, q, 7.5 Hz), 2.39-2.50 (6H, m), 2.15-2.22 (1H, m), 1.74-1.85 (8H, m), 1.43-1.52 (2H, m), 1.13 (3H, t, J=7.5 Hz)

LCMS: m/z 501 [M+H]$^+$

HPLC retention time: 1.53 min (analysis condition U)

Example 805

Compound F6-20

9-Ethyl-6,6-dimethyl-8-(4-morpholin-4-yl-piperidin-1-yl)-11-oxo-6,11-dihydro-5H-benzo[b]carbazole-3-carbonitrile

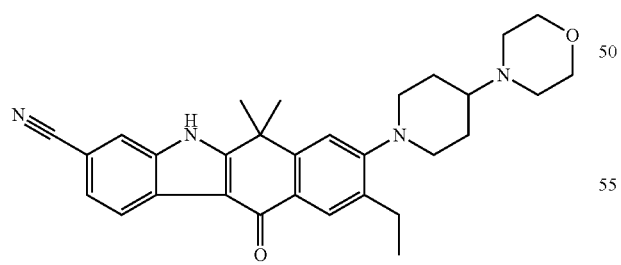

6-Cyano-2-(2-(4-ethyl-3-(4-morpholin-4-yl-piperidin-1-yl)phenyl)propan-2-yl)-1H-indole-3-carboxylic acid (500 g) was dissolved in a mixture of DMA (9.4 L), acetic anhydride (270 ml) and DIPEA (1170 ml) under nitrogen stream. The mixture was stirred at 90° C. for 1 hr. After cooling to room temperature, the mixture was added with methanol (3.525 L) and subsequently with distilled water (5.875 L). The precipitated solid was filtered, collected, washed twice with the mixture solution (methanol:water=3:5, 1.41 L), and then dried to obtain the title compound (389.6 g, 85%).

$^1$H-NMR (400 MHz, DMSO-d$_6$) δ: 12.70 (1H, s), 8.32 (1H, d, J=7.9 Hz), 8.04 (1H, s), 8.00 (1H, s), 7.61 (1H, d, J=8.5 Hz), 7.34 (1H, s), 3.64-3.57 (4H, m), 3.27-3.18 (2H, m), 2.82-2.66 (4H, m), 2.39-2.28 (1H, m), 1.96-1.87 (2H, m), 1.76 (6H, s), 1.69-1.53 (2H, m), 1.29 (3H, t, J=7.3 Hz)

LCMS: m/z 483 [M+H]$^+$

HPLC retention time: 1.98 min (analysis condition U)

Hydrochloric Acid Salt of Compound F6-20

9-Ethyl-6,6-dimethyl-8-(4-morpholin-4-yl-piperidin-1-yl)-11-oxo-6,11-dihydro-5H-benzo[b]carbazole-3-carbonitrile (400 g) was dissolved in a mixture solvent of methylethyl ketone (4.8 L), acetic acid (1.44 L) and distilled water (1.68 L) at room temperature. The resulting solution was added dropwise to the mixture of ethanol (12 L) and 2 N hydrochloric acid (0.8 L). The precipitated solid was filtered, washed with ethanol (2 L), and dried to obtain hydrochloric acid salt of Compound F6-20 (357 g).

$^1$H-NMR (400 MHz, DMSO-d$_6$) δ: 12.83 (1H, s), 10.78 (1H, s), 8.32 (1H, d, J=8.1 Hz), 8.06 (1H, s), 8.01 (1H, s), 7.61 (1H, d, J=8.1 Hz), 7.37 (1H, s), 4.02 (2H, m), 3.85 (2H, m), 3.51 (2H, m), 3.34 (1H, m), 3.32 (2H, m), 3.15 (2H, m), 2.81 (2H, dd, J=11.98, 11.7 Hz), 2.72 (2H, q, J=7.5 Hz), 2.23 (2H, m), 1.89 (2H, m), 1.77 (6H, s), 1.29 (3H, t, J=7.5 Hz)

FABMS: m/z 483.4 [M+H]$^+$

Example 806

Compound F6-22

9-Ethyl-6,6-dimethyl-10-(4-morpholin-4-yl-piperidin-1-yl)-11-oxo-6,11-dihydro-5H-benzo[b]carbazole-3-carbonitrile

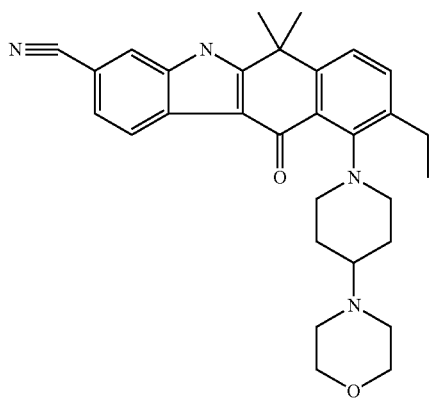 [SMILES: CCc1ccc2c(c1N1CCC(N3CCOCC3)CC1)C(=O)c1c([nH]c3cc(C#N)ccc13)C2(C)C]

From the filtrate solution obtained from the synthesis of Compound F6-20, the title compound was obtained.

$^1$H-NMR (400 MHz DMSO-D$_6$) δ: 12.56 (1H, s), 8.32 (1H, d, J=7.9 Hz), 7.96 (1H, s), 7.45-7.59 (3H, m), 3.55-3.62 (4H, m), 3.36-3.50 (2H, m), 2.75-2.86 (2H, m), 2.71 (2H, q, J=7.5 Hz), 2.45-2.56 (4H, m), 2.27-2.38 (1H, m), 1.73-1.84 (2H, m), 1.69 (6H, s), 1.43-1.58 (2H, m), 1.21 (3H, t, J=7.5 Hz).

LCMS: m/z 483 [M+H]$^+$

HPLC retention time: 1.52 min (analysis condition U)

Example 807

Compound PR8

9-Ethyl-6,6-dimethyl-8-iodo-11-oxo-6,11-dihydro-5H-benzo[b]carbazole-3-carbonitrile

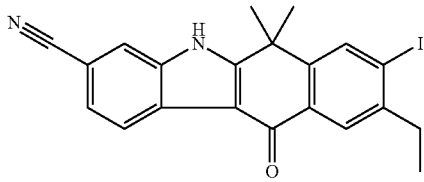 [SMILES: CCc1cc2c(cc1I)C(C)(C)c1[nH]c3cc(C#N)ccc3c1C2=O]

Tert-butyl 6-cyano-2-(2-(4-ethyl-3-iodophenyl)propan-2-yl)-1H-indole-3-carboxylic acid (11 g) was dissolved in Eaton's reagent (200 g) and stirred at room temperature for 30 min. The reaction solution was diluted with acetonitrile (200 ml) and distilled water (400 ml). The precipitated solid was collected by filtration, washed with distilled water, and then dried. The crude product was dissolved in DMA (45 ml), diluted with acetonitrile (20 ml) and distilled water (18 ml), and re-precipitated to obtain the title compound (6.62 g, 70%).

$^1$H-NMR (400 MHz DMSO-$D_6$) δ: 12.79 (1H, s), 8.32-8.29 (2H, m), 8.06 (1H, s), 8.01 (1H, s), 7.62 (1H, dd, J=1.3, 7.9 Hz), 2.78 (2H, q, J=7.5 Hz), 1.75 (6H, s), 1.20 (3H, t, J=7.5 Hz)

LCMS: m/z 441 [M+H]$^+$

HPLC retention time: 3.17 min (analysis condition U)

Example 808

Compound PR9-1

8-(1,4-Dioxa-8-aza-spiro[4.5]dec-8-yl)-9-ethyl-6,6-dimethyl-11-oxo-6,11-dihydro-5H-benzo[b]carbazole-3-carbonitrile

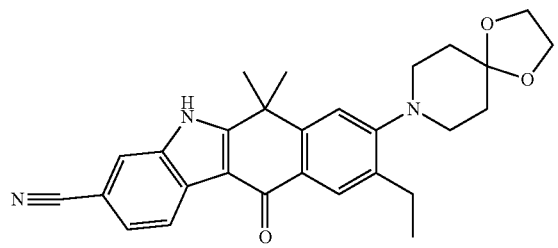 [SMILES: CCc1cc2c(cc1N1CCC3(CC1)OCCO3)C(C)(C)c1[nH]c3cc(C#N)ccc3c1C2=O]

The dioxane solution (50 ml) of 9-ethyl-6,6-dimethyl-8-iodo-11-oxo-6,11-dihydro-5H-benzo[b]carbazole-3-carbonitrile (5.0 g), 1,4-dioxa-8-aza-spiro[4.5]decane (2.08 ml), Pd$_2$(dba)$_3$ (520 mg), and S-Phos (963 mg) was flushed with nitrogen gas, added with NaHMDS (1M, THF solution 40 ml), and stirred at 60° C. for 1 hr. The resulting mixture was diluted with ethyl acetate (200 ml). The organic layer was washed three times with 10% brine, and then concentrated under reduced pressure to obtain the title compound as a crude product. This crude product was used for the next step without further purification.

LCMS: m/z 456 [M+H]$^+$

HPLC retention time: 2.78 min (analysis condition U)

Example 809

Compound PR9-2

9-Ethyl-6,6-dimethyl-11-oxo-6,11-dihydro-5H-benzo[b]carbazole-3-carbonitrile

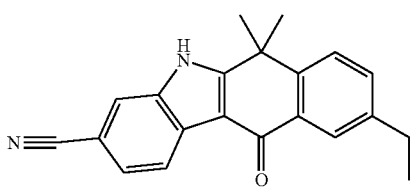 [SMILES: CCc1ccc2c(c1)C(=O)c1c([nH]c3cc(C#N)ccc13)C2(C)C]

As a by-product of Compound PR9-1, the target compound was obtained according to silica gel column separation of Example 810.

LCMS: m/z 315 [M+H]$^+$

HPLC retention time: 2.77 min (analysis condition U)

Example 810

Compound PR10-1

9-Ethyl-6,6-dimethyl-11-oxo-8-(4-oxopiperidin-1-yl)-6,11-dihydro-5H-benzo[b]carbazole-3-carbonitrile

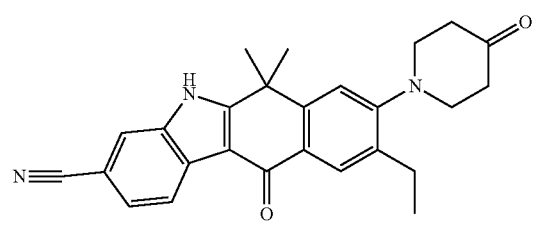 [SMILES: CCc1cc2c(cc1N1CCC(=O)CC1)C(C)(C)c1[nH]c3cc(C#N)ccc3c1C2=O]

8-(1,4-Dioxa-8-aza-spiro[4.5]dec-8-yl)-9-ethyl-6,6-dimethyl-11-oxo-6,11-dihydro-5H-benzo[b]carbazole-3-carbonitrile, which had been prepared in Example 809, was dissolved in THF (10 ml), added with 5 N hydrochloric acid (50 ml), and the mixture was stirred for 17 hrs. The reaction mixture was neutralized with 5 N aqueous solution of sodium hydroxide and diluted with ethyl acetate (200 ml). The organic layer was washed with 10% brine, and then concentrated under reduced pressure. The resulting residues were purified by silica gel column (dichloromethane/methanol=99/1 to 90/10) to obtain the title compound (2.9 g, two step yield 64%).

$^1$H-NMR (400 MHz DMSO-$D_6$) δ: 12.70 (1H, s), 8.32 (1H, d, J=8.4), 8.07 (1H, s), 7.99 (1H, s), 7.60 (1H, dd, J=1.3, 7.9 Hz), 7.42 (1H, s), 3.28 (4H, t, J=5.7), 2.80 (q, 2H, J=7.5 Hz), 2.55 (4H, t, J=5.7), 1.75 (6H, s), 1.31 (3H, t, J=7.5 Hz)

LCMS: m/z 412 [M+H]$^+$

HPLC retention time: 2.57 min (analysis condition U)

Example 811

Compound PR11-1

9-Ethyl-6,6-dimethyl-11-oxo-8-[4-(3-oxo-piperazin-1-yl)-piperidin-1-yl]-6,11-dihydro-5H-benzo[b]carbazole-3-carbonitrile

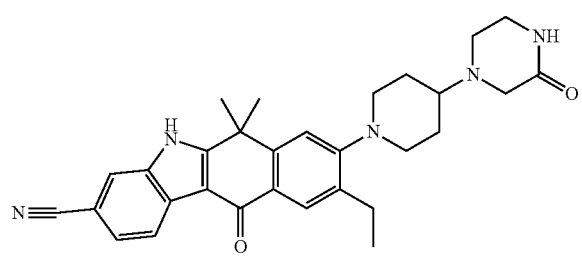 [SMILES: CCc1cc2c(cc1N1CCC(N3CCNC(=O)C3)CC1)C(C)(C)c1[nH]c3cc(C#N)ccc3c1C2=O]

9-Ethyl-6,6-dimethyl-11-oxo-8-(4-oxopiperidin-1-yl)-6,11-dihydro-5H-benzo[b]carbazole-3-carbonitrile (30 mg) and 2-ketopiperazine (10 mg) were dissolved in THF (2 ml), added with sodium triacetoxy borohydride (30 mg), and the mixture was stirred at 30° C. for 6 hrs. The reaction mixture was diluted with ethyl acetate (20 ml). The organic layer was washed with 10% brine, and then concentrated under reduced pressure. The resulting residues were purified by silica gel column (dichloromethane/methanol=99/1 to 90/10) to obtain the title compound (11.5 mg, yield 32%).

LCMS: m/z 496 [M+H]$^+$

HPLC retention time: 1.90 min (analysis condition U)

Example 812

Compound PR11-2

9-Ethyl-8-(4-hydroxy-piperidin-1-yl)-6,6-dimethyl-11-oxo-6,11-dihydro-5H-benzo[b]carbazole-3-carbonitrile

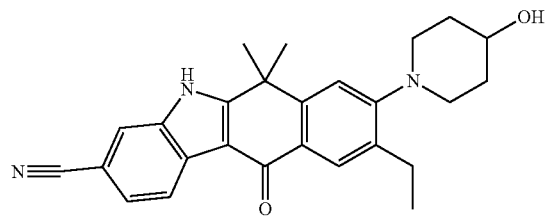 [SMILES: CCc1cc2c(cc1N1CCC(O)CC1)C(C)(C)c1[nH]c3cc(C#N)ccc3c1C2=O]

As a by-product of Compound PR11-1, the target compound was obtained.

LCMS: m/z 414 [M+H]$^+$

HPLC retention time: 2.13 min (analysis condition S)

The compounds described in the following Tables 8-10 were synthesized by introducing a corresponding amine to 9-ethyl-6,6-dimethyl-8-iodo-11-oxo-6,11-dihydro-5H-benzo[b]carbazole-3-carbonitrile according to the method used for the synthesis of Compound PR9-1. Although the relevant literatures are not entirely known, some amines in which a tertiary alkyl group is attached to the nitrogen atom were prepared according to the method described in Journal of Medicinal Chemistry, 45 (14), 3143-3160, 2002. Alternatively, the preparation was carried out by introducing a corresponding amine to 9-ethyl-6,6-dimethyl-11-oxo-8-(4-oxopiperidin-1-yl)-6,11-dihydro-5H-benzo[b]carbazole-3-carbonitrile based on the method that is used for the synthesis of Compound PR11-1 (i.e., reductive amination).

TABLE 8

| Example No. | Comp. No. | Structure | Compound Name | HPLC Condition | Retention Time | m/z |
|---|---|---|---|---|---|---|
| 813 | PR9-3 | 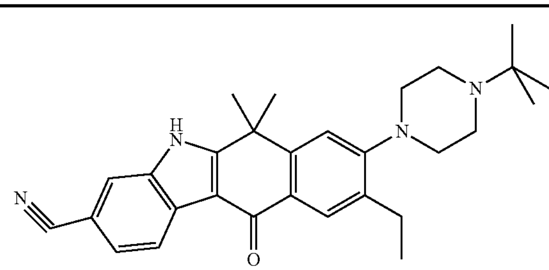 | 8-(4-tert-Butyl-piperazin-1-yl)-9-ethyl-6,6-dimethyl-11-oxo-6,11-dihydro-5H-benzo[b]carbazole-3-carbonitrile | S | 1.63 | 455 |
| 814 | PR9-4 | 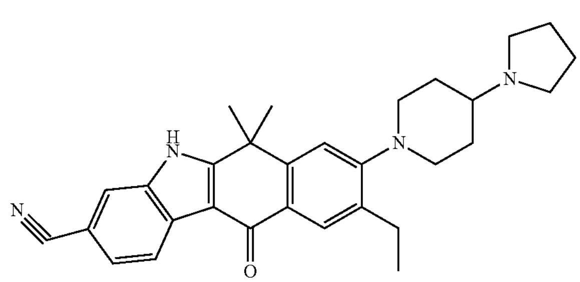 [SMILES: CCc1cc2c(cc1N1CCC(N3CCCC3)CC1)C(C)(C)c1[nH]c3cc(C#N)ccc3c1C2=O] | 9-Ethyl-6,6-dimethyl-11-oxo-8-(4-pyrrolidin-1-yl-piperidin-1-yl)-6,11-dihydro-5H-benzo[b]carbazole-3-carbonitrile | U | 2.13 | 467 |

TABLE 8-continued

| Example No. | Comp. No. | Structure | Compound Name | HPLC Condition | Retention Time | m/z |
|---|---|---|---|---|---|---|
| 815 | PR9-5 | 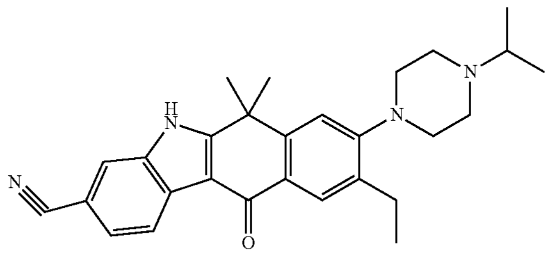 [SMILES: CCc1cc2c(cc1N1CCN(C(C)C)CC1)C(C)(C)c1[nH]c3cc(C#N)ccc3c1C2=O] | 9-Ethyl-8-(4-isopropyl-piperazin-1-yl)-6,6-dimethyl-11-oxo-6,11-dihydro-5H-benzo[b]carbazole-3-carbonitrile | U | 2.08 | 441 |
| 816 | PR9-6 | 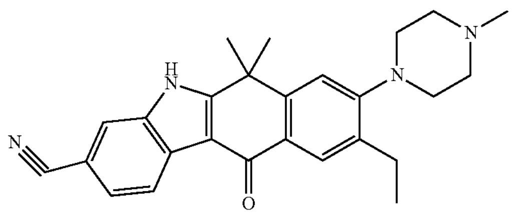 [SMILES: CCc1cc2c(cc1N1CCN(C)CC1)C(C)(C)c1[nH]c3cc(C#N)ccc3c1C2=O] | 9-Ethyl-6,6-dimethyl-8-(4-methyl-piperazin-1-yl)-11-oxo-6,11-dihydro-5H-benzo[b]carbazole-3-carbonitrile | U | 1.97 | 413 |
| 817 | PR9-7 | 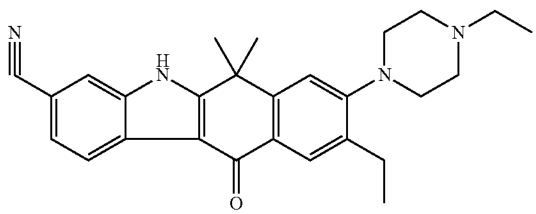 [SMILES: CCc1cc2c(cc1N1CCN(CC)CC1)C(C)(C)c1[nH]c3cc(C#N)ccc3c1C2=O] | 9-Ethyl-8-(4-ethyl-piperazin-1-yl)-6,6-dimethyl-11-oxo-6,11-dihydro-5H-benzo[b]carbazole-3-carbonitrile | U | 2.03 | 427 |
| 818 | PR9-8 | 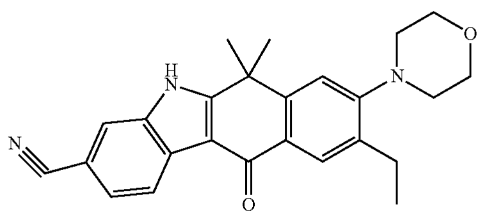 [SMILES: CCc1cc2c(cc1N1CCOCC1)C(C)(C)c1[nH]c3cc(C#N)ccc3c1C2=O] | 9-Ethyl-6,6-dimethyl-8-morpholin-4-yl-11-oxo-6,11-dihydro-5H-benzo[b]carbazole-3-carbonitrile | U | 2.65 | 400 |
| 819 | PR11-3 | 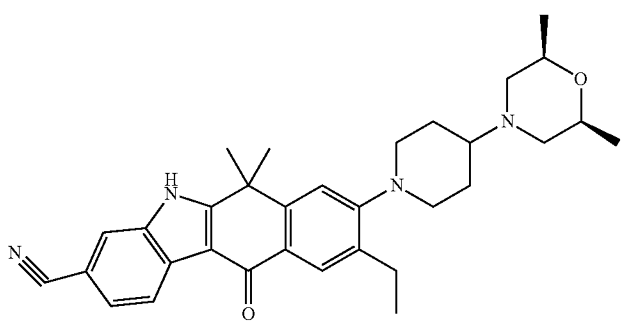 [SMILES: CCc1cc2c(cc1N1CCC(N3C[C@@H](C)O[C@@H](C)C3)CC1)C(C)(C)c1[nH]c3cc(C#N)ccc3c1C2=O] | 8-[4-((2R,6S)-2,6-Dimethyl-morpholin-4-yl)-piperidin-1-yl]-9-ethyl-6,6-dimethyl-11-oxo-6,11-dihydro-5H-benzo[b]carbazole-3-carbonitrile | S | 1.65 | 511 |
| 820 | PR11-4 | 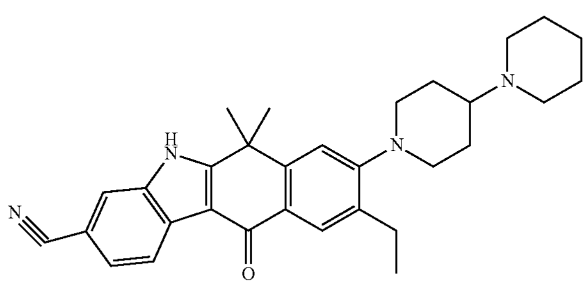 [SMILES: CCc1cc2c(cc1N1CCC(N3CCCCC3)CC1)C(C)(C)c1[nH]c3cc(C#N)ccc3c1C2=O] | 8-[1,4']Bipiperidinyl-1'-yl-9-ethyl-6,6-dimethyl-11-oxo-6,11-dihydro-5H-benzo[b]carbazole-3-carbonitrile | S | 1.63 | 481 |

TABLE 8-continued

| Example No. | Comp. No. | Structure | Compound Name | HPLC Condition | Retention Time | m/z |
|---|---|---|---|---|---|---|
| 821 | PR11-5 | 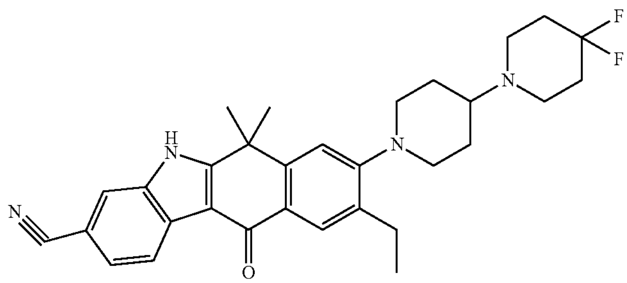 [SMILES: CCc1cc2c(cc1N1CCC(N3CCC(F)(F)CC3)CC1)C(C)(C)c1[nH]c3cc(C#N)ccc3c1C2=O] | 8-(4,4-Difluoro-[1,4']bipiperidinyl-1'-yl)-9-ethyl-6,6-dimethyl-11-oxo-6,11-dihydro-5H-benzo[b]carbazole-3-carbonitrile | S | 1.70 | 517 |
| 822 | PR11-6 | 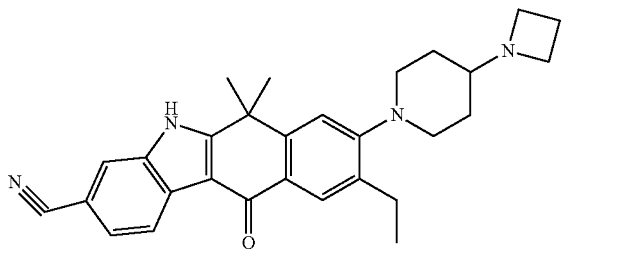 [SMILES: CCc1cc2c(cc1N1CCC(N3CCC3)CC1)C(C)(C)c1[nH]c3cc(C#N)ccc3c1C2=O] | 8-(4-Azetidin-1-yl-piperidin-1-yl)-9-ethyl-6,6-dimethyl-11-oxo-6,11-dihydro-5H-benzo[b]carbazole-3-carbonitrile | S | 1.55 | 453 |
| 823 | PR11-7 | 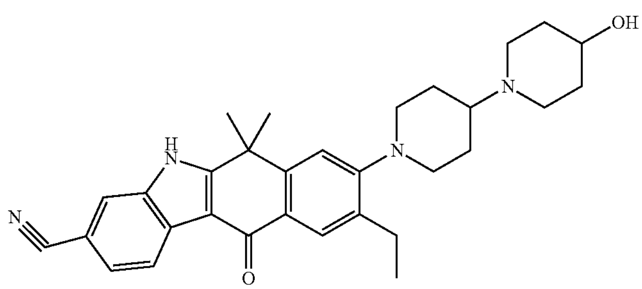 [SMILES: CCc1cc2c(cc1N1CCC(N3CCC(O)CC3)CC1)C(C)(C)c1[nH]c3cc(C#N)ccc3c1C2=O] | 9-Ethyl-8-(4-hydroxy-[1,4']bipiperidinyl-1'-yl)-6,6-dimethyl-11-oxo-6,11-dihydro-5H-benzo[b]carbazole-3-carbonitrile | U | 1.95 | 497 |
| 824 | PR9-9 | 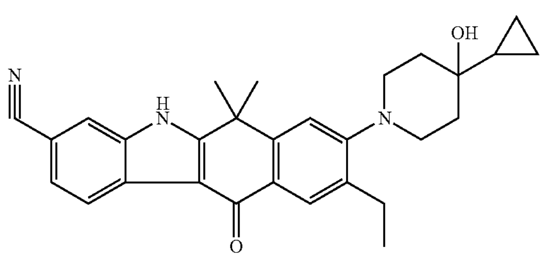 [SMILES: CCc1cc2c(cc1N1CCC(O)(C3CC3)CC1)C(C)(C)c1[nH]c3cc(C#N)ccc3c1C2=O] | 8-(4-Cyclopropyl-4-hydroxy-piperidin-1-yl)-9-ethyl-6,6-dimethyl-11-oxo-6,11-dihydro-5H-benzo[b]carbazole-3-carbonitrile | U | 2.53 | 454 |
| 825 | PR11-8 | 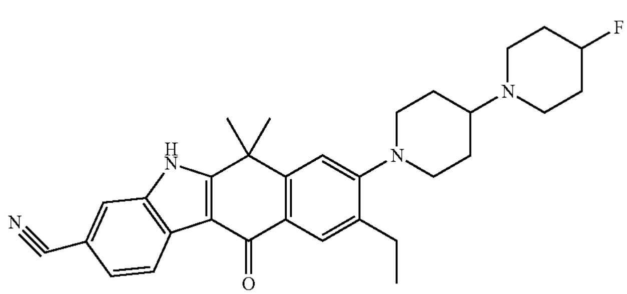 [SMILES: CCc1cc2c(cc1N1CCC(N3CCC(F)CC3)CC1)C(C)(C)c1[nH]c3cc(C#N)ccc3c1C2=O] | 9-Ethyl-8-(4-fluoro-[1,4']bipiperidinyl-1'-yl)-6,6-dimethyl-11-oxo-6,11-dihydro-5H-benzo[b]carbazole-3-carbonitrile | U | 2.13 | 499 |

TABLE 8-continued

| Example No. | Comp. No. | Structure | Compound Name | HPLC Condition | Retention Time | m/z |
|---|---|---|---|---|---|---|
| 826 | PR9-10 | 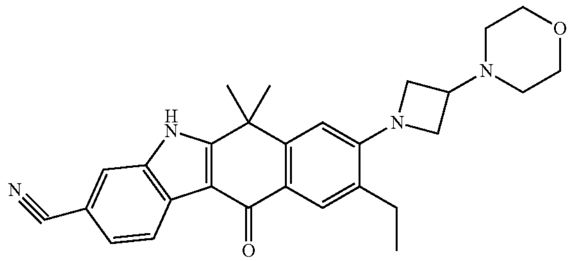 [SMILES: CCc1cc2c(cc1N1CC(N3CCOCC3)C1)C(C)(C)c1[nH]c3cc(C#N)ccc3c1C2=O] | 9-Ethyl-6,6-dimethyl-8-(3-morpholin-4-yl-azetidin-1-yl)-11-oxo-6,11-dihydro-5H-benzo[b]carbazole-3-carbonitrile | S | 1.48 | 455 |

TABLE 9

| Example No. | Comp. No. | Structure | Compound Name | HPLC Condition | Retention Time | m/z |
|---|---|---|---|---|---|---|
| 827 | PR9-11 | 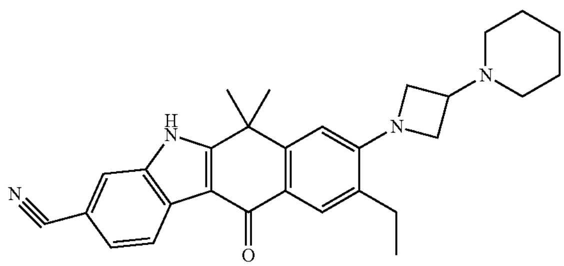 [SMILES: CCc1cc2c(cc1N1CC(N3CCCCC3)C1)C(C)(C)c1[nH]c3cc(C#N)ccc3c1C2=O] | 9-Ethyl-6,6-dimethyl-11-oxo-8-(3-piperidin-1-yl-azetidin-1-yl)-6,11-dihydro-5H-benzo[b]carbazole-3-carbonitrile | S | 1.57 | 453 |
| 828 | PR9-12 | 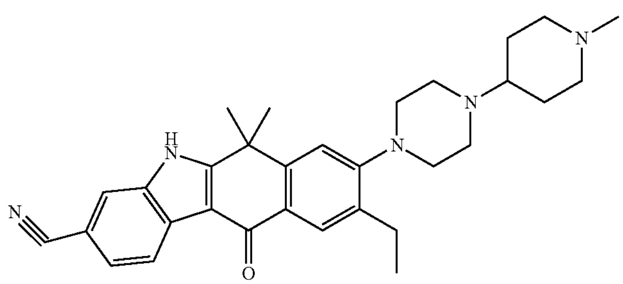 | 9-Ethyl-6,6-dimethyl-8-[4-(1-methyl-piperidin-4-yl)-piperazin-1-yl]-11-oxo-6,11-dihydro-5H-benzo[b]carbazole-3-carbonitrile | U | 1.70 | 496 |
| 829 | PR9-13 | 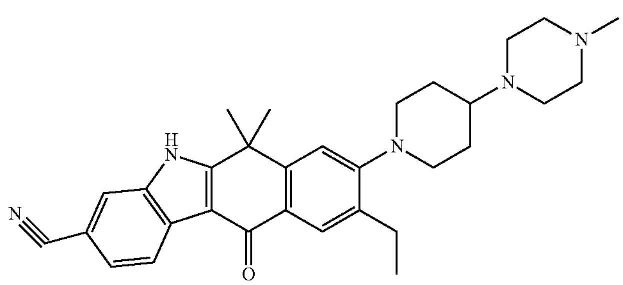 [SMILES: CCc1cc2c(cc1N1CCC(N3CCN(C)CC3)CC1)C(C)(C)c1[nH]c3cc(C#N)ccc3c1C2=O] | 9-Ethyl-6,6-dimethyl-8-[4-(4-methyl-piperazin-1-yl)-piperidin-1-yl]-11-oxo-6,11-dihydro-5H-benzo[b]carbazole-3-carbonitrile | U | 1.73 | 496 |

TABLE 9-continued

| Example No. | Comp. No. | Structure | Compound Name | HPLC Condition | Retention Time | m/z |
|---|---|---|---|---|---|---|
| 830 | PR11-9 | 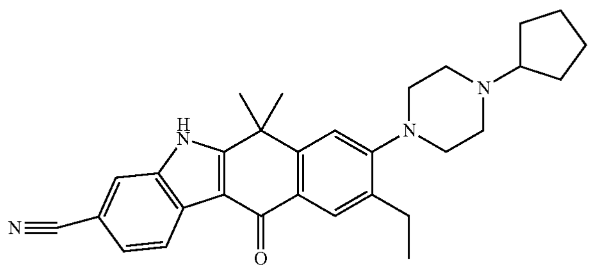 [SMILES: CCc1cc2c(cc1N1CCN(C3CCCC3)CC1)C(C)(C)c1[nH]c3cc(C#N)ccc3c1C2=O] | 8-(4-Cyclopentyl-piperazin-1-yl)-9-ethyl-6,6-dimethyl-11-oxo-6,11-dihydro-5H-benzo[b]carbazole-3-carbonitrile | U | 2.12 | 467 |
| 831 | PR11-10 | 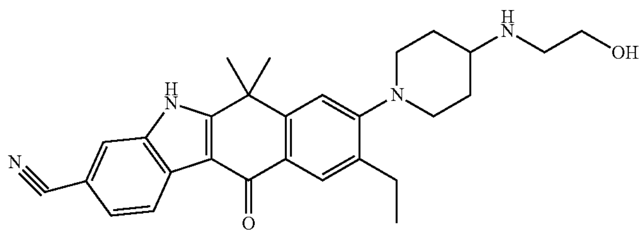 [SMILES: CCc1cc2c(cc1N1CCC(NCCO)CC1)C(C)(C)c1[nH]c3cc(C#N)ccc3c1C2=O] | 9-Ethyl-8-[4-(2-hydroxy-ethylamino)-piperidin-1-yl]-6,6-dimethyl-11-oxo-6,11-dihydro-5H-benzo[b]carbazole-3-carbonitrile | U | 1.90 | 457 |
| 832 | PR11-11 | 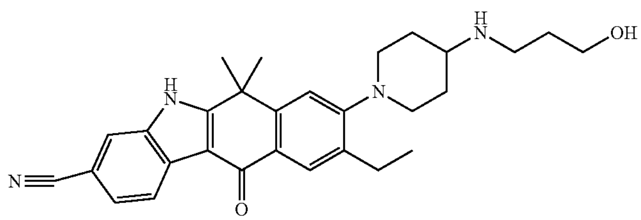 [SMILES: CCc1cc2c(cc1N1CCC(NCCCO)CC1)C(C)(C)c1[nH]c3cc(C#N)ccc3c1C2=O] | 9-Ethyl-8-[4-(3-hydroxy-propylamino)-piperidin-1-yl]-6,6-dimethyl-11-oxo-6,11-dihydro-5H-benzo[b]carbazole-3-carbonitrile | S | 1.90 | 471 |
| 833 | PR9-14 | 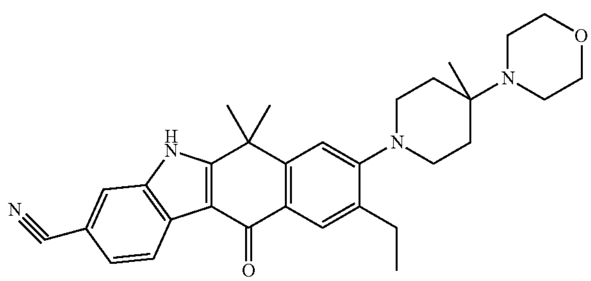 [SMILES: CCc1cc2c(cc1N1CCC(C)(N3CCOCC3)CC1)C(C)(C)c1[nH]c3cc(C#N)ccc3c1C2=O] | 9-Ethyl-6,6-dimethyl-8-(4-methyl-4-morpholine-4-yl-piperidine-1-y)-11-oxo-6,11-dihydro-5H-benzo[b]carbazole-3-carbonitrile | U | 2.00 | 497 |
| 834 | PR9-15 | 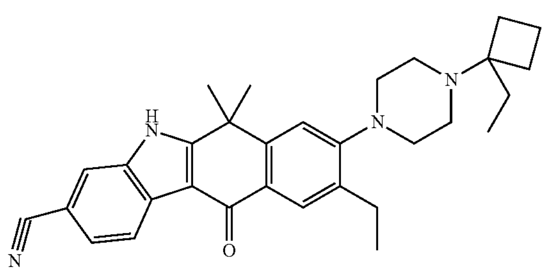 [SMILES: CCc1cc2c(cc1N1CCN(C3(CC)CCC3)CC1)C(C)(C)c1[nH]c3cc(C#N)ccc3c1C2=O] | 9-Ethyl-8-[4-(1-ethyl-cyclobutyl)-piperazine-1-yl]-6,6-dimethyl-11-oxo-6,11-dihydro-5H-benzo[b]carbazole-7-carbonitrile | Y | 2.25 | 481 |
| 835 | PR9-16 | 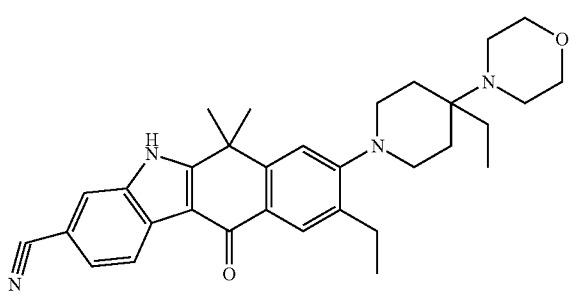 [SMILES: CCc1cc2c(cc1N1CCC(CC)(N3CCOCC3)CC1)C(C)(C)c1[nH]c3cc(C#N)ccc3c1C2=O] | 9-Ethyl-8-(4-ethyl-4-morpholine-4-yl-piperidine-1-yl)-6,6-dimethyl-11-oxo-6,11-dihydro-5H-benzo[b]carbazole-3-carbonitrile | Y | 2.17 | 511 |

TABLE 9-continued

| Example No. | Comp. No. | Structure | Compound Name | HPLC Condition | Retention Time | m/z |
|---|---|---|---|---|---|---|
| 836 | PR9-17 | 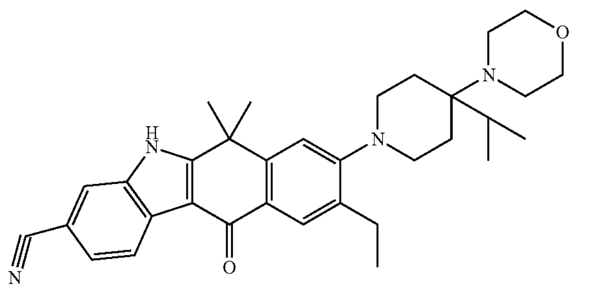 [SMILES: CCc1cc2c(cc1N1CCC(C(C)C)(N3CCOCC3)CC1)C(C)(C)c1[nH]c3cc(C#N)ccc3c1C2=O] | 9-Ethyl-8-(4-isopropyl-4-morpholine-4 yl-piperidine-1-yl)-6,6-dimethyl-11-oxo-6,11-dihydro-5H-benzo[b]carbazole-3-carbonitrile | U | 2.12 | 525 |
| 837 | PR9-18 | 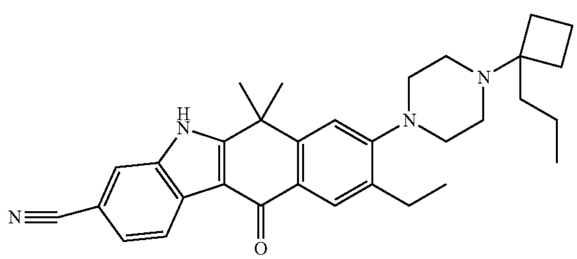 [SMILES: CCCC1(N2CCN(c3cc4c(cc3CC)C(=O)c3c([nH]c5cc(C#N)ccc35)C4(C)C)CC2)CCC1] | 9-Ethyl-6,6-dimethyl-11-oxo-8-[4-(1-propyl-cyclobutyl)-piperazine-1-yl]-6,11-dihydro-5H-benzo[b]carbazole-3-carbonitrile | U | 2.28 | 495 |
| 838 | PR9-19 | 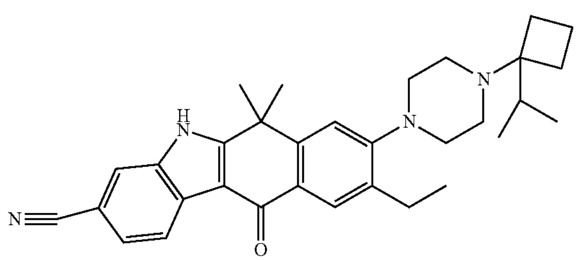 [SMILES: CCc1cc2c(cc1N1CCN(C3(C(C)C)CCC3)CC1)C(C)(C)c1[nH]c3cc(C#N)ccc3c1C2=O] | 9-Ethyl-8-[4-(1-isopropyl-cyclobutyl-piperazine-1-yl]-6,6-dimethyl-11-oxo-6,11-dihydro-5H-benzo[b]carbazole-3-carbonitrile | U | 2.25 | 495 |
| 839 | PR9-20 | 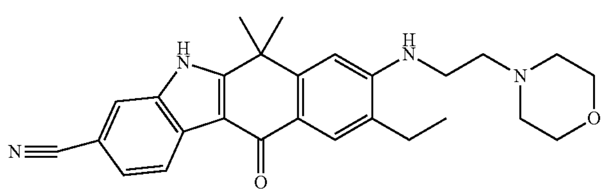 [SMILES: CCc1cc2c(cc1NCCN1CCOCC1)C(C)(C)c1[nH]c3cc(C#N)ccc3c1C2=O] | 9-Ethyl-6,6-dimethyl-8-(2-morpholine-4-yl-ethylamino)-11-oxo-6,11-dihydro-5H-benzo[b]carbazole-3-carbonitrile | Y | 1.85 | 443 |
| 840 | PR9-21 | 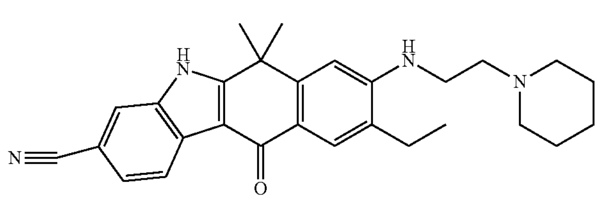 [SMILES: CCc1cc2c(cc1NCCN1CCCCC1)C(C)(C)c1[nH]c3cc(C#N)ccc3c1C2=O] | 9-Ethyl-6,6-dimethyl-11-oxo-8-(2-piperidine-1-yl-ethylamino)-6,11-dihydro-5H-benzo[b]carbazole-3-carbonitrile | Y | 1.85 | 441 |

TABLE 10

| Example No. | Comp. No. | Structure | Compound Name | HPLC Condition | Retention Time | m/z |
|---|---|---|---|---|---|---|
| 841 | PR11-12 | 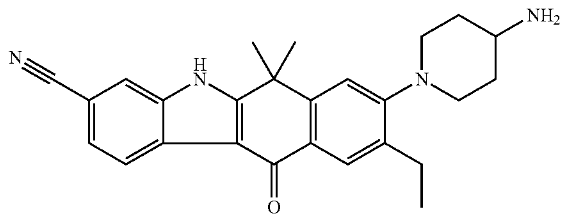 [SMILES: CCc1cc2c(cc1N1CCC(N)CC1)C(C)(C)c1[nH]c3cc(C#N)ccc3c1C2=O] | 8-(4-Amino-piperidine-1-yl)-9-ethyl-6,6-dimethyl-11-oxo-6,11-dihydro-5H-benzo[b]carbazole-3-carbonitrile | U | 1.92 | 413 |
| 842 | PR11-13 | 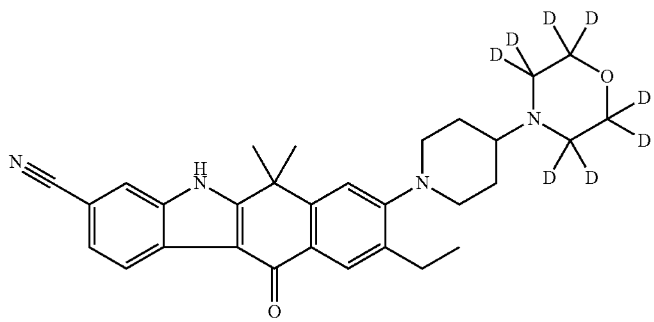 [SMILES: [2H]C1([2H])OC([2H])([2H])C([2H])([2H])N(C2CCN(c3cc4c(cc3CC)C(=O)c3c([nH]c5cc(C#N)ccc35)C4(C)C)CC2)C1([2H])[2H]] | 9-Ethyl-9,9-dimethyl-8-(4-2,2,3,3,3,5,5,6,6-d8-morpholine-4-yl-piperidine-1-yl)-11-oxo-6,11-dihydro-5H-benzo[b]carbazole-3-carbonitrile | U | 1.98 | 491 |
| 843 | PR9-22 | 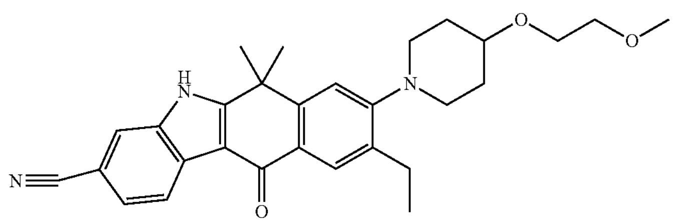 [SMILES: CCc1cc2c(cc1N1CCC(OCCOC)CC1)C(C)(C)c1[nH]c3cc(C#N)ccc3c1C2=O] | 9-Ethyl-8-[4-(2-methoxy-ethoxy)-piperidine-1-yl]-6,6-dimethyl-11-oxo-6,11-dihydro-5H-benzo[b]carbazole-3-carrbonitrile | Y | 3.23 | 472 |
| 844 | PR9-23 | 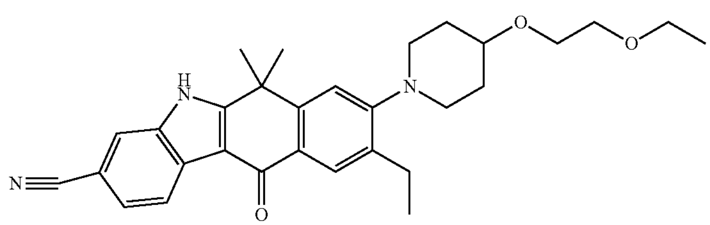 [SMILES: CCOCCOC1CCN(c2cc3c(cc2CC)C(=O)c2c([nH]c4cc(C#N)ccc24)C3(C)C)CC1] | 8-[4-(2-Ethoxy-ethoxy)-piperidine-1-yl]-9-ethyl-6,6-dimethyl-11-oxo-6,11-dihydro-5H-benzo[b]carbazole-3-carbonitrile | Y | 3.35 | 486 |
| 845 | PR9-24 | 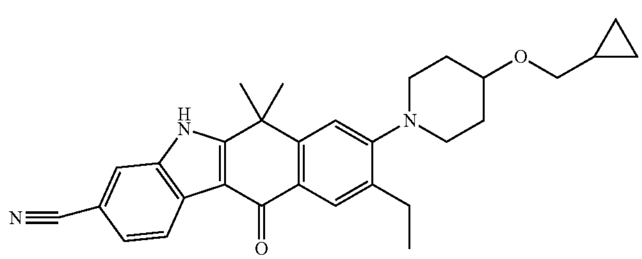 [SMILES: CCc1cc2c(cc1N1CCC(OCC3CC3)CC1)C(C)(C)c1[nH]c3cc(C#N)ccc3c1C2=O] | 8-(4-Cyclopropyl-methoxy-piperidine-1-yl)-9-ethyl-6,6-dimethyl-11-oxo-6,11-dihydro-5H-benzo[b]carbazole-3-carbonitrile | Y | 3.50 | 468 |
| 846 | PR9-25 | 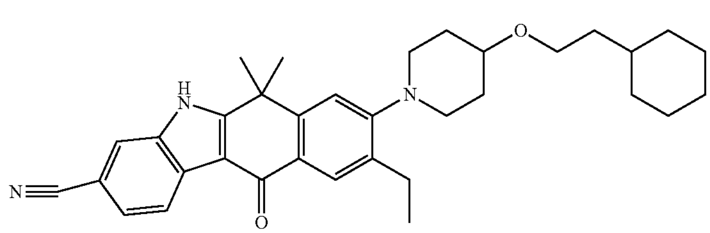 [SMILES: CCc1cc2c(cc1N1CCC(OCCC3CCCCC3)CC1)C(C)(C)c1[nH]c3cc(C#N)ccc3c1C2=O] | 8-[4-(2-Cyclohexyl-ethoxy)-piperidine-1-yl]-9-ethyl-6,6-dimethyl-11-oxo-6,11-dihydro-5H-benzo[b]carbazole-3-carbonitrile | Y | 4.00 | 524 |

TABLE 10-continued

| Example No. | Comp. No. | Structure | Compound Name | HPLC Condition | Retention Time | m/z |
|---|---|---|---|---|---|---|
| 847 | PR11-14 | 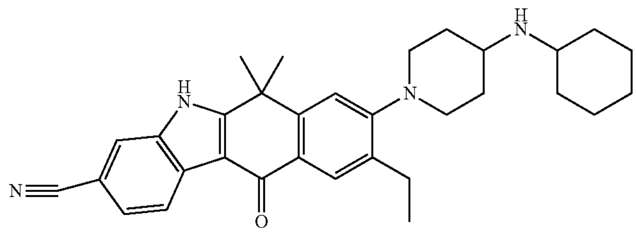 [SMILES: CCc1cc2c(cc1N1CCC(NC3CCCCC3)CC1)C(C)(C)c1[nH]c3cc(C#N)ccc3c1C2=O] | 8-(4-Cyclohexylamino-piperidine-1-yl)-9-ethyl-6,6-dimethyl-11-oxo-6,11-dihydro-5H-benzo[b]carbazole-3-carbonitrile | Y | 2.33 | 495 |
| 848 | PR11-15 | 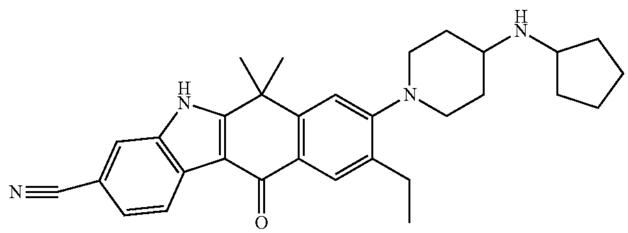 [SMILES: CCc1cc2c(cc1N1CCC(NC3CCCC3)CC1)C(C)(C)c1[nH]c3cc(C#N)ccc3c1C2=O] | 8-(4-Cyclopentylamino-piperidine-1-yl)-9-ethyl-6,6-dimethyl-11-oxo-6,11-dihydro-5H-benzo[b]carbazole-3-carbonitrile | Y | 2.15 | 481 |
| 849 | PR11-16 | 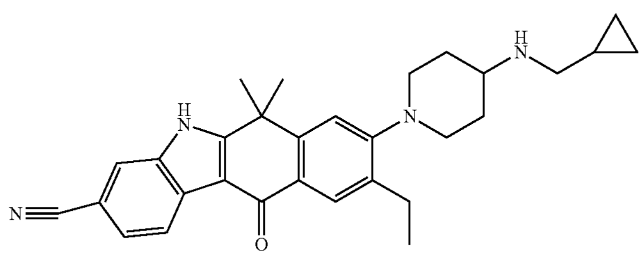 [SMILES: CCc1cc2c(cc1N1CCC(NCC3CC3)CC1)C(C)(C)c1[nH]c3cc(C#N)ccc3c1C2=O] | 8-[4-(Cyclopropylmethylamino)-piperidine-1-yl]-9-ethyl-6,6-dimethyl-11-oxo-6,11-dihydro-5H-benzo[b]carbazole-3-carbonitrile | Y | 2.15 | 467 |
| 850 | PR11-17 | 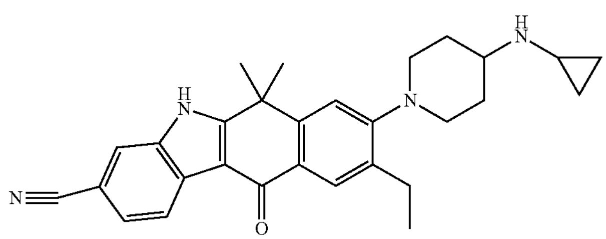 [SMILES: CCc1cc2c(cc1N1CCC(NC3CC3)CC1)C(C)(C)c1[nH]c3cc(C#N)ccc3c1C2=O] | 8-(4-Cyclopropylamino-piperidine-1-yl)-9-ethyl-6,6-dimethyl-11-oxo-6,11-dihydro-5H-benzo[b]carbazole-3-carbonitrile | Y | 2.08 | 453 |
| 851 | PR11-18 | 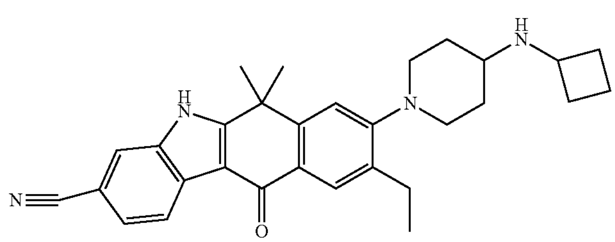 [SMILES: CCc1cc2c(cc1N1CCC(NC3CCC3)CC1)C(C)(C)c1[nH]c3cc(C#N)ccc3c1C2=O] | 8-(4-Cyclobutylamino-piperidine-1-yl)-9-ethyl-6,6-dimethyl-11-oxo-6,11-dihydro-5H-benzo[b]carbazole-3-carbonitrile | Y | 2.13 | 467 |
| 852 | PR11-19 | 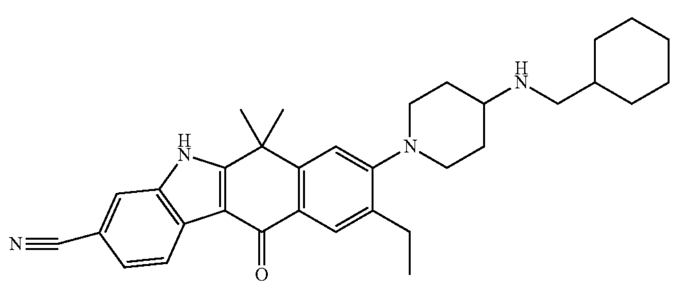 [SMILES: CCc1cc2c(cc1N1CCC(NCC3CCCCC3)CC1)C(C)(C)c1[nH]c3cc(C#N)ccc3c1C2=O] | 8-[4-(Cyclohexylmethylamino)-piperidine-1-yl]-9-ethyl-6,6-dimethyl-11-oxo-6,11-dihydro-5H-benzo[b]carbazole-3-carbonitrile | Y | 2.42 | 509 |

Example 853

Compound PR11-22

9-Ethyl-8-(4-hydroxyimino-piperidin-1-yl)-6,6-dimethyl-11-oxo-6,11-dihydro-5H-benzo[b]carbazole-3-carbonitrile

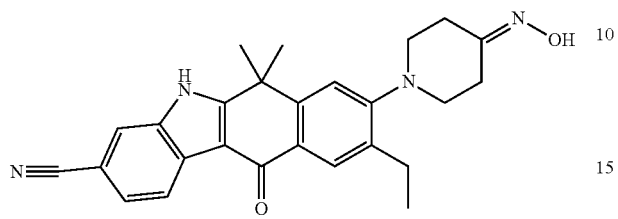

9-Ethyl-6,6-dimethyl-11-oxo-8-(4-oxopiperidin-1-yl)-6,11-dihydro-5H-benzo[b]carbazole-3-carbonitrile (30 mg) and hydroxylamine hydrochloric acid salt (10 mg) were dissolved in ethanol (5 ml) and stirred at 60° C. for 6 hrs. The reaction mixture was diluted with ethyl acetate (20 ml). The organic layer was washed with 10% brine and concentrated under reduced pressure. The resulting residues were purified by silica gel column (dichloromethane/methanol=99/1 to 90/10) to obtain the title compound (23.5 mg, yield 74%).

LCMS: m/z 427 [M+H]$^+$

HPLC retention time: 3.08 min (analysis condition Y)

Example 854

Compound PR10-2

9-Ethyl-6,6-dimethyl-5-(2-morpholin-4-yl-ethyl)-8-(2-morpholin-4-yl-ethylamino)-11-oxo-6,11-dihydro-5H-benzo[b]carbazole-3-carbonitrile

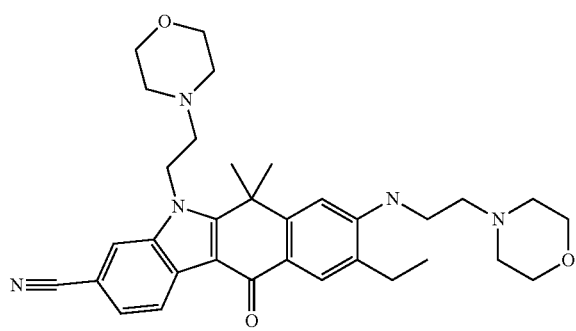 [SMILES: CCc1cc2c(cc1NCCN1CCOCC1)C(C)(C)c1c(c3ccc(C#N)cc3n1CCN1CCOCC1)C2=O]

9-Ethyl-6,6-dimethyl-8-(2-morpholin-4-yl-ethylamino)-11-oxo-6,11-dihydro-5H-benzo[b]carbazole-3-carbonitrile (10 mg) was dissolved in DMF (1 ml), added with K$_2$CO$_3$ (10 mg) and 1-(2-chloroethyl)morpholine (8 mg), and then stirred at 90° C. for 17 hrs. The reaction mixture was diluted with ethyl acetate (10 ml). The organic layer was washed with 10% brine and concentrated under reduced pressure. The resulting residues were purified by silica gel column (dichloromethane/methanol=99/1 to 90/10) to obtain the title compound (6.4 mg, yield 58%).

LCMS: m/z 556 [M+H]$^+$

HPLC retention time: 1.78 min (analysis condition Y)

Example 855

Compound F7

9-Ethyl-6,6-dimethyl-11-oxo-8-[4-(4-oxy-morpholin-4-yl)-piperidin-1-yl]-6,11-dihydro-5H-benzo[b]carbazole-3-carbonitrile

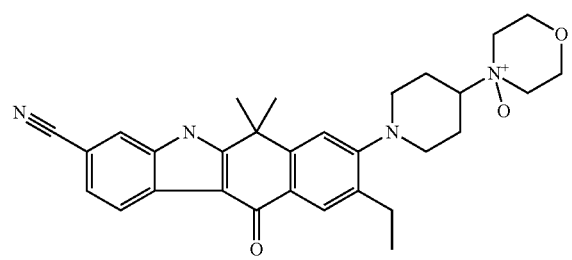 [SMILES: CCc1cc2c(cc1N1CCC([N+]3(O)CCOCC3)CC1)C(C)(C)c1[nH]c3cc(C#N)ccc3c1C2=O]

9-Ethyl-6,6-dimethyl-8-(4-morpholin-4-yl-piperidin-1-yl)-11-oxo-6,11-dihydro-5H-benzo[b]carbazole-3-carbonitrile (400 mg) was dissolved in trifluoroethanol (80 ml), added with 30% hydrogen peroxide solution (0.8 ml), and the mixture was stirred at 60° C. for 17 hrs. The reaction mixture was concentrated to 30 ml and diluted with water (20 ml). The precipitated matter was collected by filtration and dried to obtain the title compound (375 mg, yield 90%).

LCMS: m/z 499 [M+H]$^+$

HPLC retention time: 2.05 min (analysis condition U)

Example 856

Compound FR1

6-Cyano-2-[1-(4-ethyl-3-iodophenyl)-1-methylethyl]-benzofuran-3-carboxylic acid tert-butyl ester

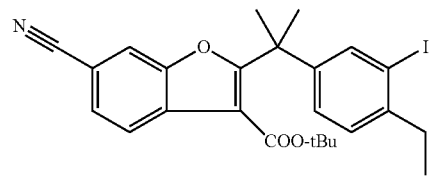

4-(4-Ethyl-3-iodo-phenyl)-4-methyl-3-oxo-pentanoic acid tert-butyl ester (1.00 g, 2.40 mmol) was dissolved in NMP (4 ml), added with cesium carbonate (1.56 g, 4.80 mmol, 2.0 eq.), and the mixture was stirred for 5 min. The NMP solution (2 ml) of 4-chloro-3-nitro-benzonitrile (542 mg, 2.88 mmol, 1.2 eq.) was added thereto, and the mixture was stirred at 50° C. for 64 hrs under nitrogen atmosphere. After cooling to room temperature, ethyl acetate (20 ml) was added and the organic layer was washed with saturated aqueous solution of ammonium chloride (20 ml). The organic layer was further washed with saturated brine and dried over sodium sulfate. The drying agent was removed by filtration and the residues obtained after concentration under reduced pressure were purified by silica gel column chromatography (ethyl acetate/hexane) to obtain the title compound (white amorphous, 320 mg, 26%).

LCMS: m/z 516 [M+H]$^+$

Example 857

Compound FR2

6-Cyano-2-{1-[4-ethyl-3-(4-morpholin-4-yl-piperidin-1-yl)-phenyl]-1-methyl-ethyl}-benzofuran-3-carboxylic acid tert-butyl ester

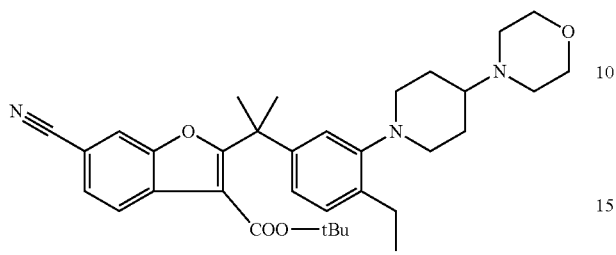

6-Cyano-2-[1-(4-ethyl-3-iodophenyl)-1-methyl-ethyl]-benzofuran-3-carboxylic acid tert-butyl ester was converted to obtain the title compound in the same manner as the method for Compound PR6.
LCMS: m/z 558 [M+H]$^+$

Example 858

Compound FR3

6-Cyano-2-{1-[4-ethyl-3-(4-morpholin-4-yl-piperidin-1-yl)-phenyl]-1-methyl-ethyl}-benzofuran-3-carboxylic acid hydroiodic acid salt

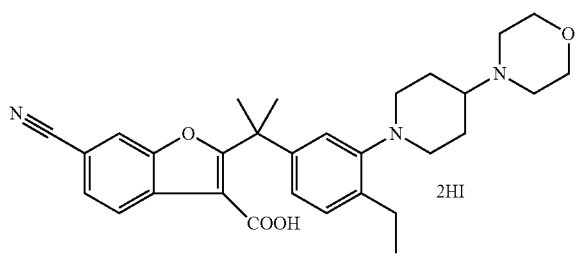 [SMILES: CCc1ccc(C(C)(C)c2oc3cc(C#N)ccc3c2C(=O)O)cc1N1CCC(N2CCOCC2)CC1]

To obtain the title compound, 6-Cyano-2-{1-[4-ethyl-3-(4-morpholin-4-yl-piperidin-1-yl)-phenyl]-1-methyl-ethyl}-benzofuran-3-carboxylic acid tert-butyl ester was deprotected by using trimethylsilyl iodide in the same manner as the method for Compound PR7.
LCMS: m/z 502 [M+H]$^+$

Example 859

Compound FR4

9-Ethyl-6,6-dimethyl-8-(4-morpholin-4-yl-piperidin-1-yl)-11-oxo-6,11-dihydro-benzo[b]naphtho[2,3-d]furan-3-carbonitrile

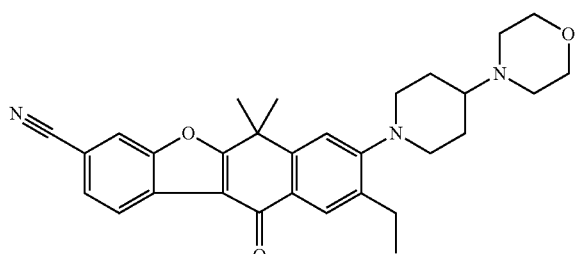

6-Cyano-2-{1-[4-ethyl-3-(4-morpholin-4-yl-piperidin-1-yl)-phenyl]-1-methyl-ethyl}-benzofuran-3-carboxylic acid hydroiodic acid salt was converted in the same method as Example 805 to obtain the target compound.
LCMS: m/z 484 [M+H]$^+$

Example 860

Compound LB1

2-[4-Ethyl-3-(4-morpholin-4-yl-piperidin-1-yl)-phenyl]-2-methyl-propionic acid

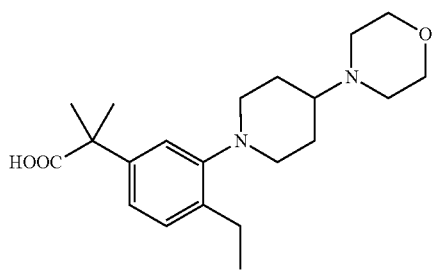 [SMILES: CCc1ccc(C(C)(C)C(=O)O)cc1N1CCC(N2CCOCC2)CC1]

The title compound was prepared from 2-(4-ethyl-3-iodophenyl)-2-methylpropanoic acid by carrying out amination in the same manner as the method for synthesizing Compound PR6.
LCMS: m/z 361 [M+H]$^+$

Example 861

Compound LB2

2-{1-[4-Ethyl-3-(4-morpholin-4-yl-piperidin-1-yl)-phenyl]-1-methyl-ethyl}-6-iodo-1H-indole-3-carboxylic acid tert-butyl ester

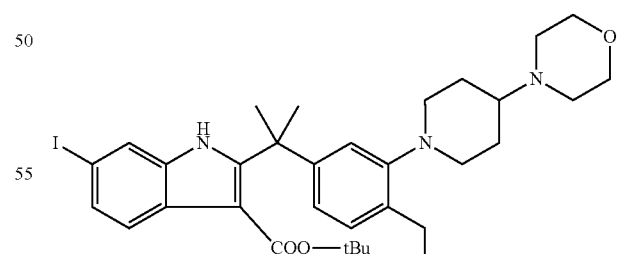

2-[4-Ethyl-3-(4-morpholin-4-yl-piperidin-1-yl)-phenyl]-2-methyl-propionic acid was converted in the same manner as the method for synthesizing Compound PR5-1 to obtain the title compound.
LCMS: m/z 658 [M+H]$^+$
HPLC retention time: 2.76 min (analysis condition U)

Example 862

Compound LB3

2-{1-[4-Ethyl-3-(4-morpholin-4-yl-piperidin-1-yl)-phenyl]-1-methyl-ethyl}-6-iodo-1H-indole-3-carboxylic acid

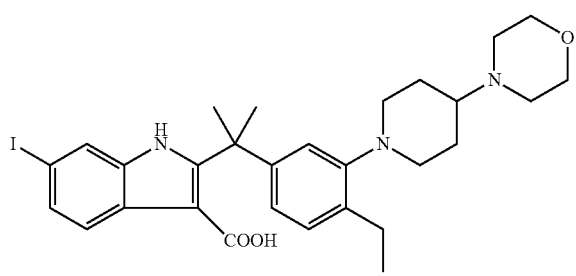 [SMILES: CCc1ccc(C(C)(C)c2[nH]c3cc(I)ccc3c2C(=O)O)cc1N1CCC(N2CCOCC2)CC1]

2-{1-[4-Ethyl-3-(4-morpholin-4-yl-piperidin-1-yl)-phenyl]-1-methyl-ethyl}-6-iodo-1H-indole-3-carboxylic acid tert-butyl ester was deprotected in the same manner as the method for preparing Compound PR7 to obtain the title compound.

LCMS: m/z 602 [M+H]$^+$

HPLC retention time: 2.17 min (analysis condition U)

Example 863

Compound LB4

9-Ethyl-3-iodo-6,6-dimethyl-8-(4-morpholin-4-yl-piperidin-1-yl)-5,6-dihydro-benzo[b]carbazol-11-one

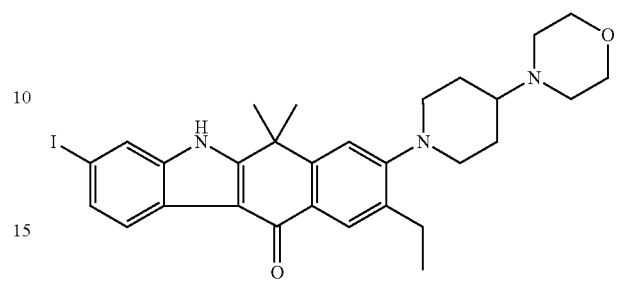

2-{1-[4-Ethyl-3-(4-morpholin-4-yl-piperidin-1-yl)-phenyl]-1-methyl-ethyl}-6-iodo-1H-indole-3-carboxylic acid was converted in the same manner as Example 805 to obtain the title compound.

LCMS: m/z 584 [M+H]$^+$

HPLC retention time: 2.25 min (analysis condition U)

The compounds described in the following Table 11 were converted and prepared from 9-ethyl-3-iodo-6,6-dimethyl-8-(4-morpholin-4-yl-piperidin-1-yl)-5,6-dihydro-benzo[b]carbazol-11-one according to the method described in the Table.

TABLE 11

| Example No. | Comp. No. | Structure | Compound Name | HPLC Condition | Retention Time | m/z | Method |
|---|---|---|---|---|---|---|---|
| 864 | LB5-1 | 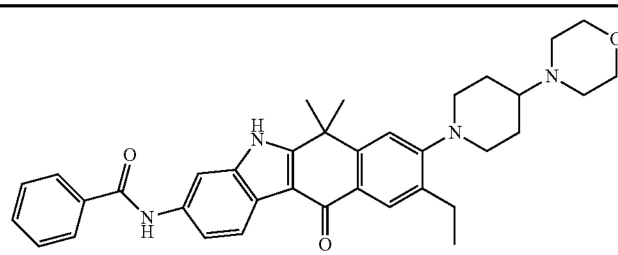 | N-[9-Ethyl-6,6-dimethyl-8-(4-morpholine-4-yl-piperidine-1-yl)-11-oxo-6,11-dihydro-5H-benzo[b]carbazole-3-yl]-benzamide | Y | 1.78 | 577 | B2-10 |
| 865 | LB5-2 | 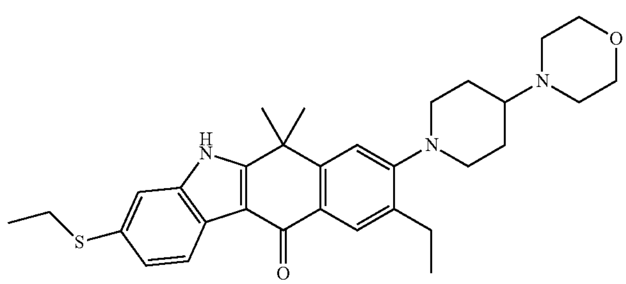 [SMILES: CCSc1ccc2c3c([nH]c2c1)C(C)(C)c1cc(N2CCC(N4CCOCC4)CC2)c(CC)cc1C3=O] | 9-Ethyl-3-ethylsulfanyl-6,6-dimethyl-8-(4-morpholine-4-yl-piperidine-1-yl)-5,6-dihydro-benzo[b]carbazole-11-one | Y | 2.28 | 518 | B2-17 |
| 866 | LB5-3 | 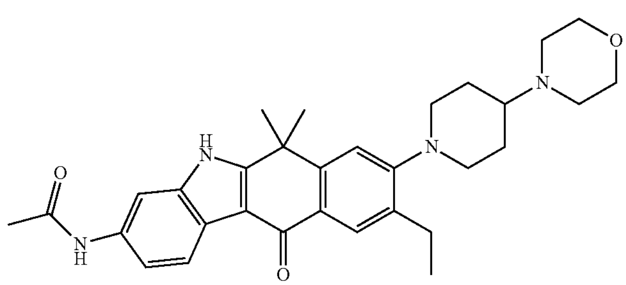 [SMILES: CCc1cc2c(cc1N1CCC(N3CCOCC3)CC1)C(C)(C)c1[nH]c3cc(NC(C)=O)ccc3c1C2=O] | N-[9-Ethyl-6,6-dimethyl-8-(4-morpholine-4-yl-piperidine-1-yl)-11-oxo-6,11-dihydro-5H-benzo[b]carbazole-3-yl]-acetamide | Y | 1.50 | 515 | B2-10 |

Example 867

Compound AZ1

Methanesulfonic acid (2-fluoropyridin-4-yl)methyl ester

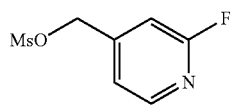 [SMILES: CS(=O)(=O)OCc1ccnc(F)c1]

(2-Fluoropyridin-4-yl) methanol (1 g) was dissolved in DCM (40 ml), added with TEA (3.3 ml) and mesyl chloride (0.67 ml), and the mixture was stirred at 0° C. for 1 hr. The mixture was concentrated and then purified by silica gel column (n-hexane/ethyl acetate=4/1) to obtain the title compound (1.18 g, 77%).

$^1$H-NMR (270 MHz DMSO-$d_6$) δ: 3.21 (3H, s), 5.38 (2H, s), 7.22 (1H, s), 7.39 (1H, d, J=5.0), 8.29 (1H, d, J=5.0)

Example 868

Compound AZ2

(2-Fluoropyridin-4-yl)acetonitrile

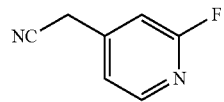

To the DMF (28 ml) solution of methanesulfonic acid (2-fluoropyridin-4-yl)methyl ester (1.16 g), sodium cyanide (0.42 g) was added and the mixture was stirred at 80° C. for 1 hr. The mixture was diluted with ethyl acetate (100 ml), and washed with 15% brine and distilled water in order. The organic layer was concentrated and purified by silica gel column (n-hexane/ethyl acetate=5/1) to obtain the title compound (278 mg, 36%).

$^1$H-NMR (270 MHz DMSO-$d_6$) δ: 4.22 (2H, s), 7.18 (1H, s), 7.36 (1H, d, J=5.0), 8.27 (1H, d, J=5.0)

Example 869

Compound AZ3

(2-Fluoropyridin-4-yl)2-methylpropionitrile

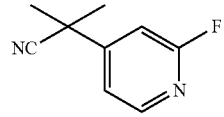

The title compound was prepared from (2-fluoropyridin-4-yl) acetonitrile in the same manner as the method for Compound K2.

$^1$H-NMR (270 MHz DMSO-$d_6$) δ: 1.72 (6H, s), 7.34 (1H, s), 7.53 (1H, d, J=5.3), 8.31 (1H, d, J=5.3)

Example 870

Compound AZ4

4-(2-Fluoropyridin-4-yl)-4-methyl-3-oxopentanoic acid ethyl ester

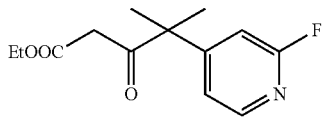 [SMILES: CCOC(=O)CC(=O)C(C)(C)c1ccnc(F)c1]

The title compound was prepared from (2-fluoropyridin-4-yl) 2-methylpropionitrile in the same manner as the method for Compound K3.

$^1$H-NMR (270 MHz DMSO-$d_6$) δ: 1.13 (3H, t, J=7.3), 1.48 (6H, s), 3.57 (2H, s), 4.01 (2H, q, J=7.3), 7.12 (1H, s), 7.25 (1H, d, J=5.3), 8.22 (1H, d, J=5.3)

Example 871

Compound AZ5

6-Cyano-2-[1-(2-fluoropyridin-4-yl)-1-methyl-ethyl]-1H-indole-3-carboxylic acid ethyl ester

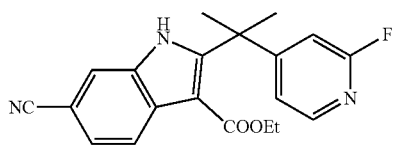 [SMILES: CCOC(=O)c1c(C(C)(C)c2ccnc(F)c2)[nH]c2cc(C#N)ccc12]

The title compound was prepared from 4-(2-fluoropyridin-4-yl)-4-methyl-3-oxopentanoic acid ethyl ester in the same manner as the method for Compound K4 and Compound K5.

LCMS: m/z 352 [M+H]$^+$ $^1$H-NMR (270 MHz DMSO-$d_6$) δ: 1.05 (3H, t, J=7.3), 1.82 (6H, s), 3.98 (2H, q, J=7.3), 6.99-7.02 (2H, m), 7.16 (1H, dd, J=8.4, 1.5), 7.97 (1H, s), 8.05-8.11 (2H, m)

Example 872

Compound AZ6

6-Cyano-2-[1-(2-(4-morpholin-4-yl-piperidin-1-yl)) pyridin-4-yl)-1-methyl-ethyl]-1H-indole-3-carboxylic acid ethyl ester

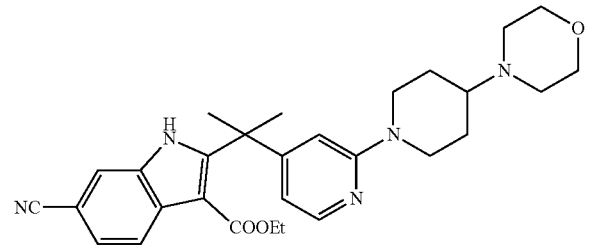 [SMILES: CCOC(=O)c1c(C(C)(C)c2ccnc(N3CCC(N4CCOCC4)CC3)c2)[nH]c2cc(C#N)ccc12]

6-Cyano-2-[1-(2-fluoropyridin-4-yl)-1-methyl-ethyl]-1H-indole-3-carboxylic acid ethyl ester (110 mg) was dissolved in NMP (3.3 ml), added with 4-morpholin-4-yl-piperidine (319 mg), and stirred in a sealing tube at 120° C. for 1 hr. The reaction mixture was diluted with ethyl acetate (50 ml) and washed with 15% brine and distilled water in order. The organic layer was concentrated and purified by silica gel column (DCM/methanol=20/1) to obtain the title compound (120 mg, 76%).
LCMS: m/z 502 [M+H]+

Example 873

Compound AZ7-1

5,5-Dimethyl-3-(4-morpholin-4-yl-piperidin-1-yl)-11-oxo-6,11-dihydro-5H-pyrido[4,3-b]carbazole-8-carboxylic acid amide

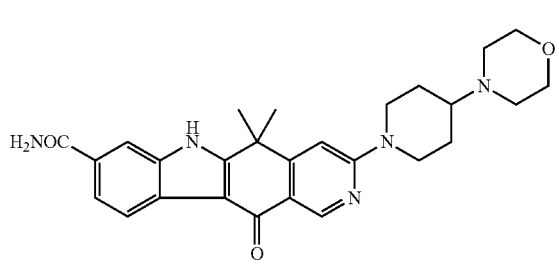 [SMILES: CC1(C)c2cc(N3CCC(N4CCOCC4)CC3)ncc2C(=O)c2c1[nH]c1cc(C(N)=O)ccc21]

6-Cyano-2-[1-(2-(4-morpholin-4-yl-piperidin-1-yl))pyridin-4-yl)-1-methyl-ethyl]-1H-indole-3-carboxylic acid ethyl ester (110 mg) was dissolved in Eaton's reagent (2.5 ml) and stirred at 55° C. for 17 hrs. The reaction mixture was neutralized with saturated aqueous solution of sodium bicarbonate. The precipitated matters were collected by filtration, and then washed with water to obtain the title compound (72 mg, 70%).
LCMS: m/z 474 [M+H]+
HPLC retention time: 1.17 min (analysis condition U)
1H-NMR (270 MHz DMSO-d6) δ: 1.38 (2H, m), 1.75 (6H, s), 1.88 (2H, m), 2.44 (5H, m), 2.94 (2H, m), 3.57 (4H, m), 4.58 (2H, m), 7.10 (1H, s), 7.32 (1H, s), 7.75 (1H, d, J=8.4), 8.00 (2H, m), 8.15 (1H, d, J=8.4), 8.85 (1H, s), 12.3 (1H, s)

Example 874

Compound AZ7-2

5,5-Dimethyl-3-(4-morpholin-4-yl-piperidin-1-yl)-11-oxo-6,11-dihydro-5H-pyrido[4,3-b]carbazole-8-carbonitrile

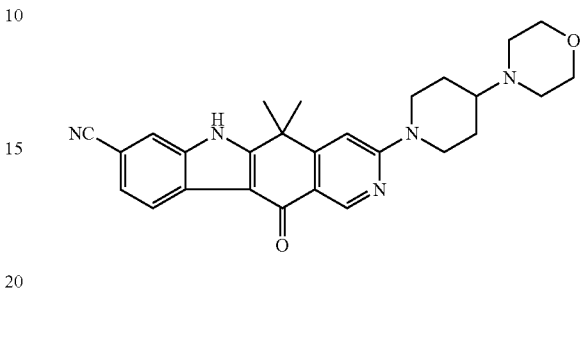

5,5-Dimethyl-3-(4-morpholin-4-yl-piperidin-1-yl)-11-oxo-6,11-dihydro-5H-pyrido[4,3-b]carbazole-8-carboxylic acid amide (54 mg) was dissolved in DMF (1 ml), added with thionyl chloride (25 μL), and the mixture was stirred at room temperature for 1 hr. The reaction mixture was diluted with water. The precipitated matters were collected by filtration to obtain the title compound (25 mg, 49%).
LCMS: m/z 456 [M+H]+
HPLC retention time: 1.55 min (analysis condition U)
1H-NMR (270 MHz DMSO-d6) δ: 1.36 (2H, m), 1.76 (6H, s), 1.89 (2H, m), 2.44 (5H, m), 2.95 (2H, m), 3.57 (4H, m) 4.58 (2H, m), 7.10 (1H, s), 7.59 (1H, d, J=8.0), 7.99 (1H, s), 8.29 (1H, d, J=8.0), 8.86 (1H, s), 12.7 (1H, s)

The compounds described in the following Tables 12-13 were synthesized by introducing a corresponding amino group to 6-cyano-2-[1-(2-fluoropyridin-4-yl)-1-methyl-ethyl]-1H-indole-3-carboxylic acid ethyl ester and forming a ring according to the method that is used for the synthesis of Compound AZ7-1. Furthermore, the preparation was carried out by converting the substituent group at position 3 from a carboxamide group to a cyano group according to the method that is used for the synthesis of Compound AZ7-2.

TABLE 12

| Example No. | Comp. No. | Structure | Compound Name | HPLC Condition | Retention Time | m/z |
|---|---|---|---|---|---|---|
| 875 | AZ7-3 | 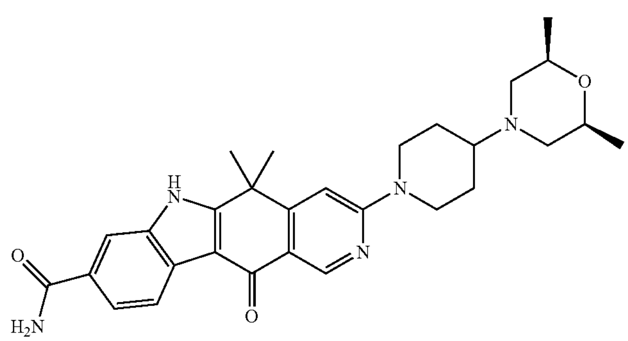 [SMILES: C[C@@H]1CN(C2CCN(c3cc4c(cn3)C(=O)c3c([nH]c5cc(C(N)=O)ccc35)C4(C)C)CC2)C[C@H](C)O1] | 3-[4-((2R,6S)-2,6-Dimethyl-morpholine-4-yl)-piperidine-1-yl]-5,5-dimethyl-11-oxo-6,11-dihydro-5H-pyrido[4,3-b]carbazole-8-carboxylic acid amide | U | 1.32 | 502 |

TABLE 12-continued

| Example No. | Comp. No. | Structure | Compound Name | HPLC Condition | Retention Time | m/z |
|---|---|---|---|---|---|---|
| 876 | AZ7-4 | 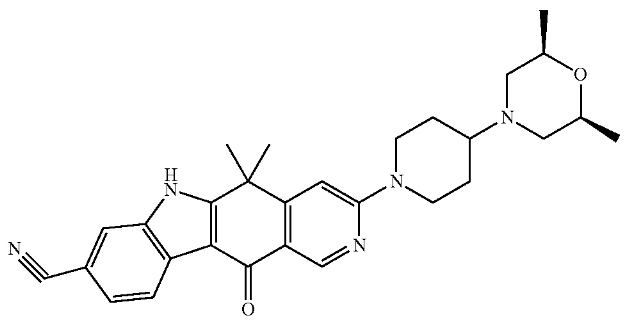 [SMILES: C[C@@H]1CN(C2CCN(c3cc4c(cn3)C(=O)c3c([nH]c5cc(C#N)ccc35)C4(C)C)CC2)C[C@H](C)O1] | 3-[4-((2R,6S)-2,6-Dimethyl-morpholine-4-yl)-piperidine-1-yl]-5,5-dimethyl-11-oxo-6,11-dihydro-5H-pyrido[4,3-b]carbazole-8-carbonitrile | U | 1.70 | 484 |
| 877 | AZ7-5 | 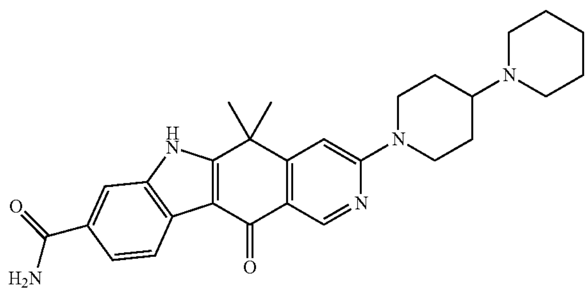 [SMILES: CC1(C)c2cc(N3CCC(N4CCCCC4)CC3)ncc2C(=O)c2c1[nH]c1cc(C(N)=O)ccc21] | 3-[1,4']Bipiperidinyl-1'-yl-5,5-dimethyl-11-oxo-6,11-dihydro-5H-pyrido[4,3-b]carbazole-8-carboxylic acid amide | U | 1.30 | 472 |
| 878 | AZ7-6 | 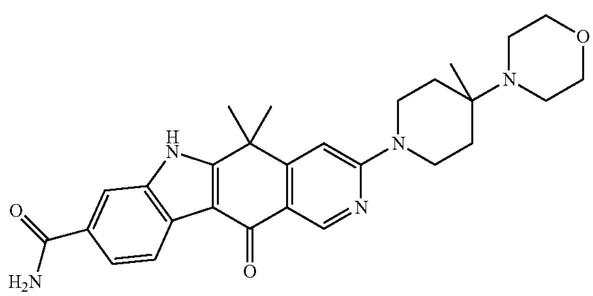 [SMILES: CC1(C)c2cc(N3CCC(C)(N4CCOCC4)CC3)ncc2C(=O)c2c1[nH]c1cc(C(N)=O)ccc21] | 5,5-Dimethyl-3-(4-methyl-4-morpholine-4-yl-piperidine-1-yl)-11-oxo-6,11-dihydro-5H-pyrido[4,3-b]carbazole-8-carboxylic acid amide | Y | 1.00 | 488 |
| 879 | AZ7-7 | 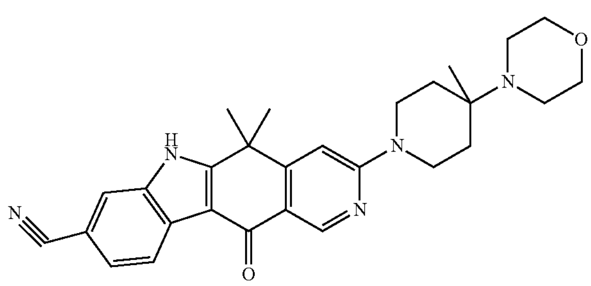 [SMILES: CC1(C)c2cc(N3CCC(C)(N4CCOCC4)CC3)ncc2C(=O)c2c1[nH]c1cc(C#N)ccc21] | 5,5-Dimethyl-3-(4-methyl-4-morpholine-4-yl-piperidine-1-yl)-11-oxo-6,11-dihydro-5H-pyrido[4,3-b]carbazole-8-carbonitrile | Y | 1.62 | 470 |
| 880 | AZ7-8 | 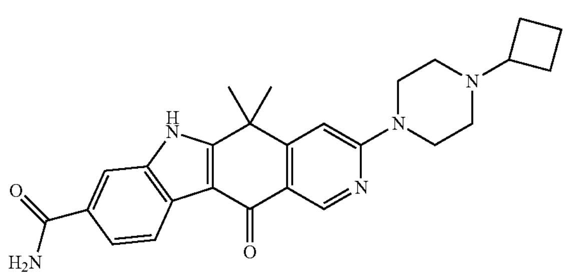 [SMILES: CC1(C)c2cc(N3CCN(C4CCC4)CC3)ncc2C(=O)c2c1[nH]c1cc(C(N)=O)ccc21] | 3-(4-Cyclobutyl-piperazine-1-yl)-5,5-dimethyl-11-oxo-6,11-dihydro-5H-pyrido[4,3-b]carbazole-8-carboxylic acid amide | Y | 1.22 | 444 |

TABLE 12-continued

| Example No. | Comp. No. | Structure | Compound Name | HPLC Condition | Retention Time | m/z |
|---|---|---|---|---|---|---|
| 881 | AZ7-9 | 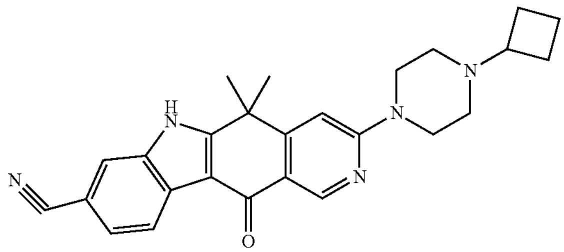 [SMILES: CC1(C)c2cc(N3CCN(C4CCC4)CC3)ncc2C(=O)c2c1[nH]c1cc(C#N)ccc21] | 3-(4-Cyclobutyl-piperazine-1-yl)-5,5-dimethyl-11-oxo-6,11-dihydro-5H-pyrido[4,3-b]carbazole-8-carbonitrile | Y | 1.55 | 426 |
| 882 | AZ7-10 | 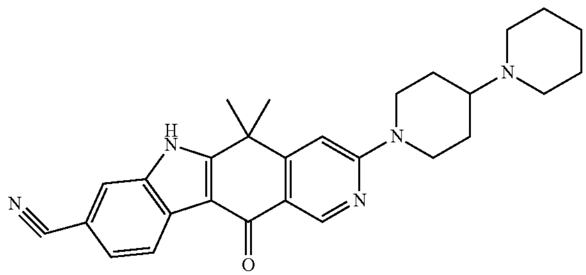 [SMILES: CC1(C)c2cc(N3CCC(N4CCCCC4)CC3)ncc2C(=O)c2c1[nH]c1cc(C#N)ccc21] | 3-[1,4']Bipiperidinyl-1'-yl-5,5-dimethyl-11-oxo-6,11-dihydro-5H-pyrido[4,3-b]carbazole-8-carbonitrile | Y | 1.73 | 454 |
| 883 | AZ7-11 | 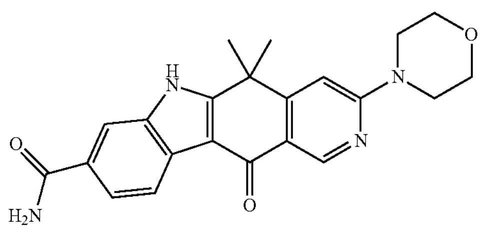 [SMILES: CC1(C)c2cc(N3CCOCC3)ncc2C(=O)c2c1[nH]c1cc(C(N)=O)ccc21] | 5,5-Dimethyl-3-morpholine-4-yl-11-oxo-6,11-dihydro-5H-pyrido[4,3-b]carbazole-8-carboxylic acid amide | U | 1.33 | 391 |
| 884 | AZ7-12 | 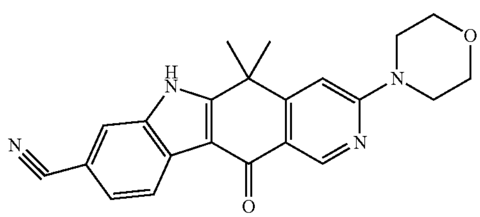 [SMILES: CC1(C)c2cc(N3CCOCC3)ncc2C(=O)c2c1[nH]c1cc(C#N)ccc21] | 5,5-Dimethyl-3-morpholine-4-yl-11-oxo-6,11-dihydro-5H-pyrido[4,3-b]carbazole-8-carbonitrile | U | 1.77 | 373 |
| 885 | AZ7-13 | 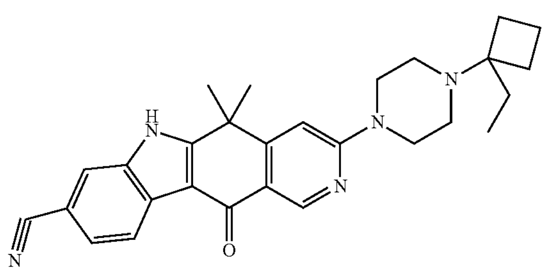 [SMILES: CCC1(N2CCN(c3cc4c(cn3)C(=O)c3c([nH]c5cc(C#N)ccc35)C4(C)C)CC2)CCC1] | 3-[4-(1-Ethyl-cyclobutyl)-piperazine-1-yl]-5,5-dimethyl-11-oxo-6,11-dihydro-5H-pyrido[4,3-b]carbazole-8-carbonitrile | Y | 1.93 | 464 |
| 886 | AZ7-14 | 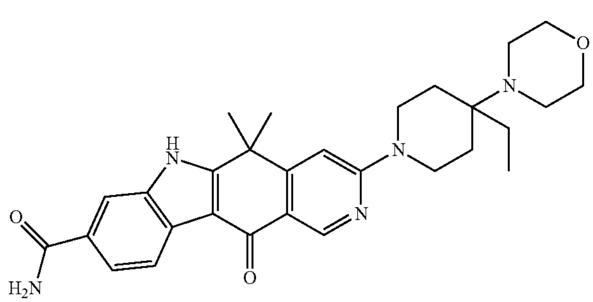 [SMILES: CCC1(N2CCOCC2)CCN(c2cc3c(cn2)C(=O)c2c([nH]c4cc(C(N)=O)ccc24)C3(C)C)CC1] | 3-(4-Ethyl-4-morpholine-4-yl-piperidine-1-yl)-5,5-dimethyl-11-oxo-6,11-dihydro-5H-pyrido[4,3-b]carbazole-8-carboxylic acid amide | Y | 1.18 | 502 |

TABLE 12-continued

| Example No. | Comp. No. | Structure | Compound Name | HPLC Condition | Retention Time | m/z |
|---|---|---|---|---|---|---|
| 887 | AZ7-15 | 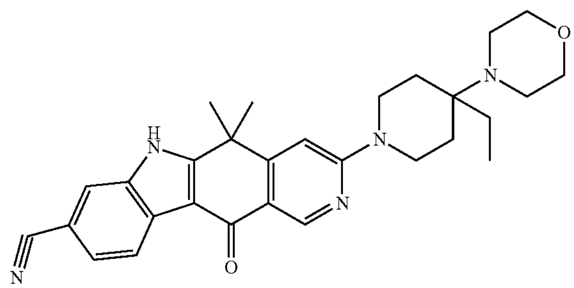 [SMILES: CCC1(N2CCOCC2)CCN(c2cc3c(cn2)C(=O)c2c([nH]c4cc(C#N)ccc24)C3(C)C)CC1] | 3-(4-Ethyl-4-morpholine-4-yl-piperidine-1-yl)-5,5-dimethyl-11-oxo-6,11-dihydro-5H-pyrido[4,3-b]carbazole-8-carbonitrile | Y | 1.78 | 484 |
| 888 | AZ7-16 | 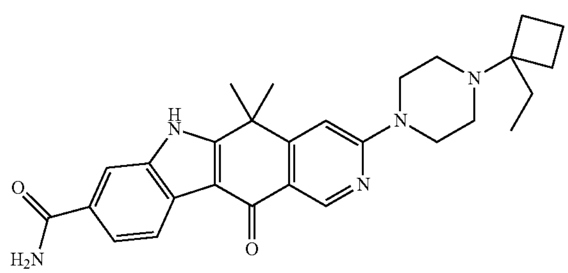 [SMILES: CCC1(N2CCN(c3cc4c(cn3)C(=O)c3c([nH]c5cc(C(N)=O)ccc35)C4(C)C)CC2)CCC1] | 3-[4-(1-Ethyl-cyclobutyl)-piperazine-1-yl]-5,5-dimethyl-11-oxo-6,11-dihydro-5H-pyrido[4,3-b]carbazole-8-carboxylic acid amide | Y | 1.25 | 472 |

TABLE 13

| Example No. | Comp. No. | Structure | Compound Name | HPLC Condition | Retention Time | m/z |
|---|---|---|---|---|---|---|
| 889 | AZ7-17 | 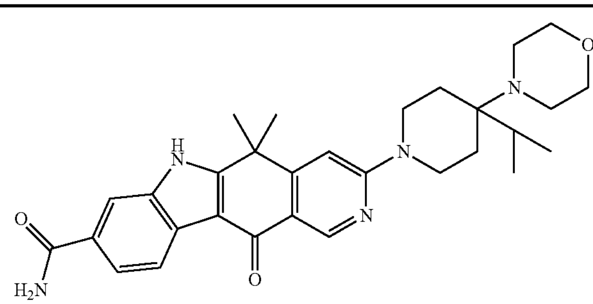 | 3-(4-Isopropyl-4-morpholine-4-yl-piperidine-1-yl)-5,5-dimethyl-11-oxo-6,11-dihydro-5H-pyrido[4,3-b]carbazole-8-carboxylic acid amide | U | 1.27 | 516 |
| 890 | AZ7-18 | 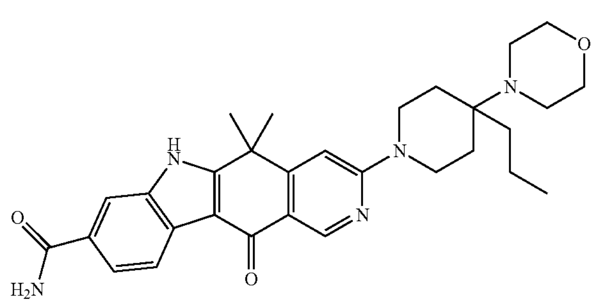 [SMILES: CCCC1(N2CCOCC2)CCN(c2cc3c(cn2)C(=O)c2c([nH]c4cc(C(N)=O)ccc24)C3(C)C)CC1] | 5,5-Dimethyl-3-(4-morpholine-4-yl-4-propyl-piperidine-1-yl)-11-oxo-6,11-dihydro-5H-pyrido[4,3-b]carbazole-8-carboxylic acid amide | U | 1.36 | 516 |

TABLE 13-continued

| Example No. | Comp. No. | Structure | Compound Name | HPLC Condition | Retention Time | m/z |
|---|---|---|---|---|---|---|
| 891 | AZ7-19 | 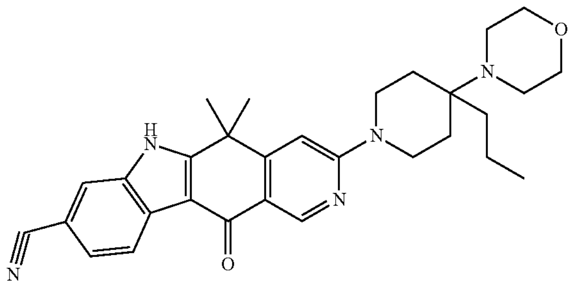 [SMILES: CCCC1(N2CCOCC2)CCN(c2cc3c(cn2)C(=O)c2c([nH]c4cc(C#N)ccc24)C3(C)C)CC1] | 5,5-Dimethyl-3-(4-morpholine-4-yl-4-propyl-piperidine-1-yl)-11-oxo-6,11-dihydro-5H-pyrido[4,3-b]carbazole-8-carbonitrile | U | 1.68 | 493 |
| 892 | AZ7-20 | 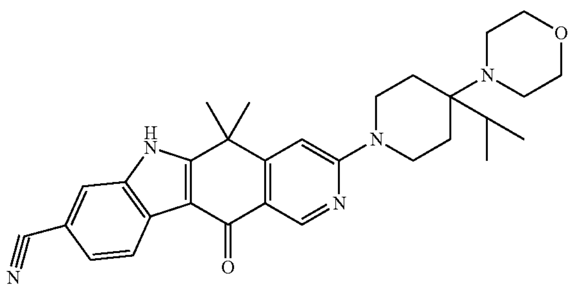 [SMILES: CC(C)C1(N2CCOCC2)CCN(c2cc3c(cn2)C(=O)c2c([nH]c4cc(C#N)ccc24)C3(C)C)CC1] | 3-(4-Isopropyl-4-morpholine-4-yl-piperidine-1-yl)-5,5-dimethyl-11-oxo-6,11-dihydro-5H-pyrido[4,3-b]carbazole-8-carbonitrile | U | 1.60 | 498 |
| 893 | AZ7-21 | 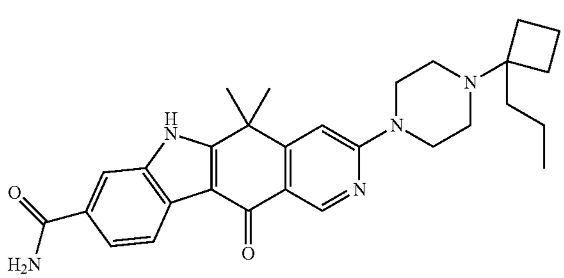 [SMILES: CCCC1(N2CCN(c3cc4c(cn3)C(=O)c3c([nH]c5cc(C(N)=O)ccc35)C4(C)C)CC2)CCC1] | 5,5-Dimethy-11-oxo-3-[4-(1-propyl-cyclobutyl)-piperazine-1-yl]-6,11-dihydro-5H-pyrido[4,3-b]carbazole-8-carboxylic acid amide | U | 1.58 | 486 |
| 894 | AZ7-22 | 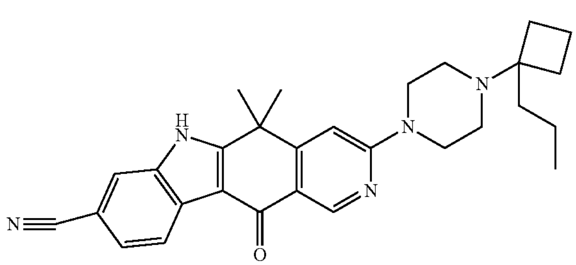 [SMILES: CCCC1(N2CCN(c3cc4c(cn3)C(=O)c3c([nH]c5cc(C#N)ccc35)C4(C)C)CC2)CCC1] | 5,5-Dimethyl-11-oxo-3-[4-(1-propyl-cyclobutyl)-piperazine-1-yl]-6,11-dihydro-5H-pyrido[4,3-b]carbazole-8-carbonitrile | U | 1.97 | 468 |

The compounds described in the following Table 14 were synthesized from (2-chloro-3-fluoropyridin-4-yl)methanol according to the method that is used for the synthesis of Compound AZ1 to AZ7-2.

TABLE 14

| Example No. | Comp. No. | Structure | Compound Name | HPLC Condition | Retention Time | m/z |
|---|---|---|---|---|---|---|
| 895 | AZ7-23 | 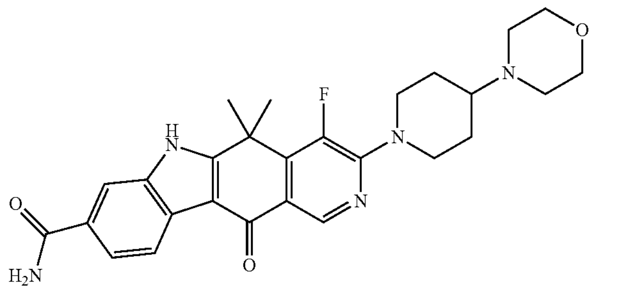 [SMILES: CC1(C)c2[nH]c3cc(C(N)=O)ccc3c2C(=O)c2cnc(N3CCC(N4CCOCC4)CC3)c(F)c21] | 4-Fluoro-5,5-dimethyl-3-(4-niorpholine-4-yl-piperidine-1-yl)-11-oxo-6,11-dihydro-5H-pyrido[4,3-b]carbazole-8-carboxylic acid amide | U | 1.37 | 492 |
| 896 | AZ7-24 | 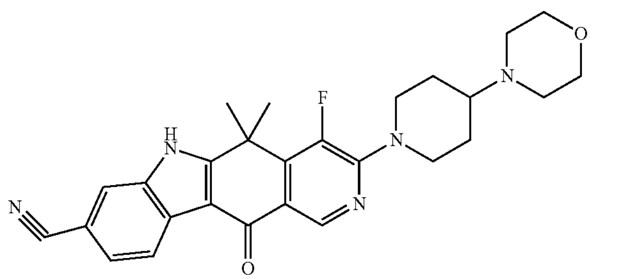 [SMILES: CC1(C)c2[nH]c3cc(C#N)ccc3c2C(=O)c2cnc(N3CCC(N4CCOCC4)CC3)c(F)c21] | 4-Fluoro-5,5-dimethyl-3-(4-morpholin-4-yl-piperidin-1-yl)-11-oxo-6,11-dihydro-5H-pyrido[4,3-b]carbazole-8-carbonitrile | U | 1.74 | 474 |
| 897 | AZ7-25 | 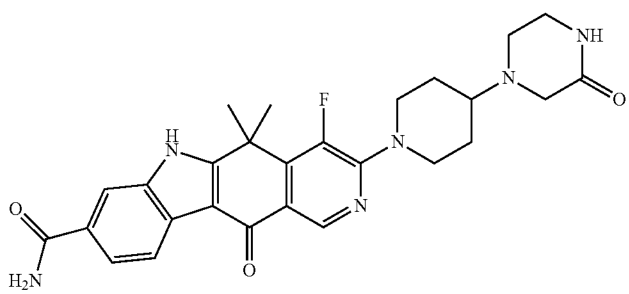 [SMILES: CC1(C)c2[nH]c3cc(C(N)=O)ccc3c2C(=O)c2cnc(N3CCC(N4CCNC(=O)C4)CC3)c(F)c21] | 4-Fluoro-5,5-dimethyl-11-oxo-3-[4-(3-oxo-piperazin-1-yl)-piperidin-1-yl]-6,11-dihydro-5H-pyrido[4,3-b]carbazole-8-carboxylic acid amide | U | 1.32 | 505 |
| 898 | AZ7-26 | 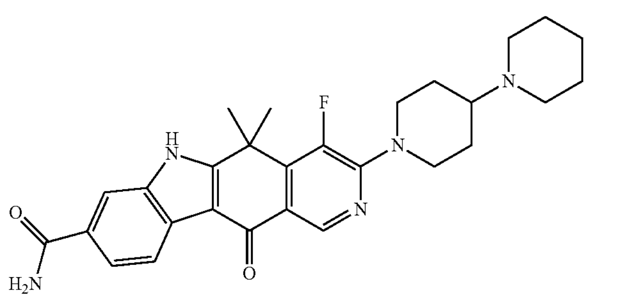 [SMILES: CC1(C)c2[nH]c3cc(C(N)=O)ccc3c2C(=O)c2cnc(N3CCC(N4CCCCC4)CC3)c(F)c21] | 3-[1,4']Bipiperidinyl-1'-yl-4-fluoro-5,5-dimethyl-11-oxo-6,11-dihydro-5H-pyrido[4,3-b]carbazole-8-carboxylic acid amide | U | 1.45 | 490 |
| 899 | AZ7-27 | 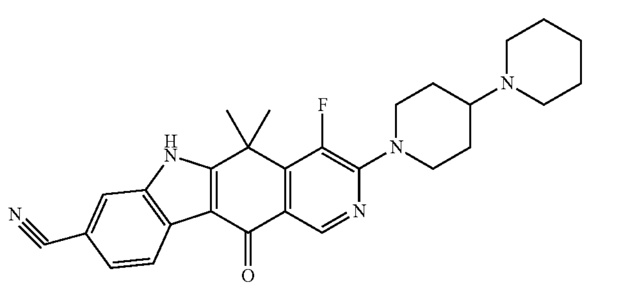 [SMILES: CC1(C)c2[nH]c3cc(C#N)ccc3c2C(=O)c2cnc(N3CCC(N4CCCCC4)CC3)c(F)c21] | 3-[1,4'] Bipiperidinyl-1'-yl-4-fluoro-5,5-dimethyl-11-oxo-6,11-dihydro-5H-pyrido[4,3-b]carbazole-8-carbonitrile | U | 1.87 | 472 |

Example 900

Compound BZ1

2-Cyano-4-hydrazinopyridine

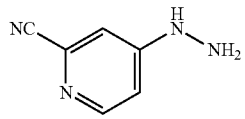

4-Chloro-2-cyanopyridine (1 g) was dissolved in hydrazine monohydrate (1 ml) and 1,4-dioxane (10 ml), and stirred overnight under reflux. The reaction solution was diluted with water (30 ml) and extracted repeatedly with ethyl acetate. The organic layer was concentrated to obtain the title compound as a crude product, which was used for the next step without further purification.

LCMS: m/z 135 [M+H]$^+$

Example 901

Compound BZ2-1

8-Methoxy-6,6-dimethyl-11-oxo-6,11-dihydro-5H-benzo[f]pyrido[4,3-b]indol-3-carbonitrile

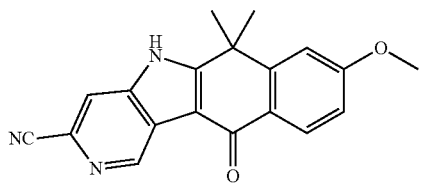 [SMILES: COc1ccc2c(c1)C(C)(C)c1[nH]c3cc(C#N)ncc3c1C2=O]

According to the method used for synthesizing Compound A3-1, the intermediate was prepared from 2-cyano-4-hydrazinopyridine and 7-methoxy-1,1-dimethyl-3,4 dihydro-1H-naphthalen-2-one. Without any purification, the intermediate was subjected to oxidation according to the method used for synthesizing Compound A4 to obtain the title compound.

LCMS: m/z 318 [M+H]$^+$
HPLC retention time: 2.10 min (analysis condition U)

Example 902

Compound BZ2-2

3-Chloro-8-methoxy-6,6-dimethyl-5,6-dihydro-benzo[f]pyrido[4,3-b]indol-11-one

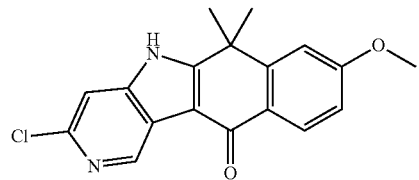 [SMILES: COc1ccc2c(c1)C(C)(C)c1[nH]c3cc(Cl)ncc3c1C2=O]

According to the method used for synthesizing Compound A3-1, the intermediate was prepared from 2-chloro-4-hydrazinopyridine and 7-methoxy-1,1-dimethyl-3,4 dihydro-1H-naphthalen-2-one. Without any purification, the intermediate was subjected to oxidation according to the method used for synthesizing Compound A4 to obtain the title compound.

LCMS: m/z 327, 329 [M+H]$^+$
HPLC retention time: 1.80 min (analysis condition S)

Example 903

Compound CZ1

2-Bromo-8-methoxy-10,10-dimethyl-10,11-dihydro-1,11-diaza-benzo[b]fluoren-5-one

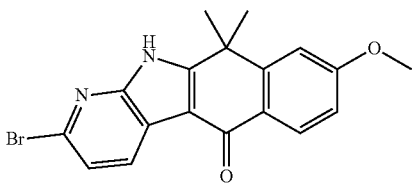

According to the method used for synthesizing Compound A3-1, the intermediate was prepared from 2-bromo-6-hydrazinopyridine and 7-methoxy-1,1-dimethyl-3,4 dihydro-1H-naphthalen-2-one. Without any purification, the intermediate was subjected to oxidation according to the method used for synthesizing Compound A4 to obtain the title compound.

LCMS: m/z 371, 373 [M+H]$^+$
HPLC retention time: 2.85 min (analysis condition U)

Example 904

Compound CZ2

8-Methoxy-10,10-dimethyl-5-oxo-10,11-dihydro-5H-1,11-diaza-benzo[b]fluorene-2-carbonitrile

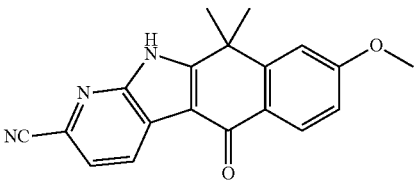 [SMILES: COc1ccc2c(c1)C(C)(C)c1[nH]c3nc(C#N)ccc3c1C2=O]

According to the method 1 for Compound A5-2, 2-bromo-8-methoxy-10,10-dimethyl-10,11-dihydro-1,11-diaza-benzo[b] fluoren-5-one was subjected to cyanation to obtain the title compound.

LCMS: m/z 318 [M+H]$^+$
HPLC retention time: 2.35 min (analysis condition U)

Example 905

Compound CZ3

8-Hydroxy-10,10-dimethyl-5-oxo-10,11-dihydro-5H-1,11-diaza-benzo[b]fluorene-2-carbonitrile

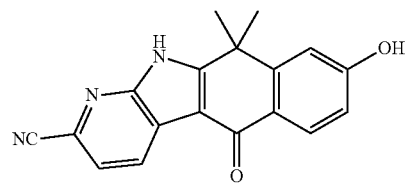 [SMILES: CC1(C)c2cc(O)ccc2C(=O)c2c1[nH]c1nc(C#N)ccc21]

According to the method used for synthesizing Compound A6,8-methoxy-10,10-dimethyl-5-oxo-10,11-dihydro-5H-1,11-diaza-benzo[b]fluorene-2-carbonitrile was subjected to demethylation to obtain the title compound.

LCMS: m/z 304 [M+H]$^+$

HPLC retention time: 1.72 min (analysis condition S)

Example 906

Compound CZ4

Trifuloromethanesulfonic acid 2-cyano-10,10-dimethyl-5-oxo-10,11-dihydro-5H-1,11-diaza-benzo[b]fluoren-8-yl ester

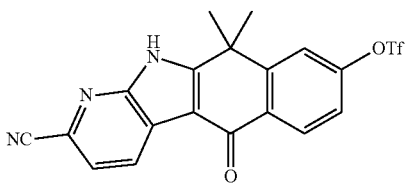 [SMILES: CC1(C)c2cc(OS(=O)(=O)C(F)(F)F)ccc2C(=O)c2c1[nH]c1nc(C#N)ccc21]

According to the method used for synthesizing Compound B1,8-hydroxy-10,10-dimethyl-5-oxo-10,11-dihydro-5H-1,11-diaza-benzo[b]fluorene-2-carbonitrile was subjected to trifluoromethanesulfone esterification to obtain the title compound.

LCMS: m/z 436 [M+H]$^+$

HPLC retention time: 3.32 min (analysis condition Y)

Example 907

Compound CZ5-1

10,10-Dimethyl-5-oxo-8-piperazin-1-yl-10,11-dihydro-5H-1,11-diaza-benzo[b]fluorene-2-carbonitrile

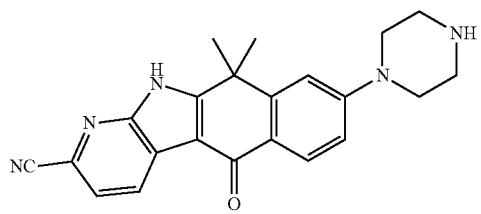 [SMILES: CC1(C)c2cc(N3CCNCC3)ccc2C(=O)c2c1[nH]c1nc(C#N)ccc21]

According to the method used for synthesizing Compound B2-1, trifluoromethanesulfonic acid 2-cyano-10,10-dimethyl-5-oxo-10,11-dihydro-5H-1,11-diaza-benzo[b]fluoren-8-yl ester was introduced with piperazine to obtain the title compound.

LCMS: m/z 372 [M+H]$^+$

HPLC retention time: 1.17 min (analysis condition S)

Example 908

Compound CZ5-2

10,10-Dimethyl-8-(4-morpholin-4-yl-piperidin-1-yl)-5-oxo-10,11-dihydro-5H-1,11-diaza-benzo[b]fluorene-2-carbonitrile

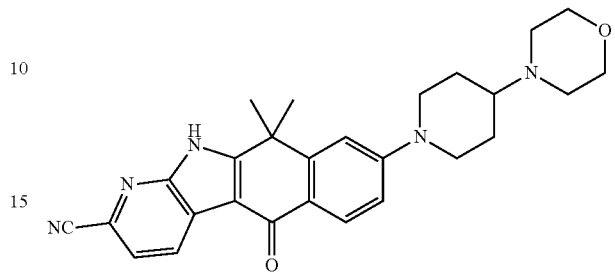

According to the method used for synthesizing Compound B2-1, trifluoromethanesulfonic acid 2-cyano-10,10-dimethyl-5-oxo-10,11-dihydro-5H-1,11-diaza-benzo[b]fluoren-8-yl ester was introduced with 4-morpholin-4-yl piperidine to obtain the title compound.

LCMS: m/z 456 [M+H]$^+$

HPLC retention time: 1.68 min (analysis condition U)

Example 909

Compound CZ6

8-(4-Cyclobutyl-piperazin-1-yl)-10,10-dimethyl-5-oxo-10,11-dihydro-5H-1,11-diaza-benzo[b]fluorene-2-carbonitrile

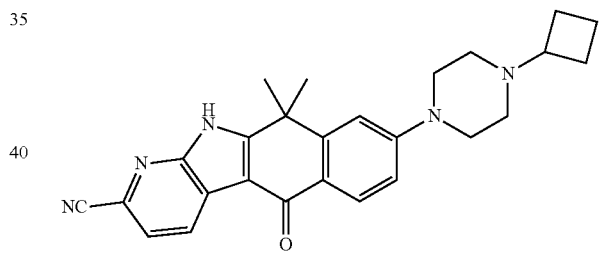

According to the method used for synthesizing Compound B3-32, 10,10-dimethyl-5-oxo-8-piperazin-1-yl-10,11-dihydro-5H-1,11-diaza-benzo[b]fluorene-2-carbonitrile was subjected to reductive amination with cyclobutanone to obtain the title compound.

LCMS: m/z 426 [M+H]$^+$

HPLC retention time: 1.60 min (analysis condition U)

Example 910

Compound DZ1

6-Ethynyl-7-methoxy-1,1-dimethyl-3,4-dihydro-1H-naphthalen-2-one

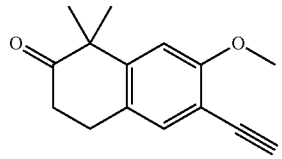 [SMILES: C#Cc1cc2c(cc1OC)C(C)(C)C(=O)CC2]

6-Bromo-7-methoxy-1,1-dimethyl-3,4-dihydro-1H-naphthalen-2-one (1 g) was dissolved in acetonitrile (50 ml), added with PdCl$_2$(CH$_3$CN)$_2$ (45 mg), X-phos (168 mg), CsCO$_3$ (1.2 g) and trimethylsilylacetylene (0.9 ml) and the mixture was stirred at 85° C. for 2 hrs. The reaction mixture was diluted with ethyl acetate (100 ml). The organic layer was washed twice with 10% brine and concentrated under reduced pressure. The resulting residues were dissolved in THF (10 ml), added with the THF solution (4 ml) comprising tetrabutylammonium fluoride and stirred at room temperature for 1 hr. The reaction mixture was diluted with ethyl acetate (100 ml). The organic layer was washed twice with 10% brine and concentrated under reduced pressure. The resulting residues were purified by silica gel column (n-hexane/ethyl acetate=9/1) to obtain the title compound (346 mg, two step yield 43%).

LCMS: m/z 229 [M+H]$^+$

Example 911

Compound DZ2

6-Ethyl-7-methoxy-1,1-dimethyl-3,4-dihydro-1H-naphthalen-2-one

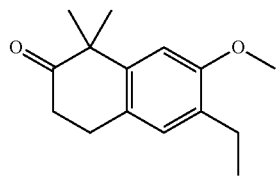 [SMILES: CCc1cc2c(cc1OC)C(C)(C)C(=O)CC2]

6-Ethynyl-7-methoxy-1,1-dimethyl-3,4-dihydro-1H-naphthalen-2-one (346 mg) was dissolved in ethanol:THF (=2:1 mixture solvent, 20 ml), added with 10% Pd/C (170 mg), and then the mixture was stirred at room temperature for 1 hr under hydrogen atmosphere. The catalyst was removed by filtration and the organic layer was concentrated under reduced pressure to obtain the title compound (322 mg, yield 91%).

LCMS: m/z 233 [M+H]$^+$

Example 912

Compound DZ3

2-Bromo-7-ethyl-8-methoxy-10,10-dimethyl-10,11-dihydro-1,11-diaza-benzo[b]fluoren-5-one

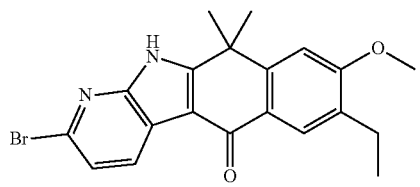 [SMILES: CCc1cc2c(cc1OC)C(C)(C)c1[nH]c3nc(Br)ccc3c1C2=O]

According to the method used for synthesizing Compound A3-1, the intermediate was prepared from 2-bromo-6-hydrazinopyridine and 6-ethyl-7-methoxy-1,1-dimethyl-3,4-dihydro-1H-naphthalen-2-one. Without any purification, the intermediate was subjected to oxidation according to the method used for synthesizing Compound A4 to obtain the title compound.

LCMS: m/z 399, 401 [M+H]$^+$
HPLC retention time: 3.35 min (analysis condition Y)

Example 913

Compound DZ4

7-Ethyl-8-methoxy-10,10-dimethyl-5-oxo-10,11-dihydro-5H-1,11-diaza-benzo[b]fluorene-2-carbonitrile

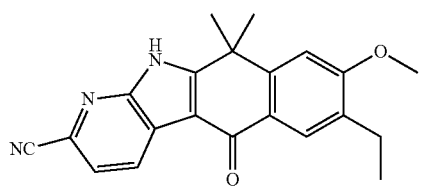 [SMILES: CCc1cc2c(cc1OC)C(C)(C)c1[nH]c3nc(C#N)ccc3c1C2=O]

According to the method 1 for Compound A5-2, 2-bromo-7-ethyl-8-methoxy-10,10-dimethyl-10,11-dihydro-1,11-diaza-benzo[b]fluoren-5-one was subjected to cyanation to obtain the title compound.

LCMS: m/z 346 [M+H]$^+$
HPLC retention time: 3.05 min (analysis condition Y)

Example 914

Compound DZ5

7-Ethyl-8-hydroxy-10,10-dimethyl-5-oxo-10,11-dihydro-5H-1,11-diaza-benzo[b]fluorene-2-carbonitrile

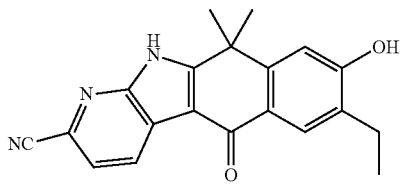 [SMILES: CCc1cc2c(cc1O)C(C)(C)c1[nH]c3nc(C#N)ccc3c1C2=O]

According to the method used for synthesizing Compound A5,7-ethyl-8-methoxy-10,10-dimethyl-5-oxo-10,11-dihydro-5H-1,11-diaza-benzo[b] fluorene-2-carbonitrile was subjected to demethylation to obtain the title compound.

LCMS: m/z 332 [M+H]$^+$
HPLC retention time: 2.60 min (analysis condition Y)

Example 915

Compound DZ6-1

Trifuloro-methanesulfonic acid 2-cyano-7-ethyl-10,10-dimethyl-5-oxo-10,11-dihydro-5H-1,11-diaza-benzo[b]fluoren-8-yl ester

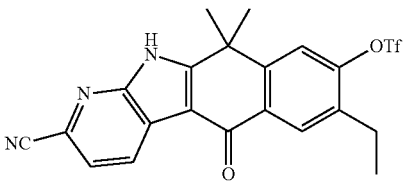 [SMILES: CCc1cc2c(cc1OS(=O)(=O)C(F)(F)F)C(C)(C)c1[nH]c3nc(C#N)ccc3c1C2=O]

According to the method used for synthesizing Compound B1,7-ethyl-8-hydroxy-10,10-dimethyl-5-oxo-10,11-dihydro-5H-1,11-diaza-benzo[b]fluorene-2-carbonitrile was subjected to trifluoromethanesulfone esterification to obtain the title compound.

LCMS: m/z 464 [M+H]+

HPLC retention time: 3.50 min (analysis condition Y)

The compounds described in the following Table 15 were prepared from trifluoro-methanesulfonic acid 2-cyano-7-ethyl-10,10-dimethyl-5-oxo-10,11-dihydro-5H-1,11-diaza-benzo[b]fluoren-8-yl ester and corresponding amine according to the method that is used for the synthesis of Compound B2-10. The compounds of Example 919 and Example 920 were obtained as a by-product of the reaction.

TABLE 15

| Example No. | Comp. No. | Structure | Compound Name | HPLC Condition | Retention Time | m/z |
|---|---|---|---|---|---|---|
| 916 | DZ7-1 | 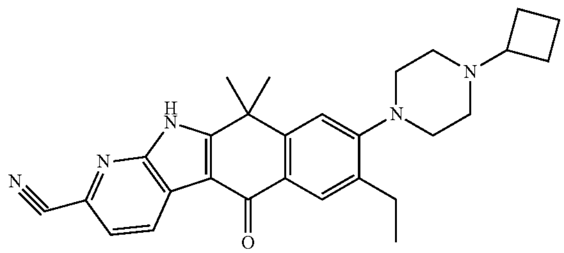 [SMILES: CCc1cc2c(cc1N1CCN(C3CCC3)CC1)C(C)(C)c1[nH]c3nc(C#N)ccc3c1C2=O] | 8-(4-Cyclobutyl-piperazine-1-yl)-7-ethyl-10,10-dimethyl-5-oxo-10,11-dihydro-5H-1,11-diaza-benzo[b]fluorene-2-carbonitrile | Y | 1.83 | 454 |
| 917 | DZ7-2 | 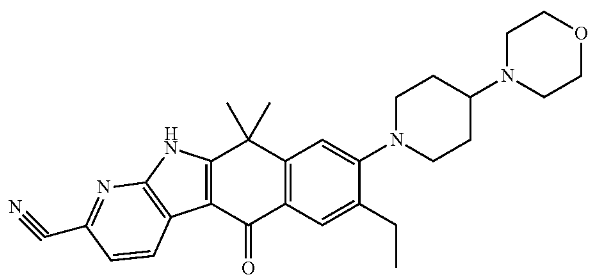 [SMILES: CCc1cc2c(cc1N1CCC(N3CCOCC3)CC1)C(C)(C)c1[nH]c3nc(C#N)ccc3c1C2=O] | 7-Ethyl-10,10-dimethyl-8-(4-morpholine-4-yl-piperidine-1-yl)-5-oxo-10,11-dihydro-5H-1,11-diaza-benzo[b]fluorene-2-carbonitrile | Y | 1.85 | 484 |
| 918 | DZ7-3 | 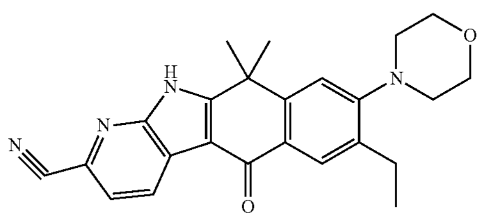 [SMILES: CCc1cc2c(cc1N1CCOCC1)C(C)(C)c1[nH]c3nc(C#N)ccc3c1C2=O] | 7-Ethyl-10,10-dimethyl-8-morpholine-4-yl-5-oxo-10,11-dihydro-5H-1,11-diaza-benzo[b]fluorene-2-carbonitrile | Y | 3.02 | 401 |
| 919 | DZ7-4 | 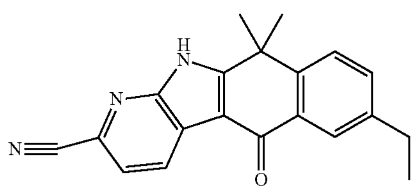 [SMILES: CCc1ccc2c(c1)C(=O)c1c([nH]c3nc(C#N)ccc13)C2(C)C] | 7-Ethyl-10,10-dimethyl-5-oxo-10,11-dihydro-5H-1,11-diaza-benzo[b]fluorene-2-carbonitrile | Y | 3.07 | 316 |
| 920 | DZ7-5 | 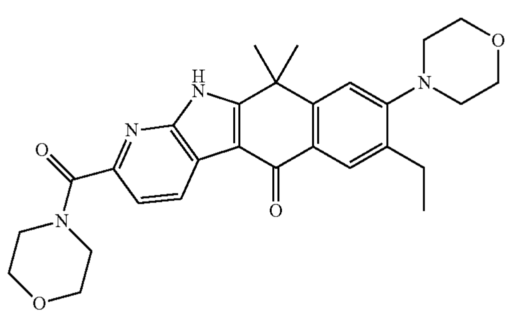 [SMILES: CCc1cc2c(cc1N1CCOCC1)C(C)(C)c1[nH]c3nc(C(=O)N4CCOCC4)ccc3c1C2=O] | 7-Ethyl-10,10-dimethyl-2-(morpholine-4-carbonyl)-8-morpholine-4-yl-10,11-dihydro-1,11-diaza-benzo[b]fluorene-5-one | Y | 2.70 | 489 |

Example 921

Compound DZ6-2

8-(2-Diethylamino-ethoxy)-11-(2-diethylamino-ethyl)-7-ethyl-10,10-dimethyl-5-oxo-10,11-dihydro-5H-1,11-diaza-benzo[b]fluorene-2-carbonitrile

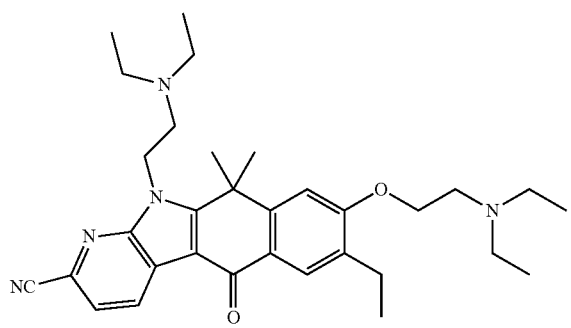 [SMILES: CCc1cc2c(cc1OCCN(CC)CC)C(C)(C)c1c(c3ccc(C#N)nc3n1CCN(CC)CC)C2=O]

According to the method used for synthesizing Compound A7-17, 7-ethyl-8-hydroxy-10,10-dimethyl-5-oxo-10,11-dihydro-5H-1,11-diaza-benzo[b]fluorene-2-carbonitrile was alkylated to obtain the title compound.

LCMS: m/z 530 [M+H]$^+$
HPLC retention time: 1.38 min (analysis condition Y)

Example 922

Compound EZ1

2-(6-Methoxy-pyridin-2-yl)-2-methyl-propionic acid ethyl ester

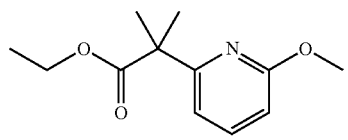 [SMILES: CCOC(=O)C(C)(C)c1cccc(OC)n1]

2-Bromo-6-methoxypyridine (7.0 g), ethyl isobutyrate (4.75 g), tri t-butylphosphine (300 mg) and Pd$_2$(dba)$_3$ (680 mg) were dissolved in toluene (200 ml) under nitrogen atmosphere, added with THF solution of LiHMDS (1.6 M, 24 ml), and the mixture was stirred at 100° C. for 6 hrs. The reaction mixture was diluted with ethyl acetate (300 ml), and washed three times with 15% brine (200 ml). The organic layer was concentrated under reduced pressure and the resulting residues were purified by silica gel column (n-hexane/ethyl acetate=4/1) to obtain the title compound (5.353 g, yield 60%).

LCMS: m/z 224 [M+H]$^+$

Example 923

Compound EZ2

2-(6-Methoxy-pyridin-2-yl)-2-methyl-propionic acid

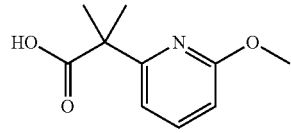

2-(6-Methoxy-pyridin-2-yl)-2-methyl-propionic acid ethyl ester (5.33 g) was dissolved in methanol (200 ml), added with 5 N aqueous solution of potassium hydroxide (25 ml), and then stirred under reflux. The reaction mixture was concentrated and neutralized with 2 N hydrochloric acid. The precipitated matters were collected by filtration and dried to obtain the title compound (3.55 g).

LCMS: m/z 196 [M+H]$^+$

Example 924

Compound EZ3

4-(6-Methoxy-pyridin-2-yl)-4-methyl-3-oxo-pentanoic acid tert-butyl ester

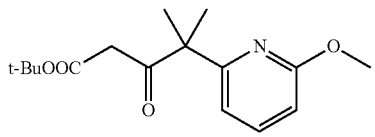

The title compound was synthesized from 2-(6-methoxy-pyridin-2-yl)-2-methyl-propionic acid and mono-tert-butyl malonic acid according to the method used for the synthesis of Compound PR4. The resultant was used for the next step without further purification.

Example 925

Compound EZ4-1

6-Cyano-2-[1-(6-methoxy-pyridin-2-yl)-1-methyl-ethyl]-1H-indole-3-carboxylic acid tert-butyl ester

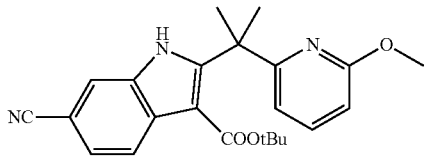

According to the method that is used for the preparation of Compound PR5-1, the title compound was synthesized from 4-(6-methoxy-pyridin-2-yl)-4-methyl-3-oxo-pentanoic acid tert-butyl ester and 4-chloro-3-nitrobenzonitrile LCMS: m/z 392 [M+H]$^+$

Example 926

Compound EZ4-2

6-Cyano-2-[1-(6-methoxy-pyridin-2-yl)-1-methyl-ethyl]-benzofuran-3-carboxylic acid tert-butyl ester

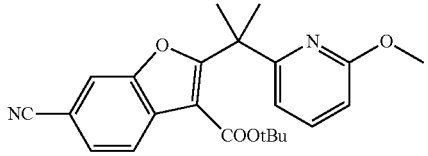

According to the method that is used for the preparation of Compound FR1, the title compound was synthesized from 4-(6-methoxy-pyridin-2-yl)-4-methyl-3-oxo-pentanoic acid tert-butyl ester and 4-chloro-3-nitrobenzonitrile.

LCMS: m/z 393 [M+H]$^+$

Example 927

Compound EZ5-1

6-Cyano-2-[1-(6-methoxy-pyridin-2-yl)-1-methyl-ethyl]-1H-indole-3-carboxylic acid

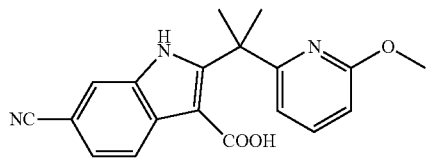 [SMILES: COc1cccc(C(C)(C)c2[nH]c3cc(C#N)ccc3c2C(=O)O)n1]

According to the method that is used for the preparation of Compound PR7, the title compound was synthesized from 6-cyano-2-[1-(6-methoxy-pyridin-2-yl)-1-methyl-ethyl]-1H-indole-3-carboxylic acid tert-butyl ester.

LCMS: m/z 336 [M+H]$^+$

Example 928

Compound EZ5-2

6-Cyano-2-[1-(6-methoxy-pyridin-2-yl)-1-methyl-ethyl]-benzofuran-3-carboxylic acid

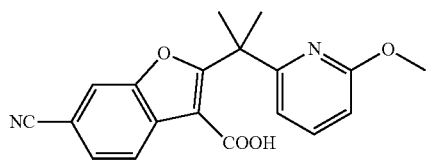 [SMILES: COc1cccc(C(C)(C)c2oc3cc(C#N)ccc3c2C(=O)O)n1]

According to the method that is used for the preparation of Compound PR7, the title compound was synthesized from 6-cyano-2-[1-(6-methoxy-pyridin-2-yl)-1-methyl-ethyl]-benzofuran-3-carboxylic acid tert-butyl ester.

LCMS: m/z 337 [M+H]$^+$

Example 929

Compound EZ6-1

2-Methoxy-11,11-dimethyl-5-oxo-10,11-dihydro-5H-pyrido[2,3-b]carbazole-8-carboxylic acid amide

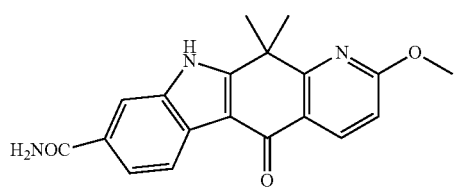 [SMILES: COc1ccc2c(n1)C(C)(C)c1[nH]c3cc(C(N)=O)ccc3c1C2=O]

According to the method that is used for the preparation of Compound AZ7-1, the title compound was synthesized from 6-cyano-2-[1-(6-methoxy-pyridin-2-yl)-1-methyl-ethyl]-1H-indole-3-carboxylic acid.

LCMS: m/z 336 [M+H]$^+$

HPLC retention time: 1.98 min (analysis condition S)

Example 930

Compound EZ6-2

2-Methoxy-11,11-dimethyl-5-oxo-5,11-dihydro-benzo[4,5]furo[3,2-g]quinoline-8-carboxylic acid amide

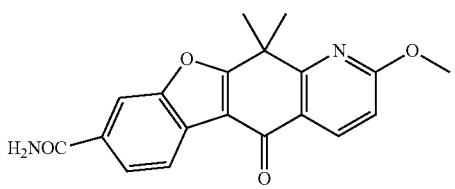 [SMILES: COc1ccc2c(n1)C(C)(C)c1oc3cc(C(N)=O)ccc3c1C2=O]

According to the method that is used for the preparation of Compound AZ7-1, the title compound was synthesized from 6-cyano-2-[1-(6-methoxy-pyridin-2-yl)-1-methyl-ethyl]-benzofuran-3-carboxylic acid.

LCMS: m/z 337 [M+H]$^+$

HPLC retention time: 2.38 min (analysis condition S)

Example 931

Compound EZ7-1

2-Methoxy-11,11-dimethyl-5-oxo-10,11-dihydro-5H-pyrido[2,3-b]carbazole-8-carbonitrile

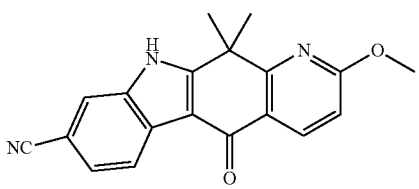 [SMILES: COc1ccc2c(n1)C(C)(C)c1[nH]c3cc(C#N)ccc3c1C2=O]

According to the method that is used for the preparation of Compound AZ7-2, the title compound was synthesized from 2-methoxy-11,11-dimethyl-5-oxo-10,11-dihydro-5H-pyrido[2,3-b]carbazole-8-carboxylic acid amide.

LCMS: m/z 318 [M+H]$^+$

HPLC retention time: 2.60 min (analysis condition S)

Example 932

Compound EZ7-2

2-Methoxy-11,11-dimethyl-5-oxo-5,11-dihydro-benzo[4,5]furo[3,2-g]quinoline-8-carbonitrile

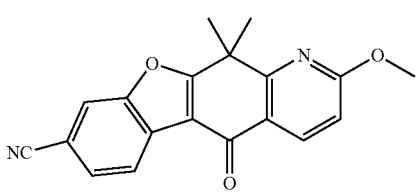 [SMILES: COc1ccc2c(n1)C(C)(C)c1oc3cc(C#N)ccc3c1C2=O]

According to the method that is used for the preparation of Compound AZ7-2, the title compound was synthesized from 2-methoxy-11,11-dimethyl-5-oxo-5,11-dihydro-benzo[4,5]furo[3,2-g]quinoline-8-carboxylic acid amide.

LCMS: m/z 319 [M+H]$^+$

HPLC retention time: 3.18 min (analysis condition S)

Example 933

Compound EZ8-1

2-Hydroxy-11,11-dimethyl-5-oxo-10,11-dihydro-5H-pyrido[2,3-b]carbazole-8-carbonitrile

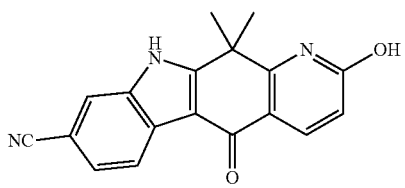 [SMILES: CC1(C)c2nc(O)ccc2C(=O)c2c1[nH]c1cc(C#N)ccc21]

According to the method that is used for the preparation of Compound A5,2-methoxy-11,11-dimethyl-5-oxo-10,11-dihydro-5H-pyrido[2,3-b]carbazole-8-carbonitrile was demethylated to synthesize the title compound.

LCMS: m/z 304 [M+H]$^+$

HPLC retention time: 1.70 min (analysis condition U)

Example 934

Compound EZ8-2

2-Hydroxy-11,11-dimethyl-5-oxo-5,11-dihydro-benzo[4,5]furo[3,2-g]quinoline-8-carbonitrile

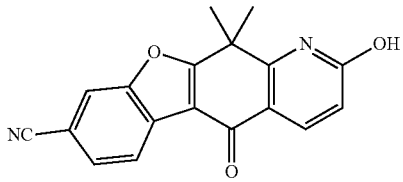 [SMILES: CC1(C)c2nc(O)ccc2C(=O)c2c1oc1cc(C#N)ccc21]

According to the method that is used for the preparation of Compound A5,2-methoxy-11,11-dimethyl-5-oxo-5,11-dihydro-benzo[4,5]furo[3,2-g]quinoline-8-carbonitrile was demethylated to synthesize the title compound.

LCMS: m/z 305 [M+H]$^+$

HPLC retention time: 2.17 min (analysis condition U)

The compounds described in the following Table 16 were synthesized from 2-hydroxy-11,11-dimethyl-5-oxo-10,11-dihydro-5H-pyrido[2,3-b]carbazole-8-carbonitrile or from 2-hydroxy-11,11-dimethyl-5-oxo-5,11-dihydro-benzo[4,5]furo[3,2-g]quinoline-8-carbonitrile according to the method described in the Table.

TABLE 16

| Example No. | Comp. No. | Structure | Compound Name | HPLC Condition | Retention Time | m/z | Method |
|---|---|---|---|---|---|---|---|
| 935 | E79-1 | 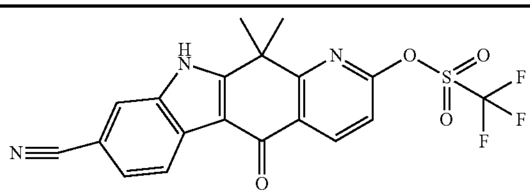 | Trifluoromethanesulfonic acid 8-cyano-11,11-dimethyl-5-oxo-10,11-dihydro-5H-pyrido[2,3-b]carbazol-2-yl ester | U | 2.93 | 436 | B1 |
| 936 | EZ9-2 | 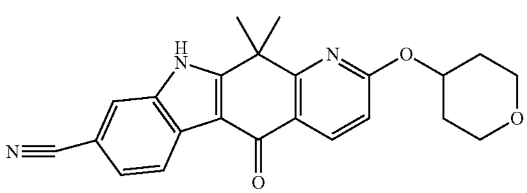 [SMILES: CC1(C)c2nc(OC3CCOCC3)ccc2C(=O)c2c1[nH]c1cc(C#N)ccc21] | 11,11-Dimethyl-5-oxo-2-(tetrahydro-pyran-4-yloxy)-10,11-dihydro-5H-pyrido[2,3-b]carbazole-8-carbonitrile | U | 2.57 | 388 | A7-1 |
| 937 | EZ9-3 | 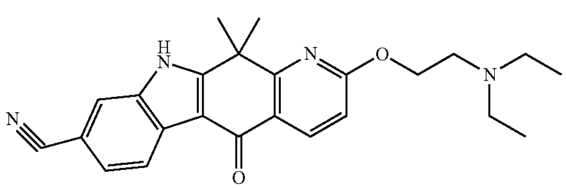 [SMILES: CCN(CC)CCOc1ccc2c(n1)C(C)(C)c1[nH]c3cc(C#N)ccc3c1C2=O] | 2-(2-Dethylamino-ethoxy)-11,11-dimethyl-5-oxo-10,11-dihydro-5H-pyrido[2,3-b]carbazole-8-carbonitrile | Y | 1.63 | 403 | A7-17 |
| 938 | EZ9-4 | 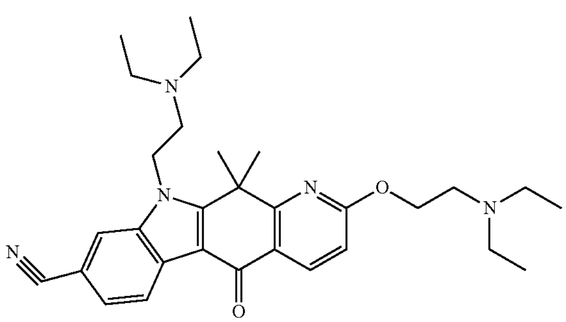 [SMILES: CCN(CC)CCOc1ccc2c(n1)C(C)(C)c1c(c3ccc(C#N)cc3n1CCN(CC)CC)C2=O] | 2-(2-Diethylamino-ethoxy)-10-(2-diethylamino-ethyl)-11,11-dimethyl-5-oxo-10,11-dihydro-5H-pyrido[2,3-b]carbazole-8-carbonitrile | Y | 1.82 | 502 | A7-17 |

TABLE 16-continued

| Example No. | Comp. No. | Structure | Compound Name | HPLC Condition | Retention Time | m/z | Method |
|---|---|---|---|---|---|---|---|
| 939 | EZ9-5 | 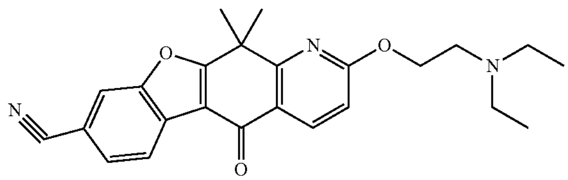 [SMILES: CCN(CC)CCOc1ccc2c(n1)C(C)(C)c1oc3cc(C#N)ccc3c1C2=O] | 2-(2-Diethylamino-ethoxy)-11,11-dimethyl-5-oxo-5,11-dihydro-benzo[4,5]furo[3,2-g]quinoline-8-carbonitrile | Y | 1.77 | 404 | A7-17 |

The compounds described in the following Table 17 were synthesized from Compound W3 and corresponding halide by alkylation of hydroxyl group according to the method that is used for the synthesis of Compound A7-17.

TABLE 17

| Example No. | Comp. No. | Structure | Compound Name | HPLC Condition | Retention Time | m/z |
|---|---|---|---|---|---|---|
| 940 | W4-3 | 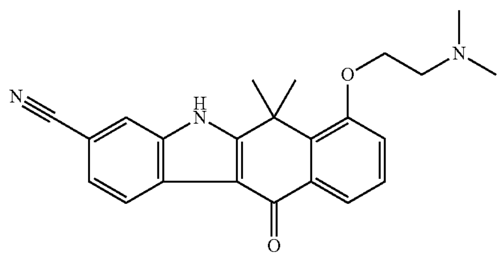 [SMILES: CN(C)CCOc1cccc2c1C(C)(C)c1[nH]c3cc(C#N)ccc3c1C2=O] | 7-(2-Dimethylamino-ethoxy)-6,6-dimethyl-11-oxo-6,11-dihydro-5H-benzo[b]carbazole-3-carbonitrile | I | 0.96 | 374.0 |
| 941 | W4-4 | 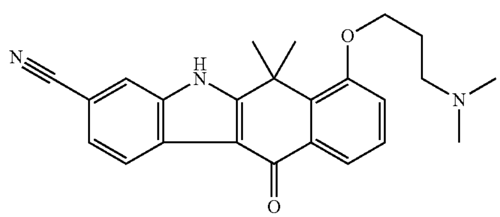 [SMILES: CN(C)CCCOc1cccc2c1C(C)(C)c1[nH]c3cc(C#N)ccc3c1C2=O] | 7-(3-Dimethylamino-propoxy)-6,6-dimethyl-11-oxo-6,11-dihydro-5H-benzo[b]carbazole-3-carbonitrile | I | 0.92 | 388.0 |

The compounds described in the following Table 18 were synthesized according to the method shown below. Specifically, Compound GT1-1 was prepared from Compound J2 and phenylhydrazine according to the method that is used for the synthesis of Compound A3 and Compound A4. Subsequently, in accordance with the methylation carried out in the same manner as Compound A10-1, Compound GT1-2 was prepared.

TABLE 18

| Example No. | Comp. No. | Structure | Compound Name | HPLC Condition | Retention Time | m/z | Method |
|---|---|---|---|---|---|---|---|
| 942 | GT1-1 | 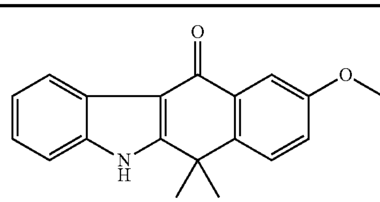 | 9-Methoxy-6,6-dimethyl-5,6-dihydro-benzo[b]carbazol-11-one | A | 2.36 | 292.0 | A3 A4 |

TABLE 18-continued

| Example No. | Comp. No. | Structure | Compound Name | HPLC Condition | Retention Time | m/z | Method |
|---|---|---|---|---|---|---|---|
| 943 | GT1-2 | 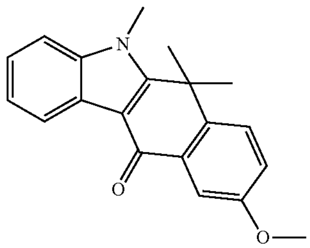 [SMILES: COc1ccc2c(c1)C(=O)c1c(n(C)c3ccccc13)C2(C)C] | 9-Methoxy-5,6,6-trimethyl-5,6-dihydro-benzo[b]carbazol-11-one | A | 2.53 | 306.0 | A10-1 |

The compounds described in the following Table 19 were synthesized according to the method shown below. Specifically, Compound GT2-1 was prepared from Compound A2 and phenylhydrazine according to the method that is used for the synthesis of Compound A3 and Compound A4.

Subsequently, by carrying out the alkylation in the same manner as Compound A10-1, Compound GT2-2 and Compound GT2-8 were prepared.

To obtain the compounds of the Table, chemical conversion of Compound GT2-1 or the 5-alkylate of Compound GT2-1 was achieved by using in combination the functional group modifications (e.g., demethylation according to the method used for the preparation of Compound A6 and subsequent introduction of a functional group, etc.) as explained before and described in the Table.

TABLE 19

| Example No. | Comp. No. | Structure | Compound Name | HPLC Condition | Retention Time | m/z | Method |
|---|---|---|---|---|---|---|---|
| 944 | GT2-1 | 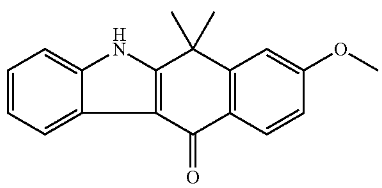 [SMILES: COc1ccc2c(c1)C(C)(C)c1[nH]c3ccccc3c1C2=O] | 8-Methoxy-6,6-dimethyl-5,6-dihydro-benzo[b]carbazol-11-one | A | 2.30 | 292.0 | A3 A4 |
| 945 | GT2-2 | 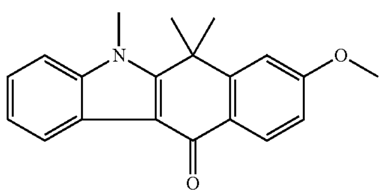 [SMILES: COc1ccc2c(c1)C(C)(C)c1c(c3ccccc3n1C)C2=O] | 8-Methoxy-5,6,6-trimethyl-5,6-dihydro-benzo[b]carbazol-11-one | A | 2.55 | 306.0 | A10-1 |
| 946 | GT2-3 | 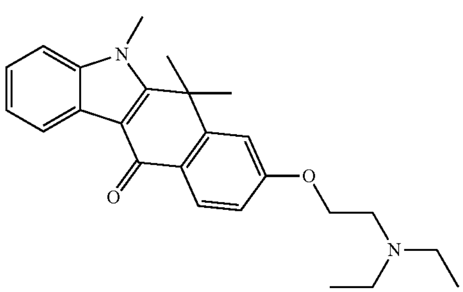 [SMILES: CCN(CC)CCOc1ccc2c(c1)C(C)(C)c1c(c3ccccc3n1C)C2=O] | 8-(2-Diethylamino-ethoxy)-5,6,6-trimethyl-5,6-dihydro-benzo[b]carbazol-11-one | A | 1.90 | 391.0 | A6 A7-17 A10-1 |
| 947 | GT2-4 | Chiral | 8-((R)-2,3-Dihydroxy-propoxy)-5,6,6-trimethyl-5,6-dihydro-benzo[b]carbazol-11-one | A | 1.90 | 366.0 | A6 A7-17 A10-1 |

TABLE 19-continued

| Example No. | Comp. No. | Structure | Compound Name | HPLC Condition | Retention Time | m/z | Method |
|---|---|---|---|---|---|---|---|
| 948 | GT2-5 | 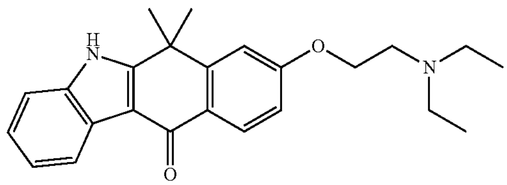 [SMILES: CCN(CC)CCOc1ccc2c(c1)C(C)(C)c1[nH]c3ccccc3c1C2=O] | 8-(2-Diethylamino-ethoxy)-6,6-dimethyl-5,6-dihydro-benzo[b]carbazol-11-one | F | 1.93 | 377.3 | A6 A7-17 |
| 949 | GT2-6 | 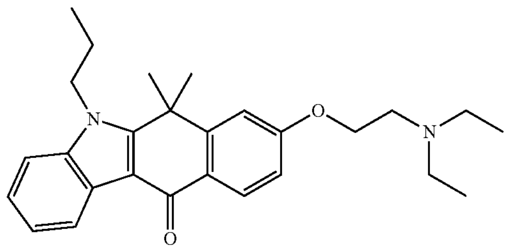 [SMILES: CCCn1c2c(c3ccccc31)C(=O)c1ccc(OCCN(CC)CC)cc1C2(C)C] | 8-(2-Diethylamino-ethoxy)-6,6-dimethyl-5-propyl-5,6-dihydro-benzo[b]carbazol-11-one | A | 2.09 | 419.0 | A6 A7-17 A10-1 |
| 950 | GT2-7 | 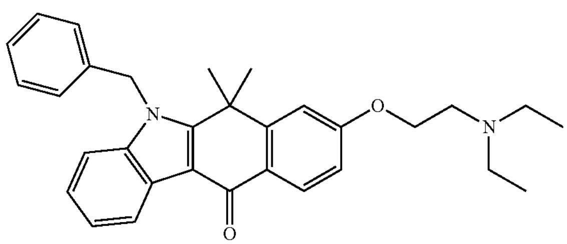 [SMILES: CCN(CC)CCOc1ccc2c(c1)C(C)(C)c1c(c3ccccc3n1Cc1ccccc1)C2=O] | 5-Benzyl-8-(2-diethylamino-ethoxy)-6,6-dimethyl-5,6-dihydro-benzo[b]carbazol-11-one | B | 4.83 | 467.3 | A6 A7-17 A10-1 |
| 951 | GT2-8 | 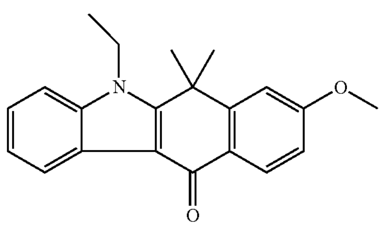 [SMILES: CCn1c2c(c3ccccc31)C(=O)c1ccc(OC)cc1C2(C)C] | 5-Ethyl-8-methoxy-6,6-dimethyl-5,6-dihydro-benzo[b]carbazol-11-one | F | 2.94 | 320.0 | A10-1 |
| 952 | GT2-9 | 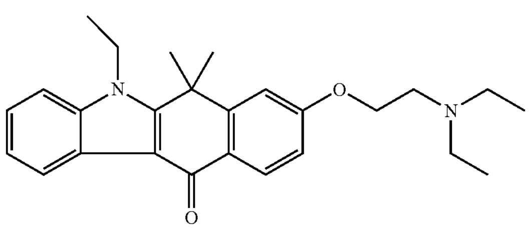 [SMILES: CCN(CC)CCOc1ccc2c(c1)C(C)(C)c1c(c3ccccc3n1CC)C2=O] | 8-(2-Diethylamino-ethoxy)-5-ethyl-6,6-dimethyl-5,6-dihydro-benzo[b]carbazol-11-one | F | 2.16 | 405.0 | A6 A7-17 A10-1 |
| 953 | GT2-10 | 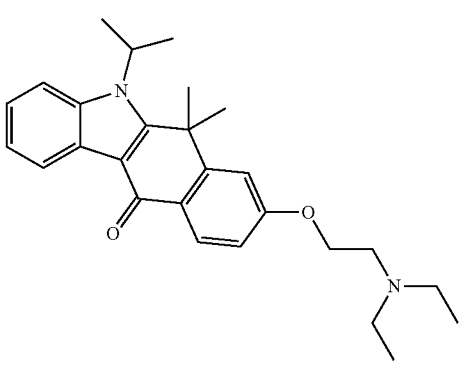 [SMILES: CCN(CC)CCOc1ccc2c(c1)C(C)(C)c1c(c3ccccc3n1C(C)C)C2=O] | 8-(2-Diethylamino-ethoxy)-5-isopropyl-6,6-dimethyl-5,6-dihydro-benzo[b]carbazol-11-one | A | 2.02 | 419.0 | A6 A7-17 A10-1 |

TABLE 19-continued

| Example No. | Comp. No. | Structure | Compound Name | HPLC Condition | Retention Time | m/z | Method |
|---|---|---|---|---|---|---|---|
| 954 | GT2-11 | 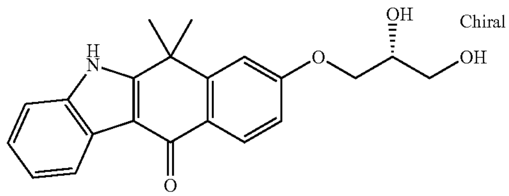 [SMILES: CC1(C)c2cc(OC[C@H](O)CO)ccc2C(=O)c2c1[nH]c1ccccc21] | 8-((R)-2,3-Dihydroxy-propoxy)-6,6-dimethyl-5,6-dihydro-benzo[b]carbazol-11-one | C | 2.17 | 352.2 | A6 A7-17 A7-14-2 |
| 955 | GT2-12 | 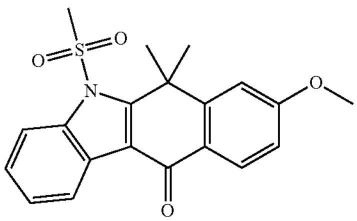 [SMILES: COc1ccc2c(c1)C(C)(C)c1c(c3ccccc3n1S(C)(=O)=O)C2=O] | 5-Methanesulfonyl-8-methoxy-6,6-dimethyl-5,6-dihydro-benzo[b]carbazol-11-one | C | 2.87 | 370.1 | A9-1 |
| 956 | GT2-13 | 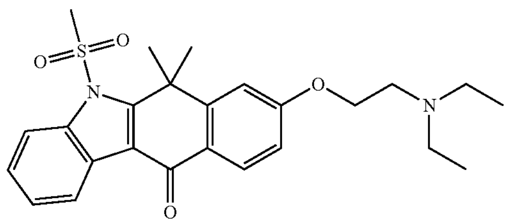 [SMILES: CCN(CC)CCOc1ccc2c(c1)C(C)(C)c1c(c3ccccc3n1S(C)(=O)=O)C2=O] | 8-(2-Diethylamino-ethoxy)-5-methanesulfonyl-6,6-dimethyl-5,6-dihydro-benzo[b]carbazol-11-one | F | 2.20 | 455.1 | A6 A7-17 A9-1 |
| 957 | GT2-14 | 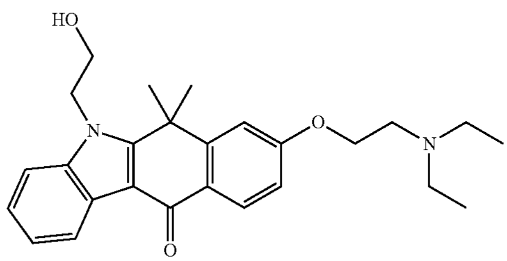 [SMILES: CCN(CC)CCOc1ccc2c(c1)C(C)(C)c1c(c3ccccc3n1CCO)C2=O] | 8-(2-Diethylamino-ethoxy)-5-(2-hydroxy-ethyl)-6,6-dimethyl-5,6-dihydro-benzo[b]carbazol-11-one | H | 3.73 | 421.0 | A6 A7-17 A10-1 |
| 958 | GT2-15 | 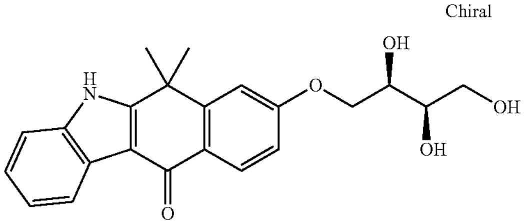 [SMILES: CC1(C)c2cc(OC[C@@H](O)[C@H](O)CO)ccc2C(=O)c2c1[nH]c1ccccc21] | 6,6-Dimethyl-8-((2R,3R)-2,3,4-trihydroxy-butoxy)-5,6-dihydro-benzo[b]carbazol-11-one | H | 3.73 | 382.4 | A7-1 A7-14-2 |

The compounds described in the following Table 20 were synthesized according to the method shown below. Specifically, by using Compound A2 and phenylhydrazine having a corresponding substituent group, 2 (or 3)-substituted-8-methoxy-6,6-dimethyl-6,11-dihydro-5H-benzo[b]carbazol-11-one was prepared according to the method that is used for the synthesis of Compound A3 and Compound A4. Subsequently, to obtain the compounds of the Table, chemical conversion of the above compounds was achieved by using in combination the functional group modifications as explained before and described in the Table.

TABLE 20

| Example No. | Comp. No. | Structure | Compound Name | HPLC Condition | Retention Time | m/z | Method |
|---|---|---|---|---|---|---|---|
| 959 | GT3-1 | 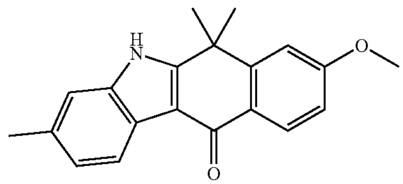 | 8-Methoxy-3,6,6-trimethyl-5,6-dihydro-benzo[b]carbazol-11-one | A | 2.39 | 306.0 | A3 A4 |
| 960 | GT3-2 | 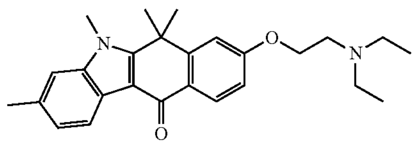 [SMILES: CCN(CC)CCOc1ccc2c(c1)C(C)(C)c1c(c3ccc(C)cc3n1C)C2=O] | 8-(2-Diethylamino-ethoxy)-3,5,6,6-tetramethyl-5,6-dihydro-benzo[b]carbazol-11-one | A | 1.97 | 405.0 | A6 A7-17 A10-1 |
| 961 | GT3-3 | 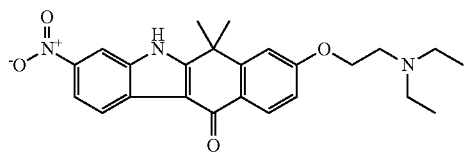 | 8-(2-Diethylamino-ethoxy)-6,6-dimethyl-3-nitro-5,6-dihydro-benzo[b]carbazol-11-one | B | 3.86 | 422.2 | A6 A7-17 |
| 962 | GT3-4 | 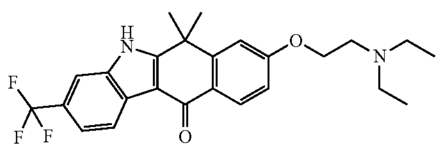 [SMILES: CCN(CC)CCOc1ccc2c(c1)C(C)(C)c1[nH]c3cc(C(F)(F)F)ccc3c1C2=O] | 8-(2-Diethylamino-ethoxy)-6,6-dimethyl-3-trifluoromethyl-5,6-dihydro-benzo[b]carbazol-11-one | A | 2.03 | 445.0 | A6 A7-17 |
| 963 | GT3-5 | 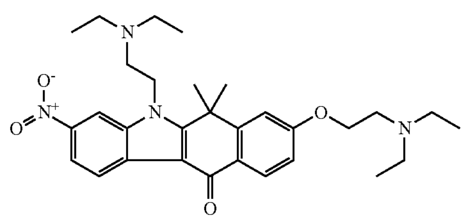 [SMILES: CCN(CC)CCOc1ccc2c(c1)C(C)(C)c1c(c3ccc([N+](=O)[O-])cc3n1CCN(CC)CC)C2=O] | 8-(2-Diethylamino-ethoxy)-5-(2-diethylamino-ethyl)-6,6-dimethyl-3-nitro-5,6-dihydro-benzo[b]carbazol-11-one | F | 1.74 | 521.3 | A6 A7-17 A10-1 |
| 964 | GT3-6 | 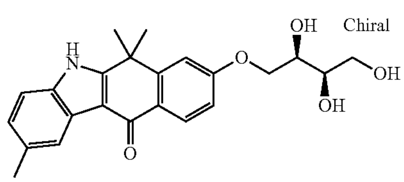 [SMILES: Cc1ccc2[nH]c3c(c2c1)C(=O)c1ccc(OC[C@@H](O)[C@H](O)CO)cc1C3(C)C] | 2,6,6-Trimethyl-8-((2R,3R)-2,3,4-trihydroxy-butoxy)-5,6-dihydro-benzo[b]carbazol-11-one | F | 2.03 | 396.0 | A6 A7-17 A7-14-2 |
| 965 | GT3-7 | 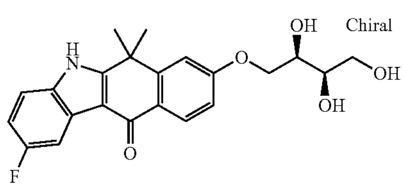 [SMILES: CC1(C)c2cc(OC[C@@H](O)[C@H](O)CO)ccc2C(=O)c2c1[nH]c1ccc(F)cc21] | 2-Fluoro-6,6-dimethyl-8-((2R,3R)-2,3,4-trihydroxy-butoxy)-5,6-dihydro-benzo[b]carbazol-11-one | F | 1.99 | 400.0 | A6 A7-17 A7-14-2 |
| 966 | GT3-8 | 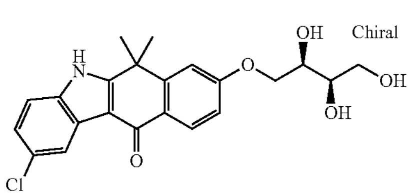 [SMILES: CC1(C)c2cc(OC[C@@H](O)[C@H](O)CO)ccc2C(=O)c2c1[nH]c1ccc(Cl)cc21] | 2-Chloro-6,6-dimethyl-8-((2R,3R)-2,3,4-trihydroxy-butoxy)-5,6-dihydro-benzo[b]carbazol-11-one | F | 2.14 | 416.0 | A6 A7-17 A7-14-2 |

TABLE 20-continued

| Example No. | Comp. No. | Structure | Compound Name | HPLC Condition | Retention Time | m/z | Method |
|---|---|---|---|---|---|---|---|
| 967 | GT3-9 | 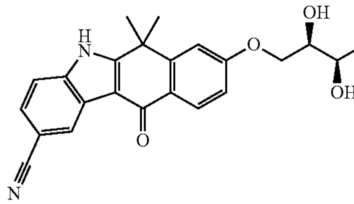 | 6,6-Dimethyl-11-oxo-8-((2R,3R)-2,3,4-trihydroxy-butoxy)-6,11-dihydro-5H-benzo[b]carbazole-2-carbonitrile | F | 1.90 | 407.4 | A6<br>A7-17<br>A7-14-2 |
| 968 | GT3-10 | 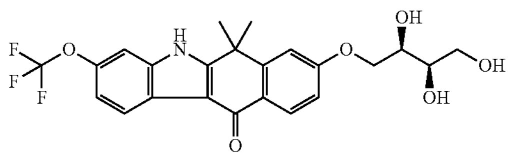 [SMILES: CC1(C)c2cc(OC[C@@H](O)[C@H](O)CO)ccc2C(=O)c2c1[nH]c1cc(OC(F)(F)F)ccc21] | 6,6-Dimethyl-3-trifluoromethoxy-8-((2R,3R)-2,3,4-trihydroxy-butoxy)-5,6-dihydro-benzo[b]carbazol-11-one | F | 2.31 | 466.4 | A6<br>A7-17<br>A7-14-2 |
| 969 | GT3-11 | 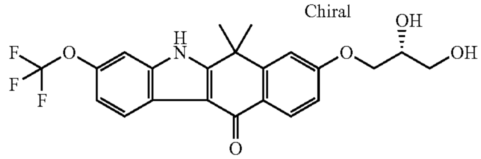 [SMILES: CC1(C)c2cc(OC[C@H](O)CO)ccc2C(=O)c2c1[nH]c1cc(OC(F)(F)F)ccc21] | 8-((R)-2,3-Dihydroxy-propoxy)-6,6-dimethyl-3-trifluoromethoxy-5,6-dihydro-benzo[b]carbazol-11-one | F | 2.43 | 436.4 | A6<br>A7-17<br>A7-14-2 |
| 970 | GT3-12 | 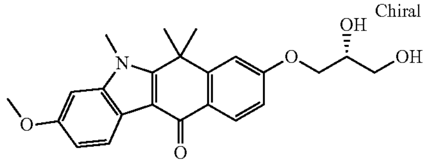 [SMILES: COc1ccc2c3c(n(C)c2c1)C(C)(C)c1cc(OC[C@H](O)CO)ccc1C3=O] | 8-((R)-2,3-Dihydroxy-propoxy)-3-methoxy-5,6,6-trimethyl-5,6-dihydro-benzo[b]carbazol-11-one | B | 3.79 | 396.5 | A6<br>A7-17<br>A10-1<br>A7-14-2 |
| 971 | GT3-13 | 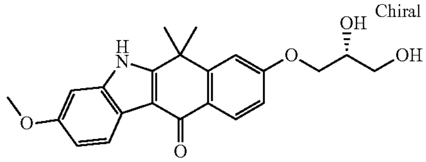 [SMILES: COc1ccc2c3c([nH]c2c1)C(C)(C)c1cc(OC[C@H](O)CO)ccc1C3=O] | 8-((R)-2,3-Dihydroxy-propoxy)-3-methoxy-6,6-dimethyl-5,6-dihydro-benzo[b]carbazol-11-one | B | 3.40 | 382.4 | A6<br>A7-17<br>A7-14-2 |

The compounds described in the following Table 21 were synthesized according to the method shown below. Specifically, by using Compound E1 and phenylhydrazine having a corresponding substituent group, 9-bromo-1-chloro-8-methoxy-6,6-dimethyl-5,6-dihydro-benzo[b]carbazol-11-one or 9-bromo-8-methoxy-6,6-dimethyl-3-trifluoromethoxy-5,6-dihydro-benzo[b]carbazol-11-one was prepared according to the method used for the synthesis of Compound A3 and Compound A4. Subsequently, to obtain the compounds of the Table, chemical conversion of the above compounds was achieved by using in combination the functional group modifications as explained before and described in the Table.

TABLE 21

| Example No. | Comp. No. | Structure | Compound Name | HPLC Condition | Retention Time | m/z | Method |
|---|---|---|---|---|---|---|---|
| 972 | GT4-1 | 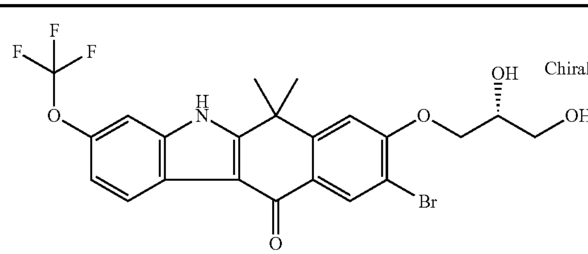 | 9-Bromo-8-((R)-2,3-dihydroxy-propoxy)-6,6-dimethyl-3-trifluoromethoxy-5,6-dihydro-benzo[b]carbazol-11-one | C | 2.68 | 514.0 | A6<br>A7-17<br>A7-14-2 |

TABLE 21-continued

| Example No. | Comp. No. | Structure | Compound Name | HPLC Condition | Retention Time | m/z | Method |
|---|---|---|---|---|---|---|---|
| 973 | GT4-2 | 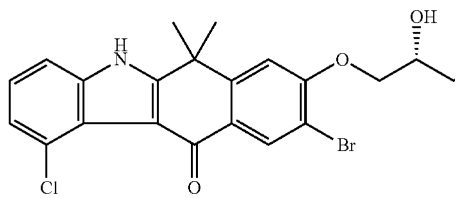 | 9-Bromo-1-chloro-8-((R)-2,3-dihydroxy-propoxy)-6,6-dimethyl-5,6-dihydro-benzo[b]carbazol-11-one | C | 2.58 | 464.0 | A6 A7-17 A7-14-2 |

The compounds described in the following Tables 22-23 were synthesized according to the method shown below. Specifically, catalytic reduction of Compound GT3-3 was carried out according to the method used for the preparation of Compound D2 to prepare Compound GT5-1.

Reductive alkylation of Compound GT5-1 was carried out according to the method used for the preparation of Compound B3-32 for the introduction of a methyl group or a benzyl group (Compound GT5-2, Compound GT5-3).

Catalytic reduction of Compound GT5-3 was carried out according to the method used for the preparation of Compound D2, and then processed to prepare Compound GT5-4.

The resulting amino derivatives of Compound GT5-1 to 4 were reacted with corresponding acyl chloride, isocynate, or chloroformate according to the method used for the preparation of Compound A9-1 to obtain the compounds of the Table.

TABLE 22

| Example No. | Comp. No. | Structure | Compound Name | HPLC Condition | Retention Time | m/z | Method |
|---|---|---|---|---|---|---|---|
| 974 | GT5-1 | 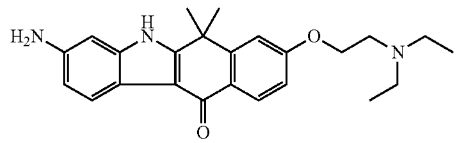 [SMILES: CCN(CC)CCOc1ccc2c(c1)C(C)(C)c1[nH]c3cc(N)ccc3c1C2=O] | 3-Amino-8-(2-diethylamino-ethoxy)-6,6-dimethyl-5,6-dihydro-benzo[b]carbazol-11-one | A | 1.15 | 392.3 | D2 |
| 975 | GT5-2 | 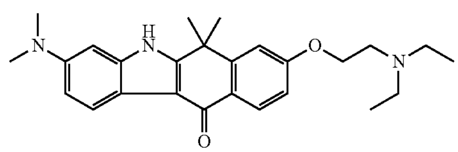 [SMILES: CCN(CC)CCOc1ccc2c(c1)C(C)(C)c1[nH]c3cc(N(C)C)ccc3c1C2=O] | 8-(2-Diethylamino-ethoxy)-3-dimethylamino-6,6-dimethyl-5,6-dihydro-benzo[b]carbazol-11-one | A | 1.18 | 420.2 | B3-32 |
| 976 | GT5-3 | 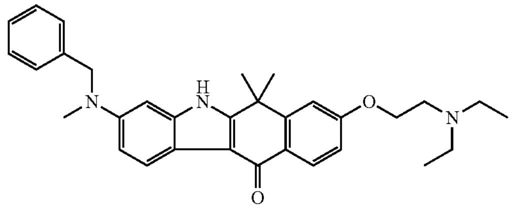 [SMILES: CCN(CC)CCOc1ccc2c(c1)C(C)(C)c1[nH]c3cc(N(C)Cc4ccccc4)ccc3c1C2=O] | 3-(Benzyl-methyl-amino)-8-(2-diethylamino-ethoxy)-6,6-dimethyl-5,6-dihydro-benzo[b]carbazol-11-one | B | 3.05 | 496.4 | B3-32 |
| 977 | GT5-4 | 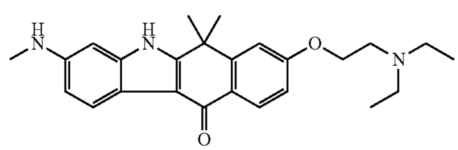 [SMILES: CCN(CC)CCOc1ccc2c(c1)C(C)(C)c1[nH]c3cc(NC)ccc3c1C2=O] | 8-(2-Diethylamino ethoxy)-6,6-dimethyl-3-methylamino-5,6-dihydro-benzo[b]carbazol-11-one | B | 2.46 | 406.3 | B3-32 D2 |
| 978 | GT5-5 | 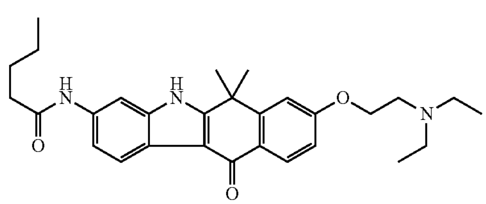 [SMILES: CCCCC(=O)Nc1ccc2c3c([nH]c2c1)C(C)(C)c1cc(OCCN(CC)CC)ccc1C3=O] | Pentanoic acid [8-(2-diethylamino-ethoxy)-6,6-dimethyl-11-oxo-6,11-dihydro-5H-benzo[b]carbazol-3-yl]-amide | C | 2.52 | 476.5 | A9-1 |

TABLE 22-continued

| Example No. | Comp. No. | Structure | Compound Name | HPLC Condition | Retention Time | m/z | Method |
|---|---|---|---|---|---|---|---|
| 979 | GT5-6 | 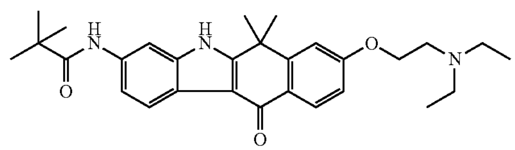 [SMILES: CCN(CC)CCOc1ccc2c(c1)C(C)(C)c1[nH]c3cc(NC(=O)C(C)(C)C)ccc3c1C2=O] | N-[8-(2-Diethylamino-ethoxy)-6,6-dimethyl-11-oxo-6,11-dihydro-5H-benzo[b]carbazol-3-yl]-2,2-dimethyl-propionamide | A | 1.74 | 476.4 | A9-1 |
| 980 | GT5-7 | 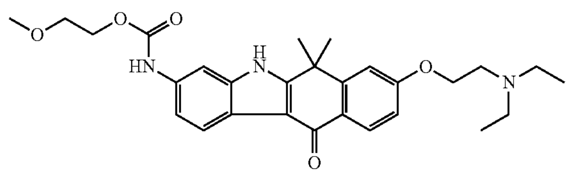 [SMILES: CCN(CC)CCOc1ccc2c(c1)C(C)(C)c1[nH]c3cc(NC(=O)OCCOC)ccc3c1C2=O] | [8-(2-Diethylamino-ethoxy)-6,6-dimethyl-11-oxo-6,11-dihydro-5H-benzo[b]carbazol-3-yl]-carbamic acid 2-methoxy-ethyl ester | A | 1.55 | 494.3 | A9-1 |
| 981 | GT5-8 | 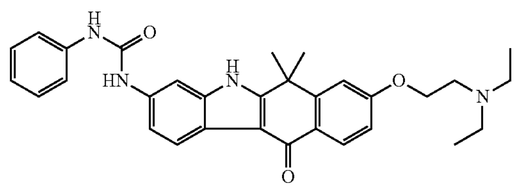 [SMILES: CCN(CC)CCOc1ccc2c(c1)C(C)(C)c1[nH]c3cc(NC(=O)Nc4ccccc4)ccc3c1C2=O] | 1-[8-(2-Diethylamino-ethoxy)-6,6-dimethyl-11-oxo-6,11-dihydro-5H-benzo[b]carbazol-3-yl]-3-phenyl-urea | B | 3.79 | 511.3 | A9-1 |
| 982 | GT5-9 | 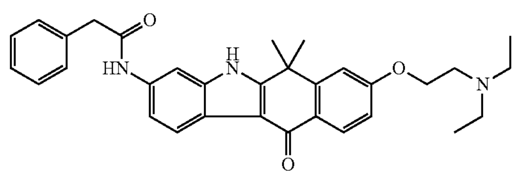 [SMILES: CCN(CC)CCOc1ccc2c(c1)C(C)(C)c1[nH]c3cc(NC(=O)Cc4ccccc4)ccc3c1C2=O] | N-[8-(2-Diethylamino-ethoxy)-6,6-dimethyl-11-oxo-6,11-dihydro-5H-benzo[b]carbazol-3-yl]-2-phenyl-acetamide | B | 3.81 | 510.4 | A9-1 |
| 983 | GT5-10 | 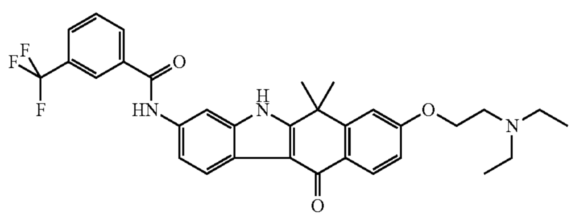 [SMILES: CCN(CC)CCOc1ccc2c(c1)C(C)(C)c1[nH]c3cc(NC(=O)c4cccc(C(F)(F)F)c4)ccc3c1C2=O] | N-[8-(2-Diethylamino-ethoxy)-6,6-dimethyl-11-oxo-6,11-dihydro-5H-benzo[b]carbazol-3-yl]-3-trifluoromethyl-benzamide | B | 4.47 | 564.4 | A9-1 |
| 984 | GT5-11 | 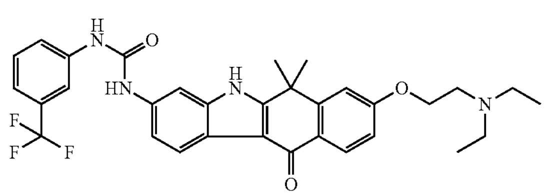 [SMILES: CCN(CC)CCOc1ccc2c(c1)C(C)(C)c1[nH]c3cc(NC(=O)Nc4cccc(C(F)(F)F)c4)ccc3c1C2=O] | 1-[8-(2-Diethylamino-ethoxy)-6,6-dimethyl-11-oxo-6,11-dihydro-5H-benzo[b]carbazol-3-yl]-3-(3-trifluoromethyl-phenyl)-urea | B | 4.55 | 579.4 | A9-1 |
| 985 | GT5-12 | 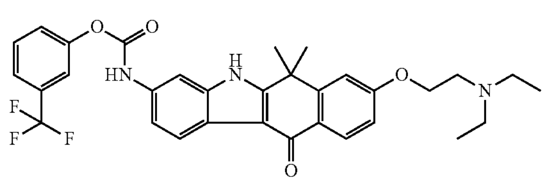 [SMILES: CCN(CC)CCOc1ccc2c(c1)C(C)(C)c1[nH]c3cc(NC(=O)Oc4cccc(C(F)(F)F)c4)ccc3c1C2=O] | [8-(2-Diethylamino-ethoxy)-6,6-dimethyl-11-oxo-6,11-dihydro-5H-benzo[b]carbazol-3-yl]-carbamic acid 3-trifluoromethyl-phenyl ester | H | 5.17 | 580.1 | A9-1 |

TABLE 22-continued

| Example No. | Comp. No. | Structure | Compound Name | HPLC Condition | Retention Time | m/z | Method |
|---|---|---|---|---|---|---|---|
| 986 | GT5-13 | 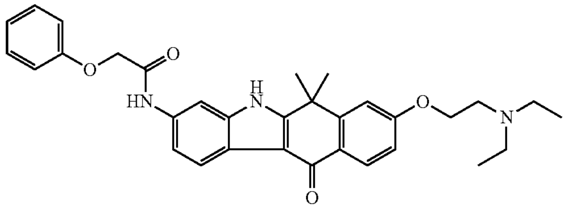 [SMILES: CCN(CC)CCOc1ccc2c(c1)C(C)(C)c1[nH]c3cc(NC(=O)COc4ccccc4)ccc3c1C2=O] | N-[8-(2-Diethylamino-ethoxy)-6,6-dimethyl-11-oxo-6,11-dihydro-5H-benzo[b]carbazol-3-yl]-2-phenoxy-acetamide | C | 2.57 | 526.1 | A9-1 |
| 987 | GT5-14 | 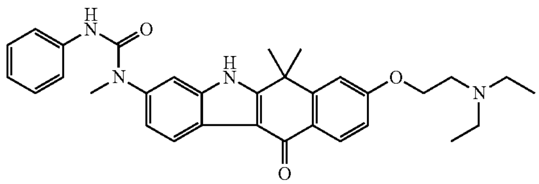 [SMILES: CCN(CC)CCOc1ccc2c(c1)C(C)(C)c1[nH]c3cc(N(C)C(=O)Nc4ccccc4)ccc3c1C2=O] | 1-[8-(2-Diethylamino-ethoxy)-6,6-dimethyl-11-oxo-6,11-dihydro-5H-benzo[b]carbazol-3-yl]-1-methyl-3-phenyl-urea | B | 3.83 | 525.6 | A9-1 |

TABLE 23

| Example No. | Comp. No. | Structure | Compound Name | HPLC Condition | Retention Time | m/z | Method |
|---|---|---|---|---|---|---|---|
| 988 | GT5-15 | 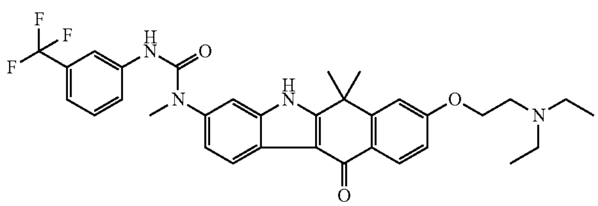 [SMILES: CCN(CC)CCOc1ccc2c(c1)C(C)(C)c1[nH]c3cc(N(C)C(=O)Nc4cccc(C(F)(F)F)c4)ccc3c1C2=O] | 1-[8-(2-Diethylamino-ethoxy)-6,6-dimethyl-11-oxo-6,11-dihydro-5H-benzo[b]carbazol-3-yl]-1-methyl-3-(3-trifluoromethyl-phenyl)-urea | B | 4.58 | 593.4 | A9-1 |
| 989 | GT5-16 | 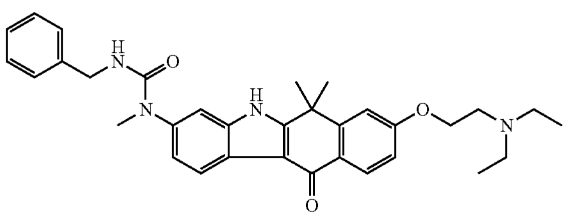 [SMILES: CCN(CC)CCOc1ccc2c(c1)C(C)(C)c1[nH]c3cc(N(C)C(=O)NCc4ccccc4)ccc3c1C2=O] | 3-Benzyl-1-[8-(2-diethylamino-ethoxy)-6,6-dimethyl-11-oxo-6,11-dihydro-5H-benzo[b]carbazol-3-yl]-1-methyl-urea | B | 3.81 | 539.4 | A9-1 |
| 990 | GT5-17 | 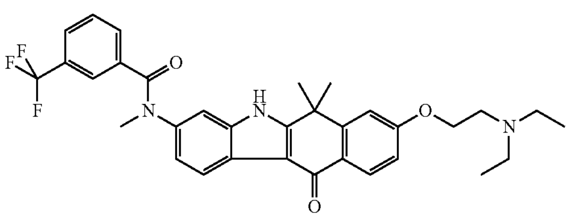 [SMILES: CCN(CC)CCOc1ccc2c(c1)C(C)(C)c1[nH]c3cc(N(C)C(=O)c4cccc(C(F)(F)F)c4)ccc3c1C2=O] | N-[8-(2-Diethylamino-ethoxy)-6,6-dimethyl-11-oxo-6,11-dihydro-5H-benzo[b]carbazol-3-yl]-N-methyl-3-trifluoromethyl-benzamide | B | 4.15 | 578.3 | A9-1 |
| 991 | GT5-18 | 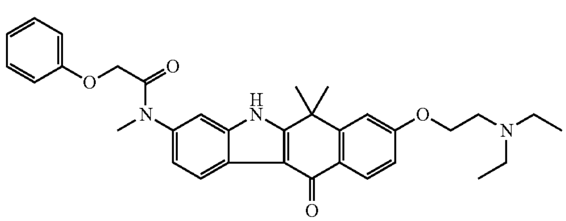 [SMILES: CCN(CC)CCOc1ccc2c(c1)C(C)(C)c1[nH]c3cc(N(C)C(=O)COc4ccccc4)ccc3c1C2=O] | N-[8-(2-Diethylamino-ethoxy)-6,6-dimethyl-11-oxo-6,11-dihydro-5H-benzo[b]carbazol-3-yl]-N-methyl-2-phenoxy-acetamide | C | 2.62 | 540.4 | A9-1 |

TABLE 23-continued

| Example No. | Comp. No. | Structure | Compound Name | HPLC Condition | Retention Time | m/z | Method |
|---|---|---|---|---|---|---|---|
| 992 | GT5-19 | 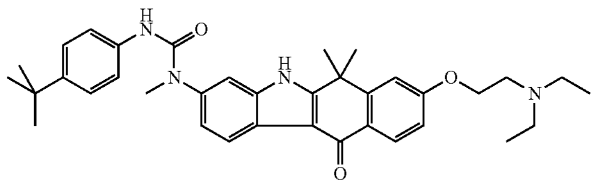 [SMILES: CCN(CC)CCOc1ccc2c(c1)C(C)(C)c1[nH]c3cc(N(C)C(=O)Nc4ccc(C(C)(C)C)cc4)ccc3c1C2=O] | 3-(4-tert-Butyl-phenyl)-1-[8-(2-diethylamino-ethoxy)-6,6-dimethyl-11-oxo-6,11-dihydro-5H-benzo[b]carbazol-3-yl]-1-methyl-urea | F | 2.45 | 581.6 | A9-1 |
| 993 | GT5-20 | 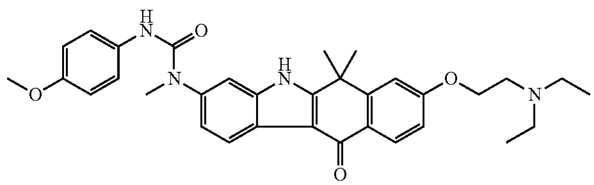 [SMILES: CCN(CC)CCOc1ccc2c(c1)C(C)(C)c1[nH]c3cc(N(C)C(=O)Nc4ccc(OC)cc4)ccc3c1C2=O] | 1-[8-(2-Diethylamino-ethoxy)-6,6-dimethyl-11-oxo-6,11-dihydro-5H-benzo[b]carbazol-3-yl]-3-(4-methoxy-phenyl)-1-methyl-urea | B | 3.77 | 555.4 | A9-1 |
| 994 | GT5-21 | 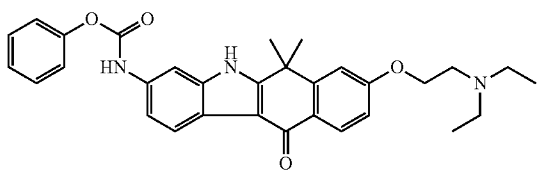 [SMILES: CCN(CC)CCOc1ccc2c(c1)C(C)(C)c1[nH]c3cc(NC(=O)Oc4ccccc4)ccc3c1C2=O] | [8-(2-Diethylamino-ethoxy)-6,6-dimethyl-11-oxo-6,11-dihydro-5H-benzo[b]carbazol-3-yl]-carbamic acid phenyl ester | A | 1.89 | 512.2 | A9-1 |

The compounds described in the following Table 24 were synthesized according to the method shown below. Specifically, having Compound T22-1 as a starting material, 8-[(4R,5R)-5-(tert-butyl-dimethylsilanyloxymethyl)-2,2-dimethyl-[1,3] dioxolan-4-yl methoxy]-6,6-dimethyl-5,6-dihydro-11-oxo-benzo[b]carbazole-3-carboxylic acid was prepared according to the method that is used for the preparation of Compound B2-28.

The resulting carboxylic acid was subjected to dehydrating condensation with corresponding amine, alcohol according to the method that is used for the preparation of Compound A9-10. Subsequently, deprotection was carried out according to the method used for the preparation of Compound T22-1-1 and Compound T22-1-2 to obtain the compounds described in the Table.

TABLE 24

| Example No. | Comp. No. | Structure | Compound Name | HPLC Condition | Retention Time | m/z | Method |
|---|---|---|---|---|---|---|---|
| 995 | GT6-1 | 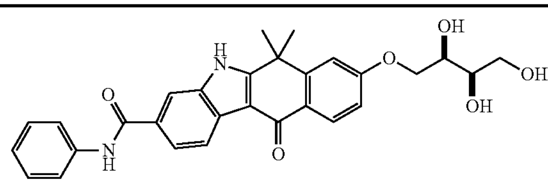 | 6,6-Dimethyl-11-oxo-8-((2R,3R)-2,3,4-trihydroxy-butoxy)-6,11-dihydro-5H-benzo[b]carbazole-3-carboxylic acid phenylamide | A | 1.79 | 501.0 | A9-10 |
| 996 | GT6-2 | 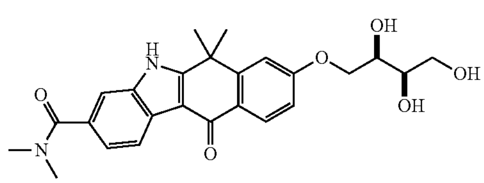 [SMILES: CN(C)C(=O)c1ccc2c3c([nH]c2c1)C(C)(C)c1cc(OC[C@@H](O)[C@H](O)CO)ccc1C3=O] | 6,6-Dimethyl-11-oxo-8-((2R,3R)-2,3,4-trihydroxy-butoxy)-6,11-dihydro-5H-benzo[b]carbazole-3-carboxylic acid diethylamide | D | 1.33 | 453.0 | A9-10 |
| 997 | GT6-3 | 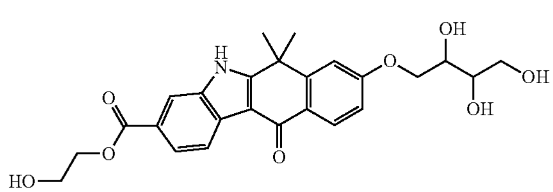 [SMILES: CC1(C)c2cc(OCC(O)C(O)CO)ccc2C(=O)c2c1[nH]c1cc(C(=O)OCCO)ccc21] | 6,6-Dimethyl-11-oxo-8-((2R,3R)-2,3,4-trihydroxy-butoxy)-6,11-dihydro-5H-benzo[b]carbazole-3-carboxylic acid 2-hydroxy-ethyl ester | A | 1.40 | 470.0 | A9-10 |

TABLE 24-continued

| Example No. | Comp. No. | Structure | Compound Name | HPLC Condition | Retention Time | m/z | Method |
|---|---|---|---|---|---|---|---|
| 998 | GT6-4 | 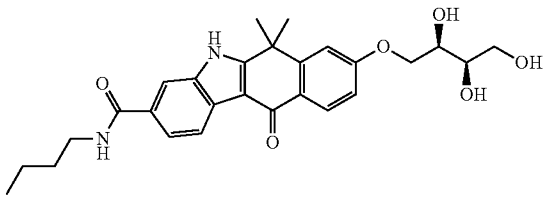 [SMILES: CCCCNC(=O)c1ccc2c3c([nH]c2c1)C(C)(C)c1cc(OC[C@@H](O)[C@H](O)CO)ccc1C3=O] | 6,6-Dimethyl-11-oxo-8-((2R,3R)-2,3,4-trihydroxy-butoxy)-6,11-dihydro-5H-benzo[b]carbazole-3-carboxylic acid butylamide | D | 1.55 | 481.0 | A9-10 |
| 999 | GT6-5 | 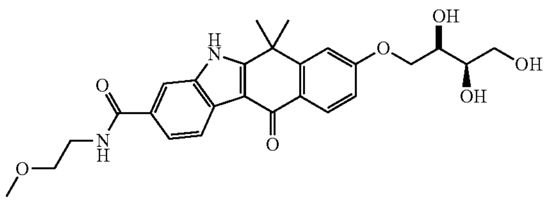 [SMILES: COCCNC(=O)c1ccc2c3c([nH]c2c1)C(C)(C)c1cc(OC[C@@H](O)[C@H](O)CO)ccc1C3=O] | 6,6-Dimethyl-11-oxo-8-((2R,3R)-2,3,4-trihydroxy-butoxy)-6,11-dihydro-5H-benzo[b]carbazole-3-carboxylic acid (2-methoxy-ethyl)-amide | D | 1.30 | 483.0 | A9-10 |
| 1000 | GT6-6 | 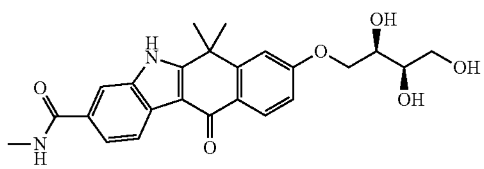 [SMILES: CNC(=O)c1ccc2c3c([nH]c2c1)C(C)(C)c1cc(OC[C@@H](O)[C@H](O)CO)ccc1C3=O] | 6,6-Dimethy-11-oxo-8-((2R,3R)-2,3,4-trihydroxy-butoxy)-6,11-dihydro-5H-benzo[b]carbazole-3-carboxylic acid methylamide | D | 1.24 | 439.0 | A9-10 |
| 1001 | GT6-7 | 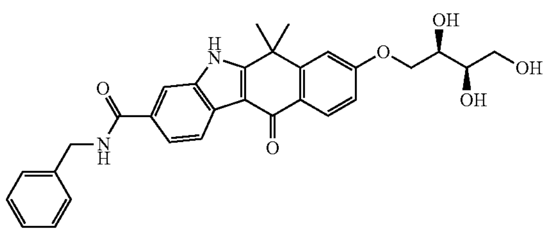 [SMILES: CC1(C)c2cc(OC[C@@H](O)[C@H](O)CO)ccc2C(=O)c2c1[nH]c1cc(C(=O)NCc3ccccc3)ccc21] | 6,6-Dimethyl-11-oxo-8-((2R,3R)-2,3,4-trihydroxy-butoxy)-6,11-dihydro-5H-benzo[b]carbazole-3-carboxylic acid benzylamide | D | 1.58 | 515.0 | A9-10 |
| 1002 | GT6-8 | 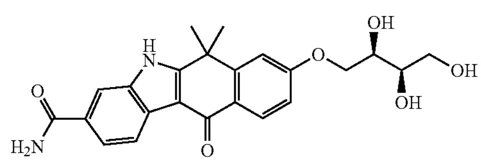 [SMILES: CC1(C)c2cc(OC[C@@H](O)[C@H](O)CO)ccc2C(=O)c2c1[nH]c1cc(C(N)=O)ccc21] | 6,6-Dimethyl-11-oxo-8-((2R,3R)-2,3,4-trihydroxy-butoxy)-6,11-dihydro-5H-benzo[b]carbazole-3-carboxylic acid amide | D | 1.16 | 425.0 | A9-10 |
| 1003 | GT6-9 | 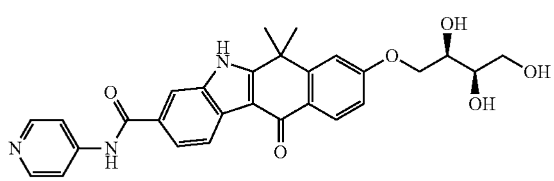 [SMILES: CC1(C)c2cc(OC[C@@H](O)[C@H](O)CO)ccc2C(=O)c2c1[nH]c1cc(C(=O)Nc3ccncc3)ccc21] | 6,6-Dimethyl-11-oxo-8-((2R,3R)-2,3,4-trihydroxy-butoxy)-6,11-dihydro-5H-benzo[b]carbazole-3-carboxylic acid pyridin-4-ylamide | D | 1.40 | 502.0 | A9-10 |
| 1004 | GT6-10 | 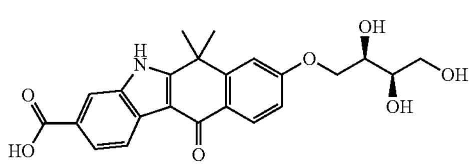 [SMILES: CC1(C)c2cc(OC[C@@H](O)[C@H](O)CO)ccc2C(=O)c2c1[nH]c1cc(C(=O)O)ccc21] | 6,6-Dimethyl-11-oxo-8-((2R,3R)-2,3,4-trihydroxy-butoxy)-6,11-dihydro-5H-benzo[b]carbazole-3-carboxylic acid | D | 1.01 | 426.0 | B2-28 |
| 1005 | GT6-11 | 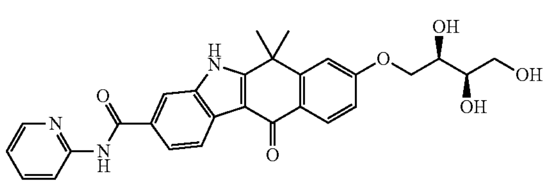 [SMILES: CC1(C)c2cc(OC[C@@H](O)[C@H](O)CO)ccc2C(=O)c2c1[nH]c1cc(C(=O)Nc3ccccn3)ccc21] | 6,6-Dimethyl-11-oxo-8-((2R,3R)-2,3,4-trihydroxy-butoxy)-6,11-dihydro-5H-benzo[b]carbazole-3-carboxylic acid pyridin-2-ylamide | D | 1.52 | 502.0 | A9-10 |

TABLE 24-continued

| Example No. | Comp. No. | Structure | Compound Name | HPLC Condition | Retention Time | m/z | Method |
|---|---|---|---|---|---|---|---|
| 1006 | GT6-12 | 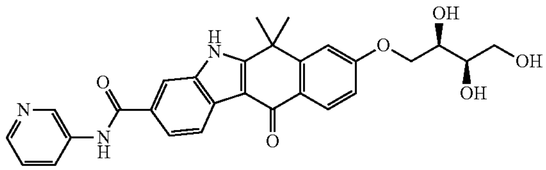 [SMILES: CC1(C)c2cc(OC[C@@H](O)[C@H](O)CO)ccc2C(=O)c2c1[nH]c1cc(C(=O)Nc3cccnc3)ccc21] | 6,6-Dmethyl-11-oxo-8-((2R,3R)-2,3,4-trihydroxy-butoxy)-6,11-dihydro-5H-benzo[b]carbazole-3-carboxylic acid pyridin-3-ylamide | D | 1.34 | 502.0 | A9-10 |
| 1007 | GT6-13 | 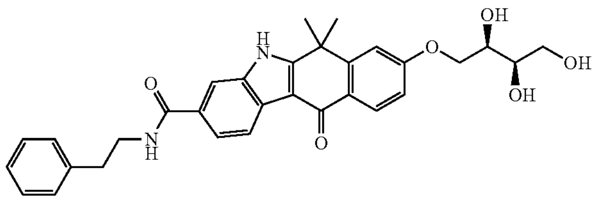 [SMILES: CC1(C)c2cc(OC[C@@H](O)[C@H](O)CO)ccc2C(=O)c2c1[nH]c1cc(C(=O)NCCc3ccccc3)ccc21] | 6,6-Dimethyl-11-oxo-8-((2R,3R)-2,3,4-trihydroxy-butoxy)-6,11-dihydro-5H-benzo[b]carbazole-3-carboxylic acid phenethyl-amide | D | 1.57 | 529.0 | A9-10 |
| 1008 | GT6-14 | 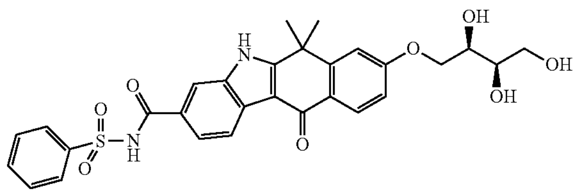 [SMILES: CC1(C)c2cc(OC[C@@H](O)[C@H](O)CO)ccc2C(=O)c2c1[nH]c1cc(C(=O)NS(=O)(=O)c3ccccc3)ccc21] | N-[6,6-Dimethyl-11-oxo-8-((2R,3R)-2,3,4-trihydroxy-butoxy)-6,11-dihydro-5H-benzo[b]carbazole-3-carbonyl]-benzenesulfonamide | D | 1.23 | 565.0 | A9-10 |

To the compounds described in the following Table 25, a hydroxyl group was introduced from Compound T17-3 according to the method described in JACS 2006, Vol. 128, page 10964. Subsequently, deprotection was carried out according to the method used for Compound A7-14-2 and Compound T22-2 to obtain the compounds shown below.

TABLE 25

| Example No. | Comp. No. | Structure | Compound Name | HPLC Condition | Retention Time | m/z |
|---|---|---|---|---|---|---|
| 1009 | GT7-1 | 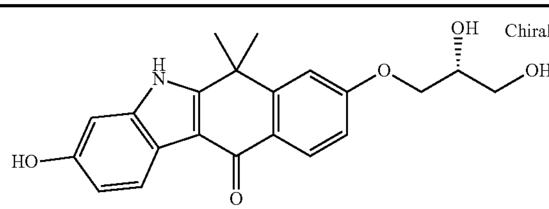 | 8-((R)-2,3-Dihydroxy-propoxy)-3-hydroxy-6,6-dimethyl-5,6-dihydro-benzo[b]carbazol-11-one | B | 2.59 | 368.4 |
| 1010 | GT7-2 | 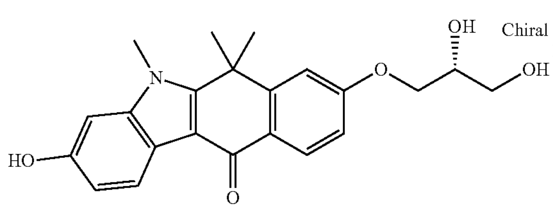 [SMILES: Cn1c2c(c3ccc(O)cc31)C(=O)c1ccc(OC[C@H](O)CO)cc1C2(C)C] | 8-((R)-2(3-Dihydroxy-propoxy)-3-hydroxy-5,6,6-trimethyl-5,6-dihydro-benzo[b]carbazol-11-one | O | 1.90 | 382.4 |

The compounds described in the following Table 26 were prepared by alkylation according to the method used for the preparation of Compound A7-1 from Compound GT7-1 or Compound GT7-2, or by carbamation according to the method used for the preparation of A9-1.

TABLE 26

| Example No. | Comp. No. | Structure | Compound Name | HPLC Condition | Retention Time | m/z | Method |
|---|---|---|---|---|---|---|---|
| 1011 | GT8-1 | 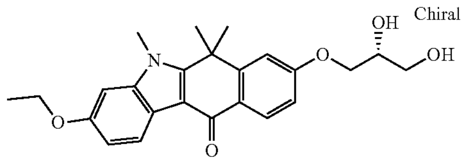 [SMILES: CCOc1ccc2c3c(n(C)c2c1)C(C)(C)c1cc(OC[C@H](O)CO)ccc1C3=O] | 8-((R)-2,3-Dihydroxy-propoxy)-3-ethoxy-5,6,6-trimethyl-5,6-dihydro-benzo[b]carbazol-11-one | O | 2.43 | 410.5 | A7-1 |
| 1012 | GT8-2 | 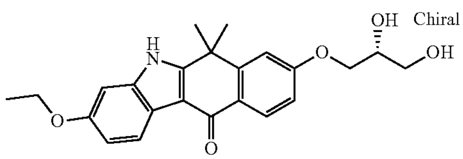 [SMILES: CCOc1ccc2c3c([nH]c2c1)C(C)(C)c1cc(OC[C@H](O)CO)ccc1C3=O] | 8-((R)-2,3-Dihydroxy-propoxy)-3-ethoxy-6,6-dimethyl-5,6-dihydro-benzo[b]carbazol-11-one | O | 2.30 | 386.5 | A7-1 |
| 1013 | GT8-3 | 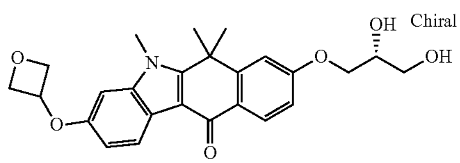 [SMILES: Cn1c2c(c3ccc(OC4COC4)cc31)C(=O)c1ccc(OC[C@H](O)CO)cc1C2(C)C] | 8-((R)-2,3-Dihydroxy-propoxy)-5,6,6-trimethyl-3-(oxetan-3-yloxy)-5,6-dihydro-benzo[b]carbazol-11-one | B | 1.72 | 438.5 | A7-1 |
| 1014 | GT8-4 | 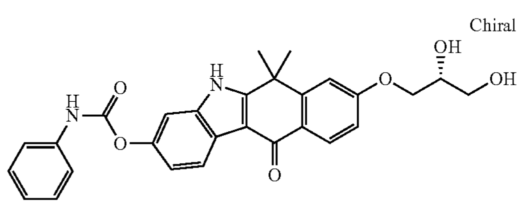 [SMILES: CC1(C)c2cc(OC[C@H](O)CO)ccc2C(=O)c2c1[nH]c1cc(OC(=O)Nc3ccccc3)ccc21] | Phenyl-carbamic acid 8-((R)-2,3-dihydroxy-propoxy)-6,6-dimethyl-11-oxo-6,11-dihydro-5H-benzo[b]carbazol-3-yl ester | B | 4.23 | 487.0 | A8-1 |

Example 1015

Compound GT9-1

8-((R)-2,3-Dihydroxy-propoxy)-6,6-dimethyl-3-(2H-tetrazol-5-yl)-5,6-dihydro-benzo[b]carbazol-11-one

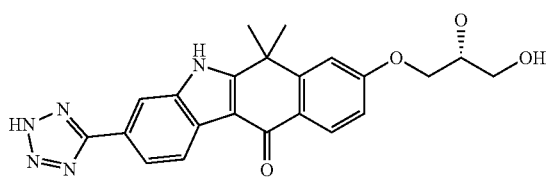 [SMILES: CC1(C)c2cc(OC[C@H](O)CO)ccc2C(=O)c2c1[nH]c1cc(-c3nn[nH]n3)ccc21]

8-((S)-2,2-Dimethyl-[1,3]dioxolan-4-yl methoxy)-6,6-dimethyl-11-oxo-6,11-dihydro-5H-benzo[b]carbazole-3-carbonitrile (20.0 mg, 0.048 mmol), ammonium chloride (1.28 mg, 0.024 mmol) and NaN₃ (6.24 mg, 0.096 mmol) were dissolved in DMF, and the mixture was stirred at 120° C. for 14 hrs. NaN₃ (6.24 mg, 0.096 mmol) was further added to the mixture, which was then stirred at 120° C. for 30 hrs. The reaction solution was added with 1 N aqueous solution of hydrochloric acid and extracted with ethyl acetate. The organic layer was washed with saturated brine and concentrated under reduced pressure. The resultant solid obtained after concentration was washed with hexane:ethyl acetate=1:1 to obtain 8-((S)-2,2-dimethyl-[1,3]dioxolan-4-yl methoxy)-6,6-dimethyl-3-(2H-tetrazol-5-yl)-5,6-dihydro-benzo[b]carbazol-11-one as a white solid.

The product was suspended in MeOH (1.0 ml), added with 1 N aqueous solution of hydrochloric acid, and then stirred at 60° C. for 1 hr and 30 min. After cooling to room temperature, the reaction solution was concentrated under reduced pressure, and the resulting solid was washed with DCM to obtain the title compound as a pale yellow solid (13.4 mg, 66.3%).

LCMS: m/z 420 [M+H]⁺

Example 1016

Compound GT9-2

8-((R)-2,3-Dihydroxy-propoxy)-6,6-dimethyl-3-thiophen-3-yl-5,6-dihydro-benzo[b]carbazol-11-one

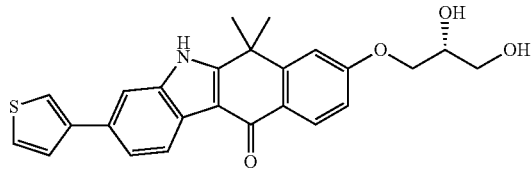 [SMILES: CC1(C)c2cc(OC[C@H](O)CO)ccc2C(=O)c2c1[nH]c1cc(-c3ccsc3)ccc21]

3-Bromo-8-((S)-2,2-dimethyl-[1,3]dioxolan-4-yl-methoxy)-6,6-dimethyl-5,6-dihydro-benzo[b]carbazol-11-one (20.0 mg, 0.043 mmol), thiophene-3-boronic acid (10.9 mg, 0.085 mmol), $K_3PO_4$ (40 mg) and Pd (PPh$_3$)$_4$ (9.9 mg, 0.0086 mmol) were dissolved in DMA (0.8 ml) and water (0.2 ml), and stirred at 140° C. for 10 min under microwave irradiation. The reaction solution was diluted with ethyl acetate and washed with saturated brine. The organic layer was concentrated under reduced pressure, and the resulting residues were purified by column chromatography (hexane/ethyl acetate) to obtain 8-((S)-2,2-dimethyl-[1,3]dioxolan-4-yl methoxy)-6,6-dimethyl-3-thiphen-3-yl-5,6-dihydro-benzo[b]carbazol-11-one.

This product was suspended in MeOH (1.0 ml), added with 1 N hydrochloric acid, and then stirred at 60° C. for 1 hr and 30 min. The reaction solution was concentrated under reduced pressure, and the resulting solid was washed with DCM to obtain the title compound as a yellow solid (12.6 mg, 67.1%).

LCMS: m/z 434 [M+H]$^+$

Using the combination of Compound T18-1 and corresponding boronic acid or the combination of (S)-8-((2,2-dimethyl-1,3-dioxolan-4-yl)methoxy)-6,6-dimethyl-3-(4,4,5,5-tetramethyl-1,3,2-dioxaborolan-2-yl)-5H-benzo[b]carbazol-11 (6H)-one and corresponding bromide, the reaction was carried out in the same manner as Compound GT9-2 to obtain the compounds of the following Table 27.

TABLE 27

| Example No. | Comp. No. | Structure | Compound Name | HPLC Condition | Retention Time | m/z |
|---|---|---|---|---|---|---|
| 1017 | GT9-3 | 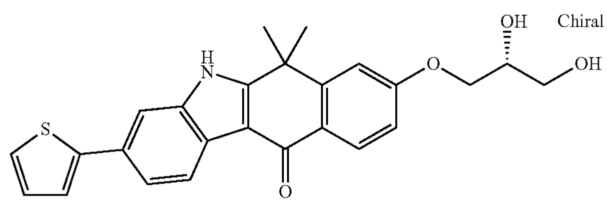 [SMILES: CC1(C)c2cc(OC[C@H](O)CO)ccc2C(=O)c2c1[nH]c1cc(-c3cccs3)ccc21] | 8-((R)-2,3-Dihydroxy-propoxy)-6,6-dimethyl-3-thiophen-2-yl-5,6-dihydro-benzo[b]carbazol-11-one | B | 4.59 | 434.0 |
| 1018 | GT9-4 | 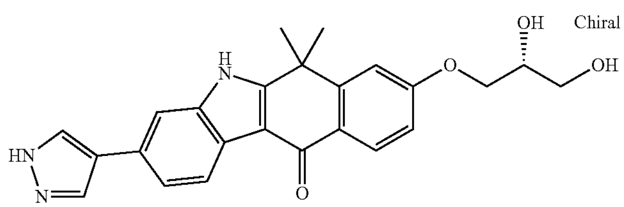 [SMILES: CC1(C)c2cc(OC[C@H](O)CO)ccc2C(=O)c2c1[nH]c1cc(-c3cn[nH]c3)ccc21] | 8-((R)-2,3-Dihydroxy-propoxy)-6,6-dimethyl-3-(1H-pyrazol-4-yl)-5,6-dihydro-benzo[b]carbazol-11-one | B | 4.04 | 418.0 |
| 1019 | GT9-5 | 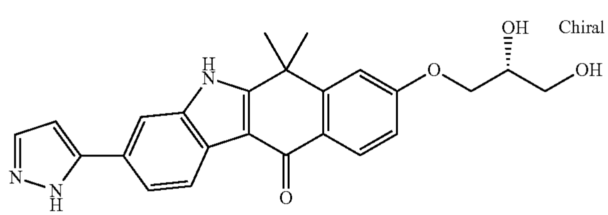 [SMILES: CC1(C)c2cc(OC[C@H](O)CO)ccc2C(=O)c2c1[nH]c1cc(-c3ccn[nH]3)ccc21] | 8-((R)-2,3-Dihydroxy-propoxy)-6,6-dimethyl-3-(2H-pyrazol-3-yl)-5,6-dihydro-benzo[b]carbazol-11-one | A | 1.51 | 418.0 |
| 1020 | GT9-6 | 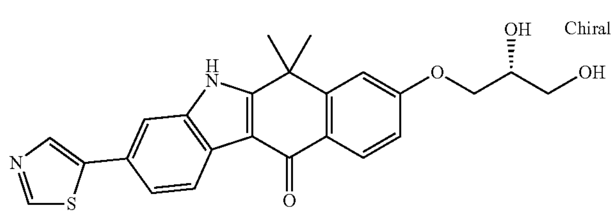 [SMILES: CC1(C)c2cc(OC[C@H](O)CO)ccc2C(=O)c2c1[nH]c1cc(-c3cncs3)ccc21] | 8-((R)-2,3-Dihydroxy-propoxy)-6,6-dimethyl-3-thiazol-5-yl-5,6-dihydro-benzo[b]carbazol-11-one | F | 1.97 | 435.0 |

TABLE 27-continued

| Example No. | Comp. No. | Structure | Compound Name | HPLC Condition | Retention Time | m/z |
|---|---|---|---|---|---|---|
| 1021 | GT9-7 | 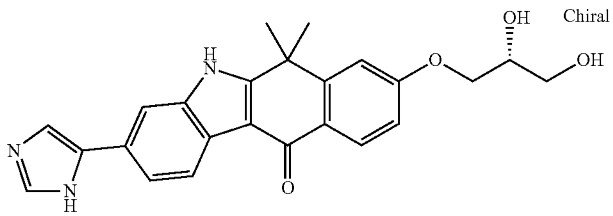 [SMILES: CC1(C)c2cc(OC[C@H](O)CO)ccc2C(=O)c2c1[nH]c1cc(-c3cnc[nH]3)ccc21] | 8-((R)-2,3-Dihydroxypropoxy)-3-(3H-imidazol-4-yl)-6,6-dimethyl-5,6-dihydrobenzo[b]carbazol-11-one | H | 2.91 | 418.0 |

Example 1022

Compound GT10-1

8-((2R,3R)-2,3,4-Trihydroxybutoxy)-2',3',5',6'-tetrahydrospiro[benzo[b]carbazole-6,4'-pyran]-11(5H)-one

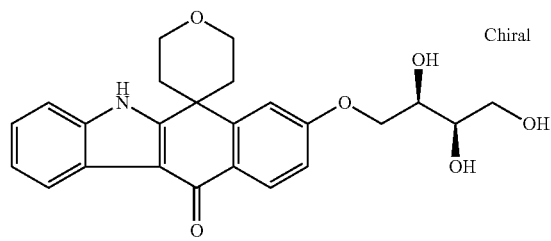 [SMILES: O=C1c2ccc(OC[C@@H](O)[C@H](O)CO)cc2C2(CCOCC2)c2[nH]c3ccccc3c21]

Preparation was carried out in the same manner as Compound N6-1-2.

LCMS: m/z 434 [M+H]$^+$

HPLC retention time: 1.56 min (analysis condition A)

The compounds described in the following Table 28—were synthesized according to the method shown below. Specifically, by using the method for the preparation of Compound Z10, Z11, Z12 and Z13, 8-hydroxy-6,6-dimethyl-6H-benzo[b]naphtho[2,3-d]furan-11-one was prepared from Compound A2 and bromophenol. To the resulting compound, a side chain or a synthetic equivalent thereof was introduced according to Mitsunobu reaction that is used for the preparation of Compound A7-1 or the method that is used for A7-17, etc. After that, if necessary, functional group modification such as deprotection, etc. was carried out to prepare the compounds listed below.

TABLE 28

| Example No. | Comp. No. | Structure | Compound Name | HPLC Condition | Retention Time | m/z |
|---|---|---|---|---|---|---|
| 1023 | GT11-1 | 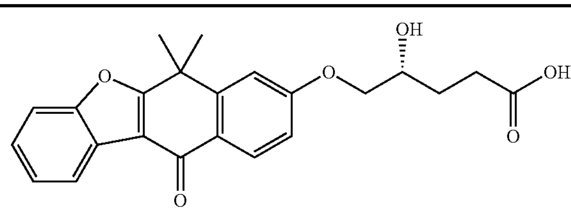 | (R)-5-(6,6-Dimethyl-11-oxo-6,11-dihydrobenzo[b]naphtho[2,3-d]furan-8-yloxy)-4-hydroxypentanoic acid | H | 5.37 | 395.0 |
| 1024 | GT11-2 | 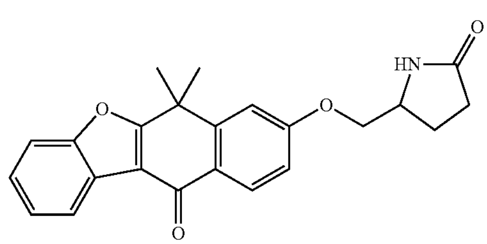 [SMILES: CC1(C)c2cc(OCC3CCC(=O)N3)ccc2C(=O)c2c1oc1ccccc21] | (R)-5-(6,6-Dimethyl-11-oxo-6,11-dihydrobenzo[b]naphtho[2,3-d]furan-8-yloxymethyl)-pyrrolidin-2-one | H | 5.50 | 376.0 |
| 1025 | GT11-3 | 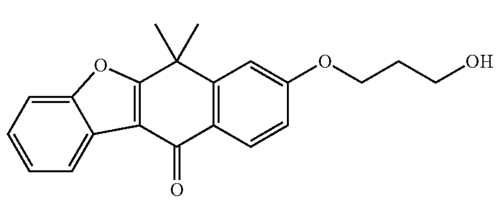 [SMILES: CC1(C)c2cc(OCCCO)ccc2C(=O)c2c1oc1ccccc21] | 8-(3-Hydroxypropoxy)-6,6-dimethyl-6H-benzo[b]naphtho[2,3-d]furan-11-one | H | 5.97 | 337.0 |

TABLE 28-continued

| Example No. | Comp. No. | Structure | Compound Name | HPLC Condition | Retention Time | m/z |
|---|---|---|---|---|---|---|
| 1026 | GT11-4 | 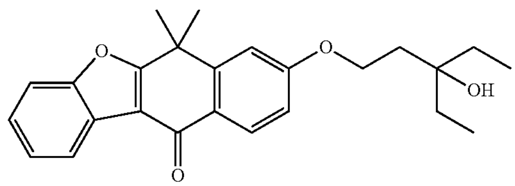 [SMILES: CCC(O)(CC)CCOc1ccc2c(c1)C(C)(C)c1oc3ccccc3c1C2=O] | 8-(3-Ethyl-3-hydroxy-pentyloxy)-6,6-dimethyl-6H-benzo[b]naphtho[2,3-d]furan-11-one | H | 9.29 | 393.0 |
| 1027 | GT11-5 | 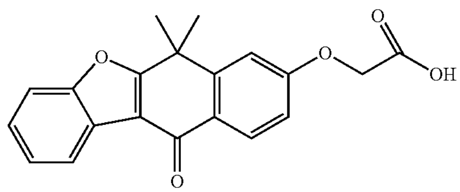 [SMILES: CC1(C)c2cc(OCC(=O)O)ccc2C(=O)c2c1oc1ccccc21] | (6,6-Dimethyl-11-oxo-6,11-dihydro-benzo[b]naphtho[2,3-d]furan-8-yloxy)-acetic acid | H | 5.65 | 336.0 |
| 1028 | GT11-6 | 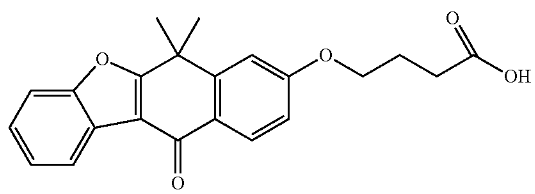 [SMILES: CC1(C)c2cc(OCCCC(=O)O)ccc2C(=O)c2c1oc1ccccc21] | 4-(6,6-Dimethyl-11-oxo-6,11-dihydro-benzo[b]naphtho[2,3-d]furan-8-yloxy)-butyric acid | H | 6.15 | 365.0 |
| 1029 | GT11-7 | 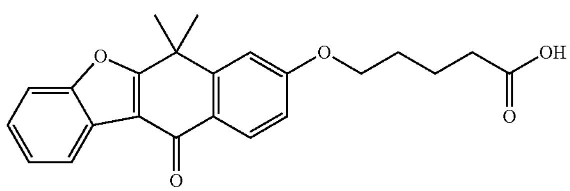 [SMILES: CC1(C)c2cc(OCCCCC(=O)O)ccc2C(=O)c2c1oc1ccccc21] | 5-(6,6-Dimethyl-11-oxo-6,11-dihydro-benzo[b]naphtho[2,3-d]furan-8-yloxy)-pentanoic acid | H | 6.44 | 379.0 |
| 1030 | GT11-8 | 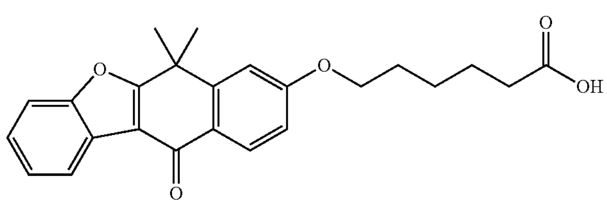 [SMILES: CC1(C)c2cc(OCCCCCC(=O)O)ccc2C(=O)c2c1oc1ccccc21] | 6-(6,6-Dimethyl-11-oxo-6,11-dihydro-benzo[b]naphtho[2,3-d]furan-8-yloxy)-hexanoic acid | H | 6.77 | 393.0 |
| 1031 | GT11-9 | 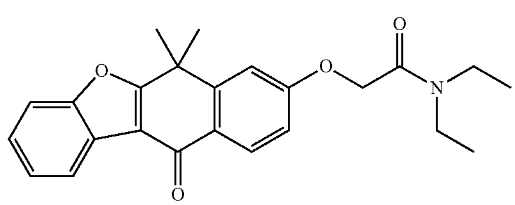 [SMILES: CCN(CC)C(=O)COc1ccc2c(c1)C(C)(C)c1oc3ccccc3c1C2=O] | 2-(6,6-Dimethyl-11-oxo-6,11-dihydro-benzo[b]naphtho[2,3-d]furan-8-yloxy)-N,N-diethyl-acetamide | H | 6.39 | 392.0 |
| 1032 | GT11-10 | 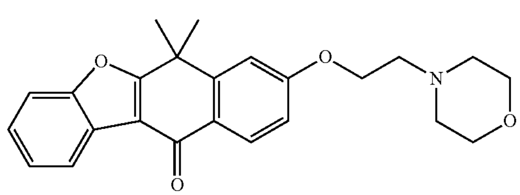 [SMILES: CC1(C)c2cc(OCCN3CCOCC3)ccc2C(=O)c2c1oc1ccccc21] | 6,6-Dimethyl-8-(2-morpholin-4-yl-ethoxy)-6H-benzo[b]naphtho[2,3-d]furan-11-one | H | 4.45 | 392.0 |

TABLE 28-continued

| Example No. | Comp. No. | Structure | Compound Name | HPLC Condition | Retention Time | m/z |
|---|---|---|---|---|---|---|
| 1033 | GT11-11 | 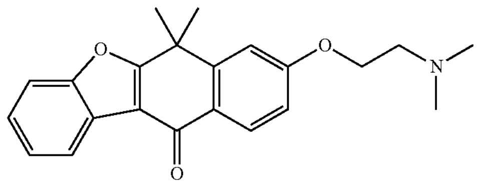 [SMILES: CN(C)CCOc1ccc2c(c1)C(C)(C)c1oc3ccccc3c1C2=O] | 8-(2-Dimethylamino-ethoxy)-6,6-dimethyl-6H-benzo[b]naphtho[2,3-d]furan-11-one | H | 4.59 | 350.0 |

TABLE 29

| Example No. | Comp. No. | Structure | Compound Name | HPLC Condition | Retention Time | m/z |
|---|---|---|---|---|---|---|
| 1034 | GT11-12 | Chiral | 8-((S)-2,3-Dihydroxy-propoxy)-6,6-dimethyl-6H-benzo[b]naphtho[2,3-d]furan-11-one | F | 2.40 | 353.0 |
| 1035 | GT11-13 | Chiral | 8-((R)-2,3-Dihydro-propoxy)-6,6-dimethyl-6H-benzo[b]naphtho[2,3-d]furan-11-one | H | 5.07 | 353.0 |
| 1036 | GT11-14 | 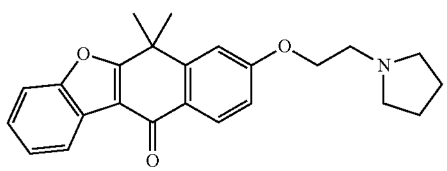 [SMILES: CC1(C)c2cc(OCCN3CCCC3)ccc2C(=O)c2c1oc1ccccc21] | 6,6-Dimethyl-8-(2-pyrrolidin-1-yl-ethoxy)-6H-benzo[b]naphtho[2,3-d]furan-11-one | C | 3.03 | 375.9 |
| 1037 | GT11-15 | 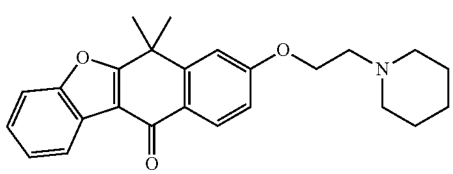 [SMILES: CC1(C)c2cc(OCCN3CCCCC3)ccc2C(=O)c2c1oc1ccccc21] | 6,6-Dimethyl-8-(2-piperidin-1-yl-ethoxy)-6H-benzo[b]naphtho[2,3-d]furan-11-one | D | 3.15 | 389.9 |
| 1038 | GT11-16 | 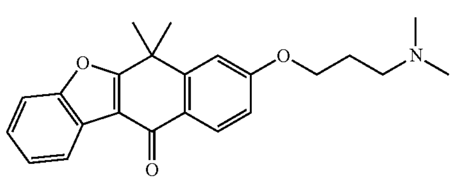 [SMILES: CN(C)CCCOc1ccc2c(c1)C(C)(C)c1oc3ccccc3c1C2=O] | 8-(3-Dimethylamino-propoxy)-6,6-dimethyl-6H-benzo[b]naphtho[2,3-d]furan-11-one | C | 3.30 | 364.2 |
| 1039 | GT11-17 | 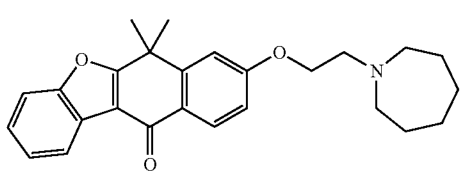 [SMILES: CC1(C)c2cc(OCCN3CCCCCC3)ccc2C(=O)c2c1oc1ccccc21] | 8-(2-Azepan-1-yl-ethoxy)-6,6-dimethyl-6H-benzo[b]naphtho[2,3-d]furan-11-one | F | 2.35 | 404.3 |

TABLE 29-continued

| Example No. | Comp. No. | Structure | Compound Name | HPLC Condition | Retention Time | m/z |
|---|---|---|---|---|---|---|
| 1040 | GT11-18 | 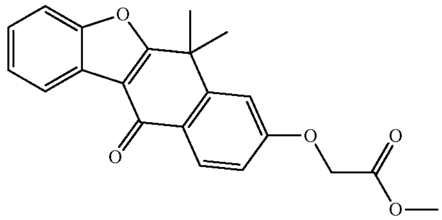 [SMILES: COC(=O)COc1ccc2c(c1)C(C)(C)c1oc3ccccc3c1C2=O] | (6,6-Dimethyl-11-oxo-6,11-dihydro-benzo[b]naphtho[2,3-d]furan-8-yloxy)-acetic acid methyl ester | D | 2.38 | 351.0 |
| 1041 | GT11-19 | 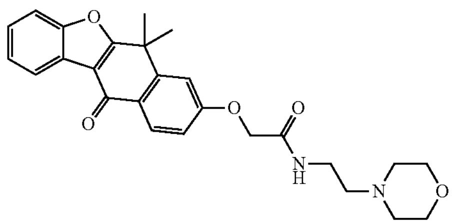 [SMILES: CC1(C)c2cc(OCC(=O)NCCN3CCOCC3)ccc2C(=O)c2c1oc1ccccc21] | 2-(6,6-Dimethyl-11-oxo-6,11-dihydro-benzo[b]naphtho[2,3-d]furan-8-yloxy)-N-(2-morpholin-4-yl-ethyl)-acetamide | D | 2.03 | 450.0 |
| 1042 | GT11-20 | 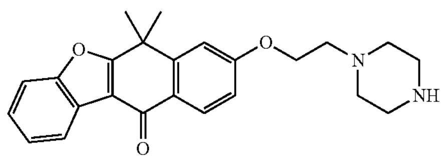 [SMILES: CC1(C)c2cc(OCCN3CCNCC3)ccc2C(=O)c2c1oc1ccccc21] | 6,6-Dimethyl-8-(2-piperazin-1-yl-ethoxy)-6H-benzo[b]naphtho[2,3-d]furan-11-one | D | 2.81 | 391.2 |
| 1043 | GT11-21 | 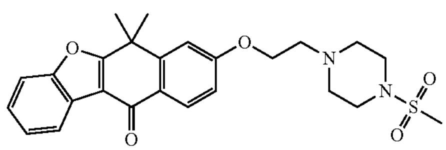 [SMILES: CC1(C)c2cc(OCCN3CCN(S(C)(=O)=O)CC3)ccc2C(=O)c2c1oc1ccccc21] | 8-[2-(4-Methanesulfonyl-piperazin-1-yl)-ethoxy]-6,6-dimethyl-6H-benzo[b]naphtho[2,3-d]furan-11-one | F | 2.21 | 469.1 |
| 1044 | GT11-22 | 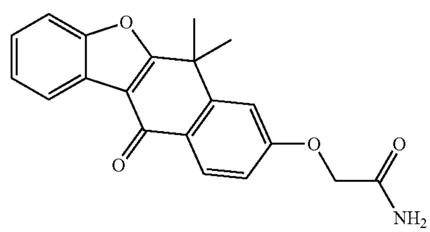 [SMILES: CC1(C)c2cc(OCC(N)=O)ccc2C(=O)c2c1oc1ccccc21] | 2-(6,6-Dimethyl-11-oxo-6,11-dihydro-benzo[b]naphtho[2,3-d]furan-8-yloxy)-acetamide | D | 1.95 | 336.0 |
| 1045 | GT11-23 | 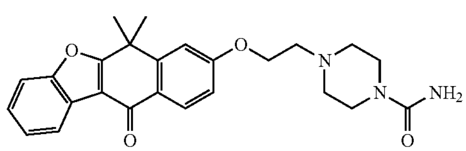 [SMILES: CC1(C)c2cc(OCCN3CCN(C(N)=O)CC3)ccc2C(=O)c2c1oc1ccccc21] | 4-[2-(6,6-Dimethyl-11-oxo-6,11-dihydro-benzo[b]naphtho[2,3-d]furan-8-yloxy)-ethyl]-piperazine-1-carboxylic acid amide | F | 2.04 | 434.0 |
| 1046 | GT11-24 | 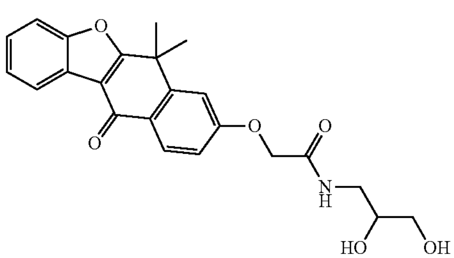 [SMILES: CC1(C)c2cc(OCC(=O)NCC(O)CO)ccc2C(=O)c2c1oc1ccccc21] | N-(2,3-Dihydroxy-propyl)-2-(6,6-dimethyl-11-oxo-6,11-dihydro-benzo[b]naphtho[2,3-d]furan-8-yloxy)-acetamide | D | 1.62 | 410.0 |

TABLE 30

| Example No. | Comp. No. | Structure | Compound Name | HPLC Condition | Retention Time | m/z |
|---|---|---|---|---|---|---|
| 1047 | GT11-25 | 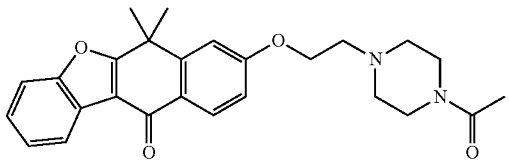 [SMILES: CC(=O)N1CCN(CCOc2ccc3c(c2)C(C)(C)c2oc4ccccc4c2C3=O)CC1] | 8-[2-(4-Acetyl-piperazin-1-yl)-ethoxy]-6,6-dimethyl-6H-benzo[b]naphtho[2,3-b]furan-11-one | F | 2.10 | 433.1 |
| 1048 | GT11-26 | 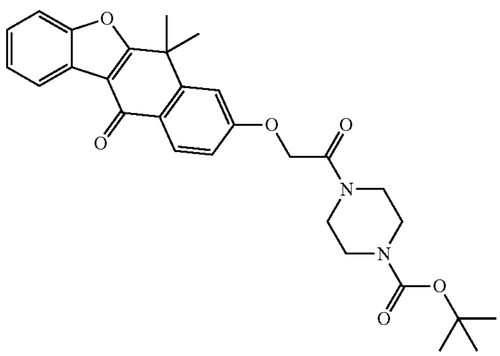 [SMILES: CC(C)(C)OC(=O)N1CCN(C(=O)COc2ccc3c(c2)C(C)(C)c2oc4ccccc4c2C3=O)CC1] | 4-[2-(6,6-Dimethyl-11-oxo-6,11-dihydro-benzo[b]naphtho[2,3-d]furan-8-yloxy)-acetyl]-piperazine-1-carboxylic acid tert-butyl ester | D | 2.53 | 505.0 |
| 1049 | GT11-27 | 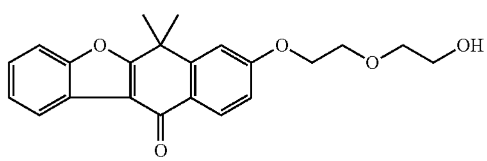 [SMILES: CC1(C)c2cc(OCCOCCO)ccc2C(=O)c2c1oc1ccccc21] | 8-[2-(2-Hydroxy-ethoxy)-ethoxy]-6,6-dimethyl-6H-benzo[b]naphtho[2,3-d]furan-11-one | H | 5.62 | 367.0 |
| 1050 | GT11-28 | 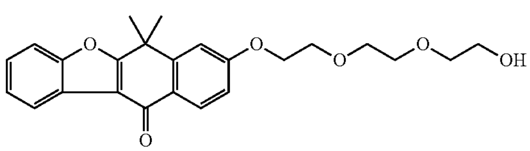 [SMILES: CC1(C)c2cc(OCCOCCOCCO)ccc2C(=O)c2c1oc1ccccc21] | 8-{2-[2-(2-Hydroxy-ethoxy)-ethoxy]-ethoxy}-6,6-dimethyl-6H-benzo[b]naphtho[2,3-d]furan-11-one | H | 5.64 | 411.0 |
| 1051 | GT11-29 | 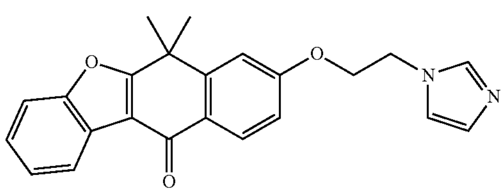 [SMILES: CC1(C)c2cc(OCCn3ccnc3)ccc2C(=O)c2c1oc1ccccc21] | 8-(2-Imidazol-1-yl-ethoxy)-6,6-dimethyl-6H-benzo[b]naphtho[2,3-d]furan-11-one | F | 2.05 | 373.1 |
| 1052 | GT11-30 | 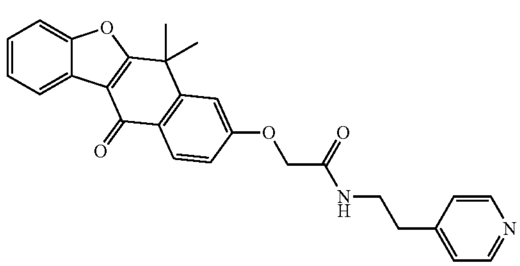 [SMILES: CC1(C)c2cc(OCC(=O)NCCc3ccncc3)ccc2C(=O)c2c1oc1ccccc21] | 2-(6,6-Dimethyl-11-oxo-6,11-dihydro-benzo[b]naphtho[2,3-d]furan-8-yloxy)-N-[2-pryidin-4-yl-ethyl)-acetamide | D | 2.10 | 441.0 |

TABLE 30-continued

| Example No. | Comp. No. | Structure | Compound Name | HPLC Condition | Retention Time | m/z |
|---|---|---|---|---|---|---|
| 1053 | GT11-31 | 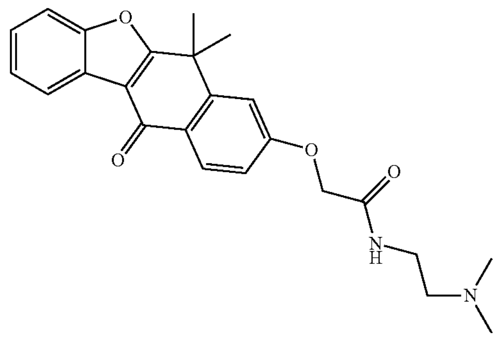 [SMILES: CN(C)CCNC(=O)COc1ccc2c(c1)C(C)(C)c1oc3ccccc3c1C2=O] | N-(2-Dimethylamino-ethyl)-2-(6,6-dimethyl-11-oxo-6,11-dihydro-benzo[b]naphtho[2,3-d]furan-8-yloxy)-acetamide | D | 2.01 | 407.0 |
| 1054 | GT11-32 | 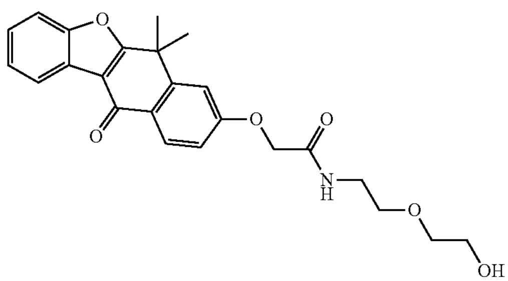 [SMILES: CC1(C)c2cc(OCC(=O)NCCOCCO)ccc2C(=O)c2c1oc1ccccc21] | 2-(6,6-Dimethyl-11-oxo-6,11-dihydro-benzo[b]naphtho[2,3-d]furan-8-yloxy)-N-[2-(2-hydroxy-ethoxy)-ethyl]-acetamide | D | 1.66 | 424.0 |
| 1055 | GT11-33 | 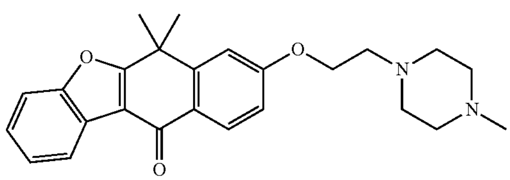 [SMILES: CN1CCN(CCOc2ccc3c(c2)C(C)(C)c2oc4ccccc4c2C3=O)CC1] | 6,6-Dimethyl-8-[2-(4-methyl-piperazin-1-yl)-ethoxy]-6H-benzo[b]naphtho[2,3-d]furan-11-one | F | 1.99 | 405.2 |
| 1056 | GT11-34 | Chiral | 6,6-Dimethyl-8-((2R,3R)-2,3,4-trihydroxy-butoxy)-6H-benzo[b]naphtho[2,3-d]furan-11-one | F | 2.21 | 383.0 |
| 1057 | GT11-35 | Chiral | 8-((R)-2-Hydroxy-3-piperidin-1-yl-propoxy)-6,6-dimethyl-6H-benzo[b]naphtho[2,3-d]furan-11-one | F | 2.25 | 420.0 |
| 1058 | GT11-36 | 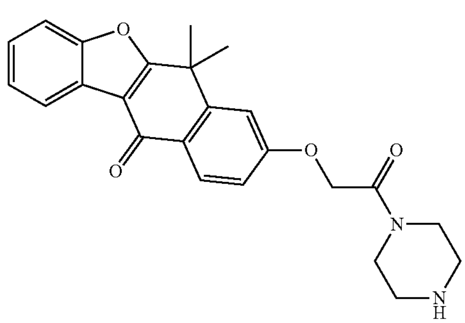 [SMILES: CC1(C)c2cc(OCC(=O)N3CCNCC3)ccc2C(=O)c2c1oc1ccccc21] | 6,6-Dimethyl-8-(2-oxo-2-piperazin-1-yl-ethoxy)-6H-benzo[b]naphtho[2,3-d]furan-11-one | D | 1.92 | 405.0 |

TABLE 30-continued

| Example No. | Comp. No. | Structure | Compound Name | HPLC Condition | Retention Time | m/z |
|---|---|---|---|---|---|---|
| 1059 | GT11-37 | 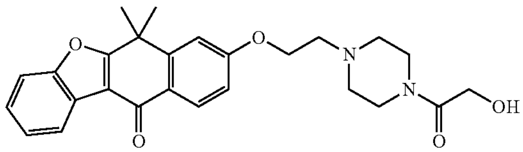 [SMILES: CC1(C)c2cc(OCCN3CCN(C(=O)CO)CC3)ccc2C(=O)c2c1oc1ccccc21] | 8-{2-[4-(2-Hydroxy-acetyl)-piperazin-1-yl]-ethoxy}-6,6-dimethyl-6H-benzo[b]naphtho[2,3-d]furan-11-one | F | 2.06 | 448.1 |
| 1060 | GT11-38 | Chiral | 8-((S)-2-Hydroxy-3-piperidin-1-yl-propoxy)-6,6-dimethyl-6H-benzo[b]naphtho[2,3-d]furan-11-one | F | 2.24 | 420.0 |

TABLE 31

| Example No. | Comp. No. | Structure | Compound Name | HPLC Condition | Retention Time | m/z |
|---|---|---|---|---|---|---|
| 1061 | GT11-39 | Chiral | 8-[2-((R)-2,3-Dihydroxy-propylamino)-ethoxy]-6,6-dimethyl-6H-benzo[b]naphtho[2,3-d]furan-11-one | H | 4.18 | 396.0 |
| 1062 | GT11-40 | Chiral | 8-((S)-4,5-Dihydroxy-pentyloxy)-6,6-dimethyl-6H-benzo[b]naphtho[2,3-d]furan-11-one | F | 2.56 | 381.0 |
| 1063 | GT11-41 | 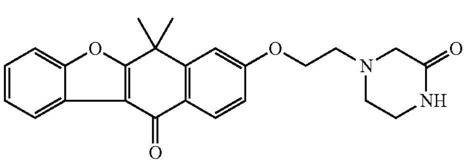 [SMILES: CC1(C)c2cc(OCCN3CCNC(=O)C3)ccc2C(=O)c2c1oc1ccccc21] | 4-[2-(6,6-Dimethyl-11-oxo-6,11-dihydro-benzo[b]naphtho[2,3-d]furan-8-yloxy)-ethyl]-piperazin-2-one | F | 2.06 | 405.0 |
| 1064 | GT11-42 | 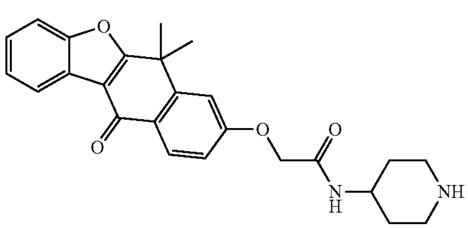 [SMILES: CC1(C)c2cc(OCC(=O)NC3CCNCC3)ccc2C(=O)c2c1oc1ccccc21] | 2-(6,6-Dimethyl-11-oxo-6,11-dihydro-benzo[b]naphtho[2,3-d]furan-8-yloxy)-N-piperidin-4-yl-acetamide | D | 1.92 | 419.0 |

TABLE 31-continued

| Example No. | Comp. No. | Structure | Compound Name | HPLC Condition | Retention Time | m/z |
|---|---|---|---|---|---|---|
| 1065 | GT11-43 | 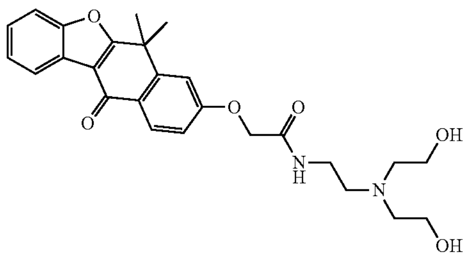 [SMILES: CC1(C)c2cc(OCC(=O)NCCN(CCO)CCO)ccc2C(=O)c2c1oc1ccccc21] | N-{2-[Bis-(2-hydroxy-ethyl)-amino]-ethyl}-2-(6,6-dimethyl-11-oxo-6,11-dihydro-benzo[b]naphtho[2,3-d]furan-8-yloxy)-acetamide | D | 1.83 | 467.0 |
| 1066 | GT11-44 | 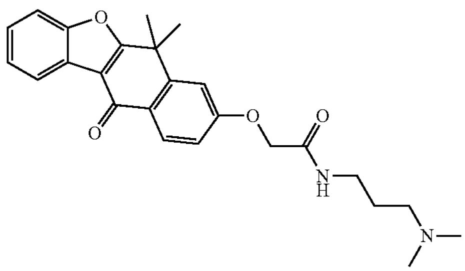 [SMILES: CN(C)CCCNC(=O)COc1ccc2c(c1)C(C)(C)c1oc3ccccc3c1C2=O] | N-(3-Dimethylamino-propyl)-2-(6,6-dimethyl-11-oxo-6,11-dihydro-benzo[b]naphtho[2,3-d]furan-8-yloxy)-acetamide | D | 2.08 | 422.0 |
| 1067 | GT11-45 | 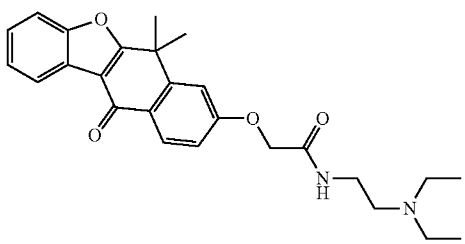 [SMILES: CCN(CC)CCNC(=O)COc1ccc2c(c1)C(C)(C)c1oc3ccccc3c1C2=O] | N-(2-Diethylamino-ethyl)-2-(6,6-dimethyl-11-oxo-6,11-dihydro-benzo[b]naphtho[2,3-d]furan-8-yloxy)-acetamide | D | 2.10 | 436.0 |
| 1068 | GT11-46 | 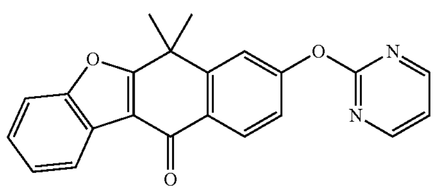 [SMILES: CC1(C)c2cc(Oc3ncccn3)ccc2C(=O)c2c1oc1ccccc21] | 6,6-Dimethyl-8-(pyrimidin-2-yloxy)-6H-benzo[b]naphtho[2,3-d]furan-11-one | H | 6.35 | 357.0 |
| 1069 | GT11-47 | 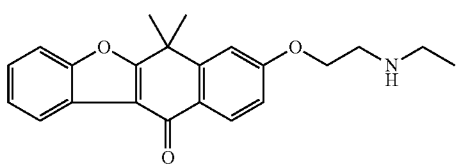 [SMILES: CCNCCOc1ccc2c(c1)C(C)(C)c1oc3ccccc3c1C2=O] | 8-(2-Ethylamino-ethoxy)-6,6-dimethyl-6H-benzo[b]naphtho[2,3-d]furan-11-one | F | 2.15 | 350.0 |
| 1070 | GT11-48 | 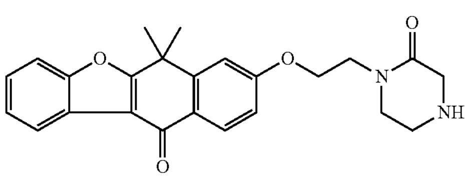 [SMILES: CC1(C)c2cc(OCCN3CCNCC3=O)ccc2C(=O)c2c1oc1ccccc21] | 1-[2-(6,6-Dimethyl-11-oxo-6,11-dihydro-benzo[b]naphtho[2,3-d]furan-8-yloxy)-ethyl]-piperazin-2-one | H | 4.42 | 405.0 |
| 1071 | GT11-49 | 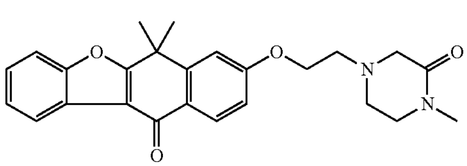 [SMILES: CN1CCN(CCOc2ccc3c(c2)C(C)(C)c2oc4ccccc4c2C3=O)CC1=O] | 4-[2-(6,6-Dimethyl-11-oxo-6,11-dihydro-benzo[b]naphtho[2,3-d]furan-8-yloxy)-ethyl]-1-methyl-piperazin-2-one | H | 4.33 | 419.0 |

TABLE 31-continued

| Example No. | Comp. No. | Structure | Compound Name | HPLC Condition | Retention Time | m/z |
|---|---|---|---|---|---|---|
| 1072 | GT11-50 | 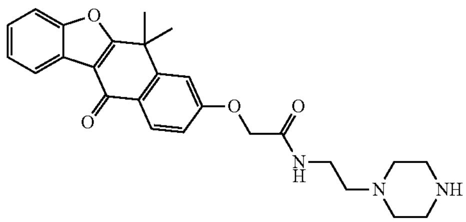 [SMILES: CC1(C)c2cc(OCC(=O)NCCN3CCNCC3)ccc2C(=O)c2c1oc1ccccc21] | 2-(6,6-Dimethyl-11-oxo-6,11-dihydro-benzo[b]naphtho[2,3-d]furan-8-yloxy)-N-(2-piperazin-1-yl-ethyl)-acetamide | A | 3.99 | 448.0 |
| 1073 | GT11-51 | 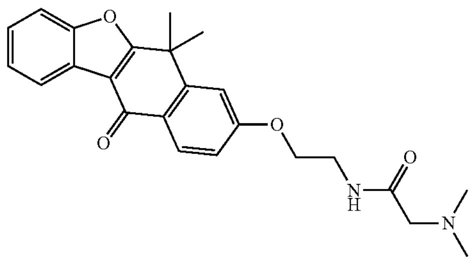 [SMILES: CN(C)CC(=O)NCCOc1ccc2c(c1)C(C)(C)c1oc3ccccc3c1C2=O] | 2-Dimethylamino-N-[2-(6,6-dimethyl-11-oxo-6,11-dihydro-benzo[b]naphtho[2,3-d]furan-8-yloxy)-ethyl]-acetamide | D | 2.13 | 408.0 |
| 1074 | GT11-52 | 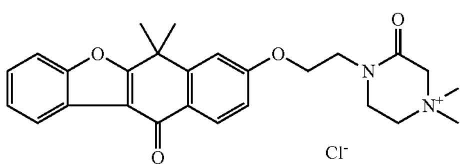 [SMILES: CC1(C)c2cc(OCCN3CC[N+](C)(C)CC3=O)ccc2C(=O)c2c1oc1ccccc21 ; [Cl-]] | 4-[2-(6,6-Dimethyl-11-oxo-6,11-dihydro-benzo[b]naphtho[2,3-d]furan-8-yloxy)-ethyl]-1,1-dimethyl-3-oxo-piperazin-1-ium; chloride | H | 4.47 | 433.0 |

TABLE 32

| Example No. | Comp. No. | Structure | Compound Name | HPLC Condition | Retention Time | m/z |
|---|---|---|---|---|---|---|
| 1075 | GT11-53 | 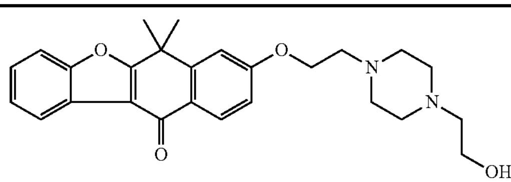 | 8-{2-[4-(2-Hydroxy-ethyl)-piperazin-1-yl]-ethoxy}-6,6-dimethyl-6H-benzo[b]naphtho[2,3-d]furan-11-one | A | 1.75 | 435.0 |
| 1076 | GT11-54 | 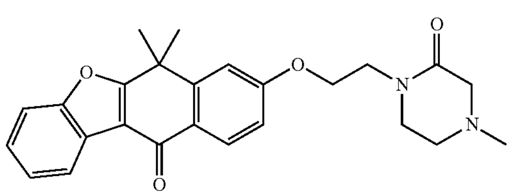 [SMILES: CN1CCN(CCOc2ccc3c(c2)C(C)(C)c2oc4ccccc4c2C3=O)C(=O)C1] | 1-[2-(6,6-Dimethyl-11-oxo-6,11-dihydro-benzo[b]naphtho[2,3-d]furan-8-yloxy)-ethyl]-4-methyl-piperazin-2-one | B | 4.09 | 418.0 |
| 1077 | GT11-55 | 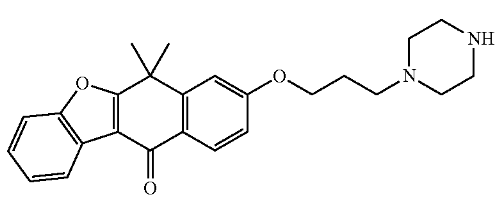 [SMILES: CC1(C)c2cc(OCCCN3CCNCC3)ccc2C(=O)c2c1oc1ccccc21] | 6,6-Dimethyl-8-(3-piperazin-1-yl-propoxy)-6H-benzo[b]naphtho[2,3-d]furan-11-one | A | 1.75 | 405.0 |
| 1078 | GT11-56 | Chiral | 8-{2-[4-((S)-2,3-Dihydroxy-propyl)-piperazin-1-yl]-ethoxy}-6,6-dimethyl-6H-benzo[b]naphtho[2,3-d]furan-11-one | A | 1.72 | 465.0 |

TABLE 32-continued

| Example No. | Comp. No. | Structure | Compound Name | HPLC Condition | Retention Time | m/z |
|---|---|---|---|---|---|---|
| 1079 | GT11-57 | 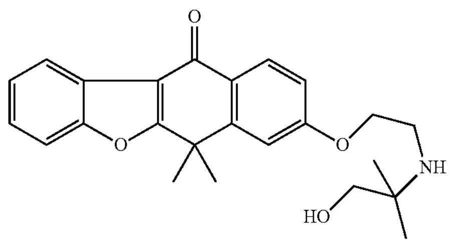 [SMILES: CC(C)(CO)NCCOc1ccc2c(c1)C(C)(C)c1oc3ccccc3c1C2=O] | 8-[2-(2-Hydroxy-1,1-dimethyl-ethylamino)-ethoxy]-6,6-dimethyl-6H-benzo[b]naphtho[2,3-d]furan-11-one | C | 2.57 | 394.0 |
| 1080 | GT11-58 | 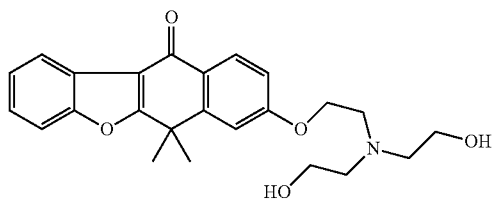 [SMILES: CC1(C)c2cc(OCCN(CCO)CCO)ccc2C(=O)c2c1oc1ccccc21] | 8-{2-[Bis-(2-hydroxy-ethyl)-amino]-ethoxy}-6,6-dimethyl-6H-benzo[b]naphtho[2,3-d]furan-11-one | C | 2.77 | 4.10 |
| 1081 | GT11-59 | 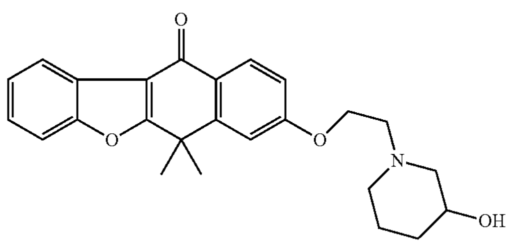 [SMILES: CC1(C)c2cc(OCCN3CCCC(O)C3)ccc2C(=O)c2c1oc1ccccc21] | 8-[2-(3-Hydroxy-piperidin-1-yl)-ethoxy]-6,6-dimethyl-6H-benzo[b]naphtho[2,3-d]furan-11-one | C | 2.88 | 406.0 |
| 1082 | GT11-60 | 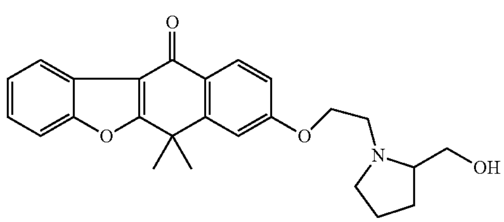 [SMILES: CC1(C)c2cc(OCCN3CCCC3CO)ccc2C(=O)c2c1oc1ccccc21] | 8-[2-(2-Hydroxymethyl-pyrrolidin-1-yl)-ethoxy]-6,6-dimethyl-6H-benzo[b]naphtho[2,3-d]furan-11-one | C | 2.82 | 406.0 |
| 1083 | GT11-61 | 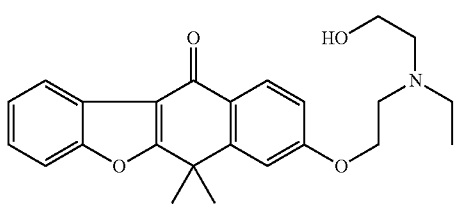 [SMILES: CCN(CCO)CCOc1ccc2c(c1)C(C)(C)c1oc3ccccc3c1C2=O] | 8-{2-[Ethyl-(2-hydroxy-ethyl)-amino]-ethoxy}-6,6-dimethyl-6H-benzo[b]naphtho[2,3-d]furan-11-one | C | 2.85 | 394.0 |
| 1084 | GT11-62 | 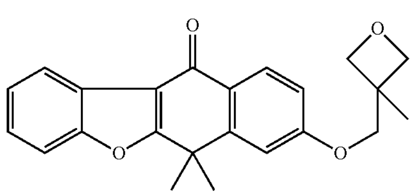 [SMILES: CC1(COc2ccc3c(c2)C(C)(C)c2oc4ccccc4c2C3=O)COC1] | 6,6-Dimethyl-8-(3-methyl-oxetan-3-ylmethoxy)-6H-benzo[b]naphtho[2,3-d]furan-11-one | C | 3.03 | 363.0 |
| 1085 | GT11-63 | 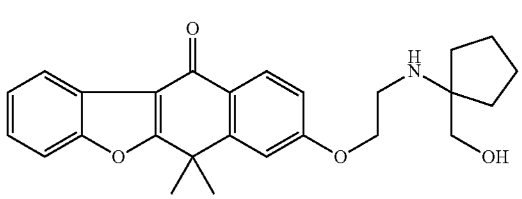 [SMILES: CC1(C)c2cc(OCCNC3(CO)CCCC3)ccc2C(=O)c2c1oc1ccccc21] | 8-[2-(1-Hydroxymethyl-cyclopentylamino)-ethoxy]-6,6-dimethyl-6H-benzo[b]naphtho[2,3-d]furan-11-one | C | 2.72 | 420.0 |

TABLE 32-continued

| Example No. | Comp. No. | Structure | Compound Name | HPLC Condition | Retention Time | m/z |
|---|---|---|---|---|---|---|
| 1086 | GT11-64 | 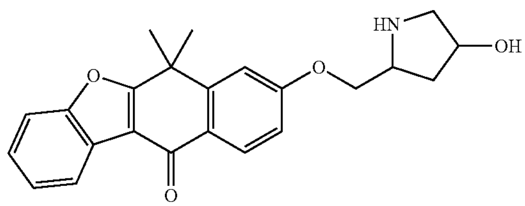 [SMILES: CC1(C)c2cc(OCC3CC(O)CN3)ccc2C(=O)c2c1oc1ccccc21] | 8-(4-Hydroxy-pyrrolidin-2-ylmethoxy)-6,6-dimethyl-6H-benzo[b]naphtho[2,3-d]furan-11-one | Y | 2.96 | 378.0 |
| 1087 | GT11-65 | 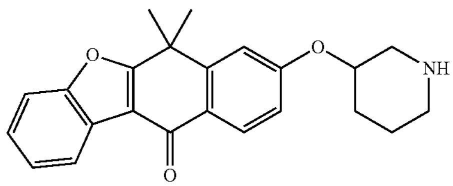 [SMILES: CC1(C)c2cc(OC3CCCNC3)ccc2C(=O)c2c1oc1ccccc21] | 6,6-Dimethyl-8-(piperidin-3-yloxy)-6H-benzo[b]naphtho[2,3-d]furan-11-one | Y | 3.03 | 362.0 |

The compounds described in the following Table 33 were synthesized according to the method shown below. From Compound A2 and 2-bromophenol having a fluorine atom at corresponding position, 8-methoxy-6H-benzo[b]naphtho[2,3-d]furan-11-one having a fluorine atom at corresponding position (Compound GT12-1, GT12-2, GT12-5 and GT12-7) was prepared according to the method used for the preparation of Compound Z10, Z11 and Z12. Further, demethylation was carried out according to the method used for the preparation of Compound A6 to obtain 8-hydroxy-6H-benzo[b]naphtho[2,3-d]furan-11-one which has a fluorine atom at corresponding position. Thereafter, according to Mitsunobu reaction used for the preparation of Compound A7-1 or the alkylation method used for the preparation of Compound A7-17, a corresponding side chain was introduced and, if necessary, functional group modification such as deprotection, etc. was carried out to prepare the compounds listed below.

TABLE 33

| Example No. | Comp. No. | Structure | Compound Name | HPLC Condition | Retention Time | m/z |
|---|---|---|---|---|---|---|
| 1088 | GT12-1 | 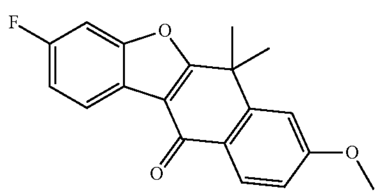 [SMILES: COc1ccc2c(c1)C(C)(C)c1oc3cc(F)ccc3c1C2=O] | 3-Fluoro-8-methoxy-6,6-dimethyl-6H-benzo[b]naphtho[2,3-d]furan-11-one | A | 3.02 | 311.0 |
| 1089 | GT12-2 | 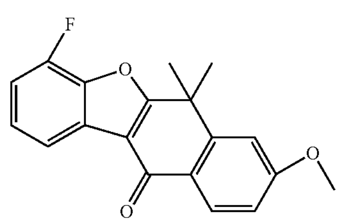 [SMILES: COc1ccc2c(c1)C(C)(C)c1oc3c(F)cccc3c1C2=O] | 4-Fluoro-8-methoxy-6,6-dimethyl-6H-benzo[b]naphtho[2,3-d]furan-11-one | A | 3.00 | 311.0 |
| 1090 | GT12-3 | 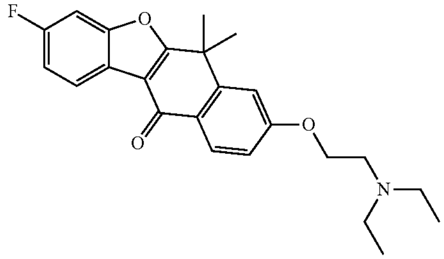 [SMILES: CCN(CC)CCOc1ccc2c(c1)C(C)(C)c1oc3cc(F)ccc3c1C2=O] | 8-(2-Diethylamino-ethoxy)-3-fluoro-6,6-dimethyl-6H-benzo[b]naphtho[2,3-d]furan-11-one | B | 4.48 | 396.0 |

TABLE 33-continued

| Example No. | Comp. No. | Structure | Compound Name | HPLC Condition | Retention Time | m/z |
|---|---|---|---|---|---|---|
| 1091 | GT12-4 | 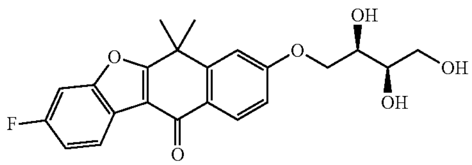 | 3-Fluoro-6,6-dimethyl-8-((2R,3R)-2,3,4-trihydroxy-butoxy)-6H-benzo[b]naphtho[2,3-d]furan-11-one | H | 4.91 | 401.4 |
| 1092 | GT12-5 | 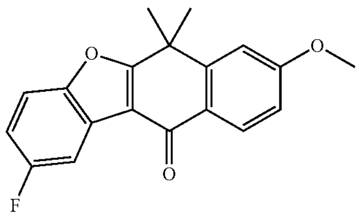 [SMILES: COc1ccc2c(c1)C(C)(C)c1oc3ccc(F)cc3c1C2=O] | 2-Fluoro-8-methoxy-6,6-dimethyl-6H-benzo[b]naphtho[2,3-d]furan-11-one | C | 3.01 | 311.0 |
| 1093 | GT12-6 | 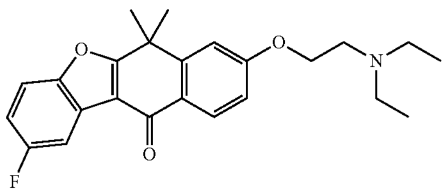 [SMILES: CCN(CC)CCOc1ccc2c(c1)C(C)(C)c1oc3ccc(F)cc3c1C2=O] | 8-(2-Diethylamino-ethoxy)-2-fluoro-6,6-dimethyl-6H-benzo[b]naphtho[2,3-d]furan-11-one | C | 2.09 | 395.0 |
| 1094 | GT12-7 | 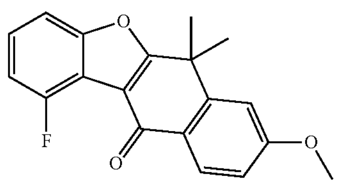 [SMILES: COc1ccc2c(c1)C(C)(C)c1oc3cccc(F)c3c1C2=O] | 1-Fluoro-8-methoxy-6,6-dimethyl-6H-benzo[b]naphtho[2,3-d]furan-11-one | B | 6.26 | 311.0 |
| 1095 | GT12-8 | 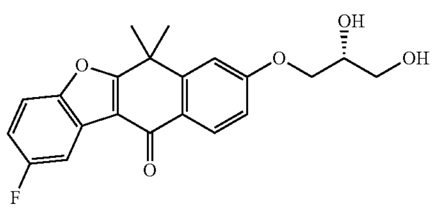 | 8-((R)-2,3-Dihydroxy-propoxy)-2-fluoro-6,6-dimethyl-6H-benzo[b]naphtho[2,3-d]furan-11-one | C | 2.22 | 371.0 |
| 1096 | GT12-9 | 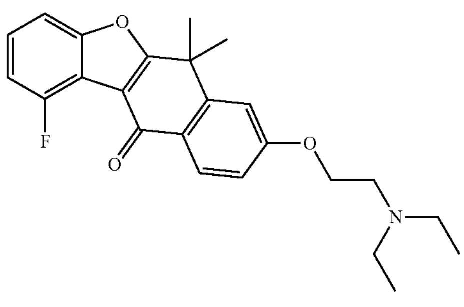 [SMILES: CCN(CC)CCOc1ccc2c(c1)C(C)(C)c1oc3cccc(F)c3c1C2=O] | 8-(2-Diethylamino-ethoxy)-1-fluoro-6,6-dimethyl-6H-benzo[b]naphtho[2,3-d]furan-11-one | B | 4.20 | 396.0 |
| 1097 | GT12-10 | 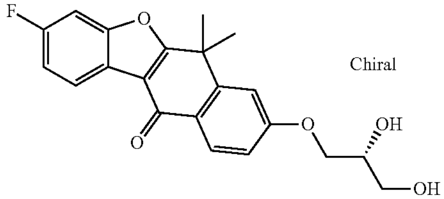 [SMILES: CC1(C)c2cc(OC[C@H](O)CO)ccc2C(=O)c2c1oc1cc(F)ccc21] | 8-((R)-2,3-Dihydroxy-propoxy)-3-fluoro-6,6-dimethyl-6H-benzo[b]naphtho[2,3-d]furan-11-one | B | 4.82 | 371.0 |

TABLE 33-continued

| Example No. | Comp. No. | Structure | Compound Name | HPLC Condition | Retention Time | m/z |
|---|---|---|---|---|---|---|
| 1098 | GT12-11 | Chiral | 8-((R)-2,3-Dihydroxy-propoxy)-4-fluoro-6,6-dimethyl-6H-benzo[b]naphtho[2,3-d]furan-11-one | D | 1.80 | 371.0 |
| 1099 | GT12-12 | Chiral | 8-((R)-2,3-Dihydroxy-propoxy)-1-fluoro-6,6-dimethyl-6H-benzo[b]naphtho[2,3-d]furan-11-one | D | 1.85 | 371.0 |

The compounds described in the following Table 34 were synthesized according to the method shown below. 8-Hydroxy-6H-benzo[b]naphtho[2,3-d]furan-11-one was transformed into trifluoromethanesulfonic acid ester according to the method used for the preparation of Compound B1. Subsequently, by carrying out the method used for the preparation of Compound B2-1 or Compound B2-18, Compound GT13-1, Compound GT13-2 and Compound GT13-3 were prepared. Compound GT13-3 was oxidized according to the method used for the preparation of Compound B3-8 to prepare Compound 13-4.

TABLE 34

| Example No. | Comp. No. | Structure | Compound Name | HPLC Condition | Retention Time | m/z | Method |
|---|---|---|---|---|---|---|---|
| 1100 | GT13-1 | 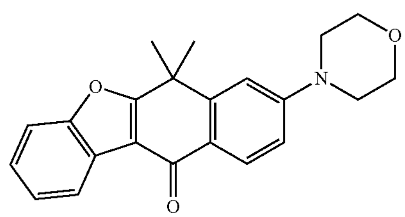 [SMILES: CC1(C)c2cc(N3CCOCC3)ccc2C(=O)c2c1oc1ccccc21] | 6,6-Dimethyl-8-morpholin-4-yl-6H-benzo[b]naphtho[2,3-d]furan-11-one | F | 3.04 | 348.2 | B1, B2-1 |
| 1101 | GT13-2 | 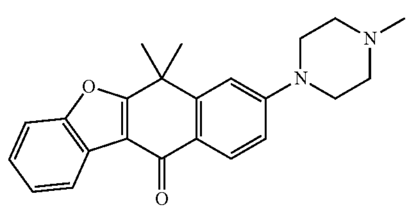 [SMILES: CN1CCN(c2ccc3c(c2)C(C)(C)c2oc4ccccc4c2C3=O)CC1] | 6,6-Dimethyl-8-(4-methyl-piperazin-1-yl)-6H-benzo[b]naphtho[2,3-d]furan-11-one | F | 2.13 | 361.3 | B1, B2-1 |
| 1102 | GT13-3 | 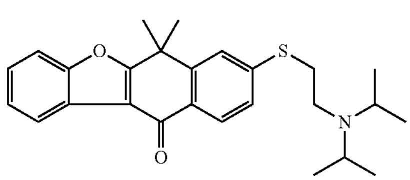 [SMILES: CC(C)N(CCSc1ccc2c(c1)C(C)(C)c1oc3ccccc3c1C2=O)C(C)C] | 8-(2-Diisopropylamino-ethylsulfanyl)-6,6-dimethyl-6H-benzo[b]naphtho[2,3-d]furan-11-one | C | 3.45 | 422.0 | B1, B2-18 |
| 1103 | GT13-4 | 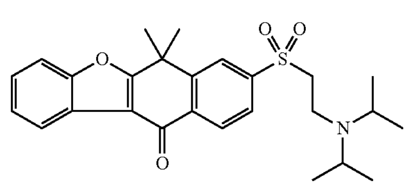 [SMILES: CC(C)N(CCS(=O)(=O)c1ccc2c(c1)C(C)(C)c1oc3ccccc3c1C2=O)C(C)C] | 8-(2-Diisopropylamino-ethanesulfonyl)-6,6-dimethyl-6H-benzo[b]naphtho[2,3-d]furan-11-one | C | 3.23 | 454.0 | B3-8 |

The compounds described in the following Table 35 were synthesized according to the method shown below. Specifically, a side chain was introduced to Compound Z13 to prepare Compound GT13-5 according to the method that is used for the preparation of Compound A7-17. Further Compound GT13-5 or trifluoromethanesulfonic acid ester of Compound Z14 was hydrolyzed to prepare Compound GT13-6 and Compound GT13-7 according to the method used for the preparation of Compound T20.

TABLE 35

| Example No. | Comp. No. | Structure | Compound Name | HPLC Condition | Retention Time | m/z | Method |
|---|---|---|---|---|---|---|---|
| 1104 | GT13-5 | 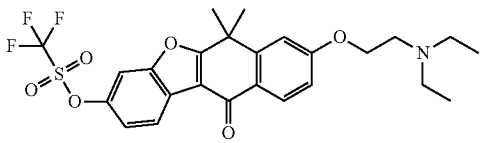 [SMILES: CCN(CC)CCOc1ccc2c(c1)C(C)(C)c1oc3cc(OS(=O)(=O)C(F)(F)F)ccc3c1C2=O] | Trifluoro-methane-sulfonic acid 8-(2-diethylamino-ethoxy)-6,6-dimethyl-11-oxo-6,11-dihydro-benzo[b]naptho[2,3-d]furan-3-yl ester | H | 5.37 | 526.0 | A7-17 |
| 1105 | GT13-6 | 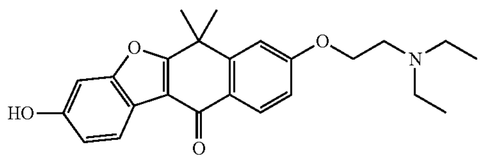 [SMILES: CCN(CC)CCOc1ccc2c(c1)C(C)(C)c1oc3cc(O)ccc3c1C2=O] | 8-(2-Diethylamino-ethoxy)-3-hydroxy-6,6-dimethyl-6H-benzo[b]naphtho[2,3-d]furan-11-one | B | 3.40 | 384.0 | T20 |
| 1106 | GT13-7 | 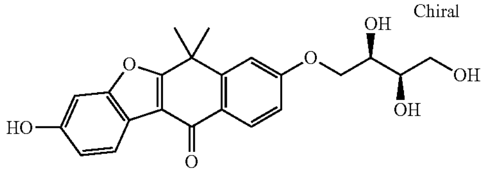 [SMILES: CC1(C)c2cc(OC[C@@H](O)[C@H](O)CO)ccc2C(=O)c2c1oc1cc(O)ccc21] | 3-Hydroxy-6,6-dimethyl-8-((2R,3R)-2,3,4-trihydroxy-butoxy)-6H-benzo[b]naphtho[2,3-d]furan-11-one | F | 1.87 | 399.0 | T20 |

The compounds described in the following Table 36 were prepared by subjecting Compound GT13-6 or GT13-7 to Mitsunobu reaction that is used for the preparation of Compound A7-1 to introduce a corresponding side chain or a synthetic equivalent. After that, by carrying out deprotection, if necessary, the compounds listed below were prepared.

TABLE 36

| Example No. | Comp. No. | Structure | Compound Name | HPLC Condition | Retention Time | m/z | Method |
|---|---|---|---|---|---|---|---|
| 1107 | GT13-8 | 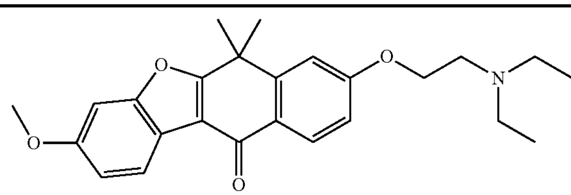 | 8-(2-Diethylamino-ethoxy)-3-methoxy-6,6-dimethyl-6H-benzo[b]naphtho[2,3-d]furan-11-one | H | 4.72 | 408.0 | A7-1 |
| 1108 | GT13-9 | 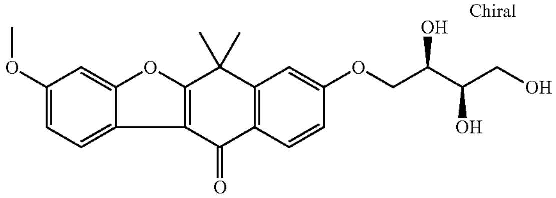 [SMILES: COc1ccc2c3c(oc2c1)C(C)(C)c1cc(OC[C@@H](O)[C@H](O)CO)ccc1C3=O] | 3-Methoxy-6,6-dimethyl-8-((2R,3R)-2,3,4-trihydroxy-butoxy)-6H-benzo[b]naphtho[2,3-d]furan-11-one | B | 4.23 | 413.2 | A7-1 |
| 1109 | GT13-10 | 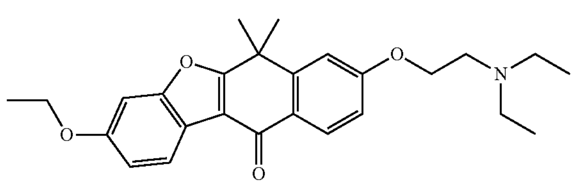 [SMILES: CCOc1ccc2c3c(oc2c1)C(C)(C)c1cc(OCCN(CC)CC)ccc1C3=O] | 8-(2-Diethylamino-ethoxy)-3-ethoxy-6,6-dimethyl-6H-benzo[b]naphtho[2,3-d]furan-11-one | H | 5.10 | 422.0 | A7-1 |

TABLE 36-continued

| Example No. | Comp. No. | Structure | Compound Name | HPLC Condition | Retention Time | m/z | Method |
|---|---|---|---|---|---|---|---|
| 1110 | GT13-11 | 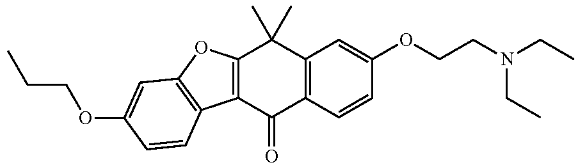 [SMILES: CCCOc1ccc2c3c(oc2c1)C(C)(C)c1cc(OCCN(CC)CC)ccc1C3=O] | 8-(2-Diethylamino-ethoxy)-6,6-dimethyl-3-propoxy-6H-benzo[b]naphtho[2,3-d]furan-11-one | H | 5.63 | 436.0 | A7-1 |
| 1111 | GT13-12 | 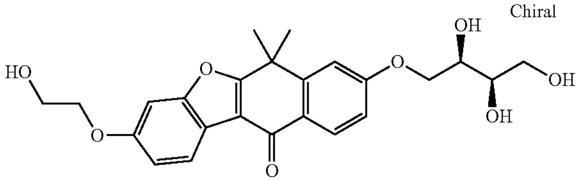 [SMILES: CC1(C)c2cc(OC[C@@H](O)[C@H](O)CO)ccc2C(=O)c2c1oc1cc(OCCO)ccc21] | 3-(2-Hydroxy-ethoxy)-6,6-dimethyl-8-((2R,3R)-2,3,4-trihydroxy-butoxy)-6H-benzo[b]naphtho[2,3-d]furan-11-one | F | 1.83 | 443.0 | A7-1 |
| 1112 | GT13-13 | 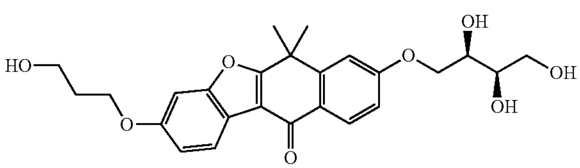 | 3-(3-Hydroxy-propoxy)-6,6-dimethyl-8-((2R,3R)-2,3,4-trihydroxy-butoxy)-6H-benzo[b]naphtho[2,3-d]furan-11-one | F | 1.94 | 457.0 | A7-1 |
| 1113 | GT13-14 | 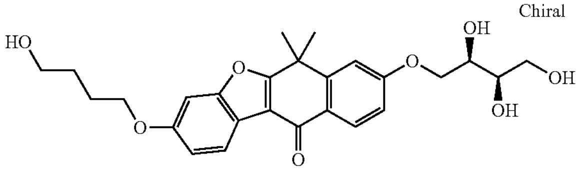 [SMILES: CC1(C)c2cc(OC[C@@H](O)[C@H](O)CO)ccc2C(=O)c2c1oc1cc(OCCCCO)ccc21] | 3-(4-Hydroxy-butoxy)-6,6-dimethyl-8-((2R,3R)-2,3,4-trihydroxy-butoxy)-6H-benzo[b]naphtho[2,3-d]furan-11-one | F | 2.01 | 471.0 | A7-1 |
| 1114 | GT13-15 | 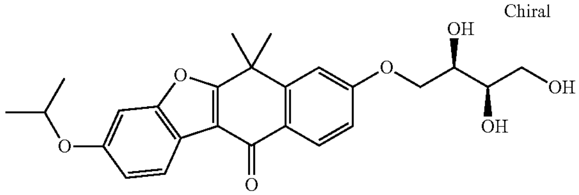 [SMILES: CC(C)Oc1ccc2c3c(oc2c1)C(C)(C)c1cc(OC[C@@H](O)[C@H](O)CO)ccc1C3=O] | 3-Isopropoxy-6,6-dimethyl-8-[(2R,3R)-2,3,4-trihydroxy-butoxy)-6H-benzo[b]naphtho[2,3-d]furan-11-one | H | 5.40 | 441.0 | A7-1 |
| 1115 | GT13-16 | 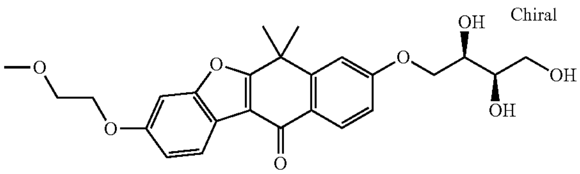 [SMILES: COCCOc1ccc2c3c(oc2c1)C(C)(C)c1cc(OC[C@@H](O)[C@H](O)CO)ccc1C3=O] | 3-(2-Methoxy-ethoxy)-6,6-dimethyl-8-((2R,3R)-2,3,4-trihydroxy-butoxy)-6H-benzo[b]naphtho[2,3-d]furan-11-one | F | 2.17 | 457.0 | A7-1 |
| 1116 | GT13-17 | 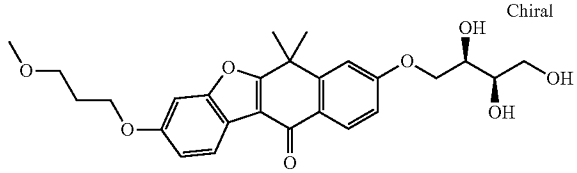 [SMILES: COCCCOc1ccc2c3c(oc2c1)C(C)(C)c1cc(OC[C@@H](O)[C@H](O)CO)ccc1C3=O] | 3-(3-Methoxy-propoxy)-6,6-dimethyl-8-((2R,3R)-2,3,4-trihydroxy-butoxy)-6H-benzo[b]naphtho[2,3-d]furan-11-one | F | 2.34 | 471.0 | A7-1 |
| 1117 | GT13-18 | 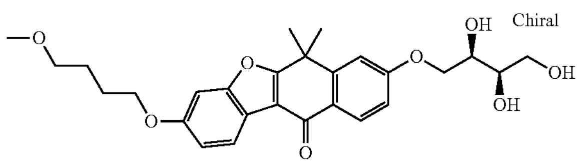 [SMILES: COCCCCOc1ccc2c3c(oc2c1)C(C)(C)c1cc(OC[C@@H](O)[C@H](O)CO)ccc1C3=O] | 3-(4-Methoxy-butoxy)-6,6-dimethyl-8-((2R,3R)-2,3,4-trihydroxy-butoxy)-6H-benzo[b]naphtho[2,3-d]furan-11-one | F | 2.45 | 485.0 | A7-1 |

TABLE 36-continued

| Example No. | Comp. No. | Structure | Compound Name | HPLC Condition | Retention Time | m/z | Method |
|---|---|---|---|---|---|---|---|
| 1118 | GT13-19 | 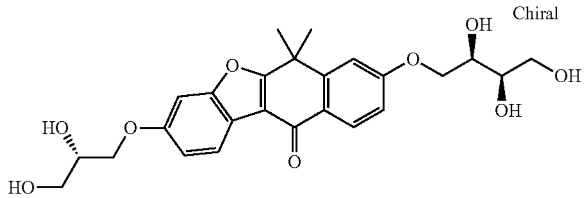 [SMILES: CC1(C)c2cc(OC[C@@H](O)[C@H](O)CO)ccc2C(=O)c2c1oc1cc(OC[C@@H](O)CO)ccc21] | 3-((S)-2,3-Dihydroxy-propoxy)-6,6-dimethyl-8-((2R,3R)-2,3,4-trihydroxy-butoxy)-6H-benzo[b]naphtho[2,3-d]furan-11-one | F | 1.69 | 473.0 | A7-1 A7-14-1 |
| 1119 | GT13-20 | 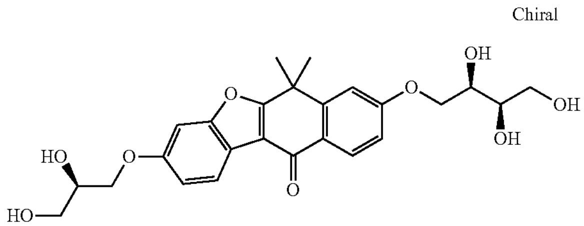 [SMILES: CC1(C)c2cc(OC[C@@H](O)[C@H](O)CO)ccc2C(=O)c2c1oc1cc(OC[C@H](O)CO)ccc21] | 3-((R)-2,3-Dihydroxy-propoxy)-6,6-dimethyl-8-((2R,3R)-2,3,4-trihydroxy-butoxy)-6H-benzo[b]naphtho[2,3-d]furan-11-one | F | 1.69 | 473.0 | A7-1 A7-14-1 |

The compounds described in the following Table 37 were prepared from Compound GT13-7 according to carbamation that is used for the preparation of Compound A9-1.

TABLE 37

| Example No. | Comp. No. | Structure | Compound Name | HPLC Condition | Retention Time | m/z | Method |
|---|---|---|---|---|---|---|---|
| 1120 | GT13-21 | 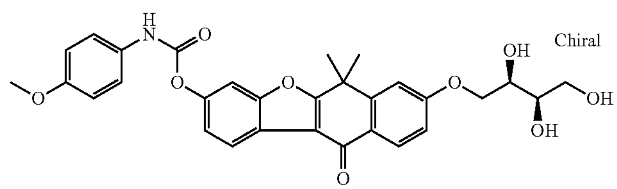 [SMILES: COc1ccc(NC(=O)Oc2ccc3c4c(oc3c2)C(C)(C)c2cc(OC[C@@H](O)[C@H](O)CO)ccc2C4=O)cc1] | (4-Methoxy-phenyl)-carbamic acid 6,6-dimethyl-11-oxo-8-((2R,3R)-2,3,4-trihydroxy-butoxy)-6,11-dihydro-benzo[b]naphtho[2,3-d]furan-3-yl ester | B | 4.34 | 548.2 | A9-1 |
| 1121 | GT13-22 | 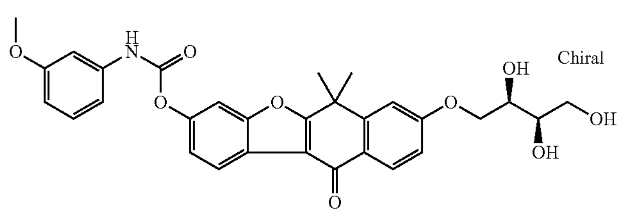 [SMILES: COc1cccc(NC(=O)Oc2ccc3c4c(oc3c2)C(C)(C)c2cc(OC[C@@H](O)[C@H](O)CO)ccc2C4=O)c1] | (3-Methoxy-phenyl)-carbamic acid 6,6-dimethyl-11-oxo-8-((2R,3R)-2,3,4-trihydroxy-butoxy)-6,11-dihydro-benzo[b]naphtho[2,3-d]furan-3-yl ester | B | 4.69 | 548.2 | A9-1 |
| 1122 | GT13-23 | 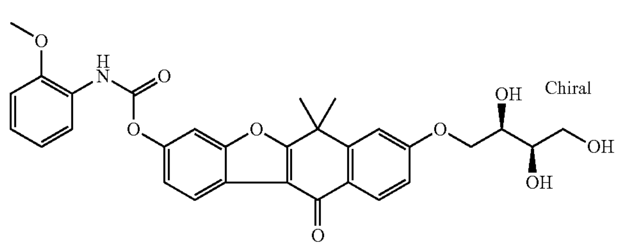 [SMILES: COc1ccccc1NC(=O)Oc1ccc2c3c(oc2c1)C(C)(C)c1cc(OC[C@@H](O)[C@H](O)CO)ccc1C3=O] | (2-Methoxy-phenyl)-carbamic acid 6,6-dimethyl-11-oxo-8-((2R,3R)-2,3,4-trihydroxy-butoxy)-6,11-dihydro-benzo[b]naphtho[2,3-d]furan-3-yl ester | B | 4.99 | 548.3 | A9-1 |

TABLE 37-continued

| Example No. | Comp. No. | Structure | Compound Name | HPLC Condition | Retention Time | m/z | Method |
|---|---|---|---|---|---|---|---|
| 1123 | GT13-24 | 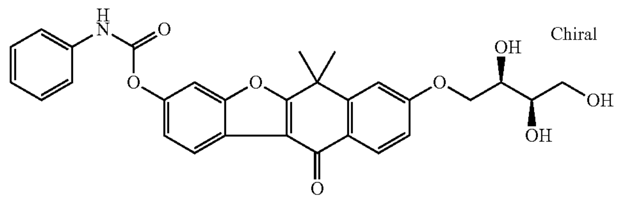 [SMILES: CC1(C)c2cc(OC[C@@H](O)[C@H](O)CO)ccc2C(=O)c2c1oc1cc(OC(=O)Nc3ccccc3)ccc21] | Phenyl-carbamic acid 6,6-dimethyl-11-oxo-8-((2R,3R)-2,3,4-trihydroxy-butoxy)-6,11-dihydro-benzo[b]naphtho[2,3-d]furan-3-yl ester | B | 4.67 | 518.2 | A9-1 |
| 1124 | GT13-25 | 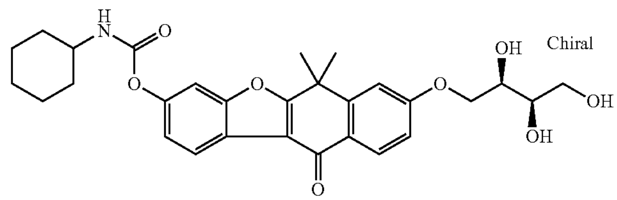 [SMILES: CC1(C)c2cc(OC[C@@H](O)[C@H](O)CO)ccc2C(=O)c2c1oc1cc(OC(=O)NC3CCCCC3)ccc21] | Cyclohexyl-carbamic acid 6,6-dimethyl-11-oxo-8-((2R,3R)-2,3,4-trihydroxy-butoxy)-6,11-dihydro-benzo[b]naphtho[2,3-d]furan-3-yl ester | B | 4.94 | 524.2 | A9-1 |
| 1125 | GT13-26 | 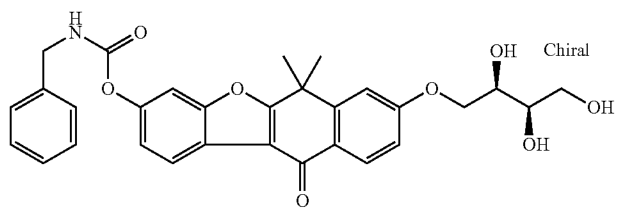 [SMILES: CC1(C)c2cc(OC[C@@H](O)[C@H](O)CO)ccc2C(=O)c2c1oc1cc(OC(=O)NCc3ccccc3)ccc21] | Benzyl-carbamic acid 6,6-dimethyl-11-oxo-8-((2R,3R)-2,3,4-trihydroxy-butoxy)-6,11-dihydro-benzo[b]naphtho[2,3-d]furan-3-yl ester | A | 2.09 | 532.3 | A9-1 |
| 1126 | GT13-27 | 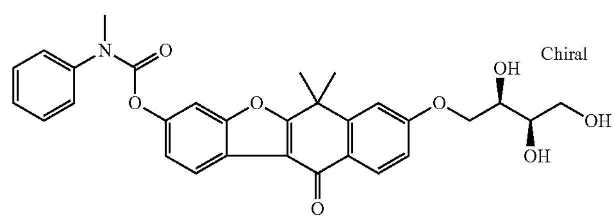 [SMILES: CN(C(=O)Oc1ccc2c3c(oc2c1)C(C)(C)c1cc(OC[C@@H](O)[C@H](O)CO)ccc1C3=O)c1ccccc1] | Methyl-phenyl-carbamic acid 6,6-dimethyl-11-oxo-8-((2R,3R)-2,3,4-trihydroxy-butoxy)-6,11-dihydro-benzo[b]naphtho[2,3-d]furan 3-yl ester | B | 4.88 | 532.3 | A9-1 |

The compounds described in the following Table 38 were prepared from corresponding intermediates by alkylation and carbamation based on the method described in the Table.

TABLE 38

| Example No. | Comp. No. | Structure | Compound Name | HPLC Condition | Retention Time | m/z | Method |
|---|---|---|---|---|---|---|---|
| 1127 | GT13-28 | 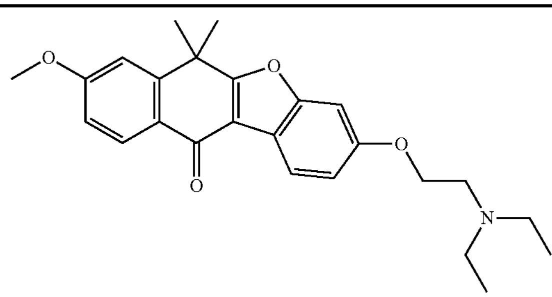 | 3-(2-Diethylamino-ethoxy)-8-methoxy-6,6-dimethyl-6H-benzo[b]naphtho[2,3-d]furan-11-one | H | 4.65 | 408.0 | A7-17 |

TABLE 38-continued

| Example No. | Comp. No. | Structure | Compound Name | HPLC Condition | Retention Time | m/z | Method |
|---|---|---|---|---|---|---|---|
| 1128 | GT13-29 | Chiral | 2-[8-((R)-2,3-Dihydroxy-propoxy)-6,6-dimethyl-11-oxo-6,11-dihydro-benzo[b]naphtho[2,3-d]furan-3-yloxy]-N-phenyl-acetamide | B | 4.70 | 502.0 | A7-17 A8-1 T13-3 |
| 1129 | GT13-30 | Chiral | (4-tert-Butyl-phenyl)-carbamic acid 8-((R)-2,3-dihydoxy-propoxy)-6,6-dimethyl-11-oxo-6,11-dihydro-benzo[b]naphtho[2,3-d]furan-3-yl ester | B | 6.19 | 544.3 | A9-1 |
| 1130 | GT13-31 | Chiral | (2-tert-Butyl-phenyl)-carbamic acid 8-((R)-2,3-dihydroxy-propoxy)-6,6-dimethyl-11-oxo-6,11-dihydro-benzo[b]naphtho[2,3-d]furan-3-yl ester | B | 5.74 | 544.3 | A9-1 |
| 1131 | GT13-32 | Chiral | (5-tert-Butyl-2-methoxy-phenyl)-carbamic acid 8-((R)-2,3-dihydroxy-propoxy)-6,6-dimethyl-11-oxo-6,11-dihydro-benzo[b]naphtho[2,3-d]furan-3-yl ester | B | 6.52 | 574.3 | A9-1 |
| 1132 | GT13-33 | Chiral | 6,6-Dimethyl-3-(pyrimidin-2-yloxy)-8-((2R,3R)-2,3,4-trihydroxy-butoxy)-6H-benzo[b]naphtho[2,3-d]furan-11-one | H | 4.14 | 477.0 | A7-17 |

Example 1133

Compound GT14-1

3-Chloro-8-((R)-2,3-dihydroxy-propoxy)-6,6-dimethyl-5,6-dihydro-benzo[f]pyrido[4,3-b]indol-11-one

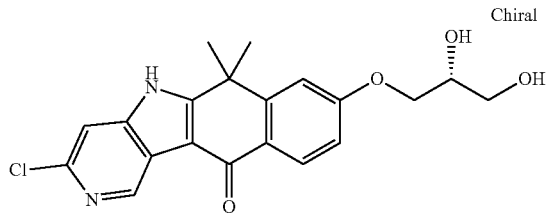 [SMILES: CC1(C)c2cc(OC[C@H](O)CO)ccc2C(=O)c2c1[nH]c1cc(Cl)ncc21]

Compound BZ2-2 was demethylated according to the method used for the preparation of Compound A6, and subsequently introduced with a substituent group and deprotected according to the method used for the preparation of Compound A7-14-1 and A7-14-2.

LCMS: m/z 386 [M+H]$^+$
HPLC retention time: 3.02 min (analysis condition B)

Example 1134

Compound GT15-1

2-Iodo-3-(4-methoxy-benzyloxy)-pyridine

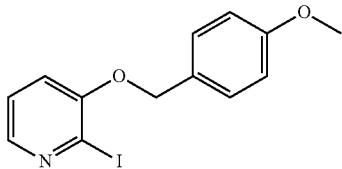 [SMILES: COc1ccc(COc2cccnc2I)cc1]

2-Iodo-pyridin-3-ol (50 mg, 0.226 mmol), K$_2$CO$_3$ (62 mg, 0.452 mmol) and DMF (2 ml) were added with para-methoxybenzyl chloride (46 µL, 0.339 mmol), and the mixture was stirred overnight at 45° C. The resultant was added with water, and then extracted with ethyl acetate. The organic layer was washed with saturated brine, and the resulting residues obtained after concentration under reduced pressure were purified by silica gel column (ethyl acetate/hexane) to obtain the title compound (21 mg, 27%).

LCMS: m/z 342 [M+H]$^+$
HPLC retention time: 3.44 min (analysis condition Y)

Example 1135

Compound GT15-2

7-Methoxy-3-[3-(4-methoxy-benzyloxy)-pyridin-2-yl]-1,1-dimethyl-3,4-dihydro-1H-naphthalen-2-one

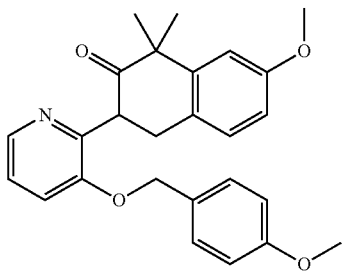 [SMILES: COc1ccc(COc2cccnc2C2Cc3ccc(OC)cc3C(C)(C)C2=O)cc1]

Toluene (0.5 ml) was added to 7-methoxy-1,1-dimethyl-3,4-dihydro-1H-naphthalen-2-one (Compound A2, 36 mg), 2-iodo-3-(4-methoxy-benzyloxy)-pyridine (Compound GT15-1, 50 mg), sodium t-butoxide (35.3 mg), Pd$_2$dba$_3$ (13.5 mg) and Xantphos (17 mg), and the mixture was stirred and heated at 80° C. for 2.5 hrs under nitrogen atmosphere. After cooling, the reaction mixture was diluted with ethyl acetate and subjected to Celite filtration. The organic layer was washed with saturated aqueous solution of sodium bicarbonate and saturated brine, and then concentrated under reduced pressure. The resulting residues were purified by silica gel column (ethyl acetate/hexane) to obtain the title compound (27 mg, 44%).

LCMS: m/z 419 [M+H]$^+$
HPLC retention time: 3.31 min (analysis condition Y)

Example 1136

Compound GT15-3

8-Methoxy-10,10-dimethyl-5,10-dihydro-11-oxa-4-aza-benzo[b] fluorene

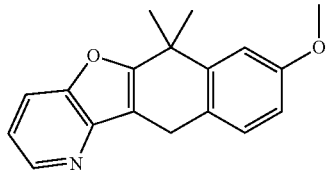 [SMILES: COc1ccc2c(c1)C(C)(C)c1oc3cccnc3c1C2]

To the mixture of 7-methoxy-3-[3-(4-methoxy-benzyloxy)-pyridin-2-yl]-1,1-dimethyl-3,4-dihydro-1H-naphthalen-2-one (Compound GT15-2, 21 mg) and ethyl acetate (0.8 ml), sulfuric acid (0.2 ml) was added. The mixture was stirred and heated at 70° C. for 5 hrs. After cooling, the reaction mixture was neutralized with 2 N aqueous solution of sodium hydroxide. The mixture was diluted with ethyl acetate. The organic layer was washed with saturated aqueous solution of sodium bicarbonate and saturated brine, and then concentrated under reduced pressure. The resulting residues were purified by silica gel column (ethyl acetate/hexane) to obtain the title compound (7 mg, 50%).

LCMS: m/z 280 [M+H]$^+$
HPLC retention time: 2.71 min (analysis condition Y)

Example 1137

Compound GT15-4

8-Methoxy-10,10-dimethyl-10H-11-oxa-4-aza-benzo[b]fluoren-5-one

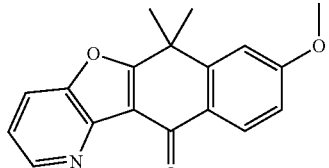

8-Methoxy-10,10-dimethyl-5,10-dihydro-11-oxa-4-aza-benzo[b]fluorene (Compound GT15-3, 22 mg) was dissolved in MeCN (0.26 ml) and water (0.13 ml), added with sodium chlorite (14 mg) and N-hydroxyphthalimide (2.6 mg), and the mixture was stirred at 40° C. for 1 hr. The reaction mixture was diluted with ethyl acetate. The organic layer was washed with saturated aqueous solution of sodium bicarbonate and saturated brine, and then concentrated under reduced pressure. The resulting residues were purified by silica gel column (ethyl acetate/hexane) to obtain the title compound (16 mg, 70%).

LCMS: m/z 294 [M+H]$^+$

HPLC retention time: 2.85 min (analysis condition Y)

Example 1138

Compound GT15-5

8-Hydroxy-10,10-dimethyl-10H-11-oxa-4-aza-benzo[b] fluoren-5-one

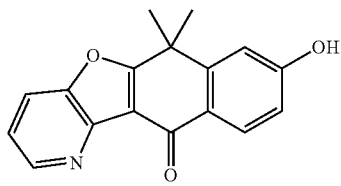 [SMILES: CC1(C)c2cc(O)ccc2C(=O)c2c1oc1cccnc21]

Mixture of 8-methoxy-10,10-dimethyl-10H-11-oxa-4-aza-benzo[b] fluoren-5-one (Compound GT15-4, 25 mg) and pyridine hydrochloric acid salt (492 mg) was stirred and heated at 178° C. overnight. The reaction mixture was cooled, and added with water. The mixture was neutralized with saturated aqueous solution of sodium bicarbonate and extracted with DCM. The organic layer was washed with saturated brine, and then concentrated under reduced pressure. The resulting residues were purified by silica gel column (DCM/MeOH) to obtain the title compound (13 mg, 54%).

LCMS: m/z 280 [M+H]$^+$

HPLC retention time: 2.30 min (analysis condition Y)

Example 1139

Compound GT15-6

8-[(4R,5R)-5-(Tert-butyl-dimethyl-silanyloxymethyl)-2,2-dimethyl-[1,3]dioxolan-4-yl methoxy]-10,10-dimethyl-10H-11-oxa-4-aza-benzo[b]fluoren-5-one

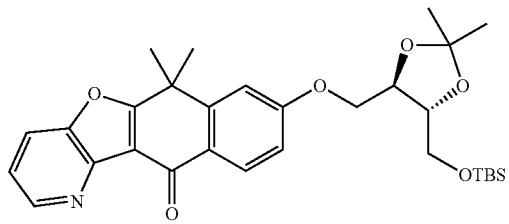 [SMILES: CC1(C)O[C@H](COc2ccc3c(c2)C(C)(C)c2oc4cccnc4c2C3=O)[C@@H](CO[Si](C)(C)C(C)(C)C)O1]

In the same manner as Compound A7-1, the title compound was synthesized from Compound GT15-5 and Compound T22-0 (29 mg, 50%).

LCMS: m/z 538 [M+H]$^+$

HPLC retention time: 3.64 min (analysis condition Y)

Example 1140

Compound GT15-7

10,10-Dimethyl-8-((2R,3R)-2,3,4-trihydroxy-butoxy)-10H-11-oxa-4-aza-benzo[b]fluoren-5-one

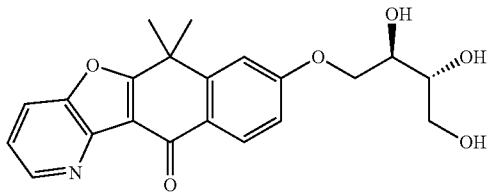 [SMILES: CC1(C)c2cc(OC[C@@H](O)[C@H](O)CO)ccc2C(=O)c2c1oc1cccnc21]

To the mixture of 8-[(4R,5R)-5-(tert-butyl-dimethyl-silanyloxymethyl)-2,2-dimethyl-[1,3]dioxolan-4-yl methoxy]-10,10-dimethyl-10H-11-oxa-4-aza-benzo[b] fluoren-5-one (Compound GT15-6, 27 mg), MeOH (0.1 ml) and THF (0.3 ml), 0.5 N sulfuric acid (0.1 ml) was added, and the mixture was stirred and heated at 55 to 60° C. for 4 hrs. The reaction mixture was neutralized with saturated aqueous solution of sodium bicarbonate. The resulting solid was filtered and washed with diethyl ether. The filtrate was extracted with the mixture solution of DCM and MeOH (DCM:MeOH=10:1). The organic layer was washed with saturated brine, and dried over magnesium sulfate. The filtered solid and the residues obtained after concentration under reduced pressure were combined and purified by silica gel column (DCM/MeOH) to obtain the title compound (5.4 mg, 28%).

LCMS: m/z 384 [M+H]$^+$

HPLC retention time: 2.02 min (analysis condition Y)

Example 1141

Compound GT15-8

7-Methoxy-3-(3-methoxymethoxy-pyridin-4-yl)-1,1-dimethyl-3,4-dihydro-1H-naphthalen-2-one

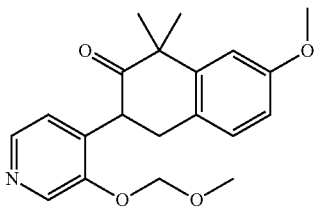 [SMILES: COCOc1cnccc1C1Cc2ccc(OC)cc2C(C)(C)C1=O]

To 7-methoxy-1,1-dimethyl-3,4-dihydro-1H-naphthalen-2-one (Compound A2, 924 mg), 4-iodo-3-methoxymethoxy-pyridine (1 g), sodium t-butoxide (906 mg), Pd$_2$dba$_3$ (173 mg) and S-Phos (185 mg), toluene (19 ml) was added, and the mixture was stirred and heated at 70° C. for 2 hrs under nitrogen atmosphere. The reaction mixture was diluted with ethyl acetate and filtered through Celite. The organic layer was washed with saturated aqueous solution of sodium bicarbonate and saturated brine, and then concentrated under reduced pressure. The resulting residues were purified by silica gel column (ethyl acetate/hexane) to obtain the title compound (610 mg, 47%).

LCMS: m/z 342 [M+H]$^+$

HPLC retention time: 2.60 min (analysis condition Y)

Example 1142

Compound GT15-9

3-(3-Hydroxy-pyridin-4-yl)-7-methoxy-1,1-dimethyl-3,4-dihydro-1H-naphthalen-2-one

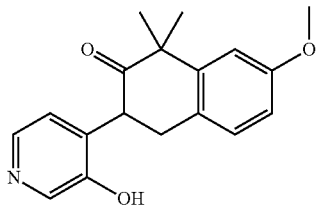 [SMILES: COc1ccc2c(c1)C(C)(C)C(=O)C(c1ccncc1O)C2]

Mixture of 7-methoxy-3-(3-methoxymethoxy-pyridin-4-yl)-1,1-dimethyl-3,4-dihydro-1H-naphthalen-2-one (Compound GT15-8, 430 mg) and 4 N hydrochloric acid dioxane solution (5 ml) was heated and stirred at room temperature for 1.5 hrs. The reaction mixture was neutralized with 2 N aqueous solution of sodium hydroxide. The resulting mixture was extracted with the mixture of DCM and MeOH (DCM:MeOH=9:1). The residues obtained after concentration under reduced pressure were purified by silica gel column (DCM/MeOH) to obtain the title compound (280 mg, 75%).

LCMS: m/z 298 [M+H]$^+$

HPLC retention time: 2.41 min (analysis condition Y)

Example 1143

Compound GT15-10

8-Methoxy-10,10-dimethyl-5,10-dihydro-11-oxa-2-aza-benzo[b]fluorene

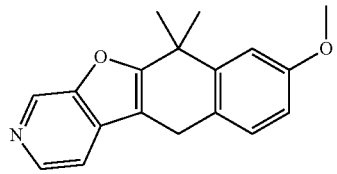 [SMILES: COc1ccc2c(c1)C(C)(C)c1oc3cnccc3c1C2]

Mixture of 3-(3-hydroxy-pyridin-4-yl)-7-methoxy-1,1-dimethyl-3,4-dihydro-1H-naphthalen-2-one (Compound GT15-9, 270 mg) and methanesulfonic acid (1 ml) was stirred and heated at 110° C. for 0.5 hrs. After cooling, the reaction mixture was neutralized with 2 N aqueous solution of sodium hydroxide. The resulting mixture was extracted with the mixture of DCM and MeOH (DCM:MeOH=9:1). The organic layer was concentrated under reduced pressure, and the resulting residues were purified by silica gel column (DCM/MeOH) to obtain the title compound (110 mg, 43%).

LCMS: m/z 280 [M+H]$^+$

HPLC retention time: 2.53 min (analysis condition Y)

Example 1144

Compound GT15-11

8-Methoxy-10,10-dimethyl-10H-11-oxa-2-aza-benzo[b]fluoren-5-one

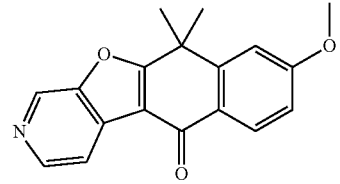 [SMILES: COc1ccc2c(c1)C(C)(C)c1oc3cnccc3c1C2=O]

8-Methoxy-10,10-dimethyl-5,10-dihydro-11-oxa-2-aza-benzo[b]fluorene (Compound GT15-10, 20 mg) was dissolved in acetonitrile (0.2 ml) and water (0.15 ml), added with sodium chlorite (16 mg) and N-hydroxyphthalimide (2.3 mg), and the mixture was stirred at 40° C. for 40 min. To the reaction mixture, ethyl acetate was added. The organic layer was washed with saturated aqueous solution of sodium bicarbonate and saturated brine, and then concentrated under reduced pressure. The resulting residues were purified by silica gel column (ethyl acetate/hexane) to obtain the title compound (12 mg, 57%).

LCMS: m/z 294 [M+H]$^+$

HPLC retention time: 2.51 min (analysis condition Y)

Example 1145

Compound GT15-12

8-Hydroxy-10,10-dimethyl-10H-11-oxa-2-aza-benzo[b]fluoren-5-one

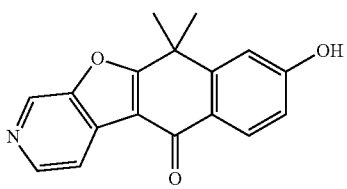 [SMILES: CC1(C)c2cc(O)ccc2C(=O)c2c1oc1cnccc21]

DCM (0.34 ml) solution of 8-methoxy-10,10-dimethyl-10H-11-oxa-2-aza-benzo[b]fluoren-5-one (Compound GT15-11, 10 mg) was cooled to −78° C., added with the DCM solution (0.17 ml) of 1.0 M BBr$_3$, and the mixture was stirred at room temperature overnight. To the reaction mixture, water and saturated aqueous solution of sodium bicarbonate were added, and the solid produced therefrom was filtered off. The filtrate was extracted with the mixture solution of DCM and MeOH (DCM:MeOH=9:1). The organic layer was washed with saturated brine. The filtered solid and the residues obtained after concentration under reduced pressure were combined to obtain the title compound (9.5 mg, 99%).

LCMS: m/z 280 [M+H]$^+$

HPLC retention time: 2.50 min (analysis condition Y)

Example 1146

Compound GT15-13

8-[(4R,5R)-5-(Tert-butyl-dimethyl-silanyloxymethyl)-2,2-dimethyl-[1,3]dioxolan-4-yl methoxy]-10,10-dimethyl-10H-11-oxa-2-aza-benzo[b]fluoren-5-one

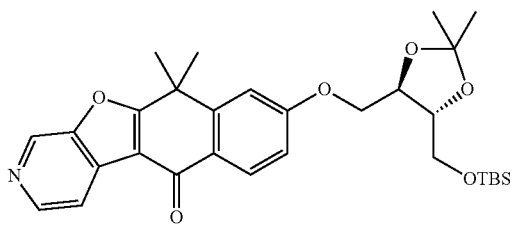 [SMILES: CC1(C)O[C@H](COc2ccc3c(c2)C(C)(C)c2oc4cnccc4c2C3=O)[C@@H](CO[Si](C)(C)C(C)(C)C)O1]

Under the same conditions as the method for synthesizing Compound A7-1, the title compound was prepared from Compound GT15-12 and Compound T22-0 (38 mg, 66%).

LCMS: m/z 538 [M+H]$^+$

HPLC retention time: 3.55 min (analysis condition Y)

Example 1147

Compound GT15-14

10,10-Dimethyl-8-((2R,3R)-2,3,4-trihydroxy-butoxy)-10H-11-oxa-2-aza-benzo[b]fluoren-5-one

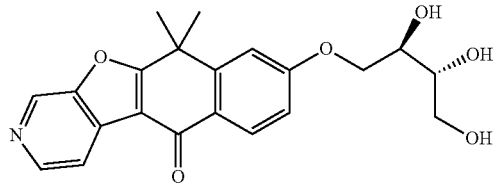 [SMILES: CC1(C)c2cc(OC[C@@H](O)[C@H](O)CO)ccc2C(=O)c2c1oc1cnccc21]

Under the same conditions as the method for synthesizing Compound GT15-7, the title compound was prepared from Compound GT15-13 (2.1 mg, 84%).

LCMS: m/z 384 [M+H]$^+$

HPLC retention time: 1.70 min (analysis condition Y)

Example 1148

Compound GT15-15

3-Bromo-2-(4-methoxy-benzyloxy)-pyridine

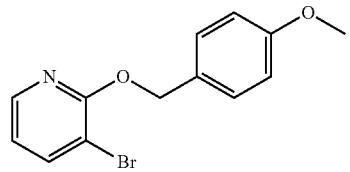 [SMILES: COc1ccc(COc2ncccc2Br)cc1]

Under the same conditions as the method for synthesizing Compound G15-1, the title compound was prepared from 3-bromo-pyridin-2-ol (740 mg, 88%).

LCMS: m/z 295 [M+H]$^+$

HPLC retention time: 2.86 min (analysis condition Y)

Example 1149

Compound GT15-16

7-Methoxy-3-[2-(4-methoxy-benzyloxy)-pyridin-3-yl]-1,1-dimethyl-3,4-dihydro-1H-naphthalen-2-one

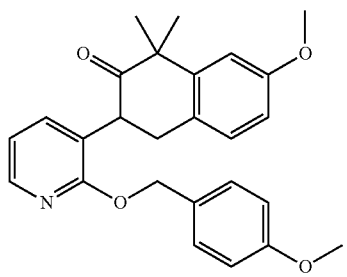 [SMILES: COc1ccc(COc2ncccc2C2Cc3ccc(OC)cc3C(C)(C)C2=O)cc1]

To 7-methoxy-1,1-dimethyl-3,4-dihydro-1H-naphthalen-2-one (Compound A2, 845 mg), 3-bromo-2-(4-methoxy-benzyloxy)-pyridine (Compound GT15-15, 1.46 g), sodium t-butoxide (597 mg), palladium acetate (18.6 mg) and tri-tert-butylphosphine tetrafluoroboric acid (21 mg), toluene (10 ml) and THF (2 ml) were added and the mixture was stirred and heated at 90° C. for 2.5 hrs under nitrogen atmosphere. After cooling, the reaction mixture was added with saturated aqueous solution of ammonium chloride, and then extracted with ethyl acetate. The organic layer was washed with saturated brine, and the residues obtained after concentration under reduced pressure were purified by silica gel column (ethyl acetate/hexane) to obtain the title compound (140 mg, 8%).

LCMS: m/z 419 [M+H]$^+$

HPLC retention time: 3.50 min (analysis condition Y)

Example 1150

Compound GT15-17

8-Methoxy-10,10-dimethyl-10H-11-oxa-1-aza-benzo[b]fluoren-5-one

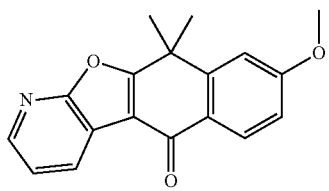 [SMILES: COc1ccc2c(c1)C(C)(C)c1oc3ncccc3c1C2=O]

Under the same conditions as the method for synthesizing Compound GT15-3, the title compound was prepared from Compound GT15-16 (49 mg, 52%).

LCMS: m/z 294 [M+H]$^+$

HPLC retention time: 3.39 min (analysis condition Y)

Example 1151

Compound GT15-18

8-Hydroxy-10,10-dimethyl-10H-11-oxa-1-aza-benzo[b]fluoren-5-one

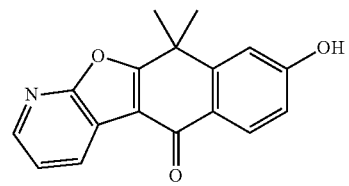 [SMILES: CC1(C)c2cc(O)ccc2C(=O)c2c1oc1ncccc21]

Under the same conditions as the method for synthesizing Compound GT15-5, the title compound was prepared from Compound GT15-17 (6.5 mg, 51%).
LCMS: m/z 280 [M+H]$^+$
HPLC retention time: 3.10 min (analysis condition Y)

Example 1152

Compound GT15-19

8-[(4R,5R)-5-(Tert-butyl-dimethyl-silanyloxymethyl)-2,2-dimethyl-[1,3]dioxolan-4-yl methoxy]-10,10-dimethyl-10H-11-oxa-1-aza-benzo[b]fluoren-5-one

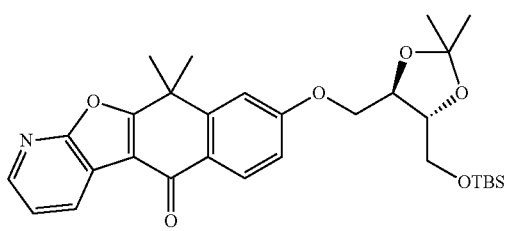 [SMILES: CC1(C)O[C@H](COc2ccc3c(c2)C(C)(C)c2oc4ncccc4c2C3=O)[C@@H](CO[Si](C)(C)C(C)(C)C)O1]

Under the same conditions as the method for synthesizing Compound A7-1, the title compound was prepared from Compound GT15-18 and Compound T22-0 (4.5 mg, 11%).
LCMS: m/z 538 [M+H]$^+$
HPLC retention time: 3.88 min (analysis condition Y)

Example 1153

Compound GT15-20

10,10-Dimethyl-8-((2R,3R)-2,3,4-trihydroxy-butoxy)-10H-11-oxa-1-aza-benzo[b]fluoren-5-one

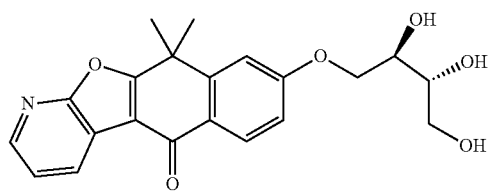 [SMILES: CC1(C)c2cc(OC[C@@H](O)[C@H](O)CO)ccc2C(=O)c2c1oc1ncccc21]

Under the same conditions as the method for synthesizing Compound GT15-7, the title compound was prepared from Compound GT15-19 (7.9 mg, 51%).

LCMS: m/z 384 [M+H]$^+$
HPLC retention time: 2.57 min (analysis condition Y)

Example 1154

Compound GT15-21

8-Methoxy-10,10-dimethyl-5,10-dihydro-11-oxa-3-aza-benzo[b]fluorene

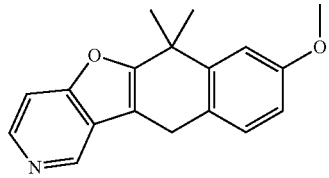 [SMILES: COc1ccc2c(c1)C(C)(C)c1oc3ccncc3c1C2]

To 7-methoxy-1,1-dimethyl-3,4-dihydro-1H-naphthalen-2-one (Compound A2, 2.5 g), 3-bromo-4-chloro-pyridine (2 g), sodium t-butoxide (3 g), Pd$_2$dba$_3$ (476 mg), and S-Phos (512 mg), toluene (20 ml) was added, and the mixture was stirred and heated at 100° C. overnight under nitrogen atmosphere. After cooling, the reaction mixture was diluted with ethyl acetate and filtered through Celite. The organic layer was washed with saturated aqueous solution of sodium bicarbonate and saturated brine. Thereafter, the organic layer was dried over sodium sulfate. The residues obtained after concentration under reduced pressure were purified by silica gel column (ethyl acetate/hexane) to obtain the title compound (112 mg, 4%).
LCMS: m/z 280 [M+H]$^+$
HPLC retention time: 2.46 min (analysis condition Y)

Example 1155

Compound GT15-22

8-Methoxy-10,10-dimethyl-10H-11-oxa-3-aza-benzo[b]fluoren-5-one

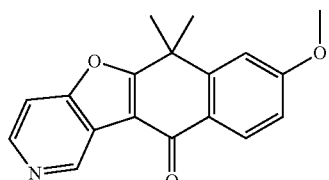

Under the same conditions as the method for synthesizing Compound GT15-3, the title compound was prepared from Compound GT15-21 (49 mg, 52%).
LCMS: m/z 294 [M+H]$^+$
HPLC retention time: 2.30 min (analysis condition Y)

Example 1156

Compound GT15-23

8-Hydroxy-10,10-dimethyl-10H-11-oxa-3-aza-benzo[b]fluoren-5-one

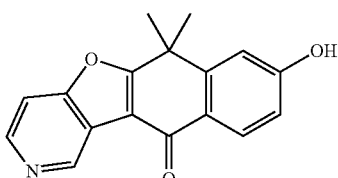

Under the same conditions as the method for synthesizing Compound GT15-12, the title compound was prepared from Compound GT15-22 (110 mg, 77%).
LCMS: m/z 280 [M+H]+
HPLC retention time: 1.95 min (analysis condition Y)

Example 1157

Compound GT15-24

8-[(4R,5R)-5-(Tert-butyl-dimethyl-silanyloxymethyl)-2,2-dimethyl-[1,3]dioxolan-4-yl methoxy]-10,10-dimethyl-10H-11-oxa-3-aza-benzo[b]fluoren-5-one

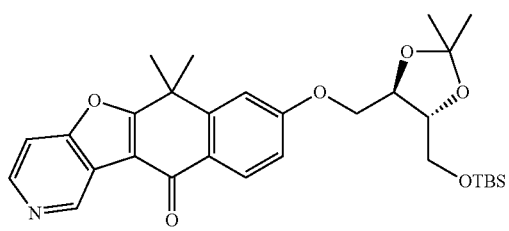 [SMILES: CC1(C)O[C@H](COc2ccc3c(c2)C(C)(C)c2oc4ccncc4c2C3=O)[C@@H](CO[Si](C)(C)C(C)(C)C)O1]

Under the same conditions as the method for synthesizing Compound A7-1, the title compound was prepared from Compound GT15-23 and Compound T22-0 (38 mg, 49%).
LCMS: m/z 538 [M+H]+
HPLC retention time: 3.40 min (analysis condition Y)

Example 1158

Compound GT15-25

10,10-Dimethyl-8-((2R,3R)-2,3,4-trihydroxy-butoxy)-10H-11-oxa-3-aza-benzo[b]fluoren-5-one

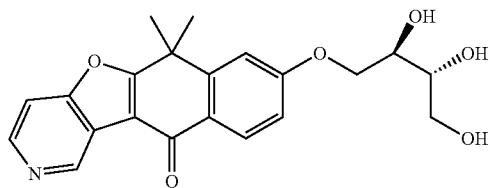 [SMILES: CC1(C)c2cc(OC[C@@H](O)[C@H](O)CO)ccc2C(=O)c2c1oc1ccncc21]

Under the same conditions as the method for synthesizing Compound GT15-7, the title compound was prepared from Compound GT15-24 (17 mg, 72%).
LCMS: m/z 384 [M+H]+
HPLC retention time: 1.48 min (analysis condition Y)

Example 1159

Compound GT16-1

2-(2-Bromo-4-methoxy-phenyl)-propan-2-ol

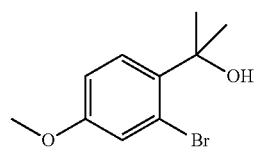

To the mixture of 1-(2-bromo-4-methoxyphenyl)-ethanone (300 mg) dissolved in THF solution (3 ml), MeMgBr (3 M THF solution, 0.52 ml) was added at 0° C. under nitrogen atmosphere. Then, the mixture was stirred at room temperature for 6 hrs. The reaction mixture was added with saturated aqueous solution of ammonium chloride and extracted with ethyl acetate. The organic layer was washed with saturated brine, and the residues obtained after concentration under reduced pressure were purified by silica gel column (ethyl acetate/hexane) to obtain the title compound (220 mg, 69%).
$^1$H-NMR (CDCL$_3$) δ: 7.55 (1H, d), 7.14 (1H, d), 6.83 (1H, dd), 3.79 (3H, s), 2.72 (1H, s), 1.73 (6H, s)

Example 1160

Compound GT16-2

2-[1-(2-Bromo-4-methoxyphenyl)-1-methylethyl]benzofuran

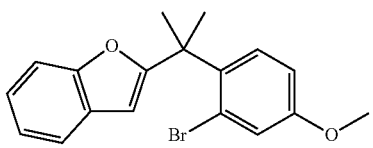 [SMILES: COc1ccc(C(C)(C)c2cc3ccccc3o2)c(Br)c1]

Mixture comprising 2-(2-bromo-4-methoxyphenyl)-propan-2-ol (100 mg), 2,3-benzofuran (0.19 ml) and polyphosphoric acid (1 g) was stirred and heated at 90° C. for 30 min. The reaction mixture was added with water and extracted with DCM. The residues obtained after concentration under reduced pressure were purified by silica gel column (DCM/hexane) to obtain the title compound (143 mg, 51%).
$^1$H-NMR (CDCL$_3$) δ: 7.4-7.5 (1H, m), 7.3-7.4 (2H, m), 7.1-7.25 (3H, m), 6.87 (1H, dd), 6.42 (1H, s) 3.79 (3H, s), 1.84 (6H, s)

Example 1161

Compound GT16-3

2-(1-Benzofuran-2-yl-1-methyl-ethyl)-5-methoxy-benzoic acid

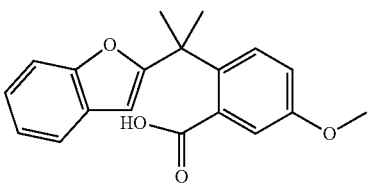 [SMILES: COc1ccc(C(C)(C)c2cc3ccccc3o2)c(C(=O)O)c1]

To the mixture comprising 2-[1-(2-bromo-4-methoxyphenyl)-1-methylethyl]benzofuran (140 mg) and THF (2 ml), n-butyl lithium (2.5 M solution, 0.17 ml) was added at −78° C. under nitrogen atmosphere. The mixture was stirred for 20 min. The resulting reaction mixture was flushed with carbon dioxide gas for 15 min. Then, the reaction mixture was added with saturated aqueous solution of ammonium chloride and extracted with ethyl acetate. The organic layer was washed with water and saturated brine, and the residues obtained after concentration under reduced pressure were purified by silica gel column (DCM/MeOH) to obtain the title compound (68 mg, 54%).
LCMS: m/z 311 [M+H]+
HPLC retention time: 2.92 min (analysis condition Y)

Example 1162

Compound GT16-4

9-Methoxy-6,6-dimethyl-6H-benzo[b]naphtho[2,3-d]furan-11-one

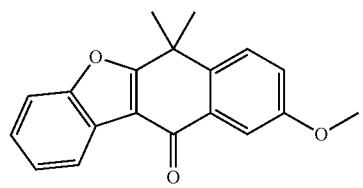 [SMILES: COc1ccc2c(c1)C(=O)c1c(oc3ccccc13)C2(C)C]

To the DCM solution (1 ml) of 2-(1-benzofuran-2-yl-1-methylethyl)-5-methoxy benzoic acid (63 mg), trifluoroacetic anhydride (0.03 ml) was added at room temperature under nitrogen atmosphere. The mixture was stirred for 30 min. The reaction mixture was then added with water and extracted with DCM. The organic layer was dried over sodium sulfate. The residues obtained after concentration under reduced pressure were purified by silica gel column (DCM) to obtain the title compound (50 mg, 84%).

LCMS: m/z 293 [M+H]$^+$
HPLC retention time: 3.49 min (analysis condition Y)

Example 1163

Compound GT16-5

9-Hydroxy-6,6-dimethyl-6H-benzo[b]naphtho[2,3-d]furan-11-one

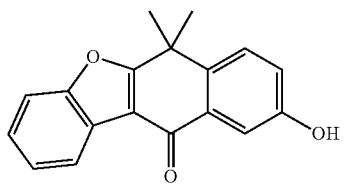 [SMILES: CC1(C)c2ccc(O)cc2C(=O)c2c1oc1ccccc21]

Under the same conditions as the method for synthesizing Compound A6, the title compound was prepared from Compound GT16-4.

LCMS: m/z 279 [M+H]$^+$
HPLC retention time: 3.05 min (analysis condition Y)

Example 1164

Compound GT16-6

9-(2-Diethylamino-ethoxy)-6,6-dimethyl-6H-benzo[b]naphtho[2,3-d]furan-11-one

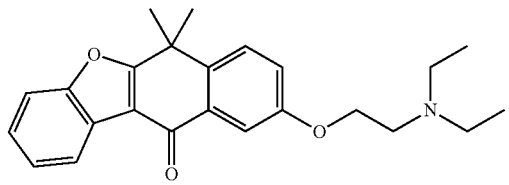 [SMILES: CCN(CC)CCOc1ccc2c(c1)C(=O)c1c(oc3ccccc13)C2(C)C]

Under the same conditions as the method for synthesizing Compound A7-17, the title compound was prepared from Compound GT16-5.

LCMS: m/z 378 [M+H]$^+$
HPLC retention time: 2.41 min (analysis condition Y)

Example 1165

Compound GT16-7

9-((S)-2,2-Dimethyl-[1,3]dioxolan-4-ylmethoxy)-6,6-dimethyl-6H-benzo[b]naphtho[2,3-d]furan-11-one

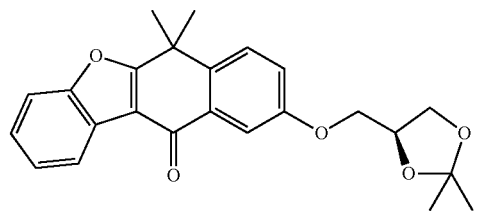 [SMILES: CC1(C)OC[C@H](COc2ccc3c(c2)C(=O)c2c(oc4ccccc24)C3(C)C)O1]

Under the same conditions as the method for synthesizing Compound A7-17, the title compound was prepared from Compound GT16-5 and toluene-4-sulfonic acid (R)-2,2-dimethyl-[1,3]dioxolan-4-yl methyl ester.

LCMS: m/z 393 [M+H]$^+$
HPLC retention time: 3.22 min (analysis condition Y)

Example 1166

Compound GT16-8

9-((R)-2,3-Dihydroxy-propoxy)-6,6-dimethyl-6H-benzo[b]naphtho[2,3-d]furan-11-one

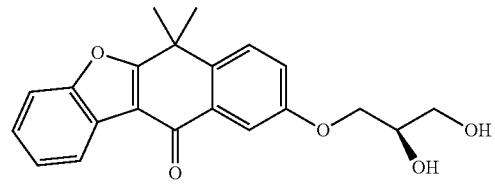 [SMILES: CC1(C)c2ccc(OC[C@H](O)CO)cc2C(=O)c2c1oc1ccccc21]

Under the same conditions as the method for synthesizing Compound A7-14-2, the title compound was prepared from Compound GT16-7.

LCMS: m/z 353 [M+H]$^+$
HPLC retention time: 2.83 min (analysis condition Y)

Example 1167

Compound GT16-9

3-(6,6-Dimethyl-11-oxo-6,11-dihydro-benzo[b]naphtho[2,3-d]furan-9-yl)-benzoic acid

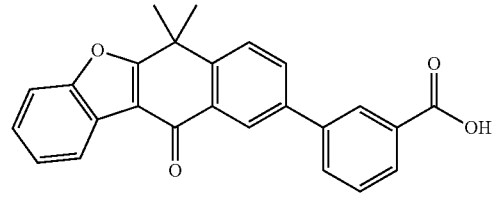 [SMILES: CC1(C)c2ccc(-c3cccc(C(=O)O)c3)cc2C(=O)c2c1oc1ccccc21]

In the same manner as Compound GT9-2, the title compound was synthesized from Compound GT16-5.

LCMS: m/z 383 [M+H]$^+$
HPLC retention time: 7.11 min (analysis condition H)

Example 1168

Compound GT16-10

9-(4-Hydroxymethyl-phenyl)-6,6-dimethyl-6H-benzo[b]naphtho[2,3-d]furan-11-one

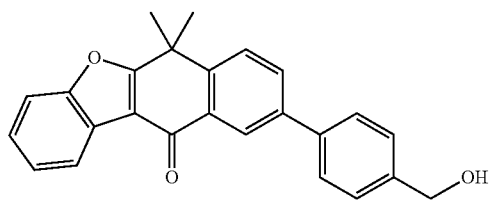 [SMILES: CC1(C)c2ccc(-c3ccc(CO)cc3)cc2C(=O)c2c1oc1ccccc21]

In the same manner as Compound GT9-2, the title compound was synthesized from Compound GT16-5.

LCMS: m/z 369 [M+H]$^+$
HPLC retention time: 6.97 min (analysis condition H)

The compounds described in the following Table 39 were synthesized according to the method shown below. Specifically, Compound GT17-1 was prepared from 8-methoxy-1,1-dimethyl-3,4-dihydro-1H naphthalen-2-one and bromophenol by following the method that is used for the preparation of Compound Z10, Z11 and Z12. Compound GT17-1 was demethylated according to the method used for the preparation of Compound A6, and as a result 7-hydroxy-6,6-dimethyl-6H-benzo[b]naphtho[2,3-d]furan-11-one was prepared. The resulting hydroxy compound was subjected to the alkylation according to the method used for the preparation of A7-1, or Mitsunobu reaction used for the preparation of Compound A7-17 for introducing a corresponding side chain or a synthetic equivalent thereof. Thereafter, if necessary, functional group modification was carried out to prepare Compound GT17-2 and Compound GT17-3.

TABLE 39

| Example No. | Comp. No. | Structure | Compound Name | HPLC Condition | Retention Time | m/z |
|---|---|---|---|---|---|---|
| 1169 | GT17-1 | 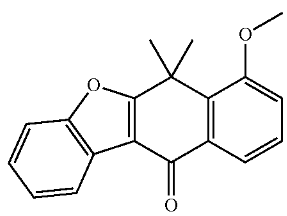 [SMILES: COc1cccc2c1C(C)(C)c1oc3ccccc3c1C2=O] | 7-Methoxy-6,6-dimethyl-6H-benzo[b]naphtho[2,3-d]furan-11-one | Y | 13.42 | 293.0 |
| 1170 | GT17-2 | 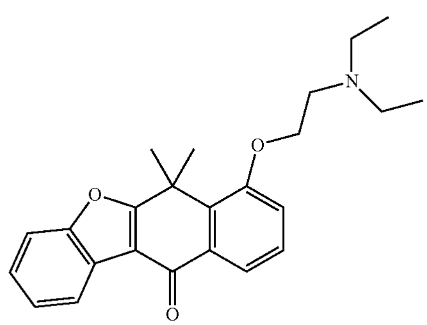 [SMILES: CCN(CC)CCOc1cccc2c1C(C)(C)c1oc3ccccc3c1C2=O] | 7-(2-Diethylamino-ethoxy)-6,6-dimethyl-6H-benzo[b]naphtho[2,3-d]furan-11-one | Y | 9.92 | 378.0 |
| 1171 | GT17-3 | Chiral | 7-(((R)-2,3-Dihydroxy-propoxy)-6,6-dimethyl-6H-benzo[b]naphtho[2,3-d]furan-11-one | Y | 11.68 | 353.0 |

The compounds described in the following Table 40 were synthesized according to the method shown below.

By using the method used for the preparation of Compound Z10, Z11 and Z12, Compound GT18-1 was prepared from Compound M1 and bromophenol. Further, according to the method used for the preparation of Compound A6, Compound GT18-1 was demethylated to prepare 8-hydroxy-11H-spiro[benzo[b]naphtho[2,3-d]furan-6,1'-cyclopentan]-11-one, which was then introduced with a side chain based on the alkylation that is used for the preparation of Compound A7-1. As a result, Compound GT18-2 was prepared.

The following spiro compounds were prepared from 7-methoxy-3,4-dihydro-1H-naphthalen-2-one and corresponding dibromide in the same manner as above.

TABLE 40

| Example No. | Comp. No. | Structure | Compound Name | HPLC Condition | Retention Time | m/z |
|---|---|---|---|---|---|---|
| 1172 | GT18-1 | 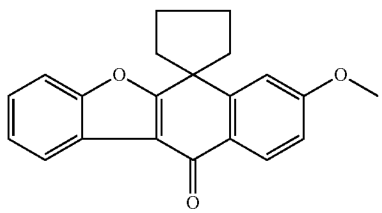 [SMILES: COc1ccc2c(c1)C1(CCCC1)c1oc3ccccc3c1C2=O] | 8-methoxy-11H-spiro[benzo[b]naphtho[2,3-d]furan-6,1'-cyclopentane]-11-one | Y | 10.00 | 319.0 |
| 1173 | GT18-2 | 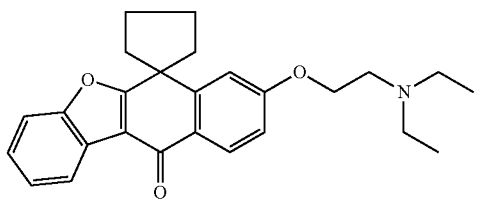 [SMILES: CCN(CC)CCOc1ccc2c(c1)C1(CCCC1)c1oc3ccccc3c1C2=O] | 8-(2-diethylamino-ethoxy)-11H-spiro[benzo[b]naphtho[2,3-d]furan-6,1'-cyclopentane]-11-one | C | 2.19 | 404.0 |
| 1174 | GT18-3 | 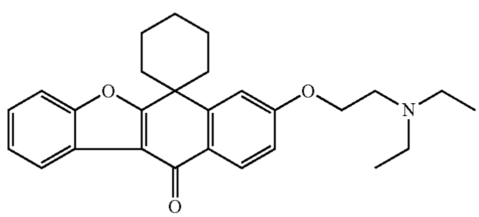 [SMILES: CCN(CC)CCOc1ccc2c(c1)C1(CCCCC1)c1oc3ccccc3c1C2=O] | 8-(2-diethylamino-ethoxy)-11H-spiro[benzo[b]naphtho[2,3-d]furan-6,1'-cyclohexane]-11-one | C | 3.28 | 418.2 |
| 1175 | GT18-4 | 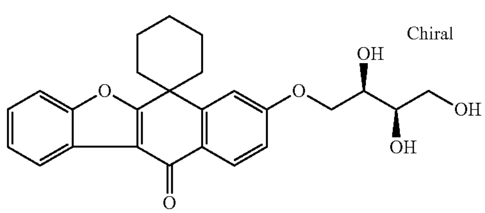 [SMILES: O=C1c2ccc(OC[C@@H](O)[C@H](O)CO)cc2C2(CCCCC2)c2oc3ccccc3c21] | 8-((2R,3R)-2,3,4-trihydroxybutoxy)-11H-spiro[benzo[b]naphtho[2,3-d]furan-6,1'-cyclohexane]-11-one | A | 2.26 | 423.2 |
| 1176 | GT18-5 | 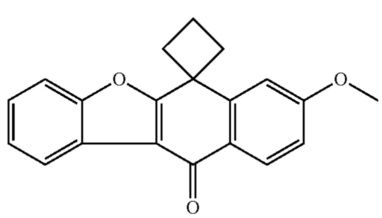 [SMILES: COc1ccc2c(c1)C1(CCC1)c1oc3ccccc3c1C2=O] | 8-methoxy-11H-spiro[benzo[b]naphtho[2,3-d]furan-6,1'-cyclobutane]-11-one | Y | 9.00 | 305.0 |
| 1177 | GT18-6 | 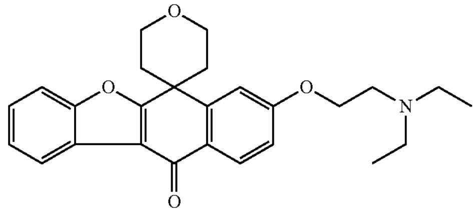 [SMILES: CCN(CC)CCOc1ccc2c(c1)C1(CCOCC1)c1oc3ccccc3c1C2=O] | 8-(2-diethylamino-ethoxy)-2',3',5',6'-tetrahydro-11H-spiro[benzo[b]naphtho[2,3-d]furan-6,4'-pyran]-11-one | B | 4.05 | 420.3 |

Example 1178

Compound GT19-1

8-(2-Diethylamino-ethoxy)-6,6-dimethyl-3-trifluoromethyl-6H-benzo[B]naphtho[2,3-d]furan-11-one

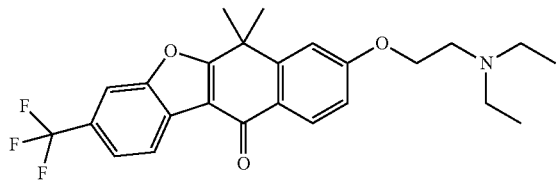 [SMILES: CCN(CC)CCOc1ccc2c(c1)C(C)(C)c1oc3cc(C(F)(F)F)ccc3c1C2=O]

According to the method described before, the preparation was carried out by using 7-methoxy-1,1-dimethyl-3,4-dihydro-1H naphthalen-2-one and 2-bromo-5-trifluorophenol.

LCMS: m/z 446 [M+H]$^+$

HPLC retention time: 3.25 min (analysis condition C)

Example 1179

Compound GT19-2

8-(2-Diethylamino-ethoxy)-6,6-dimethyl-3-phenyl-6H-benzo[b]naphtho[2,3-d]furan-11-one

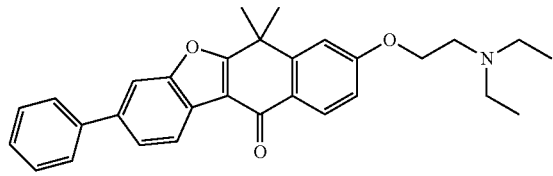 [SMILES: CCN(CC)CCOc1ccc2c(c1)C(C)(C)c1oc3cc(-c4ccccc4)ccc3c1C2=O]

By carrying out Suzuki coupling of Compound GT23-5 and a corresponding boronic acid reagent based on the method that is used for the preparation of Compound GT9-2, the title compound was prepared.

LCMS: m/z 454 [M+H]$^+$

HPLC retention time: 2.67 min (analysis condition F)

Example 1180

Compound GT20-1

8-Hydroxy-6,6-dimethyl-3-(2-phenyl-ethanesulfonyl)-5,6-dihydro-benzo[b]carbazole-11-one

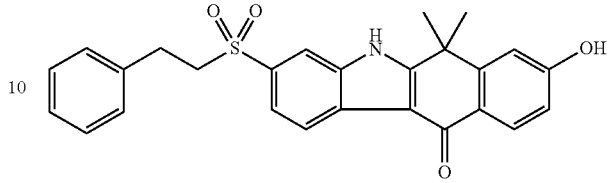

3-Bromo-8-hydroxy-6,6-dimethyl-5,6-dihydro-benzo[b]carbazol-11-one (72.2 mg, 0.203 mmol), 2-phenylethanethiol (0.0297 ml, 0.221 mmol), Pd$_2$dba$_3$ (9.3 mg, 0.0102 mmol), Xantphos (11.6 mg, 0.020 mmol) and ethyl diisopropylamine (0.068 ml, 0.40 mmol) were dissolved in dioxane (0.6 ml), and the mixture was stirred at 110° C. for 16 hrs under nitrogen atmosphere. Water and ethyl acetate were added to the mixture to give a suspension, which was then filtered. The organic layer was washed with water and saturated brine, and then concentrated under reduced pressure. The resulting residues were purified by silica gel column (ethyl acetate/hexane). The resulting residues were dissolved in THF (4 ml), and the supernatant liquid (2 ml) was taken and added with water (1 ml) and OXONE (99 mg). The resulting mixture was stirred at room temperature overnight. The reaction solution was partitioned between water and ethyl acetate. The organic layer was washed with brine, and then concentrated under reduced pressure. The resulting residues were purified by silica gel column (ethyl acetate/hexane) to obtain the title compound (37.1 mg).

LCMS: m/z 446 [M+H]$^+$

HPLC retention time: 2.51 min (analysis condition F)

Example 1181

Compound GT20-2

6,6-Dimethyl-3-(2-phenyl-ethanesulfonyl)-8-((2R,3R)-2,3,4-trihydroxy-butoxy)-5,6-dihydro-benzo[b]carbazol-11-one and

Compound GT20-3

8-Isopropoxy-6,6-dimethyl-3-(2-phenyl-ethanesulfonyl)-5,6-dihydro-benzo[b]carbazol-11-one

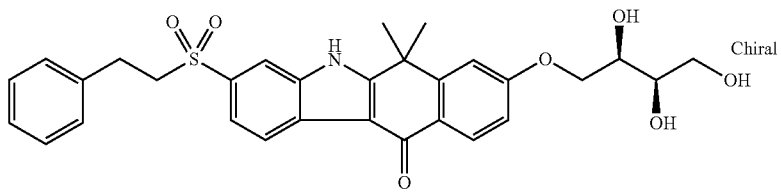

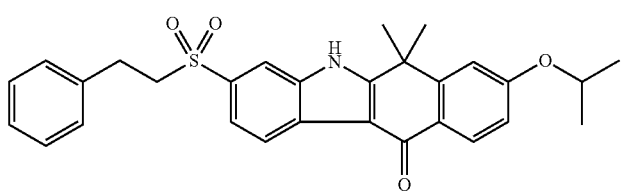

8-Hydroxy-6,6-dimethyl-3-(2-phenyl-ethanesulfonyl)-5,6-dihydro-benzo[b]carbazol-11-one (30 mg, 0.0673 mmol), [(4R,5R)-5-(tert-butyl-dimethyl-silanyloxymethyl)-2,2-dimethyl-[1,3]dioxolan-4-yl]methanol (22.3 mg, 0.0808 mmol), and PPh₃ (23 mg, 0.0875 mmol) were dissolved in THF (0.5 ml), added with DIAD (0.0169 ml, 0.0808 mmol), and the mixture was stirred at 50° C. overnight. After cooling, the reaction solution was filtered and concentrated under reduced pressure. The resulting residues were purified by silica gel column (ethyl acetate/hexane). The resulting residues were dissolved in THF (0.4 ml) and water (0.13 ml), added with camphor sulfonic acid (28.1 mg, 0.121 mmol), and then subjected to microwave irradiation at 80° C. for 15 min under nitrogen atmosphere. Ethyl acetate was added to the resultant. The organic layer was washed with saturated aqueous solution of sodium hydrocarbonate and saturated brine, and then concentrated under reduced pressure. The resulting residues were purified by thin layer chromatography (MeOH/DCM) to obtain Compound GT20-2 (10.5 mg) and Compound GT20-3 (2.4 mg).

Compound GT20-2

LCMS: m/z 550 [M+H]⁺
HPLC retention time: 2.20 min (analysis condition F)

Compound GT20-3

LCMS: m/z 488 [M+H]⁺
HPLC retention time: 3.13 min (analysis condition F)

Example 1182

Compound GT20-4

3-Methanesulfonyl-6,6-dimethyl-8-((2R,3R)-2,3,4-trihydroxy-butoxy)-5,6-dihydro-benzo[b]carbazol-11-one

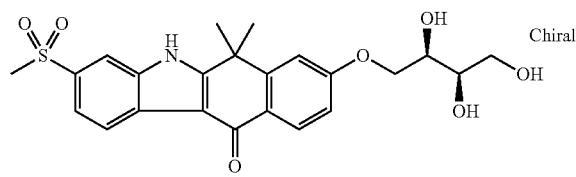 [SMILES: CC1(C)c2cc(OC[C@@H](O)[C@H](O)CO)ccc2C(=O)c2c1[nH]c1cc(S(C)(=O)=O)ccc21]

The DMA solution (0.6 ml) comprising Compound GT23-2 (59.6 mg, 0.167 mmol), sodium methanethiolate (77 mg, 1.10 mmol), Pd₂dba₃ (23.7 mg, 0.0259 mmol) and Xantphos (29.7 mg, 0.0513 mmol) was subjected to microwave irradiation at 180° C. for 30 min under nitrogen atmosphere. The reaction solution was partitioned between aqueous solution of potassium dihydrophosphoric acid and ethyl acetate. The organic layer was washed with saturated brine, and then concentrated under reduced pressure. The resulting residues were purified by silica gel column (ethyl acetate/hexane and MeOH/DCM). The resulting solids were dissolved in THF (1 ml) and water (0.5 ml), and then added with OXONE (101.4 mg). The resulting mixture was stirred at room temperature for 2 hrs. The reaction solution was partitioned between water and ethyl acetate. The organic layer was washed with saturated brine, and then concentrated under reduced pressure. The resulting residues were suspended and washed with MTBE. The resulting solid was dissolved in THF (0.4 ml), and added with PPh₃ (37 mg, 0.141 mmol), [(4R,5R)-5-(tert-butyl-dimethyl-silanyloxymethyl)-2,2-dimethyl-[1,3]dioxolan-4-yl]-methanol (39.0 mg, 0.141 mmol) and DEAD (2.2 M toluene solution, 0.064 ml, 0.141 mmol), and the mixture was stirred at 40° C. for 4 hrs under nitrogen atmosphere. The reaction solution was partitioned between water and ethyl acetate. The organic layer was washed with saturated brine, and then concentrated under reduced pressure. The resulting residues were purified by silica gel column (MeOH/DCM). Thus-obtained product was dissolved in THF (0.25 ml) and MeOH (0.05 ml), added with 0.5 M sulfuric acid (0.1 ml), and the mixture was stirred at 60° C. for 5 hrs. After cooling, the mixture was added with diethyl ether and sodium hydrocarbonate (13 mg, 0.15 mmol). The separated aqueous layer was filtered, concentrated under reduced pressure, and suspended and purified with MeOH to obtain the title compound as a white solid (10.4 mg, 14%).

LCMS: m/z 460 [M+H]⁺
HPLC retention time: 1.71 min (analysis condition F)

Example 1183

Compound GT20-5

8-((R)-2,3-Dihydroxy-propoxy)-6,6-dimethyl-3-methylsulfanyl-5,6-dihydro-benzo[b]carbazol-11-one

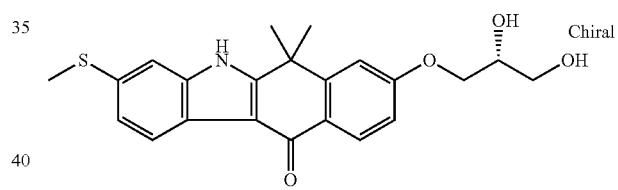

3-Bromo-8-((S)-2,2-dimethyl-[1,3]dioxolan-4-yl methoxy)-6,6-dimethyl-5,6-dihydro-benzo[b]carbazol-11-one (47.3 mg, 0.101 mmol), sodium methanethiolate (34.6 mg, 0.493 mmol), Pd₂(dba)₃ (13.1 mg, 0.0413 mmol), and Xantphos (17.9 mg, 0.0309 mmol) were dissolved in DMA (0.5 ml) and subjected to microwave irradiation at 200° C. for 30 min under nitrogen atmosphere. The resultant was partitioned between aqueous solution of potassium dihydrophosphoric acid and ethyl acetate. The organic layer was washed with saturated brine, and then concentrated under reduced pressure. The resulting residues were purified by thin layer chromatography (ethyl acetate/DCM). The resulting solid was dissolved in THF (0.23 ml) and MeOH (0.06 ml), and then added with 0.5 M sulfuric acid (0.12 ml). The resulting mixture was stirred at 60° C. for 2 hrs. The reaction solution was diluted with diethyl ether and neutralized with sodium hydrocarbonate (15.5 mg, 0.185 mmol). Thereafter, the solution was partitioned between brine and ethyl acetate. The organic layer was concentrated under reduced pressure. The resulting residues were added with diethyl ether. The precipitated solid was filtered to obtain the title compound as a white solid (15.8 mg, 39%).

LCMS: m/z 398 [M+H]⁺
HPLC retention time: 4.46 min (analysis condition H)

Example 1184

Compound GT20-5

8-((R)-2,3-Dihydroxy-propoxy)-6,6-dimethyl-3-thiazol-2-yl-5,6-dihydro-benzo[b]carbazol-11-one

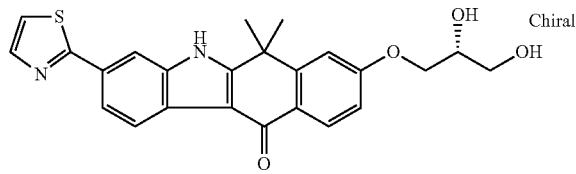 [SMILES: CC1(C)c2cc(OC[C@H](O)CO)ccc2C(=O)c2c1[nH]c1cc(-c3nccs3)ccc21]

3-Bromo-8-((S)-2,2-dimethyl-[1,3]dioxolan-4-yl-methoxy)-6,6-dimethyl-5,6-dihydrobenzo[b]carbazol-11-one (47 mg, 0.10 mmol), bis(pinacolate)diborone (33 mg, 0.13 mmol), Pd (dppf)$_2$Cl$_2$.DCM (8.2 mg, 0.010 mmol) and potassium acetate (294 mg, 0.3 mmol) were dissolved in dioxane (0.6 ml), and the mixture was stirred at 100° C. overnight under nitrogen atmosphere. The resultant was partitioned between aqueous solution of potassium dihydrophosphoric acid and ethyl acetate. The organic layer was washed with saturated brine, and then concentrated under reduced pressure. The resulting residues were purified by silica gel column (ethyl acetate/DCM) to obtain 8-((S)-2,2-dimethyl-[1,3]dioxolan-4-yl methoxy)-6,6-dimethyl-3-(4,4,5,5-tetramethyl-[1,3,2]dioxaborolan-2-yl)-5,6-dihydro-benzo[b]carbazol-11-one (30.2 mg). The product (11 mg) was dissolved in DMA (0.4 ml), added with 2-bromothiazole (0.0038 ml, 0.0428 mmol), Pd (PPh$_3$)$_4$ (5.3 mg, 0.00459 mmol), potassium phosphate (27.4 mg, 0.129 mmol) and water (0.1 ml), and the mixture was subjected to microwave irradiation at 140° C. for 7 min under nitrogen atmosphere. The resultant was partitioned between aqueous solution of potassium dihydrophosphoric acid and ethyl acetate. The organic layer was washed with saturated brine, and then concentrated under reduced pressure. The resulting residues were purified by thin layer chromatography (MeOH/DCM). The resulting solid was dissolved in MeOH (1 ml), and then added with 1 N HCl (3 drops). The resulting mixture was stirred at 60° C. for 2 hrs. The reaction solution was concentrated under reduced pressure, and the residues obtained therefrom were suspended and washed with DCM/hexane (2/1) followed by drying to obtain the title compound as a yellow solid (8.7 mg).

LCMS: m/z 435 [M+H]$^+$

HPLC retention time: 1.76 min (analysis condition A)

The compounds described in the following Table 41 were also synthesized in the same manner.

TABLE 41

| Example No. | Comp. No. | Structure | Compound Name | HPLC Condition | Retention Time | m/z |
|---|---|---|---|---|---|---|
| 1185 | GT20-6 | 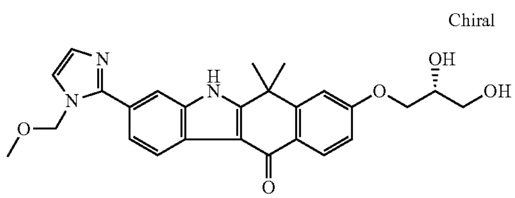 [SMILES: COCn1ccnc1-c1ccc2c3c([nH]c2c1)C(C)(C)c1cc(OC[C@H](O)CO)ccc1C3=O] | 8-((R)-2,3-Dihydroxy-propoxy)-3-(1-methoxymethyl-1H-imidazol-2-yl)-6,6-dimethyl-5,6-dihydro-benzo[b]carbazol-11-one | B | 2.63 | 462.0 |
| 1186 | GT20-7 | 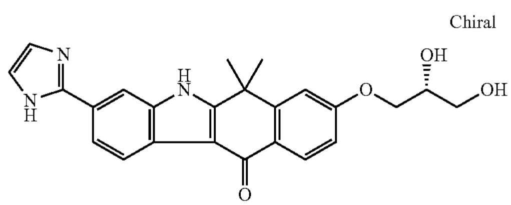 [SMILES: CC1(C)c2cc(OC[C@H](O)CO)ccc2C(=O)c2c1[nH]c1cc(-c3ncc[nH]3)ccc21] | 8-((R)-2,3-Dihydroxy-propoxy)-3-(1H-imidazol-2-yl)-6,6-dimethyl-5,6-dihydro-benzo[b]carbazol-11-one | B | 2.45 | 418.5 |

Example 1187

Compound GT20-8

8-((R)-2,3-Dihydroxy-propoxy)-3-methoxymethyl-6,6-dimethyl-5,6-dihydro-benzo[b]carbazol-11-one and

Compound GT20-9

8-((R)-2,3-Dihydroxy-propoxy)-3-hydroxymethyl-6,6-dimethyl-5,6-dihydro-benzo[b]carbazol-11-one

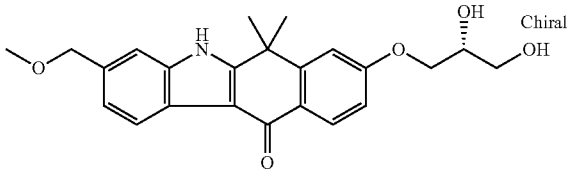

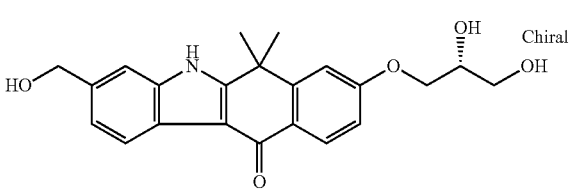

3-Bromo-8-((S)-2,2-dimethyl-[1,3]dioxolan-4-yl-methoxy)-6,6-dimethyl-5,6-dihydrobenzo[b]carbazol-11-one (200.2 mg, 0.426 mmol), palladium acetate (II) (19 mg, 0.0848 mmol), hexacarbonyl molybdenum (115.5 mg, 0.438 mmol) and tris(o-tolyl)phosphine (52.5 mg, 0.172 mmol) were dissolved in THF (1.3 ml) and ethanol (0.075 ml), added with DBU (0.195 ml), and subjected to microwave irradiation at 160° C. for 15 min under nitrogen atmosphere. The resulting reaction solution was partitioned between aqueous solution of potassium dihydrophosphoric acid and ethyl acetate. The organic layer was washed with saturated brine, and then concentrated under reduced pressure. The resulting residues were dissolved in ethanol (10 ml) and THF (3 ml), added with 2 N KOH (2 ml), and stirred at room temperature for 2 hrs, at 50° C. overnight and at 70° C. for 2 hrs. The reaction solution was partitioned between aqueous solution of potassium dihydrophosphoric acid and ethyl acetate. The organic layer was washed with saturated brine, and then concentrated under reduced pressure. The resulting residues were suspended and purified with MTBE/hexane (1/1) (155.4 mg). The THF solution (1.5 ml) of the product (109 mg) was added with TEA (0.052 ml, 0.373 mmol) and ethyl chloroformate (0.029 ml, 0.303 mmol) under ice cooling, and the mixture was stirred at 0° C. for 2 hrs. Subsequently, ethanol (1 ml) and sodium borohydride (75.7 mg, 2.0 mmol) were added to the mixture, which was then stirred at room temperature for 2 hrs. The reaction solution was partitioned between aqueous solution of potassium dihydrophosphoric acid and ethyl acetate. The organic layer was washed with saturated brine, and then concentrated under reduced pressure. The resulting residues were purified by silica gel column (MeOH/DCM) (35.2 mg). Thus-obtained solid (9.6 mg) was dissolved in MeOH (1 ml), added with 1 N HCl (3 drops), and the mixture was stirred at 60° C. for 90 min. After cooling and concentration under reduced pressure, the resultant was purified by TLC (MeOH/DCM) to obtain Compound GT20-8 (6.2 mg, white solid) and Compound GT20-9 (4.3 mg, white solid).

Compound GT20-8

LCMS: m/z 396 [M+H]+
HPLC retention time: 1.66 min (analysis condition A)

Compound GT20-9

LCMS: m/z 382 [M+H]+
HPLC retention time: 1.37 min (analysis condition A)

Example 1188

Compound GT21-1

8-[(E)-2-(2,2-Dimethyl-[1,3]dioxolan-4-yl)-vinyl]-6,6-dimethyl-6H-benzo[b]naphtho[2,3-d]furan-11-one

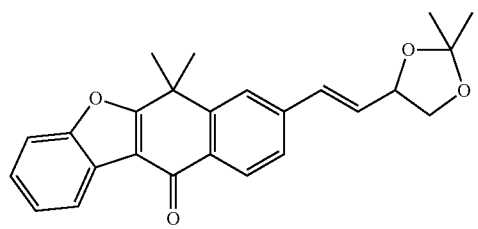 [SMILES: CC1(C)OCC(/C=C/c2ccc3c(c2)C(C)(C)c2oc4ccccc4c2C3=O)O1]

To the DMF solution (4 ml) of trifluoro-methanesulfonic acid 6,6-dimethyl-11-oxo-6,11-dihydro-benzo[b]naphtho[2,3-d]furan-8-yl ester (300 mg), 2,2-dimethyl-4-vinyl-[1,3]dioxolane (469 mg) and PdCl$_2$(PPh$_3$)$_2$ (103 mg), sodium hydrocarbonate (184 mg) was added, and the mixture was stirred at 100° C. overnight under nitrogen atmosphere. The reaction mixture was diluted with ethyl acetate. The organic layer was washed with saturated aqueous solution of sodium bicarbonate and saturated brine, and then concentrated under reduced pressure. The resulting residues were purified by silica gel column (ethyl acetate/hexane) to obtain the title compound (130 mg, 46%).

LCMS: m/z 389 [M+H]+
HPLC retention time: 3.28 min (analysis condition Y)

Example 1189

Compound GT21-2

8-(3,4-Dihydroxy-butyl)-6,6-dimethyl-6H-benzo[b]naphtho[2,3-d]furan-11-one

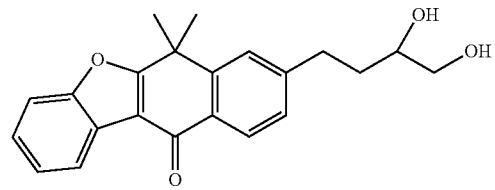 [SMILES: CC1(C)c2cc(CCC(O)CO)ccc2C(=O)c2c1oc1ccccc21]

To the MeOH solution (5 ml) of 8-[(E)-2-(2,2-dimethyl-[1,3]dioxolan-4-yl)-vinyl]-6,6-dimethyl-6H-benzo[b]naphtho[2,3-d]furan-11-one (125 mg), 10% Pd—C (25 mg) was added and the mixture was stirred overnight at room temperature under hydrogen atmosphere. The catalyst was removed by filtration. The residues obtained after concentration under reduced pressure were purified by HPLC to obtain the title compound (35 mg, 31%).

LCMS: m/z 351 [M+H]+
HPLC retention time: 1.79 min (analysis condition Y)

Example 1190

Compound GT21-3

8-Amino-6,6-dimethyl-6H-benzo[b]naphtho[2,3-d]furan-11-one

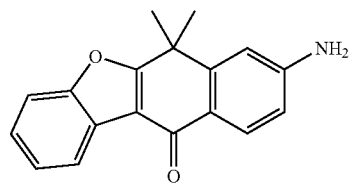 [SMILES: CC1(C)c2cc(N)ccc2C(=O)c2c1oc1ccccc21]

To trifluoro-methanesulfonic acid 6,6-dimethyl-11-oxo-6,11-dihydro-benzo[b]naphtho[2,3-d]furan-8-yl ester (100 mg), benzhydrylideneamine (0.05 ml), cesium carbonate (110 mg), palladium acetate (2 mg) and BINAP (7 mg), THF (2 ml) was added. The mixture was stirred and heated at 65° C. overnight under nitrogen atmosphere, and the reaction mixture was diluted with ethyl acetate. The organic layer was washed with saturated aqueous solution of sodium bicarbonate and saturated brine, and then concentrated under reduced pressure. The resulting residues were purified by silica gel column (ethyl acetate/hexane) to obtain the title compound (16 mg, 23%).

LCMS: m/z 278 [M+H]+
HPLC retention time: 2.52 min (analysis condition Y)

Example 1191

Compound GT21-4

8-[((S)-2,2-Dimethyl-[1,3]dioxolan-4-yl methyl)-amino]-6,6-dimethyl-6H-benzo[b]naphtho[2,3-d]furan-11-one

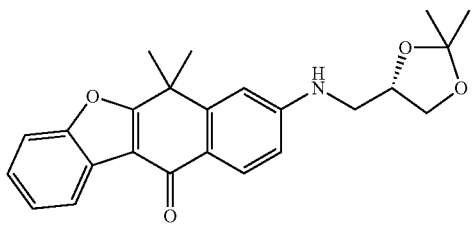 [SMILES: CC1(C)OC[C@H](CNc2ccc3c(c2)C(C)(C)c2oc4ccccc4c2C3=O)O1]

The mixture comprising 8-amino-6,6-dimethyl-6H-benzo[b]naphtho[2,3-d]furan-11-one (50 mg), (R)-4-iodomethyl-2,2-dimethyl-[1,3]dioxolane (104 mg), potassium carbonate (150 mg) and DMF (2 ml) was stirred and heated at 160° C. for 2 days under nitrogen atmosphere. The reaction mixture was diluted with ethyl acetate. The organic layer was washed with water and saturated brine, and then concentrated under reduced pressure. The resulting residues were purified by silica gel column (ethyl acetate/hexane). To the compound (71 mg) obtained therefrom, THF (1 ml) and conc. hydrochloric acid (8 drops) were added and the mixture was stirred at room temperature for 1 hr. The reaction mixture was added with saturated aqueous solution of sodium bicarbonate and then diluted with ethyl acetate. The organic layer was washed with saturated aqueous solution of sodium bicarbonate and saturated brine, and then concentrated under reduced pressure. The resulting residues were purified by silica gel column (ethyl acetate/hexane) to obtain the title compound (34 mg, 51%).

LCMS: m/z 392 [M+H]+
HPLC retention time: 3.11 min (analysis condition Y)

Example 1192

Compound GT21-5

8-((S)-2,3-Dihydroxy-propylamino)-6,6-dimethyl-6H-benzo[b]naphtho[2,3-d]furan-11-one

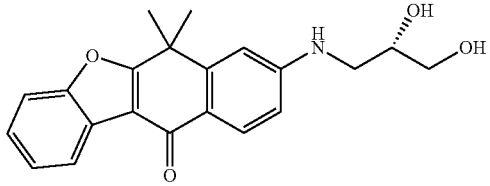 [SMILES: CC1(C)c2cc(NC[C@H](O)CO)ccc2C(=O)c2c1oc1ccccc21]

In the same manner as Compound A7-14-2, Compound GT21-4 was deprotected to obtain the title compound.

LCMS: m/z 352 [M+H]+
HPLC retention time: 2.26 min (analysis condition Y)

Example 1193

Compound GT22-1

8-(2-Diethylamino-ethoxy)-6,6-dimethyl-3-propyl-6H-benzo[b]naphtho[2,3-d]furan-11-one

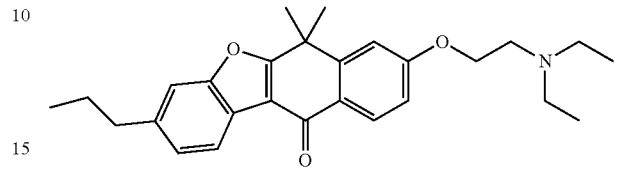

To the mixture of trifluoro-methanesulfonic acid 8-(2-diethylamino-ethoxy)-6,6-dimethyl-11-oxo-6,11-dihydro-benzo[b]naphtho[2,3-d]furan-3-yl ester (15 mg), which had been obtained in the same manner as Compound A7-25, tris(1-methyl-3-oxo-1-butenyloxy) iron (III) (1 mg), NMP (0.3 ml) and THF (0.3 ml), n-PrMgBr (0.88 M, THF solution, 0.291 ml) and zinc chloride (0.5 M THF solution, 0.114 ml) were added at 0° C. under nitrogen atmosphere, and the mixture was stirred at 0° C. for 10 min. The reaction mixture was added with water and extracted with ethyl acetate. The organic layer was washed with saturated brine, and then concentrated under reduced pressure. The resulting residues were purified by silica gel column (ethyl acetate/hexane) to obtain the title compound (4.5 mg, 3.8%).

LCMS: m/z 420 [M+H]+
HPLC retention time: 5.77 min (analysis condition H)

Example 1194

Compound GT22-2

8-(2-Diethylamino-ethoxy)-3-ethyl-6,6-dimethyl-6H-benzo[b]naphtho[2,3-d]furan-11-one

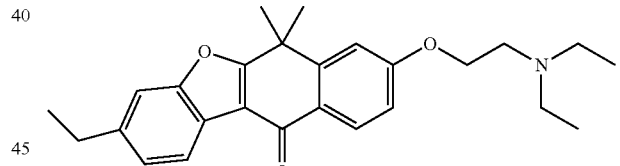

In the same manner as Compound GT22-2, the title compound was synthesized.

LCMS: m/z 406 [M+H]+
HPLC retention time: 5.12 min (analysis condition B)

Example 1195

Compound GT23-1

3-Bromo-8-methoxy-6,6-dimethyl-6H-benzo[b]naphtho[2,3-d]furan-11-one

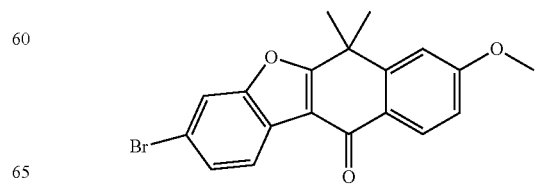

8-Methoxy-6,6-dimethyl-3-(4,4,5,5-tetramethyl-[1,3,2]dioxaborolan-2-yl)-6H-benzo[b]naphtho[2,3-d]furan-11-one (10.3 mg), which had been synthesized from Compound Z12 under the same conditions as the method for synthesizing Compound GT20-5, was mixed with copper (II) bromide (16.5 mg), MeOH (0.5 ml) and water (0.25 ml), and the mixture was stirred and heated at 70° C. for 2 hrs. DCM was added to the reaction solution for extraction. The organic layer was concentrated and purified by silica gel column to obtain the title compound (9.4 mg).

LCMS: m/z 371 [M+H]$^+$

HPLC retention time: 7.55 min (analysis condition B)

Example 1196

Compound GT23-2

3-Bromo-8-hydroxy-6,6-dimethyl-6H-benzo[b]naphtho[2,3-d]furan-11-one

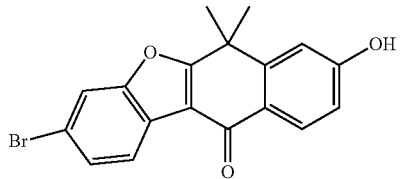 [SMILES: CC1(C)c2cc(O)ccc2C(=O)c2c1oc1cc(Br)ccc21]

In the same manner as Compound GT15-5, 3-bromo-8-methoxy-6,6-dimethyl-6H-benzo[b]naphtho[2,3-d]furan-11-one was deprotected to obtain the title compound.

LCMS: m/z 357 [M+H]$^+$

HPLC retention time: 2.82 min (analysis condition A)

The compounds described in the following Table 42 were synthesized from Compound GT23-2 according to the method given in the Table.

Example 1200

Compound GT24-1

8-((R)-2,3-Dihydroxy-propoxy)-3-iodo-6,6-dimethyl-6H-benzo[b]naphtho[2,3-d]furan-11-one

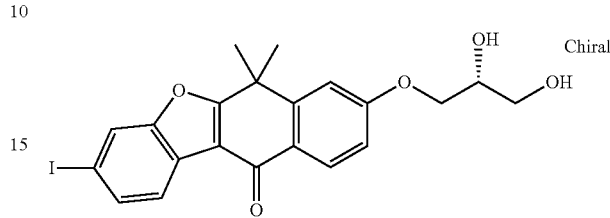

To 3-bromo-8-((S)-2,2-dimethyl-[1,3]dioxolan-4-yl-methoxy)-6,6-dimethyl-6H-benzo[b]naphtho[2,3-d]furan-11-one (15 mg, 0.032 mmol), CuI (6.2 mg, 0.032 mmol), NaI (9.6 mg, 0.064 mmol) and trans-N,N'-dimethylcyclohexane-1,2-diamine (0.01 ml) were added and the mixture was stirred for 48 hrs under nitrogen atmosphere. The reaction solution was diluted with ethyl acetate. The organic layer was washed with saturated brine, and then concentrated under reduced pressure. The resulting residues were purified by silica gel column (ethyl acetate/hexane) to obtain 8-((S)-2,2-dimethyl-[1,3]dioxolan-4-yl methoxy)-3-iodo-6,6-dimethyl-6H-benzo[b]naphtho[2,3-d]furan-11-one (16 mg, 97%), which was then deprotected according to the method of A-14-2 to give the title compound.

LCMS: m/z 479 [M+H]$^+$

HPLC retention time: 4.26 min (analysis condition A)

TABLE 42

| Example No. | Comp. No. | Structure | Compound Name | HPLC Condition | Retention Time | m/z | Method |
|---|---|---|---|---|---|---|---|
| 1197 | GT23-3 | (Chiral) | 3-Bromo-6,6-dimethyl-8-((2R,3R)-2,3,4-trihydroxy-butoxy)-6H-benzo[b]naphtho[2,3-d]furan-11-one | D | 2.30 | 461.0 | T22-1-1 T22-2 |
| 1198 | GT23-4 | (Chiral) | 3-Bromo-8-((R)-2,3-dihydroxy-propoxy)-6,6-dimethyl-6H-benzo[b]naphtho[2,3-d]furan-11-one | A | 5.42 | 431.0 | A7-14-1 A7-14-2 |
| 1199 | GT23-5 | 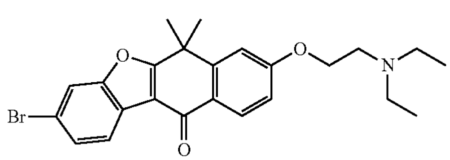 [SMILES: CCN(CC)CCOc1ccc2c(c1)C(C)(C)c1oc3cc(Br)ccc3c1C2=O] | 3-Bromo-8-[2-diethylamino-ethoxy)-6,6-dimethyl-6H-benzo[b]naphtho[2,3-d]furan-11-one | H | 5.37 | 456.0 | A7-17 |

Example 1201

Compound GT24-2

3-Iodo-6,6-dimethyl-8-((2R,3R)-2,3,4-trihydroxy-butoxy)-6H-benzo[b]naphtho[2,3-d]furan-11-one

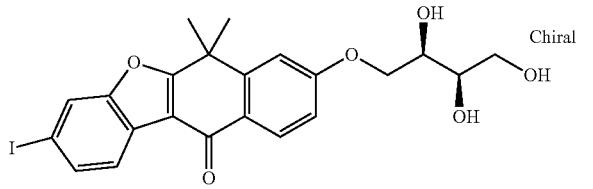 [SMILES: CC1(C)c2cc(OC[C@@H](O)[C@H](O)CO)ccc2C(=O)c2c1oc1cc(I)ccc21]

In the same manner as Compound GT24-1, 3-iodo-8-[(4R,5R)-5-(tert-butyl-dimethyl-silanyloxymethyl)-2,2-dimethyl-[1,3]dioxolan-4-ylmethoxy]-6,6-dimethyl-6H-benzo[b]naphtho[2,3-d] furan-11-one was synthesized from 3-bromo-8-[(4R,5R)-5-(tert-butyl-dimethyl-silanyloxymethyl)-2,2-dimethyl-[1,3]dioxolan-4-ylmethoxy]-6,6-dimethyl-6H-benzo[b]naphtho[2,3-d]furan-11-one. Subsequently, according to the same method as Compound T22-2, deprotection was carried out to obtain the title compound.

Example 1202

Compound GT25-1

6,6-Dimethyl-8-(4-methyl-piperazine-1-sulfonyl)-6H-benzo[b]naphtho[2,3-d]furan-11-one

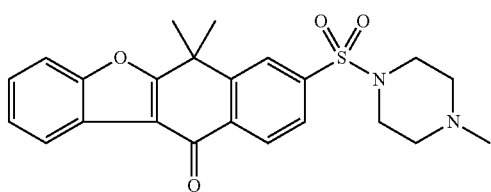 [SMILES: CN1CCN(S(=O)(=O)c2ccc3c(c2)C(C)(C)c2oc4ccccc4c2C3=O)CC1]

By using the method for preparing Compound B1, trifluoro-methanesulfonic acid 6,6-dimethyl-11-oxo-6,11-dihydro-benzo[b]naphtho[2,3-d]furan-8-yl ester was prepared from 8-hydroxy-6,6-dimethyl-6H-benzo[b]naphtho[2,3-d]furan-11-one. This trifluoromethanesulfonic acid ester (205 mg), (2R)-1-[(1R)-1-[bis(1,1-dimethylethyl)phosphino]ethyl]-2-(dicyclohexylphosphino)ferrocene (13 mg), palladium acetate (6 mg), 2-trimethylsilanyl-ethanethiol (90 μL) and potassium carbonate (85 mg) were reacted in DME to obtain a product (120 mg). To the benzyl alcohol solution (90 μL) of the product (50 mg), DCM solution of N-chlorosuccinimide (90 mg) was added, and the mixture was stirred at room temperature. The reaction solution was partitioned between water and ethyl acetate, and the organic layer was concentrated under reduced pressure. To the DCM solution of thus-obtained white solid, N-methylpiperazine (10 μL) was added and the mixture was stirred. The residues obtained after removing the solvent by distillation were purified by TLC to obtain the title compound as a white solid (6 mg).

Example 1203

Compound GT26-1

(2-Bromo-5-methoxy-phenyl)-acetonitrile

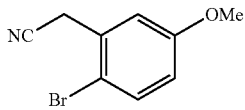 [SMILES: COc1ccc(Br)c(CC#N)c1]

To the THF solution (1000 ml) of 2-bromo-5-methoxy-benzoic acid methyl ester (20 g, 81.6 mmol), the THF suspension (50 ml) of LAH (4.07 g, 102 mmol) was added under ice cooling. The mixture was stirred for 30 min under ice cooling. The reaction solution was partitioned between saturated aqueous solution of $Na_2SO_4$ and ethyl acetate. The organic layer was washed with saturated brine and concentrated under reduced pressure. The resulting residues were dissolved in DCM (200 ml), and added with TEA (12.51 ml, 89.76 mmol) and MsCl (6.63 ml, 85.68 mmol) under ice cooling, followed by stirring overnight at room temperature. The reaction mixture was diluted with DCM, and washed in order with 10% aqueous solution of citric acid, saturated aqueous solution of $NaHCO_3$ and saturated brine. The residues obtained after concentration under reduced pressure were dissolved in DMF (100 ml), and added with the DMF (500 ml) solution of NaCN (40 g, 81.6 mmol) under ice cooling. After stirring for 2 hrs under ice cooling, the reaction mixture was extracted with ether, washed with saturated brine and dried over magnesium sulfate. The residues obtained after concentration under reduced pressure were purified by silica gel column (hexane:ethyl acetate=10:1) to obtain the title compound (12.1 g, 67%).

$^1$H-NMR (400 MHz, $CDCl_3$) δ 3.82 (s, 3H), 6.77 (d, 1H), 7.07 (s, 1H), 7.47 (d, 1H)

Example 1204

1-(2-Bromo-5-methoxy-phenyl)-cyclopropane carbonitrile

Compound GT26-2

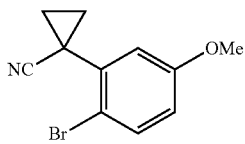 [SMILES: COc1ccc(Br)c(C2(C#N)CC2)c1]

2-Bromo-5-methoxy-phenyl)-acetonitrile (12.2 g, 53.97 mmol) was dissolved in toluene (50 ml), and added with tetrabutylammonium bromide (3.55 g, 10.79 mmol), dibromoethane (7.05 ml, 80.95 mmol) and 50% aqueous solution of NaOH (50 ml) at room temperature. The mixture was stirred at room temperature for 4 hrs. The reaction mixture was added with water and extracted with ethyl acetate. The residues obtained after concentration under reduced pressure were purified by silica gel column (hexane:ethyl acetate) to obtain the title compound (11.18 g, 82%).

$^1$H-NMR (400 MHz, $CDCl_3$) δ 1.33 (t, 1H), 1.76 (t, 1H), 3.79 (s, 3H), 6.75-6.79 (m, 1H), 6.89 (d, 1H), 7.47 (d, 1H)

Example 1205

1-(2-Bromo-5-methoxy-phenyl)-cyclopropane carboxylic acid

Compound GT26-3

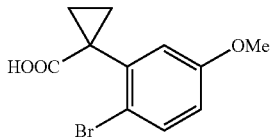

1-(2-Bromo-5-methoxy-phenyl)-cyclopropane carbonitrile (3.0 g, 11.9 mmol) was dissolved in ethylene glycol (30 ml). After adding KOH (2.1 g, 33.3 mmol) thereto, the mixture was stirred and heated at 180° C. for 7 hrs. After cooling, the reaction mixture was added with 1 N HCl (90 ml). The reaction mixture was extracted with ether, washed with water and saturated brine and dried over magnesium sulfate. After concentration under reduced pressure, the title compound was obtained (12.3 g, 72%).

LCMS: m/z 272 [M+H]$^+$

HPLC retention time: 2.03 min (analysis condition Y)

Example 1206

Compound GT26-4

2-[1-(2-Bromo-5-methoxy-phenyl)-cyclopropyl]-benzofuran

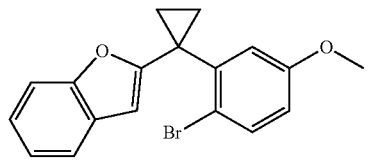 [SMILES: COc1ccc(Br)c(C2(c3cc4ccccc4o3)CC2)c1]

To the DCM solution (6 ml) of 1-(2-bromo-5-methoxy-phenyl)-cyclopropane carboxylic acid (0.3 g, 1.1 mmol), DMF (2 drops) and oxalyl chloride (0.23 ml, 2.5 mmol) were added at room temperature, and the mixture was stirred at room temperature for 2 hrs. The residues obtained from the reaction solution after concentration under reduced pressure were dissolved in toluene (6 ml), added with (2-hydroxybenzyl)triphenylphosphonium bromide (0.605 g, 1.32 mmol) and TEA (0.46 ml, 3.3 mmol), and the resulting mixture was stirred and heated at 100° C. overnight. The residues obtained after concentration under reduced pressure were purified by silica gel column (hexane:DCM) to obtain the title compound (0.309 g, 81%).

LCMS: m/z 343 [M+H]$^+$

HPLC retention time: 3.55 min (analysis condition Y)

Example 1207

Compound GT26-5

2-(1-Benzofuran-2-yl-cyclopropyl)-4-methoxy-benzoic acid

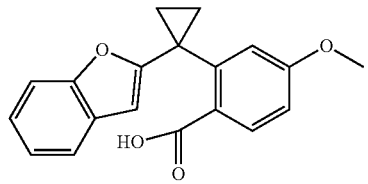 [SMILES: COc1ccc(C(=O)O)c(C2(c3cc4ccccc4o3)CC2)c1]

To the THF solution (3 ml) of 2-[1-(2-bromo-5-methoxy-phenyl)-cyclopropyl]-benzofuran (0.259 g, 0.75 mmol), n-BuLi was added at −78° C., and the mixture was stirred at −78° C. for 20 min. Thereafter, the mixture was flushed with carbon dioxide gas. The reaction mixture was added with saturated solution of NH$_4$Cl and extracted with ethyl acetate. The residues obtained after concentration under reduced pressure were purified by silica gel column (DCM:MeOH) to obtain the title compound (0.163 g, 70%).

LCMS: m/z 309 [M+H]$^+$

HPLC retention time: 2.67 min (analysis condition Y)

Example 1208

Compound GT26-6

8-Methoxy-11H-spiro[benzo[d]naphtho[2,3-b]furan-6,1'-cyclopropan]-11-one

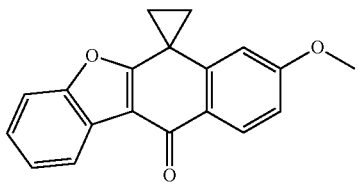 [SMILES: COc1ccc2c(c1)C1(CC1)c1oc3ccccc3c1C2=O]

To the DCM solution (10 ml) of 2-(1-benzofuran-2-yl-cyclopropyl)-4-methoxy-benzoic acid (1.0 g, 3.24 mmol), trifluoroacetic acid anhydride (0.45 ml, 3.24 mmol) was added at −78° C., and the mixture was stirred at −78° C. for 10 min, at −50° C. for 10 min, and at −30° C. for 20 min. Thereafter, the mixture was added with water and extracted with DCM. The residues obtained after concentration under reduced pressure were washed with DCM and hexane to obtain the title compound (0.163 g, 70%).

LCMS: m/z 291 [M+H]$^+$

HPLC retention time: 2.90 min (analysis condition Y)

Example 1209

Compound GT26-7

8-(2-(Diethylamino)ethoxy)-11H-spiro[benzo[d]naphtho[2,3-b]furan-6,1'-cyclopropan]-11-one

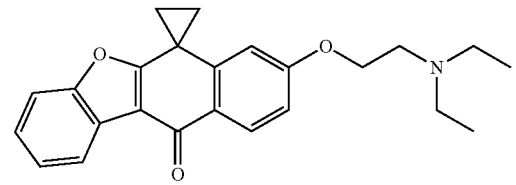 [SMILES: CCN(CC)CCOc1ccc2c(c1)C1(CC1)c1oc3ccccc3c1C2=O]

In the same manner as Compound A6 and Compound A7-17, the title compound was obtained from 8-methoxy-11H-spiro[benzo[d]naphtho[2,3-b]furan-6,1'-cyclopropan]-11-one.

LCMS: m/z 376 [M+H]$^+$

HPLC retention time: 1.65 min (analysis condition Y)

Example 1210

Compound GT27-1

2-(2-Bromo-5-methoxy-phenyl)-2-ethyl-butyric acid

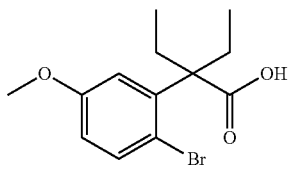 [SMILES: CCC(CC)(C(=O)O)c1cc(OC)ccc1Br]

(2-Bromo-5-methoxy-phenyl)-acetic acid methyl ester (3.51 g, 13.5 mmol) was dissolved in DMF (4.5 ml), and added with NaH (2.1 g, 67.7 mmol). Subsequently, 15-crown-5 (1.38 ml, 6.8 mmol) and EtI (5.5 ml, 67.7 mmol) cooled to 0° C. were added to the mixture. The mixture was diluted with ethyl acetate and washed with water and saturated brine. The residues obtained after concentration under reduced pressure were purified by silica gel column (hexane-ethyl acetate). Then, the resultant was dissolved in ethanol (80 ml) and water (80 ml), added with KOH (91 g), and stirred at 140° C. The reaction solution was extracted with ethyl acetate, and washed with water and saturated brine. After concentration under reduced pressure, the target compound was obtained (10.62 g, 78%).

LCMS: m/z 301 [M+H]+

HPLC retention time: 3.07 min (analysis condition Y)

Example 1211

Compound GT27-2

2-(2-Bromo-5-methoxy-phenyl)-2-ethyl-butyric acid o-tolyl ester

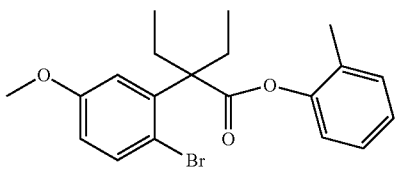 [SMILES: CCC(CC)(C(=O)Oc1ccccc1C)c1cc(OC)ccc1Br]

Compound GT27-1 (0.5 g, 1.66 mmol) was dissolved in DCM (10 ml), added with DMF (2 drops) and oxalyl chloride (0.28 ml, 3.32 mmol), and the mixture was stirred for 2 hrs. The reaction mixture obtained after concentration under reduced pressure was dissolved in toluene (5 ml), added with DMAP (406 mg, 3.32 mmol), and the mixture was heated under reflux. The reaction mixture was extracted with ethyl acetate, washed with 1 N HCl, and saturated brine. The residues obtained after concentration under reduced pressure were purified by silica gel column (hexane-ethyl acetate) to obtain the target compound (0.36 g, 86%).

LCMS: m/z 393 [M+H]+

HPLC retention time: 3.03 min (analysis condition Y)

Example 1212

Compound GT27-3

2-(2-Bromo-5-methoxy-phenyl)-2-ethyl-butyric acid 2-[(triphenyl-phosphanyl)-methyl]-phenyl ester bromate salt

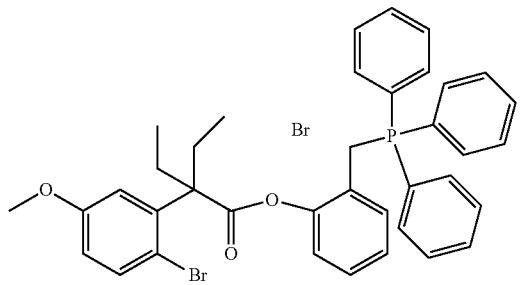

Compound GT27-2 (0.118 g, 0.302 mmol) was dissolved in carbon tetrachloride (3 ml), added with N-bromosuccinimide (54 mg, 0.302 mmol), and the mixture was heated under reflux. The reaction mixture was concentrated under reduced pressure and the resulting residues were purified by silica gel column (ethyl acetate-hexane). The product was dissolved in toluene (3 ml), added with PPh$_3$ (77 mg, 0.302 mmol), and the mixture was heated under reflux. The reaction mixture was concentrated under reduced pressure to obtain the target compound (130 mg, 57%).

Example 1213

Compound GT27-4

2-[1-(2-Bromo-5-methoxy-phenyl)-1-ethyl-propyl]-benzofuran

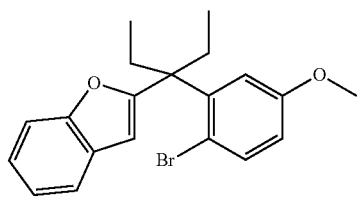 [SMILES: CCC(CC)(c1cc2ccccc2o1)c1cc(OC)ccc1Br]

To the toluene solution (3 ml) of Compound GT27-3 (0.14 g, 0.137 mmol), toluene solution (0.16 ml, 0.164 mmol) of 1 M LiHMDS was added. The mixture was heated and stirred for 4 hrs. The reaction mixture was concentrated under reduced pressure and the resulting residues were purified by silica gel column (ethyl acetate:hexane) to obtain the title compound (28 mg, 35%).

LCMS: m/z 373 [M+H]+

HPLC retention time: 2.73 min (analysis condition Y)

Example 1214

Compound GT27-5

8-(2-Diethylamino-ethoxy)-6,6-diethyl-6H-benzo[b]naphtho[2,3-d]furan-11-one

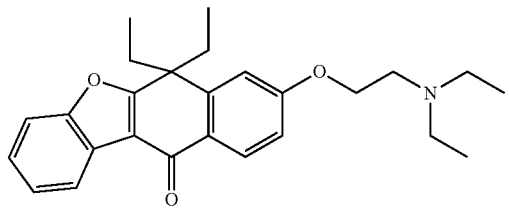 [SMILES: CCN(CC)CCOc1ccc2c(c1)C(CC)(CC)c1oc3ccccc3c1C2=O]

In the same manner as Compound A7-17, the title compound was obtained from Compound GT27-4.

LCMS: m/z 407 [M+H]$^+$

HPLC retention time: 1.92 min (analysis condition Y)

Example 1215

Compound GT27-6

8-((R)-2,3-Dihydroxy-propoxy)-6,6-diethyl-6H-benzo[b]naphtho[2,3-d]furan-11-one

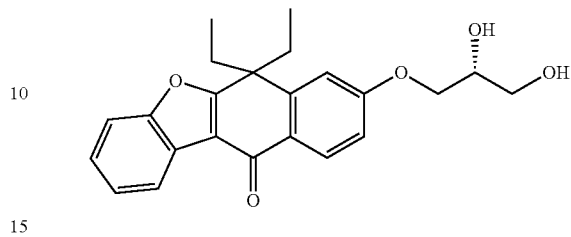

In the same manner as Compound A7-14-1 and Compound A7-14-2, the title compound was obtained from Compound GT27-4.

LCMS: m/z 381 [M+H]$^+$

HPLC retention time: 2.38 min (analysis condition Y)

The compounds described in the following Table 43 were synthesized according to the method shown below. According to the method used for the preparation of Compound Z10, Z11 and Z12, 3-chloro-8-methoxy-6H-benzo[b]naphtho[2,3-d]furan-11-one was prepared from Compound A2 and 2-bromo-5-chlorophenol. Subsequently, demethylation was carried out according to the method that is used for the preparation of Compound A6, and thus 3-chloro-8-hydroxy-6H-benzo[b]naphtho[2,3-d]furan-11-one was obtained. Thereafter, according to Mitsunobu reaction that is used for the preparation of Compound A7-1 or the alkylation method that is used for the preparation of A7-17, a corresponding side chain was introduced and, if necessary, functional group modification such as deprotection, etc. was carried out to prepare the compounds listed below.

TABLE 43

| Example No. | Comp. No. | Structure | Compound Name | HPLC Condition | Retention Time | m/z |
|---|---|---|---|---|---|---|
| 1216 | GT28-1 | 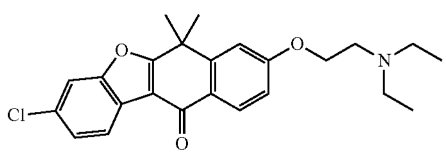 [SMILES: CCN(CC)CCOc1ccc2c(c1)C(C)(C)c1oc3cc(Cl)ccc3c1C2=O] | 3-Chloro-8-(2-diethylamino-ethoxy)-6,6-dimethyl-6H-benzo[b]naphtho[2,3-d]furan-11-one | F | 2.52 | 412.0 |
| 1217 | GT28-2 | Chiral | 3-Chloro-6,6-dimethyl-8-[(2R,3R)-2,3,4-trihydroxy-butoxy)-6H-benzo[b]naphtho[2,3-d]furan-11-one | H | 5.39 | 417.0 |
| 1218 | GT28-3 | Chiral | 3-Chloro-8-((R)-2,3-dihydroxy-propoxy)-6,6-dimethyl-6H-benzo[b]naphtho[2,3-d]furan-11-one | H | 5.77 | 387.0 |

Pharmacological Testing Method
1. Activity of Inhibiting ALK Enzyme

ALK-inhibiting activity was measured by following an activity of inhibiting phosphorylation by biotinylated peptide (EGPWLEEEEEAYGWMDF). For the detection of phosphorylation of the biotinylated peptide, time-resolved fluorescence measurement was performed using an anti-phosphorylated tyrosine antibody labeled with europium cryptate and streptavidin conjugated to XL665, i.e., an allophycocyanin derivative. From the inhibition ratio compared to the control group that does not comprise a test compound, 50% inhibitory concentration (i.e., $IC_{50}$ value) was calculated.

2. Measurement of an Activity of Inhibiting Karpas-299 Cell Growth

The test compounds were serially diluted with dimethyl sulfoxide, further diluted with phosphate buffered saline which is free of any $Ca^{2+}$, $Mg^{2+}$ (×50 dilution), and 10 μL of the resulting solution was aliquoted in a 96-well plate. Human lymphoma cell line KARPAS-299 was prepared in RPMI-1640 medium to which 10% bovine fetal serum was added to give a cell suspension with the cell density of 10,000 cells/190 μL. The resulting cell suspension was aliquoted to the plate (190 μL per well) to which the test compound had been already added, and the plate was kept in a 5% carbon dioxide gas incubator at 37° C. Ninety-six hours later, 10 μL of WST-8 (manufactured by Dojindo Laboratories) was added to each well, and subsequently the absorbance was measured at 450 nm. From the ratio of inhibition on cell growth which had been obtained from the addition of a test compound compared to the control group with no addition, 50% growth inhibitory concentration (i.e., $IC_{50}$ value) of the test compound was calculated. The results are summarized in Tables 44-49.

TABLE 44

| Examples | ALK-inhibiting activity $IC_{50}$ (μM) | Inhibitory activity on Karpas-299 cell growth $IC_{50}$ (μM) |
|---|---|---|
| 123 (Compound B2-27) | 0.00228 | 0.0138 |
| 177 (Compound B4-7) | 0.00084 | 0.0105 |
| 178 (Compound B4-8) | 0.00153 | 0.0214 |
| 304 (Compound F5-11) | 0.00081 | 0.0061 |
| 338 (Compound F5-43) | 0.00032 | 0.0086 |
| 341 (Compound F5-46) | 0.01056 | 0.0289 |
| 364 (Compound F6-18) | 0.00177 | 0.0231 |
| 366 (Compound F6-20) | 0.0053 | 0.0093 |
| 372 (Compound G6) | 0.03074 | 0.1682 |
| 380 (Compound H6-2) | 0.00053 | 0.0062 |
| 429 (Compound J7-10-2) | 0.00083 | 0.0303 |
| 543 (Compound O8-5) | 0.00032 | 0.03 |
| 550 (Compound O9-7) | 0.00090 | 0.0044 |
| 735 (Compound Z7) | 0.09385 | 1.1924 |
| 516 (Compound N6-2) | 0.003906748 | 0.0248 |
| 725 (Compound X5) | 0.687683357 | 2.8765 |
| 882 (Compound AZ7-10) | 0.000493765 | 0.005769 |
| 916 (Compound DZ7-1) | 0.001836659 | 0.357381 |
| 937 (Compound EZ9-3) | 0.006473484 | 0.056914 |
| 939 (Compound EZ9-5) | 0.399865279 | 13.421227 |
| 1175 (Compound GT18-4) | 0.093 | 2.012 |

TABLE 45

| Example No. | Compound | ALK-inhibiting activity $IC_{50}$ (μM) |
|---|---|---|
| 13 | A7-1 | 0.052707597 |
| 14 | A7-2 | 0.006159417 |
| 38 | A7-20 | 0.026183852 |
| 39 | A7-21 | 0.017713716 |
| 40 | A7-22 | 0.030434111 |
| 41 | A7-23 | 0.029469872 |
| 45 | A8-2 | 0.008009528 |
| 47 | A8-4 | 0.010253392 |
| 51 | A8-6-3 | 0.097920152 |
| 52 | A8-7 | 0.045959643 |
| 55 | A8-10 | 0.00673264 |
| 57 | A8-12 | 0.003594618 |
| 63 | A8-18 | 0.016005139 |
| 65 | A8-20 | 0.0029 |
| 67 | A9-1 | 0.004943 |
| 70 | A9-3-2 | 0.007649647 |
| 73 | A9-6-2 | 0.001398207 |
| 74 | A9-7 | 0.0034607 |
| 76 | A9-9 | 0.017148495 |
| 78 | A9-11 | 0.051123952 |
| 79 | A9-12 | 0.017501168 |
| 83 | A9-15-2 | 0.0035 |
| 84 | A9-16 | 0.08468 |
| 90 | B2-1 | 0.033572 |
| 100 | B2-9 | 0.016225317 |
| 101 | B2-10 | 0.039433518 |
| 102 | B2-11 | 0.072607257 |
| 104 | B2-13 | 0.001681324 |
| 109 | B2-16-3 | 0.000980809 |
| 117 | B2-23 | 0.005436966 |
| 118 | B2-24 | 0.014834642 |
| 122 | B2-26-2 | 0.007278245 |
| 124 | B2-28 | 0.059632226 |
| 128 | B3-2-2 | 0.003183521 |
| 130 | B3-4 | 0.063798146 |
| 135 | B3-9 | 0.01492317 |
| 137 | B3-11 | 0.071084446 |
| 141 | B3-14 | 0.011893599 |
| 142 | B3-15 | 0.030133825 |
| 143 | B3-16 | 0.027324427 |
| 146 | B3-19 | 0.010369469 |
| 147 | B3-20 | 0.026851192 |
| 149 | B3-22 | 0.272356381 |
| 150 | B3-23 | 0.023088404 |
| 151 | B3-24 | 0.003610645 |
| 157 | B3-27-2 | 0.002114607 |
| 158 | B3-28 | 0.042375341 |
| 159 | B3-29 | 0.006002322 |
| 165 | B3-34 | 0.006783031 |
| 166 | B3-35 | 0.003473067 |
| 168 | B3-37 | 0.011859342 |
| 179 | B4-9 | 0.002000975 |
| 187 | CC4-2 | 0.096115639 |
| 189 | C1-1 | 0.051102036 |
| 206 | C4-9 | 0.005101172 |
| 210 | C4-13 | 0.008752733 |
| 212 | C4-15 | 0.009616778 |
| 226 | D1 | 0.000991134 |
| 227 | D2 | 0.003611773 |
| 228 | D3-1 | 0.006279559 |
| 245 | E4-5 | 0.009450575 |
| 256 | E5-2 | 0.00133756 |
| 264 | E6-2 | 0.006668071 |
| 265 | E6-3 | 0.008113087 |
| 268 | F1-3 | 0.005054399 |
| 277 | F3-6-2 | 0.000167996 |
| 283 | F4-1-1 | 0.001625048 |
| 286 | F4-3 | 0.000951804 |
| 290 | F4-7 | 0.001133931 |
| 293 | F4-10 | 0.002098847 |
| 298 | F5-5 | 0.002385717 |
| 300 | F5-7 | 0.002575475 |
| 306 | F5-13 | 0.002051837 |
| 314 | F5-20 | 0.000996109 |
| 319 | F5-25 | 0.000881378 |
| 322 | F5-28 | 0.01227125 |
| 331 | F5-36-2 | 0.001778367 |
| 334 | F5-39 | 0.014824288 |

TABLE 46

| Example No. | Compound | ALK-inhibiting activity IC$_{50}$ (μM) |
|---|---|---|
| 346 | F5-51 | 0.002610782 |
| 350 | F6-4 | 0.00715425 |
| 353 | F6-7 | 0.020276801 |
| 355 | F6-9 | 0.001092627 |
| 358 | F6-12 | 0.015047658 |
| 359 | F6-13 | 0.000399685 |
| 389 | H9-3 | 0.002622129 |
| 403 | I6-4 | 0.000391036 |
| 407 | I7-1 | 0.001863642 |
| 421 | J7-3 | 0.015290853 |
| 422 | J7-4 | 0.004631153 |
| 423 | J7-5 | 0.012009506 |
| 424 | J7-6 | 0.001570404 |
| 426 | J7-8 | 0.001170682 |
| 431 | J7-11-2 | 0.01172814 |
| 435 | J7-15 | 0.02319 |
| 437 | J7-17 | 0.007091939 |
| 438 | J8-1 | 0.012517614 |
| 443 | J8-6 | 0.00396 |
| 455 | JJ5 | 0.862941682 |
| 458 | JJ7-2 | 0.028993627 |
| 461 | JJ9-1 | 0.004337558 |
| 465 | JJ10-1 | 0.492725332 |
| 472 | K6 | 0.029284532 |
| 486 | K10-5 | 0.000589765 |
| 501 | L10-2 | 0.00160 |
| 508 | M6-2 | 0.006136762 |
| 517 | N6-3 | 0.03272871 |
| 519 | N6-5 | 0.026853329 |
| 531 | O5-4 | 0.00431 |
| 546 | O9-3 | 0.00086 |
| 571 | Q8 | 0.005719259 |
| 579 | R8-2 | 0.000769618 |
| 591 | S4 | 1.664818863 |
| 599 | S8-2 | 0.04064 |
| 601 | S9-2 | 0.000456356 |
| 607 | T2-1 | 0.432812267 |
| 618 | T6-1 | 0.614075453 |
| 621 | T6-4 | 0.341433432 |
| 628 | T11 | 0.271479209 |
| 630 | T12-2 | 0.15422 |
| 633 | T13-3 | 0.16211 |
| 637 | T13-7 | 0.16821 |
| 639 | T13-9 | 0.16189 |
| 645 | T14-5 | 0.41327 |
| 650 | T14-10 | 0.18923 |
| 654 | T16-1 | 0.01951 |
| 657 | T16-4 | 0.07941 |
| 668 | T21 | 0.8521 |
| 671 | T22-1-1 | 0.151061541 |
| 678 | T22-7 | 2.8135 |
| 679 | T22-8 | 0.583 |
| 686 | T26-2 | 0.08320 |
| 702 | U8-6-2 | 0.00260 |
| 704 | U8-7-2 | 0.00604 |
| 706 | U8-8-2 | 0.35976 |
| 707 | U8-8-3 | 0.84884 |
| 709 | U10-1 | 0.55215 |
| 711 | U11 | 0.00193 |
| 720 | W4-2 | 0.13445 |
| 730 | Y5-2 | 0.554738402 |
| 751 | K10-10 | 0.0085 |
| 753 | K10-12 | 0.0022 |
| 755 | K10-14 | 0.0118 |
| 758 | K10-17 | 0.1422 |
| 760 | K10-19 | 0.0015 |
| 762 | L10-3 | 0.0099 |
| 770 | L10-11 | 0.0231 |
| 776 | B3-42 | 0.0042 |
| 786 | E9-4 | 0.0004 |
| 790 | E9-8 | 0.0075 |
| 796 | F4-11 | 0.0003 |
| 822 | PR11-6 | 0.0003 |
| 823 | PR11-7 | 0.0003 |
| 824 | PR9-9 | 0.0142 |
| 829 | PR9-13 | 0.0007 |
| 832 | PR11-11 | 0.0006 |
| 846 | PR9-25 | 0.021743738 |
| 847 | PR11-14 | 0.001890642 |

TABLE 47

| Example No. | Compound | ALK-inhibiting activity IC$_{50}$ (μM) |
|---|---|---|
| 849 | PR11-16 | 0.000813047 |
| 864 | LB5-1 | 0.424843491 |
| 866 | LB5-3 | 2.398295 |
| 875 | AZ7-3 | 0.113911239 |
| 892 | AZ7-20 | 0.009369855 |
| 893 | AZ7-21 | 0.142933634 |
| 920 | DZ7-5 | 0.326374265 |
| 938 | EZ9-4 | 0.300760062 |
| 949 | GT2-6 | 1.3255 |
| 956 | GT2-13 | 0.1617 |
| 960 | GT3-2 | 5.9473 |
| 962 | GT3-4 | 1.0829 |
| 963 | GT3-5 | 4.224 |
| 967 | GT3-9 | 0.8981 |
| 970 | GT3-12 | 1.6214 |
| 972 | GT4-1 | 0.29 |
| 973 | GT4-2 | 0.104 |
| 981 | GT5-8 | 2.9743 |
| 982 | GT5-9 | 21.3078 |
| 983 | GT5-10 | 3.2 |
| 994 | GT5-21 | 1.2466 |
| 995 | GT6-1 | 12.9519 |
| 996 | GT6-2 | 12.9704 |
| 997 | GT6-3 | 0.575 |
| 998 | GT6-4 | 4.3855 |
| 999 | GT6-5 | 3.9 |
| 1000 | GT6-6 | 5.4 |
| 1001 | GT6-7 | 3.7 |
| 1004 | GT6-10 | 0.9 |
| 1005 | GT6-11 | 1.4385 |
| 1007 | GT6-13 | 0.7526 |
| 1008 | GT6-14 | 4.8429 |
| 1013 | GT8-3 | 0.93 |
| 1017 | GT9-3 | 0.3785 |
| 1019 | GT9-5 | 0.77 |
| 1030 | GT11-8 | 5.9346 |
| 1031 | GT11-9 | 7.7947 |
| 1034 | GT11-12 | 2.076 |
| 1035 | GT11-13 | 1.6274 |
| 1039 | GT11-17 | 0.7938 |
| 1042 | GT11-20 | 0.5083 |
| 1043 | GT11-21 | 2.2822 |
| 1047 | GT11-25 | 1.9038 |
| 1048 | GT11-26 | 5.3708 |
| 1050 | GT11-28 | 3.2813 |
| 1051 | GT11-29 | 1.811 |
| 1052 | GT11-30 | 4.0931 |
| 1054 | GT11-32 | 7.0451 |
| 1059 | GT11-37 | 2.7739 |
| 1060 | GT11-38 | 1.1587 |
| 1061 | GT11-39 | 1.0914 |
| 1065 | GT11-43 | 3.7028 |
| 1066 | GT11-44 | 3.1203 |
| 1072 | GT11-50 | 3.3428 |
| 1073 | GT11-51 | 2.547 |
| 1074 | GT11-52 | 1.2588 |
| 1081 | GT11-59 | 1.0586 |
| 1083 | GT11-61 | 0.7928 |
| 1085 | GT11-63 | 0.9013 |
| 1086 | GT11-64 | 0.3127 |
| 1087 | GT11-65 | 0.206 |
| 1090 | GT12-3 | 0.8541 |
| 1096 | GT12-9 | 5.7571 |
| 1102 | GT13-3 | 0.4209 |
| 1105 | GT13-6 | 0.3894 |
| 1113 | GT13-14 | 0.1571 |

TABLE 47-continued

| Example No. | Compound | ALK-inhibiting activity IC$_{50}$ (μM) |
| --- | --- | --- |
| 1114 | GT13-15 | 0.7 |
| 1117 | GT13-18 | 2.2 |
| 1118 | GT13-19 | 0.5 |
| 1119 | GT13-20 | 0.42 |
| 1125 | GT13-26 | 0.028 |
| 1126 | GT13-27 | 3.0645 |
| 1127 | GT13-28 | 5.6311 |
| 1128 | GT13-29 | 17.4641 |
| 1129 | GT13-30 | 0.51 |
| 1130 | GT13-31 | 0.54 |
| 1164 | GT16-5 | 0.4149 |
| 1177 | GT18-6 | 0.7527 |
| 1185 | GT20-6 | 1.8 |

TABLE 48

| Example No. | Compound | Inhibitory activity on Karpas-299 cell growth IC$_{50}$ (μM) |
| --- | --- | --- |
| 15 | A7-3 | 0.1138 |
| 17 | A7-5 | 0.6268 |
| 19 | A7-7 | 0.3293 |
| 21 | A7-9 | 0.2037 |
| 22 | A7-10 | 0.3031 |
| 25 | A7-12 | 0.1119 |
| 46 | A8-3 | 0.0866 |
| 56 | A8-11 | 0.0677 |
| 58 | A8-13 | 0.0226 |
| 60 | A8-15 | 0.2322 |
| 61 | A8-16 | 0.0345 |
| 62 | A8-17 | 0.1269 |
| 64 | A8-19 | 0.0726 |
| 66 | A8-21 | 0.1050 |
| 68 | A9-2 | 0.1372 |
| 72 | A9-5 | 0.0523 |
| 93 | B2-4 | 0.0365 |
| 138 | B3-12 | 1.4358 |
| 154 | B3-25-3 | 0.7298 |
| 155 | B3-26 | 1.3613 |
| 160 | B3-30 | 0.2282 |
| 163 | B3-32 | 0.0652 |
| 167 | B3-36 | 0.0390 |
| 174 | B4-4 | 0.0812 |
| 229 | D3-2 | 0.9700 |
| 230 | D3-3 | 0.1320 |
| 244 | E4-4 | 0.1090 |
| 257 | E5-3 | 0.1895 |
| 260 | E5-6 | 0.0527 |
| 273 | F3-3 | 0.0162 |
| 287 | F4-4 | 0.0071 |
| 289 | F4-6 | 0.0291 |
| 291 | F4-8 | 0.0221 |
| 292 | F4-9 | 0.0650 |
| 294 | F5-1 | 0.0091 |
| 297 | F5-4 | 0.0018 |
| 301 | F5-8 | 0.0297 |
| 302 | F5-9 | 0.0043 |
| 303 | F5-10 | 0.0135 |
| 309 | F5-15-2 | 0.0098 |
| 310 | F5-16 | 0.0042 |
| 315 | F5-21 | 0.0663 |
| 316 | F5-22 | 0.0066 |
| 323 | F5-29 | 0.0076 |
| 325 | F5-31 | 0.0727 |
| 326 | F5-32 | 0.0240 |
| 335 | F5-40 | 0.0256 |
| 336 | F5-41 | 0.1491 |
| 339 | F5-44 | 0.0060 |
| 348 | F6-2 | 0.0295 |
| 351 | F6-5 | 0.0274 |
| 352 | F6-6 | 0.0364 |
| 357 | F6-11 | 0.0776 |
| 359 | F6-13 | 0.0079 |

TABLE 48-continued

| Example No. | Compound | Inhibitory activity on Karpas-299 cell growth IC$_{50}$ (μM) |
| --- | --- | --- |
| 420 | J7-2-3 | 0.0295 |
| 434 | J7-14 | 0.5567 |
| 446 | J9-3 | 0.0532 |
| 467 | JJ10-3 | 6.0632 |
| 488 | K10-7 | 0.0518 |
| 518 | N6-4 | 0.1224 |
| 562 | P5 | 27.7670 |
| 605 | T1-1 | 1.8669 |
| 636 | T13-6 | 1.2901 |
| 640 | T13-10 | 1.3775 |
| 642 | T14-2 | 0.6324 |
| 646 | T14-6 | 1.9418 |
| 649 | T14-9 | 1.08 |
| 656 | T16-3 | 2.25 |
| 672 | T22-1-2 | 1.7820 |
| 680 | T23-1 | 4.2526 |
| 681 | T23-2 | 7.0799 |
| 688 | T27-2 | 0.9970 |
| 689 | U5 | 0.1217 |
| 695 | U8-3-2 | 0.6773 |
| 698 | U8-4-3 | 1.10 |
| 700 | U8-5-2 | 0.3573 |
| 708 | U9 | 0.4070 |
| 710 | U10-2 | 0.94 |

TABLE 49

| Example No. | Compound | Inhibitory activity on Karpas-299 cell growth IC$_{50}$ (μM) |
| --- | --- | --- |
| 764 | L10-5 | 0.019 |
| 766 | L10-7 | 0.037 |
| 767 | L10-8 | 0.024 |
| 769 | L10-10 | 0.159 |
| 773 | B3-40 | 0.022 |
| 787 | E9-5 | 0.041 |
| 792 | E9-9 | 0.004 |
| 793 | PR11-20 | 0.020313 |
| 794 | PR11-21 | 0.06439 |
| 827 | PR9-11 | 0.036 |
| 839 | PR9-20 | 0.018772 |
| 844 | PR9-23 | 0.020492 |
| 845 | PR9-24 | 0.067888 |
| 850 | PR11-17 | 0.005766 |
| 852 | PR11-19 | 0.034632 |
| 865 | LB5-2 | 1.287666 |
| 878 | AZ7-6 | 1.126471 |
| 896 | AZ7-24 | 0.054 |
| 935 | EZ9-1 | 16.635 |
| 941 | W4-4 | 0.116 |
| 976 | GT5-3 | 1.868 |
| 979 | GT5-6 | 8.231 |
| 980 | GT5-7 | 17.135 |
| 984 | GT5-11 | 1.957 |
| 985 | GT5-12 | 19.989 |
| 986 | GT5-13 | 1.332 |
| 987 | GT5-14 | 3.787 |
| 990 | GT5-17 | 2.359 |
| 991 | GT5-18 | 4.255 |
| 993 | GT5-20 | 6.081 |
| 1020 | GT9-6 | 2.655 |
| 1115 | GT13-16 | 7.875 |
| 1123 | GT13-24 | 3.951 |
| 1124 | GT13-25 | 5.511 |
| 1131 | GT13-32 | 2.501 |
| 1132 | GT13-33 | 10.887 |

The invention claimed is:
1. A pharmaceutical for the treatment of cancer, cancer metastasis, or depression, comprising one or more pharmaceutically acceptable carriers and as an active ingredient a compound represented by Formula (I):

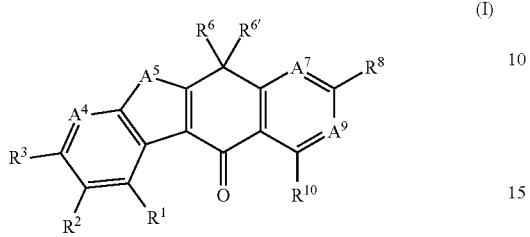

(I)

wherein,
  $A^5$ is selected from $NR^5$, O and S;
  $A^4$, $A^7$, and $A^9$ represent $CR^4$, $CR^7$, and $CR^9$ respectively, or wherein $A^4$ is N and $A^7$ and $A^9$ represent $CR^7$ and $CR^9$ respectively;
  $R^1$ and $R^{10}$ each independently represent [1] a hydrogen atom, [2] a cyano group, [3] a halogen atom or [4] a 4- to 10-membered heterocycloalkyl group which may be substituted by 4- to 10-membered heterocycloalkyl group(s);
  $R^2$ is selected from the group consisting of:
    (1) a hydrogen atom,
    (2) a $C_{1-8}$ alkyl group,
    (3) a $C_{2-8}$ alkenyl group,
    (4) a $C_{2-8}$ alkynyl group,
    (5) a cyano group,
    (6) a halogen atom,
    (7) a $(C_{1-8}$ alkyl$)_{m2}$-amino group which may be substituted by $C_{1-8}$ alkylsulfonyl group(s),
    m2: 0~2, and
    (8) a nitro group;
  $R^3$ is selected from the group consisting of:
    (1) a hydrogen atom,
    (2) a $C_{1-8}$ alkyl group which may be substituted by [1] halogen atom(s), [2] hydroxy group(s) or [3] $C_{1-8}$ alkoxy group(s),
    (3) a $C_{6-10}$ aryl group,
    (4) a cyano group,
    (5) a $C_{1-8}$ alkanoyl group which may be substituted by $C_{6-10}$ aryl group(s),
    I. (6) a (C1-8 alkyl$)_{m3a}$-aminocarbonyl group which may be substituted by one or more $R^{3A}$,
    II. $R^{3A}$: [1] a $C_{6-10}$ aryl group, [2] a $C_{1-8}$ alkoxy group, [3] a 5- to 14-membered heteroaryl group, or [4] a $C_{6-10}$ arylsulfonyl group,
    III. m3a: 0~2,
    (7) a hydroxycarbonyl group,
    (8) a $C_{1-8}$ alkoxycarbonyl group which may be substituted by [1] hydroxy group(s) or [2] $C_{1-8}$ alkoxy group(s),
    (9) a halogen atom,
    (10) a $(C_{1-8}$ alkyl$)_{m3b}$-amino group which may be substituted by $C_{6-10}$ aryl group(s),
    m3b: 0~2,
    (11) a $C_{1-8}$ alkylcarbonyl $(C_{0-8}$ alkyl) amino group which may be substituted by [1] $C_{6-10}$ aryl group(s) or [2] $C_{6-10}$ aryloxy group(s),
    (12) a $C_{6-10}$ arylcarbonyl $(C_{0-8}$ alkyl) amino group which may be substituted by $C_{1-8}$ alkyl group(s) which may be substituted by halogen atom(s),
    (13) a $(C_{1-8}$ alkyl$)_{m3c}$-aminocarbonyl $(C_{0-8}$ alkyl) amino group which may be substituted by $C_{6-10}$ aryl group(s),
    m3c: 0~2,
    (14) a nitro group,
    (15) a hydroxy group,
    (16) a $C_{1-8}$ alkoxy group which may be substituted by one or more $R^{3B}$,
    $R^{3B}$: [1] a hydroxy group, [2] a $C_{1-8}$ alkoxy group, [3] a $C_{6-10}$ aryl $(C_{0-8}$ alkyl) aminocarbonyl group, [4] a $(C_{1-8}$ alkyl$)_{m3d}$-amino group, or [5] a halogen atom,
    m3d: 0~2,
    (17) a 4- to 10-membered heterocycloalkyloxy group,
    (18) a 5- to 14-membered heteroaryloxy group,
    (19) a $(C_{1-8}$ alkyl$)_{m3e}$-aminocarbonyloxy group which may be substituted by $C_{6-10}$ aryl group(s)
    m3e: 0~2,
    (20) a 4- to 10-membered nitrogen-containing heterocycloalkylcarbonyl group,
    (21) a $C_{1-8}$ alkylsulfonyloxy group which may be substituted by halogen atom(s),
    (22) a $C_{1-8}$ alkylthio group,
    (23) a $C_{1-8}$ alkylsulfonyl group which may be substituted by $C_{6-10}$ aryl group(s),
    (24) a 5- to 14-membered heteroaryl group which may be substituted by $C_{1-8}$ alkyl group(s) which may be substituted by $C_{1-8}$ alkoxy group(s),
    (25) a $C_{1-8}$ alkoxycarbonyl $(C_{0-8}$ alkyl) amino group which may be substituted by $C_{1-8}$ alkoxy group(s),
    (26) a $C_{6-10}$ aryloxycarbonyl $(C_{0-8}$ alkyl) amino group which may be substituted by $C_{1-8}$ alkyl group(s) which may be substituted by halogen atom(s),
    (27) a $C_{6-10}$ aryl $(C_{0-8}$ alkyl) aminocarbonyl $(C_{0-8}$ alkyl) amino group which may be substituted by one or more $R^{3C}$,
    $R^{3C}$: [1] a $C_{1-8}$ alkyl group which may be substituted by halogen atom(s), or [2] a $C_{1-8}$ alkoxy group,
    (28) a $C_{3-8}$ cycloalkyl $(C_{0-8}$ alkyl) aminocarbonyloxy group, and
    (29) a $C_{6-10}$ aryl $(C_{0-8}$ alkyl) aminocarbonyloxy group which may be substituted by substituent(s) selected from the group consisting of [1] a $C_{1-8}$ alkyl group and [2] a $C_{1-8}$ alkoxy group;
  $R^4$ is selected from the group consisting of:
    (1) a hydrogen atom,
    (2) a $C_{1-8}$ alkyl group which may be substituted by halogen atom(s),
    (3) a $C_{2-8}$ alkenyl group,
    (4) a $C_{2-8}$ alkynyl group,
    (5) a $C_{3-8}$ cycloalkyl group,
    (6) a cyano group,
    (7) an aminocarbonyl group,
    (8) a $(C_{1-8}$ alkyl$)_{m4a}$-aminocarbonyl group,
    m4a: 1~2,
    (9) a hydroxycarbonyl group,
    (10) a $C_{1-8}$ alkoxycarbonyl group,
    (11) a halogen atom,
    (12) a $(C_{1-8}$ alkyl$)_{m4b}$-amino group,
    m4b: 0~2,
    (13) a hydroxy group, and
    (14) a $C_{1-8}$ alkoxy group which may be substituted by hydroxy group(s);

$R^5$ is selected from the group consisting of:
(1) a hydrogen atom,
(2) a $C_{1-8}$ alkyl group which may be substituted by one or more $R^{5A}$,
$R^{5A}$: [1] a hydroxycarbonyl group, [2] a $C_{1-8}$ alkoxycarbonyl group, [3] a hydroxy group, [4] a $C_{1-8}$ alkoxy group, [5] a $(C_{1-8}$ alkyl$)_{m5}$-amino group, [6] a $C_{6-10}$ aryl group, or [7] a $C_{1-8}$ alkylthio group,
m5: 0~2,
(3) a $C_{2-8}$ alkenyl group,
(4) a $C_{2-8}$ alkynyl group,
(5) a $C_{3-8}$ cycloalkyl group, and
(6) a $C_{1-8}$ alkylsulfonyl group;
$R^6$ and $R^{6'}$ are each independently selected from the group consisting of:
(1) a $C_{1-8}$ alkyl group which may be substituted by halogen atom(s),
(2) a $C_{2-8}$ alkenyl group, and
(3) a $C_{2-8}$ alkynyl group; or
$R^6$ and $R^{6'}$ are taken together with the carbon atoms to which they are bound to form:
(4) a $C_{3-8}$ cycloalkyl group, or
(5) a 4- to 10-membered heterocycloalkyl group which may be substituted by $C_{1-8}$ alkyl $C_{6-10}$ aryl sulfonyl group(s) which may be substituted by $C_{1-8}$ alkyl group(s);
$R^7$ is selected from the group consisting of:
(1) a hydrogen atom,
(2) a halogen atom,
IV. (3) a $C_{1-8}$ alkoxy group which may be substituted by one or more $R^{7A}$,
V. $R^{7A}$: [1] a $(C_{1-8}$ alkyl$)$m7a-amino group, [2] a hydroxy, [3] a 4- to 10-membered heterocycloalkyl group which may be substituted by $C_{1-8}$ alkyl group(s),
VI. m7a: 0~2,
(4) a $C_{1-8}$ alkylsulfonyl group,
(5) a nitro group, and
(6) a hydroxyl group;
$R^8$ is selected from the group consisting of:
(1) a hydrogen atom,
(2) a $C_{1-8}$ alkyl group which may be substituted by one or more $R^{8A}$,
$R^{8A}$: [1] a 4- to 10-membered heterocycloalkyl group which may be substituted by one or more $R^{8A1}$, [2] a $(C_{1-8}$ alkyl$)_{m8a}$-amino group which may be substituted by a halogen atom, or [3] a hydroxy group,
m8a: 0~2,
$R^{8A1}$: [1] a $C_{1-8}$ alkyl group, [2] a $C_{1-8}$ alkylsulfonyl group, [3] a $(C_{1-8}$ alkyl$)_{m8b}$-aminosulfonyl group, [4] an oxo group, [5] a $C_{1-8}$ alkoxycarbonyl, or [6] a $C_{1-8}$ alkoxycarbonyl $(C_{0-8}$ alkyl$)$ aminosulfonyl,
m8b: 0~2,
(3) a $C_{2-8}$ alkenyl group,
(4) a 4- to 10-membered heterocycloalkyl group which may be substituted by one or more $R^{8B}$,
$R^{8B}$:
<1> a $C_{1-8}$ alkyl group which may be substituted by one or more $R^{8B1}$,
<2> a $C_{2-8}$ alkeynyl group,
<3> a $C_{2-8}$ alkynyl group,
<4> a $C_{3-8}$ cycloalkyl group which may be substituted by [1] cyano group(s) or [2] $C_{1-8}$ alkyl group(s),
<5> a 4- to 10-membered heterocycloalkyl group which may be substituted by one or more $R^{8B2}$, <6> a $C_{1-8}$ alkoxy group which may be substituted by substituent(s) selected from the group consisting of [1] a $C_{1-8}$ alkoxy group and [2] a $C_{3-8}$ cycloalkyl group,
<7> a $C_{1-8}$ alkoxycarbonyl group,
<8> a $C_{1-8}$ alkylsulfonyl group,
<9> a 5- to 14-membered heteroarylsulfonyl group,
<10> an oxo group,
<11> a cyano group,
<12> a $C_{1-8}$ alkanoyl group which may be substituted by one or more $R^{8B3}$,
<13> a $C_{3-8}$ cycloalkylcarbonyl group,
<14> a $(C_{1-8}$ alkyl$)_{m8c}$-aminosulfonyl group,
<15> a $C_{1-8}$ alkylsulfonyl $(C_{0-8}$ alkyl$)$ amino group,
<16> a $(C_{1-8}$ alkyl$)_{m8d}$-amino group which may be substituted by one or more $R^{8B4}$,
<17> a hydroxy group,
<18> a $(C_{1-8}$ alkyl$)_{m8e}$-aminocarbonyl group, or
<19> a $C_{1-8}$ alkoxycarbonyl $(C_{0-8}$ alkyl$)$ amino group
m8c: 0~2
m8d: 0~2
m8e: 0~2
$R^{8B1}$: [1] a $C_{3-8}$ cycloalkyl group, [2] a hydroxy group, or [3] a $C_{1-8}$ alkoxy group(s),
$R^{8B2}$: [1] a halogen atom, [2] a $C_{1-8}$ alkyl group, [3] an oxo group, [4] a hydroxy group, or [5] a deuterium atom,
$R^{8B3}$: a $(C_{1-8}$ alkyl$)_{m8f}$-amino group,
m8f: 0~2,
$R^{8B4}$: [1] a $C_{3-8}$ cycloalkyl group, or [2] a hydroxy group,
(5) a 5- to 14-membered heteroaryl group which may be substituted by a $C_{1-8}$ alkyl group,
(6) a $(C_{1-8}$ alkyl$)_{m8g}$-aminocarbonyl group which may be substituted by one or more $R^{8C}$,
m8g: 0~2,
$R^{8C}$: [1] a hydroxy group, [2] a $(C_{1-8}$ alkyl$)_{m8h}$-amino group which may be substituted by substituent(s) selected from the group consisting of <1> a $(C_{1-8}$ alkyl$)_{m8i}$-aminosulfonyl group, <2> a $C_{1-8}$ alkylsulfonyl group, <3> a $C_{1-8}$ alkoxycarbonyl group and <4> a $C_{1-8}$ alkoxycarbonyl$(C_{0-8}$ alkyl$)$ aminosulfonyl group, [3] a $C_{1-8}$ alkylsulfonyl group, or [4] a $C_{1-8}$ alkoxy group which may be substituted by a hydroxy group,
m8h: 0~2,
m8i: 0~2,
(7) a 4- to 10-membered heterocycloalkyl $(C_{0-8}$ alkyl$)$ aminocarbonyl group which may be substituted by oxo group(s),
(8) a 4- to 10-membered nitrogen-containing heterocycloalkylcarbonyl group which may be substituted by one or more $R^{8D}$,
$R^{8D}$: [1] a $C_{1-8}$ alkyl group which may be substituted by one or more $R^{8D1}$, [2] a hydroxy group, [3] a $C_{1-8}$ alkylsulfonyl group, or [4] a $C_{1-8}$ alkoxycarbonyl group,
$R^{8D1}$: [1] a hydroxy group, or [2] a $C_{1-8}$ alkoxy group,
(9) a hydroxycarbonyl group,
(10) a $C_{0-8}$ alkoxy $(C_{0-8}$ alkyl$)$ aminocarbonyl group which may be substituted by hydroxy group(s),
(11) a halogen atom,
(12) a $(C_{1-8}$ alkyl$)_{m8j}$-amino group which may be substituted by one or more $R^{8H}$,
m8j: 0~2,
$R^{8H}$: [1] a hydroxy group, or [2] a 4- to 10-membered heterocycloalkyl group,

(13) a hydroxyl group,
(14) a $C_{1-8}$ alkoxy group which may be substituted by one or more $R^{8E}$, $R^{8E}$:
<1> a hydroxy group,
<2> halogen atom,
<3> a hydroxycarbonyl group,
<4> a $C_{1-8}$ alkoxycarbonyl group,
<5> a 4- to 10-membered nitrogen-containing heterocycloalkylcarbonyl group which may be substituted by one or more $R^{8E1}$,
<6> a $(C_{1-8}$ alkyl$)_{m8k1}$-amino group which may be substituted by one or more $R^{8E2}$,
m8k1: 0~2,
<7> a 4- to 10-membered heterocycloalkyl group which may be substituted by one or more $R^{8E3}$,
<8> a 5- to 14-membered heteroaryl group,
<9> a $(C_{1-8}$ alkyl$)_{m8k2}$-aminocarbonyl group which may be substituted by one or more $R^{8E6}$,
m8k2: 0~2,
<10> a $C_{1-8}$ alkoxy group which may be substituted by one or more $R^{8E7}$,
<11> a $C_{1-8}$ alkylthio group,
<12> a $C_{1-8}$ alkylsulfinyl group,
<13> a $C_{1-8}$ alkylsulfonyl group, $R^{8E1}$:
<1> a $C_{1-8}$ alkoxycarbonyl group,
<2> a $C_{1-8}$ alkanoyl group,
<3> a $C_{1-8}$ alkylsulfonyl group,
<4> a $(C_{1-8}$ alkyl$)_{m8k3}$-aminosulfonyl group,
m8k3: 0~2, or
<5> a 4- to 10-membered heterocycloalkyl group, $R^{8E2}$:
<1> a hydroxy group,
<2> a $C_{1-8}$ alkoxycarbonyl group which may be substituted by halogen atom(s),
<3> a $C_{3-8}$ cycloalkyl group which may be substituted by $C_{1-8}$ alkyl group(s) which may be substituted by hydroxy group(s),
<4> a $C_{1-8}$ alkanoyl group which may be substituted by substituent(s) selected from the group consisting of [1] a $(C_{1-8}$ alkyl$)_{m8k4}$-amino group and [2] a halogen atom(s),
m8k4: 0~2,
<5> a $(C_{1-8}$ alkyl$)_{m8k5}$-aminocarbonyl group,
m8k5: 0~2,
<6> a $C_{1-8}$ alkylsulfonyl group,
<7> a 4- to 10-membered nitrogen-containing heterocycloalkylsulfonyl group which may be substituted by $C_{1-8}$ alkyl group(s),
<8> a $(C_{1-8}$ alkyl$)_{m8k6}$-aminosulfonyl group which may be substituted by $C_{1-8}$ alkoxycarbonyl group(s),
m8k6: 0~2, or $R^{8E3}$:
<1> a $C_{1-8}$ alkyl group which may be substituted by substituent(s) selected from the group consisting of [1] a hydroxy group and [2] a $C_{1-8}$ alkylcarbonyloxy group,
<2> a $C_{1-8}$ alkylcarbonyloxy group,
<3> a hydroxy group,
<4> a $C_{3-8}$ cycloalkyl group,
<5> a $C_{1-8}$ alkoxy group,
<6> a $C_{1-8}$ alkoxycarbonyl group,
<7> a $C_{1-8}$ alkylsulfonyl group,
<8> a $(C_{1-8}$ alkyl$)_{m8k8}$-aminocarbonyl group
m8k8: 0~2,
<9> a $C_{1-8}$ alkanoyl group which may be substituted by hydroxy group(s),
<10> an oxo group, or
<11> a 4- to 10-membered heterocycloalkyl group which may be substituted by substituent(s) selected from the group consisting of [1] a $C_{1-8}$ alkanoyl group, [2] a $C_{1-8}$ alkoxycarbonyl group and [3] a $C_{1-8}$ alkylsulfonyl group, $R^{8E6}$:
<1> a $C_{2-8}$ alkenylcarbonyloxy group,
<2> a hydroxy group,
<3> a cyano group,
<4> a $(C_{1-8}$ alkyl$)_{m8k9}$-amino group which may be substituted by hydroxy group(s)
m8k9: 0~2,
<5> a $C_{1-8}$ alkoxy group which may be substituted by hydroxy group(s),
<6> a $C_{1-8}$ alkylcarbonyloxy group,
<7> a 4- to 10-membered heterocycloalkyl group which may be substituted by $C_{1-8}$ alkyl group(s), or
<8> a 5- to 14-membered heteroaryl group, $R^{8E7}$:
<1> a hydroxy group, or
<2> a $C_{1-8}$ alkoxy group which may be substituted by hydroxy group(s),
(15) a 4- to 10-membered heterocycloalkyloxy group which may be substituted by one or more $R^{8F}$, $R^{8F}$:
<1> a $C_{1-8}$ alkyl group which may be substituted by one or more $R^{8F1}$,
<2> a $C_{3-8}$cycloalkyl group,
<3> a $C_{1-8}$ alkanoyl group which may be substituted by halogen atom(s),
<4> a $C_{1-8}$ alkylcarbonyloxy group,
<5> a $C_{1-8}$ alkoxycarbonyl group,
<6> a 4- to 10-membered heterocycloalkyl group which may be substituted by one or more $R^{8F2}$,
<7> a $C_{1-8}$ alkyl sulfonyl group,
<8> a hydroxy group, or
[9] a $C_{6-10}$ aryl group,
$R^{8F1}$: [1] a hydroxy group, [2] a $C_{1-8}$ alkoxy group, or [3] a halogen atom,
$R^{8F2}$: [1] a 4- to 10-membered heterocycloalkyl group, [2] a $C_{1-8}$ alkoxycarbonyl group, or [3] a $C_{1-8}$ alkylsulfonyl group,
(16) a 5- to 14-membered heteroaryloxy group,
(17) a 4- to 10-membered heterocycloalkylcarbonyloxy group,
(18) a $(C_{1-8}$ alkyl$)_{m8l1}$-aminosulfonyloxy group,
m8l1: 0~2,
(19) a $C_{1-8}$ alkyl thio group which may be substituted by [1] $(C_{1-8}$ alkyl$)_{m8l2}$-amino group(s), [2] hydroxy group(s) or [3] hydroxycarbonyl group(s),
m8l2: 0~2,
(20) a $C_{1-8}$ alkylsulfonyl group which may be substituted by one or more $R^{8G}$,
$R^{8G}$: [1] a hydroxycarbonyl group, [2] a hydroxy group, or [3] a $(C_{1-8}$ alkyl$)_{m8l3}$-amino group,
m8l3: 0~2,
(21) a 4- to 10-membered nitrogen-containing heterocycloalkylsulfonyloxy group which may be substituted by $C_{1-8}$ alkyl group(s),
(22) a $C_{2-8}$ alkenyloxy group, and
(23) a $C_{1-8}$ alkylsulfonyloxy group which may be substituted by halogen atom(s);
$R^9$ is selected from the group consisting of:
(1) a hydrogen atom,
(2) a $C_{1-8}$ alkyl group which may be substituted by one or more $R^{9A}$, $R^{9A}$: [1] a $C_{3-8}$ cycloalkyl group, [2] a 4- to 10-membered heterocycloalkyl group which may be substituted by one or more $R^{9A1}$, [3] a hydroxy group, [4] a $C_{1-8}$ alkoxy group, or [5] a hydroxycarbonyl group, $R^{9A1}$: [1] a $C_{1-8}$ alkyl group, [2] a $C_{3-8}$ cycloalkyl group, or [3] a 4- to 10-membered heterocycloalkyl group, (3) a $C_{2-8}$ alkenyl group which may be substituted by one or more $R^{9B}$, $R^{9B}$: [1] a $(C_{1-8}$ alkyl$)_{m9a}$-amino group, [2] a 4- to 10-membered heterocycloalkyl group which may be substituted by one or more group $R^{9B1}$, $R^{9B1}$: [1] a $C_{3-8}$ cycloalkyl group, or [2] a 4- to 10-membered heterocycloalkyl group, m9a: 0~2, (4) a $C_{2-8}$ alkynyl group which may be substituted by one or more $R^{9C}$, $R^{9C}$: [1] a $C_{1-8}$ alkoxy group, [2] a $(C_{1-8}$ alkyl$)_{m9b}$-amino group which may be substituted by $C_{6-10}$ aryl group(s), [3] a 4- to 10-membered heterocycloalkyl group which may be substituted by one or more $R^{9C1}$, [4] a $C_{3-8}$ cycloalkyl group, [5] a hydroxy group, [6] a hydroxycarbonyl group, or [7] a $C_{1-8}$ alkyloxycarbonyl group, m9b: 0~2, $R^{9C1}$: [1] a $C_{3-8}$ cycloalkyl group, [2] a 4- to 10-membered heterocycloalkyl group, or [3] an oxo group, (5) a $C_{3-8}$ cycloalkyl group, (6) a 4- to 10-membered heterocycloalkyl group which may be substituted by one or more $R^{9D}$, $R^{9D}$: [1] a $C_{1-8}$ alkyl group which may be substituted by 4- to 10-membered heterocycloalkyl group(s), [2] a $C_{3-8}$ cycloalkyl group, [3] a 4- to 10-membered heterocycloalkyl group, or [4] a $C_{1-6}$ alkylsulfonyl group, or [5] a $C_{1-8}$ alkoxycarbonyl group, (7) a $C_{6-10}$ aryl group which may be substituted by one or more $R^{9E}$, $R^{9E}$: [1] a halogen atom, [2] a hydroxy group, [3] a hydroxycarbonyl group, or [4] a $C_{1-8}$ alkyl group which may be substituted by hydroxy group(s), or [5] a $C_{1-8}$ alkoxy group, (8) a 5- to 14-membered heteroaryl group which may be substituted by $C_{1-8}$ alkyl group(s), (9) a cyano group,

(10) a $C_{1-8}$ alkanoyl group,

(11) a 4- to 10-membered nitrogen-containing heterocycloalkylcarbonyl group which may be substituted by $C_{1-8}$ alkyl group(s),

(12) a halogen atom,

(13) a $(C_{1-8}$ alkyl$)_{m9c}$-amino group which may be substituted by one or more $R^{9F}$, m9c: 0~2, $R^{9F}$: [9F-1] a $C_{1-3}$ alkylsulfonyl group, [9F-2] a $(C_{1-3}$ alkyl$)_{m9f1}$-aminosulfonyl group (m9f1: 0~2), or [9F-3] a $C_{1-3}$ alkanoyl group which may be substituted by $(C_{1-3}$ alkyl$)_{m9f2}$-amino group(s) (m9f2: 0~2),

(14) a $C_{1-8}$ alkylcarbonyl($C_{0-8}$ alkyl)amino group which may be substituted by $(C_{1-8}$ alkyl$)_{m9d}$-amino group(s), m9d: 0~2,

(15) a $C_{1-8}$ alkylsulfonyl($C_{0-8}$ alkyl)amino group,

(16) a $(C_{1-8}$ alkyl$)_{m9e}$-aminosulfonyl($C_{0-8}$ alkyl)amino group, m9e: 0~2,

(17) a nitro group,

(18) a hydroxy group,

(19) a $C_{1-8}$ alkoxy group which may be substituted by one or more $R^{9G}$, $R^{9G}$: [1] a hydroxy group, [2] a hydroxycarbonyl group, [3] a $C_{6-10}$ aryl group which may be substituted by $C_{1-8}$ alkoxy group(s), [4] a $(C_{1-8}$ alkyl$)_{m9g1}$-amino group, [5] a $C_{1-8}$ alkoxy group which may be substituted by one or more $R^{9G1}$, [6] a 5- to 14-membered heteroaryl group, or [7] a 4- to 10-membered heterocycloalkyloxy group which may be substituted by $C_{1-8}$ alkyl group(s), m9g1: 0~2, $R^{9G1}$: [1] a $C_{1-8}$ alkoxy group, or [2] a hydroxycarbonyl group,

(20) a 4- to 10-membered heterocycloalkyloxy group which may be substituted by [1] 4- to 10-membered heterocycloalkyl group(s), or [2] $C_{1-8}$ alkoxycarbonyl group(s),

(21) a $C_{1-8}$ alkylsulfonyloxy group which may be substituted by halogen atom(s),

(22) a $C_{1-8}$ alkylthio group which may be substituted by $(C_{1-8}$ alkyl$)_{m9f}$-amino group(s), m9f: 0~2,

(23) a $C_{1-8}$ alkylsulfonyl group which may be substituted by $(C_{1-8}$ alkyl$)_{m9g}$-amino group(s), m9g: 0~2,

(24) a $(C_{1-8}$ alkyl$)_{m9h}$-aminosulfonyl group, m9h: 0~2,

(25) a 4- to 10-membered nitrogen-containing heterocycloalkylsulfonyl group which may be substituted by $C_{1-8}$ alkyl group(s), and

(26) a hydroxycarbonyl group, or a salt or solvate thereof.

2. The pharmaceutical of claim 1, wherein $R^3$ is a cyano group or a halogen atom.

3. The pharmaceutical of claim 1, wherein $A^5$ is $NR^5$ and $R^5$ is a hydrogen atom.

4. The pharmaceutical of claim 1, wherein $A^5$ is $NR^5$ and $R^5$ is a hydrogen atom.

5. The pharmaceutical of claim 1, wherein:

$A^1, A^2, A^3, A^4, A^7, A^8, A^9$ and $A^{10}$ all represent C;

$A^5$ is selected from $NR^5$, O and S;

$R^1$ represents [1] a hydrogen atom, [2] a cyano group, or [3] a halogen atom;

$R^2$ is selected from the group consisting of:

(1) a hydrogen atom, (2) a $C_{1-8}$ alkyl group, (3) a cyano group, (4) a halogen atom, and (5) a $(C_{1-8}$ alkyl$)_{m2}$-amino group which may be substituted by $C_{1-8}$ alkylsulfonyl group(s), m2: 0~2;

$R^3$ is selected from the group consisting of:

(1) a hydrogen atom, (2) a $C_{1-8}$ alkyl group which may be substituted by halogen atom(s), (3) a cyano group, VII. (4) a $(C_{1-8}$ alkyl$)_{m3a}$-aminocarbonyl group which may be substituted by one or more $R^{3A}$, VIII. $R^{3A}$: [1] a $C_{6-10}$ aryl group, [2] a $C_{1-8}$ alkoxy group, [3] a 5- to 14-membered heteroaryl group, or [4] a $C_{6-10}$ aryl sulfonyl group, m3a: 0~2, (5) a hydroxycarbonyl group, (6) a $C_{1-8}$ alkoxycarbonyl group which may be substituted by hydroxy group(s), (7) a halogen atom, (8) a $(C_{1-8}\text{ alkyl})_{m3b}$-amino group which may be substituted by $C_{6-10}$ aryl group(s),
m3b: 0~2,
(9) a $C_{1-8}$ alkylcarbonyl ($C_{0-8}$ alkyl) amino group which may be substituted by [1] $C_{6-10}$ aryl group(s) or [2] $C_{6-10}$ aryloxy group(s),
(10) a $C_{6-10}$ arylcarbonyl ($C_{0-8}$ alkyl) amino group which may be substituted by $C_{1-8}$ alkyl group(s) which may be substituted by halogen atom(s),
(11) a nitro group,
(12) a hydroxy group,
(13) a $C_{1-8}$ alkoxy group which may be substituted by one or more $R^{3B}$,
$R^{3B}$: [1] a hydroxy group, [2] a $C_{1-8}$ alkoxy group, [3] a $C_{6-10}$ aryl ($C_{0-8}$ alkyl) aminocarbonyl group, [4] a $(C_{1-8}\text{ alkyl})_{m3d}$-amino group, or [5] a halogen atom,
m3d: 0~2,
(14) a 4- to 10-membered heterocycloalkyloxy group,
(15) a 5- to 14-membered heteroaryloxy group,
(16) a $(C_{1-8}\text{ alkyl})_{m3e}$-aminocarbonyloxy group which may be substituted by $C_{6-10}$ aryl group(s),
m3e: 0~2,
(17) a 4- to 10-membered nitrogen-containing heterocycloalkylcarbonyl group,
(18) a $C_{1-8}$ alkylthio group,
(19) a 5- to 14-membered heteroaryl group which may be substituted by $C_{1-8}$ alkyl group(s) which may be substituted by $C_{1-8}$ alkoxy group(s),
(20) a $C_{1-8}$ alkoxycarbonyl ($C_{0-8}$ alkyl) amino group which may be substituted by $C_{1-8}$ alkoxy group(s),
(21) a $C_{6-10}$ aryloxycarbonyl ($C_{0-8}$ alkyl) amino group which may be substituted by $C_{1-8}$ alkyl group(s) which may be substituted by halogen atom(s),
(22) a $C_{6-10}$ aryl ($C_{0-8}$ alkyl) aminocarbonyl ($C_{0-8}$ alkyl) amino group which may be substituted by $C_{1-8}$ alkoxy group(s),
(23) a $C_{3-8}$ cycloalkyl ($C_{0-8}$ alkyl) aminocarbonyloxy group, and
(24) a $C_{6-10}$ aryl ($C_{0-8}$ alkyl) aminocarbonyloxy group which may be substituted by substituent(s) selected from the group consisting of [1] a $C_{1-8}$ alkyl group and [2] a $C_{1-8}$ alkoxy group;
$R^4$ is selected from the group consisting of:
(1) a hydrogen atom,
(2) a $C_{1-8}$ alkyl group which may be substituted by halogen atom(s),
(3) a $C_{3-8}$ cycloalkyl group,
(4) a cyano group,
(5) an aminocarbonyl group,
(6) a hydroxycarbonyl group,
(7) a halogen atom,
(8) a $(C_{1-8}\text{ alkyl})_{m4b}$-amino group,
m4b: 0~2,
(9) a hydroxy group, and
(10) a $C_{1-8}$ alkoxy group which may be substituted by hydroxy group(s);
$R^5$ is selected from the group consisting of:
(1) a hydrogen atom,
(2) a $C_{1-8}$ alkyl group which may be substituted by one or more $R^{5A}$,
$R^{5A}$: [1] a hydroxycarbonyl group, [2] a $C_{1-8}$ alkoxycarbonyl group, [3] a hydroxy group, [4] a $C_{1-8}$ alkoxy group, [5] a $(C_{1-8}\text{ alkyl})_{m5}$-amino group, or [6] a $C_{1-8}$ alkylthio group,
m5: 0~2, and
(3) a $C_{1-8}$ alkylsulfonyl group;

$R^6$ and $R^{6'}$ are each independently:
(1) a $C_{1-8}$ alkyl group, or
$R^6$ and $R^{6'}$ are taken together with the carbon atoms to which they are bound to form,
(2) a $C_{3-8}$ cycloalkyl group, or
(3) a 4- to 10-membered heterocycloalkyl group;
$R^7$ is selected from the group consisting of:
(1) a hydrogen atom,
(2) a halogen atom, and
(3) a $C_{1-8}$ alkoxy group which may be substituted by one or more $R^{7A}$,
$R^{7A}$: [1] a $(C_{1-8}\text{ alkyl})_{m7a}$-amino group, or [2] a hydroxy group,
m7a: 0~2;
$R^8$ is selected from the group consisting of:
(1) a hydrogen atom,
(2) a $C_{1-8}$ alkyl group which may be substituted by one or more $R^{8A}$,
$R^{8A}$: [1] a 4- to 10-membered heterocycloalkyl group which may be substituted by one or more $R^{8A1}$, [2] a $(C_{1-8}\text{ alkyl})_{m8a}$-amino group which may be substituted by a halogen atom, or [3] a hydroxy group,
m8a:0~2,
$R^{8A1}$: [1] a $C_{1-8}$ alkyl group, [2] a $C_{1-8}$ alkylsulfonyl group, [3] a $(C_{1-8}\text{ alkyl})_{m8b}$-aminosulfonyl group, or [4] an oxo group,
m8b: 0~2,
(3) a $C_{2-8}$ alkenyl group,
(4) a 4- to 10-membered heterocycloalkyl group which may be substituted by one or more $R^{8B}$,
$R^{8B}$:
<1> a $C_{1-8}$ alkyl group which may be substituted by one or more $R^{8B1}$,
<2> a $C_{2-8}$ alkynyl group,
<3> a $C_{3-8}$ cycloalkyl group which may be substituted by [1] cyano group(s) or [2] $C_{1-8}$ alkyl group(s),
<4> a 4- to 10-membered heterocycloalkyl group which may be substituted by one or more $R^{8B2}$,
<5> a $C_{1-8}$ alkoxy group which may be substituted by substituent(s) selected from the group consisting of [1] a $C_{1-8}$ alkoxy group and [2] a $C_{3-8}$ cycloalkyl group,
<6> a $C_{1-8}$ alkylsulfonyl group,
<7> an oxo group,
<8> a cyano group,
<9> a $C_{1-8}$ alkanoyl group which may be substituted by one or more $R^{8B3}$,
<10> a $C_{3-8}$ cycloalkylcarbonyl group,
<11> a $(C_{1-8}\text{ alkyl})_{m8c}$-aminosulfonyl group,
<12> a $C_{1-8}$ alkylsulfonyl ($C_{0-8}$ alkyl) amino group,
<13> a $(C_{1-8}\text{ alkyl})_{m8d}$-amino group which may be substituted by one or more $R^{8B4}$,
<14> a hydroxy group, or
<15> a $(C_{1-8}\text{ alkyl})_{m8e}$-aminocarbonyl group,
m8c: 0~2,
m8d: 0~2,
m8e: 0~2,
$R^{8B1}$: [1] a $C_{3-8}$ cycloalkyl group, [2] a hydroxy group, or [3] $C_{1-8}$ alkoxy group,
$R^{8B2}$: [1] a halogen atom, [2] a $C_{1-8}$ alkyl group, [3] an oxo group, or [4] a hydroxy group,
$R^{8B3}$: a $(C_{1-8}\text{ alkyl})_{m8f}$-amino group,
m8f: 0~2,
$R^{8B4}$: [1] a $C_{3-8}$ cycloalkyl group, or [2] a hydroxy group,
(5) a 5- to 14-membered heteroaryl group which may be substituted by a $C_{1-8}$ alkyl group,
(6) a $(C_{1-8}\text{ alkyl})_{m8g}$-aminocarbonyl group which may be substituted by one or more $R^{8C}$, m8g: 0~2, $R^{8C}$: [1] a hydroxy group, [2] a $(C_{1-8}$ alkyl$)_{m8h}$-amino group which may be substituted by substituent(s) selected from the group consisting of <1> a $(C_{1-8}$ alkyl$)_{m8i}$-aminosulfonyl group and <2> a $C_{1-8}$ alkylsulfonyl group, or [3] a $C_{1-8}$ alkylsulfonyl group, m8h: 0~2, m8i: 0~2, (7) a 4- to 10-membered heterocycloalkyl ($C_{0-8}$ alkyl) aminocarbonyl group which may be substituted by oxo group(s), (8) a 4- to 10-membered nitrogen-containing heterocycloalkylcarbonyl group which may be substituted by one or more $R^{8D}$, $R^{8D}$: [1] a $C_{1-8}$ alkyl group which may be substituted by one or more $R^{8D1}$, [2] a hydroxy group, or [3] a $C_{1-8}$ alkylsulfonyl group, $R^{8D1}$: [1] a hydroxy group, or [2] a $C_{1-8}$ alkoxy group, (9) a hydroxycarbonyl group,

(10) a $C_{0-8}$ alkoxy ($C_{0-8}$ alkyl) aminocarbonyl group which may be substituted by hydroxy group(s),

(11) a halogen atom,

(12) a $(C_{1-8}$ alkyl$)_{m8j}$-amino group which may be substituted by 4- to 10-membered heterocycloalkyl group(s), m8j: 0~2,

(13) a hydroxyl group,

(14) a $C_{1-8}$ alkoxy group which may be substituted by one or more $R^{8E}$, $R^{8E}$:

<1> a hydroxy group,

<2> a $C_{1-8}$ alkoxycarbonyl group,

<3> a 4- to 10-membered nitrogen-containing heterocycloalkylcarbonyl group which may be substituted by one or more $R^{8E1}$, <4> a $(C_{1-8}$ alkyl$)_{m8k1}$-amino group which may be substituted by one or more $R^{8E2}$, m8k1: 0~2, <5> a 4- to 10-membered heterocycloalkyl group which may be substituted by one or more $R^{8E3}$, <6> a 5- to 14-membered heteroaryl group, <7> a $(C_{1-8}$ alkyl$)_{m8k2}$-aminocarbonyl group which may be substituted by one or more $R^{8E6}$ m8k2: 0~2, <8> a $C_{1-8}$ alkoxy group which may be substituted by one or more $R^{8E7}$, <9> a $C_{1-8}$ alkylthio group, <10> a $C_{1-8}$ alkylsulfinyl group, or <11> a $C_{1-8}$ alkylsulfonyl group, $R^{8E1}$:

<1> a $C_{1-8}$ alkoxycarbonyl group,

<2> a $C_{1-8}$ alkanoyl group,

<3> a $C_{1-8}$ alkylsulfonyl group,

<4> a $(C_{1-8}$ alkyl$)_{m8k3}$-aminosulfonyl group m8k3: 0~2, or

<5> a 4- to 10-membered heterocycloalkyl group, $R^{8E2}$:

<1> a hydroxy group,

<2> a $C_{1-8}$ alkoxycarbonyl group,

<3> a $C_{3-8}$ cycloalkyl group which may be substituted by $C_{1-8}$ alkyl group(s) which may be substituted by hydroxy group(s), <4> a $C_{1-8}$ alkanoyl group which may be substituted by substituent(s) selected from the group consisting of [1] a $(C_{1-8}$ alkyl$)_{m8k4}$-amino group and [2] a halogen atom, m8k4: 0~2, <5> a $(C_{1-8}$ alkyl$)_{m8k5}$-aminocarbonyl group, m8k5: 0~2, <6> a $C_{1-8}$ alkylsulfonyl group, <7> a 4- to 10-membered nitrogen-containing heterocycloalkylsulfonyl group which may be substituted by $C_{1-8}$ alkyl group(s), <8> a $(C_{1-8}$ alkyl$)_{m8k6}$-aminosulfonyl group, m8k6: 0~2, or $R^{8E3}$:

<1> a $C_{1-8}$ alkyl group which may be substituted by substituent(s) selected from the group consisting of [1] a hydroxy group and [2] a $C_{1-8}$ alkylcarbonyloxy group, <2> a hydroxy group, <3> a $C_{3-8}$ cycloalkyl group, <4> a $C_{1-8}$ alkylsulfonyl group, <5> a $(C_{1-8}$ alkyl$)_{m8k8}$-aminocarbonyl group, m8k8: 0~2, <6> a $C_{1-8}$ alkanoyl group which may be substituted by hydroxy group(s), <7> an oxo group, or <8> a 4- to 10-membered heterocycloalkyl group which may be substituted by substituent(s) selected from the group consisting of [1] a $C_{1-8}$ alkanoyl group, and [2] a $C_{1-8}$ alkylsulfonyl group, $R^{8E6}$:

<1> a $C_{2-8}$ alkenylcarbonyloxy group,

<2> a hydroxy group,

<3> a cyano group,

<4> a $(C_{1-8}$ alkyl$)_{m8k9}$-amino group which may be substituted by hydroxy group(s), m8k9: 0~2, <5> a $C_{1-8}$ alkoxy group which may be substituted by hydroxy group(s), <6> a 4- to 10-membered heterocycloalkyl group which may be substituted by $C_{1-8}$ alkyl group(s), or <7> a 5- to 14-membered heteroaryl group, $R^{8E7}$:

<1> a hydroxy group, or

<2> a $C_{1-8}$ alkoxy group which may be substituted by hydroxy group(s),

(15) a 4- to 10-membered heterocycloalkyloxy group which may be substituted by one or more $R^{8F}$:

$R^{8F}$:

<1> a $C_{1-8}$ alkyl group which may be substituted by one or more $R^{8F1}$,

<2> a $C_{3-8}$ cycloalkyl group,

<3> a $C_{1-8}$ alkanoyl group which may be substituted by halogen atom(s),

<4> a $C_{1-8}$ alkoxycarbonyl group,

<5> a 4- to 10-membered heterocycloalkyl group which may be substituted by one or more $R^{8F2}$, <6> a $C_{1-8}$ alkyl sulfonyl group, or <7> a hydroxy group, $R^{8F1}$: [1] a hydroxy group, [2] a $C_{1-8}$ alkoxy group, or [3] a halogen atom, $R^{8F2}$: [1] a 4- to 10-membered heterocycloalkyl group, [2] a $C_{1-8}$ alkoxycarbonyl group, or [3] a $C_{1-8}$ alkylsulfonyl group,

(16) a 5- to 14-membered heteroaryloxy group,

(17) a $(C_{1-8}$ alkyl$)_{m8l1}$-aminosulfonyloxy group, m8l1: 0~2,

(18) a $C_{1-8}$ alkylthio group which may be substituted by $(C_{1-8}$ alkyl$)_{m8l2}$-amino group(s), m8l2: 0~2,

(19) a $C_{1-8}$ alkylsulfonyl group which may be substituted by one or more $R^{8G}$, $R^{8G}$: [1] a hydroxycarbonyl group, [2] a hydroxy group, or [3] a $(C_{1-8}$ alkyl$)_{m8l3}$-amino group, m8l3: 0~2,
(20) a $C_{2-8}$ alkenyloxy group, and
(21) a $C_{1-8}$ alkylsulfonyloxy group which may be substituted by halogen atom(s);
$R^9$ is selected from the group consisting of:
(1) a hydrogen atom,
(2) a $C_{1-8}$ alkyl group which may be substituted by one or more $R^{9A}$,
$R^{9A}$: [1] a $C_{3-8}$ cycloalkyl group, [2] a 4- to 10-membered heterocycloalkyl group which may be substituted by one or more $R^{9A1}$, [3] a hydroxy group, or [4] a $C_{1-8}$ alkoxy group,
$R^{9A1}$: [1] a $C_{1-8}$ alkyl group, [2] a $C_{3-8}$ cycloalkyl group, or [3] a 4- to 10-membered heterocycloalkyl group,
(3) a $C_{2-8}$ alkenyl group,
(4) a $C_{2-8}$ alkynyl group which may be substituted by one or more $R^{9C}$,
$R^{9C}$: [1] a $C_{1-8}$ alkoxy group, [2] a $(C_{1-8}$ alkyl$)_{m9b}$-amino group which may be substituted by $C_{6-10}$ aryl group(s), [3] a 4- to 10-membered heterocycloalkyl group which may be substituted by one or more $R^{9C1}$, [4] a $C_{3-8}$ cycloalkyl group, [5] a hydroxy group, or [6] a hydroxycarbonyl group,
m9b: 0~2,
$R^{9C1}$: [1] a $C_{3-8}$ cycloalkyl group, [2] a 4- to 10-membered heterocycloalkyl group, or [3] an oxo group,
(5) a $C_{3-8}$ cycloalkyl group,
(6) a 4- to 10-membered heterocycloalkyl group which may be substituted by one or more $R^{9D}$,
$R^{9D}$: [1] a $C_{1-8}$ alkyl group which may be substituted by 4- to 10-membered heterocycloalkyl group(s), [2] a $C_{3-8}$ cycloalkyl group, [3] a 4- to 10-membered heterocycloalkyl group, or [4] a $C_{1-6}$ alkylsulfonyl group,
(7) a $C_{6-10}$ aryl group which may be substituted by one or more $R^{9E}$,
$R^{9E}$: [1] a halogen atom, [2] a hydroxy group, [3] a hydroxycarbonyl group, or [4] a $C_{1-8}$ alkyl group which may be substituted by hydroxy group(s),
(8) a 5- to 14-membered heteroaryl group which may be substituted by $C_{1-8}$ alkyl group(s),
(9) a cyano group,
(10) a $C_{1-8}$ alkanoyl group,
(11) a 4- to 10-membered nitrogen-containing heterocycloalkylcarbonyl group which may be substituted by $C_{1-8}$ alkyl group(s),
(12) a halogen atom,
(13) a $(C_{1-8}$ alkyl$)_{m9c}$-amino group,
m9c: 0~2,
(14) a $C_{1-8}$ alkylcarbonyl($C_{0-8}$ alkyl)amino group which may be substituted by $(C_{1-8}$ alkyl$)_{m9d}$-amino group(s),
m9d: 0~2,
(15) a $C_{1-8}$ alkylsulfonyl($C_{0-8}$ alkyl)amino group,
(16) a $(C_{1-8}$ alkyl$)_{m9e}$-aminosulfonyl($C_{0-8}$ alkyl)amino group,
m9e: 0~2,
(17) a nitro group,
(18) a hydroxy group,
(19) a $C_{1-8}$ alkoxy group which may be substituted by one or more R9G,
$R^{9G}$: [1] a hydroxy group, [2] a hydroxycarbonyl group, [3] a $C_{6-10}$ aryl group which may be substituted by $C_{1-8}$ alkoxy group(s), [4] a $(C_{1-8}$ alkyl$)_{m9g1}$-amino group, [5] a $C_{1-8}$ alkoxy group which may be substituted by one or more $R^{9G1}$, or [6] a 5- to 14-membered heteroaryl group,
m9g1: 0~2,
$R^{9G1}$: [1] a $C_{1-8}$ alkoxy group, or [2] a hydroxycarbonyl group,
(20) a 4- to 10-membered heterocycloalkyloxy group which may be substituted by 4- to 10-membered heterocycloalkyl group(s),
(21) a $C_{1-8}$ alkylthio group which may be substituted by $(C_{1-8}$ alkyl$)_{m9f}$-amino group(s),
m9f: 0~2,
(22) a $C_{1-8}$ alkylsulfonyl group which may be substituted by $(C_{1-8}$ alkyl$)_{m9g}$-amino group(s),
m9g: 0~2,
(23) a $(C_{1-8}$ alkyl$)_{m9h}$-aminosulfonyl group,
m9h: 0~2, and
(24) a 4- to 10-membered nitrogen-containing heterocycloalkylsulfonyl group which may be substituted by $C_{1-8}$ alkyl group(s);
$R^{10}$ represents [1] a hydrogen atom, or [2] a 4- to 10-membered heterocycloalkyl group which may be substituted by 4- to 10-membered heterocycloalkyl group(s).

6. The pharmaceutical of claim 1, wherein the compound represented by Formula (I) is selected from the group consisting of 9-(4-isopropyl-piperazin-1-yl)-6,6-dimethyl-11-oxo-6,11-dihydro-5H-benzo[b]carbazole-3-carbonitrile; 6,6-dimethyl-8-(4-oxetan-3-yl-piperazin-1-yl)-11-oxo-9-prop-1-ynyl-6,11-dihydro-5H-benzo[b]carbazole-3-carbonitrile; 9-cyclopropylethynyl-6,6-dimethyl-8-(4-oxetan-3-yl-piperazin-1-yl)-11-oxo-6,11-dihydro-5H-benzo[b]carbazole-3-carbonitrile; 6,6-dimethyl-8-(1-oxetan-3-yl-piperidin-4-yl)-11-oxo-6,11-dihydro-5H-benzo[b]carbazole-3-carbonitrile; 9-bromo-6,6-dimethyl-8-(4-oxetan-3-yl-piperazin-1-yl)-11-oxo-6,11-dihydro-5H-benzo[b]carbazole-3-carbonitrile; 9-bromo-8-(4-cyclopropyl-piperazin-1-yl)-6,6-dimethyl-11-oxo-6,11-dihydro-5H-benzo[b]carbazole-3-carbonitrile; 9-chloro-6,6-dimethyl-8-(4-morpholin-4-yl-piperidin-1-yl)-11-oxo-6,11-dihydro-5H-benzo[b]carbazole-3-carbonitrile; 8-(4-cyclobutyl-piperazin-1-yl)-6,6-dimethyl-11-oxo-9-prop-1-ynyl-6,11-dihydro-5H-benzo[b]carbazole-3-carbonitrile; 6,6,9-trimethyl-8-(4-morpholin-4-yl-piperidin-1-yl)-11-oxo-6,11-dihydro-5H-benzo[b]carbazole-3-carbonitrile; 9-ethyl-6,6-dimethyl-8-(4-oxetan-3-yl-piperazin-1-yl)-11-oxo-6,11-dihydro-5H-benzo[b]carbazole-3-carbonitrile; 9-ethyl-6,6-dimethyl-8-(4-morpholin-4-yl-piperidin-1-yl)-11-oxo-6,11-dihydro-5H-benzo[b]carbazole-3-carbonitrile; 9-ethynyl-6,6-dimethyl-8-(4-oxetan-3-yl-piperazin-1-yl)-11-oxo-6,11-dihydro-5H-benzo[b]carbazole-3-carbonitrile; 8-(4-cyclobutyl-piperazin-1-yl)-9-ethyl-6,6-dimethyl-11-oxo-6,11-dihydro-5H-benzo[b]carbazole-3-carbonitrile; 9-ethynyl-6,6-dimethyl-11-oxo-8-(4-pyrrolidin-1-yl-piperidin-1-yl)-6,11-dihydro-5H-benzo[b]carbazole-3-carbonitrile; 6,6-dimethyl-11-oxo-8-(4-pyrrolidin-1-yl-piperidin-1-yl)-6,11-dihydro-5H-benzo[b]carbazole-3-carbonitrile; 8-(4-cyclobutyl-piperazin-1-yl)-9-ethynyl-6,6-dimethyl-11-oxo-6,11-dihydro-5H-benzo[b]carbazole-3-carbonitrile; 8-(4-cyclobutyl-piperazin-1-yl)-6,6-dimethyl-11-oxo-9-propyl-6,11-dihydro-5H-benzo[b]carbazole-3-carbonitrile; 8-(1-isopropyl-piperidin-4-yl)-6,6-dimethyl-11-oxo-6,11-dihydro-5H-benzo[b]carbazole-3-carbonitrile; 8-(4-isopropyl-piperazin-1-yl)-6,6-dimethyl-11-oxo-6,11-dihydro-5H-benzo[b]carbazole-3-carbonitrile; 8-(4-cyclobutyl-piperazin-1-yl)-9-cyclopropyl-6,6-dimethyl-11-oxo-6,11-dihydro-5H-benzo[b]carbazole-3-carbonitrile; 8-(2-tert-butylamino-ethoxy)-6,6-dimethyl-11-oxo-6,11-dihydro-5H-benzo[b]carbazole-3-carbonitrile; 9-ethynyl-8-(4-methanesulfonyl-piperazin-1-yl)-6,6-dimethyl-11-oxo-6,11- dihydro-5H-benzo[b]carbazole-3-carbonitrile; 9-bromo-8-(4-cyclobutyl-piperazin-1-yl)-6,6-dimethyl-11-oxo-6,11-dihydro-5H-benzo[b]carbazole-3-carbonitrile; 6,6-dimethyl-8-(4-oxetan-3-yl-piperazin-1-yl)-11-oxo-9-propyl-6,11-dihydro-5H-benzo[b]carbazole-3-carbonitrile; and 9-ethynyl-6,6-dimethyl-8-morpholin-4-yl-11-oxo-6,11-dihydro-5H-benzo[b]carbazole-3-carbonitrile.

7. The pharmaceutical of claim 1, wherein the pharmaceutical is for the treatment of cancer or cancer metastasis.

8. The pharmaceutical of claim 7, wherein the cancer is selected from the group consisting of lung cancer, anaplastic large cell lymphoma, inflammatory myofibroblastic tumor, esophageal cancer, and neuroblastoma.

9. The pharmaceutical of claim 1, wherein the pharmaceutical is for the treatment of depression.

10. The pharmaceutical of claim 1, wherein the compound represented by Formula (I) is 9-(4-isopropyl-piperazin-1-yl)-6,6-dimethyl-11-oxo-6,11-dihydro-5H-benzo[b]carbazole-3-carbonitrile.

11. The pharmaceutical of claim 1, wherein the compound represented by Formula (I) is 6,6-dimethyl-8-(4-oxetan-3-yl-piperazin-1-yl)-11-oxo-9-prop-1-ynyl-6,11-dihydro-5H-benzo[b]carbazole-3-carbonitrile.

12. The pharmaceutical of claim 1, wherein the compound represented by Formula (I) is 9-cyclopropylethynyl-6,6-dimethyl-8-(4-oxetan-3-yl-piperazin-1-yl)-11-oxo-6, 11-dihydro-5H-benzo[b]carbazole-3-carbonitrile.

13. The pharmaceutical of claim 1, wherein the compound represented by Formula (I) is 6,6-dimethyl-8-(1-oxetan-3-yl-piperidin-4-yl)-11-oxo-6,11-dihydro-5H-benzo[b]carbazole-3-carbonitrile.

14. The pharmaceutical of claim 1, wherein the compound represented by Formula (I) is 9-bromo-6,6-dimethyl-8-(4-oxetan-3-yl-piperazin-1-yl)-11-oxo-6,11-dihydro-5H-benzo[b]carbazole-3-carbonitrile.

15. The pharmaceutical of claim 1, wherein the compound represented by Formula (I) is 9-bromo-8-(4-cyclopropyl-piperazin-1-yl)-6,6-dimethyl-11-oxo-6,11-dihydro-5H-benzo[b]carbazole-3-carbonitrile.

16. The pharmaceutical of claim 1, wherein the compound represented by Formula (I) is 9-chloro-6,6-dimethyl-8-(4-morpholin-4-yl-piperidin-1-yl)-11-oxo-6,11-dihydro-5H-benzo[b]carbazole-3-carbonitrile.

17. The pharmaceutical of claim 1, wherein the compound represented by Formula (I) is 8-(4-cyclobutyl-piperazin-1-yl)-6,6-dimethyl-11-oxo-9-prop-1-ynyl-6,11-dihydro-5H-benzo[b]carbazole-3-carbonitrile.

18. The pharmaceutical of claim 1, wherein the compound represented by Formula (I) is 6,6,9-trimethyl-8-(4-morpholin-4-yl-piperidin-1-yl)-11-oxo-6,11-dihydro-5H-benzo[b]carbazole-3-carbonitrile.

19. The pharmaceutical of claim 1, wherein the compound represented by Formula (I) is 9-ethyl-6,6-dimethyl-8-(4-oxetan-3-yl-piperazin-1-yl)-11-oxo-6,11-dihydro-5H-benzo[b]carbazole-3-carbonitrile.

20. The pharmaceutical of claim 1, wherein the compound represented by Formula (I) is 9-ethyl-6,6-dimethyl-8-(4-morpholin-4-yl-piperidin-1-yl)-11-oxo-6,11-dihydro-5H-benzo[b]carbazole-3-carbonitrile.

21. The pharmaceutical of claim 1, wherein the compound represented by Formula (I) is 9-ethynyl-6,6-dimethyl-8-(4-oxetan-3-yl-piperazin-1-yl)-11-oxo-6,11-dihydro-5H-benzo[b]carbazole-3-carbonitrile.

22. The pharmaceutical of claim 1, wherein the compound represented by Formula (I) is 8-(4-cyclobutyl-piperazin-1-yl)-9-ethyl-6,6-dimethyl-11-oxo-6,11-dihydro-5H-benzo[b]carbazole-3-carbonitrile.

23. The pharmaceutical of claim 1, wherein the compound represented by Formula (I) is 9-ethynyl-6,6-dimethyl-11-oxo-8-(4-pyrrolidin-1-yl-piperidin-1-yl)-6,11-dihydro-5H-benzo[b]carbazole-3-carbonitrile.

24. The pharmaceutical of claim 1, wherein the compound represented by Formula (I) is 6,6-dimethyl-11-oxo-8-(4-pyrrolidin-1-yl-piperidin-1-yl)-6,11-dihydro-5H-benzo[b]carbazole-3-carbonitrile.

25. The pharmaceutical of claim 1, wherein the compound represented by Formula (I) is 8-(4-cyclobutyl-piperazin-1-yl)-9-ethynyl-6,6-dimethyl-11-oxo-6,11-dihydro-5H-benzo[b]carbazole-3-carbonitrile.

26. The pharmaceutical of claim 1, wherein the compound represented by Formula (I) is 8-(4-cyclobutyl-piperazin-1-yl)-6,6-dimethyl-11-oxo-9-propyl-6,11-dihydro-5H-benzo[b]carbazole-3-carbonitrile.

27. The pharmaceutical of claim 1, wherein the compound represented by Formula (I) is 8-(1-isopropyl-piperidin-4-yl)-6,6-dimethyl-11-oxo-6,11-dihydro-5H-benzo[b]carbazole-3-carbonitrile.

28. The pharmaceutical of claim 1, wherein the compound represented by Formula (I) is 8-(4-isopropyl-piperazin-1-yl)-6,6-dimethyl-11-oxo-6,11-dihydro-5H-benzo[b]carbazole-3-carbonitrile.

29. The pharmaceutical of claim 1, wherein the compound represented by Formula (I) is 8-(4-cyclobutyl-piperazin-1-yl)-9-cyclopropyl-6,6-dimethyl-11-oxo-6,11-dihydro-5H-benzo[b]carbazole-3-carbonitrile.

30. The pharmaceutical of claim 1, wherein the compound represented by Formula (I) is 8-(2-tert-butylamino-ethoxy)-6,6-dimethyl-11-oxo-6,11-dihydro-5H-benzo[b]carbazole-3-carbonitrile.

31. The pharmaceutical of claim 1, wherein the compound represented by Formula (I) is 9-ethynyl-8-(4-methanesulfonyl-piperazin-1-yl)-6,6-dimethyl-11-oxo-6,11-dihydro-5H-benzo[b]carbazole-3-carbonitrile.

32. The pharmaceutical of claim 1, wherein the compound represented by Formula (I) is 9-bromo-8-(4-cyclobutyl-piperazin-1-yl)-6,6-dimethyl-11-oxo-6,11-dihydro-5H-benzo[b]carbazole-3-carbonitrile.

33. The pharmaceutical of claim 1, wherein the compound represented by Formula (I) is 6,6-dimethyl-8-(4-oxetan-3-yl-piperazin-1-yl)-11-oxo-9-propyl-6,11-dihydro-5H-benzo[b]carbazole-3-carbonitrile.

34. The pharmaceutical of claim 1, wherein the compound represented by Formula (I) is 9-ethynyl-6,6-dimethyl-8-morpholin-4-yl-11-oxo-6,11-dihydro-5H-benzo[b]carbazole-3-carbonitrile.

* * * * *